US012594276B2

(12) United States Patent
Patel et al.

(10) Patent No.: US 12,594,276 B2
(45) Date of Patent: Apr. 7, 2026

(54) INHIBITORS OF HUMAN IMMUNODEFICIENCY VIRUS REPLICATION

(71) Applicant: ViiV Healthcare UK (No.5) Limited, Stevenage (GB)

(72) Inventors: Manoj Patel, Branford, CT (US); Kyle E. Parcella, Branford, CT (US); Eric P. Gillis, Branford, CT (US); B Narasimhulu Naidu, Branford, CT (US)

(73) Assignee: ViiV Healthcare UK (No. 5) Limited, Stevenage (GB)

( * ) Notice: Subject to any disclaimer, the term of this patent is extended or adjusted under 35 U.S.C. 154(b) by 0 days.

(21) Appl. No.: 19/043,910

(22) Filed: Feb. 3, 2025

(65) Prior Publication Data

US 2025/0249005 A1 Aug. 7, 2025

Related U.S. Application Data

(60) Provisional application No. 63/549,602, filed on Feb. 5, 2024.

(51) Int. Cl.

| | |
|---|---|
| ***A61K 31/519*** | (2006.01) |
| ***A61K 31/439*** | (2006.01) |
| ***A61K 31/4402*** | (2006.01) |
| ***A61K 31/4439*** | (2006.01) |
| ***A61K 31/4985*** | (2006.01) |
| ***A61K 31/505*** | (2006.01) |
| ***A61K 31/513*** | (2006.01) |
| ***A61K 31/5365*** | (2006.01) |
| ***A61K 31/5377*** | (2006.01) |
| ***A61K 31/635*** | (2006.01) |
| ***A61K 31/675*** | (2006.01) |
| ***A61P 31/18*** | (2006.01) |
| ***C07D 471/04*** | (2006.01) |

(52) U.S. Cl.

CPC .......... *A61K 31/519* (2013.01); *A61K 31/439* (2013.01); *A61K 31/4402* (2013.01); *A61K 31/4439* (2013.01); *A61K 31/4985* (2013.01); *A61K 31/505* (2013.01); *A61K 31/513* (2013.01); *A61K 31/5365* (2013.01); *A61K 31/5377* (2013.01); *A61K 31/635* (2013.01); *A61K 31/675* (2013.01); *A61P 31/18* (2018.01); *C07D 471/04* (2013.01)

(58) Field of Classification Search

CPC ................ A61K 31/519; A61K 31/439; A61K 31/4402; A61K 31/4439; A61K 31/4985; A61K 31/505; A61K 31/513; A61K 31/5365; A61K 31/5377; A61K 31/635; A61K 31/675; A61P 31/18; C07D 471/04

USPC .......................................................... 514/210

See application file for complete search history.

(56) References Cited

U.S. PATENT DOCUMENTS

| | | | | |
|---|---|---|---|---|
| 2021/0395248 | A1* | 12/2021 | Bowsher | A61P 31/18 |
| 2023/0023968 | A1 | 1/2023 | Zhang et al. | |
| 2023/0355626 | A1* | 11/2023 | Gillis | A61K 31/4985 |
| 2024/0327428 | A1 | 10/2024 | Wu et al. | |

FOREIGN PATENT DOCUMENTS

| | | | |
|---|---|---|---|
| CN | 116444499 | A | 7/2023 |
| WO | WO-2012065062 | A1 | 5/2012 |
| WO | WO-2013006738 | A1 | 1/2013 |
| WO | WO-2013006792 | A1 | 1/2013 |

(Continued)

OTHER PUBLICATIONS

Sever et al. Int. J. Mol. Sci. 2024, 25, 3659. https://doi.org/10.3390/ijms25073659 A Review of FDA-Approved Anti-HIV-1 Drugs, Anti-Gag Compounds, and Potential Strategies for HIV-1 Eradication. (Year: 2024).*

(Continued)

*Primary Examiner* — Jared Barsky

*Assistant Examiner* — Liyuan Mou

(74) *Attorney, Agent, or Firm* — Eric Myers; Nicole Ginanni

(57) ABSTRACT

A compound of Formula (I), including pharmaceutically acceptable salts thereof, and compositions and methods for treatment or prevention of human immunodeficiency virus (HIV) infection are set forth. Novel inhibitors of HIV, pharmaceutical compositions containing such compounds, and methods for using these compounds in the treatment of HIV infection are described. Formula (I) is as follows:

Formula (I)

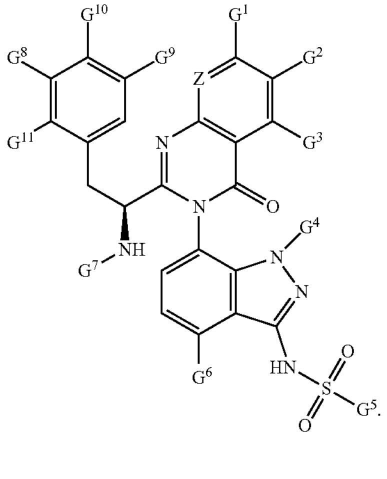

7 Claims, 23 Drawing Sheets

(56) References Cited

FOREIGN PATENT DOCUMENTS

| | | | |
|---|---|---|---|
| WO | WO-2014110296 | A1 | 7/2014 |
| WO | WO-2014110297 | A1 | 7/2014 |
| WO | WO-2014110298 | A1 | 7/2014 |
| WO | WO-2014134566 | A2 | 9/2014 |
| WO | WO-2015130964 | A1 | 9/2015 |
| WO | WO-2015130966 | A1 | 9/2015 |
| WO | WO-2016033243 | A1 | 3/2016 |
| WO | WO-2018035359 | A1 | 2/2018 |
| WO | WO-2018203235 | A1 | 11/2018 |
| WO | WO-2019035904 | A1 | 2/2019 |
| WO | WO-2019035973 | A1 | 2/2019 |
| WO | WO-2019161017 | A1 | 8/2019 |
| WO | WO-2019161280 | A1 | 8/2019 |
| WO | WO-2019198024 | A1 | 10/2019 |
| WO | WO-2020018459 | A1 | 1/2020 |
| WO | WO-2020031112 | A1 | 2/2020 |
| WO | WO-2020053811 | A1 | 3/2020 |
| WO | WO-2020058844 | A1 | 3/2020 |
| WO | WO-2020084480 | A1 | 4/2020 |
| WO | WO-2020084491 | A1 | 4/2020 |
| WO | WO-2020084492 | A1 | 4/2020 |
| WO | 2020095176 | A1 | 5/2020 |
| WO | WO-2020089778 | A1 | 5/2020 |
| WO | WO-2020095177 | A1 | 5/2020 |
| WO | WO-2020157692 | A1 | 8/2020 |
| WO | WO-2020222108 | A1 | 11/2020 |
| WO | WO-2020254985 | A1 | 12/2020 |
| WO | WO-2021064570 | A1 | 4/2021 |
| WO | WO-2021064571 | A1 | 4/2021 |
| WO | WO-2021064677 | A1 | 4/2021 |
| WO | WO-2021070054 | A1 | 4/2021 |
| WO | WO-2021104413 | A1 | 6/2021 |
| WO | WO-2021108544 | A1 | 6/2021 |
| WO | WO-2021116872 | A1 | 6/2021 |
| WO | WO-2021176366 | A1 | 9/2021 |
| WO | WO-2021176367 | A1 | 9/2021 |
| WO | WO-2021209900 | A1 | 10/2021 |
| WO | WO-2021262990 | A1 | 12/2021 |
| WO | WO-2022159877 | A1 | 7/2022 |
| WO | WO-2023062559 | A1 | 4/2023 |
| WO | WO-2023102239 | A1 | 6/2023 |
| WO | WO-2023102523 | A1 | 6/2023 |
| WO | WO-2023102529 | A1 | 6/2023 |
| WO | WO-2024175044 | A2 | 8/2024 |
| WO | WO-2024220624 | A1 | 10/2024 |
| WO | WO-2024249573 | A1 | 12/2024 |
| WO | WO-2024249592 | A1 | 12/2024 |
| WO | WO-2025029247 | A1 | 2/2025 |

OTHER PUBLICATIONS

Akther T., et al., "Quinazolinone-based Subchemotypes for Targeting HIV-1 Capsid Protein: Design and Synthesis," Medicinal Chemistry Research, 2024, vol. 33(12), pp. 2431-2447, Retrieved from [https://doi.org/10.1007/s00044-024-03305-0].

Beyrer C and Pozniak A., "HIV Drug Resistance—An Emerging Threat to Epidemic Control," New England Journal of Medicine, Oct. 26, 2017, vol. 377(17), pp. 1605-1607, Retrieved from [Doi: 10.1056/NEJMp1710608.].

Blair W., et al., "HIV Capsid Is a Tractable Target for Small Molecule Therapeutic Intervention," PLOS Pathogens, Dec. 9, 2010, vol. 6(12), e1001220, pp. 1-10, Retrieved from [Doi: 10.1371/journal.ppat.1001220].

Blair W.S., et al., New Small-molecule Inhibitor Class Targeting Human Immunodeficiency Virus Type 1 Virion Maturation, Antimicrob Agents Chemother, Dec. 2009, vol. 53(12), pp. 5080-5087, Retrieved from [Doi: 10.1128/AAC.00759-09.].

Gillis E.P., et al., "Potent Long-acting Inhibitors Targeting the HIV-1 Capsid Based on a Versatile Quinazolin-4-One Scaffold," Journal of Medicinal Chemistry, Feb. 9, 2023, vol. 66(3), pp. 1941-1954.

Gupta R.K., et al., "HIV-1 Drug Resistance Before Initiation or Re-initiation of First-line Antiretroviral Therapy in Low-income and Middle-income Countries: a Systematic Review and Meta-regression Analysis," Lancet Infectious Diseases, Mar. 2018, vol. 18(3), pp. 346-355, Retrieved from [Doi: 10.1016/S1473-3099(17)30702-8].

Link J.O., et al. "Clinical Targeting of HIV Capsid Protein with a Long-acting Small Molecule," Nature, Aug. 2020, vol. 584(7822), pp. 614-618(1-25Pages), Retrieved from [Doi:10.1038/s41586-020-2443-1].

Thenin-Houssier S and Valente S.T., "HIV-1 Capsid Inhibitors as Antiretroviral Agents," Current HIV Research, 2014, vol. 14(3), pp. 270-282(1-23 Pages).

Zazzi M., et al., "The Global Burden of HIV-1 Drug Resistance in the past 20 Years," PeerJ, May 2018, vol. 26(5), pp. 1-16, Retrieved from [DOI 10.7717/peerj.4848].

Zheng J., et al., "Lenacapavir Exhibits Atropisomerism-mechanistic Pharmacokinetics and Disposition Studies of Lenacapavir Reveal Intestinal Excretion as a Major Clearance Pathway," The Journal of Pharmacology and Experimental Therapeutics, Oct. 2024, vol. 391, pp. 91-103, Retrieved from [dx.doi.org/10.1124/jpet. 124.002302].

International Search Report and Written Opinion for International Application No. PCT/IB2025/051155, mailed Apr. 8, 2025, 13 Pages.

* cited by examiner

INHIBITORS OF HUMAN IMMUNODEFICIENCY VIRUS REPLICATION

CROSS REFERENCE TO RELATED APPLICATION

This application claims the benefit of priority to U.S. Provisional Patent Application No. 63/549,602, filed Feb. 5, 2024.

FIELD OF THE INVENTION

The invention relates to compounds, compositions, and methods for the treatment or prevention of human immunodeficiency virus (HIV) infection. More particularly, the invention provides novel inhibitors of HIV, pharmaceutical compositions containing such compounds, and methods for using these compounds in the treatment of HIV infection.

BACKGROUND OF THE INVENTION

Acquired immunodeficiency syndrome (AIDS) is the result of infection by HIV. HIV continues to be a major global public health issue. In 2015, an estimated 36.7 million people were living with HIV (including 1.8 million children)—a global HIV prevalence of 0.8%. The vast majority of this number live in low- and middle-income countries. In the same year, 1.1 million people died of AIDS-related illnesses.

Current therapy for HIV-infected individuals consists of a combination of approved anti-retroviral agents. Close to four dozen drugs are currently approved for HIV infection, either as single agents, fixed dose combinations or single tablet regimens; the latter two containing 2-4 approved agents. These agents belong to a number of different classes, targeting either a viral enzyme or the function of a viral protein during the virus replication cycle. Thus, agents are classified as either nucleotide reverse transcriptase inhibitors (NRTIs), non-nucleotide reverse transcriptase inhibitors (NNRTIs), protease inhibitors (PIs), integrase strand transfer inhibitors (INSTIs), or entry inhibitors (one, maraviroc, targets the host CCR5 protein, while the other, enfuvirtide, is a peptide that targets the gp41 region of the viral gp160 protein). In addition, a pharmacokinetic enhancer (cobicistat) can be used in combinations with antiretroviral agents (ARVs) that require boosting.

Despite the armamentarium of agents and drug combinations, there remains a medical need for new anti-retroviral agents. High viral heterogeneity, drug-associated toxicity, tolerability problems, and poor adherence can all lead to treatment failure and may result in the selection of viruses with mutations that confer resistance to one or more antiretroviral agents or even multiple drugs from an entire class (Beyrer, C., Pozniak A. HIV drug resistance—an emerging threat to epidemic control. N. Engl. J. Med. 2017, 377, 1605-1607; Gupta, R. K., Gregson J., et al. HIV-1 drug resistance before initiation or re-initiation of first-line antiretroviral therapy in low-income and middle-income countries: a systematic review and meta-regression analysis. Lancet Infect. Dis. 2017, 18, 346-355; Zazzi, M., Hu, H., Prosperi, M. The global burden of HIV-1 drug resistance in the past 20 years. PeerJ. 2018, DOI 10.7717/peerj.4848). As a result, new drugs are needed that are easier to take, have high genetic barriers to the development of resistance and have improved safety over current agents. In this panoply of choices, novel mechanisms of action (MOAs) that can be used as part of the preferred antiretroviral therapy (ART) can still have a major role to play since they should be effective against viruses resistant to current agents. Maximum benefits to HIV infected patients might be achieved if anti-HIV drugs with new mechanisms of action are discovered which have benefits which facilitate long term compliance and safety.

Certain potentially therapeutic compounds, including capsid inhibitors, have been described and are set forth in Blair, Wade S. et. al. Antimicrobial Agents and Chemotherapy (2009), 53(12), 5080-5087, Blair, Wade S. et al. PLoS Pathogens (2010), 6(12), e1001220, Thenin-Houssier, Suzie; Valente, Susana T. Current HIV Research, 2016, 14, 270-282, and published PCT Patent applications with the following numbers: WO 2012/065062, WO 2013/006738, WO 2013/006792, WO 2014/110296, WO 2014/110297, WO 2014/110298, WO 2014/134566, WO 2015/130964, WO 2015130966, WO 2016/033243, WO 2018/035359, and WO 2018/203235, WO 2019/198024, WO 2020/254985, WO 2020/031112, WO 2020/053811, WO 2020/058844, WO 2020/084480, WO 2020/084491, WO 2020/084492, WO 2020/089778, WO 2020/095177, WO 2020/095176, WO 2020/157692, WO 2020/222108, WO 2020/222108, WO 2020/254985. WO 2021/064677, WO 2021/064570, WO 2021/064571, WO 2021/070054, WO 2021/176366, and WO 2021/176367.

What is now needed are additional compounds which are novel and useful in the treatment of HIV. Additionally, these compounds should provide advantages for pharmaceutical uses, for example, with regard to one or more of their mechanisms of action, binding, inhibition efficacy, target selectivity, solubility, safety profiles, or bioavailability. Also needed are new formulations and methods of treatment which utilize these compounds.

SUMMARY OF THE INVENTION

In one aspect, the present invention provides a compound of Formula (I):

Formula (I)

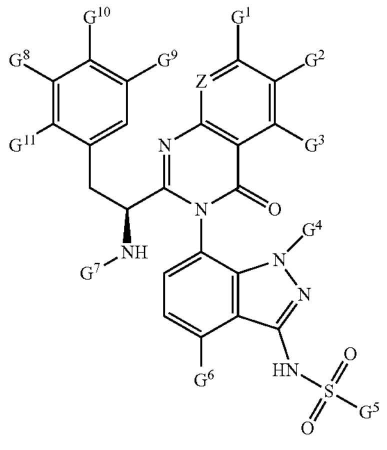

or a pharmaceutically acceptable salt thereof, wherein:

Z is CH or N;

$G^1$ is selected from

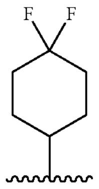

and

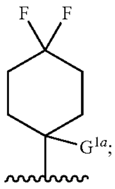

$G^{1a}$ is selected from the group consisting of —OH, —F, —Cl, —CN, —$C_{1-4}$alkyl optionally substituted with 1, 2 or 3 —F, and —$C_{1-3}$alkyl optionally substituted with one substituent selected from the group consisting of —$N(C_{1-2}alkyl)_2$, —$NH(C_{1-2}alkyl)$, and a heterocycle selected from the group consisting of azetidine, pyrrolidine, piperidine, and morpholine, wherein said heterocycle is optionally substituted with 1, 2, 3 or 4 substituents independently selected from the group consisting of —$CH_3$ and —F;

$G^2$ is selected from the group consisting of —H, —F, —Cl, —$OCH_3$, —$CH_3$, —$CHF_2$, cyclopropyl,

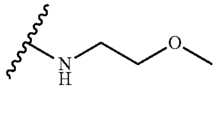

and

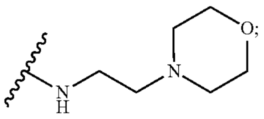

$G^3$ is selected from the group consisting of —H, —Cl, —CN, —CHO, —$C(O)C_{1-2}$alkyl; —$C_{1-3}$alkyl optionally substituted with 1, 2 or 3 —F; —$C_{1-3}$alkyl optionally substituted with one substituent select from the group consisting of —OH, —$OC_{1-2}$alkyl and —CN; —$C_{3-4}$cycloalkyl optionally substituted with 1, 2 or 3 —F; and —NH—$C_{1-3}$alkyl optionally substituted with 1, 2, or 3 substituents independently selected from the group consisting of —$OCH_3$ and —F;

or $G^3$ is —$NH(C_{1-4}alkyl\text{-}G^{3a})$, wherein $G^{3a}$ is a heterocycle selected from the group consisting of oxetane, tetrahydrofuran, and tetrahydro-2H-pyran, wherein said heterocycle is optionally substituted with one substituent selected from the group consisting of —$CH_3$, —F, —$OC_{1-3}$alkyl and —$OC_{3-4}$cycloalkyl;

or $G^3$ is selected from the group consisting of:

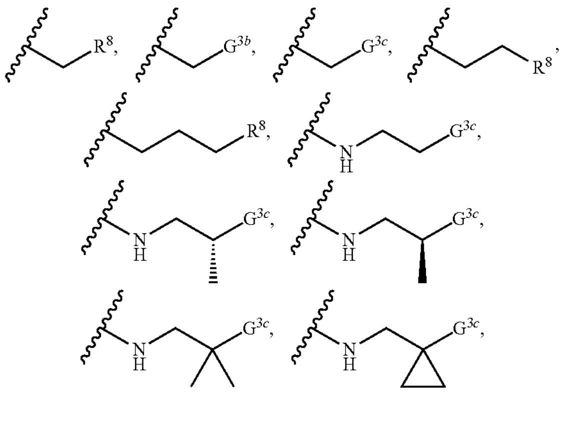

-continued

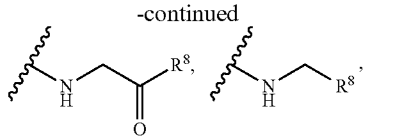

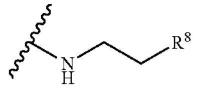

and

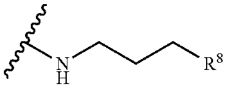

$G^{3b}$ is selected from the group consisting of —$NH(C_{1-2}alkyl)$, —$N(C_{1-2}alkyl)_2$, —$NH(CH_2CH_2OC_{1-3}alkyl)$, —$N(C_{1-2}alkyl)(CH_2CH_2OC_{1-3}alkyl)$ and —$NH(CH_2CH_2R^8)$;

$G^{3c}$ is selected from the group consisting of —H, —CN, —$OC_{1-3}$alkyl, —$C_{3-6}$cycloalkyl, —$NHC(O)C_{1-3}$alkyl, —$NH(C_{1-2}alkyl)$, —$N(C_{1-2}alkyl)_2$, —$R^8$, an aromatic heterocycle selected from the group consisting of phenyl, pyridine, thiazole, pyrazole and imidazole, wherein said aromatic heterocycle is optionally substituted with one —$CH_3$ group; and a non-aromatic heterocycle selected from the group consisting of

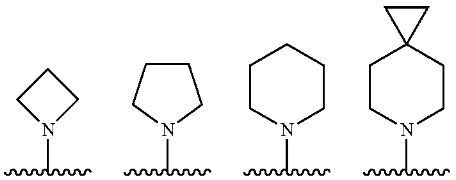

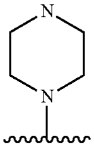

and

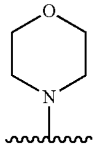

, wherein said non-aromatic heterocycle is optionally independently substituted with 1 or 2 substituents selected from the group consisting of —F, —$CH_3$, —$CF_3$, —$CHF_2$, —$OC_{1-2}$alkyl and —$C(O)C_{1-2}$alkyl;

$G^4$ is a heterocycle selected from the group consisting of pyridine, pyrimidine, pyrazole, imidazole, oxetane, tetrahydrofuran, tetrahydro-2H-pyran, azetidine, pyrrolidine and piperidine, wherein said heterocycle is optionally substituted with —$CH_2CH_2OC_{1-3}$alkyl; or $G^4$ is selected from the group consisting of:

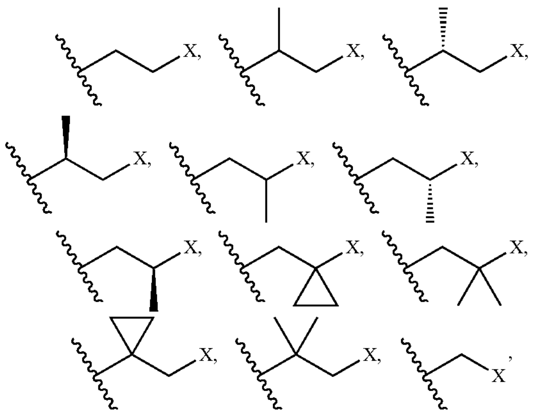

-continued

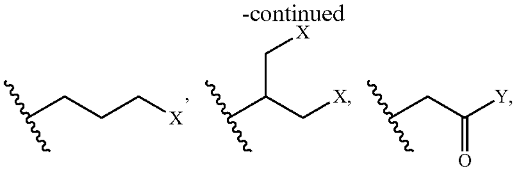

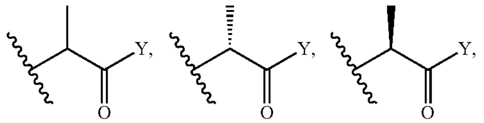

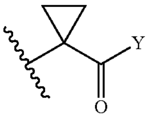
and
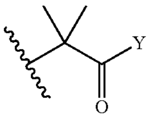

X is selected from the group consisting of —$OR^1$, —Cl, —Br, phenyl, pyridine, pyrazole, imidazole, pyrrolidin-2-one, 2,5-dihydro-pyrrole, 4-methyl-7-(methylamino)-2H-chromen-2-one, —$NR^1R^2$, —$R^6$, —$R^7$, and —$R^8$;

Y is selected from the group consisting of —$NR^1R^2$, —$R^6$, —$R^7$, and —$R^8$;

$R^1$ is selected from the group consisting of —H, phenyl, pyridine, —$R^4$, and —$C_{1-4}$alkyl optionally substituted with 1, 2 or 3 —F, 1 or 2 —$OC_{1-3}$alkyl groups, or one —CN group; —$C_{3-4}$cycloalkyl optionally substituted with 1 or 2 —F or a —$OCH_3$ group; oxetane optionally substituted with one —$CH_3$ group; tetrahydrofuran optionally substituted with one —$CH_3$ group; and tetrahydro-2H-pyran optionally substituted with one —$CH_3$ group;

$R^2$ is selected from the group consisting of —H, —$C_{1-4}$alkyl optionally substituted with 1, 2 or 3 —F, 1 or 2 —$OC_{1-3}$alkyl groups, or one —CN group; —$C_{3-4}$cycloalkyl optionally substituted with 1 or 2 substituents independently selected from the group consisting of —F and —$OCH_3$; and oxetane optionally substituted with one —$CH_3$ group;

$R^4$ is selected from the group consisting of —$(CH_2CH_2O)_nCH_2CH_2N(R^5)_2$ and —$(CH_2CH_2O)_nR^5$;

n is 2, 3, 4, 5, 6, 7 or 8;

each $R^5$ is independently selected from the group consisting of —H, —$C_{1-4}$alkyl, and —$C_{3-4}$cycloalkyl;

$R^6$ is a heterocycle selected from the group consisting of azetidine, pyrrolidine, piperidine, piperazine, and morpholine, wherein said heterocycle is optionally substituted with 1, 2, 3 or 4 —F, one —OH group, 1 or 2 —$OC_{1-4}$alkyl groups, 1 or 2 —$CH_3$ groups, one —$C_{1-3}$alkyl group optionally substituted with 1, 2 or 3 —F, one —$CH_3$ group optionally substituted with 1, 2 or 3 substituents independently selected from the group consisting of —F, —OH and —$OC_{1-3}$alkyl, or —$CH_2$pyridine optionally substituted with 1 or 2 —$CH_3$ groups;

$R^7$ is a heterocycle selected from the group consisting of azetidine, pyrrolidine, piperidine, piperazine, and morpholine, wherein said heterocycle is optionally substituted with one substituent selected from the group consisting of —$CO_2H$, —$S(O_2)R^{10}$, —$N(R^9)_2$, —$NR^9SO_2R^{10}$, —$NR^9COR^{10}$, —$C(O)R^5$, —$C(O)R^6$, a heterocycle selected from the group consisting of 1,2,4-oxadiazole, isoxazole, pyrazole, imidazole and thiazole, wherein said heterocycle is optionally substituted with one $R^{10}$ group, and a heterocycle selected from the group consisting of oxetane, tetrahydrofuran and tetrahydro-2H-pyran, wherein said heterocycle is optionally substituted with one —$CH_3$ group;

each $R^8$ is independently a heterocycle selected from the group consisting of

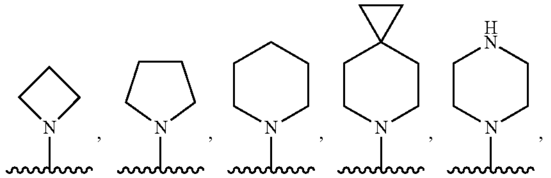

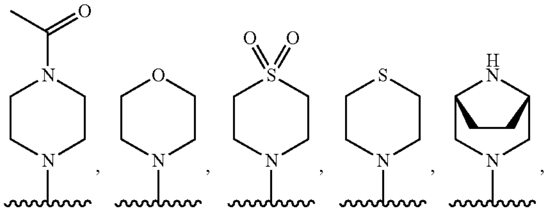

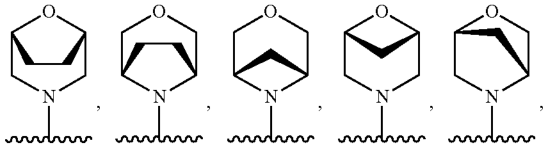

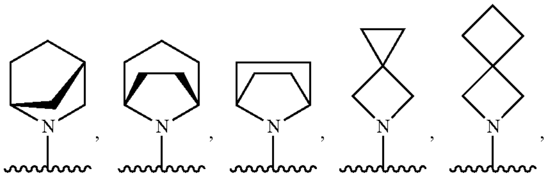

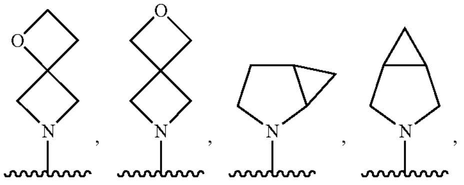

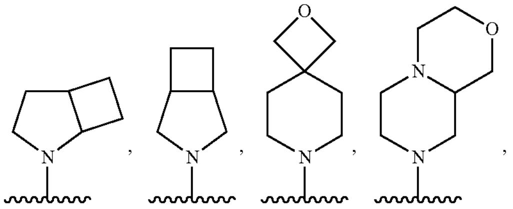

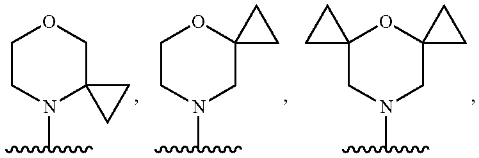

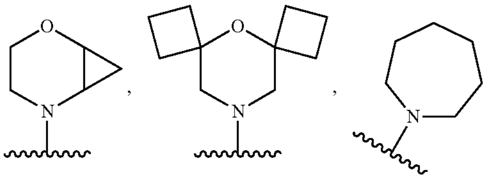
and

-continued

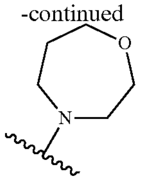

wherein said heterocycle is optionally substituted with 1, 2, 3 or 4 substituents independently selected from the group consisting of —F, —$CF_3$, —$OCH_3$, —$CHF_2$, —$CH_2F$ and —$C_{1-4}$alkyl;

each $R^9$ is independently selected from the group consisting of —H, —$CH_3$, —$C_{2-3}$alkyl optionally substituted with 1, 2 or 3 —F, and —$C_{3-4}$cycloalkyl optionally substituted with 1 or 2 —F;

$R^{10}$ is selected from the group consisting of —$CH_3$, —$CH_2F$, —$CHF_2$, —$CF_3$, —$C_{2-3}$alkyl optionally substituted with 1, 2 or 3 —F, and —$C_{3-4}$cycloalkyl optionally substituted with 1 or 2 —F;

$G^5$ is selected from the group consisting of —$C_{1-3}$alkyl optionally substituted with 1, 2 or 3 —F, and —$C_{3-4}$cycloalkyl optionally substituted with 1 or 2 —F;

$G^6$ is selected from the group consisting of —F, —C, —$CH_3$, and —$OCH_3$;

$G^7$ is selected from the group consisting of

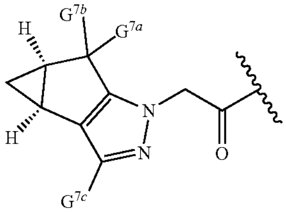

and

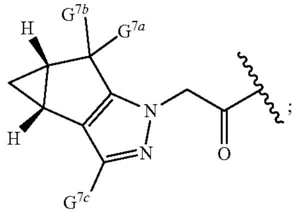

;

$G^{7a}$ is selected from the group consisting of —H and —F;

$G^{7b}$ is selected from the group consisting of —H, —$CH_3$ and —F;

$G^{7c}$ is selected from the group consisting of —$C_{1-2}$alkyl optionally substituted with 1, 2 or 3 —F, and —$C_{3-4}$cycloalkyl optionally substituted with 1 or 2 —F;

$G^8$ and $G^9$ are independently selected from the group consisting of —H, —F, —Cl, —$CH_3$ and —$OCH_3$;

$G^{10}$ is selected from the group consisting of —H and —F; and $G^{11}$ is selected from the group consisting of —H, —F, —$CH_3$ and —$OCH_3$.

In one aspect, the invention provides an Example compound of the invention, or a pharmaceutically acceptable salt thereof.

In another aspect, the invention provides a compound selected from the group consisting of:

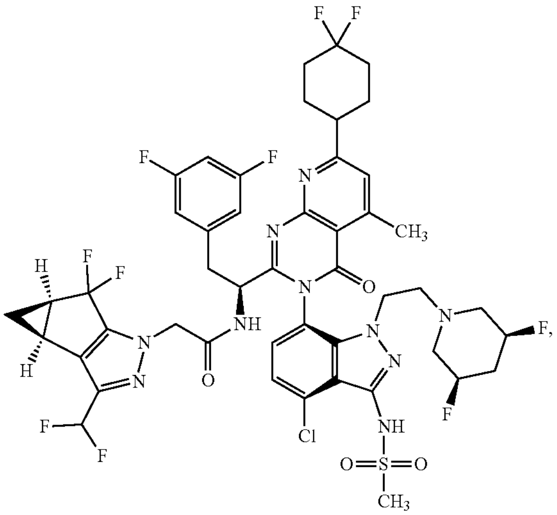

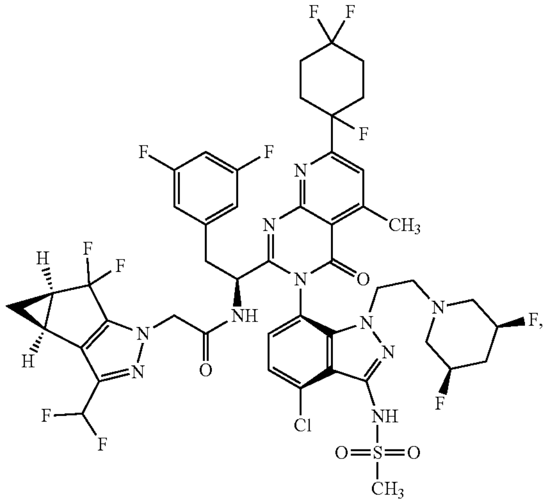

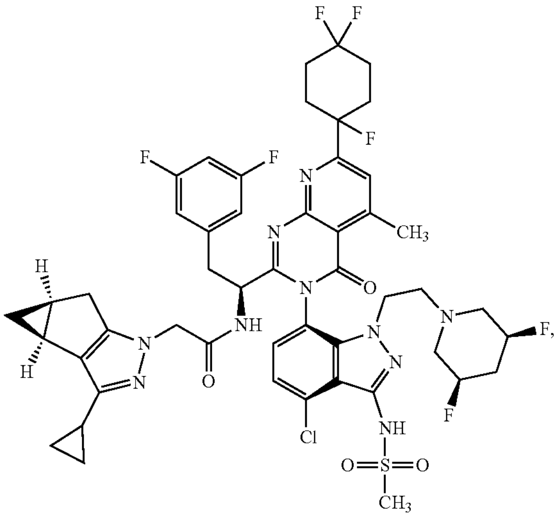

-continued
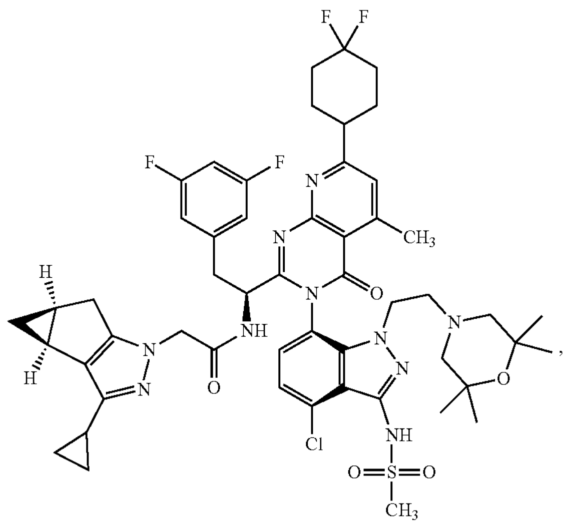
,
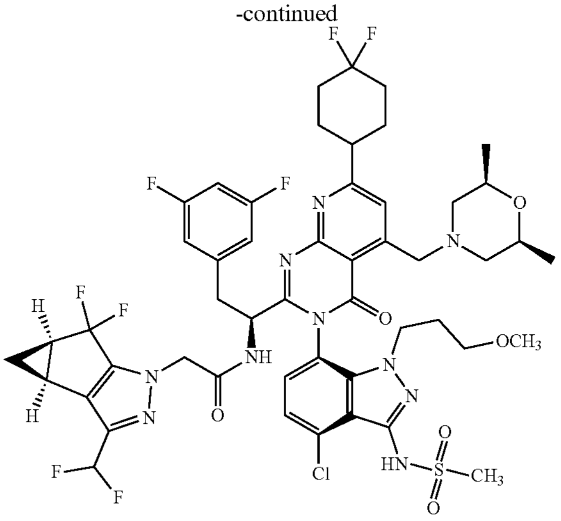
,
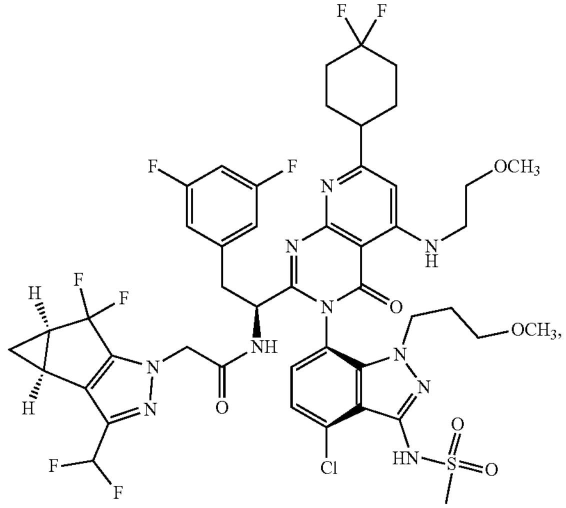
,
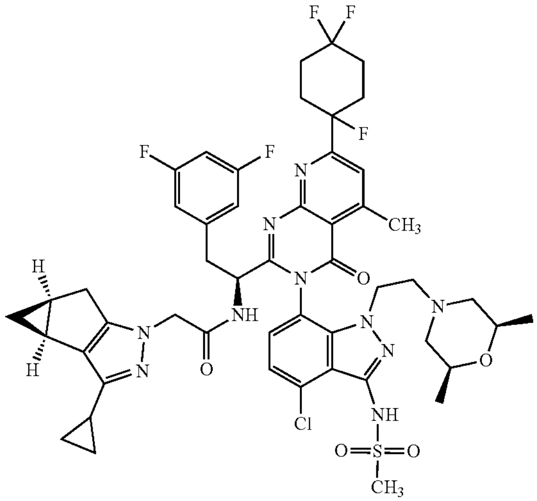
,
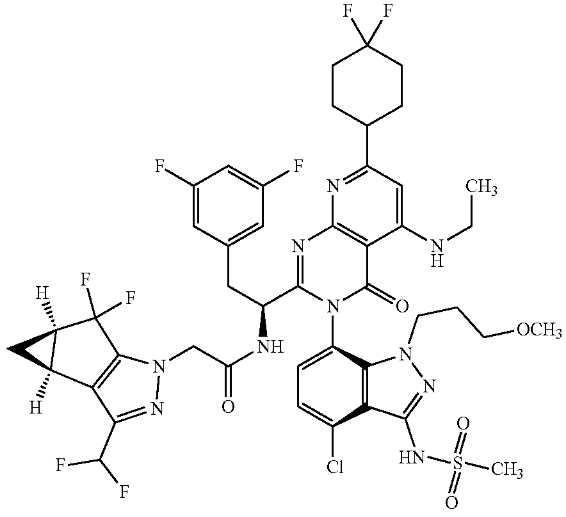
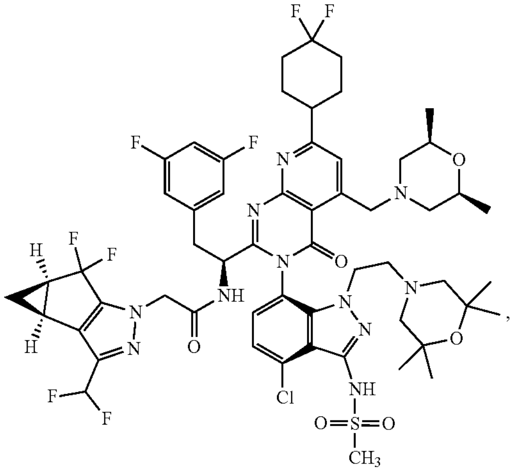
, and -continued

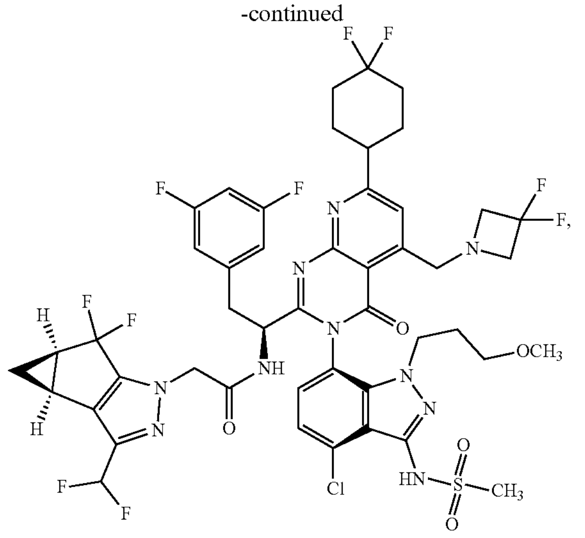

or a pharmaceutically acceptable salt thereof.

In another aspect, the invention provides a crystalline form of a compound of the invention.

In another aspect, the invention provides a composition comprising a compound of the invention, or a crystalline form of the invention, and b) a pharmaceutically acceptable excipient.

In another aspect, the invention provides a combination of a) a compound of the invention, or a crystalline form of the invention; and b) an agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors (for example an agent selected from the group consisting of Dolutegravir, lamivudine, Fostemsavir, Cabotegravir, maraviroc, rilpivirine, Reyataz, Tenofovir, Alafenamide, EfDA, Doravirine, and Prezista, or selected from the group consisting of Dolutegravir, lamivudine, Fostemsavir, and Cabotegravir).

In another aspect, the invention provides a composition comprising a) a compound of the invention, or a crystalline form of the invention; and b) an agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors (for example an agent selected from the group consisting of Dolutegravir, lamivudine, Fostemsavir, Cabotegravir, maraviroc, rilpivirine, Reyataz, Tenofovir, Alafenamide, EfDA, Doravirine, and Prezista, or selected from the group consisting of Dolutegravir, lamivudine, Fostemsavir, and Cabotegravir).

In another aspect, the invention provides a method of treatment or prevention of HIV infection in a subject in need thereof comprising administering to said subject a therapeutically effective amount of a compound of the invention, a crystalline form of the invention, a composition of the invention, or a combination of the invention.

In another aspect, the invention provides a compound of the invention, a crystalline form of the invention, a composition of the invention, or a combination of the invention, for use in therapy.

In another aspect, the invention provides a compound of the invention, a crystalline form of the invention, a composition of the invention, or a combination of the invention, for use in the treatment or prevention of HIV infection.

In another aspect, the invention provides the use of a compound of the invention, a crystalline form of the invention, or a combination of the invention, in the manufacture of a medicament for use in the treatment or prevention of HIV infection.

In another aspect, the present invention discloses the compound depicted below

Compound D

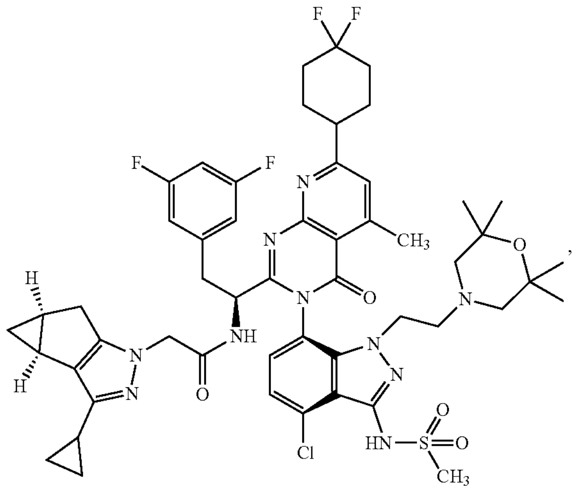

and pharmaceutically acceptable salts thereof.

In another aspect, the present invention discloses a composition comprising a composition comprising a compound or salt of the invention. In another aspect, the present invention discloses a composition comprising a composition comprising Compound D or salt of Compound D. In another aspect, the present invention discloses a method of treating HIV infection comprising administering a composition comprising a compound or salt of the invention. In another aspect, the present invention discloses a method of treating HIV infection comprising administering a composition comprising Compound D or salt of Compound D. In another aspect, the present invention discloses a compound or salt of the invention for use in therapy. In another aspect, the present invention discloses Compound D or salt of Compound D for use in therapy. In another aspect, the present invention discloses a compound or salt of the invention for use in treating HIV infection. In another aspect, the present invention discloses Compound D or salt of Compound D for use in treating HIV infection. In another aspect, the present invention discloses the use of a compound or salt of the invention in the manufacture of a medicament for the treatment of HIV infection. In another aspect, the present invention discloses the use of Compound D or salt of Compound D in the manufacture of a medicament for the treatment of HIV infection.

DETAILED DESCRIPTION OF THE INVENTION

Figure 1:
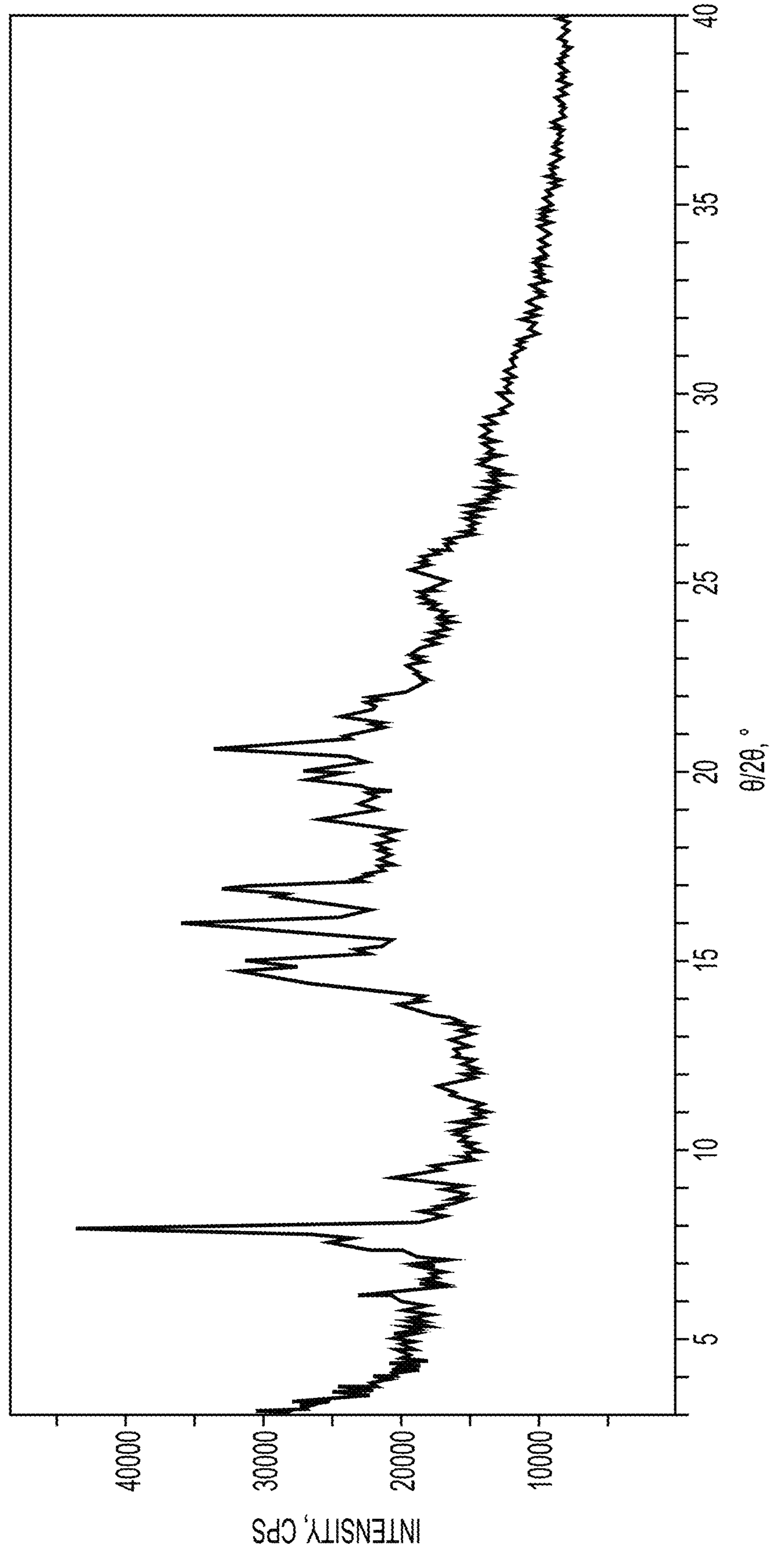
FIG. 1 depicts an X-Ray Powder Diffraction pattern (XRPD) of a crystalline form of the compound of Example 5A (Form 1), N-[(1S)-1-[(3P)-3-(4-chloro-1-{2-[(3R,5S)-3,5-difluoropiperidin-1-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide (Compound A (Form 1)).

When used herein, the term "alkyl" refers to a monovalent saturated hydrocarbon chain having the specified number of carbon member atoms. For example, —$C_{1-4}$alkyl refers to an alkyl group having from 1 to 4 carbon member atoms. Alkyl groups may be straight or branched. Representative branched alkyl groups have one, two, or three branches. Alkyl includes methyl, ethyl, propyl, (n-propyl and isopropyl), butyl (n-butyl, isobutyl, s-butyl, and t-butyl), pentyl (n-pentyl, tert-pentyl, iso-pentyl), and hexyl (n-hexyl, isohexyl, ter-hexyl).

When used herein, the term "cycloalkyl" refers to a monovalent saturated or unsaturated hydrocarbon ring having the specified number of carbon member atoms. For example, —$C_{3-4}$cycloalkyl refers to a cycloalkyl group having from 3- to 4-carbon member atoms, unless otherwise limited. Unsaturated cycloalkyl groups have one or more carbon-carbon double bonds within the ring. Cycloalkyl groups are not aromatic. Cycloalkyl includes cyclopropyl, cyclopropenyl, cyclobutyl and cyclobutenyl.

When used herein, the terms 'halogen' and 'halo' include fluorine (F), chlorine (Cl), bromine (Br) and iodine (I), and fluoro, chloro, bromo, and iodo, respectively.

When used herein, the term "independently" means that where more than one substituent is selected from a number of possible substituents, those substituents may be the same or different. That is, each substituent is separately selected from the entire group of recited possible substituents.

The term "optionally substituted" indicates that a group may be unsubstituted or substituted with one or more substituents as defined herein. When used herein, the term "substituted" in reference to a group indicates that one or more hydrogen atom attached to a member atom within the group is replaced with a substituent selected from the group of defined substituents. It should be understood that the term "substituted" includes the implicit provision that such substitution be in accordance with the permitted valence of the substituted atom and the substituent and that the substitution results in a stable compound (i.e., one that does not spontaneously undergo transformation such as by rearrangement, cyclization, or elimination and that is sufficiently robust to survive isolation from a reaction mixture). When it is stated that a group is "optionally" substituted it may or may not contain one or more substituents, one or more (as appropriate) member atoms within the group may be substituted. In addition, a single member atom within the group may be substituted with more than one substituent as long as such substitution is in accordance with the permitted valence of the atom. Suitable substituents are defined herein for each substituted or optionally substituted group.

The term "pharmaceutically acceptable" refers to those compounds (including salts), materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The term "prevention" refers to avoidance of the stated disease in a subject who is not suffering from the stated disease.

The term "therapeutically effective amount" refers to the quantity of a compound of the invention which will elicit the desired biological response in a human body. It may vary depending on the compound, the disease and its severity and the age and weight of the subject to be treated.

The term "treatment" refers to ameliorating or stabilising the specified condition, reducing or eliminating the symptoms of the condition, slowing or eliminating the progression of the condition, and preventing or delaying reoccurrence of the condition in a previously afflicted patient or subject.

As used herein, the term "prevention" or "preventing" refers to avoidance of the stated condition in a subject who is not suffering from the stated condition.

The terms "subject" or "patient" are used interchangeably to refers to a human body.

It will be understood that the term "or a salt thereof", can be a pharmaceutically acceptable salt thereof.

As used herein, the term "XRPD pattern" will be understood to comprise a diffraction angle (expressed in degrees 2θ) of "about" a value specified herein when the XRPD pattern comprises a diffraction angle within ±0.3 degrees 2θ of the specified value. Further, it is well known and understood to those skilled in the art that the apparatus employed, humidity, temperature, orientation of the powder crystals, and other parameters involved in obtaining an X-ray powder diffraction (XRPD) pattern may cause some variability in the appearance, intensities, and positions of the lines in the diffraction pattern. An X-ray powder diffraction pattern that is "substantially in accordance" with that of FIG. 1 provided herein, is an XRPD pattern that would be considered by one skilled in the art to represent a compound possessing the same crystal form as the compound that provided the XRPD pattern of FIG. 1. That is, the XRPD pattern may be identical to that of FIG. 1, or more likely it may be somewhat different. Such an XRPD pattern may not necessarily show each of the lines of any one of the diffraction patterns presented herein, and/or may show a slight change in appearance, intensity, or a shift in position of said lines resulting from differences in the conditions involved in obtaining the data. A person skilled in the art is capable of determining if a sample of a crystalline compound has the same form as, or a different form from, a form disclosed herein by comparison of their XRPD patterns. For example, one skilled in the art can overlay an XRPD pattern of a sample of crystalline N-[(1S)-1-(3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl)-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide ("Compound D") with FIG. 9 and, using expertise and knowledge in the art, readily determine whether the XRPD pattern of the sample is substantially in accordance with the XRPD pattern of crystalline Compound D. If the XRPD pattern is substantially in accordance with FIG. 9, the sample form can be readily and accurately identified as having the same form as crystalline Compound D.

During acquisition of an XRPD data, a K-Beta (Kβ) filter may be present or absent. One skilled in the art would recognize that the XRPD data acquired without the use of a Kβ filter may contain peaks attributable to Kβ. One skilled in the art would also recognize that in the XRPD data acquired with the use of a Kβ filter the peaks attributable to Kβ would be reduced or even eliminated. Further, one skilled in the art would recognize that the XRPD data specific to a material would not be substantially different whether or not a Kβ filter was used during acquisition of XRPD data.

The terms X-ray powder diffraction (XRPD) and Powder X-ray diffraction (PXRD) are used interchangeably to mean a technique to analyze the crystal structure and phase of solids.

In one embodiment, the temperature at which the crystalline form of a compound of the invention begins to melt is determined by differential scanning calorimetry ("DSC") and is referred to as the "melting onset temperature".

The invention also includes various isomers of the compounds of the invention and mixtures thereof. When used herein, the term "isomer" refers to compounds that have the same composition and molecular weight but differ in physical and/or chemical properties. The structural difference may be in constitution (geometric isomers) or in the ability to rotate the plane of polarized light (stereoisomers). The compounds of the invention contain one or more asymmetric centers, also referred to as chiral centers, and may, therefore, exist as individual enantiomers, diastereomers, including atropisomers, or other stereoisomeric forms, or as mixtures thereof. All such isomeric forms are included within the present invention, including mixtures thereof.

The Intermediates compounds and the Example compounds described herein may contain axial chirality. Axial chirality is a type of chirality where the stereogenic element is an axis of rotation. When the barrier to interconversion around an axis of axial chirality is high, the phenomenon can be termed atropisomerism. Unless otherwise noted, the term "atropisomerism" used herein is understood to refer to a barrier to interconversion sufficiently high as to allow chromatographic separation of stereoisomers that differ in their configuration about the axis of axial chirality. The term "atropisomers" used herein refers to stereoisomers that differ in their configuration about the axis of axial chirality meeting the criteria for atropisomerism which can be separated by any chromatography method. The term "atropisomer" refers to a single stereoisomer comprising a single configuration about the axis of axial chirality meeting the criteria for atropisomerism. The term "atropisomer" can be used to describe a compound possessing one or more stereogenic centers. The term "atropisomers" can be used to describe compounds possessing one or more stereogenic centers. Often, but not exclusively, when the ratio of two atropisomers is compared the comparison is between compounds wherein all of the stereogenic centers have the same configuration and only the axis of axial chirality meeting the criteria for atropisomerism differs in configuration.

Suitably, the chemical reactions described herein may produce atropisomers. The presence of absence of atropisomerism may or may not be noted. The presence of absence of atropisomers may or may not be noted. Atropisomers produced in a chemical reaction may or may not be chromatographically separated. One skilled in the art will recognize that in a chemical synthesis the point at which atropisomers form can be deduced by the identification of atropisomers is subsequent steps. One skilled in the art will recognize that in a chemical synthesis the point at which atropisomers are separated or enriched can be deduced by the enrichment of an atropisomer in a subsequent step.

Atropisomers may be designated using P/M notation consistent with IUPAC notation. Atropisomers may be indicated using wedge and dash projections on the aryl or heteroaryl rings adjacent to the axis of axial chirality which creates atropisomerism. When a compound is defined herein using P/M notation and/or using wedge and dash projections as being a single atropisomer, the material is a single atropisomer.

Chiral centers may also be present in a substituent, such as an alkyl group. Where the stereochemistry of a chiral center present in a compound of the invention, or in any chemical structure illustrated herein, is not specified the structure is intended to encompass any stereoisomer and all mixtures thereof. Thus, compounds of the invention containing one or more chiral centers may be used as racemic mixtures, enantiomerically enriched mixtures, or as enantiomerically pure individual stereoisomers.

Individual stereoisomers of a compound of the invention which contain one or more asymmetric centers may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

One skilled in the art will recognize that there may be more than one way to represent the stereochemistry of a compound. For example, one skilled in the art will recognize that each of the representations of the cyclopropyl stereochemistry below convey the same meaning.

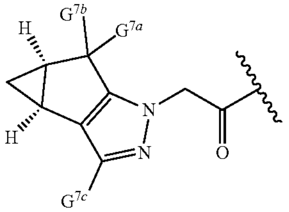

=

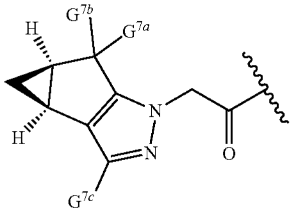

=

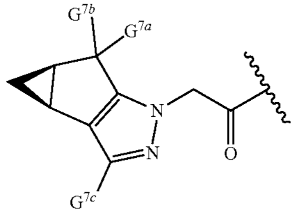

Further, one skilled in the art will recognize that each of the representations of the cyclopropyl stereochemistry below convey the same meaning.

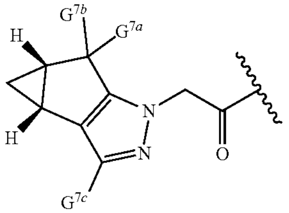

=

-continued

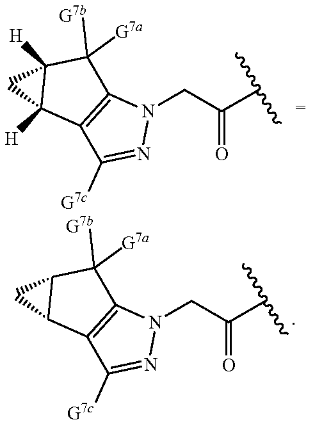

A person skilled in the art is capable of determining the proportion of a component within a chemical mixture. For example, one skilled in the art may determine the proportion of a component within a chemical mixture using HPLC to compare the area under the curve of the individual peaks. For example, typical wavelengths for detection, used by a UV detector to measure the peaks, are 220 nm or 254 nm. Alternatively, for example, one skilled in the art may determine the proportion of a component within a chemical mixture using supercritical fluid chromatography (SFC) to compare the area under the curve of the individual peaks. For example, typical wavelengths for detection, used by a UV detector to measure the peaks, are 220 nm or 254 nm.

Alternatively, for example, one skilled in the art may determine the proportion of a component within a chemical mixture using quantitative 1H-NMR.

Alternatively, for example, one skilled in the art may determine the proportion of a component within a chemical mixture using a combination of more than one method.

The compounds of the invention may exist as salts. The salts of the invention are pharmaceutically acceptable. Such salts may be acid addition salts or base addition salts. For a review of suitable pharmaceutically acceptable salts see Berge et al, J. Pharm, Sci., 66, 1-19, 1977. In one embodiment, acid addition salts are selected from the hydrochloride, hydrobromide, hydroiodide, sulphate, bisulfate, nitrate, phosphate, hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate.

In one embodiment, base addition salts include metal salts (such as sodium, potassium, aluminium, calcium, magnesium and zinc) and ammonium salts (such as isopropylamine, diethylamine, diethanolamine salts). Other salts (such as trifluoroacetates and oxalates) may be used in the manufacture of the compound of the invention and its pharmaceutically acceptable salts and are included within the scope of the invention. All possible stoichiometric and non-stoichiometric forms of the salts of the compounds of the invention are included within the scope of the invention. Acid and base addition salts may be prepared by the skilled chemist, by treating the compound of the invention with the appropriate acid or base in a suitable solvent, followed by crystallization and filtration.

As used herein, the terms "a compound of the invention" or "compounds of the invention" refer to one or more compounds according to Formula (I), Formula (Ia), Formula (Ib), Formula (II), Formula (IIa), and Formula (IIb), Compound A, Compound B, Compound C, Compound D, Compound E, Compound F, Compound G, Compound H, Compound J and Compound K, and the Example compounds described herein, or a pharmaceutically acceptable salt thereof. The compounds of the invention may exist in solid form or liquid form (which may also be referred to as "solid state" and "liquid state" respectively). The invention includes all such forms (for example, a compound of the invention in solid form). In the solid form, it may exist in crystalline or non-crystalline form, or as a mixture thereof. The invention includes all such forms (e.g. a compound of the invention crystalline or non-crystalline form, or as a mixture thereof). The skilled artisan will appreciate that pharmaceutically acceptable solvates may be formed from crystalline compounds wherein solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such hydrates and solvates.

The skilled artisan will further appreciate that certain compounds of the invention that exist in crystalline form, including the various solvates thereof, may exhibit polymorphism (i.e., the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

As used herein, the term "a crystalline form of the invention" refers to one or more compounds according to Formula (I), Formula (Ia), Formula (Ib), Formula (II), Formula (IIa), and Formula (IIb), Compound A, Compound B, Compound C, Compound D, Compound E, Compound F, Compound G, Compound H, Compound J and Compound K, and the Example compounds described herein, when in a crystalline form. In particular, the term "a crystalline form of the invention" may refer to a crystalline form selected from the group consisting of Compound A (Form 1), Compound B (Form 1), Compound C (Form 1), Compound D (Form 1), Compound E (Form 1), Compound F (Form 1), Compound G (Form 1), Compound H (Form 1), Compound J (Form 1) and Compound K (Form 1), and the crystalline Examples compounds described herein.

The subject invention also includes isotopically-labelled compounds, which are identical to those recited in Formula (I), Formula (Ia), Formula (Ib), Formula (II) and Formula (IIa), Formula (IIb), but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

Compounds of the present invention, including pharmaceutically acceptable salts of the compound of the invention, that contain the aforementioned isotopes and/or other isotopes of other atoms are within the scope of the present invention. Isotopically-labelled compounds of the present invention, for example those into which radioactive isotopes such as $^{3}H$, $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of this invention can generally be prepared by carrying out the procedures disclosed in the Schemes and/or in the Examples below, by substituting a readily available isotopically labelled reagent for a non-isotopically labelled reagent.

In the methods and uses of this invention, routes of administration are suitably oral or by injection to deliver a compound of the invention subcutaneously or intramuscularly. In one embodiment, the invention provides a compound of the invention wherein the administration is oral. In one embodiment, the invention provides a compound of the invention wherein the administration is via subcutaneous injection. In one embodiment, the invention provides a compound of the invention wherein the administration is via intramuscular injection. Pharmaceutical compositions of the invention include compositions suitable for oral administration (for example tablets) and formulations suitable for injection.

The compounds of this invention are believed to act as Capsid Inhibitors. They are believed to have as their biological target the HIV Capsid and thus their mechanism of action is to modify in one or more ways the function of the HIV capsid. As shown by the examples herein, the compounds of the invention have potent antiviral activity (see Table C below). Further, the Example compounds of the invention show significant selectivity for on-target antiviral activity versus cytotoxic activity (see also Table C below).

The compounds of the present invention and its salts, solvates, or other pharmaceutically acceptable derivatives thereof, may be employed alone or in combination with other therapeutic agents. The compound and salts of the present invention and any other pharmaceutically active agent(s) may be administered together or separately and, when administered separately, administration may occur simultaneously or sequentially, in any order. The amounts of the compound and salts of the present invention and the other pharmaceutically active agent(s) and the relative timings of administration will be selected in order to achieve the desired combined therapeutic effect.

The administration in combination of the compound of the present invention and salts, solvates, or other pharmaceutically acceptable derivatives thereof with other treatment agents may be in combination by administration concomitantly in: (1) a unitary pharmaceutical composition including multiple compounds; or (2) separate pharmaceutical compositions each including one of the compounds. Alternatively, the combination may be administered separately in a sequential manner wherein one treatment agent is administered first and the other second or vice versa, and the different agents could be administered on different schedules if appropriate. Such sequential administration may be close in time or remote in time. The amounts of the compound of the invention, or salts thereof and the other pharmaceutically active agent(s) and the relative timings of administration will be selected in order to achieve the desired combined therapeutic effect.

As such, the compound and salts of the present invention may be used in combination with one or more agents useful in the prevention or treatment of HIV. Such agents include, for example, nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Representative Embodiments

In one aspect, the invention provides a compound of Formula (I):

Formula (I)

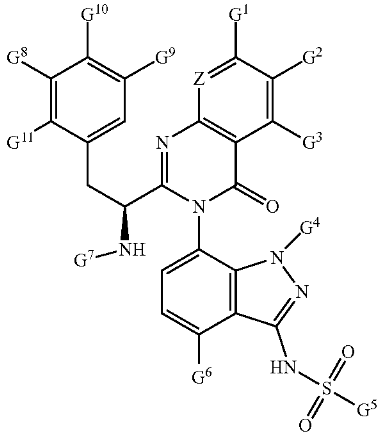

or a pharmaceutically acceptable salt thereof, wherein:

Z is CH or N;

$G^1$ is selected from

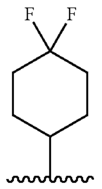

and

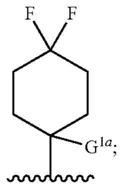

$G^{1a}$ is selected from the group consisting of —OH, —F, —Cl, —CN, —$C_{1-4}$alkyl optionally substituted with 1, 2 or 3 —F, and —$C_{1-3}$alkyl optionally substituted with one substituent selected from the group consisting of —$N(C_{1-2}alkyl)_2$, —$NH(C_{1-2}alkyl)$, and a heterocycle selected from the group consisting of azetidine, pyrrolidine, piperidine, and morpholine, wherein said heterocycle is optionally substituted with 1, 2, 3 or 4 substituents independently selected from the group consisting of-$CH_3$ and —F;

$G^2$ is selected from the group consisting of —H, —F, —C, —$OCH_3$, —$CH_3$, —$CHF_2$, cyclopropyl,

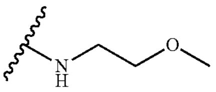

and

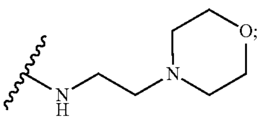

$G^3$ is selected from the group consisting of —H, —Cl, —CN, —CHO, —$C(O)C_{1-2}alkyl$, —$C_{1-3}alkyl$ optionally substituted with 1, 2 or 3 —F, —$C_{1-3}alkyl$ optionally substituted with one substituent select from the group consisting of —OH, —$OC_{1-2}alkyl$ and —CN, —$C_{3-4}cycloalkyl$ optionally substituted with 1, 2 or 3 —F, and —NH—$C_{1-3}alkyl$ optionally substituted with 1, 2, or 3 substituents independently selected from the group consisting of —$OCH_3$ and —F, or $G^3$ is —$NH(C_{1-4}alkyl\text{-}G^{3a})$, wherein $G^{3a}$ is a heterocycle selected from the group consisting of oxetane, tetrahydrofuran, and tetrahydro-2H-pyran, wherein said heterocycle is optionally substituted with one substituent selected from the group consisting of —$CH_3$, —F, —$OC_{1-3}alkyl$ and —$OC_{3-4}cycloalkyl$, or $G^3$ is selected from the group consisting of:

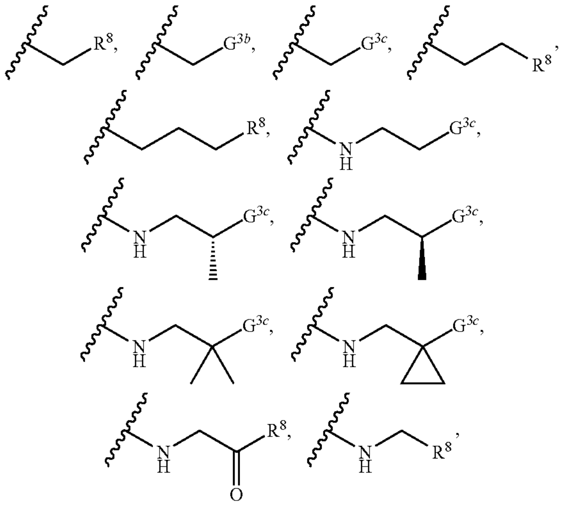

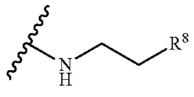

and

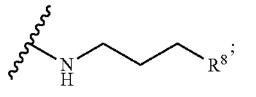

$G^{3b}$ is selected from the group consisting of —$NH(C_{1-2}alkyl)$, —$N(C_{1-2}alkyl)_2$, —$NH(CH_2CH_2OC_{1-3}alkyl)$, —$N(C_{1-2}alkyl)(CH_2CH_2OC_{1-3}alkyl)$ and —$NH(CH_2CH_2R^3)$ $G^{3c}$ is selected from the group consisting of —H, —CN, —$OC_{1-3}alkyl$, —$C_{3-6}cycloalkyl$, —$NHC(OC_{1-3}alkyl$, —$NH(C_{1-2}alkyl)$, —$N(C_{1-2}alkyl)_2$, —$R^8$, an aromatic heterocycle selected from the group consisting of phenyl, pyridine, thiazole, pyrazole and imidazole, wherein said aromatic heterocycle is optionally substituted with one —$CH_3$ group, and a non-aromatic heterocycle selected from the group consisting of

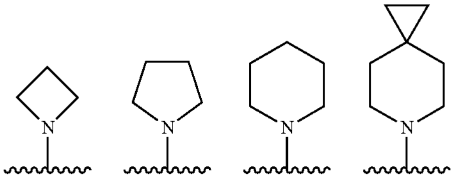

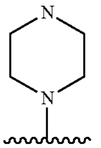

and

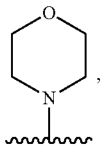

, wherein said non-aromatic heterocycle is optionally independently substituted with 1 or 2 substituents selected from the group consisting of —F, —$CH_3$, —$CF_3$, —$CHF_2$, —$O_{1-2}alky$ and —$C(O)C_{1-2}alkyl$;

$G^4$ is a heterocycle selected from the group consisting of pyridine, pyrimidine, pyrazole, imidazole, oxetane, tetrahydrofuran, tetrahydro-2H-pyran, azetidine, pyrrolidine and piperidine, wherein said heterocycle is optionally substituted with —$CH_2CH_2OC_{1-3}alkyl$; or $G^4$ is selected from the group consisting of:

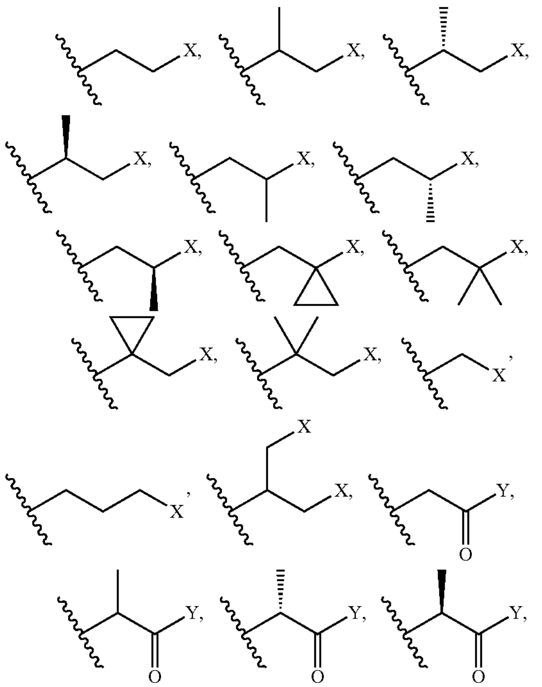

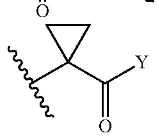

and

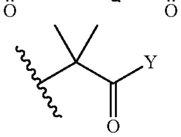

X is selected from the group consisting of —$OR^1$, —Cl, —Br, pyridine, pyrazole, imidazole, pyrrolidin-2-one, 2,5-dihydro-pyrrole, 4-methyl-7-(methylamino)-2H-chromen-2-one, —$NR^1R^2$, —$R^6$, —$R^7$, and —$R^8$;

Y is selected from the group consisting of —$NR^1R^2$, —$R^6$, —$R^7$, and —$R^8$;

$R^1$ is selected from the group consisting of —H, phenyl, pyridine, —$R^4$, and —$C_{1-4}$alkyl optionally substituted with 1, 2 or 3 —F, 1 or 2 —$OC_{1-3}$alkyl groups, or one —CN group; —$C_{3-4}$cycloalkyl optionally substituted with 1 or 2 —F or a —$OCH_3$ group; oxetane optionally substituted with one —$CH_3$ group; tetrahydrofuran optionally substituted with one —$CH_3$ group; and tetrahydro-2H-pyran optionally substituted with one —$CH_3$ group;

$R^2$ is selected from the group consisting of —H, —$C_{1-4}$alkyl optionally substituted with 1, 2 or 3 —F, 1 or 2 —$OC_{1-3}$alkyl groups, or one —CN group; —$C_{3-4}$cycloalkyl optionally substituted with 1 or 2 substituents independently selected from the group consisting of —F and —$OCH_3$; and oxetane optionally substituted with one —$CH_3$ group;

$R^4$ is selected from the group consisting of —$(CH_2CH_2O)_nCH_2CH_2N(R^5)_2$ and —$(CH_2CH_2O)_nR^5$;

n is 2, 3, 4, 5, 6, 7 or 8;

each $R^5$ is independently selected from the group consisting of —H, —$C_{1-4}$alkyl, and —$C_{3-4}$cycloalkyl;

$R^6$ is a heterocycle selected from the group consisting of azetidine, pyrrolidine, piperidine, piperazine, and morpholine, wherein said heterocycle is optionally substituted with 1, 2, 3 or 4 —F, one —OH group, 1 or 2 —$OC_{1-4}$alkyl groups, 1 or 2 —$CH_3$ groups, one —$C_{1-3}$alkyl group optionally substituted with 1, 2 or 3 —F, one —$CH_3$ group optionally substituted with 1, 2 or 3 substituents independently selected from the group consisting of —F, —OH and —$OC_{1-3}$alkyl, or —$CH_2$pyridine optionally substituted with 1 or 2 —$CH_3$ groups;

$R^7$ is a heterocycle selected from the group consisting of azetidine, pyrrolidine, piperidine, piperazine, and morpholine, wherein said heterocycle is optionally substituted with one substituent selected from the group consisting of —$CO_2H$, —$S(O_2)R^{10}$, —$N(R^9)_2$, —$NR^9SO_2R^{10}$, —$NR^9COR^{10}$, —$C(O)R^5$, —$C(O)R^6$, a heterocycle selected from the group consisting of 1,2,4-oxadiazole, isoxazole, pyrazole, imidazole and thiazole, wherein said heterocycle is optionally substituted with one $R^{10}$ group, and a heterocycle selected from the group consisting of oxetane, tetrahydrofuran and tetrahydro-2H-pyran, wherein said heterocycle is optionally substituted with one —$CH_3$ group;

each $R^8$ is independently a heterocycle selected from the group consisting of

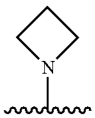, 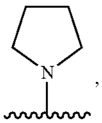, 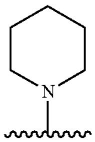, 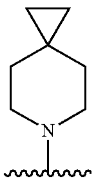, 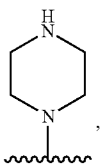, 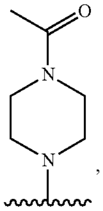, 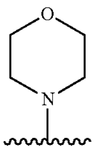, 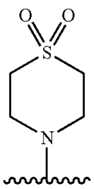, 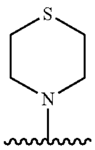, 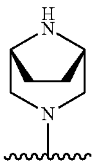, -continued

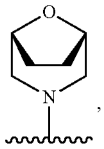, 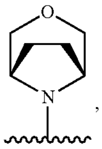, 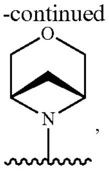, 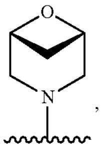, 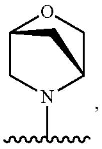, 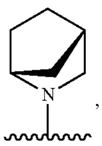, 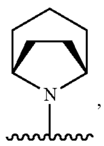, 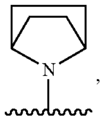, 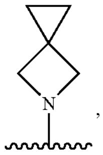, 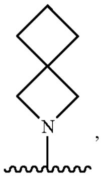, 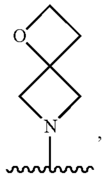, 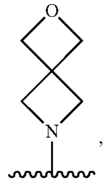, 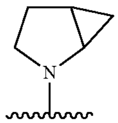, 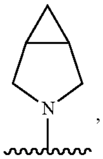, 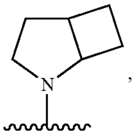, 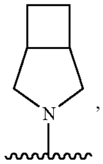, 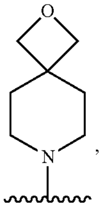, 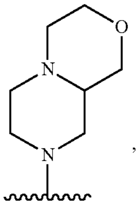, 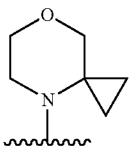, 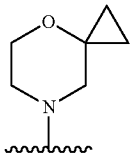, 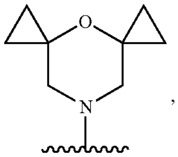, 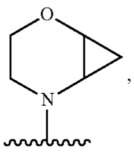, 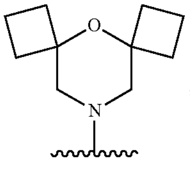, 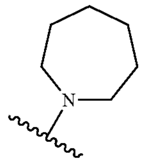 and 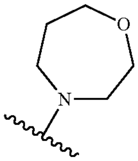

wherein said heterocycle is optionally substituted with 1, 2, 3 or 4 substituents independently selected from the group consisting of —F, —$CF_3$, —$OCH_3$, —$CHF_2$, —$CH_2F$ and —$C_{1-4}$alkyl;

each $R^9$ is independently selected from the group consisting of —H, —$CH_3$, —$C_{2-3}$alkyl optionally substituted with 1, 2 or 3 —F, and —$C_{3-4}$cycloalkyl optionally substituted with 1 or 2 —F;

$R^{10}$ is selected from the group consisting of —$CH_3$, —$CH_2F$, —$CHF_2$, —$CF_3$, —$C_{2-3}$alkyl optionally substituted with 1, 2 or 3 —F, and —$C_{3-4}$cycloalkyl optionally substituted with 1 or 2 —F;

$G^5$ is selected from the group consisting of —$C_{1-3}$alkyl optionally substituted with 1, 2 or 3 —F, and —$C_{3-4}$cycloalkyl optionally substituted with 1 or 2 —F;

$G^6$ is selected from the group consisting of —F, —Cl, —$CH_3$, and —$OCH_3$;

$G^7$ is selected from the group consisting of

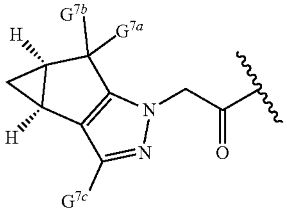

and

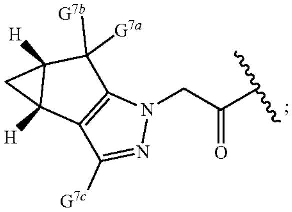

;

$G^{7a}$ is selected from the group consisting of —H and —F;

$G^{7b}$ is selected from the group consisting of —H, —$CH_3$ and —F;

$G^{7c}$ is selected from the group consisting of —$C_{1-2}$alkyl optionally substituted with 1, 2 or 3 —F, and —$C_{3-4}$cycloalkyl optionally substituted with 1 or 2 —F;

$G^8$ and $G^9$ are independently selected from the group consisting of —H, —F, —C, —$CH_3$ and —$OCH_3$;

$G^{10}$ is selected from the group consisting of —H and —F; and $G^{11}$ is selected from the group consisting of —H, —F, —$CH_3$ and —$OCH_3$.

In one embodiment Z is N.

In one embodiment, $G^1$ is selected from

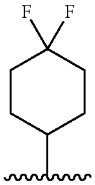

and

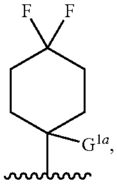

and $G^{1a}$ is selected from the group consisting of —OH, —F, —C, and —$C_{1-2}$alkyl optionally substituted with 1, 2 or 3 —F.

In one embodiment, $G^1$ is selected from

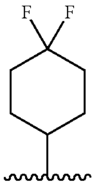

and

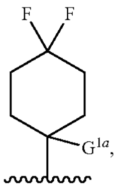

and $G^{1a}$ is —F.

In one embodiment, $G^1$ is

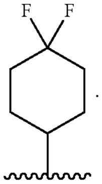

In one embodiment, $G^1$ is

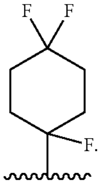

In one embodiment, $G^2$ is selected from the group consisting of —H, —$CH_3$ and —$CHF_2$. In one embodiment, $G^2$ is —H. In another embodiment, $G^2$ is —$CH_3$. In yet another embodiment, $G^2$ is —$CHF_2$.

In one embodiment, $G^3$ is selected from the group consisting of —H, —Cl, —CN, —CHO, —C(O)$C_{1-2}$alkyl; —$C_{1-3}$alkyl optionally substituted with 1, 2 or 3 —F; —$C_{1-3}$alkyl optionally substituted with one substituent select from the group consisting of —OH, —$OC_{1-2}$alkyl and —CN; —$C_{3-4}$cycloalkyl optionally substituted with 1, 2 or 3 —F; and —NH—$C_{1-3}$alkyl optionally substituted with 1, 2, or 3 substituents independently selected from the group consisting of —$OCH_3$ and —F;

or $G^3$ is —NH($C_{1-4}$alkyl-$G^{3a}$), wherein $G^{3a}$ is a heterocycle selected from the group consisting of oxetane, tetrahydrofuran, and tetrahydro-2H-pyran, wherein said heterocycle is optionally substituted with one substituent selected from the group consisting of —$CH_3$, —F, —$OC_{1-3}$alkyl and —$OC_{3-4}$cycloalkyl;

or $G^3$ is selected from the group consisting of:

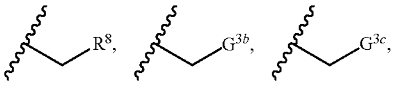

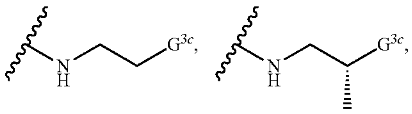

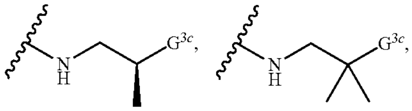

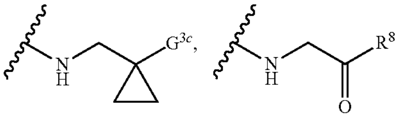

and

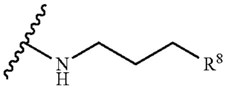

$G^{3b}$ is selected from the group consisting of —NH($C_{1-2}$alkyl), —N($C_{1-2}$alkyl)$_2$, —NH($CH_2CH_2OC_{1-3}$alkyl), —N($C_{1-2}$alkyl)($CH_2CH_2OC_{1-3}$alkyl) and —NH($CH_2CH_2R^8$);

$G^{3c}$ is selected from the group consisting of —H, —CN, —$OC_{1-3}$alkyl, —$C_{3-6}$cycloalkyl, —NHC($OC_{1-3}$alkyl, —NH($C_{1-2}$alkyl), —N($C_{1-2}$alkyl)$_2$, —$R^8$, an aromatic heterocycle selected from the group consisting of phenyl, pyridine, thiazole, pyrazole and imidazole, wherein said aromatic heterocycle is optionally substituted with one —$CH_3$ group; and a non-aromatic heterocycle selected from the group consisting of

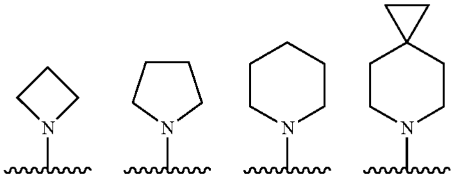

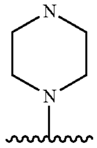

and

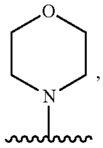

, wherein said non-aromatic heterocycle is optionally independently substituted with 1 or 2 substituents selected from the group consisting of —F, —$CH_3$, —$CF_3$, —$CHF_2$, —$OC_{1-2}$alkyl and —C(O)$C_{1-2}$alkyl; and $R^8$ is a heterocycle selected from the group consisting of

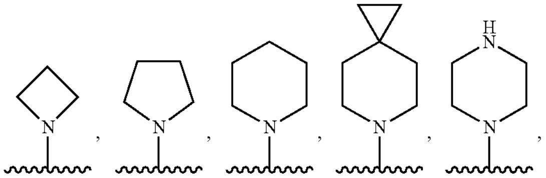

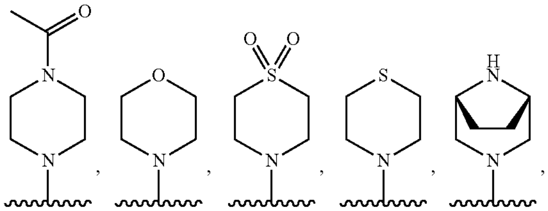

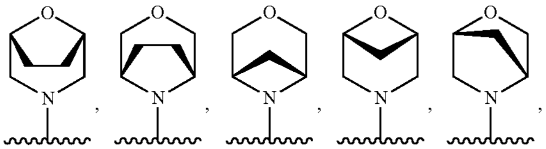

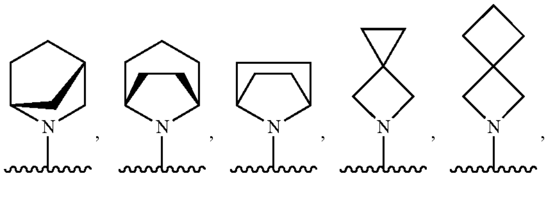

-continued

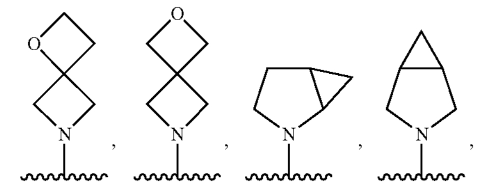

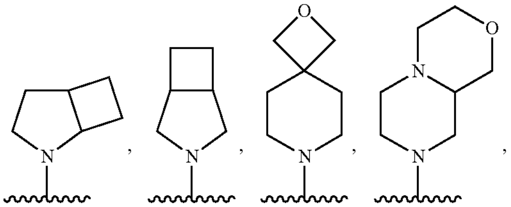

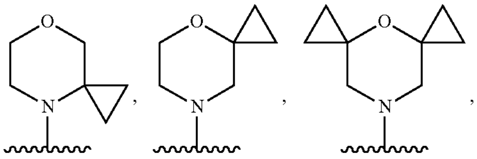

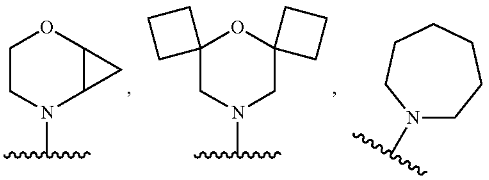

and

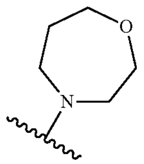

wherein said heterocycle is optionally substituted with 1, 2, 3 or 4 substituents independently selected from the group consisting of —F, —$CF_3$, —$OCH_3$, —$CHF_2$, —$CH_2F$ and —$C_{1-4}$alkyl.

In one embodiment, $G^3$ is selected from the group consisting of —H, —$C_{1-3}$alkyl optionally substituted with 1, 2 or 3 —F; —$C_{1-3}$alkyl optionally substituted with one substituent select from the group consisting of —OH, —$OC_{1-2}$alkyl and —CN; —$C_{3-4}$cycloalkyl optionally substituted with 1, 2 or 3 —F; and —NH—$C_{1-3}$alkyl optionally substituted with 1, 2, or 3 substituents independently selected from the group consisting of —$OCH_3$ and —F;

or $G^3$ is selected from the group consisting of:

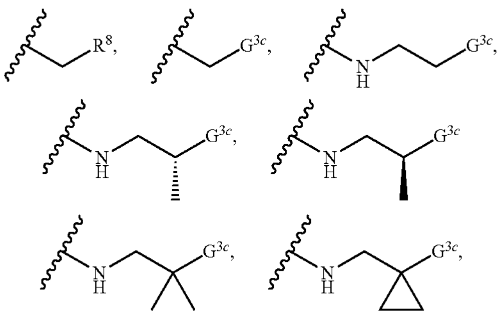

-continued

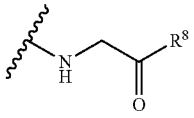

and

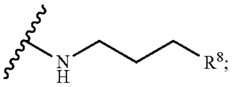

$G^{3c}$ is selected from the group consisting of —H, —CN, —$OC_{1-3}$alkyl, —$C_{3-6}$cycloalkyl, —NHC(O)$C_{1-3}$alkyl, —$R^8$, an aromatic heterocycle selected from the group consisting of phenyl, pyridine, thiazole, pyrazole and imidazole, wherein said aromatic heterocycle is optionally substituted with one —$CH_3$ group; and a non-aromatic heterocycle selected from the group consisting of

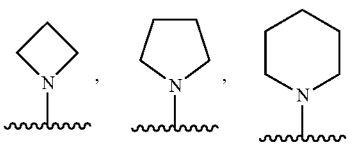

and

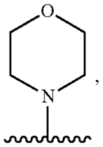

wherein said non-aromatic heterocycle is optionally independently substituted with 1 or 2 substituents selected from the group consisting of —F, —$CH_3$, —$CF_3$, —$CHF_2$ and —$OC_{1-2}$alkyl (for example $G^{3c}$ is

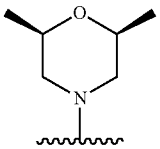

);

and $R^8$ is a heterocycle selected from the group consisting of

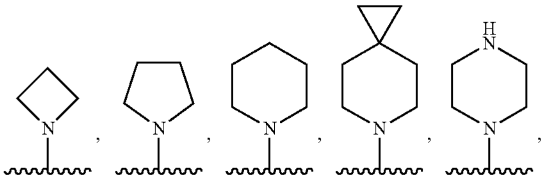

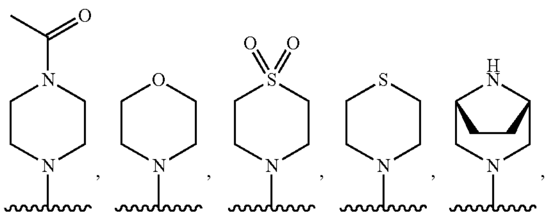

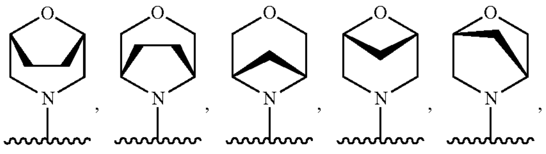

-continued

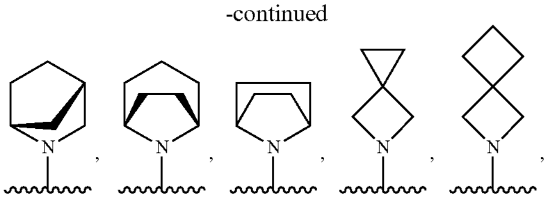

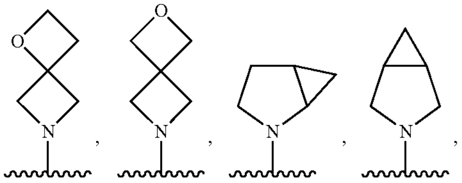

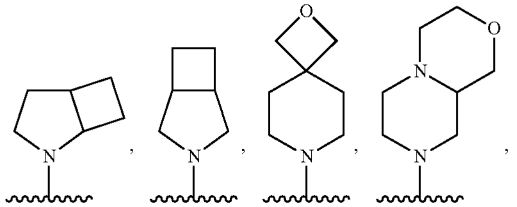

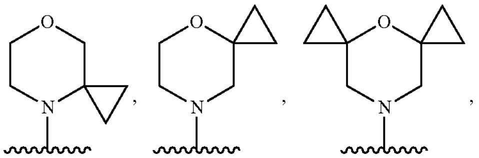

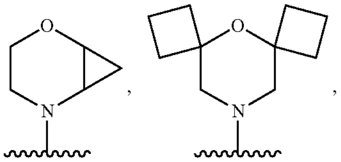

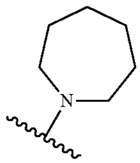

and

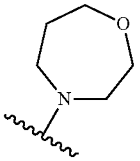

wherein said heterocycle is optionally substituted with 1, 2, 3 or 4 substituents independently selected from the group consisting of —F and —$CH_3$.

In one embodiment, $G^3$ is selected from the group consisting of —$C_{1-2}$alkyl optionally substituted with 1, 2 or 3 —F;

or $G^3$ is selected from the group consisting of:

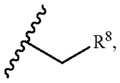

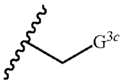

and

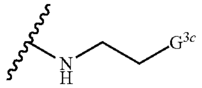

(for example,

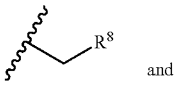

and

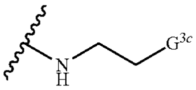

);

$G^{3c}$ is selected from the group consisting of —H, —CN, —$OC_{1-3}$alkyl, —$C_{3-6}$cycloalkyl, —NHC(O)$C_{1-3}$alkyl, —$R^8$, an aromatic heterocycle selected from the group consisting of phenyl, pyridine, thiazole, pyrazole and imidazole, wherein said aromatic heterocycle is optionally substituted with one —$CH_3$ group; and a non-aromatic heterocycle selected from the group consisting of

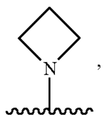, 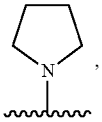, 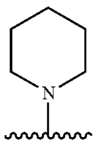 and 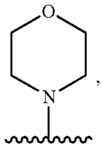, wherein said non-aromatic heterocycle is optionally independently substituted with 1 or 2 substituents selected from the group consisting of —F, —$CH_3$, —$CF_3$, —$CHF_2$ and —$OC_{1-2}$alkyl (for example $G^{3c}$ is

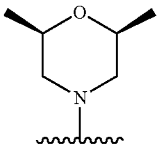);

and $R^8$ is a heterocycle selected from the group consisting of

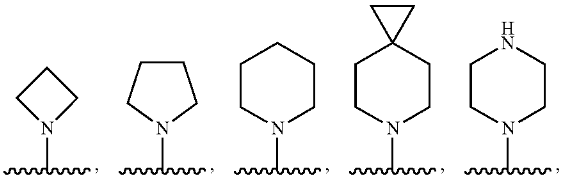

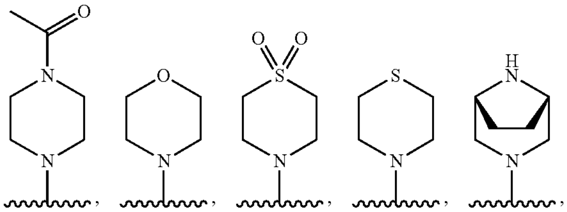

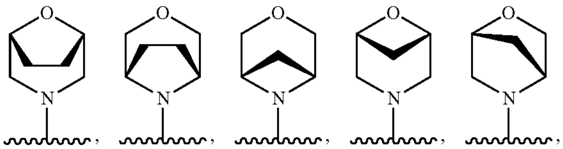

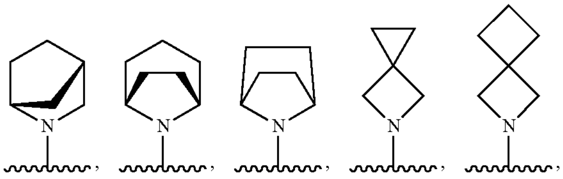

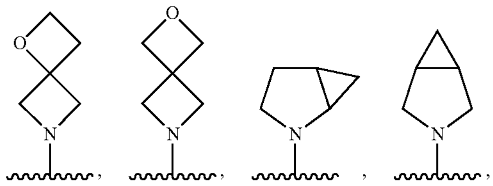

-continued

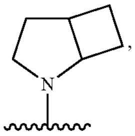, 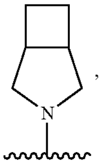, 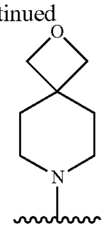, 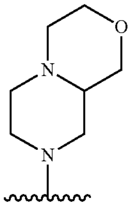,

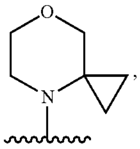, 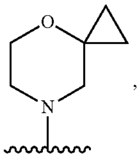, 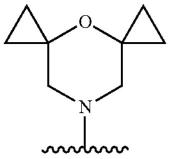,

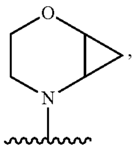, 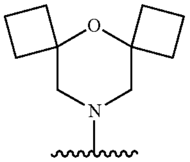, 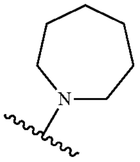 and

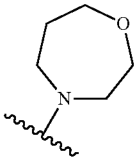

wherein said heterocycle is optionally substituted with 1, 2, 3 or 4 substituents independently selected from the group consisting of —F and —$CH_3$.

In one embodiment, $G^3$ is selected from the group consisting of —$C_{1-2}$alkyl,

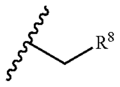 and 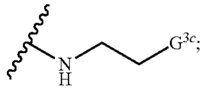;

and $G^{3c}$ is selected from the group consisting of —H, —$OC_{1-3}$alkyl, —$R^8$, and a non-aromatic heterocycle selected from the group consisting of

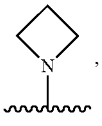, 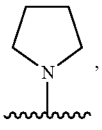, 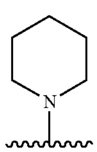 and 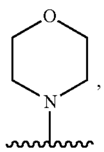, wherein said non-aromatic heterocycle is optionally independently substituted with 1 or 2 substituents selected from the group consisting of —$CH_3$, —$CF_3$, —$CHF_2$ and —$OC_{1-2}$alkyl (for example $G^{3c}$ is

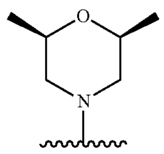);

and $R^8$ is a heterocycle selected from the group consisting of

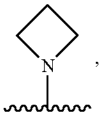, 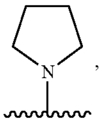, 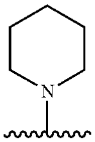 and 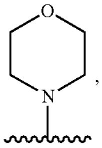, wherein said heterocycle is optionally substituted with 1, 2, 3 or 4 substituents independently selected from the group consisting of —F and —$CH_3$.

In one embodiment, $G^3$ is selected from the group consisting of —$CH_3$,

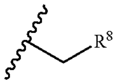 and 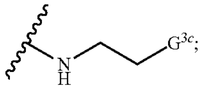;

$G^{3c}$ is selected from the group consisting of H and —$OCH_3$; and $R^8$ is a heterocycle selected from the group consisting of

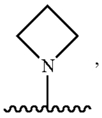, 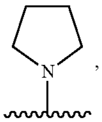, 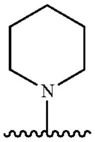 and 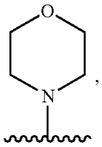, wherein said heterocycle is optionally substituted with 1 or 2 substituents independently selected from the group consisting of —F and —$CH_3$ (for example, wherein said heterocycle is optionally substituted with 1 or 2 —F or 1 or 2 —$CH_3$ substituents).

In one embodiment, $G^3$ is selected from the group consisting of —$CH_3$,

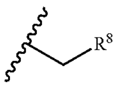 and 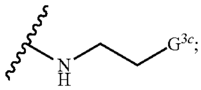;

$G^{3c}$ is selected from the group consisting of H and —$OCH_3$; and $R^8$ is a heterocycle selected from the group consisting of

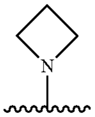 and 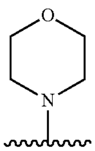, wherein said heterocycle is optionally substituted with 1 or 2 substituents independently selected from the group consisting of —F and —$CH_3$ (for example, wherein said heterocycle is optionally substituted with 1 or 2 —F or 1 or 2 —$CH_3$ substituents, or for example wherein $R^8$ is a heterocycle selected from the group consisting of

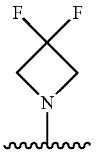 and 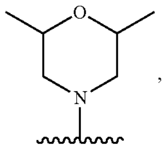, or $R^3$ is a heterocycle selected from the group consisting of

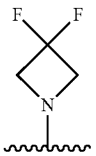 and 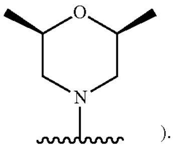).

In another embodiment, $G^3$ is selected from the group consisting of —$CH_3$,

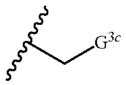 and 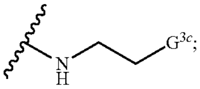;

$G^{3c}$ is selected from the group consisting of H, —$OCH_3$, and a non-aromatic heterocycle selected from the group consisting of

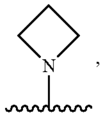, 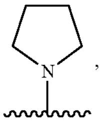, 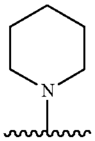 and 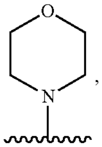, wherein said non-aromatic heterocycle is optionally independently substituted with 1 or 2 substituents selected from the group consisting of —F, —$CH_3$, —$CF_3$, —$CHF_2$ and —$OC_{1-2}$alkyl (for example, wherein said heterocycle is optionally substituted with 1 or 2 —F or 1 or 2 —$CH_3$ substituents, or, for example $G^{3c}$ is

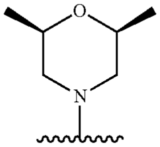).

In one embodiment, $G^3$ is selected from the group consisting of —$CH_3$,

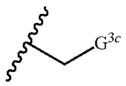 and 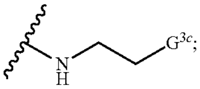;

$G^{3c}$ is selected from the group consisting of H, —$OCH_3$, and a non-aromatic heterocycle selected from the group consisting of

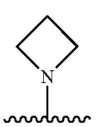 and 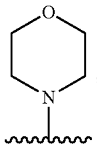, wherein said non-aromatic heterocycle is optionally substituted with 1 or 2 substituents independently selected from the group consisting of —F and —$CH_3$ (for example, wherein said non-aromatic heterocycle is optionally substituted with 1 or 2 —F or 1 or 2 —$CH_3$ substituents, or for example wherein $G^{3c}$ is a heterocycle selected from the group consisting of

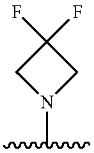 and 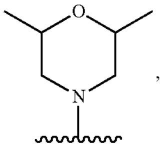, or $G^{3c}$ is a heterocycle selected from the group consisting of

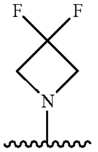 and 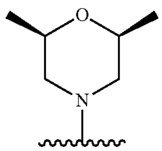).

In one embodiment, $G^3$ is —$C_{1-2}$alkyl optionally substituted with 1, 2 or 3 —F; for example, —$C_{1-2}$alkyl.

In one embodiment, $G^3$ is —$CH_3$.

In another embodiment, $G^3$ is

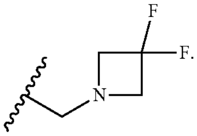 [SMILES: *CN1CC(F)(F)C1].

In another embodiment, $G^3$ is

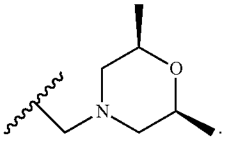 [SMILES: *CN1C[C@@H](C)O[C@@H](C)C1].

In one embodiment, $G^4$ is selected from the group consisting of:

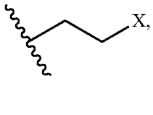, 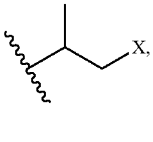, 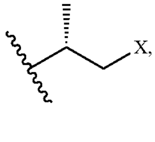,

-continued

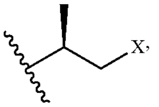, 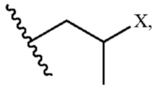, 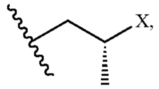,

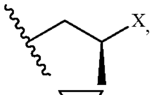, 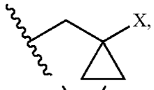, 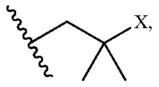,

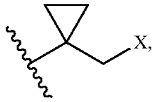, 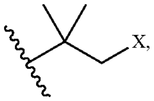, 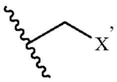,

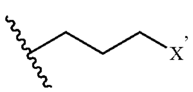, 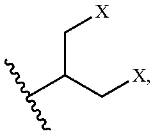, 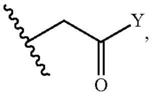,

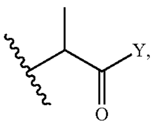, 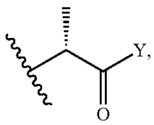, 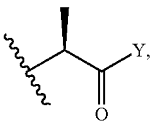,

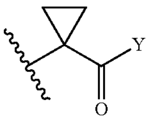 and 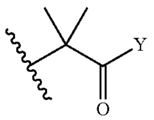

X is selected from the group consisting of —$OR^1$, —Cl, —Br, pyridine, pyrazole, imidazole, pyrrolidin-2-one, 2,5-dihydro-pyrrole, 4-methyl-7-(methylamino)-2H-chromen-2-one, —$NR^1R^2$ and —$R^8$ Y is selected from the group consisting of —$NR^1R^2$ and —$R^8$ $R^1$ is selected from the group consisting of —H, phenyl, pyridine, —$R^4$, and —$C_{1-4}$alkyl optionally substituted with 1, 2 or 3 —F, 1 or 2 —$OC_{1-3}$alkyl groups, or one —CN group; —$C_{3-4}$cycloalkyl optionally substituted with 1 or 2 —F or a —$OCH_3$ group; oxetane optionally substituted with one —$CH_3$ group; tetrahydrofuran optionally substituted with one —$CH_3$ group; and tetrahydro-2H-pyran optionally substituted with one —$CH_3$ group;

$R^2$ is selected from the group consisting of —H, —$C_{1-4}$alkyl optionally substituted with 1, 2 or 3 —F, 1 or 2 —$OC_{1-3}$alkyl groups, or one —CN group; —$C_{3-4}$cycloalkyl optionally substituted with 1 or 2 substituents independently selected from the group consisting of —F and —$OCH_3$; and oxetane optionally substituted with one —$CH_3$ group;

$R^4$ is selected from the group consisting of —$(CH_2CH_2O)_nCH_2CH_2N(R^5)_2$ and —$(CH_2CH_2O)_nR^5$;

n is 2, 3, 4, 5, 6, 7 or 8;

each $R^5$ is independently selected from the group consisting of —H, —$C_{1-4}$alkyl, and —$C_{3-4}$cycloalkyl;

$R^8$ is a heterocycle selected from the group consisting of

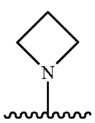, 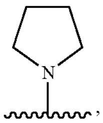, 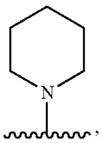, 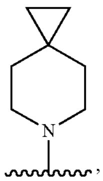, 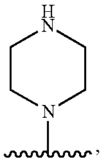,

-continued

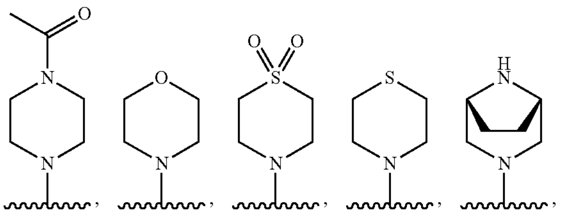

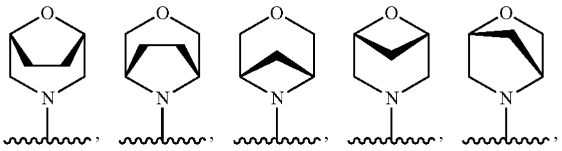

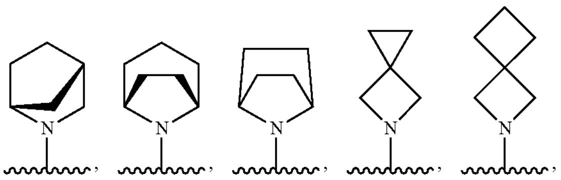

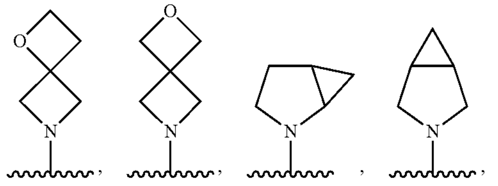

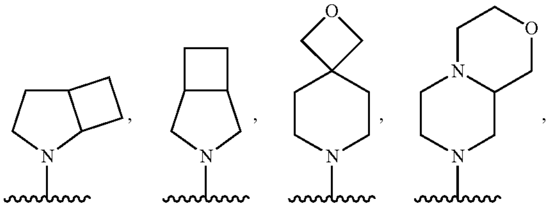

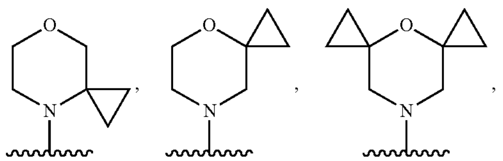

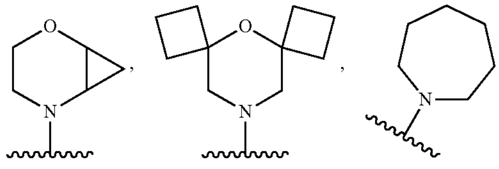

and

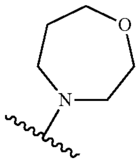

wherein said heterocycle is optionally substituted with 1, 2, 3 or 4 substituents independently selected from the group consisting of —F, —$CF_3$, —$OCH_3$, —$CHF_2$, —$CH_2F$ and —$C_{1-4}$alky (for example, 1, 2, 3 or 4 substituents independently selected from the group consisting of —F and —$C_{1-4}$alky).

In one embodiment, $G^4$ is selected from the group consisting of:

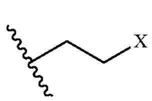

and

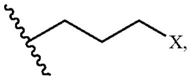

or selected from the group consisting of

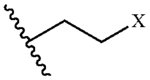

and

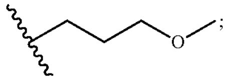

X is selected from the group consisting of —$OR^1$ and —$R^8$; $R^1$ is selected from the group consisting of H and —$C_{1-4}$alkyl optionally substituted with 1, 2 or 3 —F, 1 or 2 —$OC_{1-3}$alkyl groups, or one —CN group; and $R^8$ is a heterocycle selected from the group consisting of

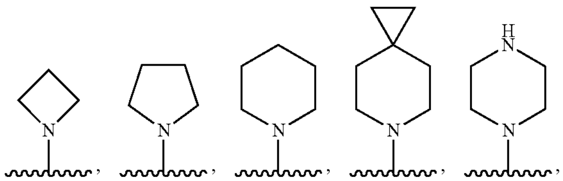

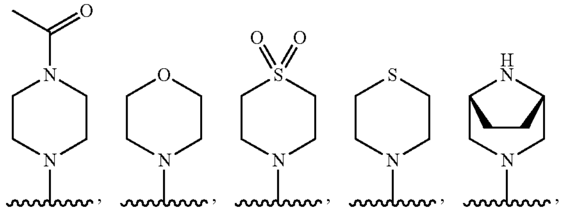

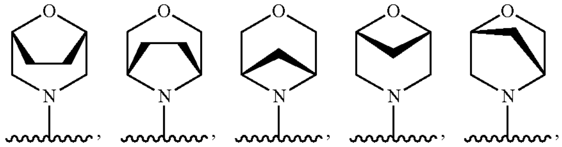

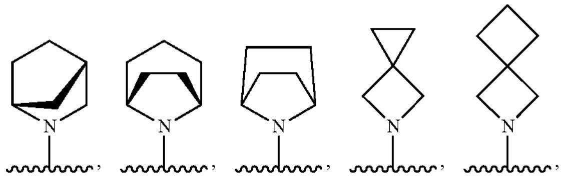

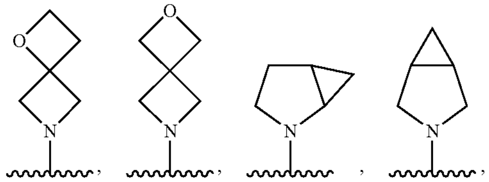

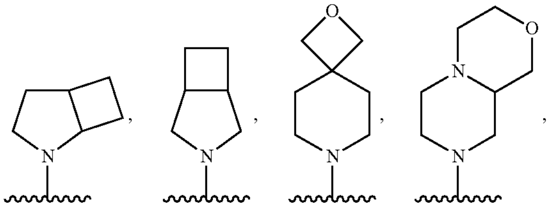

-continued

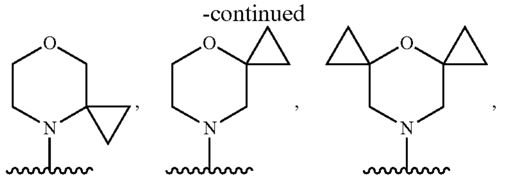

, , ,

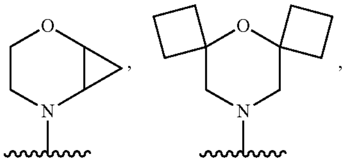

, , and

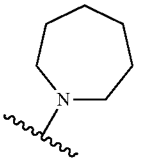

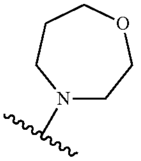

wherein said heterocycle is optionally substituted with 1, 2, 3 or 4 substituents independently selected from the group consisting of —F and —$C_{1-4}$alky (for example selected from the group consisting of —F and —$CH_3$).

In one embodiment, $G^4$ is selected from the group consisting of:

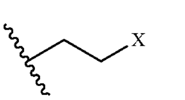

and

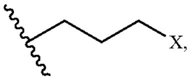

or selected from the group consisting of

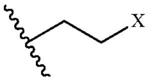

and

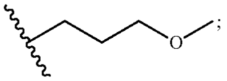

X is selected from the group consisting of —$OR^1$ and —$R^8$; $R^1$ is —$C_{1-4}$alkyl; and $R^8$ is a heterocycle selected from the group consisting of

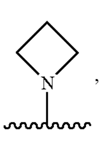

,

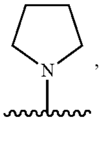

,

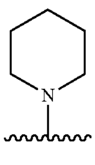

and

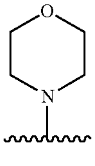

wherein said heterocycle is optionally substituted with 1, 2, 3 or 4 substituents independently selected from the group consisting of —F and —$CH_3$.

In one embodiment, $G^4$ is selected from the group consisting of:

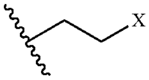

and

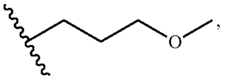

or selected from the group consisting of

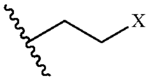

and

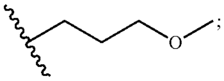

X is selected from the group consisting of —$OCH_3$ and —$R^8$; and $R^8$ is a heterocycle selected from the group consisting of

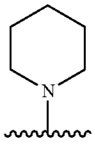

and

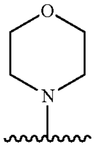

wherein said heterocycle is optionally substituted with 1, 2, 3 or 4 substituents (for example 1 or 2 substituents, or, for example, 2 substituents) independently selected from the group consisting of —F and —$CH_3$. In one embodiment, $R^3$ is a heterocycle selected from the group consisting of

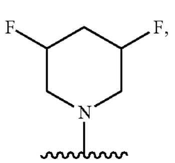

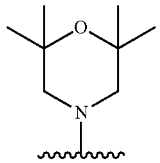

and

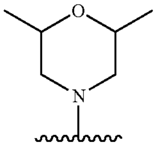

(for example, a heterocycle selected from the group consisting of

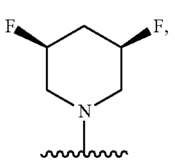

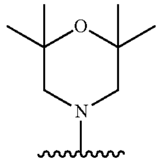

and

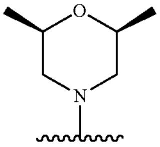

).

In one embodiment, $G^4$ is selected from the group consisting of:

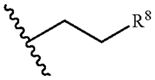

and

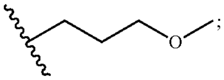

and $R^8$ is a heterocycle selected from the group consisting of

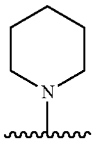 and 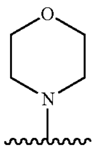

wherein said heterocycle is optionally substituted with 1, 2, 3 or 4 substituents (for example 1 or 2 substituents, or, for example, 2 substituents) independently selected from the group consisting of —F and —$CH_3$. In one embodiment, $R^8$ is a heterocycle selected from the group consisting of

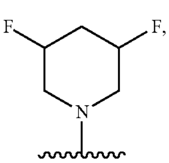 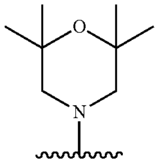 and 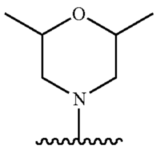

(for example, a heterocycle selected from the group consisting of

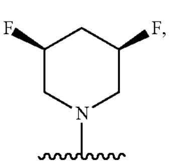 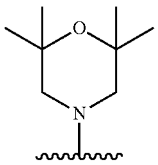 and 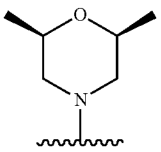 ).

In one embodiment, $G^4$ is selected from the group consisting of:

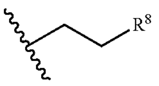 and 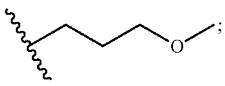;

and $R^8$ is a heterocycle selected from the group consisting of

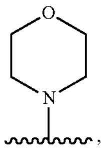, 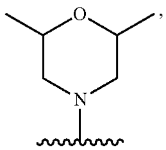, 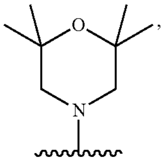, 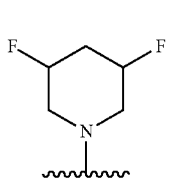 and 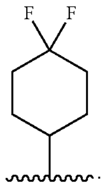.

(for example, $R^8$ is a heterocycle selected from the group consisting of

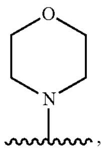, 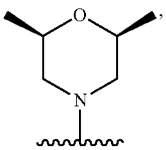, 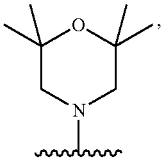, 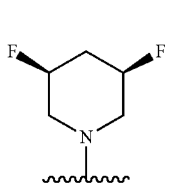 and 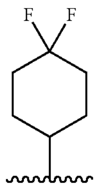 ).

In one embodiment, $G^4$ is

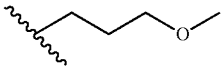.

In one embodiment, $G^{4A}$ is

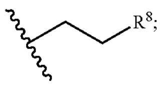;

and $R^8$

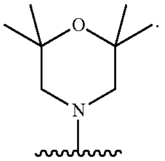

In another embodiment, each $R^8$ is independently a heterocycle selected from the group consisting of

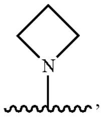, 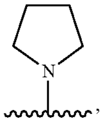, 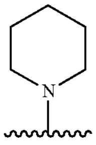 and 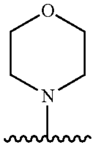

wherein said heterocycle is optionally substituted with 1, 2, 3 or 4 substituents independently selected from the group consisting of —F and —$CH_3$.

In one embodiment, each $R^8$ is independently a heterocycle selected from the group consisting of

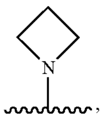, 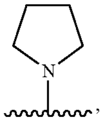, 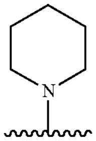 and 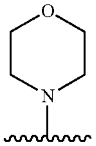

(for example,

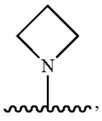, 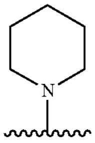 and 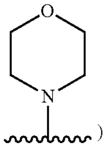)

wherein said heterocycle is optionally substituted with 1, 2, 3 or 4 substituents independently selected from the group consisting of —F and —$CH_3$ (for example, wherein said heterocycle is optionally substituted with two —F or two —$CH_3$ groups, or four —F or four —$CH_3$ groups).

In one embodiment, each $R^8$ is independently a heterocycle selected from the group consisting of

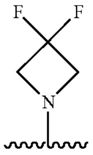, 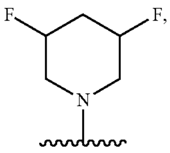, 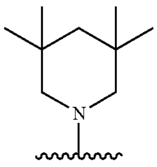 and

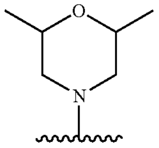

(for example, a heterocycle selected from the group consisting of

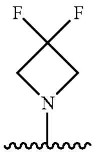, 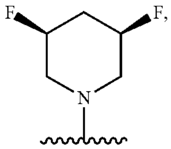, 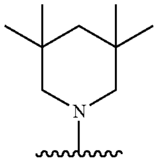 and

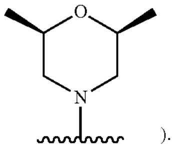).

In one embodiment, $G^3$ is selected from the group consisting of —$CH_3$,

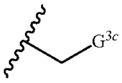 and 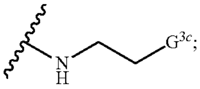;

$G^{3c}$ is selected from the group consisting of H, —$OCH_3$, and a non-aromatic heterocycle selected from the group consisting of

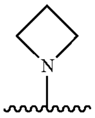 and 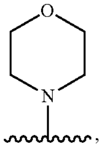, wherein said non-aromatic heterocycle is optionally substituted with 1 or 2 substituents independently selected from the group consisting of —F and —$CH_3$ (for example, wherein said non-aromatic heterocycle is optionally substituted with 1 or 2 —F or 1 or 2 —$CH_3$ substituents, or for example wherein $G^{3c}$ is a heterocycle selected from the group consisting of

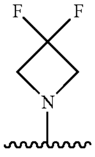 and 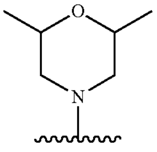, or $G^{3c}$ is a heterocycle selected from the group consisting of

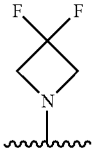 and 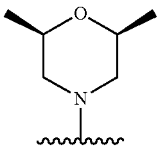);

and $G^4$ is selected from the group consisting of:

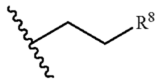 and 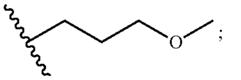 ;

and $R^8$ is a heterocycle selected from the group consisting of

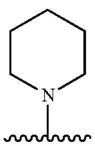 and 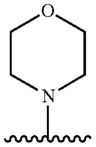

wherein said heterocycle is optionally substituted with 1, 2, 3 or 4 substituents (for example 1 or 2 substituents, or, for example, 2 substituents) independently selected from the group consisting of —F and —$CH_3$. In one embodiment, $R^3$ is a heterocycle selected from the group consisting of

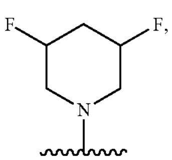 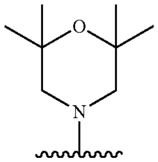 and 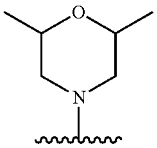

(for example, a heterocycle selected from the group consisting of

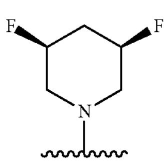 , 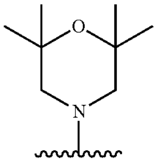 and 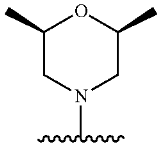 ).

In one embodiment, $G^3$ is selected from the group consisting of —$C_{1-2}$alkyl optionally substituted with 1, 2 or 3 —F (for example, —$CH_3$),

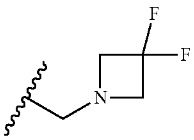 and 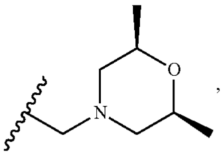 , and $G^4$ is selected from the group consisting of:

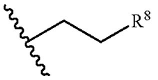 and 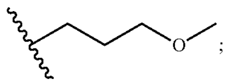 ;

and $R^8$ is a heterocycle selected from the group consisting of

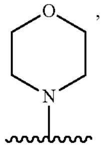 , 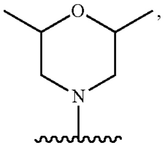 , 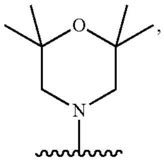 ,

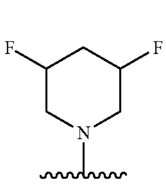 and 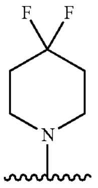

(for example, $R^8$ is a heterocycle selected from the group consisting of

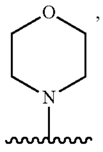 , 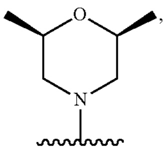 , 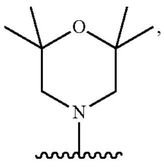 ,

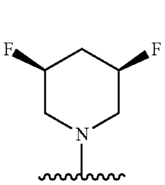 and 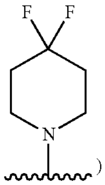 )

or $R^8$ is

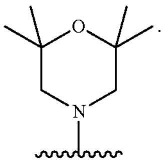

In one embodiment, $G^5$ is —$C_{1-3}$alkyl optionally substituted with 1, 2 or 3 —F. In one embodiment, $G^5$ is —$C_{1-3}$alkyl. In one embodiment, $G^5$ is —$CH_3$.

In one embodiment, $G^6$ is selected from the group consisting of —F and —Cl. In one embodiment, $G^6$ is —Cl, In one embodiment, $G^7$ is selected from the group consisting of

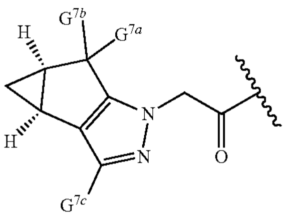 and

-continued

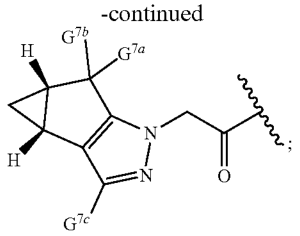

$G^{7a}$ is selected from the group consisting of —H and —F; $G^{7b}$ is selected from the group consisting of —H and —F; and $G^{7c}$ is selected from the group consisting of —$C_{1-2}$alkyl optionally substituted with 1, 2 or 3 —F, and —$C_{3-4}$cycloalkyl.

In one embodiment, $G^7$ is selected from the group consisting of

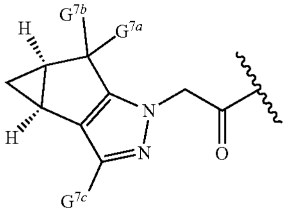

and

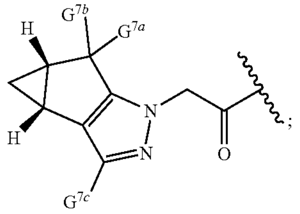

$G^{7a}$ is —H and $G^{7b}$ is —H, or $G^{7a}$ is F and $G^{7b}$ is F; and $G^{7c}$ is selected from the group consisting of —$C_{1-2}$alkyl optionally substituted with 1, 2 or 3 —F, and —$C_{3-4}$cycloalkyl.

In one embodiment, $G^7$ is

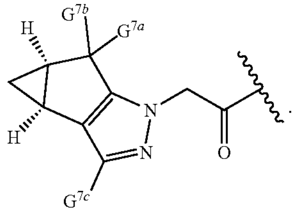

In one embodiment, $G^7$ is

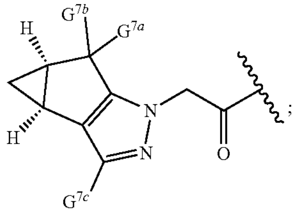

$G^{7a}$ is —H and $G^{7b}$ is —H, or $G^{7a}$ is F and $G^{7b}$ is F; and $G^{7c}$ is selected from the group consisting of —$CH_3$ optionally substituted with 1, 2 or 3 —F, and cyclopropyl.

In one embodiment, $G^7$ is

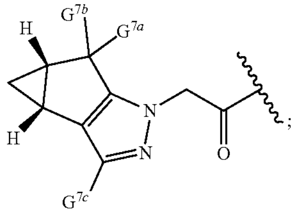

$G^{7a}$ is —H and $G^{7b}$ is —H, or $G^{7a}$ is F and $G^{7b}$ is F; and $G^{7c}$ is selected from the group consisting of —$CH_3$ optionally substituted with 1, 2 or 3 —F, and cyclopropyl.

In one embodiment, $G^7$ is selected from the group consisting of

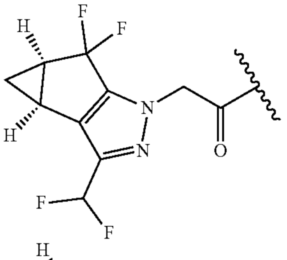

and

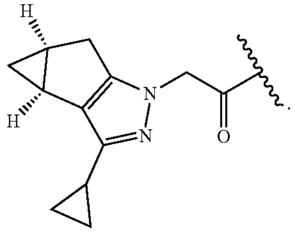 [SMILES: *C(=O)Cn1nc(C2CC2)c2c1C[C@@H]1C[C@H]21]

In one embodiment, $G^7$ is

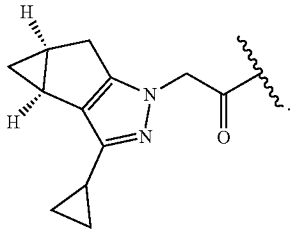

In one embodiment, $G^7$ is

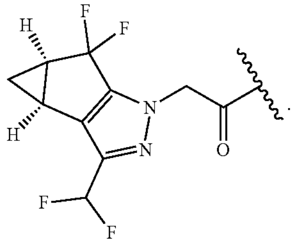 [SMILES: *C(=O)Cn1nc(C(F)F)c2c1C(F)(F)[C@@H]1C[C@H]21]

In one embodiment, $G^8$ and $G^9$ are independently selected from the group consisting of —H, and —F. In one embodiment, $G^8$ is —F and $G^9$ is —F.

In one embodiment, $G^{10}$ is selected from the group consisting of —H and —F; and $G^{11}$ is selected from the group consisting of —H and —F. In one embodiment, $G^{10}$ is H and $G^{11}$ is H.

In one aspect, the invention provides a compound of Formula (Ia):

Formula (Ia)

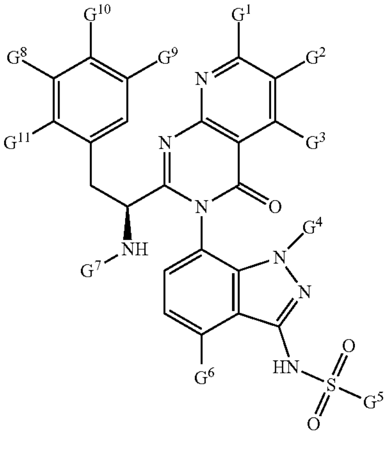

or a pharmaceutically acceptable salt thereof, wherein:

$G^1$ is selected from

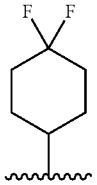

and

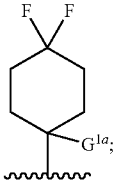

$G^{1a}$ is selected from the group consisting of —OH, —F, —Cl, —CN, —$C_{1-4}$alkyl optionally substituted with 1, 2 or 3 —F, and —$C_{1-3}$alkyl optionally substituted with one substituent selected from the group consisting of —$N(C_{1-2}alkyl)_2$, —$NH(C_{1-2}alkyl)$, and a heterocycle selected from the group consisting of azetidine, pyrrolidine, piperidine, and morpholine, wherein said heterocycle is optionally substituted with 1, 2, 3 or 4 substituents independently selected from the group consisting of-$CH_3$ and —F;

$G^2$ is selected from the group consisting of —H, —F, —Cl, —$OCH_3$ and —$CH_3$;

$G^3$ is selected from the group consisting of —H, —Cl, —CN, —CHO, —$C(O)C_{1-2}$alkyl; —$C_{1-3}$alkyl optionally substituted with 1, 2 or 3 —F; —$C_{1-3}$alkyl optionally substituted with one substituent select from the group consisting of OH, —$OC_{1-2}$alkyl and —CN; —$C_{3-4}$cycloalkyl optionally substituted with 1, 2 or 3 —F; and —NH—$C_{1-3}$alkyl optionally substituted with 1, 2, or 3 substituents independently selected from the group consisting of —$OCH_3$ and —F;

or $G^3$ is —$NH(C_{1-4}alkyl\text{-}G^{3a})$, wherein $G^{3a}$ is a heterocycle selected from the group consisting of oxetane, tetrahydrofuran, and tetrahydro-2H-pyran, wherein said heterocycle is optionally substituted with one substituent selected from the group consisting of —$CH_3$, —F, —$OC_{1-3}$alkyl and —$OC_{3-4}$cycloalkyl;

or $G^3$ is selected from the group consisting of:

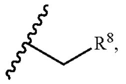
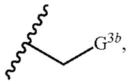
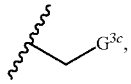
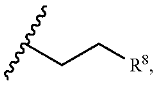
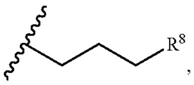
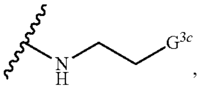
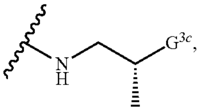
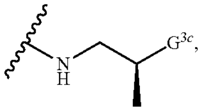
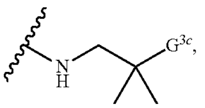
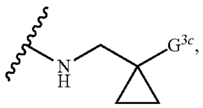
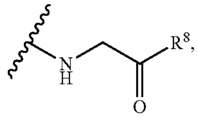
,
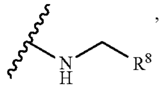
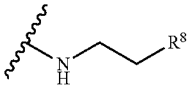

and

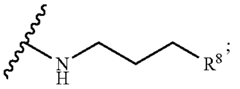

$G^{3b}$ is selected from the group consisting of —$NH(C_{1-2}alkyl)$, —$N(C_{1-2}alkyl)_2$, —$NH(CH_2CH_2OC_{1-3}alkyl)$, —$N(C_{1-2}alkyl)(CH_2CH_2OC_{1-3}alkyl)$ and —$NH(CH_2CH_2R^8)$;

$G^{3c}$ is selected from the group consisting of —H, —CN, —$OC_{1-3}$alkyl, —$C_{3-6}$cycloalkyl, —$NHC(O)C_{1-3}$alkyl, —$NH(C_{1-2}alkyl)$, —$N(C_{1-2}alkyl)_2$, —$R^8$, an aromatic heterocycle selected from the group consisting of phenyl, pyridine, thiazole, pyrazole and imidazole, wherein said aromatic heterocycle is optionally substituted with one —$CH_3$ group; and a non-aromatic heterocycle selected from the group consisting of

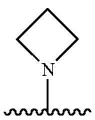
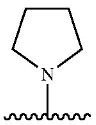
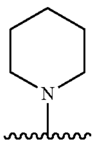
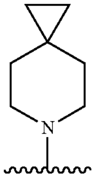
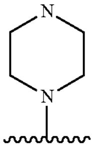

and

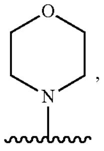
, wherein said non-aromatic heterocycle is optionally independently substituted with 1 or 2 substituents selected from the group consisting of —F, —$CH_3$, —$CF_3$, —$CHF_2$, —$OC_{1-2}$alkyl and —$C(O)C_{1-2}$alkyl;

$G^4$ is a heterocycle selected from the group consisting of pyridine, pyrimidine, pyrazole, imidazole, oxetane, tetrahydrofuran, tetrahydro-2H-pyran, azetidine, pyrrolidine and piperidine, wherein said heterocycle is optionally substituted with —$CH_2CH_2OC_{1-3}$alkyl; or $G^4$ is selected from the group consisting of:

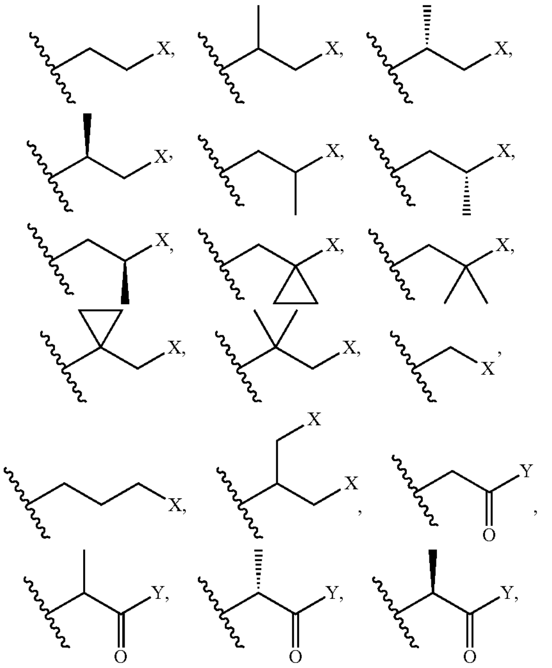

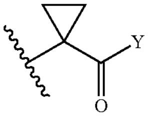 and 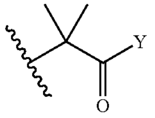

X is selected from the group consisting of —$OR^1$, —Cl, —Br, pyridine, pyrazole, imidazole, pyrrolidin-2-one, 2,5-dihydro-pyrrole, 4-methyl-7-(methylamino)-2H-chromen-2-one, —$NR^1R^2$, —$R^6$, —$R^7$, and —$R^8$;

Y is selected from the group consisting of —$NR^1R^2$, —$R^6$, —$R^7$, and —$R^8$;

$R^1$ is selected from the group consisting of —H, phenyl, pyridine, —$R^4$, and —$C_{1-4}$alkyl optionally substituted with 1, 2 or 3 —F, 1 or 2 —$OC_{1-3}$alkyl groups, or one —CN group; —$C_{3-4}$cycloalkyl optionally substituted with 1 or 2 —F or a —$OCH_3$ group; oxetane optionally substituted with one —$CH_3$ group; tetrahydrofuran optionally substituted with one —$CH_3$ group; and tetrahydro-2H-pyran optionally substituted with one —$CH_3$ group;

$R^2$ is selected from the group consisting of —H, —$C_{1-4}$alkyl optionally substituted with 1, 2 or 3 —F, 1 or 2 —$OC_{1-3}$alkyl groups, or one —CN group; —$C_{3-4}$cycloalkyl optionally substituted with 1 or 2 substituents independently selected from the group consisting of —F and —$OCH_3$; and oxetane optionally substituted with one —$CH_3$ group;

$R^4$ is selected from the group consisting of —$(CH_2CH_2O)_nCH_2CH_2N(R^5)_2$ and —$(CH_2CH_2O)_nR^5$;

n is 2, 3, 4, 5, 6, 7 or 8;

each $R^5$ is independently selected from the group consisting of —H, $C_{1-4}$alkyl, or —$C_{3-4}$cycloalkyl;

$R^6$ is a heterocycle selected from the group consisting of azetidine, pyrrolidine, piperidine, piperazine, and morpholine, wherein said heterocycle is optionally substituted with 1, 2, 3 or 4 —F, one —OH group, 1 or 2 —$OC_{1-4}$alkyl groups, 1 or 2 —$CH_3$ groups, one —$C_{1-3}$alkyl group optionally substituted with 1, 2 or 3 —F, one —$CH_3$ group optionally substituted with 1, 2 or 3 substituents independently selected from the group consisting of —F, —OH and —$OC_{1-3}$alkyl, or —$CH_2$pyridine optionally substituted with 1 or 2 —$CH_3$ groups;

$R^7$ is a heterocycle selected from the group consisting of azetidine, pyrrolidine, piperidine, piperazine, and morpholine, wherein said heterocycle is optionally substituted with one substituent selected from the group consisting of —$CO_2H$, —$S(O_2)R^{10}$, —$N(R^9)_2$, —$NR^9SO_2R^{10}$, —$NR^9COR^{10}$, —$C(O)R^5$, —$C(O)R^6$, a heterocycle selected from the group consisting of 1,2,4-oxadiazole, isoxazole, pyrazole, imidazole and thiazole, wherein said heterocycle is optionally substituted with one $R^{10}$ group, and a heterocycle selected from the group consisting of oxetane, tetrahydrofuran and tetrahydro-2H-pyran, wherein said heterocycle is optionally substituted with one —$CH_3$ group;

each $R^8$ is a heterocycle independently selected from the group consisting of:

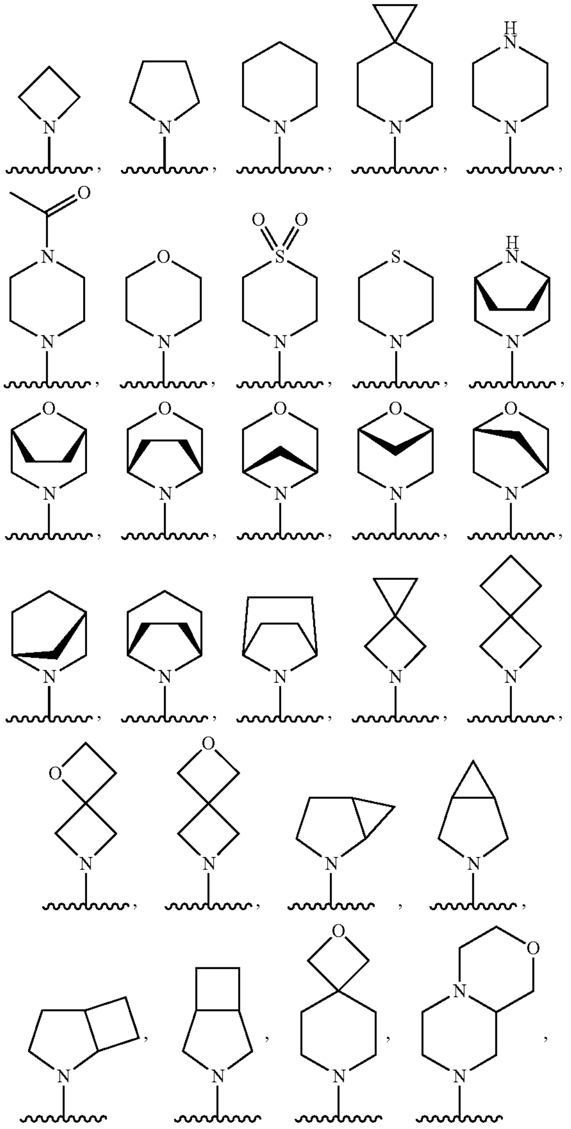

-continued

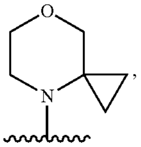,
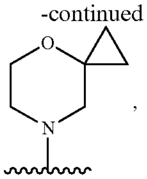,
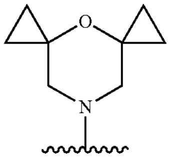,
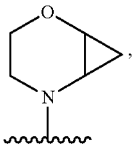,
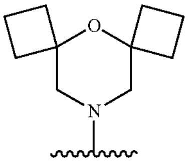,
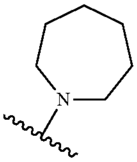 and
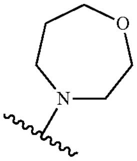

wherein said heterocycle is optionally substituted with 1, 2, 3 or 4 substituents independently selected from the group consisting of —F, —$CF_3$, —$OCH_3$, —$CHF_2$, —$CH_2F$ and —$C_{1-4}$alkyl;

each $R^9$ is independently selected from the group consisting of —H, —$CH_3$, —$C_{2-3}$alkyl optionally substituted with 1, 2 or 3 —F, and —$C_{3-4}$cycloalkyl optionally substituted with 1 or 2 —F;

$R^{10}$ is selected from the group consisting of —$CH_3$, —$CH_2F$, —$CHF_2$, —$CF_3$, —$C_{2-3}$alkyl optionally substituted with 1, 2 or 3 —F, and —$C_{3-4}$cycloalkyl optionally substituted with 1 or 2 —F;

$G^5$ is selected from the group consisting of —$C_{1-3}$alkyl optionally substituted with 1, 2 or 3 —F, and-$C_{3-4}$cycloalkyl optionally substituted with 1 or 2 —F;

$G^6$ is selected from the group consisting of —F, —Cl, —$CH_3$, and —$OCH_3$;

$G^7$ is selected from the group consisting of:

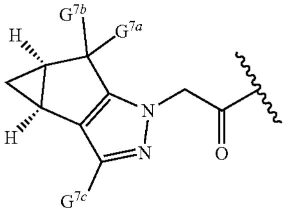 and

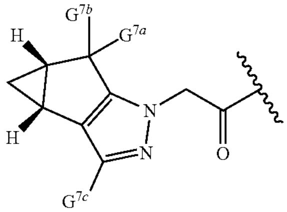;

$G^{7a}$ is selected from the group consisting of —H and —F;

$G^{7b}$ is selected from the group consisting of —H, —$CH_3$ and —F;

$G^{7c}$ is selected from the group consisting of —$C_{1-2}$alkyl optionally substituted with 1, 2 or 3 —F, and —$C_{3-4}$cycloalkyl optionally substituted with 1 or 2 —F.

$G^8$ and $G^9$ are independently selected from the group consisting of —H, —F, —C, —$CH_3$ and —$OCH_3$;

$G^{10}$ is selected from the group consisting of —H and —F; and $G^{11}$ is selected from the group consisting of —H, —F, —$CH_3$ and —$OCH_3$.

Suitably, $G^1$ is selected from

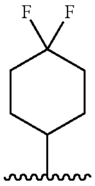 and 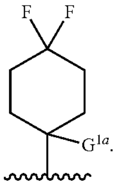.

In one embodiment, $G^1$ is

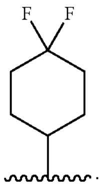.

In one embodiment, $G^1$ is

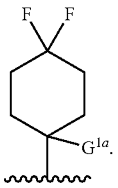.

Suitably, $G^{1a}$ is selected from the group consisting of —OH, —F, —Cl, —CN, —$C_{1-4}$alkyl optionally substituted with 1, 2 or 3 —F, and —$C_{1-3}$alkyl optionally substituted with one substituent selected from the group consisting of —$N(C_{1-2}alkyl)_2$, —$NH(C_{1-2}alkyl)$, and a heterocycle selected from the group consisting of azetidine, pyrrolidine, piperidine, and morpholine, wherein said heterocycle is optionally substituted with 1, 2, 3 or 4 substituents independently selected from the group consisting of —$CH_3$ and —F.

In one embodiment, $G^1$ is selected from

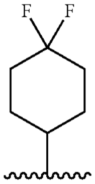 and 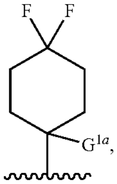, and $G^{1a}$ is selected from the group consisting of —OH, —F, —Cl, —CN, and —$C_{1-4}$alkyl optionally substituted with 1, 2 or 3 —F.

In another embodiment, $G^1$ is selected from

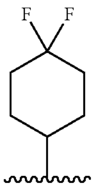

and

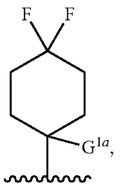

and $G^{1a}$ is selected from the group consisting of —OH, —F, —C, and —CN.

In still another embodiment, $G^1$ is selected from

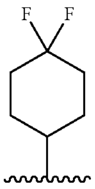

and

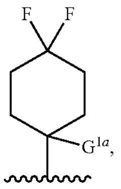

and $G^{1a}$ is

In yet another embodiment, $G^1$ is

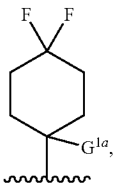

and $G^{1a}$ is —H.

In another embodiment, $G^1$ is

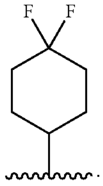

Suitably, $G^2$ is selected from the group consisting of —H, —F, —Cl, —$OCH_3$ and —$CH_3$.

In one embodiment, $G^2$ is selected from the group consisting of —H and —F.

In one embodiment, $G^2$ is H.

Suitably, $G^3$ is selected from the group consisting of —H, —Cl, —CN, —CHO, —C(O)$C_{1-2}$alkyl; —$C_{1-3}$alkyl optionally substituted with 1, 2 or 3 —F; —$C_{1-3}$alkyl optionally substituted with one substituent select from the group consisting of —OH, —$OC_{1-2}$alkyl and —CN, and —$C_{3-4}$cycloalkyl optionally substituted with 1, 2 or 3 —F;

or $G^3$ is —NH($C_{1-4}$alkyl-$G^{3a}$), wherein $G^{3a}$ is a heterocycle selected from the group consisting of oxetane, tetrahydrofuran, and tetrahydro-2H-pyran, wherein said heterocycle is optionally substituted with one substituent selected from the group consisting of —$CH_3$, —F, —$OC_{1-3}$alkyl and —$OC_{3-4}$cycloalkyl;

or $G^3$ is selected from the group consisting of:

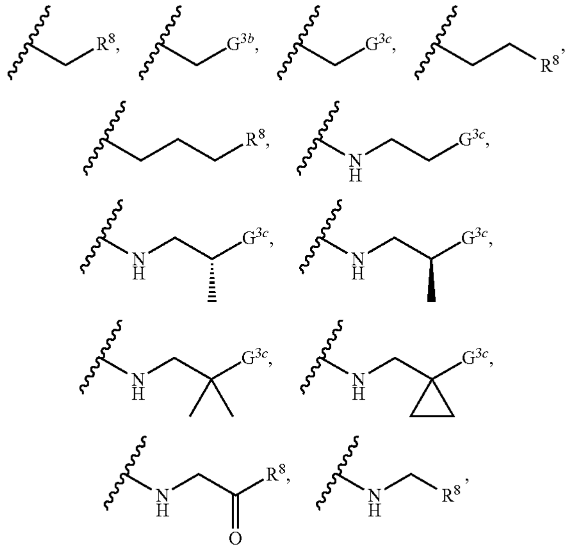

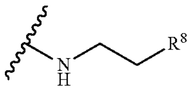

and

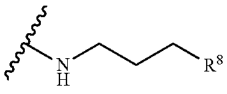

$G^{3b}$ is selected from the group consisting of —NH($C_{1-2}$alkyl), —N($C_{1-2}$alkyl)$_2$, —NH($CH_2CH_2OC_{1-3}$alkyl), —N($C_{1-2}$alkyl)($CH_2CH_2OC_{1-3}$alkyl) and —NH($CH_2CH_2R^8$);

$G^{3c}$ is selected from the group consisting of —H, —CN, —$OC_{1-3}$alkyl, —$C_{3-6}$cycloalkyl, —NHC(O)$C_{1-3}$alkyl, —NH($C_{1-2}$alkyl), —N($C_{1-2}$alkyl)$_2$, —$R^8$, an aromatic heterocycle selected from the group consisting of phenyl, pyridine, thiazole, pyrazole and imidazole, wherein said aromatic heterocycle is optionally substituted with one —$CH_3$ group, and a non-aromatic heterocycle selected from the group consisting of

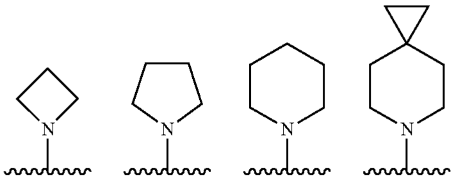

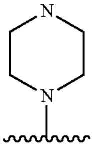

and

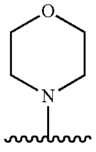

, wherein said non-aromatic heterocycle is optionally independently substituted with 1 or 2 substituents selected from the group consisting of —F, —$CH_3$, —$CF_3$, —$CHF_2$, —$OC_{1-2}$alkyl and —C(O)$C_{1-2}$alkyl.

In one embodiment, $G^3$ is selected from the group consisting of —H, —Cl, —CN, CHO, —C(O)$C_{1-2}$alkyl, —$C_{1-3}$alkyl optionally substituted with 1, 2 or 3 —F, and —$C_{3-4}$cycloalkyl optionally substituted with 1, 2 or 3 —F;

or $G^3$ is selected from the group consisting of:

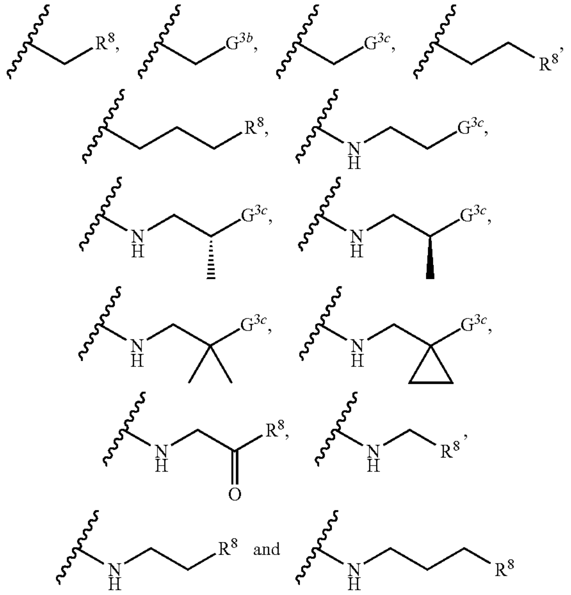

(or, for example, selected from the group consisting of

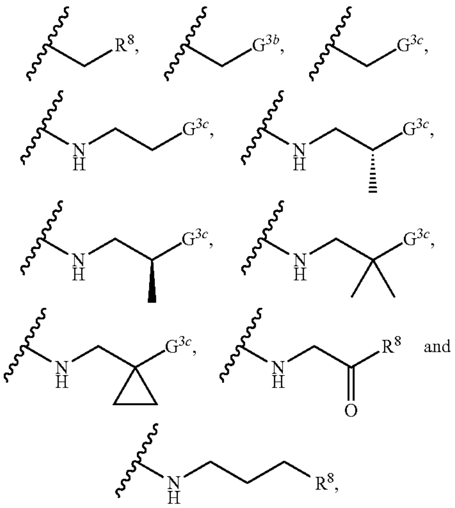

or for example, selected from the group consisting of

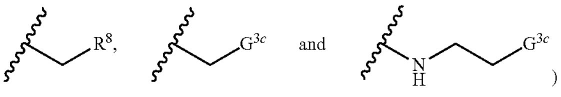

wherein, $G^{3b}$ is selected from the group consisting of $-NH(C_{1-2}alkyl)$, $-N(C_{1-2}alkyl)_2$, $-NH(CH_2CH_2OC_{1-3}alkyl)$, $-N(C_{1-2}alkyl)(CH_2CH_2OC_{1-3}alkyl)$ and $-NH(CH_2CH_2R^8)$; and wherein, $G^{3c}$ is selected from the group consisting of —H, CN, $-C_{3-6}cycloalkyl$, $-NHC(O)C_{1-3}alkyl$, $-R^8$, an aromatic heterocycle selected from the group consisting of phenyl, pyridine, and thiazole, wherein said aromatic heterocycle is optionally substituted with optionally substituted with methyl, or pyrazole optionally substituted with methyl, or imidazole optionally substituted with one $-CH_3$ group; and a non-aromatic heterocycle selected from the group consisting of

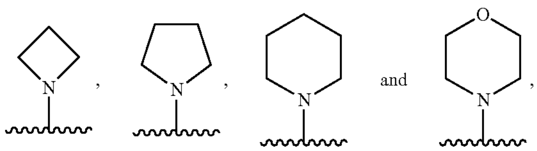

wherein said non-aromatic heterocycle is optionally independently substituted with 1 or 2 substituents selected from the group consisting of —F, $-CH_3$, $-CF_3$, $-CHF_2$ and $-OC_{1-2}alkyl$; and $R^8$ is a heterocycle selected from the group consisting of

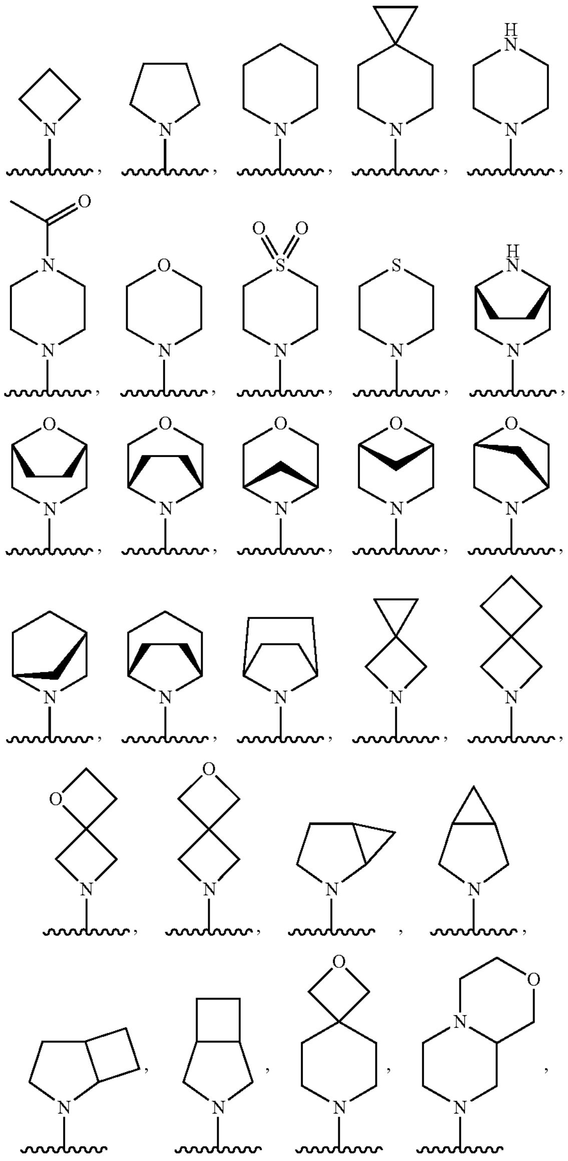

-continued

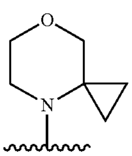, 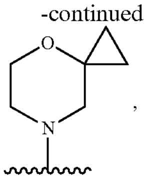, 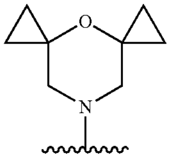,

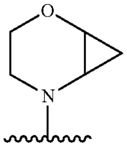, 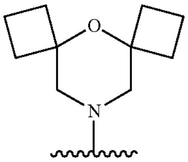, 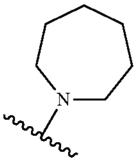 and

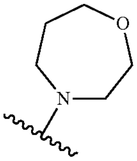

wherein said heterocycle is optionally substituted with 1, 2, 3 or 4 substituents independently selected from the group consisting of —F, —$CF_3$, —$OCH_3$, —$CHF_2$, —$CH_2F$ and —$C_{1-4}$alkyl (for example, wherein said heterocycle is optionally substituted with 1, 2, 3 or 4 substituents independently selected from the group consisting of —F and —$CH_3$).

In one embodiment, $G^3$ is selected from the group consisting of —H, —Cl, —CN, —CHO, —C(O)$C_{1-2}$alkyl, —$C_{1-2}$alkyl optionally substituted with 1, 2 or 3 —F,

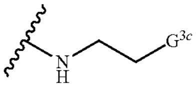 and 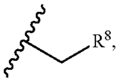, wherein $G^{3c}$ is selected from the group consisting of H and —$OC_{1-3}$alkyl (for example, H and —$OCH_3$); and wherein $R^3$ is a heterocycle selected from the group consisting of

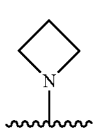 and 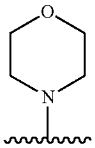

wherein said heterocycle is optionally substituted with 1 or 2 substituents independently selected from the group consisting of —F and —$CH_3$ (for example, wherein said heterocycle is optionally substituted with 1 or 2 —F or 1 or 2 —$CH_3$ substituents, or for example wherein $R^8$ is a heterocycle selected from the group consisting of

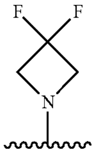 and 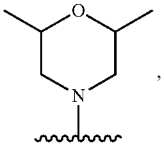, or $R^8$ is a heterocycle selected from the group consisting of

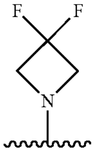 and 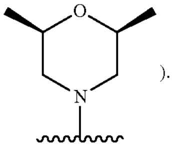).

and

In one embodiment, $G^3$ is selected from the group consisting of —$C_{1-2}$alkyl,

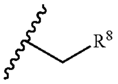 and 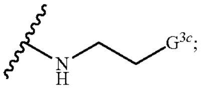;

and $G^{3c}$ is selected from the group consisting of —H, —$OC_{1-3}$alkyl, and a non-aromatic heterocycle selected from the group consisting of

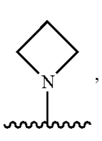, 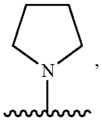, 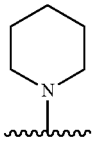 and 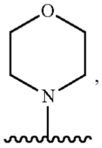, wherein said non-aromatic heterocycle is optionally independently substituted with 1 or 2 substituents selected from the group consisting of —$CH_3$, —$CF_3$, —$CHF_2$ and —$OC_{1-2}$alkyl (for example $G^{3c}$ is

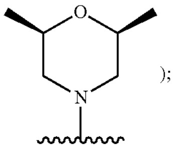);

and $R^8$ is a heterocycle selected from the group consisting of

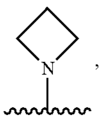, 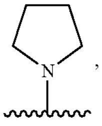, 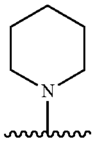 and 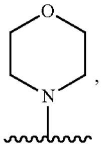, wherein said heterocycle is optionally substituted with 1, 2, 3 or 4 substituents independently selected from the group consisting of —F and —$CH_3$.

In one embodiment, $G^3$ is selected from the group consisting of —$CH_3$,

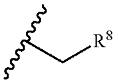 and 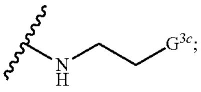;

$G^{3c}$ is selected from the group consisting of H and —$OCH_3$; and $R^8$ is a heterocycle selected from the group consisting of

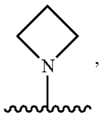, 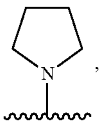, 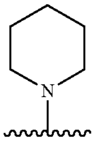 and 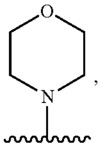, wherein said heterocycle is optionally substituted with 1 or 2 substituents independently selected from the group consisting of —F and —$CH_3$ (for example, wherein said heterocycle is optionally substituted with 1 or 2 —F or 1 or 2 —$CH_3$ substituents).

In one embodiment, $G^3$ is selected from the group consisting of —$CH_3$,

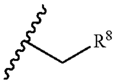 and 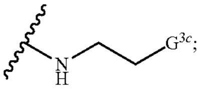

$G^{3c}$ is selected from the group consisting of H and —$OCH_3$; and $R^8$ is a heterocycle selected from the group consisting of

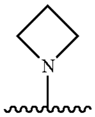 and 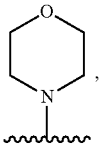, wherein said heterocycle is optionally substituted with 1 or 2 substituents independently selected from the group consisting of —F and —$CH_3$ (for example, wherein said heterocycle is optionally substituted with 1 or 2 —F or 1 or 2 —$CH_3$ substituents, or for example wherein $R^8$ is a heterocycle selected from the group consisting of

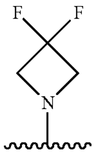 and 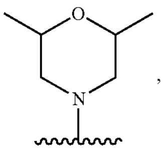, or $R^8$ is a heterocycle selected from the group consisting of

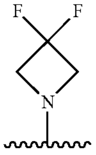 and 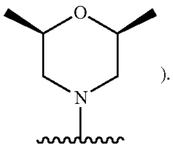).

In another embodiment, $G^3$ is selected from the group consisting of —$CH_3$,

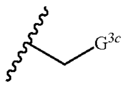 and 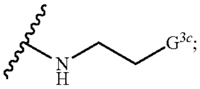

$G^{3c}$ is selected from the group consisting of H, —$OCH_3$, and a non-aromatic heterocycle selected from the group consisting of

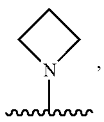, 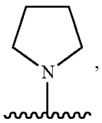, 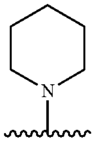 and 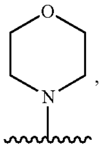, wherein said non-aromatic heterocycle is optionally independently substituted with 1 or 2 substituents selected from the group consisting of —F, —$CH_3$, —$CF_3$, —$CHF_2$ and —$OC_{1-2}$alkyl (for example, wherein said heterocycle is optionally substituted with 1 or 2 —F or 1 or 2 —$CH_3$ substituents, or, for example $G^{3c}$ is

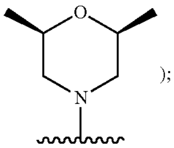);

In one embodiment, $G^3$ is selected from the group consisting of —$CH_3$,

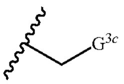 and 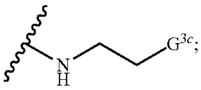

$G^{3c}$ is selected from the group consisting of H, —$OCH_3$, and a non-aromatic heterocycle selected from the group consisting of

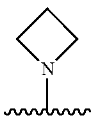 and 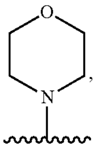, wherein said non-aromatic heterocycle is optionally substituted with 1 or 2 substituents independently selected from the group consisting of —F and —$CH_3$ (for example, wherein said non-aromatic heterocycle is optionally substituted with 1 or 2 —F or 1 or 2 —$CH_3$ substituents, or for example wherein $G^{3c}$ is a heterocycle selected from the group consisting of

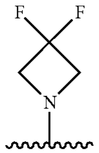 and 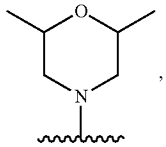, or $G^{3c}$ is a heterocycle selected from the group consisting of

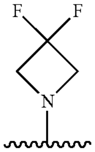 and 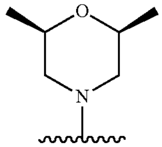).

In one embodiment, $G^3$ is selected from the group consisting of —H and —$C_{1-2}$alkyl optionally substituted with 1, 2 or 3 —F; for example, selected from the group consisting of —H, —$CHF_2$ and —$CH_3$.

In one embodiment, $G^3$ is H.

In one embodiment, $G^3$ is —$CHF_2$.

In one embodiment, $G^3$ is —$CH_3$.

In one embodiment, $G^3$ is

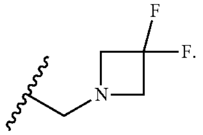 [SMILES: *CN1CC(F)(F)C1]

In one embodiment, $G^3$ is

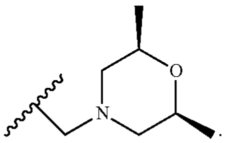 [SMILES: *CN1C[C@@H](C)O[C@@H](C)C1]

Suitably, $G^4$ is selected from the group consisting of:

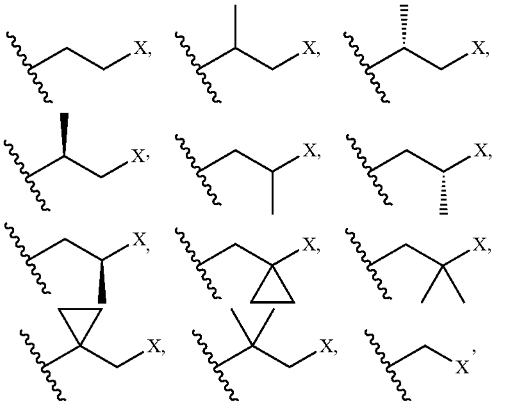

-continued

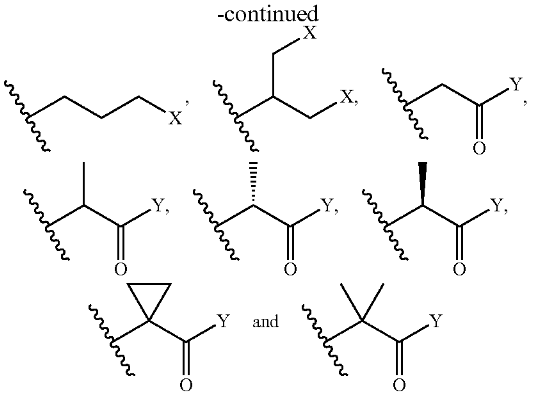

X is selected from the group consisting of —$OR^1$, —Cl, —Br, pyridine, pyrazole, imidazole, pyrrolidin-2-one, 2,5-dihydro-pyrrole, 4-methyl-7-(methylamino)-2H-chromen-2-one, —$NR^1R^2$ and —$R^8$;

Y is selected from the group consisting of —$NR^1R^2$ and —$R^8$;

$R^1$ is selected from the group consisting of —H, phenyl, pyridine, —$R^4$, and —$C_{1-4}$alkyl optionally substituted with 1, 2 or 3 —F, 1 or 2 —$OC_{1-3}$alkyl groups, or one —CN group; —$C_{3-4}$cycloalkyl optionally substituted with 1 or 2 —F or a —$OCH_3$ group; oxetane optionally substituted with one —$CH_3$ group; tetrahydrofuran optionally substituted with one —$CH_3$ group; and tetrahydro-2H-pyran optionally substituted with one —$CH_3$ group;

$R^2$ is selected from the group consisting of —H, —$C_{1-4}$alkyl optionally substituted with 1, 2 or 3 —F, 1 or 2 —$OC_{1-3}$alkyl groups, or one —CN group; —$C_{3-4}$cycloalkyl optionally substituted with 1 or 2 substituents independently selected from the group consisting of —F and —$OCH_3$; and oxetane optionally substituted with one —$CH_3$ group;

$R^4$ is selected from the group consisting of —$(CH_2CH_2O)_nCH_2CH_2N(R^5)_2$ and —$(CH_2CH_2O)_nR^5$;

n is 2, 3, 4, 5, 6, 7 or 8;

each $R^5$ is independently selected from the group consisting of —H, —$C_{1-4}$alkyl, and —$C_{3-4}$cycloalkyl;

$R^8$ is a heterocycle selected from the group consisting of

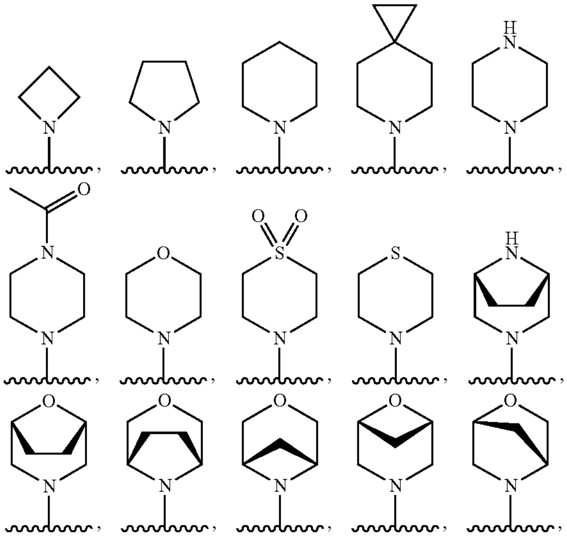

-continued

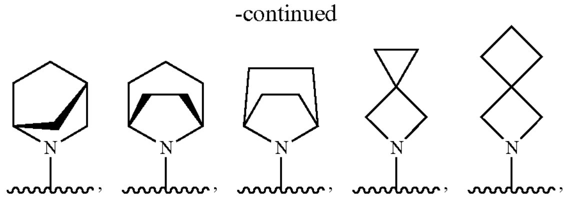

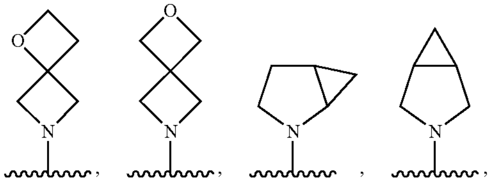

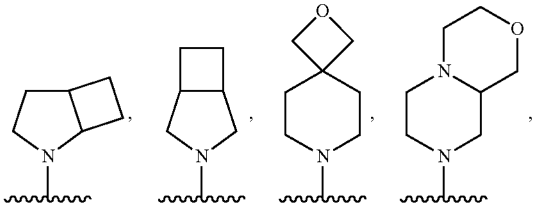

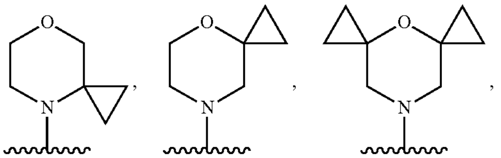

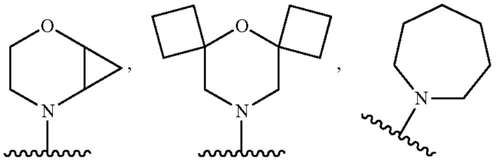

and

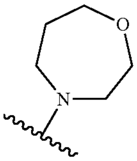

wherein said heterocycle is optionally substituted with 1, 2, 3 or 4 substituents independently selected from the group consisting of —F, —$CF_3$, —$OCH_3$, —$CHF_2$, —$CH_2F$ and —$C_{1-4}$alkyl (for example, 1, 2, 3 or 4 substituents independently selected from the group consisting of —F and —$C_{1-4}$alky).

In one embodiment, $G^4$ is selected from the group consisting of:

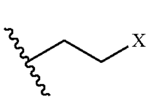

and

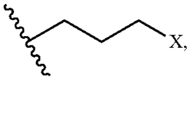

or selected from the group consisting of

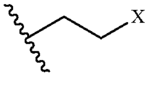

and

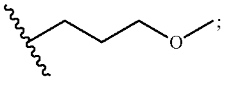

X is selected from the group consisting of —$OR^1$ and —$R^8$; $R^1$ is selected from the group consisting of H and —$C_{1-4}$alkyl optionally substituted with 1, 2 or 3 —F, 1 or 2 —$OC_{1-3}$alkyl groups, or one —CN group; and $R^8$ is a heterocycle selected from the group consisting of

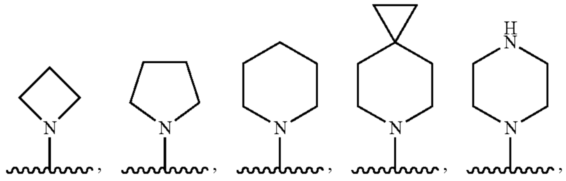

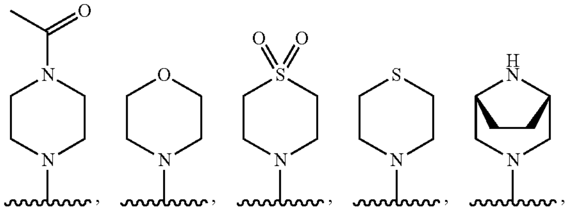

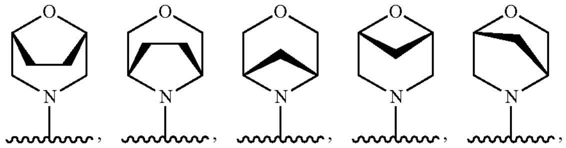

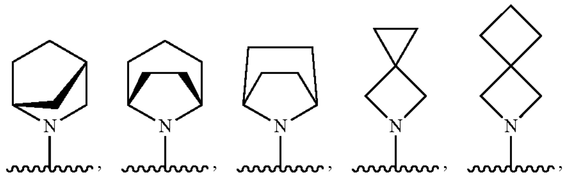

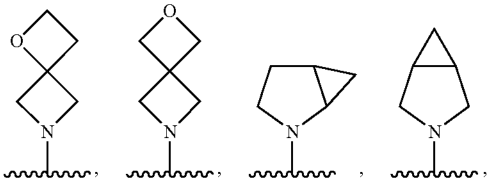

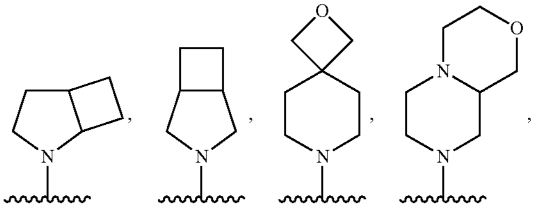

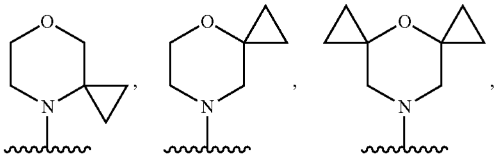

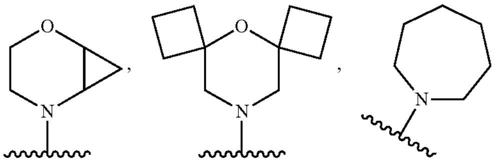

and

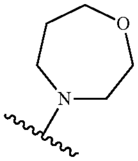

wherein said heterocycle is optionally substituted with 1, 2, 3 or 4 substituents independently selected from the group consisting of —F and —$C_{1-4}$alky (for example selected from the group consisting of —F and —$CH_3$).

In one embodiment, $G^4$ is selected from the group consisting of:

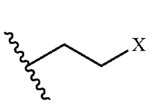
and
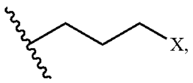

or selected from the group consisting of

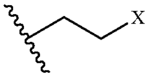
and
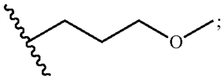

X is selected from the group consisting of —$OR^1$ and —$R^8$; $R^1$ is —$C_{1-4}$alkyl; and $R^8$ is a heterocycle selected from the group consisting of

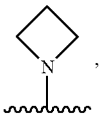
,
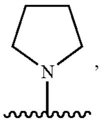
,
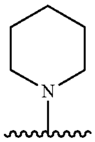
and
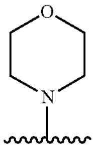

wherein said heterocycle is optionally substituted with 1, 2, 3 or 4 substituents independently selected from the group consisting of —F and —$CH_3$.

In one embodiment, $G^4$ is selected from the group consisting of:

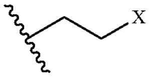
and
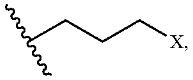

nor selected from the group consisting of

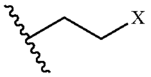
and
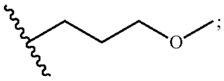

X is selected from the group consisting of —$OCH_3$ and —$R^8$; and $R^8$ is a heterocycle selected from the group consisting of

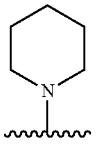
and
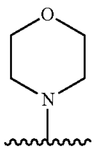

wherein said heterocycle is optionally substituted with 1, 2, 3 or 4 substituents (for example 1 or 2 substituents, or, for example, 2 substituents) independently selected from the group consisting of —F and —$CH_3$.

In one embodiment, $R^8$ is a heterocycle selected from the group consisting of

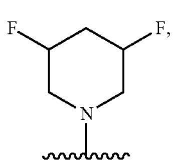
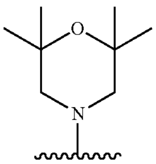
and
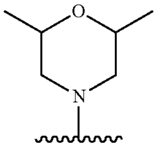

(for example, a heterocycle selected from the group consisting of

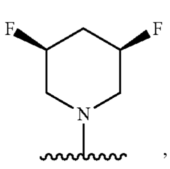
,
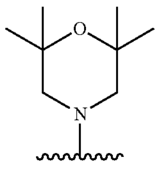
and
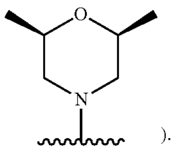
).

In one embodiment, $G^4$ is selected from the group consisting of:

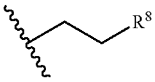
and
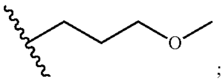

and $R^8$ is a heterocycle selected from the group consisting of

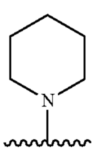
and
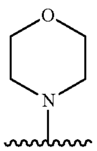

wherein said heterocycle is optionally substituted with 1, 2, 3 or 4 substituents (for example 1 or 2 substituents, or, for example, 2 substituents) independently selected from the group consisting of —F and —$CH_3$.

In one embodiment, $R^8$ is a heterocycle selected from the group consisting of

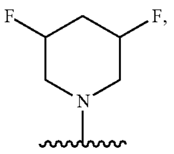
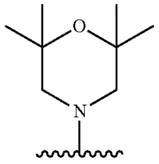
and
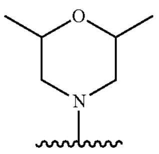

(for example, a heterocycle selected from the group consisting of

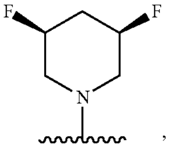, 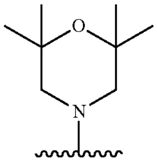 and 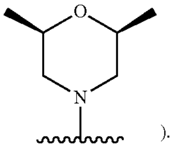).

In one embodiment, $G^4$ is selected from the group consisting of:

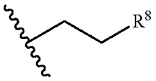 and 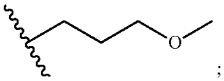;

and $R^8$ is a heterocycle selected from the group consisting of

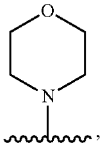, 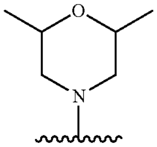, 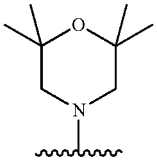, 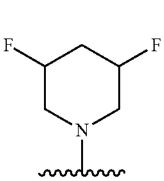 and 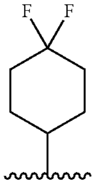

(for example, $R^8$ is a heterocycle selected from the group consisting of

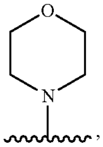, 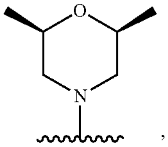, 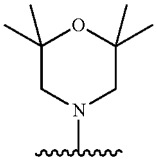, 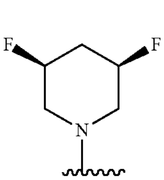 and 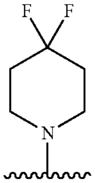).

In one embodiment, $G^4$ is

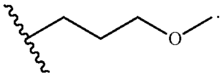 [SMILES: *CCCOC].

In one embodiment, $G^4$ is

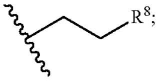

and $R^8$ is

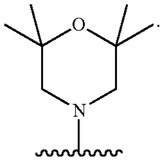.

In one embodiment, $G^3$ is selected from the group consisting of $—CH_3$,

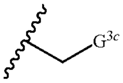 and 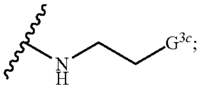;

$G^{3c}$ is selected from the group consisting of H, $—OCH_3$, and a non-aromatic heterocycle selected from the group consisting of

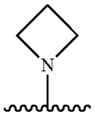 and 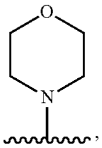, wherein said non-aromatic heterocycle is optionally substituted with 1 or 2 substituents independently selected from the group consisting of —F and $—CH_3$ (for example, wherein said non-aromatic heterocycle is optionally substituted with 1 or 2 —F or 1 or 2 $—CH_3$ substituents, or for example wherein $G^{3c}$ is a heterocycle selected from the group consisting of

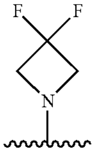 and 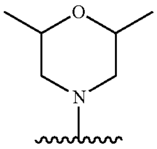, or $G^{3c}$ is a heterocycle selected from the group consisting of

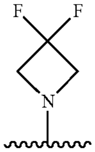 and 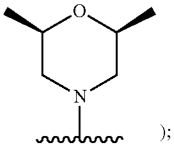);

and $G^4$ is selected from the group consisting of:

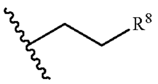 and 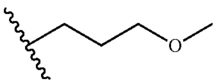 ;

and $R^8$ is a heterocycle selected from the group consisting of

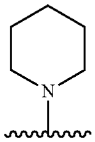 and 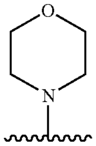

wherein said heterocycle is optionally substituted with 1, 2, 3 or 4 substituents (for example 1 or 2 substituents, or, for example, 2 substituents) independently selected from the group consisting of —F and —$CH_3$. In one embodiment, $R^3$ is a heterocycle selected from the group consisting of

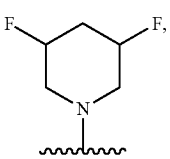 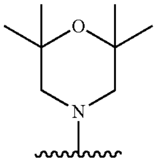 and 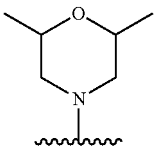

(for example, a heterocycle selected from the group consisting of

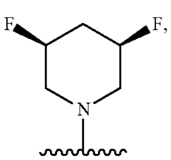 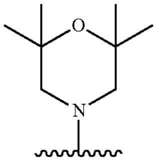 and 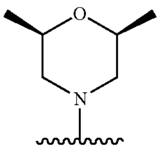 ).

In one embodiment, $G^3$ is selected from the group consisting of —$C_{1-2}$alkyl optionally substituted with 1, 2 or 3 —F (for example, —$CH_3$)

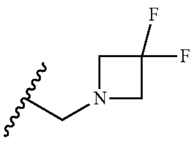 and 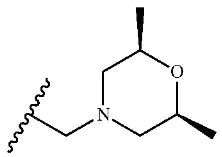 , and $G^4$ is selected from the group consisting of:

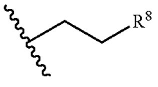 and 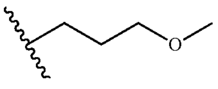 ;

and $R^8$ is a heterocycle selected from the group consisting of

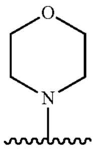 , 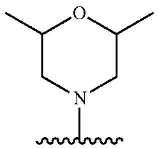 , 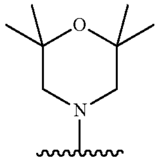 ,

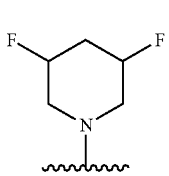 and 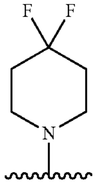

(for example, $R^8$ is a heterocycle selected from the group consisting of

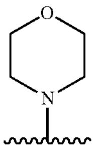 , 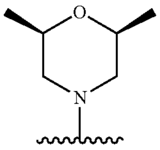 , 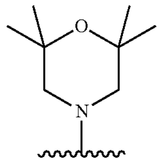 ,

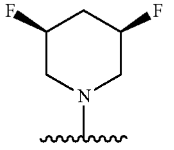 and 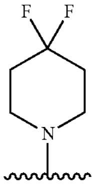 )

or $R^8$ is

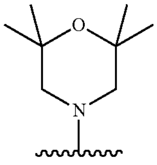 .

In certain embodiments, each $R^8$ is independently a heterocycle selected from the group consisting of

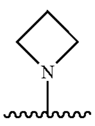 , 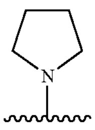 , 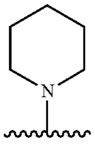 and 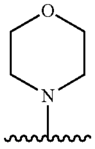

wherein said heterocycle is optionally substituted with 1, 2, 3 or 4 substituents independently selected from the group consisting of —F and —$CH_3$.

In one embodiment, each $R^8$ is independently a heterocycle selected from the group consisting of

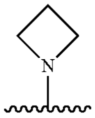 , 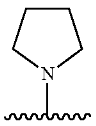 , 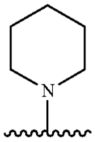 and 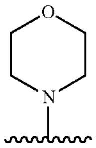

(for example,

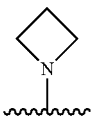 , 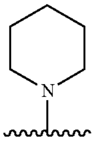 and 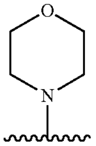 )

wherein said heterocycle is optionally substituted with 1, 2, 3 or 4 substituents independently selected from the group consisting of —F and —$CH_3$ (for example, wherein said heterocycle is optionally substituted with two —F or two —$CH_3$ groups, or four —F or four —$CH_3$ groups).

In one embodiment, each $R^8$ is independently a heterocycle selected from the group consisting of

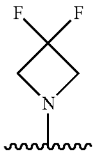 , 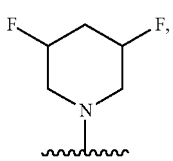 , 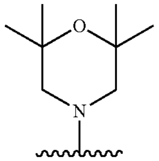 and 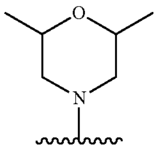

(for example, a heterocycle selected from the group consisting of

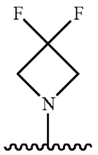 , 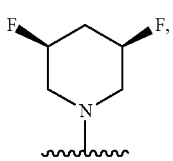 , 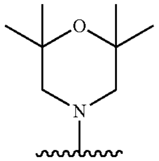 and 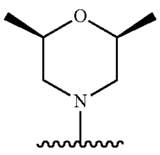 ).

Suitably, $G^5$ is selected from the group consisting of —$C_{1-3}$alkyl optionally substituted with 1, 2 or 3 —F, and-$C_{3-4}$cycloalkyl optionally substituted with 1 or 2 —F.

In one embodiment, $G^5$ is —$C_{1-3}$alkyl optionally substituted with 1, 2 or 3 —F.

In one embodiment, $G^5$ is —$C_{1-3}$alkyl.

In one embodiment, $G^5$ is —$CH_3$.

Suitably, $G^6$ is selected from the group consisting of —F, —Cl, —$CH_3$, and —$OCH_3$.

In one embodiment, $G^6$ is —$CH_3$.

Suitably, $G^7$ is selected from:

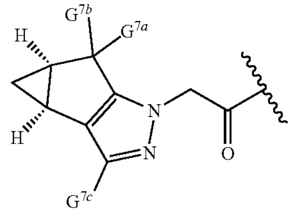

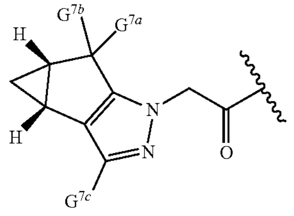 .

In one embodiment, $G^7$ is

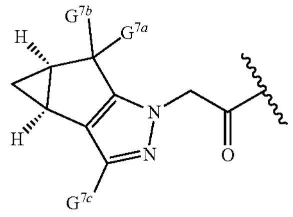

(hereinafter, formula ($G^7$A)).

In another embodiment, $G^7$ is

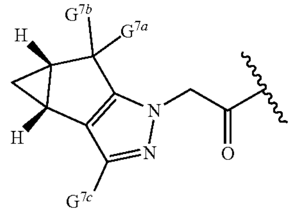

(hereinafter, formula ($G^7$B)).

Suitably, $G^{7a}$ is selected from the group consisting of —H and —F; $G^{7b}$ is selected from the group consisting of —H, —$CH_3$ and —F; and $G^{7c}$ is selected from the group consisting of —$C_{1-2}$alkyl optionally substituted with 1, 2 or 3 —F, and —$C_{3-4}$cycloalkyl optionally substituted with 1 or 2 —F.

In one embodiment, $G^{7b}$ is selected from the group consisting of —H, —$CH_3$ and —F; and $G^{7c}$ is selected from the group consisting of —$C_{1-2}$alkyl optionally substituted with 1, 2 or 3 —F, and —$C_{3-4}$cycloalkyl optionally substituted with 1 or 2 —F.

In one embodiment, $G^{7a}$ is —H.

In one embodiment, $G^{7a}$ is —F.

In one embodiment, $G^{7b}$ is selected from the group consisting of —H, —$CH_3$ and —F.

In one embodiment, $G^{7b}$ is —H.

In one embodiment, $G^{7b}$ is —$CH_3$.

In one embodiment, $G^{7b}$ is —F.

Suitably, $G^{7c}$ is selected from the group consisting of —$C_{1-2}$alkyl optionally substituted with 1, 2 or 3 —F, and —$C_{3-4}$cycloalkyl optionally substituted with 1 or 2 —F.

In one embodiment, $G^{7c}$ is —$C_{1-2}$alkyl optionally substituted with 1, 2 or 3 —F.

In another embodiment, $G^{7c}$ is —$C_{3-4}$cycloalkyl optionally substituted with 1 or 2 —F.

In one embodiment, $G^{7c}$ is selected from the group consisting of —$CHF_2$, —$CF_3$, cyclopropyl optionally substituted with 1 or 2 —F, or —$CF_2CH_3$. In another embodiment, $G^{7c}$ is selected from the group consisting of —$CHF_2$, —$CF_3$, cyclopropyl, and —$CF_2CH_3$.

In one embodiment, $G^{7c}$ is cyclopropyl optionally substituted with 1 or 2 —F.

In one embodiment, $G^{7c}$ is cyclopropyl.

In one embodiment, $G^{7a}$ and $G^{7b}$ are independently selected from the group consisting of —H and —F. In one embodiment, $G^7$ is formula ($G^7$A), and $G^{7a}$ and $G^{7b}$ are independently selected from the group consisting of —H and —F. In one embodiment, $G^7$ is formula ($G^7$B), and $G^{7a}$ and $G^{7b}$ and are independently selected from the group consisting of —H and —F.

In one embodiment, $G^7$ is formula ($G^7$A), $G^{7a}$ is —H and $G^{7b}$ is —H.

In one embodiment, $G^7$ is formula ($G^7$A), $G^{7a}$ is —F and $G^{7b}$ is —F.

In one embodiment, $G^7$ is formula ($G^7$A), and $G^{7c}$ is $C_{1-2}$alkyl optionally substituted with 1, 2 or 3 —F. In one embodiment, $G^7$ is formula ($G^7$A), and $G^{7c}$ is —$CHF_2$. In one embodiment, $G^7$ is formula ($G^7$B), and $G^{7c}$ is —$CHF_2$.

In one embodiment, $G^7$ is:

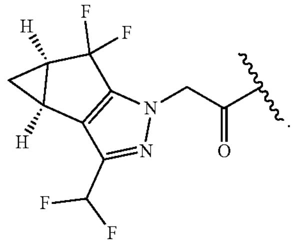 [SMILES: *C(=O)Cn1nc(C(F)F)c2c1C(F)(F)[C@@H]1C[C@H]21]

In one embodiment, $G^7$ is:

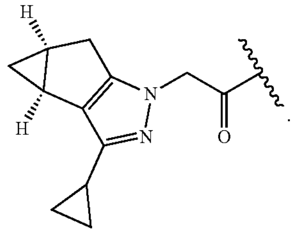 [SMILES: *C(=O)Cn1nc(C2CC2)c2c1C[C@@H]1C[C@H]21]

Suitably, $G^8$ and $G^9$ are independently selected from the group consisting of —H, —F, —Cl, —$CH_3$ and —$OCH_3$.

In one embodiment, $G^8$ and $G^9$ are independently selected from the group consisting of —H and —F.

In one embodiment, $G^3$ is —H and $G^9$ is —H.

In one embodiment, $G^8$ is —F and $G^9$ is —F.

Suitably, $G^{10}$ is selected from the group consisting of —H and —F.

In one embodiment, $G^{10}$ is H.

In one embodiment, $G^{10}$ is F.

Suitably, $G^{11}$ is selected from the group consisting of —H, —F, —$CH_3$ and —$OCH_3$.

In one embodiment, $G^{11}$ is H.

In one embodiment, the compound of Formula (I) is a compound for Formula (Ib):

Formula (Ib)

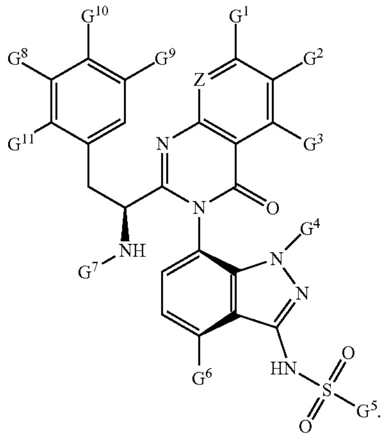

In one aspect, the invention provides a compound of Formula (II):

Formula (II)

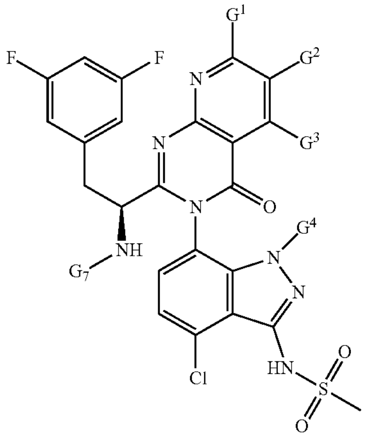

wherein:

$G^1$ is selected from the group consisting of

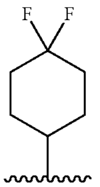

and

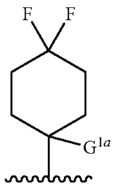

wherein $G^{1a}$ is selected from the group consisting of —F, —$CHF_2$, —$CH_2F$ and —$CH_3$;

$G^2$ is selected from the group consisting of —H, —$CH_3$ and —$CHF_2$;

$G^3$ is selected from the group consisting of —H, —$C_{1-3}$alkyl optionally substituted with 1, 2 or 3 F;

—$C_{3-4}$cycloalkyl optionally substituted with 1, 2 or 3 —F; —NH—$C_{1-3}$alkyl optionally substituted with 1, 2, or 3 substituents independently selected from the group consisting of —$OCH_3$ and F; —$C_{1-3}$alkyl-azetidine optionally substituted with 1, 2 or 3 —F; and —$C_{1-3}$alkyl-morpholine optionally substituted with 1, 2, 3 or 4 substituents independently selected from the group consisting of —$C_{1-3}$alkyl, and —F;

$G^4$ is selected from the group consisting of

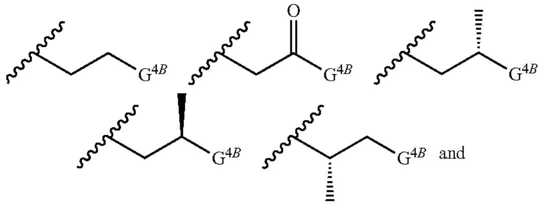

and

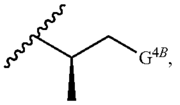

, wherein $G^{4B}$ is selected from the group consisting of —$CH_2$—O—$CH_3$, and a heterocycle selected from group consisting of

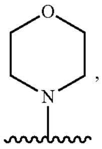

,

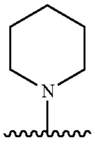

and

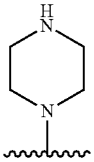

, wherein said heterocycle is optionally substituted with 1, 2, 3 or 4 substituents independently selected from the group consisting of —F and —$C_{1-3}$alkyl (for example 1, 2, 3 or 4 substituents independently selected from group consisting —F, —$CH_3$ and —$CH(CH_3)_2$); and $G^7$ is selected from the group consisting of

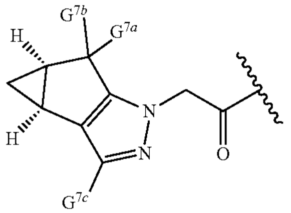

and

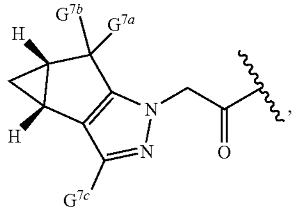

, wherein $G^{7a}$ is selected from the group consisting of —H, and —F;

$G^{7b}$ is selected from the group consisting of —H, —$CH_3$ and —F; and $G^{7c}$ is selected from the group consisting of —$C_1$-$C_2$alkyl optionally substituted with 1, 2 or 3 —F, and —$C_3$-$C_4$cycloalkyl optionally substituted with 1 or 2 —F, or a pharmaceutically acceptable salt thereof.

Suitably, $G^1$ is selected from the group consisting of

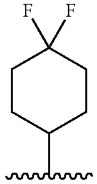

and

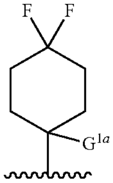

wherein $G^{1a}$ is selected from the group consisting of —F, —$CHF_2$, —$CH_2F$ and —$CH_3$.

In one embodiment, $G^1$ is

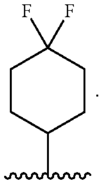

.

In one embodiment, $G^1$ is

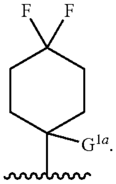

.

Suitably, $G^{1a}$ is selected from —F and —$CH_3$.

In one embodiment, $G^{1a}$ is —F.

In another embodiment, $G^{1a}$ is —$CH_3$.

Suitably, $G^2$ is selected from the group consisting of —H, —$CH_3$ and —$CHF_2$.

In one embodiment, $G^2$ is —H.

In one embodiment, $G^2$ is —$CH_3$.

In one embodiment, $G^2$ is —$CHF_2$.

Suitably, $G^3$ is selected from the group consisting of —H, —$C_{1-3}$alkyl optionally substituted with 1, 2 or 3 F; —$C_{3-4}$cycloalkyl optionally substituted with 1, 2 or 3 —F; —NH—$C_{1-3}$alkyl optionally substituted with 1, 2, or 3 substituents independently selected from the group consisting of —$OCH_3$ and F; —$C_{1-3}$alkyl-azetidine optionally substituted with 1, 2 or 3 —F; and —$C_{1-3}$alkyl-morpholine optionally substituted with 1, 2, 3 or 4 substituents independently selected from the group consisting of —$C_{1-3}$alkyl, and —F.

In one embodiment, $G^3$ is selected from the group consisting of —H, —$C_{1-3}$alkyl optionally substituted with 1, 2 or 3 —F; —$C_{3-4}$cycloalkyl, —NH—$C_{1-3}$alkyl optionally substituted with 1, 2, or 3 substituents independently selected from the group consisting of —$OCH_3$ and F; —$C_{1-3}$alkyl-azetidine optionally substituted with 1, 2 or 3 —F; and —$C_{1-3}$alkyl-morpholine optionally substituted with 1, 2, 3 or 4 substituents independently selected from the group consisting of —$CH_3$ and F.

In one embodiment, $G^3$ is selected from the group consisting of H, —$C_{1-3}$alkyl optionally substituted with 1, 2 or 3 —F; cyclopropyl, —NH—$C_{1-3}$alkyl optionally substituted with 1, 2, or 3 substituents independently selected from the group consisting of —$OCH_3$ and F; —$C_{1-3}$alkyl-azetidine optionally substituted with 1, 2 or 3 —F; and —$C_{1-3}$alkyl-morpholine optionally substituted with 1, 2, 3 or 4 substituents independently selected from the group consisting of —$C_{1-3}$alkyl and F.

In one embodiment, $G^3$ is selected from the group consisting of —$C_{1-3}$alkyl optionally substituted with 1, 2 or 3 —F; —$C_{1-3}$alkyl-azetidine optionally substituted with 1, 2 or 3 —F; —NH—$C_{1-3}$alkyl optionally substituted with 1, 2, or 3 substituents independently selected from the group consisting of —$OCH_3$ and F; and —$C_{1-3}$alkyl-morpholine optionally substituted with 1, 2, 3 or 4 substituents independently selected from the group consisting of —$CH_3$ and F.

In another embodiment, $G^3$ is selected from the group consisting of H, —$C_{1-3}$alkyl optionally substituted with 1, 2 or 3 —F, —NH—$CH_2CH_2OCH_3$, —$NHCH_2CH_3$, —$CH_2$-azetidine substituted with 2 —F; and —$C_{1-2}$alkyl-morpholine optionally substituted with 1, 2, 3 or 4 substituents independently selected from the group consisting of —$CH_3$ and F.

In one embodiment, $G^3$ is selected from the group consisting of —$CH_3$, —$CHF_2$, —NH—$CH_2CH_2OCH_3$, —$NHCH_2CH_3$, —$CH_2$-azetidine optionally substituted with 2 —F; and —$C_{1-2}$alkyl-morpholine optionally substituted with 1, 2, 3 or 4 substituents independently selected from the group consisting of —$CH_3$ and F.

In another embodiment, $G^3$ is selected from the group consisting of —$CH_3$, —$CHF_2$, —$NHCH_2CH_3$,

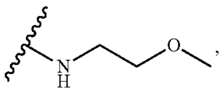 ,

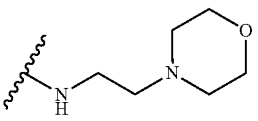

optionally substituted with 1 or 2 —$CH_3$,

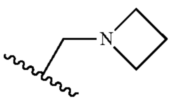 [SMILES: *CN1CCC1]

optionally substituted with 1 or 2 —F; and

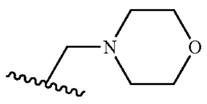 [SMILES: *CN1CCOCC1]

optionally substituted with 1 or 2 —$CH_3$.

(for example $G^3$ is selected from the group consisting of —$CH_3$, —$NHCH_2CH_3$, —$NHCH_2CH_2OCH_3$,

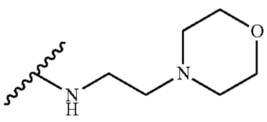

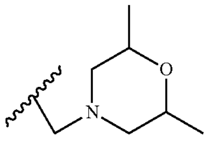 , and

-continued

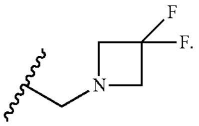

In another embodiment, $G^3$ is selected from the group consisting of —H, —$CH_3$, —$CHF_2$, cyclopropyl, —NH—$CH_2$—$CH_3$,

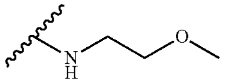 ,

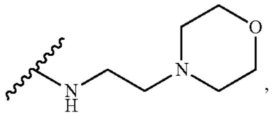 ,

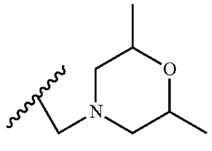 , and

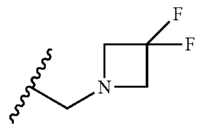

In one embodiment, $G^3$ is selected from the group consisting of —H, —$CH_3$, —$CHF_2$, cyclopropyl, —NH—$CH_2$—$CH_3$,

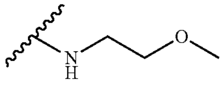 ,

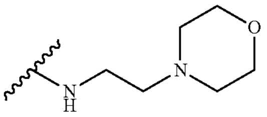

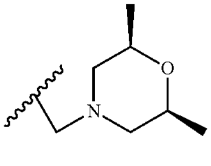 , and

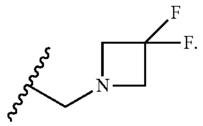

In another embodiment, $G^3$ is selected from the group consisting of —$CH_3$, —NH—$CH_2$—$CH_3$,

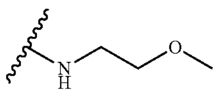 ,

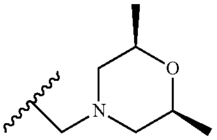 , and

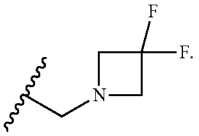

In one embodiment, $G^3$ is —NH—$CH_2$—$CH_3$.

In one embodiment, $G^3$ is

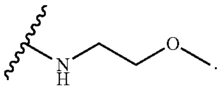 [SMILES: *NCCOC]

In one embodiment, $G^3$ is

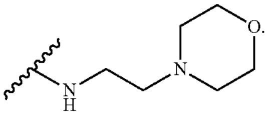 [SMILES: *NCCN1CCOCC1]

In one embodiment, $G^3$ is

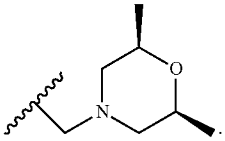 [SMILES: *CN1C[C@@H](C)O[C@@H](C)C1]

In one embodiment, $G^3$ is

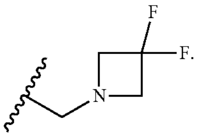 [SMILES: *CN1CC(F)(F)C1]

In one embodiment, $G^3$ is —$C_{1-3}$alkyl optionally substituted with 1, 2 or 3 —F.

In one embodiment, $G^3$ is —$CH_3$ optionally substituted with 1, 2 or 3 —F.

In another embodiment, $G^3$ is —$CHF_2$.

In one embodiment, $G^3$ is —$C_{1-3}$alkyl

In one embodiment, $G^3$ is —$CH_3$.

Suitably, $G^4$ is selected from the group consisting of

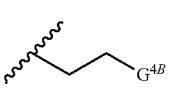 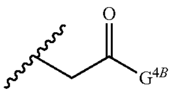 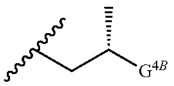 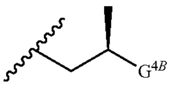 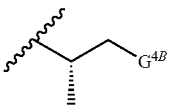 and

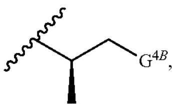

$G^{4B}$ is a heterocycle selected from group consisting of

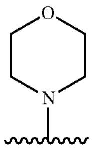 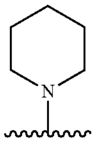 and 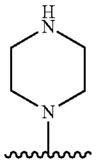 , wherein said heterocycle is optionally substituted with 1, 2, 3 or 4 substituents independently selected from the group consisting of —F and —$C_{1-3}$alkyl (for example 1, 2, 3 or 4 substituents independently selected from group consisting —F, —$CH_3$ and —$CH(CH_3)_2$).

In one embodiment, $G^4$ is

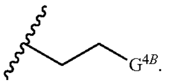

Suitably, $G^{4B}$ is selected from the group consisting of —$CH_2$—O—$CH_3$,

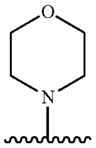 , 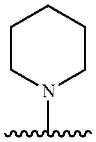 and 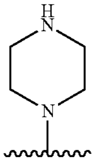 , wherein said heterocycle is optionally substituted with 1, 2, 3 or 4 substituents independently selected from group consisting of —F and —$C_{1-3}$alkyl.

In one embodiment, $G^4$ is

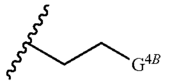

and $G^{4B}$ is —$CH_2$—O—$CH_3$.

In another embodiment, $G^4$ is

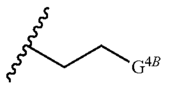

and $G^{4B}$ is a heterocycle selected from group consisting of

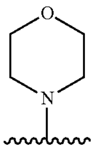 , 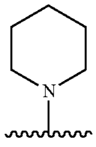 and 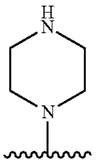

wherein said heterocycle is optionally substituted with 1, 2, 3 or 4 substituents independently selected from group consisting of —F and —$C_{1-3}$alkyl. In one embodiment, each of the heterocycles is independently substituted with 1, 2, 3 or 4 substituents independently selected from group consisting —F, —$CH_3$ and —$CH(CH_3)_2$.

In one embodiment, $G^4$ is

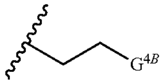

and $G^{4B}$ is selected from the group consisting of

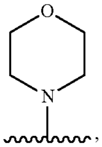, 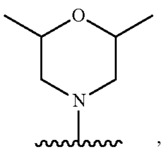, 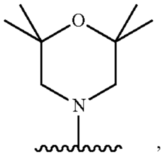,

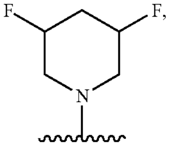 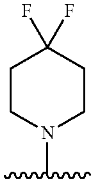 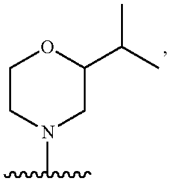,

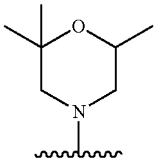, 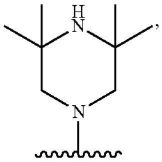, 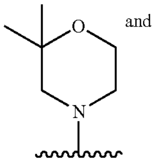 and

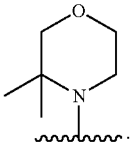

In one embodiment, $G^4$ is

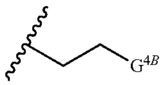

and $G^{4B}$ is selected from the group consisting of —$CH_2$—$OCH_3$,

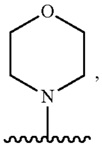, 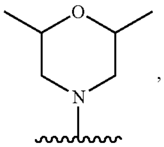, 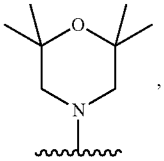,

-continued

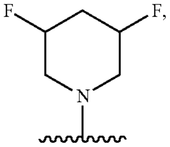 and 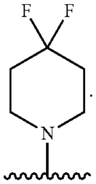

In one embodiment, $G^4$ is

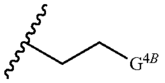

and $G^{4B}$ is selected from the group consisting of —$CH_2$—$OCH_3$,

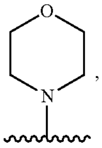, 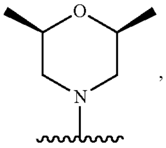, 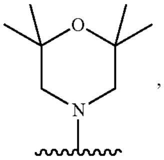,

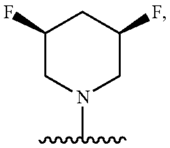 and 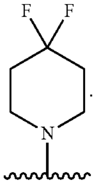

In one embodiment, $G^4$ is

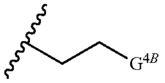

and $G^{4B}$ is selected from the group consisting of —$CH_2$—$OCH_3$,

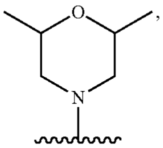, 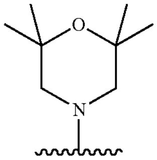 and 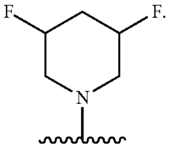

In another embodiment, $G^4$ is

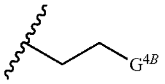

and $G^{4B}$ is selected from the group consisting of —$CH_2$—$OCH_3$,

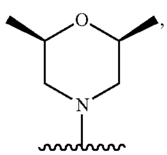,
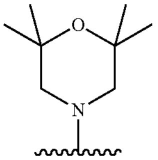
and
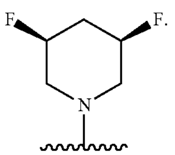

In another embodiment, $G^4$ is

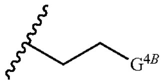

and $G^4B$ is

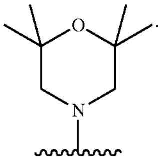

Suitably, $G^7$ is selected the group consisting of

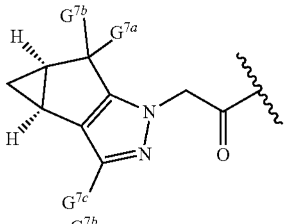
and
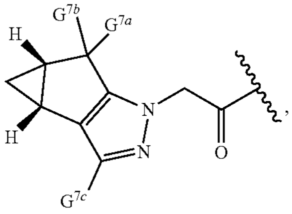, wherein $G^{7a}$ is selected from the group consisting of —H, and —F; $G^{7b}$ is selected from the group consisting of —H, —$CH_3$ and —F; $G^{7c}$ is selected from the group consisting of —$C_1$-$C_2$alkyl optionally substituted with 1, 2 or 3 —F, and —$C_3$-$C_4$cycloalkyl optionally substituted with 1 or 2 —F.

In one embodiment, $G^7$ is selected from the group consisting of

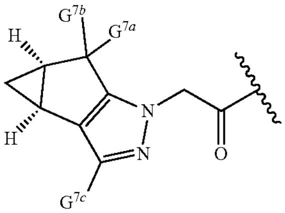
and

-continued

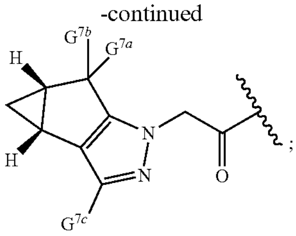;

$G^{7a}$ is —H and $G^{7b}$ is —H, or $G^{7a}$ is F and $G^{7b}$ is F; and $G^{7c}$ is selected from the group consisting of —$C_{1-2}$alkyl optionally substituted with 1, 2 or 3 —F, and —$C_{3-4}$cycloalkyl.

In one embodiment, $G^7$ is

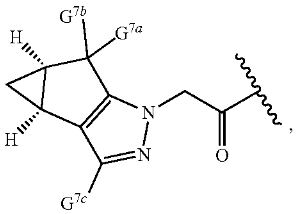, $G^{7a}$ is —H and $G^{7b}$ is —H, or $G^{7a}$ is F and $G^{7b}$ is F; and $G^{7c}$ is selected from the group consisting of —$CH_3$ optionally substituted with 1, 2 or 3 —F, and cyclopropyl.

In one embodiment, $G^7$ is

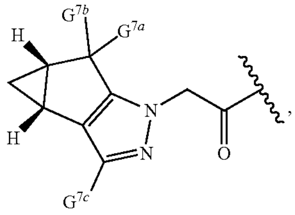, $G^{7a}$ is —H and $G^{7b}$ is —H, or $G^{7a}$ is F and $G^{7b}$ is F; and $G^{7c}$ is selected from the group consisting of —$CH_3$ optionally substituted with 1, 2 or 3 —F, and cyclopropyl.

In one embodiment, $G^7$ is selected the group consisting of

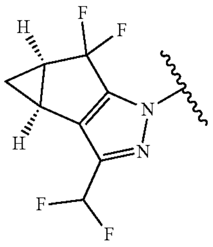
and
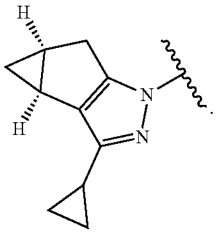.

In one embodiment, $G^7$ is

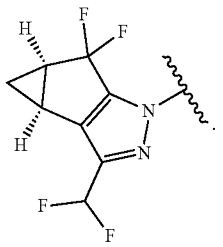 [SMILES: *n1nc(C(F)F)c2c1C(F)(F)[C@@H]1C[C@H]21]

In one embodiment, $G^7$ is

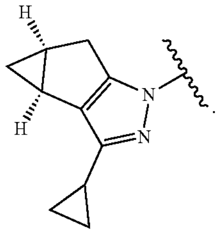 [SMILES: *n1nc(C2CC2)c2c1C[C@@H]1C[C@H]21]

In one embodiment, $G^7$ is selected from the group consisting of

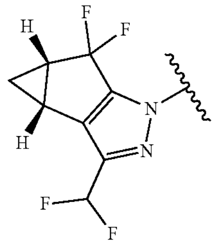

and

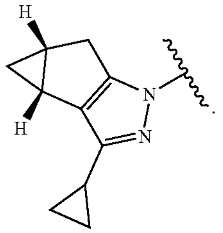

In another embodiment, $G^7$ is

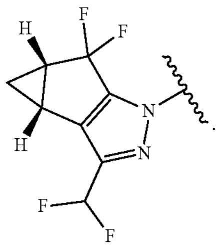 [SMILES: *n1nc(C(F)F)c2c1C(F)(F)[C@H]1C[C@@H]21]

In yet another embodiment, $G^7$ is

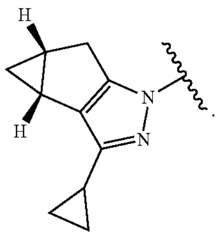 [SMILES: *n1nc(C2CC2)c2c1C[C@H]1C[C@@H]21]

In one embodiment, the invention provides a compound of Formula (II):

Formula (II)

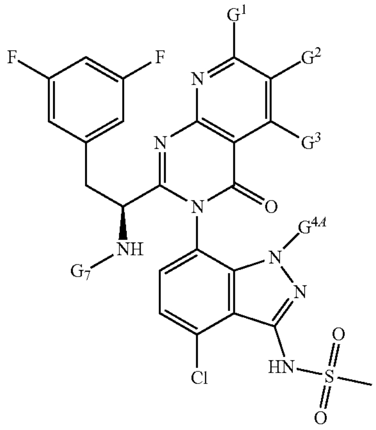

or a pharmaceutically acceptable salt thereof. wherein:

$G^1$ is

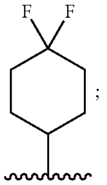

;

$G^2$ is H;

$G^3$ is selected from the group consisting of —$CH_3$,

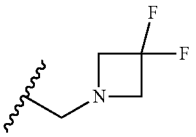

and

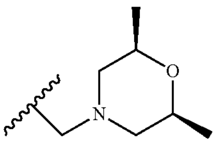

$G^4$ is

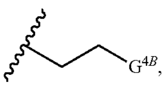

, wherein $G^{4B}$ is selected from the group consisting of $-CH_2-O-CH_3$, and

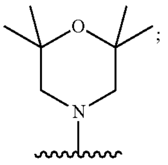

and $G^7$ is selected from the group consisting of

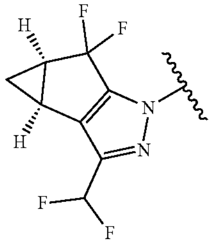

and

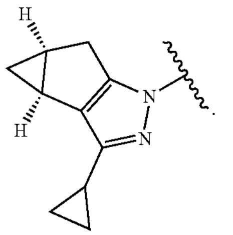

In one embodiment, the compound of Formula (II) is a compound of Formula (IIb)

Formula (IIb)

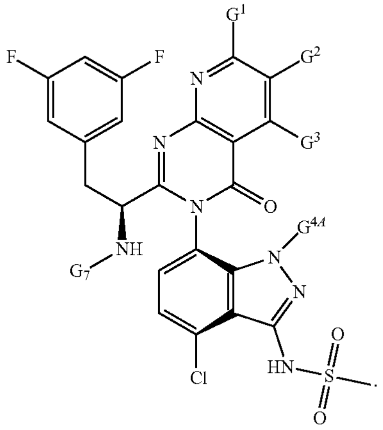

In one aspect, the invention provides a compound of Formula (IIa):

Formula (IIa)

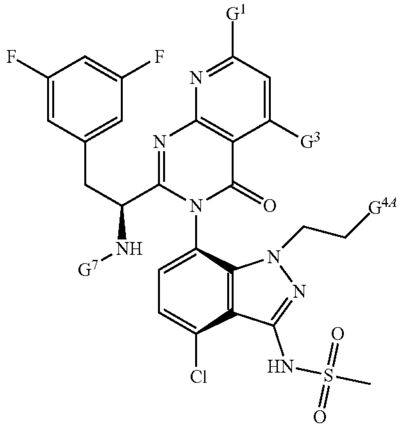

wherein:

$G^1$ is selected from:

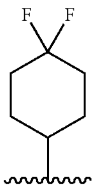

and

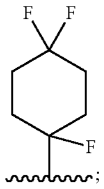

$G^3$ is selected from the group consisting of $-H$, $-CH_3$, $-CHF_2$, cyclopropyl,

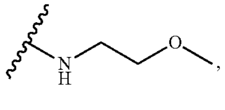

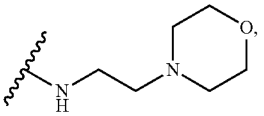

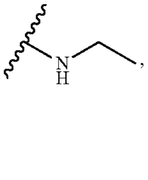

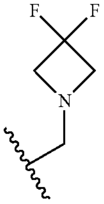

and

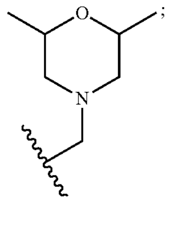

$G^{4A}$ is selected from the group consisting of $—CH_2OCH_3$,

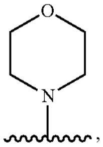
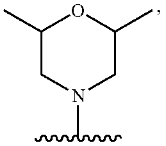
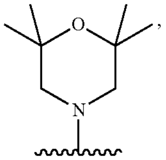
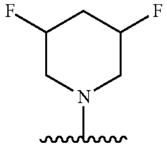
and
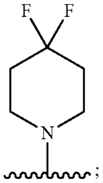

$G^7$ is selected from the group consisting of:

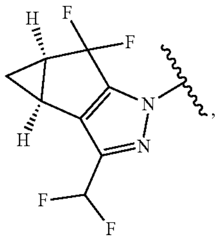
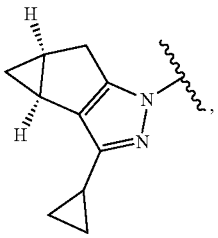
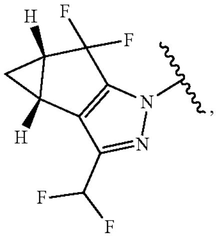
and
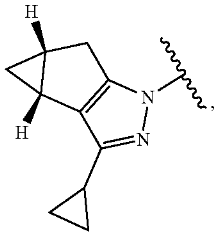

or a pharmaceutically acceptable salt thereof.

In one embodiment, $G^1$ is

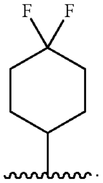

In another embodiment, $G^1$ is

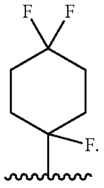 [SMILES: *C1(F)CCC(F)(F)CC1]

Suitably, $G^3$ is selected from —H, $—CH_3$, $—CHF_2$, cyclopropyl,

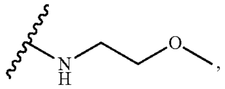
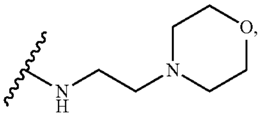
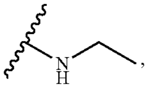
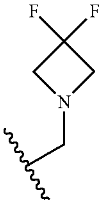
and
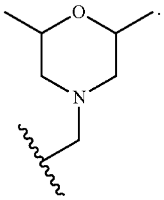

In one embodiment, $G^3$ is selected from —H, $—CH_3$, $—CHF_2$, cyclopropyl,

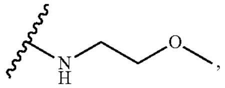
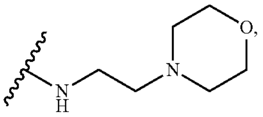
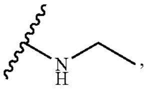
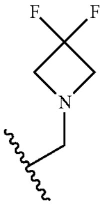
and
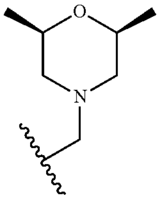

In one embodiment, $G^3$ is selected from —H, $—CH_3$, $—CHF_2$, cyclopropyl, $—NH—CH_2—CH_3$,

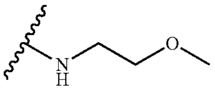
and
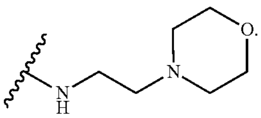

In one embodiment, $G^3$ is selected from $—CH_3$, $—NH—CH_2—CH_3$,

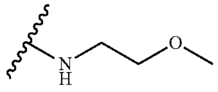

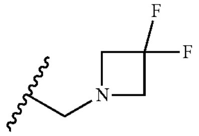

and

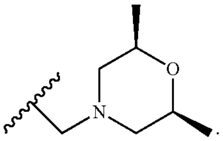

In one embodiment, $G^3$ is selected from —$CH_3$,

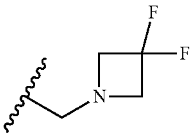

and

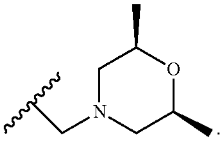

In one embodiment, $G^3$ is H or —$CH_3$.

In one embodiment, $G^3$ is H.

In one embodiment, $G^3$ is —$CH_3$.

In one embodiment, $G^3$ is —NH—$CH_2CH_3$.

In one embodiment, $G^3$ is

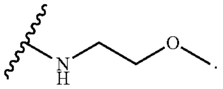 [SMILES: *NCCOC]

In another embodiment, $G^3$ is

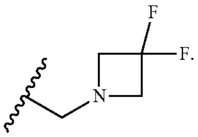 [SMILES: *CN1CC(F)(F)C1]

In another embodiment, $G^3$ is

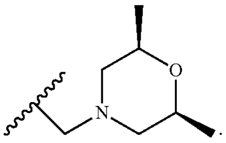 [SMILES: *CN1C[C@@H](C)O[C@@H](C)C1]

Suitably, $G^{4A}$ is selected from the group consisting of —$OCH_3$, —$CH_2OCH_3$,

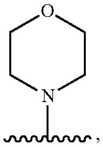

,

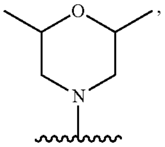

,

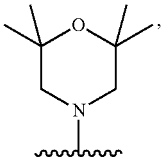

,

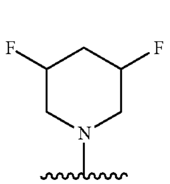

and

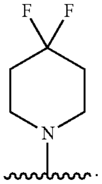

In one embodiment, $G^{4A}$ is selected from the group consisting of —$OCH_3$, —$CH_2OCH_3$,

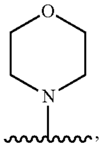

,

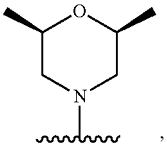

,

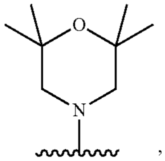

,

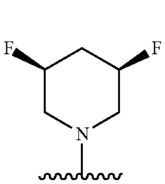

and

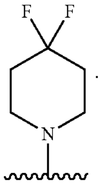

In one embodiment, $G^{4A}$ is selected from the group consisting of

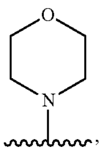

,

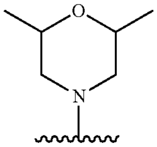

,

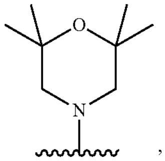

,

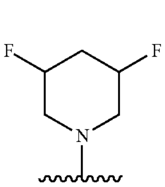

and

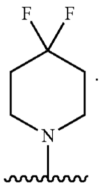

.

In one embodiment, $G^{4A}$ is selected from the group consisting of

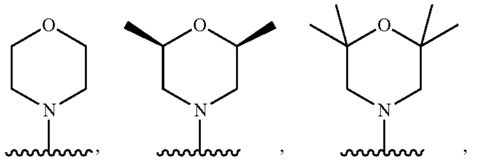

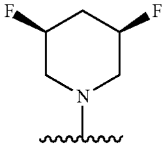

and

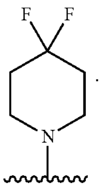

.

In one embodiment, $G^{4A}$ is selected from the group consisting of $—CH_2OCH_3$, and

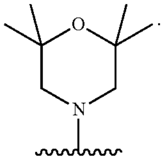

In one embodiment, $G^{4A}$ is

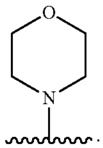

In one embodiment, $G^{4A}$ is

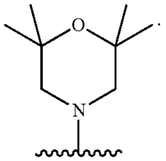

In one embodiment, $G^{4A}$ is

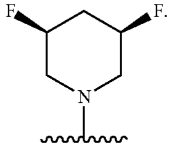

In one embodiment, $G^{4A}$ is

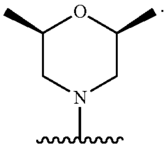

In one embodiment, $G^{4A}$ is $—CH_2OCH_3$

In one embodiment, $G^3$ is selected from —H and $—CH_3$, and $—CHF_2$; and $G^{4A}$ is selected from the group consisting of

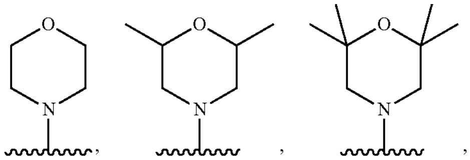

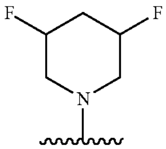

and

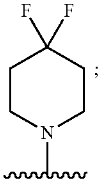

;

or $G^3$ is selected from

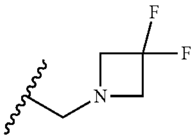

and

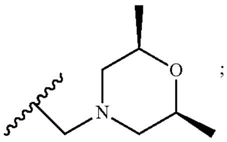

;

and $G^{4A}$ is $—CH_2OCH_3$.

In one embodiment, $G^3$ is selected from $—CH_3$,

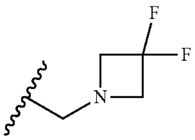

and

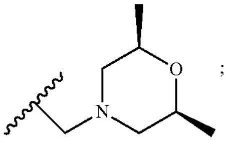

;

and $G^{4A}$ is selected from the group consisting of $—CH_2OCH_3$, and

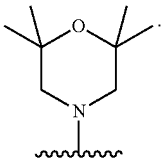

In one embodiment, $G^3$ is —$CH_3$ and $G^{4A}$ is

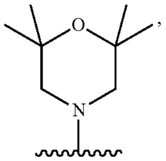

or $G^3$ is selected from

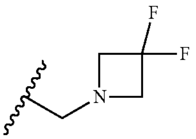

and

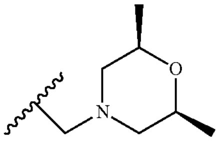

, and $G^{4A}$ is —$CH_2OCH_3$.

Suitably, $G^5$ is selected from the group consisting of

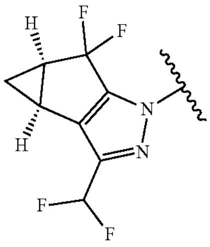

,

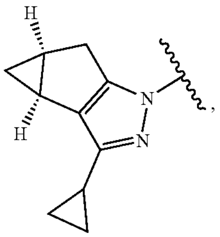

,

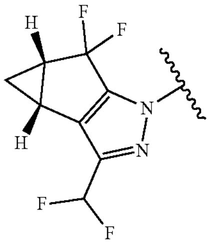

and

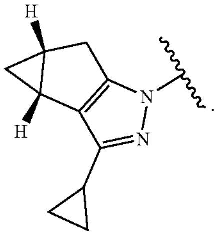

.

In one embodiment, $G^5$ is selected from the group consisting of

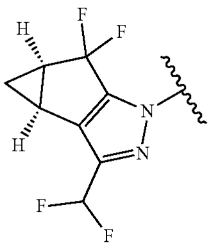

and

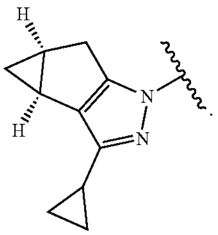

.

In one embodiment, $G^5$ is

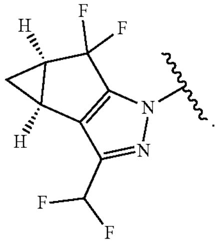 [SMILES: *n1nc(C(F)F)c2c1C(F)(F)[C@@H]1C[C@H]21]

.

In one embodiment, $G^5$ is

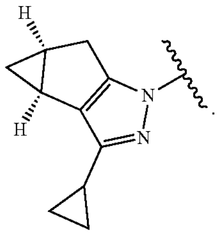 [SMILES: *n1nc(C2CC2)c2c1C[C@@H]1C[C@H]21]

.

In one embodiment, the invention provides a compound of Formula (IIa) wherein, and $G^1$ is

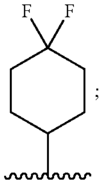 [SMILES: *C1CCC(F)(F)CC1]

;

$G^2$ is H;

$G^3$ is selected from the group consisting of —$CH_3$,

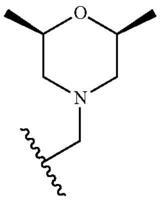

, and

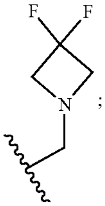

;

$G^4$ is selected from the group consisting of

In one aspect, the invention provides a compound as exemplified herein, or a pharmaceutically acceptable salt thereof.

In one aspect, the invention provides a compound selected from the group consisting of Example 1: N-[(1S)-1-[(3P)-3-(4-chloro-1-{2-[(3R,5S)-3,5-difluoropiperidin-1-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6), 8-dien-7-yl]acetamide; Example 2: N-[(1S)-1-[(3P)-3-{4-chloro-1-[2-(3,3-difluoropiperidin-1-yl)ethyl]-3- methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl] acetamide; Example 3: N-[(1S)-1-[(3P)-3-{4-chloro-1-[2-(4,4-difluoroazepan-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 4: N-[(1S)-1-[(3P)-3-(4-chloro-3-methanesulfonamido-1-{2-[(1R,5S)-8-oxa-3-azabicyclo[3.2.1]octan-3-yl]ethyl}-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 5: N-[(1S)-1-[(3P)-3-(4-chloro-1-{2-[(3R,5S)-3,5-difluoropiperidin-1-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 6: N-[(1S)-1-[(3P)-3-(4-chloro-3-methanesulfonamido-1-{2-[(1R,5S)-3-oxa-8-azabicyclo[3.2.1]octan-8-yl]ethyl}-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 7: N-[(1S)-1-[(3P)-3-(4-chloro-3-methanesulfonamido-1-{2-[(1R,5S)-6-oxa-3-azabicyclo[3.1.1]heptan-3-yl]ethyl}-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 9: N-[(1S)-1-[(3P)-3-(4-chloro-3-methanesulfonamido-1-{2-[(1R,4R)-2-oxa-5-azabicyclo[2.2.1]heptan-5-yl]ethyl}-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 10: N-[(1S)-1-[(3P)-3-(4-chloro-3-methanesulfonamido-1-{2-[(2-methoxyethyl)amino]ethyl}-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 11: N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 12: N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 13: N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 14: N-[(1S)-1-[(3P)-3-{4-chloro-1-[2-(3,3-difluoropiperidin-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 15: N-[(1S)-1-[(3P)-3-{4-chloro-1-[2-(4,4-difluoroazepan-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 17: N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 24: N-[(1S)-1-[(3P)-3-{4-chloro-1-[2-(3,3-difluoropyrrolidin-1-yl)ethyl]-3-methanesulfonamido-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 26: N-[(1S)-1-[(3P)-3-(4-chloro-1-{2-[(3R,4S)-3,4-difluoropyrrolidin-1-yl]ethyl}-3-methanesulfonamido-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 40: N-[(1S)-1-[(3P)-3-[4-chloro-3-methanesulfonamido-1-(2-{[(3R)-oxan-3-yl]amino}ethyl)-1H-indazol-7-yl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 41: N-[(1S)-1-[(3P)-3-(4-chloro-1-{2-[(3R)-3-fluoro-3-(trifluoromethyl)pyrrolidin-1-yl]ethyl}-3-methanesulfonamido-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 42: N-[(1S)-1-[(3P)-3-(4-chloro-1-{2-[(3S)-3-fluoro-3-(trifluoromethyl)pyrrolidin-1-yl]ethyl}-3-methanesulfonamido-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 43: N-[(1S)-1-[(3P)-3-(4-chloro-1-{2-[(1R,5S)-3,3-difluoro-8-azabicyclo[3.2.1]octan-8-yl]ethyl}-3-methanesulfonamido-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 46: N-[(1S)-1-[(3P)-3-(4-chloro-3-methanesulfonamido-1-{2-[(3-methyloxetan-3-yl)amino]ethyl}-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 48: N-[(1S)-1-[(3P)-3-{4-chloro-1-[2-(3,3-difluoroazetidin-1-yl)ethyl]-3-methanesulfonamido-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 59: N-[(1S)-1-[(3P)-3-{4-chloro-3-methanesulfonamido-1-[2-(propan-2-yloxy)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5- difluoro-7,8-diazatricyclo[4.3.0.$0^{2,4}$]nona-1(6),8-dien-7-yl]acetamide; Example 60: N-[(1S)-1-[(3P)-3-[4-chloro-1-(2-ethoxyethyl)-3-methanesulfonamido-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide; Example 72: N-[(1S)-1-[(3P)-3-{4-chloro-3-methanesulfonamido-1-[2-(2,2,2-trifluoroethoxy)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide; Example 77: N-[(1S)-1-[(3P)-3-{4-chloro-3-methanesulfonamido-1-[(2R)-2-methoxypropyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide; Example 78: N-[(1S)-1-[(3P)-3-{4-chloro-3-methanesulfonamido-1-[(2S)-2-methoxypropyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide; Example 84: N-[(1S)-1-[(3P)-3-[4-chloro-3-methanesulfonamido-1-(2-methoxyethyl)-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide; Example 85: N-[(1S)-1-[(3P)-3-[4-chloro-3-methanesulfonamido-1-(3-methoxypropyl)-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-cyclopropyl-5,5-difluoro-7,8-diazatricyclo[4.3.0.$0^{2,4}$]nona-1(6),8-dien-7-yl]acetamide; Example 86: N-[(1S)-1-[(3P)-3-[4-chloro-3-methanesulfonamido-1-(3-methoxypropyl)-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-(difluoromethyl)-7,8-diazatricyclo[4.3.0.$0^{2,4}$]nona-1(6),8-dien-7-yl]acetamide; Example 87: N-[(1S)-1-[(3P)-3-[4-chloro-3-methanesulfonamido-1-(3-methoxypropyl)-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.$0^{2,4}$]nona-1(6),8-dien-7-yl]acetamide; Example 88: N-[(1S)-1-[(3P)-3-[4-chloro-3-methanesulfonamido-1-(3-methoxypropyl)-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-(trifluoromethyl)-7,8-diazatricyclo[4.3.0.$0^{2,4}$]nona-1(6),8-dien-7-yl]acetamide; Example 89: N-[(1S)-1-[(3P)-3-[4-chloro-3-methanesulfonamido-1-(3-methoxypropyl)-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-5,5-difluoro-9-(trifluoromethyl)-7,8-diazatricyclo[4.3.0.$0^{2,4}$]nona-1(6),8-dien-7-yl]acetamide; Example 90: N-[(1S)-1-[(3P)-3-[4-chloro-3-methanesulfonamido-1-(3-methoxypropyl)-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide; Example 94: N-[(1S)-1-[(3P)-3-{4-chloro-1-[2-(difluoromethoxy)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide; Example 105: N-[(1S)-1-[(3P)-3-{4-chloro-3-methanesulfonamido-1-[2-(morpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide; Example 112: N-[(1S)-1-[(3P)-3-{4-chloro-3-methanesulfonamido-1-[2-(morpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-cyclopropyl-5,5-difluoro-7,8-diazatricyclo[4.3.0.$0^{2,4}$]nona-1(6),8-dien-7-yl]acetamide; Example 114: N-[(1S)-1-[(3P)-3-{4-chloro-3-methanesulfonamido-1-[2-(morpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.$0^{2,4}$]nona-1(6),8-dien-7-yl]acetamide; Example 115: N-[(1S)-1-[(3P)-3-{4-chloro-3-methanesulfonamido-1-[2-(morpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-(trifluoromethyl)-7,8-diazatricyclo[4.3.0.$0^{2,4}$]nona-1(6),8-dien-7-yl]acetamide; Example 116: N-[(1S)-1-[(3P)-3-{4-chloro-3-methanesulfonamido-1-[2-(morpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-5,5-difluoro-9-(trifluoromethyl)-7,8-diazatricyclo[4.3.0.$0^{2,4}$]nona-1(6),8-dien-7-yl]acetamide; Example 121: N-[(1S)-1-[(3P)-3-{4-chloro-3-methanesulfonamido-1-[3-(morpholin-4-yl)propyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-5,5-difluoro-9-(trifluoromethyl)-7,8-diazatricyclo[4.3.0.$0^{2,4}$]nona-1(6),8-dien-7-yl]acetamide; Example 128: N-[(1S)-1-[(3P)-3-{4-chloro-1-[2-(4,4-difluoropiperidin-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide; Example 129: N-[(1S)-1-[(3P)-3-{1-[2-(tert-butoxy)ethyl]-4-chloro-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide; Example 130: N-[(1S)-1-[(3P)-3-{4-chloro-1-[2-(4,4-difluoropiperidin-1-yl)ethyl]-3-methanesulfonamido-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide; Example 134: N-[(1S)-1-[(3P)-3-[4-chloro-3-methanesulfonamido-1-(2-methoxyethyl)-1H-indazol-7-yl]-7-(4,4-difluorocyclohexyl)-5-[(2-methoxyethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide; Example 135: N-[(1S)-1-[(3P)-3-[4-chloro-3-methanesulfonamido-1-(3-methoxypropyl)-1H-indazol-7-yl]-7-(4,4-difluorocyclohexyl)-5-[(2-methoxyethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8- diazatricyclo[4.3.0.0$^{2,4}$]nona-1(6),8-dien-7-yl]acetamide; Example 149: N-[(1S)-1-[(3P)-3-{4-chloro-1-[2-(4,4-difluoropiperidin-1-yl)ethyl]-3-methanesulfonamido-1H-indazol-7-yl}-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 150: N-[(1S)-1-[(3P)-3-[4-chloro-1-(2-ethoxyethyl)-3-methanesulfonamido-1H-indazol-7-yl]-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 154: N-[(1S)-1-[(3P)-3-{4-chloro-1-[2-(3,3-difluoropyrrolidin-1-yl)ethyl]-3-methanesulfonamido-1H-indazol-7-yl}-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 155: N-[(1S)-1-[(3P)-3-{4-chloro-3-methanesulfonamido-1-[2-(2,2,2-trifluoroethoxy)ethyl]-1H-indazol-7-yl}-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 158: N-[(1S)-1-[(3P)-3-{4-chloro-1-[2-(3,3-difluoropyrrolidin-1-yl)ethyl]-3-methanesulfonamido-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 159: N-[(1S)-1-[(3P)-3-(4-chloro-1-{2-[(2R,6S)-2,6-dimethylmorpholin-4-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 160: N-[(1S)-1-[(3P)-3-(4-chloro-1-{2-[3-(difluoromethyl)azetidin-1-yl]ethyl}-3-methanesulfonamido-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 165: N-[(1S)-1-[(3P)-3-{4-chloro-3-methanesulfonamido-1-[2-(piperidin-1-yl)ethyl]-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 166: N-[(1S)-1-[(3P)-3-{4-chloro-1-[2-(4-fluoropiperidin-1-yl)ethyl]-3-methanesulfonamido-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 167: N-[(1S)-1-[(3P)-3-{4-chloro-1-[2-(4-fluoro-4-methylpiperidin-1-yl)ethyl]-3-methanesulfonamido-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 168: N-[(1S)-1-[(3P)-3-{4-chloro-1-[2-(3,3-difluoropiperidin-1-yl)ethyl]-3-methanesulfonamido-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 170: N-[(1S)-1-[(3P)-3-[4-chloro-3-methanesulfonamido-1-(2-{2-oxa-7-azaspiro[3.5]nonan-7-yl}ethyl)-1H-indazol-7-yl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 176: N-[(1S)-1-[(3P)-3-[4-chloro-3-methanesulfonamido-1-(2-{4-oxa-7-azaspiro[2.5]octan-7-yl}ethyl)-1H-indazol-7-yl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 187: N-[(1S)-1-[(3P)-3-(4-chloro-1-{2-[2-(difluoromethyl)morpholin-4-yl]ethyl}-3-methanesulfonamido-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 189: N-[(1S)-1-[(3P)-3-(4-chloro-1-{2-[2,2-dimethyl-6-(trifluoromethyl)morpholin-4-yl]ethyl}-3-methanesulfonamido-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 191: N-[(1S)-1-[(3P)-3-(4-chloro-1-{2-[3-fluoro-3-(trifluoromethyl)pyrrolidin-1-yl]ethyl}-3-methanesulfonamido-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 195: N-[(1S)-1-[(3P)-3-(4-chloro-3-methanesulfonamido-1-{2-[4-(propane-2-sulfonyl)piperazin-1-yl]ethyl}-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 199: N-[(1S)-1-[(3P)-3-(4-chloro-3-methanesulfonamido-1-{2-[3-(trifluoromethyl)pyrrolidin-1-yl]ethyl}-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 207: N-[(1S)-1-[(3P)-3-(4-chloro-1-{2-[(3S)-3-fluoropyrrolidin-1-yl]ethyl}-3-methanesulfonamido-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 208: N-[(1S)-1-[(3P)-3-(4-chloro-1-{2-[(3R)-3-fluoropyrrolidin-1-yl]ethyl}-3-methanesulfonamido-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 211: N-[(1S)-1-[(3P)-3-{4-chloro-1-[2-(3-fluoro-3-methylpyrrolidin-1-yl)ethyl]-3-methanesulfonamido-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 214: N-[(1S)-1-[(3P)-3-[4-chloro-3-methanesulfonamido-1-(2-{6,6,7,7-tetrafluoro-3-azabicyclo[3.2.0]heptan-3-yl}ethyl)-1H-indazol-7-yl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 227: N-[(1S)-1-[(3P)-3-{4-chloro-3-methanesulfonamido-1-[2-(morpholin-4-yl)ethyl]-1H-indazol-7-yl}-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.$0^{2,4}$]nona-1(6),8-dien-7-yl]acetamide; Example 229: N-[(1S)-1-[(3P)-3-{4-chloro-1-[2-(3,3-difluoroazetidin-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide; Example 230: N-[(1S)-1-[(3P)-3-(4-chloro-1-{2-[(2R,6S)-2,6-dimethylmorpholin-4-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.$0^{2,4}$]nona-1(6),8-dien-7-yl]acetamide; Example 231: N-[(1S)-1-[(3P)-3-{4-chloro-1-[2-(3,3-difluoropyrrolidin-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide; Example 232: N-[(1S)-1-[(3P)-3-{4-chloro-1-[2-(3,3-difluoropyrrolidin-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.$0^{2,4}$]nona-1(6),8-dien-7-yl]acetamide; Example 237: N-[(1S)-1-[(3P)-3-{4-chloro-3-methanesulfonamido-1-[2-(2-methoxyethoxy)ethyl]-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.$0^{2,4}$]nona-1(6),8-dien-7-yl]acetamide; Example 239: N-[(1S)-1-[(3P)-3-{4-chloro-1-[2-(4,4-difluoropiperidin-1-yl)ethyl]-3-methanesulfonamido-1H-indazol-7-yl}-7-(4,4-difluorocyclohexyl)-6-fluoro-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.$0^{2,4}$]nona-1(6),8-dien-7-yl]acetamide; Example 240: N-[(1S)-1-[(3P)-3-(4-chloro-1-{2-[(2R,6S)-2,6-dimethylmorpholin-4-yl]ethyl}-3-methanesulfonamido-1H-indazol-7-yl)-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.$0^{2,4}$]nona-1(6),8-dien-7-yl]acetamide; Example 241: N-[(1S)-1-[(3P)-3-{4-chloro-3-methanesulfonamido-1-[2-(2-methoxyethoxy)ethyl]-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide; Example 245: N-[(1S)-1-[(3P)-3-(4-chloro-1-{2-[(1R,5S)-3,3-difluoro-8-azabicyclo[3.2.1]octan-8-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.$0^{2,4}$]nona-1(6),8-dien-7-yl]acetamide; Example 246: N-[(1S)-1-[(3P)-3-(4-chloro-1-{2-[(1R,5S)-3,3-difluoro-8-azabicyclo[3.2.1]octan-8-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide; Example 247: N-[(1S)-1-[(3P)-3-{4-chloro-3-methanesulfonamido-1-[2-(3,3,4,4-tetrafluoropyrrolidin-1-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide; Example 248: N-[(1S)-1-[(3P)-3-{4-chloro-3-methanesulfonamido-1-[2-(3,3,4,4-tetrafluoropyrrolidin-1-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.$0^{2,4}$]nona-1(6),8-dien-7-yl]acetamide; Example 257: N-[(1S)-1-[(3P)-3-(4-chloro-3-methanesulfonamido-1-{2-[(3S)-3-methoxypyrrolidin-1-yl]ethyl}-1H-indazol-7-yl)-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide; Example 259: N-[(1S)-1-[(3P)-3-(4-chloro-1-{2-[(3R,4S)-3,4-difluoropyrrolidin-1-yl]ethyl}-3-methanesulfonamido-1H-indazol-7-yl)-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide; Example 266: N-[(1S)-1-[(3P)-3-{4-chloro-3-methanesulfonamido-1-[2-(pyrrolidin-1-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide; Example 267: N-[(1S)-1-[(3P)-3-(4-chloro-1-{2-[(3R,4S)-3,4-difluoropyrrolidin-1-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide; Example 268: N-[(1S)-1-[(3P)-3-(4-chloro-1-{2-[3-(difluoromethyl)azetidin-1-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide; Example 269: N-[(1S)-1-[(3P)-3-{4-chloro-3-methanesulfonamido-1-[2-(piperidin-1-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide; Example 270: N-[(1S)-1-[(3P)-3-{4-chloro-1-[2-(4-fluoropiperidin-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide; Example 271: N-[(1S)-1-[(3P)-3-{4-chloro-1-[2-(4-fluoro-4-methylpiperidin-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide; Example 273: N-[(1S)-1-[(3P)-3-{4-chloro-3-methanesulfonamido-1-[2-(pyrrolidin-1-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.$0^{2,4}$]nona-1(6),8-dien-7-yl]acetamide; Example 275: N-[(1S)-1-[(3P)-3-(4-chloro-1-{2-[3-(difluoromethyl)azetidin-1-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)

ethyl]-2-[(2S,4S)-9-cyclopropyl-7,8-diazatricyclo[4.3.0.0$^{2,4}$]nona-1(6),8-dien-7-yl]acetamide; Example 276: N-[(1S)-1-[(3P)-3-{4-chloro-3-methanesulfonamido-1-[2-(piperidin-1-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 277: N-[(1S)-1-[(3P)-3-{4-chloro-1-[2-(4-fluoropiperidin-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 278: N-[(1S)-1-[(3P)-3-{4-chloro-1-[2-(4-fluoro-4-methylpiperidin-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 279: N-[(1S)-1-[(3P)-3-(4-chloro-3-methanesulfonamido-1-{2-[(oxetan-3-yl)amino]ethyl}-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 280: N-[(1S)-1-[(3P)-3-{4-chloro-1-[2-(3-fluoro-3-methylpyrrolidin-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 281: N-[(1S)-1-[(3P)-3-(4-chloro-1-{2-[(3R,4S)-3,4-difluoropyrrolidin-1-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 283: N-[(1S)-1-[(3P)-3-{4-chloro-1-[2-(3,3-difluoroazetidin-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 285: N-[(1S)-1-[(3P)-3-[4-chloro-3-methanesulfonamido-1-(3-methoxypropyl)-1H-indazol-7-yl]-7-(4,4-difluorocyclohexyl)-5-[(3-methoxypropyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 287: N-[(1S)-1-[(3P)-3-(4-chloro-1-{2-[(3R,5S)-3,5-difluoropiperidin-1-yl]ethyl}-3-methanesulfonamido-1H-indazol-7-yl)-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 288: N-[(1S)-1-[(3P)-3-(4-chloro-3-methanesulfonamido-1-{2-[(1R,5S)-8-oxa-3-azabicyclo[3.2.1]octan-3-yl]ethyl}-1H-indazol-7-yl)-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 289: N-[(1S)-1-[(3P)-3-(4-chloro-3-methanesulfonamido-1-{2-[(1R,5S)-3-oxa-8-azabicyclo[3.2.1]octan-8-yl]ethyl}-1H-indazol-7-yl)-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 290: N-[(1S)-1-[(3P)-3-{4-chloro-1-[2-(4-fluoro-4-methylpiperidin-1-yl)ethyl]-3-methanesulfonamido-1H-indazol-7-yl}-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 291: N-[(1S)-1-[(3P)-3-(4-chloro-1-{2-[(3R,5S)-3,5-difluoropiperidin-1-yl]ethyl}-3-methanesulfonamido-1H-indazol-7-yl)-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 292: N-[(1S)-1-[(3P)-3-{4-chloro-1-[2-(3,3-difluoropiperidin-1-yl)ethyl]-3-methanesulfonamido-1H-indazol-7-yl}-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 298: N-[(1S)-1-[(3P)-3-(4-chloro-3-methanesulfonamido-1-{2-[(1R,4R)-2-oxa-5-azabicyclo[2.2.1]heptan-5-yl]ethyl}-1H-indazol-7-yl)-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 307: N-[(1S)-1-[(3P)-3-{4-chloro-1-[2-(3,3-difluoroazetidin-1-yl)ethyl]-3-methanesulfonamido-1H-indazol-7-yl}-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 310: N-[(1S)-1-[(3P)-3-(4-chloro-1-{2-[(1S,4S)-5,5-difluoro-2-azabicyclo[2.2.1]heptan-2-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 311: N-[(1S)-1-[(3P)-3-(4-chloro-1-{2-[(1S,4S)-5,5-difluoro-2-azabicyclo[2.2.1]heptan-2-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 312: N-[(1S)-1-[(3P)-3-[4-chloro-1-(2-{6,6-difluoro-3-azabicyclo[3.1.0]hexan-3-yl}ethyl)-3-methanesulfonamido-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 315: N-[(1S)-1-[(3P)-3-(4-chloro-1-{2-[3-(difluoromethyl)azetidin-1-yl]ethyl}-3-methanesulfonamido-1H-indazol-7-yl)-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 321: N-[(1S)-1-[(3P)-3-{4-chloro-1-[2-(4,4-difluoropiperidin-1-yl)ethyl]-3-methanesulfonamido-1H-indazol-7-yl}-5-cyclopropyl-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 322: N-[(1S)-1-[(3P)-3-(4-chloro-1-{2-[(3R,5S)-3,5-difluoropiperidin-1-yl]ethyl}-3-methanesulfonamido-1H-indazol-7-yl)-5-cyclopropyl-7-(4,4-difluorocyclohexyl)-4-oxo-3H,4H-pyrido[2,3-d]pyrimidin-2-yl]-2-(3,5-difluorophenyl)ethyl]-

2-[(2S,4R)-9-(difluoromethyl)-5,5-difluoro-7,8-diazatricyclo[4.3.0.0$^{2,4}$]nona-1(6),8-dien-7-yl]acetamide; Example 324: N-[(1S)-1-[(3P)-3-(4-chloro-1-{2-[(2R,6S)-2,6-dimethylmorpholin-4-yl]ethyl}-3-methanesulfonamido-1H-indazol-7-yl)-5-cyclopropyl-7-(4,4-difluorocyclohexyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 325: N-[(1S)-1-[(3P)-3-(4-chloro-3-methanesulfonamido-1-{2-[(1R,5S)-8-oxa-3-azabicyclo[3.2.1]octan-3-yl]ethyl}-1H-indazol-7-yl)-5-cyclopropyl-7-(4,4-difluorocyclohexyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 327: N-[(1S)-1-[(3P)-3-(4-chloro-1-{2-[(3R,5S)-3,5-difluoropiperidin-1-yl]ethyl}-3-methanesulfonamido-1H-indazol-7-yl)-5-cyclopropyl-7-(4,4-difluorocyclohexyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 354: N-[(1S)-1-[(3P)-3-{4-chloro-1-[2-(3,3-difluoropyrrolidin-1-yl)ethyl]-3-methanesulfonamido-1H-indazol-7-yl}-5-cyclopropyl-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 356: N-[(1S)-1-[(3P)-3-(4-chloro-3-methanesulfonamido-1-{2-[(2R)-2-(methoxymethyl)morpholin-4-yl]ethyl}-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 360: N-[(1S)-1-[(3P)-3-(4-chloro-3-methanesulfonamido-1-{2-[(2R)-2-methylmorpholin-4-yl]ethyl}-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 370: N-[(1S)-1-[(3P)-3-{4-chloro-1-[2-(4-fluoropiperidin-1-yl)ethyl]-3-methanesulfonamido-1H-indazol-7-yl}-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 371: N-[(1S)-1-[(3P)-3-{4-chloro-1-[2-(4-fluoropiperidin-1-yl)ethyl]-3-methanesulfonamido-1H-indazol-7-yl}-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 375: N-[(1S)-1-[(3P)-3-[4-chloro-3-methanesulfonamido-1-(3-methoxypropyl)-1H-indazol-7-yl]-5-cyclopropyl-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 376: N-[(1S)-1-[(3P)-3-[4-chloro-3-methanesulfonamido-1-(3-methoxypropyl)-1H-indazol-7-yl]-5-cyclopropyl-7-(4,4-difluorocyclohexyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 381: N-[(1S)-1-[(3P)-3-(4-chloro-3-methanesulfonamido-1-{2-[(1R,5S)-3-oxa-8-azabicyclo[3.2.1]octan-8-yl]ethyl}-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 382: N-[(1S)-1-[(3P)-3-{4-chloro-3-methanesulfonamido-1-[2-(4-methanesulfonylpiperazin-1-yl)ethyl]-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 384: N-[(1S)-1-[(3P)-3-(4-chloro-1-{2-[(2R,6S)-2,6-dimethylmorpholin-4-yl]-2-oxoethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 387: 2-[(6P)-4-chloro-7-{2-[(1S)-1-{2-[(2S,4S)-9-cyclopropyl-7,8-diazatricyclo[4.3.0.0$^{2,4}$]nona-1(6),8-dien-7-yl]acetamido}-2-(3,5-difluorophenyl)ethyl]-7-(4,4-difluorocyclohexyl)-5-methyl-4-oxo-3H,4H-pyrido[2,3-d]pyrimidin-3-yl}-3-methanesulfonamido-1H-indazol-1-yl]-N,N-bis(2-methoxyethyl)acetamide; Example 393: N-[(1S)-1-[(3P)-3-[4-chloro-3-methanesulfonamido-1-({[2-(propan-2-yloxy)ethyl]carbamoyl}methyl)-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 395: N-[(1S)-1-[(3P)-3-[4-chloro-3-methanesulfonamido-1-({[(2S)-2-methoxypropyl]carbamoyl}methyl)-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 396: N-[(1S)-1-[(3P)-3-{4-chloro-3-methanesulfonamido-1-[2-oxo-2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 401: 2-[(6P)-4-chloro-7-[7-(4,4-difluorocyclohexyl)-2-[(1S)-1-{2-[(2S,4R)-9-(difluoromethyl)-5,5-difluoro-7,8-diazatricyclo[4.3.0.0$^{2,4}$]nona-1(6),8-dien-7-yl]acetamido}-2-(3,5-difluorophenyl)ethyl]-5-methyl-4-oxo-3H,4H-pyrido[2,3-d]pyrimidin-3-yl]-3-methanesulfonamido-1H-indazol-1-yl]-N,N-bis(2-methoxyethyl)acetamide; Example 405: N-[(1S)-1-[(3P)-3-[4-chloro-3-methanesulfonamido-1-({methyl[(3R)-oxolan-3-yl]carbamoyl}methyl)-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 409: N-[(1S)-1-[(3P)-3-(1-{2-[(1R,5S)-3-azabicyclo[3.1.0]hexan-3-yl]-2-oxoethyl}-4-chloro-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 413: N-[(1S)-1-[(3P)-3-{4-chloro-1-[2-(4,4-difluoropiperidin-1-yl)ethyl]-3-methanesulfonamido-1H-indazol-7-yl}-7-(4,4-difluorocyclohexyl)-5-[(2-methoxyethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 414: N-[(1S)-1-[(3P)-3-(4-chloro-1-{2-[(3R,5S)-3,5-difluoropiperidin-1-yl]ethyl}-3-methanesulfonamido-1H-indazol-7-yl)-7-(4,4-difluorocyclohexyl)-5-[(2-methoxyethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8- diazatricyclo[4.3.0.0$^{2,4}$]nona-1(6),8-dien-7-yl]acetamide; Example 415: N-[(1S)-1-[(3P)-3-{4-chloro-1-[2-(4-fluoropiperidin-1-yl)ethyl]-3-methanesulfonamido-1H-indazol-7-yl}-7-(4,4-difluorocyclohexyl)-5-[(2-methoxyethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 416: N-[(1S)-1-[(3P)-3-{4-chloro-1-[2-(3,3-difluoropiperidin-1-yl)ethyl]-3-methanesulfonamido-1H-indazol-7-yl}-7-(4,4-difluorocyclohexyl)-5-[(2-methoxyethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 417: N-[(1S)-1-[(3P)-3-(4-chloro-1-{2-[(3R,4S)-3,4-difluoropyrrolidin-1-yl]ethyl}-3-methanesulfonamido-1H-indazol-7-yl)-7-(4,4-difluorocyclohexyl)-5-[(2-methoxyethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 418: N-[(1S)-1-[(3P)-3-(4-chloro-1-{2-[(2R,6S)-2,6-dimethylmorpholin-4-yl]ethyl}-3-methanesulfonamido-1H-indazol-7-yl)-7-(4,4-difluorocyclohexyl)-5-[(2-methoxyethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 419: N-[(1S)-1-[(3P)-3-(4-chloro-3-methanesulfonamido-1-{2-[(1R,5S)-6-oxa-3-azabicyclo[3.1.1]heptan-3-yl]ethyl}-1H-indazol-7-yl)-7-(4,4-difluorocyclohexyl)-5-[(2-methoxyethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 420: N-[(1S)-1-[(3P)-3-(4-chloro-3-methanesulfonamido-1-{2-[(1R,5S)-8-oxa-3-azabicyclo[3.2.1]octan-3-yl]ethyl}-1H-indazol-7-yl)-7-(4,4-difluorocyclohexyl)-5-[(2-methoxyethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 421: N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 424: N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 427: N-[(1S)-1-[(3P)-3-[4-chloro-3-methanesulfonamido-1-(3-methoxypropyl)-1H-indazol-7-yl]-7-(4,4-difluorocyclohexyl)-5-(ethylamino)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 428: N-[(1S)-1-[(3P)-3-[4-chloro-3-methanesulfonamido-1-(3-methoxypropyl)-1H-indazol-7-yl]-7-(4,4-difluorocyclohexyl)-5-({[(3S)-oxan-3-yl]methyl}amino)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 429: N-[(1S)-1-[(3P)-3-[4-chloro-3-methanesulfonamido-1-(3-methoxypropyl)-1H-indazol-7-yl]-7-(4,4-difluorocyclohexyl)-4-oxo-5-{[2-(pyrrolidin-1-yl)ethyl]amino}-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 430: N-[(1S)-1-[(3P)-3-[4-chloro-3-methanesulfonamido-1-(3-methoxypropyl)-1H-indazol-7-yl]-7-(4,4-difluorocyclohexyl)-5-{[2-(morpholin-4-yl)ethyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 431: N-[(1S)-1-[(3P)-3-[4-chloro-3-methanesulfonamido-1-(3-methoxypropyl)-1H-indazol-7-yl]-7-(4,4-difluorocyclohexyl)-5-{[(oxan-4-yl)methyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 432: N-[(1S)-1-[(3P)-3-[4-chloro-3-methanesulfonamido-1-(3-methoxypropyl)-1H-indazol-7-yl]-7-(4,4-difluorocyclohexyl)-5-[(2-acetamidoethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 433: N-[(1S)-1-[(3P)-3-[4-chloro-3-methanesulfonamido-1-(3-methoxypropyl)-1H-indazol-7-yl]-5-[(2-cyanoethyl)amino]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 434: N-[(1S)-1-[(3P)-3-(4-chloro-3-methanesulfonamido-1-{2-[(2S)-2-(propan-2-yl)morpholin-4-yl]ethyl}-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 435: N-[(1S)-1-[(3P)-3-(4-chloro-3-methanesulfonamido-1-{2-[(2R)-2-(propan-2-yl)morpholin-4-yl]ethyl}-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 444: N-[(1S)-1-[(3P)-3-(4-chloro-1-{2-[(3S,5S)-3,5-difluoropiperidin-1-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 445: N-[(1S)-1-[(3P)-3-[4-chloro-3-methanesulfonamido-1-(2-{5-oxa-11-azadispiro[3.1.3$^{6}$.3$^{4}$]dodecan-11-yl}ethyl)-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 446: N-[(1S)-1-[(3P)-3-(4-chloro-1-{2-[(3S,5S)-3,5-difluoropiperidin-1-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 448: N-[(1S)-1-[(3P)-3-[4-chloro-3-methanesulfonamido-1-(3-methoxypropyl)-1H-indazol-7-yl]-7-(4,4-difluorocyclohexyl)-5-{[(2R,6S)-2,6-dimethylmorpholin-4-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 449: N-[(1S)-1-[(3P)-3-[4-chloro-3-methanesulfonamido-1-(3-methoxypropyl)-1H-indazol-7-yl]-7-(4,4-difluorocyclohexyl)-5-(fluoromethyl)-4-oxo-3H, 4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 453: N-[(1S)-1-[(3P)-3-(4-chloro-3-methanesulfonamido-1-{2-[(6S)-2,2,6-trimethylmorpholin-4-yl]ethyl}-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 454: N-[(1S)-1-[(3P)-3-(4-chloro-3-methanesulfonamido-1-{2-[(6R)-2,2,6-trimethylmorpholin-4-yl]ethyl}-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 456: N-[(1S)-1-[(3P)-3-(4-chloro-3-methanesulfonamido-1-{2-[(2S)-2-(propan-2-yl)morpholin-4-yl]ethyl}-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 457: N-[(1S)-1-[(3P)-3-(4-chloro-3-methanesulfonamido-1-{2-[(2R)-2-(propan-2-yl)morpholin-4-yl]ethyl}-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 458: N-[(1S)-1-[(3P)-3-(4-chloro-3-methanesulfonamido-1-{2-[(6S)-2,2,6-trimethylmorpholin-4-yl]ethyl}-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 459: N-[(1S)-1-[(3P)-3-(4-chloro-3-methanesulfonamido-1-{2-[(6R)-2,2,6-trimethylmorpholin-4-yl]ethyl}-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 462: N-[(1S)-1-[(3P)-3-(4-chloro-3-methanesulfonamido-1-{2-[(6R)-2,2,6-trimethylmorpholin-4-yl]ethyl}-1H-indazol-7-yl)-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 467: N-[(1S)-1-[(3P)-3-(4-chloro-3-methanesulfonamido-1-{2-[(2S)-2-(propan-2-yl)morpholin-4-yl]ethyl}-1H-indazol-7-yl)-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 471: N-[(1S)-1-[(3P)-3-[4-chloro-3-methanesulfonamido-1-(3-methoxypropyl)-1H-indazol-7-yl]-7-(4,4-difluorocyclohexyl)-4-oxo-5-[(2,2,6,6-tetramethylmorpholin-4-yl)methyl]-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 472: N-[(1S)-1-[(3P)-3-[4-chloro-3-methanesulfonamido-1-(3-methoxypropyl)-1H-indazol-7-yl]-7-(4,4-difluorocyclohexyl)-5-[(methylamino)methyl]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 473: N-[(1S)-1-[(3P)-3-(4-chloro-1-{2-[(3R,5S)-3,5-difluoropiperidin-1-yl]ethyl}-3-methanesulfonamido-1H-indazol-7-yl)-7-(4,4-difluoro-1-methylcyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 474: N-[(1S)-1-[(3P)-3-(4-chloro-1-{2-[(3R,5S)-3,5-difluoropiperidin-1-yl]ethyl}-3-methanesulfonamido-1H-indazol-7-yl)-7-(4,4-difluoro-1-methylcyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 475: N-[(1S)-1-[(3P)-3-[4-chloro-3-methanesulfonamido-1-(3-methoxypropyl)-1H-indazol-7-yl]-7-(4,4-difluorocyclohexyl)-5-({2-[(2R,6S)-2,6-dimethylmorpholin-4-yl]ethyl}amino)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 476: N-[(1S)-1-[(3P)-3-[4-chloro-3-methanesulfonamido-1-(3-methoxypropyl)-1H-indazol-7-yl]-7-(4,4-difluorocyclohexyl)-5-{[2-(2,2-dimethylmorpholin-4-yl)ethyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 477: N-[(1S)-1-[(3P)-3-[4-chloro-3-methanesulfonamido-1-(3-methoxypropyl)-1H-indazol-7-yl]-7-(4,4-difluorocyclohexyl)-5-{[2-(3,3-dimethylmorpholin-4-yl)ethyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 479: N-[(1S)-1-[(3P)-3-{4-chloro-1-[2-(2,2-dimethylmorpholin-4-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 480: N-[(1S)-1-[(3P)-3-{4-chloro-1-[2-(2,2-dimethylmorpholin-4-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 484: N-[(1S)-1-[(3P)-3-[4-chloro-3-methanesulfonamido-1-(3-methoxypropyl)-1H-indazol-7-yl]-7-(4,4-difluorocyclohexyl)-5-{[(4-fluorooxan-4-yl)methyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 485: N-[(1S)-1-[(3P)-3-[4-chloro-3-methanesulfonamido-1-(3-methoxypropyl)-1H-indazol-7-yl]-7-(4,4-difluorocyclohexyl)-5-{[(4-methyloxan-4-yl)methyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 488: N-[(1S)-1-[(3P)-3-[4-chloro-3-methanesulfonamido-1-(3-methoxypropyl)-1H-indazol-7-yl]-7-(4,4-difluorocyclohexyl)-5-{[(3R,5S)-3,5-difluoropiperidin-1-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 489: N-[(1S)-1-[(3P)-3-[4-chloro-3-methanesulfonamido-1-(3-methoxypropyl)-1H-indazol-7-yl]-7-(4,4-difluorocyclohexyl)-5-[(4,4-difluoropiperidin-1-yl)methyl]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 491: N-[(1S)-1-[(3P)-3-(4-chloro-1-{2-[(3R,5S)-3,5-difluoropiperidin-1-yl]ethyl}-3- methanesulfonamido-1H-indazol-7-yl)-7-(4,4-difluorocyclohexyl)-5-{[2-(morpholin-4-yl)ethyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 495: N-[(1S)-1-[(3P)-3-{4-chloro-1-[2-(3,3-dimethylmorpholin-4-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 498: N-[(1S)-1-[(3P)-3-[4-chloro-3-methanesulfonamido-1-(3-methoxypropyl)-1H-indazol-7-yl]-7-(4,4-difluorocyclohexyl)-5-{[2-(4,4-difluoropiperidin-1-yl)ethyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 500: N-[(1S)-1-[(3P)-5-{[2-(azetidin-1-yl)ethyl]amino}-3-[4-chloro-3-methanesulfonamido-1-(3-methoxypropyl)-1H-indazol-7-yl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide; Example 501: N-[(1S)-1-[(3P)-3-{4-chloro-3-methanesulfonamido-1-[2-(2,2,6,6-tetramethylmorpholin-4-yl)ethyl]-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 502: N-[(1S)-1-[(3P)-3-(4-chloro-1-{2-[(2R,6S)-2,6-dimethylmorpholin-4-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 503: N-[(1S)-1-[(3P)-3-(4-chloro-1-{2-[(2R,6S)-2,6-dimethylmorpholin-4-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 504: N-[(1S)-1-[(3P)-3-{4-chloro-3-methanesulfonamido-1-[2-(2,2,6,6-tetramethylmorpholin-4-yl)ethyl]-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2}$,$^{4}$]nona-1(6),8-dien-7-yl]acetamide; Example 505: N-[(1S)-1-[(3P)-3-(4-chloro-1-{2-[(2R,6S)-2,6-dimethylmorpholin-4-yl]ethyl}-3-methanesulfonamido-1H-indazol-7-yl)-7-(4,4-difluoro-1-methylcyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 506: N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluoro-1-methylcyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 507: N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluoro-1-methylcyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 508: N-[(1S)-1-[(3P)-3-(4-chloro-1-{2-[(2R,6S)-2,6-dimethylmorpholin-4-yl]ethyl}-3-methanesulfonamido-1H-indazol-7-yl)-7-(4,4-difluoro-1-methylcyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 509: N-[(1S)-1-[(3P)-3-[4-chloro-3-methanesulfonamido-1-(3-methoxypropyl)-1H-indazol-7-yl]-7-(4,4-difluorocyclohexyl)-5-({2-[(3R,5S)-3,5-difluoropiperidin-1-yl]ethyl}amino)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 512: N-[(1S)-1-[(3P)-3-(4-chloro-1-{2-[(3R,5S)-3,5-difluoropiperidin-1-yl]ethyl}-3-methanesulfonamido-1H-indazol-7-yl)-7-(4,4-difluorocyclohexyl)-5-(fluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 513: N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-(fluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 514: N-[(1S)-1-[(3P)-3-{4-chloro-1-[2-(4,4-difluoropiperidin-1-yl)ethyl]-3-methanesulfonamido-1H-indazol-7-yl}-7-(4,4-difluorocyclohexyl)-5-(fluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 515: N-[(1S)-1-[(3P)-5-[(2-{6-azaspiro[2.5]octan-6-yl}ethyl)amino]-3-[4-chloro-3-methanesulfonamido-1-(3-methoxypropyl)-1H-indazol-7-yl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 517: N-[(1S)-1-[(3P)-3-[4-chloro-3-methanesulfonamido-1-(3-methoxypropyl)-1H-indazol-7-yl]-5-{[2-(3,3-difluoroazetidin-1-yl)ethyl]amino}-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 519: N-[(1S)-1-[(3P)-3-[4-chloro-3-methanesulfonamido-1-(3-methoxypropyl)-1H-indazol-7-yl]-7-(4,4-difluorocyclohexyl)-4-oxo-5-{[3-(piperidin-1-yl)propyl]amino}-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 521: N-[(1S)-1-[(3P)-3-[4-chloro-3-methanesulfonamido-1-(3-methoxypropyl)-1H-indazol-7-yl]-7-(4,4-difluorocyclohexyl)-4-oxo-5-[(2-phenylethyl)amino]-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide; Example 522: N-[(1S)-1-[(3P)-3-[4-chloro-3-methanesulfonamido-1-(3-methoxypropyl)-1H-indazol-7-yl]-7-(4,4-difluorocyclohexyl)-5-{[2-(dimethylamino)ethyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 523: N-[(1S)-1-[(3P)-3-[4-chloro-3-methanesulfonamido-1-(3-methoxypropyl)-1H-indazol-7-yl]-7-(4,4-difluorocyclohexyl)-5-{[2-(4,4-dimethylpiperidin-1-yl)ethyl]amino}-4-oxo-3H,4H-pyrido

[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 525: N-[(1S)-1-[(3P)-3-{4-chloro-1-[2-(4,4-difluoropiperidin-1-yl)ethyl]-3-methanesulfonamido-1H-indazol-7-yl}-7-(4,4-difluorocyclohexyl)-5-{[(2R,6S)-2,6-dimethylmorpholin-4-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 526: N-[(1S)-1-[(3P)-3-(4-chloro-1-{2-[(3R,5S)-3,5-difluoropiperidin-1-yl]ethyl}-3-methanesulfonamido-1H-indazol-7-yl)-7-(4,4-difluorocyclohexyl)-5-{[(2R,6S)-2,6-dimethylmorpholin-4-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 527: N-[(1S)-1-[(3P)-3-{4-chloro-1-[2-(4-fluoropiperidin-1-yl)ethyl]-3-methanesulfonamido-1H-indazol-7-yl}-7-(4,4-difluorocyclohexyl)-5-{[(2R,6S)-2,6-dimethylmorpholin-4-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 528: N-[(1S)-1-[(3P)-3-(4-chloro-1-{2-[(2R,6S)-2,6-dimethylmorpholin-4-yl]ethyl}-3-methanesulfonamido-1H-indazol-7-yl)-7-(4,4-difluorocyclohexyl)-5-{[(2R,6S)-2,6-dimethylmorpholin-4-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 529: N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-{[(2R,6S)-2,6-dimethylmorpholin-4-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 530: N-[(1S)-1-[(3P)-3-[4-chloro-3-methanesulfonamido-1-(3-methoxypropyl)-1H-indazol-7-yl]-7-(4,4-difluorocyclohexyl)-5-{[(3R,4S)-3,4-difluoropyrrolidin-1-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 531: N-[(1S)-1-[(3P)-3-[4-chloro-3-methanesulfonamido-1-(3-methoxypropyl)-1H-indazol-7-yl]-7-(4,4-difluorocyclohexyl)-5-{[(1R,5S)-6-oxa-3-azabicyclo[3.1.1]heptan-3-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 535: N-[(1S)-1-[(3P)-3-[4-chloro-3-methanesulfonamido-1-(3-methoxypropyl)-1H-indazol-7-yl]-7-(4,4-difluorocyclohexyl)-5-{[2-(4-methylpiperazin-1-yl)ethyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 536: N-[(1S)-1-[(3P)-5-{[2-(4-acetylpiperazin-1-yl)ethyl]amino}-3-[4-chloro-3-methanesulfonamido-1-(3-methoxypropyl)-1H-indazol-7-yl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 538: N-[(1S)-1-[(3P)-3-[4-chloro-3-methanesulfonamido-1-(3-methoxypropyl)-1H-indazol-7-yl]-5-[(3,3-difluoroazetidin-1-yl)methyl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 539: N-[(1S)-1-[(3P)-3-[4-chloro-3-methanesulfonamido-1-(3-methoxypropyl)-1H-indazol-7-yl]-7-(4,4-difluorocyclohexyl)-5-{[2-methyl-2-(piperidin-1-yl)propyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 543: N-[(1S)-1-[(3P)-3-[4-chloro-3-methanesulfonamido-1-(3-methoxypropyl)-1H-indazol-7-yl]-7-(4,4-difluorocyclohexyl)-5-{[2-(1-methyl-1H-pyrazol-3-yl)ethyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 546: N-[(1S)-1-[(3P)-3-[4-chloro-3-methanesulfonamido-1-(3-methoxypropyl)-1H-indazol-7-yl]-7-(4,4-difluorocyclohexyl)-5-{[2-methyl-2-(morpholin-4-yl)propyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 549: N-[(1S)-1-[(3P)-3-[4-chloro-3-methanesulfonamido-1-(3-methoxypropyl)-1H-indazol-7-yl]-5-[(2-cyclohexylethyl)amino]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 550: N-[(1S)-1-[(3P)-3-[4-chloro-3-methanesulfonamido-1-(3-methoxypropyl)-1H-indazol-7-yl]-7-(4,4-difluorocyclohexyl)-5-{[2-(oxan-4-yl)ethyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 552: N-[(1S)-1-[(3P)-3-[4-chloro-3-methanesulfonamido-1-(3-methoxypropyl)-1H-indazol-7-yl]-7-(4,4-difluorocyclohexyl)-5-{[2-(3,3-difluoropyrrolidin-1-yl)ethyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 553: N-[(1S)-1-[(3P)-3-[4-chloro-3-methanesulfonamido-1-(3-methoxypropyl)-1H-indazol-7-yl]-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 556: N-[(1S)-1-[(3P)-3-(4-chloro-1-{2-[(3R,5S)-3,5-difluoropiperidin-1-yl]ethyl}-3-methanesulfonamido-1H-indazol-7-yl)-7-[4,4-difluoro-1-(fluoromethyl)cyclohexyl]-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 557: N-[(1S)-1-[(3P)-3-(4-chloro-1-{2-[(2R,6S)-2,6-dimethylmorpholin-4-yl]ethyl}-3-methanesulfonamido-1H-indazol-7-yl)-7-[4,4-difluoro-1-(fluoromethyl)cyclohexyl]-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 561: N-[(1S)-1-[(3P)-3-(4-chloro-1-{2-[(2R,6S)-2,6-dimethylmorpholin-4-yl]ethyl}-3-methanesulfonamido-1H-indazol-7-yl)-7-[1-(difluoromethyl)-4,4-difluorocyclohexyl]-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 563: N-[(1S)-1-[(3P)-3-[4-chloro-3-methanesulfonamido-1-(3-methoxypropyl)-1H-indazol-7-yl]-7-(4,4- difluorocyclohexyl)-5-{[2-(oxan-2-yl)ethyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 564: N-[(1S)-1-[(3P)-3-[4-chloro-3-methanesulfonamido-1-(3-methoxypropyl)-1H-indazol-7-yl]-7-(4,4-difluorocyclohexyl)-5-{[2-(oxetan-2-yl)ethyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 565: N-[(1S)-1-[(3P)-3-[4-chloro-3-methanesulfonamido-1-(3-methoxypropyl)-1H-indazol-7-yl]-7-(4,4-difluorocyclohexyl)-5-[(3-methoxy-3-methylbutyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 566: N-[(1S)-1-[(3P)-3-[4-chloro-3-methanesulfonamido-1-(3-methoxypropyl)-1H-indazol-7-yl]-7-(4,4-difluorocyclohexyl)-4-oxo-5-{[2-oxo-2-(piperidin-1-yl)ethyl]amino}-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 567: N-[(1S)-1-[(3P)-3-[4-chloro-3-methanesulfonamido-1-(3-methoxypropyl)-1H-indazol-7-yl]-7-(4,4-difluorocyclohexyl)-4-oxo-5-({[(3R)-oxolan-3-yl]methyl}amino)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 568: N-[(1S)-1-[(3P)-3-[4-chloro-3-methanesulfonamido-1-(3-methoxypropyl)-1H-indazol-7-yl]-7-(4,4-difluorocyclohexyl)-4-oxo-5-({[(3S)-oxolan-3-yl]methyl}amino)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 569: N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-5,5-difluoro-9-(trifluoromethyl)-7,8-diazatricyclo[4.3.0.0$^{2,4}$]nona-1(6),8-dien-7-yl]acetamide; Example 570: N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-cyclopropyl-5,5-difluoro-7,8-diazatricyclo[4.3.0.0$^{2,4}$]nona-1(6),8-dien-7-yl]acetamide; Example 571: N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-(difluoromethyl)-7,8-diazatricyclo[4.3.0.0$^{2,4}$]nona-1(6),8-dien-7-yl]acetamide; Example 572: N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-(trifluoromethyl)-7,8-diazatricyclo[4.3.0.0$^{2,4}$]nona-1(6),8-dien-7-yl]acetamide; Example 573: N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2R,4R)-9-[(1R)-2,2-difluorocyclopropyl]-7,8-diazatricyclo[4.3.0.0$^{2,4}$]nona-1(6),8-dien-7-yl]acetamide; Example 574: N-[(1S)-1-[(3P)-3-(4-chloro-3-methanesulfonamido-1-{2-[(2S)-2-(propan-2-yl)morpholin-4-yl]ethyl}-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 575: N-[(1S)-1-[(3P)-3-(4-chloro-3-methanesulfonamido-1-{2-[(2R)-2-(propan-2-yl)morpholin-4-yl]ethyl}-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 576: N-[(1S)-1-[(3P)-3-(4-chloro-3-methanesulfonamido-1-{2-[(6S)-2,2,6-trimethylmorpholin-4-yl]ethyl}-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 577: N-[(1S)-1-[(3P)-3-(4-chloro-3-methanesulfonamido-1-{2-[(6R)-2,2,6-trimethylmorpholin-4-yl]ethyl}-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 578: N-[(1S)-1-[(3P)-3-{4-chloro-1-[2-(2,2-dimethylmorpholin-4-yl)ethyl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 579: N-[(1S)-1-[(3P)-3-{4-chloro-1-[2-(3,3-dimethylmorpholin-4-yl)ethyl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 581: N-[(1S)-1-[(3P)-3-(4-chloro-3-methanesulfonamido-1-{2-[(2S)-2-(propan-2-yl)morpholin-4-yl]ethyl}-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 582: N-[(1S)-1-[(3P)-3-(4-chloro-3-methanesulfonamido-1-{2-[(2R)-2-(propan-2-yl)morpholin-4-yl]ethyl}-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 583: N-[(1S)-1-[(3P)-3-(4-chloro-3-methanesulfonamido-1-{2-[(6S)-2,2,6-trimethylmorpholin-4-yl]ethyl}-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 584: N-[(1S)-1-[(3P)-3-(4-chloro-3-methanesulfonamido-1-{2-[(6R)-2,2,6-trimethylmorpholin-4-yl]ethyl}-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 585: N-[(1S)-1-[(3P)-3-{4-chloro-1-[2-(2,2-dimethylmorpholin-4-yl)ethyl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 586: N-[(1S)-1-[(3P)-3-{4-chloro-1-[2-(3,3-dimethylmorpholin-4-yl)ethyl]-3- methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 588: N-[(1S)-1-[(3P)-3-[4-chloro-3-methanesulfonamido-1-(2-{6-oxa-3-azabicyclo[3.1.1]heptan-3-yl}ethyl)-1H-indazol-7-yl]-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 589: N-[(1S)-1-[(3P)-3-(4-chloro-3-methanesulfonamido-1-{2-[(1R,5S)-8-oxa-3-azabicyclo[3.2.1]octan-3-yl]ethyl}-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 590: N-[(1S)-1-[(3P)-3-(4-chloro-3-methanesulfonamido-1-{2-[(1R,5S)-3-oxa-8-azabicyclo[3.2.1]octan-8-yl]ethyl}-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 591: N-[(1S)-1-[(3P)-3-[4-chloro-3-methanesulfonamido-1-(2-{6-oxa-3-azabicyclo[3.1.1]heptan-3-yl}ethyl)-1H-indazol-7-yl]-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 592: N-[(1S)-1-[(3P)-3-(4-chloro-3-methanesulfonamido-1-{2-[(1R,5S)-8-oxa-3-azabicyclo[3.2.1]octan-3-yl]ethyl}-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 593: N-[(1S)-1-[(3P)-3-(4-chloro-3-methanesulfonamido-1-{2-[(1R,5S)-3-oxa-8-azabicyclo[3.2.1]octan-8-yl]ethyl}-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 594: N-[(1S)-1-[(3P)-3-(4-chloro-1-{2-[(2R,6S)-2,6-dimethylmorpholin-4-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-5,5-difluoro-9-(trifluoromethyl)-7,8-diazatricyclo[4.3.0.0$^{2,4}$]nona-1(6),8-dien-7-yl]acetamide; Example 595: N-[(1S)-1-[(3P)-3-(4-chloro-1-{2-[(2R,6S)-2,6-dimethylmorpholin-4-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-cyclopropyl-5,5-difluoro-7,8-diazatricyclo[4.3.0.0$^{2,4}$]nona-1(6),8-dien-7-yl]acetamide; Example 596: N-[(1S)-1-[(3P)-3-(4-chloro-1-{2-[(2R,6S)-2,6-dimethylmorpholin-4-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-(difluoromethyl)-7,8-diazatricyclo[4.3.0.0$^{2,4}$]nona-1(6),8-dien-7-yl]acetamide; Example 597: N-[(1S)-1-[(3P)-3-(4-chloro-1-{2-[(2R,6S)-2,6-dimethylmorpholin-4-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-(trifluoromethyl)-7,8-diazatricyclo[4.3.0.0$^{2,4}$]nona-1(6),8-dien-7-yl]acetamide; Example 598: N-[(1S)-1-[(3P)-3-(4-chloro-1-{2-[(2R,6S)-2,6-dimethylmorpholin-4-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2R,4R)-9-[(1R)-2,2-difluorocyclopropyl]-7,8-diazatricyclo[4.3.0.0$^{2,4}$]nona-1(6),8-dien-7-yl]acetamide; Example 599: N-[(1S)-1-[(3P)-3-[4-chloro-3-methanesulfonamido-1-(3-methoxypropyl)-1H-indazol-7-yl]-7-(4,4-difluorocyclohexyl)-5-{[(2R,6S)-2,6-dimethylmorpholin-4-yl]methyl}-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 600: N-[(1S)-1-[(3P)-3-[4-chloro-3-methanesulfonamido-1-(3-methoxypropyl)-1H-indazol-7-yl]-5-{[(2R,6S)-2,6-dimethylmorpholin-4-yl]methyl}-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 601: N-[(1S)-1-[(3P)-3-[4-chloro-3-methanesulfonamido-1-(3-methoxypropyl)-1H-indazol-7-yl]-7-(4,4-difluorocyclohexyl)-5-(ethylamino)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 602: N-[(1S)-1-[(3P)-3-[4-chloro-3-methanesulfonamido-1-(3-methoxypropyl)-1H-indazol-7-yl]-5-{[(2R,6S)-2,6-dimethylmorpholin-4-yl]methyl}-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 603: N-[(1S)-1-[(3P)-3-[4-chloro-3-methanesulfonamido-1-(3-methoxypropyl)-1H-indazol-7-yl]-5-[(3,3-difluoroazetidin-1-yl)methyl]-7-(4,4-difluorocyclohexyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 604: N-[(1S)-1-[(3P)-3-[4-chloro-3-methanesulfonamido-1-(3-methoxypropyl)-1H-indazol-7-yl]-7-(4,4-difluorocyclohexyl)-5-[(3-methoxyazetidin-1-yl)methyl]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 605: N-[(1S)-1-[(3P)-3-[4-chloro-3-methanesulfonamido-1-(3-methoxypropyl)-1H-indazol-7-yl]-7-(4,4-difluorocyclohexyl)-4-oxo-5-{[3-(trifluoromethyl)azetidin-1-yl]methyl}-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 606: N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2R,4R)-9-cyclopropyl-7,8-diazatricyclo[4.3.0.0$^{2,4}$]nona-1(6),8-dien-7-yl]acetamide; Example 609: N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-5,5-difluoro-9-(trifluoromethyl)-7,8-diazatricyclo[4.3.0.0$^{2,4}$]nona-1(6),8-dien-7-yl]acetamide; Example 610: N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-cyclopropyl-5,5-difluoro-7,8-diazatricyclo[4.3.0.0$^{2,4}$]nona-1(6),8-dien-7-yl]acetamide; Example 611: N-[(1S)-1-[(3P)-3-{4-chloro-3-methanesulfonamido-1-[2-(2,2,6,6- tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-(difluoromethyl)-7,8-diazatricyclo[4.3.0.0$^{2,4}$]nona-1(6),8-dien-7-yl]acetamide; Example 612: N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-(trifluoromethyl)-7,8-diazatricyclo[4.3.0.0$^{2,4}$]nona-1(6),8-dien-7-yl]acetamide; Example 613: N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2R,4R)-9-[(1R)-2,2-difluorocyclopropyl]-7,8-diazatricyclo[4.3.0.0$^{2,4}$]nona-1(6),8-dien-7-yl]acetamide; Example 615: N-[(1S)-1-[(3P)-3-[4-chloro-3-methanesulfonamido-1-(3-methoxypropyl)-1H-indazol-7-yl]-7-(1-{2-[(3R,5S)-3,5-difluoropiperidin-1-yl]ethyl}-4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 620: N-[(1S)-1-[(3P)-3-(4-chloro-1-{2-[(3R,5S)-3,5-difluoropiperidin-1-yl]ethyl}-3-methanesulfonamido-1H-indazol-7-yl)-5-[(3,3-difluoroazetidin-1-yl)methyl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 621: N-[(1S)-1-[(3P)-3-{4-chloro-3-methanesulfonamido-1-[2-(2,2,6,6-tetramethylmorpholin-4-yl)ethyl]-1H-indazol-7-yl}-5-[(3,3-difluoroazetidin-1-yl)methyl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide; Example 623: N-[(1S)-1-[(3P)-3-[4-chloro-3-methanesulfonamido-1-(3-methoxypropyl)-1H-indazol-7-yl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 632: N-[(1S)-1-[(3P)-3-[4-chloro-3-methanesulfonamido-1-(2-methoxyethyl)-1H-indazol-7-yl]-7-(4,4-difluorocyclohexyl)-5-ethyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 636: N-[(1S)-1-[(3P)-3-[4-chloro-3-methanesulfonamido-1-(2-methoxyethyl)-1H-indazol-7-yl]-7-(4,4-difluorocyclohexyl)-5-ethyl-4-oxo-3H,4H-pyrido[2,3-d]pyrimidin-2-yl]-2-(3,5-difluorophenyl)ethyl]-2-[(2R*,4R*)-9-(difluoromethyl)-7,8-diazatricyclo[4.3.0.0$^{2,4}$]nona-1(6),8-dien-7-yl]acetamide; Example 638: N-[(1S)-1-[(3P)-3-[4-chloro-3-methanesulfonamido-1-(3-methoxypropyl)-1H-indazol-7-yl]-7-(4,4-difluorocyclohexyl)-5-ethyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 639: N-[(1S)-1-[(3P)-3-[4-chloro-3-methanesulfonamido-1-(3-methoxypropyl)-1H-indazol-7-yl]-7-(4,4-difluorocyclohexyl)-5-ethyl-4-oxo-3H,4H-pyrido[2,3-d]pyrimidin-2-yl]-2-(3,5-difluorophenyl)ethyl]-2-[(2S,4R)-9-cyclopropyl-5,5-difluoro-7,8-diazatricyclo[4.3.0.0$^{2,4}$]nona-1(6),8-dien-7-yl]acetamide; Example 641: N-[(1S)-1-[(3P)-3-[4-chloro-3-methanesulfonamido-1-(3-methoxypropyl)-1H-indazol-7-yl]-7-(4,4-difluorocyclohexyl)-5-ethyl-4-oxo-3H,4H-pyrido[2,3-d]pyrimidin-2-yl]-2-(3,5-difluorophenyl)ethyl]-2-[(2R*,4R*)-9-(tifluoromethyl)-7,8-diazatricyclo[4.3.0.0$^{2,4}$]nona-1(6),8-dien-7-yl]acetamide; Example 643: N-[(1S)-1-[(3P)-3-[4-chloro-3-methanesulfonamido-1-(3-methoxypropyl)-1H-indazol-7-yl]-7-(4,4-difluorocyclohexyl)-5-ethyl-4-oxo-3H,4H-pyrido[2,3-d]pyrimidin-2-yl]-2-(3,5-difluorophenyl)ethyl]-2-[(2R*,4R*)-9-(difluoromethyl)-7,8-diazatricyclo[4.3.0.0$^{2,4}$]nona-1(6),8-dien-7-yl]acetamide; Example 671: N-[(1S)-1-[(3P)-3-(1-{2-[bis(3,3,3-trifluoropropyl)amino]ethyl}-4-chloro-3-methanesulfonamido-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 675: N-[(1S)-1-[(3P)-3-{4-chloro-1-[2-(4,4-difluoropiperidin-1-yl)ethyl]-3-methanesulfonamido-1H-indazol-7-yl}-7-(4,4-difluorocyclohexyl)-5-(hydroxymethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 676: N-[(1S)-1-[(3P)-3-{4-chloro-1-[2-(4,4-difluoropiperidin-1-yl)ethyl]-3-methanesulfonamido-1H-indazol-7-yl}-7-(4,4-difluorocyclohexyl)-5-(methoxymethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 679: N-[(1S)-1-[(3P)-3-{4-chloro-1-[(2R)-1-[(2R,6S)-2,6-dimethylmorpholin-4-yl]-1-oxopropan-2-yl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide; Example 683: N-[(1S)-1-[(3P)-3-{4-chloro-1-[(2R)-2-[(3R,5S)-3,5-difluoropiperidin-1-yl]propyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 684: N-[(1S)-1-[(3P)-3-{4-chloro-1-[(2R)-2-[(3R,5S)-3,5-difluoropiperidin-1-yl]propyl]-3-methanesulfonamido-1H-indazol-7-yl}-5-cyclopropyl-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 685: N-[(1S)-1-[(3P)-3-{4-chloro-1-[(2R)-2-[(3R,5S)-3,5-difluoropiperidin-1-yl]propyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide; Example 691: N-[(1S)-1-[(3P)-3-[4-chloro-1-({1-[(2R,6S)-2,6-dimethylmorpholin-4-yl]cyclopropyl}methyl)-3-methanesulfonamido-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide; Example 697: N-[(1S)-1-[(3P)-3-{4-chloro-1-[(2R)-2-[(3R,5S)-3,5-difluoropiperidin-1-yl]propyl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 698: N-[(1S)-1-[(3P)-3-{4-chloro-1-[2-(4,4-difluoropiperidin-1-yl)ethyl]-3- methanesulfonamido-1H-indazol-7-yl}-7-(4,4-difluorocyclohexyl)-5-[(1R**)-1-hydroxyethyl]-4-oxo-3H,4H-pyrido[2,3-d]pyrimidin-2-yl]-2-(3,5-difluorophenyl)ethyl]-2-[(2R*,4S*)-9-(difluoromethyl)-5,5-difluoro-7,8-diazatricyclo[4.3.0.0$^{2,4}$]nona-1(6),8-dien-7-yl]acetamide; Example 702: N-[(1S)-1-[(3P)-3-{4-chloro-1-[(2R)-2-[(3R,5S)-3,5-difluoropiperidin-1-yl]propyl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide; Example 703: N-[(1S)-1-[(3P)-3-{4-chloro-1-[(2S)-2-[(3R,5S)-3,5-difluoropiperidin-1-yl]propyl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 704: N-[(1S)-1-[(3P)-3-{4-chloro-1-[(2S)-2-[(3R,5S)-3,5-difluoropiperidin-1-yl]propyl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide; Example 705: N-[(1S)-1-[(3P)-3-{4-chloro-3-methanesulfonamido-1-[(2R)-2-(2,2,6,6-tetramethylmorpholin-4-yl)propyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 706: N-[(1S)-1-[(3P)-3-{4-chloro-3-methanesulfonamido-1-[(2R)-2-(2,2,6,6-tetramethylmorpholin-4-yl)propyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide; Example 707: N-[(1S)-1-[(3P)-3-{4-chloro-3-methanesulfonamido-1-[(2R)-2-(2,2,6,6-tetramethylmorpholin-4-yl)propyl]-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 711: N-[(1S)-1-[(3P)-3-{4-chloro-1-[(2R)-1-[(3R,5S)-3,5-difluoropiperidin-1-yl]propan-2-yl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 714: N-[(1S)-1-[(3P)-3-{4-chloro-3-methanesulfonamido-1-[(2S)-2-(2,2,6,6-tetramethylmorpholin-4-yl)propyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide; Example 716: N-[(1S)-1-[(3P)-3-{4-chloro-1-[(2R)-1-[(3R,5S)-3,5-difluoropiperidin-1-yl]propan-2-yl]-3-methanesulfonamido-1H-indazol-7-yl}-5-cyclopropyl-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 717: N-[(1S)-1-[(3P)-3-{4-chloro-3-methanesulfonamido-1-[(2S)-2-(2,2,6,6-tetramethylmorpholin-4-yl)propyl]-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 720: N-[(1S)-1-[(3P)-3-{4-chloro-1-[(2R)-2-[(2R,6S)-2,6-dimethylmorpholin-4-yl]propyl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 722: N-[(1S)-1-[(3P)-3-{4-chloro-1-[(2S)-2-[(2R,6S)-2,6-dimethylmorpholin-4-yl]propyl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide; Example 723: N-[(1S)-1-[(3P)-3-{4-chloro-1-[(2R)-2-[(2R,6S)-2,6-dimethylmorpholin-4-yl]propyl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide; Example 724: N-[(1S)-1-[(3P)-3-{4-chloro-3-methanesulfonamido-1-[(2S)-1-(2,2,6,6-tetramethylmorpholin-4-yl)propan-2-yl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide; Example 729: N-[(1S)-1-[(3P)-3-{4-chloro-1-[(2R)-1-[(2R,6S)-2,6-dimethylmorpholin-4-yl]propan-2-yl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 730: N-[(1S)-1-[(3P)-3-{4-chloro-1-[(2R)-1-[(2R,6S)-2,6-dimethylmorpholin-4-yl]propan-2-yl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide; Example 732: N-[(1S)-1-[(3P)-3-{4-chloro-1-[(2R)-1-[(3R,5S)-3,5-difluoropiperidin-1-yl]propan-2-yl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide; Example 733: N-[(1S)-1-[(3P)-3-{4-chloro-3-methanesulfonamido-1-[(2R)-1-(2,2,6,6-tetramethylmorpholin-4-yl)propan-2-yl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 734: N-[(1S)-1-[(3P)-3-{4-chloro-3-methanesulfonamido-1-[(2R)-1-(2,2,6,6-tetramethylmorpholin-4-yl)propan-2-yl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide; Example 735: N-[(1S)-1-[(3P)-3-{4-chloro-1-[(2S)-1-[(3R,5S)-3,5-difluoropiperidin-1-yl]propan-2-yl]-3-methanesulfonamido-1H-indazol-7-yl}-5-cyclopropyl-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 738: N-[(1S)-1-[(3P)-3-{4-chloro-3-methanesulfonamido-1-[2-(2-oxopyrrolidin-1-yl)ethyl]-1H-indazol-7-yl}-5-methyl-4- oxo-7-(1,4,4-trifluorocyclohexyl)-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.024]nona-1(6),8-dien-7-yl]acetamide; Example 740: N-[(1S)-1-[(3P)-3-{4-chloro-3-methanesulfonamido-1-[2-(pyridin-3-yl)ethyl]-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 741: N-[(1S)-1-[(3P)-3-{4-chloro-3-methanesulfonamido-1-[2-(pyridin-3-yl)ethyl]-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide; Example 742: N-[(1S)-1-[(3P)-3-{4-chloro-3-methanesulfonamido-1-[(2S)-1-(2,2,6,6-tetramethylmorpholin-4-yl)propan-2-yl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 743: N-[(1S)-1-[(3P)-3-{4-chloro-1-[(2R)-1-[(2R,6S)-2,6-dimethylmorpholin-4-yl]-1-oxopropan-2-yl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 744: N-[(1S)-1-[(3P)-3-{4-chloro-1-[(2R)-1-[(2R,6S)-2,6-dimethylmorpholin-4-yl]-1-oxopropan-2-yl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide; Example 746: N-[(1S)-1-[(3P)-5-acetyl-3-{4-chloro-1-[2-(4,4-difluoropiperidin-1-yl)ethyl]-3-methanesulfonamido-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 747: N-[(1S)-1-[(3P)-3-{4-chloro-1-[(2S)-1-[(2R,6S)-2,6-dimethylmorpholin-4-yl]propan-2-yl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 748: N-[(1S)-1-[(3P)-3-{4-chloro-1-[(2S)-1-[(2R,6S)-2,6-dimethylmorpholin-4-yl]propan-2-yl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide; Example 749: N-[(1S)-1-[(3P)-3-{4-chloro-3-methanesulfonamido-1-[(2R)-1-oxo-1-(2,2,6,6-tetramethylmorpholin-4-yl)propan-2-yl]-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 750: N-[(1S)-1-[(3P)-3-{4-chloro-3-methanesulfonamido-1-[(2R)-1-oxo-1-(2,2,6,6-tetramethylmorpholin-4-yl)propan-2-yl]-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide; Example 753: N-[(1S)-1-[(3P)-3-{4-chloro-1-[(2S)-1-[(3R,5S)-3,5-difluoropiperidin-1-yl]propan-2-yl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 754: N-[(1S)-1-[(3P)-3-{4-chloro-1-[(2S)-1-[(3R,5S)-3,5-difluoropiperidin-1-yl]propan-2-yl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide; Example 755: N-[(1S)-1-[(3P)-3-{4-chloro-1-[(2R)-1-[(3R,5S)-3,5-difluoropiperidin-1-yl]-1-oxopropan-2-yl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; and Example 756: N-[(1S)-1-[(3P)-3-{4-chloro-1-[(2R)-1-[(3R,5S)-3,5-difluoropiperidin-1-yl]-1-oxopropan-2-yl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide; or a pharmaceutically acceptable salt thereof. In one embodiment, the compound is the compound (i.e. it is not in the form of pharmaceutically acceptable salt). In another embodiment, the compound is a pharmaceutically acceptable salt.

In another aspect, the invention provides a compound selected from the group consisting of Example 5: N-[(1S)-1-[(3P)-3-(4-chloro-1-{2-[(3R,5S)-3,5-difluoropiperidin-1-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 11: N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 12: N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 13: N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 135: N-[(1S)-1-[(3P)-3-[4-chloro-3-methanesulfonamido-1-(3-methoxypropyl)-1H-indazol-7-yl]-7-(4,4-difluorocyclohexyl)-5-[(2-methoxyethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 427: N-[(1S)-1-[(3P)-3-[4-chloro-3-methanesulfonamido-1-(3-methoxypropyl)-1H-indazol-7-yl]-7-(4,4-difluorocyclohexyl)-5-(ethylamino)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8- diazatricyclo[4.3.0.0$^{2,4}$]nona-1(6),8-dien-7-yl]acetamide; Example 448: N-[(1S)-1-[(3P)-3-[4-chloro-3-methanesulfonamido-1-(3-methoxypropyl)-1H-indazol-7-yl]-7-(4,4-difluorocyclohexyl)-5-{[(2R,6S)-2,6-dimethylmorpholin-4-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 503: N-[(1S)-1-[(3P)-3-(4-chloro-1-{2-[(2R,6S)-2,6-dimethylmorpholin-4-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 529: N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-{[(2R,6S)-2,6-dimethylmorpholin-4-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; and Example 538: N-[(1S)-1-[(3P)-3-[4-chloro-3-methanesulfonamido-1-(3-methoxypropyl)-1H-indazol-7-yl]-5-[(3,3-difluoroazetidin-1-yl)methyl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; or a pharmaceutically acceptable salt thereof.

In one embodiment, the compound is the compound (i.e. the compound is not in the form of pharmaceutically acceptable salt). In such an embodiment, the invention provides a compound selected from the group consisting of Example 5: N-[(1S)-1-[(3P)-3-(4-chloro-1-{2-[(3R,5S)-3,5-difluoropiperidin-1-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 11: N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 12: N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 13: N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 135: N-[(1S)-1-[(3P)-3-[4-chloro-3-methanesulfonamido-1-(3-methoxypropyl)-1H-indazol-7-yl]-7-(4,4-difluorocyclohexyl)-5-[(2-methoxyethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 427: N-[(1S)-1-[(3P)-3-[4-chloro-3-methanesulfonamido-1-(3-methoxypropyl)-1H-indazol-7-yl]-7-(4,4-difluorocyclohexyl)-5-(ethylamino)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8- diazatricyclo[4.3.0.0$^{2,4}$]nona-1(6),8-dien-7-yl]acetamide; Example 448: N-[(1S)-1-[(3P)-3-[4-chloro-3-methanesulfonamido-1-(3-methoxypropyl)-1H-indazol-7-yl]-7-(4,4-difluorocyclohexyl)-5-{[(2R,6S)-2,6-dimethylmorpholin-4-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; Example 503: N-[(1S)-1-[(3P)-3-(4-chloro-1-{2-[(2R,6S)-2,6-dimethylmorpholin-4-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide; Example 529: N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-{[(2R,6S)-2,6-dimethylmorpholin-4-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide; and Example 538: N-[(1S)-1-[(3P)-3-[4-chloro-3-methanesulfonamido-1-(3-methoxypropyl)-1H-indazol-7-yl]-5-[(3,3-difluoroazetidin-1-yl)methyl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide. In another embodiment, the compound is a pharmaceutically acceptable salt.

One of skill in the art will understand that a compound of the invention depicted by a structure herein, may comprise a mixture, such as a mixture of isomers, including atropisomers, thereof. The invention provides a compound which is ≥80% of the mixture; ≥85% of the mixture; ≥90% of the mixture; or ≥95% of the mixture. In one embodiment, the invention provides a sample of a compound of the invention, wherein the structure depicted by the chemical drawing or the chemical name of the compound of the invention comprises that 97% of the sample.

Suitably, the invention provides a compound, or a pharmaceutically acceptable salt thereof, which is an atropisomer. In one embodiment, a compound of the invention may comprise a mixture wherein the atropisomer comprises ≥80% of the sample after storage at room temperature for ≥6 months. In another embodiment, a compound of the invention may comprise a mixture wherein the atropisomer comprises ≥85% of the sample after storage at room temperature for ≥6 months. In still another embodiment, a compound of the invention may comprise a mixture wherein the atropisomer comprises ≥90% of the sample after storage at room temperature for ≥6 months. In one embodiment, a compound of the invention may comprise a mixture wherein the atropisomer comprises ≥95% of the sample after storage at room temperature for ≥6 months. In yet another embodiment, a compound of the invention may comprise a mixture wherein the atropisomer comprises ≥97% of the sample after storage at room temperature for ≥6 months.

In one embodiment, a compound of the invention may comprise a mixture wherein the atropisomer comprises ≥80% of the sample after storage at room temperature for ≥12 months. In another embodiment, a compound of the invention may comprise a mixture wherein the atropisomer comprises ≥85% of the sample after storage at room temperature for ≥12 months. In still another embodiment, a compound of the invention may comprise a mixture wherein the atropisomer comprises ≥90% of the sample after storage at room temperature for ≥12 months. In one embodiment, a compound of the invention may comprise a mixture wherein the atropisomer comprises ≥95% of the sample after storage at room temperature for ≥12 months. In yet another embodiment, a compound of the invention may comprise a mixture wherein the atropisomer comprises ≥97% of the sample after storage at room temperature for ≥12 months.

In one aspect, the invention provides Compound A which is:

Compound A

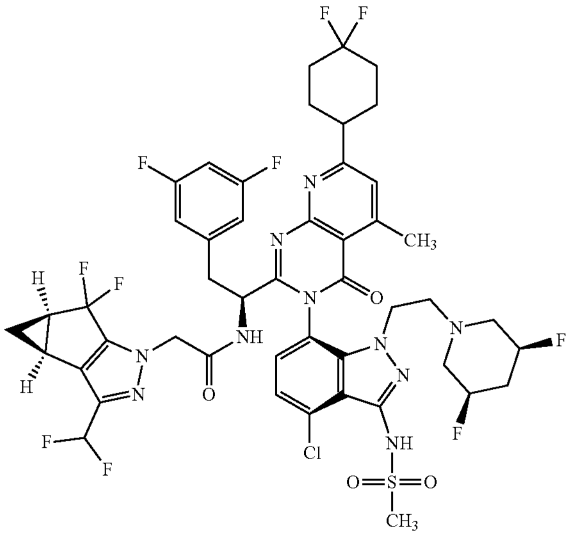

or a pharmaceutically acceptable salt thereof.

The name IUPAC of Compound A is N-[(1S)-1-[(3P)-3-(4-chloro-1-{2-[(3R,5S)-3,5-difluoropiperidin-1-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide. One of skill in the art would understand that an alternate name for Compound A is N-((S)-1-(3-(4-chloro-1-(2-((3R,5S)-3,5-difluoropiperidin-1-yl)ethyl)-3-(methylsulfonamido)-1H-indazol-7-yl)-7-(4,4-difluorocyclohexyl)-5-methyl-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.

In one embodiment, the invention provides crystalline Compound A (Form 1).

The XRPD peak list for Compound A (Form 1) (Example 5A (Form 1)) is found in Table 1.

In one embodiment, a crystalline form of Compound A (Form 1) (Example 5A (Form 1)) is characterized by an X-ray powder diffraction (XRPD) pattern comprising at least nine diffraction angles, when measured using Cu $K_\alpha$ radiation, selected from a group consisting of about 5.1, 6.2, 7.5, 7.9, 9.5, 10.4, 11.5, 13, 14.7, 15.1, 15.9, 16.1, 16.7, 17, 17.6, 18.7, 19.8, 20.2, 20.7, 21.8, 24.5, 25.4, and 34.5 degrees±0.2° 2θ.

In one embodiment, a crystalline form Compound A (Form 1) (Example 5A (Form 1)) is characterized by an XRPD pattern comprising at least eight diffraction angles, or at least seven diffraction angles, or at least six diffraction angles, or at least five diffraction angles, or at least four diffraction angles, when measured using Cu $K_\alpha$ radiation, selected from a group consisting of about 5.1, 6.2, 7.5, 7.9, 9.5, 10.4, 11.5, 13, 14.7, 15.1, 15.9, 16.1, 16.7, 17, 17.6, 18.7, 19.8, 20.2, 20.7, 21.8, 24.5, 25.4, and 34.5 degrees±0.2° 2θ.

In one embodiment, a crystalline form Compound A (Form 1) (Example 5A (Form 1)) is characterized by an XRPD pattern comprising at least eight diffraction angles, or at least seven diffraction angles, or at least six diffraction angles, or at least five diffraction angles, or at least four diffraction angles, when measured using Cu $K_\alpha$ radiation, selected from a group consisting of about 6.2, 7.5, 9.5, 11.5, 14.7, 15.1, 15.9, 16.7, 18.7, 19.8, 20.2, 20.7, and 25.4 degrees±0.2° 2θ.

In one embodiment, the invention provides a crystalline form of Compound A (Form 1) (Example 5A (Form 1)) wherein the characterizing peaks of Compound A (Form 1) (Example 5A (Form 1)), when measured using Cu $K_\alpha$ radiation, are selected from a group consisting of about 15.1, 15.9, 16.7, and 20.7 degrees±0.2° 2θ.

In one embodiment, a crystalline form Compound A (Form 1) (Example 5A (Form 1)) is characterized by an X-ray powder diffraction pattern substantially in accordance with that shown in FIG. 1.

In one embodiment, a crystalline form Compound A (Form 1) (Example 5A (Form 1)) is characterized by a DSC thermogram having a melting onset of about 209° C.

Figure 2:
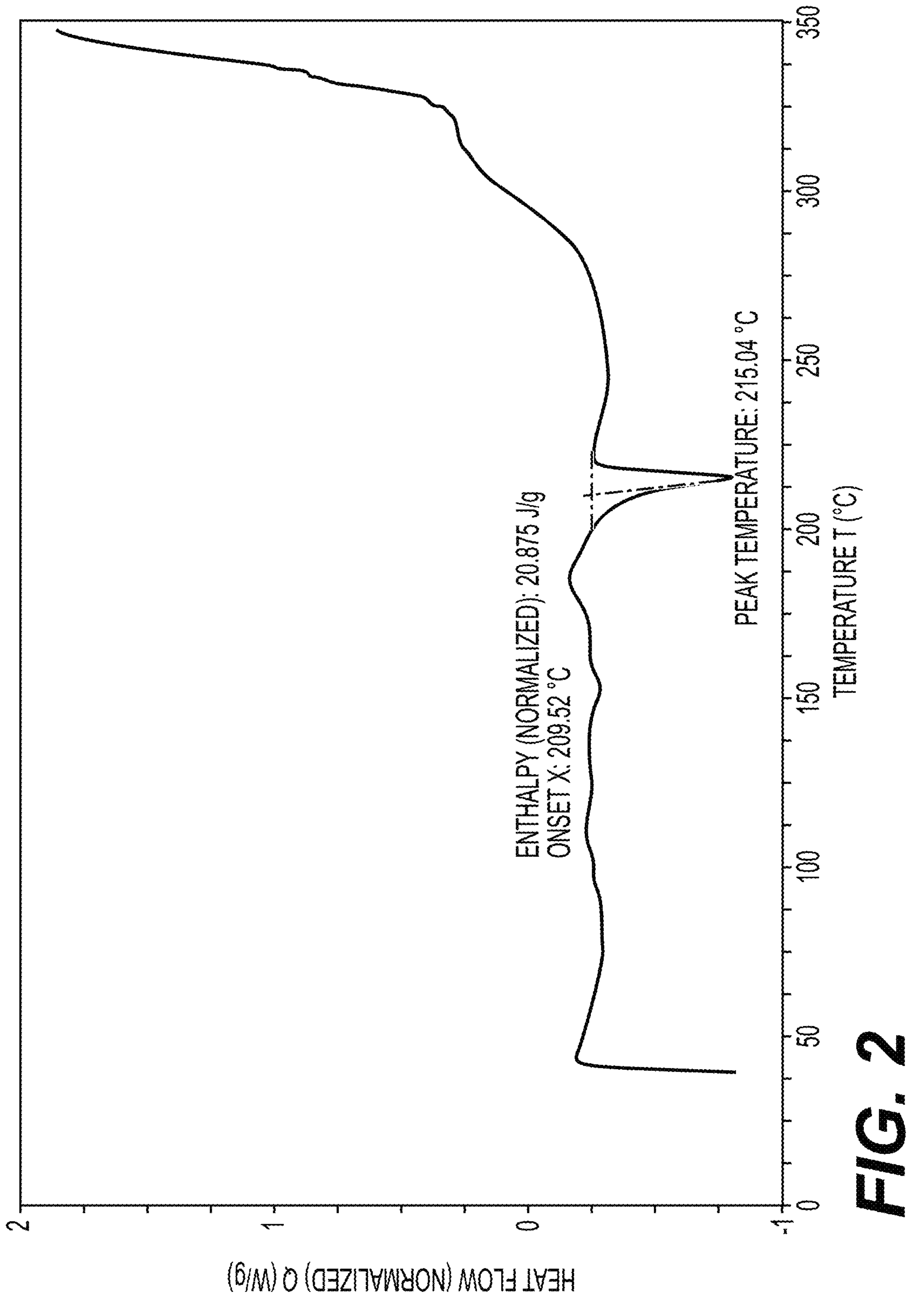
FIG. 2 depicts a Differential Scanning Calorimetry (DSC) curve of a crystalline form of the compound of Example 5A (Form 1), (Compound A (Form 1)).

In one embodiment, a crystalline form Compound A (Form 1) (Example 5A (Form 1)) is characterized by a DSC thermogram substantially in accordance with that shown in FIG. 2.

In one embodiment, the temperature at which the crystalline form of Compound A (Form 1) (Example 5A (Form 1)) begins to melt is determined by differential scanning calorimetry ("DSC") and is referred to as the "melting onset temperature". In one embodiment, a crystalline form of Compound A (Form 1) (Example 5A (Form 1)) is characterized by a melting onset temperature of 204-214° C. In one embodiment, a crystalline form of Compound A (Form 1) (Example 5A (Form 1)) is characterized by a melting onset temperature of 207-211° C. In one embodiment, a crystalline form of Compound A (Form 1) (Example 5A (Form 1)) is characterized by a melting onset temperature of 207, 208, 209, 210, or 211° C. In one embodiment, a crystalline form of Compound A (Form 1) (Example 5A (Form 1)) is characterized by a melting onset temperature of 209±5° C.

In one aspect, the invention provides Compound B which is

Compound B

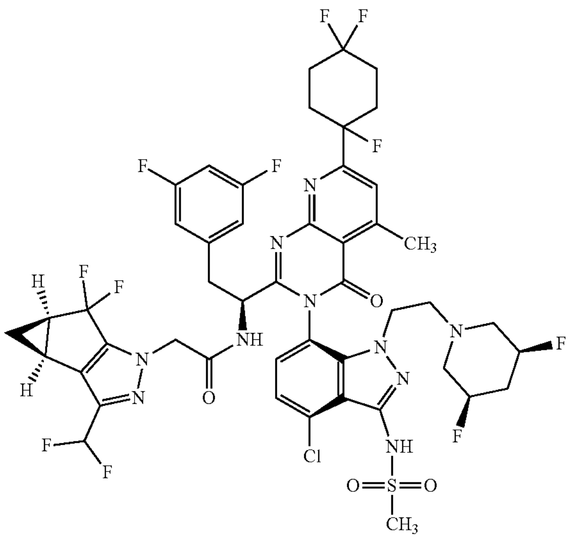

or a pharmaceutically acceptable salt thereof.

The IUPAC name of Compound B is N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide. One of skill in the art would understand that an alternate name for Compound B is N-((1S)-1-(3-(4-chloro-1-(2-((3S,5R)-3,5-difluoropiperidin-1-yl)ethyl)-3-(methylsulfonamido)-1H-indazol-7-yl)-5-methyl-4-oxo-7-(1,4,4-trifluorocyclohexyl)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.

In one embodiment, the invention provides crystalline Compound B (Form 1).

The XRPD peak list for Compound B (Form 1) (Example 11A (Form 1)) is found in Table 2.

In one embodiment, a crystalline form of Compound B (Form 1) (Example 11A (Form 1)) is characterized by an X-ray powder diffraction (XRPD) pattern comprising at least nine diffraction angles, when measured using Cu $K_\alpha$ radiation, selected from a group consisting of about 4.0, 6.3, 7.9, 9.3, 9.7, 10.5, 12.6, 12.9, 13.9, 14.5, 15.2, 15.9, 16.7, 18.7, 19.0, 20.0, 20.9, 21.2, 21.8, 22.3, 22.9, 24.6, 25.0, 25.6, 26.0, 27.0, 28.4, 29.2, 30.8, 31.6, 32.1, 32.8, 33.7, 34.7, 35.1, 35.7, 37, 37.7, and 38.6 degrees±0.2° 2θ.

In one embodiment, a crystalline form of Compound B (Form 1) (Example 11A (Form 1)) is characterized by an XRPD pattern comprising at least eight diffraction angles, or at least seven diffraction angles, or at least six diffraction angles, or at least five diffraction angles, or at least four diffraction angles, when measured using Cu $K_\alpha$ radiation, selected from a group consisting of about 4.0, 6.3, 7.9, 9.3, 9.7, 10.5, 12.6, 12.9, 13.9, 14.5, 15.2, 15.9, 16.7, 18.7, 19.0, 20.0, 20.9, 21.2, 21.8, 22.3, 22.9, 24.6, 25.0, 25.6, 26.0, 27.0, 28.4, 29.2, 30.8, 31.6, 32.1, 32.8, 33.7, 34.7, 35.1, 35.7, 37, 37.7, and 38.6 degrees±0.2° 2θ.

In one embodiment, a crystalline form of Compound B (Form 1) (Example 11A (Form 1)) is characterized by an XRPD pattern comprising at least eight diffraction angles, or at least seven diffraction angles, or at least six diffraction angles, or at least five diffraction angles, or at least four diffraction angles, when measured using Cu $K_\alpha$ radiation, selected from a group consisting of about 7.9, 9.3, 9.7, 13.9, 15.2, 15.9, 16.7, 18.7, 220.9, 21.2, 25.0, 25.6, 30.8, and 32.1 degrees±0.2° 2θ.

In one embodiment, the invention provides a crystalline form of Compound B (Form 1) (Example 11A (Form 1)) wherein the characterizing peaks of Compound B (Form 1), when measured using Cu $K_\alpha$ radiation, are selected from a group consisting of about 15.2, 15.9, 16.7, and 20.0 degrees±0.2° 2θ.

Figure 4:
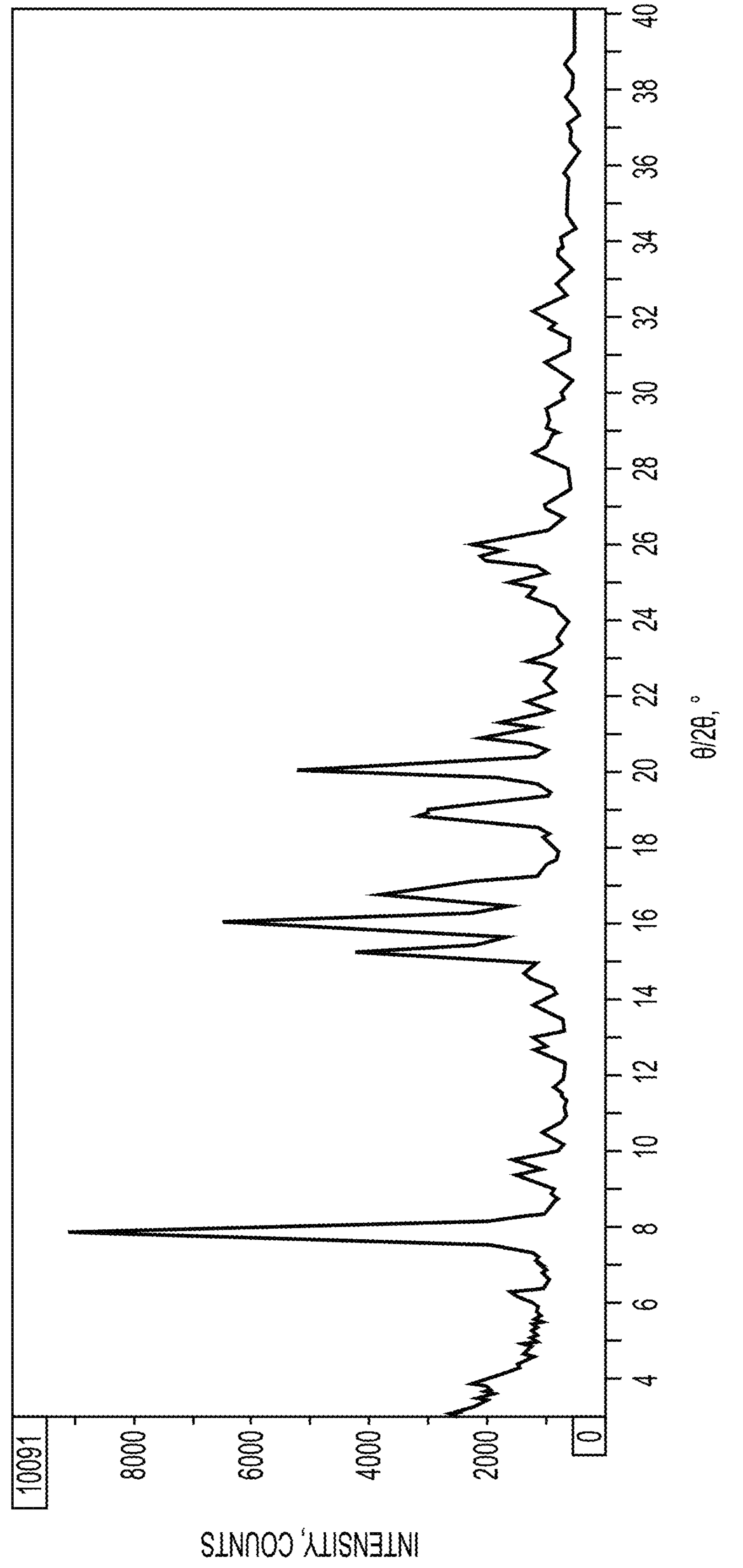
FIG. 4 depicts an XRPD pattern of a crystalline form of the compound of Example 11A (Form 1), N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide (Compound B (Form 1)).

In one embodiment, a crystalline form of Compound B (Form 1) (Example 11A (Form 1)) is characterized by an X-ray powder diffraction pattern substantially in accordance with that shown in FIG. 4.

In one embodiment, a crystalline form of Compound B (Form 1) (Example 11A (Form 1)) is characterized by a DSC thermogram having a melting onset of about 132° C.

Figure 5:
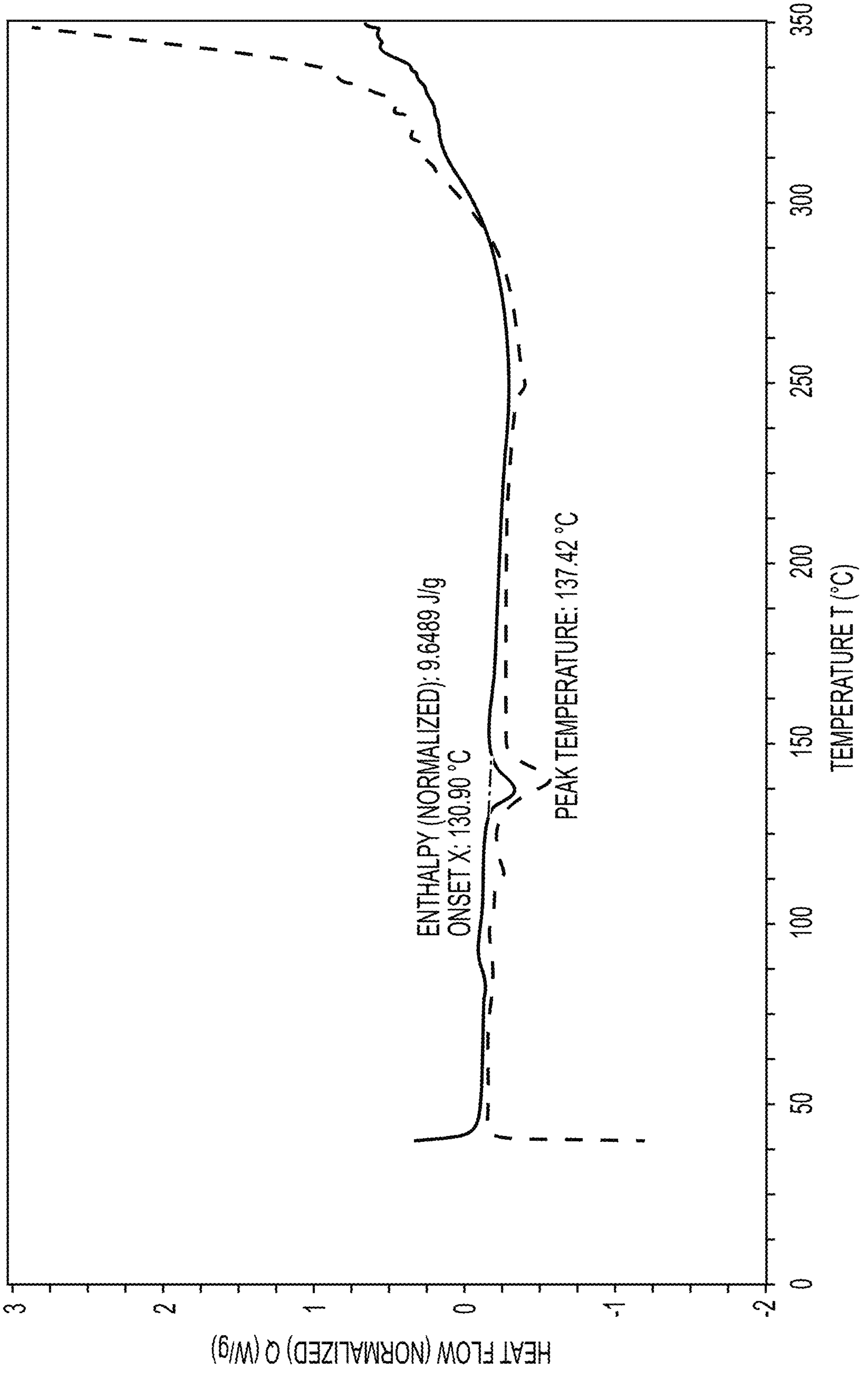
FIG. 5 depicts a DSC curve of a crystalline form of the compound of Example 11A (Form 1) (Compound B (Form 1)).

In one embodiment, a crystalline form of Compound B (Form 1) (Example 11A (Form 1)) is characterized by a DSC thermogram substantially in accordance with that shown in FIG. 5.

In one embodiment, the temperature at which the crystalline form of Compound B (Form 1) (Example 11A (Form 1)) begins to melt is determined by differential scanning calorimetry ("DSC") and is referred to as the "melting onset temperature". In one embodiment, a crystalline form of Compound B (Form 1) (Example 11A (Form 1)) is characterized by a melting onset temperature of 127-137° C. In one embodiment, a crystalline form of Compound B (Form 1) (Example 11A (Form 1)) is characterized by a melting onset temperature of 130-134° C. In one embodiment, a crystalline form of Compound B (Form 1) (Example 11A (Form 1)) is characterized by a melting onset temperature of 130, 131, 132, 133, or 134° C. In one embodiment, a crystalline form of Compound B (Form 1) (Example 11A (Form 1)) is characterized by a melting onset temperature of 132±5° C.

In one aspect, the invention provides Compound C which is:

Compound C

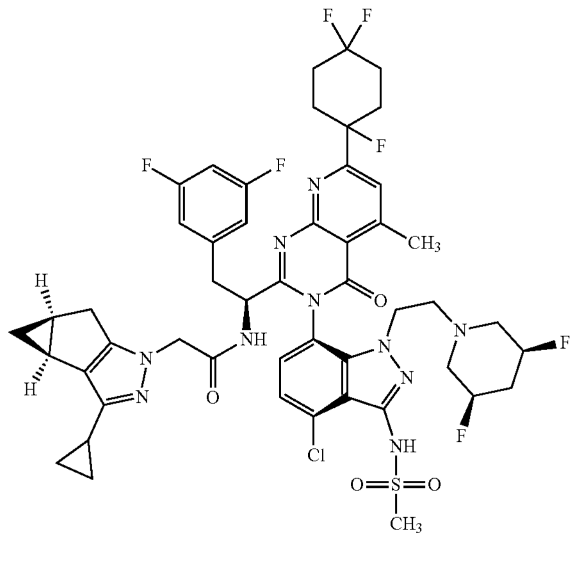

or a pharmaceutically acceptable salt thereof.

The name IUPAC of Compound C is N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d] pyrimidin-2-yl]-2-(3,5-difluorophenyl)ethyl]-2-[(2S,4S)-9-cyclopropyl-7,8-diazatricyclo[$4.3.0.0^{2,4}$]nona-1(6),8-dien-7-yl]acetamide. One of skill in the art would understand that an alternate name for Compound C is N-((1S)-1-(3-(4-chloro-1-(2-((3S,5R)-3,5-difluoropiperidin-1-yl)ethyl)-3-(methylsulfonamido)-1H-indazol-7-yl)-5-methyl-4-oxo-7-(1,4,4-trifluorocyclohexyl)-3,4-dihydropyrido[2,3-d] pyrimidin-2-yl)-2-(3,5-difluorophenyl)ethyl)-2-((3bS,4aS)-3-cyclopropyl-3b,4,4a,5-tetrahydro-1H-cyclopropa[3,4] cyclopenta[1,2-c]pyrazol-1-yl)acetamide.

In one embodiment, the invention provides crystalline Compound C (Form 1).

The XRPD peak list for Compound C (Form 1) (Example 12A (Form 1)) is found in Table 3.

In one embodiment, a crystalline form of Compound C (Form 1) (Example 12A (Form 1)) is characterized by an X-ray powder diffraction (XRPD) pattern comprising at least nine diffraction angles, when measured using Cu $K_\alpha$ radiation, selected from a group consisting of about 5.9, 6.5, 7.8, 9.2, 9.8, 10.3, 10.5, 10.9, 11.2, 12.1, 12.8, 13.9, 15.6, 16.3, 16.7, 17.2, 18.1, 19.1, 19.5, 20.0, 20.9, 21.2, 21.9, 22.2, 22.7, 23.1, 23.7, 24.4, 25.6, 26.3, 27.0, 27.7, 28.4, 30.0, 31.3, 31.9, 32.6, 33.6, 34.4, and 38.7 degrees±0.2° 2θ.

In one embodiment, a crystalline form of Compound C (Form 1) (Example 12A (Form 1)) is characterized by an XRPD pattern comprising at least eight diffraction angles, or at least seven diffraction angles, or at least six diffraction angles, or at least five diffraction angles, or at least four diffraction angles, when measured using Cu $K_\alpha$ radiation, selected from a group consisting of about 5.9, 6.5, 7.8, 9.2, 9.8, 10.3, 10.5, 10.9, 11.2, 12.1, 12.8, 13.9, 15.6, 16.3, 16.7, 17.2, 18.1, 19.1, 19.5, 20.0, 20.9, 21.2, 21.9, 22.2, 22.7, 23.1, 23.7, 24.4, 25.6, 26.3, 27.0, 27.7, 28.4, 30.0, 31.3, 31.9, 32.6, 33.6, 34.4, and 38.7 degrees±0.2° 2θ.

In one embodiment, a crystalline form Compound C (Form 1) (Example 12A (Form 1)) is characterized by an XRPD pattern comprising at least eight diffraction angles, or at least seven diffraction angles, or at least six diffraction angles, or at least five diffraction angles, or at least four diffraction angles, when measured using Cu $K_\alpha$ radiation, selected from a group consisting of about 5.9, 6.5, 10.9, 12.1, 12.8, 13.9, 16.7, 17.2, 18.1, 19.5, 220.9, 22.2, 23.7, and 25.6 degrees±0.2° 2θ.

In one embodiment, the invention provides a crystalline form of Compound C (Form 1) (Example 12A (Form 1)) wherein the characterizing peaks of Compound C (Form 1), when measured using Cu $K_\alpha$ radiation, are selected from a group consisting of about 12.1, 13.9, 18.1, 20.9, and 22.2 degrees±0.2° 2θ as measured by x-ray powder diffraction using an x-ray wavelength of 1.5406 Δ.

Figure 7:
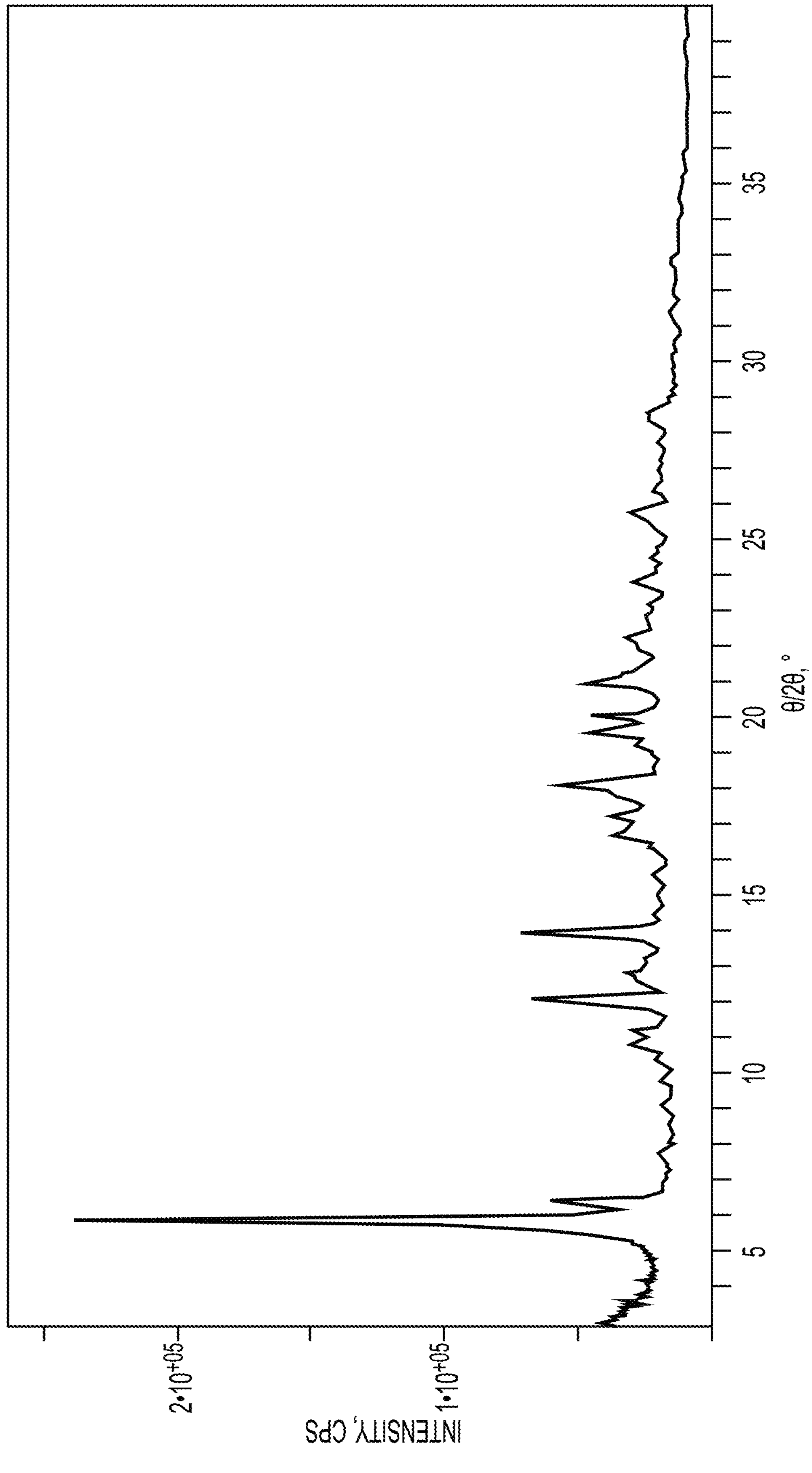
FIG. 7 depicts an XRPD pattern of a crystalline form of the compound of Example 12A (Form 1), N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide (Compound C (Form 1)).

In one embodiment, a crystalline form Compound C (Form 1) (Example 12A (Form 1)) is characterized by an X-ray powder diffraction pattern substantially in accordance with that shown in FIG. 7.

In one embodiment, a crystalline form Compound C (Form 1) (Example 12A (Form 1)) is characterized by a DSC thermogram having a melting onset of about 123° C.

Figure 8:
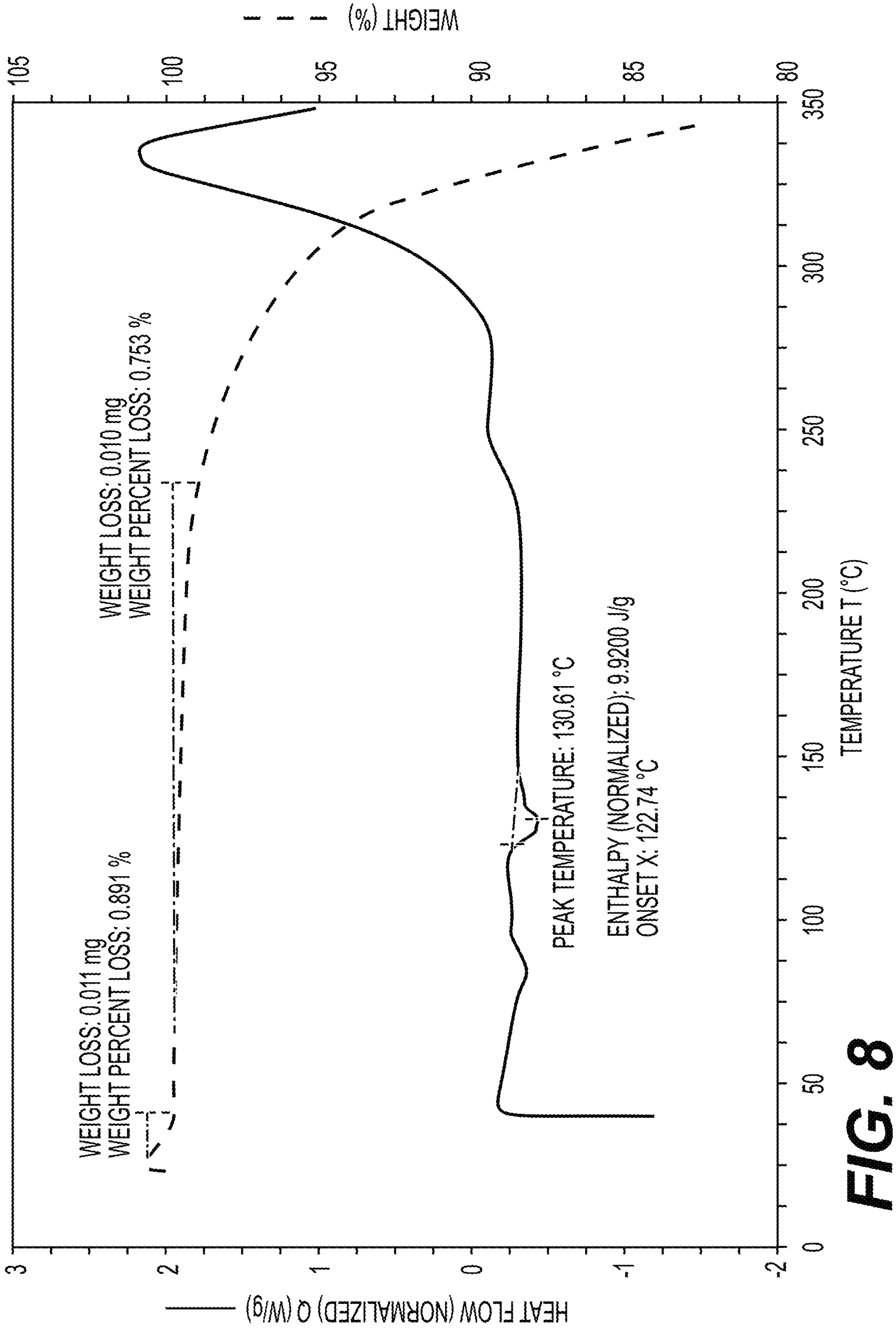
FIG. 8 depicts an overlay of DSC and TGA thermograms of a crystalline form of the compound of Example 12A (Form 1) (Compound C (Form 1)) exhibiting a melting onset of about 123° C. and a weight loss of about 0.75 wt %.

In one embodiment, a crystalline form Compound C (Form 1) (Example 12A (Form 1)) is characterized by a DSC thermogram substantially in accordance with that shown in FIG. 8.

In one embodiment, the temperature at which the crystalline form of Compound C (Form 1) (Example 12A (Form 1)) begins to melt is determined by differential scanning calorimetry ("DSC") and is referred to as the "melting onset temperature". In one embodiment, a crystalline form of Compound C (Form 1) (Example 12A (Form 1)) is characterized by a melting onset temperature of 118-128° C. In one embodiment, a crystalline form of Compound C (Form 1) (Example 12A (Form 1)) is characterized by a melting onset temperature of 121-125° C. In one embodiment, a crystalline form of Compound C (Form 1) (Example 12A (Form 1)) is characterized by a melting onset temperature of 121, 122, 123, 124, or 125° C. In one embodiment, a crystalline form of Compound C (Form 1) (Example 12A (Form 1)) is characterized by a melting onset temperature of 123±5° C.

In one aspect, the invention provides Compound D which is

Compound D

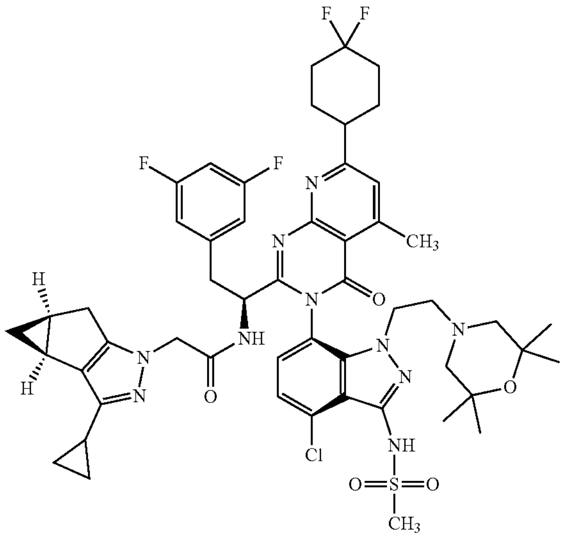

or a pharmaceutically acceptable salt thereof.

The IUPAC name of Compound D is N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d] pyrimidin-2-yl]-2-(3,5-difluorophenyl)ethyl]-2-[(2S,4S)-9-cyclopropyl-7,8-diazatricyclo[$4.3.0.0^{2,4}$]nona-1(6),8-dien-7-yl]acetamide. One of skill in the art would understand that an alternate name for Compound D is N-((S)-1-(3-(4-chloro-3-(methylsulfonamido)-1-(2-(2,2,6,6-tetramethylmorpholino)ethyl)-1H-indazol-7-yl)-7-(4,4-difluorocyclohexyl)-5-methyl-4-oxo-3,4-dihydropyrido[2,3-d]pyrimidin-2-yl)-2-(3,5-difluorophenyl)ethyl)-2-((3bS,4aS)-3-cyclopropyl-3b,4,4a,5-tetrahydro-1H-cyclopropa[3,4] cyclopenta[1,2-c]pyrazol-1-yl)acetamide.

In one embodiment, the invention provides crystalline Compound D (Form 1).

The XRPD peak list for Compound D (Form 1) (Example 13A (Form 1)) is found in Table 4.

In one embodiment, a crystalline form of Compound D (Form 1) (Example 13A (Form 1)) is characterized by an X-ray powder diffraction (XRPD) pattern comprising at least nine diffraction angles, when measured using Cu $K_\alpha$ radiation, selected from a group consisting of about 5.1, 5.6, 6.9, 7.6, 8.2, 8.7, 9.1, 9.8, 11.1, 11.3, 11.9, 13.2, 13.9, 14.4, 14.7, 15.2, 15.4, 16.0, 16.6, 16.8, 17.2, 17.5, 18.4, 18.7, 19.1, 19.4, 19.9, 20.3, 20.5, 21.0, 21.4, 22.0, 22.6, 23.8, 24.0, 24.4, 24.7, 25.1, 25.8, 26.2, 26.8, 27.0, 27.6, 27.9, 28.5, 28.8, 29.2, 29.8, 30.1, 31.1, 31.3, 31.9, 32.5, 32.7, 33.2, 34.1, 34.8, 35.4, 36.1, 37.7, 38.7, 39.0, 39.5, and 39.7 degrees±0.2° 2θ.

In one embodiment, a crystalline form of Compound D (Form 1) (Example 13A (Form 1)) is characterized by an XRPD pattern comprising at least eight diffraction angles, or at least seven diffraction angles, or at least six diffraction angles, or at least five diffraction angles, or at least four diffraction angles, when measured using Cu $K_\alpha$ radiation, selected from a group consisting of about 5.1, 5.6, 6.9, 7.6, 8.2, 8.7, 9.1, 9.8, 11.1, 11.3, 11.9, 13.2, 13.9, 14.4, 14.7, 15.2, 15.4, 16.0, 16.6, 16.8, 17.2, 17.5, 18.4, 18.7, 19.1, 19.4, 19.9, 20.3, 20.5, 21.0, 21.4, 22.0, 22.6, 23.8, 24.0, 24.4, 24.7, 25.1, 25.8, 26.2, 26.8, 27.0, 27.6, 27.9, 28.5, 28.8, 29.2, 29.8, 30.1, 31.1, 31.3, 31.9, 32.5, 32.7, 33.2, 34.1, 34.8, 35.4, 36.1, 37.7, 38.7, 39.0, 39.5, and 39.7±0.2° 2θ.

In one embodiment, a crystalline form of Compound D (Form 1) (Example 13A (Form 1)) is characterized by an XRPD pattern comprising at least eight diffraction angles, or at least seven diffraction angles, or at least six diffraction angles, or at least five diffraction angles, or at least four diffraction angles, when measured using Cu $K_\alpha$ radiation, selected from a group consisting of about 5.6, 7.6, 8.7, 9.1, 14.7, 15.4, 16.8, 17.2, 18.4, 19.1, 20.5, 21.4, 22.0, 22.6, and 27.0 degrees±0.2° 2θ.

In one embodiment, a crystalline form of Compound D (Form 1) (Example 13A (Form 1)) is characterized by an XRPD pattern comprising at least eight diffraction angles, or at least seven diffraction angles, or at least six diffraction angles, or at least five diffraction angles, or at least four diffraction angles, when measured using Cu $K_\alpha$ radiation, selected from a group consisting of about 11.9, 13.2, 14.7, 17.2, 19.4, 19.9, 21.0, 21.4, 23.8, 24.0, 24.7, 27.0, 27.6, 27.9, and 30.1 degrees±0.2° 2θ.

In one embodiment, the invention provides a crystalline form of Compound D (Form 1) (Example 13A (Form 1)) wherein the characterizing peaks of Compound D (Form 1), when measured using Cu $K_\alpha$ radiation, are selected from a group consisting of about 14.7, 17.2, 21.4, and 27.0 degrees±0.2° 2θ

Figure 9:
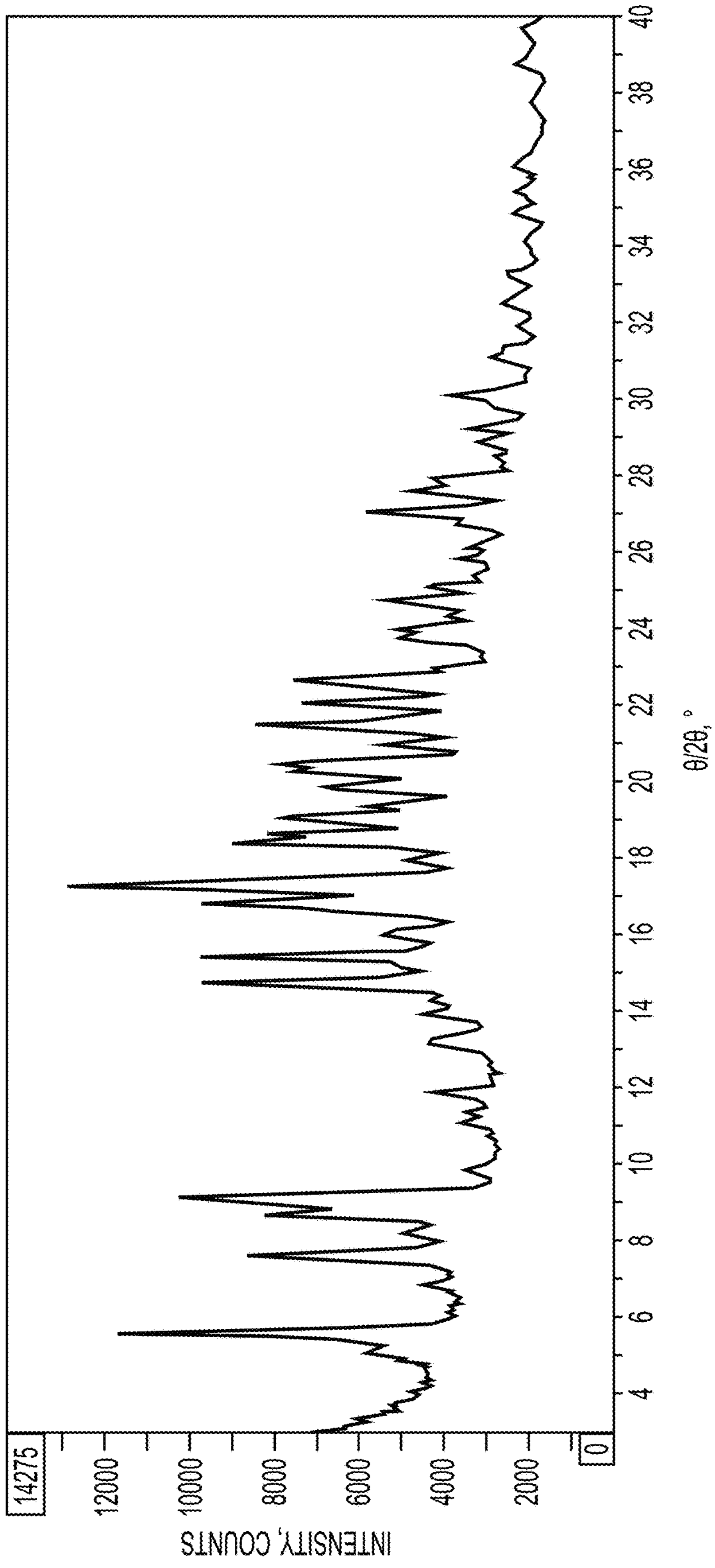
FIG. 9 depicts an XRPD pattern of a crystalline form of the compound of Example 13A (Form 1), N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide (Compound D (Form 1)).

In one embodiment, a crystalline form of Compound D (Form 1) (Example 13A (Form 1)) is characterized by an X-ray powder diffraction pattern substantially in accordance with that shown in FIG. 9.

In one embodiment, a crystalline form of Compound D (Form 1) (Example 13A (Form 1)) is characterized by a DSC thermogram having a melting onset of about 216° C.

Figure 10:
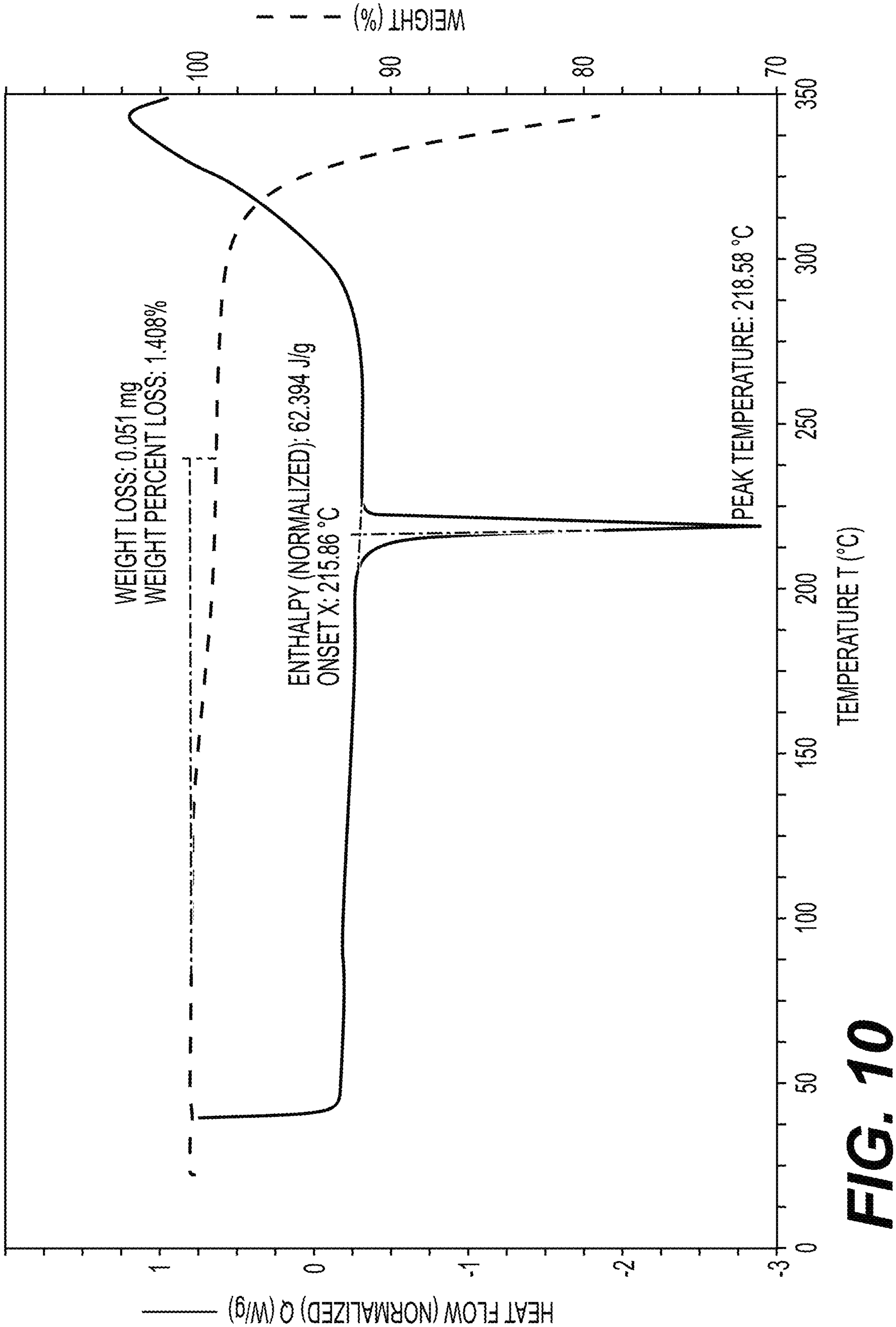
FIG. 10 depicts an overlay of DSC and TGA thermograms of a crystalline form of the compound of Example 13A (Form 1) (Compound D (Form 1)) exhibiting a melting onset of about 216° C. and a weight loss of about 1.4 wt %.

In one embodiment, a crystalline form of Compound D (Form 1) (Example 13A (Form 1)) is characterized by a DSC thermogram substantially in accordance with that shown in FIG. 10.

In one embodiment, the temperature at which the crystalline form of Compound D (Form 1) (Example 13A (Form 1)) begins to melt is determined by differential scanning calorimetry ("DSC") and is referred to as the "melting onset temperature". In one embodiment, a crystalline form of Compound D (Form 1) (Example 13A (Form 1)) is characterized by a melting onset temperature of 211-221° C. In one embodiment, a crystalline form of Compound D (Form 1) (Example 13A (Form 1)) is characterized by a melting onset temperature of 214-218° C. In one embodiment, a crystalline form of Compound D (Form 1) (Example 13A (Form 1)) is characterized by a melting onset temperature of 214, 215, 216, 217, or 218° C. In one embodiment, a crystalline form of Compound D (Form 1) (Example 13A (Form 1)) is characterized by a melting onset temperature of 216±5° C.

In one aspect, the invention provides Compound E which is:

Compound E

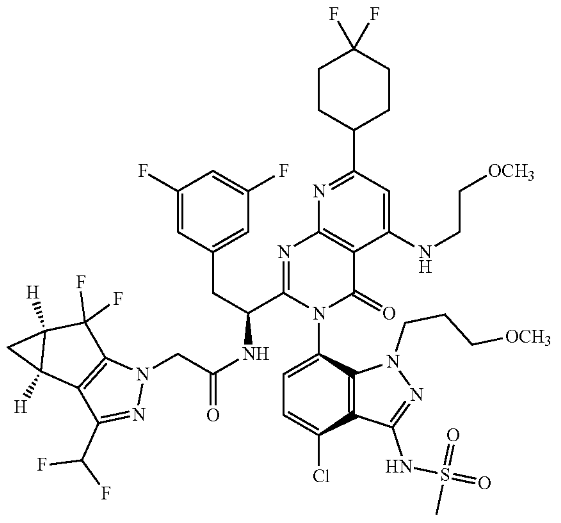

or a pharmaceutically acceptable salt thereof.

The IUPAC name of Compound E is N-[(1S)-1-[(3P)-3-[4-chloro-3-methanesulfonamido-1-(3-methoxypropyl)-1H-indazol-7-yl]-7-(4,4-difluorocyclohexyl)-5-[(2-methoxyethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide. One of skill in the art would understand that an alternate name for Compound E is N-((S)-1-(3-(4-chloro-1-(3-methoxypropyl)-3-(methylsulfonamido)-1H-indazol-7-yl)-7-(4,4-difluorocyclohexyl)-5-((2-methoxyethyl)amino)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.

In one embodiment, the invention provides crystalline Compound E (Form 1).

The XRPD peak list for Compound E (Form 1) (Example 135A (Form 1)) is found in Table 5.

In one embodiment, a crystalline form of Compound E (Form 1) (Example 135A (Form 1)) is characterized by an X-ray powder diffraction (XRPD) pattern comprising at least nine diffraction angles, when measured using Cu $K_\alpha$ radiation, selected from a group consisting of about 6.5, 7.4, 8.1, 9.0, 9.6, 10.2, 11.5, 12.7, 13.1, 13.5, 13.7, 14.1, 14.6, 14.7, 15.0, 15.9, 16.4, 16.8, 17.2, 17.5, 18.3, 18.6, 19.3, 20.0, 20.4, 21.2, 21.5, 22.1, 22.6, 23.1, 23.5, 25.0, 25.3, 25.5, 25.9, 26.1, 26.6, 26.9, 27.2, 27.6, 28.3, 28.7, 29.4, 30.1, 30.8, 31.4, 31.6, 32.1, 33.2, 34.3, 34.5, 36.0, 36.5, 37.3, 38.5, and 39.1 degrees±0.2° 2θ.

In one embodiment, a crystalline form of Compound E (Form 1) (Example 135A (Form 1)) is characterized by an XRPD pattern comprising at least eight diffraction angles, or at least seven diffraction angles, or at least six diffraction angles, or at least five diffraction angles, or at least four diffraction angles, when measured using Cu $K_\alpha$ radiation, selected from a group consisting of about 6.5, 7.4, 8.1, 9.0, 9.6, 10.2, 11.5, 12.7, 13.1, 13.5, 13.7, 14.1, 14.6, 14.7, 15.0, 15.9, 16.4, 16.8, 17.2, 17.5, 18.3, 18.6, 19.3, 20.0, 20.4, 21.2, 21.5, 22.1, 22.6, 23.1, 23.5, 25.0, 25.3, 25.5, 25.9, 26.1, 26.6, 26.9, 27.2, 27.6, 28.3, 28.7, 29.4, 30.1, 30.8, 31.4, 31.6, 32.1, 33.2, 34.3, 34.5, 36.0, 36.5, 37.3, 38.5, and 39.1 degrees±0.2° 2θ.

In one embodiment, a crystalline form of Compound E (Form 1) (Example 135A (Form 1)) is characterized by an XRPD pattern comprising at least eight diffraction angles, or at least seven diffraction angles, or at least six diffraction angles, or at least five diffraction angles, or at least four diffraction angles, when measured using Cu $K_\alpha$ radiation, selected from a group consisting of about 7.4, 8.1, 9.6, 11.5, 12.7, 13.1, 15.9, 17.2, 19.3, 20.4, 22.1, 25.3, 25.5, 30.1, and 32.1 degrees±0.2° 2θ.

In one embodiment, a crystalline form Compound E (Form 1) (Example 135A (Form 1)) is characterized by an XRPD pattern comprising at least eight diffraction angles, or at least seven diffraction angles, or at least six diffraction angles, or at least five diffraction angles, or at least four diffraction angles, when measured using Cu $K_\alpha$ radiation, selected from a group consisting of about 6.5, 9.0, 14.1, 14.6, 15.9, 16.4, 17.2, 19.3, 21.2, 22.1, 23.1, 26.1, 26.6, 27.6, and 29.4 degrees±0.2° 2θ.

In one embodiment, the invention provides a crystalline form of Compound E (Form 1) (Example 135A (Form 1)) wherein the characterizing peaks of Compound E (Form 1), when measured using Cu $K_\alpha$ radiation, are selected from a group consisting of about 15.9, 17.2, 19.3, and 22.1 degrees±0.2° 2θ.

Figure 11:
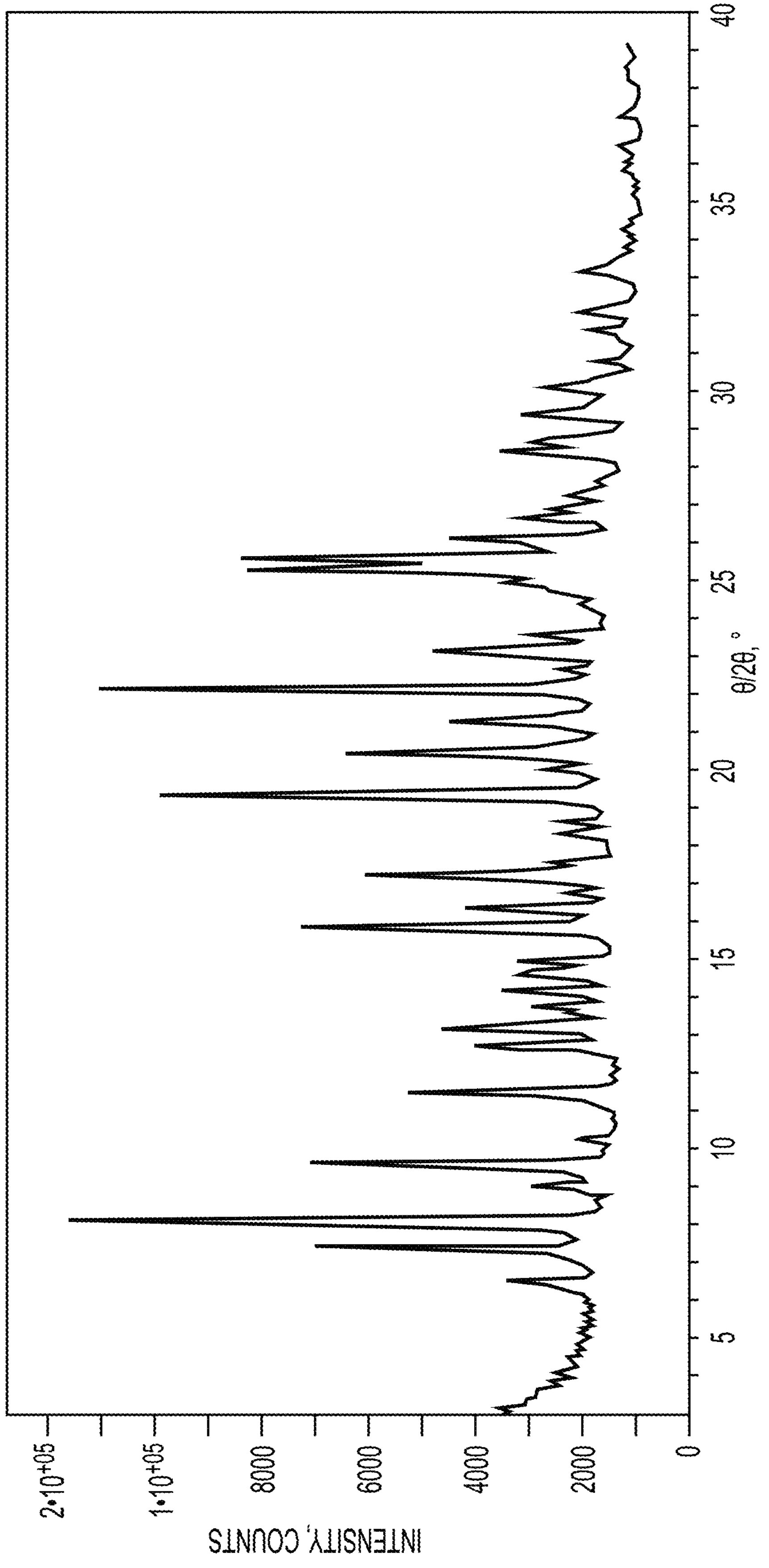
FIG. 11 depicts an XRPD pattern of a crystalline form of the compound of Example 135A (Form 1), N-[(1S)-1-[(3P)-3-[4-chloro-3-methanesulfonamido-1-(3-methoxypropyl)-1H-indazol-7-yl]-7-(4,4-difluorocyclohexyl)-5-[(2-methoxyethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide (Compound E (Form 1)).

In one embodiment, a crystalline form of Compound E (Form 1) (Example 135A (Form 1)) is characterized by an X-ray powder diffraction pattern substantially in accordance with that shown in FIG. 11.

In one embodiment, a crystalline form of Compound E (Form 1) (Example 135A (Form 1)) is characterized by a DSC thermogram having a first melting onset of about 210° C., and a second melting onset of about 225° C.

Figure 12:
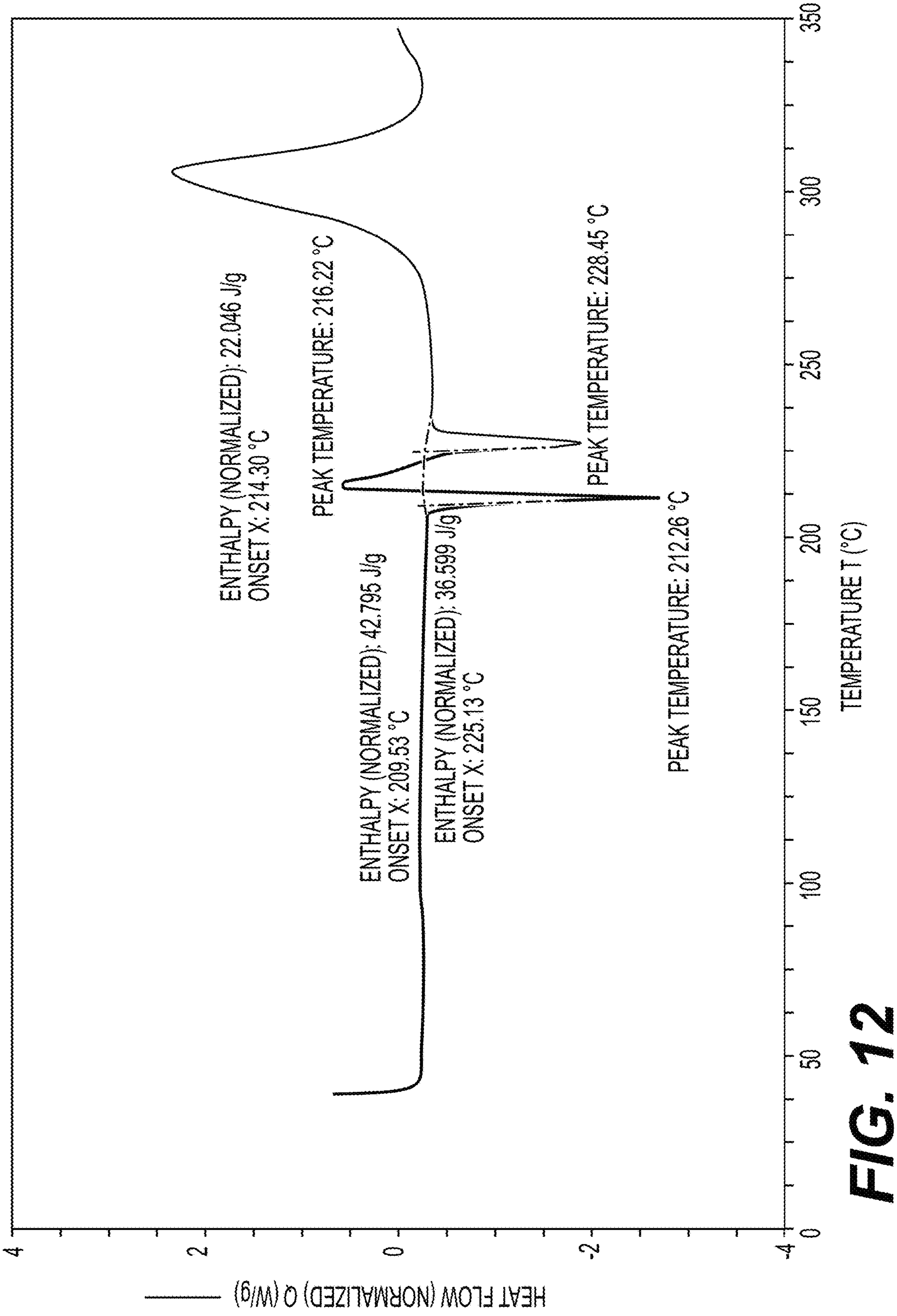
FIG. 12 depicts a DSC curve of a crystalline form of the compound of Example 135A (Form 1) (Compound E (Form 1)).

In one embodiment, a crystalline form of Compound E (Form 1) (Example 135A (Form 1)) is characterized by a DSC thermogram substantially in accordance with that shown in FIG. 12.

In one embodiment, the temperature at which the crystalline form of Compound E (Form 1) (Example 135A (Form 1)) begins to melt is determined by differential scanning calorimetry ("DSC") and is referred to as the "melting onset temperature". In one embodiment, a crystalline form of Compound E (Form 1) (Example 135A (Form 1)) is characterized by having two melting onset temperatures corresponding to two distinct melting events. In one embodiment, a crystalline form of Compound E (Form 1) (Example 135A (Form 1)) is characterized by a melting onset temperature of 205-215° C. In one embodiment, a crystalline form of Compound E (Form 1) (Example 135A (Form 1)) is characterized by a melting onset temperature of 208-212° C. In one embodiment, a crystalline form of Compound E (Form 1) (Example 135A (Form 1)) is characterized by a melting onset temperature of 208, 209, 210, 211, or 212° C. In one embodiment, a crystalline form of Compound E (Form 1) (Example 135A (Form 1)) is characterized by a melting onset temperature of 210±5° C. In one embodiment, a crystalline form of Compound E (Form 1) (Example 135A (Form 1)) is characterized by a melting onset temperature of 220-230° C. In one embodiment, a crystalline form of Compound E (Form 1) (Example 135A (Form 1)) is characterized by a melting onset temperature of 223-227° C. In one embodiment, a crystalline form of Compound E (Form 1) (Example 135A (Form 1)) is characterized by a melting onset temperature of 223, 224, 225, 226, or 227° C. In one embodiment, a crystalline form of Compound E (Form 1) (Example 135A (Form 1)) is characterized by a melting onset temperature of 225±5° C.

In one aspect, the invention provided Compound F which is:

Compound F

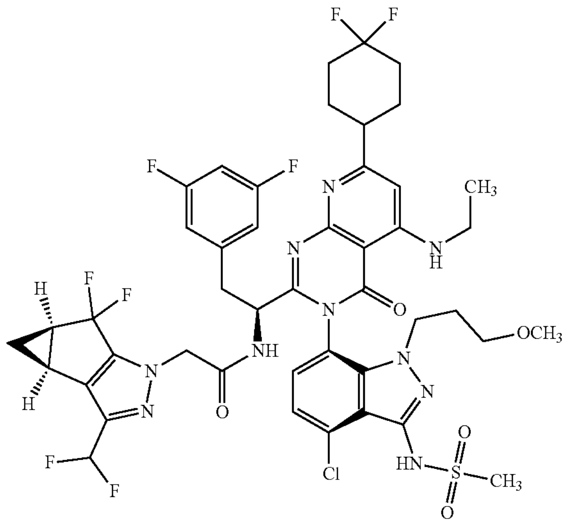

or a pharmaceutically acceptable salt thereof.

The IUPAC name of Compound F is N-[(1S)-1-[(3P)-3-[4-chloro-3-methanesulfonamido-1-(3-methoxypropyl)-1H-indazol-7-yl]-7-(4,4-difluorocyclohexyl)-5-(ethylamino)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl] acetamide. One of skill in the art would understand that an alternate name for Compound F is N-((S)-1-(3-(4-chloro-1-(3-methoxypropyl)-3-(methylsulfonamido)-1H-indazol-7-yl)-7-(4,4-difluorocyclohexyl)-5-(ethylamino)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.

In one embodiment, the invention provides crystalline Compound F (Form 1)

The XRPD peak list for Compound F (Form 1) (Example 427A (Form 1)) is found in Table 6.

In one embodiment, a crystalline form of Compound F (Form 1) (Example 427A (Form 1)) is characterized by an X-ray powder diffraction (XRPD) pattern comprising at least nine diffraction angles, when measured using Cu $K_\alpha$ radiation, selected from a group consisting of about 6.5, 7.5, 8.1, 8.4, 9.1, 9.6, 10.2, 10.3, 11.5, 12.8, 13.4, 13.8, 14.4, 14.7, 15.1, 16.0, 16.3, 17.3, 17.7, 18.3, 18.5, 18.7, 19.4, 19.6, 19.9, 20.5, 20.9, 21.1, 21.5, 22.1, 22.7, 23.0, 23.4, 23.6, 24.6, 25.2, 25.5, 26.0, 26.8, 27.0, 27.5, 28.3, 28.7, 29.1, 29.3, 29.6, 30.0, 30.7, 31.4, 31.7, 32.1, 32.5, 33.1, 33.4, 34.2, 34.6, 35.3, 36.0, 36.3, 36.5, 37.5, 38.0, 38.2, 38.6, 38.9, 39.4, and 39.6 degrees±0.2° 2θ.

In one embodiment, a crystalline form of Compound F (Form 1) (Example 427A (Form 1)) is characterized by an XRPD pattern comprising at least eight diffraction angles, or at least seven diffraction angles, or at least six diffraction angles, or at least five diffraction angles, or at least four diffraction angles, when measured using Cu $K_\alpha$ radiation, selected from a group consisting of about 6.5, 7.5, 8.1, 8.4, 9.1, 9.6, 10.2, 10.3, 11.5, 12.8, 13.4, 13.8, 14.4, 14.7, 15.1, 16.0, 16.3, 17.3, 17.7, 18.3, 18.5, 18.7, 19.4, 19.6, 19.9, 20.5, 20.9, 21.1, 21.5, 22.1, 22.7, 23.0, 23.4, 23.6, 24.6, 25.2, 25.5, 26.0, 26.8, 27.0, 27.5, 28.3, 28.7, 29.1, 29.3, 29.6, 30.0, 30.7, 31.4, 31.7, 32.1, 32.5, 33.1, 33.4, 34.2, 34.6, 35.3, 36.0, 36.3, 36.5, 37.5, 38.0, 38.2, 38.6, 38.9, 39.4, and 39.6 degrees±0.2° 2θ.

In one embodiment, a crystalline form of Compound F (Form 1) (Example 427A (Form 1)) is characterized by an XRPD pattern comprising at least eight diffraction angles, or at least seven diffraction angles, or at least six diffraction angles, or at least five diffraction angles, or at least four diffraction angles, when measured using Cu $K_\alpha$ radiation, selected from a group consisting of about 7.5, 8.1, 9.6, 11.5, 13.4, 14.7, 16.0, 16.3, 17.3, 19.6, 20.5, 22.1, 25.2, 25.5, and 26.0 degrees±0.2° 2θ.

In one embodiment, the invention provides a crystalline form Compound F (Form 1) (Example 427A (Form 1)) wherein the characterizing peaks of Compound F (Form 1), when measured using Cu $K_\alpha$ radiation, are selected from a group consisting of about 16.0, 19.6, 22.1, and 25.2 degrees±0.2° 2θ.

Figure 14:
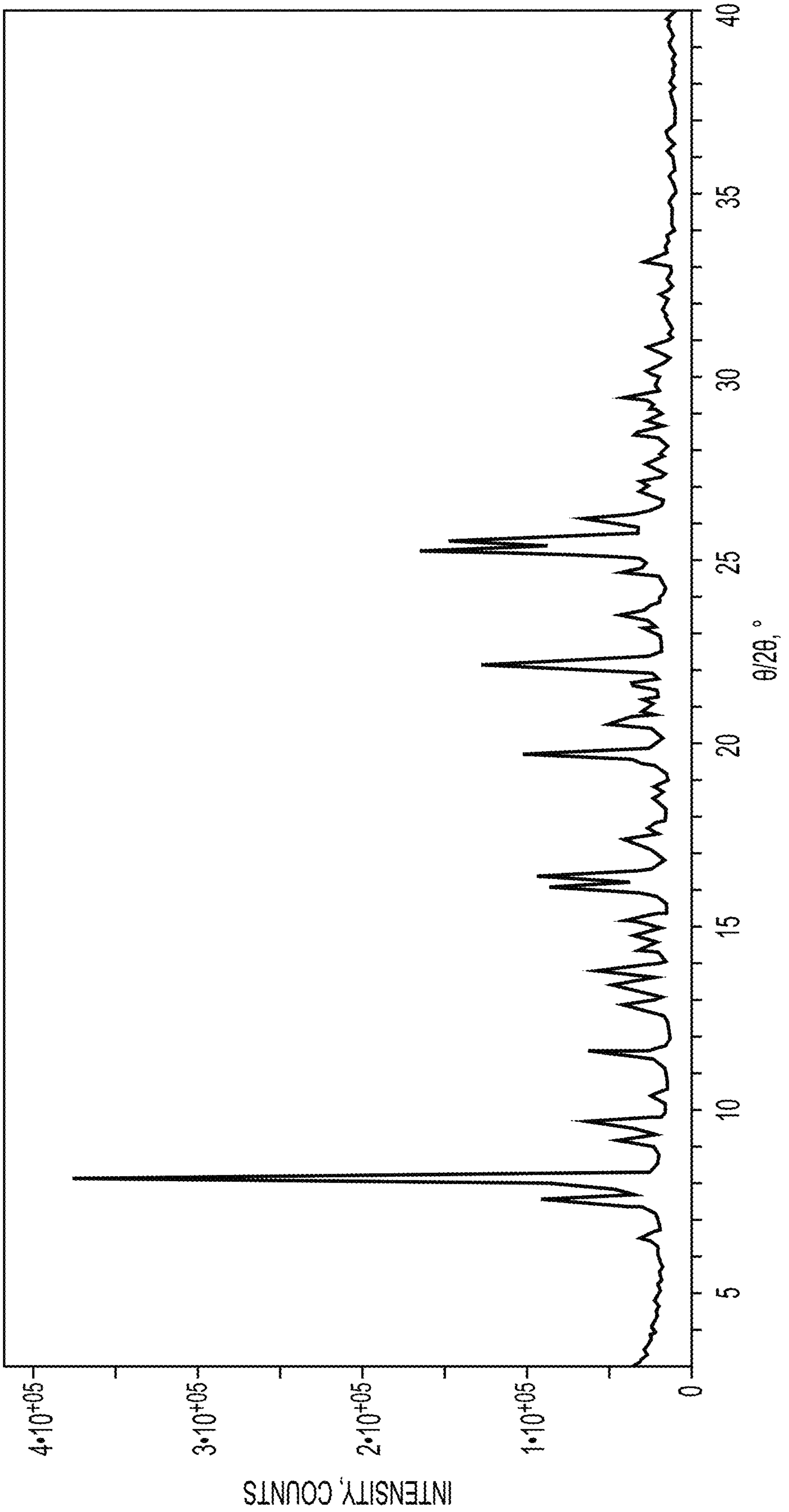
FIG. 14 depicts an X-Ray Powder Diffraction pattern (XRPD) of a crystalline form of the compound of Example 427A (Form 1), N-[(1S)-1-[(3P)-3-[4-chloro-3-methanesulfonamido-1-(3-methoxypropyl)-1H-indazol-7-yl]-7-(4,4-difluorocyclohexyl)-5-(ethylamino)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide (Compound F (Form 1)).

In one embodiment, a crystalline form of Compound F (Form 1) (Example 427A (Form 1)) is characterized by an X-ray powder diffraction pattern substantially in accordance with that shown in FIG. 14.

In one embodiment, a crystalline form of Compound F (Form 1) (Example 427A (Form 1)) is characterized by characterized by a DSC thermogram having a melting onset of about 227° C.

Figure 15:
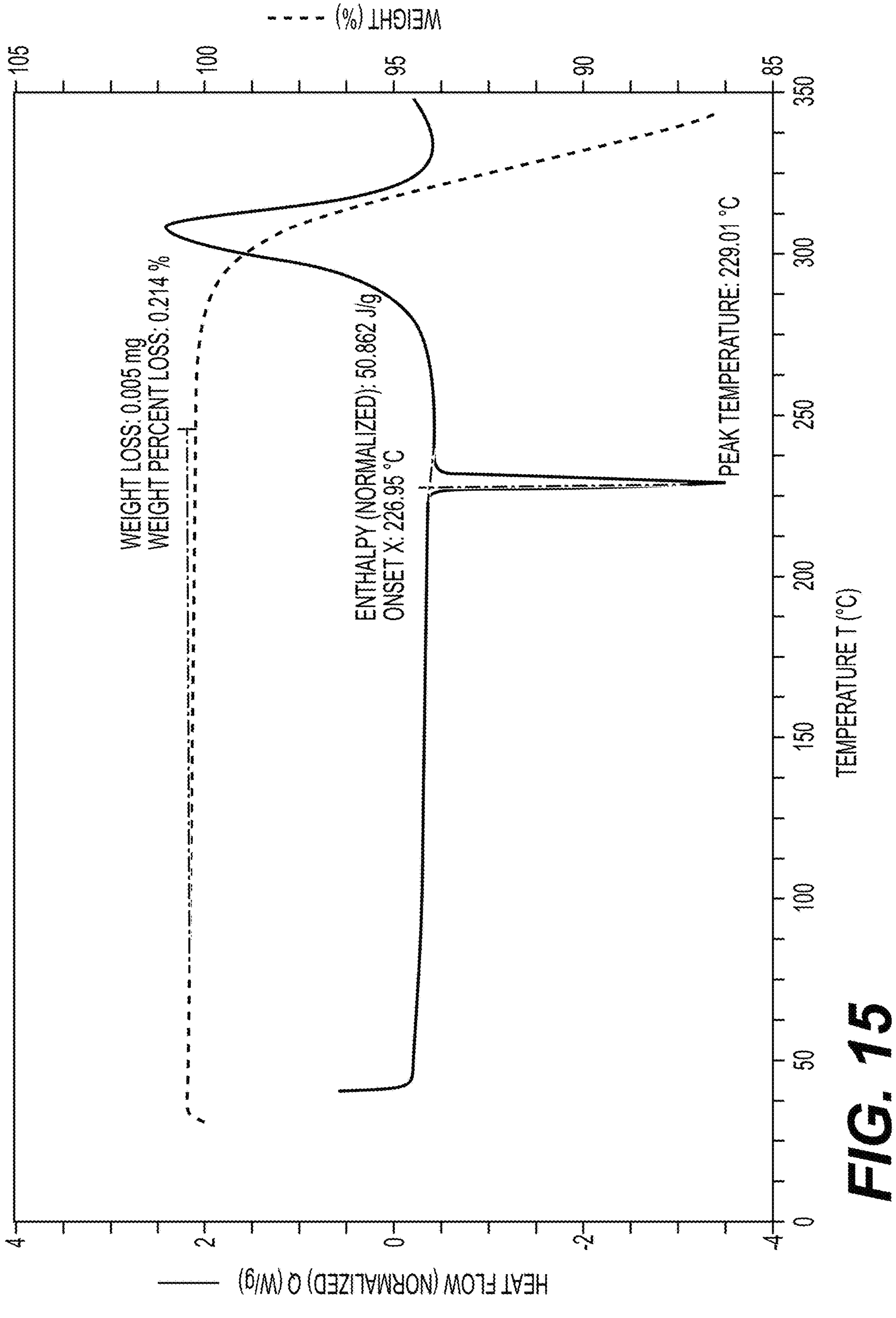
FIG. 15 depicts an overlay of DSC and TGA thermograms of a crystalline form of the compound of Example 427A (Form 1) (Compound F (Form 1)) exhibiting a melting onset of about 227° C. and a weight loss of about 0.21 wt %.

In one embodiment, a crystalline form of Compound F (Form 1) (Example 427A (Form 1)) is characterized by characterized by a DSC thermogram substantially in accordance with that shown in FIG. 15.

In one embodiment, the temperature at which the crystalline form of Compound F (Form 1) (Example 427A (Form 1)) begins to melt is determined by differential scanning calorimetry ("DSC") and is referred to as the "melting onset temperature". In one embodiment, a crystalline form of Compound F (Form 1) (Example 427A (Form 1)) is characterized by a melting onset temperature of 222-232° C. In one embodiment, a crystalline form of Compound F (Form 1) (Example 427A (Form 1)) is characterized by a melting onset temperature of 225-229° C. In one embodiment, a crystalline form of Compound F (Form 1) (Example 427A (Form 1)) is characterized by a melting onset temperature of 225, 226, 227, 228, or 229° C. In one embodiment, a crystalline form of Compound F (Form 1) (Example 427A (Form 1)) is characterized by a melting onset temperature of 227±5° C.

In one aspect, the invention provides Compound G which is:

Compound G

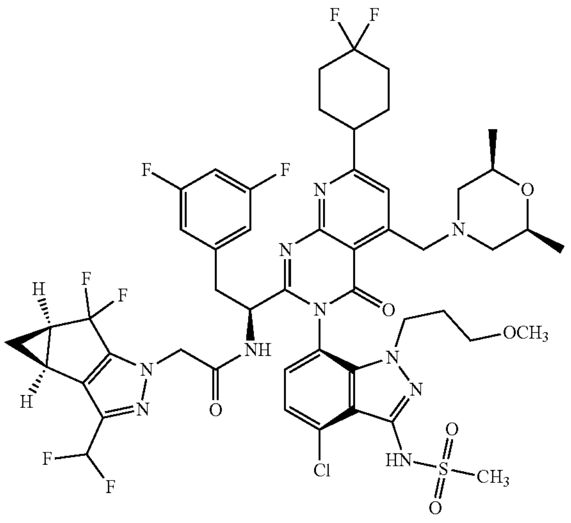

or a pharmaceutically acceptable salt thereof.

The IUPAC name of Compound G is N-[(1S)-1-[(3P)-3-[4-chloro-3-methanesulfonamido-1-(3-methoxypropyl)-1H-indazol-7-yl]-7-(4,4-difluorocyclohexyl)-5-{[(2R,6S)-2,6-dimethylmorpholin-4-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.$0.0^{2,4}$]nona-1(6),8-dien-7-yl]acetamide. One of skill in the art would understand that an alternate name for Compound G is N-((S)-1-(3-(4-chloro-1-(3-methoxypropyl)-3-(methylsulfonamido)-1H-indazol-7-yl)-7-(4,4-difluorocyclohexyl)-5-(((2S,6R)-2,6-dimethylmorpholino)methyl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.

In one embodiment, the invention provides crystalline Compound G (Form 1).

The XRPD peak list for Compound G (Form 1) (Example 448A (Form 1)) is found in Table 7.

In one embodiment, a crystalline form of Compound G (Form 1) (Example 448A (Form 1)) is characterized by an X-ray powder diffraction (XRPD) pattern comprising at least nine diffraction angles, when measured using Cu $K_\alpha$ radiation, selected from a group consisting of about 5.0, 6.8, 8.1, 9.4, 9.7, 10.0, 10.3, 10.9, 11.4, 11.9, 12.6, 13.7, 14.1, 14.4, 14.9, 16.0, 16.3, 16.9, 17.2, 18.0, 18.2, 19.6, 19.9, 20.1, 20.4, 20.7, 21.0, 21.4, 21.8, 22.7, 23.1, 23.4, 23.6, 24.9, 25.3, 25.8, 26.2, 27.4, 27.7, 28.5, 29.0, 29.4, 29.8, 30.1, 31.2, 31.5, 32.3, 33.1, 34.1, 35.1, 35.7, 36.7, 37.3, and 39.4 degrees±0.2° 2θ.

In one embodiment, a crystalline form of Compound G (Form 1) (Example 448A (Form 1)) is characterized by an XRPD pattern comprising at least eight diffraction angles, or at least seven diffraction angles, or at least six diffraction angles, or at least five diffraction angles, or at least four diffraction angles, when measured using Cu $K_\alpha$ radiation, selected from a group consisting of about 5.0, 6.8, 8.1, 9.4, 9.7, 10.0, 10.3, 10.9, 11.4, 11.9, 12.6, 13.7, 14.1, 14.4, 14.9, 16.0, 16.3, 16.9, 17.2, 18.0, 18.2, 19.6, 19.9, 20.1, 20.4, 20.7, 21.0, 21.4, 21.8, 22.7, 23.1, 23.4, 23.6, 24.9, 25.3, 25.8, 26.2, 27.4, 27.7, 28.5, 29.0, 29.4, 29.8, 30.1, 31.2, 31.5, 32.3, 33.1, 34.1, 35.1, 35.7, 36.7, 37.3, and 39.4 degrees±0.2° 2θ.

In one embodiment, a crystalline form of Compound G (Form 1) (Example 448A (Form 1)) is characterized by an XRPD pattern comprising at least eight diffraction angles, or at least seven diffraction angles, or at least six diffraction angles, or at least five diffraction angles, or at least four diffraction angles, when measured using Cu $K_\alpha$ radiation, selected from a group consisting of about 5.0, 6.8, 8.1, 111.9, 14.1, 16.3, 18.2, 19.6, 21.4, 22.7, 23.6, 24.9, 25.3, 26.2, and 27.4 degrees±0.2° 2θ.

In one embodiment, the invention provides a crystalline form of Compound G (Form 1) (Example 448A (Form 1)) wherein the characterizing peaks of Compound G (Form 1), when measured using Cu $K_\alpha$ radiation, are selected from a group consisting of about 116.3, 21.4, and 26.2 degrees±0.2° 2θ.

Figure 16:
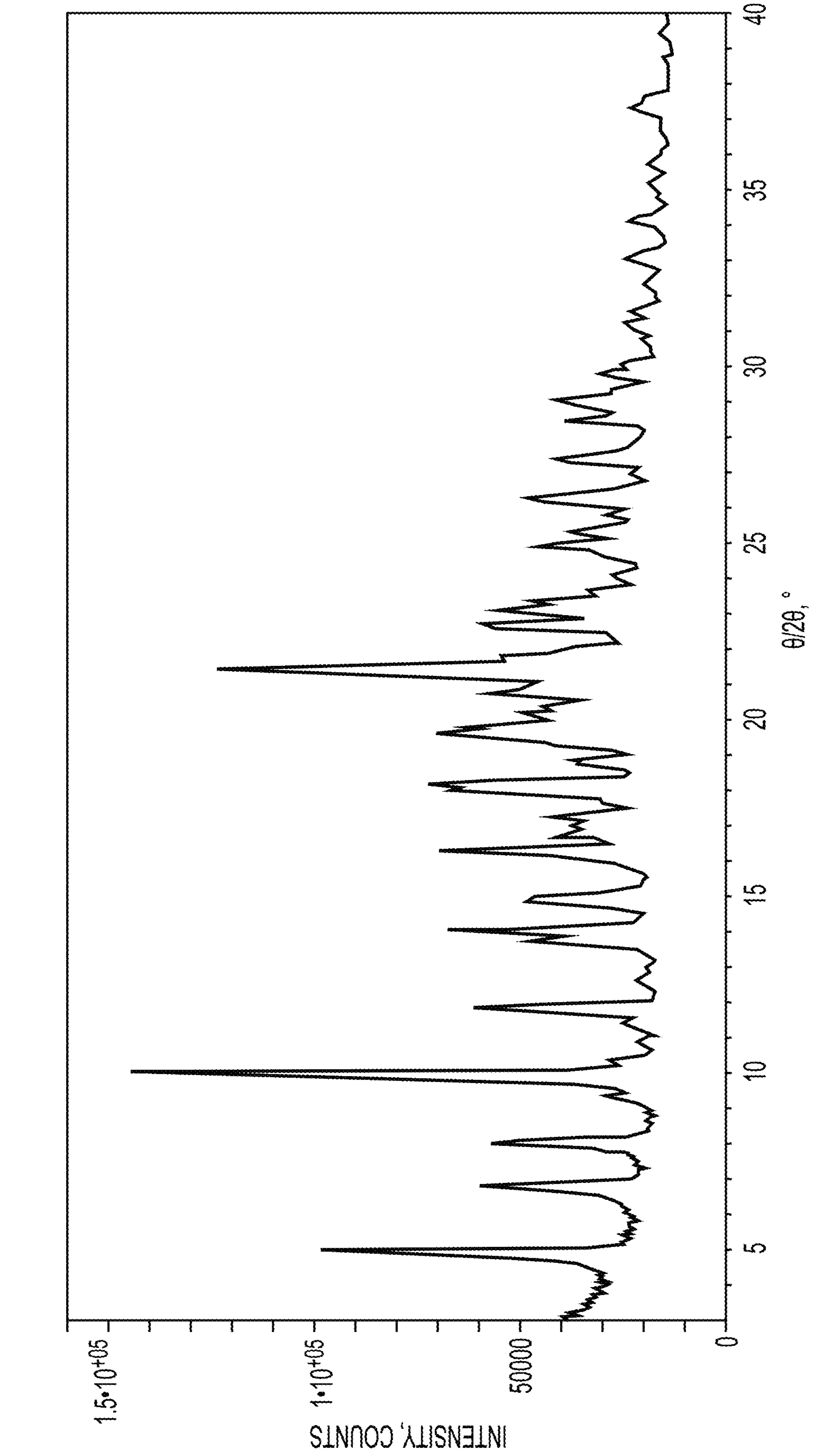
FIG. 16 depicts an X-Ray Powder Diffraction pattern (XRPD) of a crystalline form of the compound of Example 448A (Form 1), N-[(1S)-1-[(3P)-3-[4-chloro-3-methanesulfonamido-1-(3-methoxypropyl)-1H-indazol-7-yl]-7-(4,4-difluorocyclohexyl)-5-{[(2R,6S)-2,6-dimethylmorpholin-4-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide (Compound G (Form 1)).

In one embodiment, a crystalline form of Compound G (Form 1) (Example 448A (Form 1)) is characterized by an X-ray powder diffraction pattern substantially in accordance with that shown in FIG. 16.

In one embodiment, a crystalline form of Compound G (Form 1) (Example 448A (Form 1)) is characterized by a DSC thermogram having a melting onset of about 221° C.

Figure 17:
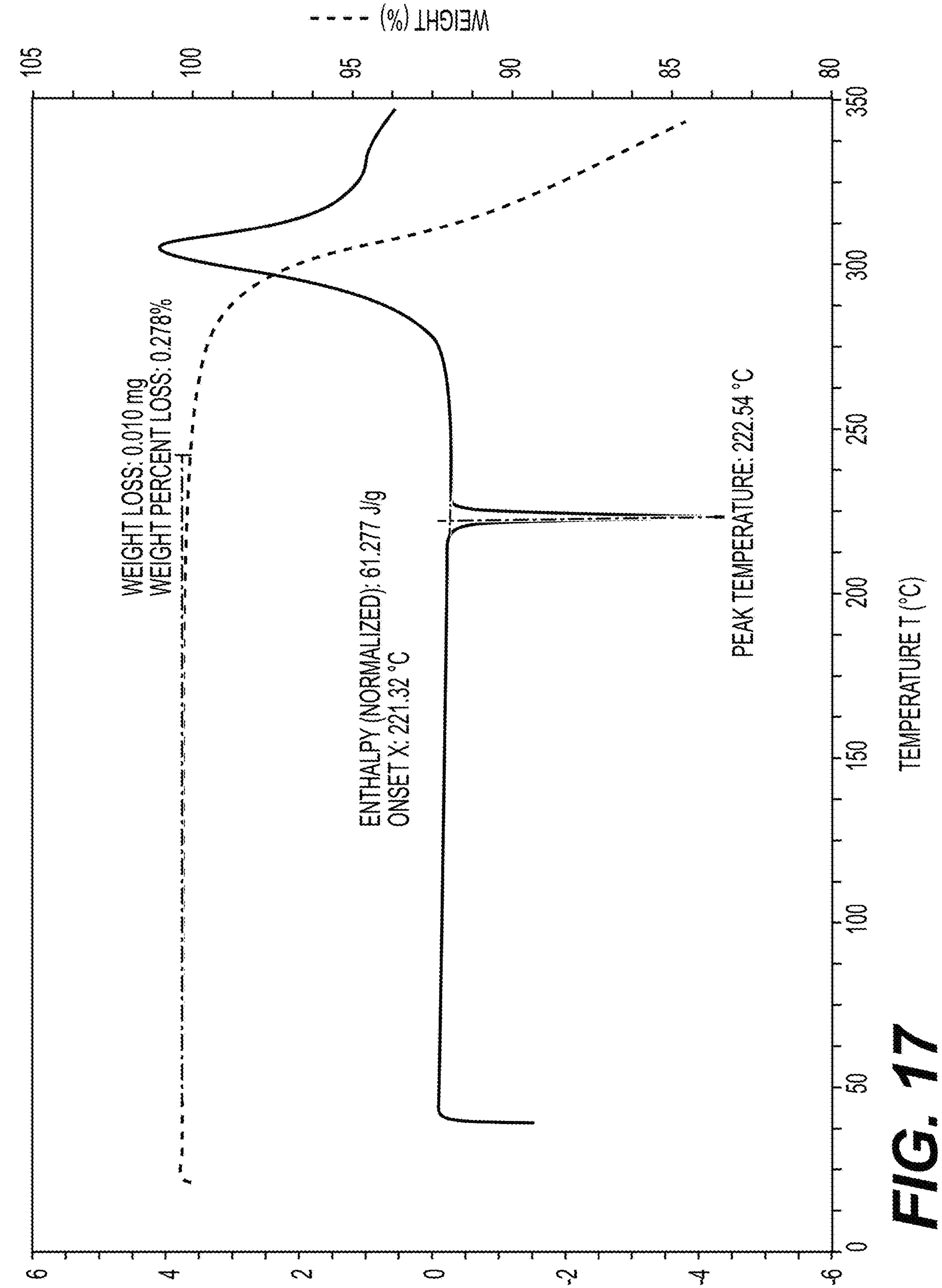
FIG. 17 depicts an overlay of DSC and TGA thermograms of a crystalline form of the compound of Example 448A (Form 1) (Compound G (Form 1)) exhibiting a melting onset of about 221° C. and a weight loss of about 0.28 wt %.

In one embodiment, a crystalline form of Compound G (Form 1) (Example 448A (Form 1)) is characterized by a DSC thermogram substantially in accordance with that shown in FIG. 17.

In one embodiment, the temperature at which the crystalline form of Compound G (Form 1) (Example 448A (Form 1)) begins to melt is determined by differential scanning calorimetry ("DSC") and is referred to as the "melting onset temperature". In one embodiment, a crystalline form of Compound G (Form 1) (Example 448A (Form 1)) is characterized by a melting onset temperature of 216-226° C. In one embodiment, a crystalline form of Compound G (Form 1) (Example 448A (Form 1)) is characterized by a melting onset temperature of 219-223° C. In one embodiment, a crystalline form of Compound G (Form 1) (Example 448A (Form 1)) is characterized by a melting onset temperature of 219, 220, 221, 222, or 223° C. In one embodiment, a crystalline form of Compound G (Form 1) (Example 448A (Form 1)) is characterized by a melting onset temperature of 221±5° C.

In one aspect, the invention provides Compound H which is:

Compound H

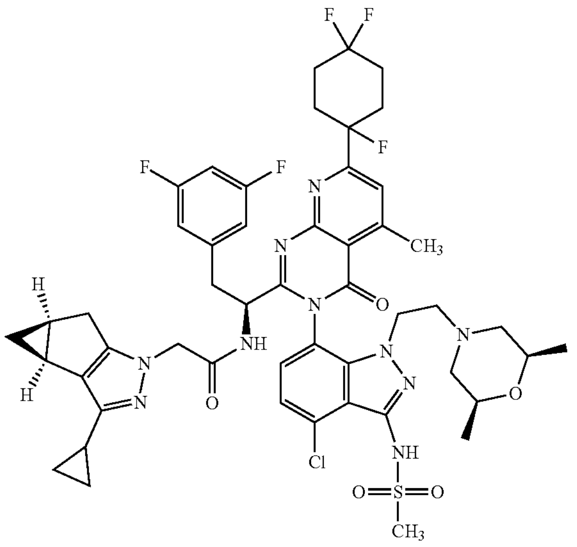

or a pharmaceutically acceptable salt thereof.

The IUPAC name of Compound H is N-[(1S)-1-[(3P)-3-(4-chloro-1-{2-[(2R,6S)-2,6-dimethylmorpholin-4-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide. One of skill in the art would understand that an alternate name for Compound H is N-((1S)-1-(3-(4-chloro-1-(2-((2R,6S)-2,6-dimethylmorpholino)ethyl)-3-(methylsulfonamido)-1H-indazol-7-yl)-5-methyl-4-oxo-7-(1,4,4-trifluorocyclohexyl)-3,4-dihydropyrido[2,3-d]pyrimidin-2-yl)-2-(3,5-difluorophenyl)ethyl)-2-((3bS,4aS)-3-cyclopropyl-3b,4,4a,5-tetrahydro-1H-cyclopropa[3,4]cyclopenta[1,2-c]pyrazol-1-yl)acetamide.

In one embodiment, the invention provides crystalline Compound H (Form 1).

The XRPD peak list for Compound H (Form 1) (Example 503A (Form 1)) is found in Table 8.

In one embodiment, a crystalline form of Compound H (Form 1) (Example 503A (Form 1)) is characterized by an X-ray powder diffraction (XRPD) pattern comprising at least nine diffraction angles, when measured using Cu $K_\alpha$ radiation, selected from a group consisting of about 6.1, 6.7, 7.6, 8.5, 9.2, 9.7, 11.0, 11.6, 12.0, 12.3, 13.0, 13.4, 14.1, 14.3, 15.1, 15.3, 16.4, 16.6, 17.2, 17.9, 18.4, 19.4, 19.6, 20.3, 20.7, 21.5, 21.9, 22.3, 23.0, 24.0, 24.3, 24.8, 25.3, 25.9, 26.9, 27.1, 28.1, 28.6, 29.6, 30.4, 30.6, 31.0, 31.2, 31.6, 32.9, 33.4, 33.7, 34.2, 34.9, 35.6, 36.4, 36.8, 37.4, 37.9, 38.5, and 39.5 degrees±0.2° 2θ.

In one embodiment, a crystalline form Compound H (Form 1) (Example 503A (Form 1)) is characterized by an XRPD pattern comprising at least eight diffraction angles, or at least seven diffraction angles, or at least six diffraction angles, or at least five diffraction angles, or at least four diffraction angles, when measured using Cu $K_\alpha$ radiation, selected from a group consisting of about 6.1, 6.7, 7.6, 8.5, 9.2, 9.7, 11.0, 11.6, 12.0, 12.3, 13.0, 13.4, 14.1, 14.3, 15.1, 15.3, 16.4, 16.6, 17.2, 17.9, 18.4, 19.4, 19.6, 20.3, 20.7, 21.5, 21.9, 22.3, 23.0, 24.0, 24.3, 24.8, 25.3, 25.9, 26.9, 27.1, 28.1, 28.6, 29.6, 30.4, 30.6, 31.0, 31.2, 31.6, 32.9, 33.4, 33.7, 34.2, 34.9, 35.6, 36.4, 36.8, 37.4, 37.9, 38.5, and 39.5 degrees±0.2° 2θ.

In one embodiment, a crystalline form of Compound H (Form 1) (Example 503A (Form 1)) is characterized by an XRPD pattern comprising at least eight diffraction angles, or at least seven diffraction angles, or at least six diffraction angles, or at least five diffraction angles, or at least four diffraction angles, when measured using Cu $K_\alpha$ radiation, selected from a group consisting of about 6.1, 8.5, 9.7, 11.0, 12.0, 15.3, 17.2, 18.4, 19.6, 20.3, 21.9, 23.0, 24.8, and 25.9 degrees±0.2° 2θ.

In one embodiment, a crystalline form of Compound H (Form 1) (Example 503A (Form 1)) is characterized by an XRPD pattern comprising at least eight diffraction angles, or at least seven diffraction angles, or at least six diffraction angles, or at least five diffraction angles, or at least four diffraction angles, when measured using Cu $K_\alpha$ radiation, selected from a group consisting of about 6.7, 9.2, 12.3, 13.0, 13.4, 14.1, 18.4, 19.6, 20.7, 21.5, 22.3, 23.0, 25.3, 25.9, 26.9, and 29.6 degrees±0.2° 2θ.

In one embodiment, the invention provides a crystalline form of Compound H (Form 1) (Example 503A (Form 1)) wherein the characterizing peaks of Compound H (Form 1), when measured using Cu $K_\alpha$ radiation, are selected from a group consisting of about 18.4, 19.6, 23.0, and 25.9 degrees±0.2° 2θ.

Figure 18:
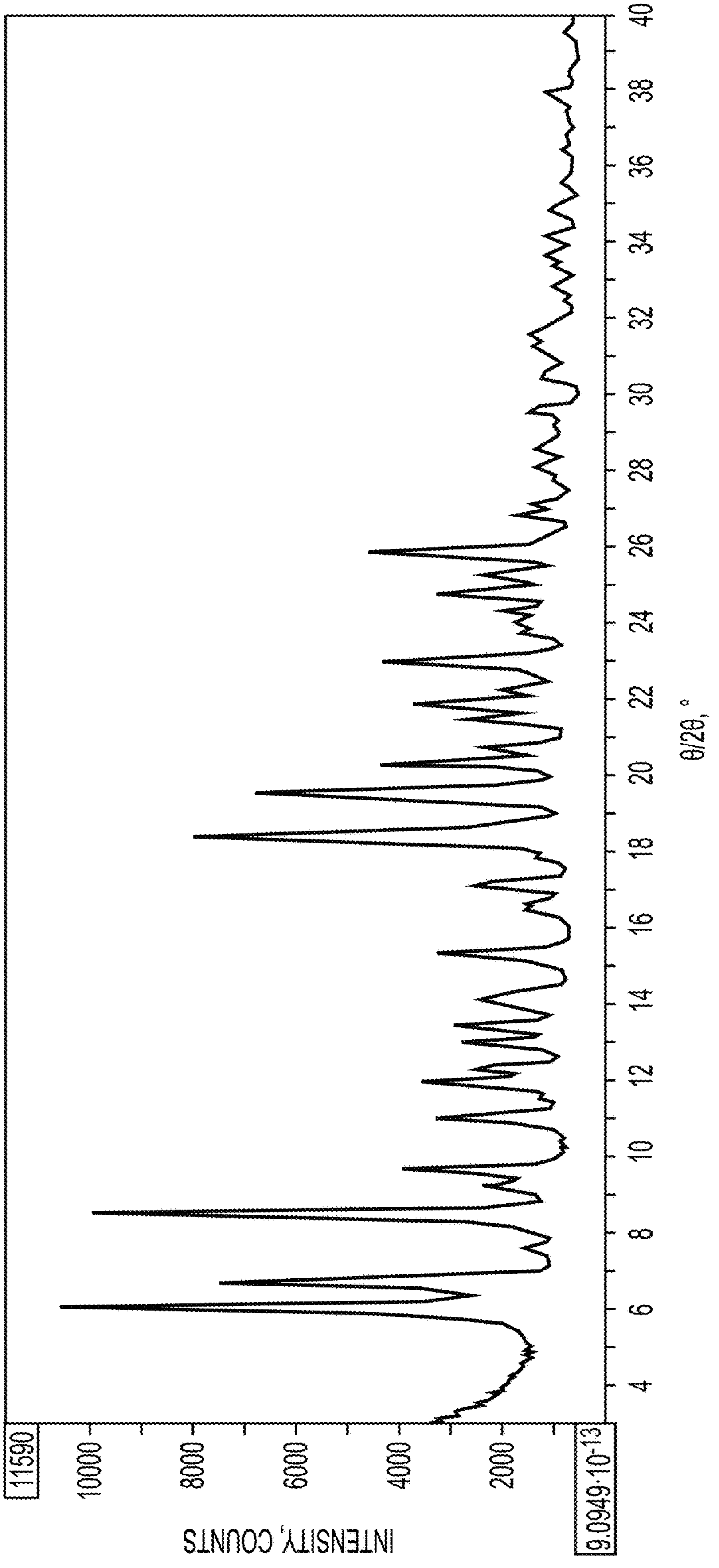
FIG. 18 depicts an XRPD pattern of a crystalline form of the compound of Example 503A (Form 1), N-[(1S)-1-[(3P)-3-(4-chloro-1-{2-[(2R,6S)-2,6-dimethylmorpholin-4-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide (Compound H (Form 1)).

In one embodiment, a crystalline form of Compound H (Form 1) (Example 503A (Form 1)) is characterized by an X-ray powder diffraction pattern substantially in accordance with that shown in FIG. 18.

In one embodiment, a crystalline form of Compound H (Form 1) (Example 503A (Form 1)) is characterized by a DSC thermogram having a melting onset of about 127° C.

Figure 19:
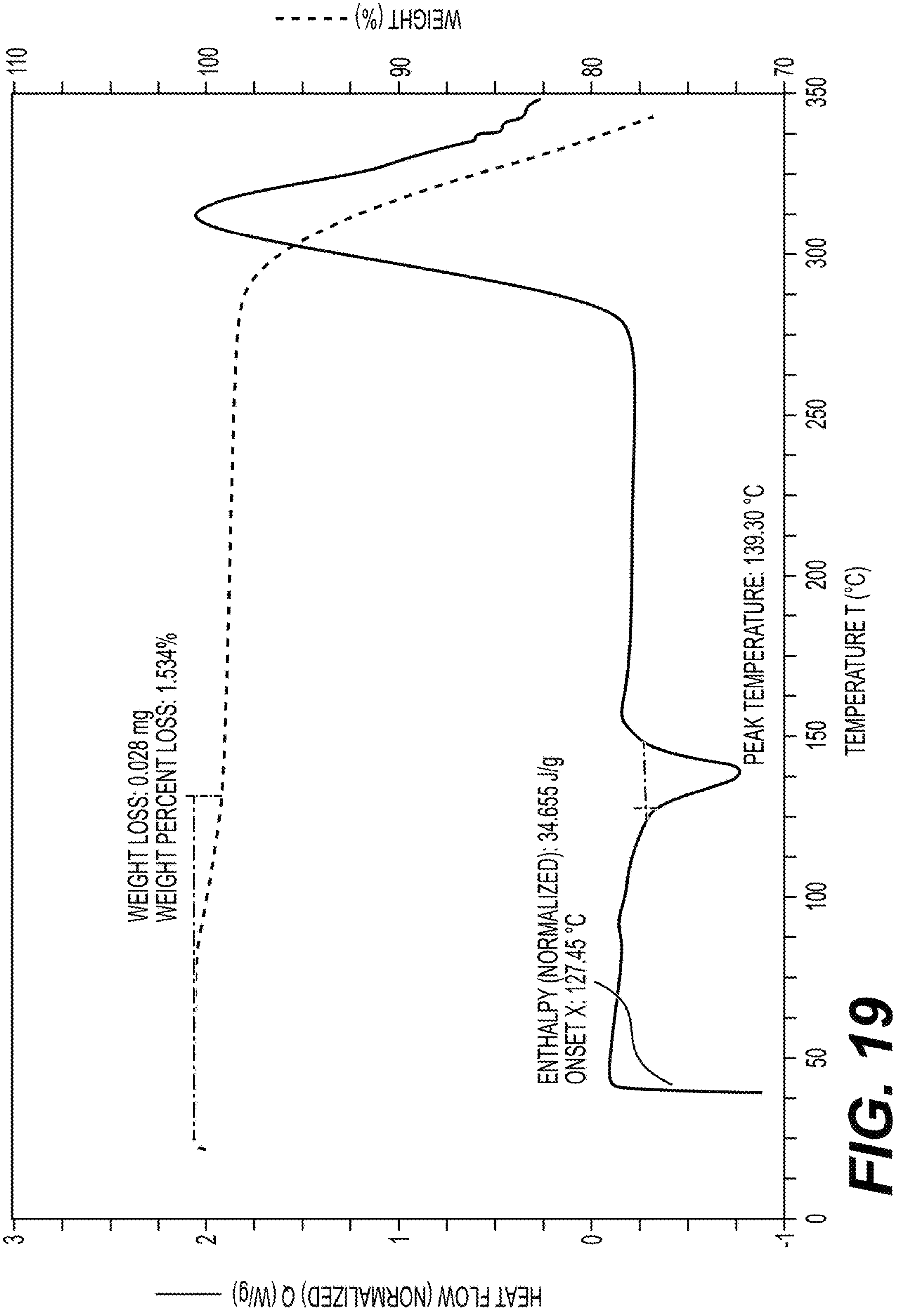
FIG. 19 depicts an overlay of DSC and TGA thermograms of a crystalline form of the compound of Example 503A (Form 1) (Compound H (Form 1)) exhibiting a melting onset of about 127° C. and a weight loss of about 1.5 wt %.

In one embodiment, a crystalline form of Compound H (Form 1) (Example 503A (Form 1)) is characterized by a DSC thermogram substantially in accordance with that shown in FIG. 19.

In one embodiment, the temperature at which the crystalline form of Compound H (Form 1) (Example 503A (Form 1)) begins to melt is determined by differential scanning calorimetry ("DSC") and is referred to as the "melting onset temperature". In one embodiment, a crystalline form of Compound H (Form 1) (Example 503A (Form 1)) is characterized by a melting onset temperature of 122-132° C. In one embodiment, a crystalline form of Compound H (Form 1) (Example 503A (Form 1)) is characterized by a melting onset temperature of 125-129° C. In one embodiment, a crystalline form of Compound H (Form 1) (Example 503A (Form 1)) is characterized by a melting onset temperature of 125, 126, 127, 128, or 129° C. In one embodiment, a crystalline form of Compound H (Form 1) (Example 503A (Form 1)) is characterized by a melting onset temperature of 127±5° C.

In one aspect, the invention provides Compound J which is:

Compound J

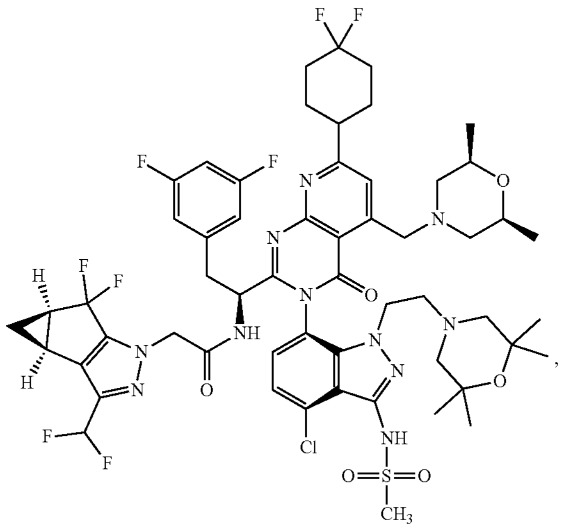

or a pharmaceutically acceptable salt thereof.

The IUPAC name of Compound J is N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-{[(2R,6S)-2,6-dimethylmorpholin-4-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide. One of skill in the art would understand that an alternate name for Compound J is N-((S)-1-(3-(4-chloro-3-(methylsulfonamido)-1-(2-(2,2,6,6-tetramethylmorpholino)ethyl)-1H-indazol-7-yl)-7-(4,4-difluorocyclohexyl)-5-(((2S,6R)-2,6-dimethylmorpholino)methyl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.

In one embodiment, the invention provides crystalline Compound J (Form 1).

The XRPD peak list for Compound J (Form 1) (Example 529A (Form 1)) is found in Table 9.

In one embodiment, a crystalline form of Compound J (Form 1) (Example 529A (Form 1)) is characterized by an X-ray powder diffraction (XRPD) pattern comprising at least nine diffraction angles, when measured using Cu $K_\alpha$ radiation, selected from a group consisting of about 4.4, 4.9, 5.5, 5.8, 6.1, 6.4, 6.7, 8.7, 9.4, 9.8, 12.2, 13.0, 13.5, 13.9, 14.4, 14.8, 15.4, 15.9, 16.2, 16.9, 17.6, 18.6, 19.9, 20.5, 21.1, 21.7, 22.6, 23.0, 23.4, 23.9, 24.9, 25.8, 27.7, 28.7, 29.3, 30.8, 33.7, and 35.0 degrees±0.2° 2θ.

In one embodiment, a crystalline form of Compound J (Form 1) (Example 529A (Form 1)) is characterized by an XRPD pattern comprising at least eight diffraction angles, or at least seven diffraction angles, or at least six diffraction angles, or at least five diffraction angles, or at least four diffraction angles, when measured using Cu $K_\alpha$ radiation, selected from a group consisting of about 4.4, 4.9, 5.5, 5.8, 6.1, 6.4, 6.7, 8.7, 9.4, 9.8, 12.2, 13.0, 13.5, 13.9, 14.4, 14.8, 15.4, 15.9, 16.2, 16.9, 17.6, 18.6, 19.9, 20.5, 21.1, 21.7, 22.6, 23.0, 23.4, 23.9, 24.9, 25.8, 27.7, 28.7, 29.3, 30.8, 33.7, and 35.0 degrees±0.2° 2θ.

In one embodiment, a crystalline form of Compound J (Form 1) (Example 529A (Form 1)) is characterized by an XRPD pattern comprising at least eight diffraction angles, or at least seven diffraction angles, or at least six diffraction angles, or at least five diffraction angles, or at least four diffraction angles, when measured using Cu $K_{\alpha}$ radiation, selected from a group consisting of about 6.1, 6.4, 8.7, 9.8, 12.2, 13.0, 14.4, 15.4, 16.9, 17.6, 18.6, 19.9, 20.5, 21.1, 24.9 and degrees±0.2° 2θ.

In one embodiment, the invention provides a crystalline form of Compound J (Form 1) (Example 529A (Form 1)) wherein the characterizing peaks of Compound J (Form 1), when measured using Cu $K_{\alpha}$ radiation, are selected from a group consisting of about 14.4, 15.4, 18.6, and 20.5 degrees±0.2° 2θ.

Figure 20:
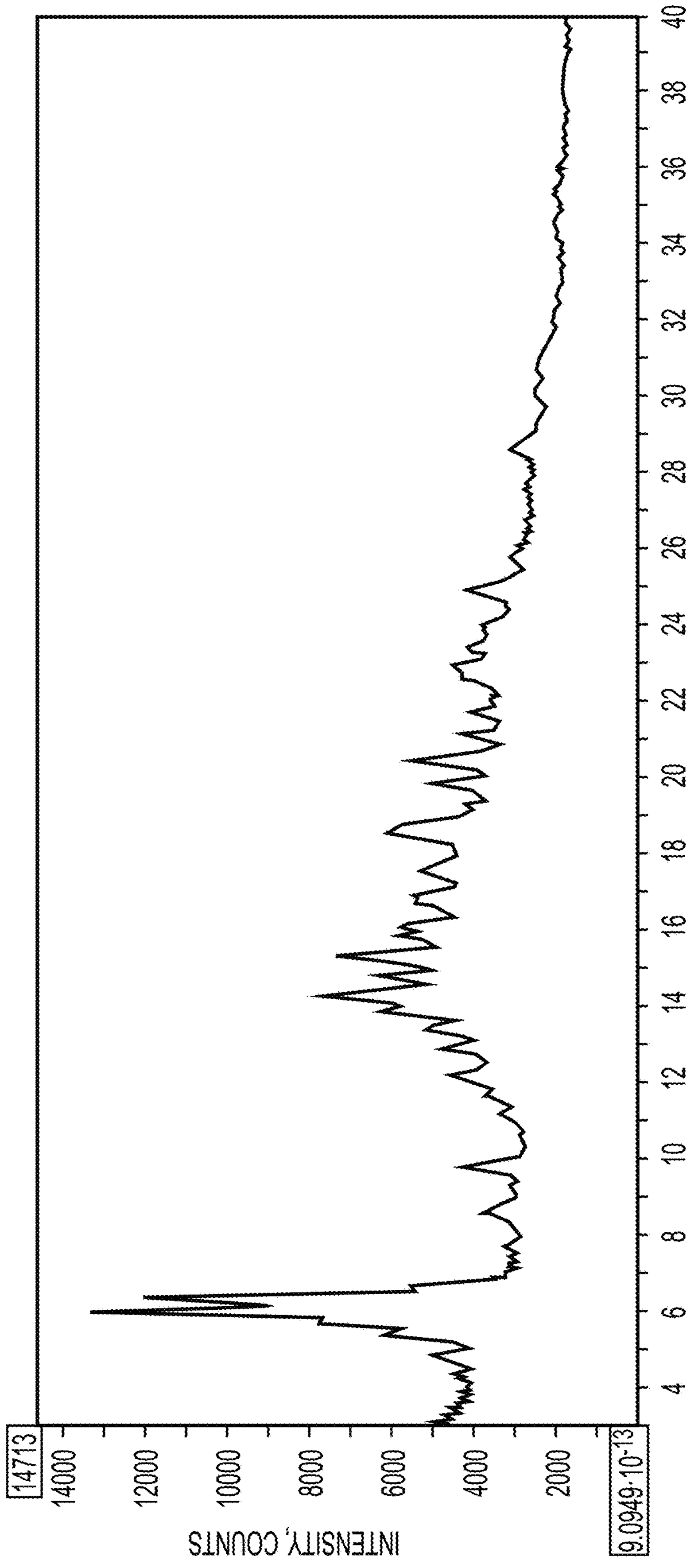
FIG. 20 depicts an XRPD pattern of a crystalline form of the compound of Example 529A (Form 1), N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-{[(2R,6S)-2,6-dimethylmorpholin-4-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide (Compound J (Form 1)).

In one embodiment, a crystalline form of Compound J (Form 1) (Example 529A (Form 1)) is characterized by an X-ray powder diffraction pattern substantially in accordance with that shown in FIG. 20.

In one embodiment, a crystalline form of Compound J (Form 1) (Example 529A (Form 1)) is characterized by a DSC thermogram having a melting onset of about 235° C.

Figure 21:
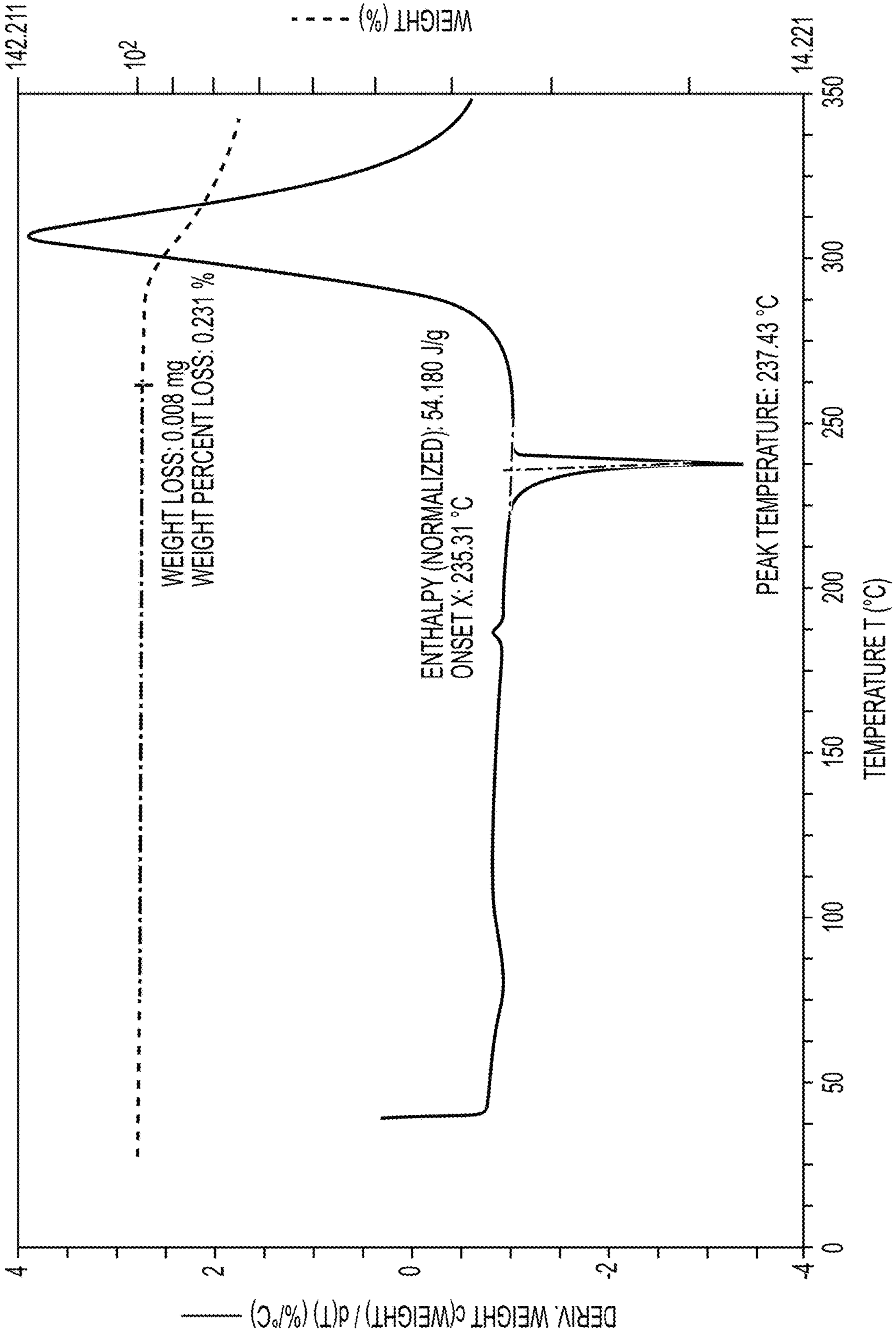
FIG. 21 depicts an overlay of DSC and TGA thermograms of a crystalline form of the compound of Example 529A (Form 1) (Compound J (Form 1)) exhibits a melting onset of about 235° C. and a weight loss of about 0.23 wt %.

In one embodiment, a crystalline form of Compound J (Form 1) (Example 529A (Form 1)) is characterized by a DSC thermogram substantially in accordance with that shown in FIG. 21.

In one embodiment, the temperature at which the crystalline form of Compound J (Form 1) (Example 529A (Form 1)) begins to melt is determined by differential scanning calorimetry ("DSC") and is referred to as the "melting onset temperature". In one embodiment, a crystalline form of Compound J (Form 1) (Example 529A (Form 1)) is characterized by a melting onset temperature of 230-240° C. In one embodiment, a crystalline form of Compound J (Form 1) (Example 529A (Form 1)) is characterized by a melting onset temperature of 233-237° C. In one embodiment, a crystalline form of Compound J (Form 1) (Example 529A (Form 1)) is characterized by a melting onset temperature of 233, 234, 235, 236, or 237° C. In one embodiment, a crystalline form of Compound J (Form 1) (Example 529A (Form 1)) is characterized by a melting onset temperature of 235±5° C.

In one aspect, the invention provides Compound K which is:

Compound K

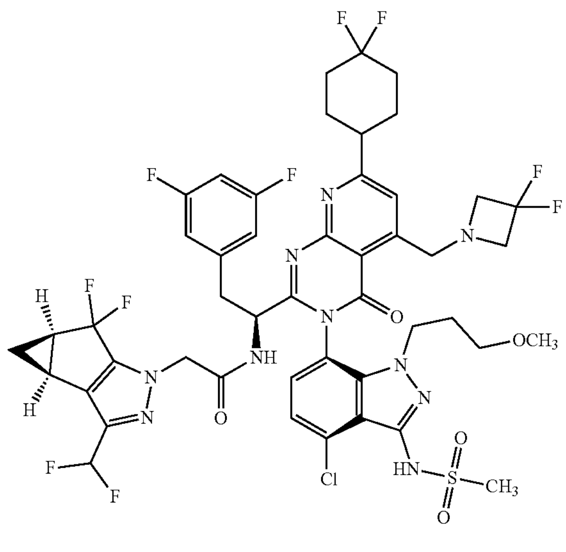

or a pharmaceutically acceptable salt thereof.

The IUPAC name of Compound K is N-[(1S)-1-[(3P)-3-[4-chloro-3-methanesulfonamido-1-(3-methoxypropyl)-1H-indazol-7-yl]-5-[(3,3-difluoroazetidin-1-yl)methyl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide. One of skill in the art would understand that an alternate name for Compound K is N-((S)-1-(3-(4-chloro-1-(3-methoxypropyl)-3-(methylsulfonamido)-1H-indazol-7-yl)-5-((3,3-difluoroazetidin-1-yl)methyl)-7-(4,4-difluorocyclohexyl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.

In one embodiment, the invention provides crystalline Compound K (Form 1).

The XRPD peak list for Compound K (Form 1) (Example 538A (Form 1)) is found in Table 10.

In one embodiment, a crystalline form of Compound K (Form 1) (Example 538A (Form 1)) is characterized by an X-ray powder diffraction (XRPD) pattern comprising at least nine diffraction angles, when measured using Cu $K_{\alpha}$ radiation, selected from a group consisting of about 6.5, 7.2, 7.9, 8.5, 8.9, 9.4, 10.1, 11.0, 11.2, 11.6, 11.9, 12.6, 12.8, 13.2, 13.9, 14.3, 14.6, 15.5, 15.9, 16.9, 17.4, 17.9, 18.1, 18.8, 19.1, 19.5, 20.0, 20.4, 20.8, 21.6, 22.0, 22.3, 22.7, 24.1, 24.6, 25.0, 25.2, 25.4, 26.0, 26.2, 26.5, 27.1, 27.6, 27.9, 28.0, 28.6, 29.1, 29.3, 29.6, 30.8, 31.3, 31.7, 32.6, 33.0, 33.5, 33.8, 35.1, 35.5, 35.8, 37.5, 37.8, 38.1, 38.7, and 39.2 degrees±0.2° 2θ.

In one embodiment, a crystalline form of Compound K (Form 1) (Example 538A (Form 1)) is characterized by an XRPD pattern comprising at least eight diffraction angles, or at least seven diffraction angles, or at least six diffraction angles, or at least five diffraction angles, or at least four diffraction angles, when measured using Cu $K_{\alpha}$ radiation, selected from a group consisting of about 6.5, 7.2, 7.9, 8.5, 8.9, 9.4, 10.1, 11.0, 11.2, 11.6, 11.9, 12.6, 12.8, 13.2, 13.9, 14.3, 14.6, 15.5, 15.9, 16.9, 17.4, 17.9, 18.1, 18.8, 19.1, 19.5, 20.0, 20.4, 20.8, 21.6, 22.0, 22.3, 22.7, 24.1, 24.6, 25.0, 25.2, 25.4, 26.0, 26.2, 26.5, 27.1, 27.6, 27.9, 28.0, 28.6, 29.1, 29.3, 29.6, 30.8, 31.3, 31.7, 32.6, 33.0, 33.5, 33.8, 35.1, 35.5, 35.8, 37.5, 37.8, 38.1, 38.7, and 39.2 degrees±0.2° 2θ.

In one embodiment, a crystalline form of Compound K (Form 1) (Example 538A (Form 1)) is characterized by an XRPD pattern comprising at least eight diffraction angles, or at least seven diffraction angles, or at least six diffraction angles, or at least five diffraction angles, or at least four diffraction angles, when measured using Cu $K_{\alpha}$ radiation, selected from a group consisting of about 7.2, 9.4, 11.2, 12.8, 13.9, 14.3, 15.5, 16.9, 18.8, 220.8, 21.6, 22.7, 24.6, and 28.0 degrees±0.2° 2θ.

In one embodiment, the invention provides a crystalline form of Compound K (Form 1) (Example 538A (Form 1)) wherein the characterizing peaks Compound K (Form 1), when measured using Cu $K_{\alpha}$ radiation, are selected from a group consisting of about 12.8, 15.5, 18.8, and 24.6 degrees±0.2° 2θ.

Figure 22:
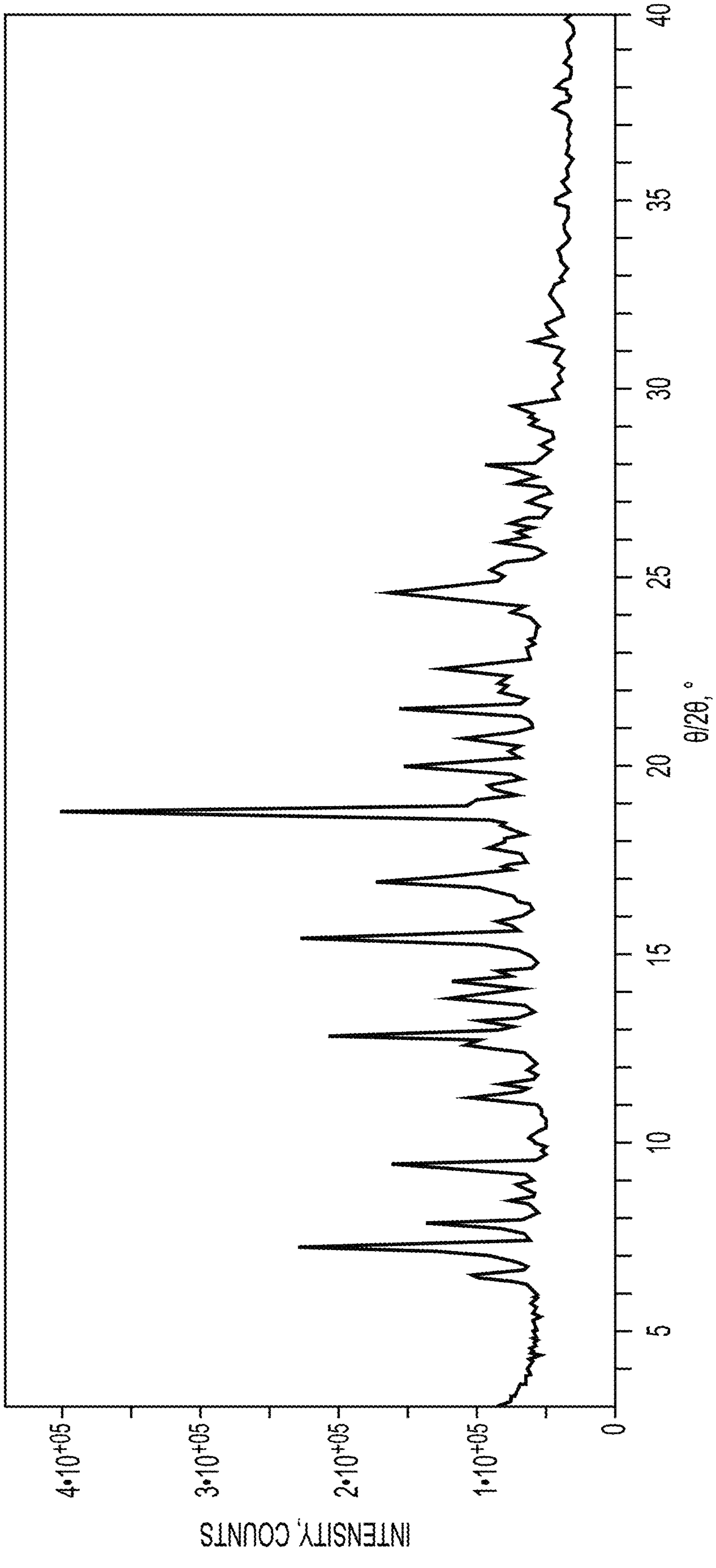
FIG. 22 depicts an XRPD pattern of a crystalline form of the compound of Example 538A (Form 1), N-[(1S)-1-[(3P)-3-[4-chloro-3-methanesulfonamido-1-(3-methoxypropyl)-1H-indazol-7-yl]-5-[(3,3-difluoroazetidin-1-yl)methyl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide (Compound K (Form 1)).

In one embodiment, a crystalline form of Compound K (Form 1) (Example 538A (Form 1)) is characterized by an X-ray powder diffraction pattern substantially in accordance with that shown in FIG. 22.

In one embodiment, a crystalline form of Compound K (Form 1) (Example 538A (Form 1)) is characterized by a DSC thermogram having a melting onset of about 162° C.

Figure 23:
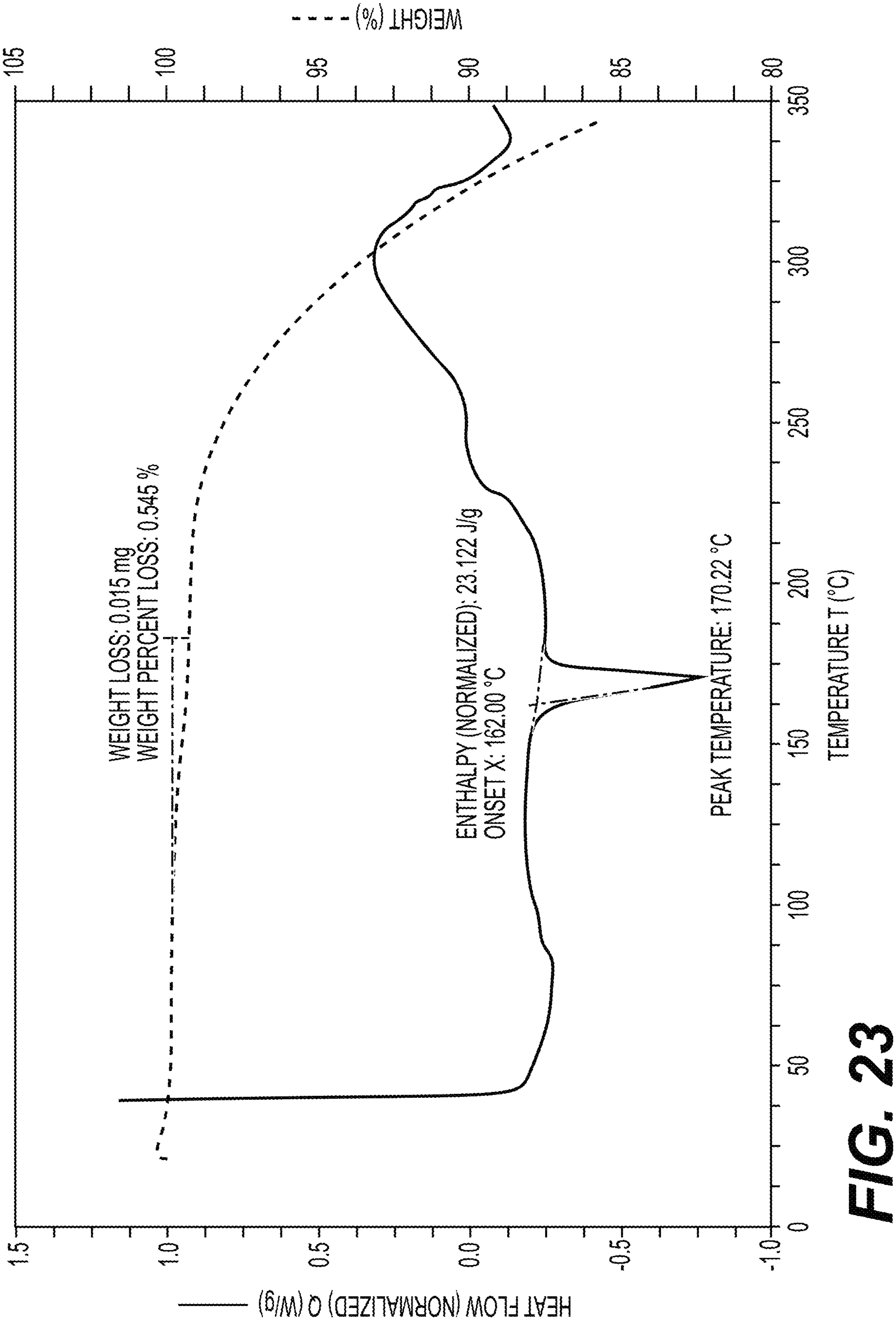
FIG. 23 depicts an overlay of DSC and TGA thermograms of a crystalline form of the compound of Example 538A (Form 1) (Compound K (Form 1)) exhibits a melting onset of about 162° C. and a weight loss of about 0.55 wt %.

In one embodiment, a crystalline form of Compound K (Form 1) (Example 538A (Form 1)) is characterized by a DSC thermogram substantially in accordance with that shown in FIG. 23.

In one embodiment, the temperature at which the crystalline form of Compound K (Form 1) (Example 538A (Form 1)) begins to melt is determined by differential scanning calorimetry ("DSC") and is referred to as the "melting onset temperature". In one embodiment, a crystalline form of Compound K (Form 1) (Example 538A (Form 1)) is characterized by a melting onset temperature of 157-167° C. In one embodiment, a crystalline form of Compound K (Form 1) (Example 538A (Form 1)) is characterized by a melting onset temperature of 160-164° C. In one embodiment, a crystalline form of Compound K (Form 1) (Example 538A (Form 1)) is characterized by a melting onset temperature of 160, 161, 162, 163, or 164° C. In one embodiment, a crystalline form of Compound K (Form 1) (Example 538A (Form 1)) is characterized by a melting onset temperature of 162±5° C.

Methods and Uses of the Invention

The present invention provides methods for treatment of HIV infection in a human in need thereof comprising administering to said human a therapeutically effective amount of a compound of the invention, a crystalline form of the invention, or a composition of the invention. The present invention also provides methods for prevention of HIV infection in a human in need thereof comprising administering to said human a therapeutically effective amount of a compound of the invention, a crystalline form of the invention, or a composition of the invention.

The invention includes a therapeutic method for treating or preventing infection with HIV in a subject in need thereof comprising administering to a subject in need thereof an antiviral effective amount of a compound of the invention or a composition comprising an effective amount of a compound of the invention and an optional pharmaceutically acceptable excipient (for example a pharmaceutically acceptable carrier and/or pharmaceutically acceptable diluent).

The present invention also provides a compound of the invention, a crystalline form of the invention, or a composition of the invention for use in therapy.

The present invention also provides a compound of the invention, a crystalline form of the invention, or a composition of the invention for use for use in the treatment or prevention of HIV infection. In one embodiment, the present invention provides a compound of the invention, a crystalline form of the invention, or a composition of the invention for use in the treatment of HIV infection. In another embodiment, the present invention provides a compound of the invention, a crystalline form of the invention, or a composition of the invention for use in the prevention of HIV infection.

The present invention also provides a compound of the invention, a crystalline form of the invention, or a composition of the invention for use as a capsid inhibitor.

In another aspect, the invention provides the use of a compound of the invention or a crystalline form of the invention, in the manufacture of a medicament for use in the treatment or prevention of HIV infection. In one embodiment, the invention provides the use of a compound of the invention a crystalline form of the invention, in the manufacture of a medicament for use in the treatment of HIV infection. In one embodiment, the invention includes the use of a compound of the invention or a crystalline form of the invention, in the manufacture of a medicament for use in the prevention of HIV infection.

In another aspect, the invention provides the use of a compound of the invention or a crystalline form of the invention, in the manufacture of a medicament for use as a capsid inhibitor.

As used herein, "HIV" or "Human Immunodeficiency Virus" refers to HIV-1 and/or HIV-2.

As used herein, the terms "treatment of infection with HIV" and "treatment of HIV infection" are used interchangeably to mean the treatment of a subject being infected with HIV.

"Treatment of HIV infection" means to inhibit the replication of the HIV virus, to inhibit viral transmission, and to ameliorate or alleviate the symptoms of the disease caused by the HIV infection. The treatment is considered "therapeutic" if there is a reduction in viral load, decrease in mortality and/or morbidity.

It will also be understood that treatment refers to a means by which the viral load of HIV (represented as the number of copies of viral RNA in a specified volume of serum) is reduced. The more effective the treatment, the lower the viral load. In one embodiment, the viral load should be reduced to as low levels as possible, e.g., below about 200 copies/ml, in particular below about 100 copies/ml, more in particular below 50 copies/ml, if possible, below the detection limit of the virus. Reductions of viral load of one, two or even three orders of magnitude are an indication of the effectiveness of the treatment. Another parameter to measure effectiveness of anti-HIV treatment is the CD4 count, which in normal adults ranges from 500 to 1500 cells per µl. Lowered CD4 counts are an indication of HIV infection and once below about 200 cells per µl, AIDS may develop. An increase of CD4 count, e.g., with about 50, 100, 200 or more cells per µl, is also an indication of the effectiveness of anti-HIV treatment. The CD4 count in particular should be increased to a level above about 200 cells per µl, or above about 350 cells per µl. Viral load or CD4 count, or both, can be used to diagnose the degree of HIV infection.

"Preventing HIV infection" or "prevention of HIV infection" means to prevent the HIV virus from establishing itself in the host or avoidance of a subject becoming infected with HIV. A treatment is considered as preventing HIV infection if the subject is exposed to the virus but does not become infected with the virus as a result of treatment.

The source of infection can be various, a material containing HIV, in particular a body fluid that contains HIV such as blood or sperm, or another subject who is infected with HIV. Prevention of HIV infection relates to the prevention of the transmission of the virus from the material containing HIV or from the HIV infected individual to an uninfected person or relates to the prevention of the virus from entering the body from an uninfected person. Transmission of the HIV virus can be by any known cause of HIV transfer such as by sexual transmission or by contact with blood of an infected subject, e.g., medical staff providing care to infected subjects. Transfer of HIV can also occur by contact with HIV infected blood, e.g., when handling blood samples or with blood transfusion. It can also be by contact with infected cells, e.g., when carrying out laboratory experiments with HIV infected cells.

In one embodiment, the invention provides a compound of the invention, or pharmaceutically acceptable salt thereof, for use in the treatment or prevention of HIV infection. In one embodiment, the invention provides a crystalline form of the invention, or pharmaceutically acceptable salt thereof, for use in the treatment or prevention of HIV infection. In one embodiment, the invention provides a composition of the invention for use in the treatment or prevention of HIV infection.

In one embodiment, the invention provides Compound A, or pharmaceutically acceptable salt thereof, for use in the treatment or prevention of HIV infection.

In one embodiment, the invention provides crystalline Compound A (Form 1), or pharmaceutically acceptable salt thereof, for use in the treatment or prevention of HIV infection.

In one embodiment, the invention provides Compound B, or pharmaceutically acceptable salt thereof, for use in the treatment or prevention of HIV infection.

In one embodiment, the invention provides crystalline Compound B (Form 1), or pharmaceutically acceptable salt thereof, for use in the treatment or prevention of HIV infection.

In one embodiment, the invention provides Compound C, or pharmaceutically acceptable salt thereof, for use in the treatment or prevention of HIV infection. In one embodiment, the invention provides crystalline Compound C (Form 1), or pharmaceutically acceptable salt thereof, for use in the treatment or prevention of HIV infection.

In one embodiment, the invention provides Compound D, or pharmaceutically acceptable salt thereof, for use in the treatment or prevention of HIV infection. In one embodiment, the invention provides crystalline Compound D (Form 1), or pharmaceutically acceptable salt thereof, for use in the treatment or prevention of HIV infection.

In one embodiment, the invention provides Compound E, or pharmaceutically acceptable salt thereof, for use in the treatment or prevention of HIV infection. In one embodiment, the invention provides crystalline Compound E (Form 1), or pharmaceutically acceptable salt thereof, for use in the treatment or prevention of HIV infection.

In one embodiment, the invention provides Compound F, or pharmaceutically acceptable salt thereof, for use in the treatment or prevention of HIV infection. In one embodiment, the invention provides crystalline Compound F (Form 1), or pharmaceutically acceptable salt thereof, for use in the treatment or prevention of HIV infection.

In one embodiment, the invention provides Compound G, or pharmaceutically acceptable salt thereof, for use in the treatment or prevention of HIV infection. In one embodiment, the invention provides crystalline Compound G (Form 1), or pharmaceutically acceptable salt thereof, for use in the treatment or prevention of HIV infection.

In one embodiment, the invention provides Compound H, or pharmaceutically acceptable salt thereof, for use in the treatment or prevention of HIV infection. In one embodiment, the invention provides crystalline Compound H (Form 1), or pharmaceutically acceptable salt thereof, for use in the treatment or prevention of HIV infection.

In one embodiment, the invention provides Compound J, or pharmaceutically acceptable salt thereof, for use in the treatment or prevention of HIV infection. In one embodiment, the invention provides crystalline Compound J (Form 1), or pharmaceutically acceptable salt thereof, for use in the treatment or prevention of HIV infection.

In one embodiment, the invention provides Compound K, or pharmaceutically acceptable salt thereof, for use in the treatment or prevention of HIV infection. In one embodiment, the invention provides crystalline Compound K (Form 1), or pharmaceutically acceptable salt thereof, for use in the treatment or prevention of HIV infection.

In one embodiment, the invention provides a compound of the invention for use in the treatment of HIV infection. In one embodiment, the invention provides a crystalline form of the invention, or a pharmaceutically acceptable salt thereof, for use in the treatment of HIV infection.

In one embodiment, the invention provides Compound A, or a pharmaceutically acceptable salt thereof; or Compound B, or a pharmaceutically acceptable salt thereof; or Compound C, or a pharmaceutically acceptable salt thereof; or Compound D, or a pharmaceutically acceptable salt thereof; or Compound E, or a pharmaceutically acceptable salt thereof; or Compound F, or a pharmaceutically acceptable salt thereof; or Compound G, or a pharmaceutically acceptable salt thereof; or Compound H, or a pharmaceutically acceptable salt thereof; or Compound J, or a pharmaceutically acceptable salt thereof; or Compound K, or a pharmaceutically acceptable salt thereof, for use in the treatment of HIV infection.

In one embodiment, the invention provides Compound A (Form 1), or a pharmaceutically acceptable salt thereof; or Compound B (Form 1), or a pharmaceutically acceptable salt thereof; or Compound C (Form 1), or a pharmaceutically acceptable salt thereof; or Compound D (Form 1), or a pharmaceutically acceptable salt thereof; or Compound E (Form 1), or a pharmaceutically acceptable salt thereof; or Compound F (Form 1), or a pharmaceutically acceptable salt thereof; or Compound G (Form 1), or a pharmaceutically acceptable salt thereof; or Compound H (Form 1), or a pharmaceutically acceptable salt thereof; or Compound J (Form 1), or a pharmaceutically acceptable salt thereof; or Compound K (Form 1), or a pharmaceutically acceptable salt thereof, for use in the treatment of HIV infection.

In one embodiment, the invention provides a pharmaceutical composition comprising a compound of the invention and one or more pharmaceutically acceptable excipients for use in the treatment of HIV infection. In one embodiment, the invention provides the use of a pharmaceutical composition comprising a crystalline form of the invention, or a pharmaceutically acceptable salt thereof, and one or more pharmaceutically acceptable excipients for use in the treatment of HIV infection.

In one embodiment, the invention provides a pharmaceutical composition comprising Compound A, or a pharmaceutically acceptable salt thereof; or Compound B, or a pharmaceutically acceptable salt thereof; or Compound C, or a pharmaceutically acceptable salt thereof; or Compound D, or a pharmaceutically acceptable salt thereof; or Compound E, or a pharmaceutically acceptable salt thereof; or Compound F, or a pharmaceutically acceptable salt thereof; or Compound G, or a pharmaceutically acceptable salt thereof; or Compound H, or a pharmaceutically acceptable salt thereof; or Compound J, or a pharmaceutically acceptable salt thereof; or Compound K, or a pharmaceutically acceptable salt thereof, and one or more pharmaceutically acceptable excipients for use in the treatment of HIV infection.

In one embodiment, the invention provides a pharmaceutical composition comprising Compound A (Form 1), or a pharmaceutically acceptable salt thereof; or Compound B (Form 1), or a pharmaceutically acceptable salt thereof; or Compound C (Form 1), or a pharmaceutically acceptable salt thereof; or Compound D (Form 1), or a pharmaceutically acceptable salt thereof; or Compound E (Form 1), or a pharmaceutically acceptable salt thereof; or Compound F (Form 1), or a pharmaceutically acceptable salt thereof; or Compound G (Form 1), or a pharmaceutically acceptable salt thereof; or Compound H (Form 1), or a pharmaceutically acceptable salt thereof; or Compound J (Form 1), or a pharmaceutically acceptable salt thereof; or Compound K (Form 1), or a pharmaceutically acceptable salt thereof, and one or more pharmaceutically acceptable excipients for use in the treatment of HIV infection.

In one embodiment, the invention provides a compound of the invention for use in the prevention of HIV infection. In one embodiment, the invention provides a crystalline form of the invention, or a pharmaceutically acceptable salt thereof, for use in the prevention of HIV infection.

In one embodiment, the invention provides Compound A, or a pharmaceutically acceptable salt thereof; or Compound B, or a pharmaceutically acceptable salt thereof; or Compound C, or a pharmaceutically acceptable salt thereof; or Compound D, or a pharmaceutically acceptable salt thereof; or Compound E, or a pharmaceutically acceptable salt thereof; or Compound F, or a pharmaceutically acceptable salt thereof; or Compound G, or a pharmaceutically acceptable salt thereof; or Compound H, or a pharmaceutically acceptable salt thereof; or Compound J, or a pharmaceutically acceptable salt thereof; or Compound K, or a pharmaceutically acceptable salt thereof, for use in the prevention of HIV infection.

In one embodiment, the invention provides Compound A (Form 1), or a pharmaceutically acceptable salt thereof; or Compound B (Form 1), or a pharmaceutically acceptable salt thereof; or Compound C (Form 1), or a pharmaceutically acceptable salt thereof; or Compound D (Form 1), or a pharmaceutically acceptable salt thereof; or Compound E (Form 1), or a pharmaceutically acceptable salt thereof; or Compound F (Form 1), or a pharmaceutically acceptable salt thereof; or Compound G (Form 1), or a pharmaceutically acceptable salt thereof; or Compound H (Form 1), or a pharmaceutically acceptable salt thereof; or Compound J (Form 1), or a pharmaceutically acceptable salt thereof; or Compound K (Form 1), or a pharmaceutically acceptable salt thereof, for use in the prevention of HIV infection.

In one embodiment, the invention provides a pharmaceutical composition comprising a compound of the invention and one or more pharmaceutically acceptable excipients for use in the prevention of HIV infection. In one embodiment, the invention provides a pharmaceutical composition comprising a crystalline form of the invention, or a pharmaceutically acceptable salt thereof, and one or more pharmaceutically acceptable excipients for use in the prevention of HIV infection.

In one embodiment, the invention provides a pharmaceutical composition comprising Compound A, or a pharmaceutically acceptable salt thereof; or Compound B, or a pharmaceutically acceptable salt thereof; or Compound C, or a pharmaceutically acceptable salt thereof; or Compound D, or a pharmaceutically acceptable salt thereof; or Compound E, or a pharmaceutically acceptable salt thereof; or Compound F, or a pharmaceutically acceptable salt thereof; or Compound G, or a pharmaceutically acceptable salt thereof; or Compound H, or a pharmaceutically acceptable salt thereof; or Compound J, or a pharmaceutically acceptable salt thereof; or Compound K, or a pharmaceutically acceptable salt thereof, and one or more pharmaceutically acceptable excipients for use in the prevention of HIV infection.

In one embodiment, the invention provides a pharmaceutical composition comprising Compound A (Form 1), or a pharmaceutically acceptable salt thereof; or Compound B (Form 1), or a pharmaceutically acceptable salt thereof; or Compound C (Form 1), or a pharmaceutically acceptable salt thereof; or Compound D (Form 1), or a pharmaceutically acceptable salt thereof; or Compound E (Form 1), or a pharmaceutically acceptable salt thereof; or Compound F (Form 1), or a pharmaceutically acceptable salt thereof; or Compound G (Form 1), or a pharmaceutically acceptable salt thereof; or Compound H (Form 1), or a pharmaceutically acceptable salt thereof; or Compound J (Form 1), or a pharmaceutically acceptable salt thereof; or Compound K (Form 1), or a pharmaceutically acceptable salt thereof, and one or more pharmaceutically acceptable excipients for use in the prevention of HIV infection.

In one aspect, the present invention provides methods of preventing HIV infection in a patient or reducing the risk of infection, comprising administering a pharmaceutical composition of the invention. "Pre-exposure prophylaxis" (or PrEP) is when people at risk for HIV infection take HIV antiretroviral medicine to lower their chances of acquiring HIV infection. PrEP has been shown to be effective in reducing the risk of infection. In one embodiment, the invention provides a compound of the invention, a crystal from of a compound of the invention, or a composition of the invention) for use in PrEP of HIV infection.

In one embodiment, the invention provides a compound of the invention for use in preventing HIV infection and/or reducing the risk of HIV infection, or for use in PrEP of HIV infection. In one embodiment, the invention provides a crystalline form of the invention, or a pharmaceutically acceptable salt thereof, for use in preventing HIV infection and/or reducing the risk of HIV infection, or for use in PrEP of HIV infection.

In one embodiment, the invention provides Compound A, or a pharmaceutically acceptable salt thereof; or Compound B, or a pharmaceutically acceptable salt thereof; or Compound C, or a pharmaceutically acceptable salt thereof; or Compound D, or a pharmaceutically acceptable salt thereof; or Compound E, or a pharmaceutically acceptable salt thereof; or Compound F, or a pharmaceutically acceptable salt thereof; or Compound G, or a pharmaceutically acceptable salt thereof; or Compound H, or a pharmaceutically acceptable salt thereof; or Compound J, or a pharmaceutically acceptable salt thereof; or Compound K, or a pharmaceutically acceptable salt thereof, for use in preventing HIV infection and/or reducing the risk of HIV infection, or for use in PrEP of HIV infection.

In one embodiment, the invention provides Compound A (Form 1), or a pharmaceutically acceptable salt thereof; or Compound B (Form 1), or a pharmaceutically acceptable salt thereof; or Compound C (Form 1), or a pharmaceutically acceptable salt thereof; or Compound D (Form 1), or a pharmaceutically acceptable salt thereof; or Compound E (Form 1), or a pharmaceutically acceptable salt thereof; or Compound F (Form 1), or a pharmaceutically acceptable salt thereof; or Compound G (Form 1), or a pharmaceutically acceptable salt thereof; or Compound H (Form 1), or a pharmaceutically acceptable salt thereof; or Compound J (Form 1), or a pharmaceutically acceptable salt thereof; or Compound K (Form 1), or a pharmaceutically acceptable salt thereof, for use in preventing HIV infection and/or reducing the risk of HIV infection, or for use in PrEP of HIV infection.

In one embodiment, the invention provides a pharmaceutical composition comprising a compound of the invention and one or more pharmaceutically acceptable excipients for use in preventing HIV infection and/or reducing the risk of HIV infection, or for use in PrEP of HIV infection. In one embodiment, the invention provides a pharmaceutical composition comprising a crystalline form of the invention, or a pharmaceutically acceptable salt thereof, and one or more pharmaceutically acceptable excipients for use in preventing HIV infection and/or reducing the risk of HIV infection, or for use in PrEP of HIV infection.

In one embodiment, the invention provides a pharmaceutical composition comprising Compound A, or a pharmaceutically acceptable salt thereof; or Compound B, or a pharmaceutically acceptable salt thereof; or Compound C, or a pharmaceutically acceptable salt thereof; or Compound D, or a pharmaceutically acceptable salt thereof; or Compound E, or a pharmaceutically acceptable salt thereof; or Compound F, or a pharmaceutically acceptable salt thereof; or Compound G, or a pharmaceutically acceptable salt thereof; or Compound H, or a pharmaceutically acceptable salt thereof; or Compound J, or a pharmaceutically acceptable salt thereof; or Compound K, or a pharmaceutically acceptable salt thereof, and one or more pharmaceutically acceptable excipients for use in preventing HIV infection and/or reducing the risk of HIV infection, or for use in PrEP of HIV infection.

In one embodiment, the invention provides a pharmaceutical composition comprising crystalline Compound A (Form 1), or a pharmaceutically acceptable salt thereof; or crystalline Compound B (Form 1), or a pharmaceutically acceptable salt thereof; or crystalline Compound C (Form 1), or a pharmaceutically acceptable salt thereof; or crystalline Compound D (Form 1), or a pharmaceutically acceptable salt thereof; or crystalline Compound E (Form 1), or a pharmaceutically acceptable salt thereof; or crystalline Compound F (Form 1), or a pharmaceutically acceptable salt thereof; or crystalline Compound G (Form 1), or a pharmaceutically acceptable salt thereof; or crystalline Compound H (Form 1), or a pharmaceutically acceptable salt thereof; or crystalline Compound J (Form 1), or a pharmaceutically acceptable salt thereof, or crystalline Compound K (Form 1), or a pharmaceutically acceptable salt thereof, and one or more pharmaceutically acceptable excipients, for use in preventing HIV infection and/or reducing the risk of HIV infection, or for use in PrEP of HIV infection.

In one embodiment, the present invention provides use of a compound of the invention or a crystalline form of the invention for in the manufacture of a medicament for use in a use or method described herein, for example in the manufacture of a medicament for use in the treatment or prevention of HIV infection; and/or use in preventing HIV infection and/or reducing the risk of HIV infection, or for use in PrEP of HIV infection.

The terms "effective treatment of HIV" and similar terms refer to that treatment that lowers the viral load, or increases CD4 count, or both, as described above. The terms "effective prevention of HIV" and similar terms refer to that situation where there is a decrease in the relative number of newly infected subjects in a population in contact with a source of HIV infection such as a material containing HIV, or a HIV infected subject. Effective prevention can be measured, for example, by measuring in a mixed population of HIV infected and non-infected individuals, if there is a decrease of the relative number of newly infected individuals, when comparing non-infected individuals treated with a pharmaceutical composition of the invention, and non-treated non-infected individuals. This decrease can be measured by statistical analysis of the numbers of infected and non-infected individuals in a given population over time.

As used herein, the terms "effective amount" and "antiviral effective amount" means any amount of a drug or pharmaceutical agent, as described herein, that will elicit the biological or medical response of a tissue, system, animal, or human that is being sought, for instance, by a researcher or clinician. Further, as compared to a corresponding subject who has not received such amount of the drug or pharmaceutical agent, as described herein, results in improved treatment, healing, or amelioration of a disease, disorder, or side effect, or a decrease in the rate of advancement of a disease or disorder. The term also includes within its scope amounts effective to enhance normal physiological function. For use in therapy, therapeutically effective amounts of a compound of the invention, as well as salts thereof, may be administered as the raw chemical. Additionally, the active ingredient may be presented as a pharmaceutical composition. Suitably, an effective amount can be the amount of the compound of the invention that result in efficacious blood plasma levels. As used herein, "efficacious blood plasma levels" is meant those blood plasma levels of the compound of the invention that provide effective treatment or effective prevention of HIV infection.

Administration methods include administering an effective amount of a compound or composition of the invention at different times during the course of therapy or concurrently in a combination form. The methods of the invention include all known therapeutic treatment regimens.

In the uses and methods of the present invention, preferred routes of administration are oral and by injection to deliver subcutaneously or intramuscularly. In one embodiment of the uses and methods of the invention, a compound of the invention, a crystalline form of the invention, or composition of the invention is administered orally. In one embodiment of the uses and methods of the invention, a compound of the invention, a crystalline form of the invention, or a composition of the invention is administered by intramuscular injection or subcutaneously injection. Preferred pharmaceutical compositions of the present invention include composition suitable for oral administration (for example tablets) and formulations suitable for injection.

A compound of the invention, a crystalline form of the invention, or a composition of the invention, may be used in combination with one or more pharmaceutically active agent (s), for example one or more agents useful in the prevention or treatment of HIV. A compound of the invention, a crystalline form of the invention, or a composition of the invention when used in combination with one or more pharmaceutically active agent(s) may be administered together or separately and, when administered separately, administration may occur simultaneously or sequentially, in any order. The amounts of the compound and salts of the present invention and the other pharmaceutically active agent(s) and the relative timings of administration will be selected in order to achieve the desired combined therapeutic effect. The administration in combination of a compound of the invention, or a crystalline form of the invention, with other treatment agents may be in combination by administration concomitantly in: (1) a unitary pharmaceutical composition including multiple compounds; or (2) separate pharmaceutical compositions each including one of the compounds. Alternatively, the combination may be administered separately in a sequential manner wherein one treatment agent is administered first and the other second or vice versa, and the different agents could be administered on different schedules if appropriate. Such sequential administration may be close in time or remote in time. The amounts of a compound of the invention, or a crystalline form of the invention, and the relative timings of administration will be selected in order to achieve the desired combined therapeutic effect.

A compound of the invention, a crystalline form of the invention, or a composition of the invention, may be used in combination with one or more agents useful in the prevention or treatment of HIV. Such agents include, for example, nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors. Examples of such agents include Dolutegravir, lamivudine, Fostemsavir, Cabotegravir, maraviroc, rilpivirine, Reyataz, Tenofovir, Alafenamide, EfDA, Doravirine, or Prezista, for example Dolutegravir, lamivudine, Fostemsavir, or Cabotegravir.

As such, in one embodiment the present invention provides a combination of a) a compound of the invention or a crystalline form of the invention; and b) an agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors (for example an agent selected from the group consisting of Dolutegravir, lamivudine, Fostemsavir, Cabotegravir, maraviroc, rilpivirine, Reyataz, Tenofovir, Alafenamide, EfDA, Doravirine, and Prezista, or selected from the group consisting of Dolutegravir, lamivudine, Fostemsavir, and Cabotegravir).

In another embodiment, the present invention provides a composition comprising a) a compound of the invention or a crystalline form of the invention; and b) an agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

In another embodiment, the present invention provides a compound of the invention, a crystalline form of the invention, or a composition of the invention for use in the treatment of prophylaxis of HIV infection wherein said use further comprises administration of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors (for example an agent selected from the group consisting of Dolutegravir, lamivudine, Fostemsavir, Cabotegravir, maraviroc, rilpivirine, Reyataz, Tenofovir, Alafenamide, EfDA, Doravirine, and Prezista, or selected from the group consisting of Dolutegravir, lamivudine, Fostemsavir, and Cabotegravir).

In one embodiment, the present invention provides use of a compound of the invention, a crystalline form of the invention, or a composition of the invention for use in the treatment of prophylaxis of HIV infection, wherein said use further comprises administration of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors (for example an agent selected from the group consisting of Dolutegravir, lamivudine, Fostemsavir, Cabotegravir, maraviroc, rilpivirine, Reyataz, Tenofovir, Alafenamide, EfDA, Doravirine, and Prezista, or selected from the group consisting of Dolutegravir, lamivudine, Fostemsavir, and Cabotegravir).

In another embodiment, the present invention provides Compound A, or pharmaceutically acceptable salt thereof, for use in the treatment or prevention of HIV infection wherein said use further comprises administration of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors (for example an agent selected from the group consisting of Dolutegravir, lamivudine, Fostemsavir, Cabotegravir, maraviroc, rilpivirine, Reyataz, Tenofovir, Alafenamide, EfDA, Doravirine, and Prezista, or selected from the group consisting of Dolutegravir, lamivudine, Fostemsavir, and Cabotegravir).

In another embodiment, the present invention discloses crystalline Compound A (Form 1), or pharmaceutically acceptable salt thereof, for use in the treatment or prevention of HIV infection wherein said use further comprises administration of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors (for example an agent selected from the group consisting of Dolutegravir, lamivudine, Fostemsavir, Cabotegravir, maraviroc, rilpivirine, Reyataz, Tenofovir, Alafenamide, EfDA, Doravirine, and Prezista, or selected from the group consisting of Dolutegravir, lamivudine, Fostemsavir, and Cabotegravir).

In another embodiment, the present invention provides Compound B, or pharmaceutically acceptable salt thereof, for use in the treatment or prevention of HIV infection wherein said use further comprises administration of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors (for example an agent selected from the group consisting of Dolutegravir, lamivudine, Fostemsavir, Cabotegravir, maraviroc, rilpivirine, Reyataz, Tenofovir, Alafenamide, EfDA, Doravirine, and Prezista, or selected from the group consisting of Dolutegravir, lamivudine, Fostemsavir, and Cabotegravir).

In another embodiment, the present invention discloses crystalline Compound B (Form 1), or pharmaceutically acceptable salt thereof, for use in the treatment or prevention of HIV infection wherein said use further comprises administration of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors (for example an agent selected from the group consisting of Dolutegravir, lamivudine, Fostemsavir, Cabotegravir, maraviroc, rilpivirine, Reyataz, Tenofovir, Alafenamide, EfDA, Doravirine, and Prezista, or selected from the group consisting of Dolutegravir, lamivudine, Fostemsavir, and Cabotegravir).

In another embodiment, the present invention provides Compound C, or pharmaceutically acceptable salt thereof, for use in the treatment of prophylaxis of HIV infection wherein said use further comprises administration of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors (for example an agent selected from the group consisting of Dolutegravir, lamivudine, Fostemsavir, Cabotegravir, maraviroc, rilpivirine, Reyataz, Tenofovir, Alafenamide, EfDA, Doravirine, and Prezista, or selected from the group consisting of Dolutegravir, lamivudine, Fostemsavir, and Cabotegravir).

In another embodiment, the present invention discloses crystalline Compound C (Form 1), or pharmaceutically acceptable salt thereof, for use in the treatment or prevention of HIV infection wherein said use further comprises administration of at least one other agent selected from the group consisting of agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors (for example an agent selected from the group consisting of Dolutegravir, lamivudine, Fostemsavir, Cabotegravir, maraviroc, rilpivirine, Reyataz, Tenofovir, Alafenamide, EfDA, Doravirine, and Prezista, or selected from the group consisting of Dolutegravir, lamivudine, Fostemsavir, and Cabotegravir).

In another aspect, the present invention provides Compound D, or pharmaceutically acceptable salt thereof, for use in the treatment of prevention of HIV infection wherein said use further comprises administration of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors (for example an agent selected from the group consisting of Dolutegravir, lamivudine, Fostemsavir, Cabotegravir, maraviroc, rilpivirine, Reyataz, Tenofovir, Alafenamide, EfDA, Doravirine, and Prezista, or selected from the group consisting of Dolutegravir, lamivudine, Fostemsavir, and Cabotegravir).

In another aspect, the present invention provides crystalline Compound D (Form 1), or pharmaceutically acceptable salt thereof, for use in the treatment or prevention of HIV infection wherein said use further comprises administration of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors (for example an agent selected from the group consisting of Dolutegravir, lamivudine, Fostemsavir, Cabotegravir, maraviroc, rilpivirine, Reyataz, Tenofovir, Alafenamide, EfDA, Doravirine, and Prezista, or selected from the group consisting of Dolutegravir, lamivudine, Fostemsavir, and Cabotegravir).

In another embodiment, the present invention provides Compound E, or pharmaceutically acceptable salt thereof, for use in the treatment or prevention of HIV infection wherein said use further comprises administration of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors (for example an agent selected from the group consisting of Dolutegravir, lamivudine, Fostemsavir, Cabotegravir, maraviroc, rilpivirine, Reyataz, Tenofovir, Alafenamide, EfDA, Doravirine, and Prezista, or selected from the group consisting of Dolutegravir, lamivudine, Fostemsavir, and Cabotegravir).

In another embodiment, the present invention discloses crystalline Compound E (Form 1), or pharmaceutically acceptable salt thereof, for use in the treatment or prevention of HIV infection wherein said use further comprises administration of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors (for example an agent selected from the group consisting of Dolutegravir, lamivudine, Fostemsavir, Cabotegravir, maraviroc, rilpivirine, Reyataz, Tenofovir, Alafenamide, EfDA, Doravirine, and Prezista, or selected from the group consisting of Dolutegravir, lamivudine, Fostemsavir, and Cabotegravir).

In another embodiment, the present invention provides Compound F, or pharmaceutically acceptable salt thereof, for use in the treatment or prevention of HIV infection wherein said use further comprises administration of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors (for example an agent selected from the group consisting of Dolutegravir, lamivudine, Fostemsavir, Cabotegravir, maraviroc, rilpivirine, Reyataz, Tenofovir, Alafenamide, EfDA, Doravirine, and Prezista, or selected from the group consisting of Dolutegravir, lamivudine, Fostemsavir, and Cabotegravir).

In another embodiment, the present invention discloses crystalline Compound F (Form 1), or pharmaceutically acceptable salt thereof, for use in the treatment or prevention of HIV infection wherein said use further comprises administration of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors (for example an agent selected from the group consisting of Dolutegravir, lamivudine, Fostemsavir, Cabotegravir, maraviroc, rilpivirine, Reyataz, Tenofovir, Alafenamide, EfDA, Doravirine, and Prezista, or selected from the group consisting of Dolutegravir, lamivudine, Fostemsavir, and Cabotegravir).

In another embodiment, the present invention provides Compound G, or pharmaceutically acceptable salt thereof, for use in the treatment or prevention of HIV infection wherein said use further comprises administration of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors (for example an agent selected from the group consisting of Dolutegravir, lamivudine, Fostemsavir, Cabotegravir, maraviroc, rilpivirine, Reyataz, Tenofovir, Alafenamide, EfDA, Doravirine, and Prezista, or selected from the group consisting of Dolutegravir, lamivudine, Fostemsavir, and Cabotegravir).

In another embodiment, the present invention discloses crystalline Compound G (Form 1), or pharmaceutically acceptable salt thereof, for use in the treatment or prevention of HIV infection wherein said use further comprises administration of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors (for example an agent selected from the group consisting of Dolutegravir, lamivudine, Fostemsavir, Cabotegravir, maraviroc, rilpivirine, Reyataz, Tenofovir, Alafenamide, EfDA, Doravirine, and Prezista, or selected from the group consisting of Dolutegravir, lamivudine, Fostemsavir, and Cabotegravir).

In another embodiment, the present invention provides Compound H, or pharmaceutically acceptable salt thereof, for use in the treatment or prevention of HIV infection wherein said use further comprises administration of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors (for example an agent selected from the group consisting of Dolutegravir, lamivudine, Fostemsavir, Cabotegravir, maraviroc, rilpivirine, Reyataz, Tenofovir, Alafenamide, EfDA, Doravirine, and Prezista, or selected from the group consisting of Dolutegravir, lamivudine, Fostemsavir, and Cabotegravir).

In another embodiment, the present invention discloses crystalline Compound H (Form 1), or pharmaceutically acceptable salt thereof, for use in the treatment or prevention of HIV infection wherein said use further comprises administration of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors (for example an agent selected from the group consisting of Dolutegravir, lamivudine, Fostemsavir, Cabotegravir, maraviroc, rilpivirine, Reyataz, Tenofovir, Alafenamide, EfDA, Doravirine, and Prezista, or selected from the group consisting of Dolutegravir, lamivudine, Fostemsavir, and Cabotegravir).

In another embodiment, the present invention provides Compound J, or pharmaceutically acceptable salt thereof, for use in the treatment or prevention of HIV infection wherein said use further comprises administration of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors (for example an agent selected from the group consisting of Dolutegravir, lamivudine, Fostemsavir, Cabotegravir, maraviroc, rilpivirine, Reyataz, Tenofovir, Alafenamide, EfDA, Doravirine, and Prezista, or selected from the group consisting of Dolutegravir, lamivudine, Fostemsavir, and Cabotegravir).

In another embodiment, the present invention discloses crystalline Compound J (Form 1), or pharmaceutically acceptable salt thereof, for use in the treatment or prevention of HIV infection wherein said use further comprises administration of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors (for example an agent selected from the group consisting of Dolutegravir, lamivudine, Fostemsavir, Cabotegravir, maraviroc, rilpivirine, Reyataz, Tenofovir, Alafenamide, EfDA, Doravirine, and Prezista, or selected from the group consisting of Dolutegravir, lamivudine, Fostemsavir, and Cabotegravir).

In another embodiment, the present invention provides Compound K, or pharmaceutically acceptable salt thereof, for use in the treatment or prevention of HIV infection wherein said use further comprises administration of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors (for example an agent selected from the group consisting of Dolutegravir, lamivudine, Fostemsavir, Cabotegravir, maraviroc, rilpivirine, Reyataz, Tenofovir, Alafenamide, EfDA, Doravirine, and Prezista, or selected from the group consisting of Dolutegravir, lamivudine, Fostemsavir, and Cabotegravir).

In another embodiment, the present invention discloses crystalline Compound K (Form 1), or pharmaceutically acceptable salt thereof, for use in the treatment or prevention of HIV infection wherein said use further comprises administration of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors (for example an agent selected from the group consisting of Dolutegravir, lamivudine, Fostemsavir, Cabotegravir, maraviroc, rilpivirine, Reyataz, Tenofovir, Alafenamide, EfDA, Doravirine, and Prezista, or selected from the group consisting of Dolutegravir, lamivudine, Fostemsavir, and Cabotegravir).

Compositions of the Invention

The compounds of the invention will normally, but not necessarily, be formulated into pharmaceutical compositions prior to administration to a patient. Accordingly, in one aspect, the invention is directed to pharmaceutical compositions comprising a compound of the invention, or a crystalline form of the invention, and one or more pharmaceutically acceptable excipients.

As used herein, "pharmaceutically acceptable excipient" means a pharmaceutically acceptable material, composition or vehicle involved in giving form or consistency to the pharmaceutical composition, for example a pharmaceutically acceptable carrier and/or pharmaceutically acceptable diluent. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

Because the compounds of this invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the purer forms used in the pharmaceutical compositions.

It is understood that samples of the compounds of the invention may contain as a weight percentage small quantities of other molecules, including small quantities of stereoisomers thereof.

In certain embodiments, this invention relates to a pharmaceutical composition comprising a compound of the invention.

In one embodiment, the invention relates to a pharmaceutical composition comprising a crystalline form of the invention.

In another embodiment, this invention relates to a pharmaceutical composition comprising a compound of the invention wherein at least 10% by weight of the compound is present as a crystalline form, or a pharmaceutically acceptable salt thereof.

In another embodiment, this invention relates to a pharmaceutical composition comprising a compound of the invention wherein at least 20% by weight, or at least 30% by weight, or at least 40% by weight, or at least 50% by weight, or at least 60% by weight, or at least 70% by weight, or at least 80% by weight, or at least 90% by weight of the compound is present as a crystalline form, or a pharmaceutically acceptable salt thereof.

In another embodiment, the invention relates to a pharmaceutical composition comprising a compound of the invention wherein at least 95% by weight, or at least 96% by weight, or at least 97% by weight, or at least 98% by weight, or at least 99% by weight, or at least 99.5% by weight, or at least 99.8% by weight, or at least 99.9% by weight of the compound, or a pharmaceutically acceptable salt thereof, is present as a crystallin form, or a pharmaceutically acceptable salt thereof.

In certain embodiments, this invention relates to a pharmaceutical composition comprising Compound A, or a pharmaceutically acceptable salt thereof.

In one embodiment, the invention relates to a pharmaceutical composition comprising crystalline Compound A (Form 1), or a pharmaceutically acceptable salt thereof.

In another embodiment, this invention relates to a pharmaceutical composition comprising Compound A, or a pharmaceutically acceptable salt thereof, wherein at least 10% by weight of Compound A, or a pharmaceutically acceptable salt thereof, is present as crystalline Compound A (Form 1), or a pharmaceutically acceptable salt thereof.

In another embodiment, this invention relates to a pharmaceutical composition comprising Compound A, or a pharmaceutically acceptable salt thereof, wherein at least 20% by weight, or at least 30% by weight, or at least 40% by weight, or at least 50% by weight, or at least 60% by weight, or at least 70% by weight, or at least 80% by weight, or at least 90% by weight of Compound A, or a pharmaceutically acceptable salt thereof, is present as crystalline Compound A (Form 1), or a pharmaceutically acceptable salt thereof.

In another embodiment, the invention relates to a pharmaceutical composition comprising Compound A, or a pharmaceutically acceptable salt thereof, wherein at least 95% by weight, or at least 96% by weight, or at least 97% by weight, or at least 98% by weight, or at least 99% by weight, or at least 99.5% by weight, or at least 99.8% by weight, or at least 99.9% by weight of Compound A, or a pharmaceutically acceptable salt thereof, is present crystalline Compound A (Form 1), or a pharmaceutically acceptable salt thereof.

In certain embodiments, this invention relates to a pharmaceutical composition comprising Compound B, or a pharmaceutically acceptable salt thereof.

In one embodiment, the invention relates to a pharmaceutical composition comprising crystalline Compound B (Form 1), or a pharmaceutically acceptable salt thereof.

In another embodiment, this invention relates to a pharmaceutical composition comprising Compound B, or a pharmaceutically acceptable salt thereof, wherein at least 10% by weight of Compound B, or a pharmaceutically acceptable salt thereof, is present as crystalline Compound B (Form 1), or a pharmaceutically acceptable salt thereof.

In another embodiment, this invention relates to a pharmaceutical composition comprising Compound B, or a pharmaceutically acceptable salt thereof, wherein at least 20% by weight, or at least 30% by weight, or at least 40% by weight, or at least 50% by weight, or at least 60% by weight, or at least 70% by weight, or at least 80% by weight, or at least 90% by weight of Compound B, or a pharmaceutically acceptable salt thereof, is present as crystalline Compound B (Form 1), or a pharmaceutically acceptable salt thereof.

In another embodiment, the invention relates to a pharmaceutical composition comprising Compound B, or a pharmaceutically acceptable salt thereof, wherein at least 95% by weight, or at least 96% by weight, or at least 97% by weight, or at least 98% by weight, or at least 99% by weight, or at least 99.5% by weight, or at least 99.8% by weight, or at least 99.9% by weight of Compound B, or a pharmaceutically acceptable salt thereof, is present as crystalline Compound B (Form 1), or a pharmaceutically acceptable salt thereof.

In certain embodiments, this invention relates to a pharmaceutical composition comprising Compound C, or a pharmaceutically acceptable salt thereof.

In one embodiment, the invention relates to a pharmaceutical composition comprising crystalline Compound C (Form 1), or a pharmaceutically acceptable salt thereof.

In another embodiment, this invention relates to a pharmaceutical composition comprising Compound C, or a pharmaceutically acceptable salt thereof, wherein at least 10% by weight of Compound C, or a pharmaceutically acceptable salt thereof, is present as crystalline Compound C (Form 1), or a pharmaceutically acceptable salt thereof.

In another embodiment, this invention relates to a pharmaceutical composition comprising Compound C, or a pharmaceutically acceptable salt thereof, wherein at least 20% by weight, or at least 30% by weight, or at least 40% by weight, or at least 50% by weight, or at least 60% by weight, or at least 70% by weight, or at least 80% by weight, or at least 90% by weight of Compound C, or a pharmaceutically acceptable salt thereof, is present as crystalline Compound C (Form 1), or a pharmaceutically acceptable salt thereof.

In another embodiment, the invention relates to a pharmaceutical composition comprising Compound C, or a pharmaceutically acceptable salt thereof, wherein at least 95% by weight, or at least 96% by weight, or at least 97% by weight, or at least 98% by weight, or at least 99% by weight, or at least 99.5% by weight, or at least 99.8% by weight, or at least 99.9% by weight of Compound C, or a pharmaceutically acceptable salt thereof, is present as crystalline Compound C (Form 1), or a pharmaceutically acceptable salt thereof.

In certain embodiments, this invention relates to a pharmaceutical composition comprising Compound D, or a pharmaceutically acceptable salt thereof.

In one embodiment, the invention relates to a pharmaceutical composition comprising crystalline Compound D (Form 1), or a pharmaceutically acceptable salt thereof.

In another embodiment, this invention relates to a pharmaceutical composition comprising Compound D, or a pharmaceutically acceptable salt thereof, wherein at least 10% by weight of Compound D, or a pharmaceutically acceptable salt thereof, is present as crystalline Compound D (Form 1), or a pharmaceutically acceptable salt thereof.

In another embodiment, this invention relates to a pharmaceutical composition comprising Compound D, or a pharmaceutically acceptable salt thereof, wherein at least 20% by weight, or at least 30% by weight, or at least 40% by weight, or at least 50% by weight, or at least 60% by weight, or at least 70% by weight, or at least 80% by weight, or at least 90% by weight of Compound D, or a pharmaceutically acceptable salt thereof, is present as crystalline Compound D (Form 1), or a pharmaceutically acceptable salt thereof.

In another embodiment, the invention relates to a pharmaceutical composition comprising Compound D, or a pharmaceutically acceptable salt thereof, wherein at least 95% by weight, or at least 96% by weight, or at least 97% by weight, or at least 98% by weight, or at least 99% by weight, or at least 99.5% by weight, or at least 99.8% by weight, or at least 99.9% by weight of Compound D, or a pharmaceutically acceptable salt thereof, is present as crystalline Compound D (Form 1), or a pharmaceutically acceptable salt thereof.

In certain embodiments, this invention relates to a pharmaceutical composition comprising Compound E, or a pharmaceutically acceptable salt thereof.

In one embodiment, the invention relates to a pharmaceutical composition comprising crystalline Compound E (Form 1), or a pharmaceutically acceptable salt thereof.

In another embodiment, this invention relates to a pharmaceutical composition comprising Compound E, or a pharmaceutically acceptable salt thereof, wherein at least 10% by weight of Compound E, or a pharmaceutically acceptable salt thereof, is present as crystalline Compound E (Form 1), or a pharmaceutically acceptable salt thereof.

In another embodiment, this invention relates to a pharmaceutical composition comprising Compound E, or a pharmaceutically acceptable salt thereof, wherein at least 20% by weight, or at least 30% by weight, or at least 40% by weight, or at least 50% by weight, or at least 60% by weight, or at least 70% by weight, or at least 80% by weight, or at least 90% by weight of Compound E, or a pharmaceutically acceptable salt thereof, is present as crystalline Compound E (Form 1), or a pharmaceutically acceptable salt thereof.

In another embodiment, the invention relates to a pharmaceutical composition comprising Compound E, or a pharmaceutically acceptable salt thereof, wherein at least 95% by weight, or at least 96% by weight, or at least 97% by weight, or at least 98% by weight, or at least 99% by weight, or at least 99.5% by weight, or at least 99.8% by weight, or at least 99.9% by weight of Compound E, or a pharmaceutically acceptable salt thereof, is present as crystalline Compound E (Form 1), or a pharmaceutically acceptable salt thereof.

In certain embodiments, this invention relates to a pharmaceutical composition comprising Compound F, or a pharmaceutically acceptable salt thereof.

In one embodiment, the invention relates to a pharmaceutical composition comprising crystalline Compound F (Form 1), or a pharmaceutically acceptable salt thereof.

In another embodiment, this invention relates to a pharmaceutical composition comprising Compound F, or a pharmaceutically acceptable salt thereof, wherein at least 10% by weight of Compound F, or a pharmaceutically acceptable salt thereof, is present as crystalline Compound F (Form 1), or a pharmaceutically acceptable salt thereof.

In another embodiment, this invention relates to a pharmaceutical composition comprising Compound F, or a pharmaceutically acceptable salt thereof, wherein at least 20% by weight, or at least 30% by weight, or at least 40% by weight, or at least 50% by weight, or at least 60% by weight, or at least 70% by weight, or at least 80% by weight, or at least 90% by weight of Compound F, or a pharmaceutically acceptable salt thereof, is present as crystalline Compound F (Form 1), or a pharmaceutically acceptable salt thereof.

In another embodiment, the invention relates to a pharmaceutical composition comprising Compound F, or a pharmaceutically acceptable salt thereof, wherein at least 95% by weight, or at least 96% by weight, or at least 97% by weight, or at least 98% by weight, or at least 99% by weight, or at least 99.5% by weight, or at least 99.8% by weight, or at least 99.9% by weight of Compound F, or a pharmaceutically acceptable salt thereof, is present as crystalline Compound F (Form 1), or a pharmaceutically acceptable salt thereof.

In certain embodiments, this invention relates to a pharmaceutical composition comprising Compound G, or a pharmaceutically acceptable salt thereof.

In one embodiment, the invention relates to a pharmaceutical composition comprising crystalline Compound G (Form 1), or a pharmaceutically acceptable salt thereof.

In another embodiment, this invention relates to a pharmaceutical composition comprising Compound G, or a pharmaceutically acceptable salt thereof, wherein at least 10% by weight of Compound G, or a pharmaceutically acceptable salt thereof, is present as crystalline Compound G (Form 1), or a pharmaceutically acceptable salt thereof.

In another embodiment, this invention relates to a pharmaceutical composition comprising Compound G, or a pharmaceutically acceptable salt thereof, wherein at least 20% by weight, or at least 30% by weight, or at least 40% by weight, or at least 50% by weight, or at least 60% by weight, or at least 70% by weight, or at least 80% by weight, or at least 90% by weight of Compound G, or a pharmaceutically acceptable salt thereof, is present as crystalline Compound G (Form 1), or a pharmaceutically acceptable salt thereof.

In another embodiment, the invention relates to a pharmaceutical composition comprising Compound G, or a pharmaceutically acceptable salt thereof, wherein at least 95% by weight, or at least 96% by weight, or at least 97% by weight, or at least 98% by weight, or at least 99% by weight, or at least 99.5% by weight, or at least 99.8% by weight, or at least 99.9% by weight of Compound G, or a pharmaceutically acceptable salt thereof, is present as crystalline Compound G (Form 1), or a pharmaceutically acceptable salt thereof.

In certain embodiments, this invention relates to a pharmaceutical composition comprising Compound H, or a pharmaceutically acceptable salt thereof.

In one embodiment, the invention relates to a pharmaceutical composition comprising crystalline Compound H (Form 1), or a pharmaceutically acceptable salt thereof.

In another embodiment, this invention relates to a pharmaceutical composition comprising Compound H, or a pharmaceutically acceptable salt thereof, wherein at least 10% by weight of Compound H, or a pharmaceutically acceptable salt thereof, is present as crystalline Compound H (Form 1), or a pharmaceutically acceptable salt thereof.

In another embodiment, this invention relates to a pharmaceutical composition comprising Compound H, or a pharmaceutically acceptable salt thereof, wherein at least 20% by weight, or at least 30% by weight, or at least 40% by weight, or at least 50% by weight, or at least 60% by weight, or at least 70% by weight, or at least 80% by weight, or at least 90% by weight of Compound H, or a pharmaceutically acceptable salt thereof, is present as crystalline Compound H (Form 1), or a pharmaceutically acceptable salt thereof.

In another embodiment, the invention relates to a pharmaceutical composition comprising Compound H, or a pharmaceutically acceptable salt thereof, wherein at least 95% by weight, or at least 96% by weight, or at least 97% by weight, or at least 98% by weight, or at least 99% by weight, or at least 99.5% by weight, or at least 99.8% by weight, or at least 99.9% by weight of Compound H, or a pharmaceutically acceptable salt thereof, is present as crystalline Compound H (Form 1), or a pharmaceutically acceptable salt thereof.

In certain embodiments, this invention relates to a pharmaceutical composition comprising Compound J, or a pharmaceutically acceptable salt thereof.

In one embodiment, the invention relates to a pharmaceutical composition comprising crystalline Compound J (Form 1), or a pharmaceutically acceptable salt thereof.

In another embodiment, this invention relates to a pharmaceutical composition comprising Compound J, or a pharmaceutically acceptable salt thereof, wherein at least 10% by weight of Compound J, or a pharmaceutically acceptable salt thereof, is present as crystalline Compound J (Form 1), or a pharmaceutically acceptable salt thereof.

In another embodiment, this invention relates to a pharmaceutical composition comprising Compound J, or a pharmaceutically acceptable salt thereof, wherein at least 20% by weight, or at least 30% by weight, or at least 40% by weight, or at least 50% by weight, or at least 60% by weight, or at least 70% by weight, or at least 80% by weight, or at least 90% by weight of Compound J, or a pharmaceutically acceptable salt thereof, is present as crystalline Compound J (Form 1), or a pharmaceutically acceptable salt thereof.

In another embodiment, the invention relates to a pharmaceutical composition comprising Compound J, or a pharmaceutically acceptable salt thereof, wherein at least 95% by weight, or at least 96% by weight, or at least 97% by weight, or at least 98% by weight, or at least 99% by weight, or at least 99.5% by weight, or at least 99.8% by weight, or at least 99.9% by weight of Compound J, or a pharmaceutically acceptable salt thereof, is present as crystalline Compound J (Form 1), or a pharmaceutically acceptable salt thereof.

In certain embodiments, this invention relates to a pharmaceutical composition comprising Compound K, or a pharmaceutically acceptable salt thereof.

In one embodiment, the invention relates to a pharmaceutical composition comprising crystalline Compound K (Form 1), or a pharmaceutically acceptable salt thereof.

In another embodiment, this invention relates to a pharmaceutical composition comprising Compound K, or a pharmaceutically acceptable salt thereof, wherein at least 10% by weight of Compound K, or a pharmaceutically acceptable salt thereof, is present as crystalline Compound K (Form 1), or a pharmaceutically acceptable salt thereof.

In another embodiment, this invention relates to a pharmaceutical composition comprising Compound K, or a pharmaceutically acceptable salt thereof, wherein at least 20% by weight, or at least 30% by weight, or at least 40% by weight, or at least 50% by weight, or at least 60% by weight, or at least 70% by weight, or at least 80% by weight, or at least 90% by weight of Compound K, or a pharmaceutically acceptable salt thereof, is present as crystalline Compound K (Form 1), or a pharmaceutically acceptable salt thereof.

In another embodiment, the invention relates to a pharmaceutical composition comprising Compound K, or a pharmaceutically acceptable salt thereof, wherein at least 95% by weight, or at least 96% by weight, or at least 97% by weight, or at least 98% by weight, or at least 99% by weight, or at least 99.5% by weight, or at least 99.8% by weight, or at least 99.9% by weight of Compound K, or a pharmaceutically acceptable salt thereof, is present as crystalline Compound K (Form 1), or a pharmaceutically acceptable salt thereof.

A compound of the invention and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixirs, suspensions, solutions, emulsions, sachets, and cachets; (2) parenteral administration, including by intramuscular injection, subcutaneous injection, intravenously, intrasternal injection or infusion technique such as sterile solutions, suspensions, or powders for reconstitution; (3) transdermal administration such as transdermal patches; (4) rectal administration such as suppositories; (5) inhalation such as dry powders, aerosols, suspensions, and solutions; and (6) topical administration such as creams, ointments, lotions, solutions, pastes, sprays, foams, and gels. One or more adjuvants may also be included.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of the invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule. Suitable pharmaceutically acceptable excipients for oral administration of a compound of the invention, include a diluent or filler. Suitable diluents and fillers include lactose, sucrose, dextrose, mannitol, sorbitol, starch (e.g., corn starch, potato starch, and pre-gelatinized starch), cellulose and its derivatives (e.g., microcrystalline cellulose), calcium sulfate, and dibasic calcium phosphate. The oral solid dosage form may further comprise a binder. Suitable binders include starch (e.g., corn starch, potato starch, and pre-gelatinized starch), gelatin, acacia, sodium alginate, alginic acid, tragacanth, guar gum, povidone, and cellulose and its derivatives (e.g., microcrystalline cellulose). The oral solid dosage form may further comprise a disintegrant. Suitable disintegrants include crospovidone, sodium starch glycolate, croscarmellose, alginic acid, and sodium carboxymethyl cellulose. The oral solid dosage form may further comprise a lubricant. Suitable lubricants include stearic acid, magnesium stearate, calcium stearate, and talc.

In one embodiment, the invention provides a pharmaceutical composition comprising a compound of the invention and one or more pharmaceutically acceptable excipients, which composition is administered as an oral dosage form. In one embodiment, the oral dosage form is a tablet. In another embodiment, the oral dosage form is a capsule.

In another embodiment, the invention provides a pharmaceutical composition comprising a crystalline form of the invention, or a pharmaceutically acceptable salt thereof, and one or more pharmaceutically acceptable excipients, which composition is administered as an oral dosage form. In one embodiment, the oral dosage form is a tablet. In another embodiment, the oral dosage form is a capsule.

In one embodiment, the invention provides a pharmaceutical composition comprising Compound A, or a pharmaceutically acceptable salt thereof, and one or more pharmaceutically acceptable excipients, which composition is administered as an oral dosage form. In one embodiment, the oral dosage form is a tablet. In another embodiment, the oral dosage form is a capsule.

In another embodiment, the invention provides a pharmaceutical composition comprising crystalline Compound A, or a pharmaceutically acceptable salt thereof, (Compound A (Form 1)), or a pharmaceutically acceptable salt thereof, and one or more pharmaceutically acceptable excipients, which composition is administered as an oral dosage form. In one embodiment, the oral dosage form is a tablet. In another embodiment, the oral dosage form is a capsule.

In one embodiment, the invention provides a pharmaceutical composition comprising Compound B, or a pharmaceutically acceptable salt thereof, and one or more pharmaceutically acceptable excipients, which composition is administered as an oral dosage form. In one embodiment, the oral dosage form is a tablet. In another embodiment, the oral dosage form is a capsule.

In another embodiment, the invention provides a pharmaceutical composition comprising crystalline Compound B, or a pharmaceutically acceptable salt thereof, (Compound B (Form 1)), or a pharmaceutically acceptable salt thereof, and one or more pharmaceutically acceptable excipients, which composition is administered as an oral dosage form. In one embodiment, the oral dosage form is a tablet. In another embodiment, the oral dosage form is a capsule.

In one embodiment, the invention provides a pharmaceutical composition comprising Compound C, or a pharmaceutically acceptable salt thereof, and one or more pharmaceutically acceptable excipients, which composition is administered as an oral dosage form. In one embodiment, the oral dosage form is a tablet. In another embodiment, the oral dosage form is a capsule.

In another embodiment, the invention provides a pharmaceutical composition comprising crystalline Compound C, or a pharmaceutically acceptable salt thereof, (Compound C (Form 1)), or a pharmaceutically acceptable salt thereof, and one or more pharmaceutically acceptable excipients, which composition is administered as an oral dosage form. In one embodiment, the oral dosage form is a tablet. In another embodiment, the oral dosage form is a capsule.

In one embodiment, the invention provides a pharmaceutical composition comprising Compound D, or a pharmaceutically acceptable salt thereof, and one or more pharmaceutically acceptable excipients, which composition is administered as an oral dosage form. In one embodiment, the oral dosage form is a tablet. In another embodiment, the oral dosage form is a capsule.

In another embodiment, the invention provides a pharmaceutical composition comprising crystalline Compound D, or a pharmaceutically acceptable salt thereof, (Compound D (Form 1)), or a pharmaceutically acceptable salt thereof, and one or more pharmaceutically acceptable excipients, which composition is administered as an oral dosage form. In one embodiment, the oral dosage form is a tablet. In another embodiment, the oral dosage form is a capsule.

In one embodiment, the invention provides a pharmaceutical composition comprising Compound E, or a pharmaceutically acceptable salt thereof, and one or more pharmaceutically acceptable excipients, which composition is administered as an oral dosage form. In one embodiment, the oral dosage form is a tablet. In another embodiment, the oral dosage form is a capsule.

In another embodiment, the invention provides a pharmaceutical composition comprising crystalline Compound E, or a pharmaceutically acceptable salt thereof, (Compound E (Form 1)), or a pharmaceutically acceptable salt thereof, and one or more pharmaceutically acceptable excipients, which composition is administered as an oral dosage form. In one embodiment, the oral dosage form is a tablet. In another embodiment, the oral dosage form is a capsule.

In one embodiment, the invention provides a pharmaceutical composition comprising Compound F, or a pharmaceutically acceptable salt thereof, and one or more pharmaceutically acceptable excipients, which composition is administered as an oral dosage form. In one embodiment, the oral dosage form is a tablet. In another embodiment, the oral dosage form is a capsule.

In another embodiment, the invention provides a pharmaceutical composition comprising crystalline Compound F, or a pharmaceutically acceptable salt thereof, (Compound F (Form 1)), or a pharmaceutically acceptable salt thereof, and one or more pharmaceutically acceptable excipients, which composition is administered as an oral dosage form. In one embodiment, the oral dosage form is a tablet. In another embodiment, the oral dosage form is a capsule.

In one embodiment, the invention provides a pharmaceutical composition comprising Compound G, or a pharmaceutically acceptable salt thereof, and one or more pharmaceutically acceptable excipients, which composition is administered as an oral dosage form. In one embodiment, the oral dosage form is a tablet. In another embodiment, the oral dosage form is a capsule.

In another embodiment, the invention provides a pharmaceutical composition comprising crystalline Compound G, or a pharmaceutically acceptable salt thereof, (Compound G (Form 1)), or a pharmaceutically acceptable salt thereof, and one or more pharmaceutically acceptable excipients, which composition is administered as an oral dosage form. In one embodiment, the oral dosage form is a tablet. In another embodiment, the oral dosage form is a capsule.

In one embodiment, the invention provides a pharmaceutical composition comprising Compound H, or a pharmaceutically acceptable salt thereof, and one or more pharmaceutically acceptable excipients, which composition is administered as an oral dosage form. In one embodiment, the oral dosage form is a tablet. In another embodiment, the oral dosage form is a capsule.

In another embodiment, the invention provides a pharmaceutical composition comprising crystalline Compound H, or a pharmaceutically acceptable salt thereof, (Compound H (Form 1)), or a pharmaceutically acceptable salt thereof, and one or more pharmaceutically acceptable excipients, which composition is administered as an oral dosage form. In one embodiment, the oral dosage form is a tablet. In another embodiment, the oral dosage form is a capsule.

In one embodiment, the invention provides a pharmaceutical composition comprising Compound J, or a pharmaceutically acceptable salt thereof, and one or more pharmaceutically acceptable excipients, which composition is administered as an oral dosage form. In one embodiment, the oral dosage form is a tablet. In another embodiment, the oral dosage form is a capsule.

In another embodiment, the invention provides a pharmaceutical composition comprising crystalline Compound J, or a pharmaceutically acceptable salt thereof, (Compound J (Form 1)), or a pharmaceutically acceptable salt thereof, and one or more pharmaceutically acceptable excipients, which composition is administered as an oral dosage form. In one embodiment, the oral dosage form is a tablet. In another embodiment, the oral dosage form is a capsule.

In one embodiment, the invention provides a pharmaceutical composition comprising Compound K, or a pharmaceutically acceptable salt thereof, and one or more pharmaceutically acceptable excipients, which composition is administered as an oral dosage form. In one embodiment, the oral dosage form is a tablet. In another embodiment, the oral dosage form is a capsule.

In another embodiment, the invention provides a pharmaceutical composition comprising crystalline Compound K, or a pharmaceutically acceptable salt thereof, (Compound K (Form 1)), or a pharmaceutically acceptable salt thereof, and one or more pharmaceutically acceptable excipients, which composition is administered as an oral dosage form. In one embodiment, the oral dosage form is a tablet. In another embodiment, the oral dosage form is a capsule.

In another aspect, the invention is directed to a dosage form adapted for administration to a subject parenterally including subcutaneous, intramuscular, intravenous or intradermal. Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In one embodiment, the invention provides a pharmaceutical composition comprising a compound of the invention and one or more pharmaceutically acceptable excipients, which composition is administered via injection. In one embodiment, the pharmaceutical composition comprises a crystalline form of the invention, or a pharmaceutically acceptable salt thereof, and is administered via injection.

In one embodiment, the invention provides a pharmaceutical composition comprising a compound of the invention and one or more pharmaceutically acceptable excipients, wherein administration is via subcutaneous injection. In one embodiment, the pharmaceutical composition comprises a crystalline form of the invention, or a pharmaceutically acceptable salt thereof, and is administered via subcutaneous injection.

In another embodiment, the invention provides a pharmaceutical composition comprising a compound of the invention and one or more pharmaceutically acceptable excipients, wherein administration is via intramuscular injection. In one embodiment, the pharmaceutical composition comprises a crystalline form of the invention, or a pharmaceutically acceptable salt thereof, and is administered via intramuscular injection.

In one embodiment, the invention provides a pharmaceutical composition comprising a compound of the invention and one or more pharmaceutically acceptable excipients, which composition is administered via injection. In one embodiment, the pharmaceutical composition comprises a crystalline form of the invention, or a pharmaceutically acceptable salt thereof, and is administered via injection.

In one embodiment, the invention provides a pharmaceutical composition comprising a compound of the invention and one or more pharmaceutically acceptable excipients, wherein administration is via subcutaneous injection. In one embodiment, the pharmaceutical composition comprises a crystalline form of the invention, or a pharmaceutically acceptable salt thereof, and is administered via subcutaneous injection.

In another embodiment, the invention provides a pharmaceutical composition comprising a compound of the invention and one or more pharmaceutically acceptable excipients, wherein administration is via intramuscular injection. In one embodiment, the pharmaceutical composition comprises a crystalline form of the invention, or a pharmaceutically acceptable salt thereof, and is administered via intramuscular injection.

In one embodiment, the invention provides a pharmaceutical composition comprising Compound A, or a pharmaceutically acceptable salt thereof, and one or more pharmaceutically acceptable excipients, which composition is administered via injection.

In one embodiment, the pharmaceutical composition comprises a crystalline form of the compound (Compound A (Form 1)), or a pharmaceutically acceptable salt thereof, and is administered via injection.

In one embodiment, the invention provides a pharmaceutical composition comprising Compound A, or a pharmaceutically acceptable salt thereof, and one or more pharmaceutically acceptable excipients, wherein administration is via subcutaneous injection. In one embodiment, the pharmaceutical composition comprises a crystalline form of the compound (Compound A (Form 1)), or a pharmaceutically acceptable salt thereof, and is administered via subcutaneous injection.

In another embodiment, the invention provides a pharmaceutical composition comprising Compound A, or a pharmaceutically acceptable salt thereof; and one or more pharmaceutically acceptable excipients, wherein administration is via intramuscular injection. In one embodiment, the pharmaceutical composition comprises a crystalline form of the compound (Compound A (Form 1)), or a pharmaceutically acceptable salt thereof, and is administered via intramuscular injection.

In one embodiment, the invention provides a pharmaceutical composition comprising Compound B, or a pharmaceutically acceptable salt thereof, and one or more pharmaceutically acceptable excipients, which composition is administered via injection. In one embodiment, the pharmaceutical composition comprises a crystalline form of the compound (Compound B (Form 1)), or a pharmaceutically acceptable salt thereof, and is administered via injection.

In one embodiment, the invention provides a pharmaceutical composition comprising Compound B, or a pharmaceutically acceptable salt thereof, and one or more pharmaceutically acceptable excipients, wherein administration is via subcutaneous injection. In one embodiment, the pharmaceutical composition comprises a crystalline form of the compound (Compound B (Form 1)), or a pharmaceutically acceptable salt thereof, and is administered via subcutaneous injection.

In another embodiment, the invention provides a pharmaceutical composition comprising Compound B, or a pharmaceutically acceptable salt thereof; and one or more pharmaceutically acceptable excipients, wherein administration is via intramuscular injection. In one embodiment, the pharmaceutical composition comprises a crystalline form of the compound (Compound B (Form 1)), or a pharmaceutically acceptable salt thereof, and is administered via intramuscular injection.

In one embodiment, the invention provides a pharmaceutical composition comprising Compound C, or a pharmaceutically acceptable salt thereof, and one or more pharmaceutically acceptable excipients, which composition is administered via injection.

In one embodiment, the pharmaceutical composition comprises a crystalline form of the compound (Compound C (Form 1)), or a pharmaceutically acceptable salt thereof, and is administered via injection.

In one embodiment, the invention provides a pharmaceutical composition comprising Compound C, or a pharmaceutically acceptable salt thereof, and one or more pharmaceutically acceptable excipients, wherein administration is via subcutaneous injection. In one embodiment, the pharmaceutical composition comprises a crystalline form of the compound (Compound C (Form 1)), or a pharmaceutically acceptable salt thereof, and is administered via subcutaneous injection.

In another embodiment, the invention provides a pharmaceutical composition comprising Compound C, or a pharmaceutically acceptable salt thereof; and one or more pharmaceutically acceptable excipients, wherein administration is via intramuscular injection. In one embodiment, the pharmaceutical composition comprises a crystalline form of the compound (Compound C (Form 1)), or a pharmaceutically acceptable salt thereof, and is administered via intramuscular injection.

In one embodiment, the invention provides a pharmaceutical composition comprising Compound D, or a pharmaceutically acceptable salt thereof, and one or more pharmaceutically acceptable excipients, which composition is administered via injection.

In one embodiment, the pharmaceutical composition comprises a crystalline form of the compound (Compound D (Form 1)), or a pharmaceutically acceptable salt thereof, and is administered via injection.

In one embodiment, the invention provides a pharmaceutical composition comprising Compound D, or a pharmaceutically acceptable salt thereof, and one or more pharmaceutically acceptable excipients, wherein administration is via subcutaneous injection. In one embodiment, the pharmaceutical composition comprises a crystalline form of the compound (Compound D (Form 1)), or a pharmaceutically acceptable salt thereof, and is administered via subcutaneous injection.

In another embodiment, the invention provides a pharmaceutical composition comprising Compound D, or a pharmaceutically acceptable salt thereof; and one or more pharmaceutically acceptable excipients, wherein administration is via intramuscular injection. In one embodiment, the pharmaceutical composition comprises a crystalline form of the compound (Compound D (Form 1)), or a pharmaceutically acceptable salt thereof, and is administered via intramuscular injection.

In one embodiment, the invention provides a pharmaceutical composition comprising Compound E, or a pharmaceutically acceptable salt thereof, and one or more pharmaceutically acceptable excipients, which composition is administered via injection.

In one embodiment, the pharmaceutical composition comprises a crystalline form of the compound (Compound E (Form 1)), or a pharmaceutically acceptable salt thereof, and is administered via injection.

In one embodiment, the invention provides a pharmaceutical composition comprising Compound E, or a pharmaceutically acceptable salt thereof, and one or more pharmaceutically acceptable excipients, wherein administration is via subcutaneous injection. In one embodiment, the pharmaceutical composition comprises a crystalline form of the compound (Compound E (Form 1)), or a pharmaceutically acceptable salt thereof, and is administered via subcutaneous injection.

In another embodiment, the invention provides a pharmaceutical composition comprising Compound E, or a pharmaceutically acceptable salt thereof; and one or more pharmaceutically acceptable excipients, wherein administration is via intramuscular injection. In one embodiment, the pharmaceutical composition comprises a crystalline form of the compound (Compound E (Form 1)), or a pharmaceutically acceptable salt thereof, and is administered via intramuscular injection.

In one embodiment, the invention provides a pharmaceutical composition comprising Compound F, or a pharmaceutically acceptable salt thereof, and one or more pharmaceutically acceptable excipients, which composition is administered via injection. In one embodiment, the pharmaceutical composition comprises a crystalline form of the compound (Compound F (Form 1)), or a pharmaceutically acceptable salt thereof, and is administered via injection.

In one embodiment, the invention provides a pharmaceutical composition comprising Compound F, or a pharmaceutically acceptable salt thereof, and one or more pharmaceutically acceptable excipients, wherein administration is via subcutaneous injection. In one embodiment, the pharmaceutical composition comprises a crystalline form of the compound (Compound F (Form 1)), or a pharmaceutically acceptable salt thereof, and is administered via subcutaneous injection.

In another embodiment, the invention provides a pharmaceutical composition comprising Compound F, or a pharmaceutically acceptable salt thereof; and one or more pharmaceutically acceptable excipients, wherein administration is via intramuscular injection. In one embodiment, the pharmaceutical composition comprises a crystalline form of the compound (Compound F (Form 1)), or a pharmaceutically acceptable salt thereof, and is administered via intramuscular injection.

In one embodiment, the invention provides a pharmaceutical composition comprising Compound G, or a pharmaceutically acceptable salt thereof, and one or more pharmaceutically acceptable excipients, which composition is administered via injection. In one embodiment, the pharmaceutical composition comprises a crystalline form of the compound (Compound G (Form 1)), or a pharmaceutically acceptable salt thereof, and is administered via injection.

In one embodiment, the invention provides a pharmaceutical composition comprising Compound G, or a pharmaceutically acceptable salt thereof, and one or more pharmaceutically acceptable excipients, wherein administration is via subcutaneous injection. In one embodiment, the pharmaceutical composition comprises a crystalline form of the compound (Compound G (Form 1)), or a pharmaceutically acceptable salt thereof, and is administered via subcutaneous injection.

In another embodiment, the invention provides a pharmaceutical composition comprising Compound G, or a pharmaceutically acceptable salt thereof; and one or more pharmaceutically acceptable excipients, wherein administration is via intramuscular injection. In one embodiment, the pharmaceutical composition comprises a crystalline form of the compound (Compound G (Form 1)), or a pharmaceutically acceptable salt thereof, and is administered via intramuscular injection.

In one embodiment, the invention provides a pharmaceutical composition comprising Compound H, or a pharmaceutically acceptable salt thereof, and one or more pharmaceutically acceptable excipients, which composition is administered via injection. In one embodiment, the pharmaceutical composition comprises a crystalline form of the compound (Compound H (Form 1)), or a pharmaceutically acceptable salt thereof, and is administered via injection.

In one embodiment, the invention provides a pharmaceutical composition comprising Compound H, or a pharmaceutically acceptable salt thereof, and one or more pharmaceutically acceptable excipients, wherein administration is via subcutaneous injection. In one embodiment, the pharmaceutical composition comprises a crystalline form of the compound (Compound H (Form 1)), or a pharmaceutically acceptable salt thereof, and is administered via subcutaneous injection.

In another embodiment, the invention provides a pharmaceutical composition comprising Compound H, or a pharmaceutically acceptable salt thereof; and one or more pharmaceutically acceptable excipients, wherein administration is via intramuscular injection. In one embodiment, the pharmaceutical composition comprises a crystalline form of the compound (Compound H (Form 1)), or a pharmaceutically acceptable salt thereof, and is administered via intramuscular injection.

In one embodiment, the invention provides a pharmaceutical composition comprising Compound J, or a pharmaceutically acceptable salt thereof, and one or more pharmaceutically acceptable excipients, which composition is administered via injection. In one embodiment, the pharmaceutical composition comprises a crystalline form of the compound (Compound J (Form 1)), or a pharmaceutically acceptable salt thereof, and is administered via injection.

In one embodiment, the invention provides a pharmaceutical composition comprising Compound J, or a pharmaceutically acceptable salt thereof, and one or more pharmaceutically acceptable excipients, wherein administration is via subcutaneous injection. In one embodiment, the pharmaceutical composition comprises a crystalline form of the compound (Compound J (Form 1)), or a pharmaceutically acceptable salt thereof, and is administered via subcutaneous injection.

In another embodiment, the invention provides a pharmaceutical composition comprising Compound J, or a pharmaceutically acceptable salt thereof; and one or more pharmaceutically acceptable excipients, wherein administration is via intramuscular injection. In one embodiment, the pharmaceutical composition comprises a crystalline form of the compound (Compound J (Form 1)), or a pharmaceutically acceptable salt thereof, and is administered via intramuscular injection.

In one embodiment, the invention provides a pharmaceutical composition comprising Compound K, or a pharmaceutically acceptable salt thereof, and one or more pharmaceutically acceptable excipients, which composition is administered via injection. In one embodiment, the pharmaceutical composition comprises a crystalline form of the compound (Compound K (Form 1)), or a pharmaceutically acceptable salt thereof, and is administered via injection.

In one embodiment, the invention provides a pharmaceutical composition comprising Compound K, or a pharmaceutically acceptable salt thereof, and one or more pharmaceutically acceptable excipients, wherein administration is via subcutaneous injection. In one embodiment, the pharmaceutical composition comprises a crystalline form of the compound (Compound K (Form 1)), or a pharmaceutically acceptable salt thereof, and is administered via subcutaneous injection.

In another embodiment, the invention provides a pharmaceutical composition comprising Compound K, or a pharmaceutically acceptable salt thereof; and one or more pharmaceutically acceptable excipients, wherein administration is via intramuscular injection. In one embodiment, the pharmaceutical composition comprises a crystalline form of the compound (Compound K (Form 1)), or a pharmaceutically acceptable salt thereof, and is administered via intramuscular injection.

In certain aspects, the present invention provides the subject matter defined by the following clauses:

§ 1. A compound of the following structure:

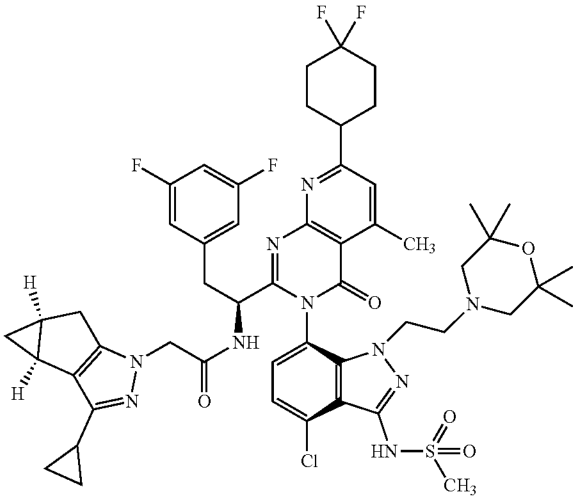

and pharmaceutically acceptable salts thereof.

§ 2. A pharmaceutical composition comprising a compound or salt according to clause § 1.

§ 3. A composition according to clause § 2 further comprising a pharmaceutically acceptable carrier, excipient, and/or diluent.

§ 4. A composition according to clause § 2 or clause § 3 suitable for oral administration, for intramuscular injection or for subcutaneous injection.

§ 5. A method of treating HIV infection comprising administering a composition according to clause § 2 to a patient.

§ 6. The method of clause § 5 wherein said administration is oral.

§ 7. The method of clause § 5 wherein said administration comprises administering by intramuscular injection or subcutaneously injection.

§ 8. The method of clause § 5 wherein said method further comprises administration of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

§ 9. The method of clause § 8 wherein said at least one other agent is selected from the group consisting of Dolutegravir, lamivudine, Fostemsavir, Cabotegravir, maraviroc, rilpivirine, Reyataz, Tenofovir, Alafenamide, EfDA, Doravirine, and Prezista.

10. The method of clause § 9 wherein said at least one other agent is selected from the group consisting of Dolutegravir, lamivudine, Fostemsavir, and Cabotegravir.

§ 11. A compound or pharmaceutically acceptable salt thereof according to clause § 1 for use in therapy § 12. A compound or pharmaceutically acceptable salt thereof according to clause § 1 for use in treating HIV infection.

§ 13. A compound or pharmaceutically acceptable salt thereof according to clause § 1 for use in the manufacture of a medicament for the treatment of HIV infection.

Examples

| | |
|---|---|
| TLC | Thin-layer chromatography |
| ABC | Ammonium bicarbonate |
| AGO | Formic acid |
| TFA | Trifluoroacetic acid |
| EtOAc | Ethyl acetate |
| Pet-ether | Petroleum ether |
| DCM | Dichloromethane |
| MeOH | Methanol |
| ACN, MeCN | Acetonitrile |
| Acq. Method | Acquisition Method |
| DIPEA | N,N-Diisopropylethylamine |
| TEA | Triethylamine |
| 2,6-Lutidine | 2,6-dimethylpyridine |
| T3P | 2,4,6-tripropyl-1,3,5,2,4,6-trioxatriphosphinane-2,4,6-trioxide |
| FA | Formic acid |

The compounds of the present invention can be generally prepared according to the following scheme:

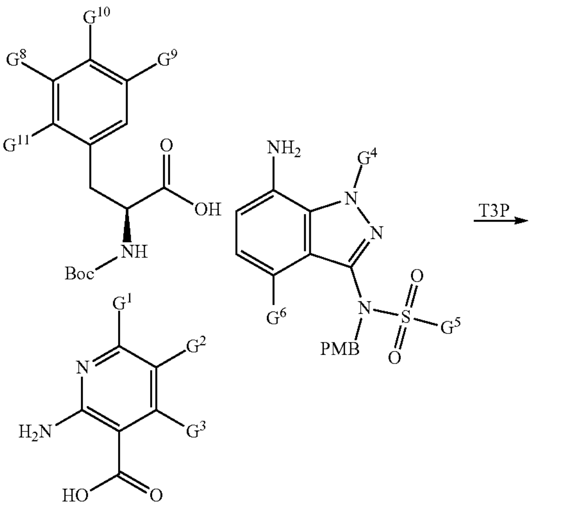

-continued
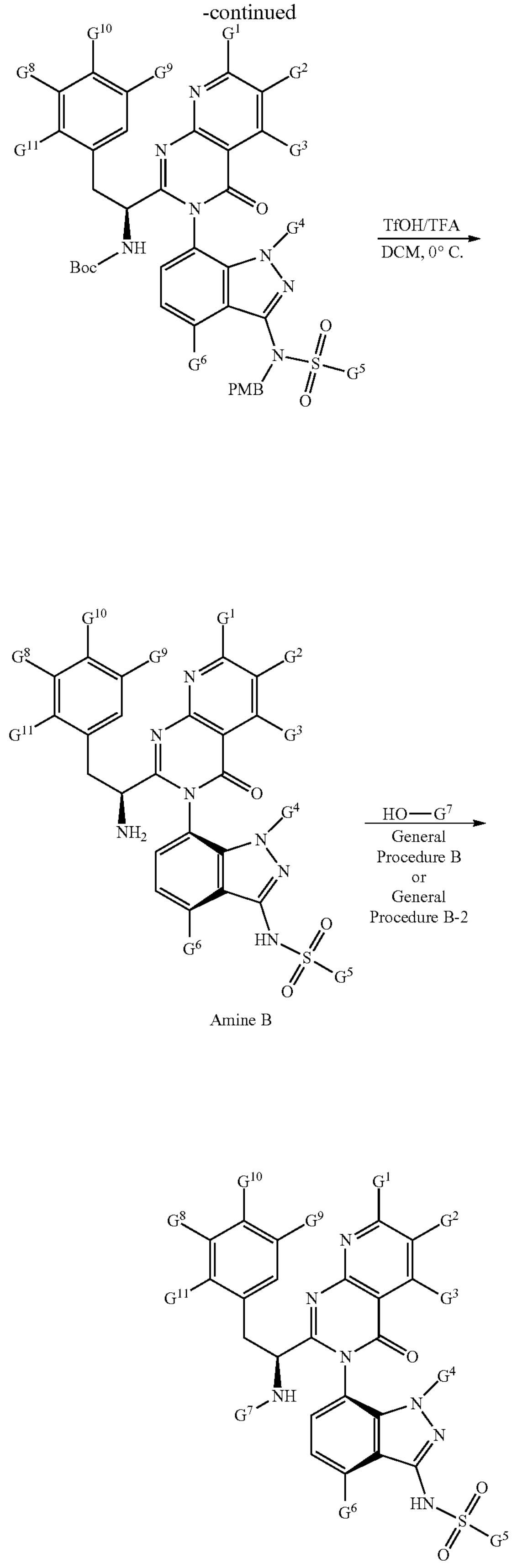
Many compounds of the present invention can also be prepared according to the following scheme:
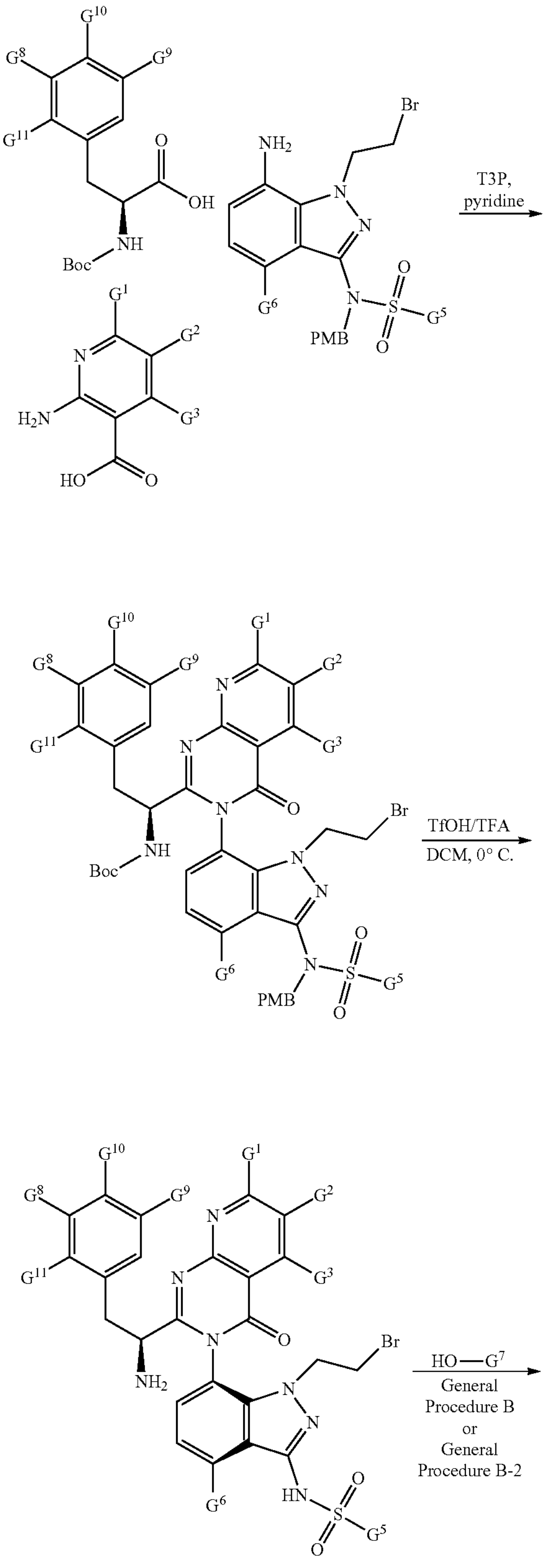
Amine B -continued
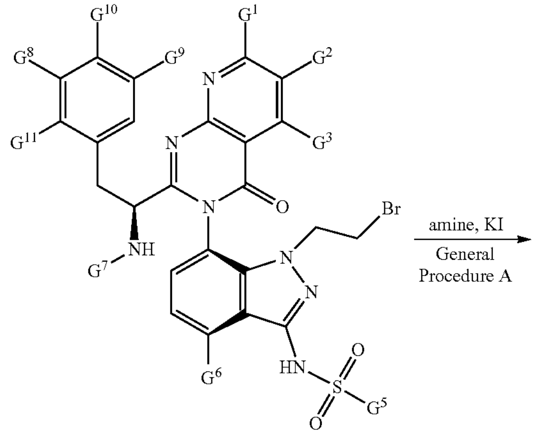
Bromide A
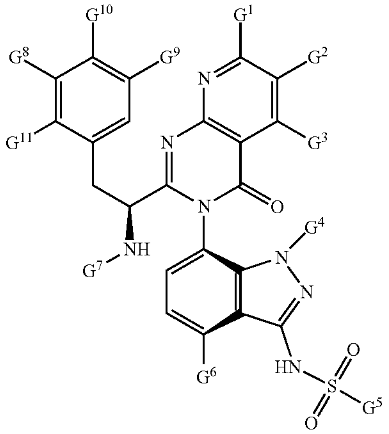
-continued
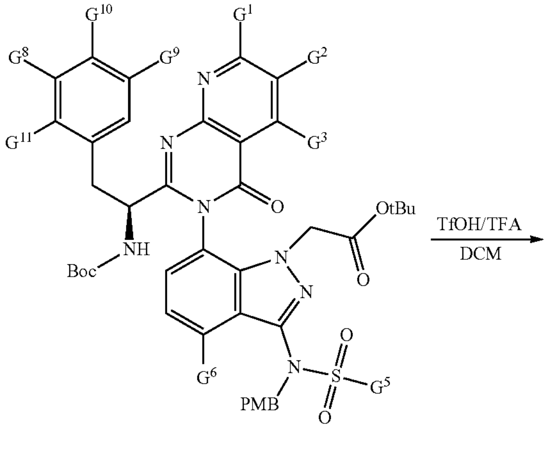
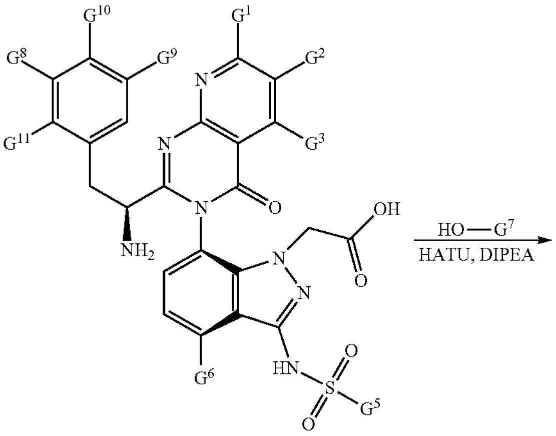
Compounds of the present invention having an amide at $G^4$ may be prepared according to the following scheme:
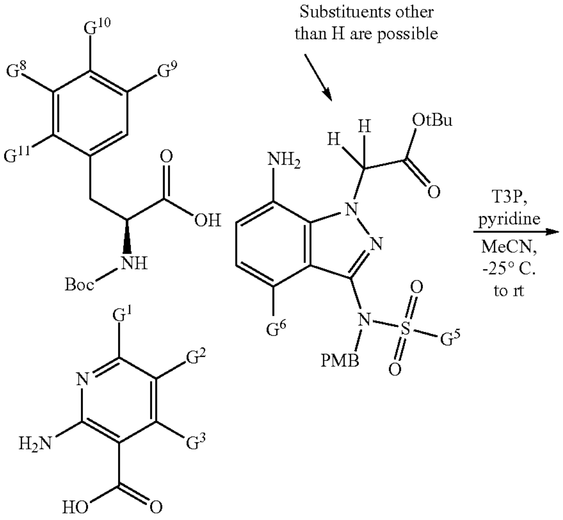
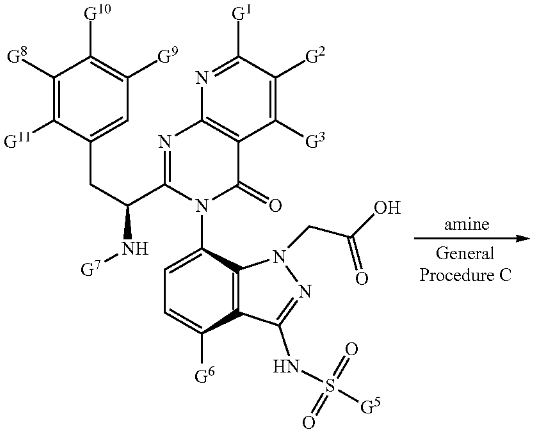
Acid C -continued
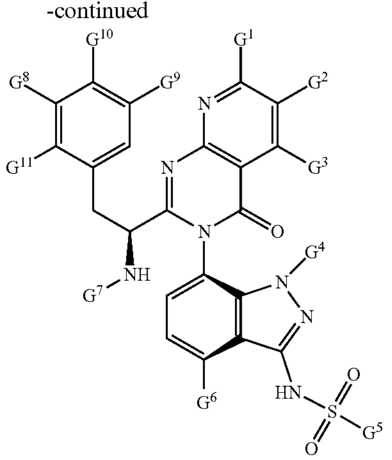
-continued
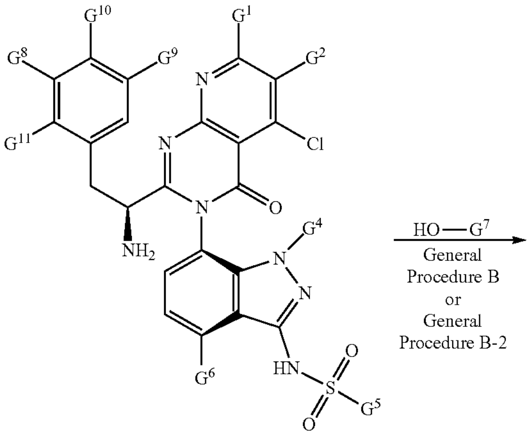
Compounds of the present invention with varied functionality at $G^3$ may be prepared according to the following scheme:
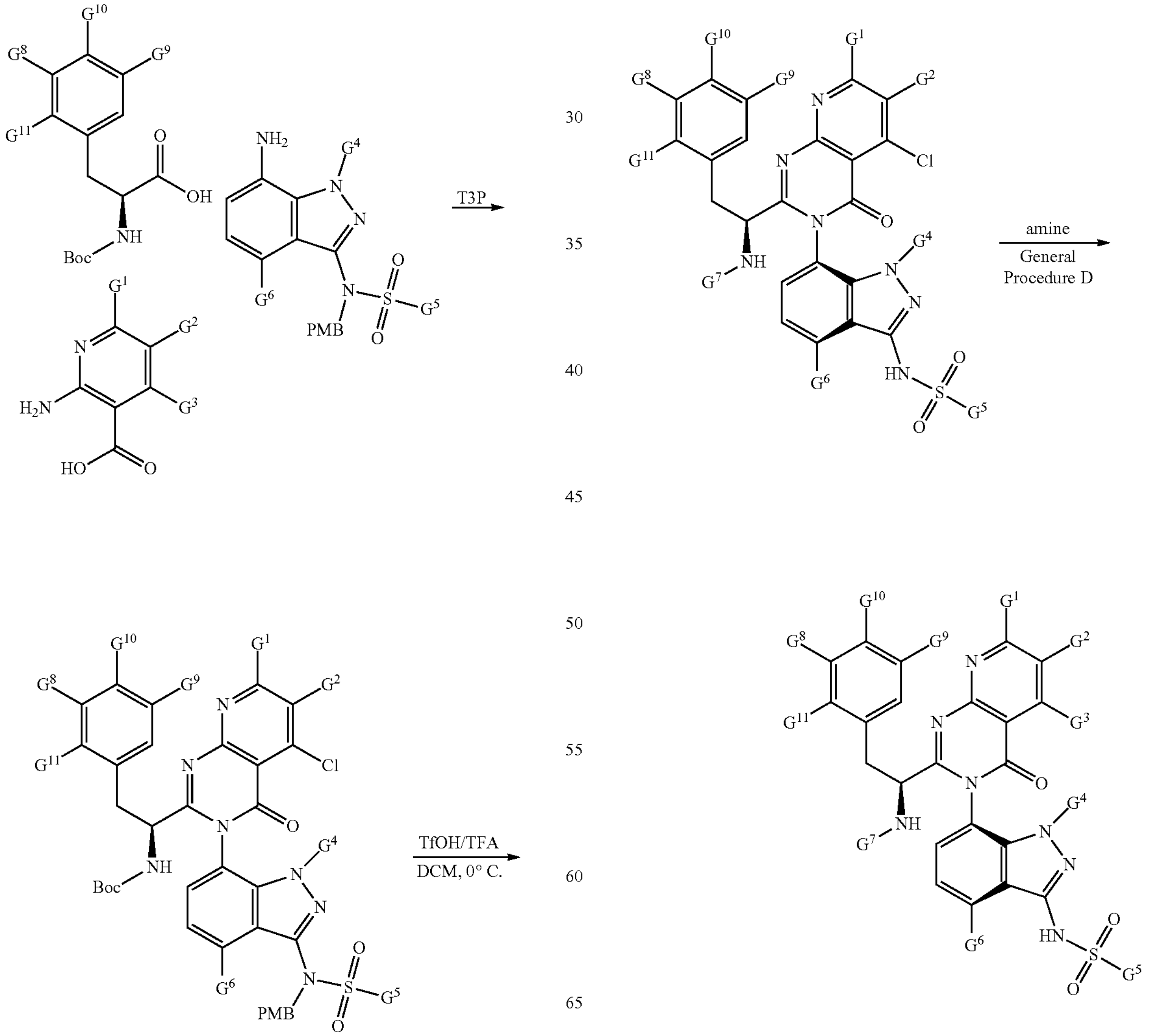

Compounds of the present invention with varied functionality at $G^3$ may also be prepared according to the following scheme:
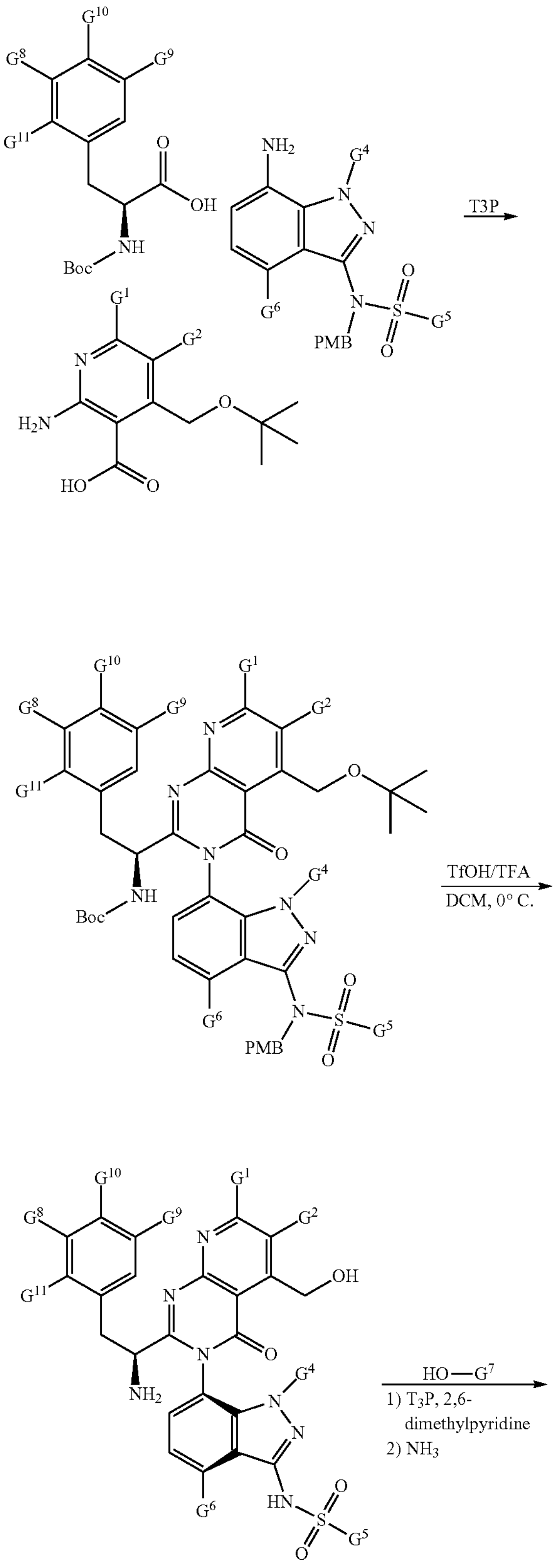
-continued
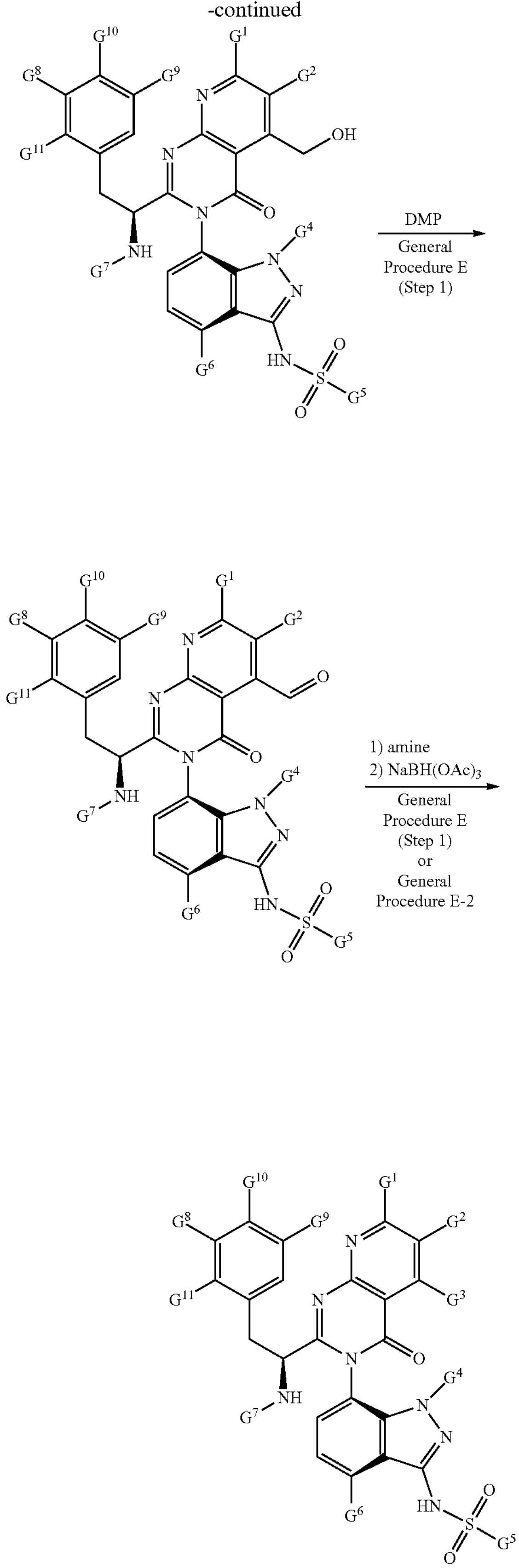

Compounds of the present invention with varied functionality at $G^{1a}$ may be prepared according to the following scheme:
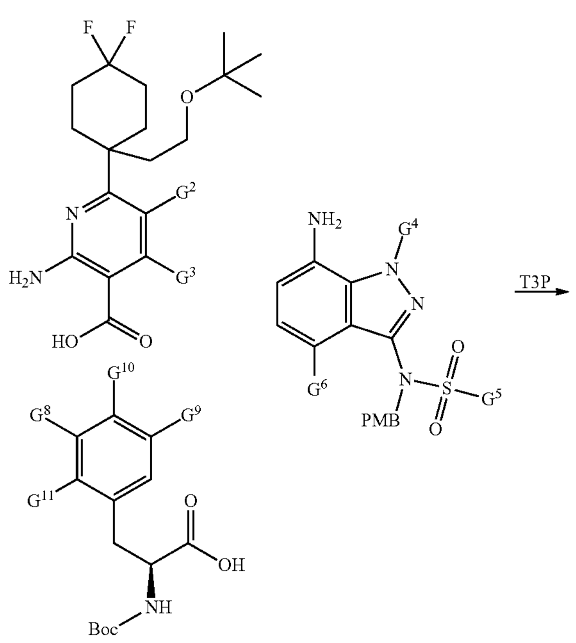
-continued
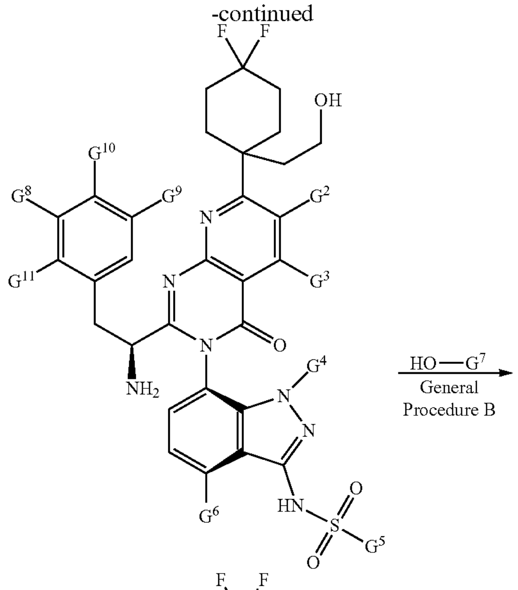
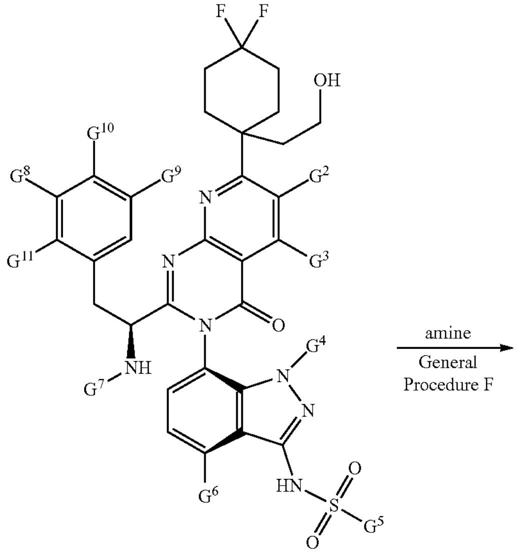
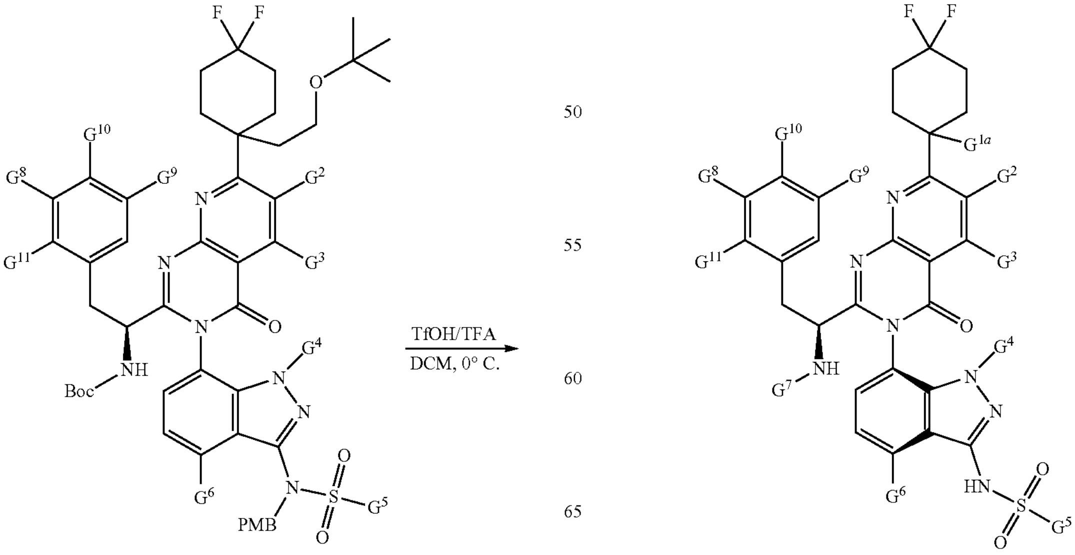

Indazole Intermediate compounds depicted in the above schemes may be prepared according to the following scheme:

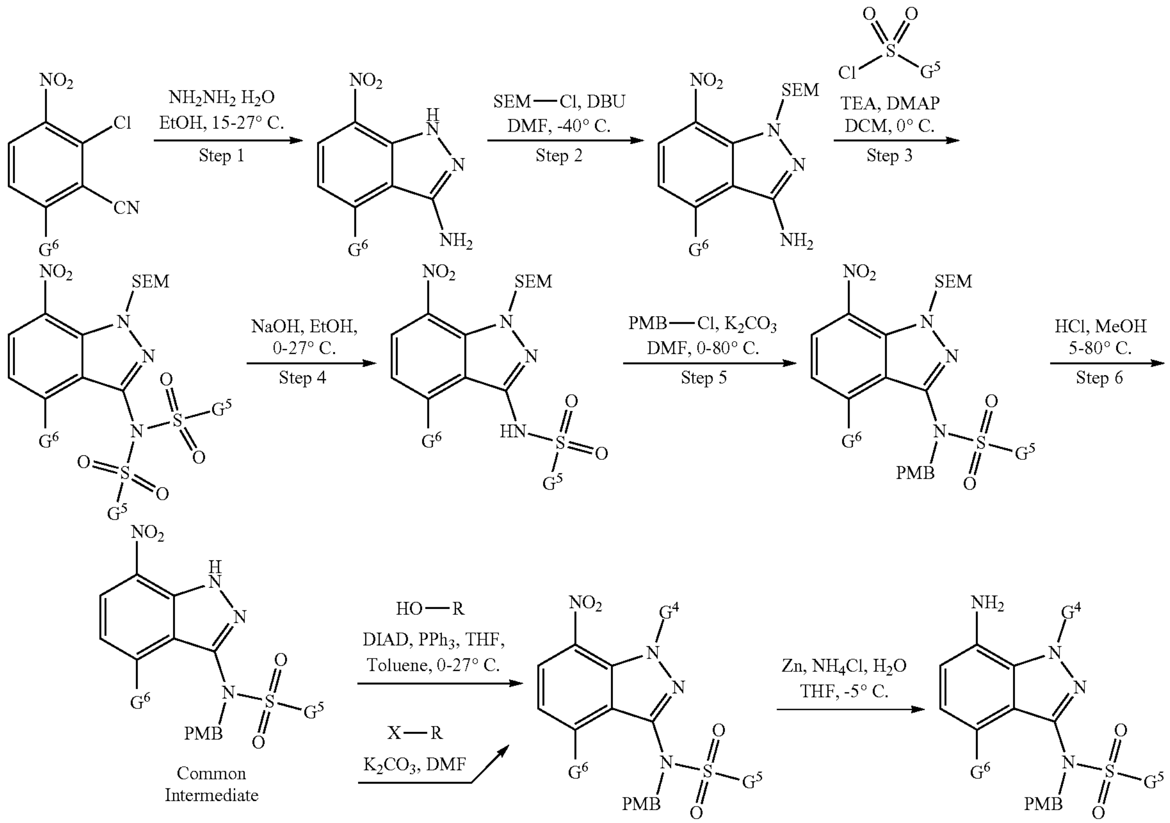

Provided below are example procedures that illustrate how the above schemes can be followed to afford the Example compounds of the present invention.

General Synthesis Methods

The General Procedures described below were typically carried out on a 0.036 mmol scale. However, it will be recognized by one skilled in the art that the scale of the reaction may be changed by modifying the amounts of reagents and solvents proportionally.

In the General Procedures, unless specifically noted otherwise, the "core reagent" is a single atropisomer, which is the atropisomer that without inversion would be required to furnish the atropisomer depicted in the example chemical structure and/or defined in the example name.

General Procedure A:

General Procedure A is as follows, and may include the modifications noted below: N-((S)-1-(3-(1-(2-bromoethyl)-4-chloro-3-(methylsulfonamido)-1H-indazol-7-yl)-7-(4,4-difluorocyclohexyl)-5-methyl-4-oxo-3,4-dihydropyrido[2,3-d]pyrimidin-2-yl)-2-(3,5-difluorophenyl)ethyl)-2-((3bS,4aS)-3-cyclopropyl-3b,4,4a,5-tetrahydro-1H-cyclopropa[3,4]cyclopenta[1,2-c]pyrazol-1-yl)acetamide ("Bromide A1", the "core reagent", 35 mg, 0.036 mmol, 1 eq.), diisopropylethylamine (DIPEA, 4-5 eq.), potassium iodide (1 eq.), and the amine required to afford the indicated product (the "diversity reagent", 4-6 eq.) were combined in acetonitrile (1 mL) at room temperature (rt). The reaction mixture was stirred overnight at 60-80° C. The reaction mixture was cooled to room temperature. To the reaction mixture was added DMF (1 mL) and the resulting solution was filtered and then subjected to HPLC purification to afford the indicated product.

The amine (the "diversity reagent") of General Procedure A was provided as the HCl salt or the free amine. Typically the HCl salt of the amine was used but in some cases the free base of the amine was used. Example compound syntheses that reference "General Procedure A" may not specify whether the free amine or HCl salt was used, and instead the name of the free amine is given with the understanding that either form is acceptable.

In General Procedure A, the mmol of the "core reagent" (for example, Bromide A1) used in the reaction may be changed with proportional changes of the other reagents and solvent amounts.

In General Procedure A, the reaction solvent may alternatively be DMF.

Depending on the structure of the Example to be made, in General Method A, the "core reagent" (Bromide A1, N-((S)-1-(3-(1-(2-bromoethyl)-4-chloro-3-(methylsulfonamido)-1H-indazol-7-yl)-7-(4,4-difluorocyclohexyl)-5-methyl-4-oxo-3,4-dihydropyrido[2,3-d]pyrimidin-2-yl)-2-(3,5-difluorophenyl)ethyl)-2-((3bS,4aS)-3-cyclopropyl-3b,4,4a,5-tetrahydro-1H-cyclopropa[3,4]cyclopenta[1,2-c]pyrazol-1-yl)acetamide) may be replaced with a different "core reagent" as would be required to afford the indicated product, for example replaced with one of the following reagents:

N-((S)-1-(3-(1-(2-bromoethyl)-4-chloro-3-(methylsulfonamido)-1H-indazol-7-yl)-7-(4,4-difluorocyclohexyl)-5- methyl-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide; or N-((1S)-1-(3-(1-(2-bromoethyl)-4-chloro-3-(methylsulfonamido)-1H-indazol-7-yl)-7-(4,4-difluorocyclohexyl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide In particular in General Procedure A, the "core reagent" Bromide A1 may be substituted for a different "core reagent" that is a bromide, as would be required to afford the indicated product. The structure of Bromide A1 and examples of alternate bromide core reagents are as follows:

Bromide A1

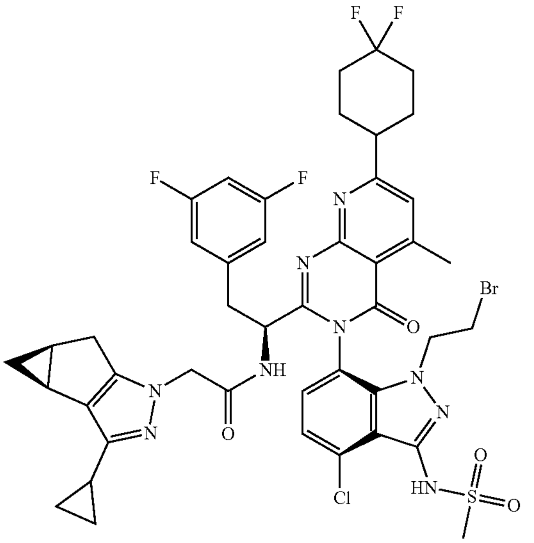

Bromide A2

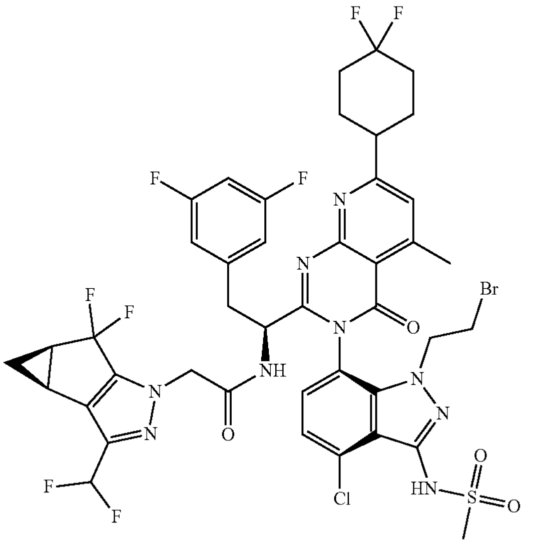

-continued

Bromide A3

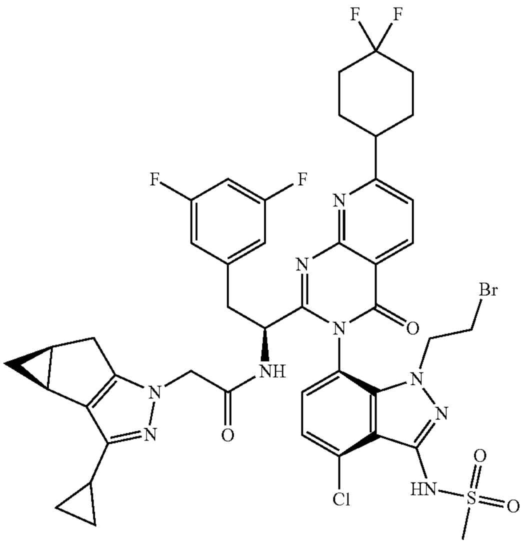

Bromide A4

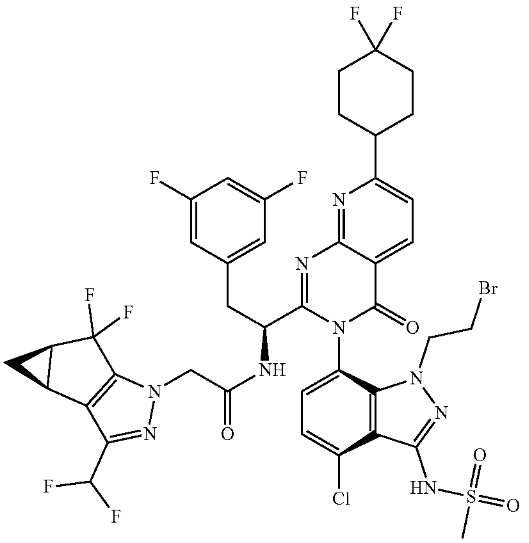

-continued
Bromide A5
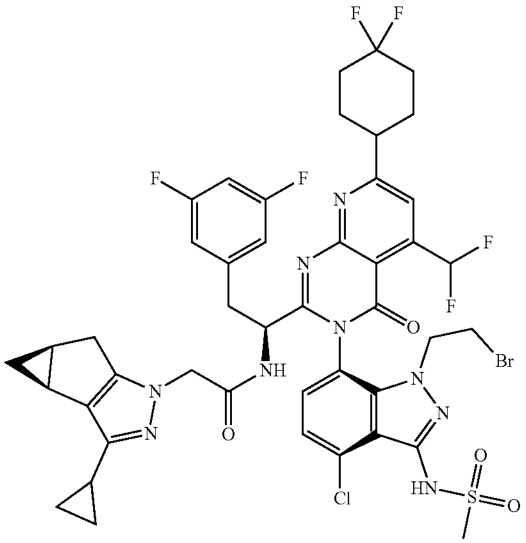
Bromide A6
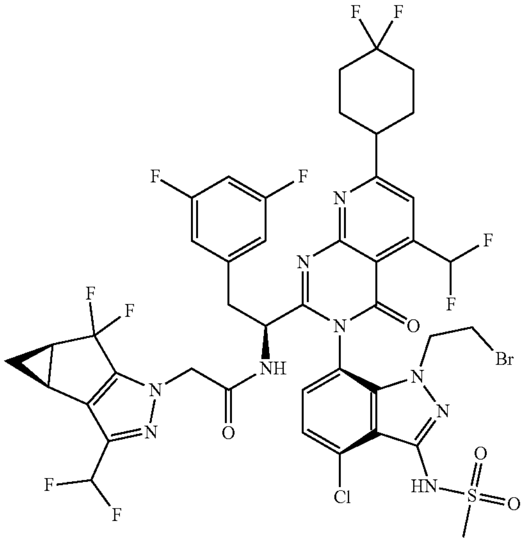
-continued
Bromide A7
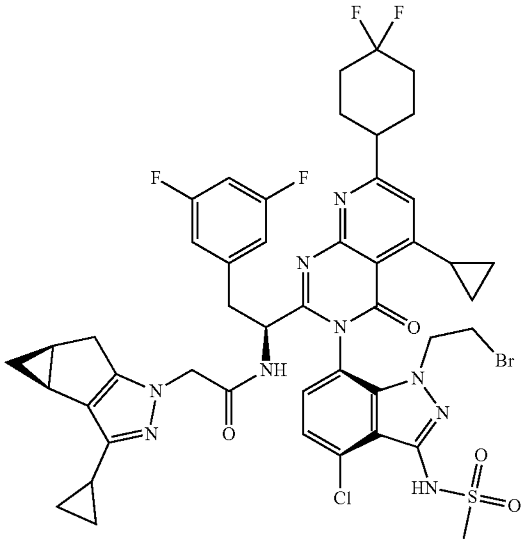
Bromide A8
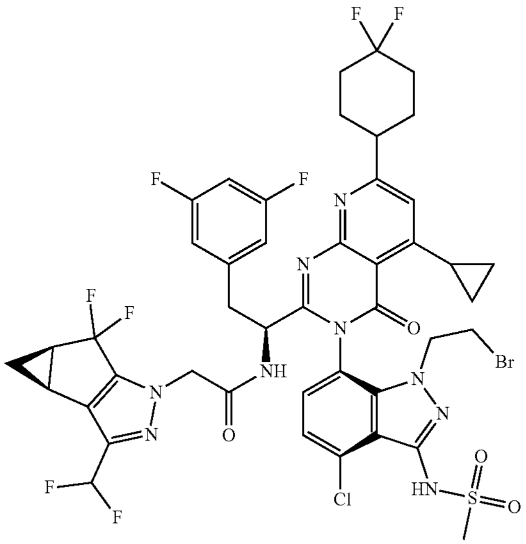

-continued
Bromide A9
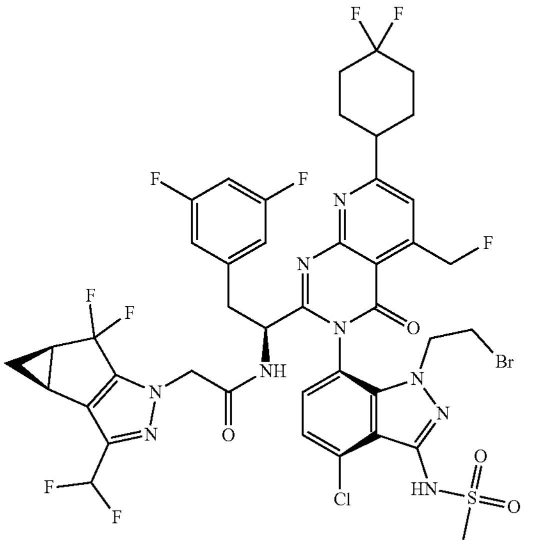
Bromide A10
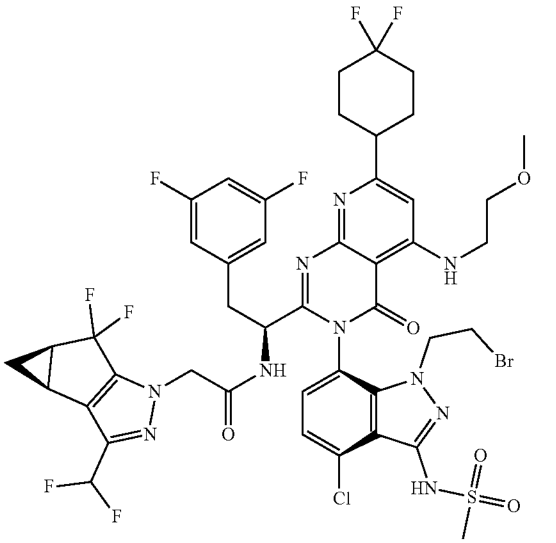
Bromide A11
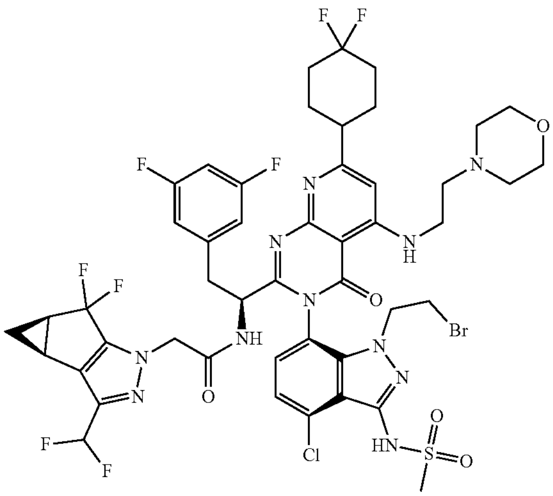
-continued
Bromide A12
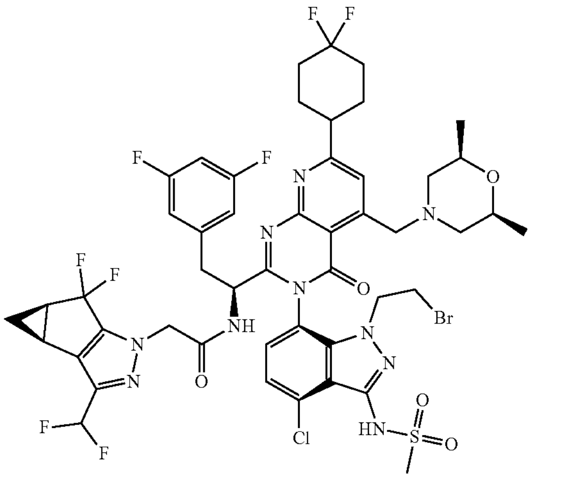
Bromide A13
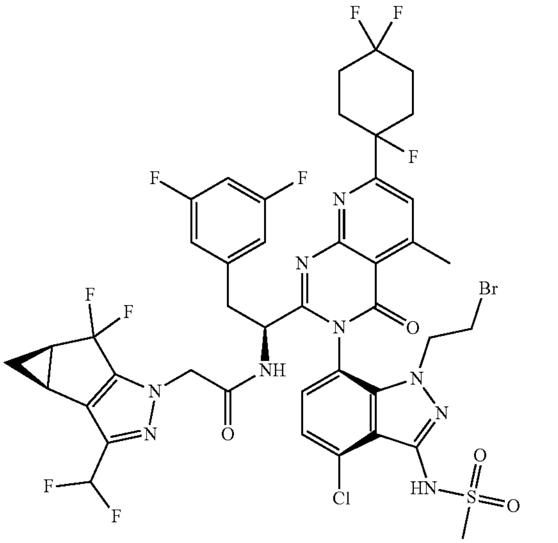
Bromide A14
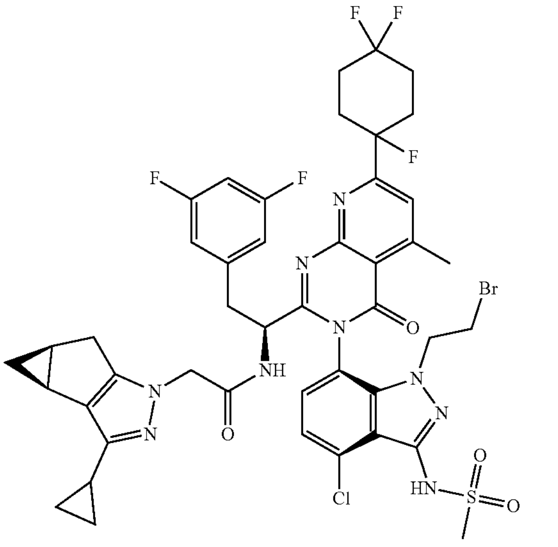

-continued

Bromide A15

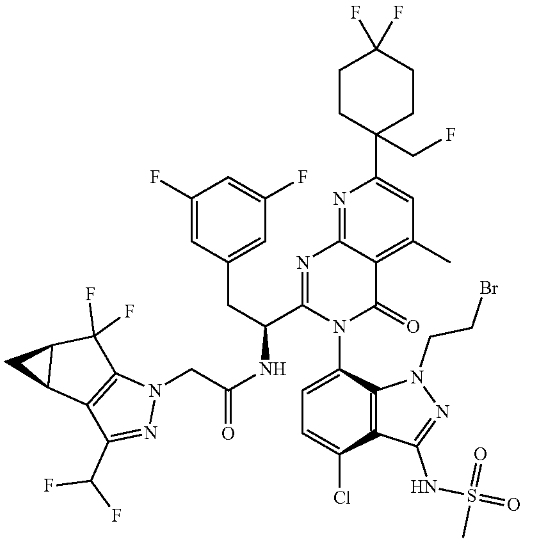

Bromide A16

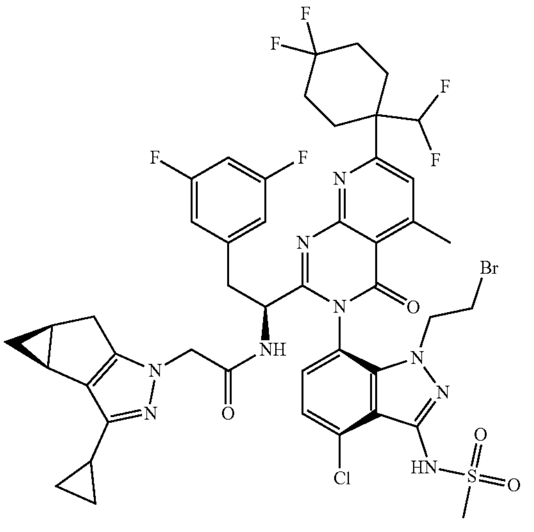

General Procedure B and General Procedure B-2:

General Procedure B is as follows, and may include the modifications noted below: N-((S)-7-(2-((S)-1-amino-2-(3,5-difluorophenyl)ethyl)-5-methyl-4-oxo-7-(1,4,4-trifluorocyclohexyl)pyrido[2,3-d]pyrimidin-3(4H)-yl)-4-chloro-1-(2-((3S,5R)-3,5-difluoropiperidin-1-yl)ethyl)-1H-indazol-3-yl)methanesulfonamide ("Amine B1", the "core reagent", 30 mg, 1 eq., 36 μmol) and the carboxylic acid required to afford the indicated product (the "diversity reagent", 1.05 eq., 37 μmol) were combined in ethyl acetate (0.36 mL). To the reaction mixture was added 2,6-dimethylpyridine (9.5 mg, 10 μL, 2.5 equiv, 89 μmol) followed by 2,4,6-tripropyl-1,3,5,2,4,6-trioxatriphosphinane 2,4,6-trioxide ("T3P", 50% wt. in ethyl acetate, 89 μmol, 2.5 eq.). The mixture was stirred 2 hr at rt. The reaction mixture was concentrated under reduced pressure and the resulting residue was subjected to preparatory HPLC purification to afford the indicated product.

General Procedure B-2 is as follows, and may include the modifications noted below: To a stirred solution of N-(7-(2-((S)-1-amino-2-(3,5-difluorophenyl)ethyl)-7-(4,4-difluorocyclohexyl)-5-methyl-4-oxopyrido[2,3-d]pyrimidin-3(4H)-yl)-4-chloro-1-((R)-2-(2,2,6,6-tetramethylmorpholino)propyl)-1H-indazol-3-yl)methanesulfonamide ("Amine B45", the "core reagent", 50 mg, 1 eq., 58 μmol) in N,N-dimethylformamide (DMF, 1 mL) at 0° C. was added HOBt (10.7 mg, 70 μmol) followed by EDC (16.7 mg, 87 μmol) and N-methylmorpholine (26 μL, 232 μmol). To the solution at 0° C. was added the carboxylic acid required to afford the indicated product (the "diversity reagent", 1.5 eq., 87 μmol). The reaction mixture was allowed to warm to room temperature and then stirring was continued for 16 h. The reaction mixture was quenched with ice-cold water (10 mL) and then extracted with ethyl acetate (2×10 mL). The combined organic layers were washed with brine, dried over anhydrous sodium sulfate, filtered, and the filtrate was concentrated under reduced pressure and the resulting residue was subjected to HPLC purification to afford the indicated product.

In General Procedure B and in General Procedure B-2, the mmol of the "core reagent" (for example, "Amine 1") used in the reaction may be changed with proportional changes of the other reagents and solvent amounts.

In General Procedure B and in General Procedure B-2, the reaction solvent may alternatively be DMF or THF.

In General Procedure B and in General Procedure B-2, the "core reagent" Amine 1 may be substituted for a different "core reagent" that is an amine as would be required to afford the indicated product. The structure of Amine 1 and examples of alternate amine core reagents are as follows:

Amide B1

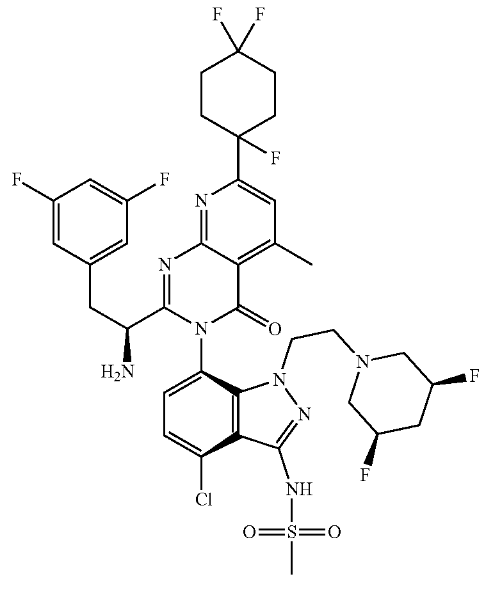

Amide B2
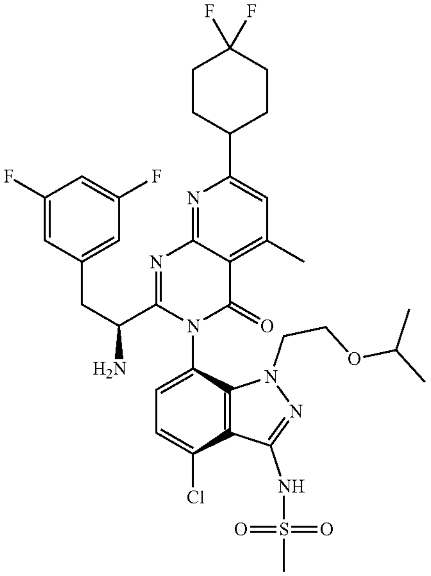
Amide B3
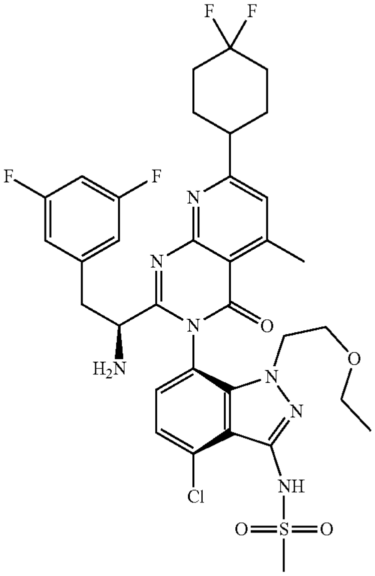
Amide B4
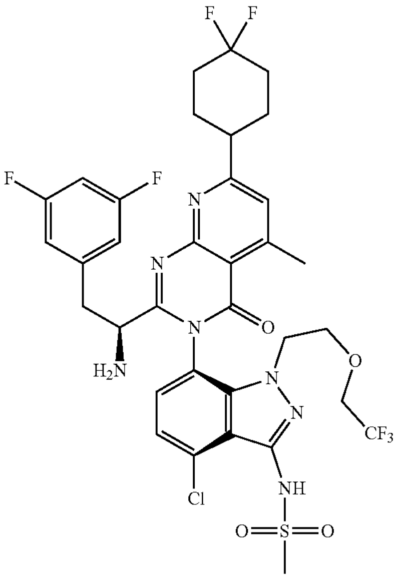
Amide B5
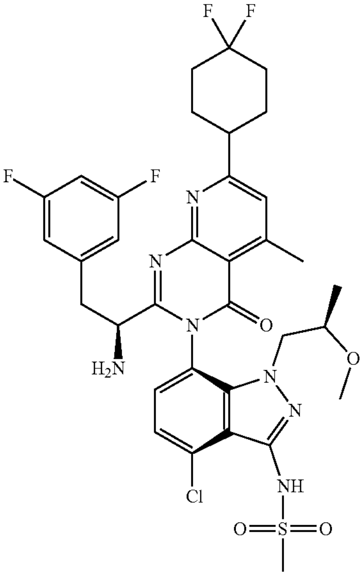

-continued
Amide B6
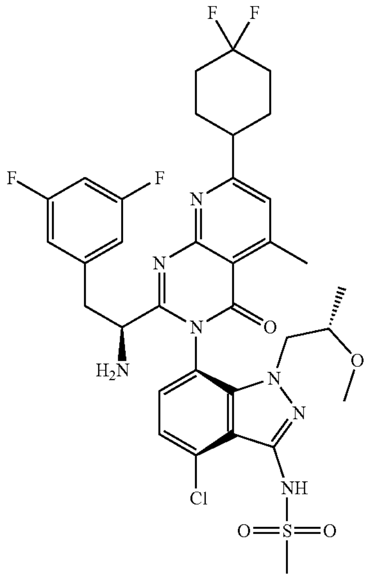
Amide B8
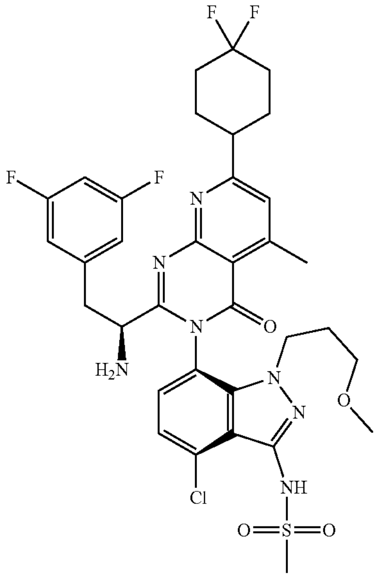
Amide B7
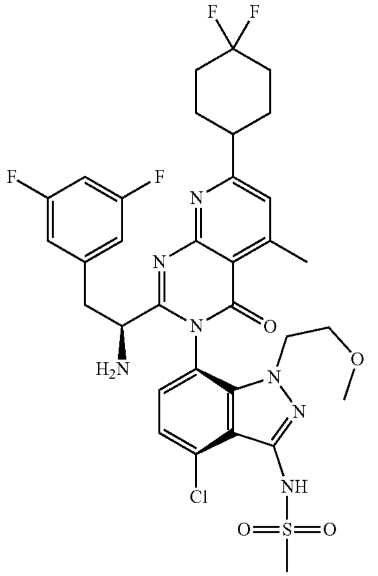
Amide A9
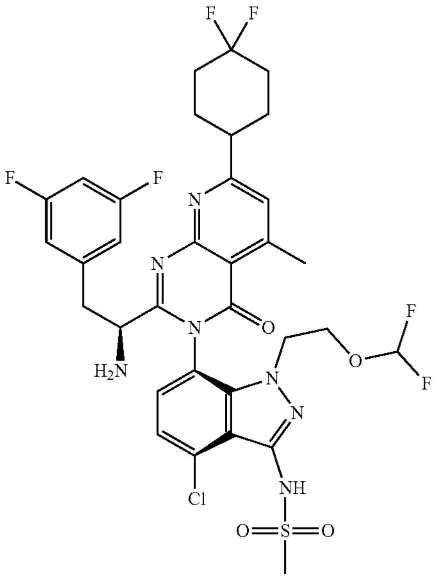

-continued
Amide 10
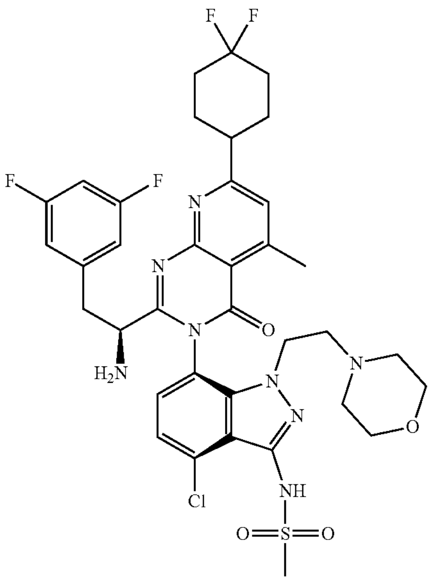
Amide B11
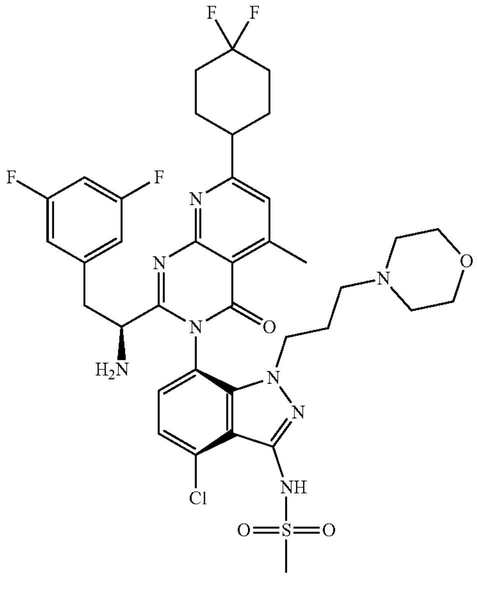
-continued
Amide B12
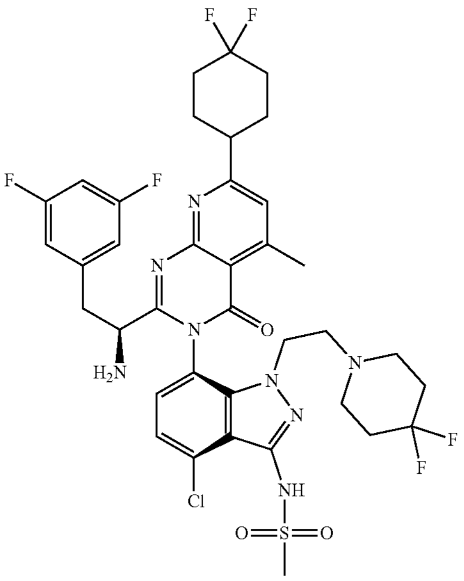
Amide B13
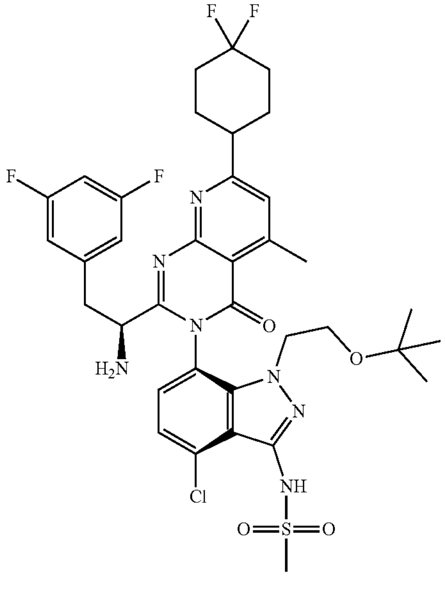

Amide B14
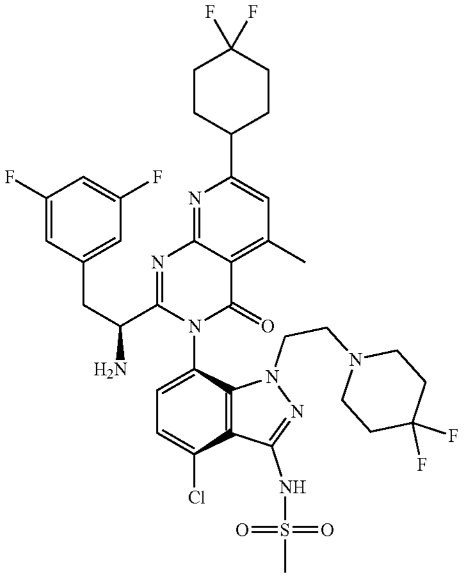
Amide B15
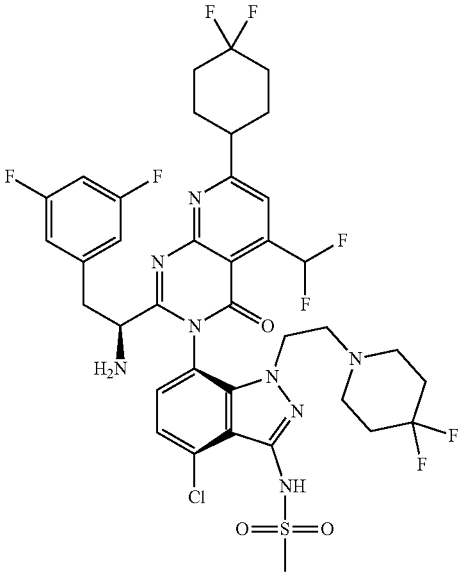
Amide B16
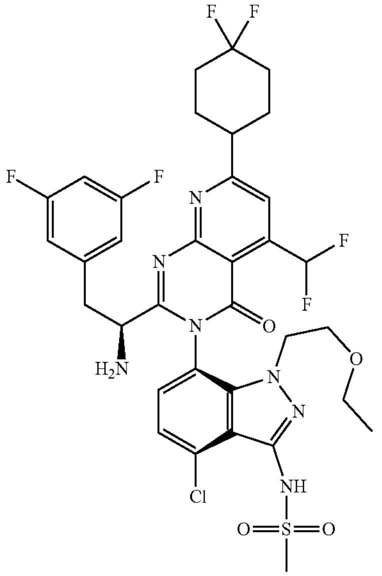
Amide B17
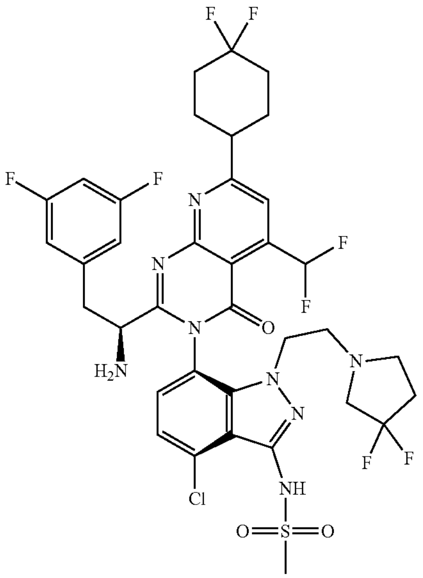

Amide B18
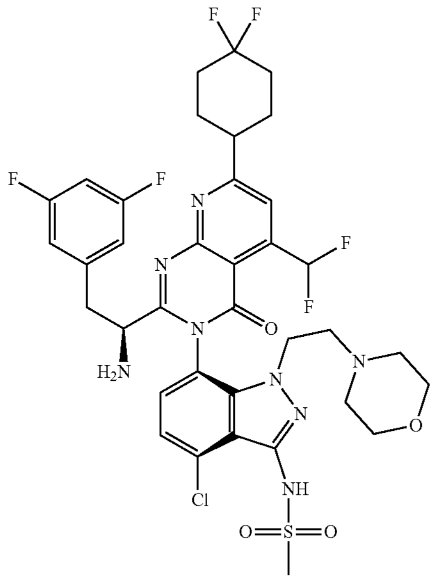
Amide B19
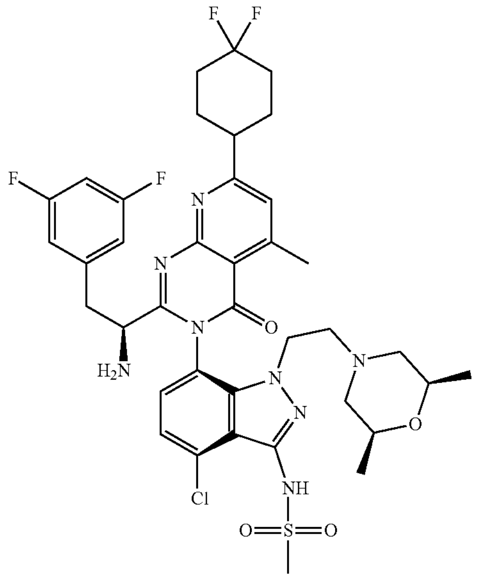
Amide B20
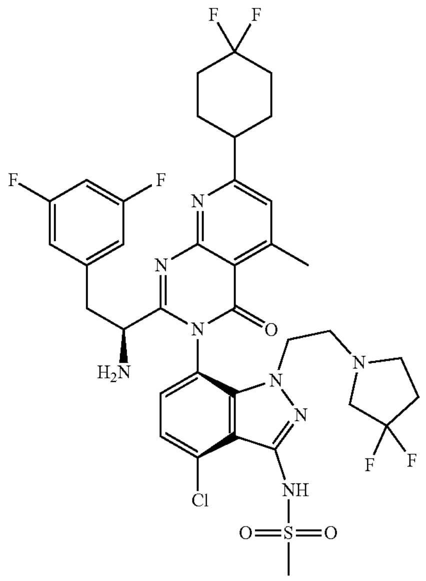
Amide B21
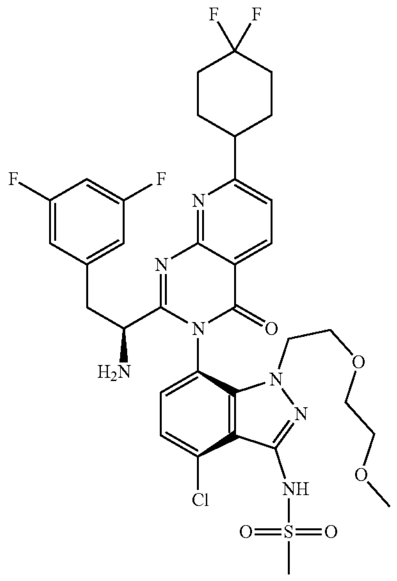

Amide B22
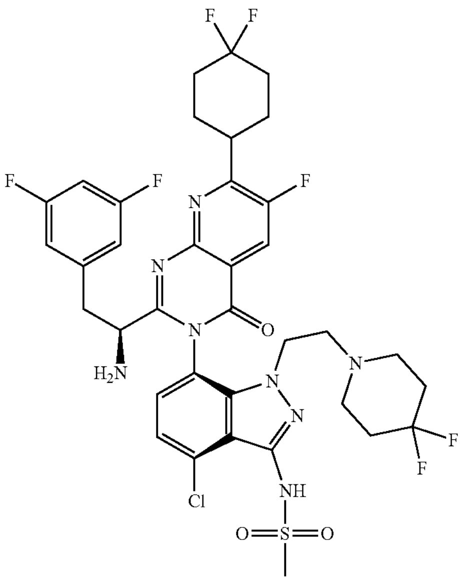
Amide B23
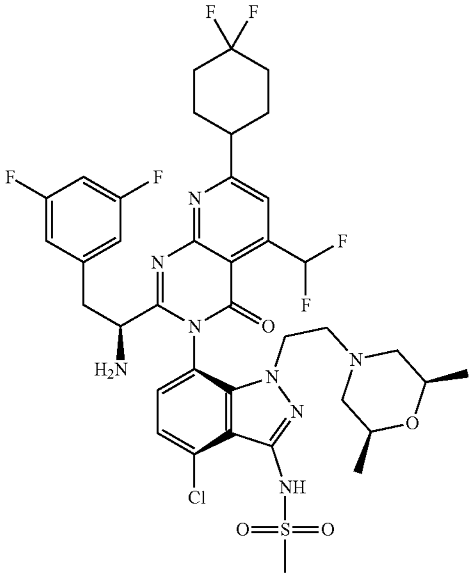
Amide 24
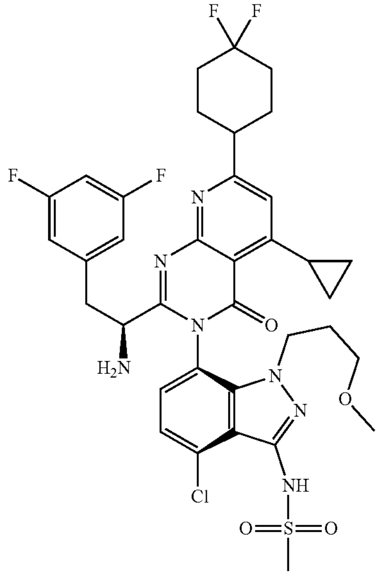
Amide B25
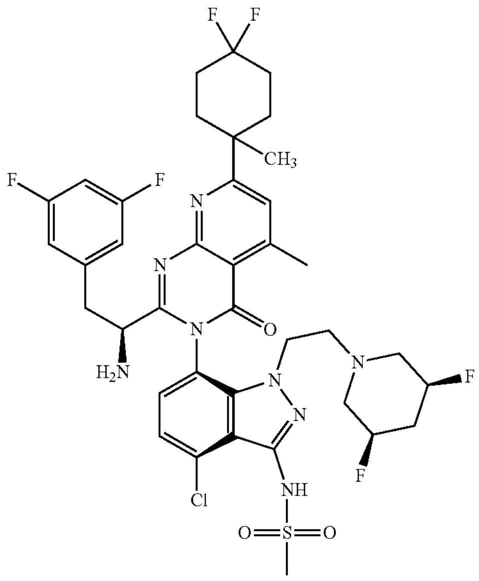

-continued
Amide B26
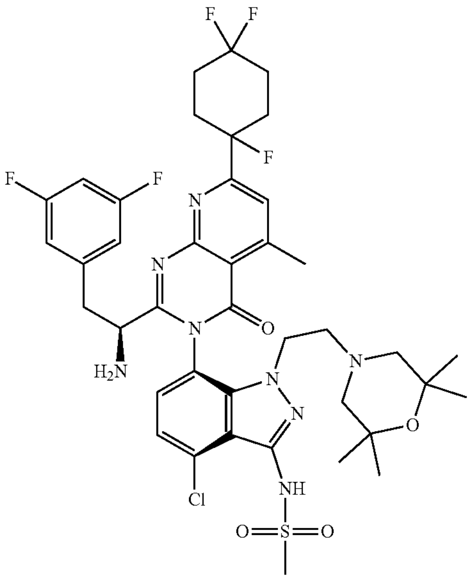
Amide B27
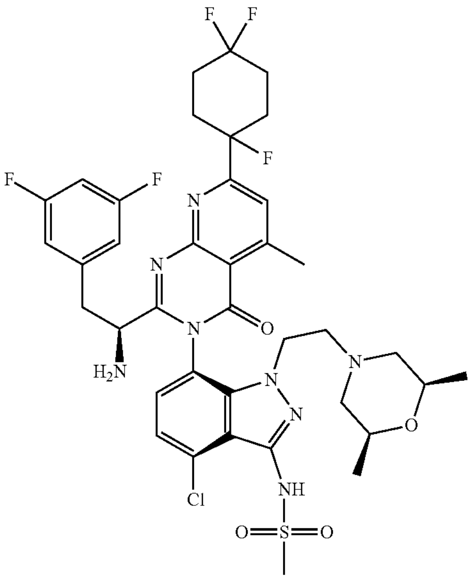
-continued
Amide B28
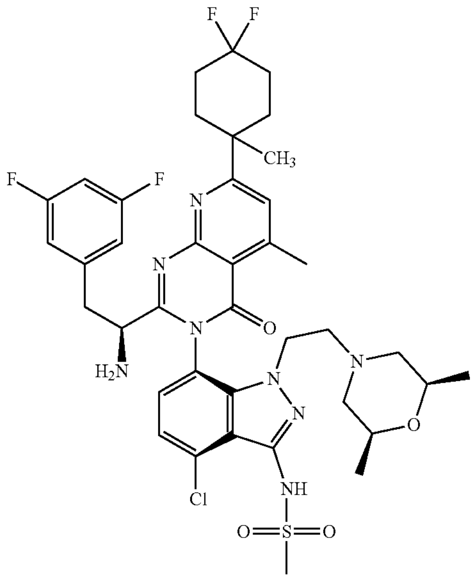
Amide B29
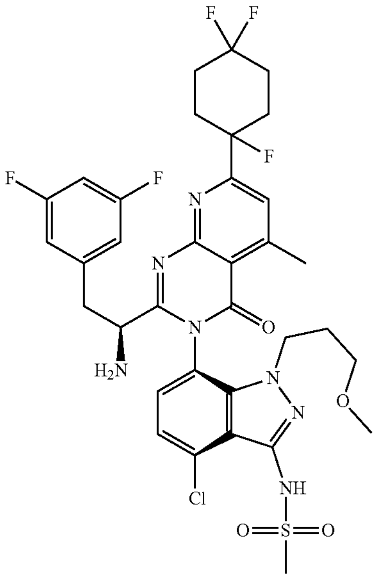

Amide B30
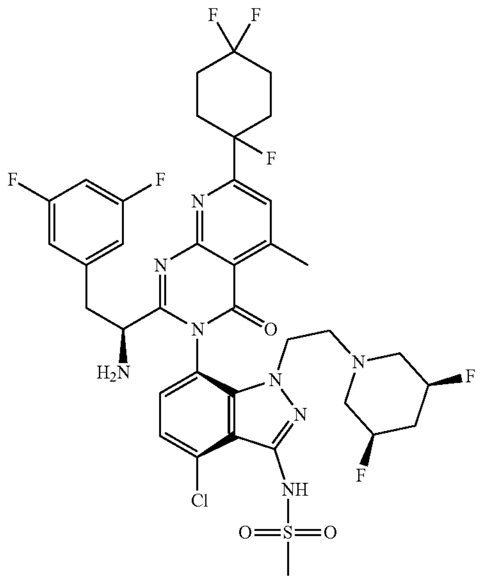
Amide B31
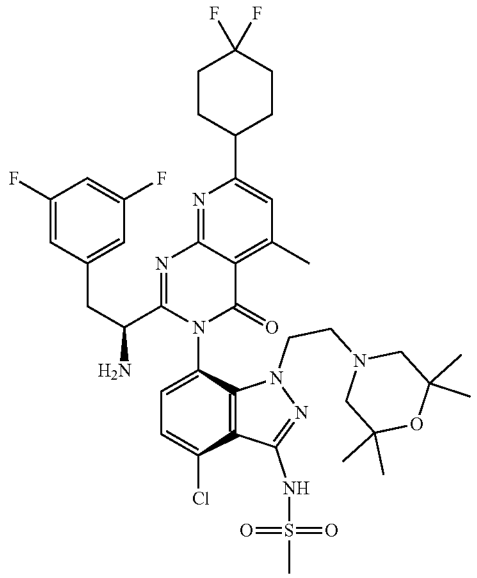
Amide B32
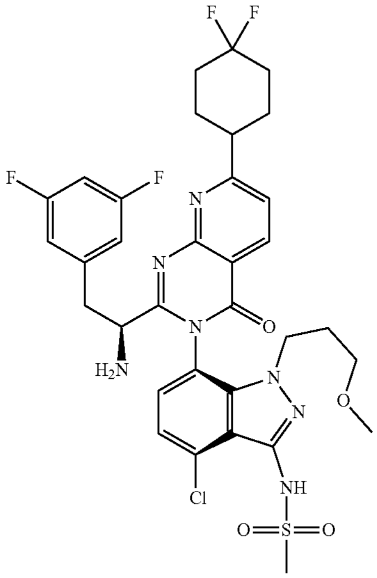
Amide B33
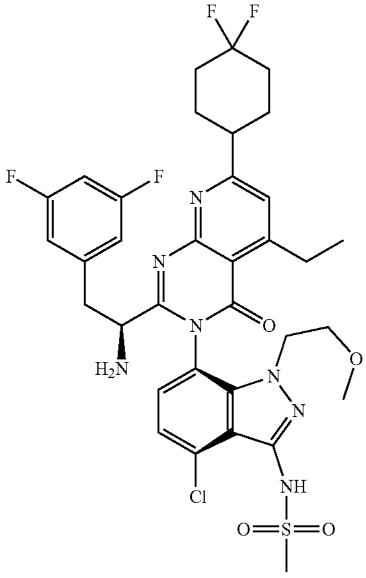

Amide B34
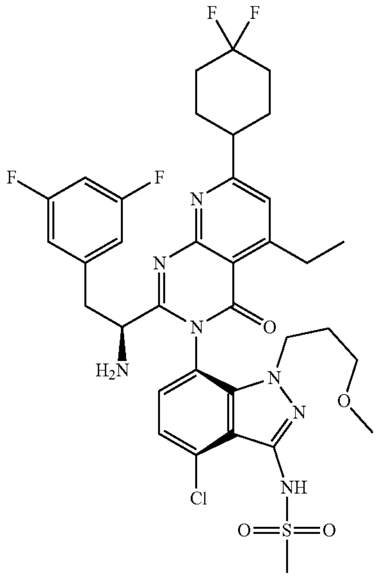
Amide B35
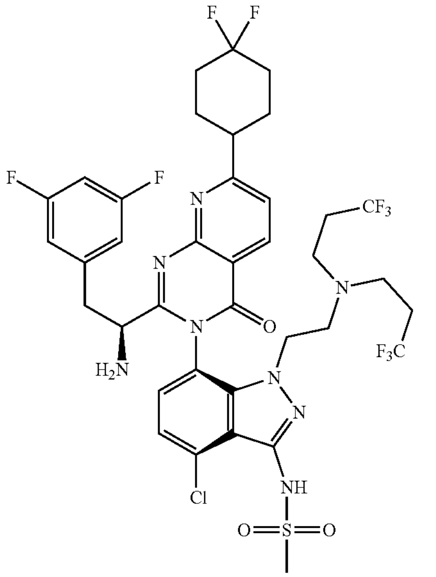
Amide B36
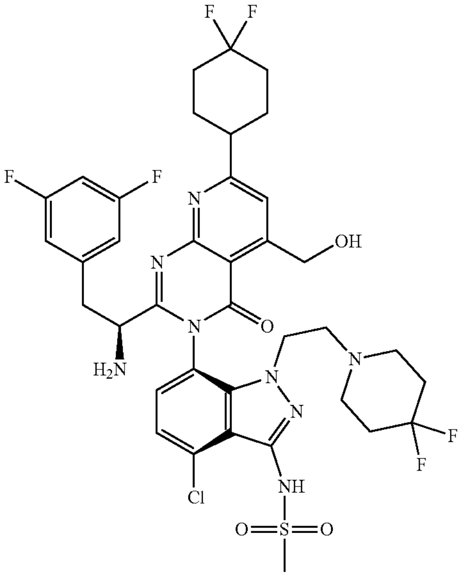
Amide B37
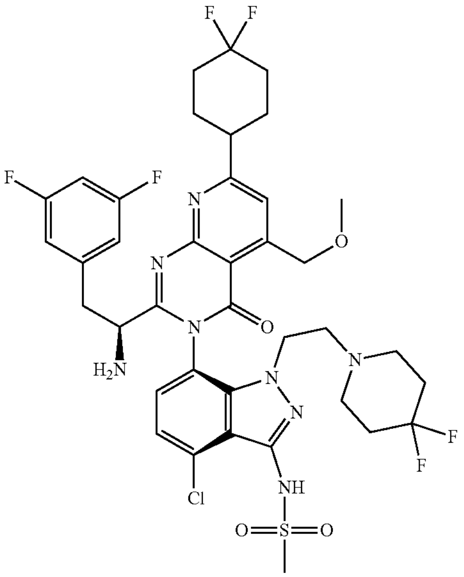

-continued
Amide B38
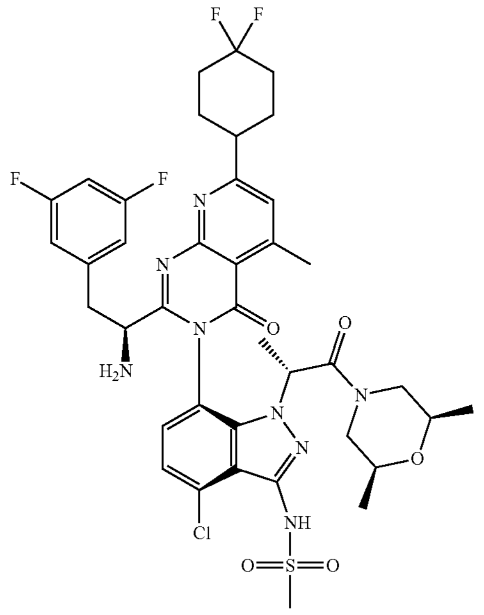
Amide B39
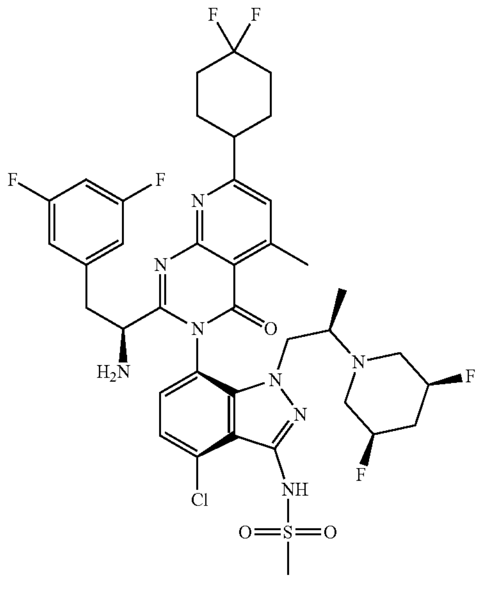
-continued
Amide B40
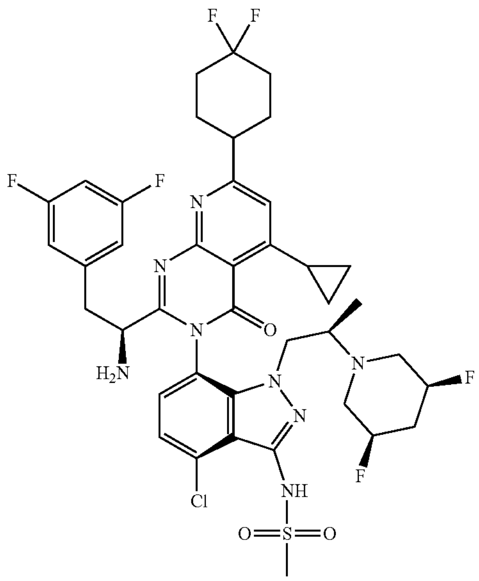
Amide B41
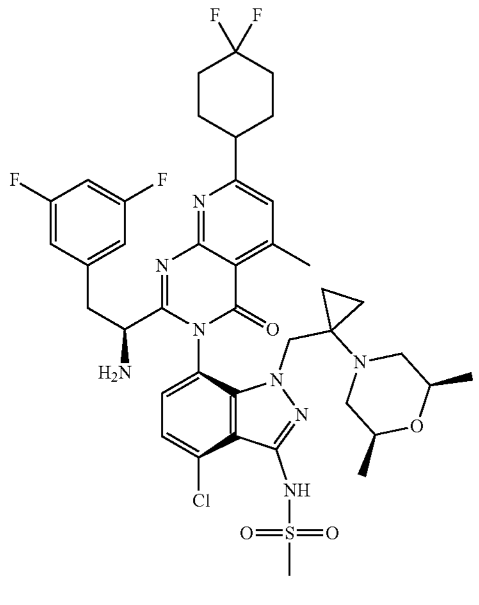

-continued
Amide B42
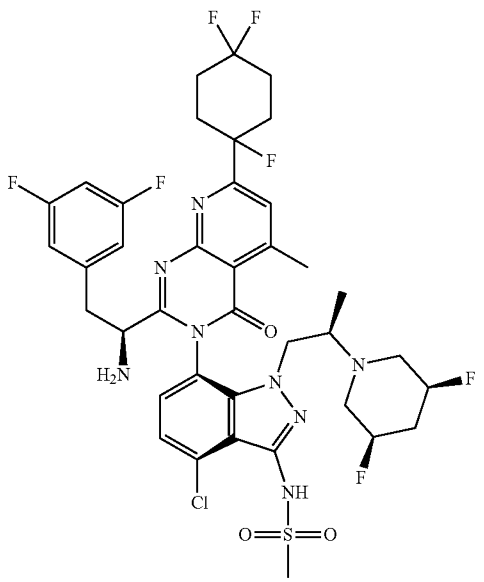
-continued
Amide B45
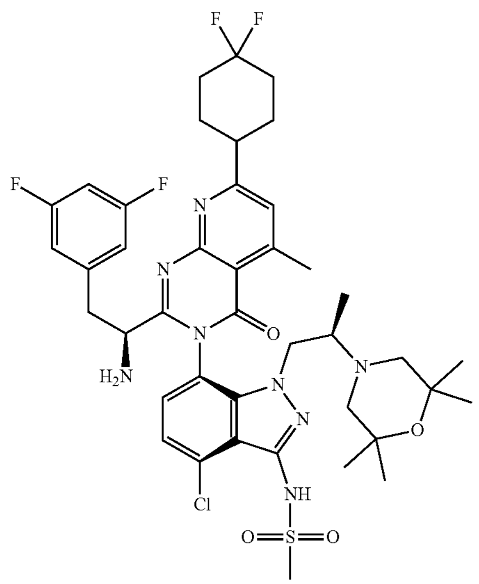
Amide B44
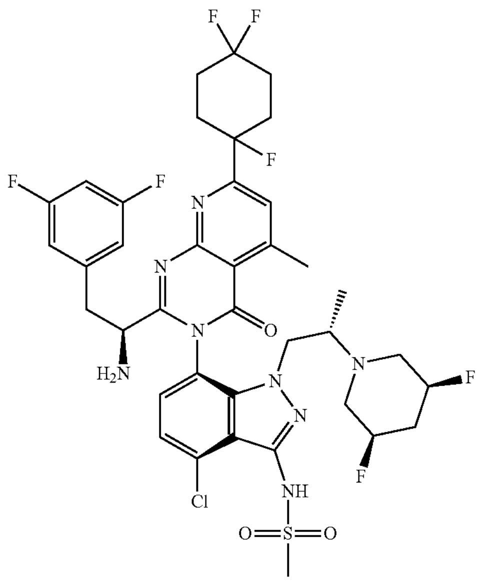
Amide B46
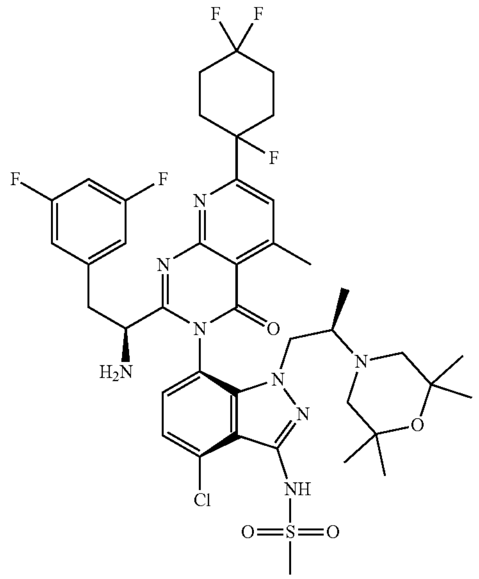

-continued
Amide B47
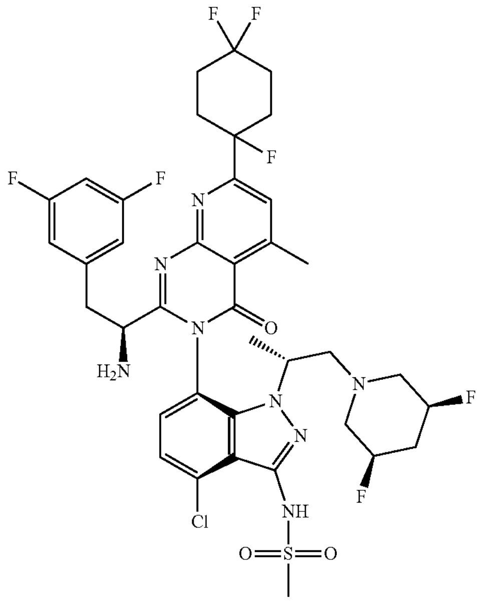
Amide B48
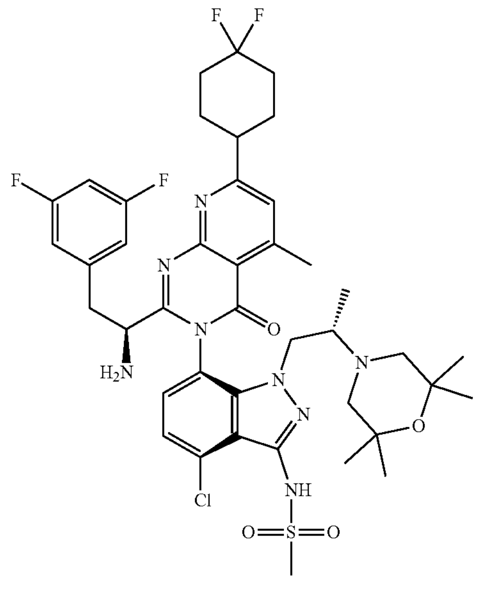
-continued
Amide B49
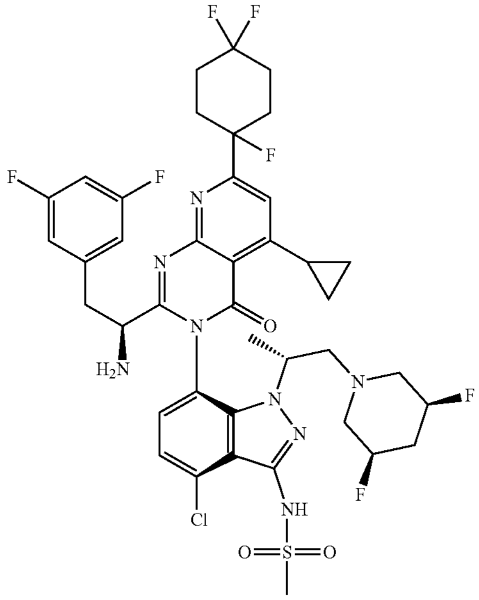
Amide B50
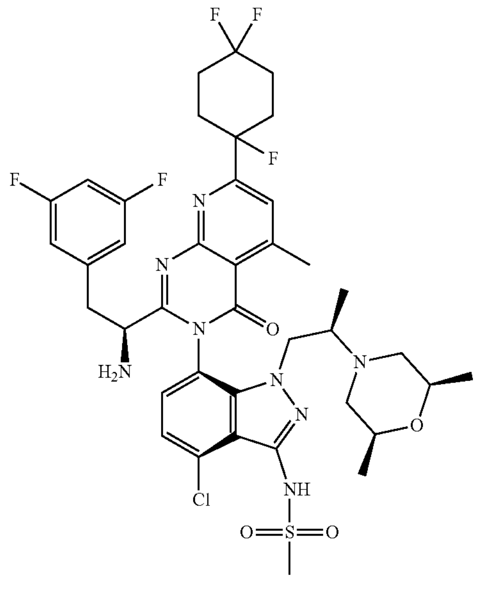

-continued
Amide B51
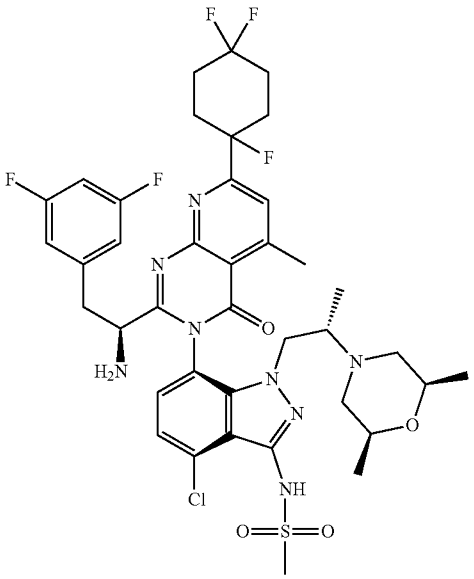
Amide B52
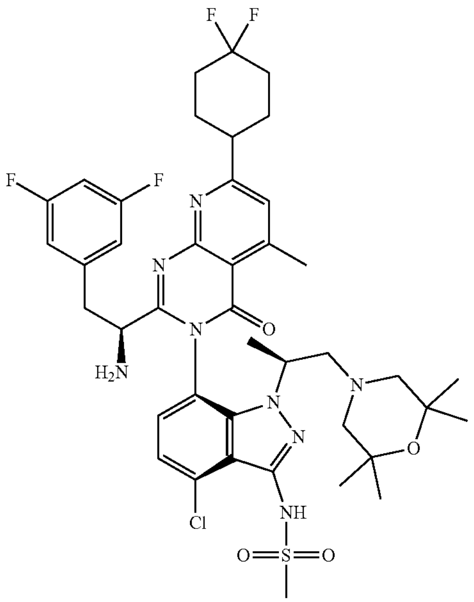
-continued
Amide B53
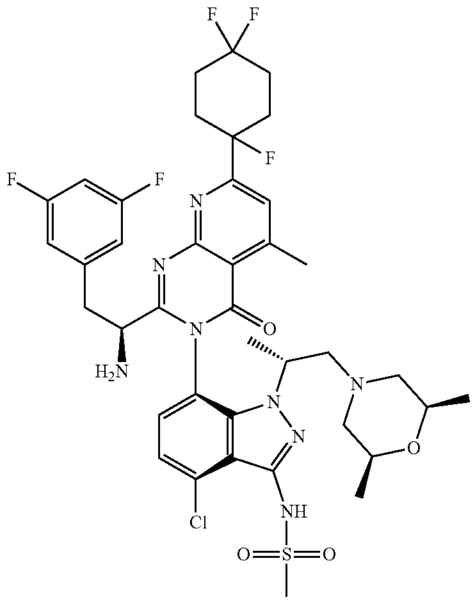
Amide B54
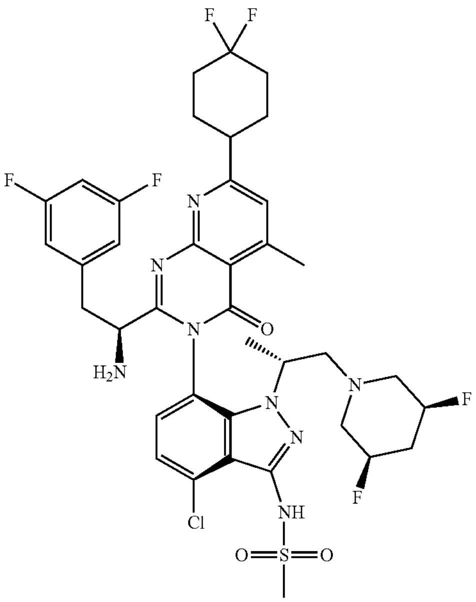

Amide B55
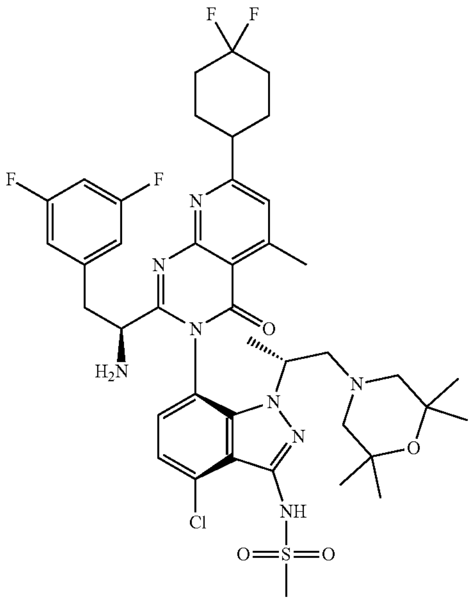
Amide B56
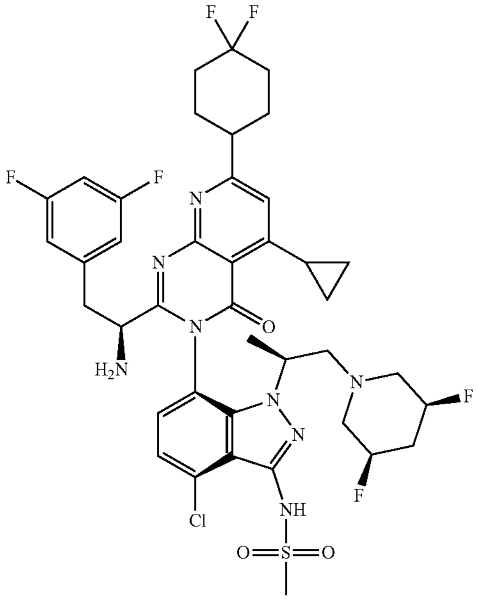
Amide B57
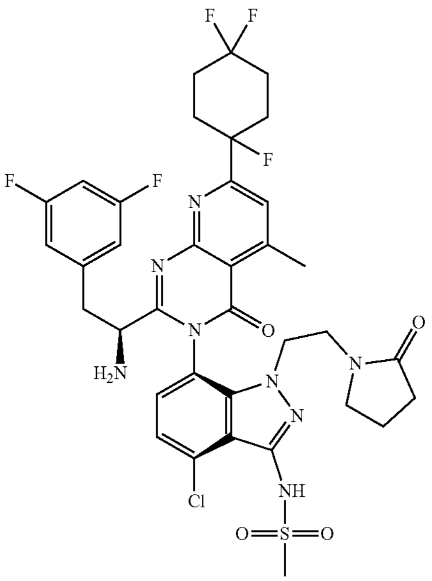
Amide B58
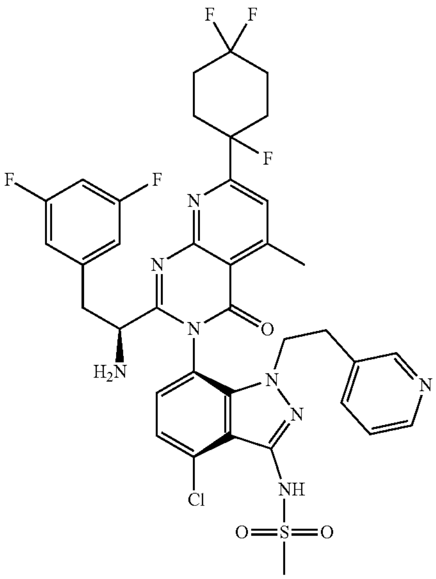

-continued
Amide B59
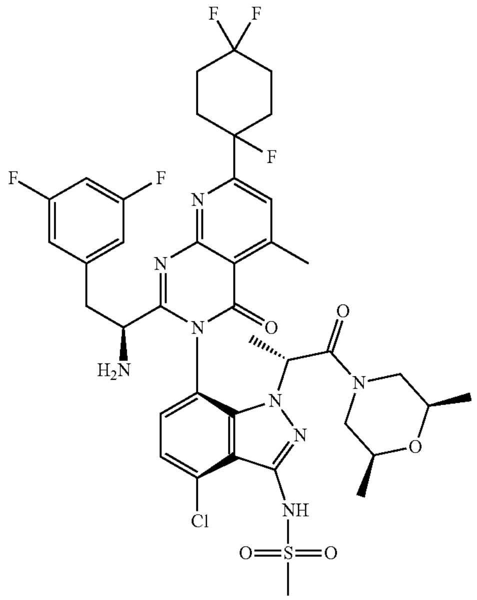
Amide 61 = Amide B62
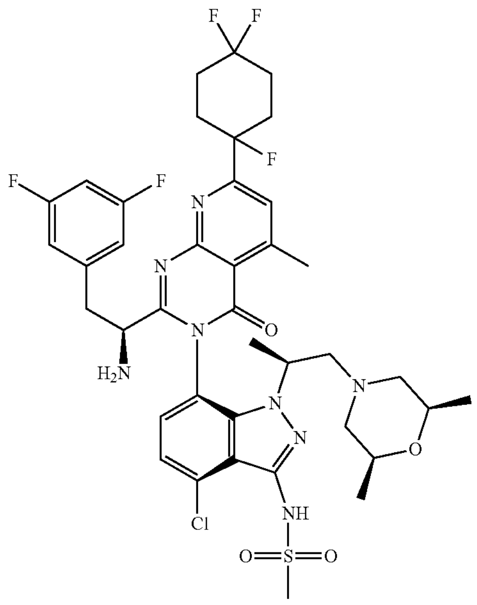
-continued
Amide B63
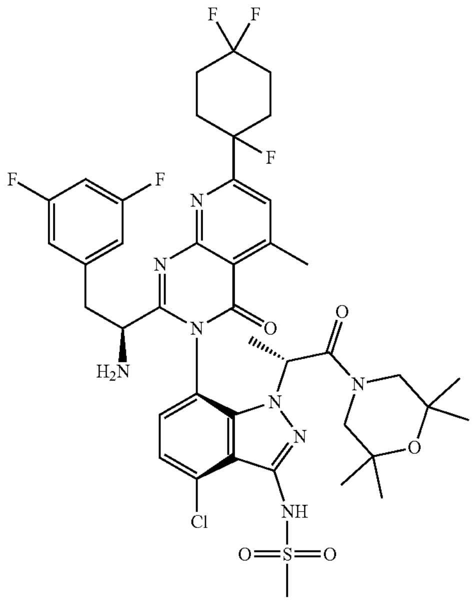
Amide B64
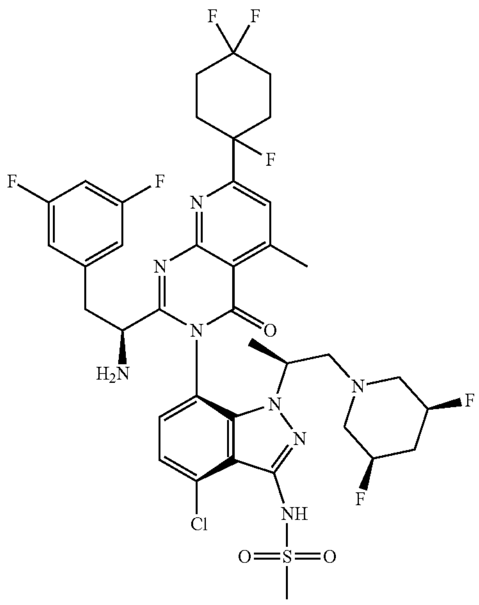

-continued

Amide B65

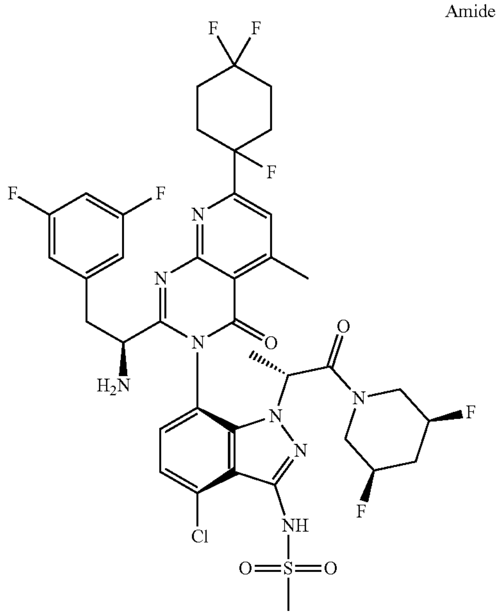

General Procedure C:

General Procedure C is as follows, and may include the modifications noted below: To a solution of 2-(4-chloro-7-(2-((S)-1-(2-((3bS,4aS)-3-cyclopropyl-3b,4,4a,5-tetrahydro-1H-cyclopropa[3,4]cyclopenta[1,2-c]pyrazol-1-yl)acetamido)-2-(3,5-difluorophenyl)ethyl)-7-(4,4-difluorocyclohexyl)-5-methyl-4-oxopyrido[2,3-d]pyrimidin-3(4H)-yl)-3-(methylsulfonamido)-1H-indazol-1-yl)acetic acid ("Acid $C_1$", the "core reagent", 25.0 mg, 26.7 μmol, 1.0 equiv) in N,N-dimethylformamide (0.4 mL) was added the amine required to afford the indicated product (the "diversity reagent", 53 μmol, 2.0 equiv). To the vial was added a solution of HATU (11.2 mg, 29.4 μmol, 1.1 equiv) in N,N-dimethylformamide (0.25 mL), followed by N,N-diisopropylethylamine (27.6 mg, 214 μmol, 8.0 equiv). The reaction mixture was stirred for 18 h. If the reaction had reached >25% conversion as determined by LC/MS, the mixture was directly subjected to HPLC purification to afford the title compound; otherwise, the mixture was charged with additional equivalents of HATU, amine, and N,N-diisopropylethylamine, stirred for 4 h, and the resulting mixture was subjected to HPLC purification to afford the title compound.

In General Procedure C, the mmol of the "core reagent" used in the reaction may be changed with proportional changes to the other reagents and solvent amounts.

In General Procedure C, the "core reagent" Acid C1 may be substituted for a different "core reagent" that is an acid as would be required to afford the indicated product. The structure of Acid C1 and examples of alternate acid core reagents are as follows:

Acid C1

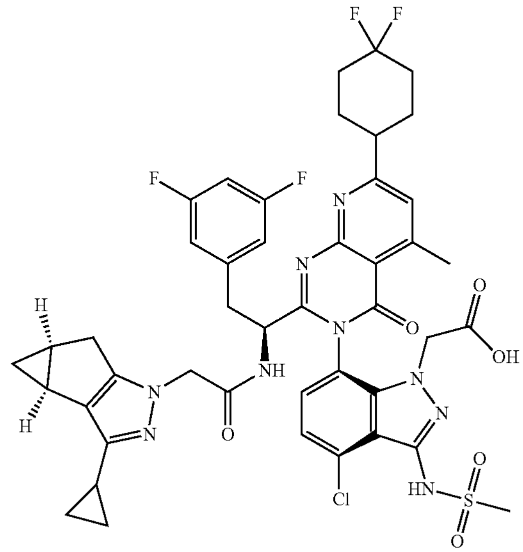

Acid C2

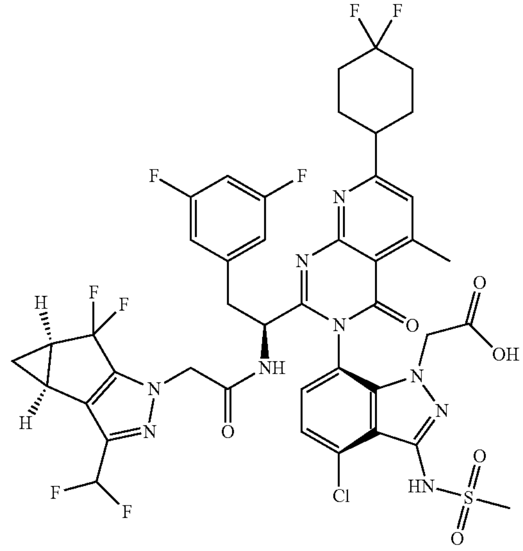

General Procedure D:

General Procedure D is as follows, and may include the modifications noted below: A solution of N-((1S)-1-(5-Chloro-3-(4-chloro-1-(3-methoxypropyl)-3-(methylsulfonamido)-1H-indazol-7-yl)-7-(4,4-difluorocyclohexyl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide ("Chloride D2", the "core reagent", 40 mg, 39 μmol), N,N-diisopropylethylamine (DIPEA, 26 mg, 200 μmol, app. 5 equiv.), and the amine required to afford the indicated product (the "diversity reagent", 200 μmol, app. 5 equiv.) in ethanol (1.0 mL) was heated at 90° C. for 2 h. (In General Procedure D, the amine used as the "diversity reagent" is in the free amine form.) The mixture was cooled to room temperature and then was subjected to preparative HPLC purification to afford the indicated product.

In General Procedure D, the mmol of the "core reagent" (for example, "Chloride D2") used in the reaction may be changed with proportional changes of the other reagents and solvent amounts.

In General Procedure D, the reaction temperature may be changed to 100° C. and the reaction time may be changed to 1 h.

In General Procedure D, the "core reagent" Chloride D2 may be substituted for a different "core reagent" this is a heteroaryl chloride, as would be required to afford the indicated product. The structure of Chloride D2 and examples of alternate chloride core reagents are as follows:

Chloride D1

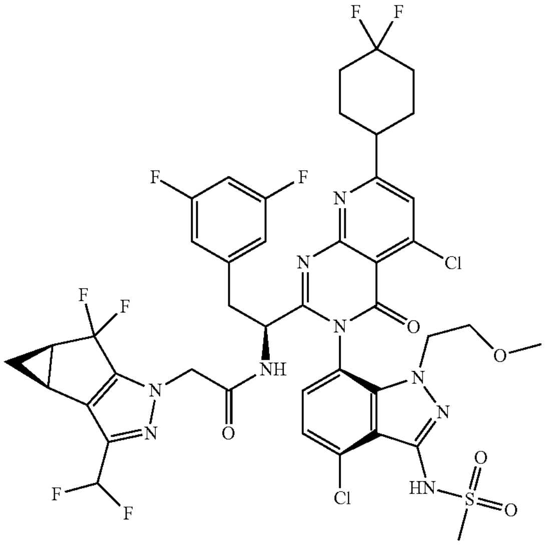

Chloride D2

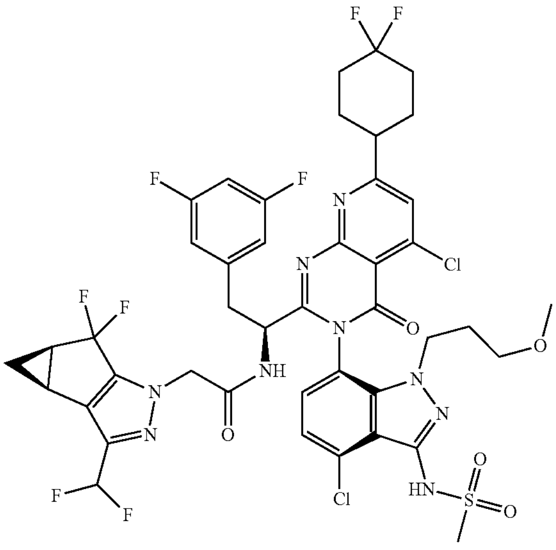

-continued

Chloride D3

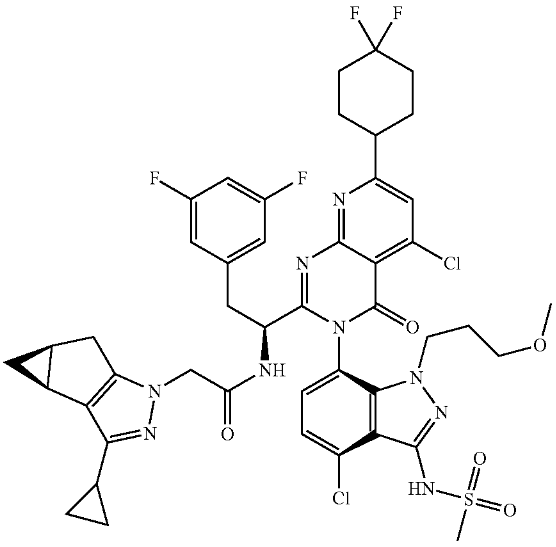

General Procedure E:

General Procedure E is as follows, and may include the modifications noted below: Step 1 (Oxidation to aldehyde): To a solution of N-((1S)-1-(3-(4-chloro-1-(3-methoxypropyl)-3-(methylsulfonamido)-1H-indazol-7-yl)-7-(4,4-difluorocyclohexyl)-5-(hydroxymethyl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide ("Alcohol E1", the "core reagent", 25 mg, 1 equiv., 25 μmol) in dichloromethane (1.0 mL) was added Dess-Martin periodinane (21 mg, 2 equiv., 50 μmol), and the resulting mixture was stirred at room temperature for 1 h. The reaction mixture was diluted with water and then was extracted with dichloromethane. The organic layer was dried over anhydrous sodium sulfate, filtered, and the filtrate was concentrated under reduced pressure to afford the crude aldehyde.

Step 2 (reductive amination): To a solution of the crude aldehyde in dichloromethane (1.0 mL) was added the amine required to afford the indicated product (the "diversity reagent", 3 equiv., 75 μmol). The mixture was stirred for 10 min, then to the mixture was added sodium triacetoxyborohydride (10.5 mg, 2 equiv., 50 μmol). The reaction mixture was stirred for 16 h at room temperature upon which LCMS analysis confirmed the formation of the desired amine product. The solvent was removed under reduced pressure and the resulting residue was subjected to preparative HPLC purification to afford the indicated product.

The amine (the "diversity reagent") of General Procedure E may be provided as the HCl salt.

In General Procedure E, typically the the ammonium salt of Step 1 is pre-treated with triethylamine before the solution is used directly in Step 2 of the procedure. A representative process is as given below:

To a solution of (3S,5R)-3,5-difluoropiperidine, hydrochloride (23.3 mg, 3 Eq, 148 μmol) in DCM (1.5000 mL) was added triethylamine ("TEA", 15 mg, 0.021 mL, 3.0 Eq, 150 μmol). The mixture was stirred for 5 minutes before being used directly in Step 2.

In General Procedure E, the mmol of the "core reagent" (for example, "Alcohol E1") used in the reaction may be changed with proportional changes of the other reagents and solvent amounts.

In General Procedure E, the "core reagent" Alcohol E1 may be substituted for a different "core reagent" that is an alcohol as would be required to afford the indicated product. The structure of Alcohol E1 and an example of an alternate alcohol core reagents are as follows:

Alcohol E1

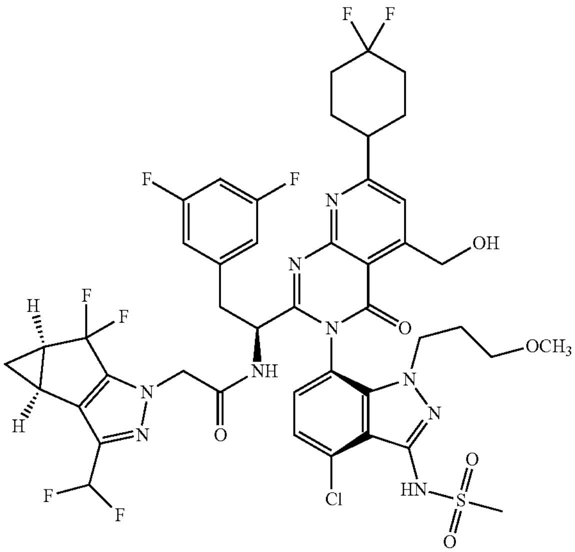

Alcohol E2

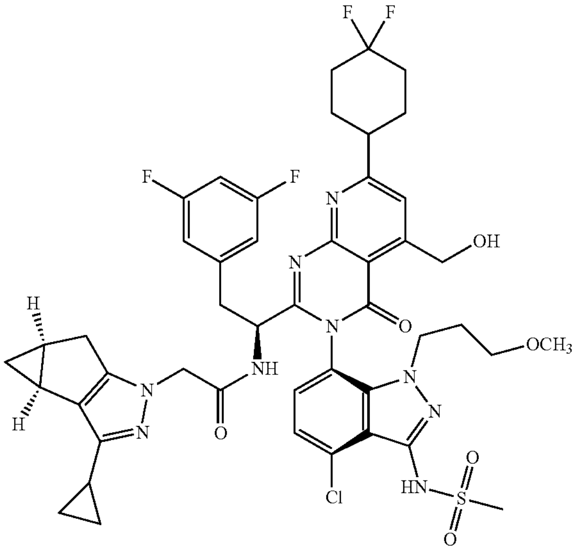

General Procedure E-2:

General Procedure E-2 is as follows, and may include the modifications noted below: To a solution of aldehyde ("Aldehyde E1", the "core reagent"), in dichloromethane (1.0 mL) was added the appropriate amine (the "Diversity Reagent", 3 equiv., 75 μmol). The mixture was stirred for 10 min, then to the mixture was added sodium triacetoxyborohydride (10.5 mg, 2 equiv., 50 μmol). The reaction mixture was stirred for 16 h at room temperature upon which LCMS analysis confirmed the formation of the desired amine product. The solvent was removed under reduced pressure and the resulting residue was subjected to preparative HPLC purification to afford the indicated product.

In General Procedure E-2 the mmol of the "core reagent" (for example, Aldehyde E1) used in the reaction may be changed with proportional changes of the other reagents and solvent amounts.

The amine (the "diversity reagent") of General Procedure E-2 may be provided as the HCl salt. When used in General Procedure E-2, typically the ammonium salt 1 is pre-treated with triethylamine before the solution is used directly in Step 2 of the procedure. A representative process is as given below:

To a solution of (3S,5R)-3,5-difluoropiperidine, hydrochloride (23.3 mg, 3 Eq, 148 μmol) in DCM (1.5000 mL) was added triethylamine ("TEA", 15 mg, 0.021 mL, 3.0 Eq, 150 μmol). The mixture was stirred for 5 minutes before being used directly in Step 2.

In General Procedure E-2, the "core reagent" Aldehyde E1 may be substituted for a different "core reagent" that is a aldehyde as would be required to afford the indicated product. The structure of Aldehyde E1 and examples of alternate aldehyde core reagents are as follows:

Aldehyde E1

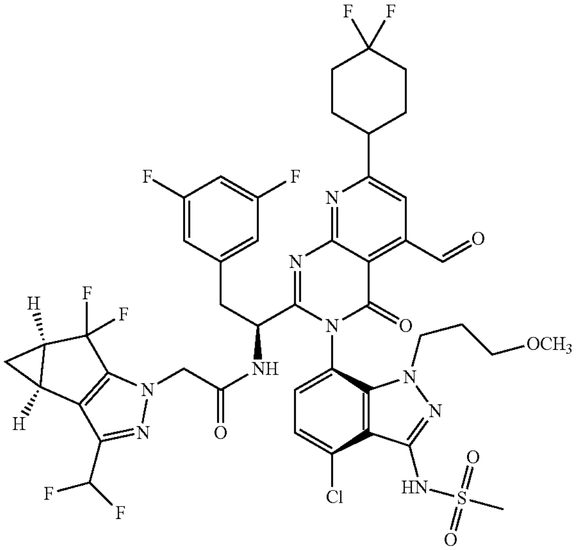

Aldehyde E2

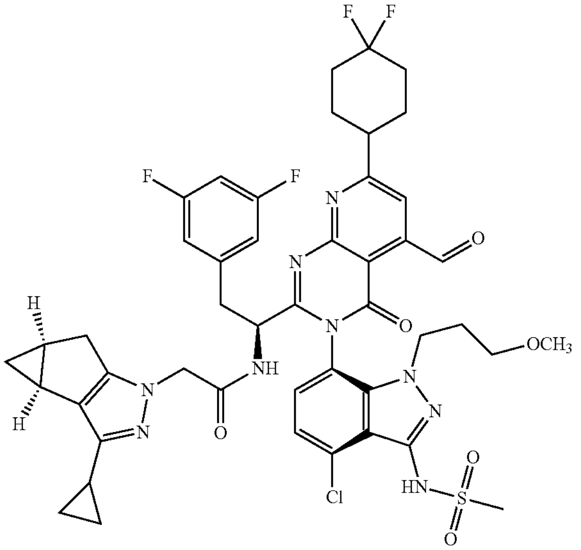

-continued

Aldehyde E3

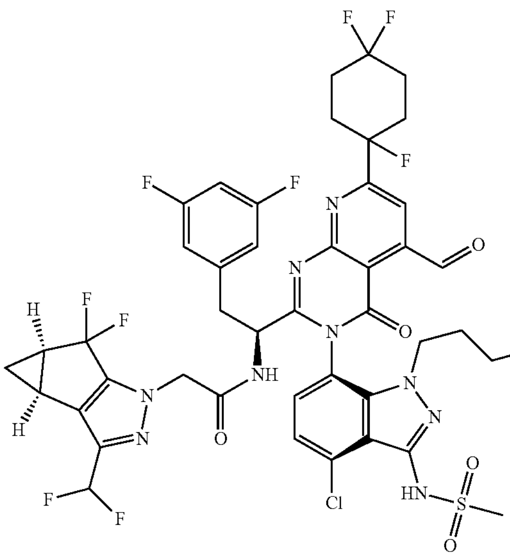

Aldehyde E4

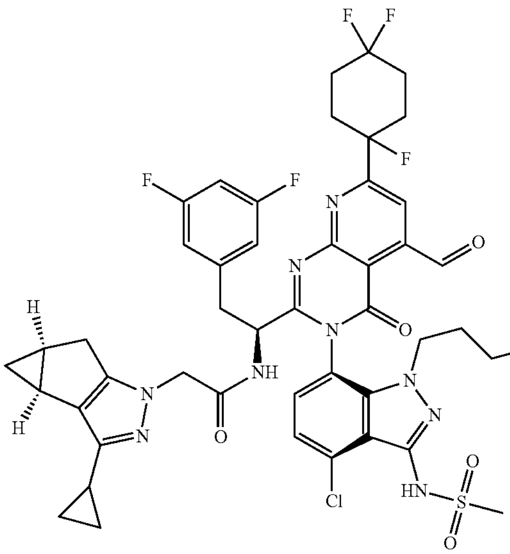

General Procedure F:

General Procedure F is as follows, and may include the modifications noted below: To a solution of N-((1S)-1-(3-(4-Chloro-1-(3-methoxypropyl)-3-(methylsulfonamido)-1H-indazol-7-yl)-7-(4,4-difluoro-1-(2-hydroxyethyl)cyclohexyl)-5-methyl-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide ("Alcohol F1", the "core reagent", 100 mg, 96.1 μmol, 1 equiv.) in dichloromethane (961 μL) was added Dess-Martin periodinane (61.1 mg, 144 μmol). The mixture was stirred at room temperature for 2 h upon which LCMS analysis indicated the presence of a mixture of product and starting material. To the mixture was added the amine required to afford the indicated product (the "diversity reagent", 961 μmol, 10 equiv.) and the mixture was stirred for app. 5-10 min. To the mixture was added sodium triacetoxyborohydride (40.7 mg, 192 μmol) and the mixture was then stirred for 1 h upon which LCMS analysis indicated the presence of the expected product ion (M+H). The reaction mixture was concentrated under reduced pressure and the resulting residue was subjected to preparatory HPLC purification to afford the indicated product.

In General Procedure F the mmol of the "core reagent" (for example, "Alcohol F1") used in the reaction may be changed with proportional changes to the other reagents and solvent amounts.

In General Procedure F, the "core reagent" Alcohol F1 may be substituted for a different "core reagent" that is an alcohol as would be required to afford the indicated product. The structure of Alcohol F1 is as follows:

Alcohol F1

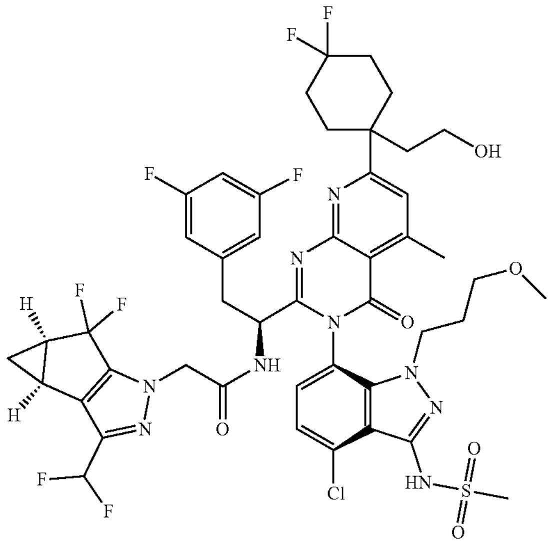

HPLC Purification:

HPLC purification was performed using one of the conditions indicated below, optionally followed by a second HPLC purification using a different condition indicated below. Based on analytical HPLC data obtained on the crude reaction mixture, the purification condition was optimized for each target compound by modifying the initial Solvent A:Solvent B ratio, the gradient time, the final Solvent A:Solvent B ratio, and the hold time at the final Solvent A:Solvent B concentration.

HPLC Condition A: Column: Two SunFire 30×100 mm (5 μM particle size) columns connected in parallel; Solvent A: 0.1% formic acid in water; Solvent B: acetonitrile. Flow Rate=40-50 mL/min. Example gradient method: 0% Solvent B 100% Solvent B.à

HPLC Condition B: Column: Zorbax Eclipse Plus C18, 21.2×100 mm, 5 μm particles; Solvent A=0.1% Formic Acid in 100% Water. Solvent B=Acetonitrile. Flow Rate=40 mL/min. Wavelength=215 and 254 nm. ESI+ Range: 150 to 1500 dalton.

HPLC Condition C: Column: Sunfire prep C18 OBD, 30×100 mm, 5 μm particles; Solvent A: water:MeCN 95:5 w/0.1% TFA, Solvent B: MeCN:water 95:5 w/0.1% TFA. Flow Rate=42 mL/min. Wavelength=220 and 254 nm.

HPLC Condition D: Column: Waters Xterra C18, 19×100 mm, 10 μm particles; Solvent A=0.1% $NH_4OH$ in 100% Water. Solvent B=Acetonitrile. Flow Rate=40 mL/min. Wavelength=215 and 254 nm. ESI+Range: 150 to 1500 dalton.

General LCMS Analysis Methods:

All LCMS methods used gradient methods which changed the percentage of Solvent B mixed with Solvent A at a linear rate over a stated time period. The gradient methods may be described using lists such as "0/3, 0.4/3, 2.5/98, 3.5/98" which should be interpreted as a list of points along the gradient profile denoting the elution time and the % B at that point. The percentage of Solvent B mixed with Solvent A changes with a linear slope between each pair of points. For example, "2.5/98" means 2% Solvent A is combined with 98% Solvent B at 2.5 minutes following the start of elution. Further, "0.4/3, 2.5/98" means the percentage of Solvent B in the eluent increases linearly from 3% at 0.4 minutes to 98% at 2.5 minutes. Alternately, the gradient may be described by giving a starting concentration (i.e., "Start % B=0"), a final concentration (i.e., "Final % B=100", and the time between these point (i.e., "Gradient Time=3.5 min") during which the percentage of Solvent B increases linearly.

LCMS Method A:

Column=Acquity UPLC BEH C18 (2.1×100 mm, 1.7 micron particles); Solvent A=water:MeCN (95:5) w/0.1% formic acid; Solvent B=water:MeCN (5:95) w/0.1% formic acid; Flow Rate=0.8 mL/min.; Start % B=0; Final % B=100; Gradient Time=3.5 min., then a 1.0 min. hold at 100% B; Wavelength=215 nm and 254 nm.

LCMS Method B:

Column=Acquity CSH C18 (2.1×30 mm, 1.7 micron particles); Solvent A=0.1% formic acid in water; Solvent B=0.1% formic acid in MeCN; Flow Rate=0.8 mL/min.; Start % B=5; Final % B=95; Gradient Time=1.7 min., then a 0.2 min. hold at 95% B; Wavelength=215 nm and 254 nm.

LCMS Method C:

Column=Acquity UPLC BEH C18 (2.1×100 mm, 1.7 µm particles); Solvent A=water:MeCN (95:5) with 10 mM $NH_4OAc$; Solvent B=water:MeCN (5:95) with 10 mM $NH_4OAc$; Flow Rate=0.8 mL/min.; Start % B=0; Final % B=100; Gradient Time=3.5 min., then a 1.0 min. hold at 100% B; Wavelength=215 nm and 254 nm.

LCMS Method D:

Column=Acquity BEH C18 (2.1×30 mm, 1.7 µm particles); Solvent A=water w/0.1% formic acid; Solvent B=MeCN w/0.1% formic acid; Flow Rate=0.8 mL/min.; Start % B=5; Final % B=95; Gradient Time=1.7 min., then a 0.2 min. hold at 95% B; Wavelength=215 nm and 254 nm.

LCMS Method E:

Column=Acquity BEH C18 (2.1×100 mm, 1.7 µm particles); Solvent A=water:MeCN (95:5) with 10 mM $NH_4OAc$; Solvent B=water:MeCN (5:95) with 10 mM $NH_4OAc$; Flow Rate=1.0 mL/min.; Start % B=0; Final % B=100; Gradient Time=3.5 min., then a 1.0 min. hold at 100% B; Wavelength=220 nm and 254 nm.

LCMS Method F:

Column=Acquity BEH C18 (2.1×50 mm, 1.7 µm particles); Solvent A=0.05% formic acid in water; Solvent B=0.05% formic acid in ACN; Flow Rate=0.6 mL/min; Gradient Method (min.)/% B: 0/3, 0.4/3, 2.5/98, 3.5/98; Wavelength=210 nm to 400 nm.

LCMS method G:

Column=Acquity BEH C18 (2.1×50 mm, 1.7 µm particles); Solvent A=0.05% Formic Acid in water; Solvent B=0.05% Formic Acid in ACN; Flow Rate=0.6 mL/min; Gradient Method (min.)/% B: 0/3, 0.4/3, 7.5/98, 9.5/98; Wavelength=210 nm to 400 nm.

LCMS method H:

Column=Acquity BEH C18 (2.1×50 mm, 1.7 µm particles); Solvent A=0.05% TFA in Water; Solvent B=0.05% TFA in ACN; Flow Rate=0.6 mL/min; Gradient Method (min.)/% B: 0/3, 0.4/3, 2.5/98, 3.5/98; Wavelength=210 nm to 400 nm.

LCMS method I:

Column=Acquity BEH C18 (2.1×50 mm, 1.7 µm particles); Solvent A=0.05% formic acid in water; Solvent B=0.05% formic acid in ACN; Flow Rate=0.6 mL/min; Gradient Method (min.)/% B: 0/3, 2.5/3, 7.5/98, 9.5/98; Wavelength=210 nm to 400 nm.

Intermediate Compounds:

Representative Intermediate compounds and Intermediate compound syntheses are provided below. The representative Intermediate compounds and syntheses illustrate methods that may be used to prepare Intermediate compounds that may be used to prepare the Example compounds of the present invention.

Preparation of 2-amino-4-chloro-6-(4,4-difluorocyclohexyl)nicotinic acid

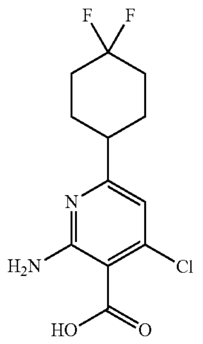 [SMILES: Nc1nc(C2CCC(F)(F)CC2)cc(Cl)c1C(=O)O]

Synthetic Scheme

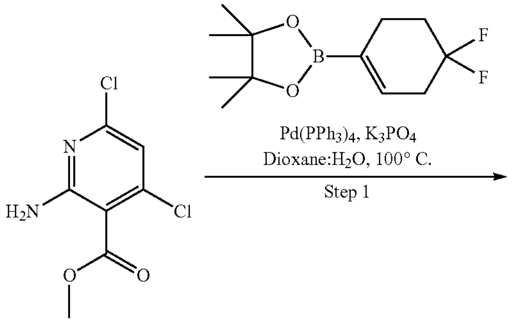

-continued

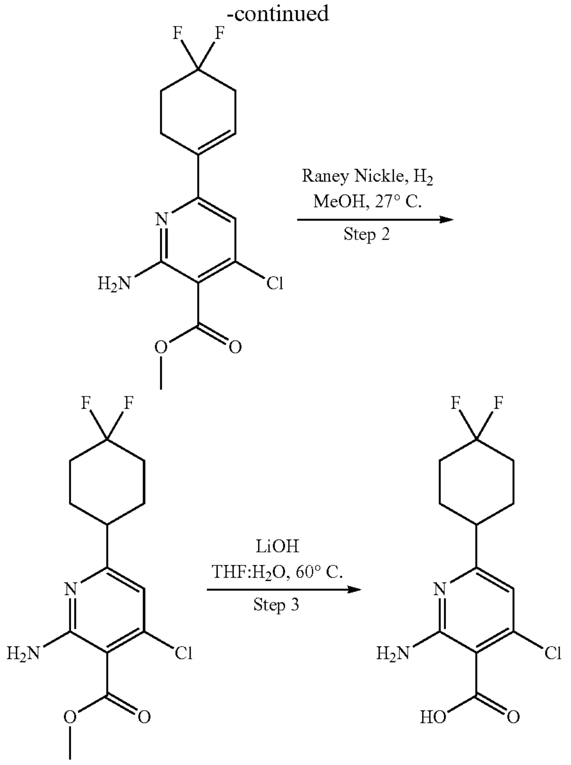

Step 1: Preparation of methyl 2-amino-4-chloro-6-(4,4-difluorocyclohex-1-en-1-yl)nicotinate

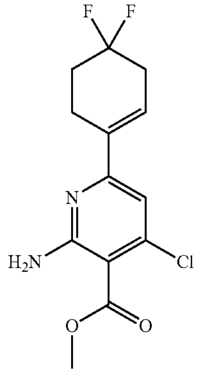 [SMILES: COC(=O)c1c(Cl)cc(C2=CCC(F)(F)CC2)nc1N]

To a stirred solution of methyl 2-amino-4,6-dichloronicotinate (100 g, 452 mmol) in 1,4-dioxane (1.25 L) was added 2-(4,4-difluorocyclohex-1-en-1-yl)-4,4,5,5-tetramethyl-1,3,2-dioxaborolane (121 g, 498 mmol), potassium phosphate tribasic (192 g, 905 mmol), and water (250 mL) at 27° C. The reaction mixture was degassed with argon for 15-20 min. To the mixture was added tetrakis(triphenylphosphine) palladium(0) (52.3 g, 45.2 mmol) and the mixture was stirred for 5 min at 27° C. The reaction mixture was then heated to 100° C. for 16 h under an argon atmosphere. Reaction progress was monitored by TLC (mobile phase: 20% ethyl acetate in hexanes). Upon completion of the reaction, the reaction mixture was filtered through a celite pad, and the filter cake was washed with ethyl acetate (1.00 L). The filtrate was concentrated under reduced pressure and the resulting residue was pre-adsorbed onto silica gel. The resulting powder was subjected to silica gel column chromatography (100-200 mesh) eluting with 0-20% ethyl acetate in petroleum ether to afford methyl 2-amino-4-chloro-6-(4,4-difluorocyclohex-1-en-1-yl)nicotinate(74.0 g, 244 mmol, yield=54%) as an off-white solid. LC/MS Method: Column=ACQUITY UPLC BEH C18, 1.7 μm, 2.1×50 mm; Mobile Phase C=0.05% formic acid in water; Mobile Phase D=0.05% formic acid in acetonitrile; Gradient=3% D for 0.3 min, 3-98% D over 1.9 min, 98% D for 1.0 min, 98-3% D over 0.1 min, 3% D for 0.7 min; Column Temperature=40° C.; Flow Rate=0.6 mL/min. LC/MS result: Retention time=2.18 min; m/z=303.0 $[M+H]^+$; Purity=97%.

Step 2: Preparation of methyl 2-amino-4-chloro-6-(4,4-difluorocyclohexyl)nicotinate

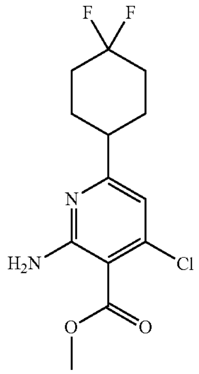 [SMILES: COC(=O)c1c(Cl)cc(C2CCC(F)(F)CC2)nc1N]

To a stirred solution of methyl 2-amino-4-chloro-6-(4,4-difluorocyclohex-1-en-1-yl)nicotinate (10.0 g, 33.0 mmol) in methanol (1.00 L) at 27° C. was added Raney nickel (6.20 g, 106 mmol). The reaction mixture was stirred for 8 h at 27° C. under a hydrogen atmosphere (balloon pressure). The progress of the reaction was monitored by TLC. Upon completion of the reaction, the mixture was filtered through a celite pad, and the filter cake was washed with methanol (300 mL). The filtrate was concentrated under reduced pressure to afford crude methyl 2-amino-4-chloro-6-(4,4-difluorocyclohexyl)nicotinate (10.1 g, purity 43%) as an off-white solid.

The above reaction was repeated, and the crude product from both reactions was combined and then pre-adsorbed onto Celite. The resulting powder was subjected to reverse-phase silica gel column chromatography on a RediSep Gold C18 column (330 g), eluting with 50-80% Mobile Phase B in Mobile Phase A at a flow rate of 50 mL/min; Mobile Phase A=95:5 water:acetonitrile+0.1% TFA, Mobile Phase B=5:95 water:acetonitrile+0.1% TFA. The pure fractions containing product were combined and concentrated under reduced pressure. The resulting aqueous mixture was diluted with saturated sodium bicarbonate solution (200 mL) and extracted with ethyl acetate (2×250 mL). The combined organic layers were dried over anhydrous sodium sulfate, filtered, and the filtrate was concentrated under reduced pressure to afford methyl 2-amino-4-chloro-6-(4,4-difluorocyclohexyl)nicotinate (10.0 g, 32.8 mmol, yield=47%) as an off-white solid. LC/MS Method: Column=ACQUITY UPLC BEH C18, 1.7 μm, 2.1×50 mm; Mobile Phase C=0.05% formic acid in water; Mobile Phase D=0.05% formic acid in acetonitrile; Gradient=3% D for 0.3 min, 3-98% D over 1.9 min, 98% D for 1.0 min, 98-3% D over 0.1 min, 3% D for 0.7 min; Column Temperature=40° C.; Flow Rate=0.6 mL/min. LC/MS result: Retention time=2.14 min; m/z=305.1 [M+H]$^+$; Purity=93%.

Step 3: Preparation of 2-amino-4-chloro-6-(4,4-difluorocyclohexyl)nicotinic Acid

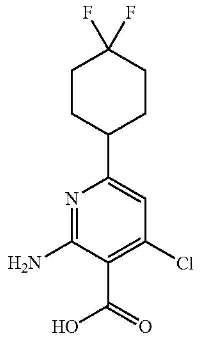 [SMILES: Nc1nc(C2CCC(F)(F)CC2)cc(Cl)c1C(=O)O]

To a stirred solution of methyl 2-amino-4-chloro-6-(4,4-difluorocyclohexyl)nicotinate (1.15 g, 3.77 mmol) in THF (15 mL) was added a solution of lithium hydroxide (181 mg, 7.55 mmol) in water (3.75 mL). The resulting mixture was heated at 60° C. for 5 h. The mixture was then concentrated under reduced pressure, diluted with water, and acidified with 0.5M citric acid. The precipitate was collected by filtration, washed with water, and dried in a vacuum oven at 40° C. to afford 2-amino-4-chloro-6-(4,4-difluorocyclohexyl)nicotinic acid (820 mg, 2.82 mmol, yield=75%) as an off-white solid. $^1$H NMR (500 MHz, DMSO-$d_6$) δ 6.60 (s, 1H), 2.65 (br t, J=11.5 Hz, 1H), 2.03-2.14 (m, 2H), 1.82-1.99 (m, 4H), 1.66-1.79 (m, 2H). LC/MS Method: Column=Acquity UPLC BEH C18, 2.1×100 mm, 1.7 μm particles; Solvent A=0.1% formic acid in 95:5 water:acetonitrile; Solvent B=0.1% formic acid in 5:95 water:acetonitrile; Flow Rate=0.8 mL/min; Start % B=0; Final % B=100; Gradient Time=3.5 min, then a 1 min hold at 100% B; Wavelength=220 and 254 nm. LC/MS result: Retention time=1.57 min; m/z=291.1 [M+H]$^+$.

Preparation of 2-amino-6-(4,4-difluorocyclohexyl)nicotinic Acid

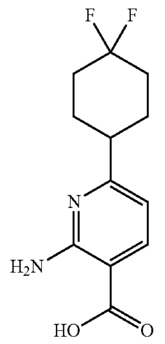 [SMILES: Nc1nc(C2CCC(F)(F)CC2)ccc1C(=O)O]

Synthetic Scheme

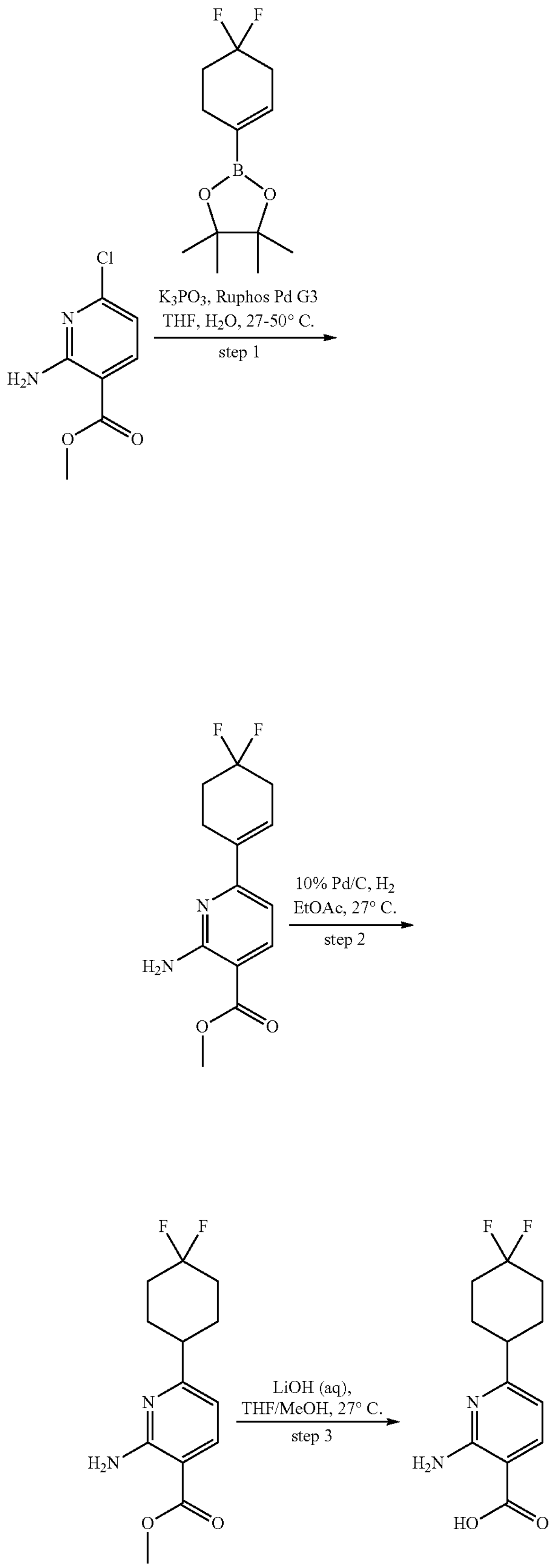

Step 1: Preparation of methyl 2-amino-6-(4,4-difluorocyclohex-1-en-1-yl)nicotinate

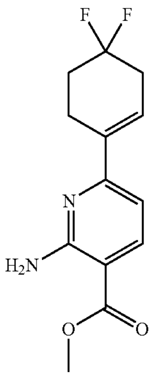 [SMILES: COC(=O)c1ccc(C2=CCC(F)(F)CC2)nc1N]

A stirred solution of methyl 2-amino-6-chloronicotinate (3.00 g, 15.9 mmol) in THF (15 mL) and water (3 mL) was degassed with nitrogen for 10 min. To the mixture was added 2-(4,4-difluorocyclohex-1-en-1-yl)-4,4,5,5-tetramethyl-1,3,2-dioxaborolane (9.71 g, 39.8 mmol), tribasic potassium phosphate (10.1 g, 47.8 mmol), and RuPhos Pd G3 (266 mg, 0.318 mmol) at 27° C. under an inert atmosphere. The reaction mixture was heated to 50° C. and stirred for 16 h. The progress of the reaction was monitored by TLC (mobile phase: 10% ethyl acetate in petroleum ether; $R_f$=0.5). Upon completion of the reaction, the reaction mixture was cooled to room temperature, diluted with water (80 mL), and extracted with ethyl acetate (2×120 mL). The combined organic layers were dried over anhydrous sodium sulfate, filtered, and the filtrate was concentrated under reduced pressure to afford crude product (3 g) as a yellow gum. The crude product was subjected to silica gel column chromatography eluting with 2-5% ethyl acetate in petroleum ether to afford methyl 2-amino-6-(4,4-difluorocyclohex-1-en-1-yl)nicotinate (1.20 g, 4.47 mmol, yield=28%) as an off-white solid. $^1H$ NMR (400 MHz, DMSO-$d_6$) δ 8.03 (d, J=8.4 Hz, 1H), 7.10 (br s, 2H), 6.83 (d, J=8.4 Hz, 1H), 6.61 (br s, 1H), 3.80 (s, 3H), 2.70-2.81 (m, 2H), 2.67-2.69 (m, 2H), 2.10-2.20 (m, 2H). LC/MS Method: Column=Acquity BEH C18 (50 mm×2.1 mm, 1.7 μm particles); Solvent A=0.05% formic acid in water; Solvent B=0.05% formic acid in acetonitrile; Flow Rate=0.6 mL/min; Gradient method (minutes/% B)=0/3, 0.4/3, 2.5/98, 3.4/98, 3.5/3, 4/3; Column Temperature=35° C. LC/MS Result: Retention time=2.23 min; observed ion=269.2 $[M+H]^+$; Purity=99%.

Step 2: Preparation of methyl 2-amino-6-(4,4-difluorocyclohexyl) nicotinate

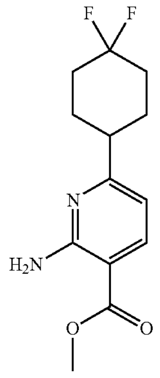

To a stirred solution of methyl 2-amino-6-(4,4-difluorocyclohex-1-en-1-yl)nicotinate (1.00 g, 3.73 mmol) in ethyl acetate (10 mL) was added 10% Pd/C (397 mg) at 27° C. The reaction mixture was stirred for 16 h under a hydrogen atmosphere (balloon pressure, ~20 psi). The progress of the reaction was monitored by TLC (mobile phase: 10% ethyl acetate in petroleum ether; $R_f$=0.4). Upon completion of the reaction, the reaction mixture was filtered through a celite pad, and the filter cake was extracted with ethyl acetate (2×50 mL). The filtrate was concentrated under reduced pressure to afford methyl 2-amino-6-(4,4-difluorocyclohexyl)nicotinate (800 mg, 2.96 mmol, yield=79%) as an off-white solid. 1H-NMR (400 MHz, DMSO-$d_6$) δ: 7.98 (d, J=8.0 Hz, 1H), 7.11 (br s, 2H), 6.54 (d, J=8.0 Hz, 1H), 3.79 (s, 3H), 2.72-2.66 (m, 1H), 2.12-1.69 (m, 8H). LC/MS Method: Column=Acquity BEH C18 (50 mm×2.1 mm, 1.7 μm particles); Solvent A=0.05% formic acid in water; Solvent B=0.05% formic acid in acetonitrile; Flow Rate=0.6 mL/min; Gradient method (minutes/% B)=0/3, 0.4/3, 2.5/98, 3.4/98, 3.5/3, 4/3; Column Temperature=35° C. LC/MS Result: Retention time=1.61 min; observed ion=271.2 $[M+H]^+$; Purity=87%.

Step 3: Preparation of 2-amino-6-(4,4-difluorocyclohexyl) nicotinic Acid

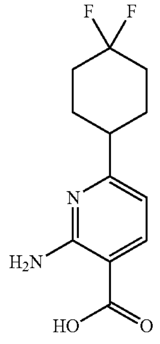

To a stirred solution of methyl 2-amino-6-(4,4-difluorocyclohexyl)nicotinate (300 mg, 1.11 mmol) in THF (8 mL) and methanol (2 mL) was added a solution of lithium hydroxide (80 mg, 3.33 mmol) in water (2.00 mL) at 27° C. The reaction mixture was stirred at 27° C. for 16 h. The progress of the reaction was monitored by TLC (mobile phase: 50% ethyl acetate in petroleum ether; $R_f$=0.1). Upon completion of the reaction, the reaction mixture was concentrated under reduced pressure, diluted with water (2 mL), and acidified with 1 N HCl (5 mL) to pH 2. The mixture was stirred for 5 min at 27° C. The precipitated solid was collected by filtration and dried under reduced pressure to afford 2-amino-6-(4,4-difluorocyclohexyl)nicotinic acid (250 mg, 0.976 mmol, yield=88%) as an off-white solid. 1H-NMR (400 MHz, DMSO-$d_6$) δ: 12.7 (br s, 1H), 7.95 (d, J=7.6 Hz, 1H), 7.15 (br s, 2H), 6.51 (d, J=8 Hz, 1H), 2.71-2.65 (m, 1H), 2.12-2.05 (m, 2H), 1.99-1.91 (m, 4H), 1.88-1.73 (m, 2H). LC/MS Method: Column=Acquity BEH C18 (50 mm×2.1 mm, 1.7 μm particles); Solvent A=0.05% formic acid in water; Solvent B=0.05% formic acid in acetonitrile; Flow Rate=0.6 mL/min; Gradient method (minutes/% B)=0/3, 0.4/3, 2.5/98, 3.4/98, 3.5/3, 4/3; Column Temperature=35° C. LC/MS Result: Retention time=1.29 min; observed ion=257.1 $[M+H]^+$; Purity=99%.

Preparation of 2-amino-6-(4,4-difluorocyclohexyl)-4-methylnicotinic Acid

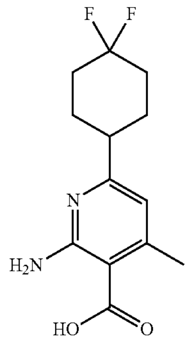

Synthetic Scheme

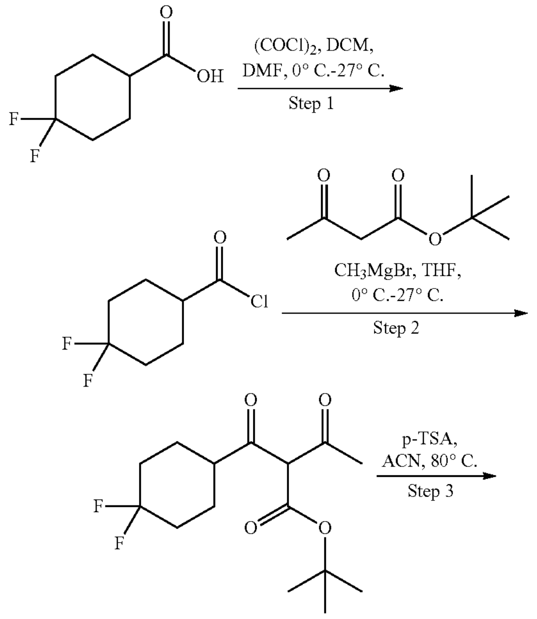

-continued

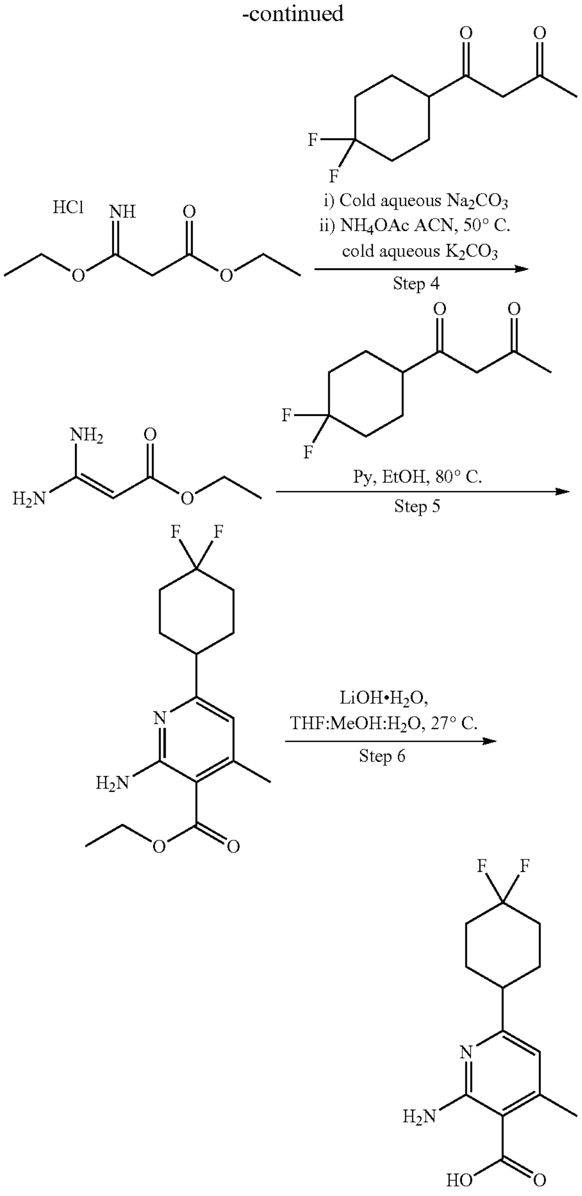

Step 1: Preparation of 4,4-difluorocyclohexane-1-carbonyl Chloride

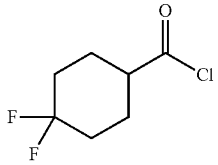 [SMILES: O=C(Cl)C1CCC(F)(F)CC1]

4,4-difluorocyclohexane-1-carboxylic acid (1.0 Kg, 6.1 mol) was dissolved in dichloromethane (DCM) (7 L) and cooled to 0° C. To this solution was added sequentially at 0° C. oxalyl chloride (0.96 L, 11 mol) followed by DMF (0.094 L, 1.2 mol). The reaction was allowed to warm to 27° C. with stirring for 2 h. The progress of the reaction was monitored by TLC ($SiO_2$, 10% EtOAc/Pet-ether Rf=0.4). On completion, the reaction solution was concentrated under reduced pressure to afford the crude product 4,4-difluorocyclohexane-1-carbonyl chloride (1.16 kg) as brown liquid. The product was used directly in the next step.

Step 2: Preparation of tert-butyl 2-(4,4-difluorocyclohexane-1-carbonyl)-3-oxobutanoate

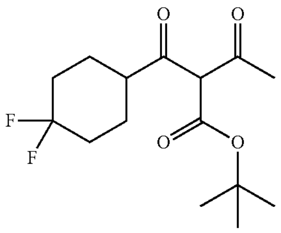 [SMILES: CC(=O)C(C(=O)OC(C)(C)C)C(=O)C1CCC(F)(F)CC1]

To a stirred solution of tert-butyl 3-oxobutanoate (1.04 L, 6.32 mol) in THF (THF) (6 L) was added methylmagnesium bromide (2.11 L, 6.32 mol) dropwise over a period of 60 min while maintaining the internal temperature between 0-5° C. under nitrogen atmosphere. The reaction mixture was warmed to 15° C. and 4,4-difluorocyclohexane-1-carbonyl chloride (1.15 kg, as prepared above) was added dropwise over the period of 10 min. The reaction mixture was warmed to 27° C. and stirred for 12 h. The progress of the reaction was monitored by TLC ($SiO_2$, 10% EtOAc/Pet-ether; Rf=0.3). On completion, the reaction mixture was quenched by dropwise addition of saturated ammonium chloride solution (3 L). The resulting mixture was extracted with EtOAc (2×5 L). The combined organics were dried over anhydrous $Na_2SO_4$ and then filtered. The filtrate was concentrated under reduced pressure to afford the crude product tert-butyl 2-(4,4-difluorocyclohexane-1-carbonyl)-3-oxobutanoate (3 kg) as a yellow liquid. The crude product was subjected to column chromatography (100-200 mesh silica gel) eluting with 10-20% EtOAc in Pet-ether to afford tert-butyl 2-(4,4-difluorocyclohexane-1-carbonyl)-3-oxobutanoate (1.8 kg, yield=97% over two steps) as a brown gummy solid. The product was used directly in the next step. LCMS retention time=2.85 min.; observed ion=303.22 (M−H); LCMS Purity=50%. LC/MS Method: Column=Acquity UPLC BEH C18 (1.7 μm, 2.1×50 mm); Solvent C=0.05% formic acid in water; Solvent D=0.05% formic acid in acetonitrile; Gradient method (minutes/% D)=0.4/3, 2.5/98, 3.4/98, 3.5/3, 4.2/3; Flow rate=0.6 mL/min.

Step 3: Preparation of 1-(4,4-difluorocyclohexyl)butane-1,3-dione

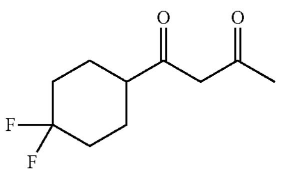

To a stirred solution of tert-butyl 2-(4,4-difluorocyclohexane-1-carbonyl)-3-oxobutanoate (1.8 kg, 5.9 mol) in acetonitrile (12 L) at 27° C. was added p-toluenesulfonic acid (p-TsOH) (1.69 Kg, 8.87 mol). The reaction mixture was heated at 80° C. for 1 h under nitrogen atmosphere. The progress of the reaction was monitored by TLC ($SiO_2$, 10% EtOAc/Pet-ether, Rf=0.3). On completion, the reaction mixture was poured into saturated aq. $NaHCO_3$ solution (800 mL). The resulting mixture was extracted with EtOAc (2×2.5 L). The combined organics were washed with brine (2 L), dried over anhydrous $Na_2SO_4$, and filtered. The filtrate was concentrated under reduced pressure to afford 1-(4,4-difluorocyclohexyl)butane-1,3-dione (1.6 kg, yield=82%) as a pale-yellow liquid. $^1$H-NMR (400 MHz, $CDCl_3$) δ=15.6 (br s, 1H), 5.56 (s, 1H), 2.51-2.39 (m, 1H), 2.21-1.97 (m, 5H), 1.96-1.74 (m, 6H).

Step 4: Preparation of ethyl 3-amino-3-iminopropanoate

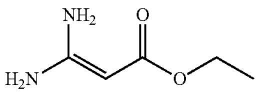

To ethyl 3-ethoxy-3-iminopropanoate hydrochloride (1.00 kg, 5.11 mol) at 27° C. was added a cold solution of aqueous 1M $Na_2CO_3$ (5.62 L, 5.62 mol) and the resulting reaction mixture was stirred at 27° C. for 2 h. The reaction mixture was extracted with EtOAc (2×3 L) and the combined organics were dried over anhydrous $Na_2SO_4$ and then filtered. The filtrate was concentrated under reduced pressure. The resulting residue (750 g) was dissolved in acetonitrile (8 L). To the solution at 27° C. was added ammonium acetate (0.591 kg, 7.67 mol). The reaction mixture was heated at 50° C. and stirred for 16 h. The progress of the reaction was monitored by TLC ($SiO_2$, 10% MeOH/DCM, Rf=0.2). On completion, the reaction mixture was cooled to room temperature and then concentrated under reduced pressure. The resulting residue was treated with cold aqueous saturated $K_2CO_3$ solution (350 mL) and the resulting mixture was stirred for 0.5 h. The mixture was extracted with EtOAc (2×2 L) and the combined organics were dried over anhydrous $Na_2SO_4$ and then filtered. The filtrate was concentrated under reduced pressure to afford ethyl 3-amino-3-iminopropanoate (550 g, yield=83%) as a pale-yellow solid. $^1$H-NMR (400 MHz, DMSO-d6) δ=6.88 (br s, 2H), 5.77 (br s, 2H), 3.87 (q, J=6.8 Hz, 2H), 3.77 (s, 1H), 1.07 (t, J=6.8 Hz, 3H).

Step 5: Preparation of ethyl 2-amino-6-(4,4-difluorocyclohexyl)-4-methylnicotinate

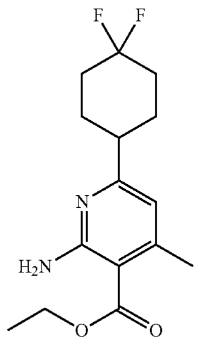 [SMILES: CCOC(=O)c1c(C)cc(C2CCC(F)(F)CC2)nc1N]

To a stirred solution of 1-(4,4-difluorocyclohexyl) butane-1,3-dione (1.5 kg, 4.55 mol) and ethyl 3-amino-3-iminopropanoate (0.711 kg, 5.46 mol) in ethanol (10 L) at 27° C. was added pyridine (0.737 L, 9.11 mol). The reaction mixture was heated at 80° C. for 16 h under nitrogen atmosphere. The progress of the reaction was monitored by TLC ($SiO_2$, 20% EtOAc/Pet-ether, Rf=0.3). On completion, the reaction mixture was cooled to room temperature and then was diluted with water (3 L). The mixture was extracted with EtOAc (2×3 L) and the combined organics were washed with brine (2.5 L), dried over with anhydrous $Na_2SO_4$, and then filtered. The filtrate was concentrated under reduced pressure to afford the crude product (1.7 kg) which was subjected to column chromatography (100-200 mesh silica gel) eluting with 20-30% EtOAc in Pet-ether to afford ethyl 2-amino-6-(4,4-difluorocyclohexyl)-4-methylnicotinate (700 g, yield=51%) as a pale-yellow solid. $^1$H-NMR (500 MHz, DMSO-$d_6$) δ=6.63 (br s, 2H), 6.39 (s, 1H), 4.36-4.22 (m, 2H), 2.62-2.56 (m, 1H), 2.34 (s, 3H), 2.12-2.04 (m, 2H), 2.02-1.89 (m, 2H), 1.88-1.80 (m, 1H), 1.79-1.70 (m, 3H), 1.33-1.25 (m, 3H). LCMS: retention time=2.41 min.; observed ion=299.49 (M+H); LCMS Purity=97%. LC/MS Method: Column=YMC Triart C18 (1.9 μm, 2.1×50 mm); Solvent A=0.05% formic acid in water; Solvent B=0.05% formic acid in acetonitrile; Gradient method (minutes/% B)=0/3, 0.4/3, 2.5/98, 3.4/98, 3.5/3, 4.5/3; Flow rate=0.6 mL/min; Column Temperature=50° C.

Step 6: Preparation of 2-amino-6-(4,4-difluorocyclohexyl)-4-methylnicotinic acid

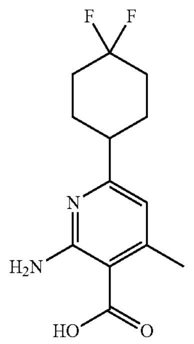 [SMILES: Cc1cc(C2CCC(F)(F)CC2)nc(N)c1C(=O)O]

To a stirred solution of ethyl 2-amino-6-(4,4-difluorocyclohexyl)-4-methylnicotinate (700 g, 2.35 mol) in THF (THF) (5 L) and methanol (1 L) at 0° C. was added water (2 L) followed by $LiOH \cdot H_2O$ (482 g, 11.5 mol). The reaction mixture was allowed to warm to 27° C. and was stirred for 16 h. The progress of the reaction was monitored by TLC ($SiO_2$, 100% EtOAc, Rf=0.2). On completion, the organics were concentrated under reduced pressure. The pH of the resulting aqueous mixture was adjusted to approximately pH=2 by addition of 2N aqueous HCl (2.5 L). The resulting solid precipitate was isolated by filtrated and was then dried in a vacuum oven to afford 2-amino-6-(4,4-difluorocyclohexyl)-4-methylnicotinic acid (550 g, yield=87%) as an off white solid. $^1$H NMR (500 MHz, DMSO-$d_6$) δ=7.96-6.55 (br s, 3H), 6.37 (s, 1H), 2.65-2.55 (m, 1H), 2.37 (s, 3H), 2.15-2.02 (m, 2H), 1.99-1.80 (m, 4H), 1.78-1.66 (m, 2H). LCMS: retention time=2.32 min.; observed ion=270.98 (M+H); LCMS Purity=95%. LC/MS Method: Column=Xbridge C18, 3.5 μm, 4.6×50 mm; Solvent A=5 mM ammonium bicarbonate in water; Solvent B=acetonitrile; Gradient method (minutes/% B)=0/5, 0.3/5, 2.5/98, 5.0/98, 5.5/5, 7.0/5; Flow rate=0.8 mL/min; Column Temperature=40° C.

Preparation of 2-amino-4-methyl-6-(1,4,4-trifluorocyclohexyl) nicotinic Acid

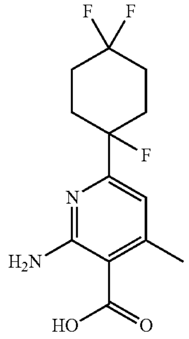

Synthetic Scheme

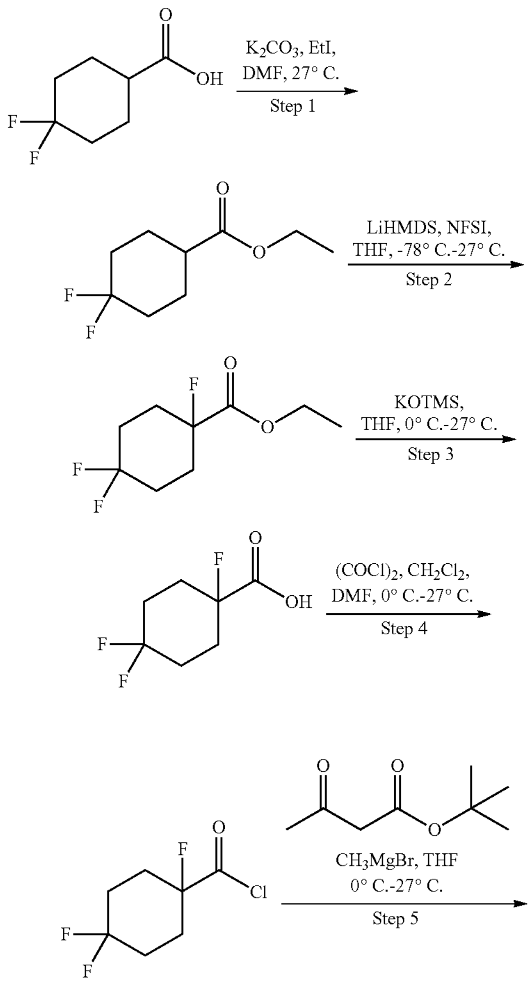

-continued

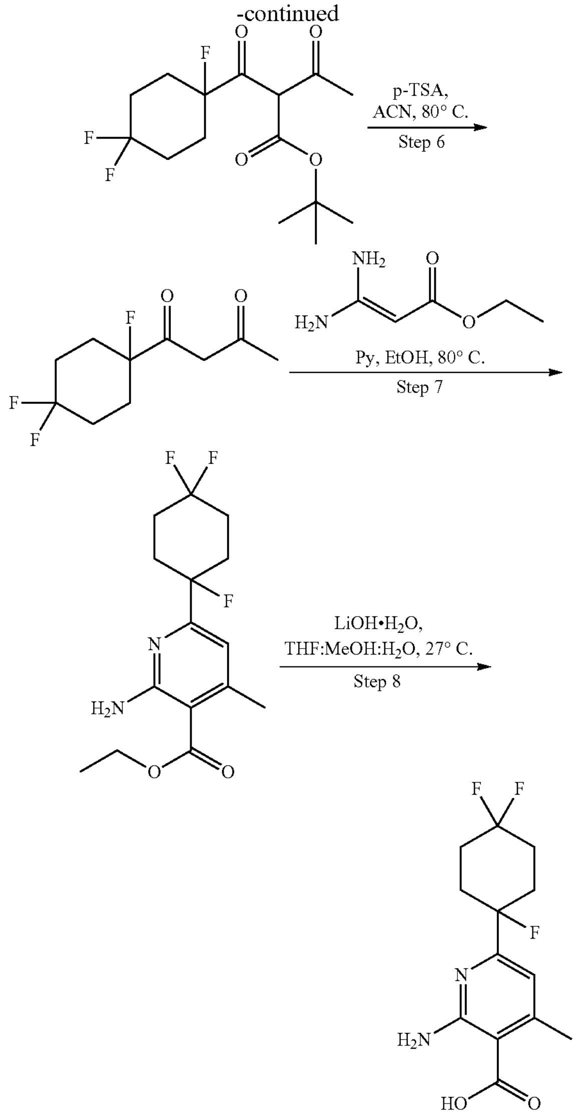

Step 1: Preparation of ethyl 4,4-difluorocyclohexane-1-carboxylate

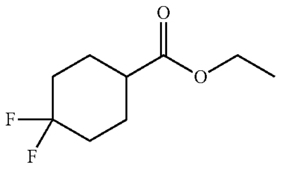

To a stirred solution of 4,4-difluorocyclohexane-1-carboxylic acid (1.50 kg, 9.14 mol) in N,N-dimethylformamide (10 L) was added potassium carbonate (2.53 kg, 18.3 mol), and the mixture was cooled to 5-10° C. To the mixture was slowly added ethyl iodide (1.11 L, 13.7 mol) over 15 min. After the addition, the reaction mixture was allowed to warm to 27° C. and was stirred for 3 h. Reaction progress was monitored by TLC (mobile phase: 30% ethyl acetate in petroleum ether; $R_f$=0.4, $KMnO_4$ active). Upon completion of the reaction, the reaction mixture was quenched with cold water (15 L) and extracted with ethyl acetate (2×10 L). The combined organic layers were washed with brine (5 L), dried over anhydrous sodium sulfate, filtered, and the filtrate was concentrated under reduced pressure to afford ethyl 4,4-difluorocyclohexane-1-carboxylate (1.70 kg, 7.96 mol, yield=87%) as a pale yellow oil. $^1$H NMR (400 MHz, $CDCl_3$) δ=4.17-4.12 (m, 2H), 2.47-2.39 (m, 1H), 2.14-2.05 (m, 2H), 2.04-1.92 (m, 2H), 1.91-1.69 (m, 4H), 1.27-1.24 (m, 3H).

Step 2: Preparation of ethyl 1,4,4-trifluorocyclohexane-1-carboxylate

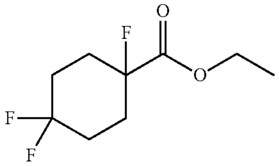

To a stirred solution of ethyl 4,4-difluorocyclohexane-1-carboxylate (500 g, 2.60 mol) in THF (2 L) at −78° C. under a nitrogen atmosphere was slowly added LiHMDS (1M in THF, 5.20 L, 5.20 mol). The reaction mixture was stirred at −78° C. for 1 h. To the reaction mixture at −78° C. was slowly added a solution of N-fluoro-N-(phenylsulfonyl)benzenesulfonamide (NFSI) (1.64 kg, 5.20 mol) in THF (2 L) under a nitrogen atmosphere. The reaction mixture was allowed to warm to 27° C. and was stirred for 3 h. The progress of the reaction was monitored by TLC (mobile phase: 10% ethyl acetate in petroleum ether; $R_f$=0.4, $KMnO_4$ active). Upon completion of the reaction, the reaction mixture was quenched with saturated aqueous ammonium chloride solution (5 L) and extracted with ethyl acetate (2×5 L). The combined organic layers were washed with brine (4 L), dried over anhydrous sodium sulfate, filtered, and the filtrate was concentrated under reduced pressure to afford the crude product as a pale brown solid. The solid material was thrice mixed with petroleum ether (2 L) and filtered. The combined filtrate was concentrated under reduced pressure to afford ethyl 1,4,4-trifluorocyclohexane-1-carboxylate (700 g) as a brown liquid. The material was used directly in the next step.

Step 3: Preparation of 1,4,4-trifluorocyclohexane-1-carboxylic Acid

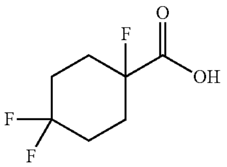 [SMILES: O=C(O)C1(F)CCC(F)(F)CC1]

To a stirred solution of potassium trimethylsilanolate (1.20 kg, 9.32 mol) in THF (7 L) under a nitrogen atmosphere at 0° C. was added dropwise over 60 min a solution of ethyl 1,4,4-trifluorocyclohexane-1-carboxylate (1.40 kg, 7.28 mol) in THF (3 L). The reaction mixture was warmed to 27° C. and stirred for 3 h. The progress of the reaction was monitored by TLC (mobile phase: 20% ethyl acetate in petroleum ether; $R_f$=0.2, $KMnO_4$ active). Upon completion of the reaction, the reaction mixture was concentrated under reduced pressure. The resulting residue was mixed with water (3 L) and then resulting solution was then washed with petroleum ether (2×2 L). The aqueous layer was acidified with 2N HCl to pH ~2. The precipitated solid was collected by filtration and dried under reduced pressure to afford 1,4,4-trifluorocyclohexane-1-carboxylic acid (720 g, 3.96 mol, yield=72%) as a pale yellow solid, which was used directly in the next step. $^1$H NMR (400 MHz, DMSO-$d_6$) δ=13.59 (br s, 1H), 2.18-1.58 (m, 8H).

Step 4: Preparation of 1,4,4-trifluorocyclohexane-1-carbonyl Chloride

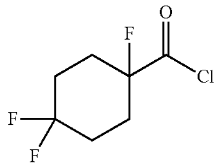 [SMILES: O=C(Cl)C1(F)CCC(F)(F)CC1]

To a stirred solution of 1,4,4-trifluorocyclohexane-1-carboxylic acid (700 g, 3.96 mol) in dichloromethane (5 L) at 0° C. was added oxalyl chloride (545 mL, 6.23 mol), followed by the dropwise addition of N,N-dimethylformamide (54 mL, 692 mmol). After the addition, the reaction mixture was allowed to warm to 27° C. and was stirred for 2 h. The reaction mixture was concentrated under reduced pressure to afford crude 1,4,4-trifluorocyclohexane-1-carbonyl chloride (750 g) as a brown liquid, which was used directly in the next step.

Step 5: tert-butyl 2-(4,4-difluorocyclohexane-1-carbonyl)-3-oxobutanoate

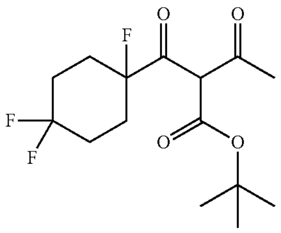 [SMILES: CC(=O)C(C(=O)OC(C)(C)C)C(=O)C1(F)CCC(F)(F)CC1]

To a stirred solution of tert-butyl 3-oxobutanoate (0.728 L, 4.43 mol) in THF (5 L) under a nitrogen atmosphere at 0° C. was added methylmagnesium bromide (3M in diethyl ether, 2.11 L, 6.32 mol) dropwise over 60 min, maintaining the internal temperature between 0-5° C. The reaction mixture was warmed to 15° C., and to the mixture was added dropwise over 30 min. 1,4,4-trifluorocyclohexane-1-carbonyl chloride (747 g, 3.54 mol). The reaction mixture was warmed to 27° C. and stirred for 5 h. The progress of the reaction was monitored by TLC (mobile phase: 10% ethyl acetate in petroleum ether; Rf=0.3). Upon completion of the reaction, the reaction mixture was quenched by dropwise addition of saturated aqueous ammonium chloride solution (7 L) and the resulting mixture was extracted with ethyl acetate (2×5 L). The combined organic layers were dried over anhydrous sodium sulfate and filtered, and the filtrate was concentrated under reduced pressure. The resulting residue (1.5 kg, a yellow liquid) was subjected to silica gel column chromatography (100-200 mesh) eluting with 0-5% ethyl acetate in petroleum ether to afford tert-butyl 3-oxo-2-(1,4,4-trifluorocyclohexane-1-carbonyl)butanoate (750 g, 2.34 mol, yield=66%) as a pale-yellow liquid. LC/MS Method: Column=XBRIDGE C18, 3.5 μm, 4.6×50 mm; Solvent A=10 mM ammonium bicarbonate in water; Solvent B=acetonitrile; Gradient method (minutes/% A)=0.3/95, 2.5/5, 5/5, 5.5/95, 7/95; Column Temperature=40.1° C.; Flow Rate=0.8 mL/min. LC/MS Result: Retention time=3.41 min; observed ion=321.0 [M−H]$^-$; Purity=60%.

Step 6: Preparation of 1-(1,4,4-trifluorocyclohexyl) butane-1,3-dione

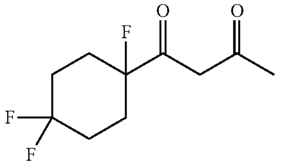

To a stirred solution of tert-butyl 3-oxo-2-(1,4,4-trifluorocyclohexane-1-carbonyl)butanoate (1.50 kg, 4.66 mol) in acetonitrile (10 L) under a nitrogen atmosphere at 27° C. was added p-toluenesulfonic acid (929 g, 4.89 mol). The reaction mixture was heated to 80° C. for 1 h. The progress of the reaction was monitored by TLC (mobile phase: 10% ethyl acetate in petroleum ether; $R_f$=0.4). Upon completion of the reaction, the reaction mixture was poured into saturated aqueous sodium bicarbonate solution (5 L) and extracted with ethyl acetate (2×5 L). The combined organic layers were washed with brine (3 L), dried over anhydrous sodium sulfate, and filtered. The filtrate was concentrated under reduced pressure to afford 1-(4,4-difluorocyclohexyl) butane-1,3-dione in quantitative yield as a pale yellow solid. $^1$H NMR (400 MHz, $CDCl_3$) δ=15.6 (br s, 1H), 5.94 (s, 1H), 2.31-2.24 (m, 2H), 2.21-2.05 (m, 6H), 1.98-1.74 (m, 3H). LC/MS Method: Column=XBRIDGE C18, 3.5 μm, 4.6×50 mm; Solvent A=10 mM ammonium bicarbonate in water; Solvent B=acetonitrile; Gradient method (minutes/% A)=0.3/95, 2.5/5, 5/5, 5.5/95, 7/95; Column Temperature=40.1° C.; Flow Rate=0.8 mL/min. LC/MS Result: Retention time=3.41 min; observed ion=221.2 [M−H]$^-$; Purity=91%.

Step 7: Preparation of Ethyl 2-amino-4-methyl-6-(1,4,4-trifluorocyclohexyl) Nicotinate

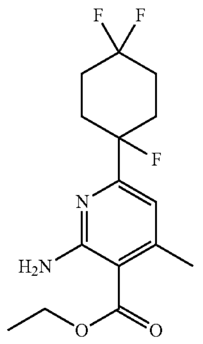 [SMILES: CCOC(=O)c1c(C)cc(C2(F)CCC(F)(F)CC2)nc1N]

To a stirred solution of 1-(4,4-difluorocyclohexyl)butane-1,3-dione (3.78 mol) and ethyl 3-amino-3-iminopropanoate (590 g, 4.54 mol) in ethanol (6 L) under a nitrogen atmosphere at 27° C. was added pyridine (612 mL, 7.56 mol). The reaction mixture was heated to 80° C. for 16 h. The progress of the reaction was monitored by TLC (mobile phase: 10% ethyl acetate in petroleum ether; $R_f$=0.3). Upon completion of the reaction, the reaction mixture was cooled to 27° C. and diluted with cold water (4 L). The mixture was extracted with ethyl acetate (2×5 L). The combined organic layers were washed with brine (2 L), dried over anhydrous sodium sulfate, and filtered. The filtrate was concentrated under reduced pressure and the resulting residue was subjected to silica gel column chromatography (100-200 mesh) eluting with 0-10% ethyl acetate in petroleum ether to afford ethyl 2-amino-6-(4,4-difluorocyclohexyl)-4-methylnicotinate (810 g, 2.56 mol, yield=67%) as a pale yellow solid. $^1$H NMR (500 MHz, DMSO-$d_6$) δ=6.71 (br s, 2H), 6.66 (s, 1H), 4.32-4.27 (m, 2H), 2.41 (s, 3H), 2.34-2.24 (m, 2H), 2.19-2.08 (m, 4H), 2.02-1.96 (m, 2H), 121-1.17 (m, 3H). LC/MS Method: Column=ACQUITY UPLC BEH C18, 1.7 μm, 2.1×50 mm; Solvent C=0.05% formic acid in water; Solvent D=0.05% formic acid in acetonitrile; Gradient method (minutes/% D)=0/3, 0.4/3, 2.5/98, 3.4/98, 3.5/3, 4.5/3; Flow rate=0.6 mL/min; Column Temperature=40° C. LC/MS Result: Retention time=2.74 min; observed ion=317.1 $[M+H]^+$; Purity=99%. HPLC Purity=99.6%.

Step 8: Preparation of 2-amino-4-methyl-6-(1,4,4-trifluorocyclohexyl) Nicotinic Acid

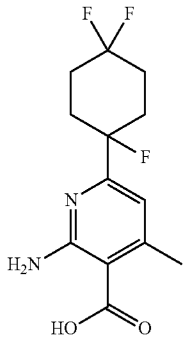 [SMILES: Cc1cc(C2(F)CCC(F)(F)CC2)nc(N)c1C(=O)O]

To a stirred solution of ethyl 2-amino-4-methyl-6-(1,4,4-trifluorocyclohexyl)nicotinate (810 g) in THF (6 L) and methanol (1 L) under a nitrogen atmosphere at 0° C. was added water (2 L) followed by lithium hydroxide monohydrate (737 g, 17.6 mol). The reaction mixture was allowed to warm to 27° C. and was stirred for 16 h. The progress of the reaction was monitored by TLC (mobile phase: ethyl acetate; $R_f$=0.2). Upon completion of the reaction, the organic solvents were removed under reduced pressure. The pH of the resulting aqueous layer was adjusted to ~2 by the addition of 2N aqueous HCl (2 L). The precipitated solid was collected by filtration, washed with water (5 L) until the washings reached pH ~7, and dried in a vacuum oven to afford 2-amino-4-methyl-6-(1,4,4-trifluorocyclohexyl)nicotinic acid (700 g, 2.43 mol, yield=95%) as an off-white solid. $^1$H NMR (500 MHz, DMSO-$d_6$) δ=12.93 (br s, 1H), 6.96 (br s, 2H), 6.65 (s, 1H), 2.41 (s, 3H), 2.35-2.25 (m, 1H), 2.20-1.90 (m, 7H). LC/MS Method: Column=ACQUITY UPLC BEH C18, 1.7 μm, 2.1×50 mm; Solvent C=0.05% formic acid in water; Solvent D=0.05% formic acid in acetonitrile; Gradient method (minutes/% D)=0/3, 0.4/3, 7.5/98, 9.5/98, 9.6/3, 10/3; Flow rate=0.6 mL/min; Column Temperature=40° C. LC/MS Result: Retention time=3.05 min; observed ion=289.1 $[M+H]^+$; Purity=98%. HPLC Purity=99.2%.

Preparation of 2-amino-4-(tert-butoxymethyl)-6-(4,4-difluorocyclohexyl)nicotinic Acid

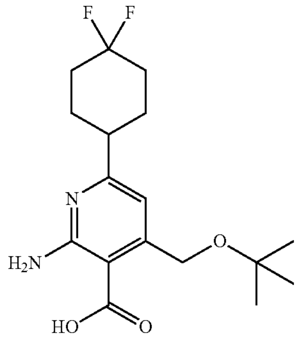 [SMILES: CC(C)(C)OCc1cc(C2CCC(F)(F)CC2)nc(N)c1C(=O)O]

Synthetic Scheme

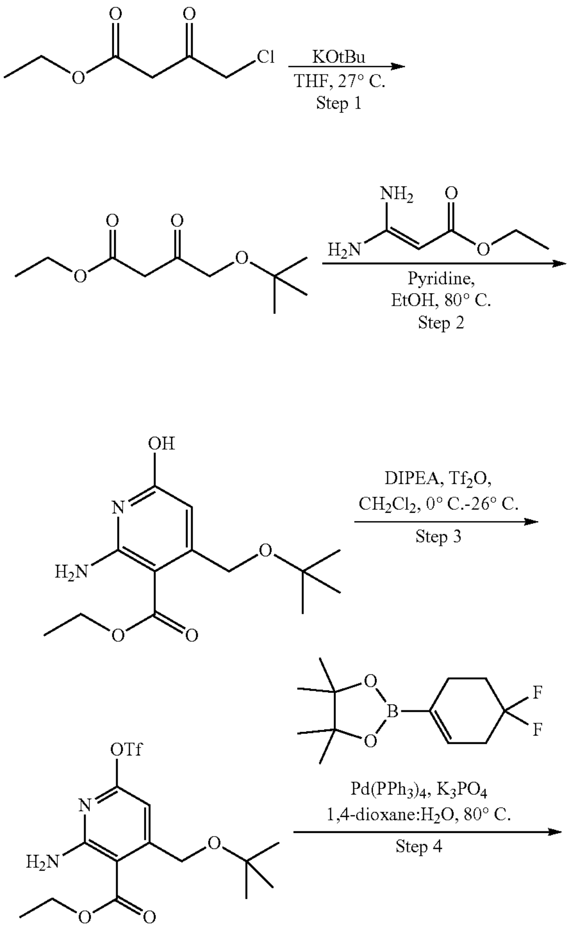

-continued

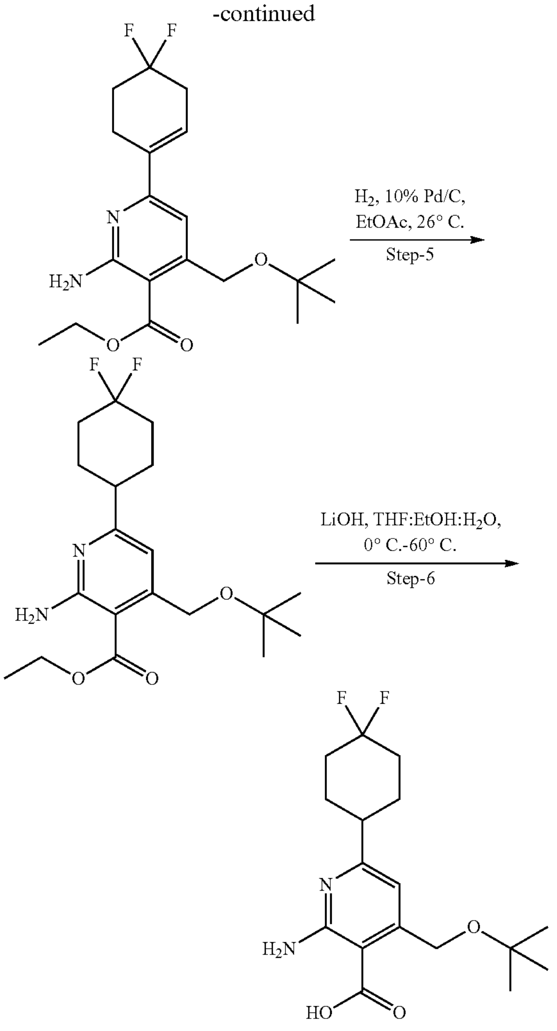

Step 1: Preparation of ethyl 4-(tert-butoxy)-3-oxobutanoate

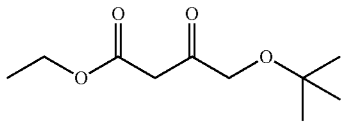

To a stirred solution of potassium tert-butoxide (102 g, 911 mmol) in THF (500 mL) under a nitrogen atmosphere at 0° C. was added a solution of ethyl 4-chlorobutanoate (75.0 g, 456 mmol) in THF (100 mL). The reaction mixture was allowed to warm to 27° C. and was stirred for 16 h. The progress of the reaction was monitored by TLC (mobile phase: 20% ethyl acetate in petroleum ether; $R_f$=0.3). Upon completion of the reaction, the solvent was removed under reduced pressure. The resulting residue was combined with 1N aqueous HCl (100 mL) and the resulting mixture was extracted with ethyl acetate (2×500 mL). The combined organic layers were washed with brine (300 mL), dried over anhydrous sodium sulfate, filtered, and the filtrate was concentrated under reduced pressure. The resulting residue was subjected to silica gel column chromatography (100-200 mesh) eluting with 9-10% ethyl acetate in petroleum ether to afford ethyl 4-(tert-butoxy)-3-oxobutanoate (24 g, 125 mmol, yield=27%) as a yellow oil. $^1$H NMR (400 MHz, DMSO-$d_6$) δ 4.13 (q, J=8.1 Hz, 2H), 4.05 (s, 2H), 3.53 (s, 2H), 1.29 (t, J=8.1 Hz, 3H), 1.09 (s, 9H).

Step 2: Preparation of ethyl 2-amino-4-(tert-butoxymethyl)-6-hydroxynicotinate

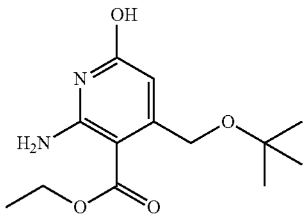 [SMILES: CCOC(=O)c1c(COC(C)(C)C)cc(O)nc1N]

To a stirred solution of ethyl 4-(tert-butoxy)-3-oxobutanoate (23.5 g, 125 mmol), ethyl 3,3-diaminoacrylate (16.6 g, 128 mmol) in ethanol (500 mL) under a nitrogen atmosphere at 27° C. was added pyridine (18.8 mL, 232 mmol). The reaction mixture was heated to 80° C. and stirred for 16 h. The progress of the reaction was monitored by TLC (mobile phase: ethyl acetate; $R_f$=0.3). Upon completion of the reaction, the reaction mixture was cooled to 27° C. and concentrated under reduced pressure. The resulting residue was combined with 10% aqueous citric acid (500 mL) and the mixture was extracted with ethyl acetate (3×550 mL). The combined organic layers were washed with brine (200 mL), dried over anhydrous sodium sulfate, and filtered. The filtrate was concentrated under reduced pressure and the resulting residue subjected to reverse-phase flash column chromatography (RediSep Gold C18 column, 275 g) eluting with 60-85% acetonitrile (containing 0.1% TFA) in water (containing 0.1% TFA). Fractions containing the pure product were combined and concentrated under reduced pressure and the resulting aqueous solution was neutralized with saturated aqueous sodium bicarbonate solution (10 mL), then extracted with ethyl acetate (3×200 mL). The combined organic layers were washed with water (3×50 mL), dried over anhydrous sodium sulfate, filtered, and the filtrate was concentrated under reduced pressure to afford the enriched product (17 g) as a brown solid, LC/MS purity=79%. The material was subjected to silica gel column chromatography (100-200 mesh) eluting with 90-100% ethyl acetate in petroleum ether to afford ethyl 2-amino-4-(tert-butoxymethyl)-6-hydroxynicotinate (5.10 g, 19.0 mmol, yield=16%) as a brown solid. $^1$H NMR (500 MHz, DMSO-$d_6$) δ 10.7 (br s, 1H), 7.30 (br s, 2H), 5.87 (s, 1H), 4.46 (s, 2H), 4.11-4.18 (m, 2H), 1.23-1.30 (m, 3H), 1.20 (s, 9H).

Step 3: Preparation of ethyl 2-amino-4-(tert-butoxymethyl)-6-(((trifluoromethyl)sulfonyl)oxy)nicotinate

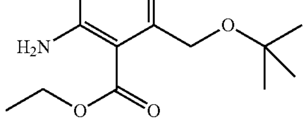

To a stirred solution of ethyl 2-amino-4-(tert-butoxymethyl)-6-hydroxynicotinate (5.00 g, 18.6 mmol) in dichloromethane (10 mL) under a nitrogen atmosphere at 0° C. was added N,N-diisopropylethylamine (19.1 mL, 110 mmol) and triflic anhydride (6.17 mL, 36.5 mmol). The reaction mixture was allowed to warm to 20° C. and was stirred for 15 min. The progress of the reaction was monitored by TLC (mobile phase: 20% ethyl acetate in petroleum ether; $R_f$=0.7). Upon completion of the reaction, the reaction mixture was concentrated under reduced pressure and the resulting residue was subjected to silica gel chromatography eluting with 10-15% ethyl acetate in petroleum ether to afford ethyl 2-amino-4-(tert-butoxymethyl)-6-(((trifluoromethyl)sulfonyl)oxy)nicotinate (6.50 g, yield=75%) as an off-white solid. 1H NMR (400 MHz, DMSO-d6) δ=7.35 (br s, 2H), 6.69 (s, 1H), 4.61 (s, 2H), 4.30 (d, J=7.1 Hz, 2H), 1.33 (t, J=7.1 Hz, 3H), 1.20 (s, 9H).

Step 4: Preparation of ethyl 2-amino-4-(tert-butoxymethyl)-6-(4,4-difluorocyclohex-1-en-1-yl)nicotinate

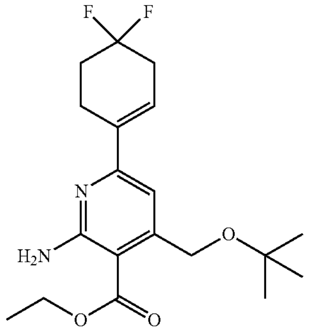 [SMILES: CCOC(=O)c1c(COC(C)(C)C)cc(C2=CCC(F)(F)CC2)nc1N]

To a stirred solution of ethyl 2-amino-4-(tert-butoxymethyl)-6-(((trifluoromethyl)sulfonyl)oxy)nicotinate (6.50 g, 16.2 mmol) and 2-(4,4-difluorocyclohex-1-en-1-yl)-4,4,5,5-tetramethyl-1,3,2-dioxaborolane (12.1 g, 49.4 mmol) in 1,4-dioxane (70 mL) was added water (10 mL). The reaction mixture was degassed with nitrogen for 10 min. To the mixture was added tripotassium phosphate (7.28 g, 34.3 mmol) and tetrakis(triphenylphosphine)palladium(0) (1.11 g, 0.961 mmol). The reaction mixture was heated to 80° C. and stirred for 3 h under a nitrogen atmosphere. The progress of the reaction was monitored by TLC (mobile phase: 20% ethyl acetate in petroleum ether; $R_f$=0.5). Upon completion of the reaction, the reaction mixture was concentrated under reduced pressure and the resulting residue was mixed with water (50 mL) and extracted with ethyl acetate (2×25 mL). The combined organics were dried over anhydrous sodium sulfate, filtered, and the filtrate was concentrated under reduced pressure to afford the crude product (7.5 g) as a brown gum. The reaction was repeated to afford additional crude product (6 g). The combined material (13.5 g) was subjected to silica gel column chromatography (230-400 mesh) eluting with 7-8% ethyl acetate in petroleum ether to afford ethyl 2-amino-4-(tert-butoxymethyl)-6-(4,4-difluorocyclohex-1-en-1-yl)nicotinate (9.00 g, yield=64%) as an off-white solid. $^1H$ NMR (400 MHz, DMSO-$d_6$) δ 7.01 (s, 1H), 6.67 (br s, 2H), 6.53-6.52 (m, 1H), 4.57 (s, 2H), 4.28 (q, J=7.1 Hz, 2H), 2.66-2.81 (m, 2H), 2.47-2.52 (m, 2H), 2.11-2.20 (m, 2H), 1.32 (t, J=7.1 Hz, 3H), 1.20 (s, 9H).

Step 5: Preparation of ethyl 2-amino-4-(tert-butoxymethyl)-6-(4,4-difluorocyclohexyl)nicotinate

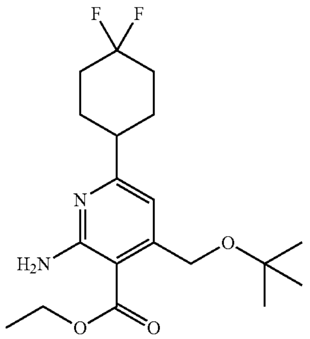 [SMILES: CCOC(=O)c1c(COC(C)(C)C)cc(C2CCC(F)(F)CC2)nc1N]

To a stirred solution of ethyl 2-amino-4-(tert-butoxymethyl)-6-(4,4-difluorocyclohex-1-en-1-yl)nicotinate (4.50 g, 11.5 mmol) in ethyl acetate (70 mL) at 26° C. was added 10% Pd/C (3.50 g). The reaction mixture was stirred at 26° C. for 16 h under a hydrogen atmosphere (20 psi). The progress of the reaction was monitored by TLC (mobile phase: 20% ethyl acetate in petroleum ether; Rf=0.4). Upon completion of the reaction, the reaction mixture was filtered through a celite pad, and the filter cake was extracted with ethyl acetate (100 mL). The filtrate was concentrated under reduced pressure to afford crude product (4.2 g) as an off-white solid. The reaction was repeated to afford additional crude product (4.2 g). The combined crude product (8.4 g) was triturated with n-pentane (3×30 mL), isolated by filtration, and dried under reduced pressure to afford ethyl 2-amino-4-(tert-butoxymethyl)-6-(4,4-difluorocyclohexyl) nicotinate (8.20 g, yield=88%) as an off-white solid. $^1H$ NMR (400 MHz, DMSO-$d_6$) δ 6.74 (s, 1H), 6.69 (br s, 2H), 4.55 (s, 2H), 4.27 (q, J=7.1 Hz, 2H), 2.61-2.73 (m, 1H), 1.62-2.37 (m, 8H), 1.32 (t, J=7.1 Hz, 3H), 1.20 (s, 9H).

Step 6: Preparation of 2-amino-4-(tert-butoxymethyl)-6-(4,4-difluorocyclohexyl) nicotinic Acid

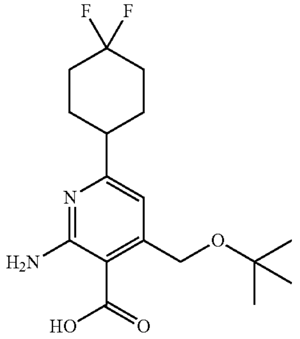 [SMILES: CC(C)(C)OCc1cc(C2CCC(F)(F)CC2)nc(N)c1C(=O)O]

To a stirred solution of ethyl 2-amino-4-(tert-butoxymethyl)-6-(4,4-difluorocyclohexyl)nicotinate (8.20 g, 22.1 mmol) in THF (50 mL) and ethanol (20 mL) at 0° C. was added a solution of lithium hydroxide (2.55 g, 106 mmol) in water (15 mL). The reaction mixture was stirred under a nitrogen atmosphere at 27° C. for 16 h and then at 60° C. for 4 h. The progress of the reaction was monitored by TLC (mobile phase: 10% methanol in dichloromethane; Rf=0.2).

Upon completion of the reaction, the reaction mixture was concentrated under reduced pressure and the resulting residue was acidified with 1 N aqueous HCl (200 mL) at 0° C., stirred for 10 min, and the resulting precipitate was collected by filtration to afford 2-amino-4-(tert-butoxymethyl)-6-(4,4-difluorocyclohexyl)nicotinic acid (7.50 g, yield=98%) as an off-white solid. 1H NMR (400 MHz, DMSO-d6) δ=9.00-7.07 (br s, 3H), 6.76 (s, 1H), 4.58 (s, 2H), 2.71-2.64 (m, 1H), 2.10-1.76 (m, 8H), 1.20 (s, 9H).

Preparation of ethyl 2-amino-4-(difluoromethyl)-6-hydroxynicotinate

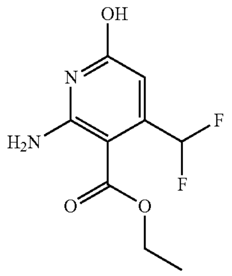 [SMILES: CCOC(=O)c1c(C(F)F)cc(O)nc1N]

To a stirred solution of ethyl 3-amino-3-iminopropanoate (13.0 g, 90.0 mmol) and ethyl 4,4-difluoro-3-oxobutanoate (13.9 mL, 135 mmol) in ethanol (50 mL) was added pyridine (14.5 mL, 180 mmol). The reaction mixture was stirred at 100° C. for 20 h. The reaction mixture was cooled to room temperature and then concentrated under reduced pressure. The resulting solid was collected by filtration and washed with a 1:1 mixture of ethanol and diethyl ether (100 mL). The filtrate was concentrated under reduced pressure, and the resulting solid was again washed with a 1:1 mixture of ethanol and diethyl ether (60 mL). The combined solids were dried under reduced pressure to afford ethyl 2-amino-4-(difluoromethyl)-6-hydroxynicotinate (6.80 g, yield=32%) as a white solid. LC/MS analysis: Retention time=1.52 min; m/z=233.10 $[M+H]^+$; Purity=99%. LC/MS Method: Column=Acquity BEH C18 (50 mm×2.1 mm, 1.7 μm particles); Solvent A=0.05% formic acid in water; Solvent B=0.05% formic acid in acetonitrile; Gradient method (minutes/% B)=0/3, 0.4/3, 2.5/98, 3.4/98, 3.5/3, 4/3; Column Temperature=35° C.; Flow Rate=0.6 mL/min.

Preparation of ethyl 2-amino-4-(difluoromethyl)-6-(((trifluoromethyl)sulfonyl)oxy)Nicotinate

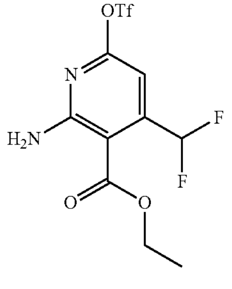 [SMILES: CCOC(=O)c1c(C(F)F)cc(OS(=O)(=O)C(F)(F)F)nc1N]

To a stirred solution of ethyl 2-amino-4-(difluoromethyl)-6-hydroxynicotinate (44.0 g, 189 mmol) in dichloromethane (1.32 L) at 0° C. was added DIPEA (99.0 mL, 570 mmol) and trifluoromethanesulfonic anhydride (35.2 mL, 209 mmol). The reaction mixture was allowed to warm to 25° C. with stirring for 1 h. The mixture was concentrated under reduced pressure and to the residue was added water (1 L). The mixture was extracted with ethyl acetate (3×500 mL). The combined organics were washed with brine (2×200 mL), dried over $Na_2SO_4$, filtered, and the filtrate was concentrated under reduced pressure. The resulting residue was subjected to flash column chromatography (330 g column) eluting with 0-10% ethyl acetate in petroleum ether to afford ethyl 2-amino-4-(difluoromethyl)-6-(((trifluoromethyl)sulfonyl)oxy)nicotinate (57.1 g) as a white solid. LC/MS Purity=100%. $^1$H NMR (400 MHz, DMSO-$d_6$) δ 7.65 (s, 2H), 7.36 (t, J=54.1 Hz, 1H), 6.79 (s, 1H), 4.34 (q, J=7.1 Hz, 2H), 1.31 (t, J=7.1 Hz, 3H).

Preparation of ethyl 2-amino-6-(4,4-difluorocyclohex-1-en-1-yl)-4-(difluoromethyl)nicotinate

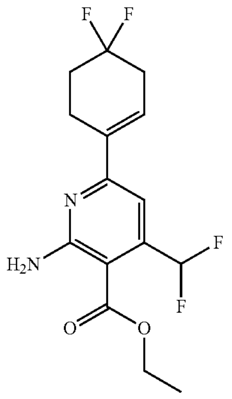 [SMILES: CCOC(=O)c1c(C(F)F)cc(C2=CCC(F)(F)CC2)nc1N]

To a stirred solution of ethyl 2-amino-4-(difluoromethyl)-6-(((trifluoromethyl)sulfonyl)oxy)nicotinate (55.0 g, 151 mmol) and 2-(4,4-difluorocyclohex-1-en-1-yl)-4,4,5,5-tetramethyl-1,3,2-dioxaborolane (55.3 g, 226 mmol) in 1,4-dioxane (1.10 L) and water (220 mL) was added cesium carbonate (148 g, 453 mmol). The reaction mixture was sparged with argon for 10 min. To the mixture was added $PdCl_2$(dppf) (2.76 g, 3.77 mmol), and the mixture was degassed for 5 min. The reaction mixture was stirred at 100° C. for 3 h under a nitrogen atmosphere. The mixture was cooled to room temperature and then concentrated under reduced pressure to remove the organic solvent. The resulting residue was diluted with water (200 mL) and then was extracted with ethyl acetate (3×500 mL). The combined organics were washed with brine (200 mL), dried over $Na_2SO_4$, filtered, and the filtrate was concentrated under reduced pressure. The resulting residue subjected to flash column chromatography eluting with 0-10% ethyl acetate in petroleum ether to afford ethyl 2-amino-6-(4,4-difluorocyclohex-1-en-1-yl)-4-(difluoromethyl)nicotinate (33.2 g) as a white solid.

Preparation of ethyl 2-amino-6-(4,4-difluorocyclohexyl)-4-(difluoromethyl) nicotinate

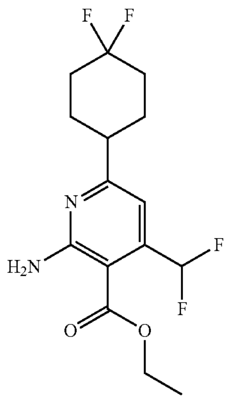 [SMILES: CCOC(=O)c1c(C(F)F)cc(C2CCC(F)(F)CC2)nc1N]

A solution of ethyl 2-amino-6-(4,4-difluorocyclohex-1-en-1-yl)-4-(difluoromethyl)nicotinate (1.80 g, 5.42 mmol) in ethyl acetate (54.2 mL) was degassed with argon. Then to the solution was added Pd/C (576 mg, 542 μmol) and the mixture was degassed with nitrogen. The atmosphere was exchanged for $H_2$ maintained under balloon pressure. The mixture was stirred at ambient temperature for 1 h. The atmosphere exchange to nitrogen and the mixture was then filtered through a pad of Celite, and the filtrate was concentrated under reduced pressure to afford ethyl 2-amino-6-(4,4-difluorocyclohexyl)-4-(difluoromethyl)nicotinate (1.32 g, yield=73%) as a pale yellow solid. $^1H$ NMR (500 MHz, $CDCl_3$ δ 7.09-7.40 (m, 1H), 6.84 (s, 1H), 6.19-6.42 (m, 2H), 4.39 (q, J=7.2 Hz, 2H), 2.61-2.71 (m, 1H), 2.15-2.26 (m, 2H), 1.76-2.01 (m, 6H), 1.41 (t, J=7.2 Hz, 3H). LC/MS analysis: m/z=335.05 $[M+H]^+$.

Preparation of 2-amino-6-(4,4-difluorocyclohexyl)-4-(difluoromethyl)nicotinic Acid

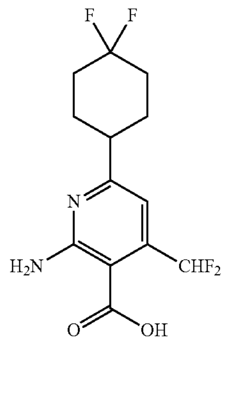 [SMILES: Nc1nc(C2CCC(F)(F)CC2)cc(C(F)F)c1C(=O)O]

To a stirred solution of ethyl 2-amino-6-(4,4-difluorocyclohexyl)-4-(difluoromethyl)nicotinate (15.7 g, 47.0 mmol) in water (160 mL) and THF (320 mL) at 0° C. was added lithium hydroxide monohydrate (7.88 g, 188 mmol). The reaction mixture was stirred at 50° C. for 2 h. The reaction mixture was concentrated under reduced pressure and to the resulting residue at 0° C. was added dropwise 1N aqueous HCl. The resulting solid was collected by filtration, washed with water (500 mL), and dried to afford 2-amino-6-(4,4-difluorocyclohexyl)-4-(difluoromethyl)nicotinic acid (11.7 g, yield=81%) as a white solid. LC/MS analysis: Retention time=1.54 min; m/z=307.32 $[M+H]^+$; Purity=99%. LC/MS Method: Column=Acquity BEH C18 (50 mm×2.1 mm, 1.7 μm particles); Solvent A=0.05% TFA in water; Solvent B=0.05% TFA in acetonitrile; Gradient method (minutes/% B)=0/3, 0.4/3, 2.5/98, 3.5/98, 3.6/3; Column Temperature=35° C.; Flow Rate=0.6 mL/min.

Preparation of ethyl 1-(2-(benzyloxy)ethyl)-4,4-difluorocyclohexane-1-carboxylate

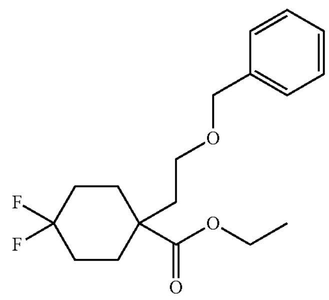 [SMILES: CCOC(=O)C1(CCOCc2ccccc2)CCC(F)(F)CC1]

To a stirred solution of ethyl 4,4-difluorocyclohexane-1-carboxylate (50.0 g, 260 mmol) in THF (400 mL) under a nitrogen atmosphere at −78° C. was added LDA (260 mL, 520 mmol). The reaction mixture was stirred at −78° C. for 1 h. To the mixture was added ((2-bromoethoxy)methyl) benzene (41.4 mL, 260 mmol) at −78° C. The reaction mixture was allowed to warm to 27° C. with stirring for 16 h. The progress of the reaction was monitored by TLC (mobile phase: 20% ethyl acetate in petroleum ether; $R_f$=0.5, $KMnO_4$ active). Upon completion of the reaction, the reaction mixture was quenched by the addition of saturated aqueous $NH_4Cl$ solution (50 mL) and then extracted with EtOAc (2×250 mL). The combined organics were dried over $Na_2SO_4$, filtered, and the filtrate was concentrated under reduced pressure to afford crude product (70 g) as a brown liquid. The crude product subjected to silica gel column chromatography eluting with 10-20% ethyl acetate in petroleum ether to afford ethyl 1-(2-(benzyloxy)ethyl)-4,4-difluorocyclohexane-1-carboxylate (68 g, yield=61%) as a pale yellow liquid. LC/MS analysis: Retention time=2.88 min; m/z=327.18 $[M+H]^+$; Purity=76%. LC/MS Method: Column=ACQUITY UPLC BEH C18, 1.7 μm, 2.1×50 mm; Solvent C=0.05% formic acid in water; Solvent D=0.05% formic acid in acetonitrile; Gradient method (minutes/% D)=0.4/3, 2.5/98, 3.4/98, 3.5/3, 4.2/3; Column Temperature=40° C.; Flow Rate=0.6 mL/min.

Preparation of 1-(2-(benzyloxy)ethyl)-4,4-difluorocyclohexane-1-carboxylic Acid

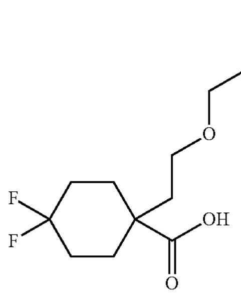

To a stirred solution of ethyl 1-(2-(benzyloxy)ethyl)-4,4-difluorocyclohexane-1-carboxylate (100 mg, 306 μmol) in THF (2 mL), methanol (2 mL), and water (1 mL) at 0° C. was added a solution of sodium hydroxide (123 mg, 3.06 mmol) in water (1 mL). The reaction mixture was heated to 80° C. and stirred for 16 h under a nitrogen atmosphere. The progress of the reaction was monitored by TLC (mobile phase: 50% EtOAc in hexanes; $R^f$=0.4, $KMnO_4$ active). Upon completion of the reaction, the organic solvents were removed under reduced pressure and the resulting residue was diluted with water (8 mL), acidified with 1N aqueous HCl (15 mL) at 0° C., and extracted with ethyl acetate (2×100 mL). The combined organics were washed with brine (20 mL), dried over $Na_2SO_4$, filtered, and the filtrate was concentrated under reduced pressure to afford 1-(2-(benzyloxy)ethyl)-4,4-difluorocyclohexane-1-carboxylic acid (70 mg, yield=77%) as a pale yellow gummy liquid. The product was used directly in the subsequent step without further purification. LC/MS analysis: Retention time=2.64 min; m/z=297.14 $[M+H]^+$; Purity=83%. LC/MS Method: Column=Xbridge C18, 3.5 μm, 4.6×50 mm; Solvent A=5 mM ammonium bicarbonate in water; Solvent B=acetonitrile; Gradient method (minutes/% B)=0/5, 0.3/5, 2.5/98, 5.0/98, 5.5/5, 7.0/5; Flow rate=0.8 mL/min; Column Temperature=40° C.

Preparation of 1-(2-(benzyloxy)ethyl)-4,4-difluoro-N-methoxy-N-methylcyclohexane-1-carboxamide

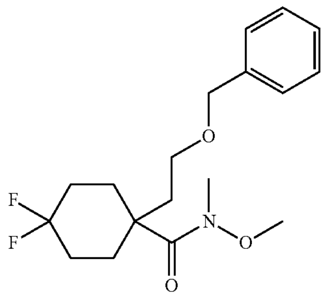 [SMILES: CON(C)C(=O)C1(CCOCc2ccccc2)CCC(F)(F)CC1]

To a stirred solution of 1-(2-(benzyloxy)ethyl)-4,4-difluorocyclohexane-1-carboxylic acid (2.00 g, 6.75 mmol) and N,O-dimethylhydroxylamine hydrochloride (785 mg, 8.04 mmol) in dichloromethane (30 mL) at 0° C. was added 1-(3-dimethylaminopropyl)-3-ethylcarbodiimide hydrochloride (1.93 g, 10.1 mmol) and DMAP (901 mg, 7.37 mmol). The reaction mixture was allowed to warm to 27° C. with stirring for 16 h under a nitrogen atmosphere. The progress of the reaction was monitored by TLC (mobile phase: 30% ethyl acetate in petroleum ether; $R_f$=0.3, $KMnO_4$ active). Upon completion of the reaction, the reaction mixture was diluted with water (30 mL) and extracted with ethyl acetate (2×50 mL). The combined organics were washed with brine (2×30 mL), dried over $Na_2SO_4$, filtered, and the filtrate was concentrated under reduced pressure to afford crude product (2.1 g) as a pale yellow oil which was subjected to silica gel column chromatography eluting with 10-20% ethyl acetate in petroleum ether to afford 1-(2-(benzyloxy)ethyl)-4,4-difluoro-N-methoxy-N-methylcyclohexane-1-carboxamide (1.30 g, yield=56%) as a colorless liquid. LC/MS analysis: Retention time=2.69 min; m/z=342.30 $[M+H]^+$; Purity=99%. LC/MS Method: Column=YMC Triart C18, 1.9 μm, 2.1×50 mm; Solvent A=0.05% formic acid in water; Solvent B=0.05% formic acid in acetonitrile; Gradient method (minutes/% B)=0/3, 0.4/3, 7.5/98, 9.5/98, 9.6/3, 10/3; Flow rate=0.6 mL/min; Column Temperature=40° C.

Preparation of 1-(1-(2-(benzyloxy)ethyl)-4,4-difluorocyclohexyl)ethan-1-one

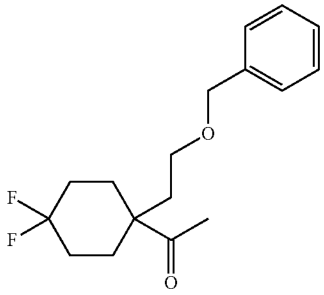 [SMILES: CC(=O)C1(CCOCc2ccccc2)CCC(F)(F)CC1]

To a stirred solution of 1-(2-(benzyloxy)ethyl)-4,4-difluoro-N-methoxy-N-methylcyclohexane-1-carboxamide (500 mg, 1.46 mmol) in THF (40 mL) at 0° C. was added methylmagnesium bromide (1.4M in THF, 5.23 mL, 7.32 mmol). The reaction mixture was heated to 50° C. with stirring for 3 h. The progress of the reaction was monitored by TLC (mobile phase: 20% ethyl acetate in hexanes; Rf=0.4, $KMnO_4$ active). Upon completion of the reaction, the reaction mixture was quenched by the addition of saturated aqueous $NH_4Cl$ (15 mL) at 0° C. and then was extracted with EtOAc (2×40 mL). The combined organics were dried over $Na_2SO_4$, filtered, and the filtrate was concentrated under reduced pressure to afford the crude product (700 mg) as a pale yellow liquid which was subjected to silica gel column chromatography eluting with 10-20% ethyl acetate in petroleum ether to afford 1-(1-(2-(benzyloxy)ethyl)-4,4-difluorocyclohexyl)ethan-1-one (360 mg, yield=83%) as a colorless liquid. LC/MS analysis: Retention time=2.68 min; m/z=297.26 $[M+H]^+$; Purity=92%. LC/MS Method: Column=YMC Triart C18, 1.9 μm, 2.1×50 mm; Solvent A=0.05% formic acid in water; Solvent B=0.05% formic acid in acetonitrile; Gradient method (minutes/% B)=0/3, 0.4/3, 2.5/98, 3.4/98, 3.5/3, 4.5/3; Flow rate=0.6 mL/min; Column temperature=40° C.

Preparation of 1-(1-(2-(benzyloxy)ethyl)-4,4-difluorocyclohexyl)butane-1,3-dione

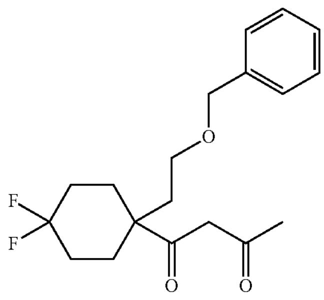 [SMILES: CC(=O)CC(=O)C1(CCOCc2ccccc2)CCC(F)(F)CC1]

To a stirred suspension of sodium hydride (101 mg, 2.53 mmol) in THF (25 mL) at 27° C. was added a solution of 1-(1-(2-(benzyloxy)ethyl)-4,4-difluorocyclohexyl)ethan-1-one (250 mg, 844 μmol) in THF (5 mL). The reaction mixture was stirred at 27° C. for 1 h. To the mixture was added ethyl acetate (83 μL, 844 μmol). The reaction mixture was heated to 75° C. in a sealed tube with stirring for 3 h. The progress of the reaction was monitored by TLC (mobile phase: 10% ethyl acetate in petroleum ether; Rf=0.4, UV active). The reaction mixture was quenched at 27° C. by the addition of saturated aqueous ammonium chloride (10 mL) and was then extracted with EtOAc (2×20 mL). The combined organics were washed with brine (20 mL), dried over $Na_2SO_4$, filtered, and the filtrate was concentrated under reduced pressure to afford crude product (300 mg) as a yellow liquid which was subjected to silica gel column chromatography eluting with 10-20% ethyl acetate in petroleum ether to afford 1-(1-(2-(benzyloxy)ethyl)-4,4-difluorocyclohexyl)butane-1,3-dione (150 mg, yield=53%) as a pale yellow liquid. LC/MS analysis: Retention time=2.86 min; m/z=339.32 $[M+H]^+$; Purity=79%. LC/MS Method: Column=YMC Triart C18, 1.9 μm, 2.1×50 mm; Solvent A=0.05% formic acid in water; Solvent B=0.05% formic acid in acetonitrile; Gradient method (minutes/% B)=0/3, 0.4/3, 2.5/98, 3.4/98, 3.5/3, 4.5/3; Flow rate=0.6 mL/min; Column temperature=40° C.

Preparation of ethyl 2-amino-6-(1-(2-(benzyloxy)ethyl)-4,4-difluorocyclohexyl)-4-methylnicotinate

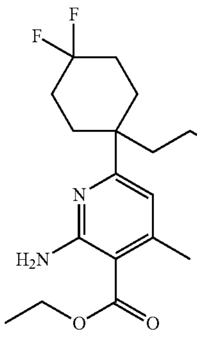

A stirred solution of 1-(1-(2-(benzyloxy)ethyl)-4,4-difluorocyclohexyl)butane-1,3-dione (2.00 g, 5.91 mmol) and ethyl 3,3-diaminoacrylate (1.54 g, 11.8 mmol) in a sealed tube was heated at 150° C. for 2 h. The reaction mixture was cooled to room temperature and then was concentrated under reduced pressure to afford the crude product (3.2 g, yellow liquid) which was subjected to silica gel column chromatography eluting with 10-20% ethyl acetate in petroleum ether to afford ethyl 2-amino-6-(1-(2-(benzyloxy)ethyl)-4,4-difluorocyclohexyl)-4-methylnicotinate (1.10 g, purity=55%, yield=43%) as a pale yellow liquid. The product was subjected to a second round of silica gel chromatography eluting with 80-100% DCM in petroleum ether to increase the purity. LC/MS analysis: Retention time=5.39 min; m/z=433.33 $[M+H]^+$; Purity=55%. LC/MS Method: Column=ACQUITY UPLC BEH C18, 1.7 μm, 2.1×50 mm; Solvent C=0.05% formic acid in water; SolventD=0.05% formic acid in acetonitrile; Gradient method (minutes/% D)=0/3, 0.4/3, 7.5/98, 9.5/98, 9.6/3, 10/3; Flow rate=0.6 mL/min; Column Temperature=40° C.

Preparation of 2-amino-6-(1-(2-(benzyloxy)ethyl)-4,4-difluorocyclohexyl)-4-methylnicotinic Acid

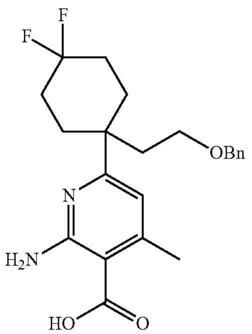 [SMILES: Cc1cc(C2(CCOCc3ccccc3)CCC(F)(F)CC2)nc(N)c1C(=O)O]

To a stirred solution of ethyl 2-amino-6-(1-(2-(benzyloxy)ethyl)-4,4-difluorocyclohexyl)-4-methylnicotinate (4.90 g, 11.1 mmol) in THF (30 mL) and methanol (15 mL) at 0° C. was added a solution of lithium hydroxide monohydrate (1.86 g, 44.4 mmol) in water (15 mL). The reaction mixture was heated to 60° C. and stirred for 16 h under a nitrogen atmosphere. The progress of the reaction was monitored by TLC (mobile phase: 10% methanol in DCM; Rf=0.3, UV active). The organic solvents were removed under reduced pressure and the resulting residue was diluted with ice-water (100 mL), acidified with 1N aqueous HCl (30 mL) at 0° C., and extracted with ethyl acetate (2×250 mL). The combined organics were washed with brine (100 mL), dried over $Na_2SO_4$, filtered, and the filtrate was concentrated under reduced pressure to afford crude product (4.7 g) as an off-white solid. The crude product was triturated with diethyl ether (3×15 mL) and n-pentane (3×20 mL), then collected by filtration and dried to afford 2-amino-6-(1-(2-(benzyloxy)ethyl)-4,4-difluorocyclohexyl)-4-methylnicotinic acid (3.95 g, yield=87%) as a white solid. LC/MS analysis: Retention time=2.00 min; m/z=405.23 $[M+H]^+$; Purity=99%. HPLC analysis: Retention time=8.81 min; Purity=99%. LC/MS Method: Column=Acquity BEH C18 (50 mm×2.1 mm, 1.7 μm particles); Gradient method (minutes/% B)=0/3, 0.4/3, 2.5/98, 3.5/98, 3.6/3, 4/3; Mobile Phase A=0.05% formic acid in water; Mobile Phase B=0.05% formic acid in acetonitrile; Column Temperature=35° C.; Flow Rate=0.6 mL/min.

Preparation of N-(7-amino-1-(2-bromoethyl)-4-chloro-1H-indazol-3-yl)-N-(4-methoxy benzyl) methanesulfonamide Synthetic Scheme

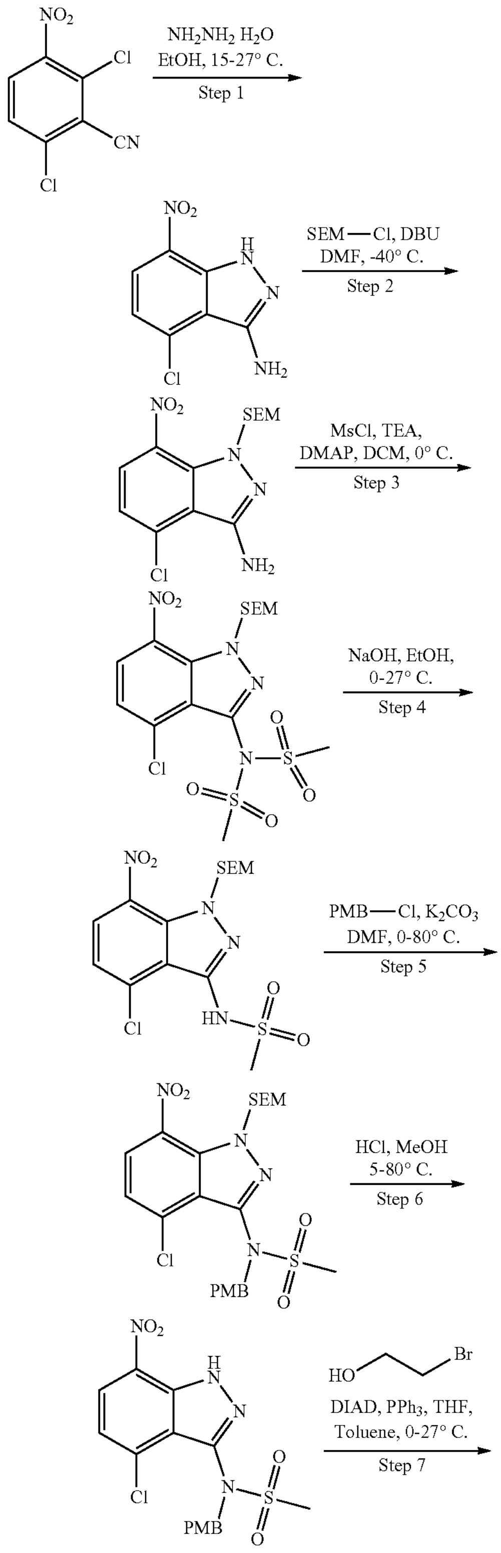

-continued

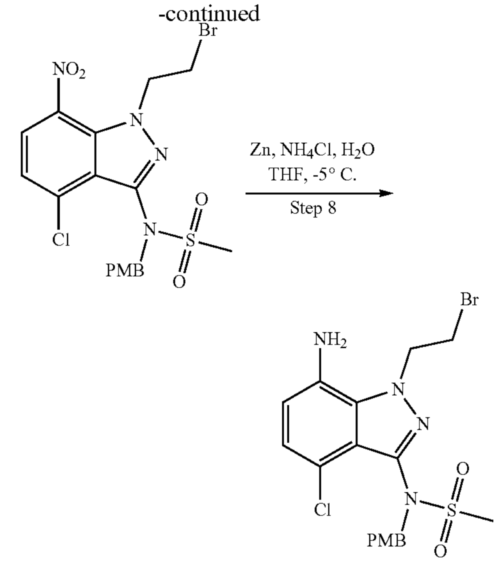

Step 1: Preparation of 4-chloro-7-nitro-1H-indazol-3-amine

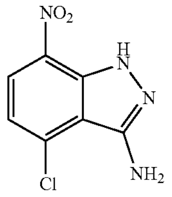 [SMILES: Nc1n[nH]c2c([N+](=O)[O-])ccc(Cl)c12]

To a stirred solution of 2,6-dichloro-3-nitrobenzonitrile (500 g, 2304 mmol) in ethanol (7500 mL) was added hydrazine hydrate (346 g, 6912 mmol) at 15-25° C. (Observation: reaction mixture color changes from pale yellow to orange red solid). After addition, the reaction mixture was slowly warmed to 27° C. and stirred for 3 hr. Reaction progress was monitored by TLC. Mobile phase: 40% EtOAc in Hexane (Rf: 0.4, UV active). The reaction mixture was diluted with water (7.5 L) and stirred for 0.5 hr. Then the precipitated compound was filtered. The wet solid was washed with Acetone and Pet-ether (1:1) ratio (3 L) and dried the compound in vacuo oven at 45-50° C. until MC reaches below 1% to get 4-chloro-7-nitro-1H-indazol-3-amine (430 g, 1800 mmol, 78% yield) as an orange red solid.

Step 2: Preparation of 4-chloro-7-nitro-1-((2-(trimethylsilyl)ethoxy)methyl)-1H-indazol-3-amine

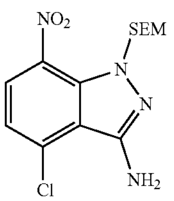 [SMILES: C[Si](C)(C)CCOCn1nc(N)c2c(Cl)ccc([N+](=O)[O-])c21]

4-chloro-7-nitro-1H-indazol-3-amine (275 g, 1294 mmol) was dissolved in N,N-Dimethylformamide (DMF) (2.7 L), cooled to −40° C. To the reaction was added DBU (1.365 L, 9055 mmol) by dropwise over 1 h. Stirred for 30 min. Then SEM-Cl (0.619 L, 3493 mmol) was added dropwise over 1 h. The total reaction mixture was stirred at −40° C. for 5 hr. The progress of reaction was monitored by TLC($SiO_2$). On completion, the reaction mixture was quenched with ice cold water (3.0 Ltr) at −40° C. dropwise and then allowed to warm to 27° C. The mixture was extracted with Ethyl acetate (3×2 Ltr). The combined organic layer was washed with water (2×2.0 Ltr), brine (1.0 Ltr) and then further dried over $Na_2SO_4$ and filtered. The filtrate was concentrated under reduced pressure to afford crude 4-chloro-7-nitro-1-((2-(trimethylsilyl)ethoxy)methyl)-1H-indazol-3-amine (360 g, 673 mmol, 52.0% yield) brown gummy solid.

Step 3: Preparation of N-(4-chloro-7-nitro-1-((2 (trimethylsilyl)ethoxy)methyl)-1H-indazol-3-yl)-N-(methylsulfonyl)methanesulfonamide

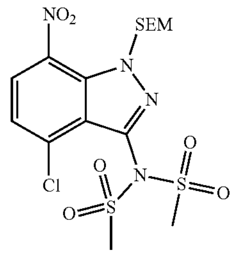 [SMILES: C[Si](C)(C)CCOCn1nc(N(S(C)(=O)=O)S(C)(=O)=O)c2c(Cl)ccc([N+](=O)[O-])c21]

To a stirred solution of 4-chloro-7-nitro-1-((2-(trimethylsilyl)ethoxy)methyl)-1H-indazol-3-amine (290 g, 846 mmol) in Dichloromethane (DCM) (2.9 L) was added methanesulfonyl chloride (0.165 L, 2118 mmol) followed by triethylamine (0.354 L, 2538 mmol), DMAP (6.20 g, 50.8 mmol) at 0° C. The reaction was stirred for 30 min at 0° C. The progress of the reaction was monitored by TLC($SiO_2$). TLC-Mobile phase: 10% Ethyl acetate in Pet-ether, Rf=0.3, UV-Active. (4 times elution). On completion of the reaction, reaction mixture was diluted with ice cold water (2500 mL) and stirred extracted with DCM (2×2500 ml) and washed with brine solution (2000 mL) and concentrated under vacuum to afford a brown solid. The above crude product was triturated with n-pentane (2×1000 mL) and dried under high vacuum to afford the desired product, N-(4-chloro-7-nitro-1-((2(trimethylsilyl)ethoxy)methyl)-1H-indazol-3-yl)-N-(methylsulfonyl)methanesulfonamide (420 g, 842 mmol, 100% yield) as a brown solid which was carried on to the next step.

Step 4: Preparation of N-(4-chloro-7-nitro-1-((2 (trimethylsilyl)ethoxy)methyl)-1H-indazol-3-yl) methanesulfonamide

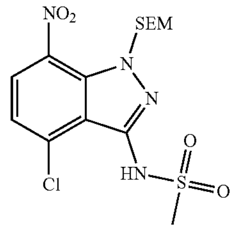 [SMILES: C[Si](C)(C)CCOCn1nc(NS(C)(=O)=O)c2c(Cl)ccc([N+](=O)[O-])c21]

To a stirred solution of N-(4-chloro-7-nitro-1-((2-(trimethylsilyl)ethoxy)methyl)-1H-indazol-3-yl)-N-(methylsulfonyl)methanesulfonamide (420 g, 842 mmol) in Ethanol (4.2 L) was added NaOH (4 L, 842 mmol, 10 wt % in water) at 0° C. The reaction was stirred for 3 hr at 27° C. The progress of the reaction was monitored by TLC($SiO_2$). TLC-Mobile phase: 30% Ethyl acetate in Pet-ether, Rf=0.2,UV-active. On completion of the reaction, reaction mixture was diluted with ice cold water (1000 mL) and acidified (pH=2) with 1 N HCl solution then precipitate was formed and then filtered and washed with water (2×2000 ml) and then dried with under vacuum to afford N-(4-chloro-7-nitro-1-((2(trimethylsilyl)ethoxy)methyl)-1H-indazol-3-yl)methanesulfonamide (320 g, 382 mmol, 45.4% yield) as a brown solid.

Step 5: Preparation of N-(4-chloro-7-nitro-1-((2-(trimethylsilyl)ethoxy)methyl)-1H-indazol-3-yl)-N-(4-methoxybenzyl)methanesulfonamide

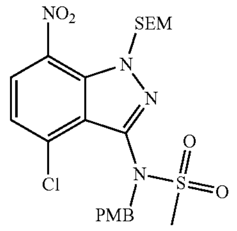

To a stirred solution of N-(4-chloro-7-nitro-1-((2-(trimethylsilyl)ethoxy)methyl)-1H-indazol-3-yl)methanesulfonamide (325 g, 772 mmol) in N,N-Dimethylformamide (DMF) (3.2 L) at 0° C., was added 4-methoxybenzyl chloride (0.116 L, 849 mmol) followed by the addition of potassium carbonate (139 g, 1004 mmol) at 0° C. The temperature was raised to 80° C. and stirred for 5 hr at 80° C. Then progress of the reaction was monitored by TLC($SiO_2$). Mobile phase: 50% Ethyl acetate in Pet-ether, Rf=0.4, UV-Active. On completion of the reaction, the reaction mixture was diluted with ice cold water (2000 mL) and stirred for extracted with ethyl acetate (2×2000 mL) and washed with cold brine solution (1000 mL) and dried over $Na_2SO_4$, concentrated under reduced pressure to afforded N-(4-chloro-7-nitro-1-((2-(trimethylsilyl)ethoxy)methyl)-1H-indazol-3-yl)-N-(4methoxybenzyl)methanesulfonamide (430 g, 438 mmol, 56.7% yield) as an brown solid.

The reaction was repeated on a similar scale with similar results and the combined crude compound was dissolved in Dichloromethane (500 ml) and absorbed 100-200 slica gel and purified through column chromatography using silica gel (100-200 mesh) and eluted with 50-70% ethyl acetate in pet-ether. The fractions containing pure product (determined by TLC) were combined and concentrated under reduced pressure to get the desired compound N-(4-chloro-7-nitro-1-((2-(trimethylsilyl)ethoxy)methyl)-1H-indazol-3yl)-N-(4-methoxybenzyl)methanesulfonamide (650 g, 1131 mmol, 68.0% yield) as brown solid.

Step 6: Preparation of N-(4-chloro-7-nitro-1H-indazol-3-yl)-N-(4-methoxybenzyl)methanesulfonamide

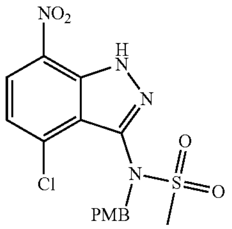

To a stirred solution of N-(4-chloro-7-nitro-1-((2-(trimethylsilyl)ethoxy)methyl)-1H-indazol-3-yl)-N-(4-methoxybenzyl)methanesulfonamide (640 g, 1183 mmol) in Methanol (2000 mL) was added MeOH-HCL (1900 mL, 7600 mmol, 4M) at 5-10° C. then stirred at 80° C. for 16 hr The progress of reaction was monitored by TLC($SiO_2$). On completion, the reaction mixture was cooled to 27° C. and obtained solid was filtered. Filtered solid was washed with water(2×2000 mL), Pet-ether (2×1000 mL) and dried under reduced pressure to afforded to get N-(4-chloro-7-nitro-1H-indazol-3-yl)-N-(4-methoxybenzyl)methanesulfonamide (401 g, 943 mmol, 80% yield) as a pale yellow solid. LCMS Method: Column=Acquity BEH C18 (50 mm×2.1 mm, 1.7 μm particles); Solvent A=0.05% formic acid in water. Solvent B=0.05% formic acid in acetonitrile. Flow Rate=0.6 mL/min. Gradient method (minutes/% B)=0/3, 0.4/3, 1.2/6, 2.6/95, 4.5/95. Column Temperature=35° C. LCMS Result: retention time=5.27 min.; observed ion=411.13 (M+H).

Step 7: Preparation of N-(1-(2-bromoethyl)-4-chloro-7-nitro-1H-indazol-3-yl)-N-(4-methoxybenzyl) methanesulfonamide

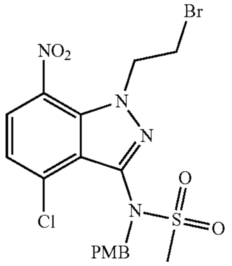

To a stirred solution of N-(4-chloro-7-nitro-1H-indazol-3-yl)-N-(4-methoxybenzyl) methanesulfonamide (10.0 g, 24.3 mmol) in Tetrahydrofuran (THF) (50 mL) and Toluene (50 mL) were added 2-bromoethan-1-ol (5.18 mL, 73.0 mmol) and triphenylphosphine (15.96 g, 60.9 mmol) followed by Diisopropyl azodicarboxylate (DIAD) (11.83 mL, 60.9 mmol) at 0° C. The reaction mixture was stirred at 27° C. for 16 h under nitrogen atmosphere. The progress of the reaction was monitored by TLC ($SiO_2$, 30% EtOAc in Hexane Rf=0.5). On completion, quenched with water (100 mL) and extracted with Ethyl acetate (2×50 mL). The combined organic layers were washed with brine solution (2×50 mL), dried over $Na_2SO_4$, filtered. The filtrate was concentrated under reduced pressure to afford crude compound as yellow solid. The crude product which was purified by to silica gel (100-200 mesh, 330 g, Teledyne ISCO on 330 g column (silica packed) and eluted with 15-20% EtOAc in Pet-ether collected pure fractions were concentrated under reduced pressure to afford the product (100 g) containing considerable amount of DIAD by product. The enriched product was washed with diethyl ether (100 mL), filtered and dried under reduced pressure to afford N-(1-(2-bromoethyl)-4-chloro-7-nitro-1H-indazol-3-yl)-N-(4-methoxybenzyl)methanesulfonamide (8.2 g, Yield: 61%) as a brown solid. 1H NMR (400 MHz, DMSO-d6) δ=8.18 (d, J=8.4 Hz, 1H), 7.42 (d, J=8.4 Hz, 1H), 7.21 (d, J=8 Hz, 2H), 6.80-6.76 (m, 2H), 4.93-4.79 (m, 4H), 3.92-3.76 (m, 2H), 3.68 (s, 3H), 3.21 (s, 3H).

Step 8: Preparation of N-(7-amino-1-(2-bromoethyl)-4-chloro-1H-indazol-3-yl)-N-(4-methoxy benzyl)methanesulfonamide

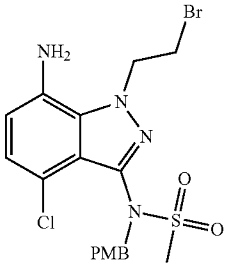

To a stirred solution of Zinc (14.75 g, 226 mmol) in Tetrahydrofuran (THF) (160 mL) was added and Water (80 mL) followed by ammonium chloride (12.07 g, 226 mmol) at −5° C. Then N-(1-(2-bromoethyl)-4-chloro-7-nitro-1H-indazol-3-yl)-N-(4-methoxybenzyl) methanesulfonamide (8.2 g, 15.05 mmol) in Tetrahydrofuran (THF) (160 mL) was added at a single lot at −5° C. and stirred for 5 min under nitrogen atmosphere. The progress of the reaction was monitored by TLC ($SiO_2$, 50% EtOAc in Hexane Rf=0.3). On completion, the reaction mixture was quenched with EtOAc (200 mL), filtered through a celite pad under suction and washed with EtOAc (100 mL). Then organic layer extracted with chilled water (2×150 mL). The combined organic layers were washed with brine solution (2×100 mL), dried over $Na_2SO_4$, filtered, and concentrated under reduced pressure to obtain the crude compound as a brown solid. The crude product was purified by silica gel (230-400 mesh, 330 g, Teledyne ISCO on 330 g column (silica packed) and eluted with 0-0.5% THF in DCM with flow rate 90 mL/minute. The fractions containing the desired product were pooled and concentrated under reduced pressure to afford N-(7-amino-1-(2-bromoethyl)-4-chloro-1H-indazol-3-yl)-N-(4-methoxybenzyl)methanesulfonamide (4.5 g, Yield: 52%) as a brown solid. 1H NMR (400 MHz, DMSO-d6) δ=7.21 (d, J=8.4 Hz, 2H), 6.88 (d, J=8 Hz, 1H), 6.82-6.76 (m, 2H), 6.21 (d, J=8.4 Hz, 1H), 5.31 (br s, 2H), 4.98-4.92 (m, 2H), 4.82-4.76 (m, 2H), 3.79-3.76 (m, 2H), 3.67 (s, 3H), 3.10 (s, 3H).

The Intermediate compound N-(4-chloro-7-nitro-1H-indazol-3-yl)-N-(4-methoxybenzyl)methanesulfonamide may be used to prepare most indazole Intermediate compounds that may be used for the preparation of the Example compounds of the present invention.

The Intermediate compound synthesis examples below are illustrative of how N-(4-chloro-7-nitro-1H-indazol-3-yl)-N-(4-methoxybenzyl)methanesulfonamide can be alkylated, using either alkyl halides and based, or using Mitsunobu reaction conditions, to provide indazole Intermediate compounds that may be used for the preparation of the Example compounds of the present invention. The Intermediate synthesis examples below are also illustrative of how the nitro group of indazole Intermediate compounds can be reduced using zinc and ammonium chloride. Although not limiting in the reaction conditions that one skilled in the art might use to generate the necessary indazole Intermediate compounds, the conditions taught by these examples are broadly general to the preparation of useful indazole Intermediate compounds and the preparation of other indazoles Intermediate compounds can be inferred from these Intermediate compound synthesis examples.

Preparation of N-(7-amino-4-chloro-1-(2-((3R,5S)-3,5-difluoropiperidin-1-yl)ethyl)-1H-indazol-3-yl)-N-(4-methoxybenzyl)methanesulfonamide

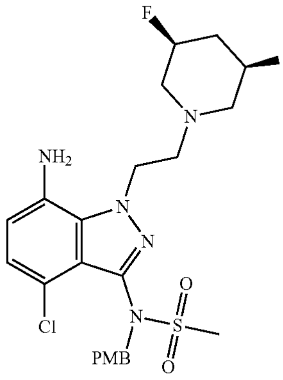

Synthetic Scheme

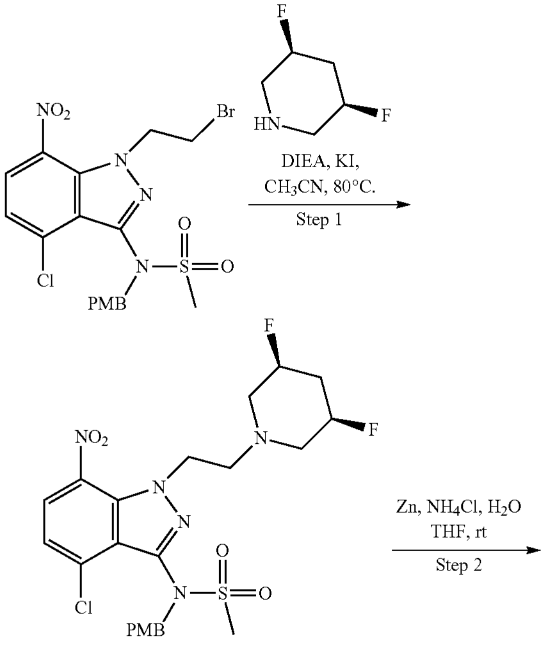

-continued

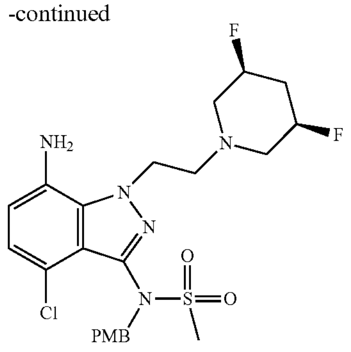

Step 1: Preparation of N-(4-chloro-1-(2-((3R,5S)-3,5-difluoropiperidin-1-yl)ethyl)-7-nitro-1H-indazol-3-yl)-N-(4-methoxybenzyl)methanesulfonamide

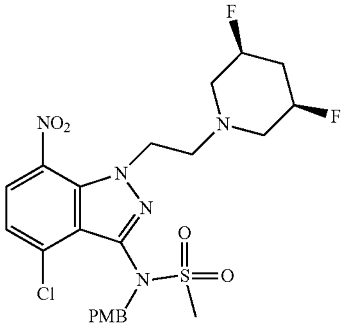

To a stirred solution of N-(1-(2-bromoethyl)-4-chloro-7-nitro-1H-indazol-3-yl)-N-(4-methoxybenzyl)methanesulfonamide (7.00 g, 13.5 mmol) in acetonitrile (27 mL) was added (3S,5R)-3,5-difluoropiperidine hydrochloride (2.10 g, 13.5 mmol), followed by N,N-diisopropylethylamine (3.50 g, 27.0 mmol) and potassium iodide (2.20 g, 13.5 mmol). The reaction mixture was heated to 80° C. and stirred overnight. The reaction mixture was concentrated under reduced pressure, and the resulting residue was subjected to silica gel column chromatography eluting with a gradient of 0-50% ethyl acetate in hexanes over 10 column volumes to afford N-(4-chloro-1-(2-((3R,5S)-3,5-difluoropiperidin-1-yl)ethyl)-7-nitro-1H-indazol-3-yl)-N-(4-methoxybenzyl) methanesulfonamide (3.60 g, 6.17 mmol, yield=48%) which was used directly in the next step. 1H NMR (500 MHz, METHANOL-d4) δ ppm 1.59-1.74 (m, 1H) 2.24-2.34 (m, 3H) 2.34-2.43 (m, 1H) 2.67-2.77 (m, 2H) 2.78-2.87 (m, 1H) 3.16-3.18 (m, 3H) 3.71 (s, 3H) 4.21-4.44 (m, 1H) 4.59-4.64 (m, 2H) 4.73-4.78 (m, 2H) 4.86-4.87 (m, 1H) 6.78-6.80 (m, 2H) 7.27 (d, J=8.64 Hz, 2H) 7.32 (d, J=8.35 Hz, 1H) 8.10 (d, J=8.35 Hz, 1H). LC/MS Method: Column=Acquity UPLC BEH C18, 1.7 μm, 2.1×100 mm; Solvent A=95:5 water: acetonitrile with 0.1% formic acid; Solvent B=5:95 water: acetonitrile with 0.1% formic acid; Gradient method (minutes/% B)=0/0, 3.5/100, 4.5/100; Flow Rate=0.8 mL/min; Injection Volume=5.00 μL; Wavelength=220 and 254 nm. LC/MS Result: Retention time=2.48 min; m/z=558.1 $[M+H]^+$.

Step 2: Preparation of N-(7-amino-4-chloro-1-(2-((3R,5S)-3,5-difluoropiperidin-1-yl)ethyl)-1H-indazol-3-yl)-N-(4-methoxybenzyl)methanesulfonamide

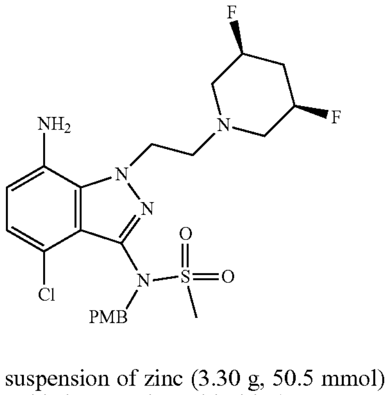

To a stirred suspension of zinc (3.30 g, 50.5 mmol) in THF (50 mL) was added ammonium chloride (2.70 g, 50.5 mmol) and water (50 mL) followed by a solution of N-(4-chloro-1-(2-((3R,5S)-3,5-difluoropiperidin-1-yl)ethyl)-7-nitro-1H-indazol-3-yl)-N-(4-methoxybenzyl)methanesulfonamide (2.80 g, 5.05 mmol) in THF (50 mL). The reaction mixture was stirred for 30 min at 21° C. The reaction mixture was filtered through a celite pad and the filtrate was concentrated under reduced pressure. The resulting residue was subjected to silica gel column chromatography eluting with a gradient of 0-100% ethyl acetate in hexanes over 10 column volumes, followed by 100% ethyl acetate for 5 column volumes, to afford N-(7-amino-4-chloro-1-(2-((3R,5S)-3,5-difluoropiperidin-1-yl)ethyl)-1H-indazol-3-yl)-N-(4-methoxybenzyl) methanesulfonamide (1.20 g, 2.27 mmol, yield=45%). 1H NMR (500 MHz, METHANOL-d4) δ ppm 1.92 (br dd, J=12.07, 5.81 Hz, 1H) 2.42-2.63 (m, 3H) 2.86 (br t, J=4.92 Hz, 2H) 3.13 (s, 3H) 3.73 (s, 3H) 4.40-4.48 (m, 1H) 4.51-4.66 (m, 3H) 4.75-4.84 (m, 4H) 6.62 (d, J=7.75 Hz, 1H) 6.75-6.82 (m, 2H) 6.89 (d, J=7.75 Hz, 1H) 7.21-7.25 (m, 2H). LC/MS Method: Column=Acquity UPLC BEH C18, 1.7 μm, 2.1×100 mm; Solvent A=95:5 water:acetonitrile with 0.1% formic acid; Solvent B=5:95 water:acetonitrile with 0.1% formic acid; Gradient method (minutes/% B)=not specified, but ends at 4.5 minutes with a gradient time of 3.5 minutes; Flow Rate=0.8 mL/min; Injection Volume=5.00 μL; Wavelength=220 and 254 nm. LC/MS Result: Retention time=2.18 min; m/z=528.2 $[M+H]^+$.

Preparation of N-(7-amino-4-chloro-1-(3-methoxypropyl)-1H-indazol-3-yl)-N-(4-methoxybenzyl) methanesulfonamide

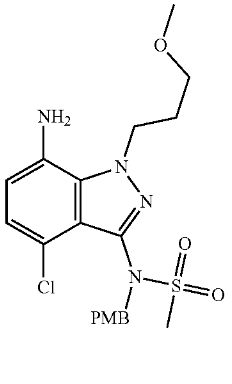

Synthetic Scheme

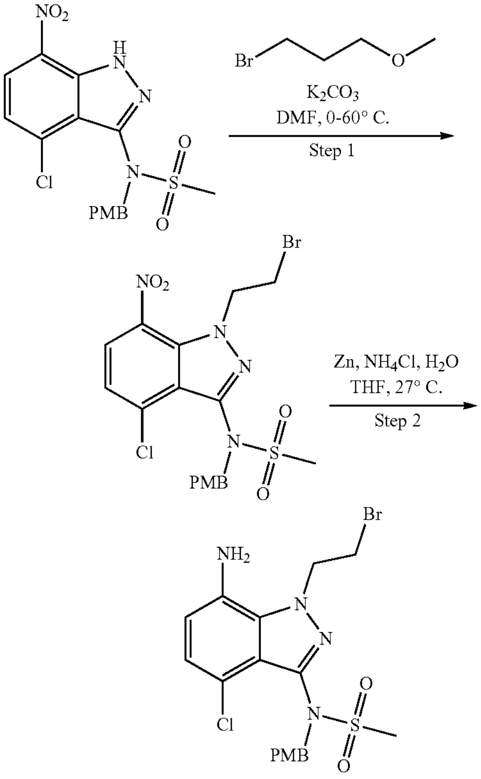

Step 1: Preparation of N-(4-chloro-1-(3-methoxypropyl)-7-nitro-1H-indazol-3-yl)-N-(4-methoxybenzyl)methanesulfonamide

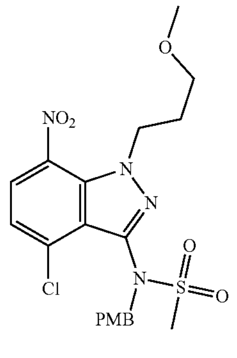

To a stirred solution of N-(4-chloro-7-nitro-1H-indazol-3-yl)-N-(4-methoxybenzyl)methanesulfonamide (3.00 g, 7.23 mmol) in N,N-dimethylformamide (30 mL) at 0° C. was added potassium carbonate (3.00 g, 21.7 mmol) and 1-bromo-3-methoxypropane (1.66 g, 10.8 mmol). The reaction mixture was stirred at 60° C. for 3 h under a nitrogen atmosphere. The progress of the reaction was monitored by TLC and LC/MS. The reaction mixture was diluted with ethyl acetate (40 mL) and washed with ice-cold water (3×50 mL). The organic layer was washed with brine (50 mL), dried over anhydrous sodium sulfate, filtered, and the filtrate was concentrated under reduced pressure. The resulting residue was subjected to silica gel column chromatography eluting with 15-25% ethyl acetate in petroleum ether to afford N-(4-chloro-1-(3-methoxypropyl)-7-nitro-1H-indazol-3-yl)-N-(4-methoxybenzyl)methanesulfonamide (3.20 g, 6.63 mmol, yield=92%) as a pale yellow solid. LC/MS Method: Column=Acquity BEH C18 (50 mm×2.1 mm, 1.7 μm); Mobile Phase A=0.05% formic acid in water; Mobile Phase B=0.05% formic acid in acetonitrile; Gradient=3% B at 0 min, 3% B at 0.4 min, 98% B at 2.5 min, 98% B at 3.4 min, 3% B at 3.5 min, 3% B at 4 min; Column Temperature=35° C.; Flow Rate=0.6 mL/min. LC/MS result: Retention time=2.15 min; m/z=483.1 $[M+H]^+$; Purity=98%.

Step 2: Preparation of N-(7-amino-4-chloro-1-(3-methoxypropyl)-1H-indazol-3-yl)-N-(4-methoxybenzyl)methanesulfonamide

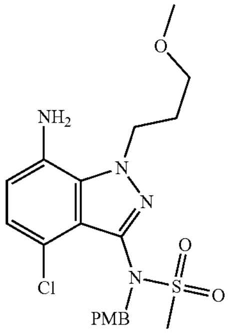

To a stirred solution of zinc (271 g, 4.14 mol) in THF (2.00 L) and water (2.00 L) was added ammonium chloride (222 g, 4.14 mol) at 27° C. Then to the mixture was added over 10 min at 27° C. a solution of N-(4-chloro-1-(3-methoxypropyl)-7-nitro-1H-indazol-3-yl)-N-(4-methoxybenzyl) methanesulfonamide (200 g, 414 mmol) in THF (4.00 L). The reaction mixture was stirred for 3 h. The mixture was diluted with ethyl acetate (3.00 L) and water (2.00 L), then filtered through a celite pad. The filter cake was washed with ethyl acetate (1.00 L). The organic layer was separated and washed with brine (2.00 L). The combined organic layers were dried over anhydrous sodium sulfate, filtered, and the filtrate was concentrated under reduced pressure to afford the crude residue as a brown gummy liquid (200 g). The crude residue was subjected to flash column chromatography on silica gel (100-200 mesh), eluting with 60-70% ethyl acetate in petroleum ether to afford N-(7-amino-4-chloro-1-(3-methoxypropyl)-1H-indazol-3-yl)-N-(4-methoxybenzyl) methanesulfonamide (165 g, 346 mmol, yield=84%) as a brown gummy solid. LC/MS Method: Column=Acquity BEH C18 (50 mm×2.1 mm, 1.7 μm); Mobile Phase A=0.05% formic acid in water; Mobile Phase B=0.05% formic acid in acetonitrile; Gradient=3% B at 0 min, 3% B at 0.4 min, 98% B at 3.2 min, 98% B at 3.8 min, 3% B at 4.2 min, 3% B at 4.5 min; Column Temperature=35° C.; Flow Rate=0.6 mL/min. LC/MS result: Retention time=2.75 min; m/z=453.2 $[M+H]^+$; Purity=96%.

Preparation of tert-butyl 2-(7-amino-4-chloro-3-(N-(4-methoxybenzyl)methylsulfonamido)-1H-indazol-1-yl)acetate

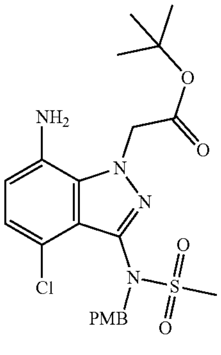

Synthetic Scheme

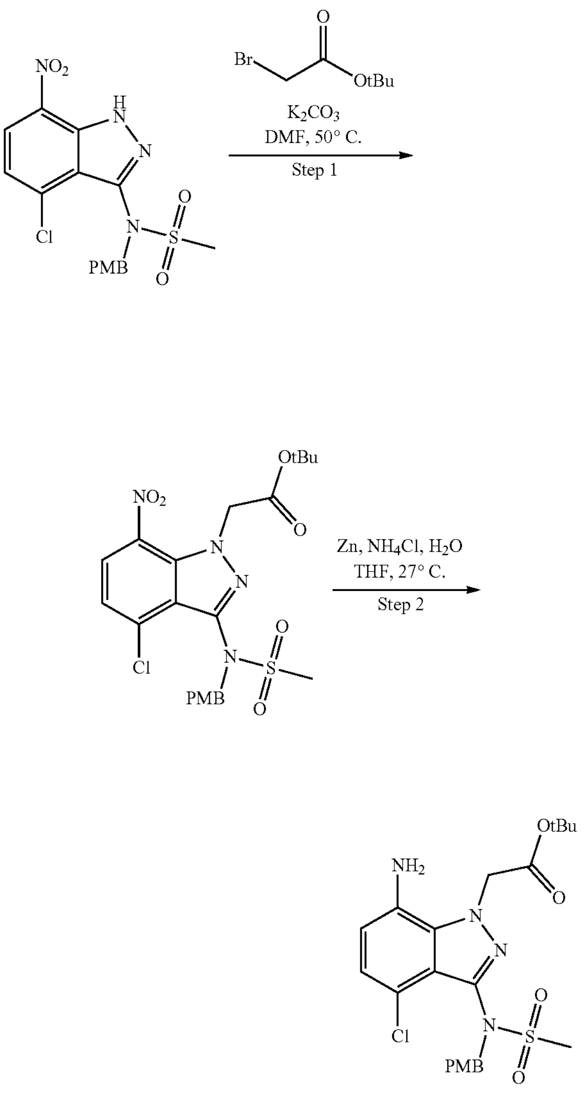

Step 1: Preparation of tert-butyl 2-(4-chloro-3-(N-(4-methoxybenzyl)methylsulfonamido)-7-nitro-1H-indazol-1-yl)acetate

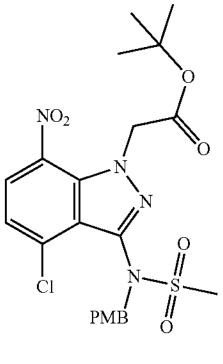

To a stirred solution of N-(4-chloro-7-nitro-1H-indazol-3-yl)-N-(4-methoxybenzyl)methanesulfonamide (500 mg, 1.22 mmol) in N,N-dimethylformamide (3 mL) was added potassium carbonate (505 mg, 3.65 mmol) and tert-butyl 2-bromoacetate (270 μL, 1.83 mmol). The reaction mixture was heated to 50° C. and stirred for 2 h under a nitrogen atmosphere. Reaction progress was monitored by TLC (mobile phase: 40% ethyl acetate in hexanes; $R_f$=0.5, UV active). Upon completion of the reaction, the reaction mixture was diluted with ice-cold water (10 mL). A solid precipitate formed, which was collected by filtration and dried under reduced pressure to afford tert-butyl 2-(4-chloro-3—(N-(4-methoxybenzyl)methylsulfonamido)-7-nitro-1H-indazol-1-yl)acetate (500 mg, 0.932 mmol, yield=77%) as an off-white solid which was used directly in the next step. LC/MS Method: Column=Acquity BEH C18 (100 mm×2.1 mm, 1.7 μm particles); Solvent A=0.05% formic acid in water; Solvent B=0.05% formic acid in acetonitrile; Gradient method (minutes/% B)=0/3, 0.4/3, 2.5/98, 3.4/98, 3.5/3, 4/3; Column Temperature=35° C.; Flow Rate=0.6 mL/min. LC/MS Result: Retention time=2.36 min; m/z=525.0 $[M+H]^+$; Purity=98%.

Step 2: Preparation of tert-butyl2-(7-amino-4-chloro-3-(N-(4-methoxybenzyl)methylsulfonamido)-1H-indazol-1-yl)acetate

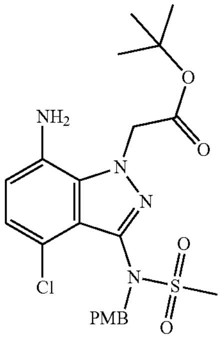

To a stirred suspension of zinc (3.24 g, 49.5 mmol) in THF (20.0 mL) was added a solution of ammonium chloride (2.65 g, 49.5 mmol) in water (20.0 mL) at ambient temperature. To the stirring suspension was added a solution of tert-butyl2-(4-chloro-3-(N-(4-methoxybenzyl)methylsulfonamido)-7-nitro-1H-indazol-1-yl)acetate (2.60 g, 4.95 mmol) in THF (10 mL). The reaction mixture was stirred at ambient temperature for 18 h, then filtered through a medium-frit glass filter. The organic phase of the biphasic filtrate was isolated and then washed with brine, dried over anhydrous magnesium sulfate, filtered, and the resulting filtrate was concentrated under reduced pressure to afford the crude product. The crude product was subjected to silica gel column chromatography (80 g RediSep Gold silica gel column) eluting with 0-100% ethyl acetate in hexanes to afford tert-butyl2-(7-amino-4-chloro-3-(N-(4-methoxybenzyl)methylsulfonamido)-1H-indazol-1-yl)acetate (2.08 g, 4.18 mmol, yield=85%) as a light brown foam. $^1$H NMR (500 MHz, DMSO-$d_6$) δ ppm 1.33 (s, 9H) 3.06 (s, 3H) 3.69 (s, 3H) 4.67-4.87 (m, 2H) 5.21 (s, 2H) 5.25-5.46 (m, 2H) 6.59 (d, J=7.75 Hz, 1H) 6.78 (d, J=8.64 Hz, 2H) 6.89 (d, J=7.75 Hz, 1H) 7.15-7.23 (m, 2H).

Preparation of N-(7-amino-4-chloro-1-(2-cyclopropoxyethyl)-1H-indazol-3-yl)-N-(4-methoxybenzyl)methanesulfonamide

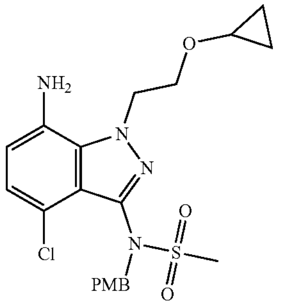

Synthetic Scheme

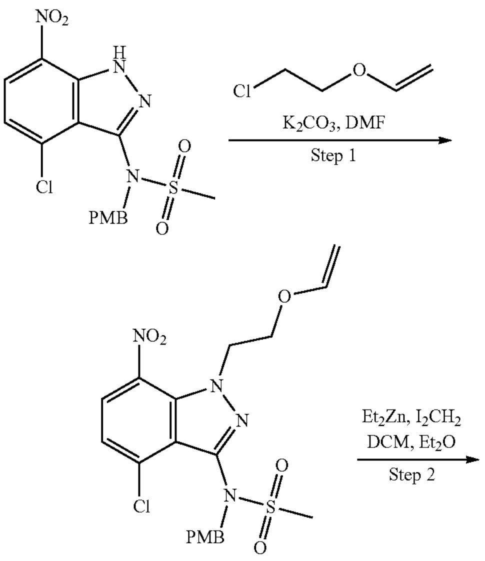

-continued

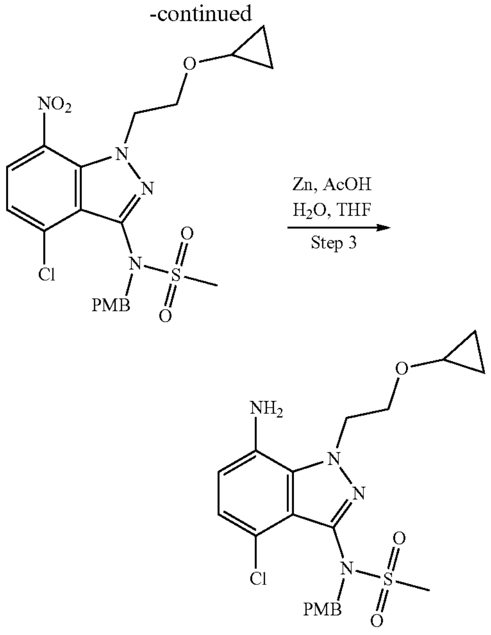

Step 1: Preparation of N-(4-chloro-7-nitro-1-(2-(vinyloxy)ethyl)-1H-indazol-3-yl)-N-(4-methoxybenzyl)methanesulfonamide

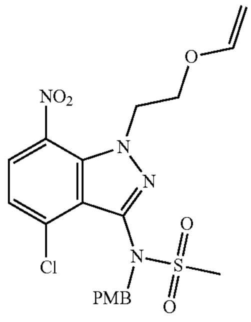

To a stirred solution of N-(4-chloro-7-nitro-1H-indazol-3-yl)-N-(4-methoxybenzyl)methanesulfonamide (10.0 g, 23.6 mmol) in N,N-dimethylformamide (150 mL) at 27° C. was added potassium carbonate (9.79 g, 70.8 mmol) and (2-chloroethoxy)ethene (4.80 mL, 47.2 mmol). The reaction mixture was heated to 60° C. and was stirred for 12 h under a nitrogen atmosphere. The progress of the reaction was monitored by TLC (mobile phase: 50% ethyl acetate in petroleum ether; $R_f$=0.3, UV active) and LC/MS. Upon completion of the reaction, the reaction mixture was diluted with ethyl acetate (200 mL) and washed with ice-cold water (3×250 mL). The organic layer was dried over anhydrous sodium sulfate, filtered, and the filtrate was concentrated under reduced pressure to afford crude product (11 g) as a yellow gummy solid which was subjected to silica gel column chromatography eluting with 40-45% ethyl acetate in petroleum ether to afford N-(4-chloro-7-nitro-1-(2-(vinyloxy)ethyl)-1H-indazol-3-yl)-N-(4-methoxybenzyl)methanesulfonamide (10.0 g, yield=88%) as a yellow gummy solid.

Step 2: Preparation of N-(4-chloro-1-(2-cyclopropoxyethyl)-7-nitro-1H-indazol-3-yl)-N-(4-methoxybenzyl)methanesulfonamide

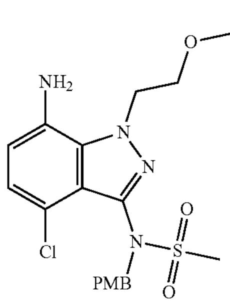

To a stirred solution of N-(4-chloro-7-nitro-1-(2-(vinyloxy)ethyl)-1H-indazol-3-yl)-N-(4-methoxybenzyl)methanesulfonamide (1.00 g, 2.08 mmol) in diethyl ether (15 mL) and dichloromethane (15 mL) under a nitrogen atmosphere at −78° C. was added diethylzinc (16.0 mL, 16.0 mmol). The mixture was stirred for 2 h, then to the mixture was added diiodomethane (8.0 mL, 99 mmol). The reaction mixture was allowed to warm to 27° C. with stirring for 5 h. Upon completion of the reaction, the reaction mixture was quenched with 1N aqueous HCl (40 mL) and extracted with ethyl acetate (2×50 mL). The combined organics were dried over anhydrous sodium sulfate, filtered, and the filtrate was concentrated under reduced pressure to afford crude product (800 mg) which was subjected to silica gel column chromatography eluting with 30-35% ethyl acetate in petroleum ether to afford N-(4-chloro-1-(2-cyclopropoxyethyl)-7-nitro-1H-indazol-3-yl)-N-(4-methoxybenzyl)methanesulfonamide (500 mg, yield=49%) as a brown gummy solid.

Step 3: Preparation of N-(7-amino-4-chloro-1-(2-cyclopropoxyethyl)-1H-indazol-3-yl)-N-(4-methoxybenzyl)methanesulfonamide

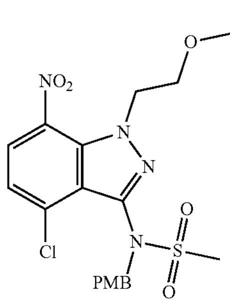

To a stirred solution of N-(4-chloro-1-(2-cyclopropoxyethyl)-7-nitro-1H-indazol-3-yl)-N-(4-methoxybenzyl)methanesulfonamide (4.20 g, 8.48 mmol) in THF (100 mL) and water (50 mL) at 0° C. was added zinc (3.50 g, 53.5 mmol). Acetic acid (5.25 mL, 91.8 mmol) was then added dropwise. The reaction mixture was allowed to warm to 27° C. with stirring for 30 min. Upon completion of the reaction, the reaction mixture was filtered through a celite pad, and the filter cake was extracted with ethyl acetate. The filtrate was concentrated under reduced pressure and the resulting residue was diluted with saturated aqueous sodium bicarbonate (80 mL) and extracted with ethyl acetate (2×120 mL). The combined organics were washed with brine (50 mL), dried over anhydrous sodium sulfate, filtered, and the filtrate was concentrated under reduced pressure to afford crude product (4.0 g) as a brown gummy solid which was subjected to silica gel column chromatography eluting with 50-60% ethyl acetate in petroleum ether to afford N-(7-amino-4-chloro-1-(2-cyclopropoxyethyl)-1H-indazol-3-yl)-N-(4-methoxybenzyl)methanesulfonamide (2.80 g, yield=67%) as a brown gummy solid.

Preparation of N-(7-amino-4-chloro-1-(2-(2,2,6,6-tetramethylmorpholino)ethyl)-1H-indazol-3-yl)-N-(4-methoxybenzyl)methanesulfonamide

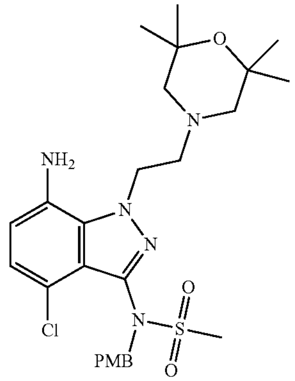

Step 1: Preparation of N-(4-chloro-7-nitro-1-(2-(2,2,6,6-tetramethylmorpholino)ethyl)-1H-indazol-3-yl)-N-(4-methoxybenzyl)methanesulfonamide

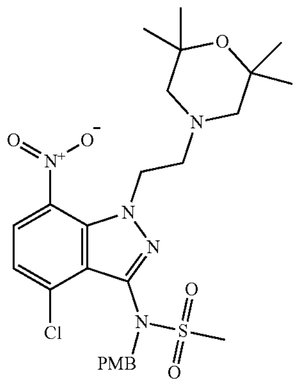

To a stirred solution of N-(1-(2-bromoethyl)-4-chloro-7-nitro-1H-indazol-3-yl)-N-(4-methoxybenzyl)methanesulfonamide (1.00 g, 1.93 mmol) and 2,2,6,6-tetramethylmorpholine (459 mg, 3.21 mmol) in N,N-dimethylformamide (12 mL) at 0° C. was added sodium iodide (58 mg, 0.386 mmol) and potassium carbonate (801 mg, 5.79 mmol). The reaction mixture was allowed to warm to 27° C. with stirring for 16 h under a nitrogen atmosphere. The progress of the reaction was monitored by TLC (mobile phase: 30% ethyl acetate in petroleum ether; $R^f$=0.3, UV active). Upon completion of the reaction, the reaction mixture was diluted with ethyl acetate (400 mL) and washed with ice-cold water (2×180 mL) and brine (2×150 mL). The organic layer was dried over Na2SO4, filtered, and the filtrate was concentrated under reduced pressure to afford the title compound (1.32 g) as a yellow liquid which was used directly in the next step. LC/MS analysis: Retention time=5.41 min; m/z=580 $[M+H]^+$; Purity=75%. LC/MS Method: Column=YMC Triart C18, 1.9 μm, 2.1×50 mm; Solvent A=0.05% formic acid in water; Solvent B=0.05% formic acid in acetonitrile; Gradient method (minutes/% B)=0/3, 0.4/3, 7.5/98, 9.5/98, 9.6/3, 10/3; Flow rate=0.6 mL/min; Column Temperature=50° C.

Step 2: Preparation of N-(7-amino-4-chloro-1-(2-(2,2,6,6-tetramethylmorpholino)ethyl)-1H-indazol-3-yl)-N-(4-methoxybenzyl)methanesulfonamide

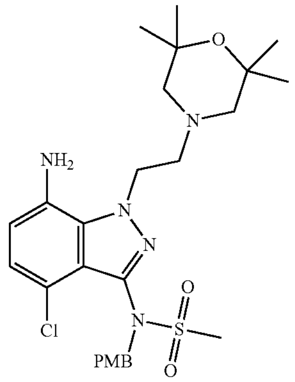

To a stirred suspension of zinc (7.52 g, 115 mmol) in THF (40 mL) and water (80 mL) at 27° C. was added $NH_4Cl$ (6.15 g, 115 mmol). To this mixture was added dropwise a solution of N-(4-chloro-7-nitro-1-(2-(2,2,6,6-tetramethylmorpholino)ethyl)-1H-indazol-3-yl)-N-(4-methoxybenzyl) methanesulfonamide (5.00 g, 8.61 mmol) in THF (80 mL). The reaction mixture was stirred at 27° C. for 1 h. The mixture was diluted with ethyl acetate (500 mL) and water (300 mL) were added, and the resulting mixture was stirred for 15 min at 27° C. The mixture was filtered through a celite pad, and the filter cake was extracted with ethyl acetate (200 mL). The organic layer of the filtrate was separated, and the aqueous layer was extracted with ethyl acetate (500 mL). The combined organics were washed with brine (370 mL), dried over $Na_2SO_4$, filtered, and the filtrate was concentrated under reduced pressure. The resulting residue was subjected to reverse-phase flash column chromatography on a RediSep Gold C18 column (275 g) eluting with 60-80% acetonitrile in water. The acetonitrile was removed from the combined pure fractions under reduced pressure and the resulting aqueous mixture was extracted with ethyl acetate (500 mL). The combined organics were washed with brine (200 mL), dried over $Na_2SO_4$, filtered, and the filtrate was concentrated under reduced pressure to afford N-(7-amino-4-chloro-1-(2-(2,2,6,6-tetramethylmorpholino)ethyl)-1H-indazol-3-yl)-N-(4-methoxybenzyl)methanesulfonamide (3.10 g, yield=65%).

Preparation of N-(4-chloro-1-((R)-2-((3R,5S)-3,5-difluoropiperidin-1-yl)propyl)-7-nitro-1H-indazol-3-yl)-N-(4-methoxybenzyl)methanesulfonamide

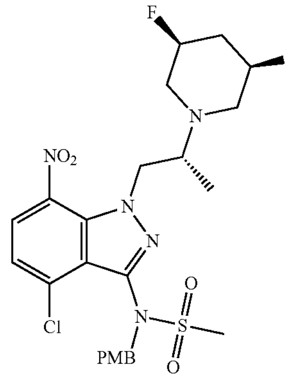

To a stirred solution of N-(4-chloro-7-nitro-1H-indazol-3-yl)-N-(4-methoxybenzyl)methanesulfonamide (1.50 g, 3.54 mmol) and (S)-2-((3R,5S)-3,5-difluoropiperidin-1-yl)propan-1-ol (952 mg, 5.31 mmol) in THF (15 mL) at 0° C. was added triphenylphosphine (1.39 g, 5.31 mmol) and di-tert-butyl azodicarboxylate (1.22 g, 5.31 mmol). The reaction mixture was allowed to warm to 27° C. under a nitrogen atmosphere with stirring for 16 h. The reaction mixture was quenched by the addition of cold water (80 mL) and the resulting mixture was extracted with ethyl acetate (3×60 mL). The combined organics were washed with brine (60 mL), dried over $Na_2SO_4$, filtered, and the filtrate was concentrated under reduced pressure. The resulting residue was subjected to silica gel column chromatography eluting with 0-20% ethyl acetate in petroleum ether to afford N-(4-chloro-1-((R)-2-((3R,5S)-3,5-difluoropiperidin-1-yl)propyl)-7-nitro-1H-indazol-3-yl)-N-(4-methoxybenzyl)methanesulfonamide (1.30 g, yield=64%) as a pale yellow semi-solid. LC/MS analysis: Retention time=2.45 min; m/z=571.21 $[M+H]^+$. LC/MS Method: Column=YMC Triart C18, 1.9 μm, 2.1×50 mm; Solvent A=0.05% formic acid in water; Solvent B=0.05% formic acid in acetonitrile; Gradient method (minutes/% B)=0/3, 0.4/3, 2.5/98, 3.4/98, 3.5/3, 4.5/3; Flow rate=0.6 mL/min; Column Temperature=50° C.

Preparation of N-(4-chloro-1-((S)-1-((3R,5S)-3,5-difluoropiperidin-1-yl)propan-2-yl)-7-nitro-1H-indazol-3-yl)-N-(4-methoxybenzyl)methanesulfonamide

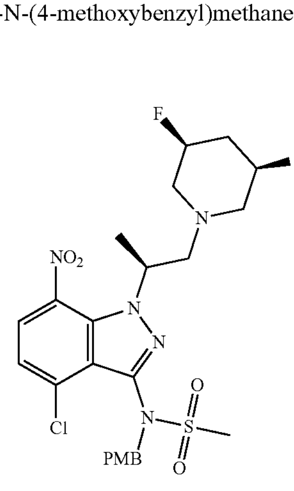

To a stirred solution of N-(4-chloro-7-nitro-1H-indazol-3-yl)-N-(4-methoxybenzyl)methanesulfonamide (1.80 g, 4.25 mmol) and (R)-1-((3R,5S)-3,5-difluoropiperidin-1-yl)propan-2-ol (1.14 g, 6.37 mmol) in THF (20 mL) and toluene (20 mL) at 0° C. was added triphenylphosphine (3.34 g, 12.8 mmol) and di-tert-butyl azodicarboxylate (2.94 g, 12.8 mmol). The reaction mixture was allowed to warm to 27° C. with stirring for 1 h under a nitrogen atmosphere. The reaction mixture was diluted with water and extracted with ethyl acetate (3×100 mL). The combined organics were washed with brine (100 mL), dried over $Na_2SO_4$, filtered, and the filtrate was concentrated under reduced pressure to afford crude product as a yellow semi-solid. The crude product was subjected to silica gel column chromatography eluting with 10-25% ethyl acetate in petroleum ether and the resulting product was further purified by reverse-phase flash column chromatography on a RediSep Gold C18 column (475 g) eluting with 50-65% MeCN (containing 0.1% TFA) in water (containing 0.1% TFA) to afford N-(4-chloro-1-((S)-1-((3R,5S)-3,5-difluoropiperidin-1-yl)propan-2-yl)-7-nitro-1H-indazol-3-yl)-N-(4-methoxybenzyl)methanesulfonamide (140 mg, yield=45%) as a yellow solid. LC/MS analysis: Retention time=2.68 min; m/z=572.24 $[M+H]^+$; Purity=96%. Chiral analysis: Retention time=5.25 min; Purity=87%. LC/MS Method: Column=ACQUITY UPLC BEH C18, 1.7 μm, 2.1×50 mm; Solvent C=0.05% formic acid in water; Solvent D=0.05% formic acid in acetonitrile; Gradient method (minutes/% D)=0.4/3, 2.5/98, 3.4/98, 3.5/3, 4.2/3; Column Temperature=40° C.; Flow rate=0.6 mL/min.

Preparation of ethyl 2-(3-cyclopropyl-3b,4,4a,5-tetrahydro-1H-cyclopropa[3,4]cyclopenta[1,2-c]pyrazol-1-yl)acetate Synthetic Scheme

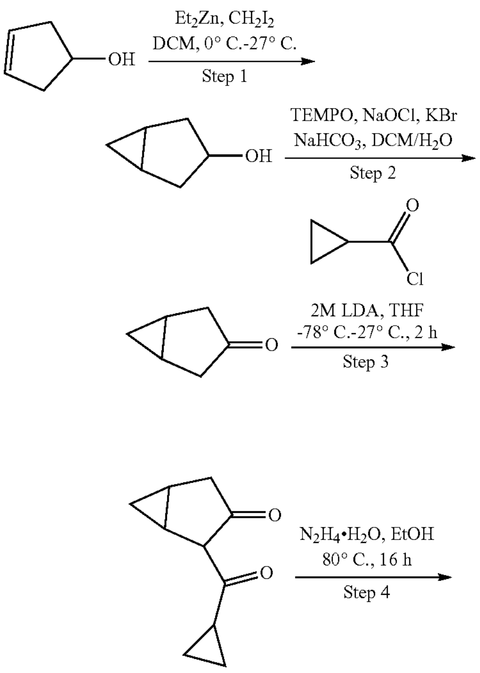

-continued

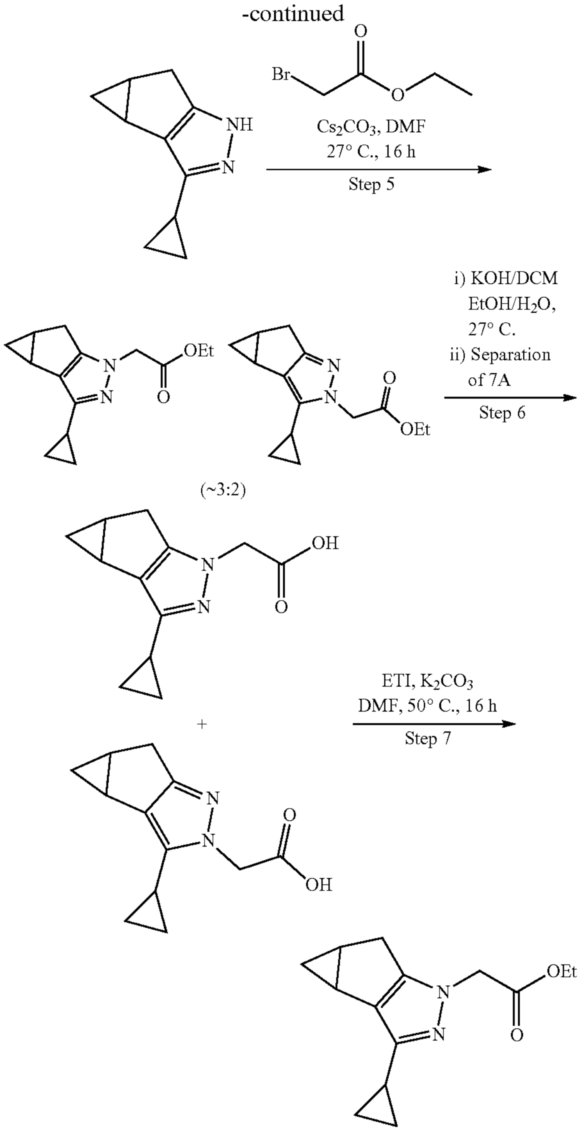

Step 1: Preparation of Bicyclo[3.1.0]hexan-3-ol

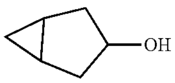

To a stirred solution of cyclopent-3-enol (250 g, 2972 mmol) in DCM (500 mL) at 0° C. to 5° C. under nitrogen atmosphere was added diethylzinc(1.0 M in hexane, 5.94 L, 5944 mmol) dropwise over 3 h. The reaction mass was stirred for 1 h, then it was added a solution of diiodomethane (0.480 L, 5944 mmol) in DCM (2 L) dropwise over 1 h. On completion of addition, the reaction mass was turned into white suspension. The reaction mixture was slowly allowed to warm to 27° C. and stirred for 18 hrs under nitrogen atmosphere. The progress of the reaction was monitored by TLC ($SiO_2$, 20% EtOAc/Pet-ether Rf=0.3). On completion, the reaction mass was slowly poured into ice cold saturated aq. $NH_4Cl$ (5 L) and stirred for 30 min. The white precipitate was appeared, it was filtered through a pad of celite and washed with DCM (500 mL). The organic layer was separated and aqueous layer was extracted with DCM (500 mL). The combined organics were dried over anhydrous $Na_2SO_4$ and filtered. The filtrate was concentrated at 27° C. (200 mbr) to afford bicyclo[3.1.0]hexan-3-ol (250 g, Yield: 81%) as reddish sticky liquid. The product was used directly in the next step without further purification. $^1$H-NMR (400 MHz, $CDCl_3$) δ: 4.39-4.37 (m, 1H), 2.13-2.07 (m, 2H), 1.73 (d, J=14.0 Hz, 2H), 1.31-1.26 (m, 2H), 1.14 (d, J=2.4 Hz, 1H), 0.56-0.48 (m, 2H). GCMS: retention time=4.12 mins.; observed ion=98.2 [M]; GCMS Purity=95%.

Step 2: Preparation of Bicyclo[3.1.0]hexan-3-one

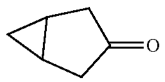

To a stirred solution of bicyclo[3.1.0]hexan-3-ol (240 g, 2445 mmol) in DCM (2.5 L) and water (1.22 L) were added sequentially sodium bicarbonate (288 g, 3424 mmol), potassium bromide (36.4 g, 306 mmol) and 2,2,6,6-tetramethylpiperidine-N-oxyl ("TEMPO", 15.28 g, 98 mmol) at 0° C. The reaction mixture was stirred for 15 min, then it was added sodium hypochlorite (12% in water, 1.937 L, 3766 mmol) by dropwise over 2 hrs at 0° C. The reaction mixture was stirred for 1 h at 0° C. The progress of the reaction was monitored by TLC ($SiO_2$, 20% EtOAc/Pet-ether Rf=0.4). On completion, the reaction mixture was filtered and washed with DCM (200 mL). From the filtrate, the organic layer was separated and washed with 15% of aq. $Na_2S_2O_3$ solution (3x300 mL). The organic layer was further washed with water (300 mL) and brine (300 mL), dried over anhydrous $Na_2SO_4$ and filtered. The filtrate was concentrated under reduced pressure at 27° C. to afford bicyclo[3.1.0]hexan-3-one (235 g, Yield: 90%) as reddish liquid. The product was used directly in the next step without further purification. $^1$H-NMR (400 MHz, $CDCl_3$) δ: 2.64-2.56 (m, 2H), 2.20-2.13 (m, 2H), 1.56-1.49 (m, 2H), 0.95-0.88 (m, 1H), 0.02-07 (m, 1H). GCMS: retention time=3.816 mins.; observed ion=96.1 [M]; GCMS Purity=91%.

Step 3: Preparation of 2-(Cyclopropanecarbonyl) bicyclo[3.1.0]hexan-3-one

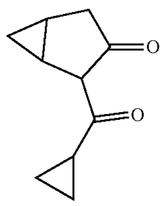 [SMILES: O=C1CC2CC2C1C(=O)C1CC1]

To a stirred solution of bicyclo[3.1.0]hexan-3-one (380 g, 3953 mmol) in THF (1500 mL) was added lithium diisopropylamide (2 M in THF, 2174 mL, 4348 mmol) at −78° C. under nitrogen atmosphere. The reaction mass was stirred for 30 minutes at −78° C., then it was added slowly a solution of cyclopropanecarbonyl chloride (395 mL, 4348 mmol) in THF (150 mL). The reaction mass was stirred at −78° C. for 1 h and then allowed to warm to 27° C. and stirred for 2 hrs. The progress of the reaction was monitored by TLC ($SiO_2$, 10% EtOAc/Pet-ether Rf=0.4). On completion, the reaction mass was quenched with 1N HCl (2.5 L) and extracted with EtOAc (2×3 L). The combined organics were washed with brine solution (2 L), dried over anhydrous $Na_2SO_4$, filtered, and then concentrated under reduced pressure to get crude compound (350 g) which was purified by silica gel chromatography eluting with 1-2% EtOAc/Pet-ether The fractions containing the desired product were pooled and concentrated under reduced pressure to afford 2-(cyclopropanecarbonyl)bicyclo[3.1.0]hexan-3-one (250 g, Yield: 30%) as brown liquid. LCMS: retention time=1.93 mins; observed ion=165.17 (M+H); LCMS Purity=61%. The product was used directly in the next step.

Step 4: Preparation of 3-Cyclopropyl-3b,4,4a,5-tetrahydro-1H-cyclopropa[3,4]cyclopenta[1,2-c]pyrazole

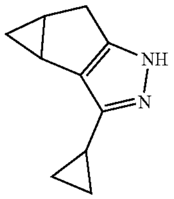 [SMILES: C1CC1c1n[nH]c2c1C1CC1C2]

To a stirred solution of 2-(cyclopropanecarbonyl)bicyclo[3.1.0]hexan-3-one (125 g, 761 mmol) in EtOH (1250 mL) were added hydrazine hydrate (29.3 mL, 933 mmol) and sulfuric acid (16.23 mL, 304 mmol) at 27° C. under nitrogen atmosphere. The reaction mass was stirred at 80° C. for 16 hrs. The progress of the reaction was monitored by TLC ($SiO_2$, 50% EtOAc/Pet-ether Rf=0.2). On completion, the reaction mass was allowed to cool to room temperature and concentrated under reduced pressure. The residue was diluted with EtOAc (2 L) and washed with saturated aqueous $NaHCO_3$ (1 L). The aqueous layer was extracted with EtOAc (500 mL). The combined organics were washed with brine (500 mL), dried over anhydrous $Na_2SO_4$, filtered, and then concentrated under reduced pressure to get crude compound (150 g) which was purified by silica gel chromatography eluting with 30-40% EtOAc/Pet-ether The fractions containing the desired product were pooled and concentrated under reduced pressure to afford 3-cyclopropyl-3b,4,4a,5-tetrahydro-1H-cyclopropa[3,4]cyclopenta[1,2-c]pyrazole (120 g, Yield: 96%) as yellow solid. $^1$H-NMR (400 MHz, $CDCl_3$) δ: 2.89 (dd, J=16.4, 6.4 Hz, 1H), 2.67 (d, J=16.4 Hz, 1H), 1.98-1.87 (m, 2H), 1.84-1.78 (m, 1H), 1.04-0.99 (m, 1H), 0.97-0.90 (m, 2H), 0.83-0.77 (m, 2H), 0.18-0.15 (m, 1H).

Step 5: Preparation of Ethyl 2-(3-cyclopropyl-3b,4,4a,5-tetrahydro-1H-cyclopropa[3,4]cyclopenta[1,2-c]pyrazol-1-yl)acetate

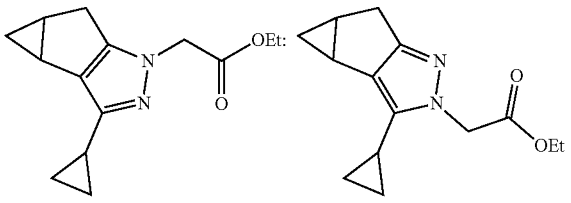

(~3:2)

To a stirred solution of 3-cyclopropyl-3b,4,4a,5-tetrahydro-1H-cyclopropa[3,4]cyclopenta[1,2-c]pyrazole (120 g, 674 mmol) in DMF (1.2 L) was added $Cs_2CO_3$ (439 g, 1348 mmol) and ethyl 2-bromoacetate (89 mL, 809 mmol) at 27° C. under nitrogen atmosphere. The reaction mass was stirred at 27° C. for 16 hrs. The progress of the reaction was monitored by TLC ($SiO_2$, 30% EtOAc/Pet-ether Rf=0.5). On completion, the reaction mass was diluted with EtOAc (250 mL) and washed with ice cold water (2×300 mL). The aqueous layer was extracted with EtOAc (2×200 mL). The combined organics were washed with brine (200 mL) and dried over anhydrous $Na_2SO_4$, filtered, and then concentrated under reduced pressure to get crude compound which was purified by silica gel chromatography eluting with 40-50% EtOAc/Pet-ether The fractions containing the desired product were pooled and concentrated under reduced pressure to afford the 3:2 mixture of ethyl 2-(3-cyclopropyl-3b,4,4a,5-tetrahydro-1H-cyclopropa[3,4]cyclopenta[1,2-c]pyrazol-1-yl)acetate and ethyl 2-(3-cyclopropyl-3b,4,4a,5-tetrahydro-2H-cyclopropa[3,4]cyclopenta[1,2-c]pyrazol-2-yl)acetate (110 g, Yield: 54%) as pale yellow liquid. The product was used directly in the next step without further purification.

Step 6: Preparation of 2-(3-Cyclopropyl-3b,4,4a,5-tetrahydro-1H-cyclopropa[3,4]cyclopenta[1,2-c]pyrazol-1-yl)acetic acid

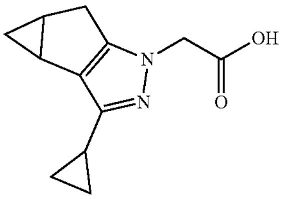 [SMILES: O=C(O)Cn1nc(C2CC2)c2c1CC1CC21]

To a stirred solution of ethyl 2-(3-cyclopropyl-3b,4,4a,5-tetrahydro-1H-cyclopropa[3,4]cyclopenta[1,2-c]pyrazol-1-yl)acetate (100 g, 333 mmol) in EtOH (200 mL) and DCM (1400 mL) was added 50% aqueous KOH (100 mL, 333 mmol) at 27° C. The reaction mass was stirred at 27° C. for 16 hrs. The progress of the reaction was monitored by TLC ($SiO_2$, 10% MeOH/DCM, Rf=0.1). On completion, the reaction mass was diluted with water (350 mL) and stirred for 10 min. The organic layer was separated and the aqueous layer was cooled to 0° C. The pH of aqueous layer was adjusted to pH 2-3 via the addition of 2 N HCl (~200 mL). The resulting precipitate was collected via filtration and was washed with n-hexane (200 mL), and then dried to obtain the crude compound (50 g, LCMS: 57% of 7A & 41% of 7B) as pale yellow solid. The aqueous filtrate contained majorly the desired isomer 7A which was extracted with 10% MeOH/DCM (4×500 mL). The combined organics were dried over anhydrous $Na_2SO_4$, filtered, and then concentrated under reduced pressure to obtain the crude compound (28 g, LCMS: 76% of 7A & 8% of 7B) as pale brown gummy liquid. The crude material (50 g, LCMS: 57% of 7A & 41% of 7B) was further purified by reverse phase column chromatography using the following method: Column=RediSep Rf Gold C18 column (275 g), Mobile Phase: A: 0.5% TFA in water/ACN (95:5); B: 0.5% TFA in ACN/water (95:5), Flow rate=50 mL/min, Load per purification=4 g; The reverse phase separation produced the desired isomer (peak-1, first peak to elute) pure fractions were collected and concentrated under reduced pressure to obtain an off-white solid which was triturated with $Et_2O$ (30 mL) and dried to afford 2-(3-cyclopropyl-3b,4,4a,5-tetrahydro-1H-cyclopropa[3,4]cyclopenta[1,2-c]pyrazol-1-yl)acetic acid (28 g, Yield: 53%) as an off-white solid. Similarly, the other crude material (28 g, LCMS: 76% of 7A & 8% of 7B) was also further purified by repeating the above described reverse phase column chromatography to afford the desired isomer, 2-(3-cyclopropyl-3b,4,4a,5-tetrahydro-1H-cyclopropa[3,4]cyclopenta[1,2-c]pyrazol-1-yl)acetic acid (18 g, Yield: 84%) as an off-white solid. $^1H$-NMR (400 MHz, DMSO-$d_6$) δ: 4.60 (s, 2H), 2.68 (dd, J=16.4, 6.4 Hz, 1H), 2.58 (d, J=16.8, 1H), 1.97-1.91 (m, 1H), 1.86-1.82 (m, 1H), 1.77-1.73 (m, 1H), 0.96-0.91 (m, 1H), 0.85-0.81 (m, 2H), 0.69-0.65 (m, 2H), 0.04-0.02 (m, 1H).

Step 7: Preparation of ethyl 2-(3-cyclopropyl-3b,4,4a,5-tetrahydro-1H-cyclopropa[3,4]cyclopenta[1,2-c]pyrazol-1-yl)acetate

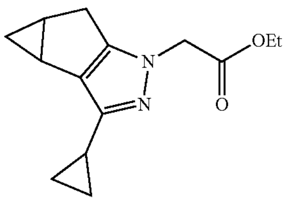 [SMILES: CCOC(=O)Cn1nc(C2CC2)c2c1CC1CC21]

To a stirred solution of 2-(3-cyclopropyl-3b,4,4a,5-tetrahydro-1H-cyclopropa[3,4]cyclopenta[1,2-c]pyrazol-1-yl) acetic acid (40.5 g, 184 mmol) in DMF (400 mL) was added $K_2CO_3$ (102 g, 735 mmol) and ethyl iodide (29.7 mL, 367 mmol) at 27° C. The reaction mass was stirred at 50° C. for 16 hrs. The progress of the reaction was monitored by TLC ($SiO_2$, 30% MeOH/DCM, Rf=0.3). On completion, the reaction mass was diluted with water (100 mL) and extracted with EtOAc (3×200 mL). The combined organics were dried over anhydrous $Na_2SO_4$, filtered, and then concentrated under reduced pressure to afford ethyl 2-(3-cyclopropyl-3b,4,4a,5-tetrahydro-1H-cyclopropa[3,4]cyclopenta[1,2-c]pyrazol-1-yl)acetate (38 g, Yield: 80%) as brown gummy liquid. The product was used directly in the next step without further purification. $^1H$-NMR (400 MHz, $CDCl_3$) δ: 4.60 (q, J=17.4 Hz, 2H), 4.19 (q, J=7.2 Hz, 2H), 2.80 (dd, J=16.4, 6.4 Hz, 1H), 2.61 (d, J=16.8 Hz, 1H), 1.89-1.85 (m, 3H), 1.26 (t, J=7.2 Hz, 3H), 0.98-0.79 (m, 5H), 0.21-0.19 (m, 1H).

Preparation of 2-((3bS,4aS)-3-cyclopropyl-3b,4,4a,5-tetrahydro-1H-cyclopropa[3,4]cyclopenta[1,2-c]pyrazol-1-yl)acetic acid and 2-((3bR,4aR)-3-cyclopropyl-3b,4,4a,5-tetrahydro-1H-cyclopropa[3,4]cyclopenta[1,2-c]pyrazol-1-yl)acetic Acid Synthetic Scheme

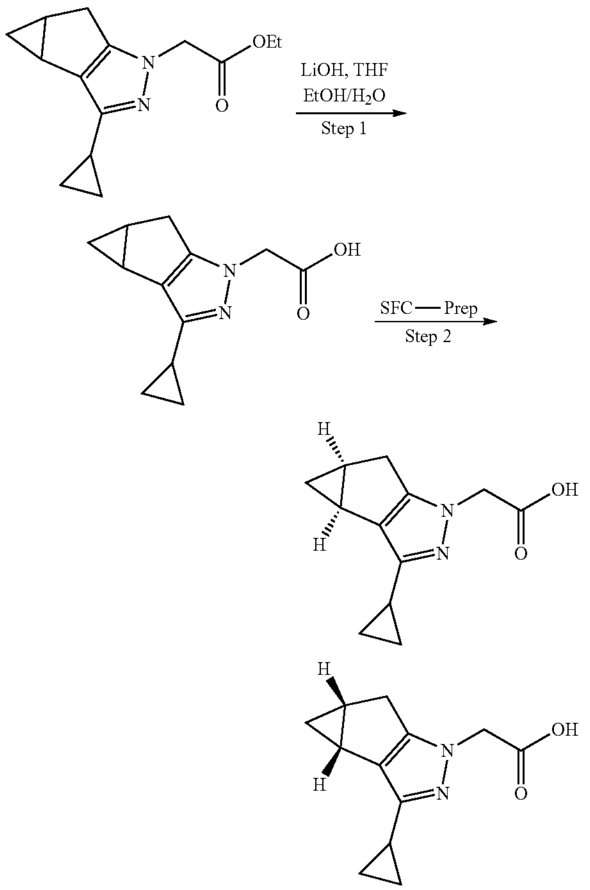

Step 1 & 2: Preparation of 2-((3bS,4aS)-3-cyclopropyl-3b,4,4a,5-tetrahydro-1H-cyclopropa[3,4]cyclopenta[1,2-c]pyrazol-1-yl)acetic acid and 2-((3bR,4aR)-3-cyclopropyl-3b,4,4a,5-tetrahydro-1H-cyclopropa[3,4]cyclopenta[1,2-c]pyrazol-1-yl)acetic Acid

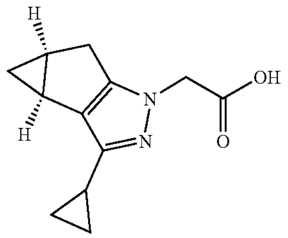

and

-continued

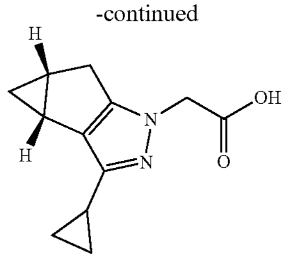

To a stirred solution of ethyl 2-(3-cyclopropyl-3b,4,4a,5-tetrahydro-1H-cyclopropa[3,4]cyclopenta[1,2-c]pyrazol-1-yl)acetate (4 g, 16.24 mmol) in Ethanol (6 mL) and THF (36 mL) was added a solution of lithium hydroxide (0.389 g, 16.24 mmol) in water (6 mL) at 27° C. under nitrogen atmosphere. The reaction mass was stirred at 27° C. for 12 hrs. The progress of the reaction was monitored by TLC ($SiO_2$, 10% MeOH/DCM, Rf=0.1). On completion, the reaction mass was concentrated under reduced pressure. The aqueous residue pH was adjust to 2-3 pH via addition of 1N HCl and extracted with EtOAc (2×100 mL). The combined organics were washed with brine (30 mL), dried over anhydrous $Na_2SO_4$, filtered, and then concentrated under reduced pressure to crude product (2.5 g, HPLC purity: 92%) which was dissolved in EtOH (10 mL) and heated at 50° C. for 30 min, then allowed to cooled to 25° C., and it was allowed to recrystallization for 16 hrs. The obtained solid was filtered and dried under vacuum to obtain the pure product (1.5 g, HPLC purity: 98%) as off-white solid. This material was dissolved in Methanol (50 mL) and was then purified by prep-SFC using the following method: Column=Chiralpak IC (250×30×5μ; eluent=$CO_2$: 0.5% Triethylamine in Methanol (70:30); Flow-rate=100 g/min; Back-pressure=100 bar; Detection=214 nm (UV); Stack time=10.1 min; Load per injection=53 mg. The SFC separation produced two peaks which were collected separately. The pure peak-1 (first peak to elute) fractions were concentrated under reduced pressure to afford 2-((3bS,4aS)-3-cyclopropyl-3b,4,4a,5-tetrahydro-1H-cyclopropa[3,4]cyclopenta[1,2-c]pyrazol-1-yl)acetic acid (0.811 g, Yield: 43%) as pale yellow sticky liquid. The product is a triethylamine salt. $^1$H-NMR (400 MHz, $CDC_3$) δ: 4.56 (d, J=17.4 Hz, 1H), 4.47 (d, J=17.4 Hz, 1H), 3.01 (q, J=7.4 Hz, 3H, $Et_3N$), 2.83-2.78 (m, 1H), 2.61 (d, J=16.1 Hz, 1H), 1.88-1.84 (m, 3H), 1.23 (t, J=7.4 Hz, 5H, $Et_3N$), 0.96-0.78 (m, 5H), 0.21-0.19 (m, 1H). LCMS: retention time=1.51 mins; observed ion=219.16 (M+H); LCMS Purity=99%; UPLC Purity=99%, Chiral HPLC Purity=99%. Similarly, the pure peak-2 (second peak to elute) fractions were concentrated under reduced pressure to afford 2-((3bR,4aR)-3-cyclopropyl-3b,4,4a,5-tetrahydro-1H-cyclopropa[3,4]cyclopenta[1,2-c]pyrazol-1-yl) acetic acid (0.7093 g, Yield: 37%) as pale yellow sticky liquid. The product is a triethylamine salt. $^1$H-NMR (400 MHz, $CDCl_3$) δ: 4.56 (d, J=17.4 Hz, 1H), 4.47 (d, J=17.4 Hz, 1H), 3.01 (q, J=7.4 Hz, 3H, $Et_3N$), 2.83-2.78 (m, 1H), 2.61 (d, J=16.1 Hz, 1H), 1.88-1.84 (m, 3H), 1.23 (t, J=7.4 Hz, 5H, $Et_3N$), 0.96-0.78 (m, 5H), 0.21-0.19 (m, 1H). LCMS Method J: retention time=1.51 mins; observed ion=219.16 (M+H); LCMS Purity=98%; UPLC Purity=98%, Chiral HPLC Purity=99%.

Preparation of (S)-N-(7-(2-(1-amino-2-(3,5-difluorophenyl)ethyl)-5-chloro-7-(4,4-difluorocyclohexyl)-4-oxopyrido[2,3-d]pyrimidin-3(4H)-yl)-4-chloro-1-(3-methoxypropyl)-1H-indazol-3-yl) methanesulfonamide Synthetic Scheme

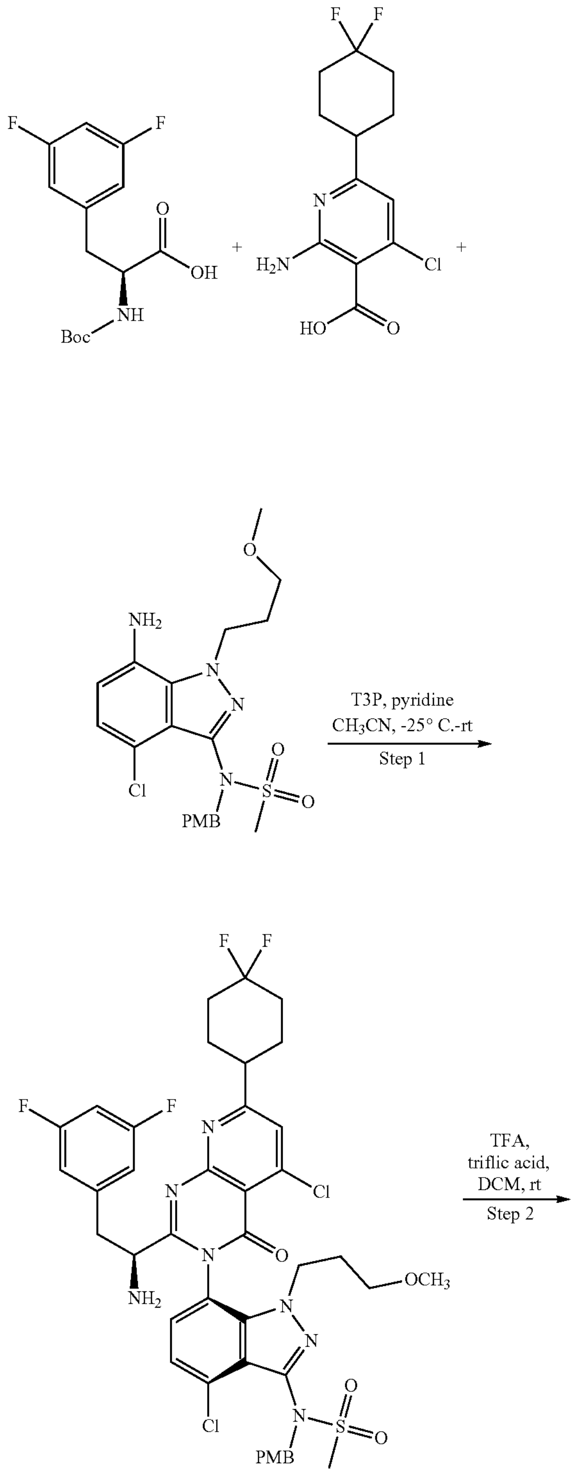

-continued

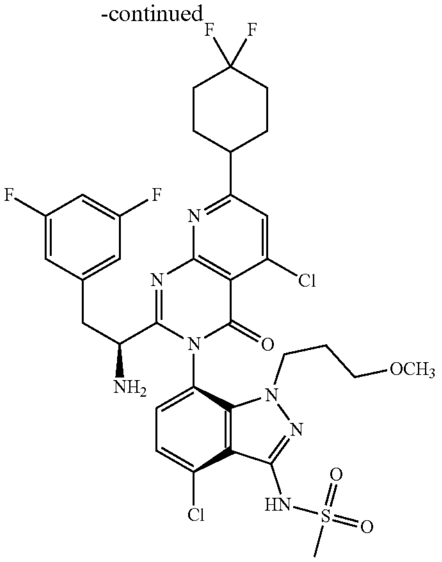

Step 1: Preparation of (S)-N-(7-(2-(1-amino-2-(3,5-difluorophenyl)ethyl)-5-chloro-7-(4,4-difluorocyclohexyl)-4-oxopyrido[2,3-d]pyrimidin-3(4H)-yl)-4-chloro-1-(3-methoxypropyl)-1H-indazol-3-yl)-N-(4-methoxybenzyl)methanesulfonamide

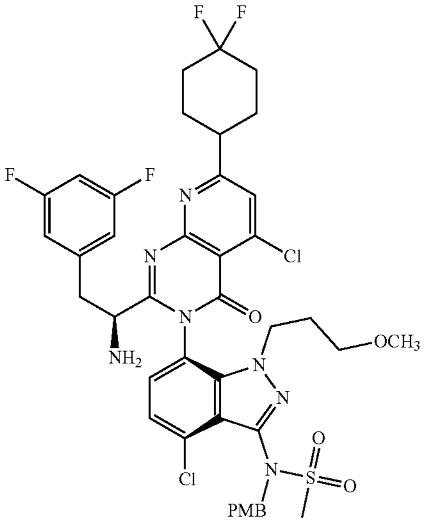

To a stirred suspension of (S)-2-((tert-butoxycarbonyl)amino)-3-(3,5-difluorophenyl)propanoic acid (1098 mg, 3.64 mmol) and 2-amino-4-chloro-6-(4,4-difluorocyclohexyl)nicotinic acid (1059 mg, 3.64 mmol) in acetonitrile (50 mL) at −25° C. was added pyridine (2.14 mL, 26.5 mmol) followed by T3P (50% wt. in ethyl acetate, 9.86 mL, 16.6 mmol). The reaction mixture was allowed to warm to 12° C. over 3 h with stirring. To the mixture was added N-(7-amino-4-chloro-1-(3-methoxypropyl)-1H-indazol-3-yl)-N-(4-methoxybenzyl)methanesulfonamide (1500 mg, 3.31 mmol) was added and the mixture was then stirred for 18 h while warming to rt (the suspension became a clear solution overnight). The solution was diluted with ethyl acetate (100 mL) and washed with 1N NaOH (25 mL), then 0.5M citric acid (25 mL), and then water (25 mL). The organic layer was dried over anhydrous sodium sulfate, filtered, and the filtrate was concentrated under reduced pressure. The resulting residue was subjected to silica gel column chromatography (40 g silica gel), eluting with 5-80% ethyl acetate in hexanes to afford tert-butyl(S)-(1-(5-chloro-3-(4-chloro-3-(N-(4-methoxybenzyl)methylsulfonamido)-1-(3-methoxypropyl)-1H-indazol-7-yl)-7-(4,4-difluorocyclohexyl)-4-oxo-3,4-dihydropyrido[2,3-d]pyrimidin-2-yl)-2-(3,5-difluorophenyl)ethyl)carbamate (1.1 g, 1.1 mmol, yield=34%), a mixture of atropisomers, as a white solid. LC/MS Method: Column=Acquity UPLC BEH C18, 2.1×100 mm, 1.7 μm particles; Solvent A=0.1% formic acid in 95:5 water:acetonitrile; Solvent B=0.1% formic acid in 5:95 water:acetonitrile; Flow Rate=0.8 mL/min; Start % B=0; Final % B=100; Gradient Time=3.5 min, then a 1 min hold at 100% B; Wavelength=220 and 254 nm. LC/MS result: Retention time=3.76 min; m/z=990.1 $[M+H]^+$.

Step 2: Preparation of (S)-N-(7-(2-(1-amino-2-(3,5-difluorophenyl)ethyl)-5-chloro-7-(4,4-difluorocyclohexyl)-4-oxopyrido[2,3-d]pyrimidin-3(4H)-yl)-4-chloro-1-(3-methoxypropyl)-1H-indazol-3-yl)methanesulfonamide

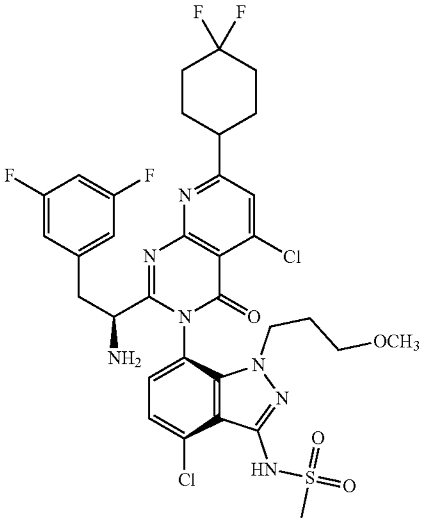

To a stirred solution of tert-butyl (1 S)-1-(5-chloro-3-(4-chloro-3-(N-(4-methoxybenzyl)methylsulfonamido)-1-(3-methoxypropyl)-1H-indazol-7-yl)-7-(4,4-difluorocyclohexyl)-4-oxo-3,4-dihydropyrido[2,3-d]pyrimidin-2-yl)-2-(3,5-difluorophenyl)ethylcarbamate (1.1 g, 1.1 mmol) in dichloromethane (10 mL) and trifluoroacetic acid (2.5 mL) was added trifluoromethanesulfonic acid (296 μL, 3.3 mmol). The resulting dark red solution was stirred at room temperature for 1 h. LCMS analysis indicated completion of the reaction. The reaction mixture was concentrated under reduced pressure, dissolved in ethyl acetate (100 mL), and washed with 1N aqueous sodium hydroxide solution (25 mL). The organic layer was separated, dried over anhydrous sodium sulfate, filtered, and the filtrate was concentrated under reduced pressure. The resulting residue was subjected to reversed-phase column chromatography (50 g C18 silica gel), eluting with 10-60% acetonitrile in water (containing 0.1% formic acid) over 25 min. Fractions containing the second-eluting, major atropisomer were combined, and acetonitrile was removed under reduced pressure. The aqueous layer was basified to pH 8 using 1N aqueous sodium hydroxide solution and then was extracted with ethyl acetate. The organic layer was washed with brine, dried over anhydrous sodium sulfate, filtered, and the filtrate was concentrated under reduced pressure to afford the desired product, the major atropisomer, (S)-N-(7-(2-(1-amino-2-(3,5-difluorophenyl)ethyl)-5-chloro-7-(4,4-difluorocyclohexyl)-4-oxopyrido[2,3-d]pyrimidin-3(4H)-yl)-4-chloro-1-(3-methoxypropyl)-1H-indazol-3-yl)methanesulfonamide (470 mg, yield=55%) as a single atropisomer. LC/MS Method: Column=Acquity UPLC BEH C18 (2.1×100 mm, 1.7 micron particles); Solvent A=water:MeCN (95:5) w/0.1% formic acid; Solvent B=water:MeCN (5:95) w/0.1% formic acid; Flow Rate=0.8 mL/min; Start % B=0; Final % B=100; Gradient Time=3.5 min, then a 1.0 min hold at 100% B; Wavelength=220 nm and 254 nm. LC/MS result: Retention time=2.36 min; m/z=770 $[M+H]^+$.

Preparation of N-(7-(2-((S)-1-amino-2-(3,5-difluorophenyl)ethyl)-7-(4,4-difluorocyclohexyl)-5-methyl-4-oxopyrido[2,3-d]pyrimidin-3(4H)-yl)-1-(2-bromoethyl)-4-chloro-1H-indazol-3-yl)methanesulfonamide Synthetic Scheme

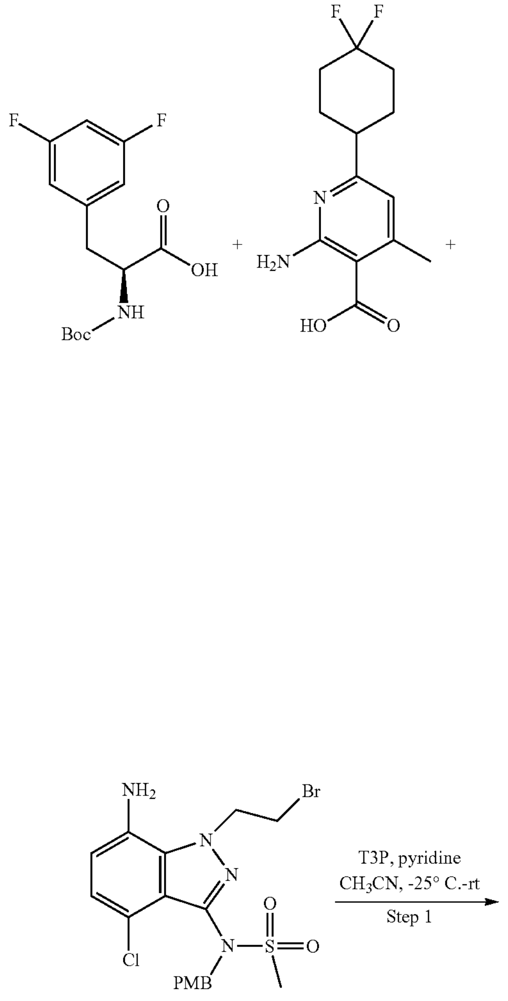

-continued

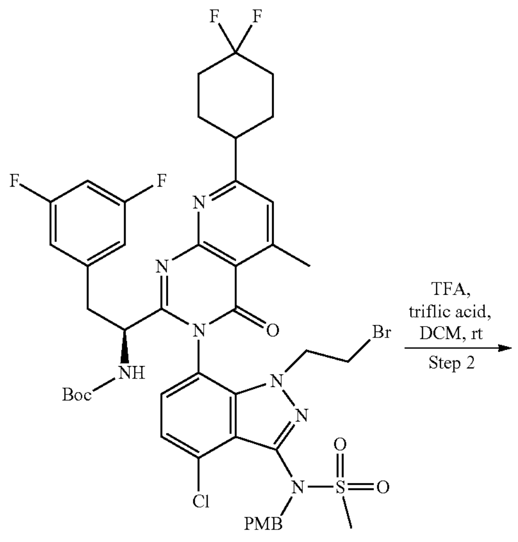

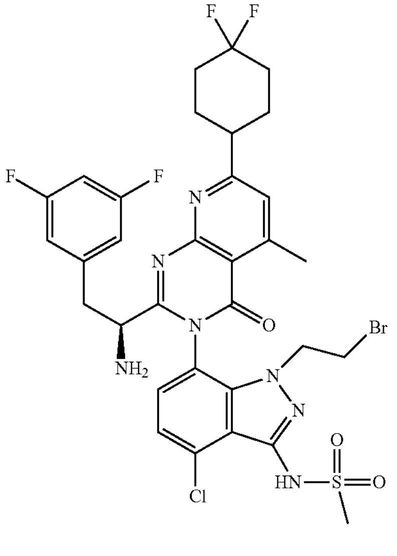

Step 1: Preparation of tert-butyl ((1S)-1-(3-(1-(2-bromoethyl)-4-chloro-3-(N-(4-methoxybenzyl)methylsulfonamido)-1H-indazol-7-yl)-7-(4,4-difluorocyclohexyl)-5-methyl-4-oxo-3,4-dihydropyrido[2,3-d]pyrimidin-2-yl)-2-(3,5-difluorophenyl)ethyl)carbamate

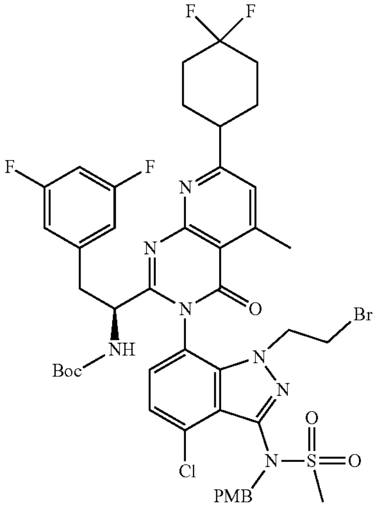

To a suspension of (S)-2-((tert-butoxycarbonyl)amino)-3-(3,5-difluorophenyl)propanoic acid (3.40 g, 1.1 Eq, 11.3 mmol) and 2-amino-6-(4,4-difluorocyclohexyl)-4-methylnicotinic acid (3.05 g, 1.1 Eq, 11.3 mmol) in Acetonitrile (100 mL) at −25° C. was added pyridine (6.49 g, 6.63 mL, 8 Eq, 82.0 mmol) followed by 2,4,6-tripropyl-1,3,5,2,4,6-trioxatriphosphinane 2,4,6-trioxide, T3P 50% in EtOAc (32.6 g, 30.5 mL, 50% Wt, 5 Eq, 51.3 mmol). The reaction mixture was stirred at −25° C. to 12° C. over 3 h and N-(7-amino-1-(2-bromoethyl)-4-chloro-1H-indazol-3-yl)-N-(4-methoxybenzyl)methanesulfonamide (5.0 g, 1 Eq, 10.3 mmol) was added and the mixture was stirred for 18 h while warming to rt (suspension became clear solution overnight). The reaction mixture was diluted with ethyl acetate (100 mL), washed with 1N NaOH (50 mL), 0.5 M citric acid (50 mL), water (50 mL), dried over $Na_2SO_4$ and concentrated. The residue was purified on silica (330 g column) using a gradient of 5-80% ethyl acetate in hexanes. The desired fractions containing the major atropisomer were concentrated to give tert-butyl ((1S)-1-(3-(1-(2-bromoethyl)-4-chloro-3-(N-(4-methoxybenzyl)methylsulfonamido)-1H-indazol-7-yl)-7-(4,4-difluorocyclohexyl)-5-methyl-4-oxo-3,4-dihydropyrido[2,3-d]pyrimidin-2-yl)-2-(3,5-difluorophenyl)ethyl)carbamate (4.9 g, 48% yield)) as an off-white solid. LCMS Method A: retention time=3.61 min.; observed ion=1006.15 (M+H).

Step 2: Preparation of N-(7-(2-((S)-1-amino-2-(3,5-difluorophenyl)ethyl)-7-(4,4-difluorocyclohexyl)-5-methyl-4-oxopyrido[2,3-d]pyrimidin-3(4H)-yl)-1-(2-bromoethyl)-4-chloro-1H-indazol-3-yl)methanesulfonamide

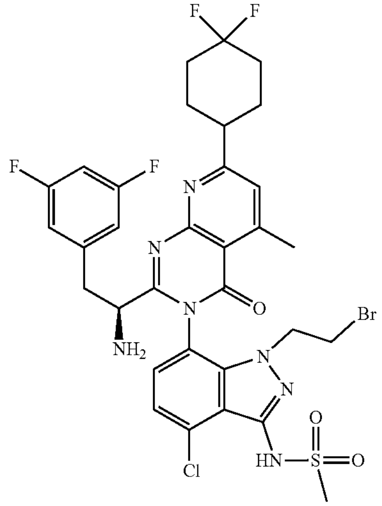 [SMILES: Cc1cc(C2CCC(F)(F)CC2)nc2nc([C@@H](N)Cc3cc(F)cc(F)c3)n(-c3ccc(Cl)c4c(NS(C)(=O)=O)nn(CCBr)c34)c(=O)c12]

Triflic acid (1.8 g, 1.1 mL, 2.5 Eq, 12.1 mmol) was added to a solution of tert-butyl ((1S)-1-(3-(1-(2-bromoethyl)-4-chloro-3-(N-(4-methoxybenzyl)methylsulfonamido)-1H-indazol-7-yl)-7-(4,4-difluorocyclohexyl)-5-methyl-4-oxo-3,4-dihydropyrido[2,3-d]pyrimidin-2-yl)-2-(3,5-difluorophenyl)ethyl)carbamate (4.9 g, 1 Eq, 4.9 mmol) and TFA (22.2 g, 15.0 mL, 40 Eq, 195 mmol) in dichloromethane (30 mL) and the resulting dark red solution was stirred at rt for 1 h. LCMS indicated the reaction was complete. The mixture was concentrated, taken up in EtOAc (200 mL) and washed with 1 N NaOH solution (50 mL). The organic layer was, collected, dried over $Na_2SO_4$, filtered and concentrated to afford N-(7-(2-((S)-1-amino-2-(3,5-difluorophenyl)ethyl)-7-(4,4-difluorocyclohexyl)-5-methyl-4-oxopyrido[2,3-d]pyrimidin-3(4H)-yl)-1-(2-bromoethyl)-4-chloro-1H-indazol-3-yl)methanesulfonamide. The crude was used as is in the next step without further purification. LCMS Method A: retention time=2.42 min.; observed ion=786.05 (M+H).

Preparation of 2-(7-(2-((S)-1-amino-2-(3,5-difluorophenyl)ethyl)-7-(4,4-difluorocyclohexyl)-5-methyl-4-oxopyrido[2,3-d]pyrimidin-3(4H)-yl)-4-chloro-3-(methylsulfonamido)-1H-indazol-1-yl)acetic Acid
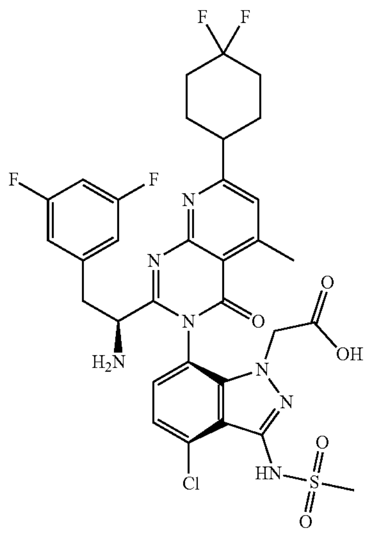
Synthetic Scheme
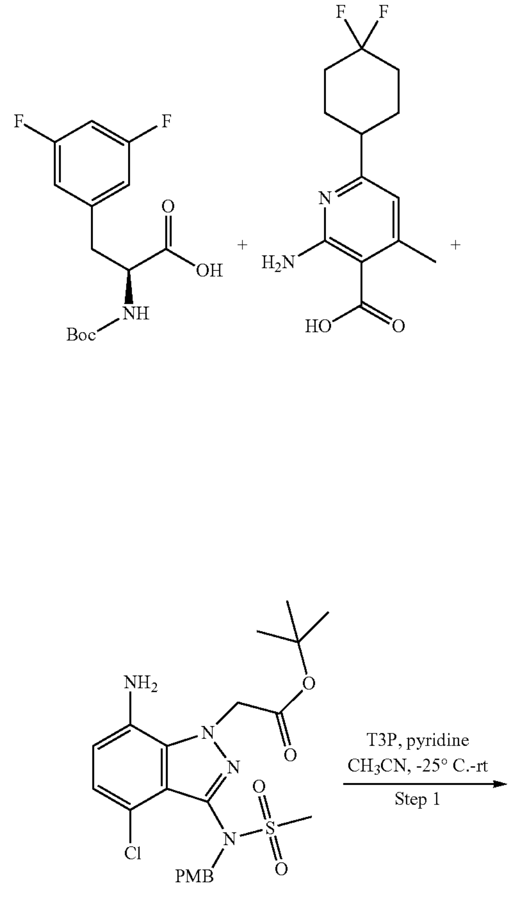
-continued
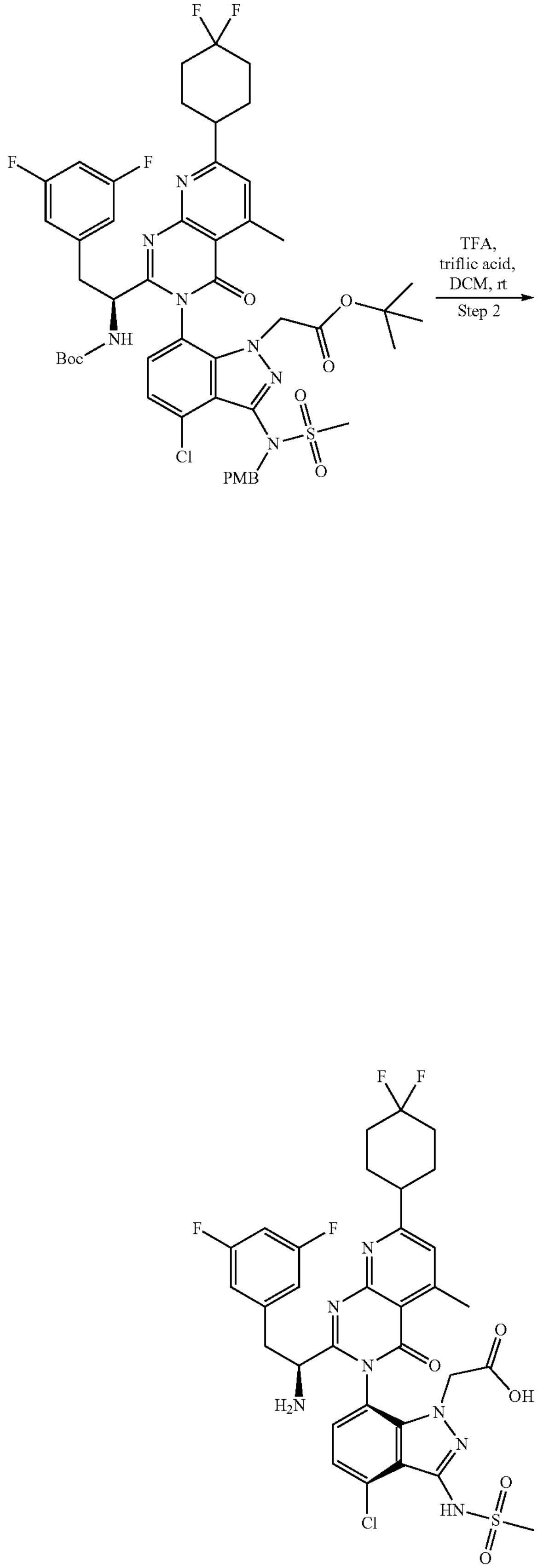

Step 1: Preparation of tert-butyl 2-(7-(2-((S)-1-((tert-butoxycarbonyl)amino)-2-(3,5-difluorophenyl)ethyl)-7-(4,4-difluorocyclohexyl)-5-methyl-4-oxopyrido[2,3-d]pyrimidin-3(4H)-yl)-4-chloro-3-(N-(4-methoxybenzyl)methylsulfonamido)-1H-indazol-1-yl)acetate

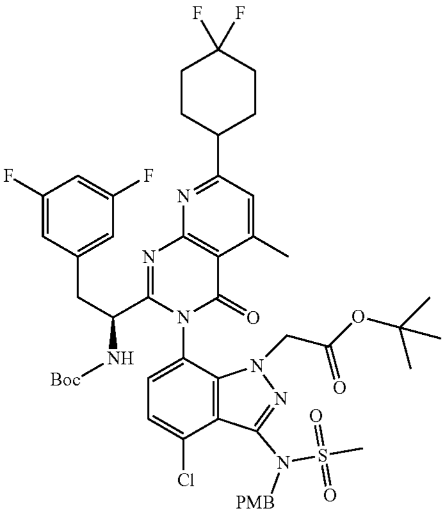

To a stirred suspension of (S)-2-((tert-butoxycarbonyl)amino)-3-(3,5-difluorophenyl)propanoic acid (1.22 g, 4.04 mmol) and 2-amino-6-(4,4-difluorocyclohexyl)-4-methylnicotinic acid (1.09 g, 4.04 mmol) in acetonitrile (25.0 mL) at −25° C. was added pyridine (2.61 mL, 32.3 mmol). To the reaction mixture was added T3P (50 wt. % in ethyl acetate, 12.0 mL, 20.2 mmol). The reaction mixture remained a slurry after the complete addition of T3P. The reaction mixture was allowed to warm slowly to ambient temperature over 2 h, during which time the slurry became a clear brown homogeneous solution. To the reaction mixture was added tert-butyl2-(7-amino-4-chloro-3-(N-(4-methoxybenzyl)methylsulfonamido)-1H-indazol-1-yl)acetate (2.00 g, 4.04 mmol), and the mixture was stirred at ambient temperature for 24 h. The reaction mixture concentrated under reduced pressure. The resulting residue was dissolved in ethyl acetate (60 mL) and washed with 1M aqueous sodium hydroxide (50 mL) and then brine. The organic layer was dried over anhydrous magnesium sulfate, filtered, and the filtrate was concentrated under reduced pressure to afford the crude product. The crude material was subjected to silica gel chromatography (80 g Isco Gold silica gel column), eluting with 15-100% ethyl acetate in hexanes to afford tert-butyl 2-(7-(2-((S)-1-((tert-butoxycarbonyl)amino)-2-(3,5-difluorophenyl)ethyl)-7-(4,4-difluorocyclohexyl)-5-methyl-4-oxopyrido[2,3-d]pyrimidin-3(4H)-yl)-4-chloro-3-(N-(4-methoxybenzyl)methylsulfonamido)-1H-indazol-1-yl)

acetate (2.69 g, 2.66 mmol, yield=66%) as an off-white foam, a mixture of atropisomers.

Step 2: Preparation of 2-(7-(2-((S)-1-amino-2-(3,5-difluorophenyl)ethyl)-7-(4,4-difluorocyclohexyl)-5-methyl-4-oxopyrido[2,3-d]pyrimidin-3(4H)-yl)-4-chloro-3-(methylsulfonamido)-1H-indazol-1-yl)acetic Acid

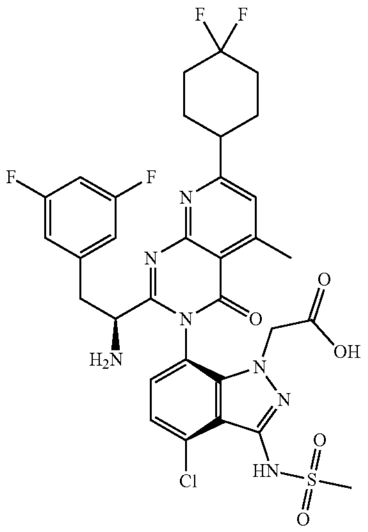

To a stirred solution of tert-butyl 2-(7-(2-((S)-1-((tert-butoxycarbonyl)amino)-2-(3,5-difluorophenyl)ethyl)-7-(4,4-difluorocyclohexyl)-5-methyl-4-oxopyrido[2,3-d]pyrimidin-3(4H)-yl)-4-chloro-3-(N-(4-methoxybenzyl)methylsulfonamido)-1H-indazol-1-yl)acetate (2.69 g, 2.66 mmol) in dichloromethane (10.0 mL) was added TFA (4.1 mL), followed by triflic acid (0.71 mL, 8.0 mmol). The reaction mixture was stirred at ambient temperature for 1 h. LC/MS analysis indicated complete deprotection and the presence of two atropisomers. The reaction mixture was concentrated under reduced pressure. The resulting residue was dissolved in acetonitrile (3 mL) and subjected to reverse-phase flash column chromatography (150 g Isco Gold C18 column), eluting with 15-75% acetonitrile in water (both solvents containing 0.1% formic acid). The desired atropisomer (second eluting peak) was collected and lyophilized to afford 2-((S)-7-(2-((S)-1-amino-2-(3,5-difluorophenyl)ethyl)-7-(4,4-difluorocyclohexyl)-5-methyl-4-oxopyrido[2,3-d]pyrimidin-3(4H)-yl)-4-chloro-3-(methylsulfonamido)-1H-indazol-1-yl)acetic acid (950 mg, 1.29 mmol, yield=49%) as a white solid.

Preparation of tert-butyl ((1S)-1-(7-(1-(2-(benzyloxy)ethyl)-4,4-difluorocyclohexyl)-3-(4-chloro-3-(N-(4-methoxybenzyl)methylsulfonamido)-1-(3-methoxypropyl)-1H-indazol-7-yl)-5-methyl-4-oxo-3,4-dihydropyrido[2,3-d]pyrimidin-2-yl)-2-(3,5-difluorophenyl)ethyl)carbamate

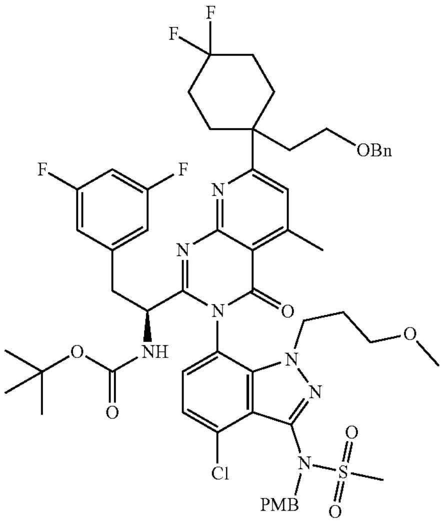

To a stirred suspension of (S)-2-((tert-butoxycarbonyl)amino)-3-(3,5-difluorophenyl)propanoic acid (752 mg, 2.49 mmol) and 2-amino-6-(1-(2-(benzyloxy)ethyl)-4,4-difluorocyclohexyl)-4-methylnicotinic acid (1.01 g, 2.49 mmol) in acetonitrile (25 mL) at −25° C. was added pyridine (1.61 mL, 20.0 mmol) followed by T3P (50 wt. % in ethyl acetate, 7.43 mL, 12.5 mmol). The reaction mixture was allowed to warm to room temperature with stirring over 3 h. To the mixture was added N-(7-amino-4-chloro-1-(3-methoxypropyl)-1H-indazol-3-yl)-N-(4-methoxybenzyl)methanesulfonamide (1.13 g, 2.49 mmol), and the resulting mixture was stirred at room temperature for 18 h. The reaction mixture was concentrated under reduced pressure and the resulting residue was subjected to silica gel column chromatography (80 g RediSep Gold silica gel column) eluting with a gradient of 0-100% ethyl acetate in hexanes over 8 column volumes, followed by 100% ethyl acetate for 3 column volumes, to afford tert-butyl ((1 S)-1-(7-(1-(2-(benzyloxy)ethyl)-4,4-difluorocyclohexyl)-3-(4-chloro-3-(N-(4-methoxybenzyl)methylsulfonamido)-1-(3-methoxypropyl)-1H-indazol-7-yl)-5-methyl-4-oxo-3,4-dihydropyrido[2,3-d]pyrimidin-2-yl)-2-(3,5-difluorophenyl)ethyl)carbamate as a mixture of atropisomers. LC/MS Method: Column=Acquity UPLC BEH C18, 1.7 μm, 2.1×100 mm; Solvent A=95:5 water:acetonitrile with 0.1% formic acid; Solvent B=5:95 water:acetonitrile with 0.1% formic acid; Gradient method (minutes/% B)=0/0, 3.5/100, 4.5/100; Flow Rate=0.8 mL/min; Injection Volume=5.00 μL; Wavelength=220 and 254 nm. LC/MS Result (major atropisomer): Retention time=3.89 min; m/z=1104.35 $[M+H]^+$.

Preparation of N-((S)-7-(2-((S)-1-amino-2-(3,5-difluorophenyl)ethyl)-7-(4,4-difluoro-1-(2-hydroxyethyl)cyclohexyl)-5-methyl-4-oxopyrido[2,3-d]pyrimidin-3(4H)-yl)-4-chloro-1-(3-methoxypropyl)-1H-indazol-3-yl)methanesulfonamide

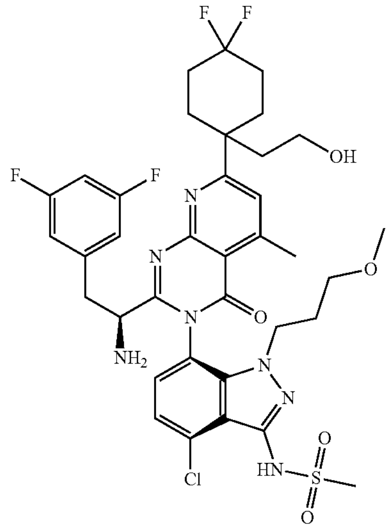

To a stirred solution of tert-butyl ((1S)-1-(7-(1-(2-(benzyloxy)ethyl)-4,4-difluorocyclohexyl)-3-(4-chloro-3-(N-(4-methoxybenzyl)methylsulfonamido)-1-(3-methoxypropyl)-1H-indazol-7-yl)-5-methyl-4-oxo-3,4-dihydropyrido[2,3-d]pyrimidin-2-yl)-2-(3,5-difluorophenyl)ethyl)carbamate (1.86 g, 1.68 mmol) in DCM (16.8 mL) at room temperature was added TFA (5.19 mL, 67.4 mmol) followed by trifluoromethanesulfonic acid (449 μL, 5.05 mmol). The reaction mixture was stirred at room temperature for 1 h. The mixture was concentrated under reduced pressure and the resulting residue was dissolved in ethyl acetate, then was washed with 1 N aqueous NaOH. The organic layer was dried over anhydrous sodium sulfate, filtered, and the filtrate was concentrated under reduced pressure. The resulting residue was subjected to silica gel column chromatography (40 g RediSep Gold silica gel column) eluting with a gradient of 40-100% of a 9:9:2 mixture of ethyl acetate:hexanes:methanol in hexanes over 8 column volumes, followed by 100% of the 9:9:2 mixture for 5 column volumes. This chromatography step separated the atropisomers. The major atropisomer was collected to afford N-((S)-7-(2-((S)-1-amino-2-(3,5-difluorophenyl)ethyl)-7-(4,4-difluoro-1-(2-hydroxyethyl)cyclohexyl)-5-methyl-4-oxo-pyrido[2,3-d]pyrimidin-3(4H)-yl)-4-chloro-1-(3-methoxypropyl)-1H-indazol-3-yl)methanesulfonamide (410 mg, yield=31%). LC/MS Method: Column=Acquity UPLC BEH C18, 1.7 μm, 2.1×100 mm; Solvent A=95:5 water:acetonitrile with 0.1% formic acid; Solvent B=5:95 water:acetonitrile with 0.1% formic acid; Gradient method (minutes/% B)=0/0, 3.5/100, 4.5/100; Flow rate=0.8 mL/min; Injection Volume=5.00 μL; Wavelength=220 and 254 nm. LC/MS Result: Retention time=2.26 min; m/z=794.15 $[M+H]^+$. $^1H$ NMR (500 MHz, METHANOL-$d_4$) δ ppm 1.70-1.85 (m, 3H) 1.88-1.99 (m, 6H) 2.67-2.73 (m, 2H) 2.83-2.86 (m, 7H) 3.12-3.17 (m, 3H) 3.30-3.30 (m, 3H) 3.36-3.40 (m, 2H) 3.59 (dd, J=8.05, 5.07 Hz, 1H) 3.99-4.07 (m, 1H) 4.13-4.20 (m, 1H) 4.58-4.63 (m, 1H) 6.52 (d, J=7.08 Hz, 2H) 6.77 (t, J=8.39 Hz, 1H) 7.09 (d, J=7.75 Hz, 1H) 7.32 (d, J=7.75 Hz, 1H) 7.61 (s, 1H).

Preparation of tert-butyl ((1S)-1-(3-(1-(2-bromoethyl)-4-chloro-3-(N-(4-methoxybenzyl)methylsulfonamido)-1H-indazol-7-yl)-5-chloro-7-(4,4-difluorocyclohexyl)-4-oxo-3,4-dihydropyrido[2,3-d]pyrimidin-2-yl)-2-(3,5-difluorophenyl)ethyl)carbamate

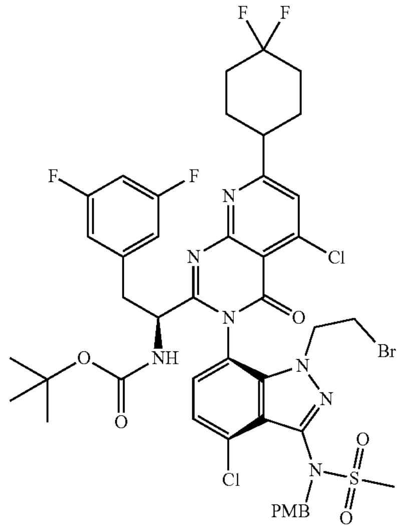

To a stirred suspension of (S)-2-((tert-butoxycarbonyl)amino)-3-(3,5-difluorophenyl)propanoic acid (1.09 g, 3.61 mmol) and 2-amino-4-chloro-6-(4,4-difluorocyclohexyl)nicotinic acid (1.05 g, 3.61 mmol) in acetonitrile (35 mL) at −25° C. was added pyridine (2.12 mL, 26.2 mmol) followed by T3P (50 wt. % in EtOAc, 9.76 mL, 16.4 mmol). The reaction mixture was allowed to warm to 12° C. over 3 h with stirring. To the mixture was added N-(7-amino-1-(2-bromoethyl)-4-chloro-1H-indazol-3-yl)-N-(4-methoxybenzyl)methanesulfonamide (1.60 g, 3.28 mmol) and the resulting mixture was allowed to warm to room temperature with stirring for 18 h. The reaction mixture was diluted with ethyl acetate (50 mL) and washed sequentially with 1N aqueous sodium hydroxide (25 mL), 0.5M aqueous citric acid (25 mL), and water (25 mL). The organic layer was dried over $Na_2SO_4$, filtered, and the filtrate was concentrated under reduced pressure. The resulting residue was subjected to silica gel column chromatography (80 g RediSep Gold silica gel column) eluting with 5-80% ethyl acetate in hexanes which led to separation of the atropisomers and allowed the peak corresponding to the major atropisomer to be collected to afford tert-butyl ((1S)-1-(3-(1-(2-bromoethyl)-4-chloro-3-(N-(4-methoxybenzyl)methylsulfonamido)-1H-indazol-7-yl)-5-chloro-7-(4,4-difluorocyclohexyl)-4-oxo-3,4-dihydropyrido[2,3-d]pyrimidin-2-yl)-2-(3,5-difluorophenyl)ethyl)carbamate (630 mg, yield=19%) as a white solid. LC/MS Method: Column=Acquity UPLC BEH C18, 2.1×100 mm, 1.7 μm particles; Solvent A=0.1% formic acid in 95:5 water:acetonitrile; Solvent B=0.1% formic acid in 5:95 water:acetonitrile; Flow Rate=0.8 mL/min; Gradient method (minutes/% B)=0/0, 3.5/100, 4.5/100; Wavelength=220 and 254 nm. LC/MS Result: Retention time=3.61 min; m/z=1026.00 $[M+H]^+$.

Preparation of N-(7-(2-((S)-1-amino-2-(3,5-difluorophenyl)ethyl)-5-chloro-7-(4,4-difluorocyclohexyl)-4-oxopyrido[2,3-d]pyrimidin-3(4H)-yl)-1-(2-bromoethyl)-4-chloro-1H-indazol-3-yl)methanesulfonamide

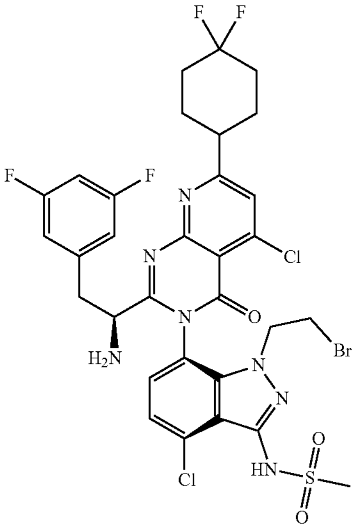

To a stirred solution of tert-butyl ((1S)-1-(3-(1-(2-bromoethyl)-4-chloro-3-(N-(4-methoxybenzyl)methylsulfonamido)-1H-indazol-7-yl)-5-chloro-7-(4,4-difluorocyclohexyl)-4-oxo-3,4-dihydropyrido[2,3-d]pyrimidin-2-yl)-2-(3,5-difluorophenyl)ethyl)carbamate (630 mg, 614 μmol) in dichloromethane (8 mL) and TFA (1.89 mL) was added triflic acid (136 μL, 1.54 mmol). The resulting dark red solution was stirred at room temperature for 1 h and then the reaction mixture was concentrated under reduced pressure. The resulting residue was dissolved in ethyl acetate (50 mL) and washed with 1N aqueous sodium hydroxide (10 mL). The organic layer was dried over $Na_2SO_4$, filtered, and the filtrate was concentrated under reduced pressure to afford N-(7-(2-((S)-1-amino-2-(3,5-difluorophenyl)ethyl)-5-chloro-7-(4,4-difluorocyclohexyl)-4-oxopyrido[2,3-d]pyrimidin-3(4H)-yl)-1-(2-bromoethyl)-4-chloro-1H-indazol-3-yl)methanesulfonamide (390 mg, yield=79%). The product was used directly in a subsequent chemistry step. LC/MS Method: Column=Acquity UPLC BEH C18, 2.1×100 mm, 1.7 μm particles; Solvent A=0.1% formic acid in 95:5 water:acetonitrile; Solvent B=0.1% formic acid in 5:95 water:acetonitrile; Flow Rate=0.8 mL/min; Gradient method (minutes/% B)=0/0, 3.5/100, 4.5/100; Wavelength=220 and 254 nm. LC/MS Result: Retention time=2.44 min; m/z=805.60 $[M+H]^+$.

Preparation of tert-butyl ((1S)-1-(3-(1-(2-bromoethyl)-4-chloro-3-(N-(4-methoxybenzyl)methylsulfonamido)-1H-indazol-7-yl)-5-(tert-butoxymethyl)-7-(4,4-difluorocyclohexyl)-4-oxo-3,4-dihydropyrido[2,3-d]pyrimidin-2-yl)-2-(3,5-difluorophenyl)ethyl)carbamate

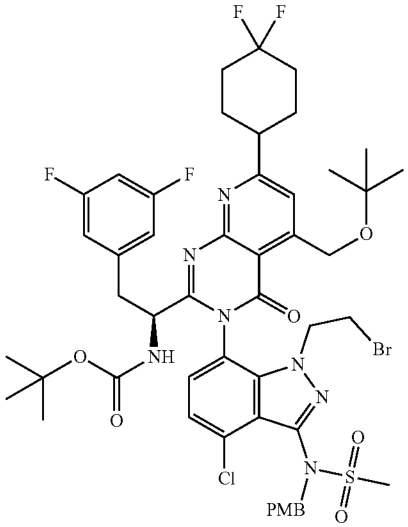

To a stirred suspension of (S)-2-((tert-butoxycarbonyl)amino)-3-(3,5-difluorophenyl)propanoic acid (1.70 g, 5.64 mmol) and 2-amino-4-(tert-butoxymethyl)-6-(4,4-difluorocyclohexyl)nicotinic acid (1.93 g, 5.64 mmol) in acetonitrile (50 mL) at −25° C. was added pyridine (3.32 mL, 41.0 mmol), followed by T3P (50 wt. % in EtOAc, 15.3 mL, 25.6 mmol). The reaction mixture was allowed to warm to 12° C. with stirring for 3 h. To the mixture was added N-(7-amino-1-(2-bromoethyl)-4-chloro-1H-indazol-3-yl)-N-(4-methoxybenzyl)methanesulfonamide (2.50 g, 5.13 mmol) and the resulting mixture was allowed to warm to room temperature with stirring for 18 h. The reaction mixture was diluted with ethyl acetate (100 mL) and washed sequentially with 1N aqueous NaOH (25 mL), 0.5M aqueous citric acid (25 mL), and water (25 mL). The organic layer was dried over $Na_2SO_4$, filtered, and the filtrate was concentrated under reduced pressure. The resulting residue was subjected to silica gel column chromatography (220 g RediSep Gold silica gel column) eluting with 5-80% ethyl acetate in hexanes to afford tert-butyl((1S)-1-(3-(1-(2-bromoethyl)-4-chloro-3-(N-(4-methoxybenzyl)methylsulfonamido)-1H-indazol-7-yl)-5-(tert-butoxymethyl)-7-(4,4-difluorocyclohexyl)-4-oxo-3,4-dihydropyrido[2,3-d]pyrimidin-2-yl)-2-(3,5-difluorophenyl)ethyl)carbamate (2.20 g, yield=40%) as an off-white solid, a mixture of atropisomers. LC/MS Method: Column=Acquity UPLC BEH C18, 2.1×100 mm, 1.7 μm particles; Solvent A=0.1% formic acid in 95:5 water:acetonitrile; Solvent B=0.1% formic acid in 5:95 water:acetonitrile; Flow Rate=0.8 mL/min; Gradient method (minutes/% B)=0/0, 3.5/100, 4.5/100; Wavelength=220 and 254 nm. LC/MS Result: Retention time=3.83 min; m/z=1078.20 $[M+H]^+$.

Preparation of N-(7-(2-((S)-1-amino-2-(3,5-difluorophenyl)ethyl)-7-(4,4-difluorocyclohexyl)-5-(hydroxymethyl)-4-oxopyrido[2,3-d]pyrimidin-3(4H)-yl)-1-(2-bromoethyl)-4-chloro-1H-indazol-3-yl)methanesulfonamide

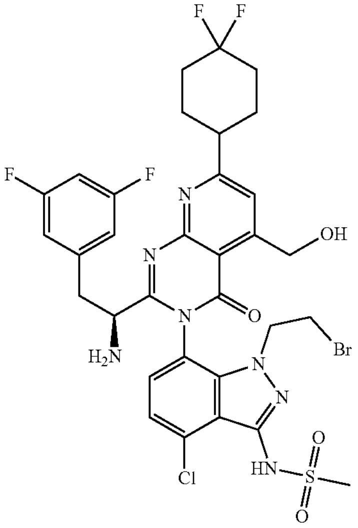 [SMILES: CS(=O)(=O)Nc1nn(CCBr)c2c(-n3c([C@@H](N)Cc4cc(F)cc(F)c4)nc4nc(C5CCC(F)(F)CC5)cc(CO)c4c3=O)ccc(Cl)c12]

To a stirred solution of tert-butyl ((1S)-1-(3-(1-(2-bromoethyl)-4-chloro-3-(N-(4-methoxybenzyl)methylsulfonamido)-1H-indazol-7-yl)-5-(tert-butoxymethyl)-7-(4,4-difluorocyclohexyl)-4-oxo-3,4-dihydropyrido[2,3-d]pyrimidin-2-yl)-2-(3,5-difluorophenyl)ethyl)carbamate (2.20 g, 2.04 mmol) in dichloromethane (30 mL) was added TFA (6.29 mL) and triflic acid (453 μL, 5.11 mmol). The resulting dark red solution was stirred at room temperature for 1 h. The reaction mixture was concentrated under reduced pressure and the residue was dissolved in ethyl acetate (100 mL) and then basified to pH 8 with 1N aqueous sodium hydroxide. The organic layer was separated, washed with brine, dried over $Na_2SO_4$, filtered, and the filtrate was concentrated under reduced pressure to afford N-(7-(2-((S)-1-amino-2-(3,5-difluorophenyl)ethyl)-7-(4,4-difluorocyclohexyl)-5-(hydroxymethyl)-4-oxopyrido[2,3-d]pyrimidin-3(4H)-yl)-1-(2-bromoethyl)-4-chloro-1H-indazol-3-yl)methanesulfonamide which was used directly in the subsequent step (amide coupling). LC/MS Method: Column=Acquity UPLC BEH C18, 2.1×100 mm, 1.7 μm particles; Solvent A=0.1% formic acid in 95:5 water:acetonitrile; Solvent B=0.1% formic acid in 5:95 water:acetonitrile; Flow Rate=0.8 mL/min; Gradient method (minutes/% B)=0/0, 3.5/100, 4.5/100; Wavelength=220 and 254 nm. LC/MS Result: Retention time=2.08 min; m/z=800.05 $[M+H]^+$.

Preparation of tert-butyl(S)-(1-(3-(4-chloro-1-(2-cyclopropoxyethyl)-3-(N-(4-methoxybenzyl)methylsulfonamido)-1H-indazol-7-yl)-7-(4,4-difluorocyclohexyl)-5-methyl-4-oxo-3,4-dihydropyrido[2,3-d]pyrimidin-2-yl)-2-(3,5-difluorophenyl)ethyl) carbamate

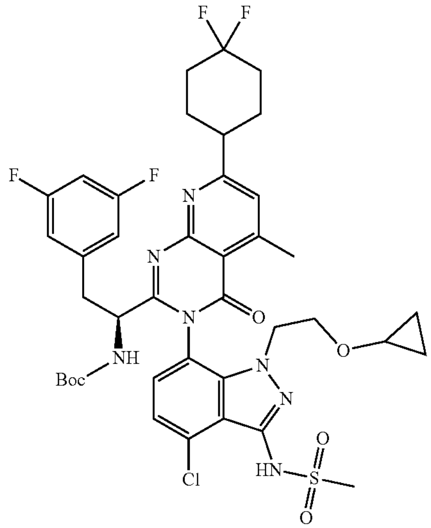 [SMILES: Cc1cc(C2CCC(F)(F)CC2)nc2nc([C@H](Cc3cc(F)cc(F)c3)NC(=O)OC(C)(C)C)n(-c3ccc(Cl)c4c(NS(C)(=O)=O)nn(CCOC5CC5)c34)c(=O)c12]

To a stirred suspension of (S)-2-((tert-butoxycarbonyl) amino)-3-(3,5-difluorophenyl)propanoic acid (713 mg, 2.37 mmol) and 2-amino-6-(4,4-difluorocyclohexyl)-4-methylnicotinic acid (639 mg, 2.37 mmol) in acetonitrile (25 mL) at −25° C. was added pyridine (1.39 mL, 17.2 mmol), followed by T3P (50 wt. % in ethyl acetate, 6.40 mL, 10.8 mmol). The reaction mixture was allowed to warm to 12° C. over 3 h with stirring, during which time the suspension became a clear solution. To the reaction mixture was added N-(7-amino-4-chloro-1-(2-cyclopropoxyethyl)-1H-indazol-3-yl)-N-(4-methoxybenzyl)methanesulfonamide (1.00 g, 2.15 mmol), and the mixture was allowed to warm to rt with stirring for 18 h. The reaction mixture was diluted with ethyl acetate and washed sequentially with 1N aqueous sodium hydroxide, water, 0.5M aqueous citric acid, and water. The organic layer was dried over anhydrous sodium sulfate, filtered, and the filtrate was concentrated under reduced pressure. The resulting residue was subjected to silica gel column chromatography (80 g RediSep Gold silica gel column) eluting with 5-80% ethyl acetate in hexanes to afford tert-butyl(S)-(1-(3-(4-chloro-1-(2-cyclopropoxyethyl)-3-(N-(4-methoxybenzyl)methylsulfonamido)-1H-indazol-7-yl)-7-(4,4-difluorocyclohexyl)-5-methyl-4-oxo-3,4-dihydropyrido[2,3-d]pyrimidin-2-yl)-2-(3,5-difluorophenyl)ethyl)carbamate (1.80 g, yield=85%), a light yellow solid, as a mixture of atropisomers. LC/MS Method: Column=Acquity UPLC BEH C18, 2.1×100 mm, 1.7 μm particles; Solvent A=0.1% formic acid in 95:5 water:acetonitrile; Solvent B=0.1% formic acid in 5:95 water:acetonitrile; Flow Rate=0.8 mL/min; Gradient method (minutes/% B)=0/0, 3.5/100, 4.5/100; Wavelength=220 and 254 nm. LC/MS Result: Retention time=3.66 min; m/z=982.25 $[M+H]^+$.

Preparation of (S)-N-(7-(2-(1-amino-2-(3,5-difluorophenyl)ethyl)-7-(4,4-difluorocyclohexyl)-5-methyl-4-oxopyrido[2,3-d]pyrimidin-3(4H)-yl)-4-chloro-1-(2-hydroxyethyl)-1H-indazol-3-yl) methanesulfonamide

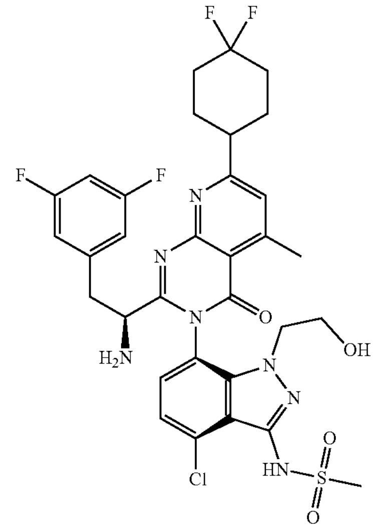

To a stirred solution of tert-butyl (S)-(1-(3-(4-chloro-1-(2-cyclopropoxyethyl)-3-(N-(4-methoxybenzyl)methylsulfonamido)-1H-indazol-7-yl)-7-(4,4-difluorocyclohexyl)-5-methyl-4-oxo-3,4-dihydropyrido[2,3-d]pyrimidin-2-yl)-2-(3,5-difluorophenyl)ethyl)carbamate (1.80 g, 1.83 mmol) in dichloromethane (5 mL) and trifluoroacetic acid (5 mL) was added triflic acid (325 μL, 3.66 mmol). The reaction mixture was stirred for 1 h and then was concentrated under reduced pressure. The resulting residue was dissolved in ethyl acetate (100 mL) and washed with 1 N aqueous sodium hydroxide (25 mL). The organic layer was dried over anhydrous sodium sulfate, filtered, and the filtrate was concentrated under reduced pressure. The resulting residue was subjected to reverse-phase flash column chromatography (50 g C18 silica gel column) eluting with 10-60% acetonitrile in water (both solvents containing 0.1% formic acid) over 25 min. The fractions containing the second-eluting diastereomer, the major atropisomer, were combined and the acetonitrile was removed under reduced pressure. The aqueous layer was basified to pH 8 with 1 N aqueous sodium hydroxide and extracted with ethyl acetate. The combined organics were washed with brine, dried over anhydrous sodium sulfate, filtered, and the filtrate was concentrated under reduced pressure to afford (S)-N-(7-(2-(1-amino-2-(3,5-difluorophenyl)ethyl)-7-(4,4-difluorocyclohexyl)-5-methyl-4-oxopyrido[2,3-d]pyrimidin-3(4H)-yl)-4-chloro-1-(2-hydroxyethyl)-1H-indazol-3-yl)methanesulfonamide (650 mg, yield 20=49%). LC/MS Method: Column=Acquity UPLC BEH C18, 2.1×100 mm, 1.7 μm particles; Solvent A=0.1% formic acid in 95:5 water:acetonitrile; Solvent B=0.1% formic acid in 5:95 water:acetonitrile; Flow Rate=0.8 mL/min; Gradient method (minutes/% B)=0/0, 3.5/100, 4.5/100; Wavelength=220 and 254 nm. LC/MS Result: Retention time=2.38 min; m/z=722.05 $[M+H]^+$.

Preparation of tert-butyl ((1S)-1-(3-(4-chloro-3-(N-(4-methoxybenzyl)methylsulfonamido)-1-(2-(2,2,6,6-tetramethylmorpholino)ethyl)-1H-indazol-7-yl)-7-(4,4-difluorocyclohexyl)-5-methyl-4-oxo-3,4-dihydropyrido[2,3-d]pyrimidin-2-yl)-2-(3,5-difluorophenyl)ethyl)carbamate

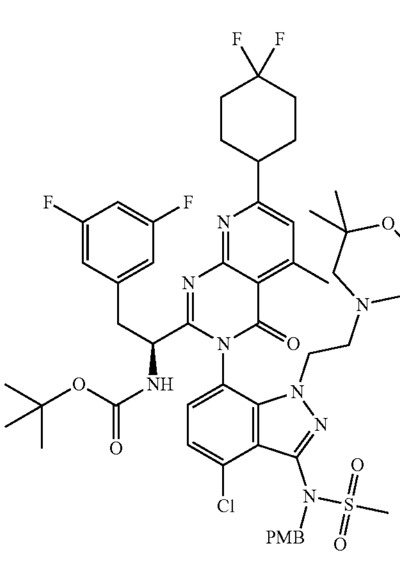

To a stirred suspension of (S)-2-((tert-butoxycarbonyl)amino)-3-(3,5-difluorophenyl)propanoic acid (8.43 g, 28.0 mmol) and 2-amino-6-(4,4-difluorocyclohexyl)-4-methylnicotinic acid (7.57 g, 28.0 mmol) in acetonitrile (200 mL) at −25° C. was added pyridine (16.5 mL, 204 mmol), followed by T3P (50 wt. % in EtOAc, 75.8 mL, 127 mmol). The reaction mixture was allowed to warm to 12° C. over 3 h with stirring. To the reaction mixture was added N-(7-amino-4-chloro-1-(2-(2,2,6,6-tetramethylmorpholino)ethyl)-1H-indazol-3-yl)-N-(4-methoxybenzyl)methanesulfonamide (14.0 g, 25.4 mmol) and the mixture was allowed to warm to room temperature with stirring for 18 h. The reaction mixture was diluted with ethyl acetate (300 mL) and washed with 1 N aqueous sodium hydroxide (2×100 mL) and then water (100 mL). The organic layer was dried over $Na_2SO_4$, filtered, and the filtrate was concentrated under reduced pressure. The resulting residue was subjected to silica gel column chromatography (330 g RediSep Gold silica gel column) eluting with 5-80% ethyl acetate in hexanes to afford tert-butyl ((1 S)-1-(3-(4-chloro-3-(N-(4-methoxybenzyl)methylsulfonamido)-1-(2-(2,2,6,6-tetramethylmorpholino)ethyl)-1H-indazol-7-yl)-7-(4,4-difluorocyclohexyl)-5-methyl-4-oxo-3,4-dihydropyrido[2,3-d]pyrimidin-2-yl)-2-(3,5-difluorophenyl)ethyl)carbamate (19.0 g, yield=70%) as an off-white solid. LC/MS Method: Column=Acquity UPLC BEH C18, 2.1×100 mm, 1.7 μm particles; Solvent A=0.1% formic acid in 95:5 water:acetonitrile; Solvent B=0.1% formic acid in 5:95 water:acetonitrile; Flow Rate=0.8 mL/min; Gradient method (minutes/% B)=0/0, 3.5/100, 4.5/100; Wavelength=220 and 254 nm. LC/MS Result: Retention time=3.78 min; m/z=1067.3 $[M+H]^+$.

Preparation of (S)-N-(7-(2-(1-amino-2-(3,5-difluorophenyl)ethyl)-7-(4,4-difluorocyclohexyl)-5-methyl-4-oxopyrido[2,3-d]pyrimidin-3(4H)-yl)-4-chloro-1-(2-(2,2,6,6-tetramethylmorpholino)ethyl)-1H-indazol-3-yl)methanesulfonamide

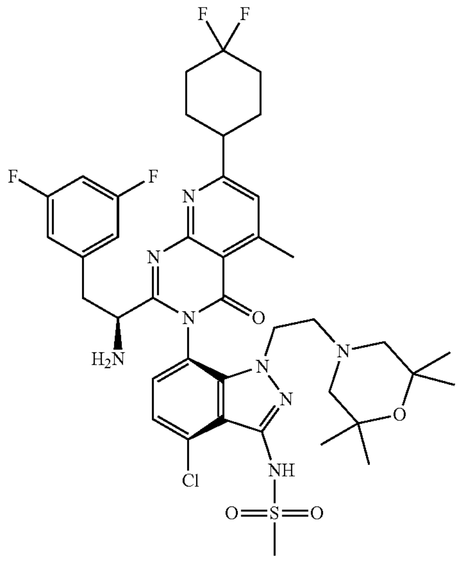

To a stirred solution of tert-butyl((1S)-1-(3-(4-chloro-3-(N-(4-methoxybenzyl)methylsulfonamido)-1-(2-(2,2,6,6-tetramethylmorpholino)ethyl)-1H-indazol-7-yl)-7-(4,4-difluorocyclohexyl)-5-methyl-4-oxo-3,4-dihydropyrido[2,3-d]pyrimidin-2-yl)-2-(3,5-difluorophenyl)ethyl)carbamate (19.0 g, 17.8 mmol) in dichloromethane (100 mL) and trifluoroacetic acid (55 mL) was added trifluoromethanesulfonic acid (3.95 mL, 44.5 mmol). The resulting dark red solution was stirred at room temperature for 1 h upon which LC/MS analysis indicated completion of the reaction. The mixture was concentrated under reduced pressure and the resulting residue was dissolved in ethyl acetate (600 mL) and washed with 1N aqueous sodium hydroxide (200 mL). The organic layer was dried over $Na_2SO_4$, filtered, and the filtrate was concentrated under reduced pressure. The resulting residue was subjected to silica gel column chromatography (330 g RediSep Gold silica gel column) eluting with a gradient of 40-100% of a 9:9:2 mixture of ethyl acetate: hexanes:methanol in hexanes over 5 column volumes, then with 100% of the 9:9:2 mixture over 3 column volumes. The first-eluting peak, corresponding to the major atropisomer, was concentrated under reduced pressure to afford the title compound, N-(7-(2-((S)-1-amino-2-(3,5-difluorophenyl)ethyl)-7-(4,4-difluorocyclohexyl)-5-methyl-4-oxopyrido[2,3-d]pyrimidin-3(4H)-yl)-4-chloro-1-(2-(2,2,6,6-tetramethylmorpholino)ethyl)-1H-indazol-3-yl)methanesulfonamide (9.80 g, yield=65%). $^1H$ NMR (500 MHz, DMSO-$d_6$) δ ppm 7.37-7.54 (m, 3H) 7.02 (tt, J=9.50, 2.27 Hz, 1H) 6.60-6.75 (m, 2H) 4.10-4.17 (m, 1H) 4.01-4.06 (m, 1H) 3.42-3.49 (m, 1H) 3.20-3.29 (m, 4H) 2.98-3.08 (m, 1H) 2.85 (dd, J=13.56, 9.09 Hz, 1H) 2.77 (s, 3H) 2.67-2.74 (m, 1H) 2.44-2.50 (m, 1H) 2.20 (td, J=6.48, 3.13 Hz, 2H) 1.80-2.12 (m, 12H) 0.87 (s, 12H). LC/MS Method: Column=Acquity UPLC BEH C18, 2.1×100 mm, 1.7 μm particles; Solvent A=0.1% formic acid in 95:5 water:acetonitrile; Solvent B=0.1% formic acid in 5:95 water:acetonitrile; Flow Rate=0.8 mL/min; Gradient method (minutes/% B)=0/0, 3.5/100, 4.5/100; Wavelength=220 and 254 nm. LC/MS Result: Retention time=2.47 min; m/z=847.40 $[M+H]^+$.

Preparation of tert-butyl ((1S)-1-(3-(4-chloro-1-(2-((2R,6S)-2,6-dimethylmorpholino)ethyl)-3-(N-(4-methoxybenzyl)methylsulfonamido)-1H-indazol-7-yl)-5-methyl-4-oxo-7-(1,4,4-trifluorocyclohexyl)-3,4-dihydropyrido[2,3-d]pyrimidin-2-yl)-2-(3,5-difluorophenyl)ethyl)carbamate

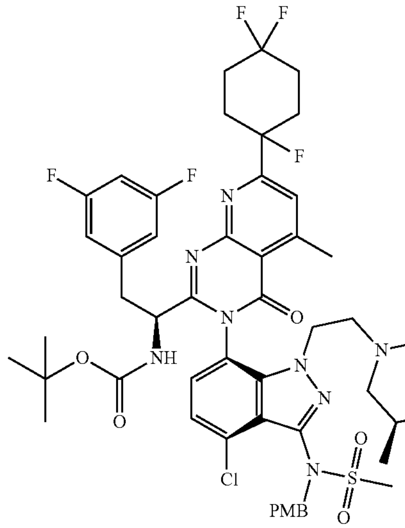

To a stirred suspension of (S)-2-((tert-butoxycarbonyl)amino)-3-(3,5-difluorophenyl)propanoic acid (173 mg, 575 μmol) and 2-amino-4-methyl-6-(1,4,4-trifluorocyclohexyl)nicotinic acid (166 mg, 575 μmol) in acetonitrile (5.75 mL) at −25° C. was added pyridine (372 μL, 4.60 mmol) followed by T3P (50 wt. % in ethyl acetate, 1.71 mL, 2.88 mmol). The reaction mixture was allowed to warm to 12° C. over 3 h with stirring. To the mixture was added N-(7-amino-4-chloro-1-(2-((2R,6S)-2,6-dimethylmorpholino)ethyl)-1H-indazol-3-yl)-N-(4-methoxybenzyl)methanesulfonamide (300 mg, 575 μmol), and the resulting mixture was allowed to warm to room temperature with stirring for 18 h. The reaction mixture was concentrated under reduced pressure and the resulting residue was subjected to silica gel column chromatography (40 g RediSep Gold silica gel column) eluting with a gradient of 0-100% ethyl acetate in hexanes over 8 column volumes, then 100% ethyl acetate for 3 column volumes to afford tert-butyl((1S)-1-(3-(4-chloro-1-(2-((2R,6S)-2,6-dimethylmorpholino)ethyl)-3-(N-(4-methoxybenzyl)methylsulfonamido)-1H-indazol-7-yl)-5-methyl-4-oxo-7-(1,4,4-trifluorocyclohexyl)-3,4-dihydropyrido[2,3-d]pyrimidin-2-yl)-2-(3,5-difluorophenyl)ethyl)carbamate as a mixture of atropisomers. LC/MS Method: Column=Acquity UPLC BEH C18, 1.7 μm, 2.1×100 mm; Solvent A=95:5 water:acetonitrile with 0.1% formic acid; Solvent B=5:95 water:acetonitrile with 0.1% formic acid; Gradient method (minutes/% B)=0/0, 3.5/100, 4.5/100; Flow rate=0.8 mL/min; Injection Volume=5.00 μL; Wavelength=220 and 254 nm. LC/MS Result: Retention time=3.22 min; m/z=1059.50 $[M+H]^+$.

Preparation of N-(7-(2-((S)-1-amino-2-(3,5-difluorophenyl)ethyl)-5-methyl-4-oxo-7-(1,4,4-trifluorocyclohexyl)pyrido[2,3-d]pyrimidin-3(4H)-yl)-4-chloro-1-(2-((2S,6R)-2,6-dimethylmorpholino)ethyl)-1H-indazol-3-yl)methanesulfonamide

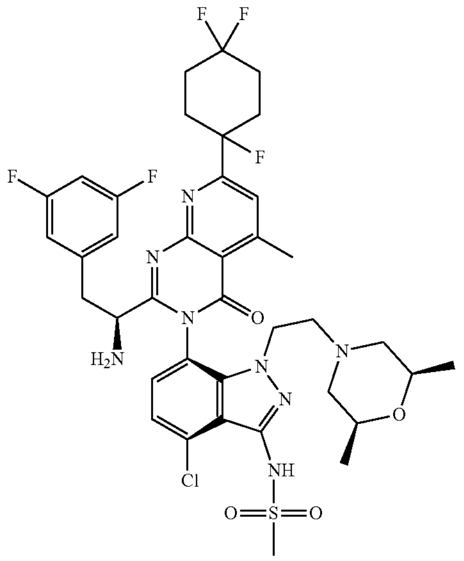

To a stirred solution of tert-butyl((1S)-1-(3-(4-chloro-1-(2-((2R,6S)-2,6-dimethylmorpholino)ethyl)-3-(N-(4-methoxybenzyl)methylsulfonamido)-1H-indazol-7-yl)-5-methyl-4-oxo-7-(1,4,4-trifluorocyclohexyl)-3,4-dihydropyrido[2,3-d]pyrimidin-2-yl)-2-(3,5-difluorophenyl)ethyl)carbamate (3.29 g, 3.11 mmol) in DCM (31 mL) at room temperature was added trifluoroacetic acid (9.59 mL, 124 mmol) followed by trifluoromethanesulfonic acid (829 μL, 9.33 mmol). The reaction mixture was stirred at room temperature for 1 h upon which LC/MS analysis indicated the presence of the expected product. The reaction mixture was concentrated under reduced pressure, diluted with ethyl acetate (100 mL), and washed with 1N aqueous sodium hydroxide (100 mL) and then brine. The organic layer was dried over $Na_2SO_4$, filtered, and the filtrate was concentrated under reduced pressure to afford 3.1 g of crude product. This material was subjected to reverse-phase flash column chromatography (RediSep Gold C18 column, 415 g) using a gradient of water and acetonitrile buffered with 0.1% formic acid. The fractions containing the major atropisomer (second eluting peak containing the product mass) were combined and lyophilized to afford N-((S)-7-(2-((S)-1-amino-2-(3,5-difluorophenyl)ethyl)-5-methyl-4-oxo-7-(1,4,4-trifluorocyclohexyl)pyrido[2,3-d]pyrimidin-3(4H)-yl)-4-chloro-1-(2-((2R,6S)-2,6-dimethylmorpholino)ethyl)-1H-indazol-3-yl)methanesulfonamide (2.05 g, yield=79%). LC/MS Method (Shimadzu): Column=Acquity UPLC BEH C18, 1.7 μm, 2.1×100 mm; Solvent A=95:5 water:acetonitrile with 0.1% formic acid; Solvent B=5:95 water:acetonitrile with 0.1% formic acid; Gradient method (minutes/% B)=0/0, 3.5/100, 4.5/100; Flow rate=0.8 mL/min; Injection volume=5.00 μL; Wavelength=220 and 254 nm. LC/MS Result: Retention time=2.31 min; m/z=837.30 $[M+H]^+$. $^1H$ NMR (500 MHz, METHANOL-$d_4$) δ ppm 0.83 (d, J=6.26 Hz, 3H) 0.96 (d, J=6.26 Hz, 3H) 1.37 (t, J=10.43 Hz, 1H) 1.57 (t, J=10.73 Hz, 1H) 2.09-2.26 (m, 5H) 2.30 (br d, J=10.73 Hz, 2H) 2.47-2.55 (m, 3H) 2.56-2.66 (m, 1H) 2.74-2.88 (m, 2H) 2.89 (d, J=0.60 Hz, 3H) 3.14-3.20 (m, 1H) 3.26-3.29 (m, 1H) 3.30-3.30 (m, 3H) 3.34-3.38 (m, 1H) 3.61 (dd, J=7.75, 5.36 Hz, 1H) 4.06-4.14 (m, 1H) 4.29 (ddd, J=14.31, 9.84, 6.26 Hz, 1H) 6.49-6.54 (m, 2H) 6.79 (t, J=8.65 Hz, 1H) 7.00 (dd, J=8.05, 0.89 Hz, 1H) 7.31 (d, J=8.05 Hz, 1H) 7.72 (s, 1H).

Preparation of N-((S)-1-(5-chloro-3-(4-chloro-1-(3-methoxypropyl)-3-(methylsulfonamido)-1H-indazol-7-yl)-7-(4,4-difluorocyclohexyl)-4-oxo-3,4-dihydro-pyrido[2,3-d]pyrimidin-2-yl)-2-(3,5-difluorophenyl) ethyl)-2-((3bS,4aR)-3-(difluoromethyl)-5,5-difluoro-3b,4,4a,5-tetrahydro-1H-cyclopropa[3,4]cyclopenta [1,2-c]pyrazol-1-yl)acetamide Synthetic Scheme

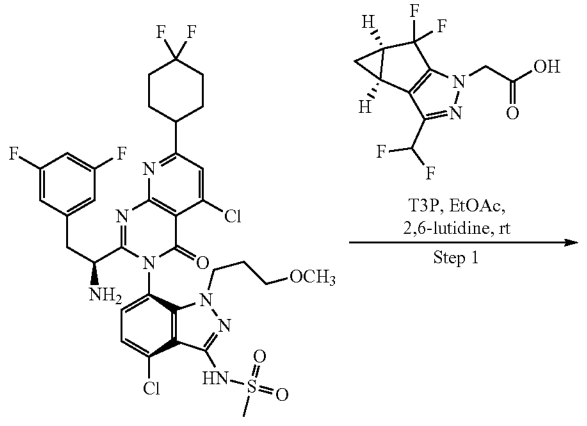

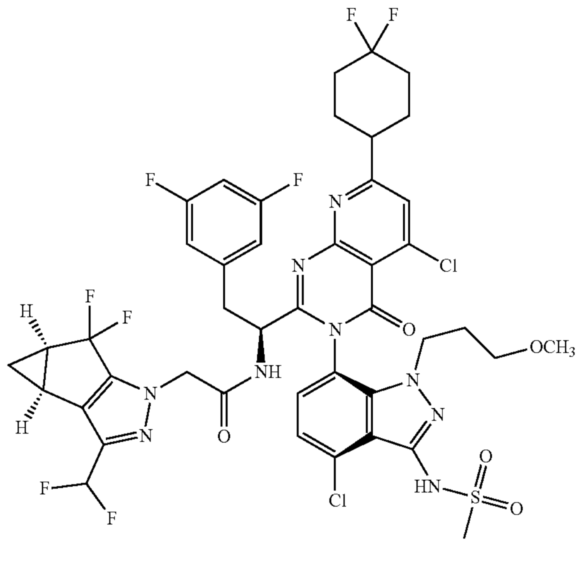

Step 1: Preparation of N-((S)-1-(5-chloro-3-(4-chloro-1-(3-methoxypropyl)-3-(methylsulfonamido)-1H-indazol-7-yl)-7-(4,4-difluorocyclohexyl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide

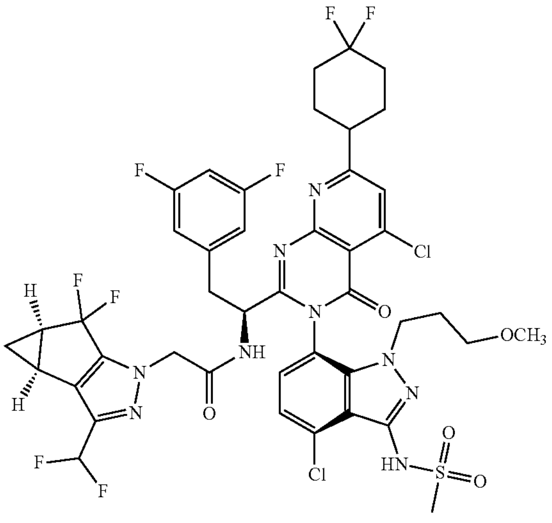

To a stirred solution of (S)-N-(7-(2-(1-Amino-2-(3,5-difluorophenyl)ethyl)-5-chloro-7-(4,4-difluorocyclohexyl)-4-oxopyrido[2,3-d]pyrimidin-3(4H)-yl)-4-chloro-1-(3-methoxypropyl)-1H-indazol-3-yl)methanesulfonamide (400 mg, 520 μmol) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (144 mg, 545 μmol) in ethyl acetate (8 mL) was added 2,6-lutidine (151 μL, 1300 μmol) followed by 2,4,6-tripropyl-1,3,5,2,4,6-trioxatriphosphinane-2,4,6-trioxide ("T3P", 50 wt % in ethyl acetate, 643 μL, 1040 μmol). The reaction mixture was stirred at room temperature for 2 h. LCMS analysis indicated a major peak with the expected $[M+H]^+$ ion. The mixture was diluted with water and then extracted with ethyl acetate. The organic layer was dried over anhydrous sodium sulfate, filtered, and the filtrate was concentrated under reduced pressure. The resulting residue was subjected to silica gel column chromatography (40 g silica gel), eluting with 5-100% ethyl acetate in hexanes to afford N-((S)-1-(5-chloro-3-(4-chloro-1-(3-methoxypropyl)-3-(methylsulfonamido)-1H-indazol-7-yl)-7-(4,4-difluorocyclohexyl)-4-oxo-3,4-dihydropyrido [2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (465 mg, yield=88%). LC/MS Method: Column=Acquity UPLC BEH C18 (2.1×100 mm, 1.7 micron particles); Solvent A=water:MeCN (95:5) w/0.1% formic acid; Solvent B=water:MeCN (5:95) w/0.1% formic acid; Flow Rate=0.8 mL/min; Start % B=0; Final % B=100; Gradient Time=3.5 min, then a 1.0 min hold at 100% B; Wavelength=220 nm and 254 nm. LC/MS result: Retention time=3.18 min; m/z=1016 $[M+H]^+$. $^1H$ NMR (500 MHz, METHANOL-$d_4$), δ ppm 1.01-1.06 (m, 1H), 1.38 (q, J=6.76 Hz, 1H), 1.85-1.92 (m, 2H), 1.95-2.14 (m, 8H), 2.23-2.29 (m, 2H), 2.41-2.47 (m, 2H), 2.82 (s, 3H), 3.05-3.13 (m, 3H), 3.13-3.19 (m, 3H), 3.26 (s, 3H), 3.40 (s, 1H), 3.83 (br d, J=9.84 Hz, 1H), 4.00-4.08 (m, 1H), 6.54-6.81 (m, 4H), 7.26-7.31 (m, 1H), 7.33-7.37 (m, 1H), 7.70 (s, 1H).

Preparation of N-((1S)-1-(3-(1-(2-bromoethyl)-4-chloro-3-(methylsulfonamido)-1H-indazol-7-yl)-7-(4,4-difluorocyclohexyl)-5-methyl-4-oxo-3,4-dihydropyrido[2,3-d]pyrimidin-2-yl)-2-(3,5-difluorophenyl)ethyl)-2-((3bS,4aS)-3-cyclopropyl-3b,4,4a,5-tetrahydro-1H-cyclopropa[3,4]cyclopenta[1,2-c]pyrazol-1-yl)acetamide

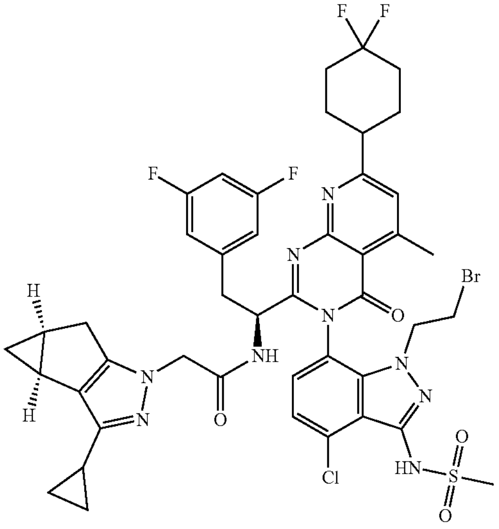 [SMILES: Cc1cc(C2CCC(F)(F)CC2)nc2nc([C@H](Cc3cc(F)cc(F)c3)NC(=O)Cn3nc(C4CC4)c4c3C[C@@H]3C[C@H]43)n(-c3ccc(Cl)c4c(NS(C)(=O)=O)nn(CCBr)c34)c(=O)c12]

Synthetic Scheme

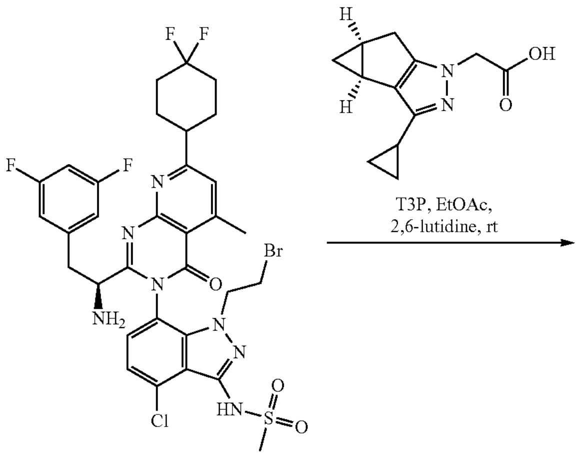

-continued

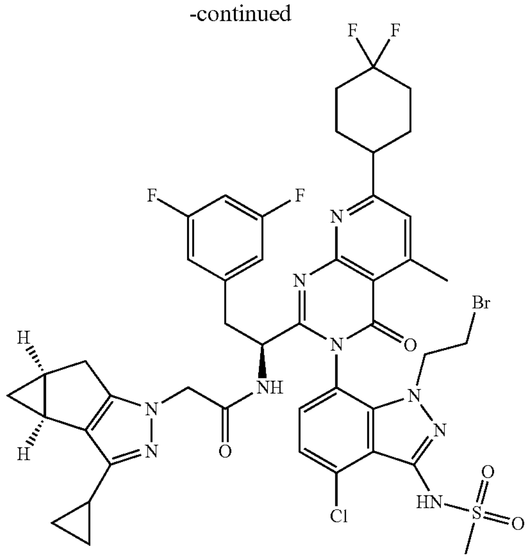

To a stirred solution of N-(7-(2-((S)-1-amino-2-(3,5-difluorophenyl)ethyl)-7-(4,4-difluorocyclohexyl)-5-methyl-4-oxopyrido[2,3-d]pyrimidin-3(4H)-yl)-1-(2-bromoethyl)-4-chloro-1H-indazol-3-yl)methanesulfonamide (2.5 g, 1 Eq, 3.2 mmol) and triethylamine 2-((3bS,4aS)-3-cyclopropyl-3b,4,4a,5-tetrahydro-1H-cyclopropa[3,4]cyclopenta[1,2-c]pyrazol-1-yl)acetate (1.0 g, 1 Eq, 3.2 mmol) in Ethyl acetate (35 mL) was added 2,6-lutidine (853 mg, 0.922 mL, 2.50 Eq, 7.96 mmol) followed by 2,4,6-tripropyl-1,3,5,2,4,6-trioxatriphosphinane 2,4,6-trioxide, 50% in EtOAc (4.05 g, 3.95 mL, 50% Wt, 2 Eq, 6.37 mmol) and the resulting mixture was stirred at room temp for 4 h. LCMS showed a major peak with the expected M+H. Water was then added and the mixture was extracted with ethyl acetate, dried ($Na_2SO_4$), filtered and concentrated. The residue was purified on silica (120 g) using gradient of 5-80% ethyl acetate in hexanes. The desired fractions were concentrated to give N-((1S)-1-(3-(1-(2-bromoethyl)-4-chloro-3-(methylsulfonamido)-1H-indazol-7-yl)-7-(4,4-difluorocyclohexyl)-5-methyl-4-oxo-3,4-dihydropyrido[2,3-d]pyrimidin-2-yl)-2-(3,5-difluorophenyl)ethyl)-2-((3bS,4aS)-3-cyclopropyl-3b,4,4a,5-tetrahydro-1H-cyclopropa[3,4]cyclopenta[1,2-c]pyrazol-1-yl)acetamide (2.6 g, 83% yield). 1H NMR (500 MHz, METHANOL-d4) δ ppm 7.41 (d, J=0.89 Hz, 1H), 7.34 (d, J=7.75 Hz, 1H), 7.22 (d, J=8.05 Hz, 1H), 6.78 (tt, J=9.20, 2.27 Hz, 1H), 6.59 (dd, J=8.05, 2.09 Hz, 2H), 4.74 (dd, J=9.39, 4.92 Hz, 1H), 4.29-4.35 (m, 1H), 4.27 (d, J=1.79 Hz, 2H), 3.86 (ddd, J=14.75, 9.54, 5.51 Hz, 1H), 3.55 (td, J=9.84, 5.66 Hz, 1H), 3.38-3.49 (m, 2H), 3.28 (s, 3H), 2.98-3.11 (m, 2H), 2.84 (d, J=0.60 Hz, 3H), 2.67 (dd, J=16.69, 6.56 Hz, 1H), 2.45 (d, J=16.39 Hz, 1H), 2.19-2.29 (m, 2H), 2.02-2.15 (m, 5H), 1.94-2.02 (m, 1H), 1.88-1.94 (m, 1H), 1.80-1.86 (m, 1H), 1.76 (tt, J=8.35, 5.07 Hz, 1H), 0.93 (td, J=7.75, 4.77 Hz, 1H), 0.85 (tdd, J=8.57, 8.57, 5.36, 3.13 Hz, 2H), 0.66-0.79 (m, 2H), 0.02-0.06 (m, 1H). LCMS Method A: retention time=3.32 min.; observed ion=986.10 (M+H).

Preparation of 2-(4-chloro-7-(2-((S)-1-(2-((3bS,4aS)-3-cyclopropyl-3b,4,4a,5-tetrahydro-1H-cyclopropa[3,4]cyclopenta[1,2-c]pyrazol-1-yl)acetamido)-2-(3,5-difluorophenyl)ethyl)-7-(4,4-difluorocyclohexyl)-5-methyl-4-oxopyrido[2,3-d]pyrimidin-3(4H)-yl)-3-(methylsulfonamido)-1H-indazol-1-yl)acetic Acid

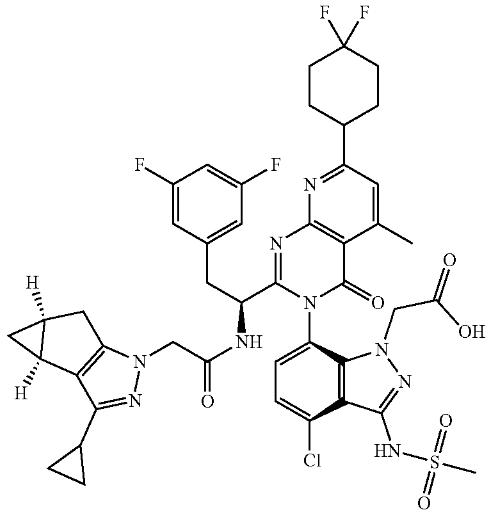

To a stirred solution of 2-((3bS,4aS)-3-cyclopropyl-3b,4,4a,5-tetrahydro-1H-cyclopropa[3,4]cyclopenta[1,2-c]pyrazol-1-yl)acetic acid (103 mg, 470 μmol) in THF (2.00 mL) was added HATU (179 mg, 470 μmol) followed by N,N-diisopropylethylamine (276 mg, 2.13 mmol). The reaction mixture was stirred for 10 min at ambient temperature. To the mixture was added a solution of 2-(7-(2-((S)-1-amino-2-(3,5-difluorophenyl)ethyl)-7-(4,4-difluorocyclohexyl)-5-methyl-4-oxopyrido[2,3-d]pyrimidin-3(4H)-yl)-4-chloro-3-(methylsulfonamido)-1H-indazol-1-yl)acetic acid, trifluoroacetic acid salt (363 mg, 427 μmol) in N,N-dimethylformamide (4.00 mL). The reaction mixture was stirred at ambient temperature for 1 h. The resulting mixture containing the title compound was used directly in the next step (General Procedure C).

Preparation of 2-(4-chloro-7-(7-(4,4-difluorocyclohexyl)-2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-5-methyl-4-oxopyrido[2,3-d]pyrimidin-3(4H)-yl)-3-(methylsulfonamido)-1H-indazol-1-yl)acetic Acid

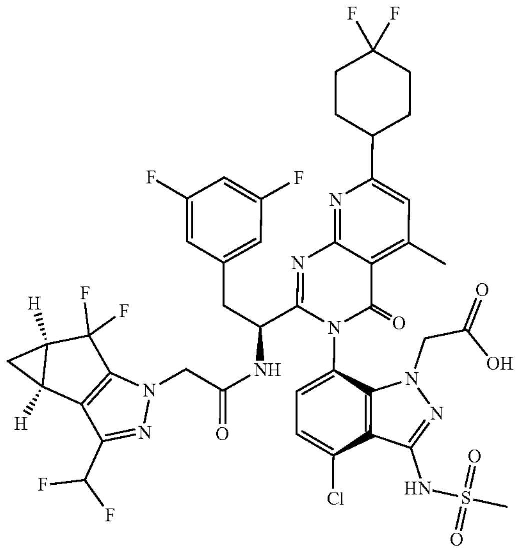

To a solution of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (137 mg, 518 μmol) in THF (1.5 mL) was added HATU (197 mg, 518 μmol) followed by N,N-diisopropylethylamine (304 mg, 2.35 mmol). The mixture was stirred at ambient temperature for 5 min. The resulting solution was combined with a solution of 2-(7-(2-((S)-1-amino-2-(3,5-difluorophenyl)ethyl)-7-(4,4-difluorocyclohexyl)-5-methyl-4-oxopyrido[2,3-d]pyrimidin-3(4H)-yl)-4-chloro-3-(methylsulfonamido)-1H-indazol-1-yl)aceticacid, trifluoroacetic acid salt (400 mg, 471 μmol) in in N,N-dimethylformamide (6.00 mL). The reaction mixture was stirred at ambient temperature for 1 h. The resulting mixture containing the title compound was used directly in the next step (General Procedure C).

Preparation of N-((1S)-1-(3-(4-chloro-1-(3-methoxypropyl)-3-(methylsulfonamido)-1H-indazol-7-yl)-7-(4,4-difluorocyclohexyl)-5-(hydroxymethyl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

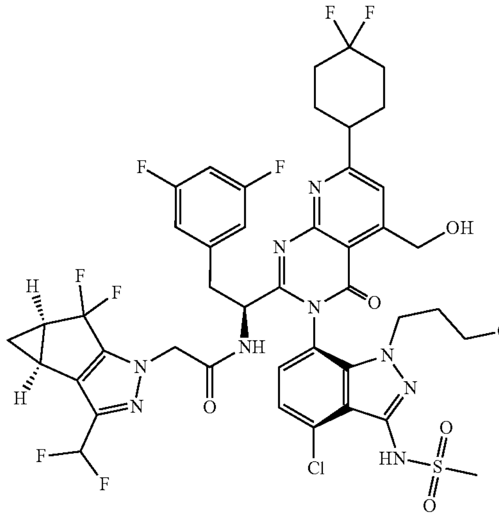

To a stirred suspension of N-(7-(2-((S)-1-amino-2-(3,5-difluorophenyl)ethyl)-7-(4,4-difluorocyclohexyl)-5-(hydroxymethyl)-4-oxopyrido[2,3-d]pyrimidin-3(4H)-yl)-4-chloro-1-(3-methoxypropyl)-1H-indazol-3-yl)methanesulfonamide (1.50 g, 1.96 mmol) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (1.03 g, 3.92 mmol) in THF (20 mL) was added HATU (2.23 g, 5.87 mmol), followed by N,N-diisopropylethylamine (1.27 g, 9.79 mmol). The resulting mixture was stirred at room temperature for 2 h. LC/MS analysis showed a major peak with the expected m/z value for the bis-adduct. Water was added to the reaction mixture, and the mixture was extracted with ethyl acetate. The organic layer was dried over anhydrous sodium sulfate, filtered, and the filtrate was concentrated under reduced pressure. The resulting residue was treated with 2M ammonia in methanol (20 mL) at room temperature for 30 min. in order to cleave the ester of the bis-adduct. The mixture was concentrated under reduced pressure, and the resulting residue was subjected to silica gel column chromatography (80 g Isco Gold silica gel column), eluting with 5-100% ethyl acetate in hexanes, to afford (3-(4-chloro-1-(3-methoxypropyl)-3-(methylsulfonamido)-1H-indazol-7-yl)-7-(4,4-difluorocyclohexyl)-2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-4-oxo-3,4-dihydropyrido[2,3-d]pyrimidin-5-yl)methyl2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetate (1.7 g, yield=86%). LC/MS retention time=3.02 min; m/z=1012.10 $[M+H]^+$. (Column: Acquity UPLC BEH C18, 2.1×100 mm, 1.7 μm particles. Solvent A=0.1% Formic acid in 95:5 Water:MeCN. Solvent B=0.1% Formic Acid in 5:95 Water:MeCN. Flow Rate=0.8 mL/min. Start % B=0. Final % B=100. Gradient Time=3.5 min, then a 1 min hold at 100% B. Wavelength=220 and 254 nm).

Preparation of N-((S)-1-(3-(4-chloro-1-(2-hydroxyethyl)-3-(methylsulfonamido)-1H-indazol-7-yl)-7-(4,4-difluorocyclohexyl)-5-methyl-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

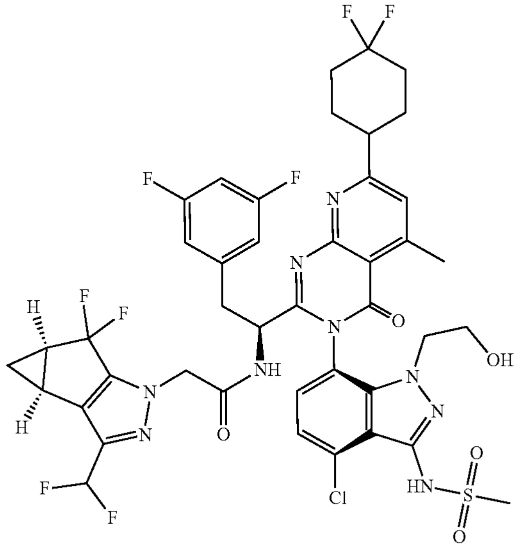

To a stirred suspension of (S)-N-(7-(2-(1-amino-2-(3,5-difluorophenyl)ethyl)-7-(4,4-difluorocyclohexyl)-5-methyl-4-oxopyrido[2,3-d]pyrimidin-3(4H)-yl)-4-chloro-1-(2-hydroxyethyl)-1H-indazol-3-yl)methanesulfonamide (640 mg, 886 μmol) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (246 mg, 931 μmol) in THF (8 mL) was added HATU (371 mg, 975 μmol), followed by N,N-diisopropylethylamine (464 μL, 2.66 mmol). The reaction mixture was stirred at room temperature for 2 h. LC/MS analysis showed a major peak with the expected product m/z value, along with some bis-coupled product (ester impurity). The mixture was diluted with water and then extracted with ethyl acetate. The organic phase was dried over anhydrous sodium sulfate, filtered, and the filtrate was concentrated under reduced pressure. The resulting residue was treated with 2M ammonia in methanol (5 mL) for 30 min to cleave the ester of the bis-adduct. The mixture was concentrated under reduced pressu and the resulting residue was subjected to silica gel column chromatography, eluting with 5-100% ethyl acetate in hexanes, to afford N-((S)-1-(3-(4-chloro-1-(2-hydroxyethyl)-3-(methylsulfonamido)-1H-indazol-7-yl)-7-(4,4-difluorocyclohexyl)-5-methyl-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (310 mg, yield=36%). 1H NMR (500 MHz, DMSO-$d_6$) δ ppm 9.84 (s, 1H), 9.34 (d, J=8.64 Hz, 1H), 7.71 (br d, J=8.05 Hz, 1H), 7.47 (br d, J=7.75 Hz, 1H), 7.43 (s, 1H), 6.72-7.07 (m, 2H), 6.56 (dd, J=8.34, 2.09 Hz, 2H), 4.64-4.74 (m, 2H), 4.48-4.61 (m, 2H), 3.82-3.89 (m, 1H), 3.62-3.70 (m, 1H), 3.47-3.59 (m, 2H), 3.34-3.37 (m, 1H), 3.29 (s, 2H), 3.17 (s, 3H), 2.92-3.08 (m, 2H), 2.75 (s, 3H), 2.43-2.48 (m, 1H), 2.15-2.23 (m, 2H), 2.00-2.09 (m, 3H), 1.89-1.98 (m, 2H), 1.31-1.39 (m, 1H), 0.83-0.90 (m, 1H). LC/MS Method: Column=Acquity UPLC BEH C18, 2.1×100 mm, 1.7 μm particles; Solvent A=0.1% formic acid in 95:5 water:acetonitrile; Solvent B=0.1% formic acid in 5:95 water:acetonitrile; Flow Rate=0.8 mL/min; Gradient method (minutes/% B)=0/0, 3.5/100, 4.5/100; Wavelength=220 and 254 nm. LC/MS Result: Retention time=3.28 min; m/z=968.10 $[M+H]^+$.

Preparation of N-((S)-1-(3-(4-chloro-3-(methylsulfonamido)-1-(2-oxoethyl)-1H-indazol-7-yl)-7-(4,4-difluorocyclohexyl)-5-methyl-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

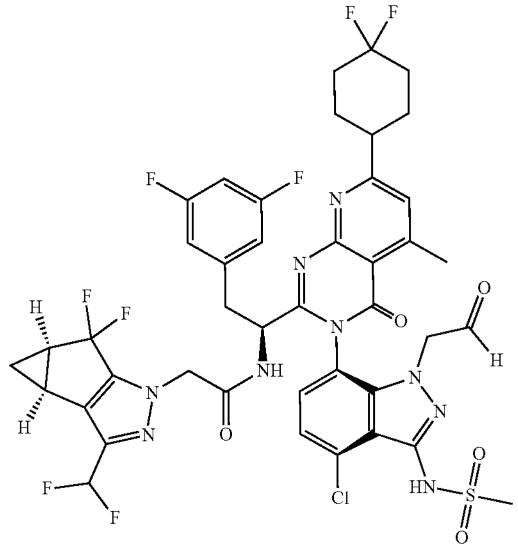

To a stirred solution of N-((S)-1-(3-(4-chloro-1-(2-hydroxyethyl)-3-(methylsulfonamido)-1H-indazol-7-yl)-7-(4,4-difluorocyclohexyl)-5-methyl-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (230 mg, 238 μmol) in dichloromethane (5 mL) was added Dess-Martin periodinane (201 mg, 475 μmol). The reaction mixture was stirred at room temperature for 3 h upon which LC/MS analysis showed a mixture of product and the +16 Da byproduct. The mixture was diluted with water and then extracted with dichloromethane. The organic phase was dried over anhydrous sodium sulfate, filtered, and the filtrate was concentrated under reduced pressure. The resulting residue was subjected to silica gel column chromatography (24 g RediSep Gold silica gel column) eluting with 5-100% ethyl acetate in hexanes to afford N-((S)-1-(3-(4-chloro-3-(methylsulfonamido)-1-(2-oxoethyl)-1H-indazol-7-yl)-7-(4,4-difluorocyclohexyl)-5-methyl-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (120 mg, yield=52%) as an off-white solid. LC/MS Method: Column=Acquity UPLC BEH C18, 2.1×100 mm, 1.7 μm particles; Solvent A=0.1% formic acid in 95:5 water:acetonitrile; Solvent B=0.1% formic acid in 5:95 water:acetonitrile; Flow Rate=0.8 mL/min; Gradient method (minutes/% B)=0/0, 3.5/100, 4.5/100; Wavelength=220 and 254 nm. LC/MS Result: Retention time=3.04 min.

Preparation of N-((1S)-1-(3-(1-(2-bromoethyl)-4-chloro-3-(methylsulfonamido)-1H-indazol-7-yl)-5-chloro-7-(4,4-difluorocyclohexyl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

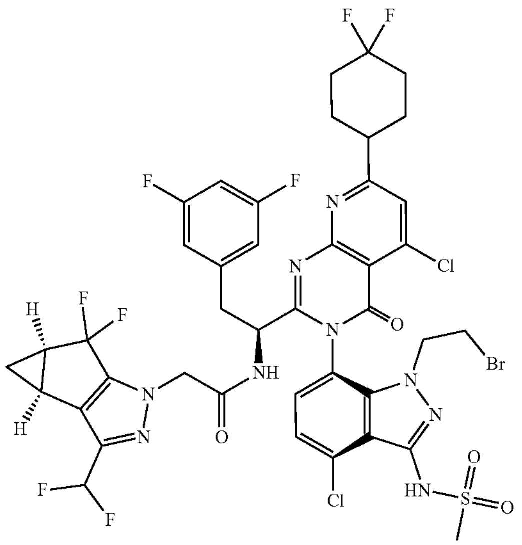

To a stirred solution of N-(7-(2-((S)-1-amino-2-(3,5-difluorophenyl)ethyl)-5-chloro-7-(4,4-difluorocyclohexyl)-4-oxopyrido[2,3-d]pyrimidin-3(4H)-yl)-1-(2-bromoethyl)-4-chloro-1H-indazol-3-yl)methanesulfonamide (209 mg, 260 μmol) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (72.0 mg, 272 μmol) in ethyl acetate (5 mL) was added 2,6-lutidine (75.1 μL, 648 μmol) followed by T3P (50 wt. % in ethyl acetate, 322 μL, 519 μmol). The reaction mixture was stirred at room temperature for 2 h, then water was added and the mixture was extracted with ethyl acetate. The organic layer was dried over $Na_2SO_4$, filtered, and the filtrate was concentrated under reduced pressure. The resulting residue was subjected to silica gel column chromatography (40 g RediSep Gold silica gel column) eluting with 5-80% ethyl acetate in hexanes to afford N-((1S)-1-(3-(1-(2-bromoethyl)-4-chloro-3-(methylsulfonamido)-1H-indazol-7-yl)-5-chloro-7-(4,4-difluorocyclohexyl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (250 mg, 238 μmol, yield=92%). LC/MS Method: Column=Acquity UPLC BEH C18, 2.1×100 mm, 1.7 μm particles; Solvent A=95:5 water:MeCN with 0.1% formic acid; Solvent B=5:95 water:MeCN with 0.1% formic acid; Gradient method (minutes/% B)=0/0, 3.5/100, 4.5/100; Flow Rate=0.8 mL/min; Injection Volume=5.00 μL; Wavelength=220 and 254 nm. LC/MS Result: Retention time=3.25 min; m/z=1051.90 [M+H]$^+$.

Preparation of N-((1S)-1-(3-(4-chloro-1-(3-methoxypropyl)-3-(methylsulfonamido)-1H-indazol-7-yl)-7-(4,4-difluorocyclohexyl)-5-formyl-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

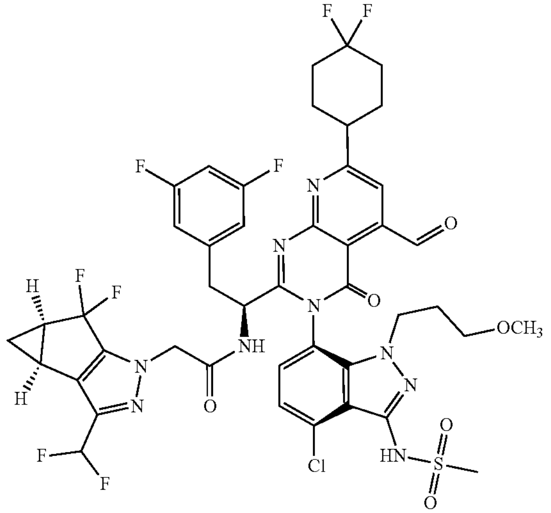

To a stirred solution of N-((1S)-1-(3-(4-chloro-1-(3-methoxypropyl)-3-(methylsulfonamido)-1H-indazol-7-yl)-7-(4,4-difluorocyclohexyl)-5-(hydroxymethyl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (1.70 g, 1.68 mmol) in DCM (50 mL) was added Dess-Martin periodinane (1.07 g, 2.52 mmol). The reaction mixture was stirred at room temperature for 2 h. To the mixture was added water and the mixture was then extracted with dichloromethane. The organic layer was dried over $Na_2SO_4$, filtered, and the filtrate was concentrated under reduced pressure. The resulting residue was subjected to silica gel column chromatography (80 g RediSep Gold silica gel column) eluting with 5-100% ethyl acetate in hexanes to afford N-((1S)-1-(3-(4-chloro-1-(3-methoxypropyl)-3-(methylsulfonamido)-1H-indazol-7-yl)-7-(4,4-difluorocyclohexyl)-5-formyl-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (1.40 g, yield=82%). LC/MS Method: Column=Acquity UPLC BEH C18, 2.1×100 mm, 1.7 μm particles; Solvent A=95:5 water:acetonitrile with 0.1% formic acid; Solvent B=5:95 water:acetonitrile with 0.1% formic acid; Gradient method (minutes/% B)=0/0, 3.5/100, 4.5/100; Flow Rate=0.8 mL/min; Injection Volume=5.00 μL; Wavelength=220 and 254 nm. LC/MS Result: Retention time=3.17 min; m/z=1010.20 [M+H]$^+$.

Preparation of N-((1S)-1-(3-(4-chloro-1-(3-methoxypropyl)-3-(methylsulfonamido)-1H-indazol-7-yl)-7-(4,4-difluoro-1-(2-hydroxyethyl)cyclohexyl)-5-methyl-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

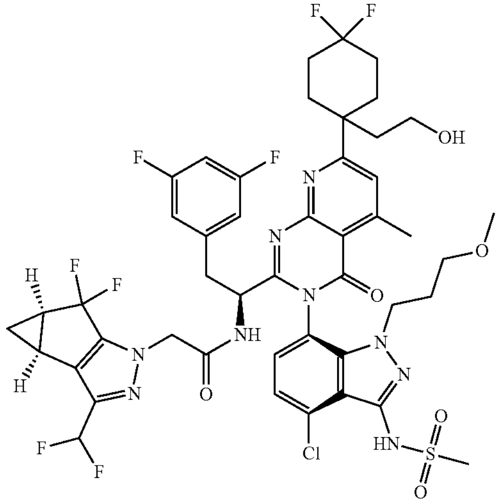

To a stirred suspension of N-((S)-7-(2-((S)-1-amino-2-(3,5-difluorophenyl)ethyl)-7-(4,4-difluoro-1-(2-hydroxyethyl)cyclohexyl)-5-methyl-4-oxopyrido[2,3-d]pyrimidin-3(4H)-yl)-4-chloro-1-(3-methoxypropyl)-1H-indazol-3-yl)methanesulfonamide (410 mg, 0.516 mol) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (273 mg, 1.03 mmol) in THF (5.16 mL) was added HATU (589 mg, 1.55 mmol) followed by DIPEA (540 μL, 3.10 mmol). The reaction mixture was stirred at room temperature for 2 h after which LC/MS analysis showed a major peak with the expected m/z value (bis-coupled product). The reaction mixture was diluted with water and then was extracted with ethyl acetate. The organic layer was dried over $Na_2SO_4$, filtered, and the filtrate was concentrated under reduced pressure. The resulting residue was treated with 2M ammonia in methanol (10 mL) for 30 min to cleave the ester of the bis-adduct. The mixture was concentrated under reduced pressure and the resulting residue was subjected to silica gel column chromatography (80 g RediSep Gold silica gel column) eluting with 5-100% ethyl acetate in hexanes to afford N-((1S)-1-(3-(4-chloro-1-(3-methoxypropyl)-3-(methylsulfonamido)-1H-indazol-7-yl)-7-(4,4-difluoro-1-(2-hydroxyethyl)cyclohexyl)-5-methyl-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (345 mg, 64%). LC/MS Method: Column=Acquity UPLC BEH C18, 1.7 μm, 2.1×100 mm; Solvent A=95:5 water:acetonitrile with 10 mM $NH_4OAc$; Solvent B=5:95 water:acetonitrile with 10 mM $NH_4OAc$; Gradient method (minutes/% B)=0/0, 3.5/100, 4.5/100; Flow rate=0.7 mL/min; Injection Volume=5.00 μL; Wavelength=220 and 254 nm. LC/MS Result: Retention time=3.25 min; m/z=1038.20 [M−H]$^-$. $^1$H NMR (500 MHz, METHANOL-$d_4$) δ ppm 1.00-1.03 (m, 1H) 1.32-1.39 (m, 1H) 1.75-1.97 (m, 6H) 2.39-2.45 (m, 2H) 2.66-2.74 (m, 2H) 2.81-2.86 (m, 5H) 3.04-3.19 (m, 4H) 3.25-3.26 (m, 3H) 3.37-3.42 (m, 3H) 3.84-3.91 (m, 1H) 4.00-4.07 (m, 1H) 4.54-4.63 (m, 3H) 4.84 (br d, J=4.77 Hz, 4H) 6.52-6.79 (m, 4H) 7.25-7.34 (m, 2H) 7.63 (s, 1H).

Preparation of N-((S)-1-(3-(1-(2-bromoethyl)-4-chloro-3-(methylsulfonamido)-1H-indazol-7-yl)-7-(4,4-difluorocyclohexyl)-5-((2-morpholinoethyl)amino)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

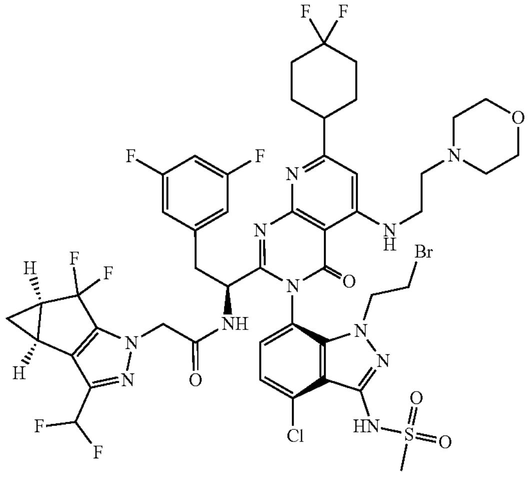

A stirred solution of N-((S)-1-(3-(1-(2-bromoethyl)-4-chloro-3-(methylsulfonamido)-1H-indazol-7-yl)-5-chloro-7-(4,4-difluorocyclohexyl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (250 mg, 238 μmol) and 2-morpholinoethan-1-amine (217 mg, 1.66 mmol) in ethanol (4 mL) was heated at 90° C. for 1 h. The reaction mixture was cooled to room temperature and concentrated under reduced pressure and the resulting residue was subjected to silica gel column chromatography (40 g RediSep Gold silica gel column) eluting with 5-100% ethyl acetate in hexanes to afford N-((S)-1-(3-(1-(2-bromoethyl)-4-chloro-3-(methylsulfonamido)-1H-indazol-7-yl)-7-(4,4-difluorocyclohexyl)-5-((2-morpholinoethyl)amino)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (180 mg, 157 μmol, yield=66%). LC/MS Method: Column=Acquity UPLC BEH C18, 2.1×100 mm, 1.7 μm particles; Solvent A=95:5 water:MeCN with 0.1% formic acid; Solvent B=5:95 water:MeCN with 0.1% formic acid; Gradient method (minutes/% B)=0/0, 3.5/100, 4.5/100; Flow Rate=0.8 mL/min; Injection Volume=5.00 μL; Wavelength=220 and 254 nm. LC/MS Result: Retention time=2.45 min; m/z=1146.0 $[M+H]^+$.

Preparation of N-((1S)-1-(3-(1-(2-bromoethyl)-4-chloro-3-(methylsulfonamido)-1H-indazol-7-yl)-7-(4,4-difluorocyclohexyl)-5-(hydroxymethyl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

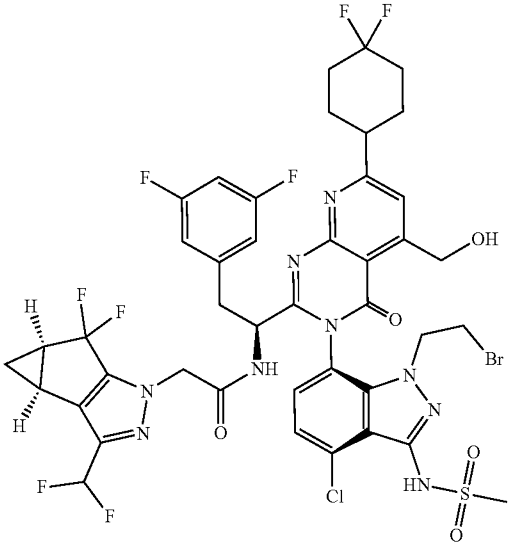

To a stirred suspension of N-(7-(2-((S)-1-amino-2-(3,5-difluorophenyl)ethyl)-7-(4,4-difluorocyclohexyl)-5-(hydroxymethyl)-4-oxopyrido[2,3-d]pyrimidin-3(4H)-yl)-1-(2-bromoethyl)-4-chloro-1H-indazol-3-yl)methanesulfonamide (1.00 g, 1.25 mmol) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (660 mg, 2.50 mmol) in THF (30 mL) was added HATU (1.42 g, 3.75 mmol) followed by DIPEA (1.09 mL, 6.24 mmol). The reaction mixture was stirred at room temperature for 2 h. LC/MS analysis showed a major peak with the expected m/z value corresponding to the bis-coupled product. To the mixture was added water was added, and the resulting mixture was extracted with ethyl acetate. The organic layer was dried over $Na_2SO_4$, filtered, and the filtrate was concentrated under reduced pressure. The resulting residue was treated with 2M ammonia in methanol (10 mL) for 30 min to cleave the ester of the bis-adduct. The mixture was concentrated under reduced pressure, and the resulting residue was subjected to silica gel column chromatography (80 g RediSep Gold silica gel column) eluting with 5-100% ethyl acetate in hexanes to afford N-((1 S)-1-(3-(1-(2-bromoethyl)-4-chloro-3-(methylsulfonamido)-1H-indazol-7-yl)-7-(4,4-difluorocyclohexyl)-5-(hydroxymethyl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (1.30 g, yield=99%). LC/MS Method: Column=Acquity UPLC BEH C18, 2.1×100 mm, 1.7 μm particles; Solvent A=0.1% formic acid in 95:5 water:acetonitrile; Solvent B=0.1% formic acid in 5:95 water:acetonitrile; Flow Rate=0.8 mL/min; Gradient method (minutes/% B)=0/0, 3.5/100, 4.5/100; Wavelength=220 and 254 nm. LC/MS Result: Retention time=3.05 min; m/z=1047.95 [M+H]+.

Preparation of N-((1S)-1-(3-(1-(2-bromoethyl)-4-chloro-3-(methylsulfonamido)-1H-indazol-7-yl)-7-(4,4-difluorocyclohexyl)-5-(((2S,6R)-2,6-dimethylmorpholino)methyl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

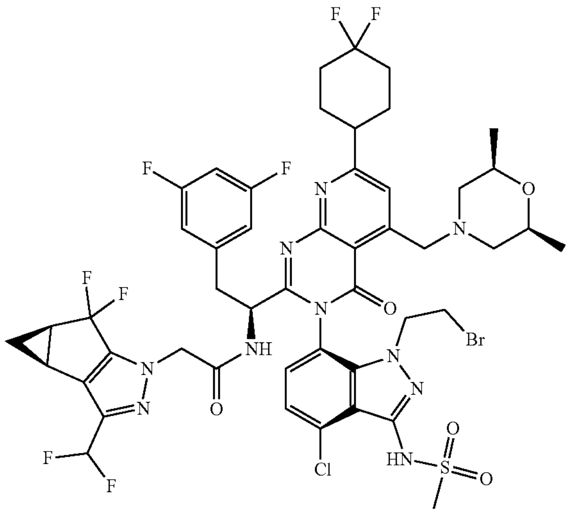

Step 1 (Formation of the Aldehyde)

To a solution of N-((1 S)-1-(3-(1-(2-bromoethyl)-4-chloro-3-(methylsulfonamido)-1H-indazol-7-yl)-7-(4,4-difluorocyclohexyl)-5-(hydroxymethyl)-4-oxo-3,4-dihydro-pyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (620 mg, 592 μmol) in DCM (15 mL) was added Dess-Martin periodinane (502 mg, 1.18 mmol) and the reaction mixture was stirred at room temperature for 1 h. The mixture was diluted with water and then was extracted with dichloromethane. The organic layer was dried over $Na_2SO_4$, filtered, and the filtrate was concentrated under reduced pressure to afford the crude aldehyde.

Step 2 (Reductive Amination Reaction)

The crude aldehyde was dissolved in DCM (15 mL). To the solution was added (2S,6R)-2,6-dimethylmorpholine (205 mg, 1.78 mmol), and the resulting mixture was stirred for 10 min. To the mixture was added sodium triacetoxy-borohydride (251 mg, 1.18 mmol), and the mixture was stirred for 16 h. The mixture was diluted with water and then was extracted with dichloromethane (25 mL). The organic layer was dried over $Na_2SO_4$, filtered, and the filtrate was concentrated under reduced pressure. The resulting residue was subjected to silica gel column chromatography (40 g RediSep Gold silica gel column) eluting with 5-100% ethyl acetate in hexanes to afford N-((1S)-1-(3-(1-(2-bromoethyl)-4-chloro-3-(methylsulfonamido)-1H-indazol-7-yl)-7-(4,4-difluorocyclohexyl)-5-(((2S,6R)-2,6-dimethylmorpholino)methyl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (350 mg, yield=52%). LC/MS Method: Column=Acquity UPLC BEH C18, 2.1×100 mm, 1.7 μm particles; Solvent A=95:5 water:acetonitrile with 0.1% formic acid; Solvent B=5:95 water:acetonitrile with 0.1% formic acid; Gradient method (minutes/% B)=0/0, 3.5/100, 4.5/100; Flow Rate=0.8 mL/min; Injection Volume=5.00 μL; Wave-length=220 and 254 nm. LC/MS Result: Retention time=2.70 min; m/z=1144.15 [M+H]+.

EXAMPLES

Preparation of Example 13: N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide

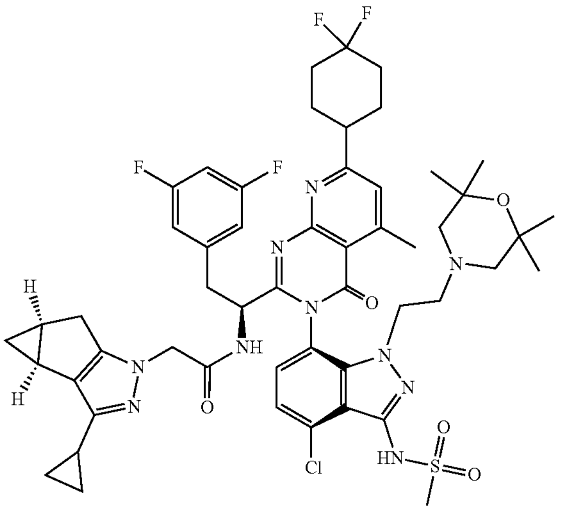

Example 13 was prepared according to General Procedure A as follows: N-((S)-1-(3-(1-(2-bromoethyl)-4-chloro-3-(methylsulfonamido)-1H-indazol-7-yl)-7-(4,4-difluorocyclohexyl)-5-methyl-4-oxo-3,4-dihydropyrido[2,3-d]pyrimidin-2-yl)-2-(3,5-difluorophenyl)ethyl)-2-((3bS,4aS)-3-cyclopropyl-3b,4,4a,5-tetrahydro-1H-cyclopropa[3,4]cyclopenta[1,2-c]pyrazol-1-yl)acetamide (35 mg, 0.036 mmol, 1 eq.), diisopropylethylamine (DIPEA, 4-5 eq.), potassium iodide (1 eq.), and 2,2,6,6-tetramethylmorpholine as the "diversity reagent" (4-6 eq.) were combined in acetonitrile (1 mL) at rt. The reaction mixture was stirred overnight at 60-80° C. The reaction mixture was cooled to room temperature. To the reaction mixture was added DMF (1 mL) and the resulting solution was filtered and then subjected to HPLC purification to afford the indicated product The experiment afforded Example 13, N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9- cyclopropyl-7,8-diazatricyclo[$4.3.0.0^{2,4}$]nona-1(6),8-dien-7-yl]acetamide. The sample was analyzed using LCMS Method B: retention time=1.52 min.; observed ion=1045.6 (M−H). $^1$H-NMR (500 MHz, METHANOL-d4) δ ppm 7.43 (d, J=0.60 Hz, 1H) 7.33 (d, J=8.05 Hz, 1H) 7.24 (d, J=7.75 Hz, 1H) 6.70-6.79 (m, 1H) 6.55 (dd, J=8.05, 2.09 Hz, 2H) 4.78-4.80 (m, 1H) 4.25 (d, J=1.49 Hz, 2H) 4.12 (ddd, J=13.71, 11.03, 5.36 Hz, 1H) 3.79 (ddd, J=13.56, 10.88, 5.07 Hz, 1H) 3.39 (dd, J=14.01, 5.07 Hz, 1H) 3.26 (s, 3H) 2.98-3.08 (m, 2H) 2.84 (s, 3H) 2.61-2.73 (m, 2H) 2.41-2.56 (m, 2H) 2.18-2.29 (m, 2H) 2.01-2.11 (m, 5H) 1.81-1.99 (m, 5H) 1.78 (tt, J=8.46, 4.95 Hz, 1H) 0.95 (d, J=3.87 Hz, 12H) 0.81-0.87 (m, 2H) 0.69-0.79 (m, 2H) 0.05-0.09 (m, 1H).

Alternative Preparation of Example 13: N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[$4.3.0.0^{2,4}$]nona-1(6),8-dien-7-yl]acetamide

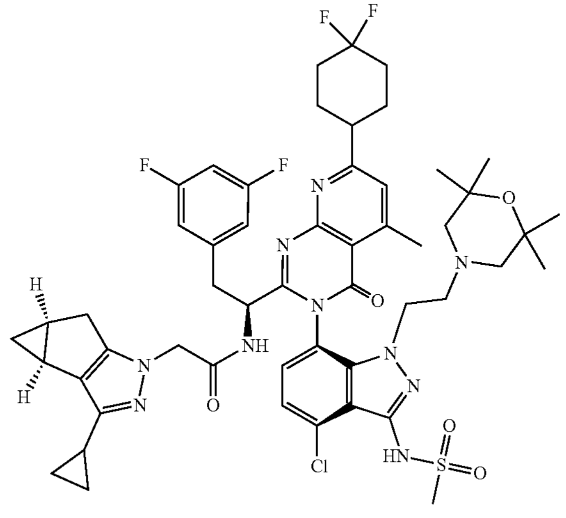

Example 13 was prepared according to General Procedure A as follows: N-((S)-1-(3-(1-(2-bromoethyl)-4-chloro-3-(methylsulfonamido)-1H-indazol-7-yl)-7-(4,4-difluorocyclohexyl)-5-methyl-4-oxo-3,4-dihydropyrido[2,3-d]pyrimidin-2-yl)-2-(3,5-difluorophenyl)ethyl)-2-((3bS,4aS)-3-cyclopropyl-3b,4,4a,5-tetrahydro-1H-cyclopropa[3,4]cyclopenta[1,2-c]pyrazol-1-yl)acetamide (150.0 mg, 1 Eq, 152.2 μmol), DIPEA (98.385 mg, 133 μL, 5 Eq, 761.20 μmol), potassium iodide (25.3 mg, 1 Eq, 152 μmol) and 2,2,6,6-tetramethylmorpholine (65.4 mg, 3 Eq, 457 μmol), were combined in acetonitrile (3.0 mL) at rt. The reaction mixture was stirred at 80° C. for approximately 18 h (overnight). The mixture was cooled to rt, diluted with ethyl acetate (20 mL), washed with water, dried over $Na_2SO_4$, filtered and the filtrate was concentrated under reduced pressure. The resulting residue was subjected to silica gel flash chromatography (40 g RediSep Gold column) eluting with 5-100% EtOAc in hexanes to afford Example 13, N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[$4.3.0.0^{2,4}$]nona-1(6),8-dien-7-yl]acetamide, (110 mg, 68% yield) as a white solid.

$^1$H NMR (500 MHz, METHANOL-d4) δ ppm 7.43 (d, J=0.60 Hz, 1H) 7.33 (d, J=8.05 Hz, 1H) 7.24 (d, J=7.75 Hz, 1H) 6.70-6.79 (m, 1H) 6.55 (dd, J=8.05, 2.09 Hz, 2H) 4.78-4.80 (m, 1H) 4.25 (d, J=1.49 Hz, 2H) 4.12 (ddd, J=13.71, 11.03, 5.36 Hz, 1H) 3.79 (ddd, J=13.56, 10.88, 5.07 Hz, 1H) 3.39 (dd, J=14.01, 5.07 Hz, 1H) 3.26 (s, 3H) 2.98-3.08 (m, 2H) 2.84 (s, 3H) 2.61-2.73 (m, 2H) 2.41-2.56 (m, 2H) 2.18-2.29 (m, 2H) 2.01-2.11 (m, 5H) 1.81-1.99 (m, 5H) 1.78 (tt, J=8.46, 4.95 Hz, 1H) 0.95 (d, J=3.87 Hz, 12H) 0.81-0.87 (m, 2H) 0.69-0.79 (m, 2H) 0.05-0.09 (m, 1H). LC/MS Method: Column=Acquity UPLC BEH C18 (1.7 μm, 2.1×100 mm); Solvent A=95:5 water:acetonitrile with 0.1% formic acid; Solvent B=5:95 water:acetonitrile with 0.1% formic acid; Gradient method (minutes/% B)=0/0, 3.5/100, 4.5/100; Flow Rate=0.8 mL/min; Injection Volume=5.00 μL; Wavelength=220 and 254 nm. LC/MS Result: Retention time=3.22 min; m/z=1047.35 [M+H]$^+$.

Alternative Reparation of Example 13: N-[(1S)-1-[(3P)-3-{4-Chloro-3-Methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[$4.3.0.0^{2,4}$]nona-1(6),8-dien-7-yl]acetamide

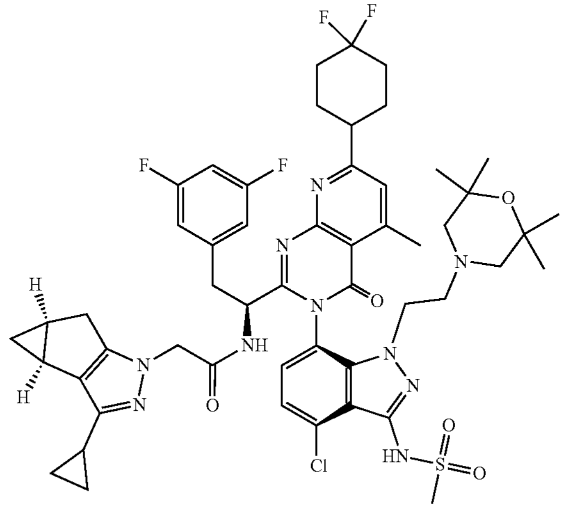

Example 13 was prepared according to General Procedure B as follows: To a stirred solution of N-(7-(2-((S)-1-amino-2-(3,5-difluorophenyl)ethyl)-7-(4,4-difluorocyclohexyl)-5-methyl-4-oxopyrido[2,3-d]pyrimidin-3(4H)-yl)-4-chloro-1-(2-(2,2,6,6-tetramethylmorpholino)ethyl)-1H-indazol-3-yl)methanesulfonamide (1.00 g, 1.18 mmol, 1.0 Eq) and 2-((3bS,4aS)-3-cyclopropyl-3b,4,4a,5-tetrahydro-1H-cyclopropa[3,4]cyclopenta[1,2-c]pyrazol-1-yl)acetate triethylamine salt (396 mg, 1.24 mmol, 1.05 Eq) in ethyl acetate (20 mL) was added 2,6-lutidine (316 mg, 0.342 mL, 2.50 Eq, 2.95 mmol) followed by 2,4,6-tripropyl-1,3,5,2,4,6-trioxatriphosphinane 2,4,6-trioxide ("T3P", 50 wt % in ethyl acetate, 1.46 mL, 2.36 mmol, 2.0 Eq) and the resulting mixture was stirred at room temp for 4 h. The mixture was diluted with water and then was extracted with ethyl acetate, dried over $Na_2SO_4$, filtered and the filtrate was concentrated under reduced pressure. The resulting residue was subjected to flash silica gel chromatography (120 g RediSep Gold column) eluting with 5-80% ethyl acetate in hexanes to afford Example 13, N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide (1.03 g, 83% yield).

$^1$H NMR (500 MHz, METHANOL-d4) δ ppm 7.43 (d, J=0.60 Hz, 1H) 7.33 (d, J=8.05 Hz, 1H) 7.24 (d, J=7.75 Hz, 1H) 6.70-6.79 (m, 1H) 6.55 (dd, J=8.05, 2.09 Hz, 2H) 4.78-4.80 (m, 1H) 4.25 (d, J=1.49 Hz, 2H) 4.12 (ddd, J=13.71, 11.03, 5.36 Hz, 1H) 3.79 (ddd, J=13.56, 10.88, 5.07 Hz, 1H) 3.39 (dd, J=14.01, 5.07 Hz, 1H) 3.26 (s, 3H) 2.98-3.08 (m, 2H) 2.84 (s, 3H) 2.61-2.73 (m, 2H) 2.41-2.56 (m, 2H) 2.18-2.29 (m, 2H) 2.01-2.11 (m, 5H) 1.81-1.99 (m, 5H) 1.78 (tt, J=8.46, 4.95 Hz, 1H) 0.95 (d, J=3.87 Hz, 12H) 0.81-0.87 (m, 2H) 0.69-0.79 (m, 2H) 0.05-0.09 (m, 1H). LC/MS Method: Column=Acquity UPLC BEH C18, 1.7 μm, 2.1×100 mm; Solvent A=95:5 water:acetonitrile with 0.1% formic acid; Solvent B=5:95 water:acetonitrile with 0.1% formic acid; Gradient method (minutes/% B)=0/0, 3.5/100, 4.5/100; Flow Rate=0.8 mL/min; Injection Volume=5.00 μL; Wavelength=220 and 254 nm. LC/MS Result: Retention time=3.32 min; m/z=1047.30 [M+H]$^+$.

Preparation of Example 159: N-[(1S)-1-[(3P)-3-(4-chloro-1-{2-[(2R,6S)-2,6-dimethylmorpholin-4-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide

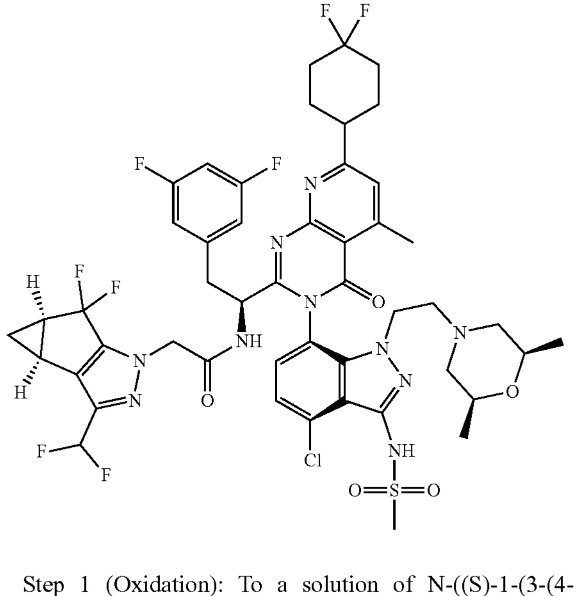

Step 1 (Oxidation): To a solution of N-((S)-1-(3-(4-chloro-1-(2-hydroxyethyl)-3-(methylsulfonamido)-1H-indazol-7-yl)-7-(4,4-difluorocyclohexyl)-5-methyl-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (25 mg, 0.026 mmol) in DCM (1 mL) was added Dess-Martin periodinane (21.90 mg, 0.052 mmol). The resulting mixture was stirred at room temperature for 17 hours upon which LCMS analysis indicated a mixture of the aldehyde product and the carboxylic acid product. The mixture was diluted with wanted and then extracted with DCM. The organic layer was dried over $Na_2SO_4$, filtered, and concentrated in vacuo to afford the crude residue.

Step 2 (Reductive amination): To a solution of the crude aldehyde residue from Step 2 in DCM (2R,6S)-2,6-was added dimethylmorpholine (8.92 mg, 0.077 mmol). The mixture was stirred for 10 minutes, then to the mixture was added sodium triacetoxyborohydride (10.94 mg, 0.052 mmol). The reaction was stirred for 16 hours upon which LCMS analysis confirmed the formation of the desired amine product. The reaction mixture was concentrated in vacuo and the resulting residue was subjected to preparative HPLC purification using 10 mM $NH_4OAc$ buffered water/acetonitrile to afford the desired product, Example 159, which was characterized using LCMS Method A: retention time=2.56 min.; observed ion=1065.2 [M+H].

1H NMR (500 MHz, METHANOL-d4), δppm7.45 (d, J=0.60 Hz, 1H), 7.32 (d, J=7.75 Hz, 1H), 7.22 (d, J=7.75 Hz, 1H), 6.56-6.80 (m, 2H), 6.51 (dd, J=8.05, 2.09 Hz, 2H), 4.75-4.79 (m, 1H), 4.57-4.69 (m, 2H), 4.17 (ddd, J=14.01, 10.73, 5.66 Hz, 1H), 3.80-3.91 (m, 1H), 3.37 (dd, J=14.31, 4.77 Hz, 1H), 3.23 (s, 3H), 3.15-3.21 (m, 1H), 2.99-3.07 (m, 2H), 2.84 (s, 3H), 2.66 (td, J=11.40, 5.51 Hz, 1H), 2.38-2.51 (m, 4H), 2.18-2.28 (m, 3H), 1.94-2.12 (m, 6H), 1.54 (t, J=10.58 Hz, 1H), 1.31-1.39 (m, 2H), 1.00-1.05 (m, 1H), 0.97 (d, J=6.26 Hz, 3H), 0.84 (d, J=6.26 Hz, 3H).

Preparation of Example 229: N-[(1S)-1-[(3P)-3-{4-chloro-1-[2-(3,3-difluoroazetidin-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide

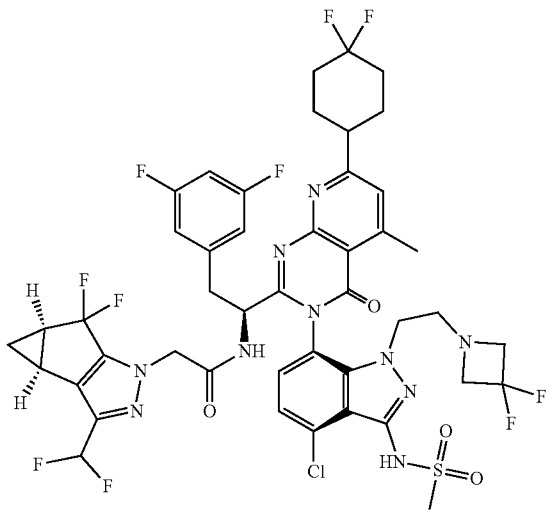

To a stirred solution of N-((S)-1-(3-(4-chloro-3-(methylsulfonamido)-1-(2-oxoethyl)-1H-indazol-7-yl)-7-(4,4-difluorocyclohexyl)-5-methyl-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (60 mg, 62 μmol) and 3,3-difluoroazetidine hydrochloride (12.1 mg, 93 μmol) in 1,2-dichloroethane (2 mL) was added triethylamine (17 μL, 124 μmol). The reaction mixture was stirred at room temperature for 15 min. To the mixture was added sodium triacetoxyborohydride (26.3 mg, 124 μmol), and the mixture was stirred at room temperature for 6 h. The reaction mixture was concentrated under reduced pressure and the resulting residue was subjected to HPLC purification to afford Example 229, which was characterized using LCMS Method A: retention time=3.04 min.; observed ion=1043.50 [M+H]+.

1H NMR (500 MHz, METHANOL-d4), δppm7.43 (d, J=0.60 Hz, 1H), 7.26-7.36 (m, 1H), 7.21 (d, J=7.75 Hz, 1H), 6.49-6.77 (m, 4H), 4.78 (dd, J=9.39, 4.92 Hz, 1H), 4.51-4.68 (m, 2H), 3.95-4.05 (m, 1H), 3.66 (dt, J=14.01, 7.00 Hz, 1H), 3.39 (dd, J=14.01, 4.77 Hz, 1H), 3.20-3.28 (m, 6H), 2.96-3.07 (m, 2H), 2.79-2.86 (m, 5H), 2.42 (ddd, J=11.18, 7.60, 3.87 Hz, 2H), 2.19-2.29 (m, 2H), 2.03-2.12 (m, 5H), 1.96-2.02 (m, 1H), 1.32-1.38 (m, 1H), 0.97-1.04 (m, 1H).

Preparation of Example 449: N-[(1S)-1-[(3P)-3-[4-chloro-3-methanesulfonamido-1-(3-methoxypropyl)-1H-indazol-7-yl]-7-(4,4-difluorocyclohexyl)-5-(fluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide

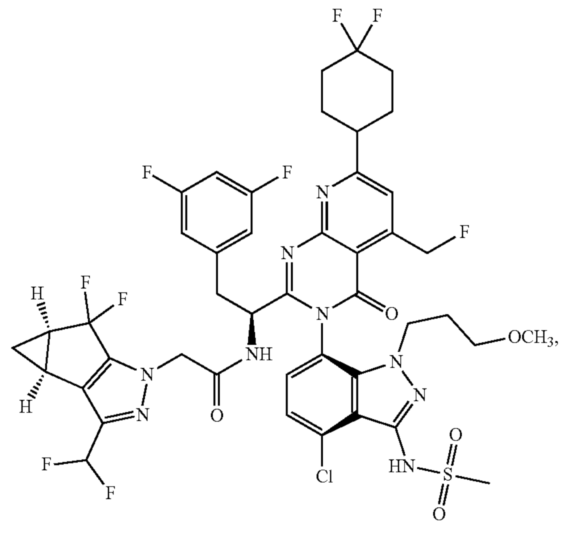

To a solution of N-((1 S)-1-(3-(4-Chloro-1-(3-methoxypropyl)-3-(methylsulfonamido)-1H-indazol-7-yl)-7-(4,4-difluorocyclohexyl)-5-(hydroxymethyl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide ("Alcohol E1", 25 mg, 25 μmol) in dichloromethane (1.0 mL) cooled to 0° C. was added diethylaminosulfur trifluoride ("DAST", 8 mg, 6.5 μL, 50 μmol). The reaction mixture was allowed to warm to room temperature with stirring for 1 h, then to the mixture was added saturated aqueous sodium bicarbonate solution. The organic layer was isolated, dried over anhydrous sodium sulfate, filtered, and the filtrate was concentrated under reduced pressure. The resulting residue was subjected to HPLC purification to afford Example 449, which was characterized using LCMS Method A: retention time=3.25 min.; observed ion=1014.00 [M+H]+.

1H NMR (500 MHz, METHANOL-d4) δ ppm 7.63 (s, 1H), 7.20 (d, J=7.75 Hz, 1H), 7.09 (d, J=7.75 Hz, 1H), 6.41-6.72 (m, 4H), 5.77-6.02 (m, 2H), 4.73 (br d, J=5.07 Hz, 1H), 4.42-4.50 (m, 2H), 3.89 (ddd, J=14.31, 10.73, 5.66 Hz, 1H), 3.71 (ddd, J=14.16, 10.88, 5.07 Hz, 1H), 3.31 (dd, J=14.01, 5.07 Hz, 1H), 3.14 (s, 3H), 3.03-3.10 (m, 2H), 2.93-3.00 (m, 2H), 2.63 (s, 3H), 2.32 (ddd, J=11.03, 7.60, 4.02 Hz, 2H), 2.10-2.20 (m, 2H), 1.94-2.05 (m, 5H), 1.86-1.93 (m, 1H), 1.65-1.82 (m, 2H), 1.22-1.30 (m, 1H), 0.85-0.95 (m, 1H).

Preparation of Example 620: N-[(1S)-1-[(3P)-3-(4-chloro-1-{2-[(3R,5S)-3,5-difluoropiperidin-1-yl]ethyl}-3-methanesulfonamido-1H-indazol-7-yl)-5-[(3,3-difluoroazetidin-1-yl)methyl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,]nona-1(6),8-dien-7-yl]acetamide

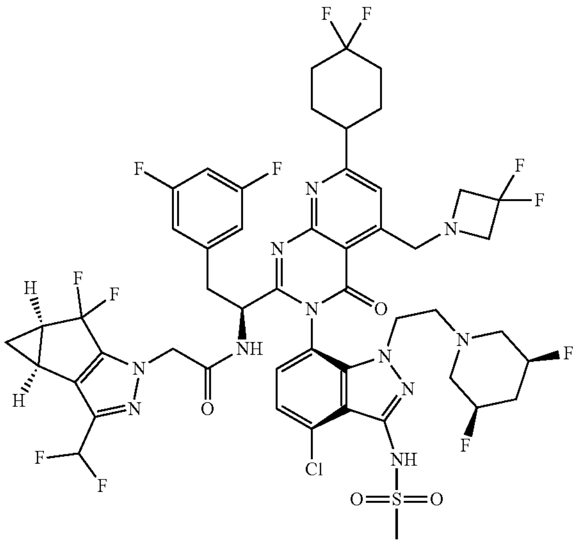

A solution of 3,3-difluoroazetidine hydrochloride (107 mg, 830 μmol), N-((1S)-1-(3-(4-chloro-1-(2-((3S,5R)-3,5-difluoropiperidin-1-yl)ethyl)-3-(methylsulfonamido)-1H-indazol-7-yl)-7-(4,4-difluorocyclohexyl)-5-formyl-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (300 mg, 276 μmol), and triethylamine ("TEA", 84 mg, 830 μmol) in 1,2-dichloroethane (6.0 mL) was heated at 60° C. for 1 h. To the solution was added sodium triacetoxyborohydride (176 mg, 830 μmol). The reaction mixture was heated at 60° C. for 16 h. The reaction mixture was cooled to room temperature and then concentrated under reduced pressure. The resulting residue was subjected to HPLC purification to afford Example 620, which was characterized by LCMS Method A: retention time=3.19 min.; observed ion=1162.30 [M+H]+.

1H NMR (500 MHz, METHANOL-d4) δ ppm 7.66 (s, 1H), 7.35 (d, J=7.75 Hz, 1H), 7.23 (d, J=7.75 Hz, 1H), 6.52-6.83 (m, 4H), 4.81 (br d, J=4.47 Hz, 1H), 4.62 (br d, J=10.73 Hz, 2H), 4.20-4.50 (m, 4H), 4.12-4.19 (m, 1H), 3.81 (t, J=12.07 Hz, 4H), 3.41 (dd, J=14.01, 4.77 Hz, 1H), 3.37 (s, 3H), 3.27 (s, 3H), 3.12-3.17 (m, 1H), 3.07 (dd, J=14.16, 9.39 Hz, 1H), 2.72-2.82 (m, 2H), 2.40-2.59 (m, 4H), 2.06-2.30 (m, 10H), 1.62-1.73 (m, 1H), 1.35-1.41 (m, 1H), 1.03 (br dd, J=2.98, 2.09 Hz, 1H).

Preparation of Example 621: N-[(1S)-1-[(3P)-3-{4-chloro-3-methanesulfonamido-1-[2-(2,2,6,6-tetramethylmorpholin-4-yl)ethyl]-1H-indazol-7-yl}-5-[(3,3-difluoroazetidin-1-yl)methyl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide

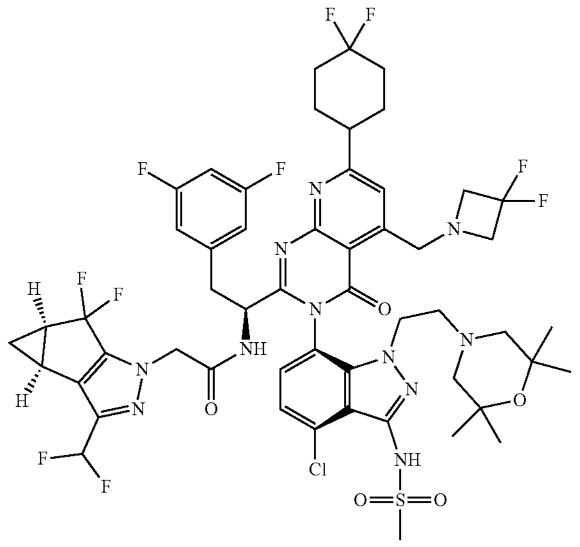

A solution of 3,3-Difluoroazetidine hydrochloride (74 mg, 570 μmol), N-((1S)-1-(3-(4-chloro-3-(methylsulfonamido)-1-(2-(2,2,6,6-tetramethylmorpholino)ethyl)-1H-indazol-7-yl)-7-(4,4-difluorocyclohexyl)-5-formyl-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (210 mg, 190 μmol), and triethylamine (TEA, 58 mg, 570 μmol) in 1,2-dichloroethane (5.0 mL) were heated at 60° C. for 1 h. To the solution was added sodium triacetoxyborohydride (121 mg, 570 μmol). The mixture was heated at 60° C. for 16 h. The reaction mixture was cooled to room temperature, diluted with dichloromethane (10 mL), and then washed with saturated aqueous sodium bicarbonate solution. The organic layer was dried over anhydrous sodium sulfate, filtered, and the filtrate concentrated under reduced pressure. The resulting residue was subjected to preparatory HPLC purification to afford Example 621, which was characterized using LCMS Method A: retention time=3.38 min.; observed ion=1184.20 [M+H]+.

1H NMR (500 MHz, METHANOL-d4) δ ppm 7.68 (s, 1H), 7.36 (d, J=8.05 Hz, 1H), 7.25 (d, J=7.75 Hz, 1H), 6.50-6.83 (m, 4H), 4.82-4.85 (m, 1H), 4.61 (s, 2H), 4.37-4.55 (m, 2H), 4.18 (ddd, J=13.71, 11.33, 5.36 Hz, 1H), 3.75-3.89 (m, 5H), 3.40 (dd, J=14.16, 4.62 Hz, 1H), 3.26 (s, 3H), 3.11-3.17 (m, 1H), 3.07 (dd, J=14.31, 9.54 Hz, 1H), 2.64 (td, J=11.62, 5.36 Hz, 1H), 2.47-2.55 (m, 1H), 2.41-2.47 (m, 2H), 2.20-2.32 (m, 2H), 2.00-2.15 (m, 6H), 1.86-1.98 (m, 4H), 1.35-1.41 (m, 1H), 1.02-1.07 (m, 1H), 0.96 (d, J=10.13 Hz, 12H).

Preparation of Example 675: N-[(1S)-1-[(3P)-3-{4-chloro-1-[2-(4,4-difluoropiperidin-1-yl)ethyl]-3-methanesulfonamido-1H-indazol-7-yl}-7-(4,4-difluorocyclohexyl)-5-(hydroxymethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide

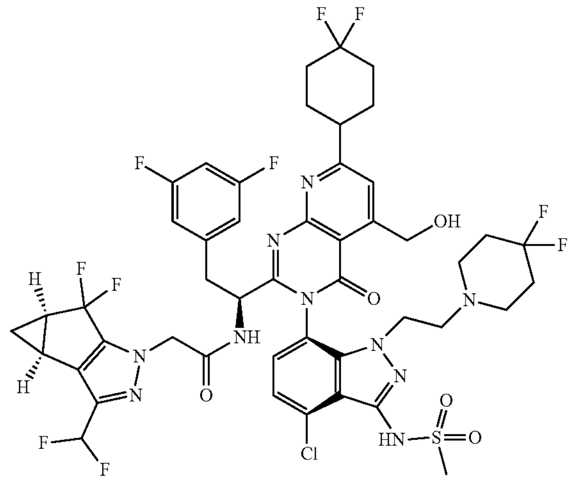

Example 675 was prepared in two steps. Step 1: General Procedure B-2 was followed using (S)-N-(7-(2-(1-amino-2-(3,5-difluorophenyl)ethyl)-7-(4,4-difluorocyclohexyl)-5-(hydroxymethyl)-4-oxopyrido[2,3-d]pyrimidin-3(4H)-yl)-4-chloro-1-(2-(4,4-difluoropiperidin-1-yl)ethyl)-1H-indazol-3-yl)methanesulfonamide (400 mg, 423 μmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (200 mg, 719 μmol), HOBt (200 mg, 1.31 mmol), EDO (600 mg, 3.13 mmol), N-methylmorpholine (2×500 μL, 2×4.55 mmol=9.1 mmol) and DMF (4 mL). Step 2: The crude product from Step 1 was dissolved in THF (2 mL) and the resulting solution was combined in a sealed tube with a solution of ammonia in methanol (2.0 mL, 23 mmol). The solution was stirred at room temperature for 6 h and then the solution was concentrated under reduced pressure. The resulting residue was treated at 0° C. with aq. 1N HCl (20 mL). The mixture was stirred for 10 min and then the solids were collected by filtration to afford crude product as a yellow solid. The crude product was subjected to preparatory HPLC purification to afford Example 675 which was characterized using the following LCMS Method:

Column=Acquity BEH C18 (2.1×50 mm, 1.7 μm); Solvent A=0.05% Formic Acid in water; Solvent B=0.05% Formic Acid in acetonitrile; Flow Rate=0.6 mL/min; Gradient Method (min.)/% B: 0/3, 0.4/3, 2.5/98, 3.5/98; Wavelength=210 nm to 400 nm.: retention time=1.96 min.; observed ion=1087.2 [M+H]+.

1H NMR (400 MHz, DMSO-d6, 298.1 K), Shift (ppm) =9.88 (br s, 1H), 9.43 (br d, J=6.8 Hz, 1H), 7.87-7.74 (m, 2H), 7.62-7.47 (m, 1H), 7.18-6.75 (m, 2H), 6.61-6.55 (m, 2H), 5.69 (br t, J=5.8 Hz, 1H), 5.16-5.00 (m, 2H), 4.72-4.63 (m, 1H), 4.60-4.48 (m, 2H), 3.94-3.85 (m, 1H), 3.81-3.71 (m, 1H), 3.58-3.49 (m, 1H), 3.23-3.16 (m, 4H), 3.02-2.93 (m, 1H), 2.47-2.34 (m, 4H), 2.23-1.95 (m, 12H), 1.64-1.51 (m, 4H), 1.40-1.33 (m, 1H), 0.89-0.83 (m, 1H).

Preparation of Example 698: N-[(1S)-1-[(3P)-3-{4-chloro-1-[2-(4,4-difluoropiperidin-1-yl)ethyl]-3-methanesulfonamido-1H-indazol-7-yl}-7-(4,4-difluorocyclohexyl)-5-[(1R**)-1-hydroxyethyl]-4-oxo-3H,4H-pyrido[2,3-d]pyrimidin-2-yl]-2-(3,5-difluorophenyl)ethyl]-2-[(2R*,4S*)-9-(difluoromethyl)-5,5-difluoro-7,8-diazatricyclo[4.3.0.0$^{2,4}$]nona-1(6),8-dien-7-yl]acetamide

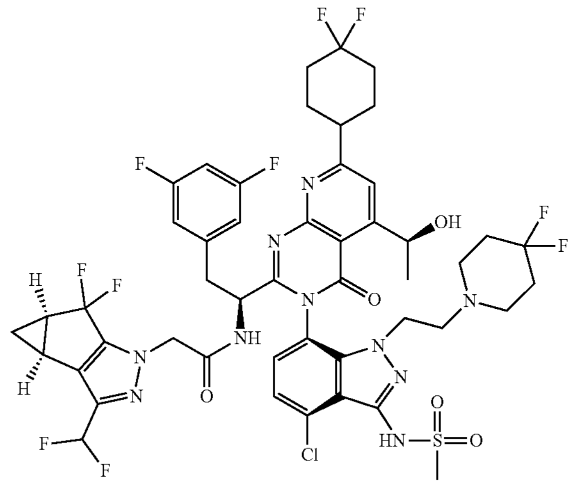

To a stirred solution of N-((S)-1-(3-(4-chloro-1-(2-(4,4-difluoropiperidin-1-yl)ethyl)-3-(methylsulfonamido)-1H-indazol-7-yl)-7-(4,4-difluorocyclohexyl)-5-formyl-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (300 mg, 0.25 mmol) in tetrahydrofuran (2 mL) at −78° C. was added methylmagnesium bromide (268 μL, 0.75 mmol). The reaction mixture was stirred at −78° C. for 45 min. The progress of the reaction was monitored by TLC (mobile phase: 60% ethyl acetate in petroleum ether). Upon completion of the reaction, the reaction mixture was quenched with saturated aqueous ammonium chloride solution (10 mL) and extracted with ethyl acetate (2×10 mL). The combined organic layers were washed with brine (2×20 mL), dried over anhydrous sodium sulfate, filtered, and the filtrate was concentrated under reduced pressure to afford crude product as a pale yellow solid. The crude product was subjected to HPLC purification to afford Example 698, which was characterized using the following LCMS method F: retention time=2.03 min.; observed ion=1101.50 [M+H]+.

1H NMR (400 MHz, DMSO-d6, 298.2 K), Shift (ppm) =9.44-9.41 (m, 1H), 7.83 (s, 1H), 7.68-7.62 (m, 1H), 7.45-7.32 (m, 1H), 7.02-6.75 (m, 2H), 6.60-6.50 (m, 2H), 5.83-5.80 (m, 1H), 5.54-5.52 (m, 1H), 4.70-4.57 (m, 3H), 3.80-3.75 (m, 2H), 3.36-3.31 (m, 1H), 3.13-2.91 (m, 5H), 2.67-2.40 (m, 4H), 2.07-1.97 (m, 12H), 1.60-1.54 (m, 4H), 1.33-1.31 (m, 4H), 1.24-1.22 (m, 1H), 0.85-0.75 (m, 1H).

Preparation of Example 746: N-[(1S)-1-[(3P)-5-acetyl-3-{4-chloro-1-[2-(4,4-difluoropiperidin-1-yl)ethyl]-3-methanesulfonamido-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide

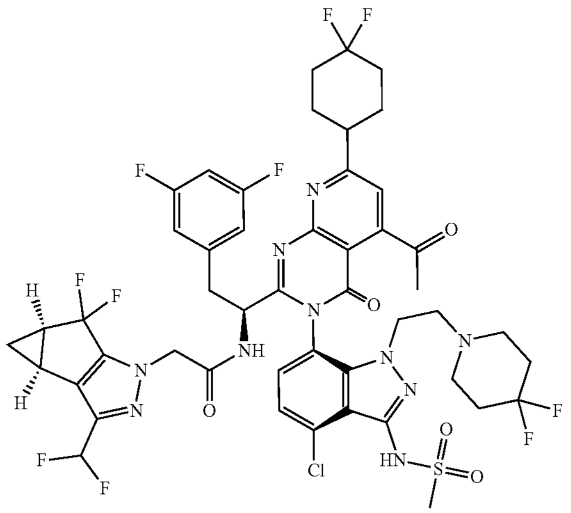

To a stirred solution of N-((1S)-1-(3-(4-chloro-1-(2-(4,4-difluoropiperidin-1-yl)ethyl)-3-(methylsulfonamido)-1H-indazol-7-yl)-7-(4,4-difluorocyclohexyl)-5-(1-hydroxyethyl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (150 mg, 133 μmol) in dichloromethane (10 mL) was added manganese dioxide (600 mg, 6.90 mmol) and the mixture was stirred at 27° C. for 2 h. To the mixture was added second portion of manganese dioxide (500 mg, 5.75 mmol) and the mixture was stirred at 27° C. for 16 h. The reaction mixture was filtered through a celite pad, and the filter cake was washed with ethyl acetate (30 mL). The filtrate was concentrated under reduced pressure and the resulting residue was subjected to HPLC purification to afford Example 746, which was characterized using the following LMCS Method F: retention time=2.03 min.; observed ion=1099.33 [M+H]+.

1H NMR (400 MHz, DMSO-d6, 298.2 K), Shift (ppm) =9.81 (br s, 1H), 9.48-9.46 (m, 1H), 7.82-7.80 (m, 1H), 7.56-7.51 (m, 2H), 7.06-6.75 (m, 2H), 6.58-6.56 (in, 2H), 4.71-4.67 (m, 1H), 4.56-4.52 (m, 2H), 3.92-3.70 (m, 2H), 3.36-3.31 (m, 1H), 3.19-3.10 (m, 4H), 2.98-2.96 (m, 1H), 2.52-2.32 (m, 7H), 2.22-1.92 (m, 12H), 1.61-1.51 (m, 4H), 1.40-1.30 (m, 1H), 0.85-0.82 (in, 1H).

Further Example compounds were synthesized as described in Table A below:

TABLE A

| Example No. (preparation of the Example) | Structure and IUPAC name | Characterising data (LCMS and/or NMR) |
|---|---|---|
| 1 (General Procedure A using Bromide A1 as the core reagent) | 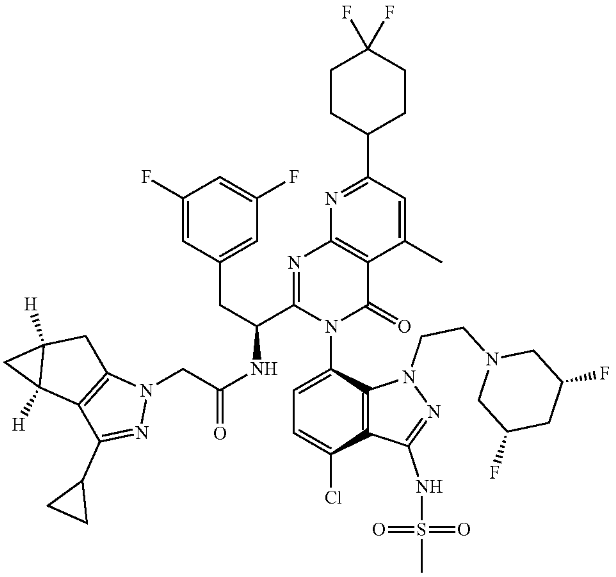 N-[(1S)-1-[(3P)-3-(4-chloro-1-{2-[(3R,5S)-3,5-difluoropiperidin-1-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.37 min.; observed ion = 1023.4 [M − H]. 1H NMR (500 MHz, METHANOL-d4) δ ppm 7.42 (d, J = 0.89 Hz, 1 H), 7.31 (d, J = 7.75 Hz, 1 H), 7.19 (d, J = 7.75 Hz, 1 H), 6.77 (tt, J = 9.20, 2.27 Hz, 1 H), 6.57 (dd, J = 8.20, 2.24 Hz, 2 H), 4.77-4.80 (m, 1 H), 4.19-4.40 (m, 4 H), 4.00-4.09 (m, 1 H), 3.68-3.77 (m, 1 H), 3.39 (dd, J = 14.01, 5.07 Hz, 1 H), 3.27 (s, 3 H), 2.98-3.08 (m, 2 H), 2.84 (s, 3 H), 2.74-2.81 (m, 1 H), 2.63-2.72 (m, 2 H), 2.42-2.58 (m, 3 H), 2.12-2.28 (m, 5 H), 1.89-2.12 (m, 7 H), 1.82-1.87 (m, 1 H), 1.77 (tt, J = 8.49, 5.07 Hz, 1 H), 1.56-1.68 (m, 1 H), 0.95 (td, J = 7.67, 4.62 Hz, 1 H), 0.81-0.90 (m, 2 H), 0.70-0.79 (m, 2 H), 0.04-0.09 (m, 1 H). |
| 2 (General Procedure A using Bromide A1 as the core reagent) | 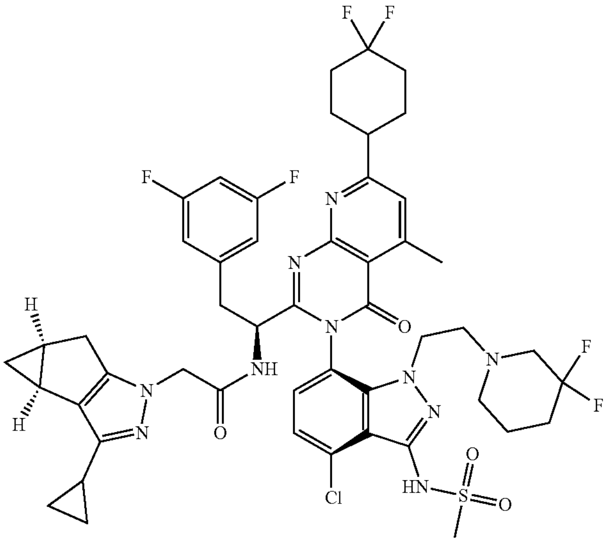 N-[(1S)-1-[(3P)-3-{4-chloro-1-[2-(3,3-difluoropiperidin-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.48 min.; observed ion = 1023.4 [M − H]. 1H NMR (500 MHz, METHANOL-d4) δ ppm 7.41 (d, J = 0.89 Hz, 1 H), 7.32 (d, J = 7.75 Hz, 1 H), 7.20 (d, J = 7.75 Hz, 1 H), 6.70-6.82 (m, 1 H), 6.50-6.62 (m, 2 H), 4.74 (br s, 1 H), 4.26 (s, 2 H), 4.07 (ddd, J = 14.01, 10.43, 5.66 Hz, 1 H), 3.70 (ddd, J = 14.23, 9.76, 4.92 Hz, 1 H), 3.40 (dd, J = 14.01, 5.07 Hz, 1 H), 3.26 (s, 3 H), 3.05 (br dd, J = 14.01, 8.94 Hz, 2 H), 2.81-2.85 (m, 3 H), 2.64-2.77 (m, 2 H), 2.52-2.62 (m, 1 H), 2.45 (br d, J = 16.69 Hz, 1 H), 2.19-2.35 (m, 4 H), 1.89-2.18 (m, 9 H), 1.81-1.87 (m, 1 H), 1.74-1.80 (m, 1 H), 1.65-1.74 (m, 2 H), 1.46 (quin, J = 5.96 Hz, 2 H), 0.95 (td, J = 7.60, 4.77 Hz, 1 H), 0.81-0.90 (m, 2 H), 0.70-0.80 (m, 2 H), 0.05-0.09 (m, 1 H). |

TABLE A-continued

| Example No. (preparation of the Example) | Structure and IUPAC name | Characterising data (LCMS and/or NMR) |
|---|---|---|
| 3 (General Procedure A using Bromide A1 as the core reagent) | 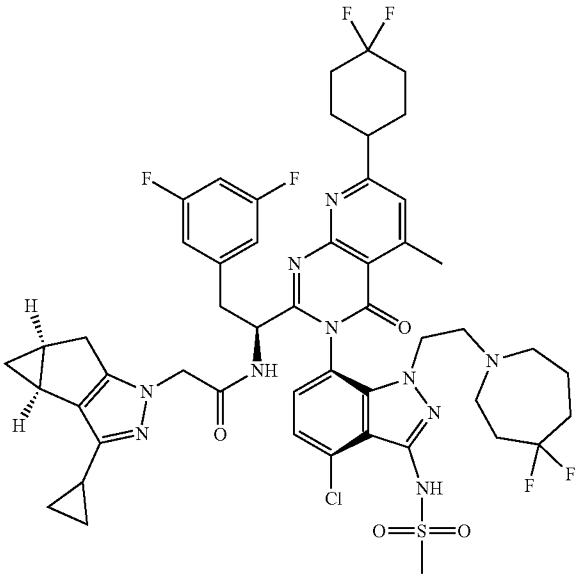 N-[(1S)-1-[(3P)-3-{4-chloro-1-[2-(4,4-difluoroazepan-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide. | LCMS Method B: retention time = 1.20 min.; observed ion = 1037.4 [M − H]. 1H NMR (500 MHz, METHANOL-d4) δ ppm 7.44 (d, J = 0.60 Hz, 1 H), 7.33 (d, J = 8.05 Hz, 1 H), 7.24 (d, J = 7.75 Hz, 1 H), 6.77 (tt, J = 9.05, 2.27 Hz, 1 H), 6.49-6.59 (m, 2 H), 4.75-4.79 (m, 1 H), 4.23-4.34 (m, 2 H), 4.04 (ddd, J = 14.01, 9.98, 5.81 Hz, 1 H), 3.63-3.74 (m, 1 H), 3.37-3.42 (m, 1 H), 3.26 (s, 3 H), 3.04 (dd, J = 14.31, 9.24 Hz, 2 H), 2.78-2.86 (m, 4 H), 2.64-2.74 (m, 2 H), 2.38-2.51 (m, 3 H), 2.16-2.37 (m, 4 H), 1.82-2.13 (m, 10 H), 1.66-1.82 (m, 3 H), 1.40-1.52 (m, 2 H), 0.96 (td, J = 7.67, 4.62 Hz, 1 H), 0.81-0.91 (m, 2 H), 0.69-0.80 (m, 2 H), 0.04-0.09 (m, 1 H). |
| 4 (General Procedure A using Bromide A1 as the core reagent) | 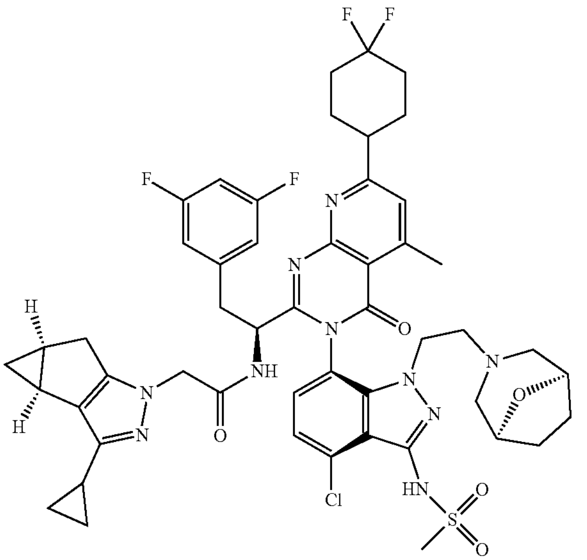 N-[(1S)-1-[(3P)-3-(4-chloro-3-methanesulfonamido-1-{2-[(1R,5S)-8-oxa-3-azabicyclo[3.2.1]octan-3-yl]ethyl}-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.23 min.; observed ion = 1015.5 [M − H]. 1H NMR (500 MHz, METHANOL-d4) δ ppm 7.44 (s, 1 H), 7.33 (d, J = 8.05 Hz, 1 H), 7.22 (d, J = 7.75 Hz, 1 H), 6.72-6.80 (m, 1 H), 6.55 (dd, J = 8.05, 2.09 Hz, 2 H), 4.75-4.80 (m, 1 H), 4.21-4.32 (m, 2 H), 3.91-4.12 (m, 3 H), 3.65 (ddd, J = 14.08, 9.91, 5.22 Hz, 1 H), 3.38 (dd, J = 14.01, 5.07 Hz, 1 H), 3.26 (s, 3 H), 2.97-3.09 (m, 2 H), 2.83 (s, 3 H), 2.71 (dd, J = 16.39, 6.56 Hz, 1 H), 2.50-2.58 (m, 1 H), 2.38-2.49 (m, 2 H), 2.32 (d, J = 10.73 Hz, 1 H), 2.18-2.28 (m, 2 H), 1.91-2.16 (m, 10 H), 1.81-1.88 (m, 1 H), 1.73-1.81 (m, 1 H), 1.44-1.66 (m, 3 H), 1.27-1.40 (m, 1 H), 0.96 (td, J = 7.67, 4.62 Hz, 1 H), 0.82-0.91 (m, 2 H), 0.71-0.80 (m, 2 H), 0.05-0.10 (m, 1 H). |

TABLE A-continued

| Example No. (preparation of the Example) | Structure and IUPAC name | Characterising data (LCMS and/or NMR) |
| --- | --- | --- |
| 5 (General Procedure A using Bromide A2 as the core reagent) | 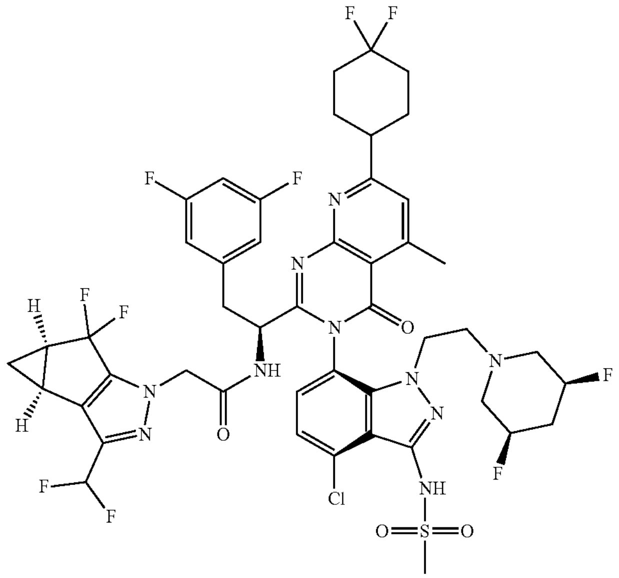 N-[(1S)-1-[(3P)-3-(4-chloro-1-{2-[(3R,5S)-3,5-difluoropiperidin-1-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^2$,$^4$]nona-1(6),8-dien-7-yl]acetamide | LCMS Method B: retention time = 1.37 min.; observed ion = 1069.6 [M − H]. 1H NMR (500 MHz, METHANOL-d4) δ ppm 7.42 (d, J = 0.60 Hz, 1 H), 7.31 (d, J = 7.75 Hz, 1 H), 7.20 (d, J = 8.05 Hz, 1 H), 6.51-6.81 (m, 4 H), 4.79 (dd, J = 9.39, 4.92 Hz, 1 H), 4.52-4.68 (m, 2 H), 4.19-4.41 (m, 2 H), 4.14 (ddd, J = 14.01, 9.84, 5.66 Hz, 1 H), 3.72-3.83 (m, 1 H), 3.39 (dd, J = 14.16, 4.92 Hz, 1 H), 3.24 (s, 3 H), 2.99-3.08 (m, 2 H), 2.84 (d, J = 0.60 Hz, 3 H), 2.79 (ddd, J = 12.67, 9.54, 6.11 Hz, 1 H), 2.67 (ddd, J = 12.67, 9.54, 5.22 Hz, 1 H), 2.47-2.59 (m, 2 H), 2.42 (ddt, J = 11.14, 7.56, 3.91, 3.91 Hz, 2 H), 2.13-2.29 (m, 5 H), 1.91-2.12 (m, 7 H), 1.55-1.69 (m, 1 H), 1.35 (q, J = 7.35 Hz, 1 H), 0.96-1.06 (m, 1 H). |
| 6 (General Procedure A using Bromide A1 as the core reagent) | 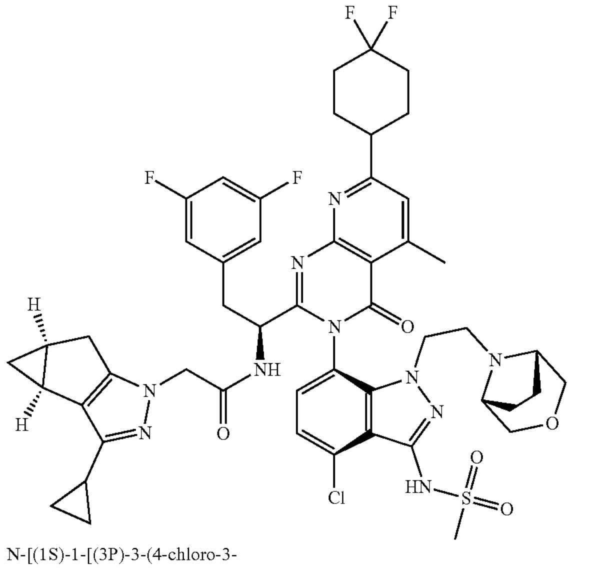 N-[(1S)-1-[(3P)-3-(4-chloro-3-methanesulfonamido-1-{2-[(1R,5S)-3-oxa-8-azabicyclo[3.2.1]octan-8-yl]ethyl}-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.$0^2$,$^4$]nona-1(6),8-dien-7-yl]acetamide | LCMS Method B: retention time = 1.15 min.; observed ion = 1015.6 [M − H]. 1H NMR (500 MHz, METHANOL-d4) δ ppm 7.42 (d, J = 0.89 Hz, 1 H), 7.29-7.41 (m, 1 H), 6.72-6.87 (m, 1 H), 6.40-6.57 (m, 2 H), 4.63-4.73 (m, 1 H), 4.15-4.57 (m, 3 H), 3.83-4.12 (m, 1 H), 3.45-3.79 (m, 3 H), 3.40 (dd, J = 14.60, 4.17 Hz, 1 H), 3.27 (s, 3 H), 3.00-3.11 (m, 2 H), 2.83 (d, J = 0.60 Hz, 3 H), 2.56-2.66 (m, 1 H), 2.44 (d, J = 16.99 Hz, 1 H), 2.19-2.28 (m, 2 H), 1.86-2.14 (m, 9 H), 1.80-1.86 (m, 1 H), 1.75 (tt, J = 8.46, 5.10 Hz, 1 H), 0.93-0.99 (m, 1 H), 0.82-0.91 (m, 2 H), 0.69-0.79 (m, 2 H), 0.04 (q, J = 4.07 Hz, 1 H). |

TABLE A-continued

| Example No. (preparation of the Example) | Structure and IUPAC name | Characterising data (LCMS and/or NMR) |
|---|---|---|
| 7 (General Procedure A using Bromide A1 as the core reagent) | 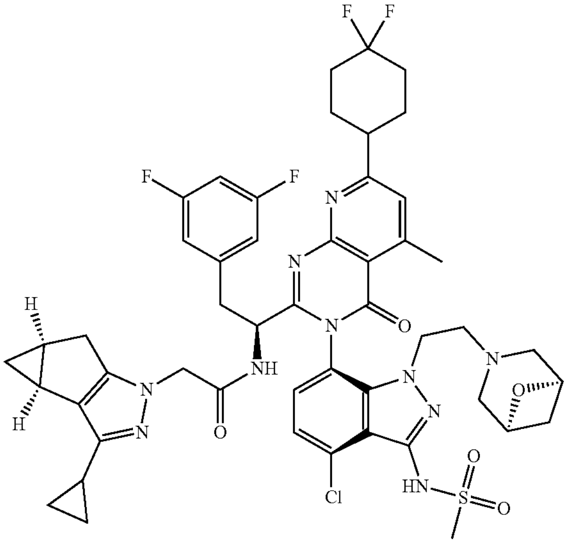 N-[(1S)-1-[(3P)-3-(4-chloro-3-methanesulfonamido-1-{2-[(1R,5S)-6-oxa-3-azabicyclo[3.1.1]heptan-3-yl]ethyl}-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.16 min.; observed ion = 1001.3 [M − H]. 1H NMR (500 MHz, METHANOL-d4) δ ppm 7.40 (s, 1 H), 7.33 (d, J = 7.75 Hz, 1 H), 7.22 (d, J = 7.75 Hz, 1 H), 6.77 (tt, J = 9.24, 2.38 Hz, 1 H), 6.47-6.59 (m, 2 H), 4.78-4.81 (m, 1 H), 4.25-4.37 (m, 3 H), 4.18-4.23 (m, 1 H), 4.07-4.15 (m, 1 H), 3.77 (ddd, J = 14.08, 9.16, 5.07 Hz, 1 H), 3.38 (dd, J = 14.01, 5.07 Hz, 1 H), 3.27 (s, 3 H), 2.98-3.09 (m, 2 H), 2.76-2.88 (m, 5 H), 2.62-2.74 (m, 3 H), 2.42-2.56 (m, 2 H), 2.32 (br d, J = 10.73 Hz, 1 H), 2.18-2.28 (m, 2 H), 1.90-2.13 (m, 7 H), 1.81-1.88 (m, 2 H), 1.76 (tt, J = 8.42, 4.99 Hz, 1 H), 0.95 (td, J = 7.67, 4.92 Hz, 1 H), 0.79-0.89 (m, 2 H), 0.70-0.78 (m, 2 H), 0.05 (q, J = 4.17 Hz, 1 H). |
| 9 (General Procedure A using Bromide A1 as the core reagent) | 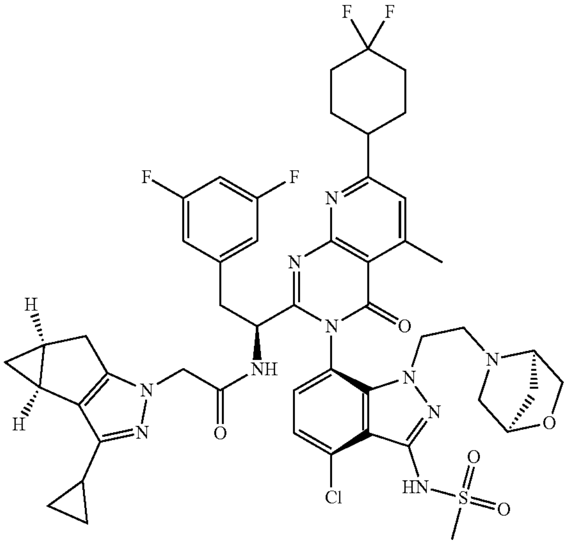 N-[(1S)-1-[(3P)-3-(4-chloro-3-methanesulfonamido-1-{2-[(1R,4R)-2-oxa-5-azabicyclo[2.2.1]heptan-5-yl]ethyl}-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.13 min.; observed ion = 1003.3 [M + H]. 1H NMR (500 MHz, METHANOL-d4) δ ppm 7.42 (d, J = 2.09 Hz, 1 H), 7.32-7.41 (m, 2 H), 6.74-6.84 (m, 1 H), 6.53 (br d, J = 5.66 Hz, 2 H), 4.63-4.71 (m, 1 H), 4.33-4.51 (m, 3 H), 4.19-4.32 (m, 1 H), 3.82-4.12 (m, 2 H), 3.57-3.68 (m, 1 H), 3.38-3.46 (m, 2 H), 2.99-3.13 (m, 3 H), 2.83 (s, 3 H), 2.56-2.66 (m, 1 H), 2.45 (br d, J = 16.39 Hz, 1 H), 2.19-2.29 (m, 2 H), 2.02-2.15 (m, 5 H), 1.88-2.00 (m, 3 H), 1.84 (br dd, J = 6.41, 2.83 Hz, 1 H), 1.70-1.78 (m, 1 H), 0.96 (td, J = 7.53, 4.62 Hz, 1 H), 0.82-0.91 (m, 2 H), 0.67-0.79 (m, 2 H), 0.02-0.06 (m, 1 H). |

TABLE A-continued

| Example No. (preparation of the Example) | Structure and IUPAC name | Characterising data (LCMS and/or NMR) |
|---|---|---|
| 10 (General Procedure A using Bromide A1 as the core reagent) | 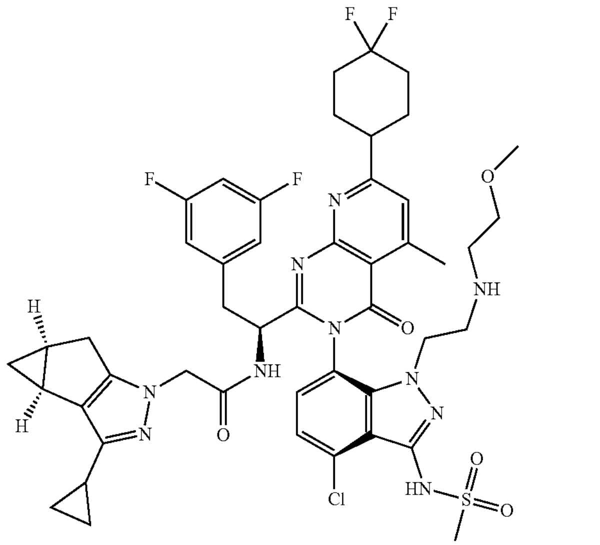 N-[(1S)-1-[(3P)-3-(4-chloro-3-methanesulfonamido-1-{2-[(2-methoxyethyl)amino]ethyl}-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide. | LCMS Method B: retention time = 1.14 min.; observed ion = 977.5 [M − H]. 1H NMR (500 MHz, METHANOL-d4) δ ppm 7.41 (s, 1 H), 7.33-7.39 (m, 2 H), 6.81 (tt, J = 9.13, 2.05 Hz, 1 H), 6.53 (br d, J = 5.96 Hz, 2 H), 4.64 (dd, J = 10.28, 4.02 Hz, 1 H), 4.36-4.50 (m, 2 H), 4.23-4.33 (m, 1 H), 3.99-4.10 (m, 1 H), 3.54 (t, J = 5.07 Hz, 2 H), 3.36-3.46 (m, 3 H), 3.32 (s, 3 H), 3.29 (s, 3 H), 3.12 (dd, J = 14.31, 10.43 Hz, 1 H), 2.96-3.08 (m, 3 H), 2.83 (s, 3 H), 2.60 (dd, J = 16.54, 6.71 Hz, 1 H), 2.44 (d, J = 16.69 Hz, 1 H), 2.19-2.29 (m, 2 H), 2.03-2.12 (m, 5 H), 1.95-2.02 (m, 1 H), 1.89-1.95 (m, 1 H), 1.81-1.86 (m, 1 H), 1.70-1.79 (m, 1 H), 0.96 (td, J = 7.60, 4.77 Hz, 1 H), 0.82-0.92 (m, 2 H), 0.69-0.79 (m, 2 H), 0.01-0.03 (m, 1 H). |
| 11 (General Procedure B using Amine B1 as the core reagent) | 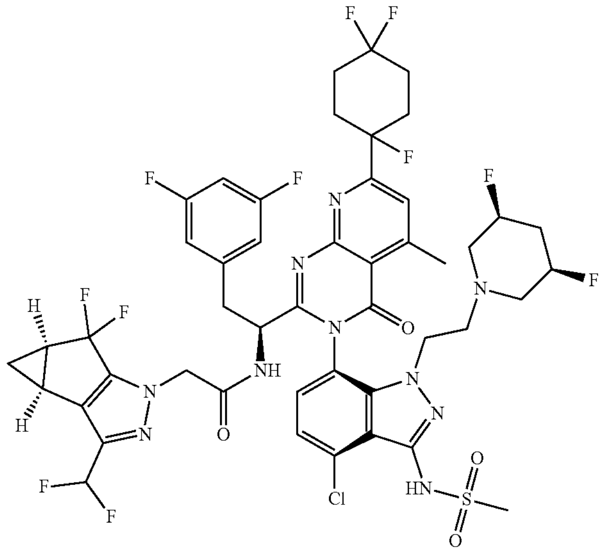 N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 3.073 min.; observed ion = 1089.10 [M + H] 1H NMR (500 MHz, METHANOL-d4) δ ppm 1.01 (br d, J = 2.09 Hz, 1 H), 1.33-1.38 (m, 1 H), 1.61-1.68 (m, 1 H), 2.10-2.32 (m, 9 H), 2.40-2.60 (m, 5 H), 2.66-2.72 (m, 1 H), 2.76-2.82 (m, 1 H), 2.90 (s, 3 H), 3.02-3.08 (m, 1 H), 3.25 (s, 3 H), 3.36-3.41 (m, 1 H), 3.76-3.83 (m, 1 H), 4.11-4.19 (m, 1 H), 4.23-4.42 (m, 1 H), 4.55-4.66 (m, 2 H), 4.77-4.80 (m, 1 H), 4.94-4.98 (m, 2 H), 6.52-6.80 (m, 4 H), 7.25-7.28 (m, 1 H), 7.33-7.36 (m, 1 H), 7.71 (s, 1 H). |

TABLE A-continued

| Example No. (preparation of the Example) | Structure and IUPAC name | Characterising data (LCMS and/or NMR) |
|---|---|---|
| 12 (General Procedure B using Amine B1 as the core reagent) | 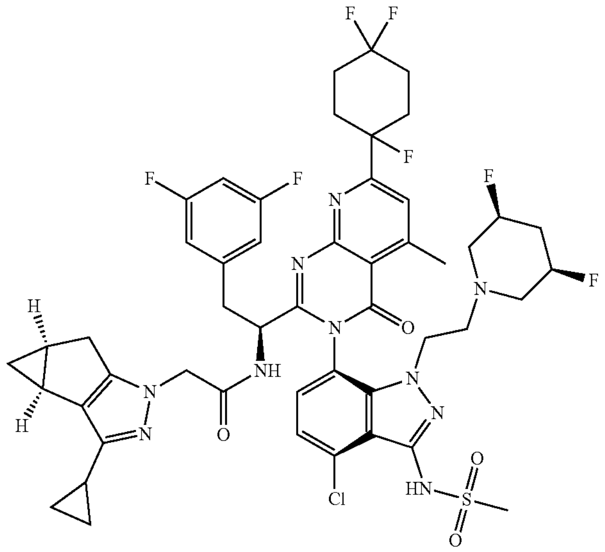 N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method A: retention time = 3.117 min.; observed ion = 1043.15 [M + H] 1H NMR (500 MHz, METHANOL-d4) δ ppm 0.06-0.09 (m, 1 H), 0.73-0.80 (m, 2 H), 0.82-0.98 (m, 4 H), 1.60-1.69 (m, 1 H), 1.78 (tt, J = 8.38, 5.03 Hz, 1 H), 1.83-1.87 (m, 1 H), 1.91-1.96 (m, 1 H), 2.15-2.31 (m, 8 H), 2.46-2.61 (m, 4 H), 2.66-2.72 (m, 2 H), 2.75-2.81 (m, 1 H), 2.89-2.91 (m, 3 H), 3.04 (dd, J = 14.01, 9.24 Hz, 1 H), 3.28-3.29 (m, 3 H), 3.36-3.40 (m, 1 H), 3.76 (ddd, J = 14.31, 9.09, 5.51 Hz, 1 H), 4.06 (ddd, J = 14.08, 9.46, 5.96 Hz, 1 H), 4.21-4.27 (m, 1 H), 4.30 (d, J = 4.47 Hz, 2 H), 4.34-4.41 (m, 1 H), 4.78 (dd, J = 9.54, 4.77 Hz, 2 H), 6.54 (d, J = 6.96 Hz, 2 H), 6.77 (t, J = 8.28 Hz, 1 H), 7.27 (d, J = 8.05 Hz, 1 H), 7.35 (d, J = 7.75 Hz, 1 H), 7.70-7.72 (m, 1 H). |
| 14 (General Procedure A using Bromide A2 as the core reagent) | 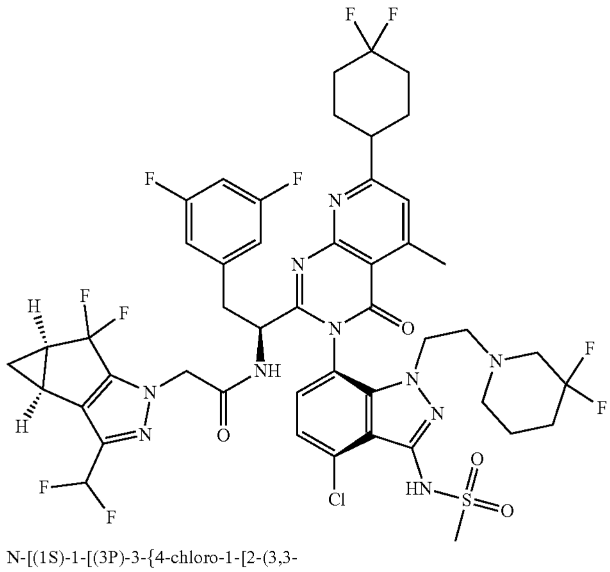 N-[(1S)-1-[(3P)-3-{4-chloro-1-[2-(3,3-difluoropiperidin-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.46 min.; observed ion = 1069.4 [M − H] 1H NMR (500 MHz, DMSO-d6) δ ppm 9.26-9.47 (m, 1 H), 7.62-7.76 (m, 1 H), 7.30-7.51 (m, 2 H), 6.49-7.08 (m, 4 H), 4.59-4.73 (m, 1 H), 4.39-4.56 (m, 2 H), 3.62-3.89 (m, 2 H), 3.10 (br d, J = 1.49 Hz, 3 H), 2.91-3.06 (m, 2 H), 2.77 (s, 3 H), 2.55-2.66 (m, 1 H), 2.24-2.32 (m, 2 H), 2.12-2.22 (m, 2 H), 1.87-2.08 (m, 8 H), 1.60-1.74 (m, 2 H), 1.13-1.42 (m, 5 H), 0.80-0.91 (m, 1 H). |

TABLE A-continued

| Example No. (preparation of the Example) | Structure and IUPAC name | Characterising data (LCMS and/or NMR) |
|---|---|---|
| 15 (General Procedure A using Bromide A2 as the core reagent) | 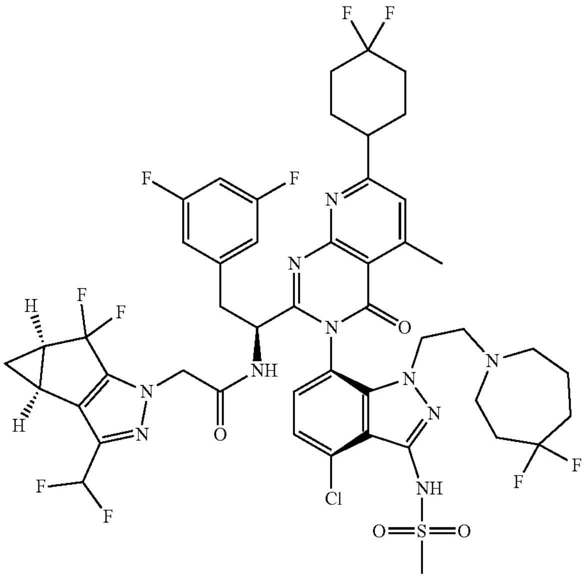 N-[(1S)-1-[(3P)-3-{4-chloro-1-[2-(4,4-difluoroazepan-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method B: retention time = 1.19 min.; observed ion = 1083.5 [M − H]. Purification (Column: Waters XSelect CSH C18 , 19 x 100 mm, 5 μm particles; Solvent A = 0.1% Formic Acid in 100% Water. Solvent B = Acetonitrile. Flow Rate = 40 mL/min. start % B = 36.7. Final % B = 56.7, Gradient Time = 6 min, then a 2 min hold at 98% B. Wavelength = 215 and 254 nm. ESI + Range: 150 to 2000 dalton. Sample was loaded at Start B % for 1 min.), 1H NMR (500 MHz, METHANOL-d4) δ ppm 7.44 (d, J = 0.60 Hz, 1 H), 7.33 (d, J = 7.75 Hz, 1 H), 7.24 (d, J = 8.05 Hz, 1 H), 6.42-6.82 (m, 4 H), 4.78 (dd, J = 9.54, 4.77 Hz, 1 H), 4.57-4.67 (m, 2 H), 4.13 (ddd, J = 14.01, 10.43, 5.66 Hz, 1 H), 3.68-3.77 (m, 1 H), 3.38 (dd, J = 14.16, 4.62 Hz, 1 H), 3.23 (s, 3 H), 3.04 (dd, J = 14.16, 9.39 Hz, 2 H), 2.84 (d, J = 0.60 Hz, 3 H), 2.76-2.82 (m, 1H), 2.66 (br dd, J = 8.94, 4.17 Hz, 1 H), 2.37-2.48 (m, 4 H), 2.18-2.35 (m, 4 H), 2.03-2.13 (m, 5 H), 1.82-2.02 (m, 3 H), 1.64-1.81 (m, 2 H), 1.40-1.50 (m, 2 H), 1.33-1.39 (m, 1 H), 0.99-1.06 (m, 1 H). |
| 17 (General Procedure A using Bromide A2 as the core reagent) | 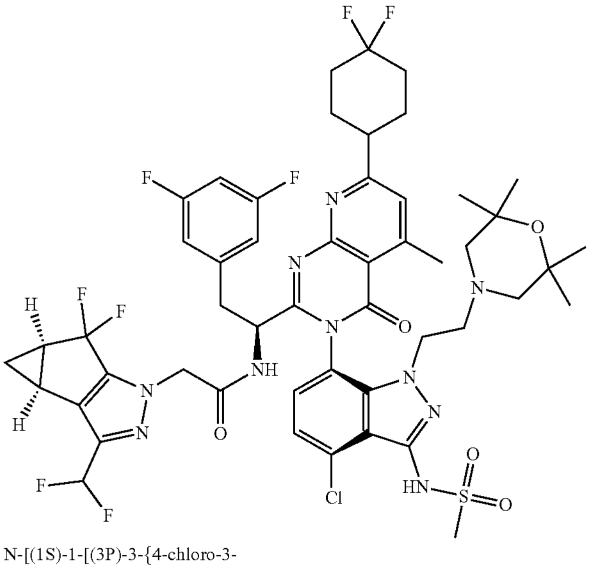 N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method B: retention time = 1.50 min.; observed ion = 1091.7 [M − H]. 1H NMR (500 MHz, METHANOL-d4) δ ppm 7.44 (d, J = 0.60 Hz, 1 H), 7.32 (d, J = 8.05 Hz, 1 H), 7.21 (d, J = 7.75 Hz, 1 H), 6.47-6.80 (m, 4 H), 4.79 (dd, J = 9.54, 4.77 Hz, 1 H), 4.58 (s, 2 H), 4.18 (ddd, J = 13.86, 11.47, 5.36 Hz, 1 H), 3.80 (ddd, J = 13.56, 11.18, 5.07 Hz, 1 H), 3.37 (dd, J = 14.16, 4.62 Hz, 1 H), 3.22 (s, 3 H), 3.04 (dd, J = 14.01, 9.54 Hz, 2 H), 2.84 (d, J = 0.60 Hz, 3 H), 2.63 (td, J = 11.70, 5.51 Hz, 1 H), 2.51 (td, J = 11.85, 5.22 Hz, 1 H), 2.36-2.46 (m, 2 H), 2.17-2.29 (m, 2 H), 2.02-2.13 (m, 5 H), 1.97 (d, J = 10.73 Hz, 2 H), 1.83-1.91 (m, 2 H), 1.32-1.39 (m, 1 H), 1.00-1.06 (m, 1 H), 0.94 (s, 12 H). |

TABLE A-continued

| Example No. (preparation of the Example) | Structure and IUPAC name | Characterising data (LCMS and/or NMR) |
|---|---|---|
| 24 (General Procedure A using Bromide A3 as the core reagent) | 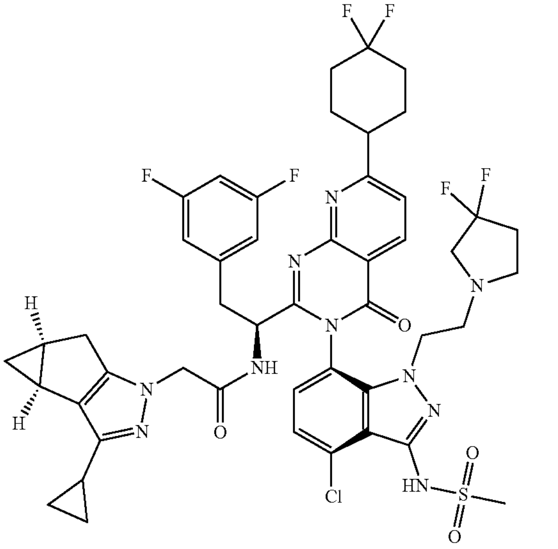<br>N-[(1S)-1-[(3P)-3-{4-chloro-1-[2-(3,3-difluoropyrrolidin-1-yl)ethyl]-3-methanesulfonamido-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.415 min.; observed ion = 995.5 [M − H].<br>1H NMR (500 MHz, CD3OD, 303 K) δ (ppm) = 8.55 (d, J = 8.0 Hz, 1H), 7.58 (d, J = 8.3 Hz, 1H), 7.28 (d, J = 7.7 Hz, 1H), 7.19 (d, J = 7.7 Hz, 1H), 6.72 (t, J = 8.8 Hz, 1H), 6.50 (d, J = 6.8 Hz, 2H), 4.77-4.73 (m, 1H), 4.28-4.22 (m, 2H), 3.98 (ddd, J = 6.1, 9.7, 14.0 Hz, 1H), 3.59 (ddd, J = 5.1, 9.4, 14.2 Hz, 1H), 3.39-3.32 (m, 1H), 3.21 (s, 3H), 3.11-2.98 (m, 2H), 2.68-2.51 (m, 3H), 2.48-2.31 (m, 5H), 2.22-2.15 (m, 2H), 2.08-1.85 (m, 9H), 1.80-1.68 (m, 2H), 0.89 (dt, J = 4.8, 7.6 Hz, 1H), 0.84-0.75 (m, 2H), 0.73-0.65 (m, 2H), 0.01--0.02 (m, 1H). |
| 26 (General Procedure A using Bromide A4 as the core reagent) | 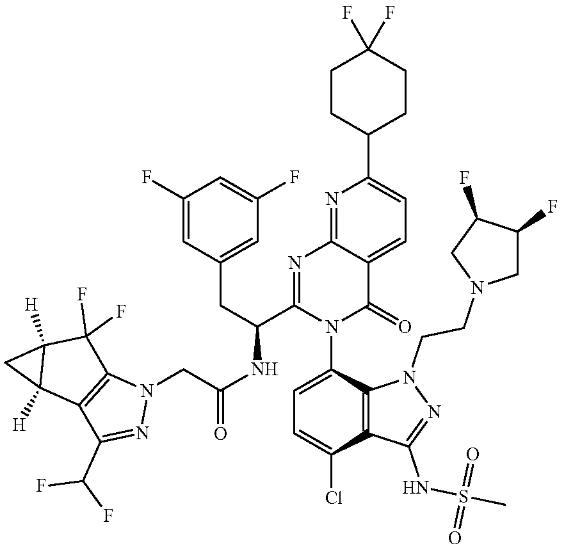<br>N-[(1S)-1-[(3P)-3-(4-chloro-1-{2-[(3R,4S)-3,4-difluoropyrrolidin-1-yl]ethyl}-3-methanesulfonamido-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide. | LCMS Method B: retention time = 1.287 min.; observed ion = 1043.4 [M + H].<br>1H NMR (500 MHz, CD3OD, 303 K), Shift (ppm) = 8.64 (d, J = 8.3 Hz, 1H), 7.67 (d, J = 8.0 Hz, 1H), 7.35 (d, J = 8.0 Hz, 1H), 7.26 (d, J = 8.0 Hz, 1H), 6.81-6.76 (m, 1H), 6.69 (t, J = 54.8 Hz, 1H), 6.56 (dd, J = 2.1, 8.0 Hz, 2H), 4.84-4.82 (m, 1H), 4.78-4.73 (m, 1H), 4.68-4.58 (m, 2H), 4.10 (ddd, J = 6.0, 9.4, 14.2 Hz, 1H), 3.72 (ddd, J = 5.5, 9.2, 14.2 Hz, 1H), 3.43 (dd, J = 4.9, 14.2 Hz, 1H), 3.26 (s, 3H), 3.20-3.06 (m, 2H), 2.83-2.77 (m, 1H), 2.74-2.69 (m, 1H), 2.68-2.49 (m, 4H), 2.44 (ddd, J = 4.0, 7.7, 11.3 Hz, 2H), 2.31-2.21 (m, 2H), 2.17-1.98 (m, 6H), 1.41-1.34 (m, 1H), 1.31 (s, 1H), 1.05-1.01 (m, 1H). |

TABLE A-continued

| Example No. (preparation of the Example) | Structure and IUPAC name | Characterising data (LCMS and/or NMR) |
|---|---|---|
| 40 (General Procedure A using Bromide A4 as the core reagent) | 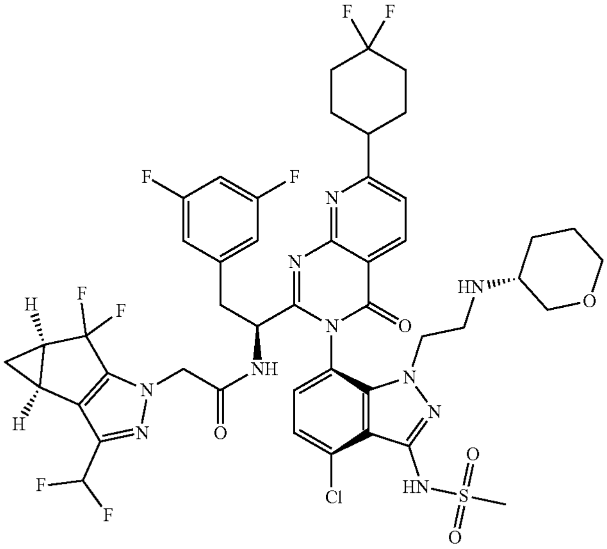 N-[(1S)-1-[(3P)-3-[4-chloro-3-methanesulfonamido-1-(2-{[(3R)-oxan-3-yl]amino}ethyl)-1H-indazol-7-yl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.1 min.; observed ion = 1035.4 [M − H]. 1H NMR (500 MHz, METHANOL-d4) δ ppm 0.97-1.01 (m, 1 H), 1.29 (s, 1 H), 1.31-1.40 (m, 1 H), 1.47-1.60 (m, 2 H), 1.66-1.74 (m, 1 H), 1.92-2.14 (m, 6 H), 2.19-2.29 (m, 2 H), 2.38-2.47 (m, 2 H), 2.82-2.93 (m, 1 H), 3.09-3.26 (m, 4 H), 3.25-3.29 (m, 2 H), 3.41-3.47 (m, 1 H), 3.47-3.54 (m, 1 H), 3.61-3.70 (m, 1 H), 3.70-3.78 (m, 1 H), 3.92-3.99 (m, 1 H), 4.20-4.27 (m, 1 H), 4.56-4.76 (m, 3 H), 4.88-4.95 (m, 2 H), 6.50-6.55 (m, 2 H), 6.66 (t, J = 54.84 Hz, 1 H), 6.75-6.81 (m, 1 H), 7.38 (s, 2 H), 7.65 (d, J = 8.35 Hz, 1 H), 8.62 (d, J = 8.05 Hz, 1 H). |
| 41 (General Procedure A using Bromide A4 as the core reagent) | 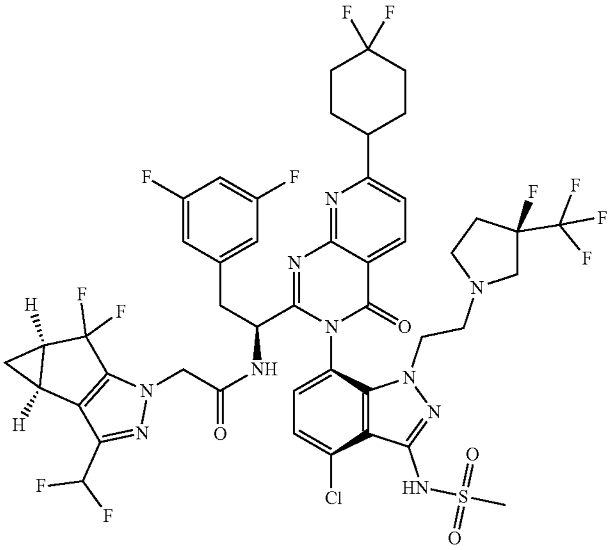 N-[(1S)-1-[(3P)-3-(4-chloro-1-{2-[(3R)-3-fluoro-3-(trifluoromethyl)pyrrolidin-1-yl]ethyl}-3-methanesulfonamido-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.5 min.; observed ion = 1091.4 [M − H]. 1H NMR (500 MHz, METHANOL-d4) δ ppm 0.98-1.05 (m, 1 H), 1.28-1.38 (m, 1 H), 2.06-2.16 (m, 4 H), 2.19-2.35 (m, 2 H), 2.39-2.44 (m, 2 H), 2.53-2.71 (m, 2 H), 2.74-2.80 (m, 1 H), 3.24 (d, J = 5.07 Hz, 3 H), 3.32-3.46 (m, 3 H), 3.74 (td, J = 9.46, 4.62 Hz, 1 H), 3.86 (ddd, J = 14.46, 11.18, 5.07 Hz, 1 H), 4.16 (ddd, J = 14.16, 9.98, 5.96 Hz, 1 H), 4.32-4.38 (m, 1 H), 4.53-4.67 (m, 2 H), 4.73-4.82 (m, 1 H), 4.86-4.93 (m, 4 H), 6.52-6.61 (m, 1 H), 6.66 (br t, J = 57.67 Hz, 1 H), 6.66 (br s, 1 H), 6.74-6.80 (m, 1 H), 7.24-7.29 (m, 1 H), 7.35 (t, J = 7.86 Hz, 1 H), 7.63-7.68 (m, 1 H), 8.62 (d, J = 8.58 Hz, 1 H), 8.65 (d, J = 8.21 Hz, 1 H). |

TABLE A-continued

| Example No. (preparation of the Example) | Structure and IUPAC name | Characterising data (LCMS and/or NMR) |
| --- | --- | --- |
| 42 (General Procedure A using Bromide A4 as the core reagent) | 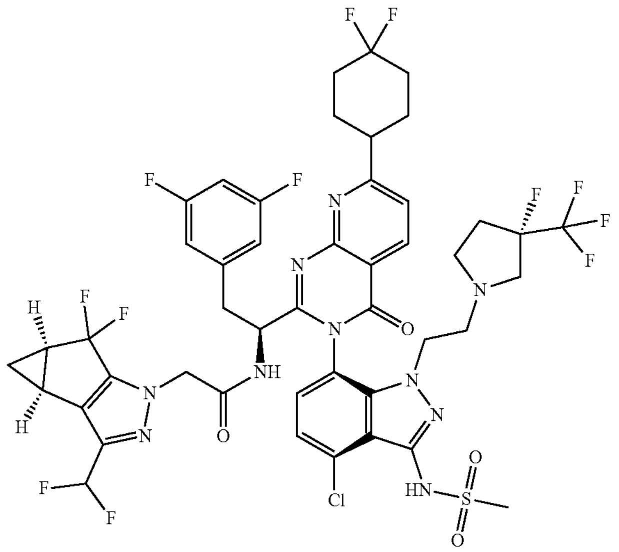 N-[(1S)-1-[(3P)-3-(4-chloro-1-{2-[(3S)-3-fluoro-3-(trifluoromethyl)pyrrolidin-1-yl]ethyl}-3-methanesulfonamido-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.5 min.; observed ion = 1093.4 [M + H]. 1H NMR (500 MHz, METHANOL-d4) δ ppm 1.00-1.03 (m, 1 H), 1.28-1.38 (m, 2 H), 1.92 (s, 1 H), 2.04-2.17 (m, 6 H), 2.20-2.34 (m, 3 H), 2.38-2.45 (m, 2 H), 2.54-2.61 (m, 1 H), 2.63-2.69 (m, 1 H), 2.74-2.81 (m, 1 H), 3.05-3.19 (m, 2 H), 3.23-3.26 (m, 3 H), 3.37-3.44 (m, 1 H), 3.69-3.90 (m, 1 H), 4.35 (dt, J = 8.94, 5.66 Hz, 1 H), 4.56-4.66 (m, 2 H), 4.74-4.82 (m, 2 H), 6.50-6.60 (m, 2 H), 6.66 (br t, J = 57.37 Hz, 1 H), 6.74-6.80 (m, 1 H), 7.24-7.29 (m, 1 H), 7.32-7.37 (m, 1 H), 7.66 (dd, J = 10.88, 8.20 Hz, 1 H), 8.62 (d, J = 8.05 Hz, 1 H), 8.65 (d, J = 8.05 Hz, 1 H). |
| 43 (General Procedure A using Bromide A4 as the core reagent) | 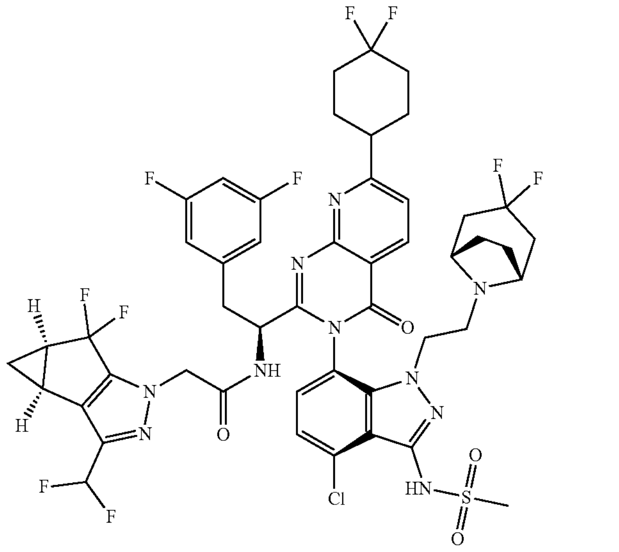 N-[(1S)-1-[(3P)-3-(4-chloro-1-{2-[(1R,5S)-3,3-difluoro-8-azabicyclo[3.2.1]octan-8-yl]ethyl}-3-methanesulfonamido-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.18 min.; observed ion = 1083.3 [M + H]. 1H NMR (500 MHz, METHANOL-d4) δ ppm 1.02-1.07 (m, 1 H), 1.33-1.42 (m, 1 H), 1.64-1.75 (m, 5 H), 1.75-1.84 (m, 2 H), 1.97-2.05 (m, 1 H), 2.07-2.16 (m, 5 H), 2.22-2.31 (m, 2 H), 2.41-2.48 (m, 2 H), 2.54-2.63 (m, 1 H), 2.65-2.72 (m, 1 H), 2.82 (br dd, J = 5.36, 2.68 Hz, 1 H), 3.01-3.20 (m, 4 H), 3.25 (s, 3 H), 3.41 (dd, J = 14.16, 4.62 Hz, 1 H), 3.71 (ddd, J = 14.23, 9.31, 5.36 Hz, 1 H), 4.13-4.18 (m, 1 H), 4.58-4.72 (m, 2 H), 4.81-4.85 (m, 1 H), 6.52-6.58 (m, 2 H), 6.69 (t, J = 54.84 Hz, 1 H), 6.76-6.81 (m, 1 H), 7.28 (d, J = 8.05 Hz, 1 H), 7.36 (d, J = 8.05 Hz, 1 H), 7.69 (d, J = 8.05 Hz, 1 H), 8.65 (d, J = 8.35 Hz, 1 H). |

TABLE A-continued

| Example No. (preparation of the Example) | Structure and IUPAC name | Characterising data (LCMS and/or NMR) |
|---|---|---|
| 46 (General Procedure A using Bromide A4 as the core reagent) | 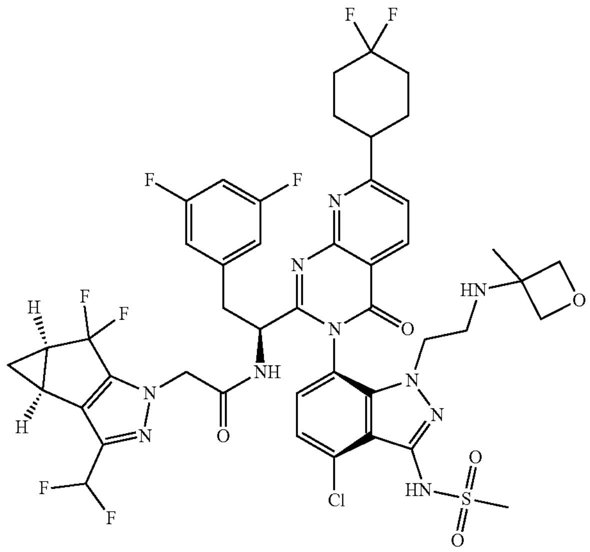 N-[(1S)-1-[(3P)-3-(4-chloro-3-methanesulfonamido-1-{2-[(3-methyloxetan-3-yl)amino]ethyl}-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.09 min.; observed ion = 1021.5 [M − H]. 1H NMR (500 MHz, METHANOL-d4) δ ppm 1.00 (br dd, J = 3.43, 1.94 Hz, 1 H), 1.33 (s, 3 H), 1.34-1.38 (m, 1 H), 2.07-2.16 (m, 5 H), 2.20-2.29 (m, 2 H), 2.42 (ddd, J = 11.55, 7.53, 3.87 Hz, 2 H), 2.95 (br d, J = 1.19 Hz, 1 H), 2.99 (br s, 1 H), 3.03-3.20 (m, 3 H), 3.27-3.29 (m, 3 H), 3.40-3.45 (m, 1 H), 3.84 (br d, J = 14.31 Hz, 1 H), 4.15 (br d, J = 12.52 Hz, 1 H), 4.24 (t, J = 5.96 Hz, 2 H), 4.37 (d, J = 6.56 Hz, 1 H), 4.44 (d, J = 6.56 Hz, 1 H), 4.59-4.70 (m, 2 H), 4.77-4.80 (m, 1 H), 6.52-6.79 (m, 4 H), 7.28-7.38 (m, 2 H), 7.65 (d, J = 8.35 Hz, 1 H), 8.61 (d, J = 8.05 Hz, 1 H). |
| 48 (General Procedure A using Bromide A4 as the core reagent) | 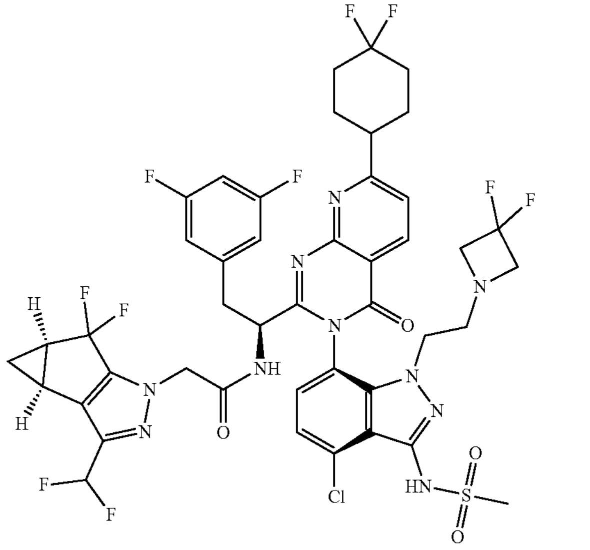 N-[(1S)-1-[(3P)-3-{4-chloro-1-[2-(3,3-difluoroazetidin-1-yl)ethyl]-3-methanesulfonamido-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.38 min.; observed ion = 1027.6 [M − H]. 1H NMR (500 MHz, METHANOL-d4) δ ppm 1.01 (br d, J = 2.98 Hz, 1 H), 1.36 (br d, J = 7.45 Hz, 1 H), 1.96-2.03 (m, 1 H), 2.06-2.16 (m, 4 H), 2.25 (br d, J = 7.45 Hz, 2 H), 2.42 (td, J = 7.38, 4.02 Hz, 2 H), 2.80 (br d, J = 4.77 Hz, 2 H), 3.07 (br dd, J = 14.31, 9.54 Hz, 3 H), 3.22-3.30 (m, 7 H), 3.39 (d, J = 4.77 Hz, 1 H), 3.64 (s, 1 H), 4.00 (s, 1 H), 4.55-4.69 (m, 2 H), 4.79-4.83 (m, 1 H), 6.54 (br dd, J = 8.20, 2.24 Hz, 2 H), 6.67 (br t, J = 54.84 Hz, 1 H), 6.74-6.80 (m, 1 H), 7.25 (d, J = 7.75 Hz, 1 H), 7.33 (d, J = 8.05 Hz, 1 H), 7.66 (d, J = 8.05 Hz, 1 H), 8.62 (d, J = 8.05 Hz, 1 H). |

TABLE A-continued

| Example No. (preparation of the Example) | Structure and IUPAC name | Characterising data (LCMS and/or NMR) |
| --- | --- | --- |
| 59 (General Procedure B using Amine B2 as the core reagent) | 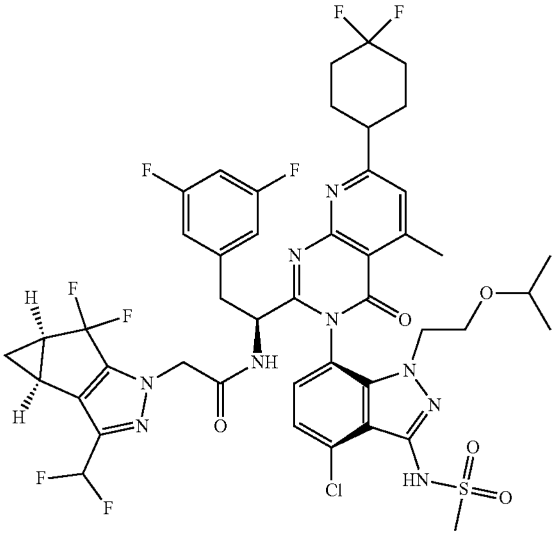 N-[(1S)-1-[(3P)-3-{4-chloro-3-methanesulfonamido-1-[2-(propan-2-yloxy)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 3.32 min.; observed ion = 1010.15 [M + H]. 1H NMR (500 MHz, METHANOL-d4) δ ppm 7.42 (s, 1 H), 7.31 (d, J = 7.75 Hz, 1 H), 7.19 (d, J = 7.75 Hz, 1H), 6.49-6.79 (m, 4 H), 4.80-4.84 (m, 1 H), 4.53-4.63 (m, 2H), 4.14 (dt, J = 13.64, 6.74 Hz, 1 H), 3.72 (dt, J = 13.86, 6.78 Hz, 1 H), 3.58-3.66 (m, 1 H), 3.45-3.55 (m, 1H), 3.38 (br dd, J = 14.01, 4.77 Hz, 1H), 3.24 (s, 3H), 3.03 (br dd, J = 13.41, 9.24 Hz, 2 H), 2.83 (s, 3 H), 2.41 (br s, 2 H), 2.24 (br d, J = 6.56 Hz, 2 H), 1.89-2.13 (m, 6 H), 1.35 (q, J = 6.85 Hz, 1 H), 1.01 (br s, 1 H), 0.89 (d, J = 6.26 Hz, 3H), 0.81 (d, J = 5.96 Hz, 3H). |
| 60 (General Procedure B using Amine B3 as the core reagent) | 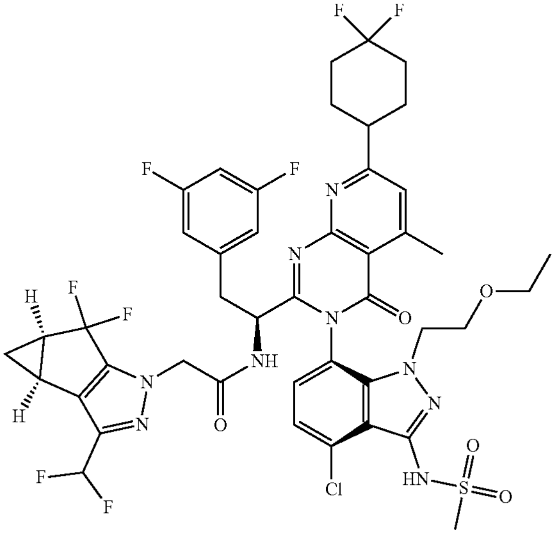 N-[(1S)-1-[(3P)-3-[4-chloro-1-(2-ethoxyethyl)-3-methanesulfonamido-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 3.26 min.; observed ion = 996.15 [M + H]. 1H NMR (500 MHz, METHANOL-d4) δ ppm 7.42 (s, 1 H), 7.31 (d, J = 8.05 Hz, 1 H), 7.19 (d, J = 8.05 Hz, 1 H), 6.49-6.80 (m, 4 H), 4.81-4.85 (m, 1 H), 4.50-4.65 (m, 2 H), 4.09-4.21 (m, 1 H), 3.71-3.81 (m, 1 H), 3.58-3.66 (m, 1 H), 3.50-3.57 (m, 1 H), 3.38 (br dd, J = 14.01, 4.47 Hz, 1 H), 3.24 (s, 3 H), 3.15-3.22 (m, 2H), 3.03 (br dd, J = 13.71, 9.24 Hz, 2 H), 2.83 (s, 3H), 2.42 (br t, J = 6.71 Hz, 2 H), 2.24 (br d, J = 6.56 Hz, 2 H), 1.92-2.13 (m, 6 H), 1.30-1.39 (m, 1 H), 1.01 (br s, 1H), 0.86 (t, J = 6.85 Hz, 3H). |

TABLE A-continued

| Example No. (preparation of the Example) | Structure and IUPAC name | Characterising data (LCMS and/or NMR) |
| --- | --- | --- |
| 72 (General Procedure B using Amine B4 as the core reagent) | 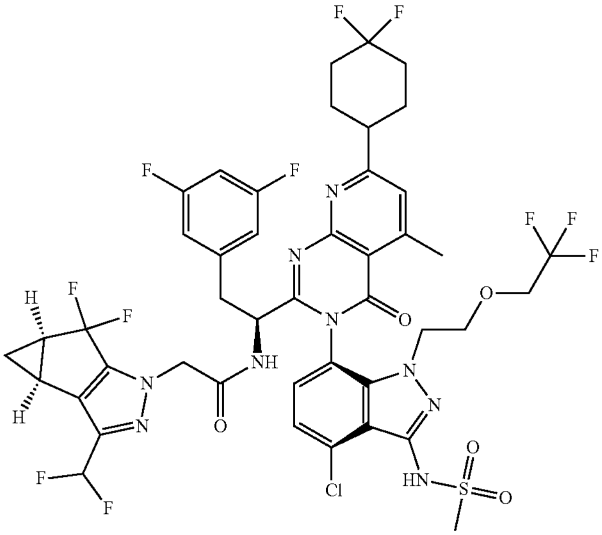 N-[(1S)-1-[(3P)-3-{4-chloro-3-methanesulfonamido-1-[2-(2,2,2-trifluoroethoxy)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method A: retention time = 3.31 min.; observed ion = 1050.15 [M + H]. 1H NMR (500 MHz, METHANOL-d4) δ ppm 7.41 (s, 1 H), 7.33 (d, J = 7.75 Hz, 1 H), 7.19 (d, J = 7.75 Hz, 1H), 6.50-6.80 (m, 4H), 4.81 (dd, J = 9.39, 4.92 Hz, 1H), 4.61 (q, J = 16.39 Hz, 2H), 4.14-4.22 (m, 1 H), 3.74-3.85 (m, 3 H), 3.57-3.70 (m, 2 H), 3.38 (dd, J = 14.16, 4.92 Hz, 1 H), 3.25 (s, 3 H), 2.99-3.09 (m, 2H), 2.81 (s, 3H), 2.41 (ddd, J = 11.03, 7.60, 4.02 Hz, 2H), 2.17-2.30 (m, 2 H), 1.91-2.15 (m, 6 H), 1.31-1.38 (m, 1 H), 0.96-1.03 (m, 1H). |
| 77 (General Procedure B using Amine B5 as the core reagent) | 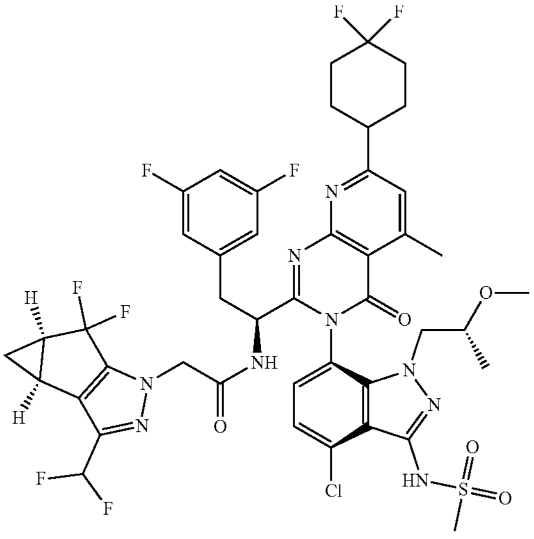 N-[(1S)-1-[(3P)-3-{4-chloro-3-methanesulfonamido-1-[(2R)-2-methoxypropyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method A: retention time = 3.24 min.; observed ion = 996.15 [M + H]. 1H NMR (500 MHz, METHANOL-d4) δ ppm 7.43 (d, J = 0.89 Hz, 1 H), 7.34 (d, J = 7.75 Hz, 1 H), 7.25 (d, J = 7.75 Hz, 1 H), 6.48-6.80 (m, 4 H), 4.78 (dd, J = 9.09, 4.92 Hz, 1 H), 4.54-4.68 (m, 2 H), 3.99-4.09 (m, 1 H), 3.56-3.64 (m, 2 H), 3.35 (dd, J = 14.01, 4.77 Hz, 1 H), 3.25 (s, 3 H), 3.02 (s, 3 H), 2.96-3.06 (m, 1 H), 2.83 (d, J = 0.60 Hz, 3 H), 2.39-2.46 (m, 2 H), 2.19-2.29 (m, 2 H), 1.93-2.12 (m, 6 H), 1.32-1.40 (m, 1 H), 0.97-1.07 (m, 1 H), 0.72 (d, J = 5.96 Hz, 3H). |

TABLE A-continued

| Example No. (preparation of the Example) | Structure and IUPAC name | Characterising data (LCMS and/or NMR) |
|---|---|---|
| 78 (General Procedure B using Amine B6 as the core reagent) | 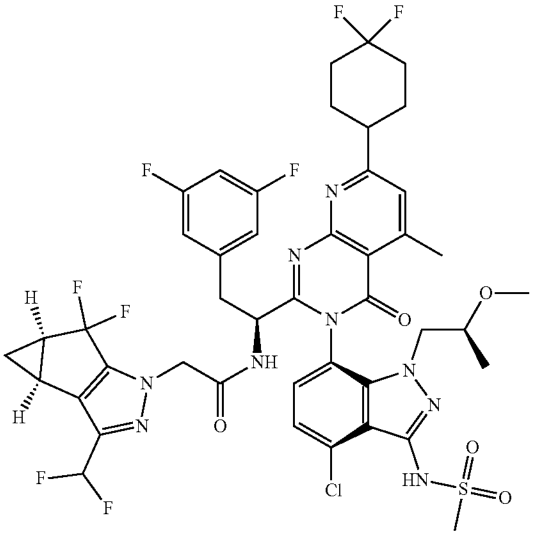 N-[(1S)-1-[(3P)-3-{4-chloro-3-methanesulfonamido-1-[(2S)-2-methoxypropyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 3.26 min.; observed ion = 996.15 [M + H]. 1H NMR (500 MHz, METHANOL-d4) δ ppm 7.40 (s, 1 H), 7.33 (d, J = 7.75 Hz, 1 H), 7.19 (d, J = 7.75 Hz, 1 H), 6.54-6.80 (m, 2 H), 6.43-6.50 (m, 2 H), 4.81-4.84 (m, 1 H), 4.70-4.76 (m, 1 H), 4.58-4.67 (m, 1 H), 3.99 (dd, J = 14.01, 3.87 Hz, 1 H), 3.45-3.50 (m, 1 H), 3.36-3.44 (m, 1 H), 3.22 (s, 3H), 2.94-3.07 (m, 2H), 2.82 (s, 3H), 2.77 (s, 3H), 2.43 (ddd, J = 11.33, 7.60, 4.02 Hz, 2 H), 2.15-2.30 (m, 2 H), 1.91-2.12 (m, 7 H), 1.36 (q, J = 7.25 Hz, 1 H), 0.98-1.09 (m, 1 H), 0.72 (d, J = 5.96 Hz, 3 H). |
| 84 (General Procedure B using Amine B7 as the core reagent) | 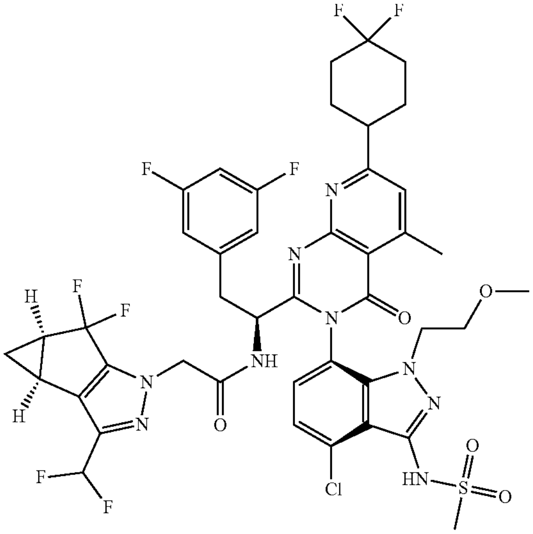 N-[(1S)-1-[(3P)-3-[4-chloro-3-methanesulfonamido-1-(2-methoxyethyl)-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.52 min.; observed ion = 982.3 [M + H]. 1H NMR (500 MHz, METHANOL-d4) δ ppm 7.41 (d, J = 0.89 Hz, 1 H), 7.31 (d, J = 7.75 Hz, 1 H), 7.18 (d, J = 8.05 Hz, 1 H), 6.47-6.79 (m, 4 H), 4.54-4.64 (m, 3H), 4.14 (dt, J = 14.60, 5.36 Hz, 1 H), 3.72-3.80 (m, 1 H), 3.49-3.58 (m, 2 H), 3.37 (dd, J = 14.01, 5.07 Hz, 1 H), 3.23 (s, 3 H), 3.04 (d, J = 8.94 Hz, 1 H), 3.03 (s, 3 H), 3.00-3.02 (m, 1 H), 2.83 (d, J = 0.60 Hz, 3 H), 2.38-2.46 (m, 2 H), 2.19-2.28 (m, 2 H), 2.03-2.15 (m, 5 H), 1.92-2.01 (m, 1 H), 1.32-1.38 (m, 1 H), 0.98-1.04 (m, 1 H). |

TABLE A-continued

| Example No. (preparation of the Example) | Structure and IUPAC name | Characterising data (LCMS and/or NMR) |
|---|---|---|
| 85 (General Procedure B using Amine B8 as the core reagent) | 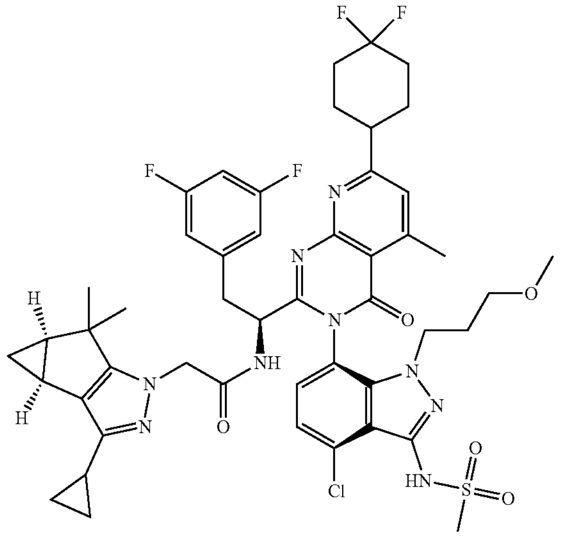 N-[(1S)-1-[(3P)-3-[4-chloro-3-methanesulfonamido-1-(3-methoxypropyl)-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-cyclopropyl-5,5-difluoro-7,8-diazatricyclo[4.3.0.0$^{2,4}$]nona-1(6),8-dien-7-yl]acetamide | LCMS Method B: retention time = 1.57 min.; observed ion = 986.4 [M + H]. 1H NMR (500 MHz, METHANOL-d4) δ ppm 7.41 (d, J = 0.60 Hz, 1H), 7.30 (d, J = 7.75 Hz, 1H), 7.12 (d, J = 8.05 Hz, 1H), 6.76 (tt, J = 9.24, 2.38 Hz, 1H), 6.54 (dd, J = 8.05, 2.09 Hz, 2H), 4.80-4.82 (m, 1 H), 4.44 (d, J = 1.49 Hz, 2 H), 4.01 (ddd, J = 14.31, 9.84, 5.96 Hz, 1 H), 3.76-3.87 (m, 1 H), 3.34-3.41 (m, 1 H), 3.25 (s, 3 H), 3.11-3.15 (m, 1H), 2.98-3.11 (m, 3 H), 2.81 (d, J = 0.60 Hz, 3 H), 2.77 (s, 3 H), 2.27-2.33 (m, 1 H), 2.20-2.27 (m, 3 H), 1.96-2.13 (m, 6 H), 1.79-1.89 (m, 3 H), 1.26-1.31 (m, 1 H), 0.87-0.95 (m, 3 H), 0.76-0.82 (m, 2 H). |
| 86 (General Procedure B using Amine B8 as the core reagent) | 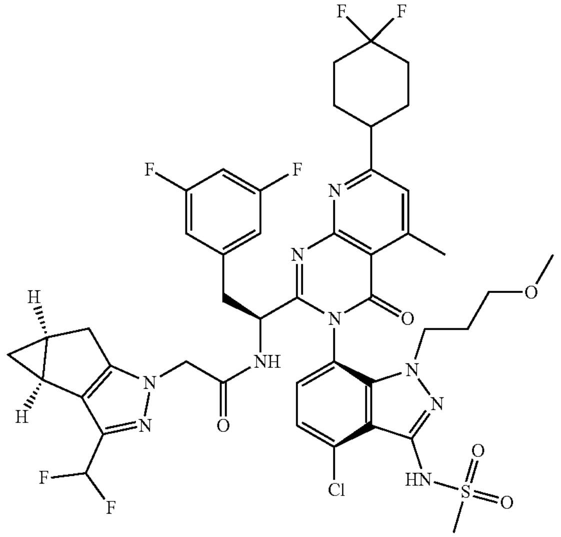 N-[(1S)-1-[(3P)-3-[4-chloro-3-methanesulfonamido-1-(3-methoxypropyl)-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-(difluoromethyl)-7,8-diazatricyclo[4.3.0.0$^{2,4}$]nona-1(6),8-dien-7-yl]acetamide | LCMS Method B: retention time = 1.52 min.; observed ion = 960.2 [M + H]. 1H NMR (500 MHz, METHANOL-d4) δ ppm 7.42 (d, J = 0.89 Hz, 1 H), 7.30 (d, J = 7.75 Hz, 1 H), 7.20 (d, J = 7.75 Hz, 1 H), 6.70-6.78 (m, 1 H), 6.40-6.68 (m, 3 H), 4.88-4.91 (m, 1 H), 4.39 (d, J = 16.39 Hz, 1 H), 4.23 (d, J = 16.39 Hz, 1 H), 3.90-3.97 (m, 1H), 3.83 (ddd, J = 14.16, 10.28, 5.36 Hz, 1 H), 3.42 (dd, J = 14.01, 5.07 Hz, 1H), 3.26 (s, 3 H), 2.99-3.15 (m, 4 H), 2.81 (d, J = 0.60 Hz, 3 H), 2.77 (s, 3 H), 2.60-2.67 (m, 1 Hz), 2.51-2.59 (m, 1 H), 2.18-2.27 (m, 2 H), 1.94-2.13 (m, 8H), 1.79-1.93 (m, 2 H), 1.03 (td, J = 7.75, 4.77 Hz, 1 H), 0.17-0.21 (m, 1H). |

TABLE A-continued

| Example No. (preparation of the Example) | Structure and IUPAC name | Characterising data (LCMS and/or NMR) |
| --- | --- | --- |
| 87 (General Procedure B using Amine B8 as the core reagent) | 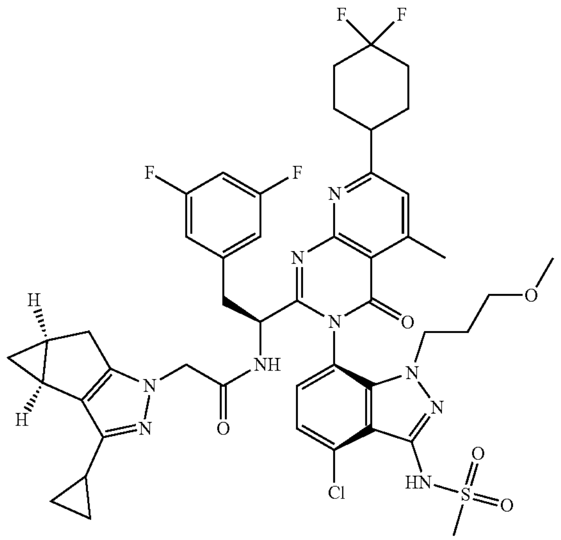 N-[(1S)-1-[(3P)-3-[4-chloro-3-methanesulfonamido-1-(3-methoxypropyl)-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.55 min.; observed ion = 950.2 [M + H]. 1H NMR (500 MHz, METHANOL-d4) δ ppm 7.42 (d, J = 0.60 Hz, 1 H), 7.30 (d, J = 8.05 Hz, 1 H), 7.15 (d, J = 7.75 Hz, 1 H), 6.76 (tt, J = 9.09, 2.38 Hz, 1 H), 6.53-6.62 (m, 2H), 4.79-4.83 (m, 1H), 4.25 (s, 2H), 3.91 (ddd, J = 14.16, 10.28, 5.96 Hz, 1H), 3.76-3.85 (m, 1H), 3.40 (dd, J = 14.01, 5.36 Hz, 1 H), 3.27 (s, 3 H), 3.08-3.15 (m, 2H), 3.04 (dd, J = 14.16, 8.79 Hz, 2H), 2.81 (d, J = 0.60 Hz, 3 H), 2.78 (s, 3 H), 2.66 (dd, J = 16.39, 6.56 Hz, 1 H), 2.44 (d, J = 16.39 Hz, 1 H), 2.18-2.28 (m, 2 H), 2.02-2.13 (m, 5 H), 1.81-2.01 (m, 5H), 1.77 (tt, J = 8.49, 5.07 Hz, 1H), 0.95 (td, J = 7.60, 4.77 Hz, 1 H), 0.82-0.89 (m, 2 H), 0.69-0.80 (m, 2 H), 0.04-0.10 (m, 1H) |
| 88 (General Procedure B using Amine B8 as the core reagent) | 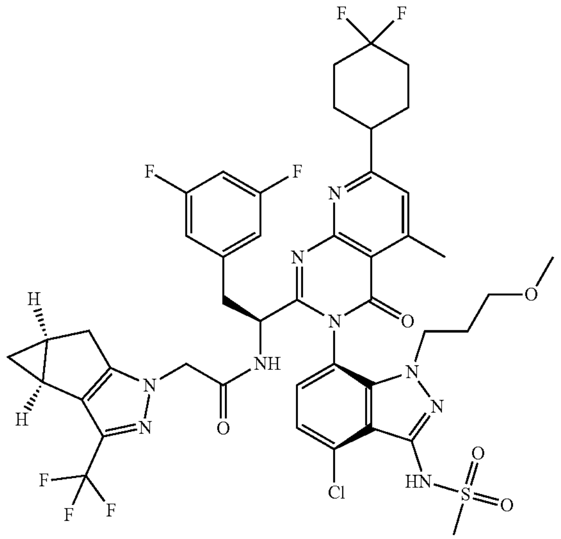 N-[(1S)-1-[(3P)-3-[4-chloro-3-methanesulfonamido-1-(3-methoxypropyl)-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-(trifluoromethyl)-7,8-diazatricyclo[4.3.0.0$^{2,4}$]nona-1(6),8-dien-7-yl]acetamide | LCMS Method B: retention time = 1.57 min.; observed ion = 978.4 [M + H]. 1H NMR (500 MHz, METHANOL-d4) δ ppm 7.42 (s, 1 H), 7.29 (d, J = 7.75 Hz, 1 H), 7.16 (d, J = 7.75 Hz, 1 H), 6.71-6.79 (m, 1 H), 6.59 (br d, J = 6.56 Hz, 2 H), 4.54-4.60 (m, 1 H), 4.33-4.47 (m, 2 H), 3.89-3.99 (m, 1 H), 3.84 (br dd, J = 10.13, 5.07 Hz, 1 H), 3.42 (dd, J = 14.01, 5.07 Hz, 1 H), 3.26 (s, 3 H), 2.98-3.16 (m, 4 H), 2.81 (s, 3 H), 2.76 (s, 3 H), 2.70-2.75 (m, 1 H), 2.53-2.60 (m, 1 H), 2.17-2.29 (m, 2 H), 2.02-2.13 (m, 7 H), 1.92-2.01 (m, 1 H), 1.77-1.92 (m, 2 H), 1.06 (td, J = 7.67, 5.51 Hz, 1 H), 0.19 (q, J = 4.17 Hz, 1 H). |

TABLE A-continued

| Example No. (preparation of the Example) | Structure and IUPAC name | Characterising data (LCMS and/or NMR) |
| --- | --- | --- |
| 89 (General Procedure B using Amine B8 as the core reagent) | 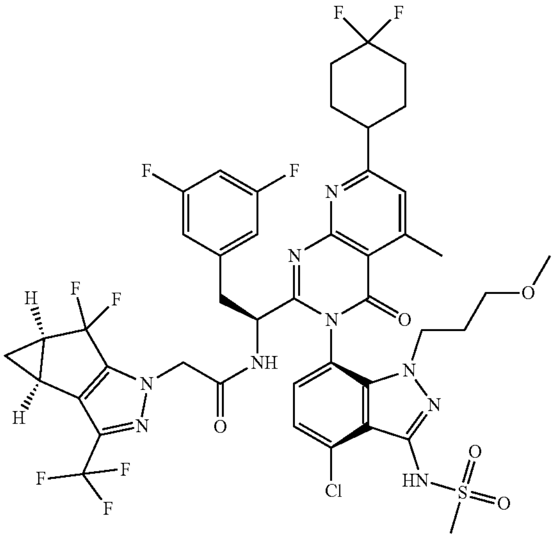 N-[(1S)-1-[(3P)-3-[4-chloro-3-methanesulfonamido-1-(3-methoxypropyl)-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-5,5-difluoro-9-(trifluoromethyl)-7,8-diazatricyclo[4.3.0.0$^{2}$,$^{4}$]nona-1(6),8-dien-7-yl]acetamide | LCMS Method B: retention time = 1.58 min.; observed ion = 1014.2 [M + H]. 1H NMR (500 MHz, METHANOL-d4) δ ppm 7.42 (d, J = 0.60 Hz, 1H), 7.30 (d, J = 8.05 Hz, 1 H), 7.15 (d, J = 7.75 Hz, 1 H), 6.76 (tt, J = 9.24, 2.38 Hz, 1 H), 6.50-6.59 (m, 2H), 4.80-4.82 (m, 2H), 4.65 (q, J = 16.49 Hz, 2H), 3.99 (ddd, J = 14.16, 9.84, 6.11 Hz, 1H), 3.83 (ddd, J = 14.08, 9.76, 5.96 Hz, 1H), 3.40 ( dd, J = 14.01, 5.07 Hz, 1 H), 3.24 (s, 3 H), 3.11-3.14 (m, 1 H), 2.98-3.11 (m, 3 H), 2.81 (d, J = 0.60 Hz, 3H), 2.77 (s, 3 H), 2.40-2.51 (m, 2 H), 2.17-2.27 (m, 2 H), 2.02-2.13 (m, 5 H), 1.94-2.01 (m, 1 H), 1.79-1.90 (m, 2 H), 1.35-1.41 (m, 1 H), 1.04-1.09 (m, 1 H). |
| 90 (General Procedure B using Amine B8 as the core reagent) | 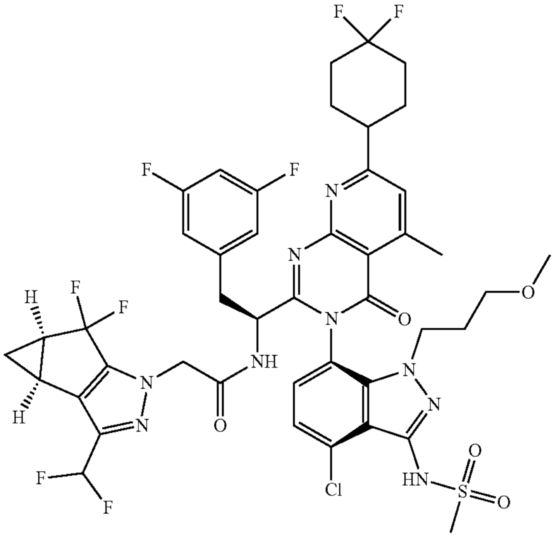 N-[(1S)-1-[(3P)-3-[4-chloro-3-methanesulfonamido-1-(3-methoxypropyl)-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method B: retention time = 1.53 min.; observed ion = 996.2 [M + H]. 1H NMR (500 MHz, METHANOL-d4) δ ppm 7.38-7.44 (m, 1 H), 7.27-7.33 (m, 1 H), 7.16 (d, J = 7.75 Hz, 1 H), 6.52-6.78 (m, 4 H), 4.76-4.80 (m, 1 H), 4.53-4.62 (m, 3 H), 4.01 (ddd, J = 14.01, 10.13, 5.96 Hz, 1H), 3.82 (ddd, J = 14.16, 10.28, 5.66 Hz, 1 H), 3.40 (dd, J = 13.86, 5.22 Hz, 1 H), 3.23 (s, 3 H), 2.9 8-3.14 (m, 4 H), 2.81 (d, J = 0.60 Hz, 3 H), 2.77 (s, 3 H), 2.42 (ddd, J = 11.18, 7.60, 4.17 Hz, 2 H), 2.18-2.29 (m, 2 H), 2.02-2.14 (m, 5 H), 1.94-2.02 (m, 1 H), 1.77-1.92 (m, 2 H), 1.33-1.39 (m, 1 H), 0.99-1.05 (m, 1 H). |

TABLE A-continued

| Example No. (preparation of the Example) | Structure and IUPAC name | Characterising data (LCMS and/or NMR) |
|---|---|---|
| 94 (General Procedure B using Amine B9 as the core reagent) | 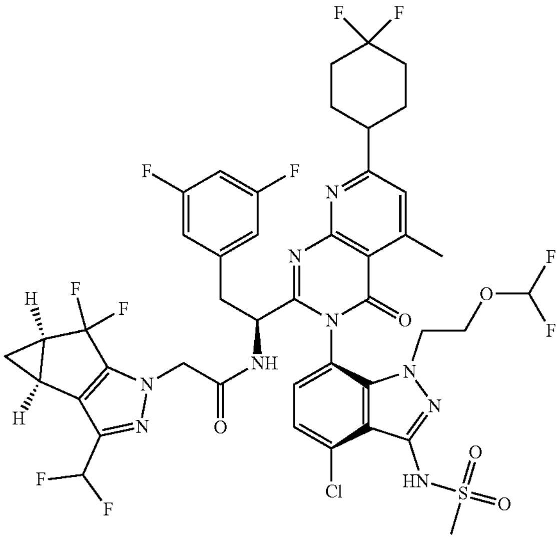 N-[(1S)-1-[(3P)-3-{4-chloro-1-[2-(difluoromethoxy)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 3.23 min.; observed ion = 1018.25 [M + H]. 1H NMR (500 MHz, METHANOL-d4) δ ppm 7.41 (d, J = 0.89 Hz, 1 H), 7.33 (d, J = 7.75 Hz, 1 H), 7.19 (d, J = 8.05 Hz, 1 H), 6.48-6.80 (m, 4 H), 5.95-6.30 (m, 1H), 4.78 (dd, J = 9.39, 4.92 Hz, 1 H), 4.62 (q, J = 16.39 Hz, 2H), 4.23 (dt, J = 14.45, 5.29 Hz, 1 H), 4.04-4.14 (m, 1H), 3.98 (dt, J = 10.88, 5.29 Hz, 1 H), 3.81-3.91 (m, 1H), 3.38 (dd, J = 14.16, 4.92 Hz, 1H), 3.23 (s, 3H), 2.97-3.09 (m, 2 H), 2.81 (d, J = 0.89 Hz, 3 H), 2.41 (ddd, J = 11.10, 7.53, 4.02 Hz, 2 H), 2.18-2.28 (m, 2 H), 2.01-2.15 (m, 5 H), 1.91-2.01 (m, 1 H), 1.29-1.38 (m, 1 H), 0.95-1.04 (m, 1H). |
| 105 (General Procedure B using Amine B10 as the core reagent) | 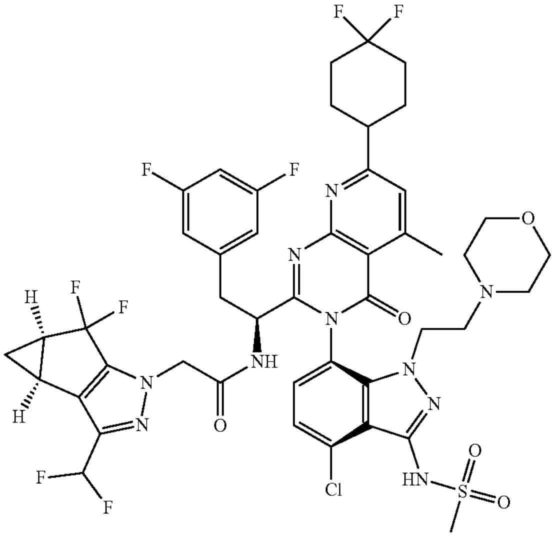 N-[(1S)-1-[(3P)-3-{4-chloro-3-methanesulfonamido-1-[2-(morpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.63 min.; observed ion = 1037.05 [M + H]. 1H NMR (500 MHz, METHANOL-d4) δ ppm 7.44 (d, J = 0.60 Hz, 1 H), 7.33 (d, J = 8.05 Hz, 1 H), 7.23 (d, J = 7.75 Hz, 1H), 6.49-6.80 (m, 4 H), 4.78 (dd, J = 9.54, 4.77 Hz, 1 H), 4.56-4.68 (m, 2H), 4.17 (ddd, J = 14.16, 9.98, 5.96 Hz, 1H), 3.79 (ddd, J = 14.38, 9.76, 5.07 Hz, 1 H), 3.34-3.41 (m, 5H), 3.24 (s, 3H), 3.04 (dd, J = 14.16, 9.39 Hz, 2H), 2.83 (s, 3H), 2.64 (ddd, J = 12.14, 10.06, 5.81 Hz, 1 H), 2.46-2.55 (m, 1 H), 2.42 (ddd, J = 11.10, 7.53, 4.02 Hz, 2 H), 2.19-2.28 (m, 2 H), 1.96-2.15 (m, 10 H), 1.32-1.39 (m, 1 H), 0.98-1.05 (m, 1 H). |

TABLE A-continued

| Example No. (preparation of the Example) | Structure and IUPAC name | Characterising data (LCMS and/or NMR) |
| --- | --- | --- |
| 112 (General Procedure B using Amine B10 as the core reagent) | 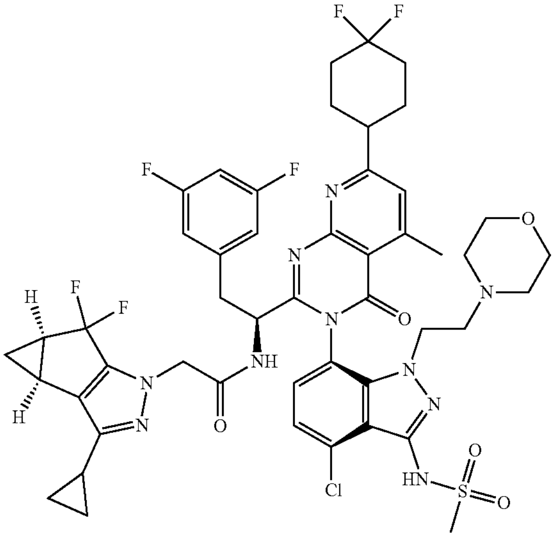 N-[(1S)-1-[(3P)-3-{4-chloro-3-methanesulfonamido-1-[2-(morpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-cyclopropyl-5,5-difluoro-7,8-diazatricyclo[4.3.0.0$^{2,4}$]nona-1(6),8-dien-7-yl]acetamide | LCMS Method B: retention time = 1.17 min.; observed ion = 1025.5 [M − H]. 1H NMR (500 MHz, METHANOL-d4) δ ppm 7.43 (d, J = 0.60 Hz, 1H), 7.34 (d, J = 8.05 Hz, 1H), 7.24 (d, J = 8.05 Hz, 1H), 6.77 (tt, J = 9.13, 2.35 Hz, 1H), 6.51 (dd, J = 8.20, 2.24 Hz, 2H), 4.75 (dd, J = 9.69, 4.62 Hz, 1 H), 4.42-4.54 (m, 2 H), 4.17-4.26 (m, 1 H), 3.78-3.87 (m, 1 H), 3.34-3.43 (m, 5 H), 3.26 (s, 3 H), 2.97-3.09 (m, 2 H), 2.83 (s, 3 H), 2.69-2.78 (m, 1 H), 2.54-2.66 (m, 1 H), 2.19-2.33 (m, 7 H), 2.03-2.13 (m, 5 H), 1.94-2.02 (m, 1 H), 1.83 (tt, J = 8.46, 4.95 Hz, 1 H), 1.24-1.30 (m, 1 H), 1.02 (t, J = 7.00 Hz, 1 H), 0.88-0.93 (m, 3 H), 0.75-0.80 (m, 2H). |
| 114 (General Procedure B using Amine B10 as the core reagent) | 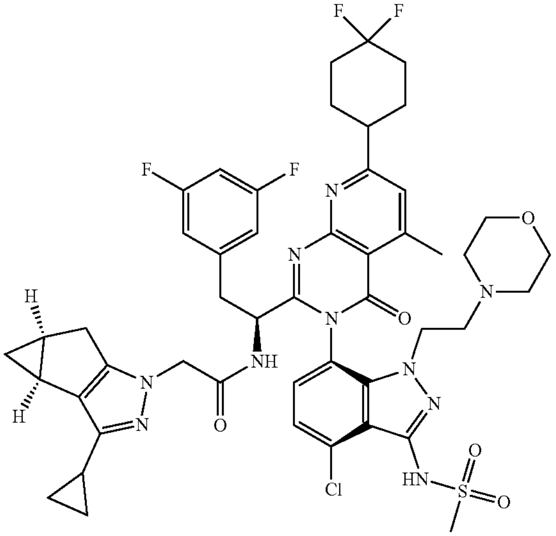 N-[(1S)-1-[(3P)-3-{4-chloro-3-methanesulfonamido-1-[2-(morpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.19 min.; observed ion = 989.5 [M − H]. 1H NMR (500 MHz, METHANOL-d4) δ ppm 7.43 (s, 1 H), 7.34 (d, J = 7.75 Hz, 1 H), 7.25 (d, J = 7.75 Hz, 1 H), 6.77 (tt, J = 9.13, 2.35 Hz, 1 H), 6.51-6.58 (m, 2 H), 4.76 (br d, J = 5.07 Hz, 1H), 4.25-4.36 (m, 2 H), 4.05-4.16 (m, 1 H), 3.74-3.83 (m, 1 H), 3.36-3.43 (m, 5 H), 3.27 (s, 3 H), 3.05 (br dd, J = 14.16, 9.39 Hz, 2 H), 2.83 (s, 3H), 2.53-2.76 (m, 3 H), 2.45 (d, J = 16.09 Hz, 1 H), 2.19-2.27 (m, 5 H), 2.03-2.12 (m, 5 H), 1.90-2.01 (m, 2 H), 1.81-1.86 (m, 1 H), 1.77 (tt, J = 8.46, 5.10 Hz, 2 H), 0.99-1.04 (m, 1H), 0.95 (td, J = 7.75, 4.77 Hz, 1 H), 0.82-0.89 (m, 2 H), 0.70-0.79 (m, 2H), 0.06 (q, J = 4.27 Hz, 1H). |

TABLE A-continued

| Example No. (preparation of the Example) | Structure and IUPAC name | Characterising data (LCMS and/or NMR) |
|---|---|---|
| 115 (General Procedure B using Amine B10 as the core reagent) | 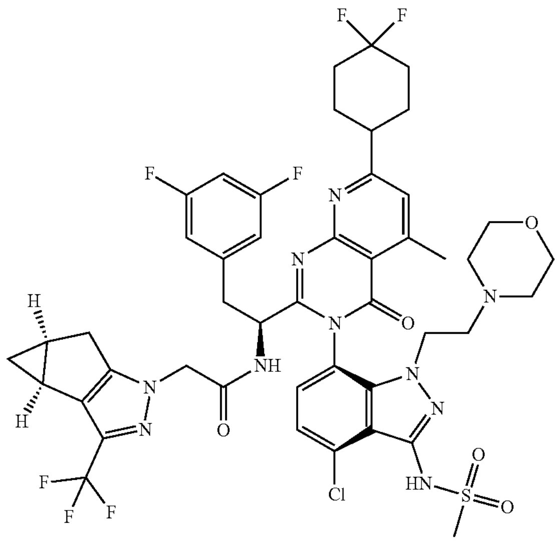 N-[(1S)-1-[(3P)-3-{4-chloro-3-methanesulfonamido-1-[2-(morpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-(trifluoromethyl)-7,8-diazatricyclo[4.3.0.0$^{2}$,$^{4}$]nona-1(6),8-dien-7-yl]acetamide | LCMS Method B: retention time = 1.21 min.; observed ion = 1017.5 [M − H]. 1H NMR (500 MHz, METHANOL-d4) δ ppm 7.44 (d, J = 0.60 Hz, 1 H), 7.29-7.36 (m, 1 H), 7.23 (d, J = 7.75 Hz, 1 H), 6.73-6.80 (m, 1 H), 6.55 (dd, J = 8.20, 2.24 Hz, 2 H), 4.78-4.81 (m, 1H), 4.41-4.52 (m, 2 H), 4.13 (ddd, J = 14.08, 9.76, 5.96 Hz, 1 H), 3.80 (ddd, J = 14.08, 9.46, 5.07 Hz, 1 H), 3.36-3.43 (m, 5 H), 3.26 (s, 3 H), 3.01-3.09 (m, 2 H), 2.83 (d, J = 0.60 Hz, 3H), 2.63-2.75 (m, 2 H), 2.50-2.61 (m, 2 H), 2.14-2.28 (m, 5 H), 2.02-2.11 (m, 7 H), 1.04-1.09 (m, 1 H), 0.98-1.03 (m, 1 H), 0.16-0.21 (m, 1 H). |
| 116 (General Procedure B using Amine B10 as the core reagent) | 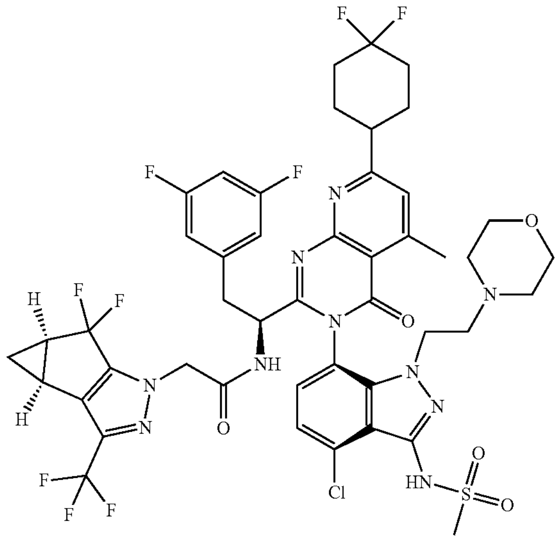 N-[(1S)-1-[(3P)-3-{4-chloro-3-methanesulfonamido-1-[2-(morpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-5,5-difluoro-9-(trifluoromethyl)-7,8-diazatricyclo[4.3.0.0$^{2}$,$^{4}$]nona-1(6),8-dien-7-yl]acetamide | LCMS Method B: retention time = 1.18 min.; observed ion = 1053.5 [M − H]. 1H NMR (500 MHz, METHANOL-d4) δ ppm 7.44 (d, J = 0.60 Hz, 1 H), 7.35 (d, J = 8.05 Hz, 1 H), 7.27 (d, J = 8.05 Hz, 1H), 6.76 (tt, J = 9.16, 2.31 Hz, 1 H), 6.51 (dd, J = 8.05, 2.09 Hz, 2H), 4.77-4.79 (m, 1 H), 4.73-4.76 (m, 1 H), 4.58-4.69 (m, 1H), 4.20 (ddd, J = 14.45, 8.64, 5.81 Hz, 1 H), 3.86 (ddd, J = 14.23, 8.87, 5.22 Hz, 1 H), 3.37-3.45 (m, 5 H), 3.25 (s, 3H), 3.05 (dd, J = 14.01, 9.54 Hz, 2 H), 2.83 (d, J = 0.60 Hz, 3 H), 2.61-2.79 (m, 2 H), 2.40-2.53 (m, 3 H), 2.21-2.32 (m, 5 H), 1.95-2.11 (m, 6 H), 1.36-1.42 (m, 1 H), 1.03-1.08 (m, 1 H). |

TABLE A-continued

| Example No. (preparation of the Example) | Structure and IUPAC name | Characterising data (LCMS and/or NMR) |
|---|---|---|
| 121 (General Procedure B using Amine B11 as the core reagent) | 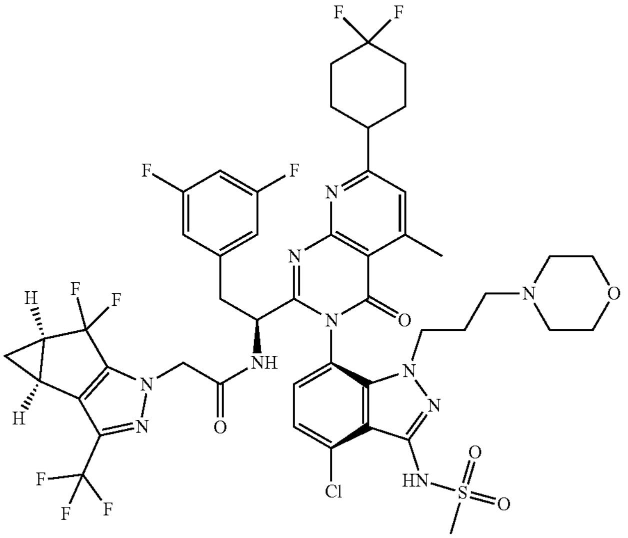<br>N-[(1S)-1-[(3P)-3-{4-chloro-3-methanesulfonamido-1-[3-(morpholin-4-yl)propyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-5,5-difluoro-9-(trifluoromethyl)-7,8-diazatricyclo[4.3.0.0$^{2}$,$^{4}$]nona-1(6),8-dien-7-yl]acetamide | LCMS Method B: retention time = 1.15 min.; observed ion = 1067.4 [M − H].<br>1H NMR (500 MHz, METHANOL-d4) δ ppm 7.44 (s, 1 H), 7.35 (d, J = 8.05 Hz, 1 H), 7.26 (d, J = 8.05 Hz, 1 H), 6.73-6.80 (m, 1 H), 6.51 (br d, J = 5.66 Hz, 2 H), 4.74 (br d, J = 10.13 Hz, 3 H), 4.04-4.11 (m, 1 H), 3.77-3.85 (m, 1 H), 3.57-3.69 (m, 4 H), 3.38-3.42 (m, 1 H), 3.28 (s, 3 H), 3.02-3.09 (m, 2 H), 2.84 (s, 3 H), 2.61-2.75 (m, 4 H), 2.40-2.53 (m, 4 H), 2.19-2.30 (m, 2 H), 2.06-2.12 (m, 4 H), 1.96-2.02 (m, 2 H), 1.66-1.80 (m, 2 H), 1.37-1.44 (m, 1 H), 0.97-1.08 (m, 3 H). |
| 128 (General Procedure B using Amine B12 as the core reagent) | 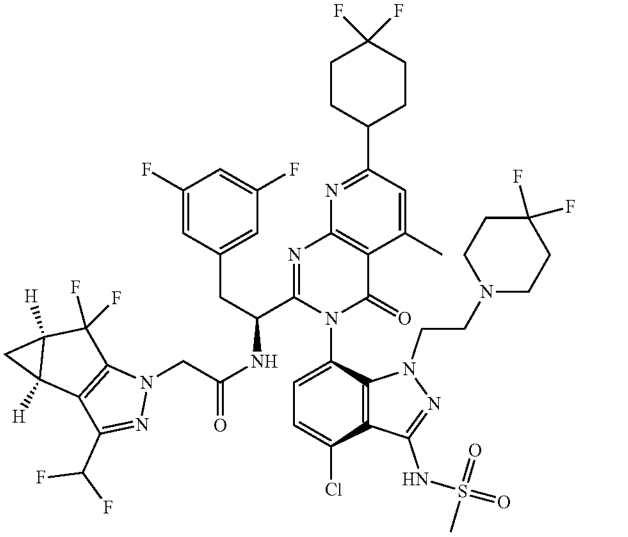<br>N-[(1S)-1-[(3P)-3-{4-chloro-1-[2-(4,4-difluoropiperidin-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method A: retention time = 2.94 min.; observed ion = 1071.15 [M + H]. 1H NMR (500 MHz, METHANOL-d4) δ ppm 7.40-7.47 (m, 1 H), 7.34 (d, J = 7.75 Hz, 1 H), 7.25 (d, J = 8.05 Hz, 1 H), 6.47-6.79 (m, 4 H), 4.75-4.79 (m, 1 H), 4.53-4.68 (m, 2 H), 4.17 (ddd, J = 14.16, 9.98, 5.96 Hz, 1 H), 3.77 (ddd, J = 14.23, 9.61, 5.07 Hz, 1 H), 3.37 (dd, J = 14.01, 4.77 Hz, 1 H), 3.24 (s, 3 H), 2.98-3.08 (m, 2 H), 2.83 (d, J = 0.60 Hz, 3 H), 2.69 (ddd, J = 12.37, 9.98, 5.96 Hz, 1 H), 2.49-2.58 (m, 1 H), 2.42 (ddd, J = 11.10, 7.67, 3.87 Hz, 2 H), 2.18-2.28 (m, 6 H), 1.97-2.12 (m, 6 H), 1.57-1.70 (m, 4 H), 1.31-1.40 (m, 1 H), 0.95-1.05 (m, 1H). |

TABLE A-continued

| Example No. (preparation of the Example) | Structure and IUPAC name | Characterising data (LCMS and/or NMR) |
|---|---|---|
| 129 (General Procedure B using Amine B13 as the core reagent) | 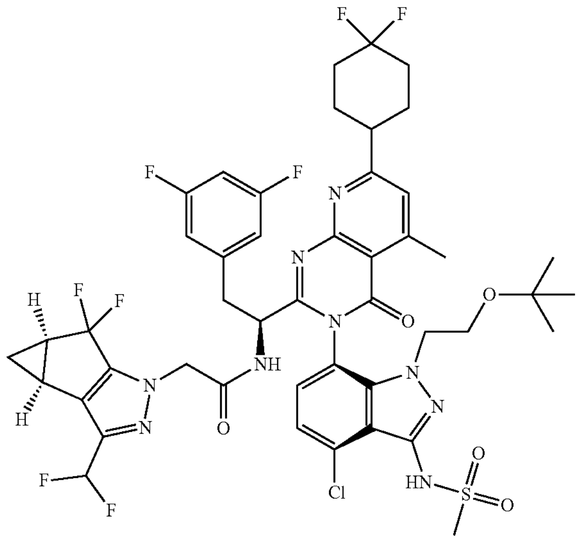 N-[(1S)-1-[(3P)-3-{1-[2-(tert-butoxy)ethyl]-4-chloro-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 3.48 min.; observed ion = 1024.10 [M + H]. 1H NMR (500 MHz, METHANOL-d4) δ ppm 7.42 (d, J = 0.89 Hz, 1 H), 7.31 (d, J = 8.05 Hz, 1 H), 7.17 (d, J = 8.05 Hz, 1 H), 6.48-6.81 (m, 4 H), 4.81 (d, J = 5.07 Hz, 1 H), 4.54-4.66 (m, 2 H), 4.12 (ddd, J = 14.01, 7.45, 6.26 Hz, 1 H), 3.63-3.73 (m, 1 H), 3.56 (ddd, J = 9.46, 7.23, 6.26 Hz, 1 H), 3.41-3.48 (m, 1 H), 3.36 (dd, J = 13.86, 5.22 Hz, 1 H), 3.24 (s, 3 H), 2.97-3.09 (m, 2 H), 2.84 (s, 3 H), 2.42 (ddd, J = 11.18, 7.60, 3.87 Hz, 2 H), 2.19-2.29 (m, 2 H), 2.02-2.13 (m, 5 H), 1.95-2.01 (m, 1 H), 1.30-1.39 (m, 1 H), 0.99-1.06 (m, 1 H), 0.90 (s, 9 H). |
| 130 (General Procedure B using Amine B14 as the core reagent) | 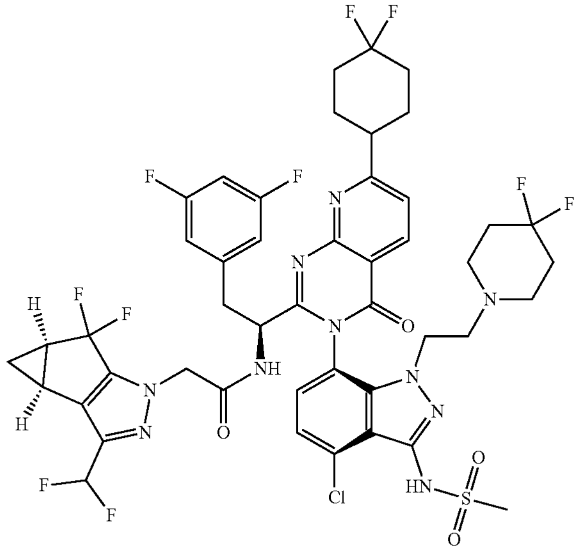 N-[(1S)-1-[(3P)-3-{4-chloro-1-[2-(4,4-difluoropiperidin-1-yl)ethyl]-3-methanesulfonamido-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.905 min.; observed ion = 1057.10 [M + H]. 1H NMR (500 MHz, CD3OD, 303 K) δ (ppm) = 8.64 (d, J = 8.0 Hz, 1H), 7.69 (d, J = 8.0 Hz, 1H), 7.38 (d, J = 7.7 Hz, 1H), 7.32 (d, J = 7.7 Hz, 1H), 6.81-6.76 (m, 1H), 6.69 (br t, J = 54.8 Hz, 1H), 6.58-6.51 (m, 2H), 4.83 (br d, J = 4.8 Hz, 2H), 4.72-4.59 (m, 2H), 4.24-4.16 (m, 1H), 3.82-3.75 (m, 1H), 3.42 (dd, J = 4.6, 14.2 Hz, 1H), 3.26 (s, 3H), 3.19-3.06 (m, 2H), 2.77-2.58 (m, 2H), 2.47-2.41 (m, 2H), 2.32-2.23 (m, 4H), 2.18-2.06 (m, 6H), 2.06-1.97 (m, 1H), 1.77-1.60 (m, 4H), 1.40-1.35 (m, 1H), 1.05-1.01 (m, 1H). |

TABLE A-continued

| Example No. (preparation of the Example) | Structure and IUPAC name | Characterising data (LCMS and/or NMR) |
|---|---|---|
| 134 (General Procedure D using Chloride D1 as the core reagent) | 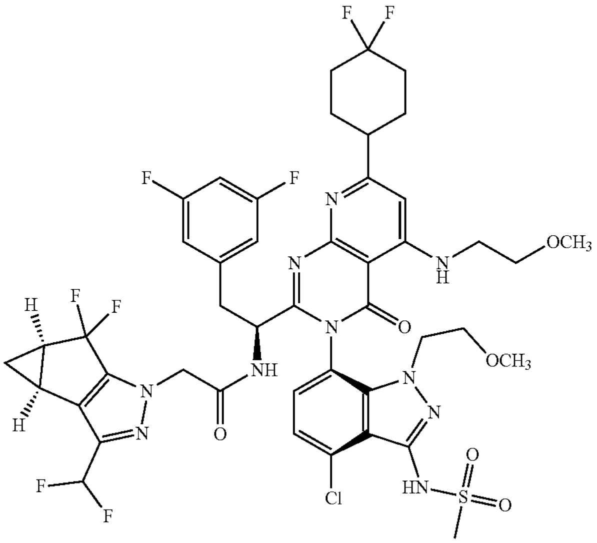 N-[(1S)-1-[(3P)-3-[4-chloro-3-methanesulfonamido-1-(2-methoxyethyl)-1H-indazol-7-yl]-7-(4,4-difluorocyclohexyl)-5-[(2-methoxyethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.80 min.; observed ion = 1041.10 [M + H]. 1H NMR (500 MHz, METHANOL-d4), δ ppm 9.12 (t, J = 5.22 Hz, 1H), 7.28 (d, J = 7.75 Hz, 1H), 7.07 (d, J = 7.75 Hz, 1H), 6.48-6.80 (m, 5 H), 4.50-4.62 (m, 2 H), 4.15 (dt, J = 14.31, 5.36 Hz, 1 H), 3.69-3.82 (m, 1 H), 3.59-3.64 (m, 2 H), 3.47-3.57 (m, 4 H), 3.33-3.37 (m, 1 H), 3.33 (s, 3 H), 3.23 (s, 3 H), 3.06 (s, 3 H), 3.01 (dd, J = 13.71, 8.94 Hz, 1 H), 2.77-2.89 (m, 1 H), 2.37-2.48 (m, 2 H), 2.19-2.27 (m, 2 H), 1.90-2.12 (m, 6 H), 1.30-1.39 (m, 1H), 0.98-1.04 (m, 1 H). |
| 135 (General Procedure D using Chloride D2 as the core reagent) | 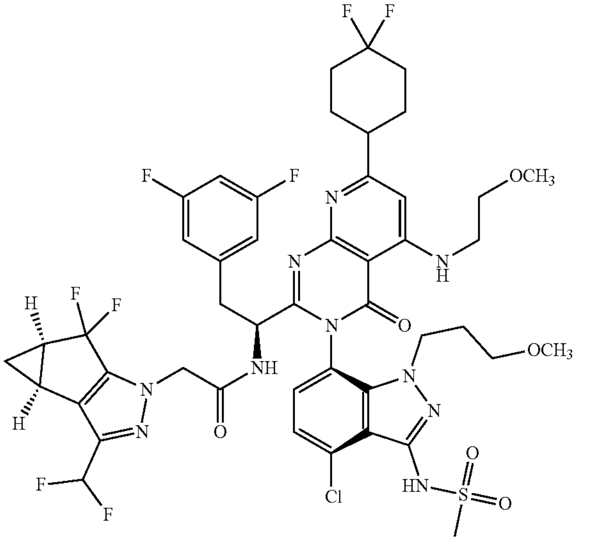 N-[(1S)-1-[(3P)-3-[4-chloro-3-methanesulfonamido-1-(3-methoxypropyl)-1H-indazol-7-yl]-7-(4,4-difluorocyclohexyl)-5-[(2-methoxyethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.84 min.; observed ion = 1055.15 [M + H]. 1H NMR (500 MHz, METHANOL-d4), δ ppm 9.10 (t, J = 5.36 Hz, 1H), 7.27 (d, J = 7.75 Hz, 1H), 7.07 (d, J = 8.05 Hz, 1H), 6.45-6.85 (m, 5 H), 4.77-4.81 (m, 1H), 4.57 (d, J = 2.38 Hz, 2 H), 3.94-4.08 (m, 1H), 3.74-3.85 (m, 1H), 3.58-3.63 (m, 2H), 3.49-3.54 (m, 2H), 3.37 (dd, J = 14.01, 5.36 Hz, 1 H), 3.33 (s, 3H), 3.23 (s, 3H), 3.09-3.17 (m, 2H), 3.02 (dd, J = 14.01, 8.94 Hz, 1H), 2.92 (s, 3H), 2.79-2.89 (m, 1H), 2.42 (ddd, J = 11.55, 7.67, 4.02 Hz, 2 H), 2.17-2.27 (m, 2 H), 1.94-2.11 (m, 6 H), 1.80-1.89 (m, 2 H), 1.32-1.38 (m, 1 H), 0.98-1.04 (m, 1 H) |

TABLE A-continued

| Example No. (preparation of the Example) | Structure and IUPAC name | Characterising data (LCMS and/or NMR) |
|---|---|---|
| 149 (General Procedure B using Amine B15 as the core reagent) | 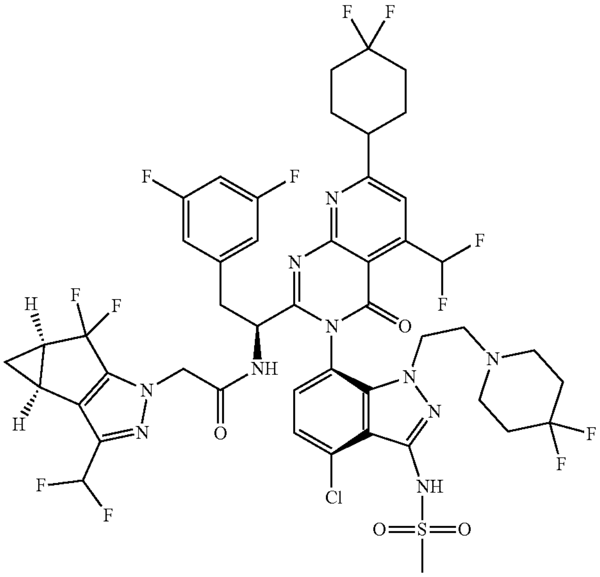 N-[(1S)-1-[(3P)-3-{4-chloro-1-[2-(4,4-difluoropiperidin-1-yl)ethyl]-3-methanesulfonamido-1H-indazol-7-yl}-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 3.19 min.; observed ion = 1107.2 [M + H]. 1H NMR (500 MHz, METHANOL-d4) δ ppm 7.67-7.93 (m, 2 H), 7.35 (s, 1 H), 7.31-7.33 (m, 1 H), 6.49-6.81 (m, 4 H), 4.78-4.82 (m, 2 H), 4.56-4.71 (m, 2 H), 4.18 (ddd, J = 14.53, 9.16, 5.81 Hz, 1 H), 3.80 (br d, J = 9.24 Hz, 1 H), 3.36-3.41 (m, 1 H), 3.23-3.25 (m, 3 H), 3.18-3.23 (m, 1 H), 3.06 (dd, J = 14.31, 9.84 Hz, 1 H), 2.63-2.71 (m, 1 H), 2.54-2.62 (m, 1 H), 2.42 (ddd, J = 11.25, 7.67, 4.02 Hz, 2 H), 2.21-2.30 (m, 5 H), 1.97-2.15 (m, 6 H), 1.60-1.70 (m, 4 H), 1.33-1.39 (m, 1 H), 0.99-1.03 (m, 1 H). |
| 150 (General Procedure B using Amine B16 as the core reagent) | 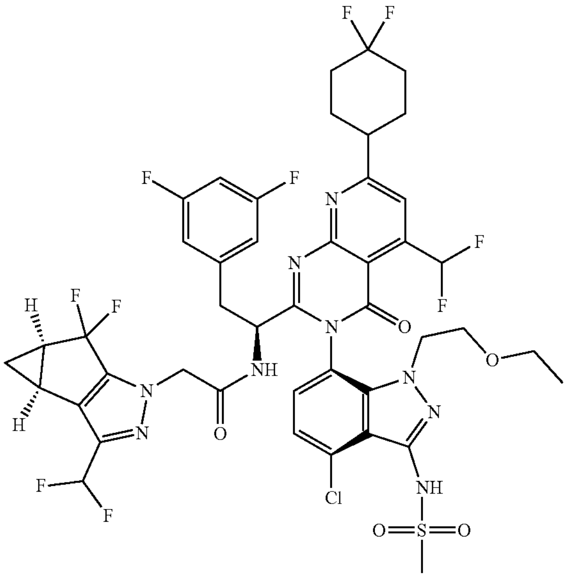 N-[(1S)-1-[(3P)-3-[4-chloro-1-(2-ethoxyethyl)-3-methanesulfonamido-1H-indazol-7-yl]-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 3.25 min.; observed ion = 1032.2 [M + H]. 1H NMR (500 MHz, METHANOL-d4) δ ppm 7.65-7.90 (m, 2 H), 7.32-7.36 (m, 1 H), 7.25-7.30 (m, 1 H), 6.51-6.78 (m, 4 H), 4.87 (dd, J = 9.39, 4.62 Hz, 1 H), 4.54-4.63 (m, 2 H), 4.15 (dt, J = 14.38, 6.22 Hz, 1 H), 3.74 (dt, J = 14.46, 6.33 Hz, 1 H), 3.57-3.64 (m, 1 H), 3.49-3.55 (m, 1 H), 3.39 (dd, J = 14.31, 4.77 Hz, 1 H), 3.16-3.25 (m, 6 H), 3.06 (dd, J = 14.31, 9.54 Hz, 1 H), 2.41 (ddd, J = 11.03, 7.60, 4.02 Hz, 2 H), 2.20-2.30 (m, 2 H), 2.06-2.16 (m, 5 H), 1.32-1.38 (m, 1 H), 0.98-1.03 (m, 1 H), 0.85 (t, J = 7.00 Hz, 3 H). |

TABLE A-continued

| Example No. (preparation of the Example) | Structure and IUPAC name | Characterising data (LCMS and/or NMR) |
|---|---|---|
| 154 (General Procedure B using Amine B17 as the core reagent) | 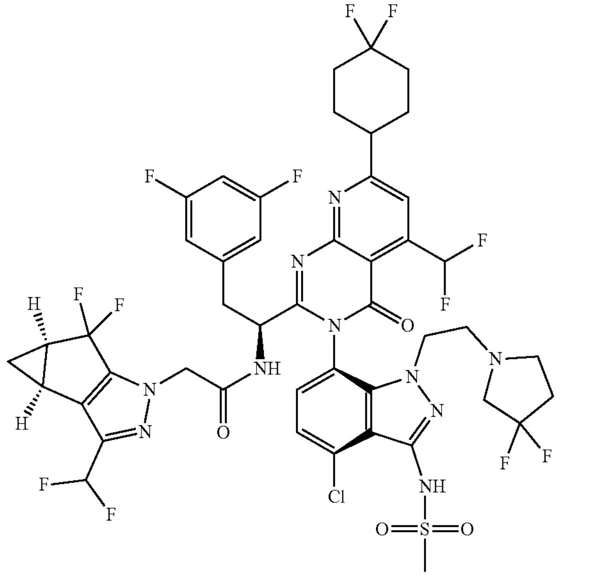 N-[(1S)-1-[(3P)-3-{4-chloro-1-[2-(3,3-difluoropyrrolidin-1-yl)ethyl]-3-methanesulfonamido-1H-indazol-7-yl}-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 3.09 min.; observed ion = 1093.1 [M + H]. 1H NMR (500 MHz, METHANOL-d4) δ ppm 7.65-7.90 (m, 2 H), 7.33-7.37 (m, 1 H), 7.26-7.31 (m, 1 H), 6.51-6.80 (m, 4 H), 4.81 (br d, J = 4.77 Hz, 1 H), 4.54-4.69 (m, 2 H), 4.13 (ddd, J = 14.31, 9.54, 5.96 Hz, 1 H), 3.74 (ddd, J = 14.16, 9.24, 5.22 Hz, 1 H), 3.40 (dd, J = 14.01, 4.47 Hz, 1 H), 3.17-3.25 (m, 4 H), 3.08 (dd, J = 14.16, 9.69 Hz, 1 H), 2.74 (ddd, J = 11.92, 9.69, 6.11 Hz, 1 H), 2.59-2.65 (m, 1 H), 2.38-2.59 (m, 6 H), 2.19-2.31 (m, 2 H), 2.06-2.17 (m, 5 H), 1.93-2.04 (m, 3 H), 1.32-1.38 (m, 1 H), 0.97-1.03 (m, 1 H). |
| 155 (General Procedure B using Amine B17 as the core reagent) | 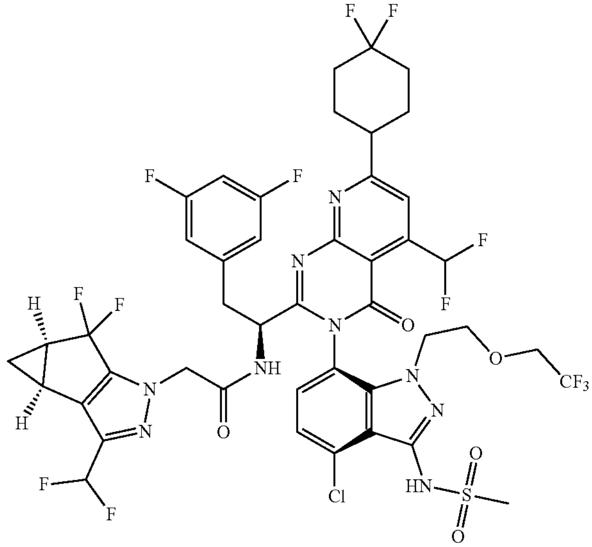 N-[(1S)-1-[(3P)-3-{4-chloro-3-methanesulfonamido-1-[2-(2,2,2-trifluoroethoxy)ethyl]-1H-indazol-7-yl}-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 3.28 min.; observed ion = 1086.1 [M + H]. 1H NMR (500 MHz, METHANOL-d4) δ ppm 7.62-7.89 (m, 2 H), 7.33-7.37 (m, 1 H), 7.26-7.30 (m, 1 H), 6.50-6.81 (m, 4 H), 4.56-4.69 (m, 2 H), 4.15-4.22 (m, 1 H), 3.72-3.85 (m, 3 H), 3.57-3.70 (m, 2 H), 3.38 (dd, J = 14.01, 4.47 Hz, 1 H), 3.16-3.25 (m, 4 H), 3.07 (dd, J = 14.16, 9.69 Hz, 1 H), 2.41 (ddd, J = 11.62, 7.90, 4.02 Hz, 2 H), 2.20-2.29 (m, 2 H), 1.97-2.18 (m, 6 H), 1.31-1.38 (m, 1 H), 0.97-1.02 (m, 1 H). |

TABLE A-continued

| Example No. (preparation of the Example) | Structure and IUPAC name | Characterising data (LCMS and/or NMR) |
|---|---|---|
| 158 (General Procedure A using Bromide A4 as the core reagent) | 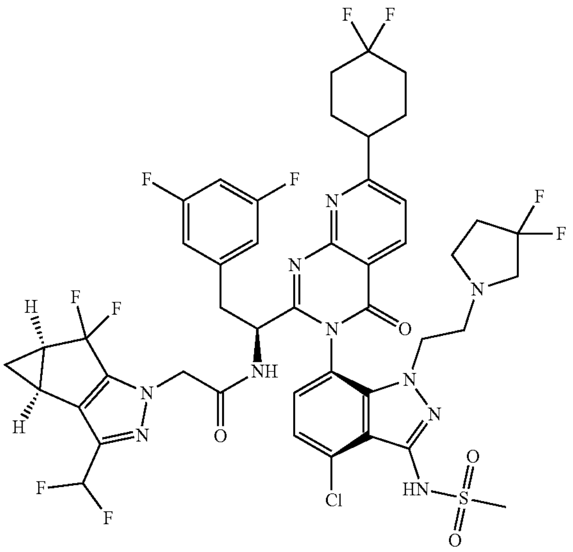 N-[(1S)-1-[(3P)-3-{4-chloro-1-[2-(3,3-difluoropyrrolidin-1-yl)ethyl]-3-methanesulfonamido-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.960 min.; observed ion = 1043.05 [M + H]. 1H NMR (500 MHz, CD3OD, 303 K) δ (ppm) = 8.52 (d, J = 8.0 Hz, 1H), 7.55 (d, J = 8.3 Hz, 1H), 7.25 (d, J = 8.0 Hz, 1H), 7.16 (d, J = 8.0 Hz, 1H), 6.69-6.65 (m, 1H), 6.56 (br t, J = 55.4 Hz, 1H), 6.47-6.42 (m, 2H), 4.72-4.70 (m, 1H), 4.59-4.46 (m, 2H), 4.03 (ddd, J = 6.0, 9.8, 14.3 Hz, 1H), 3.60 (ddd, J = 5.1, 9.5, 14.3 Hz, 1H), 3.31 (dd, J = 4.6, 14.2 Hz, 1H), 3.14 (s, 3H), 3.07-2.94 (m, 2H), 2.63 (ddd, J = 5.8, 9.9, 11.7 Hz, 1H), 2.51 (ddd, J = 4.9, 9.9, 12.0 Hz, 1H), 2.43-2.28 (m, 6H), 2.18-2.10 (m, 2H), 2.06-1.97 (m, 4H), 1.93-1.83 (m, 3H), 1.28-1.20 (m, 2H), 0.93-0.89 (m, 1H). |
| 160 (General Procedure A using Bromide A4 as the core reagent) | 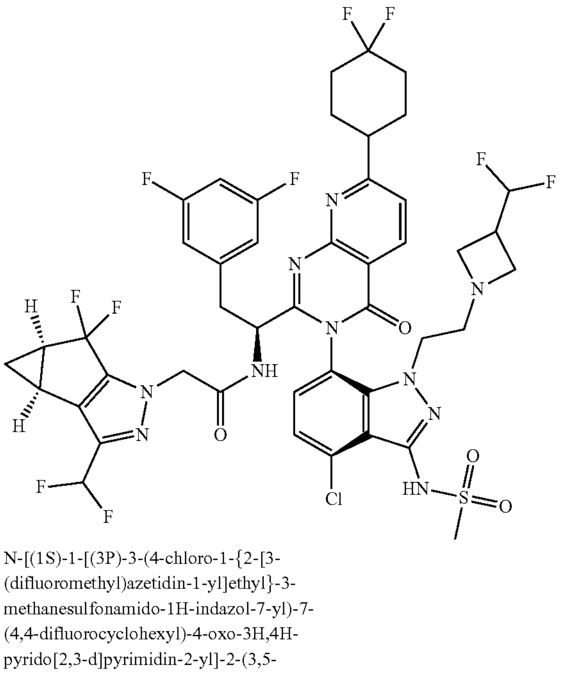 N-[(1S)-1-[(3P)-3-(4-chloro-1-{2-[3-(difluoromethyl)azetidin-1-yl]ethyl}-3-methanesulfonamido-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.12 min.; observed ion = 1041.4 [M − H]. 1H NMR (500 MHz, CD3OD, 303 K) δ (ppm) = 8.65 (d, J = 8.0 Hz, 1H), 7.68 (d, J = 8.0 Hz, 1H), 7.40-7.33 (m, 2H), 6.82-6.77 (m, 1H), 6.69 (t, J = 54.8 Hz, 1H), 6.58-6.53 (m, 2H), 6.07-5.75 (m, 1H), 4.83-4.77 (m, 2H), 4.73-4.58 (m, 2H), 4.09-4.02 (m, 1H), 3.77-3.71 (m, 1H), 3.48-3.41 (m, 1H), 3.29 (s, 3H), 3.26-3.18 (m, 2H), 3.15-3.08 (m, 2H), 3.02-2.88 (m, 2H), 2.88-2.77 (m, 1H), 2.49-2.40 (m, 2H), 2.31-2.22 (m, 2H), 2.18-2.08 (m, 5H), 2.06-1.98 (m, 1H), 1.42-1.35 (m, 1H), 1.33-1.28 (m, 1H), 1.04-1.00 (m, 1H). |

TABLE A-continued

| Example No. (preparation of the Example) | Structure and IUPAC name | Characterising data (LCMS and/or NMR) |
|---|---|---|
| 165 (General Procedure A using Bromide A4 as the core reagent) | 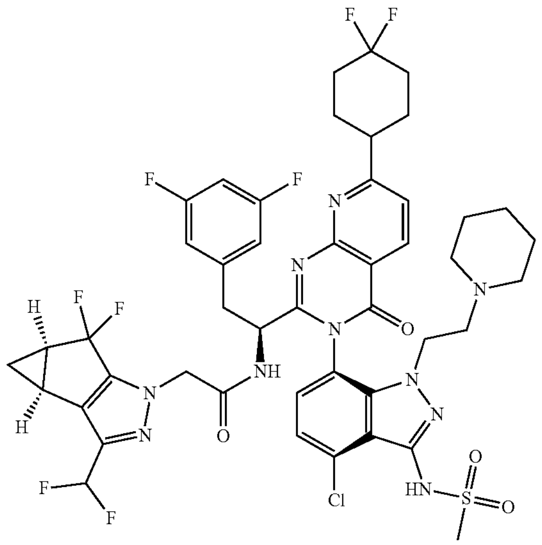 N-[(1S)-1-[(3P)-3-{4-chloro-3-methanesulfonamido-1-[2-(piperidin-1-yl)ethyl]-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.12 min.; observed ion = 1019.4 [M − H]. 1H NMR (500 MHz, CD3OD, 303 K) δ (ppm) = 8.64 (d, J = 8.0 Hz, 1H), 7.67 (d, J = 8.0 Hz, 1H), 7.43-7.38 (m, 2H), 6.83-6.79 (m, 1H), 6.70 (s, 1H), 6.68 (t, J = 54.8 Hz, 1H), 6.55 (dd, J = 2.1, 8.0 Hz, 2H), 4.91-4.88 (m, 1H), 4.77-4.63 (m, 3H), 4.36-4.30 (m, 1H), 4.07-4.01 (m, 1H), 3.48-3.44 (m, 1H), 3.27 (s, 3H), 3.20-3.12 (m, 2H), 2.49-2.40 (m, 2H), 2.31-2.22 (m, 2H), 2.15-1.98 (m, 6H), 1.78-1.66 (m, 4H), 1.65-1.48 (m, 2H), 1.42-1.27 (m, 3H), 1.24 (s, 1H), 1.02-0.98 (m, 1H), 0.93 (br d, J = 6.9 Hz, 1H). |
| 166 (General Procedure A using Bromide A4 as the core reagent) | 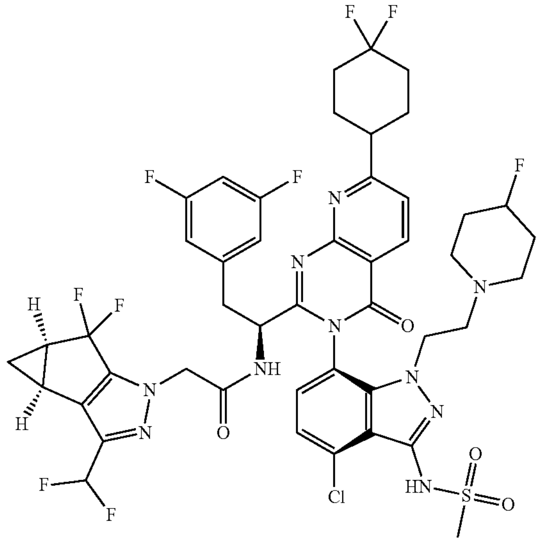 N-[(1S)-1-[(3P)-3-{4-chloro-1-[2-(4-fluoropiperidin-1-yl)ethyl]-3-methanesulfonamido-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.12 min.; observed ion = 1037.4 [M − H]. 1H NMR (500 MHz, CD3OD, 303 K) δ (ppm) = 8.64 (d, J = 8.0 Hz, 1H), 7.68 (d, J = 8.3 Hz, 1H), 7.38 (q, J = 7.9 Hz, 2H), 6.84-6.52 (m, 4H), 4.83-4.77 (m, 1H), 4.74-4.58 (m, 3H), 4.30-4.23 (m, 1H), 3.94-3.88 (m, 1H), 3.47-3.42 (m, 1H), 3.27 (s, 3H), 3.21-3.08 (m, 3H), 2.66-2.52 (m, 3H), 2.50-2.39 (m, 3H), 2.31-2.22 (m, 2H), 2.16-2.06 (m, 5H), 1.83-1.66 (m, 3H), 1.40-1.36 (m, 1H), 1.34-1.29 (m, 2H), 1.02 (tdd, J = 1.9, 3.8, 5.8 Hz, 1H), 0.97-0.87 (m, 1H). |

TABLE A-continued

| Example No. (preparation of the Example) | Structure and IUPAC name | Characterising data (LCMS and/or NMR) |
| --- | --- | --- |
| 167 (General Procedure A using Bromide A4 as the core reagent) | 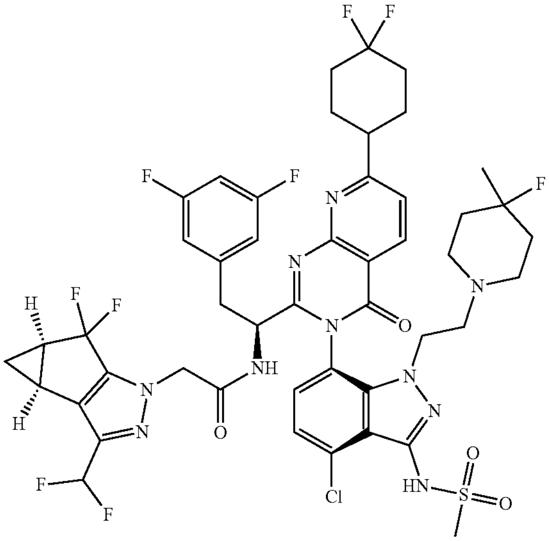 N-[(1S)-1-[(3P)-3-{4-chloro-1-[2-(4-fluoro-4-methylpiperidin-1-yl)ethyl]-3-methanesulfonamido-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method B: retention time = 1.14 min.; observed ion = 1051.6 [M − H]. 1H NMR (500 MHz, CD3OD, 303 K) δ (ppm) = 8.64 (d, J = 8.0 Hz, 1H), 7.68 (d, J = 8.0 Hz, 1H), 7.40 (s, 2H), 6.83-6.78 (m, 1H), 6.69 (t, J = 54.7 Hz, 1H), 6.57-6.53 (m, 2H), 4.94-4.88 (m, 1H), 4.78-4.61 (m, 3H), 4.33-4.27 (m, 1H), 4.02-3.94 (m, 1H), 3.48-3.43 (m, 1H), 3.28 (br s, 1H), 3.27 (s, 2H), 3.19-3.02 (m, 4H), 3.02-2.91 (m, 1H), 2.44 (ddd, J = 4.0, 7.6, 11.3 Hz, 2H), 2.31-2.22 (m, 2H), 2.17-2.01 (m, 6H), 1.87-1.72 (m, 3H), 1.42-1.35 (m, 3H), 1.33-1.23 (m, 3H), 1.03-0.99 (m, 1H), 0.93 (br d, J = 6.0 Hz, 1H). |
| 168 (General Procedure A using Bromide A4 as the core reagent) | 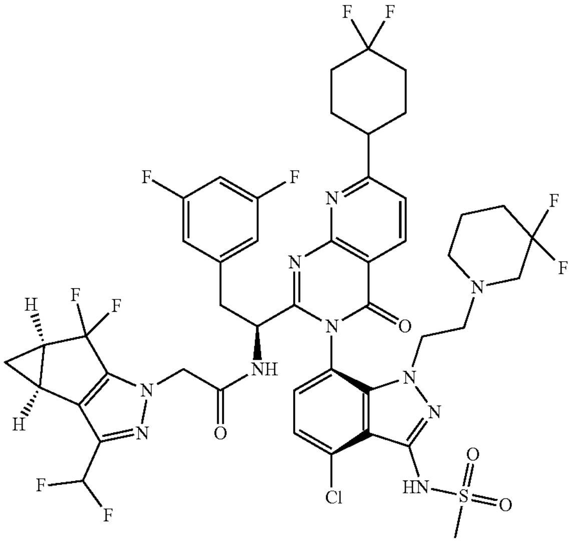 N-[(1S)-1-[(3P)-3-{4-chloro-1-[2-(3,3-difluoropiperidin-1-yl)ethyl]-3-methanesulfonamido-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method B: retention time = 1.42 min.; observed ion = 1055.4 [M − H]. 1H NMR (500 MHz, CD3OD, 303 K) δ (ppm) = 8.64 (d, J = 8.0 Hz, 1H), 7.67 (d, J = 8.3 Hz, 1H), 7.35 (d, J = 8.0 Hz, 1H), 7.25 ( d, J = 8.0 Hz, 1H), 6.81-6.55 (m, 4H), 4.85-4.78 (m, 1H), 4.66-4.56 (m, 2H), 4.18 (ddd, J = 5.8, 10.5, 14.1 Hz, 1H), 3.74 (ddd, J = 4.9, 10.4, 13.9 Hz, 1H), 3.48-3.41 (m, 1H), 3.25 (s, 3H), 3.20-3.07 (m, 2H), 2.76-2.69 (m, 1H), 2.64-2.58 (m, 1H), 2.44 (ddd, J = 4.2, 7.6, 11.5 Hz, 2H), 2.39-2.21 (m, 5H), 2.18-2.06 (m, 6H), 1.76-1.67 (m, 2H), 1.50-1.43 (m, 2H), 1.40-1.31 (m, 2H), 1.04 (dt, J = 1.9, 3.8 Hz, 1H). |

TABLE A-continued

| Example No. (preparation of the Example) | Structure and IUPAC name | Characterising data (LCMS and/or NMR) |
|---|---|---|
| 170 (General Procedure A using Bromide A4 as the core reagent) | 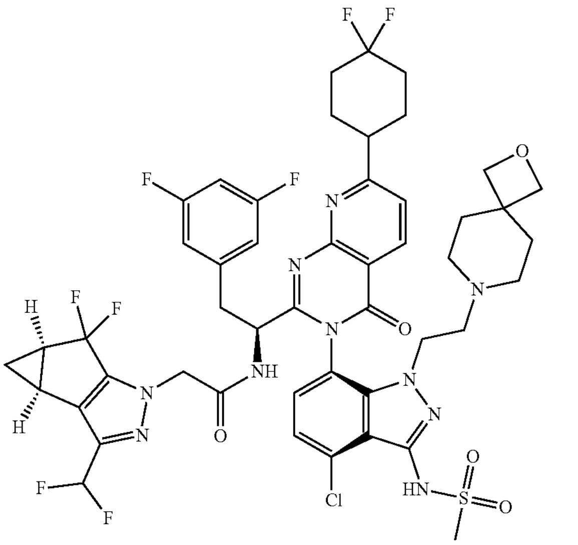 N-[(1S)-1-[(3P)-3-[4-chloro-3-methanesulfonamido-1-(2-{2-oxa-7-azaspiro[3.5]nonan-7-yl}ethyl)-1H-indazol-7-yl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.09 min.; observed ion = 1061.5 [M − H]. 1H NMR (500 MHz, CD3OD, 303 K) δ (ppm) = 8.64 (d, J = 8.0 Hz, 1H), 7.69 (d, J = 8.3 Hz, 1H), 7.39 (s, 2H), 6.82-6.77 (m, 1H), 6.71 (s, 1H), 6.60 (s, 1H), 6.70 (br t, J = 54.7 Hz, 1H), 6.55 (d, J = 6.5 Hz, 2H), 4.77-4.61 (m, 3H), 4.37 (s, 4H), 4.31-4.24 (m, 1H), 3.99-3.91 (m, 1H), 3.49-3.41 (m, 2H), 3.27 (s, 3H), 3.20-3.09 (m, 2H), 3.05-2.92 (m, 2H), 2.49-2.42 (m, 3H), 2.32-2.22 (m, 2H), 2.17-2.08 (m, 5H), 1.88-1.78 (m, 3H), 1.41-1.32 (m, 2H), 1.31 (s, 1H), 1.04-1.00 (m, 1H). |
| 176 (General Procedure A using Bromide A4 as the core reagent) | 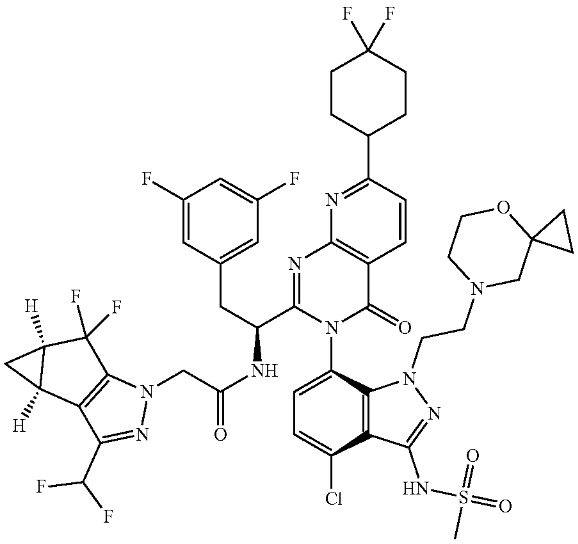 N-[(1S)-1-[(3P)-3-[4-chloro-3-methanesulfonamido-1-(2-{4-oxa-7-azaspiro[2.5]octan-7-yl}ethyl)-1H-indazol-7-yl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.14 min.; observed ion = 1047.4 [M − H]. 1H NMR (500 MHz, CD3OD, 303 K), Shift (ppm) = 8.62 (d, J = 8.3 Hz, 1H), 7.67 (d, J = 8.0 Hz, 1H), 7.34 (d, J = 7.7 Hz, 1H), 7.26 (d, J = 7.7 Hz, 1H), 6.77 (br t, J = 9.2 Hz, 1H), 6.69 (br t, J = 54.8 Hz, 1H), 6.56-6.51 (m, 2H), 4.83-4.80 (m, 1H), 4.63-4.55 (m, 2H), 4.18-4.11 (m, 1H), 3.83-3.78 (m, 1H), 3.50-3.41 (m, 2H), 3.24 (s, 3H), 3.18-3.04 (m, 2H), 2.70-2.56 (m, 2H), 2.45-2.40 (m, 2H), 2.29-2.21 (m, 4H), 2.17-1.93 (m, 9H), 1.39-1.33 (m, 1H), 1.04-1.00 (m, 1H), 0.59-0.50 (m, 2H), 0.28-0.17 (m, 2H). |

TABLE A-continued

| Example No. (preparation of the Example) | Structure and IUPAC name | Characterising data (LCMS and/or NMR) |
|---|---|---|
| 187 (General Procedure A using Bromide A4 as the core reagent) | 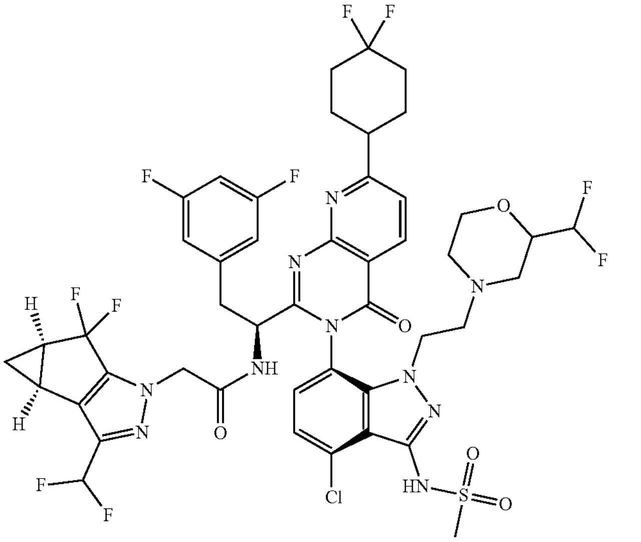 N-[(1S)-1-[(3P)-3-(4-chloro-1-{2-[2-(difluoromethyl)morpholin-4-yl]ethyl}-3-methanesulfonamido-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.36 min.; observed ion = 1071.5 [M − H]. 1H NMR (500 MHz, CD3OD, 303 K), Shift (ppm) = 8.63 (t, J = 8.2 Hz, 1H), 7.67 (dd, J = 7.2, 8.0 Hz, 1H), 7.36 (dd, J = 1.6, 7.9 Hz, 1H), 7.29 (dd, J = 6.7, 7.9 Hz, 1H), 6.82-6.52 (m, 4H), 5.75-5.44 (m, 1H), 4.84-4.77 (m, 2H), 4.70-4.58 (m, 2H), 4.26-4.15 (m, 1H), 3.81-3.59 (m, 2H), 3.44-3.37 (m, 2H), 3.26 (s, 3H), 3.23-3.13 (m, 2H), 3.12-3.04 (m, 1H), 2.70-2.60 (m, 1H), 2.57-2.51 (m, 1H), 2.47-2.42 (m, 2H), 2.36-2.22 (m, 3H), 2.16-2.02 (m, 6H), 1.96-1.88 (m, 1H), 1.83 (t, J = 10.6 Hz, 1H), 1.42-1.34 (m, 1H), 1.04 (br dd, J = 1.3, 2.8 Hz, 1H). |
| 189 (General Procedure A using Bromide A4 as the core reagent) | 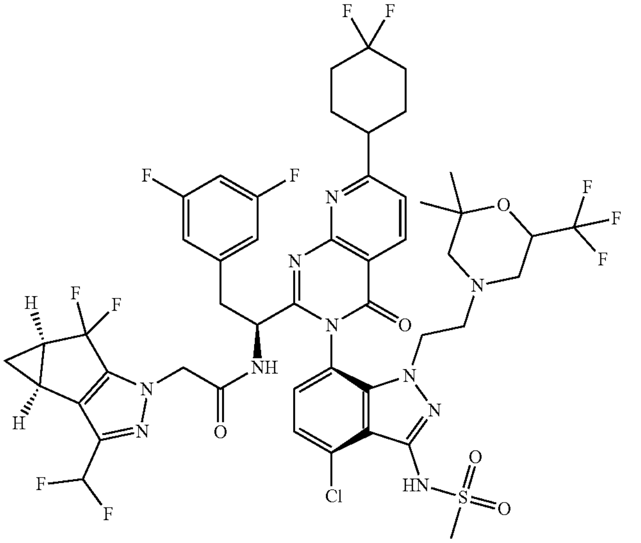 N-[(1S)-1-[(3P)-3-(4-chloro-1-{2-[2,2-dimethyl-6-(trifluoromethyl)morpholin-4-yl]ethyl}-3-methanesulfonamido-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.6 min.; observed ion = 1117.4 [M − H]. 1H NMR (500 MHz, CD3OD, 303 K), Shift (ppm) = 8.63 (d, J = 8.0 Hz, 1H), 7.68 (dd, J = 5.4, 8.0 Hz, 1H), 7.38-7.28 (m, 2H), 6.83-6.46 (m, 4H), 4.84-4.79 (m, 2H), 4.70-4.58 (m, 2H), 4.30-4.25 (m, 1H), 4.14-4.03 (m, 1H), 3.79-3.72 (m, 1H), 3.41-3.36 (m, 1H), 3.28-3.24 (m, 3H), 3.20-3.12 (m, 1H), 3.06 (ddd, J = 7.0, 9.8, 14.2 Hz, 1H), 2.61 (br d, J = 5.1 Hz, 1H), 2.48-2.41 (m, 3H), 2.31-2.21 (m, 2H), 2.17-2.06 (m, 6H), 1.77-1.72 (m, 1H), 1.41-1.28 (m, 2H), 0.90 (s, 2H), 1.08-0.81 (m, 6H). |

TABLE A-continued

| Example No. (preparation of the Example) | Structure and IUPAC name | Characterising data (LCMS and/or NMR) |
|---|---|---|
| 191 (General Procedure A using Bromide A4 as the core reagent) | 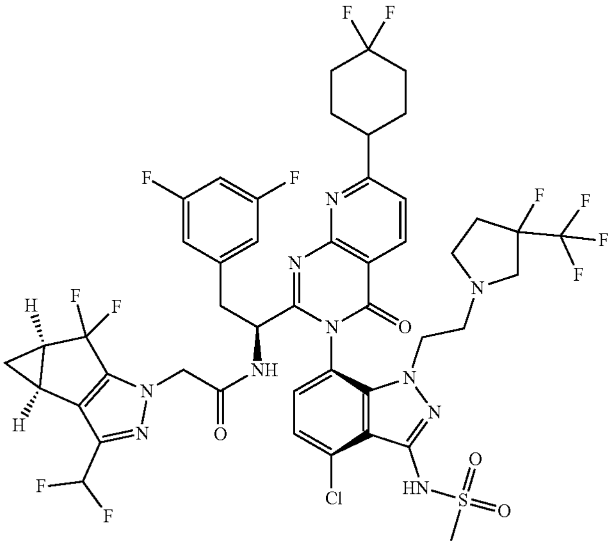<br>N-[(1S)-1-[(3P)-3-(4-chloro-1-{2-[3-fluoro-3-(trifluoromethyl)pyrrolidin-1-yl]ethyl}-3-methanesulfonamido-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.54 min.; observed ion = 1093.4 [M + H].<br>1H NMR (500 MHz, CD3OD, 303 K), Shift (ppm) = 8.66-8.60 (m, 1H), 7.68-7.63 (m, 1H), 7.36-7.32 (m, 1H), 7.29-7.24 (m, 1H), 6.82-6.50 (m, 4H), 4.92-4.86 (m, 1H), 4.82-4.78 (m, 1H), 4.64-4.53 (m, 2H), 4.38-4.12 (m, 1H), 3.91-3.70 (m, 1H), 3.46-3.39 (m, 1H), 3.26-3.22 (m, 3H), 3.22-3.07 (m, 3H), 2.79-2.74 (m, 1H), 2.70-2.54 (m, 2H), 2.41 (ddd, J = 3.9, 7.5, 11.3 Hz, 2H), 2.35-2.20 (m, 3H), 2.15-1.96 (m, 7H), 1.37-1.29 (m, 2H), 1.03-1.00 (m, 1H). |
| 195 (General Procedure A using Bromide A4 as the core reagent) | 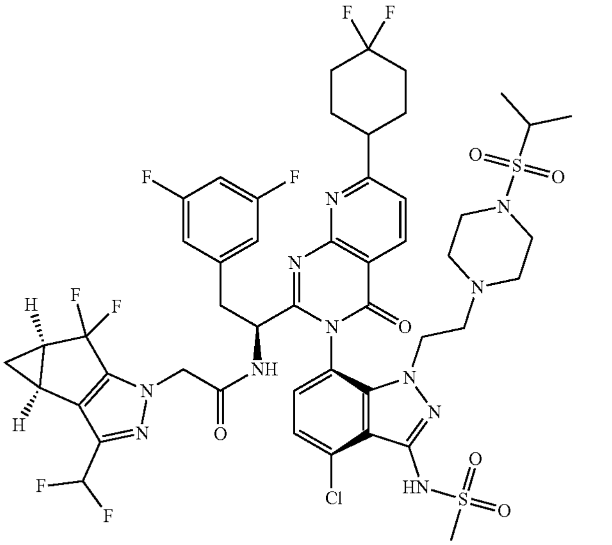<br>N-[(1S)-1-[(3P)-3-(4-chloro-3-methanesulfonamido-1-{2-[4-(propane-2-sulfonyl)piperazin-1-yl]ethyl}-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.245 min.; observed ion = 1126.5 [M − H].<br>1H NMR (500 MHz, CD3OD, 303 K), Shift (ppm) = 8.63 (d, J = 8.0 Hz, 1H), 7.67 (d, J = 8.0 Hz, 1H), 7.36-7.29 (m, 2H), 6.79-6.74 (m, 1H), 6.68 (t, J = 54.8 Hz, 1H), 6.52 (d, J = 6.8 Hz, 2H), 4.83-4.80 (m, 1H), 4.70-4.56 (m, 2H), 4.15 (ddd, J = 5.7, 9.8, 14.1 Hz, 1H), 3.74 (ddd, J = 5.1, 9.7, 14.5 Hz, 1H), 3.40 (dd, J = 4.5, 14.0 Hz, 1H), 3.24 (s, 3H), 3.23-3.12 (m, 2H), 3.06 (dd, J = 9.7, 14.2 Hz, 1H), 3.00 (t, J = 4.6 Hz, 4H), 2.68-2.61 (m, 1H), 2.53 (ddd, J = 4.9, 10.0, 12.5 Hz, 1H), 2.43 (ddd, J = 3.9, 7.7, 11.3 Hz, 2H), 2.31-2.18 (m, 2H), 2.18-2.07 (m, 8H), 2.04-1.98 (m, 1H), 1.40-1.33 (m, 1H), 1.29 (br s, 1H), 1.25 (d, J = 6.9 Hz, 6H), 1.05-0.99 (m, 1H). |

TABLE A-continued

| Example No. (preparation of the Example) | Structure and IUPAC name | Characterising data (LCMS and/or NMR) |
|---|---|---|
| 199 (General Procedure A using Bromide A4 as the core reagent) | 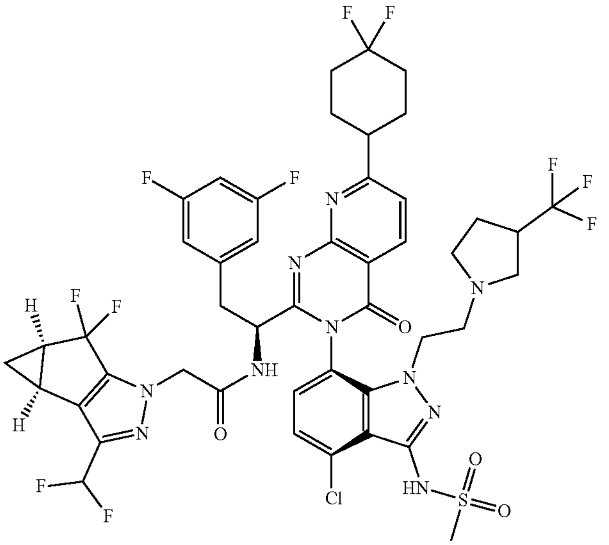 N-[(1S)-1-[(3P)-3-(4-chloro-3-methanesulfonamido-1-{2-[3-(trifluoromethyl)pyrrolidin-1-yl]ethyl}-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.193 min.; observed ion = 1073.4 [M − H]. 1H NMR (500 MHz, CD3OD, 303 K), Shift (ppm) = 8.61 (dd, J = 2.5, 8.2 Hz, 1H), 7.65 (dd, J = 1.9, 8.2 Hz, 1H), 7.34 (d, J = 8.0 Hz, 1H), 7.25 (d, J = 7.7 Hz, 1H), 6.80-6.52 (m, 4H), 4.82-4.80 (m, 1H), 4.66-4.55 (m, 2H), 4.18-4.12 (m, 1H), 3.79-3.73 (m, 1H), 3.45-3.36 (m, 1H), 3.24 (s, 3H), 3.18-3.04 (m, 2H), 2.78-2.61 (m, 3H), 2.48-2.35 (m, 3H), 2.31-2.17 (m, 5H), 2.16-2.05 (m, 5H), 1.83-1.76 (m, 1H), 1.65-1.56 (m, 1H), 1.39-1.27 (m, 2H), 1.03-0.99 (m, 1H). |
| 207 (General Procedure A using Bromide A4 as the core reagent) | 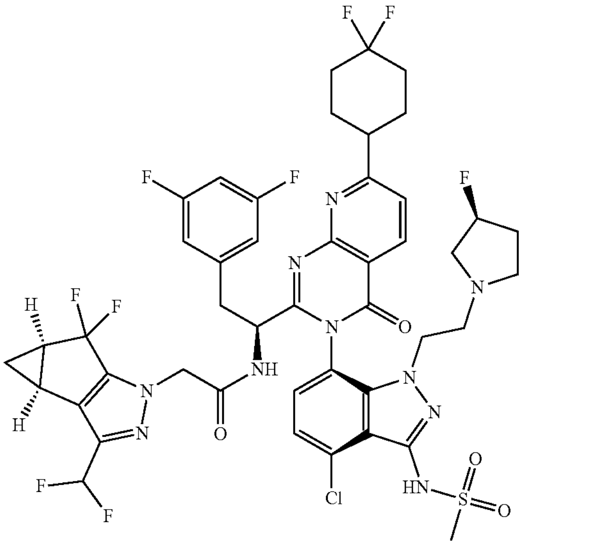 N-[(1S)-1-[(3P)-3-(4-chloro-1-{2-[(3S)-3-fluoropyrrolidin-1-yl]ethyl}-3-methanesulfonamido-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.114 min.; observed ion = 1023.6 [M − H]. 1H NMR (500 MHz, CD3OD, 303 K), Shift (ppm) = 8.62 (d, J = 8.0 Hz, 1H), 7.65 (d, J = 8.0 Hz, 1H), 7.36 (d, J = 7.7 Hz, 1H), 7.30 (d, J = 7.7 Hz, 1H), 6.80-6.75 (m, 1H), 6.67 (t, J = 55.4 Hz, 1H), 6.58-6.52 (m, 2H), 5.11-4.96 (m, 1H), 4.82-4.78 (m, 2H), 4.71-4.55 (m, 3H), 4.21 (s, 1H), 3.87 (s, 1H), 3.46-3.39 (m, 1H), 3.25 (s, 3H), 3.15-3.06 (m, 2H), 3.02-2.96 (m, 1H), 2.47-2.37 (m, 3H), 2.30-2.19 (m, 2H), 2.14-1.96 (m, 8H), 1.39-1.25 (m, 3H), 1.02-0.98 (m, 1H). |

TABLE A-continued

| Example No. (preparation of the Example) | Structure and IUPAC name | Characterising data (LCMS and/or NMR) |
|---|---|---|
| 208 (General Procedure A using Bromide A4 as the core reagent) | 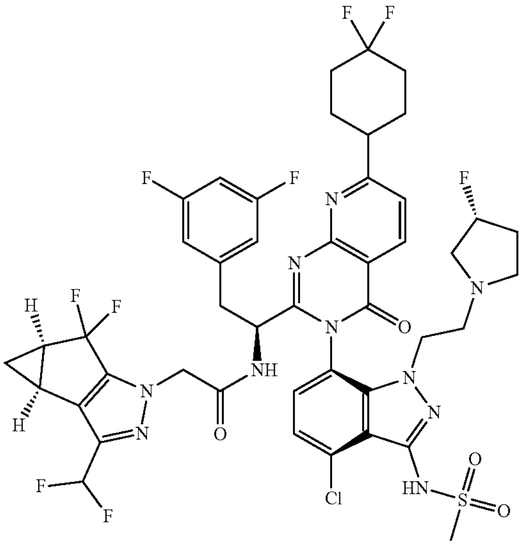 N-[(1S)-1-[(3P)-3-(4-chloro-1-{2-[(3R)-3-fluoropyrrolidin-1-yl]ethyl}-3-methanesulfonamido-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.115 min.; observed ion = 1023.6 [M − H]. 1H NMR (500 MHz, CD3OD, 303 K), Shift (ppm) = 8.62 (d, J = 8.0 Hz, 1H), 7.65 (d, J = 8.0 Hz, 1H), 7.38-7.30 (m, 2H), 6.81-6.53 (m, 4H), 5.00 (br s, 1H), 4.80-4.77 (m, 1H), 4.70-4.56 (m, 2H), 4.24-4.18 (m, 1H), 3.92-3.85 (m, 1H), 3.43 (dd, J = 4.5, 14.0 Hz, 1H), 3.26-3.25 (m, 3H), 3.17-2.94 (m, 4H), 2.89-2.68 (m, 3H), 2.47-2.37 (m, 3H), 2.27-2.20 (m, 2H), 2.14-2.00 (m, 7H), 1.38-1.28 (m, 2H), 1.02-0.98 (m, 1H). |
| 211 (General Procedure A using Bromide A4 as the core reagent) | 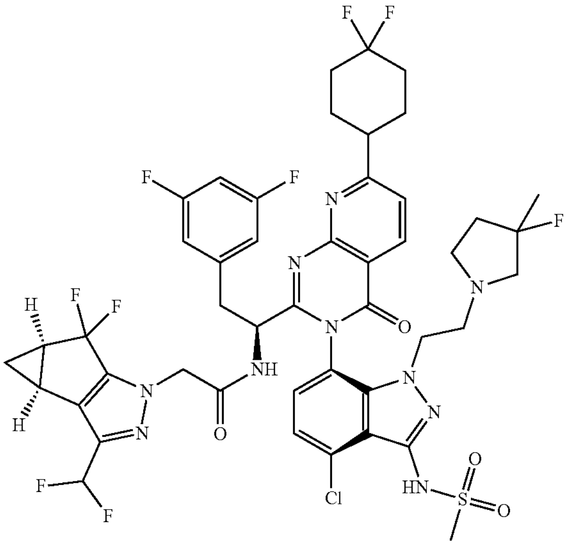 N-[(1S)-1-[(3P)-3-{4-chloro-1-[2-(3-fluoro-3-methylpyrrolidin-1-yl)ethyl]-3-methanesulfonamido-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.131 min.; observed ion = 1037.5 [M − H]. 1H NMR (500 MHz, CD3OD, 303 K), Shift (ppm) = 8.62 (dd, J = 3.3, 8.0 Hz, 1H), 7.66 (dd, J = 2.2, 8.2 Hz, 1H), 7.38-7.32 (m, 2H), 6.80-6.76 (m, 1H), 6.67 (dd, J = 54.7, 56.5 Hz, 1H), 6.57-6.53 (m, 2H), 4.90-4.86 (m, 1H), 4.81-4.75 (m, 1H), 4.71-4.53 (m, 2H), 4.25-4.19 (m, 1H), 3.94-3.88 (m, 1H), 3.46-3.40 (m, 1H), 3.26 (d, J = 0.6 Hz, 3H), 3.17-3.07 (m, 3H), 3.01-2.85 (m, 2H), 2.42 (ddd, J = 4.0, 7.6, 11.3 Hz, 2H), 2.28-2.21 (m, 2H), 2.14-1.96 (m, 8H), 1.42-1.29 (m, 6H), 1.02-0.98 (m, 1H). |

TABLE A-continued

| Example No. (preparation of the Example) | Structure and IUPAC name | Characterising data (LCMS and/or NMR) |
|---|---|---|
| 214 (General Procedure A using Bromide A4 as the core reagent) | 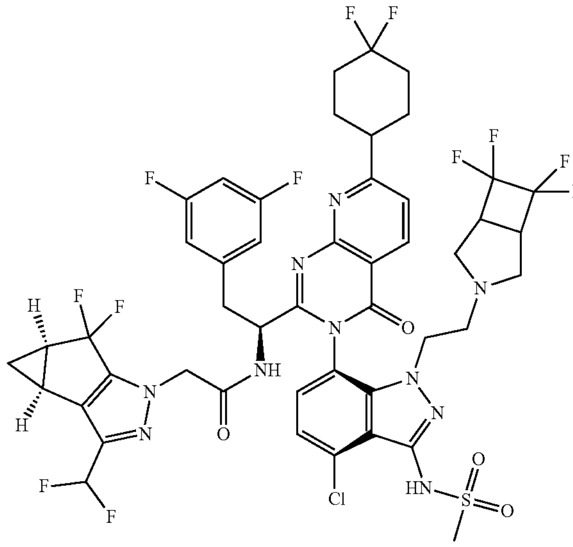 N-[(1S)-1-[(3P)-3-[4-chloro-3-methanesulfonamido-1-(2-{6,6,7,7-tetrafluoro-3-azabicyclo[3.2.0]heptan-3-yl}ethyl)-1H-indazol-7-yl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.517 min.; observed ion = 1105.4 [M + H]. 1H NMR (500 MHz, CD3OD, 303 K), Shift (ppm) = 8.66-8.61 (m, 1H), 7.68-7.63 (m, 1H), 7.34 (t, J = 8.8 Hz, 1H), 7.29-7.23 (m, 1H), 6.80-6.53 (m, 4H), 4.90-4.85 (m, 1H), 4.82-4.78 (m, 1H), 4.62-4.53 (m, 2H), 4.39-4.10 (m, 1H), 3.89-3.67 (m, 1H), 3.53-3.40 (m, 1H), 3.30-3.23 (m, 4H), 3.21-2.98 (m, 4H), 2.79-2.66 (m, 1H), 2.44-2.38 (m, 2H), 2.29-2.19 (m, 2H), 2.16-1.94 (m, 7H), 1.38-1.26 (m, 2H), 1.04-0.99 (m, 1H), 0.89 (br d, J = 11.9 Hz, 1H). |
| 227 (General Procedure B using Amine B18 as the core reagent) | 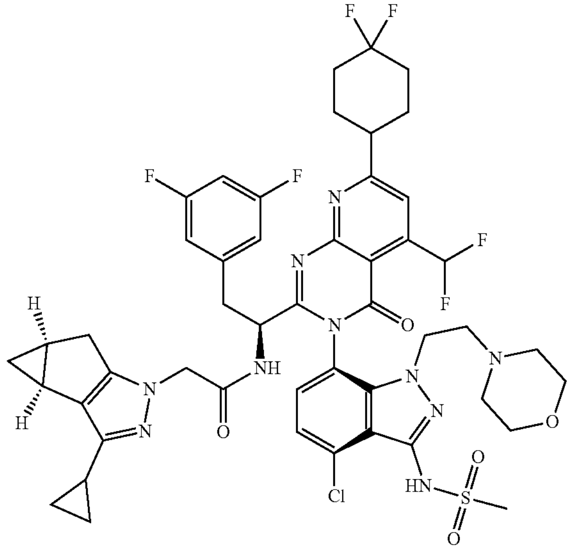 N-[(1S)-1-[(3P)-3-{4-chloro-3-methanesulfonamido-1-[2-(morpholin-4-yl)ethyl]-1H-indazol-7-yl}-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.21 min.; observed ion = 1026.5 [M + H]. 1H NMR (500 MHz, METHANOL-d4) δ ppm 7.63-7.95 (m, 2 H), 7.25-7.40 (m, 2 H), 6.78 (tt, J = 9.16, 2.31 Hz, 1 H), 6.44-6.59 (m, 2 H), 4.76-4.81 (m, 2 H), 4.26-4.39 (m, 2 H), 4.10-4.19 (m, 1 H), 3.77-3.87 (m, 1 H), 3.37-3.48 (m, 5 H), 3.27-3.29 (m, 3 H), 3.07 (dd, J = 14.01, 9.84 Hz, 1 H), 2.61-2.76 (m, 3 H), 2.45 (d, J = 16.09 Hz, 1 H), 2.21-2.32 (m, 5 H), 2.07-2.17 (m, 5 H), 1.90-1.96 (m, 1 H), 1.82-1.87 (m, 1 H), 1.74-1.80 (m, 2 H), 1.02 (t, J = 7.30 Hz, 1 H), 0.96 (td, J = 7.60, 4.77 Hz, 1 H), 0.83-0.91 (m, 2 H), 0.72-0.80 (m, 2 H), 0.03-0.07 (m, 1 H). |

TABLE A-continued

| Example No. (preparation of the Example) | Structure and IUPAC name | Characterising data (LCMS and/or NMR) |
|---|---|---|
| 230 (General Procedure B using Amine B19 as the core reagent) | 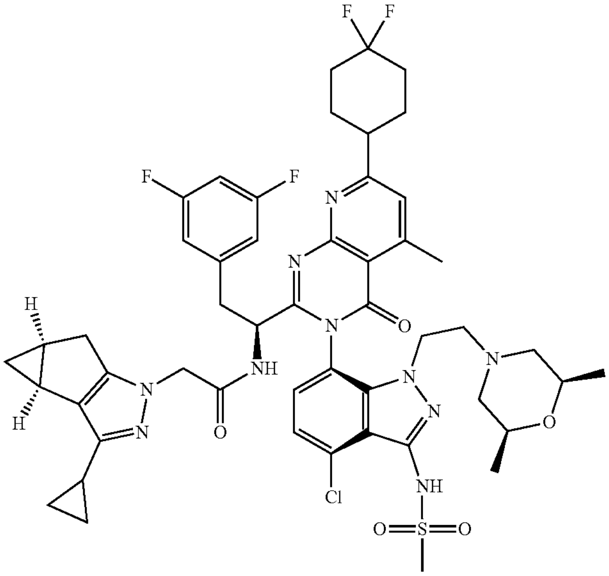 N-[(1S)-1-[(3P)-3-(4-chloro-1-{2-[(2R,6S)-2,6-dimethylmorpholin-4-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2}$,$^{4}$]nona-1(6),8-dien-7-yl]acetamide | LCMS Method A: retention time = 1.20 min.; observed ion = 1019.5 [M + H]+. 1H NMR (500 MHz, METHANOL-d4) δ ppm 7.44 (d, J = 0.60 Hz, 1 H), 7.33 (d, J = 8.05 Hz, 1 H), 7.22 (d, J = 7.75 Hz, 1 H), 6.67-6.80 (m, 1 H), 6.54 (dd, J = 8.05, 2.09 Hz, 2 H), 4.77-4.80 (m, 1 H), 4.29 (s, 2 H), 4.07-4.18 (m, 1 H), 3.83 (ddd, J = 14.31, 9.69, 4.92 Hz, 1 H), 3.34-3.40 (m, 2 H), 3.27 (s, 3 H), 3.04 (br dd, J = 14.16, 9.09 Hz, 2 H), 2.84 (d, J = 0.60 Hz, 3 H), 2.68 (dd, J = 16.54, 6.71 Hz, 2 H), 2.39-2.54 (m, 3 H), 2.17-2.35 (m, 3 H), 2.03-2.13 (m, 5 H), 1.88-2.01 (m, 2 H), 1.81-1.87 (m, 1 H), 1.74-1.80 (m, 1 H), 1.55-1.63 (m, 1 H), 1.37-1.46 (m, 1 H), 0.93-1.03 (m, 4 H), 0.81-0.90 (m, 5 H), 0.70-0.79 (m, 2 H), 0.04-0.10 (m, 1 H). |
| 231 (General Procedure B using Amine B20 as the core reagent) | 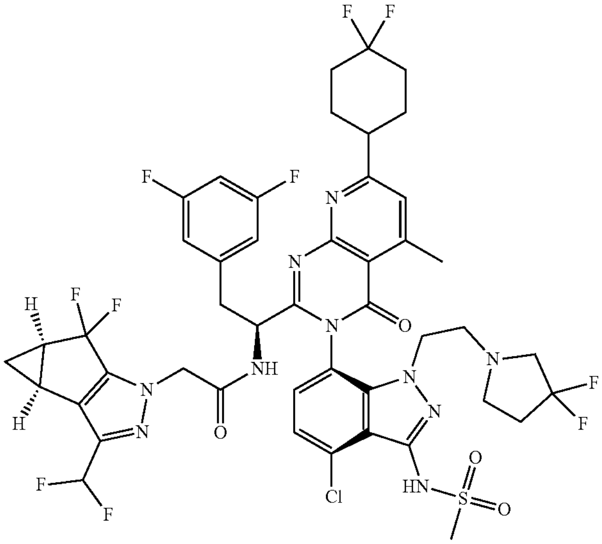 N-[(1S)-1-[(3P)-3-{4-chloro-1-[2-(3,3-difluoropyrrolidin-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method A: retention time = 1.45 min.; observed ion = 1055.5 [M − H]. 1H NMR (500 MHz, METHANOL-d4) δ ppm 7.42 (s, 1 H), 7.32 (d, J = 7.75 Hz, 1 H), 7.22 (d, J = 7.75 Hz, 1 H), 6.44-6.82 (m, 4 H), 4.76-4.80 (m, 1 H), 4.52-4.68 (m, 2 H), 4.08-4.17 (m, 1 H), 3.73 (ddd, J = 14.31, 9.54, 5.36 Hz, 1 H), 3.39 (dd, J = 14.16, 4.62 Hz, 1 H), 3.23 (s, 3 H), 3.00-3.09 (m, 2 H), 2.84 (s, 3 H), 2.76-2.82 (m, 1 H), 2.60-2.67 (m, 1 H), 2.36-2.56 (m, 6 H), 2.18-2.30 (m, 2 H), 1.92-2.14 (m, 8 H), 1.35 (td, J = 7.53, 5.51 Hz, 1 H), 0.96-1.04 (m, 1 H). |

TABLE A-continued

| Example No. (preparation of the Example) | Structure and IUPAC name | Characterising data (LCMS and/or NMR) |
| --- | --- | --- |
| 232 (General Procedure B using Amine B20 as the core reagent) | 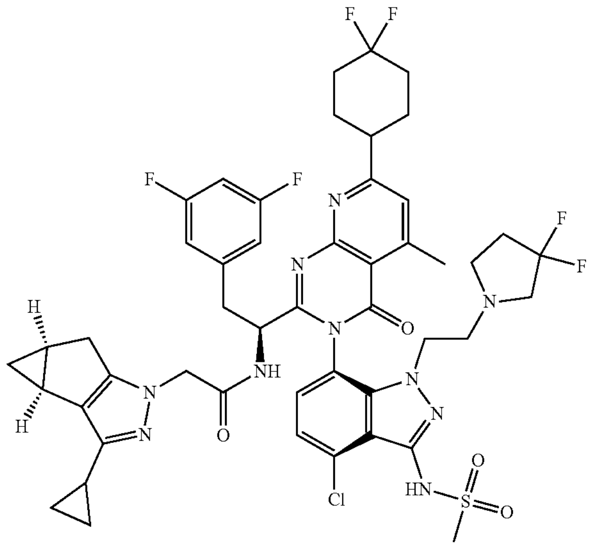 N-[(1S)-1-[(3P)-3-{4-chloro-1-[2-(3,3-difluoropyrrolidin-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method A: retention time = 1.46 min.; observed ion = 1009.6 [M − H]. 1H NMR (500 MHz, METHANOL-d4) δ ppm 7.42 (d, J = 0.60 Hz, 1 H), 7.32 (d, J = 8.05 Hz, 1 H), 7.21 (d, J = 7.75 Hz, 1 H), 6.72-6.81 (m, 1 H), 6.56 (dd, J = 8.05, 2.09 Hz, 2 H), 4.76-4.80 (m, 1 H), 4.22-4.36 (m, 2 H), 4.03 (ddd, J = 14.16, 9.39, 5.96 Hz, 1 H), 3.69 (ddd, J = 14.23, 9.31, 5.07 Hz, 1 H), 3.40 (dd, J = 14.16, 4.92 Hz, 1 H), 3.26 (s, 3 H), 3.00-3.09 (m, 2 H), 2.83 (d, J = 0.60 Hz, 3 H), 2.74-2.80 (m, 1 H), 2.68 (dd, J = 16.39, 6.56 Hz, 1 H), 2.61 (ddd, J = 12.07, 9.24, 5.51 Hz, 1 H), 2.37-2.56 (m, 5 H), 2.17-2.30 (m, 2 H), 2.05-2.13 (m, 4 H), 1.89-2.04 (m, 5 H), 1.80-1.86 (m, 1 H), 1.71-1.79 (m, 1 H), 0.95 (td, J = 7.60, 4.77 Hz, 1 H), 0.81-0.89 (m, 2 H), 0.69-0.78 (m, 2 H), 0.03-0.07 (m, 1 H). |
| 237 (General Procedure B using Amine B21 as the core reagent) | 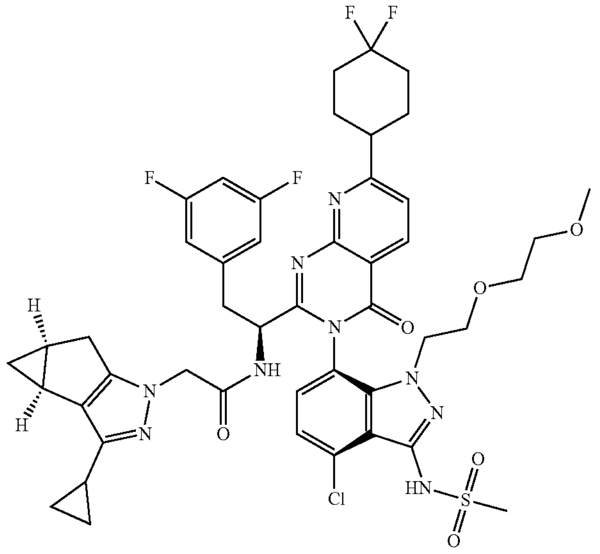 N-[(1S)-1-[(3P)-3-{4-chloro-3-methanesulfonamido-1-[2-(2-methoxyethoxy)ethyl]-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.47 min.; observed ion = 966.4 [M + H]+. 1H NMR (500 MHz, METHANOL-d4) δ ppm 8.60 (d, J = 8.05 Hz, 1 H), 7.64 (d, J = 8.35 Hz, 1 H), 7.32 (d, J = 7.75 Hz, 1 H), 7.21 (d, J = 7.75 Hz, 1 H), 6.74-6.80 (m, 1 H), 6.56 (dd, J = 8.05, 2.09 Hz, 2 H), 4.89-4.92 (m, 3 H), 4.19-4.32 (m, 2 H), 4.07 (d, J = 14.01 Hz, 1 H), 3.66-3.79 (m, 2 H), 3.56-3.64 (m, 1 H), 3.40 (dd, J = 14.16, 5.22 Hz, 1 H), 3.28 (s, 3 H), 3.23-3.26 (m, 2 H), 3.17 (s, 3 H), 3.01-3.07 (m, 1 H), 2.66 (dd, J = 16.39, 6.56 Hz, 1 H), 2.46 (d, J = 17.29 Hz, 1 H), 2.20-2.28 (m, 2 H), 2.05-2.15 (m, 5 H), 1.89-1.94 (m, 1 H), 1.89-2.03 (m, 3 H), 1.74-1.86 (m, 2 H), 0.91-1.02 (m, 2 H), 0.81-0.90 (m, 2 H), 0.69-0.80 (m, 2 H), 0.06 (q, J = 4.17 Hz, 1 H). |

TABLE A-continued

| Example No. (preparation of the Example) | Structure and IUPAC name | Characterising data (LCMS and/or NMR) |
| --- | --- | --- |
| 239 (General Procedure B using Amine B22 as the core reagent) | 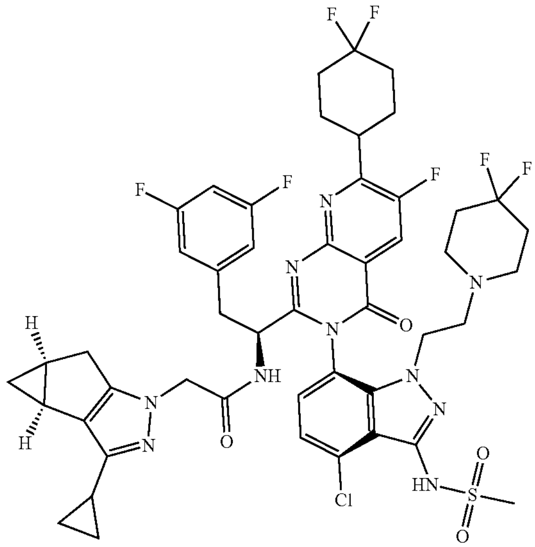 N-[(1S)-1-[(3P)-3-{4-chloro-1-[2-(4,4-difluoropiperidin-1-yl)ethyl]-3-methanesulfonamido-1H-indazol-7-yl}-7-(4,4-difluorocyclohexyl)-6-fluoro-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.30 min.; observed ion = 1029.7 [M + H]+. 1H NMR (500 MHz, METHANOL-d4) δ ppm 8.32 (d, J = 8.64 Hz, 1 H), 7.34-7.39 (m, 1 H), 7.28-7.33 (m, 1 H), 6.74-6.82 (m, 1 H), 6.47-6.56 (m, 2 H), 4.31 (q, J = 16.69 Hz, 2 H), 4.08 (ddd, J = 14.01, 9.39, 6.11 Hz, 1 H), 3.68 (ddd, J = 14.01, 9.09, 5.51 Hz, 1 H), 3.42-3.50 (m, 2 H), 3.35-3.39 (m, 1 H), 3.26-3.27 (m, 3 H), 3.04 (dd, J = 14.16, 9.69 Hz, 1 H), 2.67-2.73 (m, 1 H), 2.54-2.66 (m, 2 H), 2.46 (d, J = 16.99 Hz, 1 H), 2.18-2.32 (m, 7 H), 2.03-2.12 (m, 4 H), 1.90-1.97 (m, 1 H), 1.81-1.87 (m, 1 H), 1.74-1.81 (m, 1 H), 1.61-1.71 (m, 4 H), 0.93-0.99 (m, 1 H), 0.82-0.91 (m, 2 H), 0.72-0.80 (m, 2 H), 0.04-0.08 (m, 1 H). |
| 240 (General Procedure B using Amine B23 as the core reagent) | 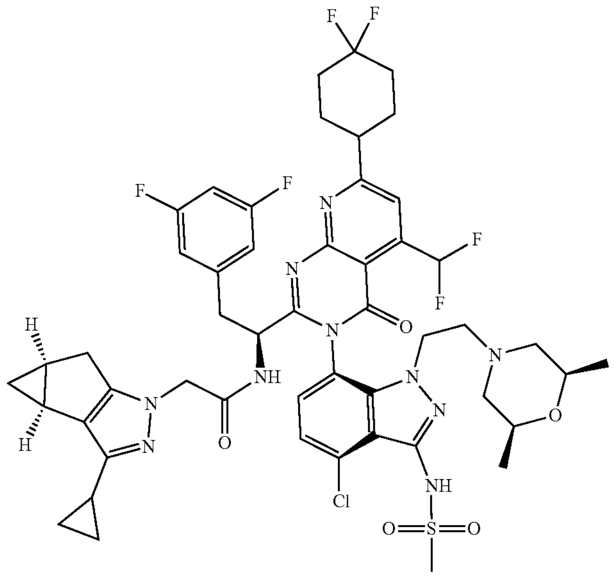 N-[(1S)-1-[(3P)-3-(4-chloro-1-{2-[(2R,6S)-2,6-dimethylmorpholin-4-yl]ethyl}-3-methanesulfonamido-1H-indazol-7-yl)-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.22 min.; observed ion = 1055.2 [M + H]+. 1H NMR (500 MHz, METHANOL-d4) δ ppm 7.65-7.94 (m, 2 H), 7.33-7.42 (m, 2 H), 6.74-6.83 (m, 1 H), 6.50-6.58 (m, 2 H), 4.74-4.79 (m, 1 H), 4.29-4.40 (m, 2 H), 4.18-4.28 (m, 1 H), 3.88-4.00 (m, 1 H), 3.37-3.42 (m, 1 H), 3.28-3.29 (m, 3 H), 3.19-3.24 (m, 1 H), 3.09 (dd, J = 14.16, 9.69 Hz, 1 H), 2.65 (dd, J = 16.69, 6.85 Hz, 1 H), 2.44 (d, J = 16.69 Hz, 1 H), 2.19-2.29 (m, 2 H), 2.06-2.15 (m, 5 H), 1.97-2.03 (m, 1 H), 1.90-1.95 (m, 1 H), 1.82-1.86 (m, 2 H), 1.74-1.80 (m, 2 H), 1.63-1.71 (m, 2 H), 0.93-1.05 (m, 9 H), 0.82-0.91 (m, 3 H), 0.71-0.80 (m, 2 H), 0.03-0.08 (m, 1 H). |

TABLE A-continued

| Example No. (preparation of the Example) | Structure and IUPAC name | Characterising data (LCMS and/or NMR) |
|---|---|---|
| 241 (General Procedure B using Amine B21 as the core reagent) | 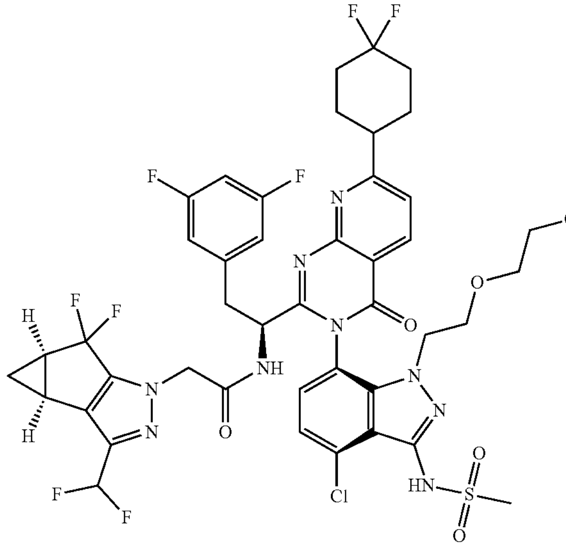 N-[(1S)-1-[(3P)-3-{4-chloro-3-methanesulfonamido-1-[2-(2-methoxyethoxy)ethyl]-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method B: retention time = 1.49 min.; observed ion = 1012.4 [M + H]+. 1H NMR (500 MHz, METHANOL-d4) δ ppm 8.61 (d, J = 8.05 Hz, 1 H), 7.64 (d, J = 8.05 Hz, 1 H), 7.31 (d, J = 7.75 Hz, 1 H), 7.21 (d, J = 8.05 Hz, 1 H), 6.53-6.81 (m, 4 H), 4.91 (dd, J = 9.09, 5.22 Hz, 1 H), 4.49-4.60 (m, 2 H), 4.12 (dt, J = 14.16, 5.74 Hz, 1 H), 3.69-3.83 (m, 2 H), 3.59 (dt, J = 10.13, 5.96 Hz, 1 H), 3.42 (dd, J = 14.16, 4.92 Hz, 1 H), 3.24-3.27 (m, 5 H), 3.17 (s, 3 H), 3.02-3.08 (m, 1 H), 2.38-2.45 (m, 2 H), 2.20-2.29 (m, 2 H), 1.95-2.16 (m, 7 H), 1.32-1.38 (m, 1 H), 0.98-1.03 (m, 1 H). |
| 245 (General Procedure A using Bromide A1 as the core reagent) | 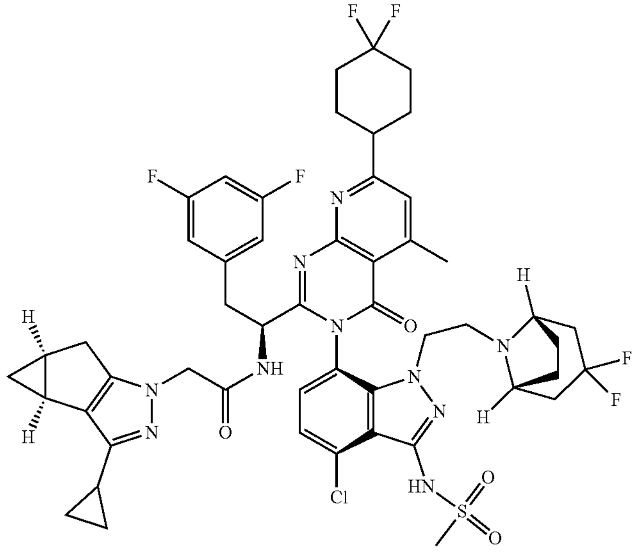 N-[(1S)-1-[(3P)-3-(4-chloro-1-{2-[(1R,5S)-3,3-difluoro-8-azabicyclo[3.2.1]octan-8-ylethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2}$,$^{4}$]nona-1(6),8-dien-7-yl]acetamide | (LCMS Method A: retention time = 2.87 min.; observed ion = 1051.20 [M + H]+. 1H NMR (500 MHz, METHANOL-d4) δ ppm 7.43 (d, J = 0.60 Hz, 1 H), 7.34 (d, J = 7.75 Hz, 1 H), 7.23 (d, J = 7.75 Hz, 1 H), 6.77 (tt, J = 9.20, 2.27 Hz, 1 H), 6.54 (dd, J = 8.05, 2.09 Hz, 2 H), 4.78 (dd, J = 9.39, 4.92 Hz, 1 H), 4.23-4.38 (m, 2 H), 4.01-4.15 (m, 1 H), 3.70 (ddd, J = 14.23, 9.02, 5.36 Hz, 1 H), 3.37 (dd, J = 14.16, 4.92 Hz, 1 H), 3.26 (s, 3 H), 3.07-3.14 (m, 1 H), 3.04 (dd, J = 14.16, 9.39 Hz, 2 H), 2.87-2.93 (m, 1 H), 2.83 (s, 3 H), 2.72-2.80 (m, 1 H), 2.69 (dd, J = 16.69, 6.56 Hz, 1 H), 2.55-2.63 (m, 1 H), 2.46 (d, J = 16.09 Hz, 1 H), 2.17-2.28 (m, 2 H), 2.01-2.13 (m, 5 H), 1.89-2.00 (m, 2 H), 1.62-1.88 (m, 10 H), 0.96 (td, J = 7.67, 4.62 Hz, 1 H), 0.81-0.91 (m, 2 H), 0.71-0.80 (m, 2 H), 0.07 (q, J = 4.17 Hz, 1 H).) |

TABLE A-continued

| Example No. (preparation of the Example) | Structure and IUPAC name | Characterising data (LCMS and/or NMR) |
|---|---|---|
| 246 (General Procedure A using Bromide A2 as the core reagent) | 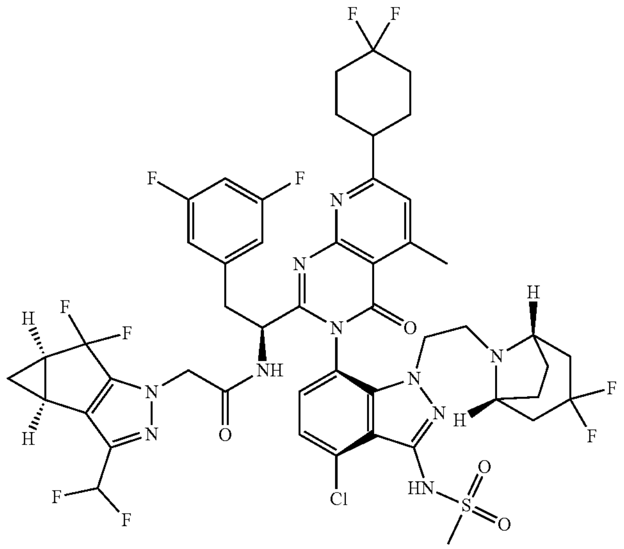 N-[(1S)-1-[(3P)-3-(4-chloro-1-{2-[(1R,5S)-3,3-difluoro-8-azabicyclo[3.2.1]octan-8-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.79 min.; observed ion = 1097.25 [M + H]+. 1H NMR (500 MHz, METHANOL-d4) δ ppm 7.44 (d, J = 0.60 Hz, 1 H), 7.34 (d, J = 8.05 Hz, 1 H), 7.23 (d, J = 7.75 Hz, 1 H), 6.46-6.80 (m, 4 H), 4.78 (dd, J = 9.54, 4.77 Hz, 1 H), 4.55-4.70 (m, 2 H), 4.17 (ddd, J = 14.31, 9.54, 5.96 Hz, 1 H), 3.74 (ddd, J = 14.31, 9.09, 5.22 Hz, 1 H), 3.37 (dd, J = 14.16, 4.92 Hz, 1 H), 3.23 (s, 3 H), 2.99-3.12 (m, 3 H), 2.88 (br s, 1 H), 2.84 (s, 3 H), 2.74 (ddd, J = 12.29, 9.31, 6.41 Hz, 1 H), 2.55-2.64 (m, 1 H), 2.42 (ddd, J = 11.10, 7.53, 4.02 Hz, 2 H), 2.18-2.30 (m, 2 H), 1.93-2.12 (m, 6 H), 1.57-1.85 (m, 8 H), 1.31-1.40 (m, 1 H), 0.98-1.05 (m, 1 H). |
| 247 (General Procedure A using Bromide A2 as the core reagent, where the general procedure was modified as follows: the reaction run at 80° C. for 2 days) | 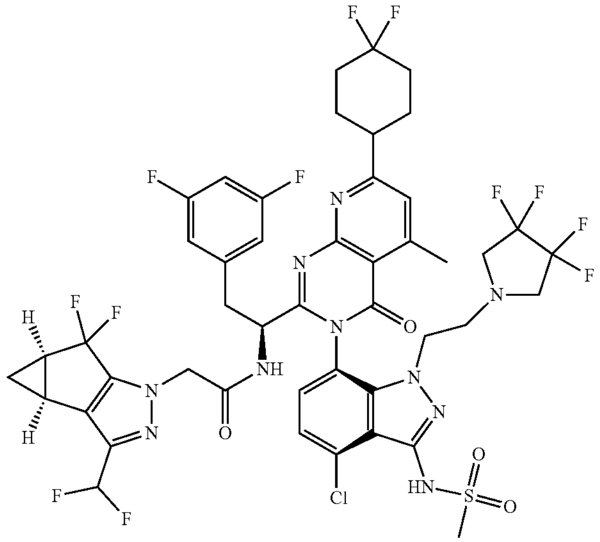 N-[(1S)-1-[(3P)-3-{4-chloro-3-methanesulfonamido-1-[2-(3,3,4,4-tetrafluoropyrrolidin-1-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 3.29 min.; observed ion = 1093.15 [M + H]+. 1H NMR (500 MHz, METHANOL-d4) δ ppm 7.43 (d, J = 0.60 Hz, 1 H), 7.34 (d, J = 8.05 Hz, 1 H), 7.25 (d, J = 8.05 Hz, 1 H), 6.49-6.81 (m, 4 H), 4.73-4.76 (m, 1 H), 4.53-4.68 (m, 3 H), 4.07-4.18 (m, 1 H), 3.72 (ddd, J = 14.31, 9.09, 5.51 Hz, 1 H), 3.40 (dd, J = 14.31, 4.77 Hz, 1 H), 3.23 (s, 3 H), 2.98-3.09 (m, 2 H), 2.77-2.88 (m, 7 H), 2.68-2.76 (m, 1 H), 2.36-2.46 (m, 2 H), 2.19-2.27 (m, 2 H), 1.94-2.11 (m, 6 H), 1.32-1.39 (m, 1 H), 0.97-1.05 (m, 1 H) |

TABLE A-continued

| Example No. (preparation of the Example) | Structure and IUPAC name | Characterising data (LCMS and/or NMR) |
|---|---|---|
| 248 (General Procedure A using Bromide A1 as the core reagent, where the general procedure was modified as follows: the reaction run at 80° C. for 2 days) | 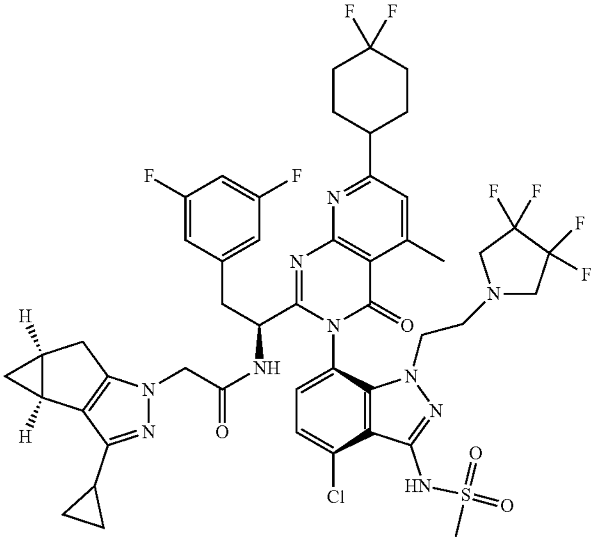<br>N-[(1S)-1-[(3P)-3-{4-chloro-3-methanesulfonamido-1-[2-(3,3,4,4-tetrafluoropyrrolidin-1-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method A: retention time = 3.38 min.; observed ion = 1047.20 [M + H]+. 1H NMR (500 MHz, METHANOL-d4) δ ppm 7.42 (s, 1 H), 7.34 (d, J = 7.75 Hz, 1 H), 7.22 (d, J = 7.75 Hz, 1 H), 6.78 (tt, J = 9.20, 2.42 Hz, 1 H), 6.56 (dd, J = 8.05, 2.09 Hz, 2 H), 4.77 (dd, J = 9.54, 5.07 Hz, 1 H), 4.18-4.36 (m, 2 H), 4.04 (ddd, J = 14.31, 8.49, 6.11 Hz, 1 H), 3.69 (ddd, J = 14.16, 8.64, 5.51 Hz, 1 H), 3.40 (dd, J = 14.16, 4.92 Hz, 1 H), 3.26 (s, 3 H), 3.00-3.10 (m, 2 H), 2.77-2.89 (m, 8 H), 2.62-2.75 (m, 2 H), 2.44 (d, J = 16.39 Hz, 1 H), 2.18-2.29 (m, 2 H), 1.89-2.12 (m, 7 H), 1.80-1.86 (m, 1 H), 1.72-1.79 (m, 1 H), 0.95 (td, J = 7.67, 4.62 Hz, 1 H), 0.82-0.90 (m, 2 H), 0.70-0.79 (m, 2 H), 0.02-0.07 (m, 1 H). |
| 257 (General Procedure A using Bromide A6 as the core reagent) | 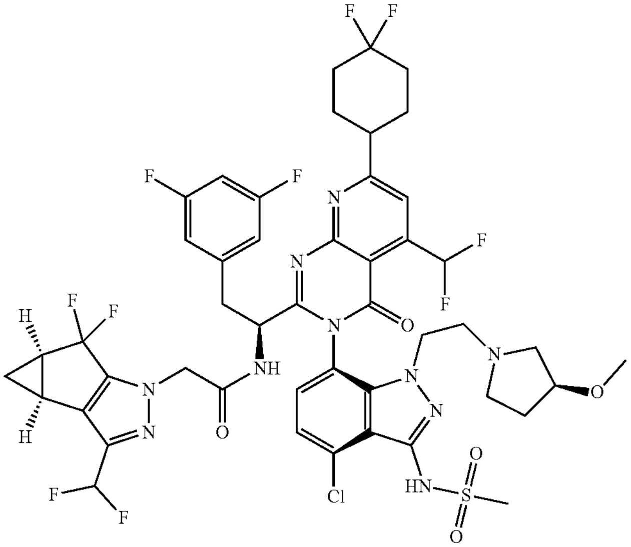<br>N-[(1S)-1-[(3P)-3-(4-chloro-3-methanesulfonamido-1-{2-[(3S)-3-methoxypyrrolidin-1-yl]ethyl}-1H-indazol-7-yl)-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method C: retention time = 3.27 min.; observed ion = 1087.3 [M + H]+.<br>1H NMR (500 MHz, METHANOL-d4) δ ppm 7.64-7.90 (m, 2 H), 7.29-7.32 (m, 1 H), 7.23-7.28 (m, 1 H), 6.54-6.80 (m, 4 H), 4.53-4.64 (m, 2 H), 4.11-4.19 (m, 1 H), 3.75-3.90 (m, 2 H), 3.41-3.47 (m, 1 H), 3.21-3.23 (m, 3 H), 3.15-3.20 (m, 3 H), 3.09 (dd, J = 14.16, 9.69 Hz, 1 H), 2.80-2.91 (m, 2 H), 2.47-2.62 (m, 2 H), 2.42 (ddd, J = 11.03, 7.60, 4.02 Hz, 3 H), 2.21-2.31 (m, 3 H), 1.86-2.17 (m, 8 H), 1.60-1.75 (m, 1 H), 1.32-1.39 (m, 1 H), 0.97-1.04 (m, 1 H). |

TABLE A-continued

| Example No. (preparation of the Example) | Structure and IUPAC name | Characterising data (LCMS and/or NMR) |
|---|---|---|
| 259 (General Procedure A using Bromide A6 as the core reagent) | 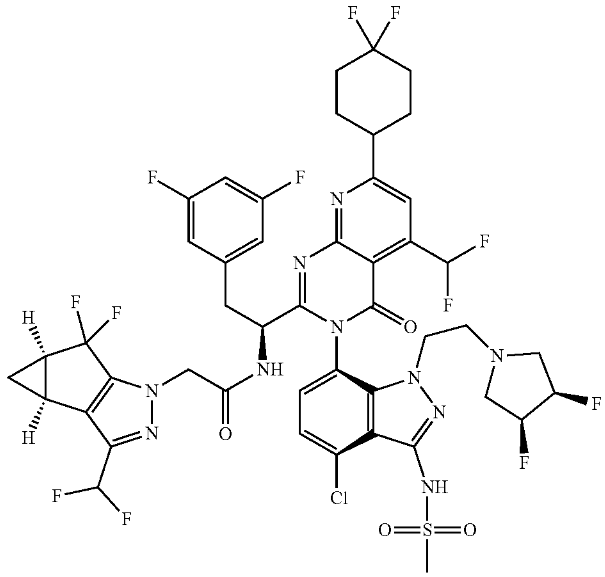 N-[(1S)-1-[(3P)-3-(4-chloro-1-{2-[(3R,4S)-3,4-difluoropyrrolidin-1-yl]ethyl}-3-methanesulfonamido-1H-indazol-7-yl)-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method C: retention time = 3.35 min.; observed ion = 1093.2 [M + H]+. 1H NMR (500 MHz, METHANOL-d4) δ ppm 7.63-7.90 (m, 2 H), 7.33-7.36 (m, 1 H), 7.27 (d, J = 7.75 Hz, 1 H), 6.52-6.80 (m, 4 H), 4.86-4.92 (m, 1 H), 4.73-4.80 (m, 1 H), 4.54-4.68 (m, 2 H), 4.10 (ddd, J = 14.08, 9.16, 5.96 Hz, 1 H), 3.75 (ddd, J = 14.23, 9.02, 5.66 Hz, 1 H), 3.41 (dd, J = 14.31, 4.47 Hz, 1 H), 3.24 (s, 3 H), 3.15-3.22 (m, 1 H), 3.08 (dd, J = 14.31, 9.54 Hz, 1 H), 2.68-2.83 (m, 2 H), 2.53-2.66 (m, 4 H), 2.42 (ddd, J = 11.10, 7.67, 3.87 Hz, 2 H), 2.19-2.29 (m, 2 H), 1.95-2.17 (m, 7 H), 1.31-1.39 (m, 1 H), 0.97-1.03 (m, 1 H). |
| 266 (General Procedure A using Bromide A2 as the core reagent) | 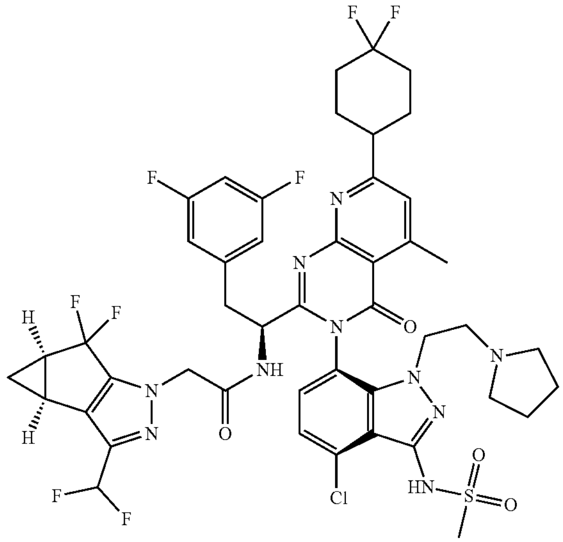 N-[(1S)-1-[(3P)-3-{4-chloro-3-methanesulfonamido-1-[2-(pyrrolidin-1-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.13 min.; observed ion = 1019.6 [M − H]. 1H NMR (500 MHz, METHANOL-d4) δ ppm 7.42 (s, 1 H), 7.33-7.39 (m, 2 H), 6.48-6.81 (m, 4 H), 4.70-4.77 (m, 1 H), 4.61-4.67 (m, 2 H), 4.56 (s, 1 H), 4.25-4.36 (m, 1 H), 3.99-4.0918 hr (m, 1 H), 3.33-3.46 (m, 3 H), 3.24 (s, 3 H), 3.07-3.13 (m, 2 H), 2.99-3.06 (m, 2 H), 2.95-3.19 (m, 2 H), 2.83 (s, 2 H), 2.38-2.45 (m, 1 H), 2.36-2.52 (m, 1 H), 2.19-2.28 (m, 2 H), 1.74-2.12 (m, 12 H), 1.33-1.39 (m, 1 H), 0.97 (dt, J = 3.50, 1.97 Hz, 1 H). |

TABLE A-continued

| Example No. (preparation of the Example) | Structure and IUPAC name | Characterising data (LCMS and/or NMR) |
|---|---|---|
| 267 (General Procedure A using Bromide A2 as the core reagent) | 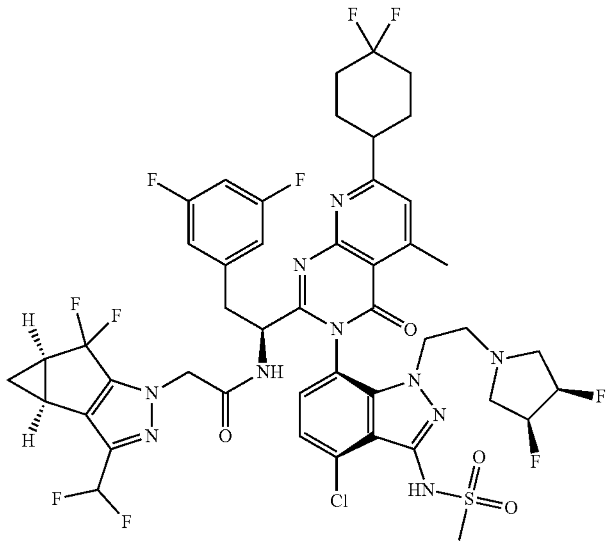 N-[(1S)-1-[(3P)-3-(4-chloro-1-{2-[(3R,4S)-3,4-difluoropyrrolidin-1-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.33 min.; observed ion = 1055.6 [M − H]. 1H NMR (500 MHz, METHANOL-d4) δ ppm 7.42 (d, J = 0.60 Hz, 1 H), 7.31 (d, J = 8.05 Hz, 1 H), 7.20 (d, J = 8.05 Hz, 1 H), 6.50-6.83 (m, 4 H), 4.74-4.80 (m, 3 H), 4.50-4.68 (m, 2 H), 4.01-18 hr 4.14 (m, 1 H), 3.67-3.79 (m, 1 H), 3.40 (dd, J = 14.01, 4.77 Hz, 1 H), 3.23 (s, 3 H), 2.99-3.09 (m, 2 H), 2.80-2.88 (m, 4 H), 2.46-2.75 (m, 5 H), 2.42 (ddd, J = 11.25, 7.67, 4.02 Hz, 2 H), 2.18-2.29 (m, 2 H), 1.91-2.15 (m, 6 H), 1.35 (q, J = 7.15 Hz, 1 H), 1.00 (td, J = 3.65, 1.64 Hz, 1 H) |
| 268 (General Procedure A using Bromide A2 as the core reagent) | 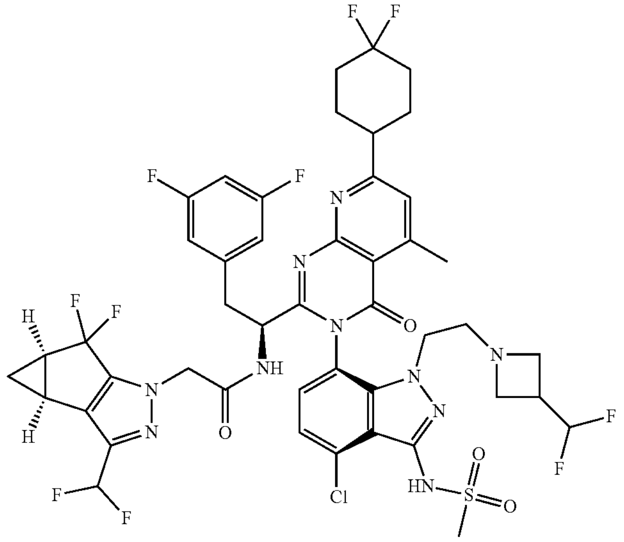 N-[(1S)-1-[(3P)-3-(4-chloro-1-{2-[3-(difluoromethyl)azetidin-1-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.14 min.; observed ion = 1055.6 [M − H]. 1H NMR (500 MHz, METHANOL-d4) δ ppm 7.25-7.47 (m, 3 H), 6.42-6.84 (m, 4 H), 5.75-6.09 (m, 1 H), 4.55-4.74 (m, 3 H), 4.48-4.76 (m, 1 H), 4.06-4.17 (m, 1 H), 3.79-3.92 (m, 118 hr H), 3.39-3.47 (m, 1 H), 3.36-3.70 (m, 2 H), 3.01-3.13 (m, 2 H), 2.88-3.20 (m, 4 H), 2.82-2.87 (m, 3 H), 2.42 (ddd, J = 11.33, 7.75, 3.87 Hz, 2 H), 2.20-2.31 (m, 2 H), 1.93-2.14 (m, 6 H), 1.33-1.39 (m, 1 H), 0.95-1.03 (m, 1 H). |

TABLE A-continued

| Example No. (preparation of the Example) | Structure and IUPAC name | Characterising data (LCMS and/or NMR) |
|---|---|---|
| 269 (General Procedure A using Bromide A2 as the core reagent) | 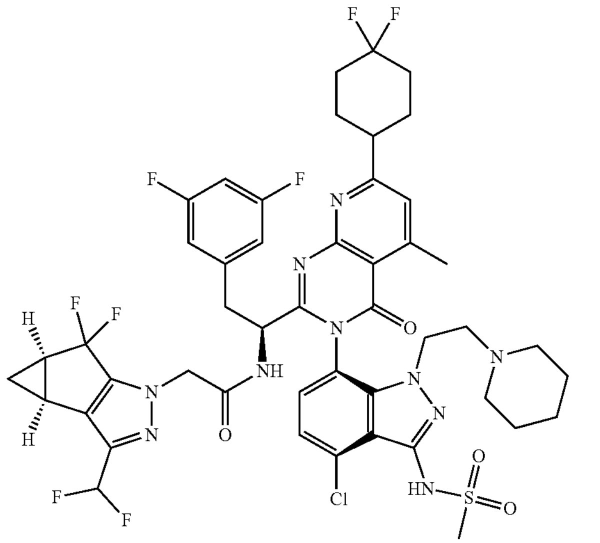 N-[(1S)-1-[(3P)-3-{4-chloro-3-methanesulfonamido-1-[2-(piperidin-1-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.14 min.; observed ion = 1033.4 [M − H]. 1H NMR (500 MHz, METHANOL-d4) δ ppm 7.43 (d, J = 0.89 Hz, 1 H), 7.38 (s, 2 H), 6.49-6.82 (m, 4 H), 4.54-4.78 (m, 4 H), 4.29-4.39 (m, 1 H), 4.02-4.12 (m, 1 H), 3.42 (dd, J = 14.75, 18 hr 4.02 Hz, 1 H), 3.25 (s, 3 H), 2.99-3.13 (m, 3 H), 3.16 (br d, J = 1.79 Hz, 1 H), 2.83 (s, 3 H), 2.42 (ddd, J = 11.40, 7.67, 3.87 Hz, 2 H), 2.19-2.29 (m, 2 H), 1.93-2.10 (m, 5 H), 1.88-2.10 (m, 1 H), 1.68-1.79 (m, 3 H), 1.64-1.82 (m, 1 H), 1.49-1.63 (m, 2 H), 1.32-1.40 (m, 1 H), 0.98 (br dd, J = 5.36, 2.09 Hz, 1 H). |
| 270 (General Procedure A using Bromide A2 as the core reagent) | 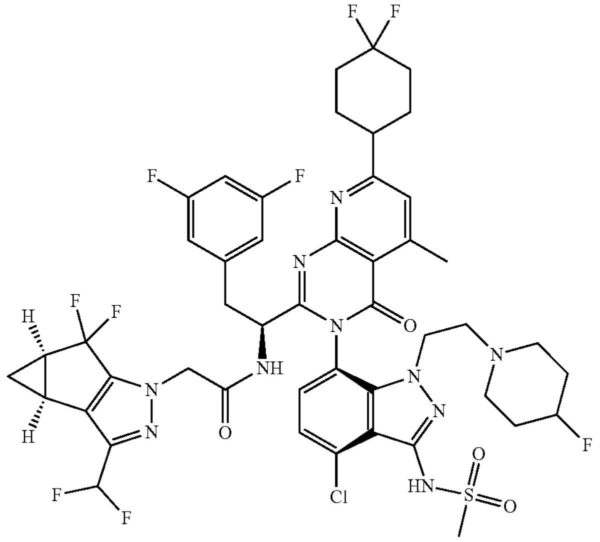 N-[(1S)-1-[(3P)-3-{4-chloro-1-[2-(4-fluoropiperidin-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.14 min.; observed ion = 1051.5 [M − H]. 1H NMR (500 MHz, METHANOL-d4) δ ppm 7.43 (d, J = 0.89 Hz, 1 H), 7.30-7.39 (m, 2 H), 6.47-6.82 (m, 4 H), 4.68-4.74 (m, 2 H), 4.53-4.66 (m, 2 H), 4.22-4.32 (m, 1 H), 3.91-4.01 (m, 18 hr 1 H), 3.41 (dd, J = 14.31, 4.17 Hz, 1 H), 3.25 (s, 3 H), 2.96-3.11 (m, 3 H), 2.84 (d, J = 0.89 Hz, 3 H), 2.53-2.78 (m, 3 H), 2.42 (ddd, J = 11.33, 7.60, 4.02 Hz, 2 H), 2.19-2.29 (m, 2 H), 1.97-2.12 (m, 6 H), 1.70-1.92 (m, 3 H), 1.33-1.39 (m, 1 H), 0.96-1.02 (m, 1 H). |

TABLE A-continued

| Example No. (preparation of the Example) | Structure and IUPAC name | Characterising data (LCMS and/or NMR) |
|---|---|---|
| 271 (General Procedure A using Bromide A2 as the core reagent) | 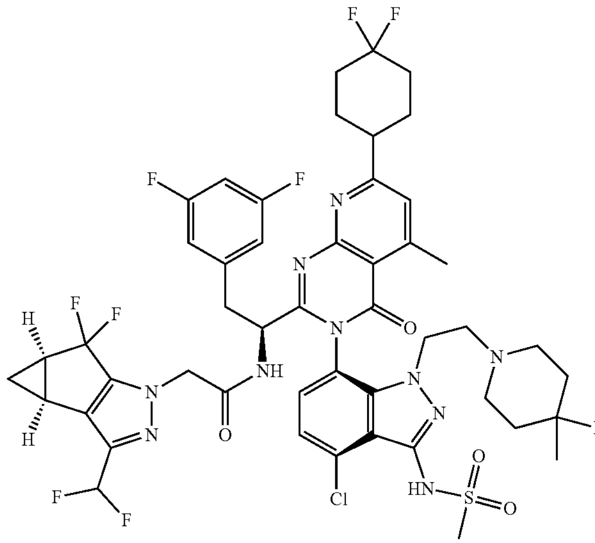 N-[(1S)-1-[(3P)-3-{4-chloro-1-[2-(4-fluoro-4-methylpiperidin-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method B: retention time = 1.16 min.; observed ion = 1065.5 [M − H]. 1H NMR (500 MHz, METHANOL-d4) δ ppm 0.99 (td, J = 3.73, 1.79 Hz, 1 H), 1.28-1.40 (m, 4 H), 1.67-1.91 (m, 4 H), 1.95-2.12 (m, 6 H), 2.17-2.28 (m, 2 H), 2.42 (ddd, J = 11.33, 7.60, 18 hr 4.02 Hz, 2 H), 2.83 (d, J = 0.60 Hz, 3 H), 2.98-3.13 (m, 4 H), 3.25 (s, 3 H), 3.42 (dd, J = 14.45, 4.02 Hz, 1 H), 3.97-4.06 (m, 1 H), 4.25-4.34 (m, 1 H), 4.54-4.75 (m, 4 H), 6.47-6.82 (m, 4 H), 7.32-7.40 (m, 2 H), 7.43 (d, J = 0.60 Hz, 1 H). |
| 273 (General Procedure A using Bromide A1 as the core reagent) | 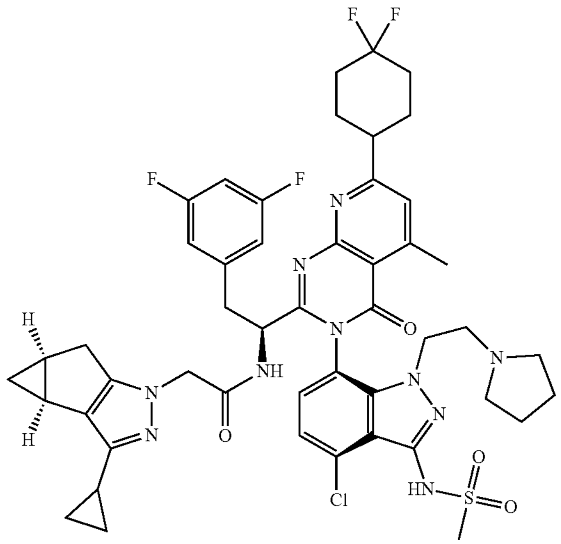 N-[(1S)-1-[(3P)-3-{4-chloro-3-methanesulfonamido-1-[2-(pyrrolidin-1-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2}$,$^{4}$]nona-1(6),8-dien-7-yl]acetamide | 1H NMR (500 MHz, METHANOL-d4) δ ppm 7.41 (s, 1 H), 7.34-7.39 (m, 2 H), 6.74-6.86 (m, 1 H), 6.54 (br d, J = 6.26 Hz, 2 H), 4.66 (dd, J = 10.73, 3.58 Hz, 1 H), 4.45-4.52 (m, 1 H), 4.35-4.42 (m, 1 H), 4.26-4.34 (m, 1 H), 4.02-4.13 (m, 1 H), 3.39-3.49 (m, 3 H), 3.26 (s, 3 H), 3.08-3.19 (m, 2 H), 3.00-3.07 (m, 1 H), 2.83 (s, 3 H), 2.54-2.61 (m, 1 H), 2.40-2.49 (m, 1 H), 2.18-2.29 (m, 2 H), 2.02-2.12 (m, 5 H), 1.89-2.01 (m, 6 H, 1.80-1.86 (m, 1 H), 1.69-1.78 (m, 1 H), 0.93-0.99 (m, 1 H), 0.82-0.92 (m, 2 H), 0.66-0.79 (m, 2 H). |

TABLE A-continued

| Example No. (preparation of the Example) | Structure and IUPAC name | Characterising data (LCMS and/or NMR) |
|---|---|---|
| 275 (General Procedure A using Bromide A1 as the core reagent) | 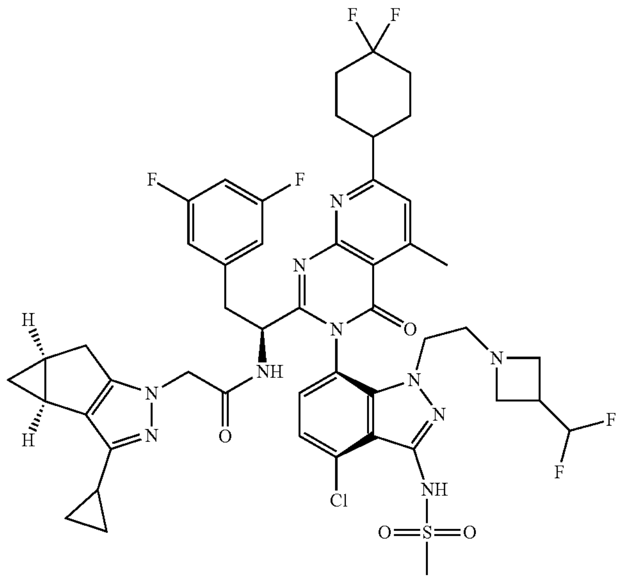 N-[(1S)-1-[(3P)-3-(4-chloro-1-{2-[3-(difluoromethyl)azetidin-1-ylethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.16 min.; observed ion = 1009.4 [M − H]. 1H NMR (500 MHz, METHANOL-d4) δ ppm 7.42 (s, 1 H), 7.30-7.40 (m, 2 H), 6.70-6.87 (m, 1 H), 6.55 (dd, J = 7.90, 1.94 Hz, 2 H), 5.78-6.11 (m, 1 H), 4.68 (dd, J = 10.28, 3.73 Hz, 1 H), 4.32-4.49 (m, 2 H), 4.03-4.20 (m, 1 H), 3.83-3.96 (m, 1 H), 3.52-3.77 (m, 2 H), 3.39-3.47 (m, 1 H), 3.10 (br dd, J = 14.45, 9.98 Hz, 2 H), 2.97-3.05 (m, 2 H), 2.84 (s, 3 H), 2.61 (dd, J = 16.54, 6.41 Hz, 1 H), 2.46 (d, J = 16.39 Hz, 1 H), 2.18-2.29 (m, 2 H), 1.89-2.12 (m, 8 H), 1.79-1.86 (m, 1 H), 1.75 (tt, J = 8.53, 5.03 Hz, 1 H), 0.95 (td, J = 7.67, 4.92 Hz, 1 H), 0.80-0.90 (m, 2H), 0.66-0.79 (m, 2 H), 0.01-0.05 (m, 1 H). |
| 276 (General Procedure A using Bromide A1 as the core reagent) | 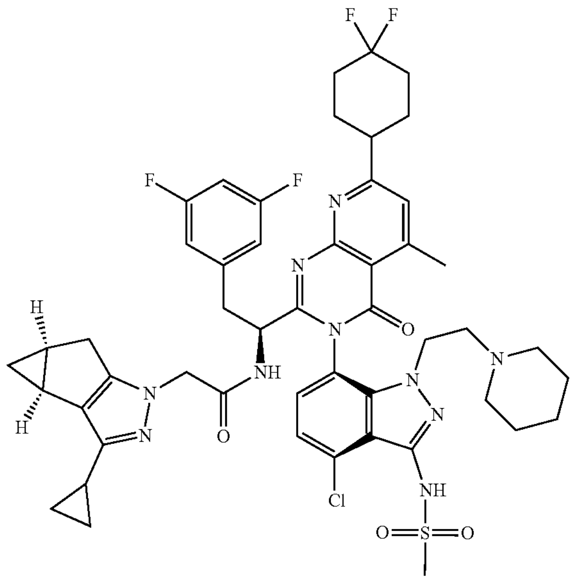 N-[(1S)-1-[(3P)-3-{4-chloro-3-methanesulfonamido-1-[2-(piperidin-1-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.15 min.; observed ion = 987.7 [M − H]. 1H NMR (500 MHz, METHANOL-d4) δ ppm 7.42 (d, J = 0.89 Hz, 1 H), 7.37 (s, 2 H), 6.81 (tt, J = 9.24, 2.38 Hz, 1 H), 6.53 (dd, J = 8.05, 2.09 Hz, 2 H), 4.66 (dd, J = 9.98, 3.73 Hz, 1 H), 4.42-4.51 (m, 1 H), 4.33-4.40 (m, 1 H), 4.24-4.32 (m, 1 H), 3.99-4.13 (m, 1 H), 3.40-3.45 (m, 1 H), 3.27 (s, 3 H), 3.11 (dd, J = 14.45, 10.28 Hz, 1 H), 2.99-3.06 (m, 1 H), 2.83 (d, J = 0.60 Hz, 3 H), 2.58 (dd, J = 16.54, 6.71 Hz, 1 H), 2.43 (d, J = 16.39 Hz, 1 H), 2.18-2.29 (m, 2 H), 1.89-2.12 (m, 6 H), 1.80-1.86 (m, 1 H), 1.66-1.78 (m, 4 H), 1.52-1.62 (m, 1 H), 0.93-0.99 (m, 1 H), 0.83-0.92 (m, 2 H), 0.65-0.79 (m, 2 H), 0.01-0.04 (m, 1 H). |

TABLE A-continued

| Example No. (preparation of the Example) | Structure and IUPAC name | Characterising data (LCMS and/or NMR) |
|---|---|---|
| 277 (General Procedure A using Bromide A1 as the core reagent) | 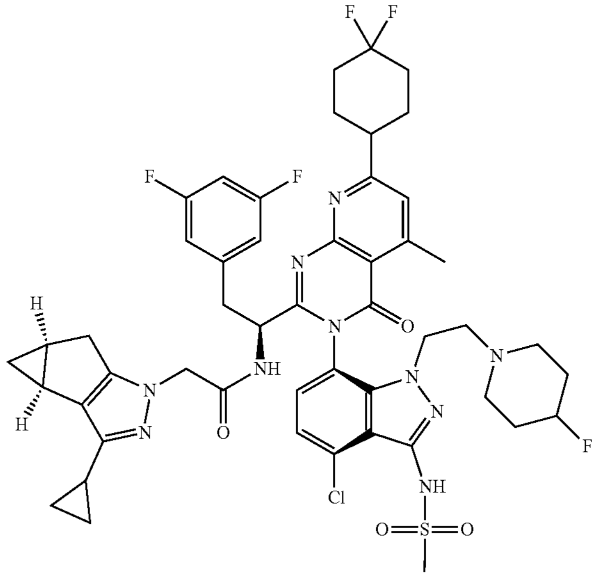 N-[(1S)-1-[(3P)-3-{4-chloro-1-[2-(4-fluoropiperidin-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2}$,$^{4}$]nona-1(6),8-dien-7-yl]acetamide | LCMS Method B: retention time = 1.16 min.; observed ion = 1005.6 [M − H]. 1H NMR (500 MHz, METHANOL-d4) δ ppm 7.42 (s, 1 H), 7.32-7.40 (m, 2 H), 6.73-6.86 (m, 1 H), 6.45-6.62 (m, 2 H), 4.70 (br dd, J = 9.24, 3.28 Hz, 1 H), 4.30-4.46 (m, 2 H), 4.19-4.29 (m, 1 H), 3.94-4.08 (m, 1 H), 3.40-3.47 (m, 1 H), 3.28 (s, 3 H), 2.98-3.12 (m, 3 H), 2.83 (s, 3 H), 2.56-2.64 (m, 1 H), 2.44 (d, J = 16.69 Hz, 1 H), 2.18-2.29 (m, 2 H), 1.87-2.13 (m, 10 H), 1.80-1.86 (m, 2 H), 1.71-1.79 (m, 1 H), 0.96 (td, J = 7.53, 4.62 Hz, 1 H), 0.81-0.92 (m, 2 H), 0.68-0.79 (m, 2 H), 0.01-0.05 (m, 1 H). |
| 278 (General Procedure A using Bromide A1 as the core reagent) | 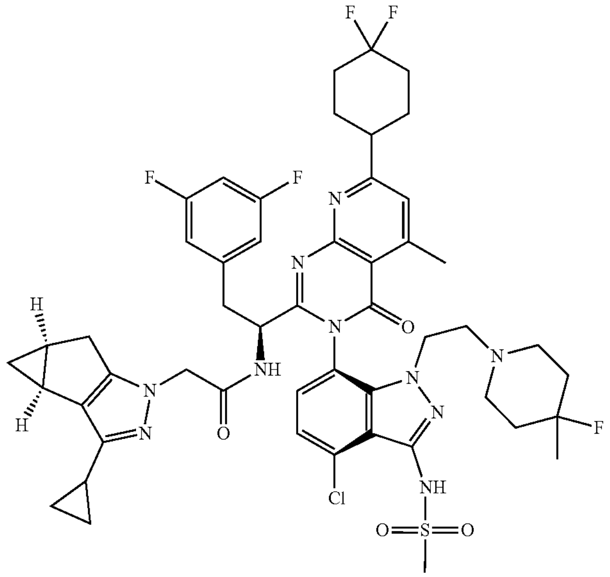 N-[(1S)-1-[(3P)-3-{4-chloro-1-[2-(4-fluoro-4-methylpiperidin-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2}$,$^{4}$]nona-1(6),8-dien-7-yl]acetamide | LCMS Method B: retention time = 1.18 min.; observed ion = 1019.7 [M − H]. 1H NMR (500 MHz, METHANOL-d4) δ ppm 7.42 (s, 1 H), 7.33-7.40 (m, 2 H), 6.73-6.85 (m, 1 H), 6.54 (br d, J = 5.96 Hz, 2 H), 4.68-4.73 (m, 2 H), 4.41-4.48 (m, 1 H), 4.32-4.39 (m, 1H), 4.23-4.31 (m, 1 H), 3.99-4.11 (m, 1 H), 3.42 (br dd, J = 14.60, 4.17 Hz, 1 H), 3.28 (s, 3 H), 3.16-3.21 (m, 2 H), 3.10 (br dd, J = 14.16, 9.69 Hz, 2 H), 3.01-3.07 (m, 1 H), 2.83 (s, 3 H), 2.60 (br dd, J = 16.69, 6.56 Hz, 1 H), 2.44 (brd, J = 17.29 Hz, 1H), 2.19-2.29 (m, 2 H), 2.02-2.13 (m, 5 H), 1.79-2.01 (m, 7H), 1.72-1.78 (m, 1H), 1.30-1.40 (m, 3H), 0.96 (td, J = 7.534 Hz, 1H), 0.83-0.92 (m, 2H), 0.70-0.78 (, 2H), 0.02 (br d, J = 3.87 Hz, 1 H). |

TABLE A-continued

| Example No. (preparation of the Example) | Structure and IUPAC name | Characterising data (LCMS and/or NMR) |
|---|---|---|
| 279 (General Procedure A using Bromide A1 as the core reagent) | 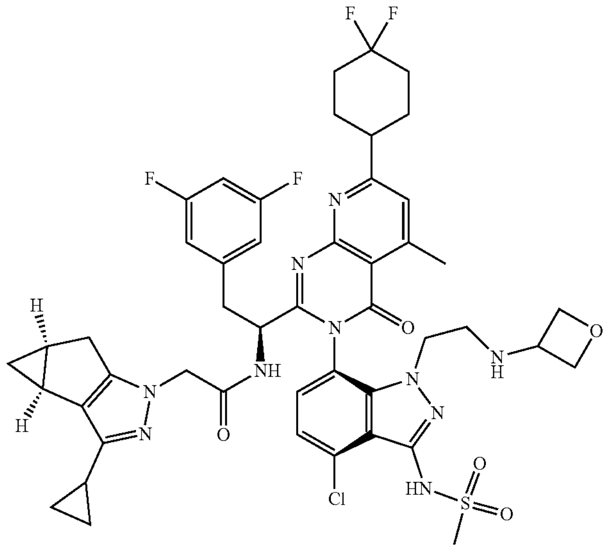 N-[(1S)-1-[(3P)-3-(4-chloro-3-methanesulfonamido-1-{2-[(oxetan-3-yl)amino]ethyl}-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.13 min.; observed ion = 975.4 [M − H]. 1H NMR (500 MHz, METHANOL-d4) δ ppm 7.42 (s, 1 H), 7.33-7.38 (m, 1 H), 7.26-7.31 (m, 1 H), 6.76-6.82 (m, 1 H), 6.54 (br d, J = 6.56 Hz, 2 H), 4.72 (dd, J = 9.54, 4.47 Hz, 1 H), 4.57-4.66 (m, 2 H), 4.26-4.42 (m, 4 H), 4.05-4.14 (m, 1 H), 3.75-3.91 (m, 2 H), 3.39-3.46 (m, 1 H), 3.01-3.11 (m, 2 H), 2.91-3.00 (m, 2 H), 2.83 (s, 3 H), 2.62 (dd, J = 16.54, 6.71 Hz, 1 H), 2.44 (br d, J = 16.39 Hz, 1 H), 2.18-2.29 (m, 2 H), 1.89-2.13 (m, 7 H), 1.81-1.87 (m, 1 H), 1.71-1.80 (m, 1 H), 0.93-0.99 (m, 1 H), 0.87 (tdd, J = 8.31, 8.31, 4.99, 3.13 Hz, 2 H), 0.67-0.80 (m, 2H), 0.04 (q, J = 4.27 Hz, 1 H). |
| 280 (General Procedure A using Bromide A1 as the core reagent) | 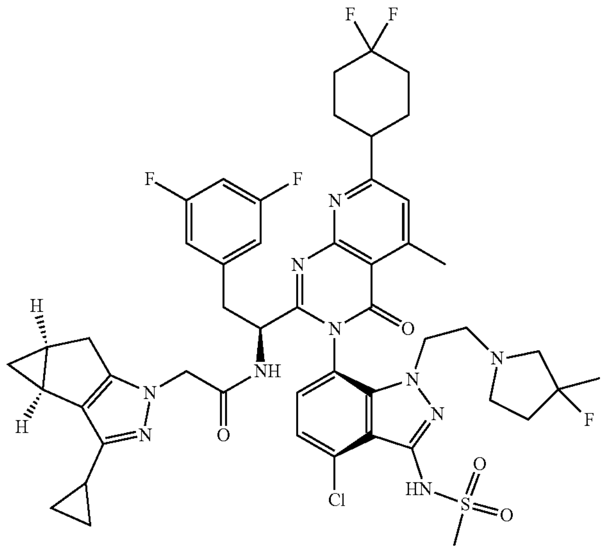 N-[(1S)-1-[(3P)-3-{4-chloro-1-[2-(3-fluoro-3-methylpyrrolidin-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.17 min.; observed ion = 1005.4 [M − H]. 1H NMR (500 MHz, METHANOL-d4) δ ppm 7.42 (s, 1 H), 7.28-7.40 (m, 2 H), 6.80 (tt, J = 9.13, 2.35 Hz, 1 H), 6.51-6.59 (m, 2 H), 4.67-4.74 (m, 1 H), 4.31-4.43 (m, 2 H), 4.21-4.29 (m, 1H), 3.94-4.08 (m, 1 H), 3.41-3.48 (m, 1 H), 3.10 (br dd, J = 14.01, 10.43 Hz, 2 H), 2.97-3.05 (m, 2 H), 2.83 (d, J = 0.60 Hz, 3 H), 2.63 (ddd, J = 16.39, 6.56, 2.38 Hz, 1 H), 2.45 (d, J = 16.39 Hz, 1H), 2.19-2.28 (m, 2 H), 2.02-2.14 (m, 6 H), 1.88-2.01 (m, 3 H), 1.84 (ddd, J = 7.67, 5.74, 2.09 Hz, 1 H), 1.69-1.78 (m, 1 H), 1.37-1.48 (m, 3 H), 0.92-1.00 (m, 1 H), 0.81-0.91 (m, 2 H), 0.68-0.79 (m, 2 H), 0.02-0.06 (m, 1 H). |

TABLE A-continued

| Example No. (preparation of the Example) | Structure and IUPAC name | Characterising data (LCMS and/or NMR) |
|---|---|---|
| 281 (General Procedure A using Bromide A1 as the core reagent) | 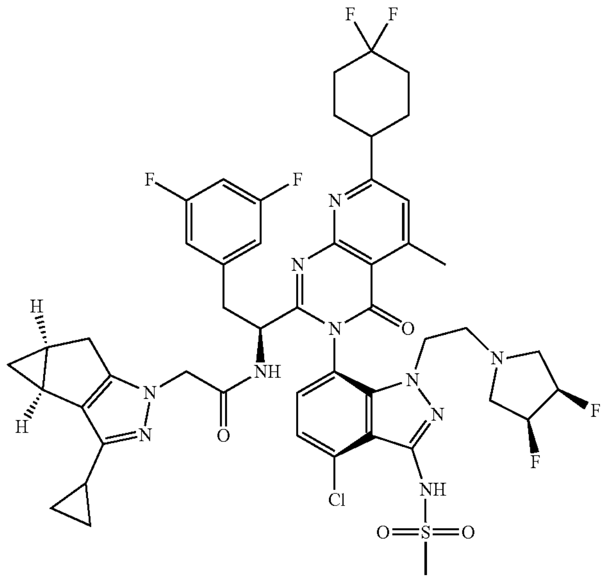 N-[(1S)-1-[(3P)-3-(4-chloro-1-{2-[(3R,4S)-3,4-difluoropyrrolidin-1-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.33 min.; observed ion = 1009.3 [M − H]. 1H NMR (500 MHz, METHANOL-d4) δ ppm 7.42 (s, 1 H), 7.28-7.40 (m, 2 H), 6.80 (tt, J = 9.13, 2.35 Hz, 1 H), 6.51-6.59 (m, 2 H), 4.67-4.74 (m, 1 H), 4.31-4.43 (m, 2 H), 4.21-4.29 (m, 1H), 3.94-4.08 (m, 1 H), 3.41-3.48 (m, 1 H), 3.10 (br dd, J = 14.01, 10.43 Hz, 2 H), 2.97-3.05 (m, 2 H), 2.83 (d, J = 0.60 Hz, 3 H), 2.63 (ddd, J = 16.39, 6.56, 2.38 Hz, 1 H), 2.45 (d, J = 16.39 Hz, 1H), 2.19-2.28 (m, 2H), 2.02-2.14 (m, 6 H), 1.88-2.01 (m, 3 H), 1.84 (ddd, J = 7.67, 5.74, 2.09 Hz, 1 H), 1.69-1.78 (m, 1 H), 1.37-1.48 (m, 3H), 0.92-1.00 (m, 1H), 0.81-0.91 (m, 2H), 0.68-0.79 (m, 2H), 0.02-0.06 (m, 1 H). |
| 283 (General Procedure A using Bromide A1 as the core reagent) | 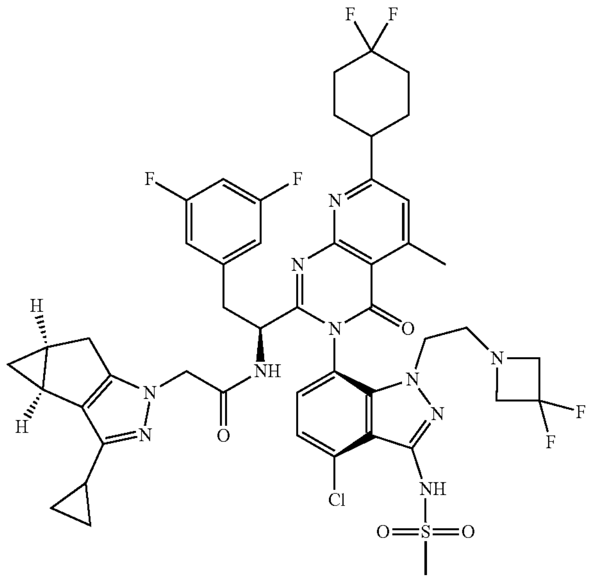 N-[(1S)-1-[(3P)-3-{4-chloro-1-[2-(3,3-difluoroazetidin-1-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.45 min.; observed ion = 995.5 [M − H]. 1H NMR (500 MHz, METHANOL-d4) δ ppm 7.42 (s, 1 H), 7.32 (d, J = 7.75 Hz, 1 H), 7.20 (d, J = 7.75 Hz, 1 H), 6.69-6.81 (m, 1 H), 6.55 (br d, J = 7.15 Hz, 2 H), 5.48 (s, 1 H), 4.77-4.80 (m, 1 H), 4.23-4.34 (m, 2 H), 3.93 (dt, J = 13.56, 6.93 Hz, 1 H), 3.56-3.69 (m, 1 H), 3.35-3.46 (m, 1 H), 3.28 (s, 3 H), 3.23-3.27 (m, 2 H), 3.04 (br dd, J = 13.56, 9.09 Hz, 2 H), 2.84 (s, 3 H), 2.80-2.83 (m, 1 H), 2.67 (dd, J = 16.54, 6.71 Hz, 1 H), 2.45 (d, J = 16.69 Hz, 1 H), 2.19-2.28 (m, 2 H), 1.89-2.15 (m, 7 H), 1.81-1.86 (m, 1 H), 1.73-1.80 (m, 1 H), 0.91-0.98 (m, 1 H), 0.80-0.89 (m, 2 H), 0.68-0.79 (m, 2 H), 0.05 (q, J = 3.87 Hz, 1 H). |

TABLE A-continued

| Example No. (preparation of the Example) | Structure and IUPAC name | Characterising data (LCMS and/or NMR) |
|---|---|---|
| 285 (General Procedure D using Chloride D2 as the core reagent) | 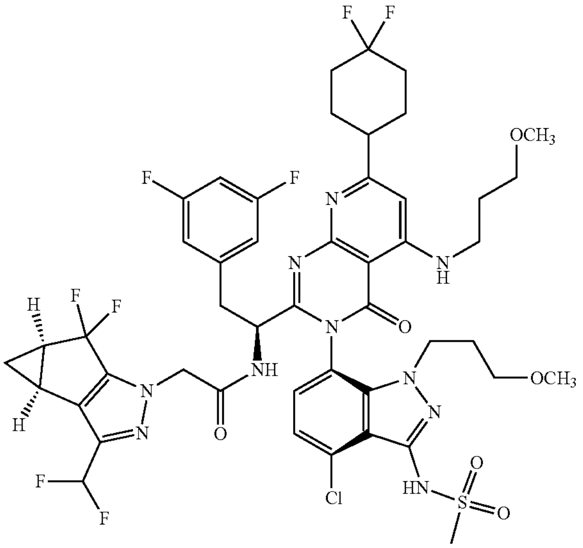 N-[(1S)-1-[(3P)-3-[4-chloro-3-methanesulfonamido-1-(3-methoxypropyl)-1H-indazol-7-yl]-7-(4,4-difluorocyclohexyl)-5-[(3-methoxypropyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.63 min.; observed ion = 1069.15 [M + H]+. 1H NMR (500 MHz, METHANOL-d4) δ ppm 8.96-9.10 (m, 1 H), 9.04 (t, J = 5.66 Hz, 1 H), 7.27 (d, J = 7.75 Hz, 1 H), 7.06 (d, J = 7.75 Hz, 1 H), 6.52-6.80 (m, 5 H), 4.73-4.80 (m, 1 H), 4.57 (d, J = 2.38 Hz, 2 H), 4.03 (ddd, J = 14.23, 9.76, 6.11 Hz, 1 H), 3.72-3.86 (m, 1 H), 3.42-3.50 (m, 4 H), 3.37 (dd, J = 14.01, 5.36 Hz, 1 H), 3.23 (s, 3 H), 3.14 (t, J = 5.66 Hz, 2 H), 3.02 (dd, J = 14.01, 8.94 Hz, 1 H), 2.91 (s, 3 H), 2.80-2.88 (m, 1 H), 2.42 (ddd, J = 11.55, 7.67, 4.02 Hz, 2 H), 2.16-2.28 (m, 2 H), 1.77-2.09 (m, 10 H), 1.27-1.40 (m, 1 H), 0.92-1.06 (m, 1 H). |
| 287 (General Procedure A using Bromide A5 as the core reagent) | 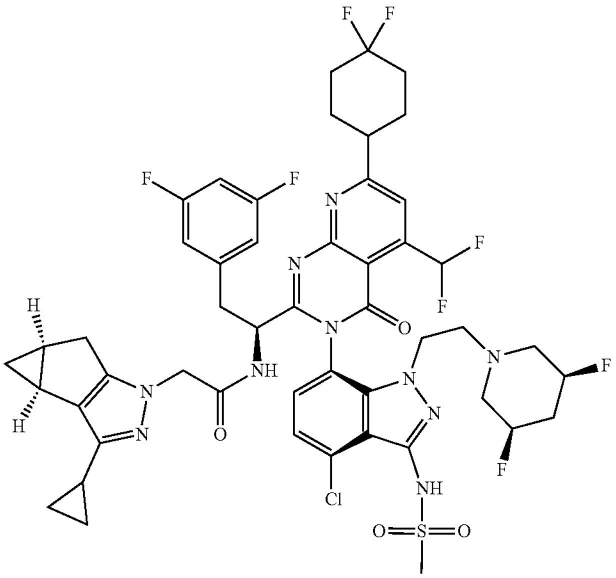 N-[(1S)-1-[(3P)-3-(4-chloro-1-{2-[(3R,5S)-3,5-difluoropiperidin-1-yl]ethyl}-3-methanesulfonamido-1H-indazol-7-yl)-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method D: retention time = 1.41 min.; observed ion = 1061.4 [M + H]+. 1H NMR (500 MHz, METHANOL-d4) δ ppm 0.04-0.10 (m, 1 H), 0.71-0.80 (m, 2 H), 0.82-0.91 (m, 2 H), 0.94-1.00 (m, 1 H), 1.58-1.70 (m, 1 H), 1.74-2.30 (m, 16 H), 2.41-2.56 (m, 3 H), 2.62-2.81 (m, 3 H), 3.06 (dd, J = 13.86, 9.69 Hz, 1 H), 3.15-3.23 (m, 1 H), 3.26-3.28 (m, 3 H), 3.40-3.42 (m, 1 H), 3.71-3.79 (m, 1 H), 4.01-4.09 (m, 1 H), 4.24-4.33 (m, 3 H), 4.38 (dt, J = 7.08, 3.46 Hz, 1 H), 6.52-6.60 (m, 2 H), 6.73-6.80 (m, 1 H), 7.25-7.30 (m, 1 H), 7.32-7.37 (m, 1 H), 7.63-7.90 (m, 2 H). |

TABLE A-continued

| Example No. (preparation of the Example) | Structure and IUPAC name | Characterising data (LCMS and/or NMR) |
|---|---|---|
| 288 (General Procedure A using Bromide A5 as the core reagent) | 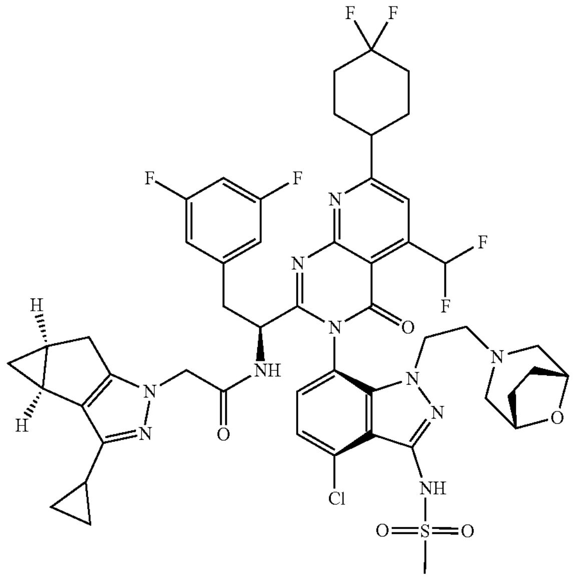 N-[(1S)-1-[(3P)-3-(4-chloro-3-methanesulfonamido-1-{2-[(1R,5S)-8-oxa-3-azabicyclo[3.2.1]octan-3-yl]ethyl}-1H-indazol-7-yl)-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method D: retention time = 1.16 min.; observed ion = 1051.4 [M − H]+. 1H NMR (500 MHz, METHANOL-d4) δ ppm 0.05-0.09 (m, 1 H), 0.73-0.81 (m, 2 H), 0.83-0.91 (m, 2 H), 0.96 (td, J = 7.60, 4.77 Hz, 1 H), 1.27-1.35 (m, 2 H), 1.42-1.47 (m, 1 H), 1.51-1.61 (m, 2 H), 1.74-1.87 (m, 2 H), 1.95-2.19 (m, 11 H), 2.23-2.31 (m, 3 H), 2.44-2.53 (m, 3 H), 2.71 (dd, J = 16.24, 6.41 Hz, 1 H), 3.01-3.08 (m, 1 H), 3.26 (s, 3 H), 3.38 (br s, 1 H), 3.62-3.71 (m, 2 H), 3.96-4.07 (m, 3 H), 4.25-4.38 (m, 2 H), 6.47-6.56 (m, 2 H), 6.72-6.80 (m, 1 H), 7.28-7.38 (m, 2 H), 7.65-7.89 (m, 1 H), 7.91 (s, 1 H). |
| 289 (General Procedure A using Bromide A5 as the core reagent) | 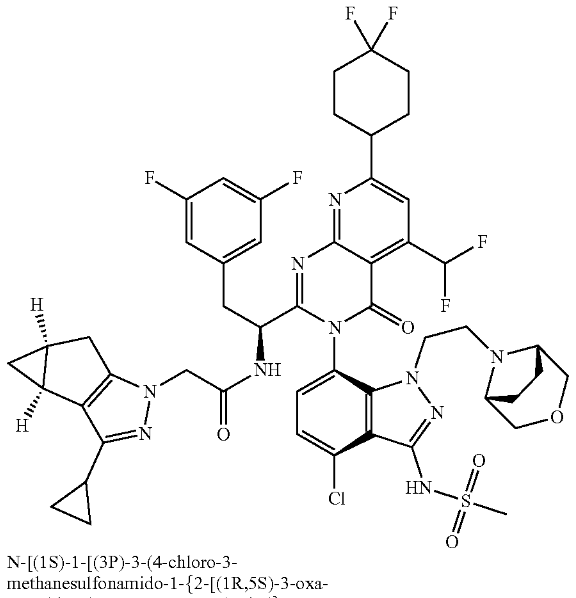 N-[(1S)-1-[(3P)-3-(4-chloro-3-methanesulfonamido-1-{2-[(1R,5S)-3-oxa-8-azabicyclo[3.2.1]octan-8-yl]ethyl}-1H-indazol-7-yl)-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method D: retention time = 1.19 min.; observed ion = 1051.4 [M − H]+. 1H NMR (500 MHz, METHANOL-d4) δ ppm 0.03-0.07 (m, 1 H), 0.70-0.80 (m, 2 H), 0.83-0.92 (m, 3 H), 0.93-0.99 (m, 1 H), 1.71-2.18 (m, 17 H), 2.19-2.30 (m, 3 H), 2.45 (d, J = 16.39 Hz, 1 H), 2.61-2.68 (m, 1 H), 3.08 (dd, J = 14.31, 9.84 Hz, 2 H), 3.17-3.24 (m, 2 H), 3.25-3.28 (m, 4 H), 3.41 (br d, J = 3.58 Hz, 1 H), 3.81-3.93 (m, 1 H), 4.13-4.24 (m, 1 H), 4.29-4.42 (m, 2 H), 4.73-4.79 (m, 1 H), 6.52 (dd, J = 8.20, 1.94 Hz, 2 H), 6.74-6.83 (m, 1 H), 7.35-7.41 (m, 2 H), 7.64-7.94 (m, 2 H) |

TABLE A-continued

| Example No. (preparation of the Example) | Structure and IUPAC name | Characterising data (LCMS and/or NMR) |
|---|---|---|
| 290 (General Procedure A using Bromide A6 as the core reagent) | 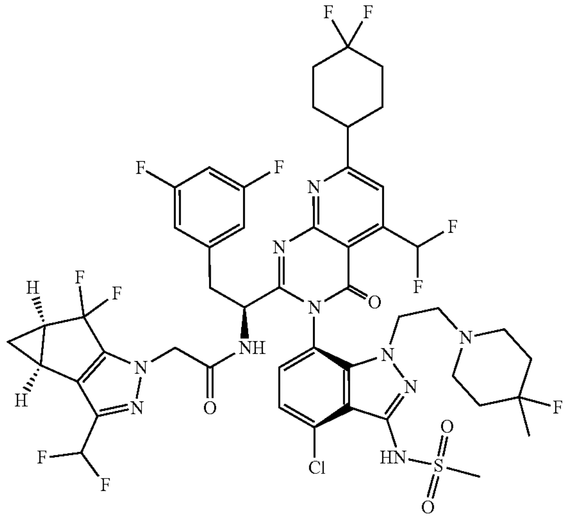 N-[(1S)-1-[(3P)-3-{4-chloro-1-[2-(4-fluoro-4-methylpiperidin-1-yl)ethyl]-3-methanesulfonamido-1H-indazol-7-yl}-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method D: retention time = 1.20 min.; observed ion = 1103.4 [M + H]+. 1H NMR (500 MHz, METHANOL-d4) δ ppm 0.94-1.01 (m, 1 H), 1.21-1.42 (m, 5 H), 1.75-2.17 (m, 9 H), 2.19-2.30 (m, 2 H), 2.38-2.51 (m, 2 H), 3.09-3.24 (m, 3 H), 3.24-3.28 (m, 3 H), 3.41-3.45 (m, 1 H), 3.96-4.07 (m, 1 H), 4.26-4.38 (m, 1 H), 4.58-4.75 (m, 3 H), 6.50-6.86 (m, 4 H), 7.36-7.46 (m, 2 H), 7.63-7.92 (m, 2 H) |
| 291 (General Procedure A using Bromide A6 as the core reagent) | 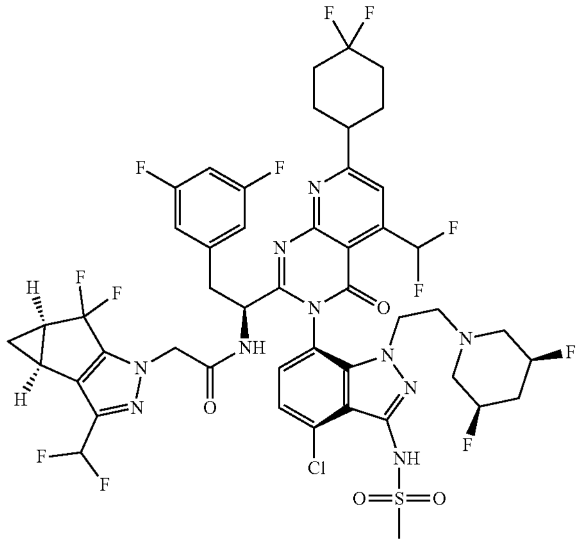 N-[(1S)-1-[(3P)-3-(4-chloro-1-{2-[(3R,5S)-3,5-difluoropiperidin-1-yl]ethyl}-3-methanesulfonamido-1H-indazol-7-yl)-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method D: retention time = 1.41 min.; observed ion = 1107.4 [M + H]+. 1H NMR (500 MHz, METHANOL-d4) δ ppm 0.99-1.03 (m, 1 H), 1.32-1.39 (m, 1 H), 1.60-1.71 (m, 1 H), 1.94-2.30 (m, 12 H), 2.39-2.54 (m, 4 H), 2.62-2.70 (m, 1 H), 2.72-2.81 (m, 1 H), 3.07 (dd, J = 14.01, 9.54 Hz, 1 H), 3.17-3.21 (m, 1 H), 3.22-3.25 (m, 3 H), 3.37-3.43 (m, 1 H), 3.74-3.83 (m, 1 H), 4.10-4.18 (m, 1 H), 4.26-4.33 (m, 1 H), 4.34-4.42 (m, 1 H), 4.54-4.68 (m, 2 H), 6.50-6.80 (m, 4 H), 7.23-7.30 (m, 1 H), 7.30-7.36 (m, 1 H), 7.65-7.90 (m, 2 H). |

TABLE A-continued

| Example No. (preparation of the Example) | Structure and IUPAC name | Characterising data (LCMS and/or NMR) |
|---|---|---|
| 292 (General Procedure A using Bromide A6 as the core reagent) | 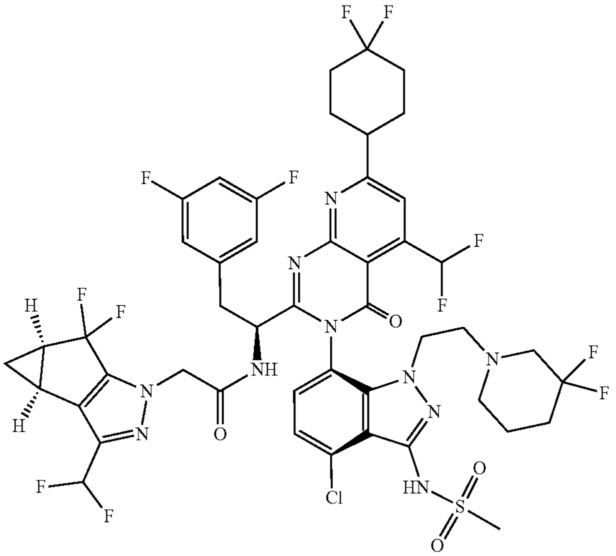 N-[(1S)-1-[(3P)-3-{4-chloro-1-[2-(3,3-difluoropiperidin-1-yl)ethyl]-3-methanesulfonamido-1H-indazol-7-yl}-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method D: retention time = 1.50 min.; observed ion = 1107.2 [M + H]+. 1H NMR (500 MHz, METHANOL-d4) δ ppm 0.99-1.04 (m, 1 H), 1.33-1.39 (m, 1 H), 1.43-1.50 (m, 2 H), 1.76 (s, 2 H), 2.05-2.18 (m, 7 H), 2.20-2.36 (m, 6 H), 2.39-2.46 (m, 2 H), 2.55-2.63 (m, 1 H), 2.70 (ddd, J = 12.37, 10.73, 6.11 Hz, 1 H), 3.07 (dd, J = 14.01, 9.84 Hz, 1 H), 3.18-3.25 (m, 4 H), 3.40 (dd, J = 14.01, 4.47 Hz, 1 H), 3.75 (ddd, J = 14.16, 10.13, 5.22 Hz, 1 H), 4.16 (ddd, J = 14.23, 10.51, 5.66 Hz, 1 H), 4.60 (q, J = 16.69 Hz, 2 H), 6.51-6.80 (m, 4 H), 7.26 (d, J = 8.05 Hz, 1 H), 7.31-7.36 (m, 1 H), 7.64-7.91 (m, 2 H). |
| 298 (General Procedure A using Bromide A5 as the core reagent) | 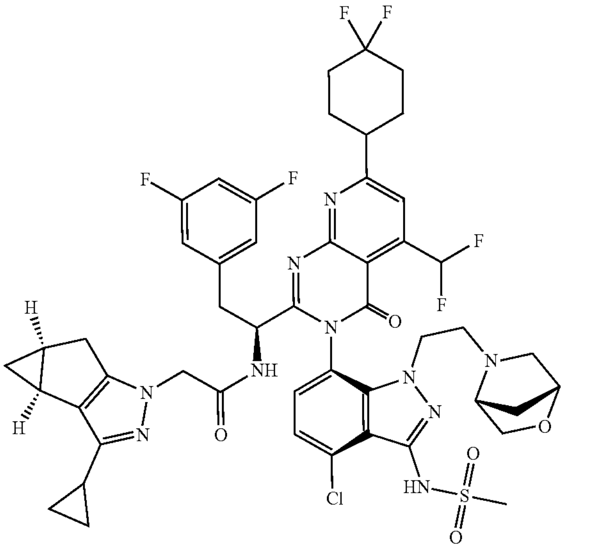 N-[(1S)-1-[(3P)-3-(4-chloro-3-methanesulfonamido-1-{2-[(1R,4R)-2-oxa-5-azabicyclo[2.2.1]heptan-5-yl]ethyl}-1H-indazol-7-yl)-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method D: retention time = 1.17 min.; observed ion = 1039.3 [M + H]+. 1H NMR (500 MHz, METHANOL-d4) δ ppm 0.02-0.06 (m, 1 H), 0.68-0.80 (m, 2 H), 0.81-0.91 (m, 2 H), 0.92-1.01 (m, 1 H), 1.70-2.16 (m, 12 H), 2.19-2.29 (m, 2 H), 2.45 (d, J = 16.39 Hz, 1 H), 2.59-2.67 (m, 1 H), 3.07-3.13 (m, 1 H), 3.18-3.25 (m, 1 H), 3.28 (s, 3 H), 3.39-3.46 (m, 1 H), 3.53-3.63 (m, 1 H), 3.79-3.99 (m, 2 H), 4.15-4.27 (m, 1 H), 4.30-4.44 (m, 3 H), 4.70-4.76 (m, 1 H), 6.49-6.59 (m, 2 H), 6.76-6.84 (m, 1 H), 7.39 (s, 2 H), 7.63-7.91 (m, 2 H) |

TABLE A-continued

| Example No. (preparation of the Example) | Structure and IUPAC name | Characterising data (LCMS and/or NMR) |
| --- | --- | --- |
| 307 (General Procedure A using Bromide A6 as the core reagent) | 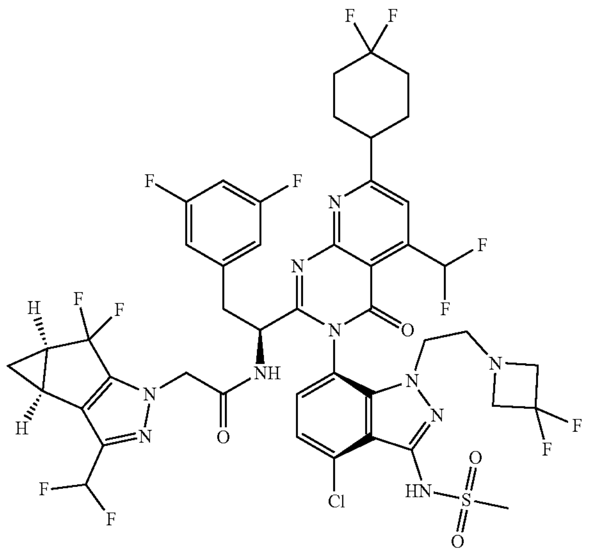 N-[(1S)-1-[(3P)-3-{4-chloro-1-[2-(3,3-difluoroazetidin-1-yl)ethyl]-3-methanesulfonamido-1H-indazol-7-yl}-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method D: retention time = 1.48 min.; observed ion = 1079.4 [M + H]+. 1H NMR (500 MHz, METHANOL-d4) δ ppm 0.96-1.03 (m, 1 H), 1.32-1.39 (m, 1 H), 1.94-2.17 (m, 6 H), 2.20-2.30 (m, 2 H), 2.37-2.47 (m, 2 H), 2.76-2.93 (m, 2 H), 3.08 (dd, J = 14.01, 9.54 Hz, 1 H), 3.17-3.27 (m, 5 H), 3.28 (br d, J = 2.98 Hz, 3 H), 3.38-3.43 (m, 1 H), 3.61-3.71 (m, 1 H), 3.97-4.07 (m, 1 H), 4.54-4.68 (m, 2 H), 6.52-6.80 (m, 4 H), 7.25-7.29 (m, 1 H), 7.31-7.35 (m, 1 H), 7.67-7.92 (m, 2 H). |
| 310 (General Procedure A using Bromide A2 as the core reagent) | 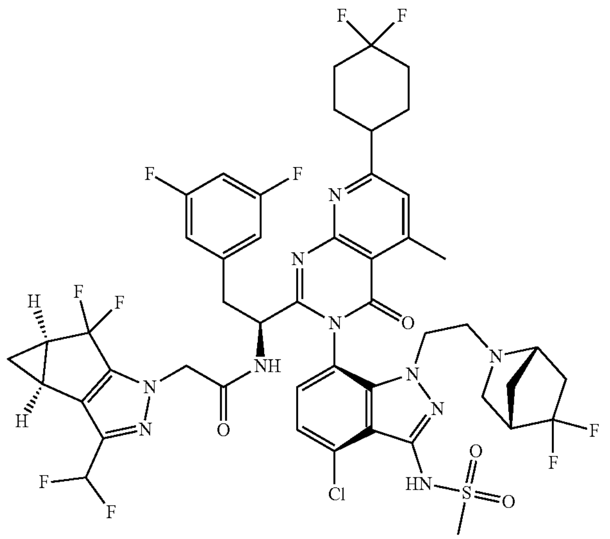 N-[(1S)-1-[(3P)-3-(4-chloro-1-{2-[(1S,4S)-5,5-difluoro-2-azabicyclo[2.2.1]heptan-2-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method B: retention time = 1.16 min.; observed ion = 1081.6 [M − H]. 1H NMR (500 MHz, METHANOL-d4) δ ppm 7.43 (dd, J = 2.24, 0.74 Hz, 1 H), 7.32 (dd, J = 7.75, 2.09 Hz, 1 H), 7.21 (dd, J = 7.90, 6.41 Hz, 1 H), 6.43-6.83 (m, 4 H), 4.76-4.80 (m, 1 H), 4.52-4.67 (m, 2 H), 4.05-4.17 (m, 1 H), 3.69-3.78 (m, 1 H), 3.35-3.41 (m, 1 H), 3.23 (d, J = 1.19 Hz, 3 H), 2.98-3.09 (m, 3 H), 2.83 (s, 3 H), 2.64-2.76 (m, 1 H), 2.28-2.47 (m, 5 H), 2.18-2.27 (m, 2 H), 2.03-2.13 (m, 5 H), 1.95-2.02 (m, 1 H), 1.56-1.87 (m, 4 H), 1.33-1.38 (m, 1 H), 0.96-1.05 (m, 1 H). |

TABLE A-continued

| Example No. (preparation of the Example) | Structure and IUPAC name | Characterising data (LCMS and/or NMR) |
| --- | --- | --- |
| 311 (General Procedure A using Bromide A1 as the core reagent) | 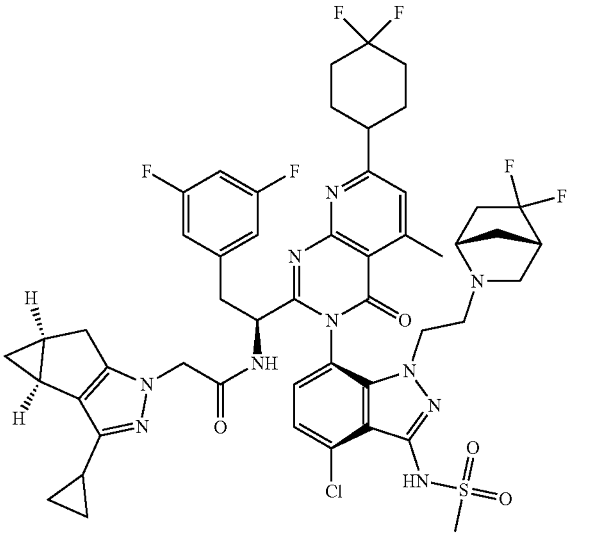<br>N-[(1S)-1-[(3P)-3-(4-chloro-1-{2-[(1S,4S)-5,5-difluoro-2-azabicyclo[2.2.1]heptan-2-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2}$,$^{4}$]nona-1(6),8-dien-7-yl]acetamide | LCMS Method B: retention time = 1.18 min.; observed ion = 1035.6 [M − H]<br>1H NMR (500 MHz, METHANOL-d4) δ ppm 7.40-7.48 (m, 1 H), 7.34 (dd, J = 8.05, 1.49 Hz, 1 H), 7.24 (dd, J = 7.90, 3.73 Hz, 1 H), 6.63-6.83 (m, 1 H), 6.39-6.57 (m, 2 H), 4.77 (dd, J = 9.24, 4.77 Hz, 1 H), 4.22-4.34 (m, 2 H), 3.97-4.12 (m, 1 H), 3.64-3.76 (m, 1 H), 3.39 (dd, J = 14.31, 4.47 Hz, 1 H), 3.27 (d, J = 1.19 Hz, 3 H), 2.99-3.13 (m, 3 H), 2.86-2.96 (m, 1 H), 2.81-2.85 (m, 3 H), 2.59-2.76 (m, 2 H), 2.36-2.50 (m, 3 H), 2.19-2.28 (m, 2 H), 1.95-2.11 (m, 6 H), 1.89-1.94 (m, 1 H), 1.80-1.87 (m, 2 H), 1.74-1.79 (m, 1 H), 1.57-1.69 (m, 2 H), 0.93-0.97 (m, 1 H), 0.82-0.90 (m, 2 H), 0.70-0.79 (m, 2 H), 0.04-0.08 (m, 1 H) |
| 312 (General Procedure A using Bromide A2 as the core reagent) | 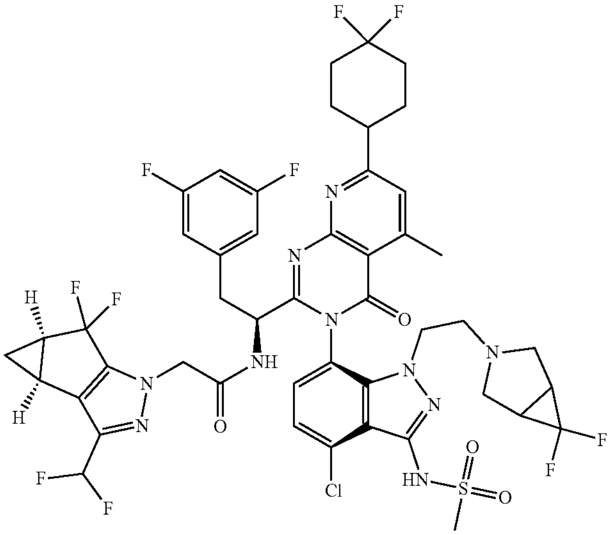<br>N-[(1S)-1-[(3P)-3-[4-chloro-1-(2-{6,6-difluoro-3-azabicyclo[3.1.0]hexan-3-yl}ethyl)-3-methanesulfonamido-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method B: retention time = 1.21 min.; observed ion = 1067.3 [M − H].<br>1H NMR (500 MHz, METHANOL-d4) δ ppm 7.43 (d, J = 0.60 Hz, 1 H), 7.31 (d, J = 8.05 Hz, 1 H), 7.19 (d, J = 7.75 Hz, 1 H), 6.51-6.81 (m, 4 H), 4.79 (dd, J = 9.39, 4.92 Hz, 1 H), 4.53-4.67 (m, 2 H), 4.08 (ddd, J = 14.01, 10.28, 5.81 Hz, 1 H), 3.71 (ddd, J = 14.16, 10.13, 5.22 Hz, 1 H), 3.39 (dd, J = 14.01, 5.07 Hz, 1 H), 3.23 (s, 3 H), 3.04 (dd, J = 14.01, 9.24 Hz, 2 H), 2.83 (d, J = 0.60 Hz, 3 H), 2.72 (td, J = 10.95, 5.51 Hz, 1 H), 2.50-2.65 (m, 5 H), 2.42 (ddd, J = 11.40, 7.67, 4.17 Hz, 2 H), 2.18-2.30 (m, 2 H), 1.94-2.13 (m, 8 H), 1.32-1.39 (m, 1 H), 0.97-1.05 (m, 1 H) |

TABLE A-continued

| Example No. (preparation of the Example) | Structure and IUPAC name | Characterising data (LCMS and/or NMR) |
|---|---|---|
| 315 (General Procedure A using Bromide A6 as the core reagent) | 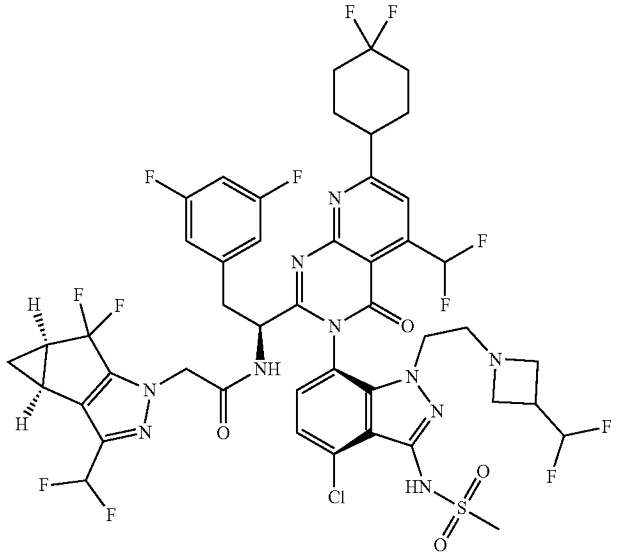 N-[(1S)-1-[(3P)-3-(4-chloro-1-{2-[3-(difluoromethyl)azetidin-1-yl]ethyl}-3-methanesulfonamido-1H-indazol-7-yl)-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.19 min.; observed ion = 1093.3 [M + H]+. 1H NMR (500 MHz, METHANOL-d4) δ ppm 1.32-1.38 (m, 1 H), 1.95-2.17 (m, 7 H), 2.19-2.29 (m, 2 H), 2.38-2.46 (m, 2 H), 2.63-2.74 (m, 3 H), 2.84-2.95 (m, 2 H), 3.03-3.13 (m, 3 H), 3.16-3.25 (m, 5 H), 3.40 (dd, J = 14.01, 4.47 Hz, 1 H), 3.62 (ddd, J = 14.16, 7.90, 6.56 Hz, 1 H), 3.96 (ddd, J = 14.31, 8.20, 6.41 Hz, 1 H), 4.52-4.68 (m, 3 H), 5.69-5.96 (m, 1 H), 6.47-6.80 (m, 4 H), 7.23-7.28 (m, 1 H), 7.30-7.34 (m, 1 H), 7.65-7.94 (m, 2 H). |
| 321 (General Procedure A using Bromide A8 as the core reagent) | 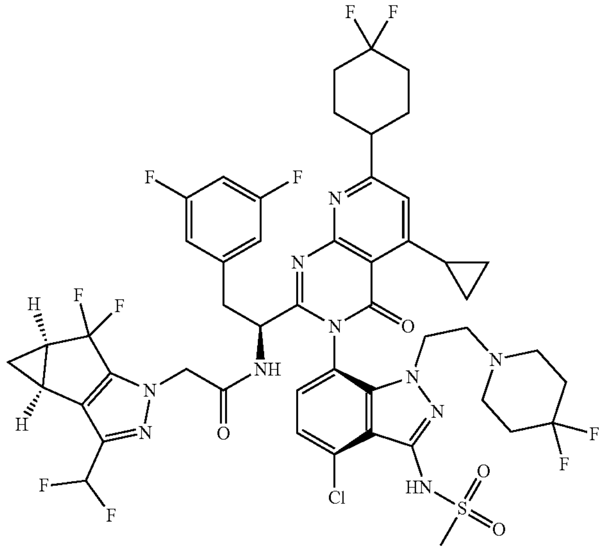 N-[(1S)-1-[(3P)-3-{4-chloro-1-[2-(4,4-difluoropiperidin-1-yl)ethyl]-3-methanesulfonamido-1H-indazol-7-yl}-5-cyclopropyl-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.32 min.; observed ion = 1095.4 [M − H]. 1H NMR (500 MHz, METHANOL-d4) δ ppm 7.33 (d, J = 8.05 Hz, 1 H), 7.25 (d, J = 8.05 Hz, 1 H), 7.01 (s, 1 H), 6.49-6.80 (m, 4 H), 4.78 (dd, J = 9.54, 4.77 Hz, 1 H), 4.55-4.69 (m, 2 H), 4.13-4.23 (m, 1 H), 3.78 (ddd, J = 14.16, 9.84, 4.92 Hz, 1 H), 3.60-3.69 (m, 1 H), 3.38 (dd, J = 14.16, 4.62 Hz, 1 H), 3.23 (s, 3 H), 2.96-3.09 (m, 2 H), 2.66-2.76 (m, 1 H), 2.52-2.61 (m, 1 H), 2.42 (ddd, J = 11.25, 7.53, 3.87 Hz, 2 H), 2.17-2.31 (m, 6 H), 1.92-2.11 (m, 6 H), 1.55-1.70 (m, 4 H), 1.33-1.39 (m, 1 H), 1.24 (d, J = 8.64 Hz, 2 H), 0.95-1.07 (m, 3 H) |

TABLE A-continued

| Example No. (preparation of the Example) | Structure and IUPAC name | Characterising data (LCMS and/or NMR) |
|---|---|---|
| 322 (General Procedure A using Bromide A8 as the core reagent) | 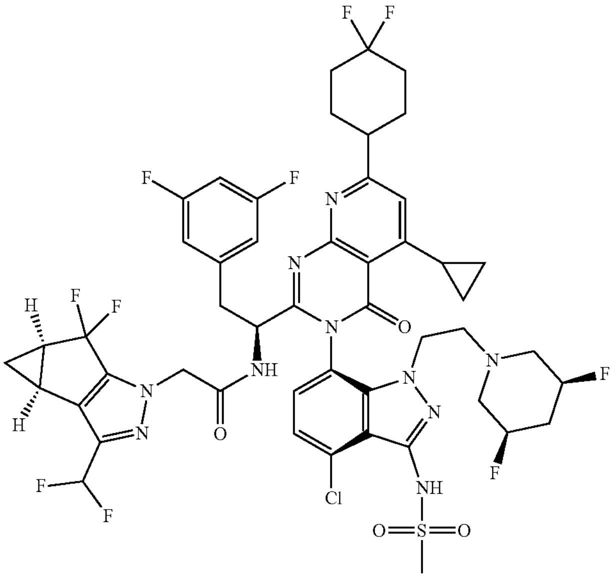<br>N-[(1S)-1-[(3P)-3-(4-chloro-1-{2-[(3R,5S)-3,5-difluoropiperidin-1-yl]ethyl}-3-methanesulfonamido-1H-indazol-7-yl)-5-cyclopropyl-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.44 min.; observed ion = 1095.4 [M − H]. 1H NMR (500 MHz, METHANOL-d4) δ ppm 7.31 (d, J = 8.05 Hz, 1 H), 7.21 (d, J = 7.75 Hz, 1 H), 7.00 (s, 1 H), 6.51-6.81 (m, 4 H), 4.77-4.80 (m, 1 H), 4.54-4.66 (m, 2 H), 4.12-4.40 (m, 3 H), 3.73-3.83 (m, 1 H), 3.63 (tt, J = 8.42, 5.14 Hz, 1 H), 3.40 (dd, J = 14.01, 4.77 Hz, 1 H), 3.24 (s, 3 H), 2.96-3.10 (m, 2 H), 2.80 (ddd, J = 12.74, 9.91, 5.66 Hz, 1 H), 2.66-2.74 (m, 1 H), 2.57-2.64 (m, 1 H), 2.47-2.56 (m, 1 H), 2.42 (ddd, J = 11.40, 7.67, 3.87 Hz, 2 H), 2.10-2.27 (m, 5 H), 1.92-2.09 (m, 6 H), 1.55-1.64 (m, 1 H), 1.32-1.39 (m, 1 H), 1.21-1.27 (m, 2 H), 0.92-1.06 (m, 3 H). |
| 324 (General Procedure A using Bromide A7 as the core reagent) | 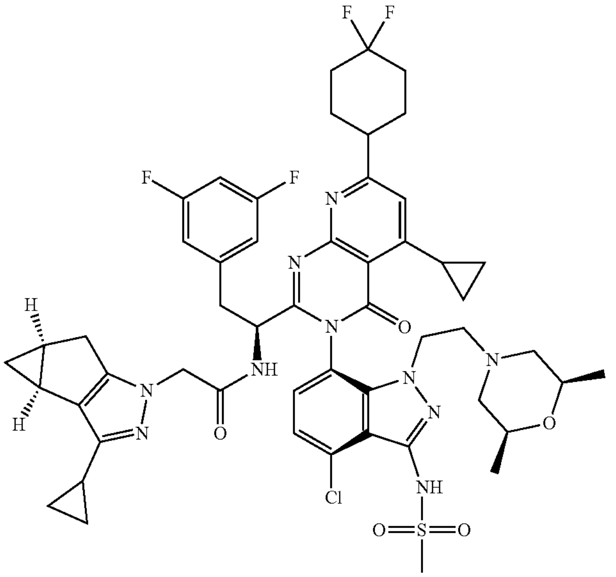<br>N-[(1S)-1-[(3P)-3-(4-chloro-1-{2-[(2R,6S)-2,6-dimethylmorpholin-4-yl]ethyl}-3-methanesulfonamido-1H-indazol-7-yl)-5-cyclopropyl-7-(4,4-difluorocyclohexyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.24 min.; observed ion = 1043.7 [M − H].<br>1H NMR (500 MHz, METHANOL-d4) δ ppm 7.33 (d, J = 7.75 Hz, 1 H), 7.22 (d, J = 8.05 Hz, 1 H), 7.03 (s, 1 H), 6.71-6.80 (m, 1 H), 6.55 (dd, J = 8.05, 2.09 Hz, 2 H), 4.76-4.81 (m, 1 H), 4.28 (s, 2 H), 4.14 (ddd, J = 14.16, 10.28, 5.66 Hz, 1 H), 3.81-3.90 (m, 1 H), 3.61 (ddd, J = 8.42, 5.29, 2.98 Hz, 1 H), 3.34-3.42 (m, 2 H), 3.27 (s, 3 H), 2.94-3.08 (m, 2 H), 2.63-2.73 (m, 2 H), 2.41-2.55 (m, 3 H), 2.17-2.30 (m, 3 H), 2.00-2.09 (m, 5 H), 1.90-1.97 (m, 2 H), 1.84 (tt, J = 7.41, 1.68 Hz, 1 H), 1.78 (tt, J = 8.49, 5.07 Hz, 1 H), 1.53-1.61 (m, 1 H), 1.37-1.46 (m, 1 H), 1.20-1.26 (m, 2 H), 1.03-1.08 (m, 1 H), 0.94-0.99 (m, 4 H), 0.94 (s, 1 H), 0.83-0.87 (m, 4 H), 0.82-0.90 (m, 1 H), 0.72-0.80 (m, 2 H), 0.05-0.10 (m, 1 H). |

TABLE A-continued

| Example No. (preparation of the Example) | Structure and IUPAC name | Characterising data (LCMS and/or NMR) |
|---|---|---|
| 325 (General Procedure A using Bromide A7 as the core reagent) | 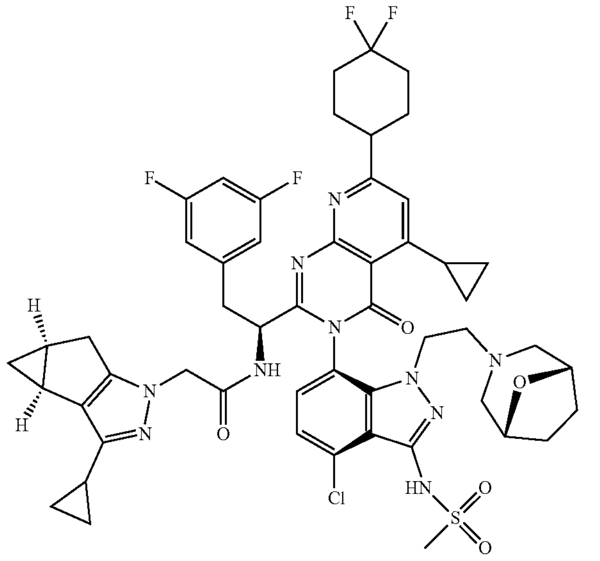 N-[(1S)-1-[(3P)-3-(4-chloro-3-methanesulfonamido-1-{2-[(1R,5S)-8-oxa-3-azabicyclo[3.2.1]octan-3-yl]ethyl}-1H-indazol-7-yl)-5-cyclopropyl-7-(4,4-difluorocyclohexyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.28 min.; observed ion = 1041.6 [M − H]. 1H NMR (500 MHz, METHANOL-d4) δ ppm 7.29-7.37 (m, 1 H), 7.23 (d, J = 7.75 Hz, 1 H), 7.02 (s, 1 H), 6.76 (tt, J = 9.24, 2.38 Hz, 1 H), 6.55 (dd, J = 8.20, 2.24 Hz, 2 H), 4.77-4.80 (m, 1 H), 4.23-4.32 (m, 2 H), 3.99-4.09 (m, 2 H), 3.96 (br d, J = 6.56 Hz, 1 H), 3.58-3.70 (m, 2 H), 3.39 (dd, J = 14.01, 5.36 Hz, 1 H), 3.26 (s, 3 H), 2.96-3.09 (m, 2 H), 2.71 (dd, J = 16.54, 6.71 Hz, 1 H), 2.51-2.59 (m, 1 H), 2.43-2.50 (m, 2 H), 2.35 (d, J = 10.43 Hz, 1 H), 2.15-2.27 (m, 3 H), 1.99-2.13 (m, 7 H), 1.89-1.97 (m, 2 H), 1.82-1.87 (m, 1 H), 1.73-1.80 (m, 1 H), 1.46-1.64 (m, 3 H), 1.28-1.35 (m, 1 H), 1.20-1.28 (m, 2 H), 0.94-1.07 (m, 3 H), 0.82-0.90 (m, 2 H), 0.71-0.79 (m, 2 H), 0.05-0.10 (m, 1 H). |
| 327 (General Procedure A using Bromide A7 as the core reagent) | 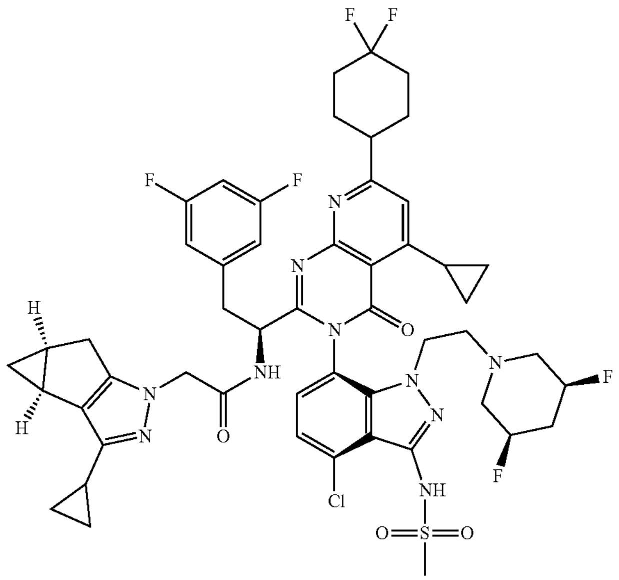 N-[(1S)-1-[(3P)-3-(4-chloro-1-{2-[(3R,5S)-3,5-difluoropiperidin-1-yl]ethyl}-3-methanesulfonamido-1H-indazol-7-yl)-5-cyclopropyl-7-(4,4-difluorocyclohexyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.44 min.; observed ion = 1049.5 [M − H]. 1H NMR (500 MHz, METHANOL-d4) δ ppm 7.31 (d, J = 8.05 Hz, 1 H), 7.20 (d, J = 8.05 Hz, 1 H), 6.99 (s, 1 H), 6.77 (tt, J = 9.16, 2.31 Hz, 1 H), 6.57 (dd, J = 8.20, 2.24 Hz, 2 H), 4.77-4.81 (m, 1 H), 4.16-4.39 (m, 4 H), 4.07 (ddd, J = 14.01, 9.98, 6.11 Hz, 1 H), 3.74 (ddd, J = 14.23, 9.46, 5.22 Hz, 1 H), 3.58-3.66 (m, 1 H), 3.40 (dd, J = 14.16, 5.22 Hz, 1 H), 3.27 (s, 3 H), 2.95-3.09 (m, 2 H), 2.79 (ddd, J = 12.82, 9.69, 5.81 Hz, 1 H), 2.66-2.73 (m, 2 H), 2.51-2.65 (m, 2 H), 2.46 (d, J = 16.39 Hz, 1 H), 2.10-2.26 (m, 5 H), 2.01-2.07 (m, 4 H), 1.90-1.99 (m, 2 H), 1.81-1.86 (m, 1 H), 1.77 (tt, J = 8.42, 4.99 Hz, 1 H), 1.50-1.66 (m, 1 H), 1.21-1.26 (m, 2 H), 0.98-1.04 (m, 2 H), 0.93-0.97 (m, 1 H), 0.81-0.91 (m, 2 H), 0.70-0.80 (m, 2 H), 0.04-0.09 (m, 1 H). |

TABLE A-continued

| Example No. (preparation of the Example) | Structure and IUPAC name | Characterising data (LCMS and/or NMR) |
|---|---|---|
| 354 (General Procedure A using Bromide A8 as the core reagent) | 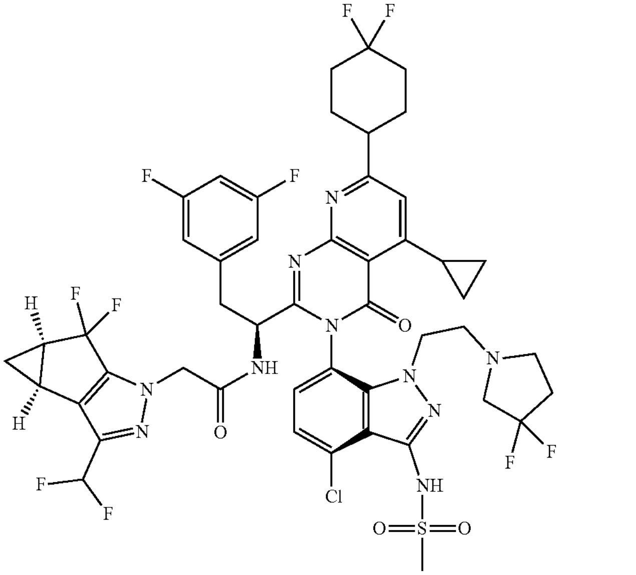 N-[(1S)-1-[(3P)-3-{4-chloro-1-[2-(3,3-difluoropyrrolidin-1-yl)ethyl]-3-methanesulfonamido-1H-indazol-7-yl}-5-cyclopropyl-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.51 min.; observed ion = 1081.5 [M − H]. 1H NMR (500 MHz, METHANOL-d4) δ ppm 7.32 (d, J = 7.75 Hz, 1 H), 7.22 (d, J = 7.75 Hz, 1 H), 7.01 (s, 1 H), 6.50-6.82 (m, 4 H), 4.75-4.79 (m, 1 H), 4.52-4.68 (m, 2 H), 4.06-4.18 (m, 1 H), 3.74 (ddd, J = 14.45, 9.69, 5.07 Hz, 1 H), 3.60 (ddd, J = 8.27, 5.29, 3.13 Hz, 1 H), 3.40 (dd, J = 14.31, 5.07 Hz, 1 H), 3.23 (s, 3 H), 2.96-3.09 (m, 2 H), 2.76-2.86 (m, 1 H), 2.63 (ddd, J = 11.70, 10.36, 5.36 Hz, 1 H), 2.36-2.57 (m, 6 H), 2.16-2.28 (m, 2 H), 1.90-2.11 (m, 8 H), 1.33-1.38 (m, 1 H), 1.23 (dd, J = 8.49, 2.53 Hz, 2 H), 0.94-1.05 (m, 3 H). |
| 356 (General Procedure A using Bromide A4 as the core reagent) | 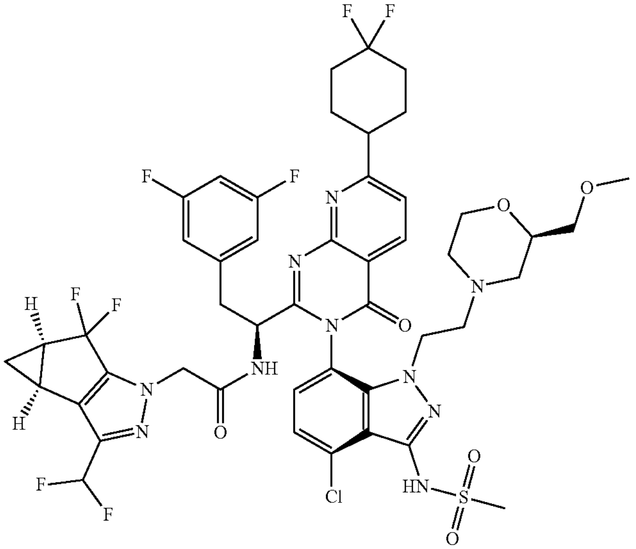 N-[(1S)-1-[(3P)-3-(4-chloro-3-methanesulfonamido-1-{2-[(2R)-2-(methoxymethyl)morpholin-4-yl]ethyl}-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.14 min.; observed ion = 1065.4 [M − H]. 1H NMR (500 MHz, METHANOL-d4) δ ppm 1.02 (br dd, J = 5.51, 2.24 Hz, 1 H), 1.34-1.39 (m, 1 H), 1.73 (s, 1 H), 1.83 (br d, J = 0.89 Hz, 1 H), 1.97-2.15 (m, 6 H), 2.15-2.29 (m, 3 H), 2.40-2.61 (m, 5 H), 3.06 (dd, J = 14.16, 9.69 Hz, 1 H), 3.12-3.22 (m, 3 H), 3.24 (s, 3 H), 3.29-3.30 (m, 3 H), 3.40 (dd, J = 14.16, 4.92 Hz, 1 H), 3.49-3.59 (m, 1 H), 3.76 (dt, J = 9.31, 4.43 Hz, 1 H), 4.14-4.19 (m, 1 H), 4.55-4.70 (m, 3 H), 4.77-4.82 (m, 2 H), 6.53 (dd, J = 8.05, 2.09 Hz, 2 H), 6.68 (br t, J = 54.69 Hz, 1 H), 6.74-6.79 (m, 1 H), 7.27 (d, J = 8.05 Hz, 1 H), 7.35 (d, J = 7.75 Hz, 1 H), 7.67 (d, J = 8.05 Hz, 1 H), 8.62 (d, J = 8.35 Hz, 1 H) |

TABLE A-continued

| Example No. (preparation of the Example) | Structure and IUPAC name | Characterising data (LCMS and/or NMR) |
|---|---|---|
| 360 (General Procedure A using Bromide A4 as the core reagent) | 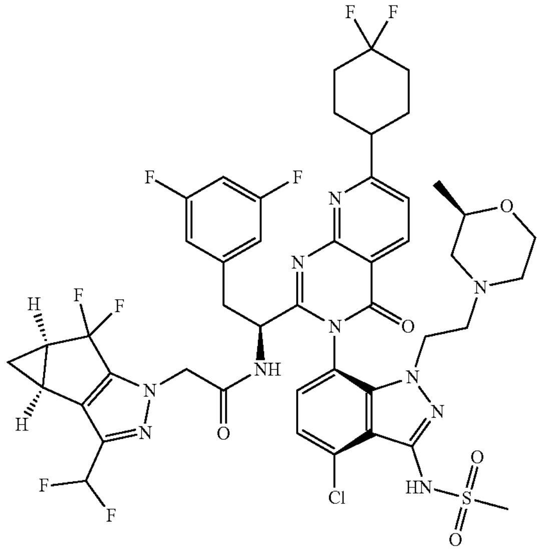 N-[(1S)-1-[(3P)-3-(4-chloro-3-methanesulfonamido-1-{2-[(2R)-2-methylmorpholin-4-yl]ethyl}-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method B: retention time = 1.13 min.; observed ion = 1035.4 [M − H]. 1H NMR (500 MHz, METHANOL-d4) δ ppm 0.93-0.97 (m, 3 H), 1.03 (td, J = 3.73, 1.79 Hz, 1 H), 1.33-1.39 (m, 1 H), 1.61 (br s, 1 H), 1.84 (br d, J = 2.98 Hz, 1 H), 1.97-2.16 (m, 7 H), 2.19-2.31 (m, 3 H), 2.39-2.51 (m, 3 H), 2.52-2.63 (m, 2 H), 3.06 (dd, J = 14.16, 9.69 Hz, 1 H), 3.21-3.28 (m, 5 H), 3.40 (dd, J = 14.01, 4.47 Hz, 1 H), 3.48-3.56 (m, 1 H), 3.78 (ddd, J = 14.31, 9.54, 5.07 Hz, 1 H), 4.14-4.20 (m, 1 H), 4.54-4.80 (m, 3 H), 6.50-6.56 (m, 2 H), 6.67 (br t, J = 54.69 Hz, 1 H), 6.74-6.79 (m, 1 H), 7.28 (d, J = 8.17 Hz, 1 H), 7.33-7.36 (m, 1 H), 7.67 (d, J = 8.05 Hz, 1 H), 8.62 (d, J = 8.05 Hz, 1 H) |
| 370 (General Procedure A using Bromide A5 as the core reagent) | 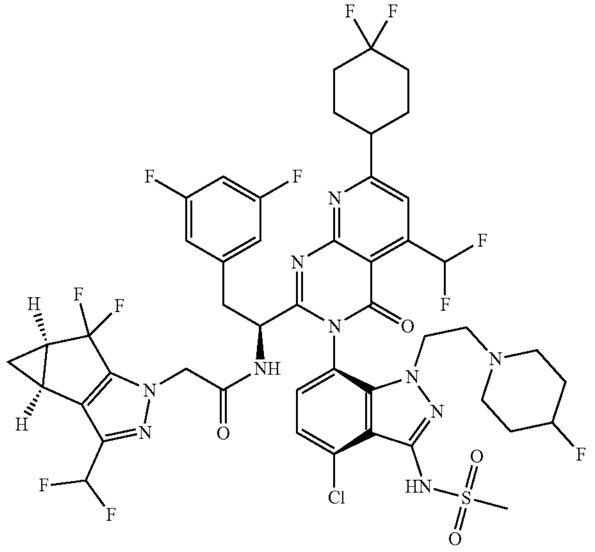 N-[(1S)-1-[(3P)-3-{4-chloro-1-[2-(4-fluoropiperidin-1-yl)ethyl]-3-methanesulfonamido-1H-indazol-7-yl}-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method A: retention time = 2.82 min.; observed ion = 1089.1 [M + H]+. 1H NMR (500 MHz, METHANOL-d4) δ ppm 0.83-0.95 (m, 1 H), 0.98-1.03 (m, 1 H), 1.26-1.40 (m, 5 H), 1.53-1.79 (m, 4 H), 1.96-2.19 (m, 7 H), 2.20-2.31 (m, 3 H), 2.38-2.48 (m, 3 H), 3.04-3.11 (m, 1 H), 3.45 (br s, 3 H), 3.79-3.89 (m, 1 H), 4.16-4.26 (m, 1 H), 4.55-4.69 (m, 3 H), 6.49-6.82 (m, 4 H), 7.29-7.38 (m, 2 H), 7.64-7.94 (m, 2 H) |

TABLE A-continued

| Example No. (preparation of the Example) | Structure and IUPAC name | Characterising data (LCMS and/or NMR) |
|---|---|---|
| 371 (General Procedure A using Bromide A5 as the core reagent) | 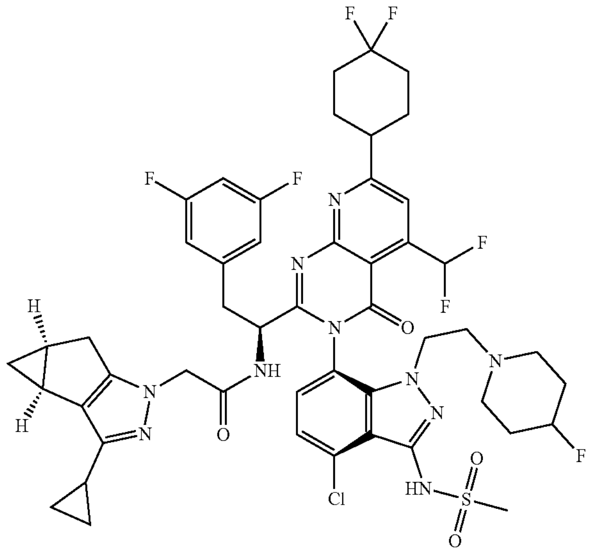 N-[(1S)-1-[(3P)-3-{4-chloro-1-[2-(4-fluoropiperidin-1-yl)ethyl]-3-methanesulfonamido-1H-indazol-7-yl}-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method A: retention time = 2.73 min.; observed ion = 1043.15 [M + H]+. 1H NMR (500 MHz, METHANOL-d4) δ ppm 0.70-0.82 (m, 3 H), 0.83-1.00 (m, 5 H), 1.25-1.34 (m, 2 H), 1.74-1.80 (m, 2 H), 1.82-1.87 (m, 1 H), 1.90-1.96 (m, 1 H), 2.04-2.17 (m, 8 H), 2.21-2.31 (m, 4 H), 2.42-2.49 (m, 2 H), 2.62-2.73 (m, 2 H), 3.15-3.17 (m, 2 H), 3.37-3.46 (m, 5 H), 3.76 (s, 1 H), 4.05-4.17 (m, 1 H), 4.25-4.37 (m, 2 H), 6.50-6.60 (m, 2 H), 6.73-6.81 (m, 1 H), 7.28-7.41 (m, 2 H), 7.65-7.93 (m, 2 H). |
| 375 (General Procedure B using Amine B24 as the core reagent) | 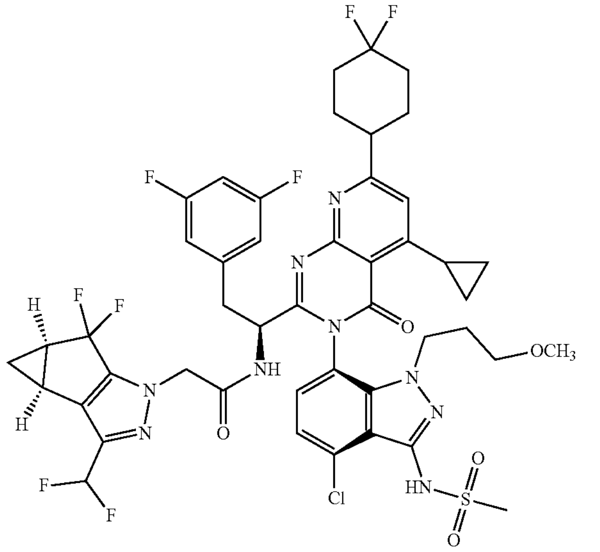 N-[(1S)-1-[(3P)-3-[4-chloro-3-methanesulfonamido-1-(3-methoxypropyl)-1H-indazol-7-yl]-5-cyclopropyl-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 3.27 min.; observed ion = 1022.20 [M + H]. 1H NMR (500 MHz, METHANOL-d4) δ ppm 7.24-7.35 (m, 1 H), 7.18 (d, J = 8.05 Hz, 1 H), 7.05 (s, 1 H), 6.52-6.81 (m, 4 H), 4.82-4.85 (m, 1 H), 4.58 (d, J = 3.28 Hz, 2 H), 3.99-4.07 (m, 1 H), 3.79-3.87 (m, 1 H), 3.44-3.49 (m, 1 H), 3.40 (dd, J = 14.01, 5.07 Hz, 1 H), 3.24 (s, 3 H), 3.11 (t, J = 5.66 Hz, 2 H), 3.05 (br dd, J = 14.01, 9.24 Hz, 2H), 2.79 (s, 3 H), 2.42 (td, J = 7.60, 3.87 Hz, 2 H), 2.17-2.27 (m, 2 H), 1.92-2.12 (m, 6 H), 1.83-1.91 (m, 2 H), 1.32-1.38 (m, 1 H), 1.18 (dq, J = 8.38, 2.27 Hz, 2 H), 0.88-1.05 (m, 3 H). |

TABLE A-continued

| Example No. (preparation of the Example) | Structure and IUPAC name | Characterising data (LCMS and/or NMR) |
|---|---|---|
| 376 (General Procedure B using Amine B24 as the core reagent) | 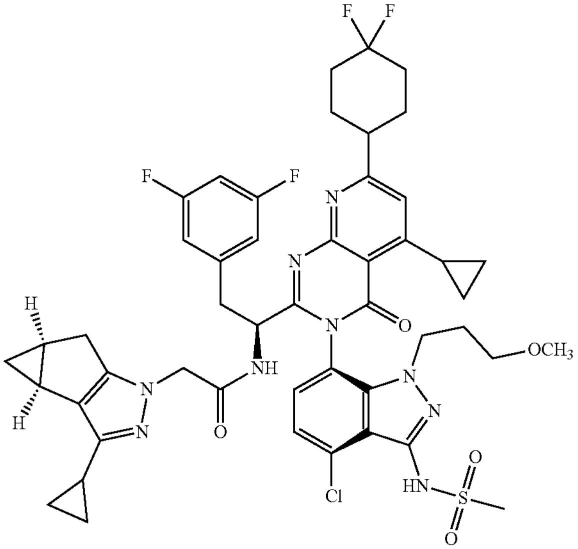 N-[(1S)-1-[(3P)-3-[4-chloro-3-methanesulfonamido-1-(3-methoxypropyl)-1H-indazol-7-yl]-5-cyclopropyl-7-(4,4-difluorocyclohexyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method A: retention time = 3.31 min.; observed ion = 976.20 [M + H]. 1H NMR (500 MHz, METHANOL-d4) δ ppm 7.31 (d, J = 7.75 Hz, 1 H), 7.18 (d, J = 8.05 Hz, 1 H), 7.05 (s, 1 H), 6.72-6.81 (m, 1 H), 6.58 (dd, J = 8.05, 2.09 Hz, 2 H), 4.81-4.84 (m, 1 H), 4.25 (s, 2 H), 3.88-4.00 (m, 1 H), 3.78-3.86 (m, 1 H), 3.45-3.50 (m, 1 H), 3.37-3.42 (m, 1 H), 3.27 (s, 3 H), 3.09-3.14 (m, 2 H), 2.96-3.08 (m, 2 H), 2.79 (s, 3 H), 2.65 (dd, J = 16.39, 6.56 Hz, 1 H), 2.43 (d, J = 16.69 Hz, 1 H), 2.16-2.28 (m, 2 H), 1.81-2.12 (m, 10 H), 1.77 (tt, J = 8.46, 4.95 Hz, 1 H), 1.14-1.22 (m, 2 H), 0.89-1.02 (m, 3 H), 0.82-0.88 (m, 2 H), 0.75 (dtd, J = 15.05, 5.14, 5.14, 2.98 Hz, 2 H), 0.07 (q, J = 4.17 Hz, 1 H). |
| 381 (General Procedure A using Bromide A3 as the core reagent) | 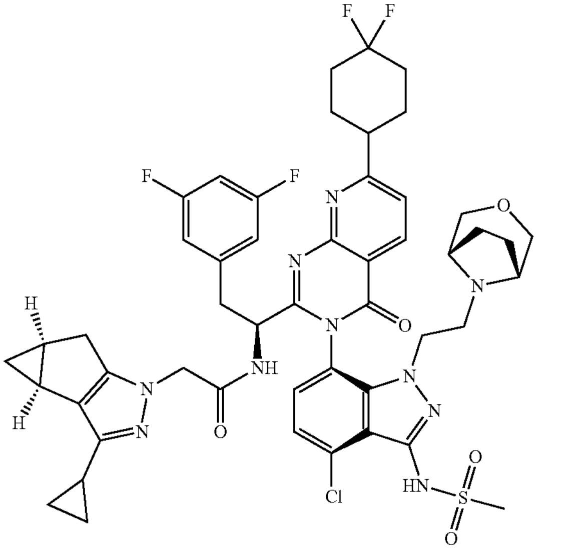 N-[(1S)-1-[(3P)-3-(4-chloro-3-methanesulfonamido-1-{2-[(1R,5S)-3-oxa-8-azabicyclo[3.2.1]octan-8-yl]ethyl}-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.13 min.; observed ion = 1001.6 [M − H]. 1H NMR (500 MHz, METHANOL-d 4) δ ppm 0.72-0.78 (m, 2 H), 0.84-0.91 (m, 2 H), 0.94-0.98 (m, 1 H), 1.29-1.32 (m, 1 H), 1.73-1.78 (m, 1 H), 1.82-1.86 (m, 1 H), 1.88-2.03 (m, 5 H), 2.04-2.13 (m, 5 H), 2.22-2.28 (m, 2 H), 2.43 (br d, J = 0.89 Hz, 1 H), 2.59-2.64 (m, 1 H), 3.07-3.27 (m, 3 H), 3.27-3.29 (m, 3 H), 3.34-3.57 (m, 7 H), 3.63-3.65 (m, 1 H), 4.33-4.38 (m, 1 H), 4.41-4.46 (m, 1 H), 4.71-4.85 (m, 3 H), 4.93-4.99 (m, 1 H), 6.53 (br d, J = 6.26 Hz, 2 H), 6.78-6.83 (m, 1 H), 7.40 (br s, 2 H), 7.65 (d, J = 8.05 Hz, 1 H), 8.62 (d, J = 8.35 Hz, 1 H). |

TABLE A-continued

| Example No. (preparation of the Example) | Structure and IUPAC name | Characterising data (LCMS and/or NMR) |
|---|---|---|
| 382 (General Procedure A using Bromide A3 as the core reagent) | 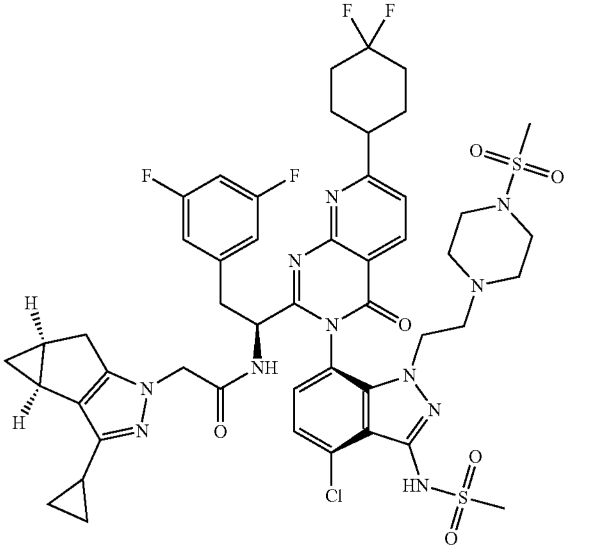 N-[(1S)-1-[(3P)-3-{4-chloro-3-methanesulfonamido-1-[2-(4-methanesulfonylpiperazin-1-yl)ethyl]-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.25 min.; observed ion = 1052.3 [M − H]. 1H NMR (500 MHz, DMSO-d 6) δ ppm 0.58-0.62 (m, 2 H), 0.77 (ddd, J = 8.57, 4.99, 2.53 Hz, 2 H), 0.86 (td, J = 7.60, 4.17 Hz, 1 H), 1.65-1.71 (m, 1 H), 1.74-1.83 (m, 2 H), 1.90-2.11 (m, 11 H), 2.12-2.21 (m, 2 H), 2.23-2.32 (m, 1 H), 2.34-2.48 (m, 6 H), 2.74-2.79 (m, 7 H), 2.97-3.05 (m, 2 H), 3.64-3.70 (m, 2 H), 3.83-3.97 (m, 2 H), 4.20 (d, J = 16.09 Hz, 1 H), 4.30 (d, J = 16.39 Hz, 1H), 4.49-4.56 (m, 1 H), 6.54-6.62 (m, 2 H), 7.02-7.07 (m, 1 H), 7.40-7.53 (m, 1 H), 7.65 (d, J = 8.35 Hz, 1 H), 7.75 (br s, 1 H), 8.56 (d, J = 8.35 Hz, 1 H), 9.06-9.16 (m, 1 H). |
| 384 (General Procedure C using Acid C1 as the core reagent) | 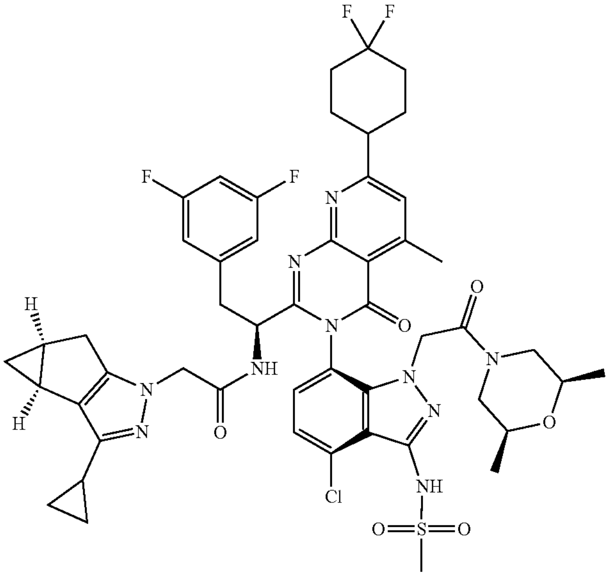 N-[(1S)-1-[(3P)-3-(4-chloro-1-{2-[(2R,6S)-2,6-dimethylmorpholin-4-yl]-2-oxoethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.55 min.; observed ion = 1031.5 [M − H]. 1H NMR (500 MHz, METHANOL-d4) δ ppm 0.64 (ddt, J = 11.70, 4.99, 2.53, 2.53 Hz, 1 H), 0.68-0.73 (m, 1 H), 0.74-0.96 (m, 9 H), 1.55-1.61 (m, 1 H), 1.68-1.75 (m, 2 H), 1.77-2.04 (m, 8 H), 2.10-2.19 (m, 2 H), 2.37 (br d, J = 16.39 Hz, 1 H), 2.51-2.62 (m, 2 H), 2.63-2.85 (m, 5 H), 2.88-2.99 (m, 2 H), 3.16 (d, J = 2.98 Hz, 3 H), 3.30-3.37 (m, 1 H), 3.83 (br d, J = 12.82 Hz, 1 H), 3.99 (br dd, J = 16.69, 3.28 Hz, 1 H), 4.12 (dd, J = 16.69, 5.66 Hz, 1 H), 6.53-6.61 (m, 2 H), 6.62-6.69 (m, 1 H), 7.24-7.33 (m, 2 H), 7.36 (d, J = 4.47 Hz, 1 H). |

TABLE A-continued

| Example No. (preparation of the Example) | Structure and IUPAC name | Characterising data (LCMS and/or NMR) |
|---|---|---|
| 387 (General Procedure C using Acid C1 as the core reagent) | 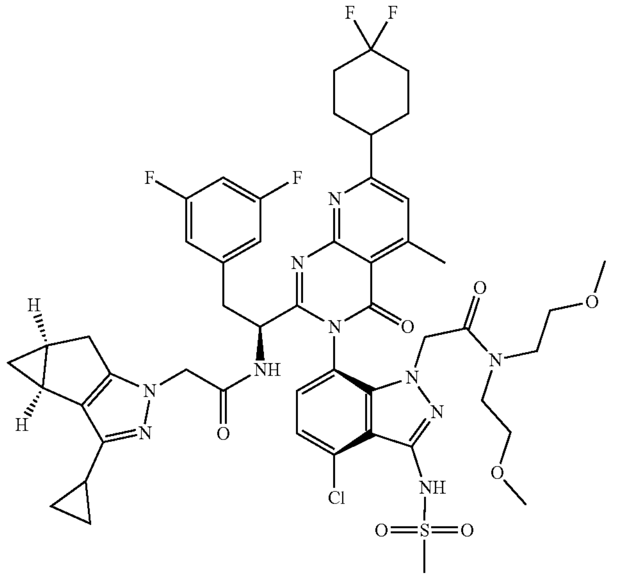 2-[(6P)-4-chloro-7-{2-[(1S)-1-{2-[(2S,4S)-9-cyclopropyl-7,8-diazatricyclo[4.3.0.0$^{2}$,$^{4}$]nona-1(6),8-dien-7-yl]acetamido}-2-(3,5-difluorophenyl)ethyl]-7-(4,4-difluorocyclohexyl)-5-methyl-4-oxo-3H,4H-pyrido[2,3-d]pyrimidin-3-yl}-3-methanesulfonamido-1H-indazol-1-yl]-N,N-bis(2-methoxyethyl)acetamide | LCMS Method B: retention time = 1.52 min.; observed ion = 1049.3 [M − H]. 1H NMR (500 MHz, DMSO-d6) δ ppm 0.65 (ddd, J = 7.15, 4.92, 2.53 Hz, 2 H), 0.78-0.83 (m, 2 H), 0.88-0.94 (m, 1 H), 1.69-1.75 (m, 1 H), 1.77-1.88 (m, 2 H), 1.91-2.12 (m, 6 H), 2.15-2.24 (m, 2 H), 2.39 (br d, J = 1.49 Hz, 1 H), 2.73 (br d, J = 0.60 Hz, 3 H), 2.92 (br dd, J = 13.56, 9.69 Hz, 2 H), 2.98-3.07 (m, 5 H), 3.08 (s, 3 H), 3.15 (s, 3 H), 3.16-3.23 (m, 3 H), 4.29 (br d, J = 2.68 Hz, 2 H), 4.53-4.60 (m, 1 H), 4.79-4.90 (m, 1 H), 4.94-5.07 (m, 1 H), 6.48-6.61 (m, 2 H), 7.06 (tt, J = 9.50, 2.12 Hz, 1 H), 7.38-7.45 (m, 1 H), 7.45-7.57 (m, 1 H), 7.64-7.80 (m, 1 H), 9.04 (br d, J = 8.94 Hz, 1 H), 9.90-10.08 (m, 1 H). |
| 393 (General Procedure C using Acid C1 as the core reagent) | 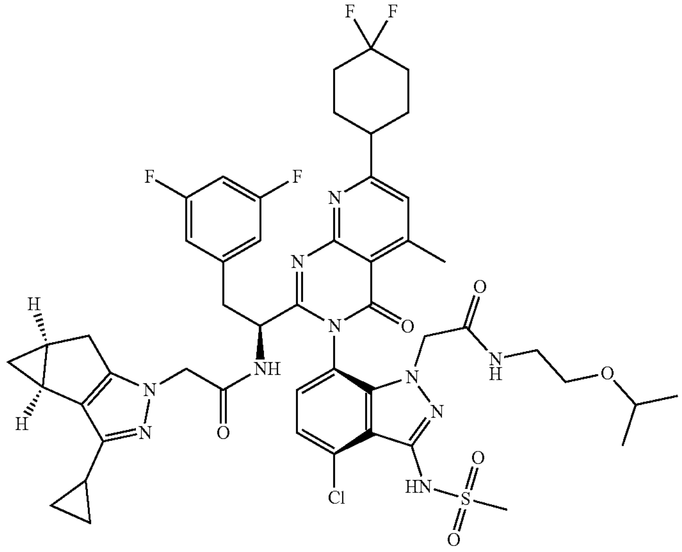 N-[(1S)-1-[(3P)-3-[4-chloro-3-methanesulfonamido-1-({[2-(propan-2-yloxy)ethyl]carbamoyl}methyl)-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2}$,$^{4}$]nona-1(6),8-dien-7-yl]acetamide | LCMS Method B: retention time = 1.54 min.; observed ion = 511.2 [M + 2H]. 1H NMR (500 MHz, METHANOL-d4) δ ppm 0.63-0.68 (m, 1 H), 0.69-0.74 (m, 1 H), 0.75-0.84 (m, 2 H), 0.84-0.90 (m, 1 H), 0.94 (d, J = 6.26 Hz, 3 H), 0.97 (d, J = 5.96 Hz, 3 H), 1.68-1.78 (m, 2 H), 1.82-2.06 (m, 7 H), 2.12-2.20 (m, 2 H), 2.35-2.41 (m, 1 H), 2.57 (dd, J = 16.69, 6.56 Hz, 1 H), 2.73 (d, J = 0.60 Hz, 3 H), 2.87-3.03 (m, 4 H), 3.18-3.22 (m, 5 H), 3.34-3.41 (m, 2 H), 4.08-4.20 (m, 2 H), 4.43 (d, J = 17.58 Hz, 1 H), 4.64 (br d, J = 17.29 Hz, 1 H), 6.57 (br dd, J = 8.20, 2.24 Hz, 2 H), 6.67-6.73 (m, 1 H), 7.16 (d, J = 8.05 Hz, 1 H), 7.23-7.29 (m, 1 H), 7.32 (d, J = 0.89 Hz, 1 H). |

TABLE A-continued

| Example No. (preparation of the Example) | Structure and IUPAC name | Characterising data (LCMS and/or NMR) |
|---|---|---|
| 395 (General Procedure C using Acid C1 as the core reagent) | 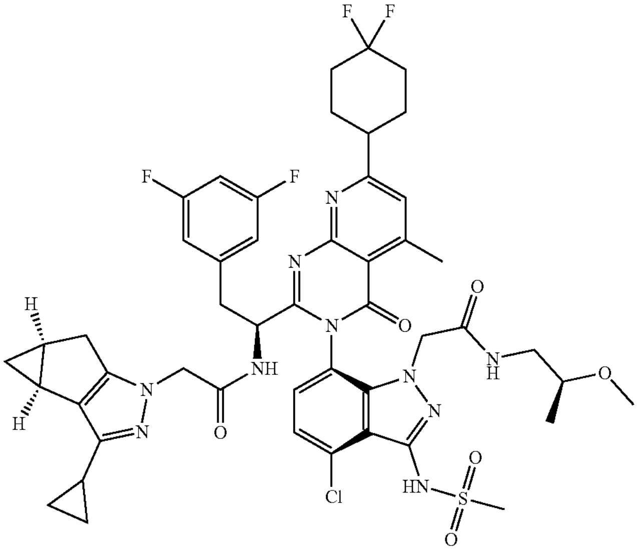 N-[(1S)-1-[(3P)-3-[4-chloro-3-methanesulfonamido-1-({[(2S)-2-methoxypropyl]carbamoyl}methyl)-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.5 min.; observed ion = 1007.3 [M + H]. 1H NMR (500 MHz, METHANOL-d4) δ ppm 0.62-0.68 (m, 1 H), 0.68-0.73 (m, 1 H), 0.75-0.80 (m, 2 H), 0.86 (d, J = 6.26 Hz, 4 H), 1.67-1.77 (m, 2 H), 1.80-2.05 (m, 7 H), 2.11-2.21 (m, 2 H), 2.37 (br d, J = 16.39 Hz, 1 H), 2.53-2.59 (m, 1 H), 2.69-2.75 (m, 3 H), 2.79 (dd, J = 13.71, 6.26 Hz, 1 H), 2.88 (dd, J = 13.71, 4.77 Hz, 1 H), 2.91-3.01 (m, 2 H), 3.08-3.11 (m, 1 H), 3.12 (s, 3 H), 3.20 (s, 3 H), 3.33-3.39 (m, 1 H), 4.04-4.18 (m, 2 H), 4.46 (d, J = 17.58 Hz, 1 H), 4.50-4.56 (m, 1 H), 4.63 (br d, J = 17.58 Hz, 1 H), 6.57 (br dd, J = 8.05, 2.09 Hz, 2 H), 6.66-6.72 (m, 1 H), 7.15 (d, J = 8.05 Hz, 1 H), 7.26 (d, J = 7.75 Hz, 1 H), 7.32 (d, J = 0.60 Hz, 1 H). |
| 396 (General Procedure C using Acid C1 as the core reagent) | 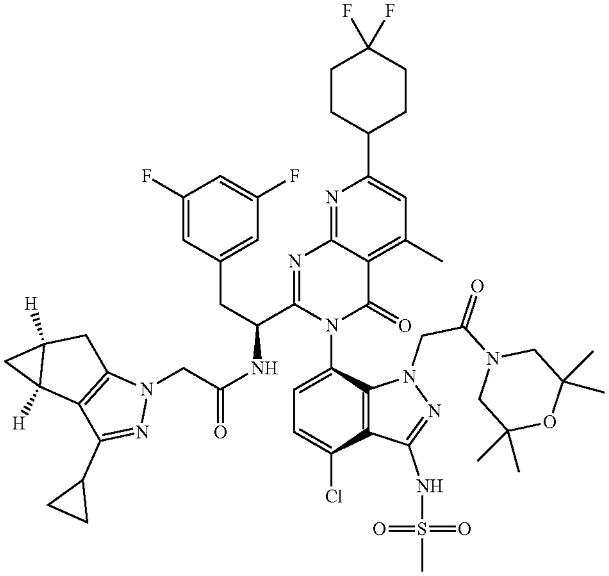 N-[(1S)-1-[(3P)-3-{4-chloro-3-methanesulfonamido-1-[2-oxo-2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.6 min.; observed ion = 1061.5 [M + H]. 1H NMR (500 MHz, METHANOL-d4) δ ppm 0.50-0.96 (m, 17 H), 1.67-1.75 (m, 2 H), 1.78-2.04 (m, 6 H), 2.08-2.18 (m, 2 H), 2.34-2.46 (m, 2 H), 2.58 (br dd, J = 16.69, 6.56 Hz, 1 H), 2.63-2.82 (m, 3 H), 2.77-2.97 (m, 4 H), 3.16 (s, 3 H), 3.32 (dd, J = 13.86, 4.92 Hz, 1 H), 3.95-4.13 (m, 2 H), 4.92 (br d, J = 17.58 Hz, 1 H), 4.98-5.03 (m, 1 H), 6.48-6.59 (m, 2 H), 6.61-6.67 (m, 1 H), 7.20-7.37 (m, 3 H). |

TABLE A-continued

| Example No. (preparation of the Example) | Structure and IUPAC name | Characterising data (LCMS and/or NMR) |
|---|---|---|
| 401 (General Procedure C using Acid C2 as the core reagent) | 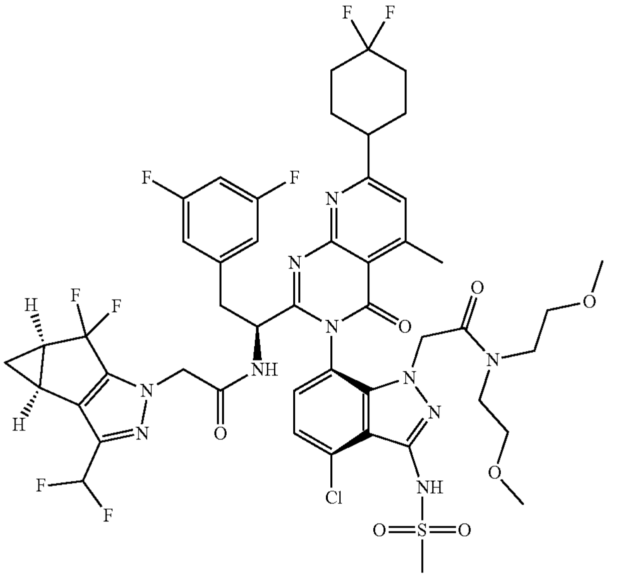<br>2-[(6P)-4-chloro-7-[7-(4,4-difluorocyclohexyl)-2-[(1S)-1-{2-[(2S,4R)-9-(difluoromethyl)-5,5-difluoro-7,8-diazatricyclo[4.3.0.02, 4]nona-1(6),8-dien-7-yl]acetamido}-2-(3,5-difluorophenyl)ethyl]-5-methyl-4-oxo-3H,4H-pyrido[2,3-d]pyrimidin-3-yl]-3-methanesulfonamido-1H-indazol-1-yl]-N,N-bis(2-methoxyethyl)acetamide | LCMS Method B: retention time = 1.51 min.; observed ion = 1095.3 [M − H].<br>1H NMR (500 MHz, METHANOL-d4) δ ppm 1.03-1.07 (m, 1 H), 1.36-1.41 (m, 1 H), 1.95-2.03 (m, 2 H), 2.04-2.13 (m, 4 H), 2.21-2.29 (m, 2 H), 2.42-2.50 (m, 2 H), 2.84 (d, J = 0.60 Hz, 2 H), 2.99-3.10 (m, 3 H), 3.15 (s, 3 H), 3.17-3.26 (m, 9 H), 3.27-3.31 (m, 4 H), 3.44 (dd, J = 14.31, 5.36 Hz, 1 H), 4.49-4.59 (m, 2 H), 4.97-5.01 (m, 1 H), 5.04-5.10 (m, 1 H), 6.61-6.85 (m, 4 H), 7.30-7.39 (m, 2 H), 7.43 (d, J = 0.60 Hz, 1 H). |
| 405 (General Procedure C using Acid C2 as the core reagent) | 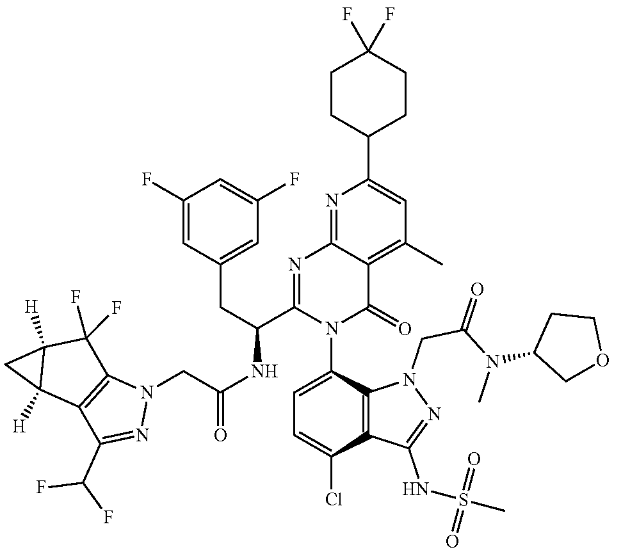<br>N-[(1S)-1-[(3P)-3-[4-chloro-3-methanesulfonamido-1-({methyl[(3R)-oxolan-3-yl]carbamoyl}methyl)-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.46 min.; observed ion = 1063.5 [M − H].<br>1H NMR (500 MHz, METHANOL-d4) δ ppm 1.04-1.09 (m, 1 H), 1.36-1.44 (m, 2 H), 1.71-1.80 (m, 1 H), 1.96-2.05 (m, 2 H), 2.06-2.14 (m, 5 H), 2.23-2.31 (m, 2 H), 2.44 (d, J = 5.07 Hz, 3 H), 2.47 (br dd, J = 8.20, 2.83 Hz, 2 H), 2.81-2.85 (m, 3 H), 3.00-3.10 (m, 3 H), 3.26 (d, J = 3.87 Hz, 3 H), 3.39-3.46 (m, 3 H), 3.50-3.55 (m, 1 H), 3.80-3.91 (m, 2 H), 4.16-4.24 (m, 1 H), 4.57 (s, 1 H), 5.02 (br d, J = 2.68 Hz, 1 H), 6.55-6.86 (m, 6 H), 7.37-7.47 (m, 3 H). |

TABLE A-continued

| Example No. (preparation of the Example) | Structure and IUPAC name | Characterising data (LCMS and/or NMR) |
|---|---|---|
| 409 (General Procedure C using Acid C2 as the core reagent) | 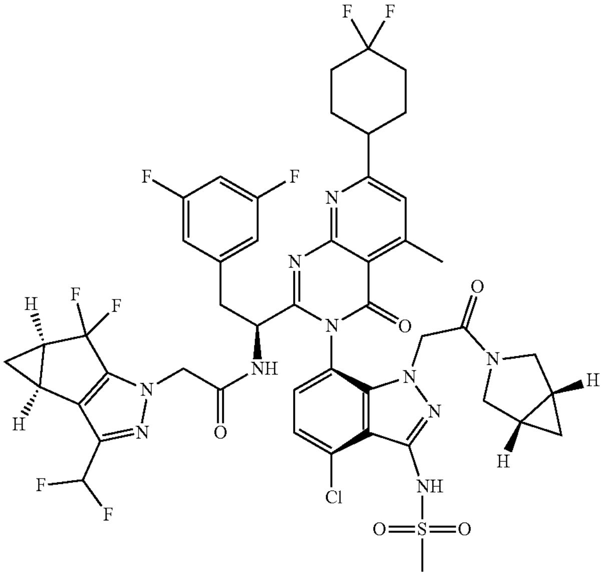 N-[(1S)-1-[(3P)-3-(1-{2-[(1R,5S)-3-azabicyclo[3.1.0]hexan-3-yl]-2-oxoethyl}-4-chloro-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.51 min.; observed ion = 1047.3 [M + H]. 1H NMR (500 MHz, METHANOL-d4) δ ppm 0.54-0.65 (m, 1 H), 1.08 (br dd, J = 3.73, 1.94 Hz, 1 H), 1.36-1.42 (m, 2 H), 1.97-2.14 (m, 6 H), 2.23-2.30 (m, 2 H), 2.43-2.50 (m, 2 H), 2.57-2.62 (m, 1 H), 2.76-2.82 (m, 1 H), 2.84 (dd, J = 2.98, 0.60 Hz, 3 H), 2.97-3.11 (m, 4 H), 3.16 (br d, J = 10.43 Hz, 1 H), 3.25 (d, J = 11.62 Hz, 3 H), 3.40-3.46 (m, 1 H), 4.53 (s, 1 H), 4.59-4.71 (m, 2 H), 6.58-6.88 (m, 5 H), 7.35-7.46 (m, 3 H) |
| 413 (General Procedure A using Bromide A10 as the core reagent) | 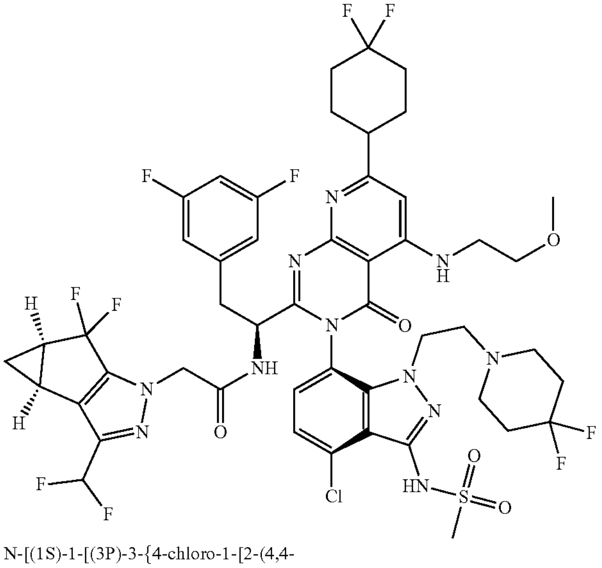 N-[(1S)-1-[(3P)-3-{4-chloro-1-[2-(4,4-difluoropiperidin-1-yl)ethyl]-3-methanesulfonamido-1H-indazol-7-yl}-7-(4,4-difluorocyclohexyl)-5-[(2-methoxyethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.08 min.; observed ion = 1128.5 [M − H]. 1H NMR (500 MHz, METHANOL-d4) δ ppm 7.31 (d, J = 8.05 Hz, 1 H), 7.15 (d, J = 8.05 Hz, 1 H), 6.51-6.79 (m, 5 H), 4.75 (br d, J = 4.17 Hz, 1 H), 4.55-4.65 (m, 3 H), 4.19 (ddd, J = 14.08, 10.21, 5.81 Hz, 1 H), 3.72-3.78 (m, 1 H), 3.60-3.64 (m, 2 H), 3.51 (br dd, J = 5.22, 3.13 Hz, 2 H), 3.36-3.39 (m, 1 H), 3.23 (s, 3 H), 3.02 (dd, J = 14.16, 9.39 Hz, 1 H), 2.83-2.89 (m, 1 H), 2.66-2.73 (m, 1 H), 2.54 (br dd, J = 10.88, 4.62 Hz, 1 H), 2.42 (ddd, J = 11.40, 7.67, 4.17 Hz, 2 H), 2.19-2.33 (m, 5 H), 1.95-2.11 (m, 6 H), 1.63-1.74 (m, 7 H), 1.33-1.38 (m, 1 H), 1.02 (td, J = 3.65, 1.94 Hz, 1 H). |

TABLE A-continued

| Example No. (preparation of the Example) | Structure and IUPAC name | Characterising data (LCMS and/or NMR) |
|---|---|---|
| 414 (General Procedure A using Bromide A10 as the core reagent) | 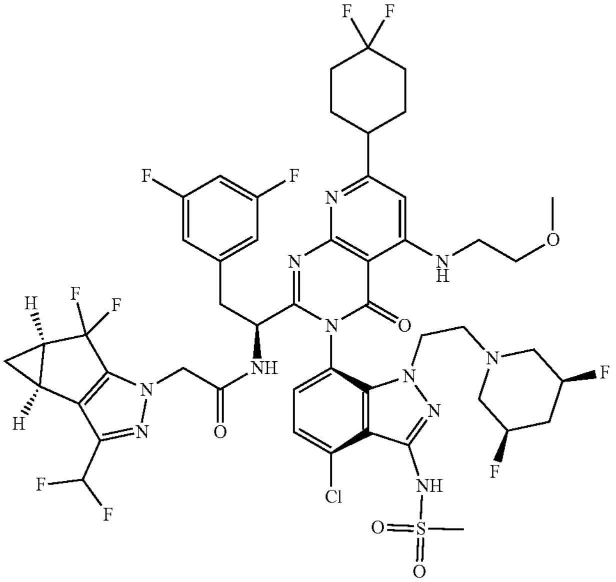 N-[(1S)-1-[(3P)-3-(4-chloro-1-{2-[(3R,5S)-3,5-difluoropiperidin-1-yl]ethyl}-3-methanesulfonamido-1H-indazol-7-yl)-7-(4,4-difluorocyclohexyl)-5-[(2-methoxyethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.11 min.; observed ion = 565.8 [M + 2H]. 1H NMR (500 MHz, METHANOL-d4) δ ppm 7.30 (d, J = 8.05 Hz, 1 H), 7.12 (d, J = 8.05 Hz, 1 H), 6.54-6.80 (m, 5 H), 4.76 (br d, J = 3.87 Hz, 1 H), 4.52-4.59 (m, 2 H), 4.14-4.36 (m, 3 H), 3.75 (td, J = 9.39, 5.07 Hz, 1 H), 3.61-3.64 (m, 2 H), 3.49-3.53 (m, 2 H), 3.37-3.41 (m, 1 H), 3.34 (s, 3 H), 3.24 (s, 3 H), 3.03 (dd, J = 14.01, 9.24 Hz, 1 H), 2.77-2.88 (m, 2 H), 2.61-2.69 (m, 2 H), 2.52-2.59 (m, 1 H), 2.42 (ddd, J = 11.10, 7.53, 4.02 Hz, 2 H), 2.15-2.26 (m, 5 H), 1.95-2.11 (m, 6 H), 1.62 (dt, J = 12.22, 8.35 Hz, 1 H), 1.32-1.38 (m, 1 H), 0.97-1.04 (m, 1 H) |
| 415 (General Procedure A using Bromide A10 as the core reagent) | 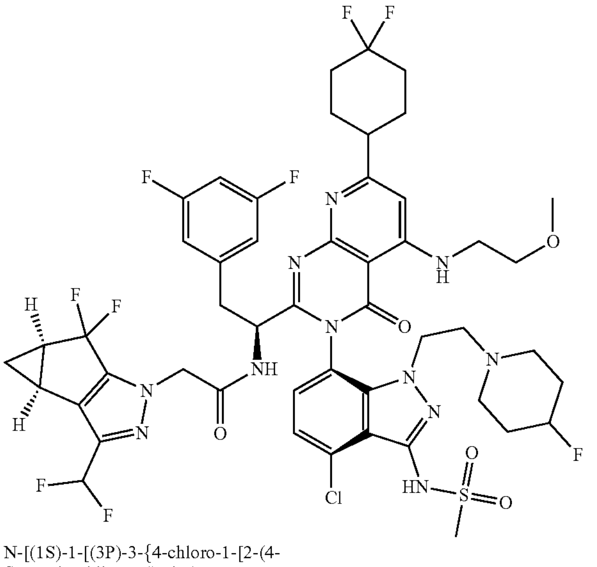 N-[(1S)-1-[(3P)-3-{4-chloro-1-[2-(4-fluoropiperidin-1-yl)ethyl]-3-methanesulfonamido-1H-indazol-7-yl}-7-(4,4-difluorocyclohexyl)-5-[(2-methoxyethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 0.97 min.; observed ion = 1110.2 [M − H]. 1H NMR (500 MHz, METHANOL-d4) δ ppm 7.33 (d, J = 7.75 Hz, 1 H), 7.18-7.23 (m, 1 H), 6.52-6.81 (m, 5 H), 4.71 (br d, J = 4.77 Hz, 1 H), 4.57-4.67 (m, 4 H), 4.19-4.28 (m, 1 H), 3.83-3.94 (m, 1 H), 3.61-3.64 (m, 2 H), 3.50-3.54 (m, 2 H), 3.37-3.41 (m, 2 H), 3.34 (s, 3 H), 3.24 (s, 3 H), 3.05 (dd, J = 14.01, 9.54 Hz, 1 H), 2.80-2.92 (m, 2 H), 2.49-2.67 (m, 2 H), 2.42 (ddd, J = 11.10, 7.53, 4.02 Hz, 2 H), 2.18-2.27 (m, 2 H), 1.91-2.11 (m, 7 H), 1.62-1.88 (m, 3 H), 1.33-1.38 (m, 1 H), 1.00 (br dd, J = 5.36, 2.09 Hz, 1 H). |

TABLE A-continued

| Example No. (preparation of the Example) | Structure and IUPAC name | Characterising data (LCMS and/or NMR) |
|---|---|---|
| 416 (General Procedure A using Bromide A10 as the core reagent) | 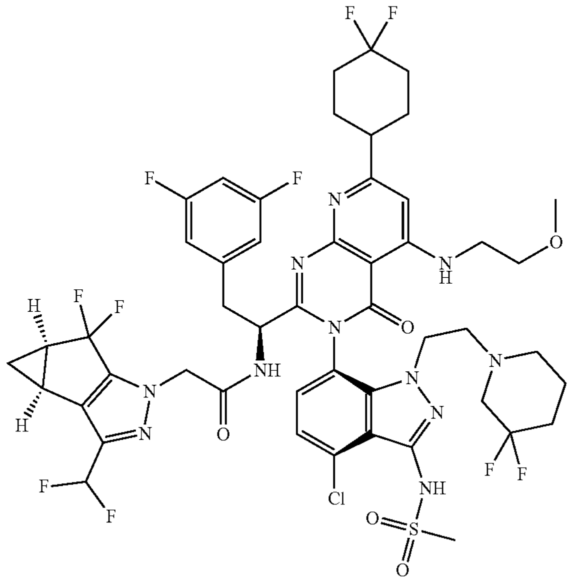 N-[(1S)-1-[(3P)-3-{4-chloro-1-[2-(3,3-difluoropiperidin-1-yl)ethyl]-3-methanesulfonamido-1H-indazol-7-yl}-7-(4,4-difluorocyclohexyl)-5-[(2-methoxyethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide. | LCMS Method B: retention time = 1.18 min.; observed ion = 1128.3 [M − H]. 1H NMR (500 MHz, METHANOL-d4) δ ppm 7.28 (d, J = 8.05 Hz, 1 H), 7.09 (d, J = 7.75 Hz, 1 H), 6.55-6.79 (m, 6 H), 4.77 (br d, J = 3.58 Hz, 1 H), 4.56 (d, J = 8.35 Hz, 2 H), 4.14-4.21 (m, 1 H), 3.71-3.77 (m, 1 H), 3.60-3.64 (m, 2 H), 3.48-3.52 (m, 2 H), 3.38-3.42 (m, 1 H), 3.34 (s, 3 H), 3.23 (s, 3 H), 3.04 (dd, J = 14.01, 8.94 Hz, 1 H), 2.82-2.89 (m, 1 H), 2.75 (td, J = 11.70, 5.51 Hz, 1 H), 2.55-2.62 (m, 1 H), 2.34-2.46 (m, 4 H), 2.28-2.34 (m, 1 H), 2.19-2.25 (m, 2 H), 1.92-2.13 (m, 7 H), 1.69-1.78 (m, 2 H), 1.48-1.54 (m, 2 H), 1.33-1.37 (m, 1 H), 1.02 (td, J = 2.91, 1.64 Hz, 1 H). |
| 417 (General Procedure A using Bromide A10 as the core reagent) | 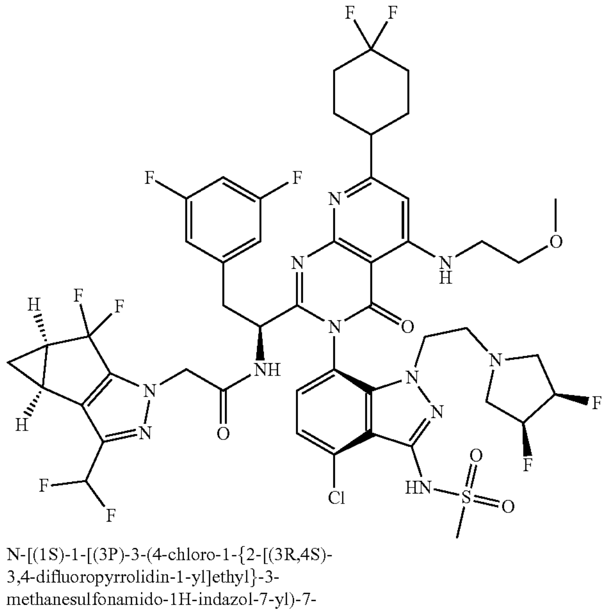 N-[(1S)-1-[(3P)-3-(4-chloro-1-{2-[(3R,4S)-3,4-difluoropyrrolidin-1-yl]ethyl}-3-methanesulfonamido-1H-indazol-7-yl)-7-(4,4-difluorocyclohexyl)-5-[(2-methoxyethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.09 min.; observed ion = 1114.3 [M − H]. 1H NMR (500 MHz, METHANOL-d4) δ ppm 7.29 (d, J = 8.05 Hz, 1 H), 7.11 (d, J = 7.75 Hz, 1 H), 6.52-6.79 (m, 5 H), 4.77 (br s, 1 H), 4.54-4.63 (m, 3 H), 4.06-4.14 (m, 1 H), 3.68-3.75 (m, 1 H), 3.61-3.64 (m, 2 H), 3.49-3.53 (m, 2 H), 3.37-3.41 (m, 1 H), 3.34 (s, 3 H), 3.23 (s, 3 H), 3.03 (dd, J = 13.71, 9.24 Hz, 1 H), 2.81-2.88 (m, 2 H), 2.51-2.75 (m, 4 H), 2.39-2.45 (m, 2 H), 2.17-2.28 (m, 2 H), 1.93-2.11 (m, 5 H), 1.33-1.38 (m, 1 H), 1.01 (ddd, J = 5.44, 3.80, 1.49 Hz, 1 H). |

TABLE A-continued

| Example No. (preparation of the Example) | Structure and IUPAC name | Characterising data (LCMS and/or NMR) |
| --- | --- | --- |
| 418 (General Procedure A using Bromide A10 as the core reagent) | 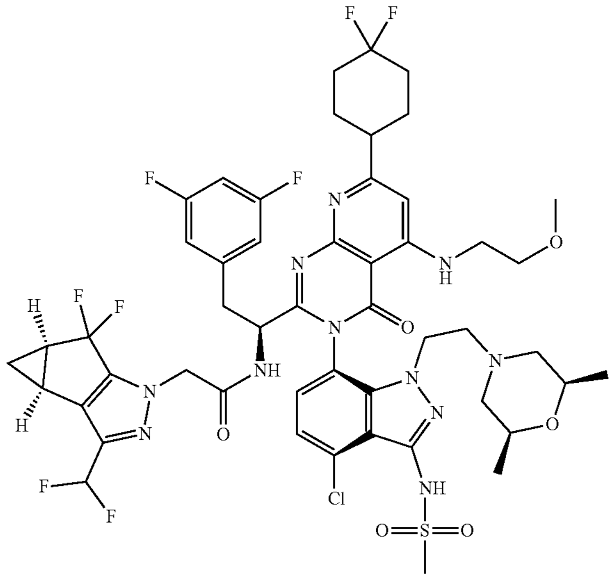 N-[(1S)-1-[(3P)-3-(4-chloro-1-{2-[(2R,6S)-2,6-dimethylmorpholin-4-yl]ethyl}-3-methanesulfonamido-1H-indazol-7-yl)-7-(4,4-difluorocyclohexyl)-5-[(2-methoxyethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method B: retention time = 0.99 min.; observed ion = 1122.4 [M − H]. 1H NMR (500 MHz, METHANOL-d4) δ ppm 7.30 (d, J = 7.75 Hz, 1 H), 7.14 (d, J = 8.05 Hz, 1 H), 6.52-6.80 (m, 5 H), 4.72-4.74 (m, 1 H), 4.55-4.64 (m, 3 H), 4.15-4.25 (m, 1 H), 3.82-3.91 (m, 1 H), 3.60-3.65 (m, 2 H), 3.49-3.54 (m, 2 H), 3.41-3.45 (m, 1 H), 3.35 (s, 3 H), 3.24 (s, 3 H), 3.01-3.06 (m, 1 H), 2.83-2.90 (m, 1 H), 2.65-2.75 (m, 1 H), 2.47-2.59 (m, 2 H), 2.40-2.46 (m, 2 H), 2.30-2.36 (m, 1 H), 2.20-2.27 (m, 2 H), 1.94-2.09 (m, 7 H), 1.60-1.66 (m, 1 H), 1.48 (s, 1 H), 1.34-1.39 (m, 1 H), 1.03 (br d, J = 6.26 Hz, 1 H), 1.00 (d, J = 6.26 Hz, 3 H), 0.89 (d, J = 6.26 Hz, 3 H), 0.84 (br d, J = 5.96 Hz, 1 H) |
| 419 (General Procedure A using Bromide A10 as the core reagent) | 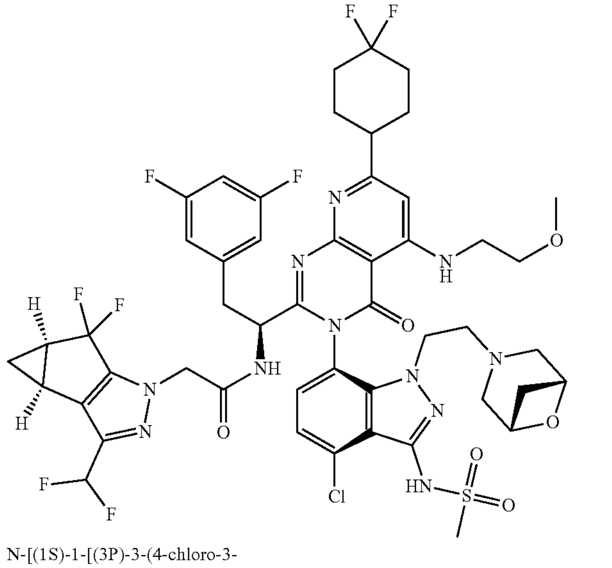 N-[(1S)-1-[(3P)-3-(4-chloro-3-methanesulfonamido-1-{2-[(1R,5S)-6-oxa-3-azabicyclo[3.1.1]heptan-3-yl]ethyl}-1H-indazol-7-yl)-7-(4,4-difluorocyclohexyl)-5-[(2-methoxyethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method B: retention time = 0.95 min.; observed ion = 1106.7 [M − H]. 1H NMR (500 MHz, METHANOL-d4) δ ppm 7.31 (d, J = 7.75 Hz, 1 H), 7.15 (d, J = 8.05 Hz, 1 H), 6.47-6.81 (m, 5 H), 4.76 (br d, J = 3.87 Hz, 1 H), 4.54-4.63 (m, 3 H), 4.30-4.35 (m, 1 H), 4.20-4.27 (m, 2 H), 3.76-3.83 (m, 1 H), 3.58-3.61 (m, 2 H), 3.48 (br d, J = 4.17 Hz, 2 H), 3.38 (br d, J = 4.47 Hz, 1 H), 3.33 (s, 3 H), 3.24 (s, 3 H), 2.99-3.06 (m, 1 H), 2.78-2.89 (m, 4 H), 2.71-2.76 (m, 2 H), 2.55 (br d, J = 11.03 Hz, 1 H), 2.38-2.46 (m, 3 H), 2.17-2.27 (m, 2 H), 1.93-2.11 (m, 6 H), 1.88 (d, J = 7.45 Hz, 1 H), 1.32-1.38 (m, 1 H), 1.01 (td, J = 3.73, 2.98 Hz, 1 H) |

TABLE A-continued

| Example No. (preparation of the Example) | Structure and IUPAC name | Characterising data (LCMS and/or NMR) |
|---|---|---|
| 420 (General Procedure A using Bromide A10 as the core reagent) | 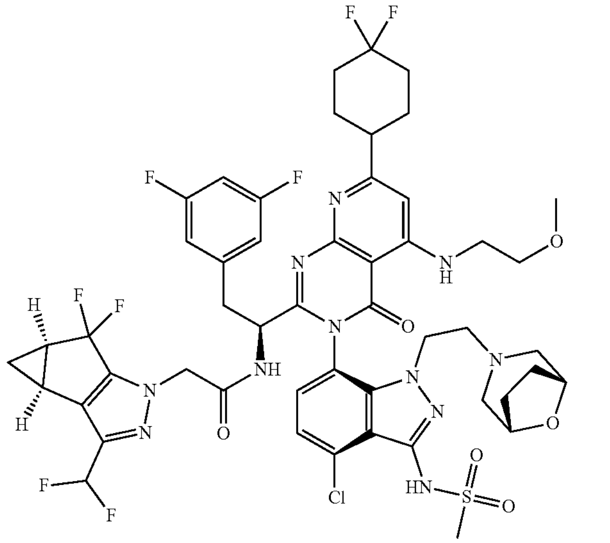 N-[(1S)-1-[(3P)-3-(4-chloro-3-methanesulfonamido-1-{2-[(1R,5S)-8-oxa-3-azabicyclo[3.2.1]octan-3-yl]ethyl}-1H-indazol-7-yl)-7-(4,4-difluorocyclohexyl)-5-[(2-methoxyethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.01 min.; observed ion = 1120.6 [M − H]. 1H NMR (500 MHz, METHANOL-d4) δ ppm 7.30 (d, J = 7.75 Hz, 1 H), 7.14 (d, J = 8.05 Hz, 1 H), 6.52-6.80 (m, 5 H), 4.74 (br d, J = 4.17 Hz, 1 H), 4.55-4.63 (m, 3 H), 4.12-4.18 (m, 1 H), 4.09 (br d, J = 6.26 Hz, 1 H), 3.96-4.00 (m, 1 H), 3.65-3.70 (m, 1 H), 3.59-3.63 (m, 2 H), 3.49-3.53 (m, 2 H), 3.34 (s, 3 H), 3.22 (s, 3 H), 3.01 (dd, J = 14.01, 9.24 Hz, 1 H), 2.81-2.90 (m, 1 H), 2.51-2.58 (m, 1 H), 2.37-2.46 (m, 4 H), 2.16-2.27 (m, 3 H), 2.12 (dd, J = 10.73, 2.09 Hz, 1 H), 2.00-2.09 (m, 6 H), 1.93-1.99 (m, 1 H), 1.53-1.66 (m, 3 H), 1.34-1.46 (m, 2 H), 1.00-1.05 (m, 1 H). |
| 421 (General Procedure A using Bromide A5 as the core reagent) | 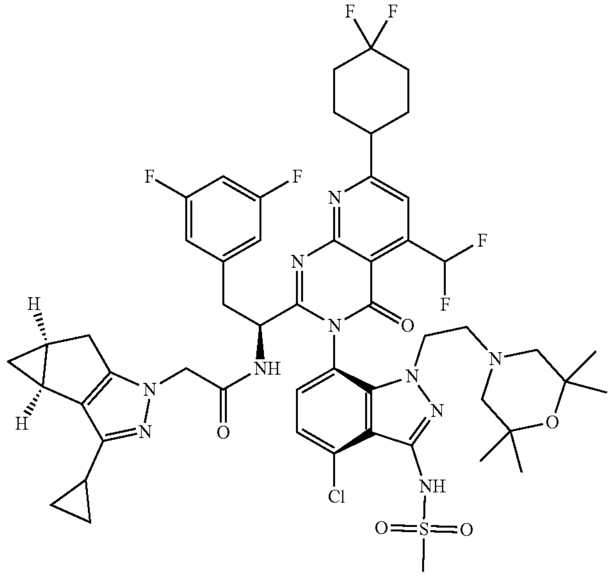 N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method A: retention time = 3.26 min.; observed ion = 1083.3 [M + H]+. 1H NMR (500 MHz, METHANOL-d4) δ ppm 0.06-0.10 (m, 1 H), 0.73-0.81 (m, 2 H), 0.83-0.90 (m, 3 H), 0.93 (d, J = 1.79 Hz, 12 H), 1.75-1.98 (m, 8 H), 2.05-2.14 (m, 5 H), 2.19-2.29 (m, 2 H), 2.42-2.56 (m, 2 H), 2.57-2.65 (m, 1 H), 2.69 (dd, J = 16.54, 6.41 Hz, 1 H), 3.02-3.09 (m, 1 H), 3.26 (s, 3 H), 3.36-3.41 (m, 1 H), 4.09-4.16 (m, 1 H), 4.27 (s, 2 H), 4.81-4.83 (m, 2 H), 6.49-6.58 (m, 2 H), 6.72-6.83 (m, 1 H), 7.29-7.39 (m, 2 H), 7.65-7.92 (m, 2 H). |

TABLE A-continued

| Example No. (preparation of the Example) | Structure and IUPAC name | Characterising data (LCMS and/or NMR) |
|---|---|---|
| 424 (General Procedure A using Bromide A3 as the core reagent) | 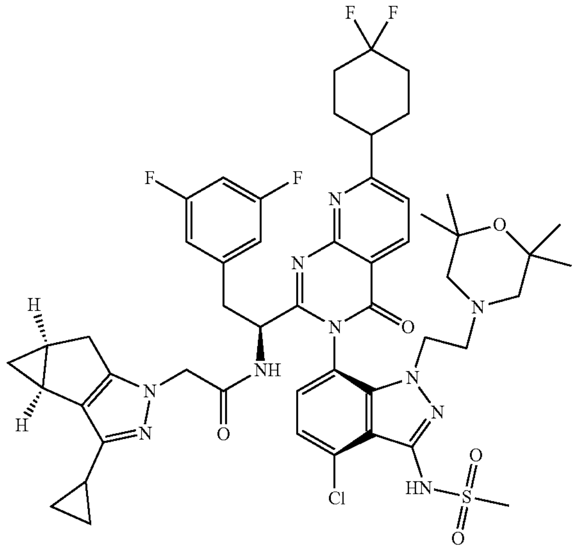 N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.458 min.; observed ion = 1034.2 [M + H]. 1H NMR (500 MHz, METHANOL-d4) δ ppm 0.06-0.10 (m, 1 H), 0.73-0.80 (m, 2 H), 0.83-0.90 (m, 3 H), 0.95 (d, J = 5.96 Hz, 12 H), 1.78 (tt, J = 8.53, 5.03 Hz, 1 H), 1.82-1.89 (m, 3 H), 1.90-2.11 (m, 10 H), 2.19-2.29 (m, 2 H), 2.43-2.64 (m, 3 H), 2.66-2.72 (m, 1 H), 3.03-3.08 (m, 1 H), 3.10-3.16 (m, 1 H), 3.27-3.28 (m, 3 H), 3.40 (dd, J = 14.16, 4.92 Hz, 1 H), 3.74-3.83 (m, 1 H), 4.07-4.15 (m, 1 H), 4.25-4.28 (m, 2 H), 6.52-6.57 (m, 2 H), 6.73-6.80 (m, 1 H), 7.27-7.37 (m, 2 H), 7.62-7.69 (m, 1 H), 8.63 (d, J = 8.05 Hz, 1 H). |
| 427 (General Procedure D using Chloride D2 as the core reagent) | 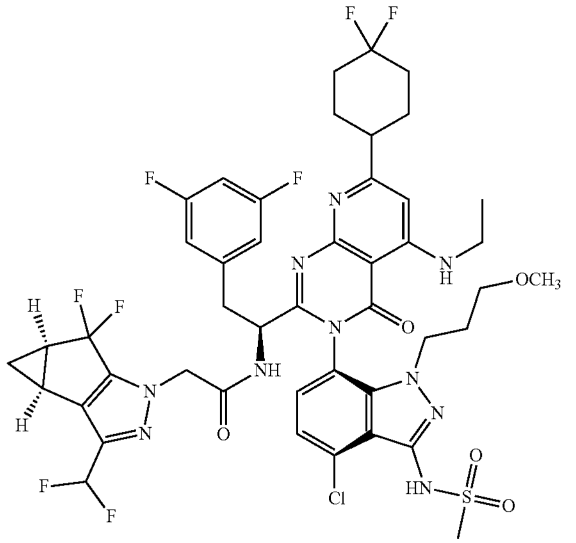 N-[(1S)-1-[(3P)-3-[4-chloro-3-methanesulfonamido-1-(3-methoxypropyl)-1H-indazol-7-yl]-7-(4,4-difluorocyclohexyl)-5-(ethylamino)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.65 min.; observed ion = 1025.15 [M + H]+. 1H NMR (500 MHz, METHANOL-d4) δ ppm 8.88 (br t, J = 5.22 Hz, 1 H), 7.27 (d, J = 7.75 Hz, 1 H), 7.07 (d, J = 8.05 Hz, 1 H), 6.47-6.84 (m, 5 H), 4.77-4.80 (m, 1 H), 4.57 (d, J = 2.38 Hz, 2 H), 3.98-4.06 (m, 1 H), 3.78-3.86 (m, 1 H), 3.34-3.41 (m, 3 H), 3.23 (s, 3 H), 3.11-3.16 (m, 2 H), 3.02 (dd, J = 14.01, 8.94 Hz, 1 H), 2.92 (s, 3 H), 2.81-2.88 (m, 1 H), 2.37-2.46 (m, 2 H), 2.17-2.27 (m, 2 H), 1.93-2.13 (m, 6 H), 1.81-1.89 (m, 2 H), 1.32-1.38 (m, 1 H), 1.28 (t, J = 7.15 Hz, 3 H), 0.97-1.05 (m, 1 H). |

TABLE A-continued

| Example No. (preparation of the Example) | Structure and IUPAC name | Characterising data (LCMS and/or NMR) |
|---|---|---|
| 428 (General Procedure D using Chloride D2 as the core reagent) | 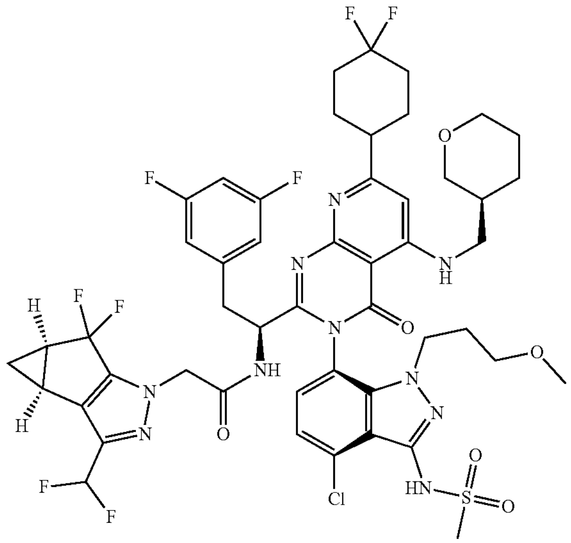<br>N-[(1S)-1-[(3P)-3-[4-chloro-3-methanesulfonamido-1-(3-methoxypropyl)-1H-indazol-7-yl]-7-(4,4-difluorocyclohexyl)-5-({[(3S)-oxan-3-yl]methyl}amino)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.21 min.; observed ion = 1095.3 [M + H]+. 1H NMR (500 MHz, METHANOL-d4) δ ppm 8.98-9.11 (m, 1 H), 7.30 (d, J = 7.75 Hz, 1 H), 7.11 (d, J = 7.75 Hz, 1 H), 6.53-6.82 (m, 5 H), 4.82 (br s, 1 H), 4.63 (s, 2 H), 4.59 (s, 2 H), 3.99-4.11 (m, 1 H), 3.74-3.93 (m, 3 H), 3.39-3.50 (m, 2 H), 3.26 (s, 3 H), 3.12-3.21 (m, 3 H), 3.01-3.09 (m, 2 H), 2.91 (s, 3 H), 2.41-2.48 (m, 2 H), 2.20-2.31 (m, 2 H), 1.81-2.13 (m, 11 H), 1.66-1.73 (m, 1 H), 1.56-1.66 (m, 1 H), 1.35-1.46 (m, 2 H), 1.02-1.08 (m, 1 H). |
| 429 (General Procedure D using Chloride D2 as the core reagent) | 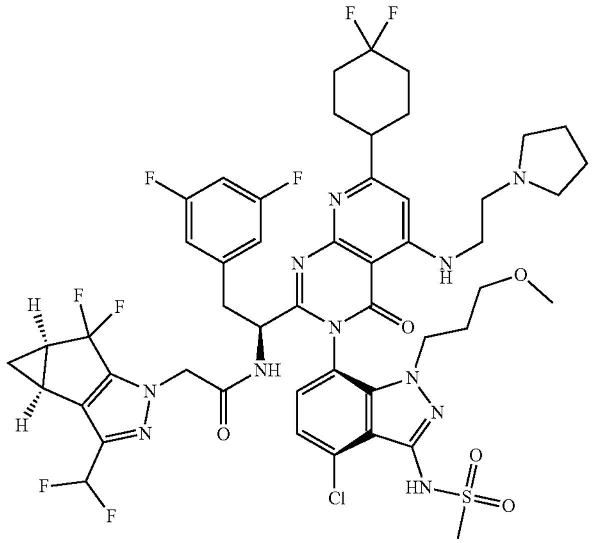<br>N-[(1S)-1-[(3P)-3-[4-chloro-3-methanesulfonamido-1-(3-methoxypropyl)-1H-indazol-7-yl]-7-(4,4-difluorocyclohexyl)-4-oxo-5-{[2-(pyrrolidin-1-yl)ethyl]amino}-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 0.94 min.; observed ion = 1094.5 [M + H]+.<br>1H NMR (500 MHz, METHANOL-d4) δ ppm 8.49 (br d, J = 1.19 Hz, 1 H), 7.30 (d, J = 7.75 Hz, 1 H), 7.06 (d, J = 8.35 Hz, 1 H), 6.56-6.85 (m, 5 H), 4.84 (br d, J = 1.49 Hz, 1 H), 4.61 (s, 2 H), 3.98-4.10 (m, 1 H), 3.79-3.89 (m, 1 H), 3.63-3.75 (m, 2 H), 3.37-3.49 (m, 1 H), 3.27 (s, 3 H), 3.12-3.21 (m, 5 H), 2.97-3.09 (m, 6 H), 2.93 (s, 3 H), 2.90 (br s, 1 H), 2.41-2.48 (m, 2 H), 2.21-2.33 (m, 2 H), 2.03-2.15 (m, 5 H), 1.87-1.97 (m, 6 H), 1.35-1.42 (m, 1 H), 1.04 (br d, J = 1.79 Hz, 1 H). |

TABLE A-continued

| Example No. (preparation of the Example) | Structure and IUPAC name | Characterising data (LCMS and/or NMR) |
|---|---|---|
| 430 (General Procedure D using Chloride D2 as the core reagent) | 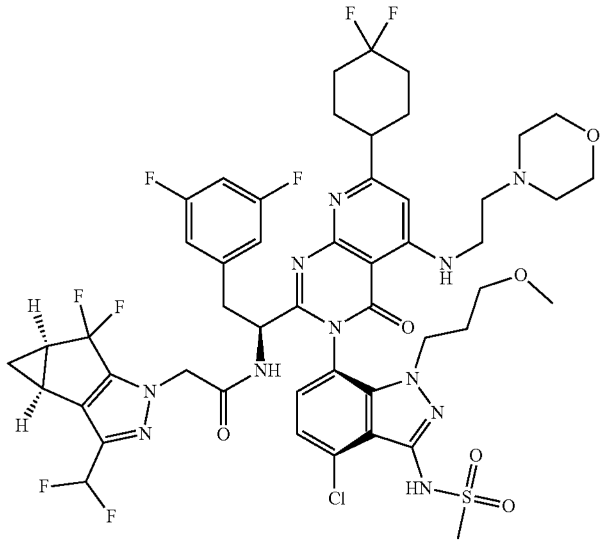 N-[(1S)-1-[(3P)-3-[4-chloro-3-methanesulfonamido-1-(3-methoxypropyl)-1H-indazol-7-yl]-7-(4,4-difluorocyclohexyl)-5-{[2-(morpholin-4-yl)ethyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 0.97 min.; observed ion = 1110.4 [M + H]+. 1H NMR (500 MHz, METHANOL-d4) δ ppm 7.31 (d, J = 8.05 Hz, 1 H), 7.10 (d, J = 8.05 Hz, 1 H), 6.54-6.84 (m, 5 H), 4.81 (br d, J = 3.58 Hz, 1 H), 4.59 (d, J = 2.98 Hz, 2 H), 4.05 (ddd, J = 14.16, 9.98, 6.26 Hz, 1 H), 3.77-3.87 (m, 1 H), 3.59-3.68 (m, 4 H), 3.45-3.50 (m, 2 H), 3.40 (dd, J = 13.86, 5.51 Hz, 1 H), 3.26 (s, 3 H), 3.13-3.16 (m, 2 H), 3.01-3.08 (m, 2 H), 2.93 (s, 3 H), 2.85-2.90 (m, 1 H), 2.68 (dq, J = 16.76, 6.33 Hz, 2 H), 2.41-2.52 (m, 6 H), 2.21-2.29 (m, 2 H), 1.98-2.13 (m, 6 H), 1.83-1.93 (m, 2 H), 1.36-1.41 (m, 1 H), 1.02-1.07 (m, 1 H). |
| 431 (General Procedure D using Chloride D2 as the core reagent) | 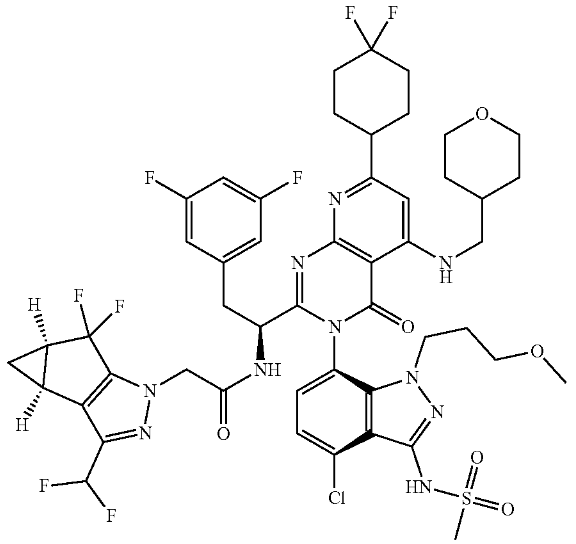 N-[(1S)-1-[(3P)-3-[4-chloro-3-methanesulfonamido-1-(3-methoxypropyl)-1H-indazol-7-yl]-7-(4,4-difluorocyclohexyl)-5-{[(oxan-4-yl)methyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.16 min.; observed ion = 1095.4 [M + H]+. 1H NMR (500 MHz, METHANOL-d4) δ ppm 7.29 (d, J = 7.75 Hz, 1 H), 7.10 (d, J = 8.05 Hz, 1 H), 6.56-6.83 (m, 5 H), 4.84 (d, J = 3.58 Hz, 1 H), 4.59 (d, J = 1.19 Hz, 2 H), 4.04 (ddd, J = 14.01, 10.13, 5.96 Hz, 1 H), 3.95 (dd, J = 11.47, 3.13 Hz, 2 H), 3.79-3.89 (m, 1 H), 3.38-3.45 (m, 3 H), 3.28 (s, 1 H), 3.26 (s, 3 H), 3.13-3.17 (m, 2 H), 3.05 (dd, J = 13.71, 8.94 Hz, 1 H), 2.92 (s, 3 H), 2.86-2.90 (m, 1 H), 2.41-2.48 (m, 2 H), 2.21-2.31 (m, 2 H), 2.00-2.13 (m, 5 H), 1.88-1.99 (m, 3 H), 1.79-1.87 (m, 1 H), 1.68-1.75 (m, 2 H), 1.35-1.45 (m, 3 H), 1.01-1.07 (m, 1 H). |

TABLE A-continued

| Example No. (preparation of the Example) | Structure and IUPAC name | Characterising data (LCMS and/or NMR) |
|---|---|---|
| 432 (General Procedure D using Chloride D2 as the core reagent) | 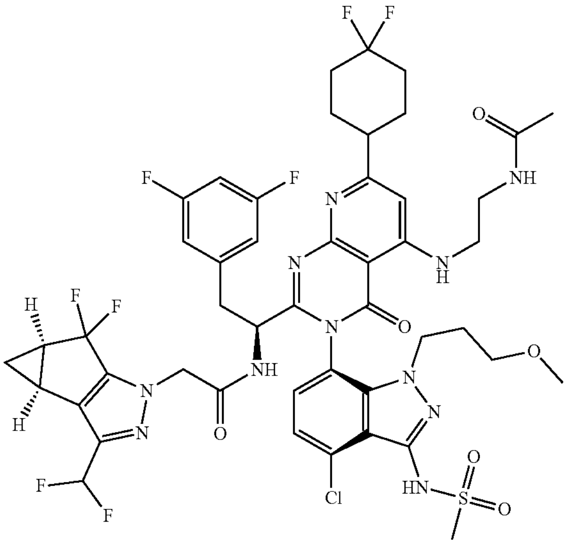 N-[(1S)-1-[(3P)-3-[4-chloro-3-methanesulfonamido-1-(3-methoxypropyl)-1H-indazol-7-yl]-7-(4,4-difluorocyclohexyl)-5-[(2-acetamidoethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.10 min.; observed ion = 1080.8 [M − H]. 1H NMR (500 MHz, METHANOL-d4) δ ppm 7.30 (d, J = 7.75 Hz, 1 H), 7.10 (d, J = 7.75 Hz, 1 H), 6.56-6.85 (m, 5 H), 4.82 (br d, J = 3.87 Hz, 1 H), 4.59 (d, J = 2.09 Hz, 2 H), 4.05 (ddd, J = 14.23, 9.76, 6.11 Hz, 1 H), 3.83 (ddd, J = 14.16, 9.69, 5.66 Hz, 1 H), 3.36-3.57 (m, 4 H), 3.26 (s, 3 H), 3.16 (d, J = 5.36 Hz, 2 H), 3.05 (dd, J = 13.86, 9.09 Hz, 1 H), 2.94 (s, 3 H), 2.83-2.92 (m, 2 H), 2.41-2.49 (m, 2 H), 2.19-2.29 (m, 2 H), 1.95-2.15 (m, 6 H), 1.91 (s, 3 H), 1.84-1.89 (m, 2 H), 1.35-1.41 (m, 1 H), 1.00-1.08 (m, 1 H). |
| 433 (General Procedure D using Chloride D2 as the core reagent) | 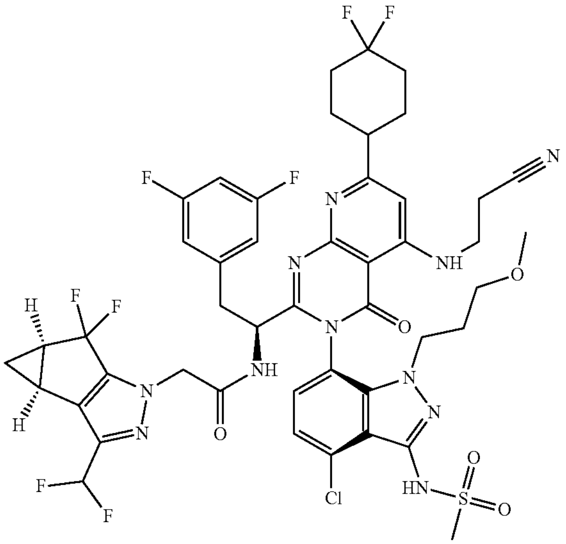 N-[(1S)-1-[(3P)-3-[4-chloro-3-methanesulfonamido-1-(3-methoxypropyl)-1H-indazol-7-yl]-5-[(2-cyanoethyl)amino]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.20 min.; observed ion = 1050.2 [M + H]+. 1H NMR (500 MHz, METHANOL-d4) δ ppm 7.24-7.33 (m, 1 H), 7.12 (d, J = 7.75 Hz, 1 H), 6.56-6.82 (m, 5 H), 4.84 (br d, J = 3.87 Hz, 1 H), 4.59 (s, 2 H), 4.01-4.10 (m, 1 H), 3.80-3.87 (m, 1 H), 3.72-3.79 (m, 2 H), 3.39-3.44 (m, 1 H), 3.25 (s, 3 H), 3.16-3.21 (m, 3 H), 3.05 (dd, J = 13.86, 8.79 Hz, 1 H), 2.92 (s, 3 H), 2.87-2.91 (m, 1 H), 2.82 (t, J = 6.56 Hz, 2 H), 2.41-2.48 (m, 2 H), 2.20-2.31 (m, 2 H), 2.03-2.14 (m, 5 H), 1.95-2.02 (m, 1 H), 1.85-1.92 (m, 2 H), 1.34-1.41 (m, 1 H), 1.02-1.08 (m, 1 H). |

TABLE A-continued

| Example No. (preparation of the Example) | Structure and IUPAC name | Characterising data (LCMS and/or NMR) |
|---|---|---|
| 434 (General Procedure A using Bromide A3 as the core reagent) | 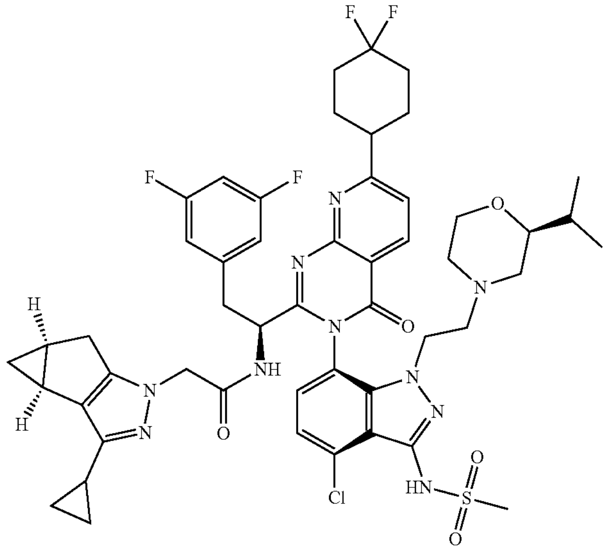 N-[(1S)-1-[(3P)-3-(4-chloro-3-methanesulfonamido-1-{2-[(2S)-2-(propan-2-yl)morpholin-4-yl]ethyl}-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.2 min.; observed ion = 1017.5 [M − H]. 1H NMR (500 MHz, METHANOL-d4) δ ppm 0.07 (d, J = 3.87 Hz, 1 H), 0.73-0.75 (m, 1 H), 0.78 (d, J = 6.85 Hz, 4 H), 0.84 (d, J = 6.56 Hz, 4 H), 0.86-0.89 (m, 2 H), 0.93-0.98 (m, 2 H), 1.28 (br d, J = 6.85 Hz, 2 H), 1.67-1.80 (m, 3 H), 1.84 (br d, J = 0.89 Hz, 1 H), 1.93 (s, 1 H), 2.02 (s, 1 H), 2.06-2.16 (m, 7 H), 2.22-2.28 (m, 2 H), 2.48-2.57 (m, 2 H), 3.04 (dd, J = 13.86, 9.09 Hz, 1 H), 3.22 (s, 3 H), 3.48-3.54 (m, 2 H), 3.67-3.77 (m, 2 H), 4.08-4.16 (m, 1 H), 4.28 (d, J = 3.87 Hz, 2 H), 4.60 (br d, J = 7.45 Hz, 2 H), 6.54-6.57 (m, 2 H), 6.77 (t, J = 8.17 Hz, 1 H), 7.22 (br d, J = 1.49 Hz, 2 H), 7.66 (d, J = 8.05 Hz, 1 H), 8.61 (d, J = 8.35 Hz, 1 H). |
| 435 (General Procedure A using Bromide A3 as the core reagent) | 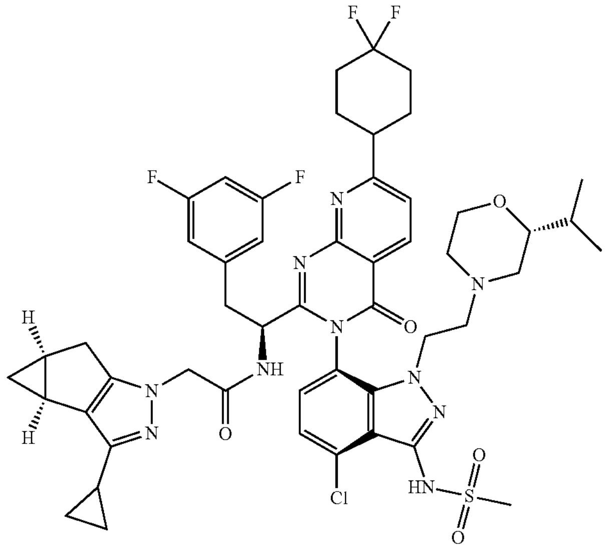 N-[(1S)-1-[(3P)-3-(4-chloro-3-methanesulfonamido-1-{2-[(2R)-2-(propan-2-yl)morpholin-4-yl]ethyl}-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.22 min.; observed ion = 1019.2 [M + H]. 1H NMR (500 MHz, METHANOL-d4) δ ppm 0.06-0.09 (m, 1 H), 0.73 (d, J = 6.85 Hz, 3 H), 0.82 (d, J = 6.85 Hz, 3 H), 0.83-0.90 (m, 2 H), 0.93-0.98 (m, 1 H), 1.19-1.37 (m, 9 H), 1.52-1.58 (m, 1 H), 1.75-1.85 (m, 2 H), 1.88-1.96 (m, 2 H), 2.07-2.15 (m, 5 H), 2.20-2.33 (m, 3 H), 2.38-2.53 (m, 3 H), 2.60-2.66 (m, 1 H), 2.69-2.73 (m, 1 H), 3.01-3.06 (m, 1 H), 3.20 (s, 3 H), 3.64 (dd, J = 10.13, 1.49 Hz, 1 H), 3.73-3.79 (m, 1 H), 4.06-4.12 (m, 1 H), 4.28 (d, J = 4.77 Hz, 2 H), 6.55 (d, J = 7.09 Hz, 2 H), 6.76 (t, J = 8.31 Hz, 1 H), 7.17-7.24 (m, 2 H), 7.65 (d, J = 8.35 Hz, 1 H), 8.60 (d, J = 7.75 Hz, 1 H). |

TABLE A-continued

| Example No. (preparation of the Example) | Structure and IUPAC name | Characterising data (LCMS and/or NMR) |
|---|---|---|
| 444 (General Procedure A using Bromide A1 as the core reagent) | 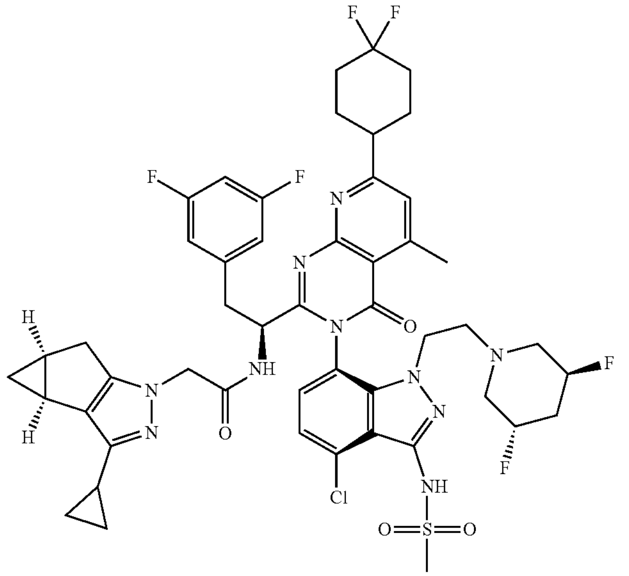 N-[(1S)-1-[(3P)-3-(4-chloro-1-{2-[(3S,5S)-3,5-difluoropiperidin-1-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.51 min.; observed ion = 1023.4 [M − H]. 1H NMR (500 MHz, METHANOL-d4) δ ppm 7.34 (dd, J = 6.41, 0.75 Hz, 1 H), 7.24 (br d, J = 7.45 Hz, 1 H), 7.13 (dd, J = 7.90, 1.64 Hz, 1 H), 6.65-6.74 (m, 1 H), 6.51 (dd, J = 6.85, 1.19 Hz, 2 H), 4.73 (br s, 1 H), 4.48-4.55 (m, 2 H), 4.37-4.46 (m, 1 H), 4.16-4.23 (m, 2 H), 3.96-4.04 (m, 1 H), 3.58-3.69 (m, 1 H), 3.31-3.36 (m, 1 H), 3.19 (s, 3 H), 2.93-3.01 (m, 2 H), 2.77 (dd, J = 5.36, 0.60 Hz, 3 H), 2.67-2.73 (m, 1 H), 2.58-2.66 (m, 2 H), 2.36-2.52 (m, 2 H), 2.12-2.30 (m, 5 H), 1.95-2.06 (m, 4 H), 1.75-1.94 (m, 4 H), 1.67-1.73 (m, 1 H), 1.27 (d, J = 6.56 Hz, 1 H), 0.86-0.92 (m, 1 H), 0.74-0.83 (m, 2 H), 0.64-0.73 (m, 2 H), −0.02-0.02 (m, 1 H). |
| 445 (General Procedure A using Bromide A1 as the core reagent) | 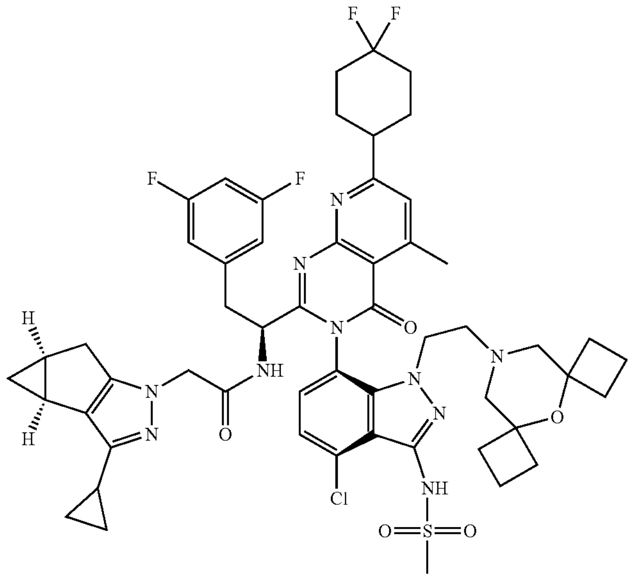 N-[(1S)-1-[(3P)-3-[4-chloro-3-methanesulfonamido-1-(2-{5-oxa-11-azadispiro[3.1.3$^{6}$.3$^{4}$]dodecan-11-yl}ethyl)-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.48 min.; observed ion = 1069.4 [M − H]. 1H NMR (500 MHz, METHANOL-d4) δ ppm 7.34 (s, 1 H), 7.19-7.26 (m, 1 H), 7.13 (br d, J = 7.75 Hz, 1 H), 6.63-6.72 (m, 1 H), 6.47 (br d, J = 6.85 Hz, 2 H), 4.73 (br s, 1 H), 4.06-4.22 (m, 2 H), 3.75-3.84 (m, 1 H), 3.32 (br dd, J = 14.60, 4.17 Hz, 1 H), 3.18 (s, 3 H), 2.88-2.99 (m, 2 H), 2.77 (s, 3 H), 2.57-2.71 (m, 2 H), 2.42-2.50 (m, 1 H), 2.37 (br d, J = 17.29 Hz, 1 H), 2.04-2.18 (m, 3 H), 1.88-2.01 (m, 7 H), 1.77-1.87 (m, 5 H), 1.73-1.77 (m, 1 H), 1.66-1.71 (m, 1 H), 1.44-1.58 (m, 6 H), 1.09-1.28 (m, 4 H), 0.84-0.90 (m, 1 H), 0.74-0.81 (m, 2 H), 0.63-0.72 (m, 2 H),-0.03-0.03 (m, 1 H). |

TABLE A-continued

| Example No. (preparation of the Example) | Structure and IUPAC name | Characterising data (LCMS and/or NMR) |
|---|---|---|
| 446 (General Procedure A using Bromide A2 as the core reagent) | 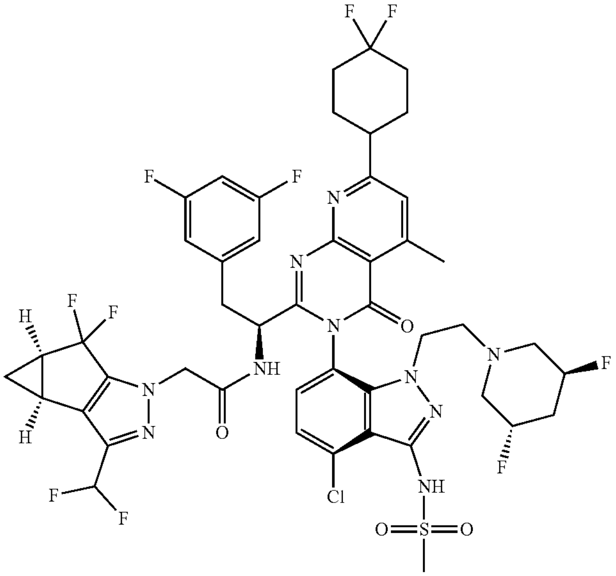 N-[(1S)-1-[(3P)-3-(4-chloro-1-{2-[(3S,5S)-3,5-difluoropiperidin-1-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.50 min.; observed ion = 1069.5 [M − H]. 1H NMR (500 MHz, METHANOL-d4) δ ppm 7.41-7.47 (m, 1 H), 7.34 (dd, J = 7.90, 2.24 Hz, 1 H), 7.19-7.26 (m, 1 H), 6.54-6.84 (m, 4 H), 4.81 (br d, J = 4.47 Hz, 1 H), 4.56-4.68 (m, 4 H), 4.45-4.54 (m, 1 H), 4.15-4.24 (m, 1 H), 3.74-3.84 (m, 1 H), 3.42 (dd, J = 14.16, 4.92 Hz, 1 H), 3.25 (s, 3 H), 3.03-3.11 (m, 2 H), 2.87 (dd, J = 4.47, 0.60 Hz, 2 H), 2.67-2.84 (m, 2 H), 2.49-2.61 (m, 1 H), 2.42-2.48 (m, 2 H), 2.21-2.38 (m, 5 H), 2.04-2.15 (m, 5 H), 1.97-2.04 (m, 1 H), 1.82-1.95 (m, 2 H), 1.36-1.41 (m, 1 H), 0.99-1.08 (m, 1 H). |
| 448 (General Procedure E using Alcohol E1 as the core reagent) | 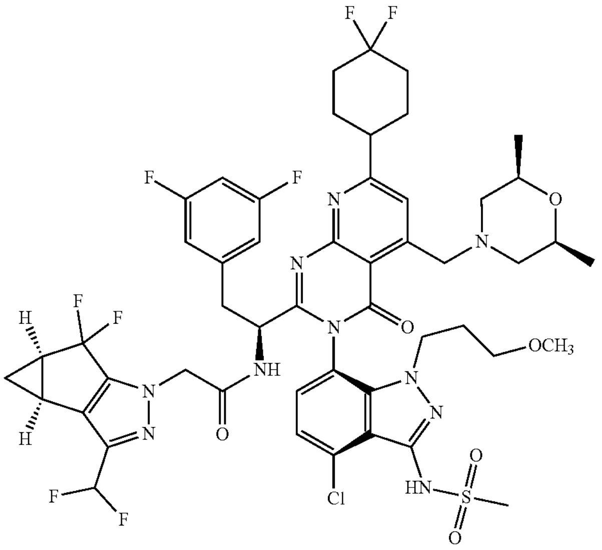 N-[(1S)-1-[(3P)-3-[4-chloro-3-methanesulfonamido-1-(3-methoxypropyl)-1H-indazol-7-yl]-7-(4,4-difluorocyclohexyl)-5-{[(2R,6S)-2,6-dimethylmorpholin-4-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.72 min.; observed ion = 1109.15 [M + H]+. 1H NMR (500 MHz, METHANOL-d4) δ ppm 7.71 (s, 1 H), 7.20 (d, J = 7.75 Hz, 1 H), 7.05 (d, J = 7.75 Hz, 1 H), 6.41-6.72 (m, 4 H), 4.47-4.50 (m, 2 H), 3.94-4.12 (m, 2 H), 3.86-3.93 (m, 1 H), 3.60-3.75 (m, 3 H), 3.29-3.34 (m, 1 H), 3.14 (s, 3 H), 2.93-3.05 (m, 5 H), 2.66-2.74 (m, 2 H), 2.64 (s, 3 H), 2.32 (ddd, J = 11.10, 7.53, 4.02 Hz, 2 H), 2.11-2.19 (m, 2 H), 1.89-2.04 (m, 6 H), 1.70-1.84 (m, 4 H), 1.22-1.30 (m, 1 H), 1.02 (dd, J = 6.26, 1.79 Hz, 6 H), 0.89-0.94 (m, 1 H). |

TABLE A-continued

| Example No. (preparation of the Example) | Structure and IUPAC name | Characterising data (LCMS and/or NMR) |
|---|---|---|
| 453 (General Procedure A using Bromide A2 as the core reagent) | 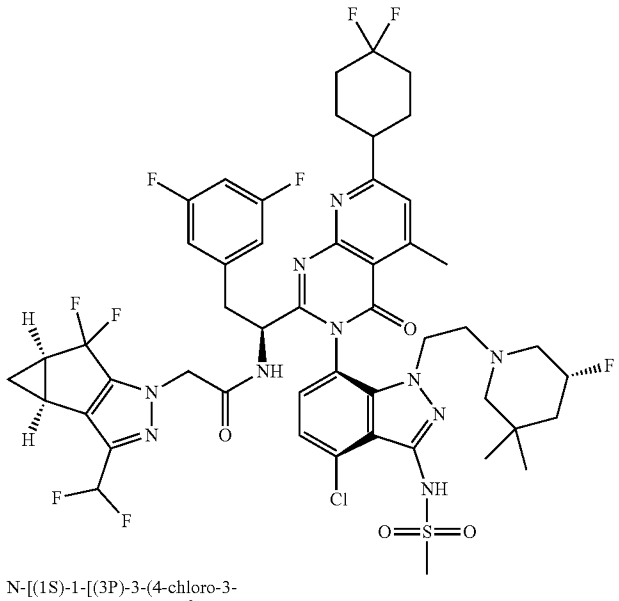 N-[(1S)-1-[(3P)-3-(4-chloro-3-methanesulfonamido-1-{2-[(6S)-2,2,6-trimethylmorpholin-4-yl]ethyl}-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.30 min.; observed ion = 1077.7 [M − H]. 1H NMR (500 MHz, METHANOL-d4) δ ppm 7.48 (d, J = 0.89 Hz, 1 H), 7.35 (d, J = 7.75 Hz, 1 H), 7.27 (d, J = 8.05 Hz, 1 H), 6.49-6.82 (m, 4 H), 4.79 (d, J = 4.77 Hz, 1 H), 4.65 (d, J = 5.96 Hz, 2 H), 4.25 (ddd, J = 13.93, 10.95, 5.81 Hz, 1 H), 3.74-3.82 (m, 1 H), 3.37-3.40 (m, 1 H), 3.25 (s, 3 H), 3.01-3.08 (m, 2 H), 2.87 (d, J = 0.60 Hz, 3 H), 2.56 (td, J = 11.33, 5.96 Hz, 1 H), 2.39-2.49 (m, 3 H), 2.32 (d, J = 10.13 Hz, 1 H), 2.23-2.29 (m, 2 H), 2.16-2.22 (m, 1 H), 2.06-2.13 (m, 5 H), 1.98-2.04 (m, 1 H), 1.62 (d, J = 11.33 Hz, 1 H), 1.32-1.41 (m, 2 H), 1.04-1.08 (m, 1 H), 1.01 (s, 3 H), 0.93 (s, 3 H), 0.82 (d, J = 6.26 Hz, 3 H). |
| 454 (General Procedure A using Bromide A2 as the core reagent) | 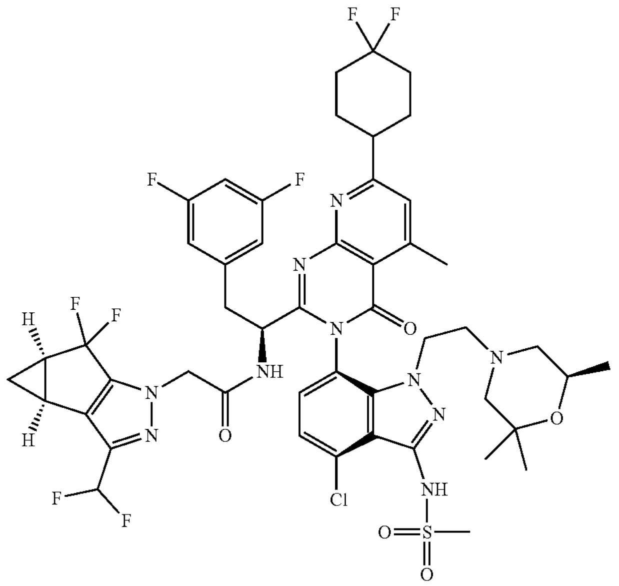 N-[(1S)-1-[(3P)-3-(4-chloro-3-methanesulfonamido-1-{2-[(6R)-2,2,6-trimethylmorpholin-4-yl]ethyl}-1H-indazol-7-yl)-7-(4,4-difluorocyclohexyl)-5-methyl-4-oxo-3H, 4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.27 min.; observed ion = 1077.6 [M − H]. 1H NMR (500 MHz, METHANOL-d4) δ ppm 7.48 (d, J = 0.89 Hz, 1 H), 7.34 (d, J = 7.75 Hz, 1 H), 7.25 (d, J = 7.75 Hz, 1 H), 6.51-6.81 (m, 4 H), 4.80 (br s, 1 H), 4.63 (s, 2 H), 4.12-4.20 (m, 1 H), 4.06-4.25 (m, 1 H), 3.82-3.89 (m, 1 H), 3.60-3.67 (m, 1 H), 3.38-3.41 (m, 1 H), 3.25 (s, 3 H), 3.05 (dd, J = 14.01, 9.54 Hz, 2 H), 2.87 (d, J = 0.89 Hz, 3 H), 2.42-2.62 (m, 5 H), 2.22-2.30 (m, 2 H), 1.98-2.13 (m, 7 H), 1.47-1.55 (m, 2 H), 1.35-1.41 (m, 1 H), 1.04-1.07 (m, 1 H), 0.94 (d, J = 6.26 Hz, 3 H), 0.92 (s, 3 H), 0.88 (s, 3 H). |

TABLE A-continued

| Example No. (preparation of the Example) | Structure and IUPAC name | Characterising data (LCMS and/or NMR) |
|---|---|---|
| 456 (General Procedure A using Bromide A1 as the core reagent) | 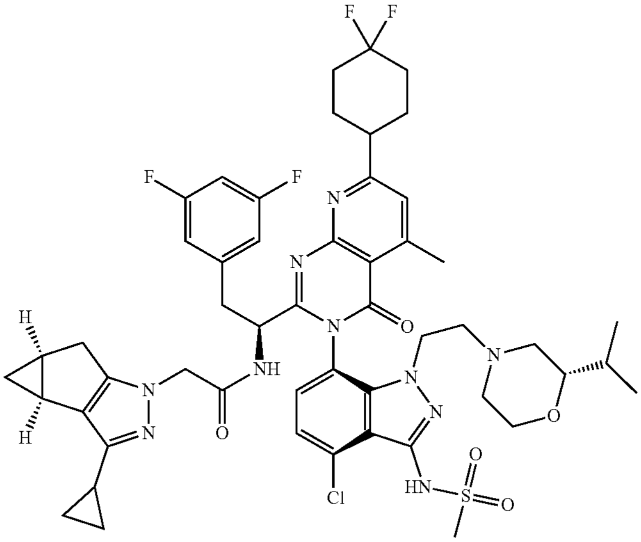 N-[(1S)-1-[(3P)-3-(4-chloro-3-methanesulfonamido-1-{2-[(2S)-2-(propan-2-yl)morpholin-4-yl]ethyl}-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.24 min.; observed ion = 1031.6 [M − H]. 1H NMR (500 MHz, METHANOL-d4) δ ppm 7.37 (s, 1 H), 7.25 (br d, J = 7.45 Hz, 1 H), 7.16 (s, 1 H), 6.64-6.74 (m, 1 H), 6.43-6.52 (m, 2 H), 4.54 (br s, 2 H), 4.21 (s, 2 H), 4.00-4.09 (m, 1 H), 3.71-3.81 (m, 1 H), 3.58 (br s, 1 H), 3.27-3.35 (m, 2 H), 3.20 (br s, 3 H), 2.93-3.01 (m, 2 H), 2.77 (s, 3 H), 2.55-2.72 (m, 3 H), 2.43-2.51 (m, 1 H), 2.33-2.41 (m, 2 H), 2.25 (br d, J = 5.66 Hz, 1 H), 2.14-2.21 (m, 2 H), 1.97-2.07 (m, 5 H), 1.84-1.96 (m, 3 H), 1.75-1.79 (m, 1 H), 1.69 (br d, J = 7.75 Hz, 1 H), 1.44-1.53 (m, 1 H), 1.20-1.30 (m, 1 H), 0.86-0.92 (m, 1 H), 0.77-0.83 (m, 2 H), 0.74 (br d, J = 6.26 Hz, 3 H), 0.67-0.71 (m, 1 H), 0.64 (br d, J = 6.85 Hz, 3 H), 0.00 (br s, 1 H). |
| 457 (General Procedure A using Bromide A1 as the core reagent) | 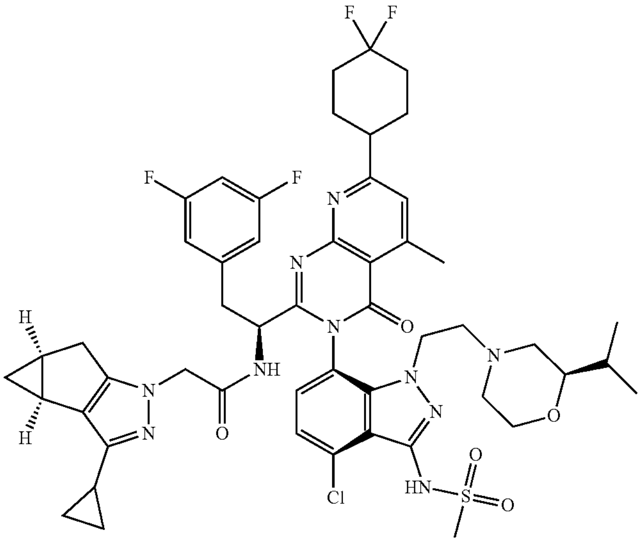 N-[(1S)-1-[(3P)-3-(4-chloro-3-methanesulfonamido-1-{2-[(2R)-2-(propan-2-yl)morpholin-4-yl]ethyl}-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.23 min.; observed ion = 1031.5 [M − H]. 1H NMR (500 MHz, METHANOL-d4) δ ppm 7.37 (s, 1 H), 7.25 (br d, J = 7.75 Hz, 1 H), 7.16 (d, J = 7.75 Hz, 1 H), 6.65-6.73 (m, 1 H), 6.42-6.52 (m, 2 H), 4.53 (s, 2 H), 4.20 (s, 2 H), 4.03-4.11 (m, 1 H), 3.67-3.76 (m, 1 H), 3.42-3.47 (m, 1 H), 3.32 (br dd, J = 14.16, 4.92 Hz, 2 H), 3.19 (s, 3 H), 2.93-2.99 (m, 2 H), 2.78-2.83 (m, 1 H), 2.76 (s, 3 H), 2.60 (br dd, J = 16.39, 6.26 Hz, 2 H), 2.32-2.51 (m, 3 H), 2.13-2.21 (m, 2 H), 2.07-2.12 (m, 1 H), 1.97-2.05 (m, 5 H), 1.82-1.94 (m, 2 H), 1.74-1.79 (m, 1 H), 1.58-1.73 (m, 3 H), 1.38-1.45 (m, 1 H), 0.88 (td, J = 7.67, 4.62 Hz, 1 H), 0.78-0.84 (m, 2 H), 0.77 (d, J = 6.56 Hz, 3 H), 0.71 (d, J = 6.85 Hz, 3 H), 0.63-0.69 (m, 1 H),-0.03-0.01 (m, 1 H). |

TABLE A-continued

| Example No. (preparation of the Example) | Structure and IUPAC name | Characterising data (LCMS and/or NMR) |
|---|---|---|
| 458 (General Procedure A using Bromide A2 as the core reagent) | 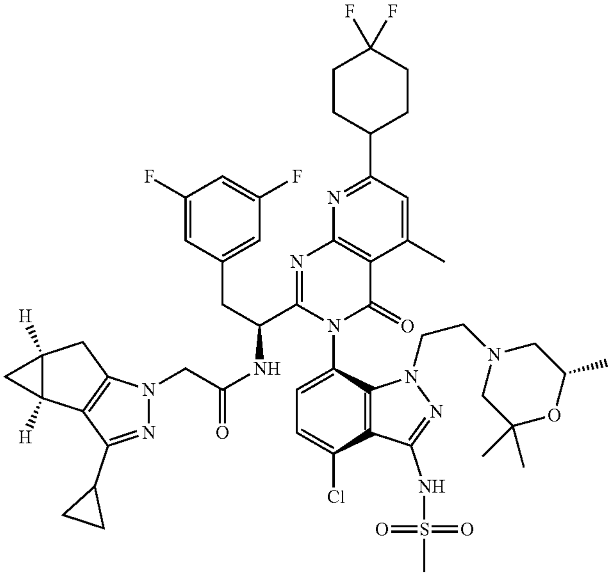<br>N-[(1S)-1-[(3P)-3-(4-chloro-3-methanesulfonamido-1-{2-[(6S)-2,2,6-trimethylmorpholin-4-yl]ethyl}-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.30 min.; observed ion = 1031.4 [M − H]. 1H NMR (500 MHz, METHANOL-d4) δ ppm 7.34-7.39 (m, 1 H), 7.24 (d, J = 7.75 Hz, 1 H), 7.13 (d, J = 8.05 Hz, 1 H), 6.61-6.71 (m, 1 H), 6.45 (dd, J = 8.05, 2.09 Hz, 2 H), 4.71 (br s, 1 H), 4.52 (s, 2 H), 4.20 (s, 2 H), 4.08 (ddd, J = 14.01, 10.88, 6.11 Hz, 1 H), 3.62-3.72 (m, 1 H), 3.28-3.32 (m, 1 H), 3.18 (s, 3 H), 2.95 (br dd, J = 14.16, 9.39 Hz, 2 H), 2.76 (d, J = 0.60 Hz, 3 H), 2.62 (dd, J = 16.24, 6.71 Hz, 1 H), 2.47 (td, J = 11.33, 5.66 Hz, 1 H), 2.28-2.41 (m, 2 H), 2.09-2.25 (m, 4 H), 1.95-2.04 (m, 5 H), 1.82-1.87 (m, 1 H), 1.74-1.80 (m, 1 H), 1.70 (tt, J = 8.38, 5.03 Hz, 1 H), 1.53 (d, J = 10.73 Hz, 1 H), 1.24 (t, J = 10.58 Hz, 1 H), 0.91 (s, 3 H), 0.86-0.90 (m, 1 H), 0.84 (s, 3 H), 0.76-0.81 (m, 2 H), 0.72 (d, J = 6.26 Hz, 3 H), 0.64-0.70 (m, 2 H), −0.03-0.03 (m, 1 H). |
| 459 (General Procedure A using Bromide A2 as the core reagent) | 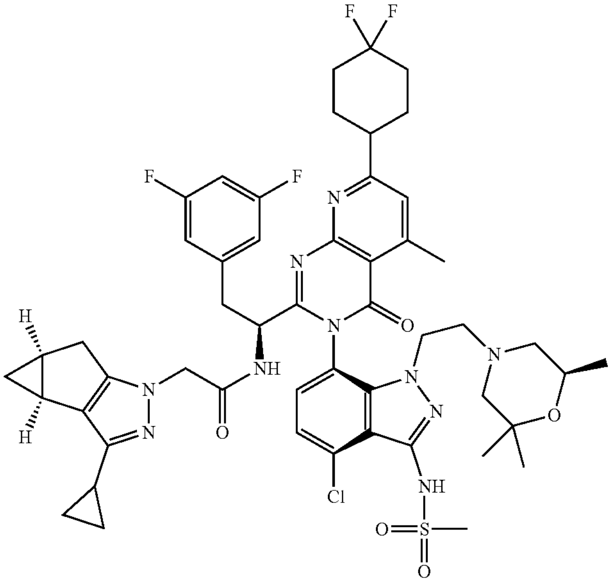<br>N-[(1S)-1-[(3P)-3-(4-chloro-3-methanesulfonamido-1-{2-[(6R)-2,2,6-trimethylmorpholin-4-yl]ethyl}-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.28 min.; observed ion = 1031.4 [M − H].<br>1H NMR (500 MHz, METHANOL-d4) δ ppm 7.37 (d, J = 0.89 Hz, 1 H), 7.24 (d, J = 8.05 Hz, 1 H), 7.15 (d, J = 7.75 Hz, 1 H), 6.61-6.72 (m, 1 H), 6.46 (dd, J = 8.05, 2.09 Hz, 2 H), 4.71 (br s, 1 H), 4.52 (s, 2 H), 4.19 (s, 2 H), 3.94-4.01 (m, 1 H), 3.71 (ddd, J = 13.93, 10.65, 5.81 Hz, 1 H), 3.50-3.59 (m, 1 H), 3.30 (br dd, J = 14.16, 4.92 Hz, 1 H), 3.18 (s, 3 H), 2.95 (br dd, J = 14.16, 9.39 Hz, 2 H), 2.76 (d, J = 0.60 Hz, 3 H), 2.60 (dd, J = 16.54, 6.71 Hz, 1 H), 2.34-2.54 (m, 4 H), 2.11-2.20 (m, 2 H), 1.91-2.02 (m, 6 H), 1.81-1.86 (m, 1 H), 1.74-1.79 (m, 1 H), 1.65-1.73 (m, 1 H), 1.38-1.48 (m, 2 H), 0.88 (dd, J = 7.90, 4.62 Hz, 1 H), 0.85 (d, J = 6.26 Hz, 3 H), 0.81 (s, 3 H), 0.79 (s, 3 H), 0.76 (br dd, J = 4.32, 2.53 Hz, 1 H), 0.65-0.71 (m, 2 H), 0.00 (d, J = 3.58 Hz, 1 H). |

TABLE A-continued

| Example No. (preparation of the Example) | Structure and IUPAC name | Characterising data (LCMS and/or NMR) |
|---|---|---|
| 462 (General Procedure A using Bromide A5 as the core reagent) | 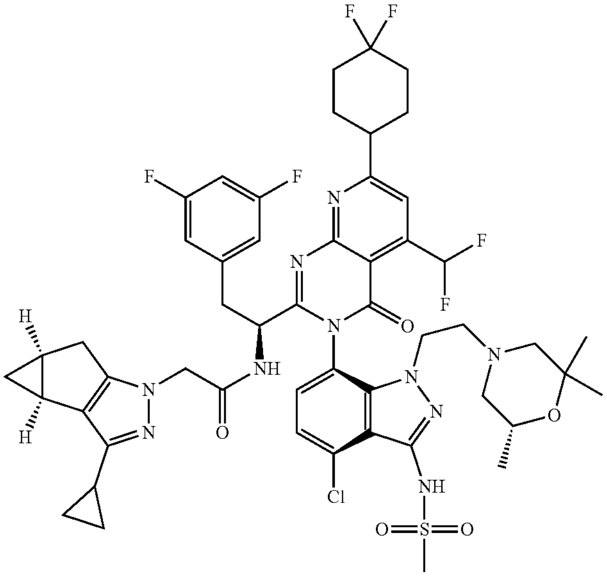 N-[(1S)-1-[(3P)-3-(4-chloro-3-methanesulfonamido-1-{2-[(6R)-2,2,6-trimethylmorpholin-4-yl]ethyl}-1H-indazol-7-yl)-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.31 min.; observed ion = 1069.4 [M + H]+. 1H NMR (500 MHz, METHANOL-d4) δ ppm 0.12 (s, 1 H), 0.74-0.84 (m, 2 H), 0.86-0.93 (m, 8 H), 0.94-1.01 (m, 4 H), 1.47-1.58 (m, 2 H), 1.76-1.84 (m, 1 H), 1.84-1.90 (m, 1 H), 1.91-1.98 (m, 1 H), 1.99-2.19 (m, 7 H), 2.21-2.32 (m, 2 H), 2.43-2.51 (m, 2 H), 2.52-2.60 (m, 2 H), 2.70 (dd, J = 16.69, 6.56 Hz, 1 H), 3.06 (dd, J = 14.16, 9.69 Hz, 1 H), 3.20-3.27 (m, 2 H), 3.29 (s, 3 H), 3.41 (s, 1 H), 3.59-3.68 (m, 1 H), 3.75-3.89 (m, 1 H), 4.06-4.19 (m, 1 H), 6.49-6.60 (m, 2 H), 6.74-6.85 (m, 1 H), 7.30-7.41 (m, 2 H), 7.68-7.98 (m, 1 H), 7.77-7.78 (m, 1 H). |
| 467 (General Procedure A using Bromide A5 as the core reagent) | 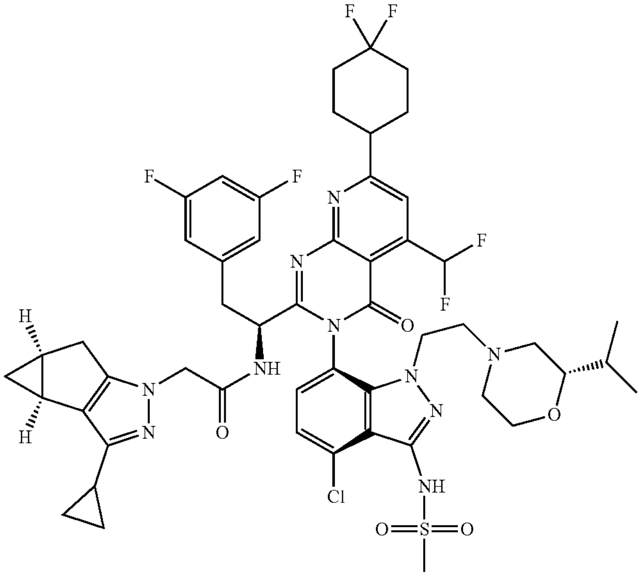 N-[(1S)-1-[(3P)-3-(4-chloro-3-methanesulfonamido-1-{2-[(2S)-2-(propan-2-yl)morpholin-4-yl]ethyl}-1H-indazol-7-yl)-7-(4,4-difluorocyclohexyl)-5-(difluoromethyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.27 min.; observed ion = 1069.4 [M + H]+. 1H NMR (500 MHz, METHANOL-d4) δ ppm 0.05-0.12 (m, 1 H), 0.73-0.84 (m, 5 H), 0.84-0.92 (m, 5 H), 0.94-1.02 (m, 1 H), 1.47-1.56 (m, 1 H), 1.68-1.98 (m, 4 H), 2.09-2.19 (m, 5 H), 2.22-2.32 (m, 3 H), 2.43-2.50 (m, 1 H), 2.52-2.61 (m, 1 H), 2.67-2.74 (m, 1 H), 2.86-2.94 (m, 1 H), 3.03-3.12 (m, 1 H), 3.21-3.27 (m, 2 H), 3.28-3.30 (m, 3 H), 3.41-3.45 (m, 1 H), 3.54-3.59 (m, 1 H), 3.78-3.87 (m, 1 H), 4.16-4.23 (m, 1 H), 4.30-4.34 (m, 2 H), 6.51-6.60 (m, 2 H), 6.76-6.84 (m, 1 H), 7.30-7.41 (m, 2 H), 7.66-7.97 (m, 2 H). |

TABLE A-continued

| Example No. (preparation of the Example) | Structure and IUPAC name | Characterising data (LCMS and/or NMR) |
|---|---|---|
| 471 (General Procedure E using Alcohol E1 as the core reagent) | 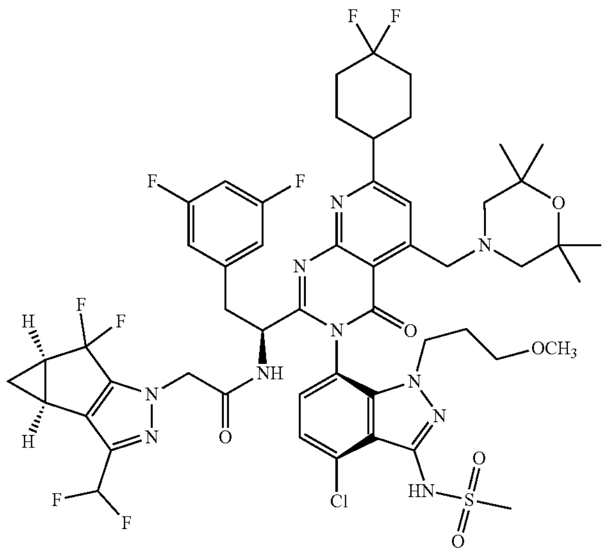 N-[(1S)-1-[(3P)-3-[4-chloro-3-methanesulfonamido-1-(3-methoxypropyl)-1H-indazol-7-yl]-7-(4,4-difluorocyclohexyl)-4-oxo-5-[(2,2,6,6-tetramethylmorpholin-4-yl)methyl]-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 3.34 min.; observed ion = 1137.25 [M + H]+. 1H NMR (500 MHz, METHANOL-d4) δ ppm 8.06 (s, 1 H), 7.32 (d, J = 7.75 Hz, 1 H), 7.16 (d, J = 7.75 Hz, 1 H), 6.57-6.82 (m, 4 H), 4.87 (br s, 1 H), 4.59 (d, J = 1.49 Hz, 2 H), 4.08-4.22 (m, 2 H), 4.02 (ddd, J = 14.23, 10.65, 5.81 Hz, 1 H), 3.79-3.88 (m, 1 H), 3.44 (dd, J = 13.86, 5.22 Hz, 1 H), 3.26 (s, 3 H), 3.16-3.20 (m, 1 H), 3.05-3.13 (m, 3 H), 2.76 (s, 3 H), 2.45 (ddd, J = 11.18, 7.60, 3.87 Hz, 2 H), 2.34 (s, 3 H), 2.27 (br d, J = 5.66 Hz, 2 H), 2.14-2.20 (m, 2 H), 2.01-2.12 (m, 4 H), 1.79-1.97 (m, 2 H), 1.36-1.40 (m, 1 H), 1.32 (d, J = 2.09 Hz, 12 H), 1.00-1.07 (m, 1 H). |
| 472 (General Procedure E using Alcohol E1 as the core reagent) | 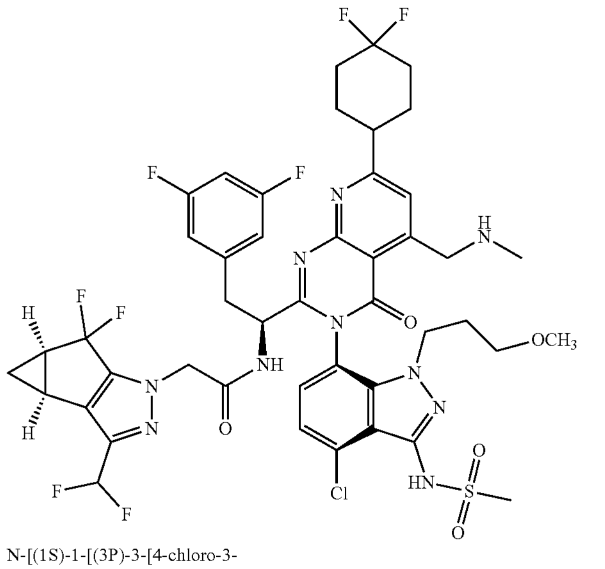 N-[(1S)-1-[(3P)-3-[4-chloro-3-methanesulfonamido-1-(3-methoxypropyl)-1H-indazol-7-yl]-7-(4,4-difluorocyclohexyl)-5-[(methylamino)methyl]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.61 min.; observed ion = 1025.15 [M + H]+. 1H NMR (500 MHz, METHANOL-d4) δ ppm 8.45 (s, 1 H), 7.72 (s, 1 H), 7.34 (d, J = 7.75 Hz, 1 H), 7.17 (d, J = 8.05 Hz, 1 H), 6.58-6.85 (m, 4 H), 5.51 (s, 1 H), 4.71 (d, J = 13.41 Hz, 1 H), 4.58-4.65 (m, 2 H), 4.44 (d, J = 13.41 Hz, 1 H), 4.02 (ddd, J = 14.31, 10.73, 5.66 Hz, 1 H), 3.81-3.92 (m, 1 H), 3.46 (dd, J = 13.86, 5.22 Hz, 1 H), 3.27 (s, 3 H), 3.26 (br d, J = 4.47 Hz, 1 H), 3.17-3.22 (m, 1 H), 3.08-3.15 (m, 2 H), 2.74 (s, 3 H), 2.71 (s, 3 H), 2.41-2.48 (m, 2H), 2.24-2.32 (m, 2 H), 2.08-2.18 (m, 5 H), 2.01-2.07 (m, 1 H), 1.90-1.98 (m, 1 H), 1.81-1.90 (m, 1 H), 1.38 (q, J = 6.95 Hz, 1 H), 1.01-1.07 (m, 1H). |

TABLE A-continued

| Example No. (preparation of the Example) | Structure and IUPAC name | Characterising data (LCMS and/or NMR) |
|---|---|---|
| 473 (General Procedure B using Amine B25 as the core reagent) | 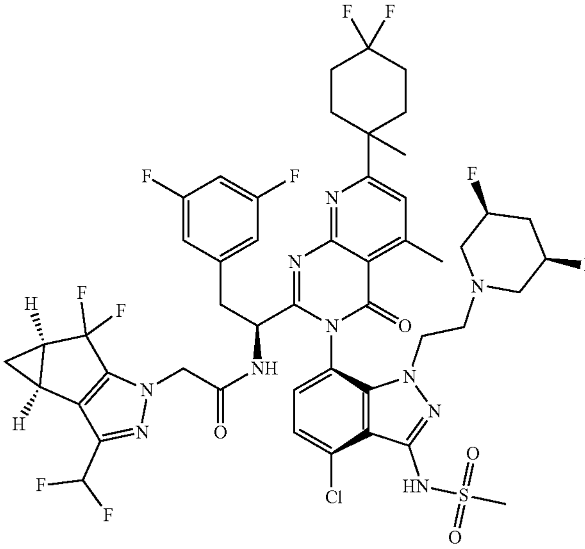 N-[(1S)-1-[(3P)-3-(4-chloro-1-{2-[(3R,5S)-3,5-difluoropiperidin-1-yl]ethyl}-3-methanesulfonamido-1H-indazol-7-yl)-7-(4,4-difluoro-1-methylcyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 3.096 min.; observed ion = 1085.60 [M + H]. 1H NMR (500 MHz, METHANOL-d4) δ ppm 1.02 (dtd, J = 5.70, 3.78, 3.78, 2.24 Hz, 1 H), 1.32-1.40 (m, 4 H), 1.58-1.70 (m, 1 H), 1.79-1.94 (m, 4 H), 2.02-2.25 (m, 4 H), 2.40-2.46 (m, 2 H), 2.48-2.55 (m, 1 H), 2.56-2.73 (m, 4 H), 2.78-2.83 (m, 1 H), 2.87 (s, 2 H), 2.97-3.09 (m, 1 H), 3.26 (s, 3 H), 3.36-3.41 (m, 1 H), 3.78-3.85 (m, 1 H), 4.14-4.39 (m, 3 H), 4.55-4.68 (m, 3 H), 4.80 (dd, J = 9.24, 4.77 Hz, 2 H), 6.50-6.57 (m, 2 H), 6.67 (br t, J = 54.69 Hz, 1 H), 6.76 (tt, J = 9.13, 2.35 Hz, 1 H), 7.25-7.29 (m, 1 H), 7.35 (d, J = 8.05 Hz, 1 H), 7.62 (d, J = 0.89 Hz, 1 H). |
| 474 (General Procedure B using Amine B25 as the core reagent) | 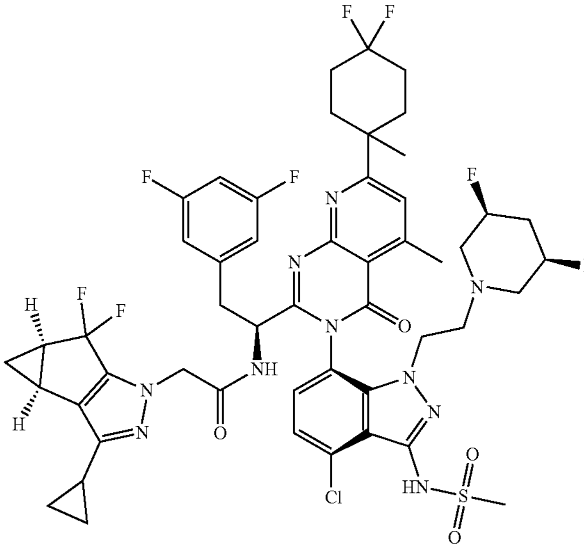 N-[(1S)-1-[(3P)-3-(4-chloro-1-{2-[(3R,5S)-3,5-difluoropiperidin-1-yl]ethyl}-3-methanesulfonamido-1H-indazol-7-yl)-7-(4,4-difluoro-1-methylcyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method A: retention time = 3.149 min.; observed ion = 1039.30 [M + H]. 1H NMR (500 MHz, METHANOL-d4) δ ppm 0.06-0.09 (m, 1 H), 0.72-0.91 (m, 4 H), 0.96 (td, J = 7.60, 4.47 Hz, 1 H), 1.36 (s, 3 H), 1.60-1.69 (m, 1 H), 1.75-1.95 (m, 7 H), 1.99-2.08 (m, 2 H), 2.13-2.28 (m, 3 H), 2.42-2.51 (m, 1 H), 2.54-2.72 (m, 5 H), 2.78-2.86 (m, 1 H), 2.87 (s, 3 H), 3.06 (dd, J = 14.01, 9.24 Hz, 1 H), 3.28-3.29 (m, 3 H), 3.38 (dd, J = 14.16, 4.92 Hz, 1 H), 3.77 (ddd, J = 14.16, 9.09, 5.36 Hz, 1 H), 4.09 (ddd, J = 14.01, 9.39, 6.11 Hz, 1 H), 4.19-4.40 (m, 4 H), 4.79-4.82 (m, 2 H), 6.53-6.58 (m, 2 H), 6.77 (tt, J = 9.16, 2.16 Hz, 1 H), 7.26 (d, J = 7.75 Hz, 1 H), 7.35 (d, J = 7.75 Hz, 1 H), 7.62 (s, 1 H). |

TABLE A-continued

| Example No. (preparation of the Example) | Structure and IUPAC name | Characterising data (LCMS and/or NMR) |
|---|---|---|
| 475 (General Procedure D using Chloride D2 as the core reagent) | 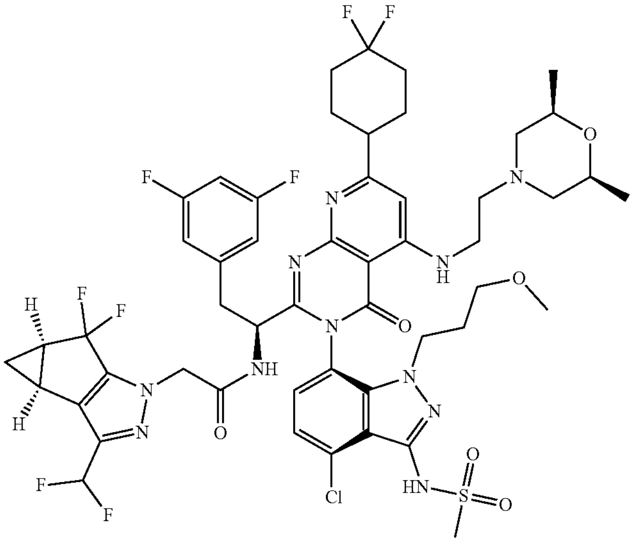 N-[(1S)-1-[(3P)-3-[4-chloro-3-methanesulfonamido-1-(3-methoxypropyl)-1H-indazol-7-yl]-7-(4,4-difluorocyclohexyl)-5-({2-[(2R,6S)-2,6-dimethylmorpholin-4-ylethyl}amino)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.47 min.; observed ion = 1138.3 [M + H]+. 1H NMR (500 MHz, METHANOL-d4) δ ppm 8.24 (s, 1 H), 7.31 (d, J = 7.75 Hz, 1 H), 7.10 (d, J = 7.75 Hz, 1 H), 6.57-6.84 (m, 6 H), 4.81 (dd, J = 8.94, 5.36 Hz, 1 H), 4.53-4.62 (m, 2 H), 4.05 (ddd, J = 14.08, 10.21, 5.81 Hz, 1 H), 3.82 (ddd, J = 14.23, 9.91, 5.36 Hz, 1 H), 3.58-3.64 (m, 2 H), 3.49 (br t, J = 6.11 Hz, 2 H), 3.42 (br d, J = 5.07 Hz, 1 H), 3.26 (s, 3 H), 3.10-3.17 (m, 2 H), 3.05 (dd, J = 14.01, 9.24 Hz, 1 H), 2.94 (s, 3 H), 2.76-2.83 (m, 2 H), 2.60-2.71 (m, 2 H), 2.45 (ddd, J = 11.47, 7.75, 4.02 Hz, 2 H), 2.21-2.30 (m, 2 H), 1.97-2.14 (m, 6 H), 1.84-1.94 (m, 2 H), 1.74-1.84 (m, 2 H), 1.35-1.41 (m, 1 H), 1.09 (dd, J = 6.41, 2.83 Hz, 6 H), 1.02-1.05 (m, 1 H). |
| 476 (General Procedure D using Chloride D2 as the core reagent) | 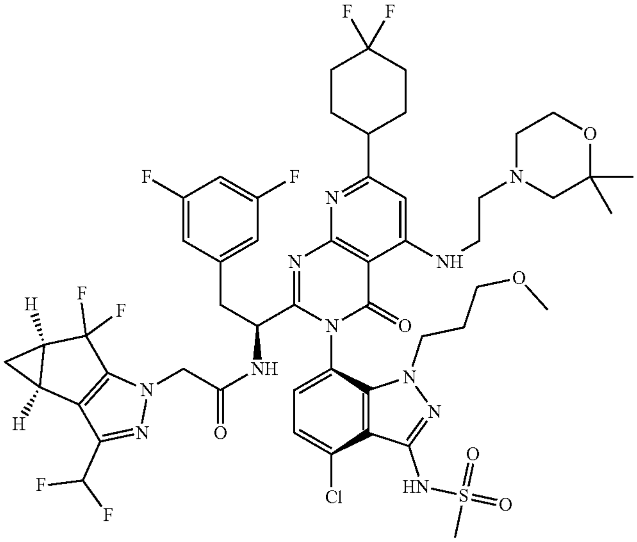 N-[(1S)-1-[(3P)-3-[4-chloro-3-methanesulfonamido-1-(3-methoxypropyl)-1H-indazol-7-yl]-7-(4,4-difluorocyclohexyl)-5-{[2-(2,2-dimethylmorpholin-4-yl)ethyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.27 min.; observed ion = 1138.3 [M + H]+. 1H NMR (500 MHz, METHANOL-d4) δ ppm 7.30 (d, J = 7.75 Hz, 1 H), 7.07 (d, J = 8.05 Hz, 1 H), 6.56-6.84 (m, 5 H), 4.82 (d, J = 3.58 Hz, 1 H), 4.56-4.64 (m, 2 H), 4.05 (ddd, J = 14.31, 9.98, 6.41 Hz, 1 H), 3.78-3.89 (m, 1 H), 3.65 (t, J = 4.77 Hz, 2 H), 3.39-3.47 (m, 3 H), 3.26 (s, 3 H), 3.15 (t, J = 5.81 Hz, 2 H), 3.05 (dd, J = 13.71, 8.94 Hz, 1 H), 2.94 (s, 3 H), 2.86-2.92 (m, 1 H), 2.58-2.66 (m, 2 H), 2.37-2.49 (m, 4 H), 2.21-2.30 (m, 4 H), 1.97-2.14 (m, 6 H), 1.83-1.92 (m, 2 H), 1.38 (br d, J = 6.85 Hz, 1 H), 1.14 (d, J = 3.58 Hz, 6 H), 1.03-1.06 (m, 1 H). |

TABLE A-continued

| Example No. (preparation of the Example) | Structure and IUPAC name | Characterising data (LCMS and/or NMR) |
|---|---|---|
| 477 (General Procedure D using Chloride D2 as the core reagent) | 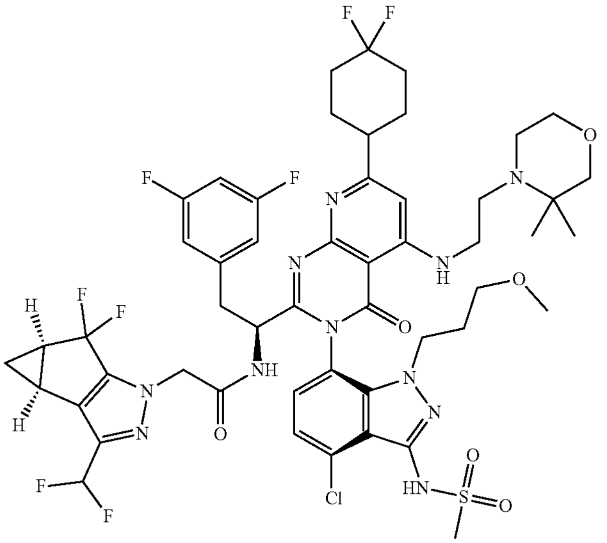 N-[(1S)-1-[(3P)-3-[4-chloro-3-methanesulfonamido-1-(3-methoxypropyl)-1H-indazol-7-yl]-7-(4,4-difluorocyclohexyl)-5-{[2-(3,3-dimethylmorpholin-4-yl)ethyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.45 min.; observed ion = 1138.3 [M + H]+. 1H NMR (500 MHz, METHANOL-d4) δ ppm 8.20 (s, 1 H), 7.31 (d, J = 8.05 Hz, 1 H), 7.10 (d, J = 7.75 Hz, 1 H), 6.56-6.83 (m, 5 H), 4.77-4.80 (m, 1 H), 4.55-4.62 (m, 2 H), 4.07 (ddd, J = 14.38, 9.91, 6.41 Hz, 1 H), 3.84 (ddd, J = 14.53, 9.46, 5.51 Hz, 1 H), 3.61-3.70 (m, 2 H), 3.38-3.45 (m, 4 H), 3.26 (s, 3 H), 3.16 (dd, J = 6.26, 5.36 Hz, 2 H), 3.05 (dd, J = 13.71, 8.94 Hz, 1 H), 2.94 (s, 3 H), 2.87-2.92 (m, 1 H), 2.70-2.80 (m, 2 H), 2.63 (t, J = 5.07 Hz, 2 H), 2.41-2.49 (m, 2 H), 2.21-2.31 (m, 2 H), 1.98-2.17 (m, 6 H), 1.83-1.93 (m, 2 H), 1.35-1.42 (m, 1 H), 1.04-1.07 (m, 1 H), 1.01 (d, J = 3.87 Hz, 6 H). |
| 479 (General Procedure A using Bromide A2 as the core reagent) | 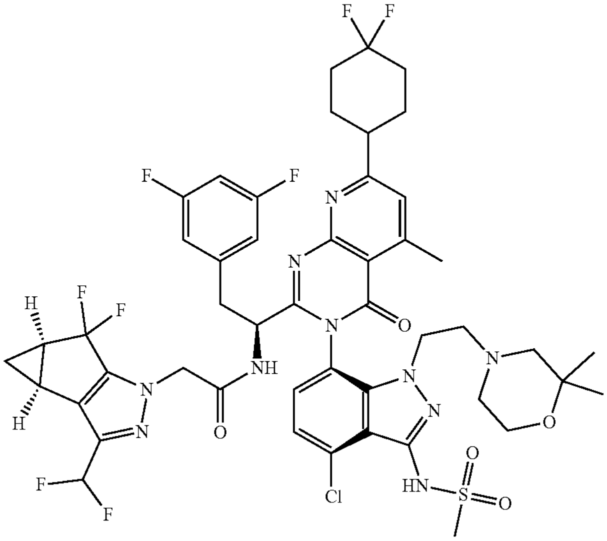 N-[(1S)-1-[(3P)-3-{4-chloro-1-[2-(2,2-dimethylmorpholin-4-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.77 min.; observed ion = 1065.30 [M + H]+. 1H NMR (500 MHz, METHANOL-d4) δ ppm 7.48 (d, J = 0.60 Hz, 1 H), 7.32-7.39 (m, 1 H), 7.28 (d, J = 7.75 Hz, 1 H), 6.49-6.84 (m, 4 H), 4.80 (dd, J = 9.54, 4.77 Hz, 1 H), 4.57-4.70 (m, 2 H), 4.20 (ddd, J = 13.93, 10.80, 5.66 Hz, 1 H), 3.75-3.84 (m, 1 H), 3.37-3.45 (m, 3 H), 3.26 (s, 3 H), 3.05 (br dd, J = 14.16, 9.39 Hz, 2 H), 2.86 (s, 3 H), 2.54-2.62 (m, 1 H), 2.41-2.51 (m, 3 H), 2.21-2.32 (m, 2 H), 2.07-2.15 (m, 6 H), 1.95-2.03 (m, 2 H), 1.86 (br d, J = 11.03 Hz, 1 H), 1.34-1.42 (m, 1 H), 1.01-1.07 (m, 1 H), 0.96 (s, 3 H), 0.89 (s, 3 H). |

TABLE A-continued

| Example No. (preparation of the Example) | Structure and IUPAC name | Characterising data (LCMS and/or NMR) |
|---|---|---|
| 480 (General Procedure A using Bromide A1 as the core reagent) | 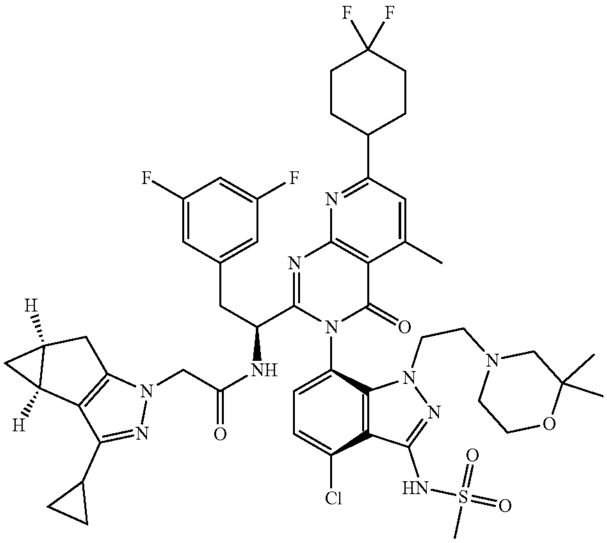 N-[(1S)-1-[(3P)-3-{4-chloro-1-[2-(2,2-dimethylmorpholin-4-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2}$,$^{4}$]nona-1(6),8-dien-7-yl]acetamide | LCMS Method A: retention time = 2.89 min.; observed ion = 1019.35 [M + H]+. 1H NMR (500 MHz, METHANOL-d4) δ ppm 7.32-7.41 (m, 1 H), 7.23-7.29 (m, 1 H), 7.16 (d, J = 7.75 Hz, 1 H), 6.64-6.74 (m, 1 H), 6.46 (dd, J = 8.05, 2.09 Hz, 2 H), 4.70 (dd, J = 9.24, 5.07 Hz, 1 H), 4.20 (d, J = 0.89 Hz, 2 H), 4.02 (ddd, J = 14.08, 10.36, 5.36 Hz, 1 H), 3.61-3.71 (m, 1 H), 3.28-3.38 (m, 3 H), 3.19 (s, 3 H), 2.95 (br dd, J = 13.86, 9.39 Hz, 2 H), 2.76 (d, J = 0.60 Hz, 3 H), 2.61 (dd, J = 16.54, 6.71 Hz, 1 H), 2.45-2.53 (m, 1 H), 2.33-2.42 (m, 2 H), 2.12-2.20 (m, 2 H), 1.97-2.06 (m, 6 H), 1.82-1.92 (m, 3 H), 1.73-1.80 (m, 2 H), 1.66-1.72 (m, 1 H), 0.86-0.91 (m, 1 H), 0.85 (s, 3 H), 0.80 (s, 3 H), 0.75-0.78 (m, 1 H), 0.63-0.72 (m, 2 H),-0.04-0.03 (m, 1 H). |
| 484 (General Procedure D using Chloride D2 as the core reagent) | 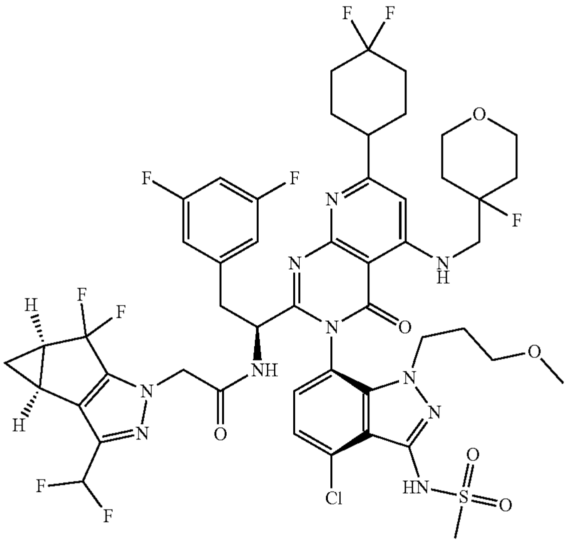 N-[(1S)-1-[(3P)-3-[4-chloro-3-methanesulfonamido-1-(3-methoxypropyl)-1H-indazol-7-yl]-7-(4,4-difluorocyclohexyl)-5-{[(4-fluorooxan-4-yl)methyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method B: retention time = 1.19 min.; observed ion = 1111.7 [M − H]. 1H NMR (500 MHz, METHANOL-d4) δ ppm 7.29 (d, J = 7.75 Hz, 1 H), 7.11 (d, J = 7.75 Hz, 1 H), 6.57-6.85 (m, 5 H), 4.83 (br d, J = 5.36 Hz, 1 H), 4.58 (s, 2 H), 4.04 (ddd, J = 14.16, 10.13, 5.81 Hz, 1 H), 3.79-3.87 (m, 3 H), 3.64-3.71 (m, 3 H), 3.56-3.64 (m, 1 H), 3.41 (dd, J = 14.01, 5.36 Hz, 2 H), 3.25 (s, 3 H), 3.12-3.17 (m, 2 H), 3.05 (dd, J = 13.86, 9.09 Hz, 1 H), 2.89 (s, 3 H), 2.83-2.88 (m, 1 H), 2.41-2.48 (m, 2 H), 2.21-2.28 (m, 2 H), 1.98-2.11 (m, 6 H), 1.77-1.92 (m, 6 H), 1.35-1.41 (m, 1 H), 1.00-1.07 (m, 1 H). |

TABLE A-continued

| Example No. (preparation of the Example) | Structure and IUPAC name | Characterising data (LCMS and/or NMR) |
|---|---|---|
| 485 (General Procedure D using Chloride D2 as the core reagent) | 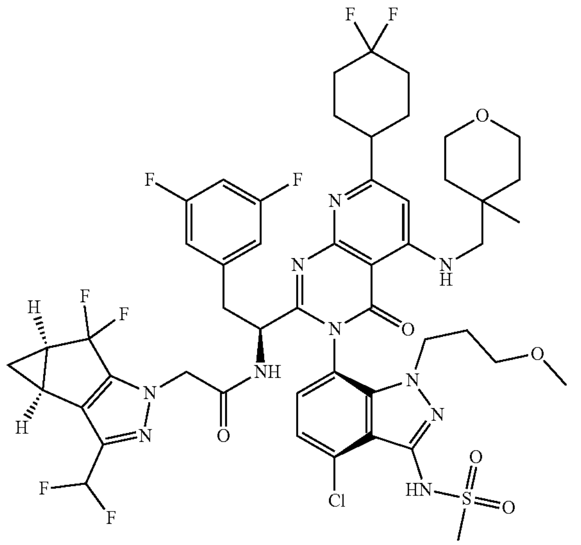 N-[(1S)-1-[(3P)-3-[4-chloro-3-methanesulfonamido-1-(3-methoxypropyl)-1H-indazol-7-yl]-7-(4,4-difluorocyclohexyl)-5-{[(4-methyloxan-4-yl)methyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method B: retention time = 1.19 min.; observed ion = 1107.4 [M − H]. 1H NMR (500 MHz, METHANOL-d4) δ ppm 9.16-9.26 (m, 1 H), 7.28 (d, J = 8.05 Hz, 1 H), 7.10 (d, J = 8.05 Hz, 1 H), 6.59-6.83 (m, 5 H), 4.85 (br d, J = 3.58 Hz, 1 H), 4.58 (s, 2 H), 4.00-4.08 (m, 1 H), 3.83 (ddd, J = 14.45, 9.98, 4.77 Hz, 1 H), 3.72-3.78 (m, 2 H), 3.62-3.69 (m, 2 H), 3.41 (dd, J = 14.16, 5.22 Hz, 1 H), 3.24 (s, 3 H), 3.15-3.19 (m, 2 H), 3.04-3.08 (m, 1 H), 2.90 (s, 3 H), 2.85-2.88 (m, 1 H), 2.44 (ddd, J = 11.62, 7.75, 4.17 Hz, 2 H), 2.21-2.30 (m, 2 H), 1.97-2.12 (m, 7 H), 1.82-1.93 (m, 2 H), 1.63 (ddd, J = 13.71, 9.39, 4.62 Hz, 2 H), 1.37-1.44 (m, 3 H), 1.34 (d, J = 6.56 Hz, 2 H), 1.12 (s, 3 H), 1.02-1.06 (m, 1 H). |
| 488 (General Procedure E-2 using Aldehyde E1 as the core reagent where the general procedure was modified as follows: the HCl salt of the amine was used; the reductive amination was conducted at 40° C.) | 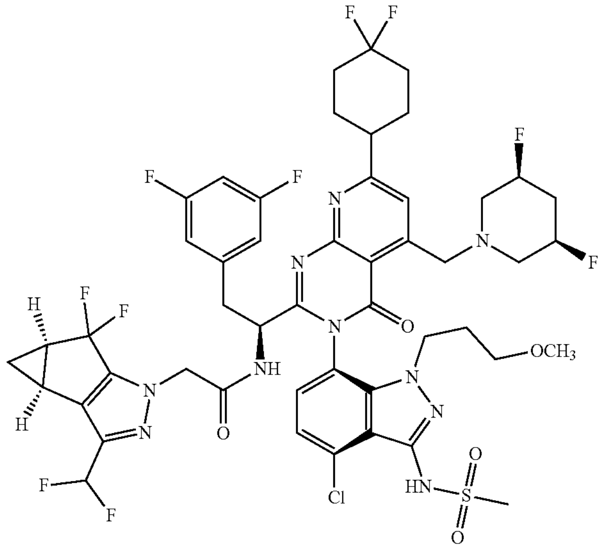 N-[(1S)-1-[(3P)-3-[4-chloro-3-methanesulfonamido-1-(3-methoxypropyl)-1H-indazol-7-yl]-7-(4,4-difluorocyclohexyl)-5-{[(3R,5S)-3,5-difluoropiperidin-1-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method A: retention time = 2.92 min.; observed ion = 1115.25 [M + H]+. 1H NMR (500 MHz, METHANOL-d4) δ ppm 8.06 (s, 1 H), 7.33 (d, J = 7.75 Hz, 1 H), 7.19 (d, J = 8.05 Hz, 1 H), 6.56-6.84 (m, 4 H), 4.82 (br d, J = 0.89 Hz, 1 H), 4.72 (br d, J = 3.58 Hz, 1 H), 4.60 (d, J = 2.38 Hz, 2 H), 4.26 (d, J = 2.68 Hz, 2 H), 4.02 (ddd, J = 14.38, 10.65, 5.66 Hz, 1 H), 3.84 (ddd, J = 14.23, 10.65, 5.22 Hz, 1 H), 3.43 (dd, J = 14.31, 5.07 Hz, 1 H), 3.26 (s, 3 H), 3.16-3.19 (m, 1 H), 3.05-3.13 (m, 3 H), 2.82-2.90 (m, 2 H), 2.70-2.80 (m, 5 H), 2.44 (td, J = 7.45, 3.87 Hz, 2 H), 2.22-2.32 (m, 2 H), 2.06-2.18 (m, 7 H), 1.98-2.04 (m, 1 H), 1.79-1.93 (m, 2 H), 1.35-1.41 (m, 1 H), 1.04 (dt, J = 3.73, 2.01 Hz, 1 H). |

TABLE A-continued

| Example No. (preparation of the Example) | Structure and IUPAC name | Characterising data (LCMS and/or NMR) |
|---|---|---|
| 489 (General Procedure E-2 using Aldehyde E1 as the core reagent, where the general procedure was moified as follows: the HCl salt of the amine was used; the reductive amination was conducted at 40° C.) | 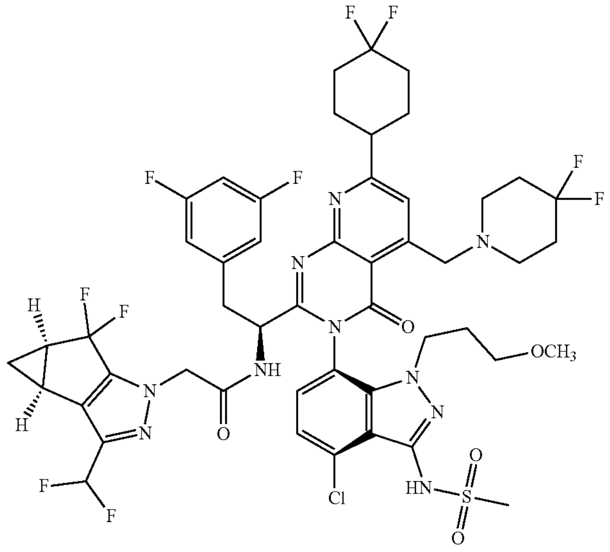 N-[(1S)-1-[(3P)-3-[4-chloro-3-methanesulfonamido-1-(3-methoxypropyl)-1H-indazol-7-yl]-7-(4,4-difluorocyclohexyl)-5-[(4,4-difluoropiperidin-1-yl)methyl]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.86 min.; observed ion = 1115.20 [M + H]+. 1H NMR (500 MHz, METHANOL-d4) δ ppm 7.84 (s, 1 H), 7.33 (d, J = 8.05 Hz, 1 H), 7.18 (d, J = 8.05 Hz, 1 H), 6.54-6.83 (m, 4 H), 4.86 (br d, J = 5.07 Hz, 1 H), 4.60 (d, J = 3.28 Hz, 2 H), 4.13-4.29 (m, 2 H), 3.98-4.08 (m, 1 H), 3.84 (ddd, J = 14.23, 10.36, 5.22 Hz, 1 H), 3.43 (dd, J = 14.01, 5.07 Hz, 1 H), 3.26 (s, 3 H), 3.03-3.20 (m, 5 H), 2.76 (s, 3 H), 2.70 (br t, J = 5.36 Hz, 4 H), 2.39-2.50 (m, 2 H), 2.22-2.33 (m, 2 H), 1.98-2.17 (m, 11 H), 1.79-1.92 (m, 2 H), 1.35-1.42 (m, 1 H), 0.99-1.07 (m, 1 H). |
| 491 (General Procedure A using Bromide A11 as the core reagent) | 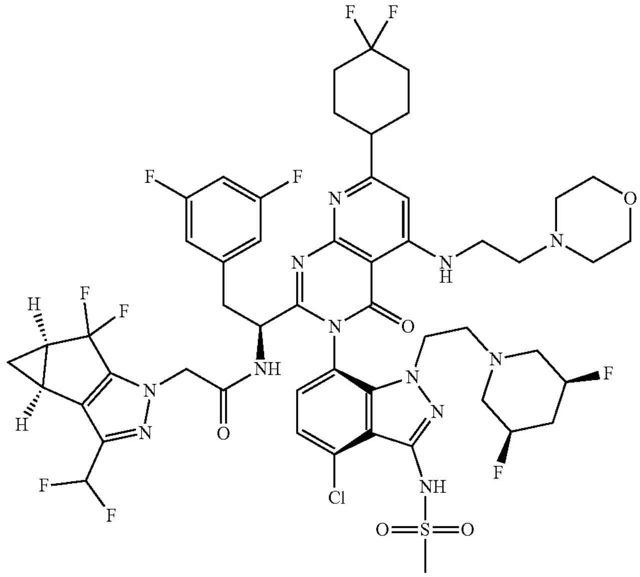 N-[(1S)-1-[(3P)-3-(4-chloro-1-{2-[(3R,5S)-3,5-difluoropiperidin-1-yl]ethyl}-3-methanesulfonamido-1H-indazol-7-yl)-7-(4,4-difluorocyclohexyl)-5-{[2-(morpholin-4-yl)ethyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 0.94 min.; observed ion = 1183.6 [M − H]. 1H NMR (500 MHz, METHANOL-d4) δ ppm 7.30 (d, J = 7.75 Hz, 1 H), 7.12 (d, J = 7.75 Hz, 1 H), 6.56-6.84 (m, 5 H), 4.76 (br d, J = 3.87 Hz, 1 H), 4.62 (d, J = 12.22 Hz, 2 H), 4.16-4.41 (m, 3 H), 3.71-3.78 (m, 1 H), 3.65 (t, J = 4.62 Hz, 4 H), 3.45-3.49 (m, 2 H), 3.41 (br d, J = 5.36 Hz, 1 H), 3.24 (s, 3 H), 3.04 (dd, J = 13.71, 8.94 Hz, 1 H), 2.79-2.92 (m, 2 H), 2.58-2.74 (m, 5 H), 2.42-2.53 (m, 6 H), 2.20-2.31 (m, 3 H), 1.97-2.16 (m, 7 H), 1.55-1.65 (m, 1 H), 1.30-1.41 (m, 3 H), 1.00-1.07 (m, 1 H). |

TABLE A-continued

| Example No. (preparation of the Example) | Structure and IUPAC name | Characterising data (LCMS and/or NMR) |
|---|---|---|
| 495 (General Procedure A using Bromide A1 as the core reagent) | 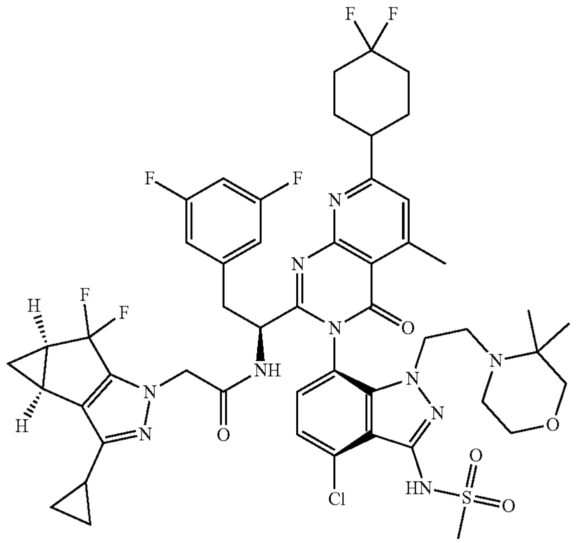 N-[(1S)-1-[(3P)-3-{4-chloro-1-[2-(3,3-dimethylmorpholin-4-yl)ethyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.18 min.; observed ion = 1017.6 [M − H]. 1H NMR (500 MHz, METHANOL-d4) δ ppm 7.35 (d, J = 0.60 Hz, 1 H), 7.22 (br d, J = 7.45 Hz, 1 H), 7.12 (d, J = 7.75 Hz, 1 H), 6.65-6.74 (m, 1 H), 6.45 (dd, J = 8.05, 2.09 Hz, 2 H), 4.72 (br d, J = 4.17 Hz, 1 H), 4.51-4.54 (m, 1 H), 4.23 (s, 2 H), 3.81-3.91 (m, 1 H), 3.51-3.60 (m, 1 H), 3.31-3.35 (m, 1 H), 3.26-3.30 (m, 2 H), 3.19 (br s, 3 H), 3.03 (br s, 2 H), 2.91-2.98 (m, 2 H), 2.76 (d, J = 0.60 Hz, 3 H), 2.58-2.69 (m, 2 H), 2.40 (d, J = 16.99 Hz, 1 H), 2.24-2.33 (m, 1 H), 2.07-2.20 (m, 3 H), 1.94-2.04 (m, 6 H), 1.82-1.87 (m, 1 H), 1.74-1.79 (m, 1 H), 1.66-1.73 (m, 1 H), 1.26 (s, 1 H), 0.88 (td, J = 7.60, 4.77 Hz, 1 H), 0.76-0.82 (m, 2 H), 0.63-0.71 (m, 7 H), 0.00 (q, J = 4.07 Hz, 1 H). |
| 498 (General Procedure D using Chloride D2 as the core reagent) | 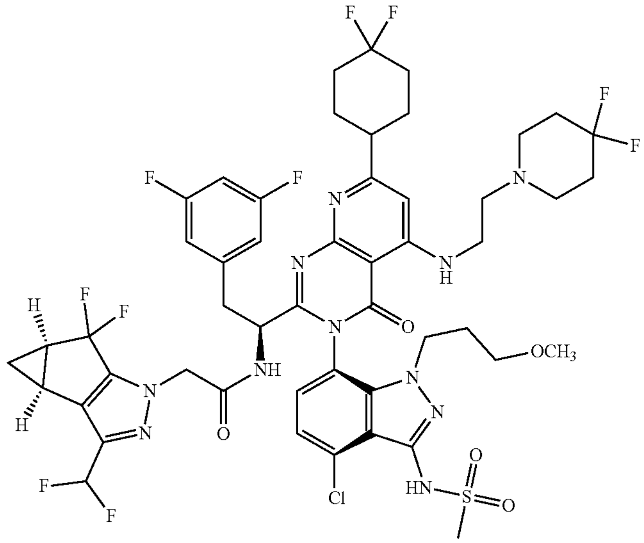 N-[(1S)-1-[(3P)-3-[4-chloro-3-methanesulfonamido-1-(3-methoxypropyl)-1H-indazol-7-yl]-7-(4,4-difluorocyclohexyl)-5-{[2-(4,4-difluoropiperidin-1-yl)ethyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.60 min.; observed ion = 1144.25 [M + H]+. 1H NMR (500 MHz, METHANOL-d4) δ ppm 7.31 (d, J = 8.05 Hz, 1 H), 7.10 (d, J = 8.05 Hz, 1 H), 6.56-6.82 (m, 5 H), 4.80-4.82 (m, 1 H), 4.59 (d, J = 2.98 Hz, 2 H), 4.06 (ddd, J = 14.08, 10.06, 6.26 Hz, 1 H), 3.80-3.87 (m, 1 H), 3.47 (t, J = 6.11 Hz, 2 H), 3.40 (br dd, J = 13.86, 5.22 Hz, 2 H), 3.25 (s, 3 H), 3.14-3.18 (m, 2 H), 3.05 (dd, J = 13.86, 9.09 Hz, 1 H), 2.94 (s, 3 H), 2.88 (br dd, J = 11.62, 7.45 Hz, 1 H), 2.69-2.77 (m, 2 H), 2.61 (br s, 4 H), 2.45 (ddd, J = 11.40, 7.53, 4.02 Hz, 2 H), 2.21-2.30 (m, 2 H), 1.99-2.15 (m, 6 H), 1.81 (s, 6 H), 1.39 (t, J = 6.85 Hz, 1 H), 1.02-1.07 (m, 1 H). |

TABLE A-continued

| Example No. (preparation of the Example) | Structure and IUPAC name | Characterising data (LCMS and/or NMR) |
|---|---|---|
| 500 (General Procedure D using Chloride D2 as the core reagent) | 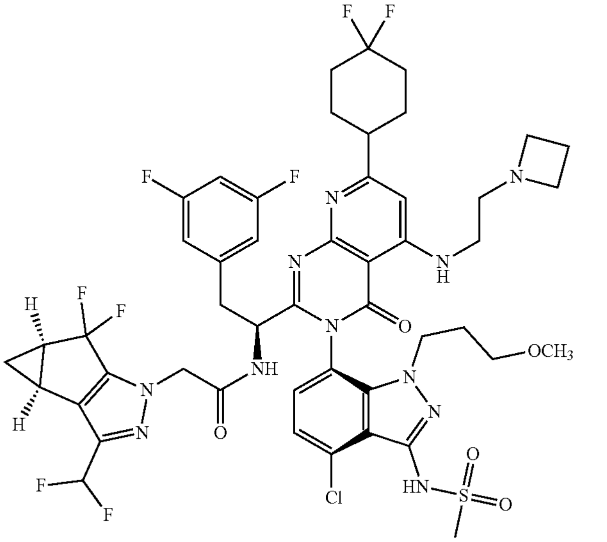<br>N-[(1S)-1-[(3P)-5-{[2-(azetidin-1-yl)ethyl]amino}-3-[4-chloro-3-methanesulfonamido-1-(3-methoxypropyl)-1H-indazol-7-yl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.35 min.; observed ion = 1080.15 [M + H]+.<br>1H NMR (500 MHz, METHANOL-d4) δ ppm 7.29 (d, J = 7.75 Hz, 1 H), 7.07 (d, J = 7.75 Hz, 1 H), 6.55-6.83 (m, 5 H), 4.82-4.85 (m, 1 H), 4.60 (d, J = 2.38 Hz, 2 H), 4.04 (ddd, J = 14.16, 9.98, 5.96 Hz, 1 H), 3.79-3.88 (m, 1 H), 3.62 (t, J = 7.45 Hz, 3 H), 3.47-3.52 (m, 2 H), 3.40 (dd, J = 13.86, 5.51 Hz, 1 H), 3.26 (s, 3 H), 3.13-3.18 (m, 2 H), 2.97-3.07 (m, 3 H), 2.93 (s, 3 H), 2.90 (br dd, J = 3.43, 1.64 Hz, 1 H), 2.40-2.47 (m, 2 H), 2.21-2.30 (m, 4 H), 1.96-2.13 (m, 7 H), 1.81-1.92 (m, 2 H), 1.35-1.41 (m, 1 H), 1.04 (ddd, J = 5.59, 3.80, 2.24 Hz, 1 H). |
| 501 (General Procedure B using Amine B26 as the core reagent) | 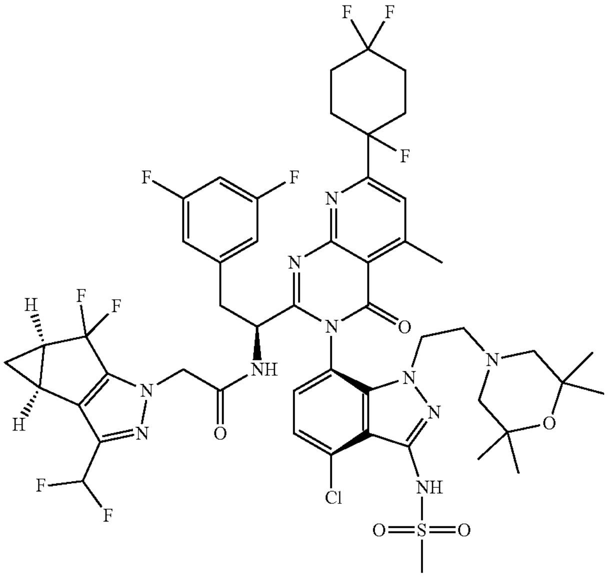<br>N-[(1S)-1-[(3P)-3-{4-chloro-3-methanesulfonamido-1-[2-(2,2,6,6-tetramethylmorpholin-4-yl)ethyl]-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 3.304 min.; observed ion = 1111.20 [M + H]+.<br>1H NMR (500 MHz, METHANOL-d4) δ ppm 0.94 (d, J = 2.98 Hz, 12 H), 1.01-1.06 (m, 1 H), 1.34-1.39 (m, 1 H), 1.85-1.93 (m, 2 H), 1.96-2.04 (m, 2 H), 2.09-2.31 (m, 6 H), 2.40-2.46 (m, 2 H), 2.47-2.67 (m, 4 H), 2.90 (s, 3 H), 3.05 (dd, J = 14.16, 9.69 Hz, 1 H), 3.24 (s, 3 H), 3.35-3.39 (m, 1 H), 3.82 (ddd, J = 13.78, 10.95, 4.77 Hz, 1 H), 4.20 (ddd, J = 13.71, 11.33, 5.36 Hz, 1 H), 4.59 (d, J = 5.36 Hz, 2 H), 4.93-5.00 (m, 1 H), 6.49-6.54 (m, 2 H), 6.66 (t, J = 54.84 Hz, 1 H), 6.74-6.79 (m, 1 H), 7.28 (d, J = 7.75 Hz, 1 H), 7.35 (d, J = 8.05 Hz, 1 H), 7.71-7.72 (m, 1 H). |

TABLE A-continued

| Example No. (preparation of the Example) | Structure and IUPAC name | Characterising data (LCMS and/or NMR) |
|---|---|---|
| 502 (General Procedure B using Amine B27 as the core reagent) | 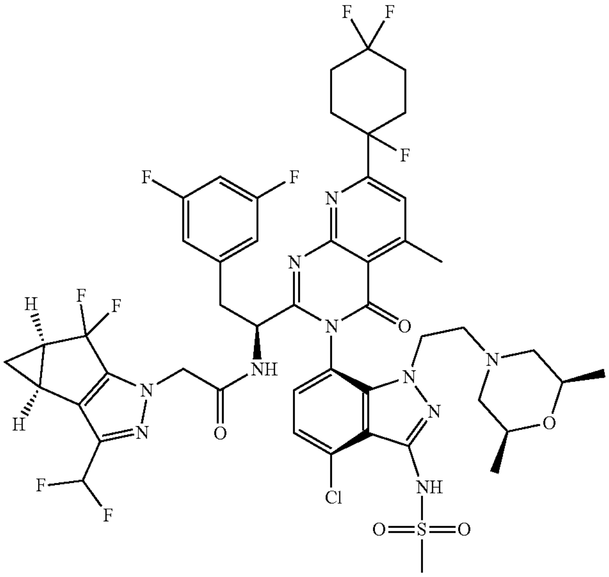 N-[(1S)-1-[(3P)-3-(4-chloro-1-{2-[(2R,6S)-2,6-dimethylmorpholin-4-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.891 min.; observed ion = 1083.15 [M + H]+. 1H NMR (500 MHz, METHANOL-d4) δ ppm 0.88 (d, J = 6.26 Hz, 3 H), 0.98-1.04 (m, 5 H), 1.34-1.39 (m, 1 H), 1.49 (br d, J = 2.38 Hz, 1 H), 1.61-1.70 (m, 1 H), 2.11-2.25 (m, 5 H), 2.27-2.45 (m, 4 H), 2.50-2.66 (m, 4 H), 2.70-2.77 (m, 1 H), 2.89-2.92 (m, 3 H), 3.05 (dd, J = 14.16, 9.69 Hz, 1 H), 3.25 (s, 3 H), 3.38 (br s, 1 H), 3.91 (td, J = 9.39, 4.47 Hz, 1 H), 4.18-4.25 (m, 1 H), 4.57-4.68 (m, 3 H), 4.76 (br s, 1 H), 6.48-6.52 (m, 2 H), 6.68 (t, J = 54.69 Hz, 1 H), 6.74-6.78 (m, 1 H), 7.31 (d, J = 8.05 Hz, 1 H), 7.36 (d, J = 7.75 Hz, 1 H), 7.73 (dd, J = 1.64, 0.74 Hz, 1 H). |
| 503 (General Procedure B using Amine B27 as the core reagent) | 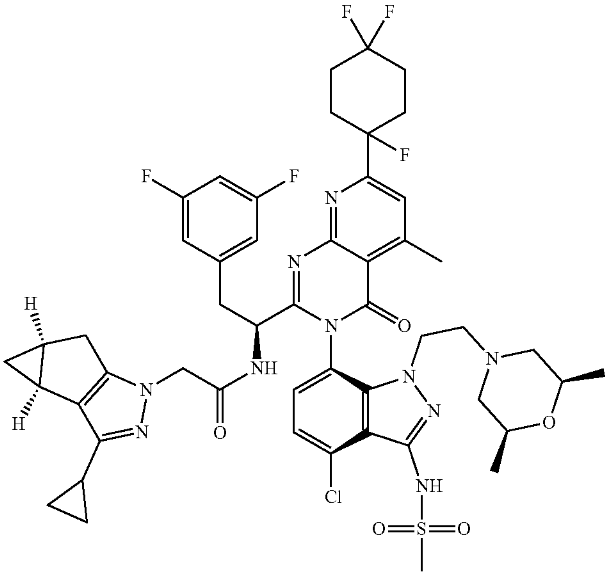 N-[(1S)-1-[(3P)-3-(4-chloro-1-{2-[(2R,6S)-2,6-dimethylmorpholin-4-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method A: retention time = 2.958 min.; observed ion = 1037.25 [M + H]+. 1H NMR (500 MHz, METHANOL-d4) δ ppm 0.06-0.09 (m, 1 H), 0.73-0.80 (m, 2 H), 0.83-1.02 (m, 11 H), 1.46 (br s, 1 H), 1.60-1.66 (m, 1 H), 1.75-1.81 (m, 1 H), 1.83-1.87 (m, 1 H), 1.90-1.95 (m, 1 H), 2.11-2.34 (m, 7 H), 2.47 (s, 1 H), 2.50-2.67 (m, 5 H), 2.69-2.75 (m, 1 H), 2.90 (s, 3 H), 3.04 (dd, J = 14.31, 9.54 Hz, 1 H), 3.28-3.29 (m, 3 H), 3.38 (d, J = 4.47 Hz, 1 H), 3.85-3.90 (m, 1 H), 4.13-4.19 (m, 1 H), 4.31 (d, J = 4.47 Hz, 2 H), 4.78 (br d, J = 4.77 Hz, 1 H), 6.52 (d, J = 6.90 Hz, 2 H), 6.78 (t, J = 8.34 Hz, 1 H), 7.29 (d, J = 7.75 Hz, 1 H), 7.36 (d, J = 8.05 Hz, 1 H), 7.73 (dd, J = 1.64, 0.75 Hz, 1 H). |

TABLE A-continued

| Example No. (preparation of the Example) | Structure and IUPAC name | Characterising data (LCMS and/or NMR) |
|---|---|---|
| 504 (General Procedure B using Amine B26 as the core reagent) | 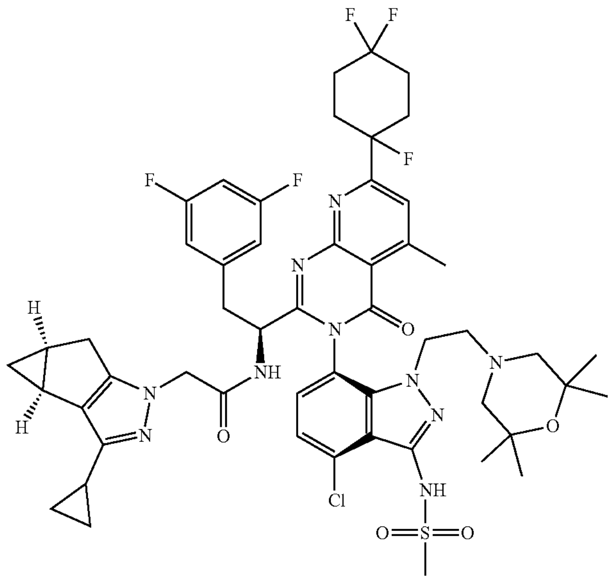 N-[(1S)-1-[(3P)-3-{4-chloro-3-methanesulfonamido-1-[2-(2,2,6,6-tetramethylmorpholin-4-yl)ethyl]-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method A: retention time = 3.398 min.; observed ion = 1065.25 [M + H]+. 1H NMR (500 MHz, METHANOL-d4) δ ppm 0.09 (q, J = 4.27 Hz, 1 H), 0.72-0.80 (m, 2 H), 0.86-1.00 (m, 15 H), 1.76-1.81 (m, 1 H), 1.83-1.91 (m, 3 H), 1.97-2.02 (m, 2 H), 2.09-2.27 (m, 5 H), 2.30 (br s, 1 H), 2.46 (d, J = 16.39 Hz, 1 H), 2.49-2.58 (m, 2 H), 2.62-2.73 (m, 2 H), 2.90 (d, J = 0.60 Hz, 3 H), 3.04 (dd, J = 14.31, 9.54 Hz, 1 H), 3.28 (s, 3 H), 3.34-3.39 (m, 1 H), 3.80-3.86 (m, 1 H), 4.11-4.17 (m, 1 H), 4.27 (s, 2 H), 4.78 (br dd, J = 9.54, 4.77 Hz, 3 H), 6.52 (dd, J = 8.05, 2.09 Hz, 2 H), 6.77 (t, J = 8.73 Hz, 1 H), 7.31 (d, J = 7.75 Hz, 1 H), 7.35-7.37 (m, 1 H), 7.72 (s, 1 H). |
| 505 (General Procedure B using Amine B28 as the core reagent) | 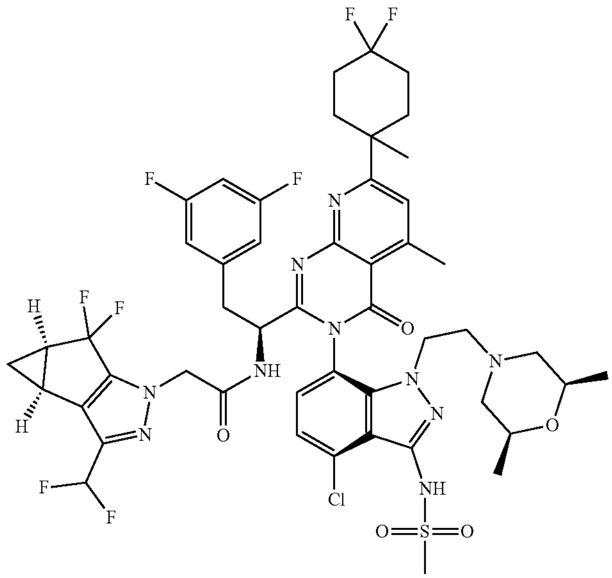 N-[(1S)-1-[(3P)-3-(4-chloro-1-{2-[(2R,6S)-2,6-dimethylmorpholin-4-yl]ethyl}-3-methanesulfonamido-1H-indazol-7-yl)-7-(4,4-difluoro-1-methylcyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.885 min.; observed ion = 1079.35 [M + H]+. 1H NMR (500 MHz, METHANOL-d4) δ ppm 0.87 (d, J = 6.56 Hz, 3 H), 0.98 (d, J = 6.26 Hz, 3 H), 1.00-1.04 (m, 1 H), 1.33-1.41 (m, 4 H), 1.48 (br t, J = 10.73 Hz, 1 H), 1.60 (br t, J = 10.43 Hz, 1 H), 1.81-1.94 (m, 4 H), 1.98-2.08 (m, 2 H), 2.32 (br dd, J = 11.47, 1.04 Hz, 1 H), 2.38-2.47 (m, 2 H), 2.51-2.59 (m, 2 H), 2.59-2.71 (m, 3 H), 2.85-2.89 (m, 3 H), 3.05 (dd, J = 14.16, 9.39 Hz, 1 H), 3.25 (s, 3 H), 3.37-3.39 (m, 1 H), 3.90 (td, J = 9.61, 4.92 Hz, 1 H), 4.22 (ddd, J = 14.31, 10.13, 5.96 Hz, 1 H), 4.56-4.70 (m, 4 H), 4.91-4.92 (m, 1 H), 6.50 (d, J = 6.89 Hz, 2 H), 6.68 (t, J = 54.69 Hz, 1 H), 6.73-6.78 (m, 1 H), 7.29 (d, J = 8.05 Hz, 1 H), 7.36 (d, J = 7.75 Hz, 1 H), 7.64 (d, J = 0.89 Hz, 1 H). |

TABLE A-continued

| Example No. (preparation of the Example) | Structure and IUPAC name | Characterising data (LCMS and/or NMR) |
|---|---|---|
| 506 (General Procedure B using Amine B26 as the core reagent) | 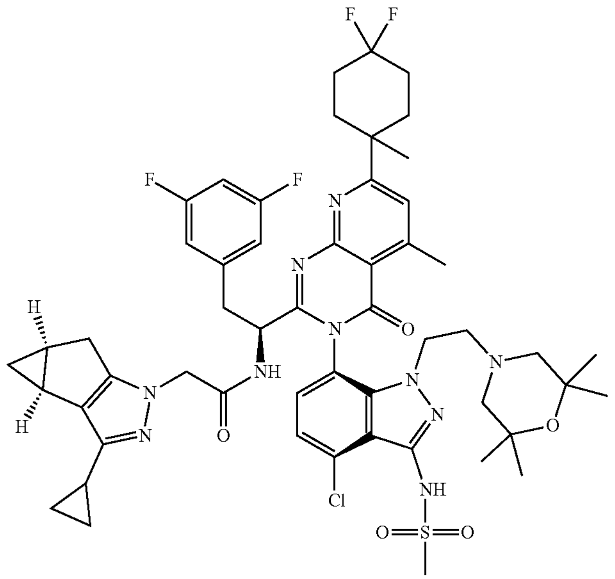 N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluoro-1-methylcyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method A: retention time = 3.406 min.; observed ion = 1061.25 [M + H]+. 1H NMR (500 MHz, METHANOL-d4) δ ppm 0.09 (d, J = 3.58 Hz, 1 H), 0.73-0.80 (m, 2 H), 0.84-0.89 (m, 2 H), 0.96 (s, 12 H), 1.36 (s, 3 H), 1.73-1.95 (m, 10 H), 1.98-2.08 (m, 4 H), 2.46 (d, J = 16.39 Hz, 1 H), 2.56-2.72 (m, 5 H), 2.86 (s, 3 H), 3.05 (dd, J = 14.01, 9.54 Hz, 1 H), 3.28 (s, 3 H), 3.37 (s, 1 H), 3.78-3.88 (m, 1 H), 4.10-4.20 (m, 1 H), 4.27 (s, 2 H), 6.51-6.57 (m, 2 H), 6.73-6.78 (m, 1 H), 7.29 (d, J = 8.05 Hz, 1 H), 7.36 (d, J = 7.75 Hz, 1 H), 7.63 (d, J = 0.60 Hz, 1 H), 8.10 (s, 1 H). |
| 507 (General Procedure B using Amine B26 as the core reagent) | 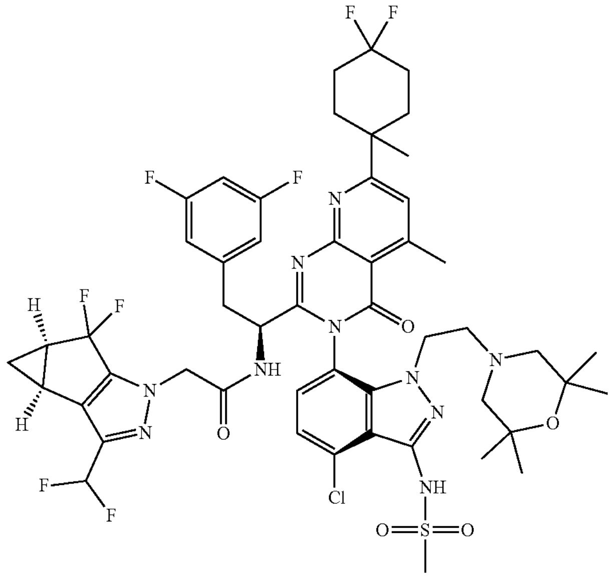 N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluoro-1-methylcyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 3.310 min.; observed ion = 1107.20 [M + H]+. 1H NMR (500 MHz, METHANOL-d4) δ ppm 0.95 (d, J = 5.36 Hz, 12 H), 1.01-1.05 (m, 1 H), 1.33-1.39 (m, 4 H), 1.76-1.97 (m, 7 H), 1.99-2.08 (m, 4 H), 2.38-2.47 (m, 2 H), 2.54-2.70 (m, 4 H), 2.85-2.88 (m, 3 H), 3.06 (dd, J = 14.16, 9.39 Hz, 1 H), 3.24 (s, 3 H), 3.36-3.39 (m, 1 H), 3.83-3.88 (m, 1 H), 4.22 (ddd, J = 13.64, 11.40, 5.66 Hz, 1 H), 4.60 (d, J = 4.77 Hz, 2 H), 6.49-6.54 (m, 2 H), 6.66 (br t, J = 54.69 Hz, 1 H), 6.73-6.78 (m, 1 H), 7.28 (d, J = 7.75 Hz, 1 H), 7.35 (d, J = 8.05 Hz, 1 H), 7.63 (d, J = 0.60 Hz, 1 H). |

TABLE A-continued

| Example No. (preparation of the Example) | Structure and IUPAC name | Characterising data (LCMS and/or NMR) |
|---|---|---|
| 508 (General Procedure B using Amine B28 as the core reagent) | 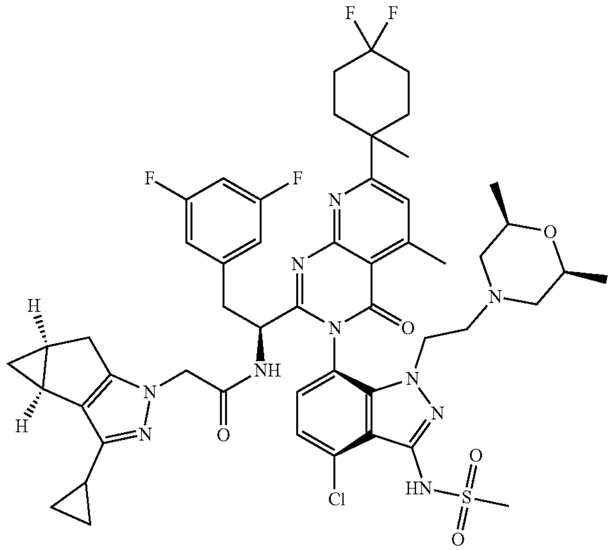<br>N-[(1S)-1-[(3P)-3-(4-chloro-1-{2-[(2R,6S)-2,6-dimethylmorpholin-4-yl]ethyl}-3-methanesulfonamido-1H-indazol-7-yl)-7-(4,4-difluoro-1-methylcyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method A: retention time = 2.958 min.; observed ion = 1033.25 [M + H]+. 1H NMR (500 MHz, METHANOL-d4) δ ppm 0.06-0.09 (m, 1 H), 0.72-0.81 (m, 2 H), 0.84-0.94 (m, 5 H), 1.02 (d, J = 6.26 Hz, 3 H), 1.37 (s, 3 H), 1.68 (s, 1 H), 1.74-1.95 (m, 9 H), 1.99-2.09 (m, 2 H), 2.44 (d, J = 16.39 Hz, 1 H), 2.51 (br d, J = 10.73 Hz, 1 H), 2.58-2.74 (m, 6 H), 2.87 (d, J = 0.60 Hz, 3 H), 3.07 (dd, J = 14.31, 9.54 Hz, 1 H), 3.29 (s, 3 H), 3.36-3.41 (m, 2 H), 3.93 (s, 1 H), 4.18-4.23 (m, 1 H), 4.29-4.37 (m, 2 H), 4.77 (d, J = 4.77 Hz, 1 H), 6.53 (d, J = 6.74 Hz, 2 H), 6.78 (t, J = 8.75 Hz, 1 H), 7.32 (d, J = 7.75 Hz, 1 H), 7.35-7.39 (m, 1 H), 7.64 (d, J = 0.89 Hz, 1 H), 8.16 (s, 1 H). |
| 509 (General Procedure D using Chloride D2 as the core reagent) | 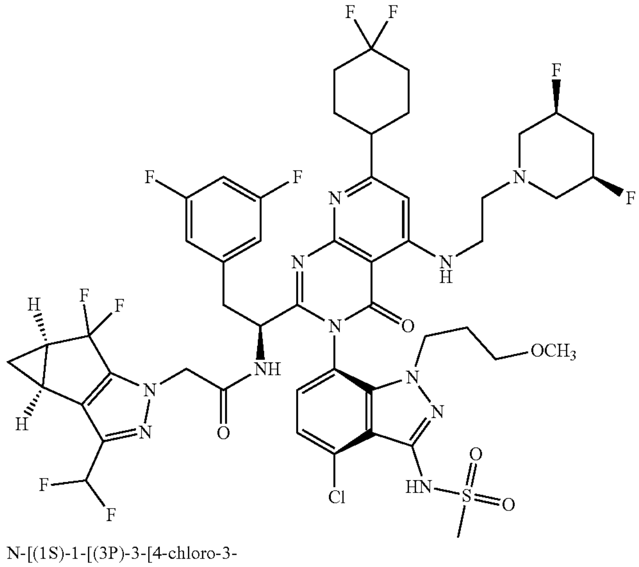<br>N-[(1S)-1-[(3P)-3-[4-chloro-3-methanesulfonamido-1-(3-methoxypropyl)-1H-indazol-7-yl]-7-(4,4-difluorocyclohexyl)-5-({2-[(3R,5S)-3,5-difluoropiperidin-1-yl]ethyl}amino)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.65 min.; observed ion = 1144.15 [M + H]+. 1H NMR (500 MHz, METHANOL-d4) δ ppm 7.19 (d, J = 7.75 Hz, 1 H), 6.98 (d, J = 8.05 Hz, 1 H), 6.43-6.70 (m, 5 H), 4.68 (dd, J = 8.94, 5.36 Hz, 1 H), 4.49-4.53 (m, 1 H), 4.47 (d, J = 2.98 Hz, 2 H), 4.34-4.41 (m, 1 H), 3.93 (ddd, J = 14.08, 10.21, 6.11 Hz, 1 H), 3.67-3.75 (m, 1 H), 3.36-3.39 (m, 2 H), 3.26-3.30 (m, 1 H), 3.14 (s, 3 H), 3.00-3.07 (m, 2 H), 2.92 (dd, J = 13.86, 9.09 Hz, 1 H), 2.75-2.86 (m, 5 H), 2.64-2.72 (m, 2 H), 2.23-2.36 (m, 4 H), 2.07-2.16 (m, 2 H), 1.85-2.02 (m, 5 H), 1.68-1.82 (m, 2 H), 1.58-1.66 (m, 1 H), 1.26 (t, J = 6.71 Hz, 1 H), 0.89-0.95 (m, 1 H). |

TABLE A-continued

| Example No. (preparation of the Example) | Structure and IUPAC name | Characterising data (LCMS and/or NMR) |
|---|---|---|
| 512 (General Procedure A using Bromide A9 as the core reagent) | 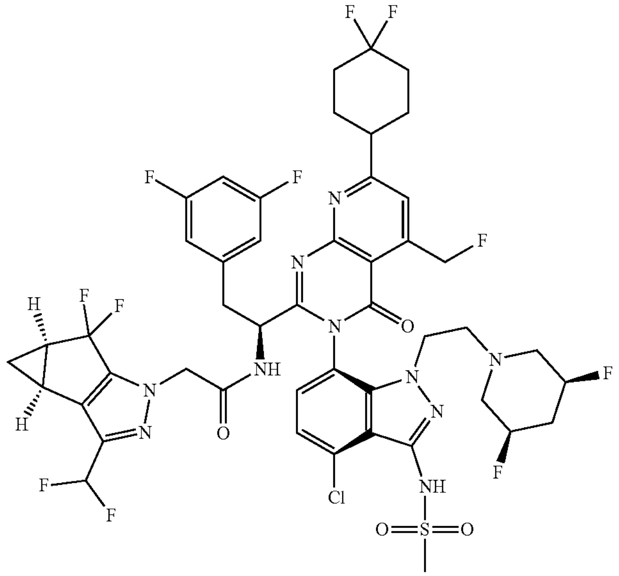 N-[(1S)-1-[(3P)-3-(4-chloro-1-{2-[(3R,5S)-3,5-difluoropiperidin-1-yl]ethyl}-3-methanesulfonamido-1H-indazol-7-yl)-7-(4,4-difluorocyclohexyl)-5-(fluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.99 min.; observed ion = 1089.20 [M + H]+. 1H NMR (500 MHz, METHANOL-d4) δ ppm 7.75 (s, 1 H), 7.31-7.40 (m, 1 H), 7.21-7.30 (m, 1 H), 6.52-6.85 (m, 5 H), 5.90-6.15 (m, 2 H), 4.83 (dd, J = 9.54, 4.77 Hz, 1 H), 4.53-4.67 (m, 2 H), 4.26-4.46 (m, 2 H), 4.10-4.20 (m, 1 H), 3.73-3.83 (m, 1 H), 3.40-3.44 (m, 1 H), 3.27 (s, 3 H), 3.13-3.20 (m, 1 H), 3.08 (dd, J = 14.16, 9.39 Hz, 1 H), 2.66-2.82 (m, 2 H), 2.42-2.55 (m, 4 H), 2.19-2.31 (m, 5 H), 1.97-2.18 (m, 8 H), 1.65-1.77 (m, 1 H), 1.38 (br d, J = 7.15 Hz, 1 H), 0.98-1.06 (m, 1 H). |
| 513 (General Procedure A using Bromide A9 as the core reagent) | 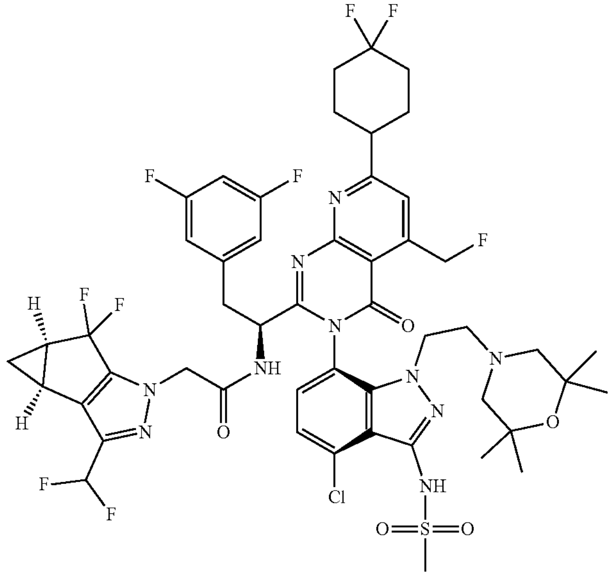 N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-(fluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide. | LCMS Method A: retention time = 3.22 min.; observed ion = 1111.20 [M + H]+. 1H NMR (500 MHz, METHANOL-d4) δ ppm 7.76 (s, 1 H), 7.34-7.40 (m, 1 H), 7.26-7.33 (m, 1 H), 6.51-6.82 (m, 4 H), 6.06-6.10 (m, 1 H), 5.99 (d, J = 1.79 Hz, 1 H), 4.82-4.84 (m, 1 H), 4.61 (d, J = 2.68 Hz, 2 H), 4.20 (ddd, J = 13.71, 11.33, 5.36 Hz, 1 H), 3.79 (ddd, J = 13.86, 11.18, 5.07 Hz, 1 H), 3.40 (dd, J = 14.01, 4.47 Hz, 1 H), 3.25 (s, 3 H), 3.14-3.19 (m, 1 H), 3.08 (dd, J = 14.16, 9.69 Hz, 1 H), 2.63 (td, J = 11.62, 5.36 Hz, 1 H), 2.48-2.55 (m, 1 H), 2.40-2.47 (m, 2 H), 2.21-2.33 (m, 2 H), 2.05-2.16 (m, 5 H), 1.99 (d, J = 11.03 Hz, 2 H), 1.90 (d, J = 10.73 Hz, 2 H), 1.36-1.42 (m, 1 H), 1.03-1.07 (m, 1 H), 0.96 (d, J = 2.09 Hz, 12 H). |

TABLE A-continued

| Example No. (preparation of the Example) | Structure and IUPAC name | Characterising data (LCMS and/or NMR) |
|---|---|---|
| 514 (General Procedure A using Bromide A9 as the core reagent) | 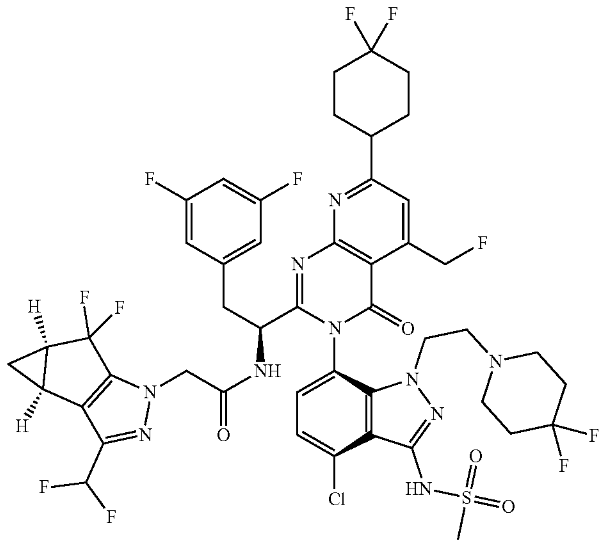 N-[(1S)-1-[(3P)-3-{4-chloro-1-[2-(4,4-difluoropiperidin-1-yl)ethyl]-3-methanesulfonamido-1H-indazol-7-yl}-7-(4,4-difluorocyclohexyl)-5-(fluoromethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.89 min.; observed ion = 1089.15 [M + H]+. 1H NMR (500 MHz, METHANOL-d4) δ ppm 7.77 (s, 1 H), 7.35-7.41 (m, 1 H), 7.29-7.34 (m, 1 H), 6.50-6.82 (m, 4 H), 5.89-6.13 (m, 2 H), 4.81 (dd, J = 9.69, 4.32 Hz, 1 H), 4.56-4.73 (m, 2 H), 4.19 (ddd, J = 14.01, 9.84, 5.96 Hz, 1 H), 3.78 (ddd, J = 14.16, 9.39, 5.07 Hz, 1 H), 3.41 (dd, J = 14.31, 4.47 Hz, 1 H), 3.26 (s, 3 H), 3.15-3.21 (m, 1 H), 3.08 (dd, J = 14.31, 9.84 Hz, 1 H), 2.70 (ddd, J = 12.37, 9.69, 5.96 Hz, 1 H), 2.56 (ddd, J = 12.37, 9.69, 4.77 Hz, 1 H), 2.45 (ddd, J = 11.18, 7.60, 3.87 Hz, 2 H), 2.20-2.32 (m, 6 H), 1.98-2.18 (m, 7 H), 1.61-1.74 (m, 4 H), 1.35-1.43 (m, 1 H), 1.01-1.08 (m, 1 H). |
| 515 (General Procedure D using Chloride D2 as the core reagent) | 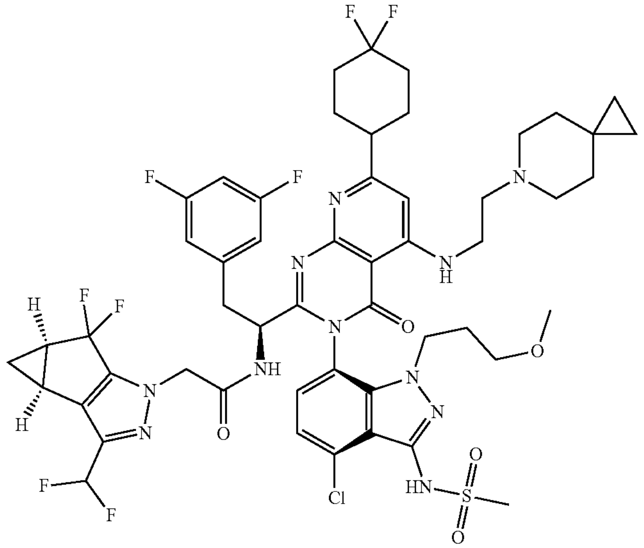 N-[(1S)-1-[(3P)-5-[(2-{6-azaspiro[2.5]octan-6-yl}ethyl)amino]-3-[4-chloro-3-methanesulfonamido-1-(3-methoxypropyl)-1H-indazol-7-yl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 0.99 min.; observed ion = 1134.3 [M + H]. 1H NMR (500 MHz, METHANOL-d4) δ ppm 7.30 (d, J = 7.75 Hz, 1 H), 7.06 (d, J = 7.75 Hz, 1 H), 6.52-6.84 (m, 5 H), 4.82-4.84 (m, 1 H), 4.61 (d, J = 2.68 Hz, 2 H), 4.03-4.11 (m, 1 H), 3.80-3.88 (m, 1 H), 3.48 (br d, J = 3.28 Hz, 2 H), 3.39-3.43 (m, 1 H), 3.26 (s, 3 H), 3.14-3.18 (m, 2 H), 3.02-3.08 (m, 1 H), 2.95 (s, 3 H), 2.85-2.92 (m, 1 H), 2.61-2.74 (m, 2 H), 2.40-2.50 (m, 3 H), 2.17-2.31 (m, 4 H), 1.94-2.14 (m, 7 H), 1.84-1.91 (m, 2 H), 1.54-1.64 (m, 2 H), 1.36-1.41 (m, 1 H), 1.25 (br d, J = 5.36 Hz, 2 H), 1.18 (d, J = 5.96 Hz, 1 H), 1.05 (br dd, J = 3.58, 1.19 Hz, 1 H). |

TABLE A-continued

| Example No. (preparation of the Example) | Structure and IUPAC name | Characterising data (LCMS and/or NMR) |
|---|---|---|
| 517 (General Procedure D using Chloride D2 as the core reagent) | 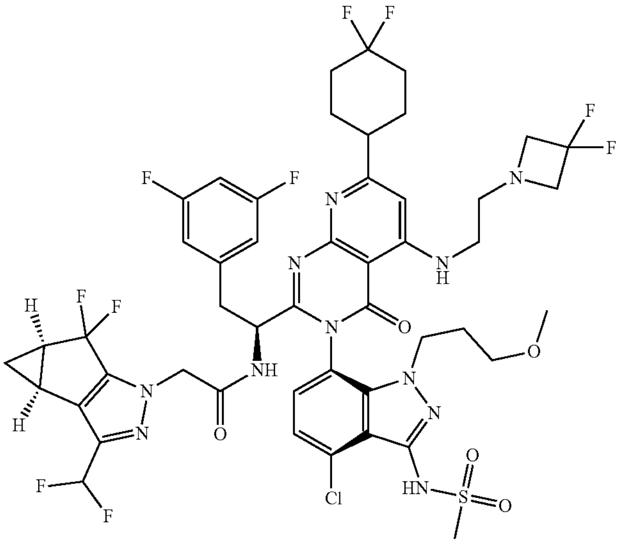 N-[(1S)-1-[(3P)-3-[4-chloro-3-methanesulfonamido-1-(3-methoxypropyl)-1H-indazol-7-yl]-5-{[2-(3,3-difluoroazetidin-1-yl)ethyl]amino}-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.17 min.; observed ion = 1116.4 [M + H]. 1H NMR (500 MHz, METHANOL-d4) δ ppm 7.29 (d, J = 8.05 Hz, 1 H), 7.09 (d, J = 8.05 Hz, 1 H), 6.55-6.82 (m, 5 H), 4.83 (br d, J = 3.87 Hz, 1 H), 4.60 (d, J = 2.68 Hz, 2 H), 4.04 (ddd, J = 13.93, 10.06, 6.11 Hz, 1 H), 3.78-3.88 (m, 1 H), 3.65 (t, J = 12.22 Hz, 4 H), 3.40-3.44 (m, 2 H), 3.25 (s, 3 H), 3.16 (t, J = 5.81 Hz, 2 H), 3.04 (dd, J = 13.86, 9.09 Hz, 2 H), 2.93 (s, 3 H), 2.84-2.91 (m, 4 H), 2.41-2.48 (m, 2 H), 2.21-2.30 (m, 2 H), 1.96-2.14 (m, 7 H), 1.82-1.92 (m, 2 H), 1.35-1.40 (m, 1 H), 1.03-1.07 (m, 1 H). |
| 519 (General Procedure D using Chloride D2 as the core reagent) | 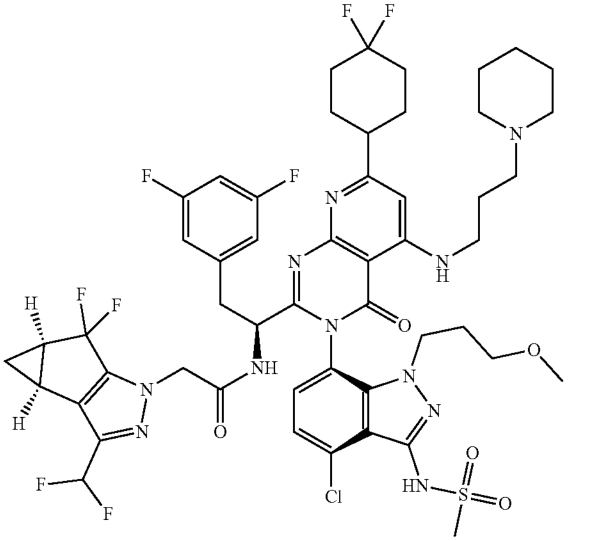 N-[(1S)-1-[(3P)-3-[4-chloro-3-methanesulfonamido-1-(3-methoxypropyl)-1H-indazol-7-yl]-7-(4,4-difluorocyclohexyl)-4-oxo-5-{[3-(piperidin-1-yl)propyl]amino}-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 0.91 min.; observed ion = 1120.5 [M − H]. 1H NMR (500 MHz, METHANOL-d4) δ ppm 7.41-7.46 (m, 1 H), 7.18-7.23 (m, 1 H), 6.71-6.99 (m, 6 H), 4.95-4.98 (m, 1 H), 4.74 (s, 2 H), 4.15-4.24 (m, 1 H), 3.95-4.00 (m, 1 H), 3.60-3.64 (m, 3 H), 3.53-3.57 (m, 4 H), 3.44-3.45 (m, 1 H), 3.41 (s, 3 H), 3.28-3.36 (m, 2 H), 3.06-3.09 (m, 3 H), 2.95-3.05 (m, 5 H), 2.59 (br d, J = 2.09 Hz, 2 H), 2.36-2.43 (m, 2 H), 2.14-2.28 (m, 8 H), 1.87 (br d, J = 6.56 Hz, 4 H), 1.72 (td, J = 3.28, 2.38 Hz, 2 H), 1.50-1.55 (m, 1 H), 1.29-1.34 (m, 1 H), 1.16-1.20 (m, 1 H). |

TABLE A-continued

| Example No. (preparation of the Example) | Structure and IUPAC name | Characterising data (LCMS and/or NMR) |
|---|---|---|
| 521 (General Procedure D using Chloride D2 as the core reagent) | 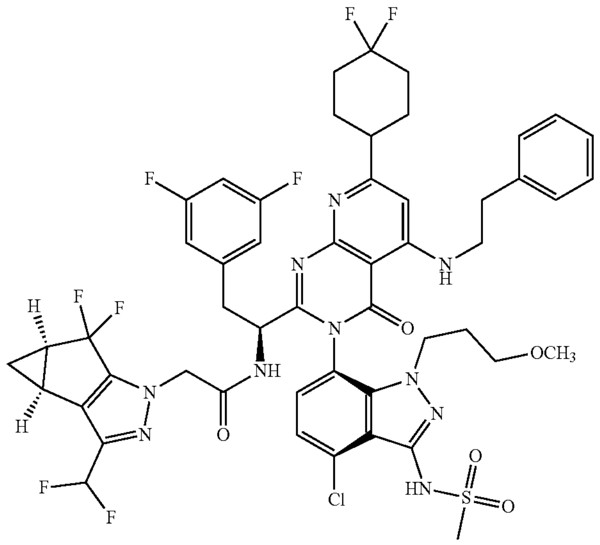 N-[(1S)-1-[(3P)-3-[4-chloro-3-methanesulfonamido-1-(3-methoxypropyl)-1H-indazol-7-yl]-7-(4,4-difluorocyclohexyl)-4-oxo-5-[(2-phenylethyl)amino]-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method B: retention time = 1.27 min.; observed ion = 1101.3 [M + H]. 1H NMR (500 MHz, METHANOL-d4) δ ppm 7.15-7.34 (m, 7 H), 7.07 (d, J = 8.05 Hz, 1 H), 6.54-6.82 (m, 5 H), 6.53 (s, 1 H), 4.81 (br d, J = 5.36 Hz, 1 H), 4.58 (d, J = 1.49 Hz, 2 H), 4.01 (ddd, J = 14.08, 10.21, 5.51 Hz, 1 H), 3.78 (ddd, J = 14.38, 9.91, 4.92 Hz, 1 H), 3.61-3.68 (m, 2 H), 3.37-3.41 (m, 1 H), 3.26 (s, 3 H), 3.07-3.10 (m, 1 H), 2.92-3.05 (m, 5 H), 2.91-3.13 (m, 1 H), 2.85 (s, 3 H), 2.79-2.84 (m, 1 H), 2.43 (td, J = 7.60, 3.87 Hz, 2 H), 2.20-2.28 (m, 2 H), 1.93-2.10 (m, 6 H), 1.91-2.10 (m, 1 H), 1.73-1.87 (m, 1 H), 1.66-1.87 (m, 1 H), 1.35-1.40 (m, 1 H), 1.04 (td, J = 3.95, 2.24 Hz, 1 H). |
| 522 (General Procedure D using Chloride D2 as the core reagent) | 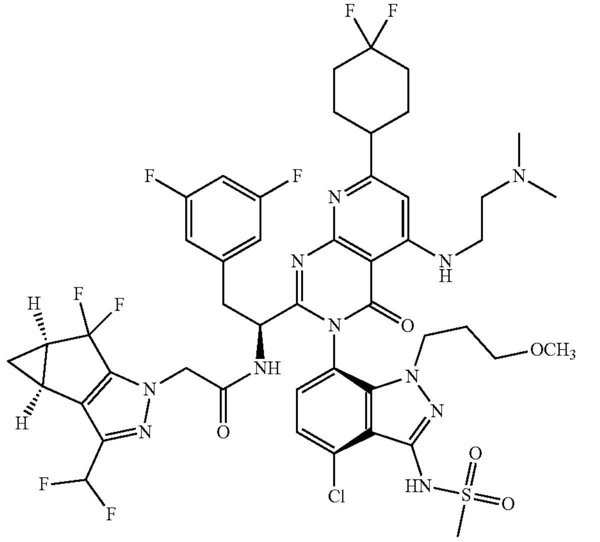 N-[(1S)-1-[(3P)-3-[4-chloro-3-methanesulfonamido-1-(3-methoxypropyl)-1H-indazol-7-yl]-7-(4,4-difluorocyclohexyl)-5-{[2-(dimethylamino)ethyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method B: retention time = 0.92 min.; observed ion = 1066.5 [M − H]. 1H NMR (500 MHz, METHANOL-d4) δ ppm 7.30 (d, J = 8.05 Hz, 1 H), 7.08 (d, J = 8.05 Hz, 1 H), 6.57-6.83 (m, 6 H), 4.83 (d, J = 3.58 Hz, 1 H), 4.59 (d, J = 1.79 Hz, 2 H), 4.00-4.08 (m, 1 H), 3.80-3.87 (m, 1 H), 3.54-3.58 (m, 2 H), 3.41 (br dd, J = 13.56, 5.22 Hz, 2 H), 3.26 (s, 3 H), 3.15-3.18 (m, 2 H), 3.05 (dd, J = 13.86, 8.79 Hz, 1 H), 2.94 (s, 3 H), 2.87-2.92 (m, 1 H), 2.76-2.83 (m, 2 H), 2.44 (s, 6 H), 2.22-2.30 (m, 2 H), 1.97-2.14 (m, 6 H), 1.81-1.92 (m, 2 H), 1.35-1.42 (m, 1 H), 1.04 (dt, J = 3.43, 1.86 Hz, 1 H). |

TABLE A-continued

| Example No. (preparation of the Example) | Structure and IUPAC name | Characterising data (LCMS and/or NMR) |
|---|---|---|
| 523 (General Procedure D using Chloride D2 as the core reagent) | 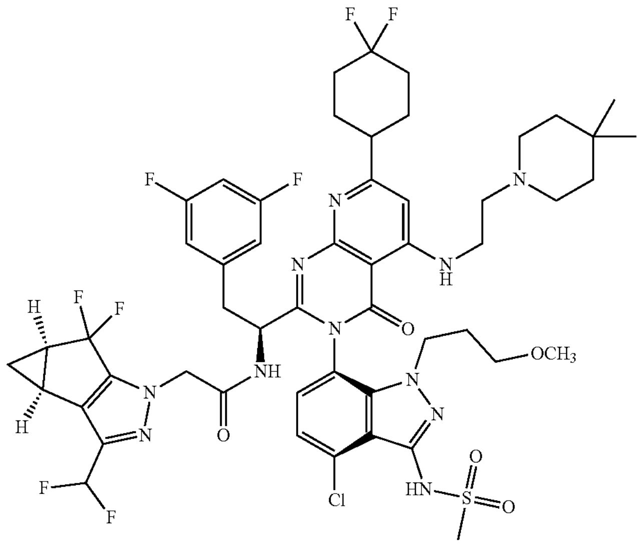 N-[(1S)-1-[(3P)-3-[4-chloro-3-methanesulfonamido-1-(3-methoxypropyl)-1H-indazol-7-yl]-7-(4,4-difluorocyclohexyl)-5-{[2-(4,4-dimethylpiperidin-1-yl)ethyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.00 min.; observed ion = 1136.4 [M + H]. 1H NMR (500 MHz, METHANOL-d4) δ ppm 7.30 (d, J = 7.75 Hz, 1 H), 7.09 (d, J = 8.05 Hz, 1 H), 6.53-6.83 (m, 6 H), 4.82 (br s, 1 H), 4.59 (d, J = 2.09 Hz, 2 H), 4.01-4.10 (m, 1 H), 3.81-3.88 (m, 1 H), 3.53 (br t, J = 6.71 Hz, 2 H), 3.42 (br d, J = 5.36 Hz, 1 H), 3.25 (s, 3 H), 3.16 (t, J = 5.81 Hz, 2 H), 3.05 (dd, J = 13.71, 8.94 Hz, 1 H), 2.93 (s, 3 H), 2.87-2.92 (m, 1 H), 2.71-2.79 (m, 2 H), 2.58 (br s, 4 H), 2.41-2.47 (m, 2 H), 2.22-2.29 (m, 2 H), 2.00-2.13 (m, 6 H), 1.84-1.93 (m, 2 H), 1.37-1.44 (m, 5 H), 1.03-1.06 (m, 1 H), 0.93 (s, 6 H). |
| 525 (General Procedure A using Bromide A12 as the core reagent) | 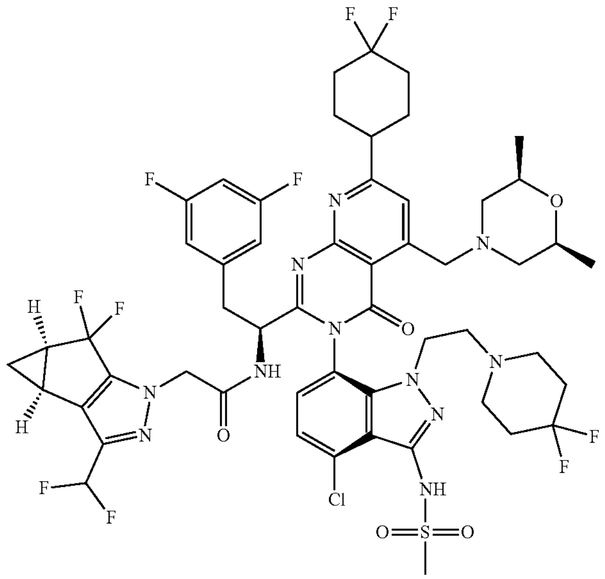 N-[(1S)-1-[(3P)-3-{4-chloro-1-[2-(4,4-difluoropiperidin-1-yl)ethyl]-3-methanesulfonamido-1H-indazol-7-yl}-7-(4,4-difluorocyclohexyl)-5-{[(2R,6S)-2,6-dimethylmorpholin-4-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.61 min.; observed ion = 1184.15 [M + H]+. 1H NMR (500 MHz, METHANOL-d4) δ ppm 7.85 (s, 1 H), 7.34-7.44 (m, 1 H), 7.28 (d, J = 8.05 Hz, 1 H), 6.51-6.84 (m, 4 H), 4.81 (d, J = 4.77 Hz, 1 H), 4.62-4.69 (m, 2 H), 4.22-4.29 (m, 1 H), 4.18 (dt, J = 14.16, 5.14 Hz, 1 H), 4.09 (d, J = 16.99 Hz, 1 H), 3.74-3.88 (m, 3 H), 3.40-3.44 (m, 1 H), 3.27 (s, 3 H), 3.12-3.17 (m, 1 H), 3.07 (dd, J = 14.01, 9.54 Hz, 1 H), 2.84 (br t, J = 9.98 Hz, 2 H), 2.73-2.80 (m, 1 H), 2.60 (ddd, J = 12.29, 10.06, 5.36 Hz, 1 H), 2.41-2.49 (m, 2 H), 2.21-2.33 (m, 6 H), 2.07-2.17 (m, 5 H), 1.89-2.01 (m, 2 H), 1.62-1.76 (m, 4 H), 1.35-1.43 (m, 1 H), 1.15 (dd, J = 6.26, 1.79 Hz, 6 H), 1.01-1.06 (m, 1 H). |

TABLE A-continued

| Example No. (preparation of the Example) | Structure and IUPAC name | Characterising data (LCMS and/or NMR) |
|---|---|---|
| 526 (General Procedure A using Bromide A12 as the core reagent) | 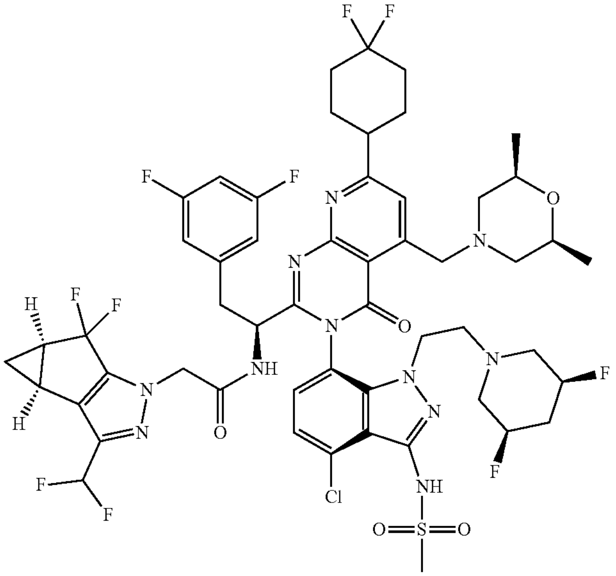<br>N-[(1S)-1-[(3P)-3-(4-chloro-1-{2-[(3R,5S)-3,5-difluoropiperidin-1-yl]ethyl}-3-methanesulfonamido-1H-indazol-7-yl)-7-(4,4-difluorocyclohexyl)-5-{[(2R,6S)-2,6-dimethylmorpholin-4-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method A: retention time = 2.72 min.; observed ion = 1184.30 [M + H]+.<br>1H NMR (500 MHz, METHANOL-d4) δ ppm 7.83 (s, 1 H), 7.35 (d, J = 8.05 Hz, 1 H), 7.23 (d, J = 8.05 Hz, 1 H), 6.54-6.82 (m, 4 H), 4.82 (d, J = 4.47 Hz, 1 H), 4.63 (d, J = 11.62 Hz, 2 H), 4.27-4.44 (m, 2 H), 4.12-4.24 (m, 3 H), 3.73-3.84 (m, 3 H), 3.40-3.45 (m, 1 H), 3.27 (s, 3 H), 3.04-3.15 (m, 3 H), 2.81-2.87 (m, 2 H), 2.68-2.80 (m, 2 H), 2.42-2.61 (m, 4 H), 2.20-2.32 (m, 3 H), 2.06-2.19 (m, 8 H), 2.00-2.05 (m, 1 H), 1.89-1.97 (m, 2 H), 1.60-1.67 (m, 1 H), 1.34-1.42 (m, 1 H), 1.14 (dd, J = 6.26, 2.98 Hz, 6 H), 0.98-1.06 (m, 1 H). |
| 527 (General Procedure A using Bromide A12 as the core reagent) | 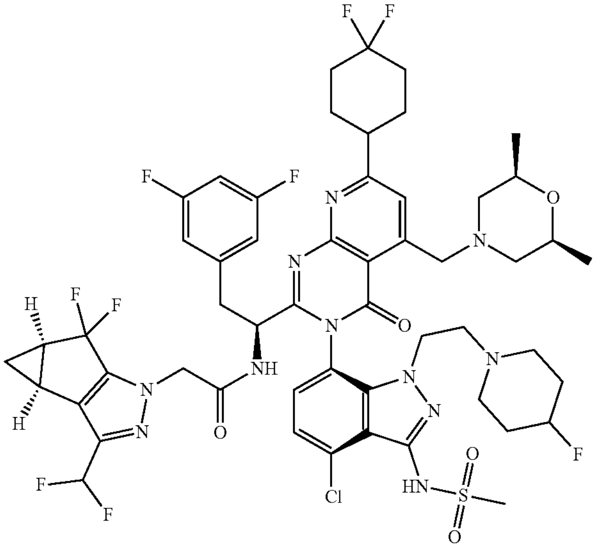<br>N-[(1S)-1-[(3P)-3-{4-chloro-1-[2-(4-fluoropiperidin-1-yl)ethyl]-3-methanesulfonamido-1H-indazol-7-yl}-7-(4,4-difluorocyclohexyl)-5-{[(2R,6S)-2,6-dimethylmorpholin-4-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method E: retention time = 3.43 min.; observed ion = 1166.30 [M + H]+.<br>1H NMR (500 MHz, METHANOL-d4) δ ppm 7.85 (s, 1 H), 7.38 (d, J = 8.05 Hz, 1 H), 7.28-7.34 (m, 1 H), 6.52-6.84 (m, 4 H), 4.77-4.80 (m, 1 H), 4.64-4.70 (m, 2 H), 4.18-4.27 (m, 2 H), 4.07-4.13 (m, 1 H), 3.89-3.98 (m, 1 H), 3.73-3.82 (m, 2 H), 3.42-3.46 (m, 1 H), 3.27 (s, 3 H), 3.06-3.16 (m, 2 H), 2.71-2.93 (m, 4 H), 2.42-2.56 (m, 4 H), 2.23-2.40 (m, 4 H), 2.03-2.16 (m, 6 H), 1.92-1.97 (m, 1 H), 1.55-1.83 (m, 4 H), 1.36-1.42 (m, 1 H), 1.14 (dd, J = 6.26, 0.89 Hz, 6 H), 1.03 (ddd, J = 5.51, 3.58, 1.94 Hz, 1 H). |

TABLE A-continued

| Example No. (preparation of the Example) | Structure and IUPAC name | Characterising data (LCMS and/or NMR) |
|---|---|---|
| 528 (General Procedure A using Bromide A12 as the core reagent) | 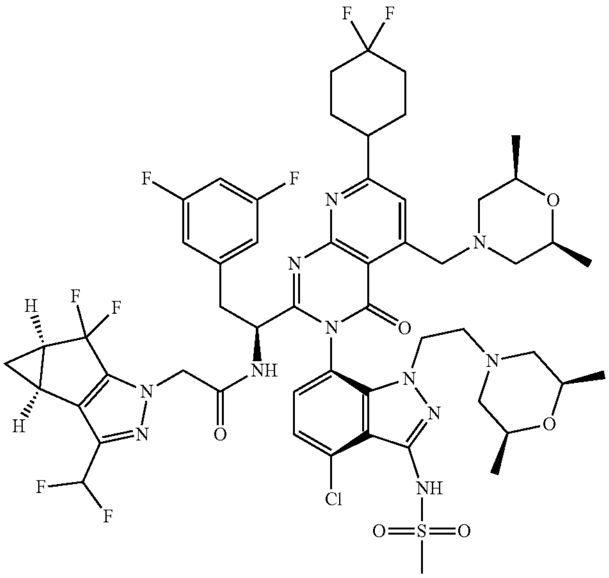 N-[(1S)-1-[(3P)-3-(4-chloro-1-{2-[(2R,6S)-2,6-dimethylmorpholin-4-yl]ethyl}-3-methanesulfonamido-1H-indazol-7-yl)-7-(4,4-difluorocyclohexyl)-5-{[(2R,6S)-2,6-dimethylmorpholin-4-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method E: retention time = 3.47 min.; observed ion = 1178.35 [M + H]+. 1H NMR (500 MHz, METHANOL-d4) δ ppm 7.85 (s, 1 H), 7.36 (d, J = 8.05 Hz, 1 H), 7.26 (d, J = 7.75 Hz, 1 H), 6.49-6.83 (m, 4 H), 4.80 (d, J = 4.77 Hz, 1 H), 4.65 (d, J = 13.71 Hz, 2 H), 4.15-4.24 (m, 2 H), 4.06-4.13 (m, 1 H), 3.87-3.96 (m, 1 H), 3.74-3.83 (m, 2 H), 3.40-3.44 (m, 1 H), 3.27 (s, 3 H), 3.12-3.17 (m, 1 H), 3.07 (dd, J = 14.01, 9.24 Hz, 1 H), 2.81-2.86 (m, 2 H), 2.66-2.74 (m, 1 H), 2.48-2.55 (m, 2 H), 2.41-2.47 (m, 2 H), 2.23-2.31 (m, 3 H), 2.06-2.15 (m, 5 H), 1.92-1.98 (m, 2 H), 1.56-1.63 (m, 1 H), 1.32-1.42 (m, 2 H), 1.15 (dd, J = 6.26, 1.19 Hz, 6 H), 1.05 (br dd, J = 5.51, 1.94 Hz, 1 H), 0.99 (d, J = 6.56 Hz, 3 H), 0.84 (d, J = 6.26 Hz, 3 H). |
| 529 (General Procedure A using Bromide A12 as the core reagent) | 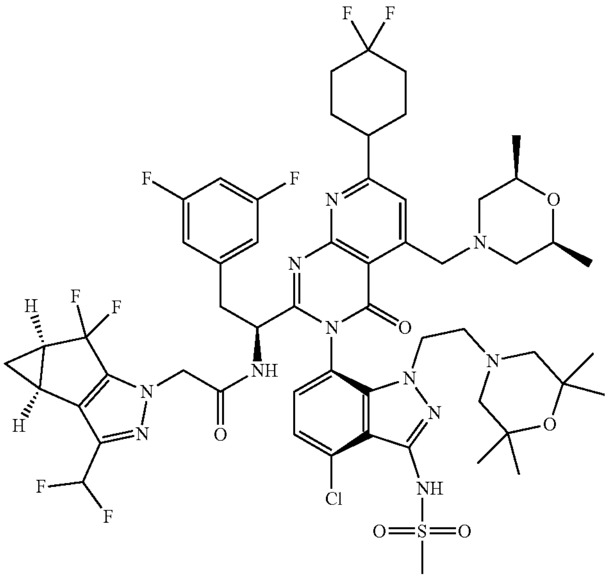 N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-{[(2R,6S)-2,6-dimethylmorpholin-4-yl]methyl}-4-oxo-3H,4H-pyrido[2,3-d]pyrimidin-2-yl]-2-(3,5- | LCMS Method E: retention time = 3.64 min.; observed ion = 1206.35 [M + H]+. 1H NMR (500 MHz, METHANOL-d4) δ ppm 7.84 (s, 1 H), 7.36 (d, J = 7.75 Hz, 1 H), 7.25 (d, J = 7.75 Hz, 1 H), 6.50-6.83 (m, 4 H), 4.85 (br d, J = 4.77 Hz, 1 H), 4.62 (s, 2 H), 4.23 (d, J = 17.29 Hz, 1 H), 4.13-4.20 (m, 1 H), 4.05-4.11 (m, 1 H), 3.86 (ddd, J = 13.78, 11.25, 5.36 Hz, 1 H), 3.73-3.81 (m, 2 H), 3.41 (dd, J = 14.01, 4.77 Hz, 1 H), 3.26 (s, 3 H), 3.04-3.15 (m, 2 H), 2.79-2.86 (m, 2 H), 2.64 (td, J = 11.77, 5.36 Hz, 1 H), 2.50-2.56 (m, 1 H), 2.45 (ddd, J = 11.33, 7.60, 4.02 Hz, 2 H), 2.22-2.32 (m, 2 H), 2.03-2.17 (m, 6 H), 1.87-1.98 (m, 6 H), 1.36-1.41 (m, 1 H), 1.14 (dd, J = 6.26, 0.60 Hz, 6 H), 1.04-1.07 (m, 1 H), 0.99 (s, 6 H), 0.95 (s, 6 H). |

TABLE A-continued

| Example No. (preparation of the Example) | Structure and IUPAC name | Characterising data (LCMS and/or NMR) |
|---|---|---|
| | difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | |
| 530 (General Procedure E-2 using Aldehyde E1 as the core reagent, where the general procedure was modified as follows: the HCl salt of the amine was used; the reductive amination was conducted at 40° C.) | 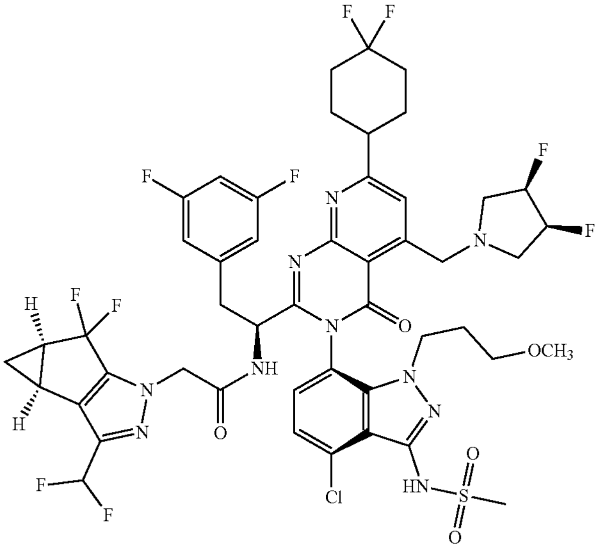 N-[(1S)-1-[(3P)-3-[4-chloro-3-methanesulfonamido-1-(3-methoxypropyl)-1H-indazol-7-yl]-7-(4,4-difluorocyclohexyl)-5-{[(3R,4S)-3,4-difluoropyrrolidin-1-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.99 min.; observed ion = 1101.15 [M + H]+. 1H NMR (500 MHz, METHANOL-d4) δ ppm 7.80 (s, 1 H), 7.33 (d, J = 7.75 Hz, 1 H), 7.18 (d, J = 7.75 Hz, 1 H), 6.56-6.83 (m, 4 H), 5.19 (dd, J = 9.69, 4.62 Hz, 1 H), 5.06-5.11 (m, 1 H), 4.84-4.88 (m, 1 H), 4.60 (d, J = 2.68 Hz, 2 H), 4.38 (d, J = 4.47 Hz, 2 H), 4.02 (ddd, J = 14.23, 10.51, 5.96 Hz, 1 H), 3.84 (ddd, J = 14.23, 10.51, 5.36 Hz, 1 H), 3.43 (dd, J = 14.01, 5.07 Hz, 1 H), 3.26 (s, 3 H), 3.00-3.18 (m, 8 H), 2.76 (s, 3 H), 2.44 (ddd, J = 11.18, 7.75, 4.02 Hz, 2 H), 2.22-2.31 (m, 2 H), 2.08-2.17 (m, 5 H), 1.98-2.05 (m, 1 H), 1.80-1.93 (m, 2 H), 1.32-1.43 (m, 1 H), 0.97-1.07 (m, 1 H). |
| 531 (General Procedure E-2 using Aldehyde E1 as the core reagent, where the general procedure was modified as follows: the HCl salt of the amine was used; the reductive amination was conducted at 40° C.) | 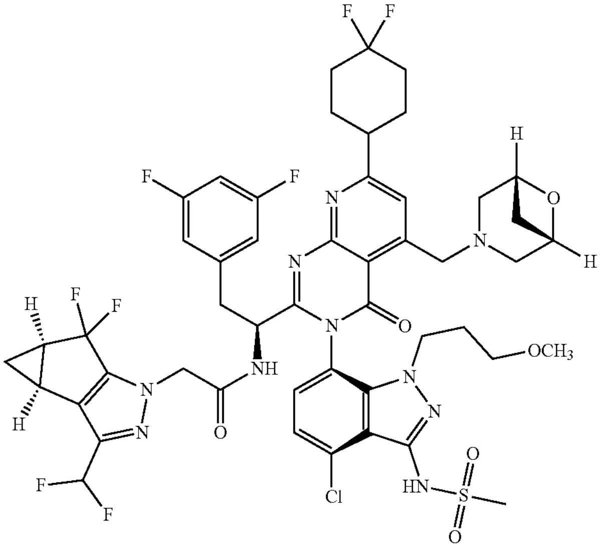 N-[(1S)-1-[(3P)-3-[4-chloro-3-methanesulfonamido-1-(3-methoxypropyl)-1H-indazol-7-yl]-7-(4,4-difluorocyclohexyl)-5-{[(1R,5S)-6-oxa-3-azabicyclo[3.1.1]heptan-3-yl]methyl}-4-oxo-3H,4H-pyrido[2,3-d]pyrimidin-2-yl]-2-(3,5-difluorophenyl)ethyl]-2-[(2S,4R)-9- | LCMS Method A: retention time = 2.70 min.; observed ion = 1093.20 [M + H]+. 1H NMR (500 MHz, METHANOL-d4) δ ppm 7.84 (s, 1 H), 7.33 (d, J = 8.05 Hz, 1 H), 7.18 (d, J = 8.05 Hz, 1 H), 6.55-6.83 (m, 4 H), 4.87 (br d, J = 5.07 Hz, 1 H), 4.61 (d, J = 3.28 Hz, 2 H), 4.57 (d, J = 5.96 Hz, 2 H), 4.41-4.52 (m, 2 H), 4.03 (ddd, J = 14.31, 10.43, 5.96 Hz, 1 H), 3.85 (ddd, J = 14.23, 10.51, 5.36 Hz, 1 H), 3.43 (dd, J = 14.01, 5.07 Hz, 1 H), 3.29 (br s, 1 H), 3.26 (s, 3 H), 3.23 (s, 1 H), 2.99-3.18 (m, 7 H), 2.75 (s, 3 H), 2.41-2.47 (m, 3 H), 2.22-2.31 (m, 2 H), 1.98-2.18 (m, 6 H), 1.80-1.95 (m, 2 H), 1.35-1.41 (m, 1 H), 1.01-1.07 (m, 1 H). |

TABLE A-continued

| Example No. (preparation of the Example) | Structure and IUPAC name | Characterising data (LCMS and/or NMR) |
|---|---|---|
| | (difluoromethyl)-5,5-difluoro-7,8-diazatricyclo[4.3.0.0$^{2}$,$^{4}$]nona-1(6),8-dien-7-yl]acetamide | |
| 535 (General Procedure D using Chloride D2 as the core reagent) | 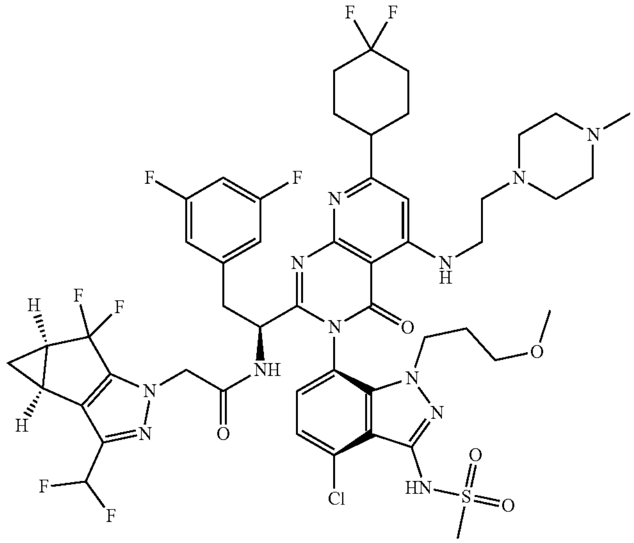 N-[(1S)-1-[(3P)-3-[4-chloro-3-methanesulfonamido-1-(3-methoxypropyl)-1H-indazol-7-yl]-7-(4,4-difluorocyclohexyl)-5-{[2-(4-methylpiperazin-1-yl)ethyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method B: retention time = 0.86 min.; observed ion = 1121.8 [M − H]. 1H NMR (500 MHz, METHANOL-d4) δ ppm 7.28 (d, J = 7.75 Hz, 1 H), 7.08 (d, J = 7.75 Hz, 1 H), 6.52-6.83 (m, 5 H), 4.81-4.83 (m, 1 H), 4.59 (d, J = 2.38 Hz, 2 H), 4.01-4.07 (m, 1 H), 3.77-3.85 (m, 1 H), 3.44-3.49 (m, 3 H), 3.42 (br d, J = 5.36 Hz, 1 H), 3.37-3.43 (m, 3 H), 3.24 (s, 3 H), 3.15 (t, J = 5.81 Hz, 2 H), 3.04 (dd, J = 14.01, 8.94 Hz, 1 H), 2.93 (s, 3 H), 2.84-2.91 (m, 1 H), 2.63-2.74 (m, 3 H), 2.40-2.48 (m, 3 H), 2.39-2.61 (m, 4 H), 2.21-2.29 (m, 5 H), 1.98-2.14 (m, 6 H), 1.86-1.92 (m, 1 H), 1.35-1.41 (m, 1 H), 1.02-1.07 (m, 1 H). |
| 536 (General Procedure D using Chloride D2 as the core reagent) | 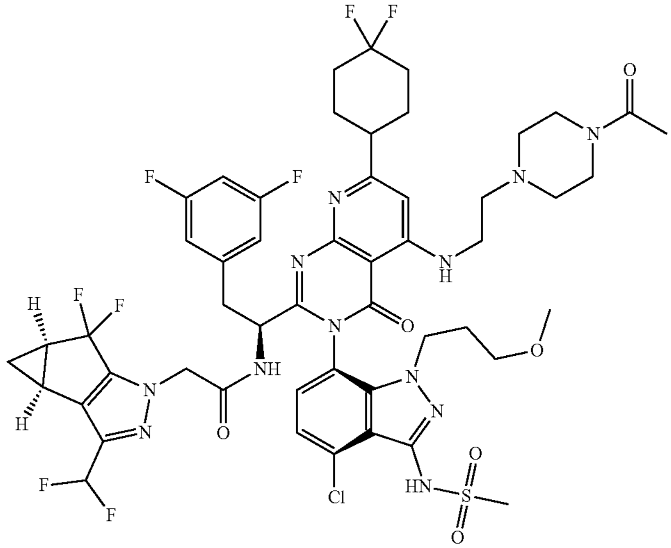 N-[(1S)-1-[(3P)-5-{[2-(4-acetylpiperazin-1-yl)ethyl]amino}-3-[4-chloro-3-methanesulfonamido-1-(3-methoxypropyl)-1H-indazol-7-yl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method B: retention time = 0.96 min.; observed ion = 1149.5 [M − H]. 1H NMR (500 MHz, METHANOL-d4) δ ppm 7.20-7.34 (m, 1 H), 7.08 (d, J = 8.05 Hz, 1 H), 6.54-6.85 (m, 5 H), 4.80-4.83 (m, 1 H), 4.59 (d, J = 2.98 Hz, 2 H), 4.04 (ddd, J = 14.16, 9.98, 5.96 Hz, 1 H), 3.76-3.86 (m, 1 H), 3.46-3.55 (m, 7 H), 3.40 (br dd, J = 14.01, 5.36 Hz, 2 H), 3.24 (s, 3 H), 3.13-3.17 (m, 2 H), 3.04 (dd, J = 13.71, 8.94 Hz, 1 H), 2.94 (s, 3 H), 2.84-2.91 (m, 1 H), 2.66-2.76 (m, 2 H), 2.50-2.54 (m, 2 H), 2.41-2.48 (m, 4 H), 2.21-2.30 (m, 2 H), 2.01-2.12 (m, 8 H), 1.81-1.95 (m, 2 H), 1.35-1.41 (m, 1 H), 1.02-1.07 (m, 1 H). |

TABLE A-continued

| Example No. (preparation of the Example) | Structure and IUPAC name | Characterising data (LCMS and/or NMR) |
|---|---|---|
| 538 (General Procedure E-2 using Aldehyde E1 as the core reagent) | 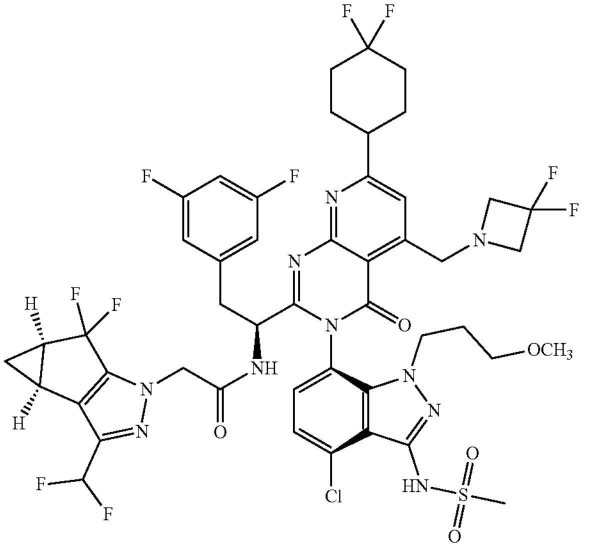 N-[(1S)-1-[(3P)-3-[4-chloro-3-methanesulfonamido-1-(3-methoxypropyl)-1H-indazol-7-yl]-5-[(3,3-difluoroazetidin-1-yl)methyl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 3.24 min.; observed ion = 1087.15 [M + H]+. 1H NMR (500 MHz, METHANOL-d4) δ ppm 7.55 (s, 1 H), 7.20 (d, J = 8.05 Hz, 1 H), 7.06 (d, J = 7.75 Hz, 1 H), 6.42-6.71 (m, 4 H), 4.48 (d, J = 3.58 Hz, 2 H), 4.22-4.39 (m, 2 H), 3.89 (ddd, J = 14.31, 10.43, 5.66 Hz, 1 H), 3.61-3.77 (m, 5 H), 3.28-3.32 (m, 1 H), 3.13 (s, 3 H), 3.01-3.08 (m, 2 H), 2.90-2.99 (m, 2 H), 2.62 (s, 3 H), 2.32 (ddd, J = 11.10, 7.53, 4.02 Hz, 2 H), 2.09-2.20 (m, 2 H), 1.86-2.05 (m, 6 H), 1.66-1.84 (m, 2 H), 1.26 (q, J = 6.76 Hz, 1 H), 0.86-0.96 (m, 1 H). |
| 539 (General Procedure D using Chloride D2 as the core reagent) | 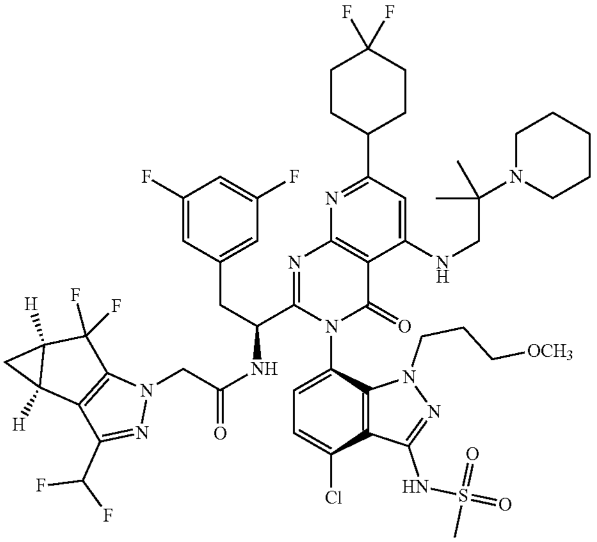 N-[(1S)-1-[(3P)-3-[4-chloro-3-methanesulfonamido-1-(3-methoxypropyl)-1H-indazol-7-yl]-7-(4,4-difluorocyclohexyl)-5-{[2-methyl-2-(piperidin-1-yl)propyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.40 min.; observed ion = 1136.25 [M + H]+. 1H NMR (500 MHz, METHANOL-d4) δ ppm 7.31 (d, J = 7.75 Hz, 1 H), 7.10 (d, J = 7.75 Hz, 1 H), 6.57-6.83 (m, 5 H), 4.81 (br s, 1 H), 4.59 (d, J = 2.38 Hz, 2 H), 4.06 (ddd, J = 14.08, 10.36, 5.96 Hz, 1 H), 3.79-3.91 (m, 1 H), 3.40-3.43 (m, 2 H), 3.26 (s, 3 H), 3.13-3.18 (m, 2 H), 3.05 (dd, J = 13.86, 9.09 Hz, 1 H), 2.90 (s, 3 H), 2.71-2.88 (m, 3 H), 2.42-2.47 (m, 2 H), 2.21-2.32 (m, 2 H), 1.95-2.14 (m, 7 H), 1.79-1.93 (m, 2 H), 1.61 (br dd, J = 5.22, 1.34 Hz, 4 H), 1.42-1.51 (m, 2 H), 1.36-1.41 (m, 1 H), 1.31 (br s, 2 H), 1.20-1.28 (m, 6 H), 1.01-1.06 (m, 1 H). |

TABLE A-continued

| Example No. (preparation of the Example) | Structure and IUPAC name | Characterising data (LCMS and/or NMR) |
|---|---|---|
| 543 (General Procedure D using Chloride D2 as the core reagent) | 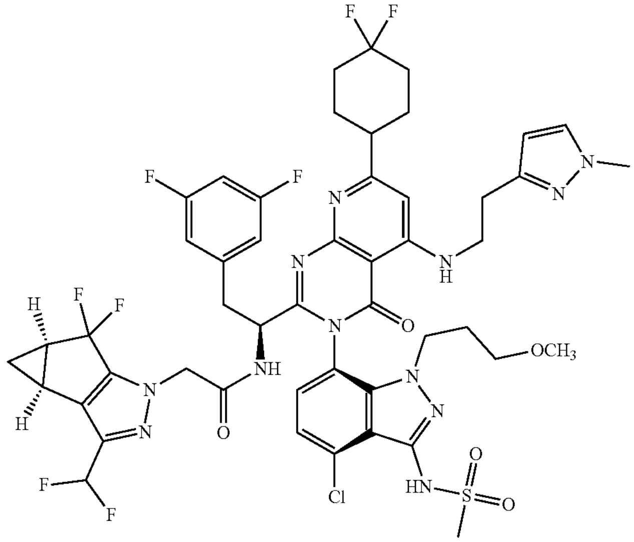 N-[(1S)-1-[(3P)-3-[4-chloro-3-methanesulfonamido-1-(3-methoxypropyl)-1H-indazol-7-yl]-7-(4,4-difluorocyclohexyl)-5-{[2-(1-methyl-1H-pyrazol-3-yl)ethyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method A: retention time = 2.58 min.; observed ion = 1105.30 [M + H]+. 1H NMR (500 MHz, METHANOL-d4) δ ppm 9.04 (t, J = 5.66 Hz, 1 H), 7.44 (d, J = 2.09 Hz, 1 H), 7.29 (d, J = 7.75 Hz, 1 H), 7.08 (d, J = 8.05 Hz, 1 H), 6.57-6.82 (m, 5 H), 6.15 (d, J = 2.38 Hz, 1 H), 4.83 (d, J = 3.87 Hz, 1 H), 4.58 (s, 2 H), 4.01 (ddd, J = 14.31, 10.43, 5.96 Hz, 1 H), 3.80 (dt, J = 9.39, 4.84 Hz, 1 H), 3.75 (s, 3 H), 3.60-3.70 (m, 2 H), 3.38-3.43 (m, 1 H), 3.27 (s, 3 H), 3.10-3.15 (m, 1 H), 3.03-3.08 (m, 2 H), 2.94-2.98 (m, 2 H), 2.89 (s, 3 H), 2.83-2.88 (m, 1 H), 2.44 (td, J = 7.53, 3.73 Hz, 2 H), 2.21-2.31 (m, 2 H), 1.95-2.15 (m, 6 H), 1.74-1.89 (m, 2 H), 1.34-1.41 (m, 1 H), 1.01-1.06 (m, 1 H). |
| 546 (General Procedure D using Chloride D2 as the core reagent) | 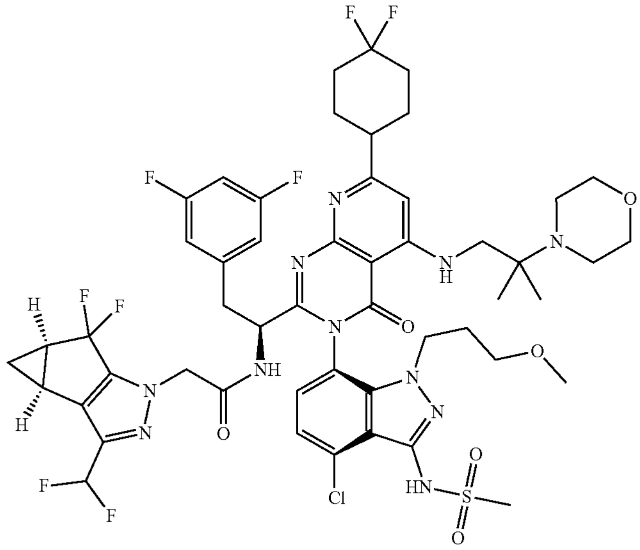 N-[(1S)-1-[(3P)-3-[4-chloro-3-methanesulfonamido-1-(3-methoxypropyl)-1H-indazol-7-yl]-7-(4,4-difluorocyclohexyl)-5-{[2-methyl-2-(morpholin-4-yl)propyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method B: retention time = 1.04 min.; observed ion = 1136.4 [M − H]. 1H NMR (500 MHz, METHANOL-d4) δ ppm 7.32 (d, J = 8.05 Hz, 1 H), 7.10 (d, J = 7.75 Hz, 1 H), 6.55-6.83 (m, 5 H), 4.79 (dd, J = 8.94, 5.36 Hz, 1 H), 4.57-4.63 (m, 2 H), 4.07 (ddd, J = 14.08, 10.36, 6.26 Hz, 1 H), 3.79-3.89 (m, 1 H), 3.57 (t, J = 4.32 Hz, 3 H), 3.40 (dd, J = 14.01, 5.36 Hz, 1 H), 3.26 (s, 3 H), 3.12-3.16 (m, 2 H), 3.04 (dd, J = 14.01, 8.94 Hz, 1 H), 2.90 (s, 3 H), 2.83-2.88 (m, 1 H), 2.50-2.57 (m, 3 H), 2.41-2.48 (m, 2 H), 2.20-2.30 (m, 2 H), 1.82-2.15 (m, 8 H), 1.35-1.40 (m, 1 H), 1.14 (d, J = 6.85 Hz, 6 H), 1.03-1.07 (m, 1 H). |

TABLE A-continued

| Example No. (preparation of the Example) | Structure and IUPAC name | Characterising data (LCMS and/or NMR) |
|---|---|---|
| 549 (General Procedure D using Chloride D2 as the core reagent) | 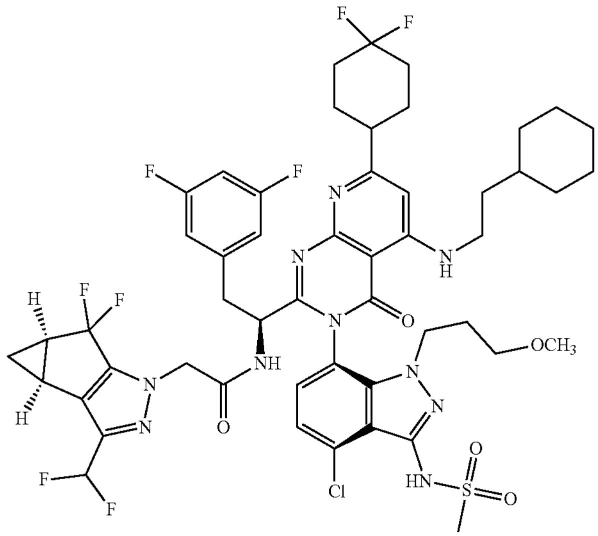 N-[(1S)-1-[(3P)-3-[4-chloro-3-methanesulfonamido-1-(3-methoxypropyl)-1H-indazol-7-yl]-5-[(2-cyclohexylethyl)amino]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method A: retention time = 3.08 min.; observed ion = 1107.20 [M + H]+. 1H NMR (500 MHz, METHANOL-d4) δ ppm 8.88-8.98 (m, 1 H), 7.30 (d, J = 7.75 Hz, 1 H), 7.11 (d, J = 8.05 Hz, 1 H), 6.56-6.83 (m, 5 H), 4.82 (dd, J = 8.94, 5.36 Hz, 1 H), 4.59 (d, J = 2.09 Hz, 2 H), 4.05 (ddd, J = 14.23, 10.06, 6.11 Hz, 1 H), 3.84 (td, J = 9.61, 4.92 Hz, 1 H), 3.36-3.43 (m, 3 H), 3.26 (s, 3 H), 3.16 (dd, J = 6.41, 4.92 Hz, 2 H), 3.05 (dd, J = 13.86, 9.09 Hz, 1 H), 2.92 (s, 3 H), 2.82-2.90 (m, 1 H), 2.44 (ddd, J = 11.55, 7.67, 4.02 Hz, 2 H), 2.20-2.29 (m, 2 H), 1.96-2.15 (m, 6 H), 1.83-1.94 (m, 2 H), 1.66-1.82 (m, 5 H), 1.58 (q, J = 7.15 Hz, 2 H), 1.35-1.48 (m, 2 H), 1.16-1.32 (m, 3 H), 0.93-1.07 (m, 3 H). |
| 550 (General Procedure D using Chloride D2 as the core reagent) | 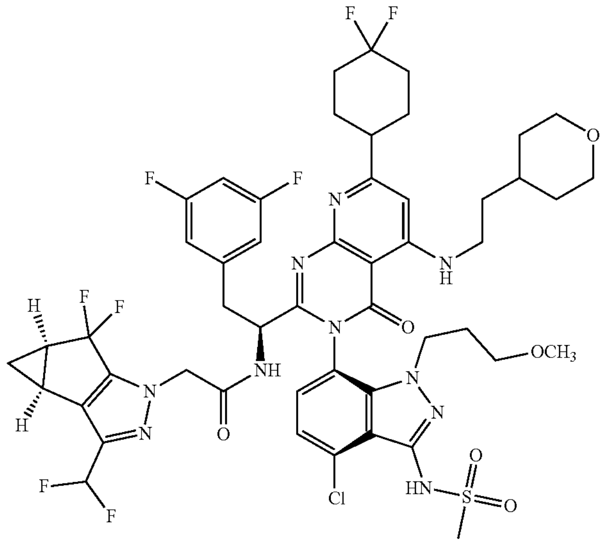 N-[(1S)-1-[(3P)-3-[4-chloro-3-methanesulfonamido-1-(3-methoxypropyl)-1H-indazol-7-yl]-7-(4,4-difluorocyclohexyl)-5-{[2-(oxan-4-yl)ethyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method A: retention time = 2.66 min.; observed ion = 1109.20 [M + H]+. 1H NMR (500 MHz, METHANOL-d4) δ ppm 8.89-9.03 (m, 1 H), 7.30 (d, J = 7.75 Hz, 1 H), 7.10 (d, J = 7.75 Hz, 1 H), 6.55-6.83 (m, 5 H), 4.80-4.84 (m, 1 H), 4.59 (d, J = 2.38 Hz, 2 H), 4.05 (ddd, J = 14.23, 10.21, 5.96 Hz, 1 H), 3.89-3.95 (m, 2 H), 3.84 (td, J = 9.54, 4.77 Hz, 1 H), 3.38-3.46 (m, 4 H), 3.26 (s, 3 H), 3.12-3.19 (m, 2 H), 3.01-3.07 (m, 1 H), 2.92 (s, 3 H), 2.81-2.88 (m, 1 H), 2.44 (td, J = 7.75, 3.87 Hz, 2 H), 2.19-2.30 (m, 2 H), 1.95-2.13 (m, 6 H), 1.80-1.93 (m, 2 H), 1.60-1.74 (m, 5 H), 1.26-1.42 (m, 3 H), 0.98-1.07 (m, 1 H). |

TABLE A-continued

| Example No. (preparation of the Example) | Structure and IUPAC name | Characterising data (LCMS and/or NMR) |
|---|---|---|
| 552 (General Procedure D using Chloride D2 as the core reagent) | 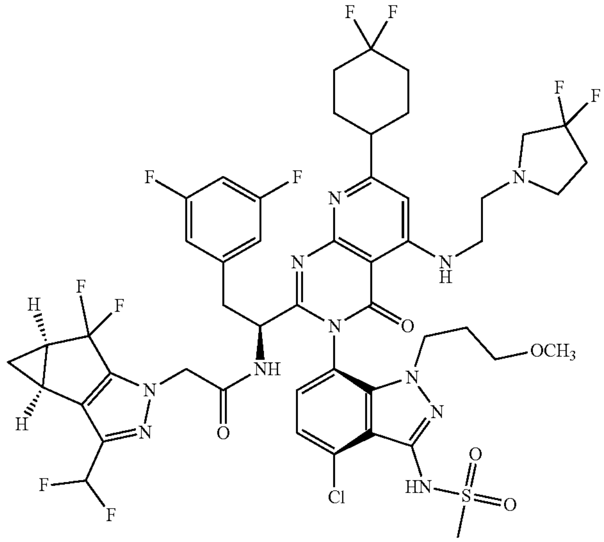 N-[(1S)-1-[(3P)-3-[4-chloro-3-methanesulfonamido-1-(3-methoxypropyl)-1H-indazol-7-yl]-7-(4,4-difluorocyclohexyl)-5-{[2-(3,3-difluoropyrrolidin-1-yl)ethyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method A: retention time = 2.75 min.; observed ion = 1130.15 [M + H]+. 1H NMR (500 MHz, METHANOL-d4) δ ppm 8.19 (s, 1 H), 7.31 (d, J = 7.75 Hz, 1 H), 7.11 (d, J = 8.05 Hz, 1 H), 6.58-6.83 (m, 5 H), 4.80-4.83 (m, 1 H), 4.57 (d, J = 2.09 Hz, 2 H), 4.05 (ddd, J = 14.23, 10.21, 6.26 Hz, 1 H), 3.83 (ddd, J = 14.08, 10.06, 5.66 Hz, 1 H), 3.47-3.51 (m, 2 H), 3.39-3.43 (m, 1 H), 3.26 (s, 3 H), 3.13-3.18 (m, 1 H), 3.12-3.20 (m, 1 H), 3.03-3.09 (m, 1 H), 2.92-2.93 (m, 1 H), 2.87-2.99 (m, 4 H), 2.87-3.00 (m, 1 H), 2.78-2.85 (m, 3 H), 2.73-2.85 (m, 1 H), 2.44 (ddd, J = 11.62, 7.75, 4.17 Hz, 2 H), 2.18-2.30 (m, 4 H), 2.01-2.14 (m, 5 H), 1.95-2.15 (m, 1 H), 1.84-1.92 (m, 1 H), 1.35-1.40 (m, 1 H), 1.02-1.06 (m, 1 H). |
| 553 (General Procedure B using Amine B29 as the core reagent) | 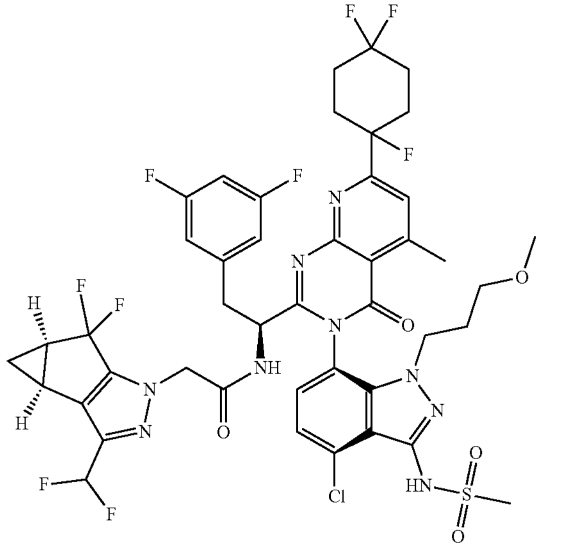 N-[(1S)-1-[(3P)-3-[4-chloro-3-methanesulfonamido-1-(3-methoxypropyl)-1H-indazol-7-yl]-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method B: retention time = 1.58 min.; observed ion = 1014.3 [M + H]. 1H NMR (500 MHz, METHANOL-d4) δ ppm 1.01-1.04 (m, 1 H), 1.31-1.38 (m, 1 H), 1.82-1.90 (m, 2 H), 2.14-2.25 (m, 4 H), 2.29 (br d, J = 12.52 Hz, 1 H), 2.40-2.45 (m, 2 H), 2.50-2.56 (m, 1 H), 2.62 (br d, J = 1.79 Hz, 1 H), 2.76 (s, 3 H), 2.87 (s, 3 H), 3.05-3.18 (m, 3 H), 3.25 (s, 3 H), 3.41 (d, J = 4.77 Hz, 1 H), 3.82-3.88 (m, 1 H), 3.97-4.06 (m, 1 H), 4.54-4.63 (m, 4 H), 6.52-6.79 (m, 4 H), 7.22 (d, J = 7.75 Hz, 1 H), 7.33 (d, J = 7.75 Hz, 1 H), 7.71 (s, 1 H). |

TABLE A-continued

| Example No. (preparation of the Example) | Structure and IUPAC name | Characterising data (LCMS and/or NMR) |
|---|---|---|
| 556 (General Procedure A using Bromide A15 as the core reagent) | 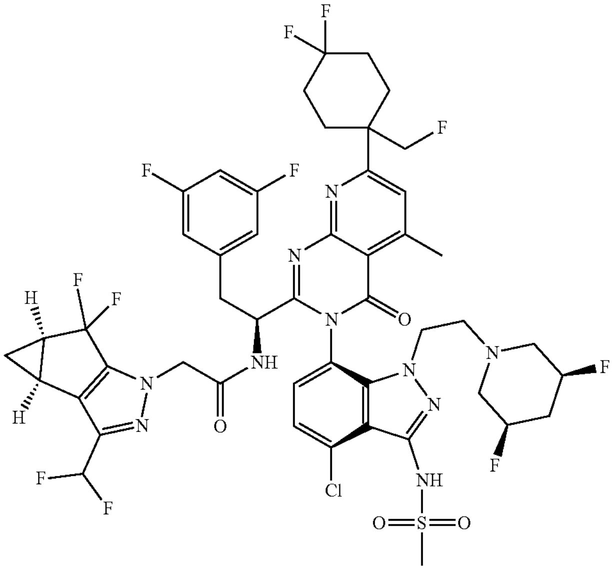 N-[(1S)-1-[(3P)-3-(4-chloro-1-{2-[(3R,5S)-3,5-difluoropiperidin-1-yl]ethyl}-3-methanesulfonamido-1H-indazol-7-yl)-7-[4,4-difluoro-1-(fluoromethyl)cyclohexyl]-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.40 min.; observed ion = 1103.4 [M + H]. 1H NMR (500 MHz, METHANOL-d4) δ ppm 1.00-1.03 (m, 1 H), 1.36 (br d, J = 7.15 Hz, 1 H), 1.64 (br d, J = 12.82 Hz, 1 H), 1.84 (br d, J = 2.09 Hz, 2 H), 1.91-2.01 (m, 2 H), 2.02-2.13 (m, 3 H), 2.16-2.27 (m, 2 H), 2.39-2.46 (m, 2 H), 2.52 (br dd, J = 16.09, 12.82 Hz, 2 H), 2.64-2.75 (m, 3 H), 2.75-2.82 (m, 1 H), 2.85-2.92 (m, 3 H), 3.06 (dd, J = 14.01, 9.54 Hz, 1 H), 3.25 (s, 3 H), 3.35-3.40 (m, 1 H), 3.81 (ddd, J = 14.31, 9.54, 5.36 Hz, 1 H), 4.14-4.21 (m, 1 H), 4.25 (br dd, J = 6.71, 3.43 Hz, 1 H), 4.48 (s, 1 H), 4.56-4.62 (m, 5 H), 6.53 (dd, J = 8.05, 2.09 Hz, 2 H), 6.67 (br t, J = 54.69 Hz, 1 H), 6.73-6.79 (m, 1 H), 7.29 (d, J = 8.05 Hz, 1 H), 7.35 (d, J = 8.05 Hz, 1 H), 7.68 (s, 1 H). |
| 557 (General Procedure A using Bromide A15 as the core reagent) | 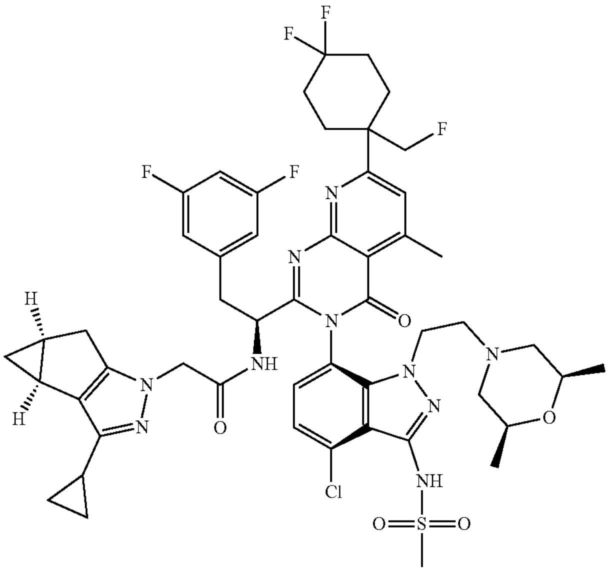 N-[(1S)-1-[(3P)-3-(4-chloro-1-{2-[(2R,6S)-2,6-dimethylmorpholin-4-yl]ethyl}-3-methanesulfonamido-1H-indazol-7-yl)-7-[4,4-difluoro-1-(fluoromethyl)cyclohexyl]-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.22 min.; observed ion = 1049.5 [M − H]. 1H NMR (500 MHz, METHANOL-d4) δ ppm 0.07-0.10 (m, 1 H), 0.74-0.79 (m, 1 H), 0.84-0.91 (m, 5 H), 0.93-1.04 (m, 4 H), 1.27-1.32 (m, 1 H), 1.49 (s, 1 H), 1.58-1.62 (m, 1 H), 1.75-1.87 (m, 3 H), 1.91-2.03 (m, 3 H), 2.08-2.14 (m, 2 H), 2.28 (br s, 1 H), 2.51-2.56 (m, 1 H), 2.64-2.75 (m, 4 H), 2.88 (s, 3 H), 3.04 (dd, J = 14.01, 9.54 Hz, 1 H), 3.15-3.19 (m, 1 H), 3.28 (s, 3 H), 3.37-3.38 (m, 1 H), 3.82-3.89 (m, 1 H), 4.13-4.19 (m, 1 H), 4.30 (d, J = 1.49 Hz, 2 H), 4.51 (s, 1 H), 4.58-4.63 (m, 4 H), 4.80-4.82 (m, 2 H), 6.53 (d, J = 6.97 Hz, 2 H), 6.76 (t, J = 8.30 Hz, 1 H), 7.29 (d, J = 7.75 Hz, 1 H), 7.36 (d, J = 8.05 Hz, 1 H), 7.69 (s, 1 H). |

TABLE A-continued

| Example No. (preparation of the Example) | Structure and IUPAC name | Characterising data (LCMS and/or NMR) |
|---|---|---|
| 561 (General Procedure A using Bromide A16 as the core reagent) | 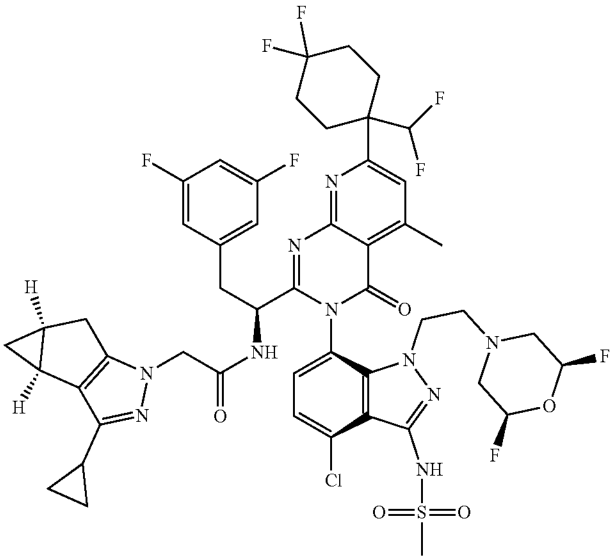 N-[(1S)-1-[(3P)-3-(4-chloro-1-{2-[(2R,6S)-2,6-dimethylmorpholin-4-yl]ethyl}-3-methanesulfonamido-1H-indazol-7-yl)-7-[1-(difluoromethyl)-4,4-difluorocyclohexyl]-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.24 min.; observed ion = 1067.5 [M − H]. 1H NMR (500 MHz, METHANOL-d4) δ ppm 0.06-0.09 (m, 1 H), 0.73-0.92 (m, 8 H), 0.94-1.01 (m, 4 H), 1.57 (br d, J = 2.09 Hz, 1 H), 1.62-1.71 (m, 2 H), 1.72-1.87 (m, 4 H), 1.92 (br dd, J = 11.18, 3.13 Hz, 1 H), 2.02-2.14 (m, 4 H), 2.36 (br s, 1 H), 2.44 (d, J = 16.99 Hz, 1 H), 2.53-2.73 (m, 4 H), 2.90 (s, 3 H), 3.05 (dd, J = 14.01, 9.24 Hz, 1 H), 3.28 (s, 3 H), 3.35-3.39 (m, 1 H), 3.88 (s, 1 H), 4.16-4.23 (m, 1 H), 4.27-4.34 (m, 2 H), 4.59-4.63 (m, 3 H), 5.99 (t, J = 56.18 Hz, 1 H), 6.52 (d, J = 7.24 Hz, 2 H), 6.76 (t, J = 8.42 Hz, 1 H), 7.31-7.38 (m, 2 H), 7.75 (s, 1 H). |
| 563 (General Procedure D using Chloride D2 as the core reagent) | 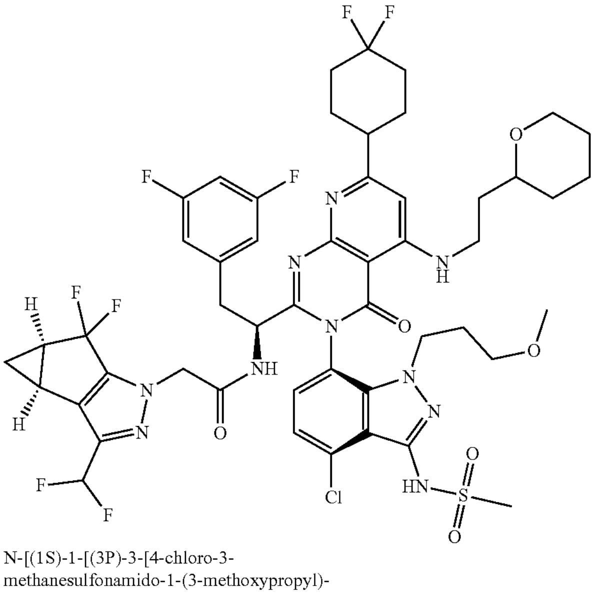 N-[(1S)-1-[(3P)-3-[4-chloro-3-methanesulfonamido-1-(3-methoxypropyl)-1H-indazol-7-yl]-7-(4,4-difluorocyclohexyl)-5-{[2-(oxan-2-yl)ethyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.23 min.; observed ion = 1109.4 [M + H]. 1H NMR (500 MHz, METHANOL-d4) δ ppm 9.10 (br d, J = 8.35 Hz, 1 H), 7.29 (d, J = 7.75 Hz, 1 H), 7.09 (dd, J = 7.75, 1.19 Hz, 1 H), 6.54-6.84 (m, 5 H), 4.82 (br d, J = 2.09 Hz, 1 H), 4.59 (d, J = 2.38 Hz, 2 H), 4.00-4.11 (m, 1 H), 3.90-3.97 (m, 1 H), 3.79-3.88 (m, 1 H), 3.45-3.53 (m, 2 H), 3.37-3.42 (m, 4 H), 3.26 (s, 3 H), 3.13-3.18 (m, 2 H), 3.04 (dd, J = 14.01, 8.94 Hz, 1 H), 2.94 (s, 2 H), 2.83-2.90 (m, 1 H), 2.41-2.46 (m, 2 H), 2.21-2.29 (m, 2 H), 1.98-2.15 (m, 6 H), 1.85-1.92 (m, 2 H), 1.83 (br dd, J = 8.05, 3.87 Hz, 1 H), 1.75-1.80 (m, 2 H), 1.58-1.64 (m, 1 H), 1.48-1.55 (m, 3 H), 1.33-1.41 (m, 2 H), 1.03-1.07 (m, 1 H). |

TABLE A-continued

| Example No. (preparation of the Example) | Structure and IUPAC name | Characterising data (LCMS and/or NMR) |
|---|---|---|
| 564 (General Procedure D using Chloride D2 as the core reagent) | 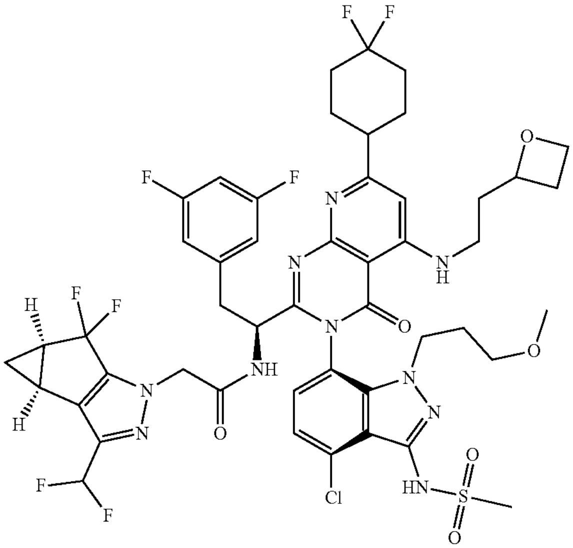 N-[(1S)-1-[(3P)-3-[4-chloro-3-methanesulfonamido-1-(3-methoxypropyl)-1H-indazol-7-yl]-7-(4,4-difluorocyclohexyl)-5-{[2-(oxetan-2-yl)ethyl]amino}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.12 min.; observed ion = 1081.3 [M + H]. 1H NMR (500 MHz, METHANOL-d4) δ ppm 7.29 (dd, J = 7.90, 1.34 Hz, 1 H), 7.09 (dd, J = 7.90, 5.22 Hz, 1 H), 6.56-6.85 (m, 5 H), 4.98 (br d, J = 3.87 Hz, 1 H), 4.84 (br s, 1 H), 4.68-4.71 (m, 1 H), 4.59 (d, J = 2.09 Hz, 2 H), 4.55 (dt, J = 9.09, 5.89 Hz, 2 H), 4.01-4.09 (m, 1 H), 3.80-3.87 (m, 1 H), 3.45-3.49 (m, 2 H), 3.41 (br d, J = 5.07 Hz, 1 H), 3.26 (s, 3 H), 3.17 (td, J = 5.81, 1.49 Hz, 2 H), 3.04 (dd, J = 14.01, 8.94 Hz, 1 H), 2.94 (s, 3 H), 2.86-2.92 (m, 1 H), 2.69-2.77 (m, 1 H), 2.39-2.50 (m, 3 H), 2.21-2.30 (m, 2 H), 2.14-2.20 (m, 1 H), 1.98-2.13 (m, 7 H), 1.83-1.93 (m, 2 H), 1.35-1.41 (m, 1 H), 1.02-1.06 (m, 1 H). |
| 565 (General Procedure D using Chloride D2 as the core reagent) | 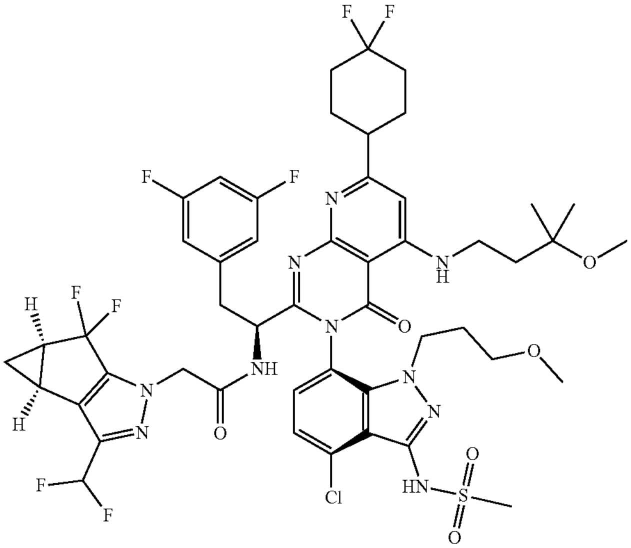 N-[(1S)-1-[(3P)-3-[4-chloro-3-methanesulfonamido-1-(3-methoxypropyl)-1H-indazol-7-yl]-7-(4,4-difluorocyclohexyl)-5-[(3-methoxy-3-methylbutyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.20 min.; observed ion = 1097.4 [M + H]. 1H NMR (500 MHz, METHANOL-d4) δ ppm 7.29 (d, J = 7.75 Hz, 1 H), 7.08 (d, J = 8.05 Hz, 1 H), 6.52-6.84 (m, 5 H), 4.82 (br s, 1 H), 4.59 (d, J = 2.09 Hz, 2 H), 4.03 (s, 1 H), 3.79-3.87 (m, 1 H), 3.41-3.48 (m, 2 H), 3.25 (s, 3 H), 3.19 (s, 3 H), 3.13-3.17 (m, 2 H), 3.04 (dd, J = 14.01, 9.24 Hz, 1 H), 2.94 (s, 3 H), 2.85-2.90 (m, 1 H), 2.20-2.29 (m, 2 H), 1.97-2.15 (m, 6 H), 1.85-1.90 (m, 3 H), 1.35-1.40 (m, 1 H), 1.23 (s, 6 H), 1.03-1.07 (m, 1 H). |

TABLE A-continued

| Example No. (preparation of the Example) | Structure and IUPAC name | Characterising data (LCMS and/or NMR) |
|---|---|---|
| 566 (General Procedure D using Chloride D2 as the core reagent) | 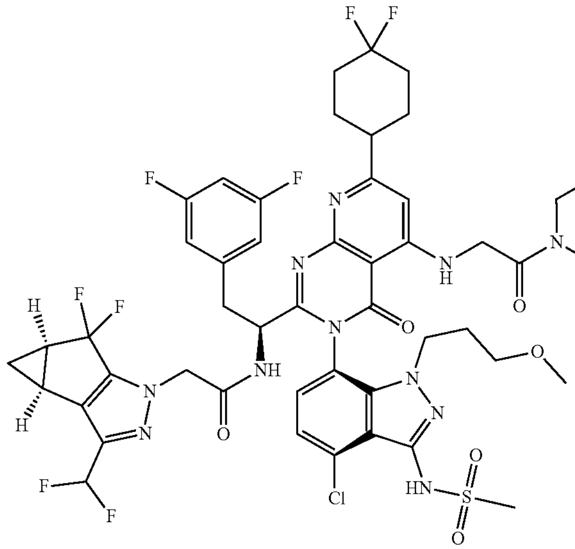 N-[(1S)-1-[(3P)-3-[4-chloro-3-methanesulfonamido-1-(3-methoxypropyl)-1H-indazol-7-yl]-7-(4,4-difluorocyclohexyl)-4-oxo-5-{[2-oxo-2-(piperidin-1-yl)ethyl]amino}-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.19 min.; observed ion = 1122.4 [M + H]. 1H NMR (500 MHz, METHANOL-d4) δ ppm 7.29 (d, J = 7.75 Hz, 1 H), 7.10 (d, J = 8.05 Hz, 1 H), 6.57-6.82 (m, 5 H), 4.85 (br s, 1 H), 4.60 (d, J = 2.09 Hz, 2 H), 4.21-4.27 (m, 2 H), 4.02-4.10 (m, 1 H), 3.80-3.88 (m, 1 H), 3.55-3.61 (m, 2 H), 3.51-3.55 (m, 2 H), 3.41 (dd, J = 13.71, 5.07 Hz, 1 H), 3.25 (s, 3 H), 3.11-3.19 (m, 3 H), 3.05 (dd, J = 14.01, 8.94 Hz, 1 H), 2.94 (s, 3 H), 2.88-2.92 (m, 1 H), 2.41-2.47 (m, 2 H), 2.21-2.30 (m, 2 H), 2.00-2.14 (m, 6 H), 1.85-1.92 (m, 2 H), 1.64-1.74 (m, 5 H), 1.55-1.60 (m, 2 H), 1.35-1.40 (m, 1 H), 1.04 (dt, J = 3.50, 1.97 Hz, 1 H). |
| 567 (General Procedure D using Chloride D2 as the core reagent) | 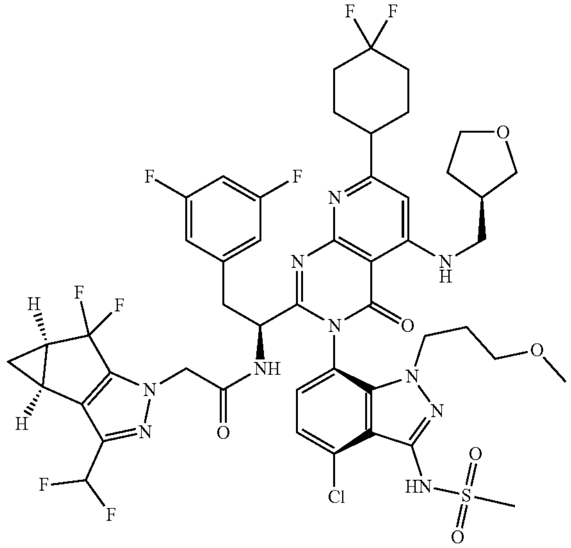 N-[(1S)-1-[(3P)-3-[4-chloro-3-methanesulfonamido-1-(3-methoxypropyl)-1H-indazol-7-yl]-7-(4,4-difluorocyclohexyl)-4-oxo-5-({[(3R)-oxolan-3-yl]methyl}amino)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.14 min.; observed ion = 1081.3 [M + H]. 1H NMR (500 MHz, METHANOL-d4) δ ppm 7.30 (d, J = 7.75 Hz, 1 H), 7.10 (d, J = 8.05 Hz, 1 H), 6.55-6.83 (m, 5 H), 4.82-4.84 (m, 2 H), 4.59 (d, J = 1.79 Hz, 2 H), 4.04 (ddd, J = 14.38, 10.21, 5.81 Hz, 1 H), 3.91 (td, J = 8.35, 5.36 Hz, 1 H), 3.80-3.86 (m, 2 H), 3.71-3.78 (m, 1 H), 3.59 (dd, J = 8.79, 5.22 Hz, 1 H), 3.39-3.43 (m, 2 H), 3.25 (s, 3 H), 3.13-3.19 (m, 2 H), 3.05 (dd, J = 14.01, 8.94 Hz, 1 H), 2.91 (s, 3 H), 2.88 (br dd, J = 7.45, 3.28 Hz, 1 H), 2.61-2.69 (m, 1 H), 2.44 (ddd, J = 11.55, 7.67, 4.02 Hz, 2 H), 2.20-2.30 (m, 2 H), 2.01-2.16 (m, 6 H), 1.82-1.95 (m, 2 H), 1.68-1.77 (m, 1 H), 1.36-1.41 (m, 1 H), 1.02-1.08 (m, 1 H). |

TABLE A-continued

| Example No. (preparation of the Example) | Structure and IUPAC name | Characterising data (LCMS and/or NMR) |
| --- | --- | --- |
| 568 (General Procedure D using Chloride D2 as the core reagent) | 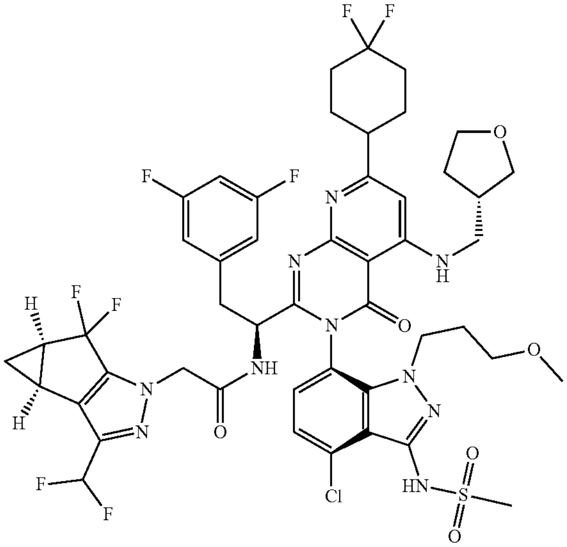 N-[(1S)-1-[(3P)-3-[4-chloro-3-methanesulfonamido-1-(3-methoxypropyl)-1H-indazol-7-yl]-7-(4,4-difluorocyclohexyl)-4-oxo-5-({[(3S)-oxolan-3-yl]methyl}amino)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.14 min.; observed ion = 1081.3 [M + H]. 1H NMR (500 MHz, METHANOL-d4) δ ppm 7.30 (d, J = 7.75 Hz, 1 H), 7.10 (d, J = 8.05 Hz, 1 H), 6.55-6.83 (m, 5 H), 4.82-4.84 (m, 2 H), 4.59 (d, J = 1.79 Hz, 2 H), 4.04 (ddd, J = 14.38, 10.21, 5.81 Hz, 1 H), 3.91 (td, J = 8.35, 5.36 Hz, 1 H), 3.80-3.86 (m, 2 H), 3.71-3.78 (m, 1 H), 3.59 (dd, J = 8.79, 5.22 Hz, 1 H), 3.39-3.43 (m, 2 H), 3.25 (s, 3 H), 3.13-3.19 (m, 2 H), 3.05 (dd, J = 14.01, 8.94 Hz, 1 H), 2.91 (s, 3 H), 2.88 (br dd, J = 7.45, 3.28 Hz, 1 H), 2.61-2.69 (m, 1 H), 2.44 (ddd, J = 11.55, 7.67, 4.02 Hz, 2 H), 2.20-2.30 (m, 2 H), 2.01-2.16 (m, 6 H), 1.82-1.95 (m, 2 H), 1.68-1.77 (m, 1 H), 1.36-1.41 (m, 1 H), 1.02-1.08 (m, 1 H). |
| 569 (General Procedure B using Amine B30 as the core reagent) | 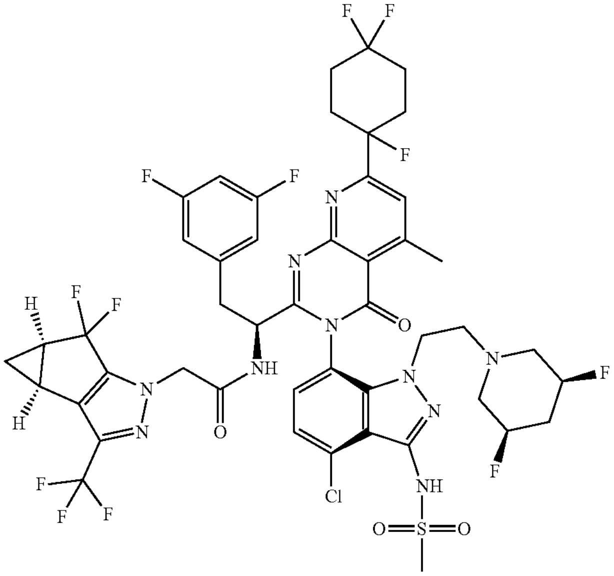 N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-5,5-difluoro-9-(trifluoromethyl)-7,8-diazatricyclo[4.3.0.0$^{2,4}$]nona-1(6),8-dien-7-yl]acetamide | LCMS Method B: retention time = 1.494 min.; observed ion = 1107.2 [M + H]. 1H NMR (500 MHz, METHANOL-d4) δ ppm 1.07 (td, J = 4.77, 2.38 Hz, 1 H), 1.37-1.41 (m, 1 H), 1.66 (br d, J = 7.75 Hz, 1 H), 2.12-2.22 (m, 8 H), 2.25-2.32 (m, 1 H), 2.43-2.64 (m, 7 H), 2.66-2.79 (m, 2 H), 2.89-2.91 (m, 3 H), 3.05 (dd, J = 14.01, 9.54 Hz, 1 H), 3.26 (s, 3 H), 3.77-3.84 (m, 1 H), 4.14 (ddd, J = 14.08, 9.46, 5.96 Hz, 1 H), 4.23-4.40 (m, 2 H), 4.61-4.73 (m, 3 H), 6.52 (d, J = 7.28 Hz, 2 H), 6.76 (t, J = 8.22 Hz, 1 H), 7.24-7.36 (m, 2 H), 7.71 (s, 1 H). |

TABLE A-continued

| Example No. (preparation of the Example) | Structure and IUPAC name | Characterising data (LCMS and/or NMR) |
|---|---|---|
| 570 (General Procedure B using Amine B30 as the core reagent) | 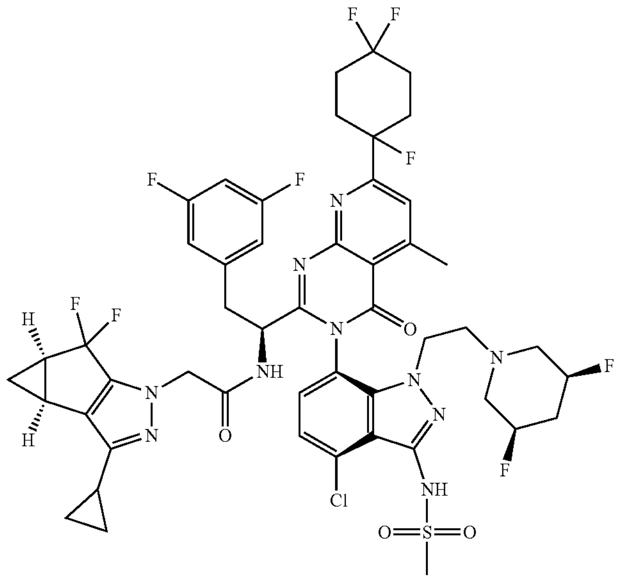 N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-cyclopropyl-5,5-difluoro-7,8-diazatricyclo[4.3.0.0$^{2,4}$]nona-1(6),8-dien-7-yl]acetamide | LCMS Method B: retention time = 1.461 min.; observed ion = 1079.4 [M + H]. 1H NMR (500 MHz, METHANOL-d4) δ ppm 0.77-0.81 (m, 2 H), 0.88-0.95 (m, 3 H), 1.25-1.30 (m, 1 H), 1.57-1.65 (m, 1 H), 1.84 (tt, J = 8.31, 4.95 Hz, 1 H), 2.12-2.34 (m, 11 H), 2.51-2.73 (m, 4 H), 2.75-2.81 (m, 1 H), 2.89-2.91 (m, 3 H), 3.02 (dd, J = 14.16, 9.39 Hz, 1 H), 3.27 (s, 3 H), 3.37 (d, J = 5.07 Hz, 1 H), 3.74-3.81 (m, 1 H), 4.13-4.25 (m, 1 H), 4.30 (dd, J = 43.36, 26.08 Hz, 1 H), 4.26-4.34 (m, 1 H), 4.38 (br d, J = 4.47 Hz, 1 H), 4.42-4.52 (m, 2 H), 4.76-4.79 (m, 1 H), 6.49-6.54 (m, 2 H), 6.74-6.79 (m, 1 H), 7.25 (d, J = 8.05 Hz, 1 H), 7.34 (d, J = 8.05 Hz, 1 H), 7.71 (dd, J = 1.64, 0.74 Hz, 1 H). |
| 571 (General Procedure B using Amine B30 as the core reagent) | 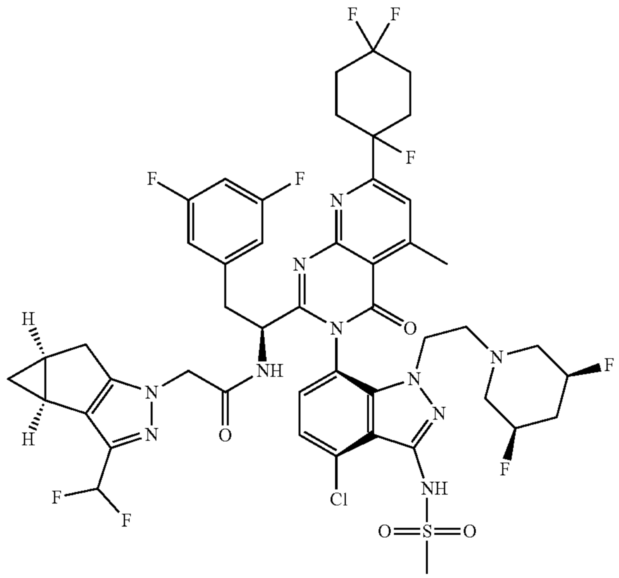 N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-(difluoromethyl)-7,8-diazatricyclo[4.3.0.0$^{2,4}$]nona-1(6),8-dien-7-yl]acetamide | LCMS Method B: retention time = 1.422 min.; observed ion = 1053.4 [M + H]. 1H NMR (500 MHz, METHANOL-d4) δ ppm 0.19 (q, J = 4.17 Hz, 1 H), 1.04 (td, J = 7.75, 4.77 Hz, 1 H), 1.65-1.72 (m, 1 H), 1.99-2.07 (m, 2 H), 2.10-2.32 (m, 9 H), 2.45-2.64 (m, 5 H), 2.66-2.72 (m, 1 H), 2.81 (ddd, J = 12.37, 9.54, 5.51 Hz, 1 H), 2.89-2.91 (m, 3 H), 3.06-3.09 (m, 1 H), 3.27-3.28 (m, 3 H), 3.40 (dd, J = 13.71, 4.47 Hz, 1 H), 3.79-3.85 (m, 1 H), 4.08-4.14 (m, 1 H), 4.26-4.45 (m, 4 H), 4.82-4.86 (m, 2 H), 6.57 (br t, J = 55.14 Hz, 2 H), 6.53-6.58 (m, 1 H), 6.76 (t, J = 8.84 Hz, 1 H), 7.30-7.36 (m, 2 H), 7.71 (dd, J = 1.49, 0.89 Hz, 1 H). |

TABLE A-continued

| Example No. (preparation of the Example) | Structure and IUPAC name | Characterising data (LCMS and/or NMR) |
|---|---|---|
| 572 (General Procedure B using Amine B30 as the core reagent) | 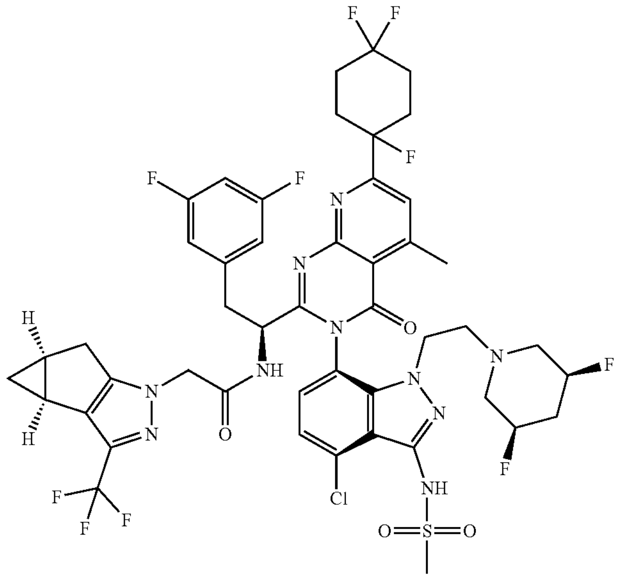 N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-(trifluoromethyl)-7,8-diazatricyclo[4.3.0.0$^{2,4}$]nona-1(6),8-dien-7-yl]acetamide | LCMS Method B: retention time = 1.485 min.; observed ion = 1071.3 [M + H]. 1H NMR (500 MHz, METHANOL-d4) δ ppm 0.19-0.22 (m, 1 H), 1.05-1.09 (m, 1 H), 1.64-1.72 (m, 1 H), 2.05-2.08 (m, 2 H), 2.11-2.27 (m, 9 H), 2.43-2.62 (m, 5 H), 2.64-2.78 (m, 3 H), 2.88-2.92 (m, 3 H), 3.03-3.09 (m, 1 H), 3.27-3.28 (m, 3 H), 3.38-3.43 (m, 1 H), 3.74-3.84 (m, 1 H), 4.05-4.15 (m, 1 H), 4.24-4.42 (m, 1 H), 4.45 (s, 2 H), 4.81-4.85 (m, 2 H), 6.57 (d, J = 7.11 Hz, 2 H), 6.74-6.79 (m, 1 H), 7.26 (d, J = 8.05 Hz, 1 H), 7.34 (d, J = 8.05 Hz, 1 H), 7.71 (d, J = 1.79 Hz, 1 H). |
| 573 (General Procedure B using Amine B30 as the core reagent) | 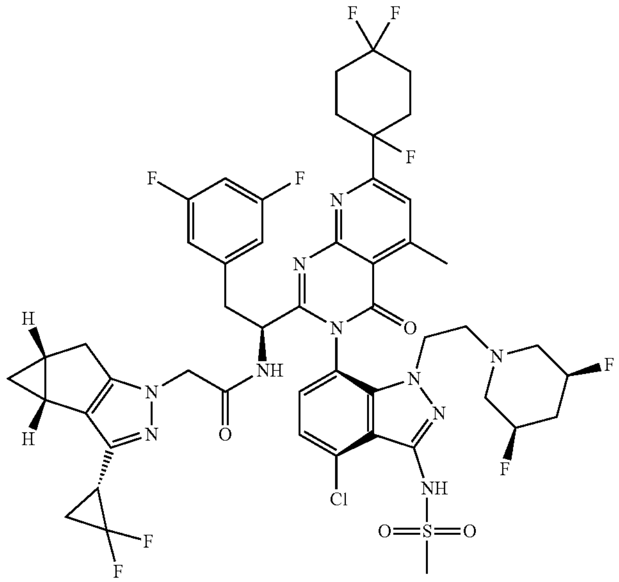 N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2R,4R)-9-[(1R)-2,2-difluorocyclopropyl]-7,8-diazatricyclo[4.3.0.0$^{2,4}$]nona-1(6),8-dien-7-yl]acetamide | LCMS Method B: retention time = 1.462 min.; observed ion = 1079.4 [M + H]. 1H NMR (500 MHz, METHANOL-d4) δ ppm 0.05-0.14 (m, 1 H), 0.94-1.03 (m, 1 H), 1.56-1.69 (m, 1 H), 1.77-1.85 (m, 2 H), 1.93-2.00 (m, 2 H), 2.11-2.33 (m, 10 H), 2.47-2.58 (m, 4 H), 2.64-2.70 (m, 2 H), 2.74-2.80 (m, 2 H), 2.90 (s, 3 H), 3.02-3.10 (m, 1 H), 3.41 (br d, J = 5.07 Hz, 1 H), 3.71 (ddd, J = 14.31, 8.94, 5.36 Hz, 2 H), 3.94-4.02 (m, 1 H), 4.24-4.41 (m, 5 H), 4.80 (br dd, J = 9.39, 4.92 Hz, 2 H), 6.54-6.59 (m, 2 H), 6.74-6.79 (m, 1 H), 7.23-7.37 (m, 2 H), 7.67-7.73 (m, 1 H). |

TABLE A-continued

| Example No. (preparation of the Example) | Structure and IUPAC name | Characterising data (LCMS and/or NMR) |
|---|---|---|
| 574 (General Procedure A using Bromide A13 as the core reagent) | 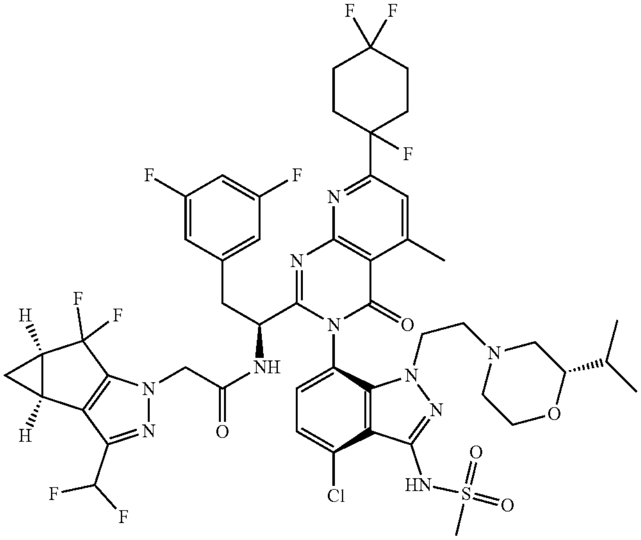 N-[(1S)-1-[(3P)-3-(4-chloro-3-methanesulfonamido-1-{2-[(2S)-2-(propan-2-yl)morpholin-4-yl]ethyl}-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method B: retention time = 1.27 min.; observed ion = 1097.2 [M + H]. 1H NMR (500 MHz, METHANOL-d4) δ ppm 7.74 (dd, J = 1.49, 0.89 Hz, 1 H), 7.34-7.40 (m, 1 H), 7.29 (d, J = 7.75 Hz, 1 H), 6.52-6.82 (m, 4 H), 4.80-4.82 (m, 1 H), 4.64 (q, J = 16.69 Hz, 3 H), 4.19-4.26 (m, 1 H), 3.84-3.93 (m, 1 H), 3.64-3.70 (m, 1 H), 3.41 (br d, J = 4.47 Hz, 1 H), 3.26 (s, 3 H), 3.06 (dd, J = 14.31, 9.84 Hz, 1 H), 2.92 (d, J = 0.60 Hz, 3 H), 2.54-2.77 (m, 5 H), 2.41-2.49 (m, 3 H), 2.14-2.38 (m, 8 H), 1.89-1.98 (m, 1 H), 1.53-1.61 (m, 1 H), 1.34-1.41 (m, 2 H), 1.04 (dt, J = 3.73, 2.01 Hz, 1 H), 0.83 (d, J = 6.56 Hz, 3 H), 0.73 (d, J = 6.85 Hz, 3 H). |
| 575 (General Procedure A using Bromide A13 as the core reagent) | 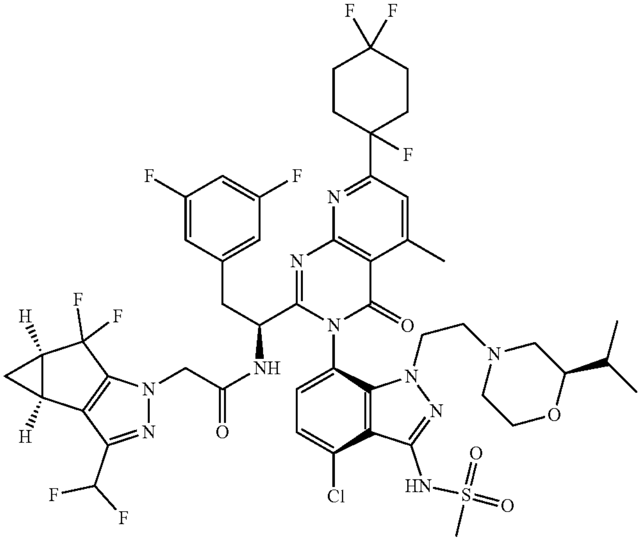 N-[(1S)-1-[(3P)-3-(4-chloro-3-methanesulfonamido-1-{2-[(2R)-2-(propan-2-yl)morpholin-4-yl]ethyl}-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method B: retention time = 1.27 min.; observed ion = 1097.4 [M + H]. 1H NMR (500 MHz, METHANOL-d4) δ ppm 7.71-7.76 (m, 1 H), 7.34-7.39 (m, 1 H), 7.30 (d, J = 7.75 Hz, 1 H), 6.52-6.82 (m, 4 H), 4.80-4.82 (m, 1 H), 4.64 (q, J = 16.69 Hz, 3 H), 4.19-4.28 (m, 1 H), 3.85 (ddd, J = 14.23, 9.91, 4.77 Hz, 1 H), 3.56 (br dd, J = 2.53, 1.34 Hz, 1 H), 3.40 (dd, J = 14.01, 4.47 Hz, 1 H), 3.26 (s, 3 H), 3.07 (dd, J = 14.16, 9.69 Hz, 1 H), 2.92 (d, J = 0.60 Hz, 3 H), 2.53-2.73 (m, 5 H), 2.42-2.49 (m, 2 H), 2.15-2.37 (m, 8 H), 1.68-1.80 (m, 2 H), 1.48-1.56 (m, 1 H), 1.35-1.41 (m, 1 H), 1.02-1.07 (m, 1 H), 0.86 (d, J = 6.56 Hz, 3 H), 0.80 (d, J = 6.85 Hz, 3 H). |

TABLE A-continued

| Example No. (preparation of the Example) | Structure and IUPAC name | Characterising data (LCMS and/or NMR) |
|---|---|---|
| 576 (General Procedure A using Bromide A13 as the core reagent) | 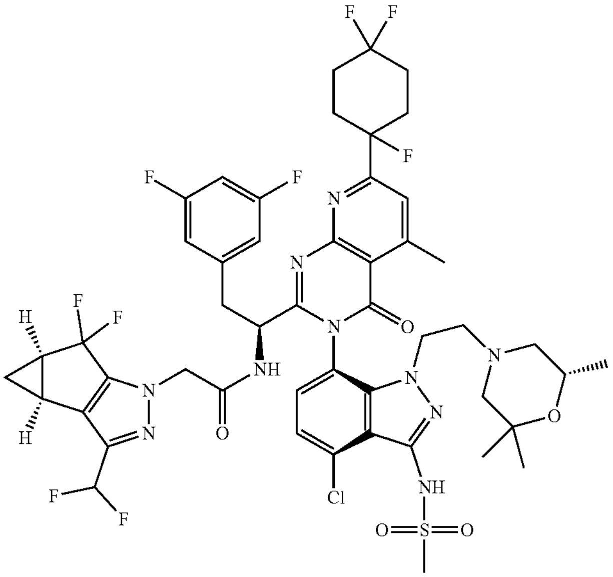 N-[(1S)-1-[(3P)-3-(4-chloro-3-methanesulfonamido-1-{2-[(6S)-2,2,6-trimethylmorpholin-4-yl]ethyl}-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method B: retention time = 1.35 min.; observed ion = 1097.2 [M + H]. 1H NMR (500 MHz, METHANOL-d4) δ ppm 7.64 (d, J = 0.89 Hz, 1 H), 7.24-7.29 (m, 1 H), 7.18-7.23 (m, 1 H), 6.37-6.71 (m, 4 H), 4.70 (br d, J = 5.36 Hz, 1 H), 4.50-4.60 (m, 3 H), 4.15 (ddd, J = 14.23, 10.95, 6.41 Hz, 1 H), 3.65-3.72 (m, 1 H), 3.28 (br s, 1 H), 3.15 (s, 3 H), 2.93 (dd, J = 14.31, 9.54 Hz, 1 H), 2.82 (d, J = 0.60 Hz, 3 H), 2.43-2.51 (m, 2 H), 2.30-2.38 (m, 3 H), 1.98-2.27 (m, 9 H), 1.51 (d, J = 11.33 Hz, 1 H), 1.23-1.31 (m, 2 H), 0.95 (ddd, J = 5.59, 3.50, 2.24 Hz, 1 H), 0.91 (s, 3 H), 0.82 (s, 3 H), 0.71 (d, J = 6.26 Hz, 3 H). |
| 577 (General Procedure A using Bromide A13 as the core reagent) | 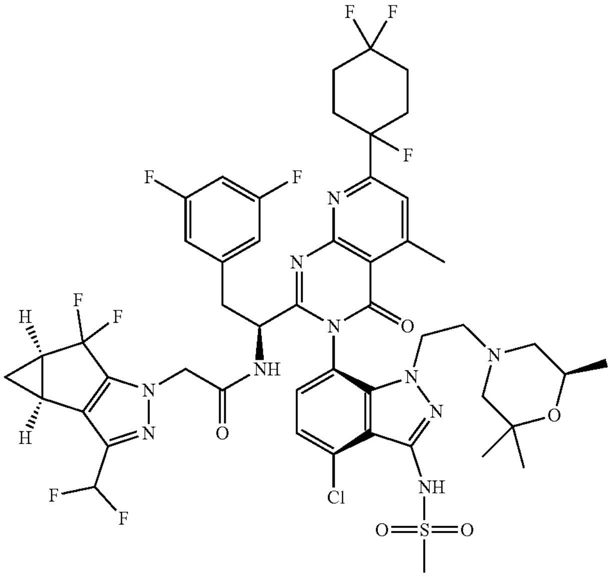 N-[(1S)-1-[(3P)-3-(4-chloro-3-methanesulfonamido-1-{2-[(6R)-2,2,6-trimethylmorpholin-4-yl]ethyl}-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method B: retention time = 1.32 min.; observed ion = 1097.4 [M + H]. 1H NMR (500 MHz, METHANOL-d4) δ ppm 7.60-7.65 (m, 1 H), 7.25-7.29 (m, 1 H), 7.18-7.23 (m, 1 H), 6.40-6.71 (m, 4 H), 4.69 (dd, J = 9.69, 4.62 Hz, 1 H), 4.46-4.58 (m, 2 H), 4.06 (ddd, J = 14.08, 10.80, 4.92 Hz, 1 H), 3.76 (ddd, J = 14.01, 10.58, 5.81 Hz, 1 H), 3.50-3.56 (m, 1 H), 3.26-3.30 (m, 1 H), 3.16 (s, 3 H), 2.95 (dd, J = 14.16, 9.69 Hz, 1 H), 2.82 (d, J = 0.89 Hz, 3 H), 2.32-2.54 (m, 7 H), 2.01-2.26 (m, 7 H), 1.96 (dd, J = 10.73, 0.89 Hz, 1 H), 1.37-1.47 (m, 2 H), 1.28 (br d, J = 6.85 Hz, 1 H), 0.93-0.97 (m, 1 H), 0.83 (d, J = 5.96 Hz, 3 H), 0.79 (d, J = 6.56 Hz, 6 H). |

TABLE A-continued

| Example No. (preparation of the Example) | Structure and IUPAC name | Characterising data (LCMS and/or NMR) |
|---|---|---|
| 578 (General Procedure A using Bromide A13 as the core reagent) | 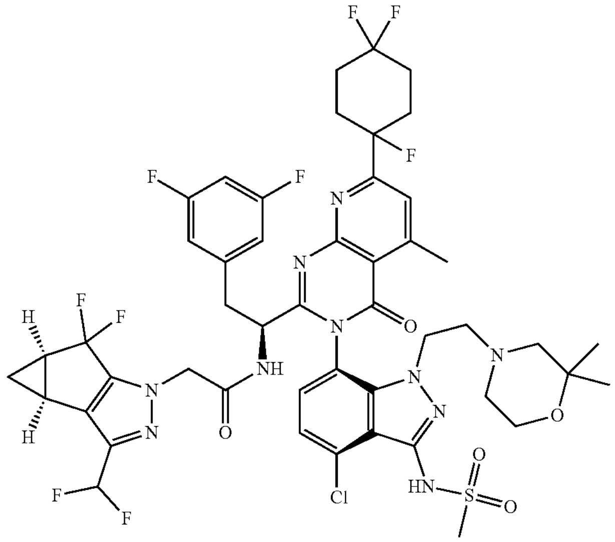 N-[(1S)-1-[(3P)-3-{4-chloro-1-[2-(2,2-dimethylmorpholin-4-yl)ethyl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.30 min.; observed ion = 1083.4 [M + H]. 1H NMR (500 MHz, METHANOL-d4) δ ppm 7.65 (s, 1 H), 7.24-7.30 (m, 1 H), 7.18-7.23 (m, 1 H), 6.39-6.71 (m, 4 H), 4.70 (br d, J = 4.47 Hz, 1 H), 4.54 (q, J = 16.69 Hz, 3 H), 4.10 (ddd, J = 14.01, 10.58, 5.51 Hz, 1 H), 3.66-3.73 (m, 1 H), 3.31-3.33 (m, 1 H), 3.26-3.29 (m, 2 H), 3.15 (s, 3 H), 2.94 (dd, J = 14.16, 9.69 Hz, 1 H), 2.81 (d, J = 0.60 Hz, 3 H), 2.32-2.55 (m, 6 H), 2.04-2.26 (m, 6 H), 1.97-2.02 (m, 2 H), 1.89 (br d, J = 11.03 Hz, 1 H), 1.75 (d, J = 10.73 Hz, 1 H), 1.26-1.30 (m, 1 H), 0.93-0.97 (m, 1 H), 0.84 (s, 3 H), 0.78 (s, 3 H). |
| 579 (General Procedure A using Bromide A13 as the core reagent) | 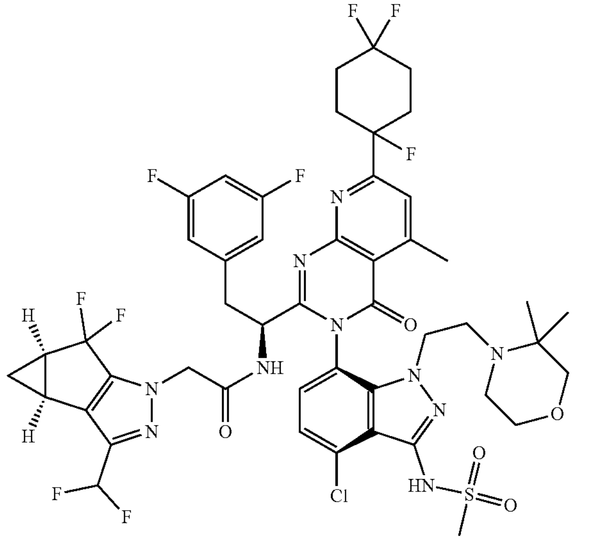 N-[(1S)-1-[(3P)-3-{4-chloro-1-[2-(3,3-dimethylmorpholin-4-yl)ethyl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.21 min.; observed ion = 1083.6 [M + H]. 1H NMR (500 MHz, METHANOL-d4) δ ppm 7.74 (d, J = 0.60 Hz, 1 H), 7.36 (d, J = 8.05 Hz, 1 H), 7.28 (d, J = 8.05 Hz, 1 H), 6.48-6.82 (m, 4 H), 4.80 (br dd, J = 9.84, 4.47 Hz, 2 H), 4.60-4.73 (m, 2 H), 4.02-4.12 (m, 1 H), 3.67-3.75 (m, 1 H), 3.42-3.46 (m, 1 H), 3.36-3.39 (m, 1 H), 3.28 (s, 3 H), 3.13 (br d, J = 3.87 Hz, 2 H), 3.03 (dd, J = 14.01, 9.54 Hz, 1 H), 2.92 (d, J = 0.60 Hz, 3 H), 2.71-2.80 (m, 1 H), 2.51-2.67 (m, 2 H), 2.45 (ddd, J = 11.10, 7.53, 4.02 Hz, 3 H), 2.29-2.37 (m, 1 H), 2.08-2.27 (m, 7 H), 1.35-1.42 (m, 1 H), 1.02-1.08 (m, 1 H), 0.76 (br d, J = 9.54 Hz, 6 H). |

TABLE A-continued

| Example No. (preparation of the Example) | Structure and IUPAC name | Characterising data (LCMS and/or NMR) |
|---|---|---|
| 581 (General Procedure A using Bromide A14 as the core reagent) | 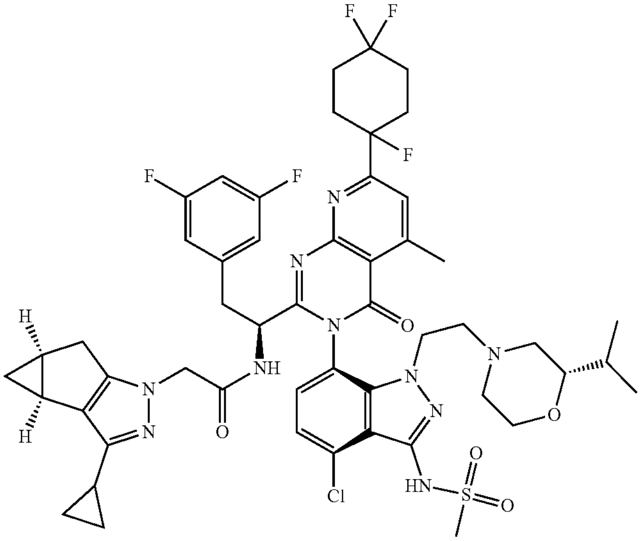 N-[(1S)-1-[(3P)-3-(4-chloro-3-methanesulfonamido-1-{2-[(2S)-2-(propan-2-yl)morpholin-4-yl]ethyl}-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.34 min.; observed ion = 1049.5 [M − H]. 1H NMR (500 MHz, METHANOL-d4) δ ppm 7.61-7.66 (m, 1 H), 7.25-7.30 (m, 1 H), 7.19-7.23 (m, 1 H), 6.65-6.72 (m, 1 H), 6.43 (dd, J = 8.05, 2.09 Hz, 2 H), 4.69 (dd, J = 9.54, 4.47 Hz, 1 H), 4.21 (d, J = 1.19 Hz, 2 H), 4.00 (ddd, J = 13.93, 10.36, 5.22 Hz, 1 H), 3.73 (ddd, J = 13.93, 10.36, 5.81 Hz, 1 H), 3.52-3.58 (m, 1 H), 3.26-3.29 (m, 2 H), 3.19 (s, 3 H), 2.93 (dd, J = 14.16, 9.69 Hz, 1 H), 2.82 (d, J = 0.60 Hz, 3 H), 2.60 (dd, J = 16.69, 6.56 Hz, 1 H), 2.35-2.55 (m, 6 H), 1.99-2.26 (m, 7 H), 1.95 (d, J = 10.43 Hz, 1 H), 1.81-1.88 (m, 1 H), 1.74-1.79 (m, 1 H), 1.70 (tt, J = 8.35, 5.07 Hz, 1 H), 1.38-1.49 (m, 2 H), 0.87-0.90 (m, 1 H), 0.84 (d, J = 6.26 Hz, 3 H), 0.79 (d, J = 2.38 Hz, 6 H), 0.74-0.78 (m, 1 H), 0.64-0.72 (m, 2 H),-0.02-0.03 (m, 1 H). |
| 582 (General Procedure A using Bromide A14 as the core reagent) | 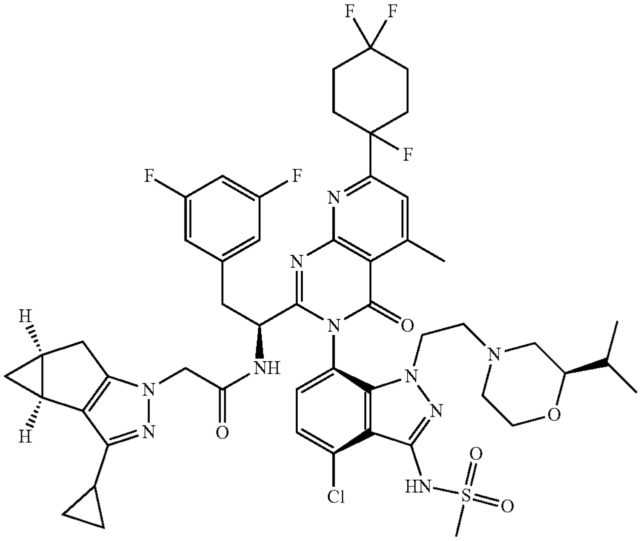 N-[(1S)-1-[(3P)-3-(4-chloro-3-methanesulfonamido-1-{2-[(2R)-2-(propan-2-yl)morpholin-4-yl]ethyl}-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.30 min.; observed ion = 1049.5 [M − H]. 1H NMR (500 MHz, METHANOL-d4) δ ppm 7.60-7.66 (m, 1 H), 7.24-7.30 (m, 1 H), 7.20 (d, J = 8.05 Hz, 1 H), 6.69 (tt, J = 9.09, 2.24 Hz, 1 H), 6.44 (dd, J = 8.20, 2.24 Hz, 2 H), 4.69-4.72 (m, 1 H), 4.18-4.27 (m, 2 H), 4.03-4.11 (m, 1 H), 3.77 (td, J = 9.54, 5.07 Hz, 1 H), 3.59 (br dd, J = 10.73, 2.09 Hz, 1 H), 3.27-3.31 (m, 2 H), 3.20 (s, 3 H), 2.95 (dd, J = 14.16, 9.39 Hz, 1 H), 2.82 (d, J = 0.60 Hz, 3 H), 2.62 (dd, J = 16.54, 6.71 Hz, 2 H), 2.43-2.59 (m, 4 H), 2.33-2.40 (m, 2 H), 2.02-2.29 (m, 8 H), 1.83-1.89 (m, 2 H), 1.75-1.80 (m, 1 H), 1.70 (tt, J = 8.38, 5.03 Hz, 1 H), 1.46-1.54 (m, 1 H), 1.23-1.32 (m, 1 H), 0.87-0.92 (m, 1 H), 0.77-0.83 (m, 2 H), 0.73 (d, J = 6.85 Hz, 3 H), 0.67-0.71 (m, 2 H), 0.64 (d, J = 6.85 Hz, 3 H), −0.04-0.02 (m, 1 H). |

TABLE A-continued

| Example No. (preparation of the Example) | Structure and IUPAC name | Characterising data (LCMS and/or NMR) |
|---|---|---|
| 583 (General Procedure A using Bromide A14 as the core reagent) | 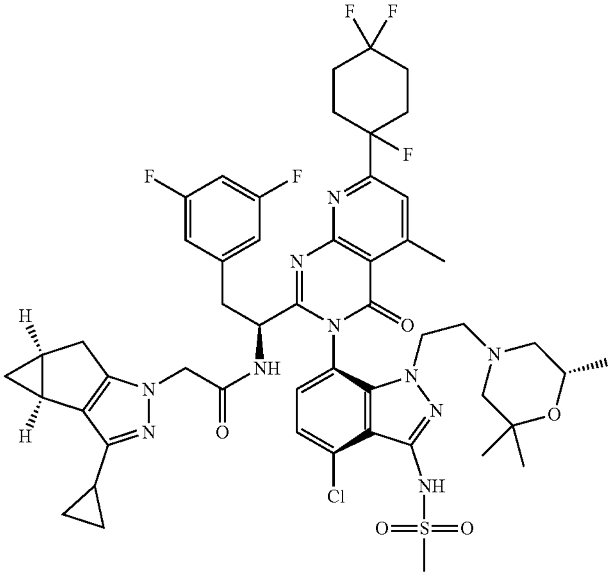 N-[(1S)-1-[(3P)-3-(4-chloro-3-methanesulfonamido-1-{2-[(6S)-2,2,6-trimethylmorpholin-4-yl]ethyl}-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | |
| 584 (General Procedure A using Bromide A14 as the core reagent) | 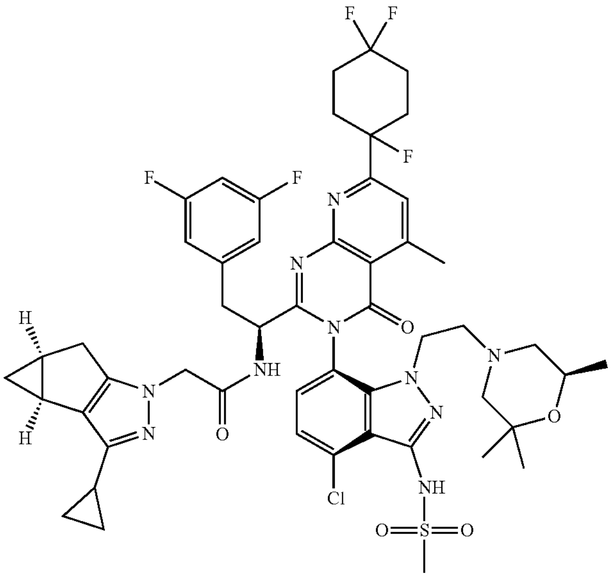 N-[(1S)-1-[(3P)-3-(4-chloro-3-methanesulfonamido-1-{2-[(6R)-2,2,6-trimethylmorpholin-4-yl]ethyl}-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.39 min.; observed ion = 1049.5 [M − H]. 1H NMR (500 MHz, METHANOL-d4) δ ppm 7.65 (d, J = 0.89 Hz, 1 H), 7.24-7.30 (m, 1 H), 7.15-7.22 (m, 1 H), 6.68 (tt, J = 9.13, 2.35 Hz, 1 H), 6.42 (dd, J = 8.05, 2.09 Hz, 2 H), 4.70 (dd, J = 9.54, 4.77 Hz, 1 H), 4.18-4.26 (m, 2 H), 4.05-4.14 (m, 1 H), 3.68 (ddd, J = 14.31, 10.28, 4.62 Hz, 1 H), 3.26-3.30 (m, 1 H), 3.18 (s, 3 H), 2.89-2.96 (m, 1 H), 2.82 (s, 3 H), 2.62 (dd, J = 16.69, 6.56 Hz, 1 H), 2.41-2.56 (m, 3 H), 2.29-2.40 (m, 2 H), 2.19-2.26 (m, 2 H), 1.99-2.17 (m, 6 H), 1.82-1.88 (m, 1 H), 1.74-1.80 (m, 1 H), 1.67-1.73 (m, 1 H), 1.52 (d, J = 10.73 Hz, 1 H), 1.26 (t, J = 10.73 Hz, 1 H), 0.91 (s, 3 H), 0.86-0.90 (m, 1 H), 0.82 (s, 3 H), 0.75-0.81 (m, 2 H), 0.72 (d, J = 6.26 Hz, 3 H), 0.64-0.71 (m, 2 H), −0.04-0.03 (m, 1 H). |

TABLE A-continued

| Example No. (preparation of the Example) | Structure and IUPAC name | Characterising data (LCMS and/or NMR) |
| --- | --- | --- |
| 585 (General Procedure A using Bromide A14 as the core reagent) | 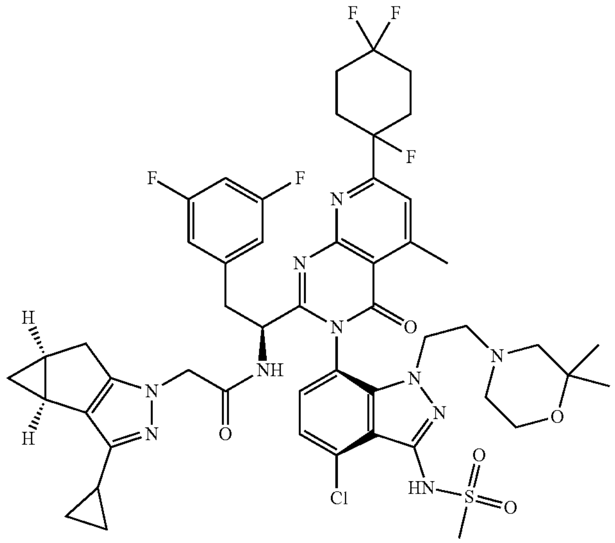 N-[(1S)-1-[(3P)-3-{4-chloro-1-[2-(2,2-dimethylmorpholin-4-yl)ethyl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method A: retention time = 2.933 min.; observed ion = 1037.25 [M + H]. 1H NMR (500 MHz, METHANOL-d4) δ ppm 7.61-7.66 (m, 1 H), 7.25-7.30 (m, 1 H), 7.19-7.23 (m, 1 H), 6.65-6.72 (m, 1 H), 6.43 (dd, J = 8.05, 2.09 Hz, 2 H), 4.69 (dd, J = 9.54, 4.47 Hz, 1 H), 4.21 (d, J = 1.19 Hz, 2 H), 4.00 (ddd, J = 13.93, 10.36, 5.22 Hz, 1 H), 3.73 (ddd, J = 13.93, 10.36, 5.81 Hz, 1 H), 3.52-3.58 (m, 1 H), 3.26-3.29 (m, 2 H), 3.19 (s, 3 H), 2.93 (dd, J = 14.16, 9.69 Hz, 1 H), 2.82 (d, J = 0.60 Hz, 3 H), 2.60 (dd, J = 16.69, 6.56 Hz, 1 H), 2.35-2.55 (m, 6 H), 1.99-2.26 (m, 7 H), 1.95 (d, J = 10.43 Hz, 1 H), 1.81-1.88 (m, 1 H), 1.74-1.79 (m, 1 H), 1.70 (tt, J = 8.35, 5.07 Hz, 1 H), 1.38-1.49 (m, 2 H), 0.87-0.90 (m, 1 H), 0.84 (d, J = 6.26 Hz, 3 H), 0.79 (d, J = 2.38 Hz, 6 H), 0.74-0.78 (m, 1 H), 0.64-0.72 (m, 2 H), −0.02-0.03 (m, 1 H). |
| 586 (General Procedure A using Bromide A14 as the core reagent) | 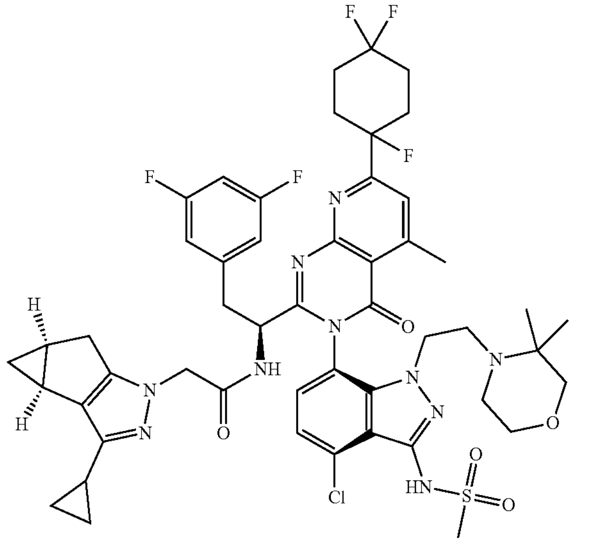 N-[(1S)-1-[(3P)-3-{4-chloro-1-[2-(3,3-dimethylmorpholin-4-yl)ethyl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.23 min.; observed ion = 1035.7 [M − H]. 1H NMR (500 MHz, METHANOL-d4) δ ppm 7.65 (s, 1 H), 7.27-7.32 (m, 1 H), 7.19-7.25 (m, 1 H), 6.64-6.75 (m, 1 H), 6.42 (dd, J = 8.20, 2.24 Hz, 2 H), 4.67-4.70 (m, 1 H), 4.18-4.33 (m, 2 H), 3.86-3.98 (m, 1 H), 3.55-3.67 (m, 1 H), 3.22 (s, 3 H), 3.09 (br dd, J = 3.13, 1.64 Hz, 3 H), 2.94 (dd, J = 14.31, 9.54 Hz, 1 H), 2.82 (s, 3 H), 2.67-2.76 (m, 1 H), 2.58-2.65 (m, 1 H), 2.44-2.56 (m, 2 H), 2.39 (br d, J = 17.29 Hz, 1 H), 2.05-2.26 (m, 8 H), 1.83-1.89 (m, 1 H), 1.74-1.80 (m, 1 H), 1.65-1.72 (m, 1 H), 0.89 (td, J = 7.67, 4.62 Hz, 1 H), 0.76-0.83 (m, 2 H), 0.65-0.74 (m, 8 H), 0.00 (d, J = 3.58 Hz, 1 H). |

TABLE A-continued

| Example No. (preparation of the Example) | Structure and IUPAC name | Characterising data (LCMS and/or NMR) |
|---|---|---|
| 588 (General Procedure A using Bromide A13 as the core reagent) | 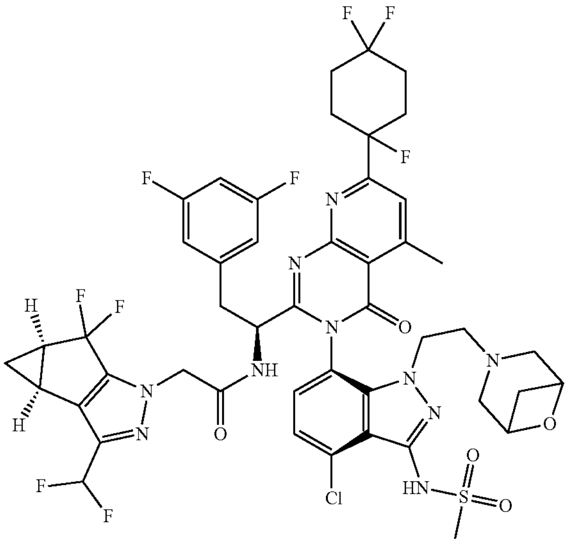 N-[(1S)-1-[(3P)-3-[4-chloro-3-methanesulfonamido-1-(2-{6-oxa-3-azabicyclo[3.1.1]heptan-3-yl}ethyl)-1H-indazol-7-yl]-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.19 min.; observed ion = 1067.3 [M + H]. 1H NMR (500 MHz, METHANOL-d4) δ ppm 7.61 (d, J = 0.89 Hz, 1 H), 7.25-7.29 (m, 1 H), 7.20-7.24 (m, 1 H), 6.42-6.72 (m, 4 H), 4.71 (d, J = 5.07 Hz, 1 H), 4.49-4.62 (m, 3 H), 4.20-4.23 (m, 1 H), 4.09-4.17 (m, 2 H), 3.76 (ddd, J = 14.38, 9.31, 5.22 Hz, 1 H), 3.28-3.32 (m, 1 H), 3.16 (s, 3 H), 2.95 (dd, J = 14.16, 9.69 Hz, 1 H), 2.80 (d, J = 0.60 Hz, 3 H), 2.55-2.77 (m, 6 H), 2.47-2.54 (m, 1 H), 2.40-2.46 (m, 2 H), 2.34 (td, J = 7.30, 3.87 Hz, 2 H), 2.19-2.28 (m, 2 H), 2.00-2.17 (m, 6 H), 1.77 (d, J = 8.05 Hz, 1 H), 1.25-1.32 (m, 1 H), 0.88-0.96 (m, 1 H). |
| 589 (General Procedure A using Bromide A13 as the core reagent) | 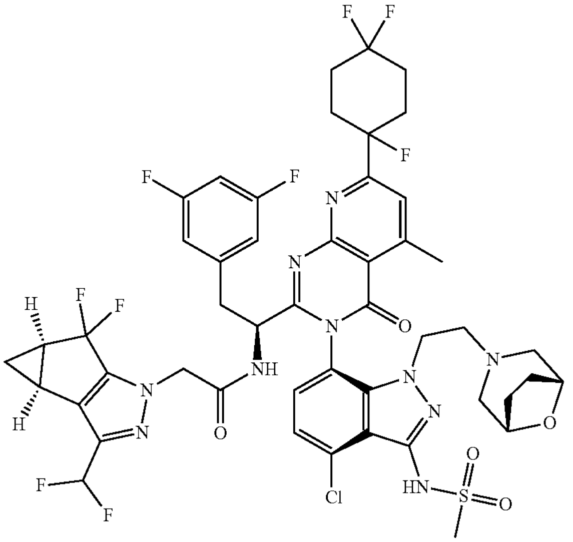 N-[(1S)-1-[(3P)-3-(4-chloro-3-methanesulfonamido-1-{2-[(1R,5S)-8-oxa-3-azabicyclo[3.2.1]octan-3-yl]ethyl}-1H-indazol-7-yl)-5-methyl-4-oxo-7-(1,4,4-trifluorocyclohexyl)-3H, 4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method B: retention time = 1.28 min.; observed ion = 1081.3 [M + H]. 1H NMR (500 MHz, METHANOL-d4) δ ppm 7.72-7.78 (m, 1 H), 7.35-7.39 (m, 1 H), 7.29-7.34 (m, 1 H), 6.50-6.82 (m, 4 H), 4.80 (d, J = 5.36 Hz, 1 H), 4.58-4.71 (m, 3 H), 4.12-4.19 (m, 1 H), 4.08 (br d, J = 6.56 Hz, 1 H), 3.95-4.00 (m, 1 H), 3.70-3.78 (m, 1 H), 3.37-3.42 (m, 2 H), 3.25 (s, 3 H), 3.05 (dd, J = 14.01, 9.54 Hz, 1 H), 2.92 (s, 3 H), 2.52-2.69 (m, 3 H), 2.43-2.50 (m, 3 H), 2.29-2.37 (m, 2 H), 2.17-2.28 (m, 5 H), 2.08-2.15 (m, 2 H), 1.97 (dd, J = 10.88, 1.94 Hz, 1 H), 1.54-1.66 (m, 2 H), 1.46-1.53 (m, 1 H), 1.30-1.42 (m, 2 H), 1.01-1.07 (m, 1 H). |

TABLE A-continued

| Example No. (preparation of the Example) | Structure and IUPAC name | Characterising data (LCMS and/or NMR) |
| --- | --- | --- |
| 590 (General Procedure A using Bromide A13 as the core reagent) | 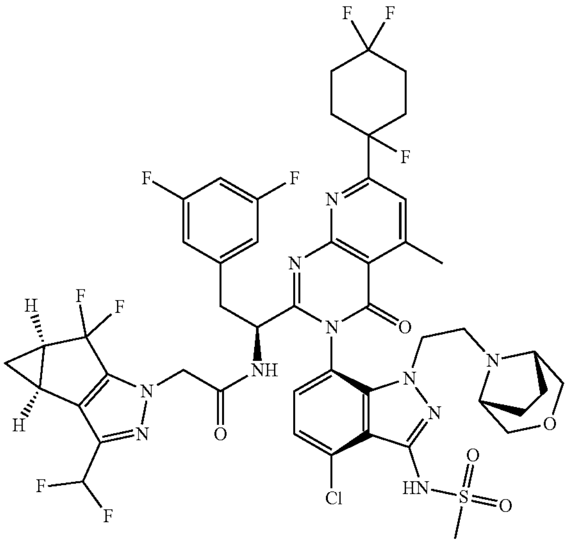 N-[(1S)-1-[(3P)-3-(4-chloro-3-methanesulfonamido-1-{2-[(1R,5S)-3-oxa-8-azabicyclo[3.2.1]octan-8-yl]ethyl}-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method B: retention time = 1.18 min.; observed ion = 1081.3 [M + H]. 1H NMR (500 MHz, METHANOL-d4) δ ppm 7.70-7.76 (m, 1 H), 7.44-7.46 (m, 1 H), 7.38-7.49 (m, 1 H), 6.49-6.84 (m, 4 H), 4.79 (s, 1 H), 4.63-4.72 (m, 3 H), 4.33-4.43 (m, 1 H), 3.92-4.13 (m, 1 H), 3.49-3.78 (m, 3 H), 3.41-3.48 (m, 1 H), 3.28 (s, 3 H), 3.08-3.14 (m, 2 H), 2.91 (d, J = 0.60 Hz, 3 H), 2.51-2.67 (m, 2 H), 2.41-2.49 (m, 2 H), 2.11-2.37 (m, 8 H), 1.89-2.05 (m, 4 H), 1.35-1.42 (m, 1 H), 1.00-1.05 (m, 1 H). |
| 591 (General Procedure A using Bromide A14 as the core reagent) | 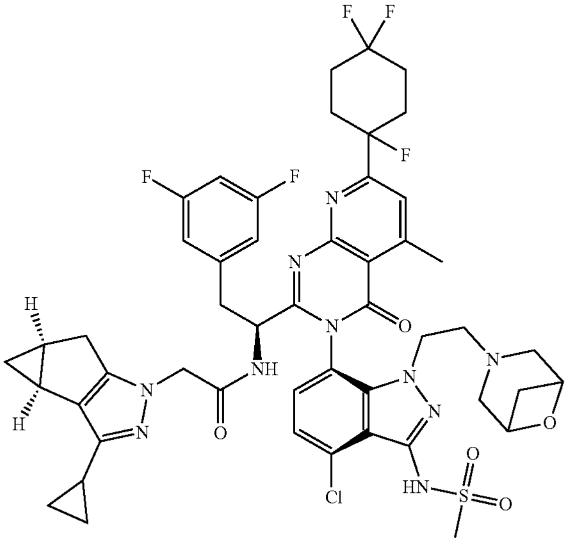 N-[(1S)-1-[(3P)-3-[4-chloro-3-methanesulfonamido-1-(2-{6-oxa-3-azabicyclo[3.1.1]heptan-3-yl}ethyl)-1H-indazol-7-yl]-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2}$,$^{4}$]nona-1(6),8-dien-7-yl]acetamide | LCMS Method B: retention time = 1.21 min.; observed ion = 1019.5 [M − H]. 1H NMR (500 MHz, METHANOL-d4) δ ppm 7.63 (d, J = 0.89 Hz, 1 H), 7.28-7.34 (m, 1 H), 7.22 (d, J = 8.05 Hz, 1 H), 6.66-6.76 (m, 1 H), 6.46 (dd, J = 8.05, 2.09 Hz, 2 H), 4.72-4.75 (m, 1 H), 4.22-4.32 (m, 3 H), 4.16 (br d, J = 3.28 Hz, 1 H), 4.07 (ddd, J = 14.23, 9.31, 6.26 Hz, 1 H), 3.68-3.78 (m, 1 H), 3.31 (dd, J = 14.31, 4.77 Hz, 1 H), 3.22 (s, 3 H), 2.97 (dd, J = 14.31, 9.54 Hz, 1 H), 2.82 (d, J = 0.60 Hz, 3 H), 2.70-2.80 (m, 3 H), 2.59-2.69 (m, 3 H), 2.37-2.57 (m, 4 H), 2.03-2.31 (m, 7 H), 1.82-1.91 (m, 1 H), 1.75-1.81 (m, 2 H), 1.70 (tt, J = 8.35, 5.07 Hz, 1 H), 0.89 (td, J = 7.60, 4.77 Hz, 1 H), 0.75-0.84 (m, 2 H), 0.64-0.72 (m, 2 H), 0.00 (d, J = 3.58 Hz, 1 H). |

TABLE A-continued

| Example No. (preparation of the Example) | Structure and IUPAC name | Characterising data (LCMS and/or NMR) |
|---|---|---|
| 592 (General Procedure A using Bromide A14 as the core reagent) | 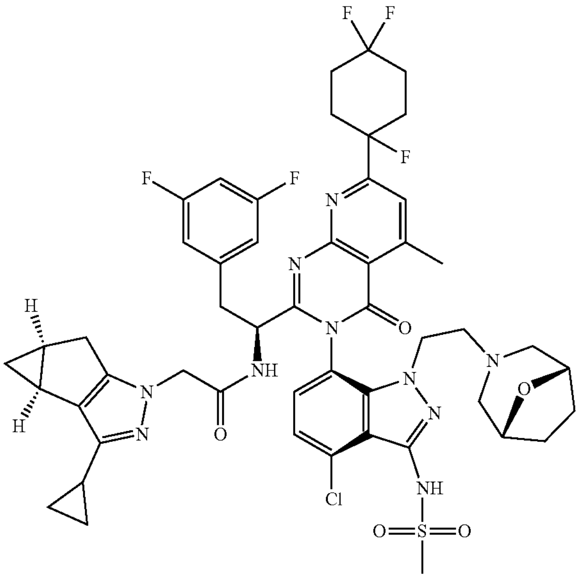<br>N-[(1S)-1-[(3P)-3-(4-chloro-3-methanesulfonamido-1-{2-[(1R,5S)-8-oxa-3-azabicyclo[3.2.1]octan-3-yl]ethyl}-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.29 min.; observed ion = 1033.5 [M − H].<br>1H NMR (500 MHz, METHANOL-d4) δ ppm 7.66 (d, J = 0.60 Hz, 1 H), 7.25-7.32 (m, 1 H), 7.18-7.24 (m, 1 H), 6.66-6.74 (m, 1 H), 6.45 (dd, J = 8.05, 2.09 Hz, 2 H), 4.68-4.72 (m, 1 H), 4.17-4.27 (m, 2 H), 3.92-4.03 (m, 2 H), 3.89 (br d, J = 6.26 Hz, 1 H), 3.60 (td, J = 9.39, 4.77 Hz, 1 H), 3.29 (dd, J = 14.01, 4.77 Hz, 1 H), 3.19 (s, 3 H), 2.95 (dd, J = 14.16, 9.39 Hz, 1 H), 2.81 (s, 3 H), 2.64 (dd, J = 16.54, 6.71 Hz, 1 H), 2.51-2.59 (m, 1 H), 2.45 (ddd, J = 12.15, 9.91, 5.96 Hz, 2 H), 2.35-2.41 (m, 2 H), 2.20-2.28 (m, 2 H), 2.03-2.18 (m, 6 H), 2.00 (dd, J = 10.88, 1.94 Hz, 1 H), 1.84-1.92 (m, 2 H), 1.75-1.79 (m, 1 H), 1.70 (tt, J = 8.46, 4.95 Hz, 1 H), 1.45-1.56 (m, 2 H), 1.36-1.42 (m, 1 H), 1.18-1.28 (m, 1 H), 0.89 (td, J = 7.75, 4.77 Hz, 1 H), 0.75-0.83 (m, 2 H), 0.69 (qd, J = 5.12, 2.83 Hz, 2 H), −0.03-0.02 (m, 1 H). |
| 593 (General Procedure A using Bromide A14 as the core reagent) | 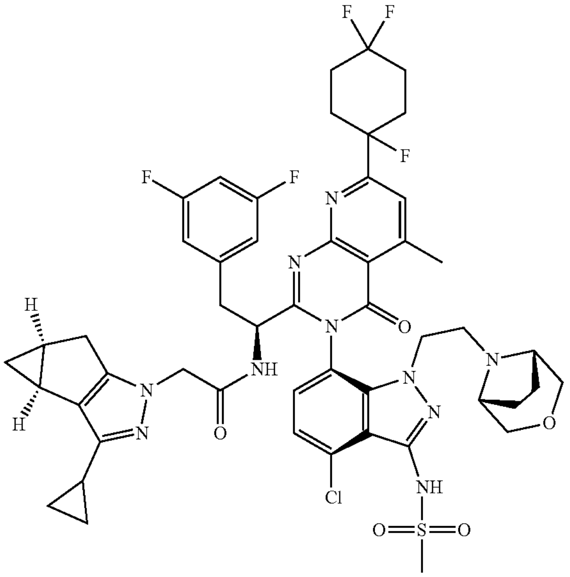<br>N-[(1S)-1-[(3P)-3-(4-chloro-3-methanesulfonamido-1-{2-[(1R,5S)-3-oxa-8-azabicyclo[3.2.1]octan-8-yl]ethyl}-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method B: retention time = 1.20 min.; observed ion = 1033.6 [M − H].<br>1H NMR (500 MHz, METHANOL-d4) δ ppm 7.63-7.71 (m, 1 H), 7.33-7.45 (m, 2 H), 6.72-6.81 (m, 1 H), 6.46 (dd, J = 8.05, 2.09 Hz, 2 H), 4.63 (br dd, J = 9.98, 3.43 Hz, 1 H), 4.24-4.45 (m, 2 H), 3.91-4.07 (m, 1 H), 3.40-3.76 (m, 5 H), 3.35 (br dd, J = 14.31, 3.58 Hz, 2 H), 3.24 (s, 3 H), 3.03 (dd, J = 14.46, 10.28 Hz, 2 H), 2.85 (s, 3 H), 2.44-2.62 (m, 3 H), 2.41 (s, 1 H), 2.05-2.30 (m, 6 H), 1.84-2.02 (m, 4 H), 1.77-1.82 (m, 1 H), 1.70 (tt, J = 8.46, 4.95 Hz, 1 H), 0.92 (td, J = 7.67, 4.62 Hz, 1 H), 0.77-0.87 (m, 2 H), 0.66-0.75 (m, 2 H), 0.00 (q, J = 4.17 Hz, 1 H). |

TABLE A-continued

| Example No. (preparation of the Example) | Structure and IUPAC name | Characterising data (LCMS and/or NMR) |
|---|---|---|
| 594 (General Procedure B using Amine B27 as the core reagent) | 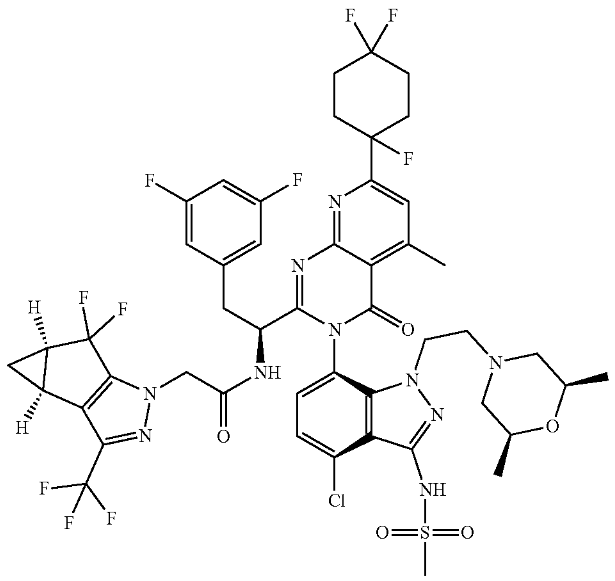 N-[(1S)-1-[(3P)-3-(4-chloro-1-{2-[(2R,6S)-2,6-dimethylmorpholin-4-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-5,5-difluoro-9-(trifluoromethyl)-7,8-diazatricyclo[4.3.0.0$^{2,4}$]nona-1(6),8-dien-7-yl]acetamide | LCMS Method B: retention time = 1.271 min.; observed ion = 1101.3 [M + H]. 1H NMR (500 MHz, METHANOL-d4) δ ppm 0.87 (d, J = 6.26 Hz, 3 H), 0.95-1.02 (m, 4 H), 1.07 (br dd, J = 5.66, 1.79 Hz, 1 H), 1.37-1.42 (m, 1 H), 1.47 (br d, J = 5.66 Hz, 1 H), 1.55-1.64 (m, 1 H), 2.01-2.07 (m, 2 H), 2.11-2.25 (m, 5 H), 2.43-2.57 (m, 5 H), 2.65-2.69 (m, 1 H), 2.81-2.84 (m, 3 H), 2.90 (s, 3 H), 3.04 (dd, J = 14.31, 9.84 Hz, 1 H), 3.25-3.26 (m, 3 H), 3.37-3.40 (m, 1 H), 3.86-3.93 (m, 1 H), 4.16-4.22 (m, 1 H), 4.60-4.72 (m, 2 H), 6.49 (d, J = 6.92 Hz, 2 H), 6.76 (t, J = 8.76 Hz, 1 H), 7.30 (d, J = 7.75 Hz, 1 H), 7.36 (d, J = 8.05 Hz, 1 H), 7.73 (s, 1 H). |
| 595 (General Procedure B using Amine B27 as the core reagent) | 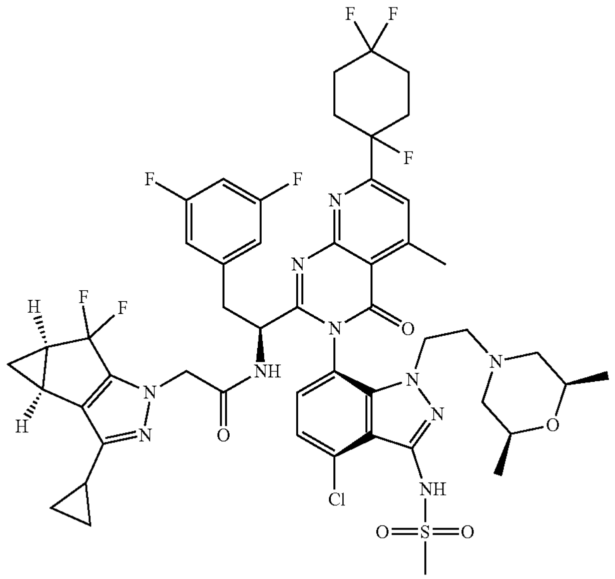 N-[(1S)-1-[(3P)-3-(4-chloro-1-{2-[(2R,6S)-2,6-dimethylmorpholin-4-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-cyclopropyl-5,5-difluoro-7,8-diazatricyclo[4.3.0.0$^{2,4}$]nona-1(6),8-dien-7-yl]acetamide | LCMS Method B: retention time = 1.254 min.; observed ion = 1073.4 [M + H]. 1H NMR (500 MHz, METHANOL-d4) δ ppm 0.76-0.80 (m, 2 H), 0.89-0.95 (m, 6 H), 0.97-1.04 (m, 5 H), 1.25-1.32 (m, 1 H), 1.59-1.71 (m, 2 H), 1.79-1.87 (m, 2 H), 2.01-2.07 (m, 1 H), 2.15-2.30 (m, 6 H), 2.49-2.63 (m, 3 H), 2.65-2.74 (m, 2 H), 2.82-2.83 (m, 1 H), 2.90 (d, J = 0.60 Hz, 3 H), 3.00-3.06 (m, 1 H), 3.28 (s, 3 H), 3.36-3.46 (m, 2 H), 3.91-3.97 (m, 1 H), 4.24-4.30 (m, 1 H), 4.51 (d, J = 11.03 Hz, 1 H), 4.70-4.74 (m, 1 H), 6.47-6.52 (m, 2 H), 6.74-6.81 (m, 1 H), 7.32-7.39 (m, 2 H), 7.73 (s, 1 H). |

TABLE A-continued

| Example No. (preparation of the Example) | Structure and IUPAC name | Characterising data (LCMS and/or NMR) |
|---|---|---|
| 596 (General Procedure B using Amine B27 as the core reagent) | 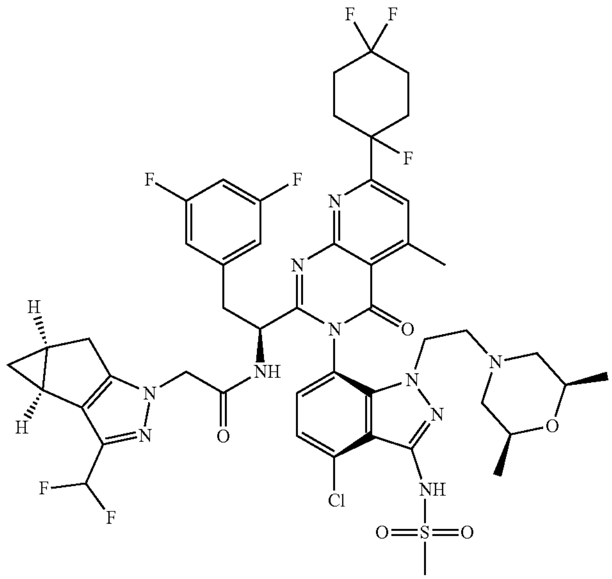 N-[(1S)-1-[(3P)-3-(4-chloro-1-{2-[(2R,6S)-2,6-dimethylmorpholin-4-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-(difluoromethyl)-7,8-diazatricyclo[4.3.0.0$^{2,4}$]nona-1(6),8-dien-7-yl]acetamide | LCMS Method B: retention time = 1.222 min.; observed ion = 1047.6 [M + H]. 1H NMR (500 MHz, METHANOL-d4) δ ppm 0.19-0.22 (m, 1 H), 0.87 (d, J = 6.26 Hz, 3 H), 0.98-1.02 (m, 3 H), 1.02-1.06 (m, 1 H), 1.57-1.68 (m, 1 H), 1.99-2.07 (m, 3 H), 2.15-2.25 (m, 4 H), 2.27-2.38 (m, 3 H), 2.49-2.68 (m, 6 H), 2.74 (br d, J = 2.68 Hz, 1 H), 2.83 (t, J = 0.75 Hz, 1 H), 2.90 (d, J = 0.60 Hz, 3 H), 3.06 (dd, J = 14.31, 9.84 Hz, 1 H), 3.17 (dt, J = 3.28, 1.64 Hz, 1 H), 3.27-3.28 (m, 3 H), 3.39-3.41 (m, 1 H), 3.43-3.47 (m, 1 H), 3.89-3.94 (m, 1 H), 4.13-4.18 (m, 1 H), 4.31-4.45 (m, 2 H), 6.46-6.71 (m, 3 H), 6.73-6.79 (m, 1 H), 7.31-7.37 (m, 2 H), 7.74 (s, 1 H). |
| 597 (General Procedure B using Amine B27 as the core reagent) | 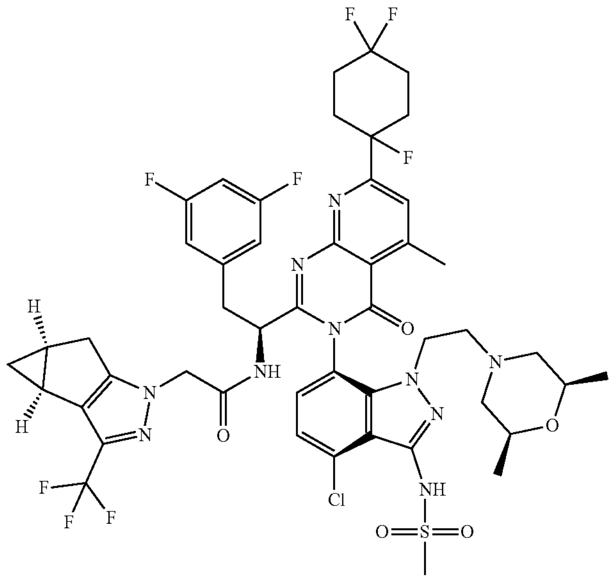 N-[(1S)-1-[(3P)-3-(4-chloro-1-{2-[(2R,6S)-2,6-dimethylmorpholin-4-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-(trifluoromethyl)-7,8-diazatricyclo[4.3.0.0$^{2,4}$]nona-1(6),8-dien-7-yl]acetamide | LCMS Method B: retention time = 1.267 min.; observed ion = 1065.5 [M + H]. 1H NMR (500 MHz, METHANOL-d4) δ ppm 0.19-0.22 (m, 1 H), 0.86 (d, J = 6.26 Hz, 3 H), 0.98 (d, J = 6.56 Hz, 3 H), 1.07 (td, J = 7.67, 4.92 Hz, 1 H), 1.29 (s, 1 H), 1.43 (br d, J = 2.09 Hz, 1 H), 1.57 (br s, 1 H), 2.02-2.08 (m, 3 H), 2.12-2.32 (m, 7 H), 2.33-2.38 (m, 1 H), 2.50-2.56 (m, 2 H), 2.58-2.61 (m, 1 H), 2.63-2.67 (m, 1 H), 2.70-2.75 (m, 1 H), 2.82-2.83 (m, 1 H), 2.90 (s, 3 H), 3.06 (dd, J = 14.16, 9.39 Hz, 1 H), 3.27 (s, 3 H), 3.38-3.41 (m, 1 H), 3.42-3.47 (m, 1 H), 3.87 (br dd, J = 9.09, 4.92 Hz, 1 H), 4.13-4.19 (m, 1 H), 4.42-4.51 (m, 2 H), 6.54 (d, J = 6.88 Hz, 2 H), 6.77 (t, J = 8.34 Hz, 1 H), 7.26 (d, J = 8.05 Hz, 1 H), 7.34 (d, J = 7.52 Hz, 1 H), 7.73 (s, 1 H). |

TABLE A-continued

| Example No. (preparation of the Example) | Structure and IUPAC name | Characterising data (LCMS and/or NMR) |
|---|---|---|
| 598 (General Procedure B using Amine B27 as the core reagent) | 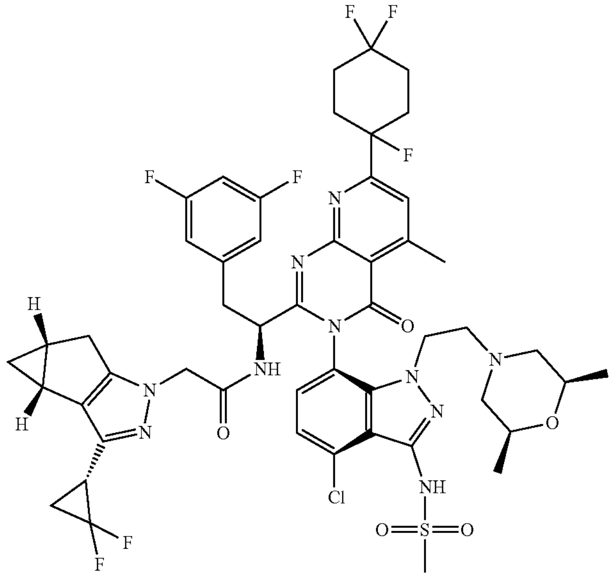 N-[(1S)-1-[(3P)-3-(4-chloro-1-{2-[(2R,6S)-2,6-dimethylmorpholin-4-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2R,4R)-9-[(1R)-2,2-difluorocyclopropyl]-7,8-diazatricyclo[4.3.0.0$^{2,4}$]nona-1(6),8-dien-7-yl]acetamide | LCMS Method B: retention time = 1.252 min.; observed ion = 1073.2 [M + H]. 1H NMR (500 MHz, METHANOL-d4) δ ppm 0.07-0.10 (m, 1 H), 0.94-1.08 (m, 9 H), 1.65-1.88 (m, 6 H), 1.92-2.02 (m, 2 H), 2.11-2.32 (m, 6 H), 2.52-2.64 (m, 3 H), 2.65-2.76 (m, 3 H), 2.90 (d, J = 0.60 Hz, 3 H), 3.07 (dd, J = 14.31, 9.84 Hz, 1 H), 3.28 (s, 3 H), 3.39-3.43 (m, 2 H), 3.88-3.95 (m, 1 H), 4.14-4.20 (m, 1 H), 4.34-4.43 (m, 2 H), 4.73-4.76 (m, 1 H), 6.52-6.56 (m, 2 H), 6.78 (t, J = 8.68 Hz, 1 H), 7.32-7.39 (m, 2 H), 7.73 (s, 1 H). |
| 599 (General Procedure E-2 using Aldehyde E2 as the core reagent) | 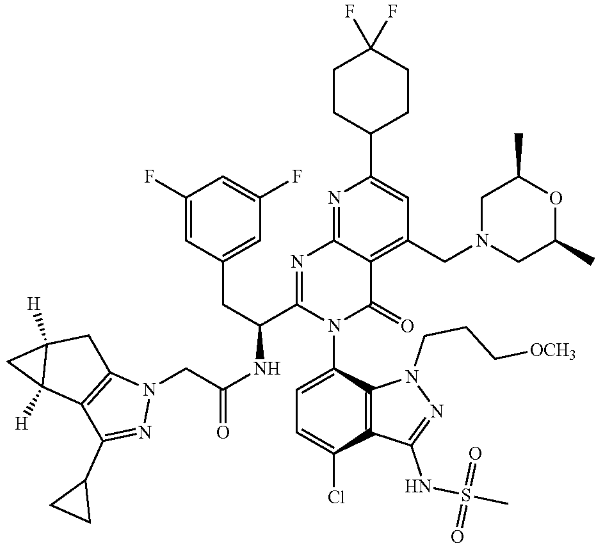 N-[(1S)-1-[(3P)-3-[4-chloro-3-methanesulfonamido-1-(3-methoxypropyl)-1H-indazol-7-yl]-7-(4,4-difluorocyclohexyl)-5-{[(2R,6S)-2,6-dimethylmorpholin-4-yl]methyl}-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method A: retention time = 2.74 min.; observed ion = 1063.35 [M + H]+. 1H NMR (500 MHz, METHANOL-d4) δ ppm 7.74 (s, 1 H), 7.23 (d, J = 8.05 Hz, 1 H), 7.08 (d, J = 7.75 Hz, 1 H), 6.70 (tt, J = 9.24, 2.38 Hz, 1 H), 6.51 (dd, J = 8.05, 2.09 Hz, 2 H), 4.77 (d, J = 5.36 Hz, 1 H), 4.18 (s, 2 H), 4.05-4.12 (m, 1 H), 3.94-4.01 (m, 1 H), 3.79-3.88 (m, 1 H), 3.63-3.76 (m, 3 H), 3.34 (dd, J = 14.01, 5.36 Hz, 1 H), 3.20 (s, 3 H), 2.96-3.10 (m, 4 H), 2.69-2.76 (m, 2 H), 2.67 (s, 3 H), 2.59 (dd, J = 16.69, 6.56 Hz, 1 H), 2.37 (d, J = 16.09 Hz, 1 H), 2.13-2.22 (m, 2 H), 1.90-2.08 (m, 6 H), 1.65-1.86 (m, 7 H), 1.04 (dd, J = 6.26, 1.19 Hz, 6 H), 0.85-0.90 (m, 1 H), 0.74-0.82 (m, 2 H), 0.62-0.73 (m, 2 H), 0.00 (q, J = 4.27 Hz, 1 H). |

TABLE A-continued

| Example No. (preparation of the Example) | Structure and IUPAC name | Characterising data (LCMS and/or NMR) |
|---|---|---|
| 600 (General Procedure E-2 using Aldehyde E3 as the core reagent) | 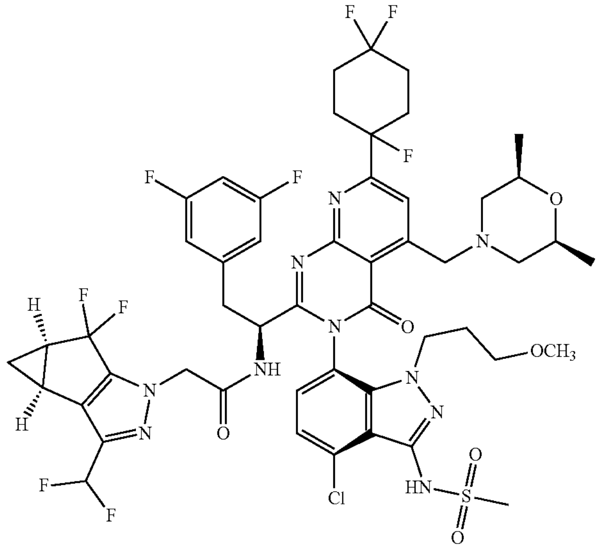 N-[(1S)-1-[(3P)-3-[4-chloro-3-methanesulfonamido-1-(3-methoxypropyl)-1H-indazol-7-yl]-5-{[(2R,6S)-2,6-dimethylmorpholin-4-yl]methyl}-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.78 min.; observed ion = 1127.20 [M + H]+. 1H NMR (500 MHz, METHANOL-d4) δ ppm 8.17 (d, J = 1.79 Hz, 1 H), 7.34 (d, J = 8.05 Hz, 1 H), 7.23 (d, J = 7.75 Hz, 1 H), 6.54-6.84 (m, 4 H), 4.86 (br s, 1 H), 4.59-4.65 (m, 2 H), 4.11-4.24 (m, 2 H), 4.02 (ddd, J = 14.16, 10.28, 5.96 Hz, 1 H), 3.83-3.89 (m, 1 H), 3.71-3.80 (m, 2 H), 3.40-3.44 (m, 1 H), 3.26 (s, 3 H), 3.15-3.20 (m, 1 H), 3.05-3.12 (m, 2 H), 2.79-2.86 (m, 2 H), 2.75 (s, 3 H), 2.55-2.71 (m, 2 H), 2.42-2.48 (m, 2 H), 2.14-2.38 (m, 6 H), 1.78-1.98 (m, 4 H), 1.35-1.42 (m, 1 H), 1.14 (dd, J = 6.26, 2.09 Hz, 6 H), 1.02-1.06 (m, 1 H). |
| 601 (General Procedure D using Chloride D3 as the core reagent) | 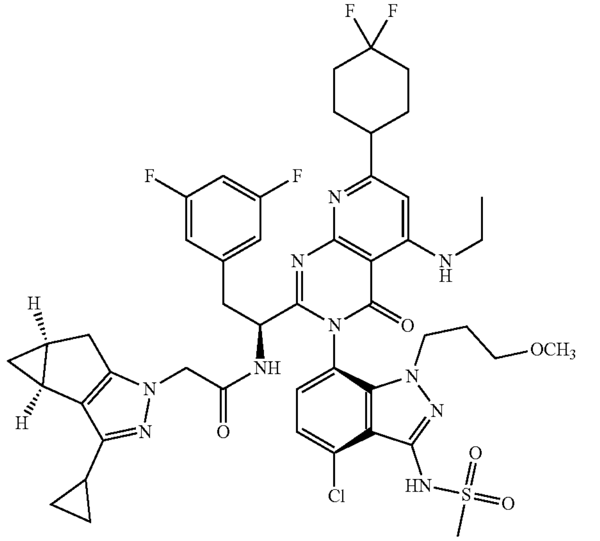 N-[(1S)-1-[(3P)-3-[4-chloro-3-methanesulfonamido-1-(3-methoxypropyl)-1H-indazol-7-yl]-7-(4,4-difluorocyclohexyl)-5-(ethylamino)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method A: retention time = 2.68 min.; observed ion = 979.20 [M + H]+. 1 H NMR (500 MHz, METHANOL-d4) δ ppm 8.81 (s, 1 H), 7.21 (d, J = 7.75 Hz, 1 H), 7.00 (d, J = 7.75 Hz, 1 H), 6.65-6.78 (m, 1 H), 6.44-6.57 (m, 3 H), 4.73 (dd, J = 8.94, 5.36 Hz, 1 H), 4.18 (s, 2 H), 3.87 (ddd, J = 14.16, 9.84, 6.11 Hz, 1 H), 3.66-3.77 (m, 1 H), 3.29-3.36 (m, 3 H), 3.20 (s, 3 H), 3.07 (t, J = 5.81 Hz, 2 H), 2.96 (dd, J = 13.86, 9.09 Hz, 1 H), 2.86 (s, 3 H), 2.75-2.83 (m, 1 H), 2.58 (dd, J = 16.39, 6.56 Hz, 1 H), 2.34-2.42 (m, 1 H), 2.11-2.22 (m, 2 H), 1.74-2.04 (m, 10 H), 1.70 (tt, J = 8.49, 5.07 Hz, 1 H), 1.21 (t, J = 7.15 Hz, 3 H), 0.86-0.91 (m, 1 H), 0.75-0.83 (m, 2 H), 0.61-0.73 (m, 2 H), −0.04-0.04 (m, 1 H) |

TABLE A-continued

| Example No. (preparation of the Example) | Structure and IUPAC name | Characterising data (LCMS and/or NMR) |
|---|---|---|
| 602 (General Procedure E-2 using Aldehyde E4 as the core reagent) | 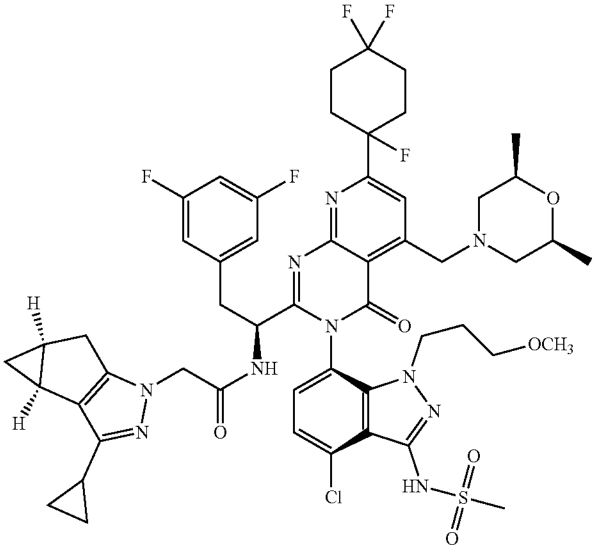 N-[(1S)-1-[(3P)-3-[4-chloro-3-methanesulfonamido-1-(3-methoxypropyl)-1H-indazol-7-yl]-5-{[(2R,6S)-2,6-dimethylmorpholin-4-yl]methyl}-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method A: retention time = 2.87 min.; observed ion = 1081.35 [M + H]+. 1H NMR (500 MHz, METHANOL-d4) δ ppm 8.07 (d, J = 2.09 Hz, 1 H), 7.24 (d, J = 8.05 Hz, 1 H), 7.13 (d, J = 7.75 Hz, 1 H), 6.63-6.77 (m, 1 H), 6.48 (dd, J = 8.05, 2.09 Hz, 2 H), 4.74-4.77 (m, 1 H), 4.19 (s, 2 H), 3.99-4.16 (m, 2 H), 3.79-3.88 (m, 1 H), 3.72-3.77 (m, 1 H), 3.62-3.70 (m, 2 H), 3.29-3.33 (m, 1 H), 3.20 (s, 3 H), 3.07 (dt, J = 9.54, 4.77 Hz, 1 H), 2.93-3.02 (m, 2 H), 2.68-2.75 (m, 2 H), 2.65 (s, 3 H), 2.55-2.63 (m, 2 H), 2.44-2.53 (m, 1 H), 2.36 (d, J = 16.99 Hz, 1 H), 2.04-2.29 (m, 6 H), 1.66-1.89 (m, 7 H), 1.04 (dd, J = 6.26, 1.79 Hz, 6 H), 0.88 (td, J = 7.60, 4.47 Hz, 1 H), 0.74-0.83 (m, 2 H), 0.62-0.73 (m, 2 H), −0.03-0.02 (m, 1 H). |
| 603 (General Procedure E-2 using Aldehyde E2 as the core reagent, where the general procedure was modified as follows: the HCl salt of the amine was used; the reductive amination was conducted at 50° C. for 16 h) | 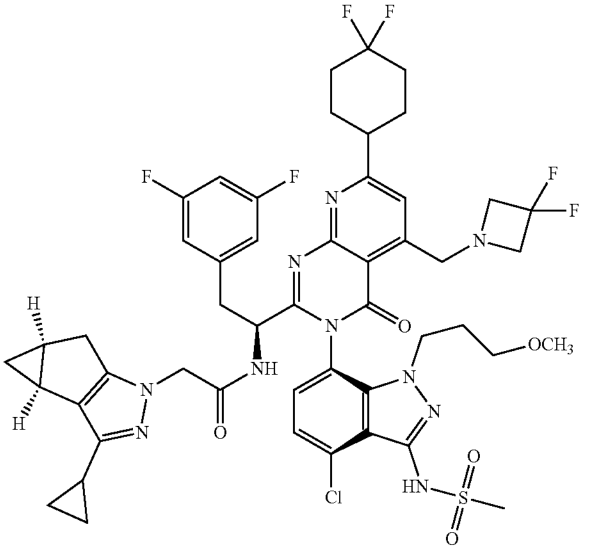 N-[(1S)-1-[(3P)-3-[4-chloro-3-methanesulfonamido-1-(3-methoxypropyl)-1H-indazol-7-yl]-5-[(3,3-difluoroazetidin-1-yl)methyl]-7-(4,4-difluorocyclohexyl)-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | LCMS Method A: retention time = 3.36 min.; observed ion = 1041.25 [M + H]+. 1H NMR (500 MHz, METHANOL-d4) δ ppm 7.58 (s, 1 H), 7.23 (d, J = 8.05 Hz, 1 H), 7.09 (d, J = 8.05 Hz, 1 H), 6.65-6.75 (m, 1 H), 6.52 (dd, J = 7.90, 2.24 Hz, 2 H), 4.28-4.44 (m, 2 H), 4.18 (d, J = 0.89 Hz, 2 H), 3.80-3.87 (m, 1 H), 3.71 (td, J = 12.15, 5.51 Hz, 5 H), 3.32-3.38 (m, 2 H), 3.20 (s, 3 H), 3.06-3.13 (m, 3 H), 2.96-3.02 (m, 2 H), 2.66 (s, 3 H), 2.60 (dd, J = 16.99, 6.56 Hz, 1 H), 2.37 (d, J = 16.69 Hz, 1 H), 2.14-2.22 (m, 2 H), 1.98-2.08 (m, 5 H), 1.90-1.97 (m, 1 H), 1.67-1.88 (m, 5 H), 0.88 (td, J = 7.60, 4.77 Hz, 1 H), 0.76-0.82 (m, 2 H), 0.63-0.73 (m, 2 H), 0.00 (d, J = 3.58 Hz, 1 H). |

TABLE A-continued

| Example No. (preparation of the Example) | Structure and IUPAC name | Characterising data (LCMS and/or NMR) |
|---|---|---|
| 604 (General Procedure E-2 using Aldehyde E1 as the core reagent, where the general procedure was modified as follows: the HCl salt of the amine was used; the reductive amination was conducted at 50° C. for 16 h) | 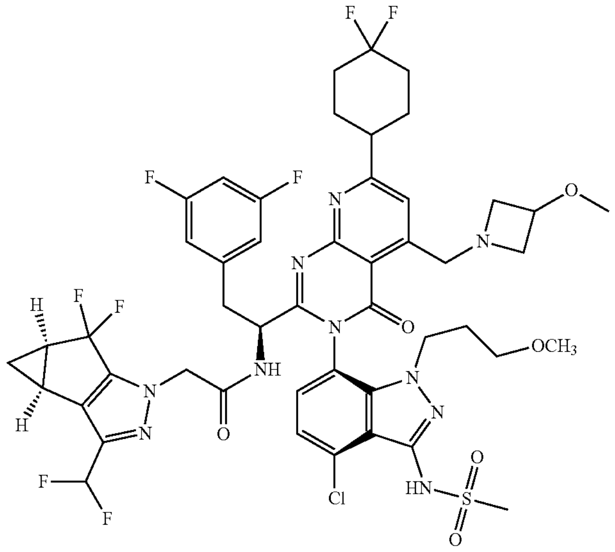 N-[(1S)-1-[(3P)-3-[4-chloro-3-methanesulfonamido-1-(3-methoxypropyl)-1H-indazol-7-yl]-7-(4,4-difluorocyclohexyl)-5-[(3-methoxyazetidin-1-yl)methyl]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.63 min.; observed ion = 1081.20 [M + H]+. 1H NMR (500 MHz, METHANOL-d4) δ ppm 7.48 (s, 1 H), 7.21 (d, J = 7.75 Hz, 1 H), 7.07 (d, J = 8.05 Hz, 1 H), 6.43-6.70 (m, 5 H), 4.74 (br s, 1 H), 4.47 (d, J = 3.28 Hz, 2 H), 4.31 (br d, J = 17.88 Hz, 1 H), 4.13 (br d, J = 18.18 Hz, 1 H), 4.04 (quin, J = 5.51 Hz, 1 H), 3.87-3.93 (m, 1 H), 3.63-3.75 (m, 3 H), 3.29-3.33 (m, 1 H), 3.17 (s, 3 H), 3.14 (s, 3 H), 2.93-3.09 (m, 9 H), 2.61 (s, 3 H), 2.29-2.35 (m, 2 H), 2.11-2.20 (m, 2 H), 1.84-2.05 (m, 8 H), 1.68-1.82 (m, 2 H), 1.22-1.29 (m, 2 H), 0.90-0.95 (m, 1 H). |
| 605 (General Procedure E-2 using Aldehyde E1 as the core reagent, where the general procedure was modified as follows: the HCl salt of the amine was used; the reductive amination was conducted at 50° C. for 16 h) | 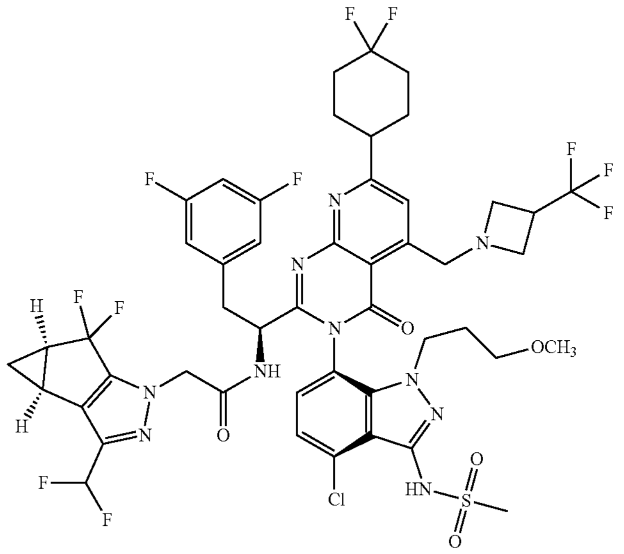 N-[(1S)-1-[(3P)-3-[4-chloro-3-methanesulfonamido-1-(3-methoxypropyl)-1H-indazol-7-yl]-7-(4,4-difluorocyclohexyl)-4-oxo-5-{[3-(trifluoromethyl)azetidin-1-yl]methyl}-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method A: retention time = 2.88 min.; observed ion = 1119.20 [M + H]+. 1H NMR (500 MHz, METHANOL-d4) δ ppm 7.52 (s, 1 H), 7.21 (d, J = 7.75 Hz, 1 H), 7.07 (d, J = 8.05 Hz, 1 H), 6.43-6.70 (m, 4 H), 4.72-4.75 (m, 1 H), 4.47 (d, J = 2.98 Hz, 2 H), 4.12-4.30 (m, 2 H), 3.89 (ddd, J = 14.23, 10.65, 5.81 Hz, 1 H), 3.67-3.78 (m, 1 H), 3.52-3.60 (m, 2 H), 3.28-3.36 (m, 4 H), 3.14 (s, 3 H), 2.92-3.09 (m, 4 H), 2.61 (s, 3 H), 2.32 (ddd, J = 11.25, 7.67, 4.02 Hz, 2 H), 2.10-2.20 (m, 2 H), 1.86-2.06 (m, 6 H), 1.66-1.84 (m, 2 H), 1.26 (q, J = 7.45 Hz, 1 H), 0.89-0.98 (m, 1 H). |

TABLE A-continued

| Example No. (preparation of the Example) | Structure and IUPAC name | Characterising data (LCMS and/or NMR) |
|---|---|---|
| 606 (General Procedure B using Amine B8 as the core reagent) | 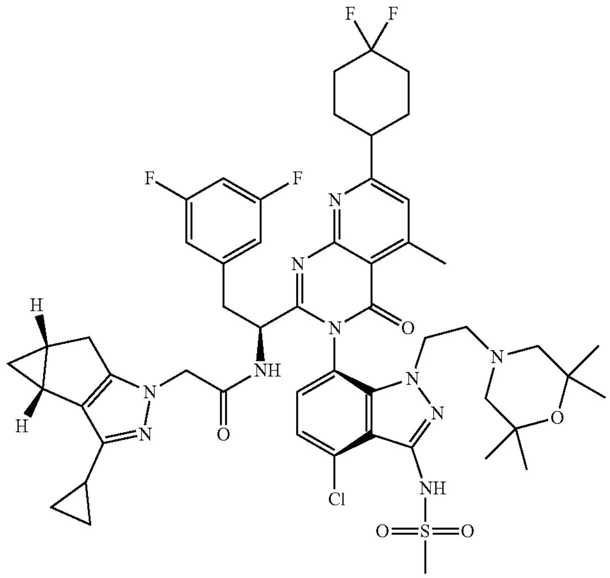 N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2R,4R)-9-cyclopropyl-7,8-diazatricyclo[4.3.0.0$^{2,4}$]nona-1(6),8-dien-7-yl]acetamide | LCMS Method A: retention time = 3.324 min.; observed ion = 1047.30 [M + H]+. 1H NMR (500 MHz, METHANOL-d4) δ ppm 0.21 (q, J = 4.37 Hz, 1 H), 0.76-0.80 (m, 1 H), 0.84-1.04 (m, 18 H), 1.81-1.92 (m, 3 H), 1.96-2.11 (m, 10 H), 2.19-2.31 (m, 2 H), 2.60-2.68 (m, 2 H), 2.73-2.79 (m, 1 H), 2.83 (d, J = 0.60 Hz, 3 H), 2.89 (dd, J = 13.41, 5.36 Hz, 1 H), 3.02-3.10 (m, 1 H), 3.29-3.30 (m, 3 H), 3.53 (br dd, J = 12.82, 9.24 Hz, 2 H), 4.46 (d, J = 1.49 Hz, 2 H), 4.68 (dd, J = 8.94, 5.66 Hz, 1 H), 6.69 (br d, J = 6.26 Hz, 2 H), 6.81 (tt, J = 9.05, 2.27 Hz, 1 H), 7.20 (d, J = 8.05 Hz, 1 H), 7.34 (d, J = 8.05 Hz, 1 H), 7.46 (d, J = 0.89 Hz, 1 H). |
| 609 (General Procedure B using Amine B31 as the core reagent) | 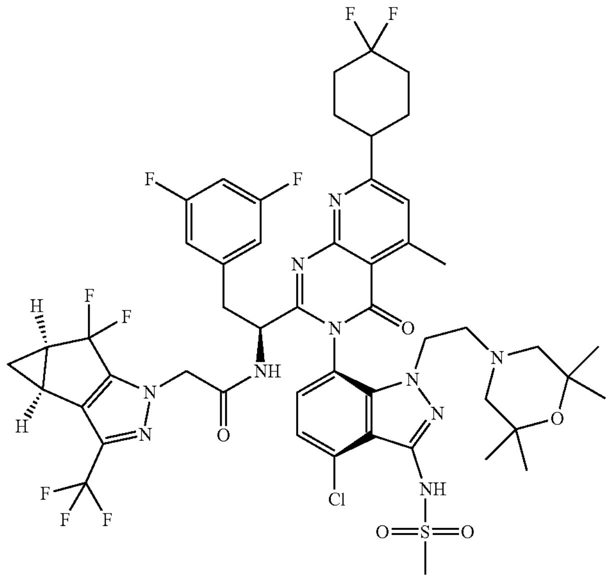 N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-5,5-difluoro-9-(trifluoromethyl)-7,8-diazatricyclo[4.3.0.0$^{2,4}$]nona-1(6),8-dien-7-yl]acetamide | LCMS Method B: retention time = 1.556 min.; observed ion = 1109.4 [M − H]. 1H NMR (500 MHz, METHANOL-d4) δ ppm 0.94 (d, J = 4.47 Hz, 12 H), 1.05-1.11 (m, 1 H), 1.38-1.41 (m, 1 H), 1.86-1.90 (m, 2 H), 1.98 (d, J = 10.73 Hz, 2 H), 2.04-2.11 (m, 5 H), 2.20-2.26 (m, 2 H), 2.43-2.55 (m, 3 H), 2.60 (dd, J = 11.33, 5.36 Hz, 1 H), 2.84-2.85 (m, 3 H), 3.05 (br dd, J = 14.16, 9.69 Hz, 2 H), 3.23 (s, 3 H), 3.38-3.41 (m, 1 H), 3.81 (ddd, J = 13.78, 11.40, 4.92 Hz, 1 H), 4.17 (ddd, J = 13.71, 11.47, 5.51 Hz, 1 H), 4.59-4.63 (m, 3 H), 4.80 (br d, J = 4.77 Hz, 1 H), 6.51-6.54 (m, 2 H), 6.74-6.80 (m, 1 H), 7.21 (d, J = 7.75 Hz, 1 H), 7.33 (d, J = 7.75 Hz, 1 H), 7.44 (d, J = 0.60 Hz, 1 H). |

| Example No. (preparation of the Example) | Structure and IUPAC name | Characterising data (LCMS and/or NMR) |
|---|---|---|
| 610 (General Procedure B using Amine B31 as the core reagent) | 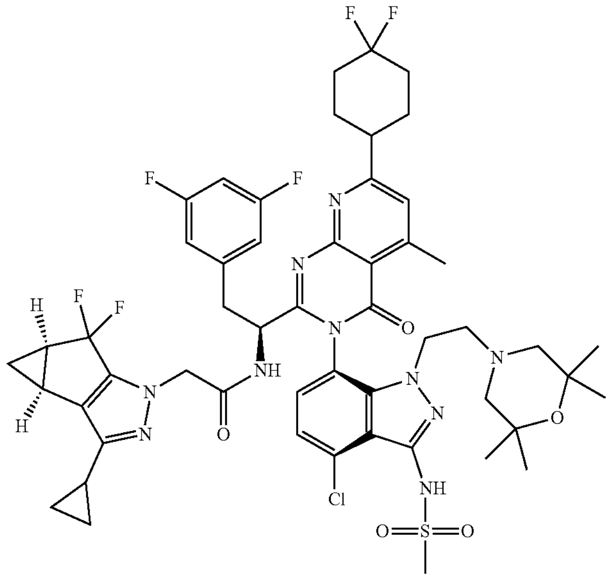 N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-cyclopropyl-5,5-difluoro-7,8-diazatricyclo[4.3.0.0$^{2,4}$]nona-1(6),8-dien-7-yl]acetamide | LCMS Method B: retention time = 1.531 min.; observed ion = 1081.6 [M − H]. 1H NMR (500 MHz, METHANOL-d4) δ ppm 0.77-0.82 (m, 2 H), 0.89-0.93 (m, 3 H), 0.95 (s, 12 H), 1.24-1.31 (m, 1 H), 1.81-1.90 (m, 3 H), 1.98 (d, J = 10.73 Hz, 3 H), 2.06 (br d, J = 4.77 Hz, 4 H), 2.19-2.28 (m, 3 H), 2.51 (td, J = 11.77, 5.07 Hz, 1 H), 2.61-2.68 (m, 1 H), 2.81-2.87 (m, 3 H), 2.97-3.06 (m, 2 H), 3.25 (s, 3 H), 3.35-3.39 (m, 1 H), 3.79 (ddd, J = 13.49, 11.25, 5.07 Hz, 1 H), 4.17-4.25 (m, 1 H), 4.45 (s, 2 H), 4.59-4.62 (m, 2 H), 4.80 (br d, J = 4.77 Hz, 1 H), 6.49-6.54 (m, 2 H), 6.77 (tt, J = 9.24, 2.38 Hz, 1 H), 7.20 (d, J = 8.05 Hz, 1 H), 7.32 (d, J = 7.75 Hz, 1 H), 7.44 (d, J = 0.89 Hz, 1 H). |
| 611 (General Procedure B using Amine B31 as the core reagent) | 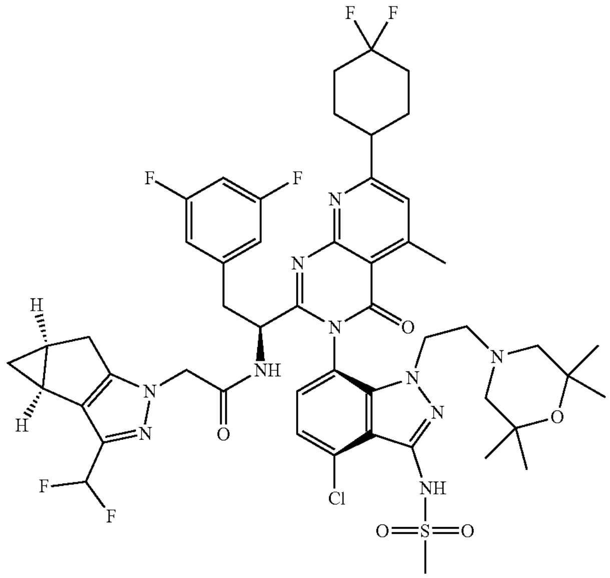 N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5- | LCMS Method B: retention time = 1.486 min.; observed ion = 1055.7 [M − H]. 1H NMR (500 MHz, METHANOL-d4) δ ppm 0.95 (d, J = 1.19 Hz, 12 H), 1.04 (td, J = 7.75, 5.07 Hz, 1 H), 1.86-1.90 (m, 2 H), 1.94-2.08 (m, 10 H), 2.20-2.28 (m, 2 H), 2.49-2.59 (m, 2 H), 2.63-2.68 (m, 2 H), 2.82-2.87 (m, 3 H), 3.02-3.11 (m, 2 H), 3.27 (s, 3 H), 3.37-3.43 (m, 2 H), 3.79-3.89 (m, 1 H), 4.11-4.20 (m, 1 H), 4.23-4.44 (m, 2 H), 4.60 (s, 2 H), 6.45-6.79 (m, 3 H), 7.28-7.35 (m, 2 H), 7.42-7.46 (m, 1 H). |

TABLE A-continued

| Example No. (preparation of the Example) | Structure and IUPAC name | Characterising data (LCMS and/or NMR) |
|---|---|---|
| | difluorophenyl)ethyl]-2-[(2S,4S)-9-(difluoromethyl)-7,8-diazatricyclo[4.3.0.0$^{2,4}$]nona-1(6),8-dien-7-yl]acetamide. | |
| 612 (General Procedure B using Amine B31 as the core reagent) | 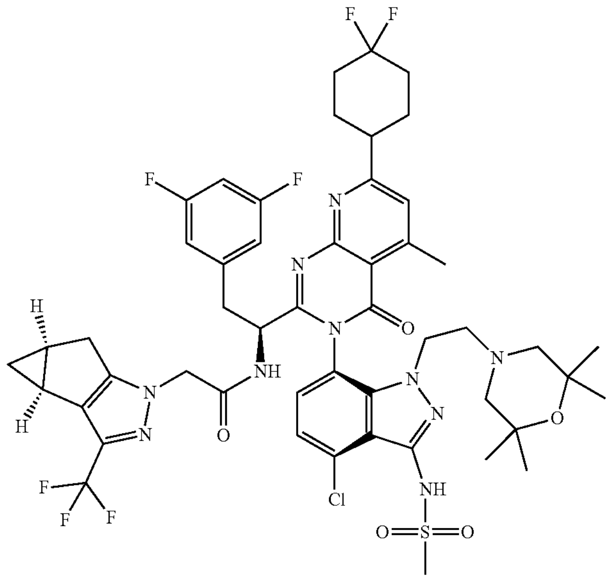 N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-(trifluoromethyl)-7,8-diazatricyclo[4.3.0.0$^{2,4}$]nona-1(6),8-dien-7-yl]acetamide | LCMS Method B: retention time = 1.55 min.; observed ion = 1073.5 [M − H]. 1H NMR (500 MHz, METHANOL-d4) δ ppm 0.18-0.24 (m, 1 H), 0.94 (d, J = 3.28 Hz, 11 H), 1.07 (td, J = 7.67, 4.92 Hz, 1 H), 1.85-1.89 (m, 2 H), 1.96-2.10 (m, 10 H), 2.19-2.29 (m, 2 H), 2.48-2.67 (m, 3 H), 2.69-2.76 (m, 1 H), 2.84 (d, J = 0.60 Hz, 3 H), 2.99-3.13 (m, 2 H), 3.25 (s, 3 H), 3.40-3.44 (m, 1 H), 3.81 (ddd, J = 13.71, 11.18, 5.22 Hz, 1 H), 4.12-4.20 (m, 1 H), 4.43 (s, 2 H), 4.57-4.64 (m, 2 H), 6.57 (d, J = 7.30 Hz, 2 H), 6.72-6.80 (m, 1 H), 7.19 (d, J = 8.05 Hz, 2 H), 7.42-7.46 (m, 1 H). |
| 613 (General Procedure B using Amine B31 as the core reagent) | 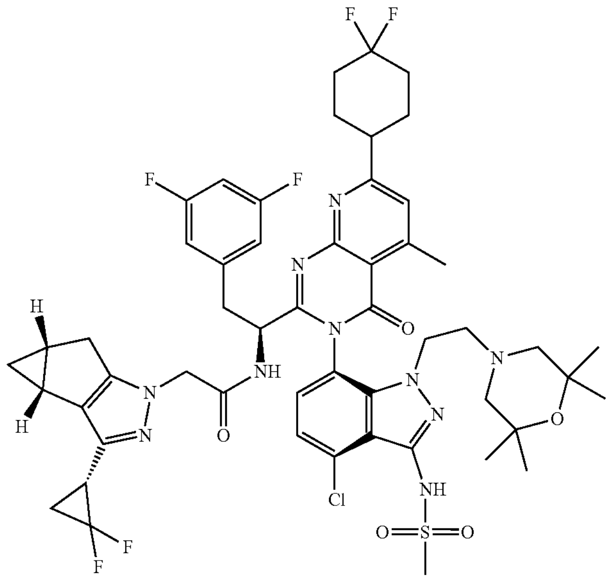 N-[(1S)-1-[(3P)-3-{4-chloro-3-methanesulfonamido-1-[2-(2,2,6,6-tetramethylmorpholin-4-yl) ethyl]-1H-indazol-7-yl}-7-(4,4-difluorocyclohexyl)-5-methyl-4-oxo-3H,4H-pyrido[2,3- | LCMS Method B: retention time = 1.526 min.; observed ion = 1081.7 [M − H]. 1H NMR (500 MHz, METHANOL-d4) δ ppm 0.10-0.13 (m, 1 H), 0.95 (d, J = 4.17 Hz, 12 H), 1.76-1.89 (m, 4 H), 1.91-1.99 (m, 5 H), 2.02-2.09 (m, 5 H), 2.20-2.27 (m, 2 H), 2.47-2.55 (m, 2 H), 2.60-2.70 (m, 2 H), 2.74-2.80 (m, 1 H), 2.84 (d, J = 0.89 Hz, 3 H), 2.98-3.12 (m, 3 H), 3.26-3.27 (m, 3 H), 3.37-3.43 (m, 1 H), 3.76 (ddd, J = 13.78, 10.80, 5.22 Hz, 1 H), 4.03-4.10 (m, 1 H), 4.25-4.32 (m, 2 H), 4.60 (s, 1 H), 6.55-6.60 (m, 2 H), 6.76 (t, J = 8.62 Hz, 1 H), 7.24 (d, J = 7.75 Hz, 1 H), 7.33 (d, J = 7.75 Hz, 1 H), 7.44 (d, J = 0.60 Hz, 1 H). |

TABLE A-continued

| Example No. (preparation of the Example) | Structure and IUPAC name | Characterising data (LCMS and/or NMR) |
|---|---|---|
| | d]pyrimidin-2-yl]-2-(3,5-difluorophenyl)ethyl]-2-[(2R,4R)-9-[(1R)-2,2-difluorocyclopropyl]-7,8-diazatricyclo$[4.3.0.0^{2,4}]$nona-1(6),8-dien-7-yl]acetamide | |
| 615 (General Procedure F using Alcohol F1 as the core reagent) | 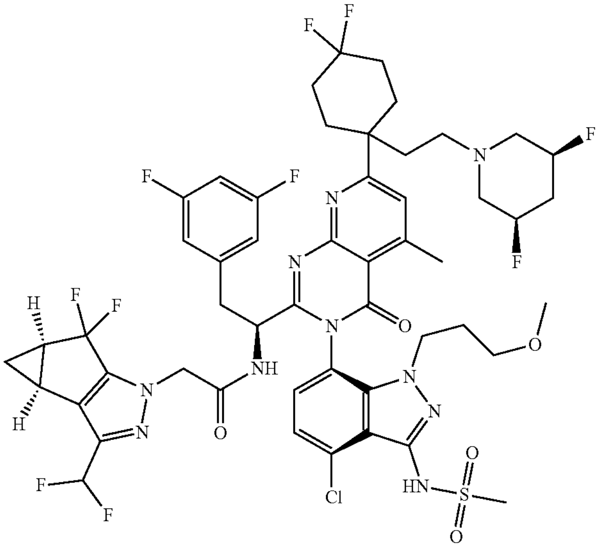 N-[(1S)-1-[(3P)-3-[4-chloro-3-methanesulfonamido-1-(3-methoxypropyl)-1H-indazol-7-yl]-7-(1-{2-[(3R,5S)-3,5-difluoropiperidin-1-ylethyl}-4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo$[4.3.0.0^{2,4}]$nona-1(6),8-dien-7-yl]acetamide | LCMS Method B: retention time = 1.12 min.; observed ion = 1141.6 [M − H]. 1H NMR (500 MHz, METHANOL-d4) δ ppm 1.01-1.03 (m, 1 H), 1.33-1.38 (m, 2 H), 1.76-1.83 (m, 1 H), 1.86-1.93 (m, 4 H), 1.97-2.01 (m, 2 H), 2.03-2.08 (m, 2 H), 2.22-2.27 (m, 2 H), 2.40-2.55 (m, 6 H), 2.66-2.75 (m, 2 H), 2.85 (s, 5 H), 3.02-3.08 (m, 1 H), 3.11-3.15 (m, 1 H), 3.24-3.26 (m, 4 H), 3.39-3.42 (m, 1 H), 3.84-3.90 (m, 1 H), 4.04 (td, J = 7.23, 3.13 Hz, 1 H), 4.50-4.53 (m, 1 H), 4.58-4.63 (m, 6 H), 4.95 (dt, J = 2.91, 1.38 Hz, 1 H), 6.54-6.78 (m, 4 H), 7.21 (d, J = 7.84 Hz, 1 H), 7.32 (d, J = 7.75 Hz, 1 H), 7.64 (s, 1 H) |
| 623 (General Procedure B-2 using Amine B32 as the core reagent) | 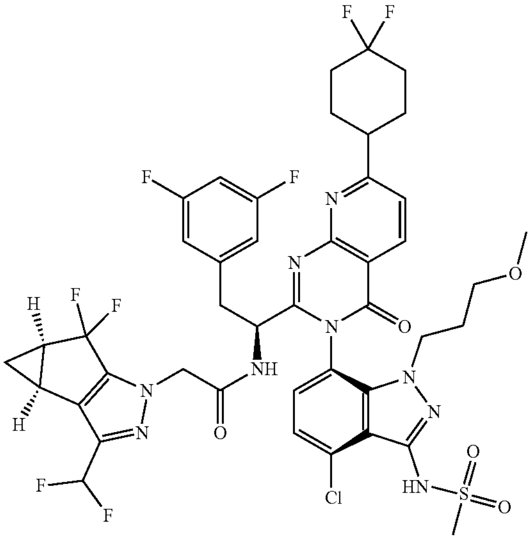 N-[(1S)-1-[(3P)-3-[4-chloro-3-methanesulfonamido-1-(3-methoxypropyl)-1H-indazol-7-yl]-7-(4,4-difluorocyclohexyl)-4-oxo-3H,4H-pyrido[2,3-d]pyrimidin-2-yl]- | LCMS Method: Column = Acquity BEH C18 (2.1 × 50 mm, 1.7 μm); Solvent A = 0.05% Formic Acid in acetonitrile; Solvent B = 0.1% Formic Acid in water; Flow Rate = 0.6 mL/min; Gradient Method (min.)/% B: 0/3, 0.4/3, 7.5/98, 9.5/98; Wavelength = 210 nm to 400 nm.: retention time = 5.19 min.; observed ion = 982.1 [M + H]+ 1H NMR (400 MHz, DMSO-d6, 298.2 K), Shift (ppm) = 9.95-9.85 (m, 1H), 9.37 (br d, J = 8.8 Hz, 1H), 8.53 (d, J = 8.1 Hz, 1H), 7.77 (br d, J = 7.8 Hz, 1H), 7.62 (d, J = 8.1 Hz, 1H), 7.54-7.47 (m, 1H), 7.08-6.75 (m, 2H), 6.68-6.51 (m, 2H), 4.77-4.64 (m, 1H), 4.57-4.46 (m, 2H), 3.90-3.68 (m, 2H), 3.50-3.39 (m, 1H), 3.26-3.14 (m, 4H), 3.04-2.94 (m, 3H), 2.78-2.72 (m, 3H), 2.47-2.39 (m, 2H), 2.20-1.92 (m, 8H), 1.77-1.65 (m, 2H), 1.39-1.31 (m, 1H), 0.88-0.82 (m, 1H) |

TABLE A-continued

| Example No. (preparation of the Example) | Structure and IUPAC name | Characterising data (LCMS and/or NMR) |
|---|---|---|
| | 2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | |
| 632 (General Procedure B-2 using Amine B33 as the core reagent) | 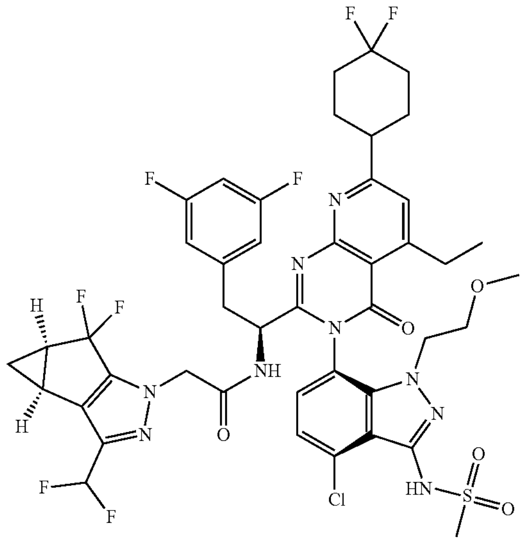 N-[(1S)-1-[(3P)-3-[4-chloro-3-methanesulfonamido-1-(2-methoxyethyl)-1H-indazol-7-yl]-7-(4,4-difluorocyclohexyl)-5-ethyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS method G: retention time = 6.00 min.; observed ion = 996.4 [M + H]+ 1H NMR (400 MHz, DMSO-d6, 298.2 K), Shift (ppm) 9.88 (s, 1H), 9.39 (br d, J = 8.7 Hz, 1H), 7.80-7.67 (m, 1H), 7.55-7.49 (m, 1H), 7.43 (s, 1H), 7.09-6.71 (m, 2H), 6.64-6.50 (m, 2H), 4.72 (d, J = 16.7 Hz, 1H), 4.61-4.44 (m, 2H), 4.00-3.86 (m, 1H), 3.82-3.68 (m, 1H), 3.53-3.41 (m, 2H), 3.39-3.33 (m, 1H), 3.26-3.14 (m, 5H), 3.10-2.93 (m, 5H), 2.47-2.39 (m, 2H), 2.24-2.13 (m, 2H), 2.10-1.88 (m, 6H), 1.39-1.30 (m, 1H), 1.19 (t, J = 7.4 Hz, 3H), 0.87-0.79 (m, 1H) |
| 636 (General Procedure B-2 using Amine B33 as the core reagent) | 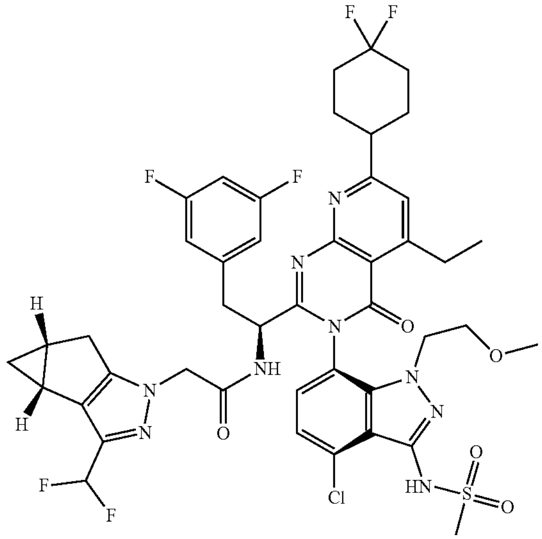 N-[(1S)-1-[(3P)-3-[4-chloro-3-methanesulfonamido-1-(2-methoxyethyl)-1H-indazol-7-yl]-7-(4,4-difluorocyclohexyl)-5-ethyl-4-oxo-3H,4H-pyrido[2,3-d]pyrimidin-2-yl]-2-(3,5-difluorophenyl)ethyl]-2-[(2R*,4R*)-9-(difluoromethyl)-7,8-diazatricyclo[4.3.0.0$^{2,4}$]nona-1(6),8-dien-7-yl]acetamide | LCMS Method: Column = Acquity BEH C18 (2.1 × 50 mm, 1.7 μm); Solvent A = 0.05% Formic Acid in water; Solvent B = 0.05% Formic Acid in ACN; Flow Rate = 0.6 ml/min; Gradient Method (min.)/% B: 0/3, 0.4/3, 3.2/98, 3.8/98; Wavelength = 210 nm to 400 nm.: retention time = 3.27 min.; observed ion = 960.4 [M + H]+ 1H NMR (400 MHz, DMSO-d6, 298.2 K), Shift (ppm) = 9.91 (s, 1H), 9.33-9.25 (m, 1H), 7.77-7.70 (m, 1H), 7.53-7.46 (m, 1H), 7.43 (s, 1H), 7.10-7.01 (m, 1H), 6.89-6.53 (m, 3H), 4.58-4.38 (m, 3H), 4.03-3.89 (m, 1H), 3.78-3.69 (m, 1H), 3.56-3.41 (m, 2H), 3.40-3.34 (m, 1H), 3.25-3.17 (m, 5H), 3.11-2.93 (m, 5H), 2.46-2.40 (m, 2H), 2.25-2.12 (m, 2H), 2.11-1.89 (m, 8H), 1.19 (t, J = 7.2 Hz, 3H), 0.97-0.91 (m, 1H), 0.04-0.00 (m, 1H) |

TABLE A-continued

| Example No. (preparation of the Example) | Structure and IUPAC name | Characterising data (LCMS and/or NMR) |
|---|---|---|
| 638 (General Procedure B-2 using Amine B34 as the core reagent) | 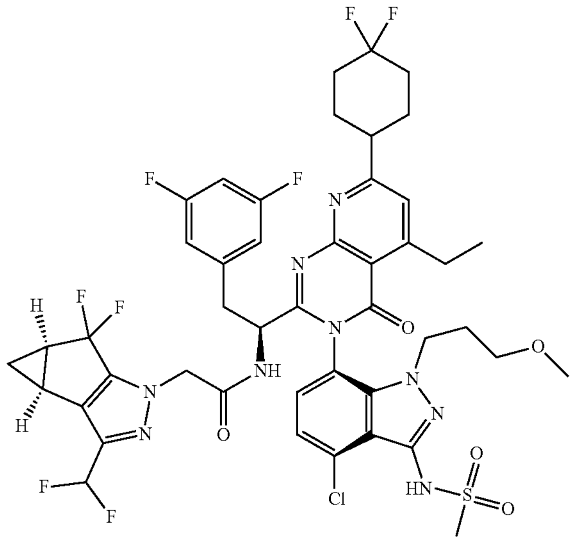 N-[(1S)-1-[(3P)-3-[4-chloro-3-methanesulfonamido-1-(3-methoxypropyl)-1H-indazol-7-yl]-7-(4,4-difluorocyclohexyl)-5-ethyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS method G: retention time = 6.05 min.; observed ion = 1010.5 [M + H]+ 1H NMR (400 MHz, DMSO-d6, 298.2 K), Shift (ppm) = 1H NMR (400 MHz, DMSO-d6), Shift (ppm) = 9.87 (br s, 1H), 9.36 (br d, J = 7.2 Hz, 1H), 7.82-7.68 (m, 1H), 7.53-7.44 (m, 1H), 7.44-7.33 (m, 1H), 7.09-6.83 (m, 2H), 6.64-6.51 (m, 2H), 4.71-4.60 (m, 1H), 4.54-4.45 (m, 2H), 3.89-3.67 (m, 2H), 3.39-3.33 (m, 1H), 3.18 (s, 5H), 3.09-2.89 (m, 4H), 2.72 (s, 3H), 2.47-2.41 (m, 2H), 2.24-1.93 (m, 8H), 1.80-1.64 (m, 2H), 1.40-1.32 (m, 1H), 1.18 (t, J = 7.4 Hz, 3H), 0.88-0.81 (m, 1H) |
| 639 (General Procedure B using Amine B34 as the core reagent) | 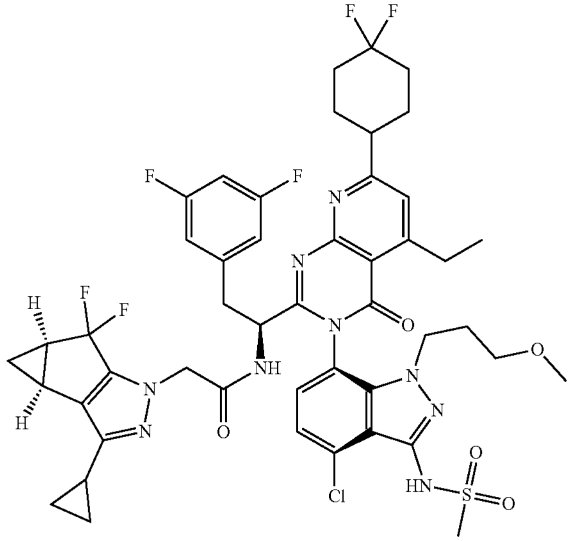 N-[(1S)-1-[(3P)-3-[4-chloro-3-methanesulfonamido-1-(3-methoxypropyl)-1H-indazol-7-yl]-7-(4,4-difluorocyclohexyl)-5-ethyl-4-oxo-3H,4H-pyrido[2,3-d]pyrimidin-2-yl]-2-(3,5-difluorophenyl)ethyl]-2-[(2S,4R)-9-cyclopropyl-5,5-difluoro-7,8-diazatricyclo[4.3.0.0$^{2,4}$]nona-1(6),8-dien-7-yl]acetamide | LCMS method G: retention time = 6.16 min.; observed ion = 1000.5 [M + H]+ 1H NMR (400 MHz, DMSO-d6, 298.2 K), Shift (ppm) = 9.89 (br s, 1H), 9.16 (br d, J = 8.8 Hz, 1H), 7.73 (br d, J = 7.8 Hz, 1H), 7.51-7.43 (m, 2H), 7.05-6.99 (m, 1H), 6.61-6.56 (m, 2H), 4.54-4.39 (m, 2H), 4.35-4.25 (m, 1H), 3.88-3.68 (m, 2H), 3.35-3.31 (m, 1H), 3.25-3.13 (m, 5H), 3.09-2.94 (m, 4H), 2.74 (s, 3H), 2.34-2.12 (m, 4H), 2.11-1.86 (m, 6H), 1.82-1.75 (m, 3H), 1.29-1.26 (m, 4H), 0.84-0.76 (m, 2H), 0.77-0.71 (m, 1H), 0.69-0.58 (m, 2H) |

TABLE A-continued

| Example No. (preparation of the Example) | Structure and IUPAC name | Characterising data (LCMS and/or NMR) |
|---|---|---|
| 641 (General Procedure B-2 using Amine B34 as the core reagent) | 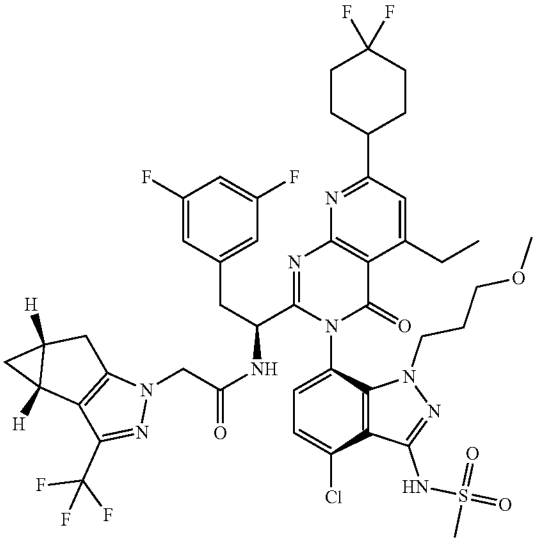 N-[(1S)-1-[(3P)-3-[4-chloro-3-methanesulfonamido-1-(3-methoxypropyl)-1H-indazol-7-yl]-7-(4,4-difluorocyclohexyl)-5-ethyl-4-oxo-3H,4H-pyrido[2,3-d]pyrimidin-2-yl]-2-(3,5-difluorophenyl)ethyl]-2-[(2R*,4R*)-9-(trifluoromethyl)-7,8-diazatricyclo[4.3.0.0$^{2,4}$]nona-1(6),8-dien-7-yl]acetamide | LCMS method G: retention time = 6.18 min.; observed ion = 992.5 [M + H]+ 1H NMR (400 MHz, DMSO-d6, 298.2 K), Shift (ppm) = 9.92 (br s, 1H), 9.36-9.22 (m, 1H), 7.71 (d, J = 7.9 Hz, 1H), 7.51-7.40 (m, 2H), 7.03-6.99 (m, 1H), 6.64-6.58 (m, 2H), 4.61-4.54 (m, 1H), 4.53-4.41 (m, 1H), 4.42-4.32 (m, 1H), 3.87-3.72 (m, 2H), 3.46-3.35 (m, 1H), 3.26-3.09 (m, 5H), 3.08-2.93 (m, 4H), 2.70 (s, 3H), 2.54-2.51 (m, 2H), 2.24-2.11 (m, 2H), 2.12-1.89 (m, 8H), 1.83-1.67 (m, 2H), 1.20 (t, J = 7.8 Hz, 3H), 1.12-1.04 (m, 1H), 0.14-0.08 (m, 1H) |
| 643 (General Procedure B-2 using Amine B34 as the core reagent) | 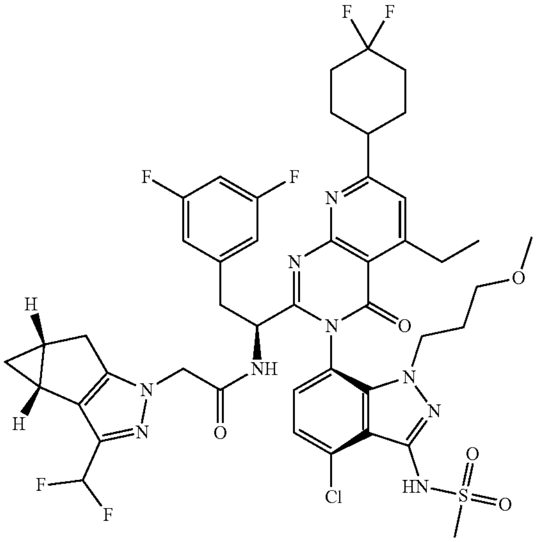 N-[(1S)-1-[(3P)-3-[4-chloro-3-methanesulfonamido-1-(3-methoxypropyl)-1H-indazol-7-yl]-7-(4,4-difluorocyclohexyl)-5-ethyl-4-oxo-3H,4H-pyrido[2,3-d]pyrimidin-2-yl]-2-(3,5-difluorophenyl)ethyl]-2-[(2R*,4R*)-9-(difluoromethyl)-7,8-diazatricyclo[4.3.0.0$^{2,4}$]nona-1(6),8-dien-7-yl]acetamide | LCMS Method: Column = Acquity BEH C18 (2.1 × 50 mm, 1.7 μm); Solvent A = 0.05% Formic Acid in water; Solvent B = 0.05% Formic Acid in acetonitrile; Flow Rate = 0.6 mL/min; Gradient Method (min.)/% B: 0/3, 0.4/3, 7.5/98, 9.5/98; Wavelength = 210 nm to 400 nm.: retention time = 5.99 min.; observed ion = 974.2 [M + H]+ 1H NMR (400 MHz, DMSO-d6, 298.1 K), Shift (ppm) = 9.92 (br s, 1H), 9.33-9.24 (m, 1H), 7.78-7.67 (m, 1H), 7.50-7.42 (m, 2H), 7.09-7.01 (m, 1H), 6.87-6.54 (m, 3H), 4.55-4.38 (m, 3H), 3.89-3.71 (m, 2H), 3.40-3.34 (m, 1H), 3.24-3.15 (m, 5H), 3.11-2.95 (m, 4H), 2.72 (s, 3H), 2.47-2.37 (m, 2H), 2.23-2.14 (m, 2H), 2.07-1.89 (m, 8H), 1.79-1.63 (m, 2H), 1.18 (t, J = 7.4 Hz, 3H), 1.01-0.94 (m, 1H), 0.04-0.00 (m, 1H) |

| Example No. (preparation of the Example) | Structure and IUPAC name | Characterising data (LCMS and/or NMR) |
|---|---|---|
| 671 (General Procedure B-2 using Amine B35 as the core reagent) | 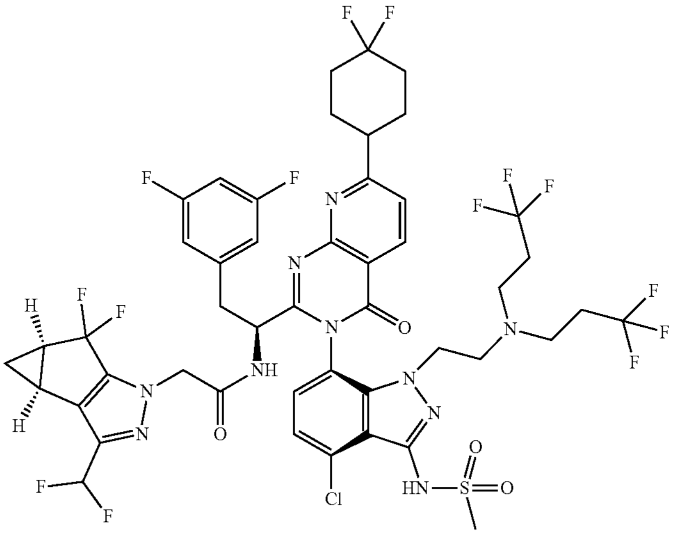 N-[(1S)-1-[(3P)-3-(1-{2-[bis(3,3,3-trifluoropropyl)amino]ethyl}-4-chloro-3-methanesulfonamido-1H-indazol-7-yl)-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method: Column = Acquity BEH C18 (2.1 × 50 mm, 1.7 μm); Solvent A = 0.05% Formic Acid in water; Solvent B = 0.05% Formic Acid in acetonitrile; Flow Rate = 0.6 mL/min; Gradient Method (min.)/% B: 0/3, 0.4/3, 2.5/98, 3.4/98; Wavelength = 210 nm to 400 nm.: retention time = 2.43 min.; observed ion = 1145.3 [M + H]+ 1H NMR (400 MHz, DMSO-d6, 299.4 K), Shift (ppm) = 9.98-9.82 (m, 1H), 9.57-9.35 (m, 1H), 8.59-8.41 (m, 1H), 7.83-7.74 (m, 1H), 7.69-7.56 (m, 1H), 7.54-7.43 (m, 1H), 7.11-6.66 (m, 2H), 6.64-6.42 (m, 2H), 4.72-4.37 (m, 1H), 4.01-3.74 (m, 1H), 3.71-3.55 (m, 1H), 3.44-3.34 (m, 1H), 3.23-3.09 (m, 4H), 3.05-2.92 (m, 1H), 2.72-2.62 (m, 2H), 2.47-2.35 (m, 6H), 2.25-1.87 (m, 12H), 1.42-1.30 (m, 1H), 1.27-1.17 (m, 2H), 0.90-0.81 (m, 1H) |
| 676 (General Procedure B-2 using Amine B37 as the core reagent, where the general procedure was modified as follows: A large excess of reagents (EDC, HOBt, N-methyl-morpholine) were used) | 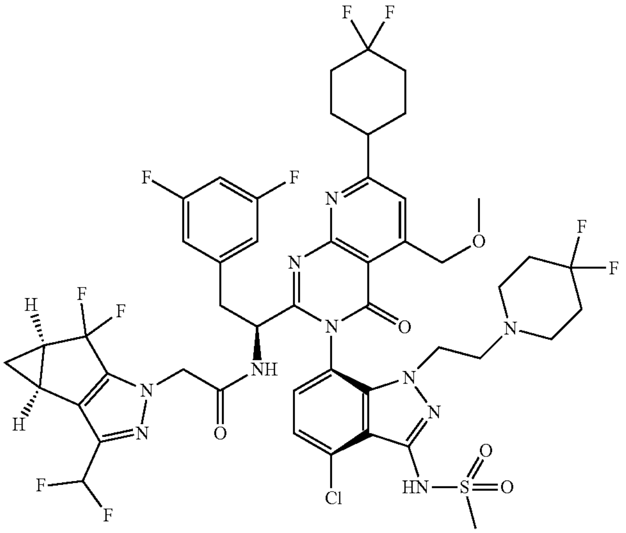 N-[(1S)-1-[(3P)-3-{4-chloro-1-[2-(4,4-difluoropiperidin-1-yl)ethyl]-3-methanesulfonamido-1H-indazol-7-yl}-7-(4,4-difluorocyclohexyl)-5-(methoxymethyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method: Column = ACQUITY BEH C18 (2.1 × 50 mm, 1.7 μm); Solvent A = 0.05% TFA in water; Solvent B = 0.05% TFA in acetonitrile; Flow rate = 0.6 mL/min; Gradient Method (min.)/% B: 0/3, 0.4/3, 2.5/98, 3.4/98; Wavelength = 210 nm to 400 nm.: retention time = 2.17 min.; observed ion = 1101.4 [M + H]+ 1H NMR (400 MHz, DMSO-d6, 298.2 K), Shift (ppm) = 9.88 (br s, 1H), 9.45 (br d, J = 7.1 Hz, 1H), 7.77 (d, J = 7.6 Hz, 1H), 7.66 (s, 1H), 7.51 (d, J = 7.6 Hz, 1H), 7.02-6.74 (m, 2H), 6.59-6.57 (m, 2H), 5.03-4.90 (m, 2H), 4.68-4.64 (m, 1H), 4.55-4.49 (m, 2H), 3.88-3.74 (m, 2H), 3.45 (s, 3H), 3.37-3. 36 (m, 1H), 3.18-3.16 (m, 4H), 2.99-2.93 (m, 1H), 2.50-2.40 (m, 4H), 2.17-1.91 (m, 12H), 1.59-1.52 (m, 4H), 1.37-1.32 (m, 1H), 0.86-0.81 (m, 1H) |

TABLE A-continued

| Example No. (preparation of the Example) | Structure and IUPAC name | Characterising data (LCMS and/or NMR) |
|---|---|---|
| 679 (General Procedure B-2 using Amine B38 as the core reagent) | 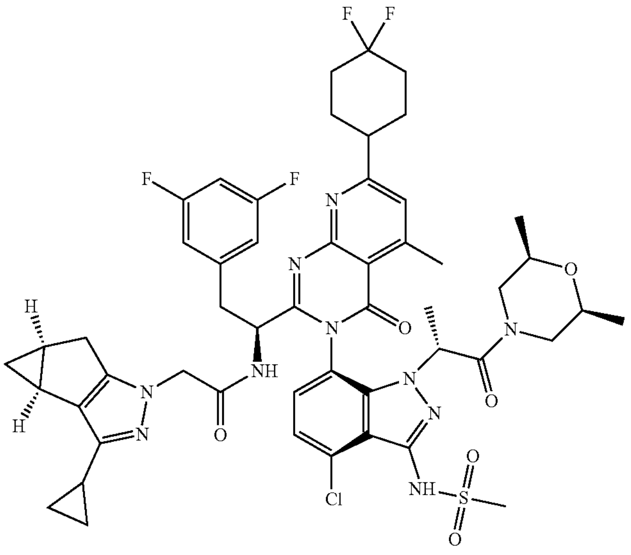 N-[(1S)-1-[(3P)-3-{4-chloro-1-[(2R)-1-[(2R,6S)-2,6-dimethylmorpholin-4-yl]-1-oxopropan-2-yl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide | LCMS Method: Column = Acquity BEH C18 (2.1 x 50 mm, 1.7 μm); Solvent A = 0.05% Formic Acid in water; Solvent B = 0.05% Formic Acid in acetonitrile; Flow Rate = 0.6 mL/min; Gradient Method (min.)/% B: 0/3, 0.4/3, 2.5/98, 3.5/98; Wavelength = 210 nm to 400 nm.: retention time = 2.50 min.; observed ion = 1047.64 [M + H]+ 1H NMR (400 MHz, DMSO-d6, 298.2 K), Shift (ppm) = 9.97 (br s, 1H), 8.28-8.20 (m, 1H), 7.81-7.76 (m, 1H), 7.51-7.48 (m, 2H), 7.04-7.00 (m, 1H), 6.74-6.64 (m, 2H), 5.20-5.13 (m, 1H), 4.62-4.53 (m, 1H), 4.27-4.14 (m, 1H), 4.12-4.00 (m, 1H), 3.91-3.85 (m, 1H), 3.36-3.30 (m, 2H), 3.28-3.26 (m, 3H), 3.20-3.15 (m, 1H), 3.15-3.05 (m, 2H), 3.01-2.94 (m, 1H), 2.93-2.87 (m, 1H), 2.86-2.78 (m, 4H), 2.46-2.44 (m, 1H), 2.34-2.32 (m, 1H), 2.31-2.23 (m, 2H), 2.22-2.01 (m, 6H), 1.81-1.70 (m, 3H), 1.61-1.56 (m, 3H), 1.03-0.96 (m, 3H), 0.92-0.78 (m, 4H), 0.69-0.52 (m, 4H), 0.03--0.01 (m, 1H) |
| 683 (following General Procedure B-2 using Amine B39 as the core reagent) | 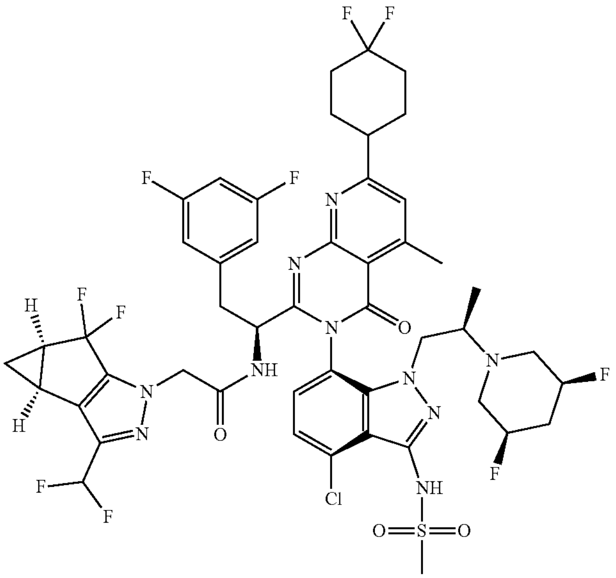 N-[(1S)-1-[(3P)-3-{4-chloro-1-[(2R)-2-[(3R,5S)-3,5-difluoropiperidin-1-yl]propyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method: Column = Acquity BEH C18 (2.1 x 50 mm, 1.7 μm); Solvent A = 0.05% formic acid in water; Solvent B = 0.05% formic acid in acetonitrile; Flow Rate = 0.6 mL/min; Gradient Method (min.)/% B: 0/3, 2.5/3, 7.5/98, 9.5/98; Wavelength = 210 nm to 400 nm .: retention time = 6.20 min.; observed ion = 1085.49 [M + H]+ 1H NMR (400 MHz, DMSO-d6, 298.6 K), Shift (ppm) = 9.90 (br s, 1H), 9.46 (d, J = 8.8 Hz, 1H), 7.85-7.80 (m, 1H), 7.60-7.44 (m, 2H), 7.06-6.70 (m, 2H), 6.60-6.57 (m, 2H), 4.62 (d, J = 16.8 Hz, 1H), 4.52-4.46 (m, 2H), 4.18-3.80 (m, 3H), 3.80-3.67 (m, 1H), 3.45-3.35 (m, 1H), 3.22-3.17 (m, 3H), 3.10-3.00 (m, 1H), 2.96-2.88 (m, 1H), 2.76 (s, 3H), 2.7-2.6 (m, 3H), 2.48-2.38 (m, 2H), 2.40-1.85 (m, 11H), 1.48-1.30 (m, 2H), 0.89-0.82 (m, 1H), 0.49 (d, J = 6.4 Hz, 3H) |

TABLE A-continued

| Example No. (preparation of the Example) | Structure and IUPAC name | Characterising data (LCMS and/or NMR) |
|---|---|---|
| 684 (General Procedure B-2 using Amine B40 as the core reagent) | 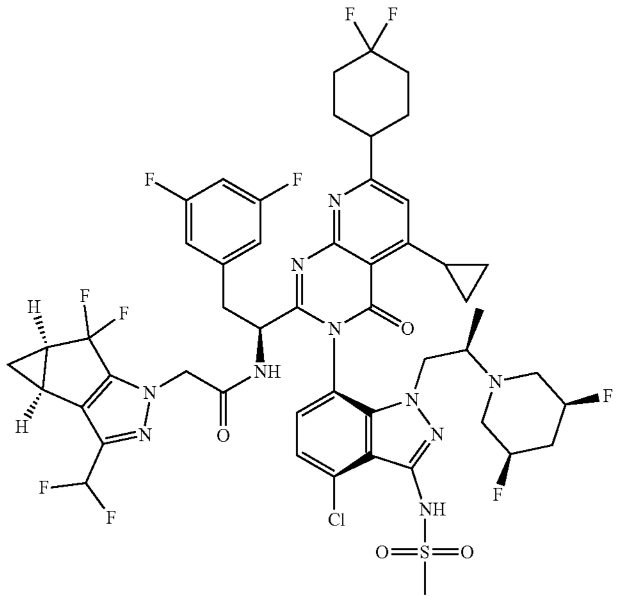 N-[(1S)-1-[(3P)-3-{4-chloro-1-[(2R)-2-[(3R,5S)-3,5-difluoropiperidin-1-yl]propyl]-3-methanesulfonamido-1H-indazol-7-yl}-5-cyclopropyl-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method: Column = Acquity BEH C18 (2.1 × 50 mm, 1.7 μm); Solvent A = 0.05% formic acid in water; Solvent B = 0.05% formic acid in acetonitrile; Flow Rate = 0.6 mL/min; Gradient Method (min.)/% B: 0/3, 2.5/3, 7.5/98, 9.5/98; Wavelength = 210 nm to 400 nm.: retention time = 6.34 min.; observed ion = 1109.49 [M − H]+ 1H NMR (400 MHz, DMSO-d6, 298.1 K), Shift (ppm) = 9.90 (br s, 1H), 9.48 (d, J = 6.8 Hz, 1H), 7.90-7.78 (m, 1H), 7.65-7.45 (m, 1H), 7.09 (s, 1H), 7.08-7.01 (m, 1H), 6.85 (t, J = 54 Hz, 1H), 6.62-6.57 (m, 2H), 4.62 (d, J = 16.8 Hz, 1H), 4.55-4.47 (m, 2H), 4.15-3.87 (m, 3H), 3.81-3.68 (m, 1H), 3.51-3.44 (m, 1H), 3.42-3.37 (m, 1H), 3.24-3.20 (br m, 3H), 3.09-2.98 (m, 1H), 2.97-2.86 (m, 1H), 2.78-2.58 (m, 2H), 2.51-2.38 (m, 3H), 2.27-2.21 (m, 4H), 2.06-1.87 (m, 7H), 1.42-1.31 (m, 2H), 1.18-1.11 (m, 2H), 1.06-1.01 (m, 1H), 0.88-0.82 (m, 2H), 0.51-0.49 (d, J = 6.8 Hz, 3H) |
| 685 (General Procedure B-2 using Amine B39 as the core reagent) | 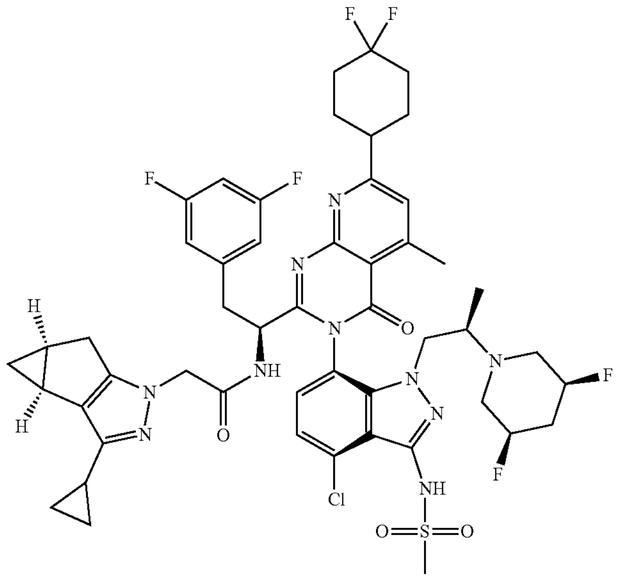 N-[(1S)-1-[(3P)-3-{4-chloro-1-[(2R)-2-[(3R,5S)-3,5-difluoropiperidin-1-yl]propyl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2}$,$^{4}$]nona-1(6),8-dien-7-yl]acetamide | LCMS Method: Column = Xbridge C18 (4.6 × 150 mm, 3.5 μm); Solvent A = 10 mM Ammonium Bicarbonate in water; Solvent B = ACN; Flow Rate = 1.0 ml/min; Gradient Method (min.)/% B: 0/5, 16.0/98; Wavelength = 210 nm to 1.0/5, 3.0/15, 7.0/55, 11.0/98, 400 nm.: retention time = 12.14 min.; observed ion = 1039.58 [M + H]+ 1H NMR (400 MHz, DMSO-d6, 298.1 K), Shift (ppm) = 9.90 (br s, 1H), 9.15 (d, J = 6.8 Hz, 1H), 7.80-7.75 (m, 1H), 7.55-7.48 (m, 1H), 7.45 (s, 1H), 7.09-7.02 (m, 1H), 6.63-6.59 (m, 2H), 4.52-4.48 (m, 1H), 4.30 (d, J = 16.4 Hz, 1H), 4.21-3.96 (m, 3H), 3.92-3.86 (m, 1H), 3.64-3.56 (m, 1H), 3.41-3.36 (m, 1H), 3.23-3.17 (br m, 3H), 3.08-2.92 (m, 2H), 2.82-2.72 (m, 4H), 2.70-2.58 (m, 1H), 2.60-2.53 (m, 1H), 2.38-2.28 (m, 2H), 2.27-1.86 (m, 11H), , 1.83-1.72 (m, 2H), 1.70-1.65 (m, 1H), 1.48-1.38 (m, 1H), 0.92-0.82 (m, 1H), 0.80-0.74 (m, 2H), 0.61-0.56 (m, 2H), 0.45 (d, J = 6.8 Hz, 3H), −0.02-−0.06 (m, 1H) |

TABLE A-continued

| Example No. (preparation of the Example) | Structure and IUPAC name | Characterising data (LCMS and/or NMR) |
| --- | --- | --- |
| 691 (General Procedure B-2 using Amine B41 as the core reagent) | 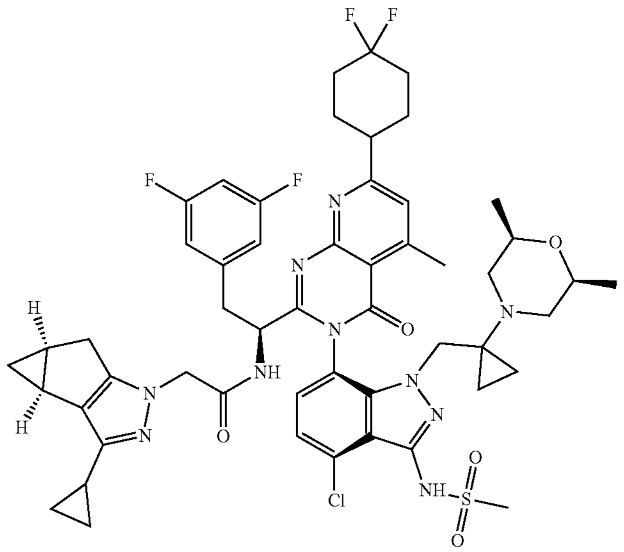 N-[(1S)-1-[(3P)-3-[4-chloro-1-({1-[(2R,6S)-2,6-dimethylmorpholin-4-yl]cyclopropyl}methyl)-3-methanesulfonamido-1H-indazol-7-yl]-7-(4,4-difluorocyclohexyl)-5-methyl-4-oxo-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2}$,$^{4}$]nona-1(6),8-dien-7-yl]acetamide | LCMS Method: Column = Acquity BEH C18 (2.1 × 50 mm, 1.7 μm); Solvent A = 0.05% formic acid in water; Solvent B = 0.05% formic acid in ACN; Flow Rate = 0.6 mL/min; Gradient Method (min.)/% B: 0/3, 0.4/3, 2.5/98, 3.5/98; Column Temp: 35° C.; Wavelength = 210 nm to 400 nm.: retention time = 2.39 min.; observed ion = 1045.57 [M + H]+ 1H NMR (400 MHz, DMSO-d6, 298.2 K), Shift (ppm) = 9.95 (br s, 1H), 9.11 (br d, J = 7.6 Hz, 1H), 7.69 (d, J = 7.2 Hz, 1H), 7.50-7.42 (m, 2H), 7.08-6.98 (m, 1H), 6.50-6.46 (m, 2H), 4.52-4.45 (m, 1H), 4.35-4.22 (m, 2H), 4.15-4.04 (m, 2H), 3.30-3.15 (m, 5H), 3.15-2.90 (m, 3H), 2.77 (s, 3H), 2.48-2.35 (m, 3H), 2.25-2.12 (m, 2H), 2.10-1.88 (m, 8H), 1.86-1.75 (m, 2H), 1.73-1.65 (m, 1H), 1.51-1.43 (m, 1H), 0.94-0.88 (m, 4H), 0.81-0.75 (m, 2H), 0.69-0.49 (m, 6H), 0.40-0.29 (m, 2H), 0.11-0.03 (m, 1H), 0.01--0.04 (m, 1H) |
| 697 (General Procedure B-2 using Amine B42 as the core reagent) | 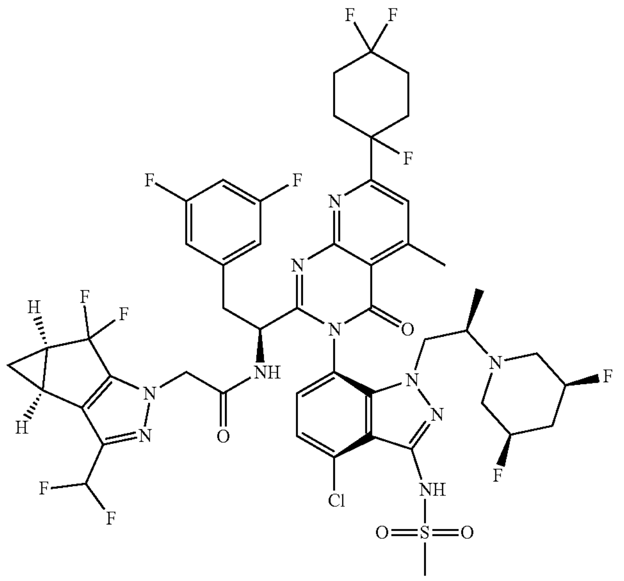 N-[(1S)-1-[(3P)-3-{4-chloro-1-[(2R)-2-[(3R,5S)-3,5-difluoropiperidin-1-yl]propyl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method H .: retention time = 2.15 min.; observed ion = 1103.18 [M + H]+ 1H NMR (400 MHz, DMSO-d6, 298.1 K), Shift (ppm) = 9.89 (s, 1 H), 9.475 (d, J = 9.2 Hz, 1 H), 7.85 (d, J = 7.6 Hz, 1 H), 7.72 (s, 1 H), 7.57 (d, J = 7.2 Hz, 1 H), 7.04-6.85 (m, 2 H), 6.58 (m, 2 H), 4.65-4.45 (m, 3 H), 3.92-3.69 (m, 4 H), 3.38-3.17 (m, 4 H), 2.94-2.86 (m, 4 H), 2.67-2.66 (m, 2 H), 2.49-2.43 (m, 4 H), 2.33-2.25 (m, 9 H), 2.14-2.12 (m, 1 H), 1.34-1.23 (m, 2 H), 0.84 (br s, 1 H), 0.50-0.48 (m, 3 H) |

TABLE A-continued

| Example No. (preparation of the Example) | Structure and IUPAC name | Characterising data (LCMS and/or NMR) |
|---|---|---|
| 702 (General Procedure B-2 using Amine B42 as the core reagent) | 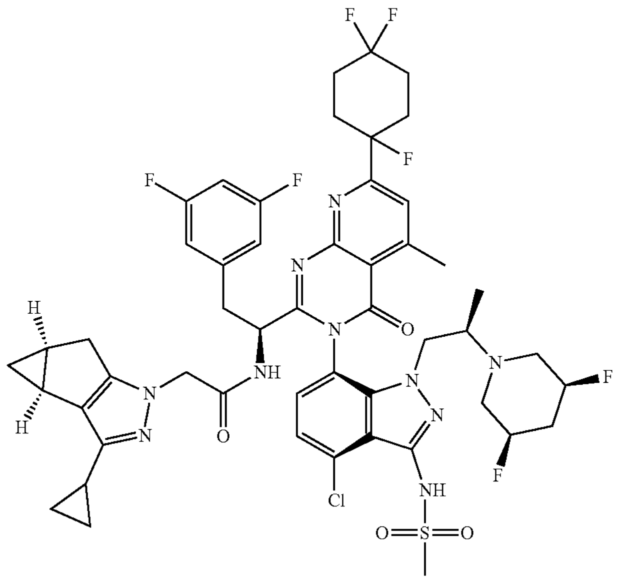 N-[(1S)-1-[(3P)-3-{4-chloro-1-[(2R)-2-[(3R,5S)-3,5-difluoropiperidin-1-yl]propyl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2}$,$^{4}$]nona-1(6),8-dien-7-yl]acetamide | LCMS method H: retention time = 2.15 min.; observed ion = 1057.29 [M + H]+ 1H NMR (400 MHz, DMSO-d6 298.2 K), Shift (ppm) = 9.93 (s, 1 H), 9.19 (d, J = 9.2 Hz, 1 H), 7.81 (d, J = 8.0 Hz, 1 H), 7.71 (s, 1 H), 7.54 (d, J = 7.6 Hz, 1 H), 7.07-7.03 (m, 1 H), 6.60 (d, J = 6.4 Hz, 2 H), 4.47-4.33 (m, 2 H), 4.28-4.15 (m, 4 H), 3.65-3.6 (m, 1 H), 3.36-3.22 (m, 4 H), 2.96-2.84 (m, 3H), 2.66-2.50 (m, 2 H), 2.49-2.14 (m, 13 H), 1.77-1.66 (m, 4 H), 1.66 (m, 1 H), 0.87-0.86 (m, 1 H), 0.77-0.73 (m, 2H), 0.59-0.57 (m, 2H), 0.46-0.45 (m, 3H) |
| 703 (General Procedure B-2 using Amine B44 as the core reagent) | 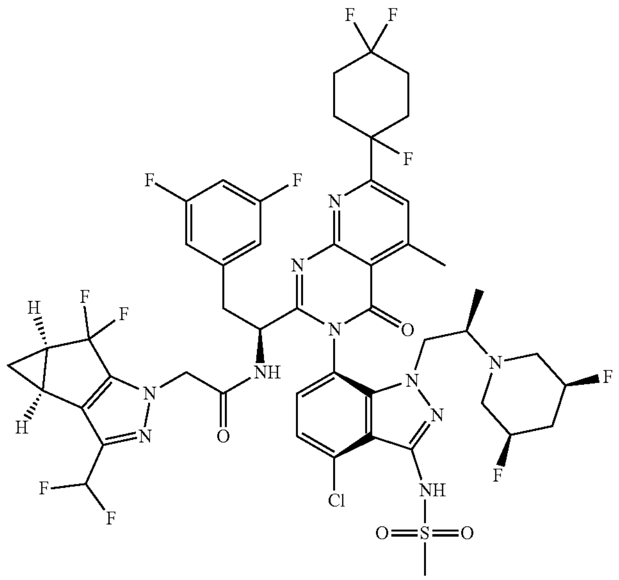 N-[(1S)-1-[(3P)-3-{4-chloro-1-[(2S)-2-[(3R,5S)-3,5-difluoropiperidin-1-yl]propyl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method F.: retention time = 2.34 min.; observed ion = 1103.45 [M + H]+ 1H NMR (400 MHz, DMSO-d6, 298.1 K), Shift (ppm) = 9.93 (s, 1H), 9.43 (s, 1H), 7.76-7.71 (m, 2H), 7.52 (d, J = 8.0 Hz, 1H), 7.04-6.73 (m, 2H), 6.49-6.47 (m, 2H), 4.76-4.72 ( m, 1H), 4.57-4.52 (m, 2H), 4.10-3.88 (m, 1H), 3.77-3.76 (m, 2H), 3.56-3.45 (m, 1H), 3.25-3.24 (m, 1H), 3.15 (s, 3H), 2.92-2.79 (m, 5H), 2.62-2.60 (m, 1H), 2.45-2.32 (m, 5H), 2.28-2.05 (m, 8H), 1.95-1.83 (m, 1H), 1.37-1.30 (m, 2H), 0.87-0.86 (m, 1H), 0.81 (d, J = 4.0 Hz, 3H) |

TABLE A-continued

| Example No. (preparation of the Example) | Structure and IUPAC name | Characterising data (LCMS and/or NMR) |
|---|---|---|
| 704 (General Procedure B-2 using Amine B44 as the core reagent) | 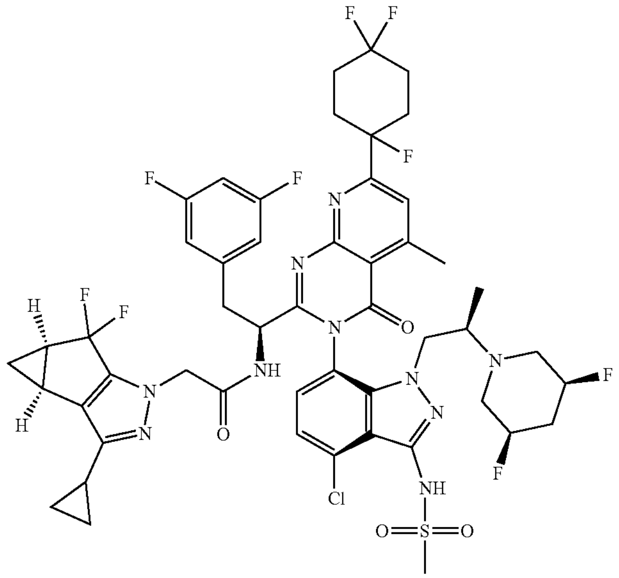 N-[(1S)-1-[(3P)-3-{4-chloro-1-[(2S)-2-[(3R,5S)-3,5-difluoropiperidin-1-yl]propyl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide | LCMS method F: retention time = 2.39 min.; observed ion = 1057.48 [M + H]+. 1H NMR (400 MHz, DMSO-d6, 298.1 K), Shift (ppm) = 9.96 (s, 1H), 9.12 (d, J = 8.0 Hz, 1H), 7.70 (s, 2H), 7.49 (br s, 1H), 7.06-7.01 (m, 1H), 6.52 (d, J = 8.0 Hz, 1H), 4.59-4.52 (m, 1H), 4.23-4.19 (m, 1H), 4.10-3.90 (m, 1H), 3.85-3.70 (m, 2H), 3.60-3.40 (m, 1H), 3.25-3.15 (m, 4H), 3.00-2.90 (m, 1H), 2.83 (s, 4H), 2.60-2.59 (m, 1H), 2.42-2.38 (m, 3H), 2.33-2.31 (m, 1H), 2.29-2.05 (m, 8H), 1.95-1.85 (m, 1H), 1.84-1.75 (m, 2H), 1.70-1.68 (m, 1H), 1.40-1.20 (m, 3H), 0.90-0.62 (m, 6H), 0.61-0.55 (m, 2H) |
| 705 (General Procedure B-2 using Amine B45 as the core reagent) | 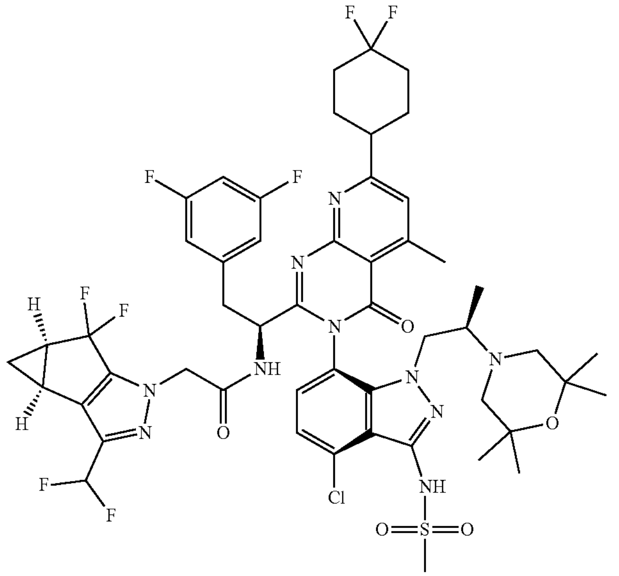 N-[(1S)-1-[(3P)-3-{4-chloro-3-methanesulfonamido-1-[(2R)-2-(2,2,6,6-tetramethylmorpholin-4-yl)propyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method: Column = Xbridge C18 (4.6 x 75 mm, 3.5 μm); Solvent A = 10 mM Ammonium Bicarbonate in water; Solvent B = ACN; Flow Rate = 1.3 mL/min; Gradient Method (min.)/% B: 0/5, 0.5/5, 1.0/15, 4.0/98, 7.0/98; Wavelength = 210 nm to 400 nm.: retention time = 4.86 min.; observed ion = 1107.54 [M + H]+ 1H NMR (400 MHz, DMSO-d6, 298.2 K), Shift (ppm) = 9.91 (s, 1H), 9.42-9.40 (m, 1H), 7.86-7.75 (m, 1H), 7.59-7.49 (m, 1H), 7.46 (s, 1H), 7.07-6.97 (m, 1H), 6.95-6.77 (m, 1H), 6.57-6.56 (m, 2H), 4.55-4.51 (m, 3H), 4.05-3.97 (m, 1H), 3.69-3.59 (m, 1H), 3.41-3.36 (m, 1H), 3.28-3.18 (m, 3H), 3.07-2.93 (m, 2H), 2.85-2.61 (s, 4H), 2.45-2.38 (m, 2H), 2.26-2.12 (m, 2H), 2.12-1.88 (m, 11H), 1.39-1.31 (m, 1H), 0.90-0.65 (m, 12H), 0.51-0.44 (m, 3H) |

TABLE A-continued

| Example No. (preparation of the Example) | Structure and IUPAC name | Characterising data (LCMS and/or NMR) |
|---|---|---|
| 706 (following General Procedure B-2 using Amine B45 as the core reagent) | 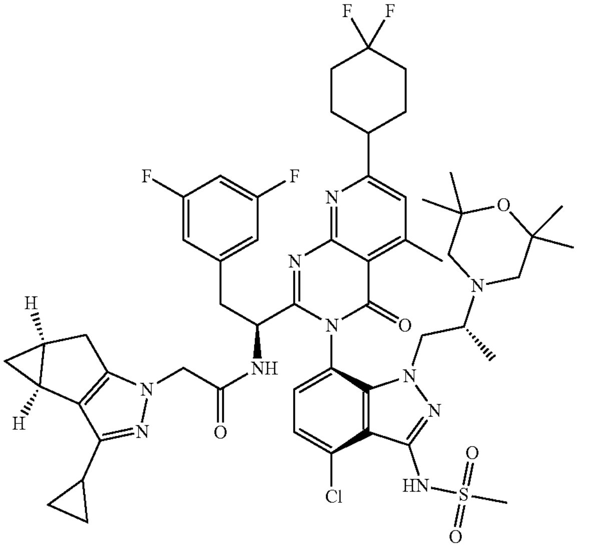 N-[(1S)-1-[(3P)-3-{4-chloro-3-methanesulfonamido-1-[(2R)-2-(2,2,6,6-tetramethylmorpholin-4-yl)propyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2}$,$^{4}$]nona-1(6),8-dien-7-yl]acetamide | LCMS method F: retention time = 2.46 min.; observed ion = 1061.58 [M + H]+ 1H NMR (400 MHz, DMSO-d6, 298.2 K), Shift (ppm) = 10.05-9.90 (m, 1H), 9.15-9.02 (m, 1H), 7.84-7.64 (m, 1H), 7.55-7.45 (m, 2H), 7.09-7.03 (m, 1H), 6.62-6.52 (m, 2H), 4.59-4.47 (m, 1H), 4.23 (s, 2H), 4.07-3.95 (m, 1H), 3.66-3.52 (m, 1H), 3.25-3.05 (m, 3H), 3.07-2.80 (m, 3H), 2.76 (s, 3H), 2.41-2.31 (m, 2H), 2.25-2.16 (m, 2H), 2.11-1.90 (m, 10H), 1.83-1.76 (m, 2H), 1.70-1.62 (m, 1H), 0.94-0.74 (m, 16H), 0.65-0.55 (m, 2H), 0.51-0.41 (m, 3H), −0.02-−0.05 (m, 1H) |
| 707 (General Procedure B-2 using Amine B46 as the core reagent) | 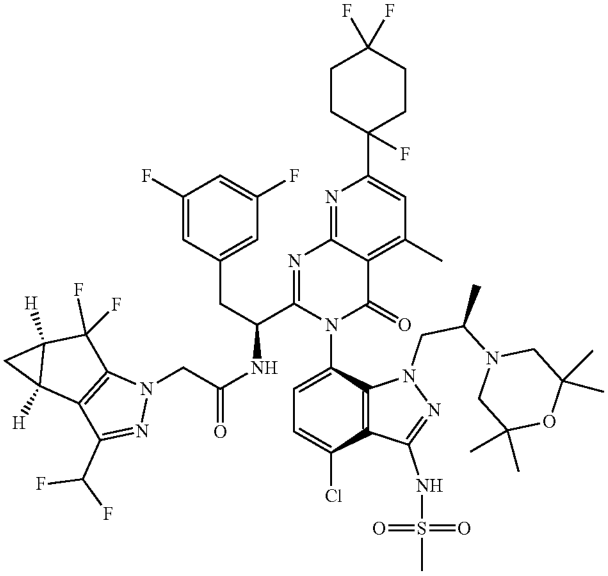 N-[(1S)-1-[(3P)-3-{4-chloro-3-methanesulfonamido-1-[(2R)-2-(2,2,6,6-tetramethylmorpholin-4-yl)propyl]-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS Method: Column = Xbridge C18 (4.6 × 75 mm, 3.5 μm); Solvent A = 10 mM Ammonium Bicarbonate in Water; Solvent B = 100% Acetonitrile; Flow Rate = 1.0 mL/min; Gradient Method (min.)/% B: 0/5, 1/5, 3/15, 7/55, 11/98, 16/98; Wavelength = 210 nm to 400 nm. Retention time = 11.23 min.; observed ion = 1123.59 (M − H).: retention time = 11.23 min.; observed ion = 1123.59 [M − H] 1H NMR (400 MHz, DMSO-d6, 298.2 K), Shift (ppm) = 9.99-9.81 (m, 1H), 9.47-9.32 (m, 1H), 7.91-7.76 (m, 1H), 7.73-7.68 (m, 1H), 7.63-7.49 (m, 1H), 7.05-6.96 (m, 1H), 6.94-6.67 (m, 1H), 6.59-6.52 (m, 2H), 4.59-4.52 (m, 3H), 4.05-3.95 (m, 1H), 3.75-3.64 (m, 1H), 3.42-3.35 (m, 1H), 3.29-3.08 (m, 3H), 2.99-2.89 (m, 1H), 2.83-2.72 (m, 4H), 2.47-2.36 (m, 3H), 2.35-2.03 (m, 7H), 2.00-1.76 (m, 4H), 1.40-1.29 (m, 1H), 0.85-0.75 (m, 13H), 0.49-0.47 (m, 3H) |

TABLE A-continued

| Example No. (preparation of the Example) | Structure and IUPAC name | Characterising data (LCMS and/or NMR) |
|---|---|---|
| 711 (General Procedure B using Amine B47 as the core reagent) | 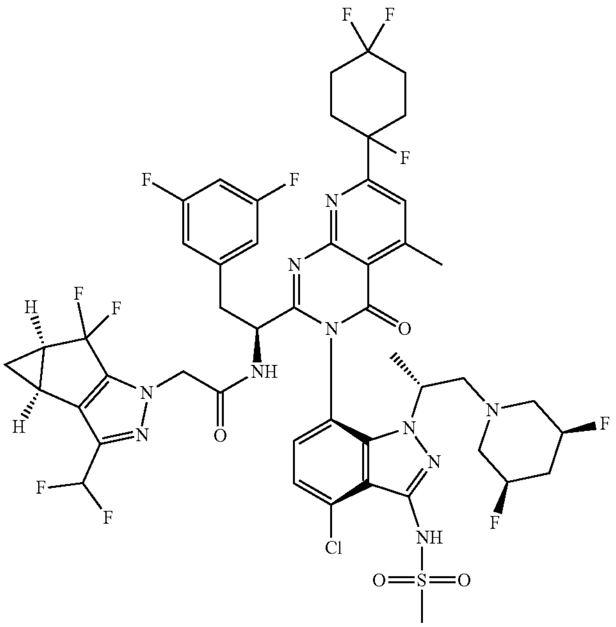 N-[(1S)-1-[(3P)-3-{4-chloro-1-[(2R)-1-[(3R,5S)-3,5-difluoropiperidin-1-yl]propan-2-yl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS method F: retention time = 2.38 min.; observed ion = 1103.41 [M + H]+ 1H NMR (400 MHz, DMSO-d6, 298.2 K), Shift (ppm) = 9.94-9.80 (m, 1H), 9.56-9.45 (m, 1H), 7.96-7.85 (m, 1H), 7.72-7.71 (m, 1H), 7.63-7.56 (m, 1H), 7.05-6.98 (m, 1H), 6.87-6.67 (m, 1H), 6.66-6.59 (m, 2H), 4.69-4.61 (m, 1H), 4.57-4.48 (m, 3H), 4.42-4.34 (m, 1H), 4.30-4.23 (m, 1H), 3.87-3.75 (m, 1H), 3.45-3.35 (m, 1H), 3.18 (s, 3H), 2.95-2.90 (m, 1H), 2.90-2.75 (m, 3H), 2.75-2.65 (m, 1H), 2.47-2.30 (m, 4H), 2.27-1.95 (m, 7H), 1.78-1.66 (m, 1H), 1.39-1.31 (m, 1H), 1.28-1.21 (m, 3H), 1.16-1.11 (m, 3H), 0.87-0.86 (m, 2H) |
| 714 (General Procedure B-2 using Amine B48 as the core reagent) | 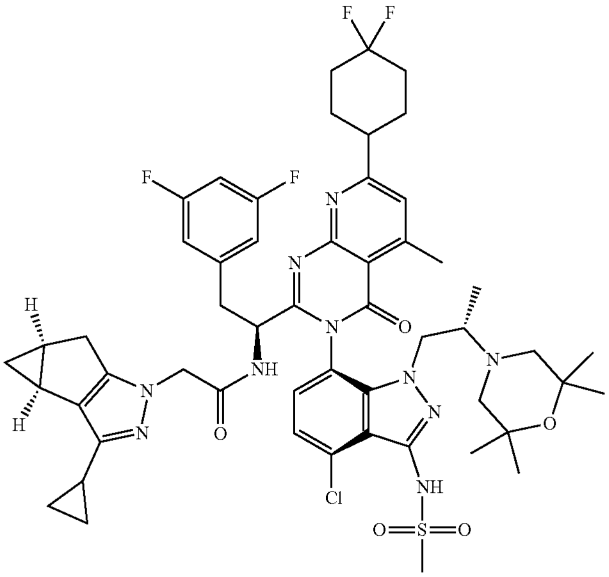 N-[(1S)-1-[(3P)-3-{4-chloro-3-methanesulfonamido-1-[(2S)-2-(2,2,6,6-tetramethylmorpholin-4-yl)propyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2R*,4R*)-9- | LCMS method I: retention time = 6.37 min.; observed ion = 1061.54 [M + H]+ 1H NMR (400 MHz, DMSO-d6, 297.7 K), Shift (ppm) = 9.95 (br s, 1H), 9.18-9.11 (m, 1H), 7.75-7.67 (m, 1H), 7.53-7.44 (m, 2H), 7.08-7.01 (m, 1H), 6.56-6.48 (m, 2H), 4.56-4.46 (m, 1H), 4.37-4.19 (m, 2H), 4.00-3.92 (m, 1H), 3.89-3.77 (m, 1H), 3.28-3.19 (m, 4H), 3.05-2.82 (m, 3H), 2.74 (s, 3H), 2.40-2.35 (m, 2H), 2.25-2.12 (m, 2H), 2.05-1.78 (m, 12H), 1.72-1.59 (m, 1H), 0.95-0.87 (m, 1H), 0.85-0.82 (m, 6H), 0.80-0.72 (m, 11H), 0.67-0.59 (m, 2H), −0.01-−0.05 (m, 1H) |

TABLE A-continued

| Example No. (preparation of the Example) | Structure and IUPAC name | Characterising data (LCMS and/or NMR) |
|---|---|---|
| | cyclopropyl-7,8-diazatricyclo[4.3.0.0$^{2,4}$]nona-1(6),8-dien-7-yl]acetamide | |
| 716 (General Procedure B using Amine B49 as the core reagent) | 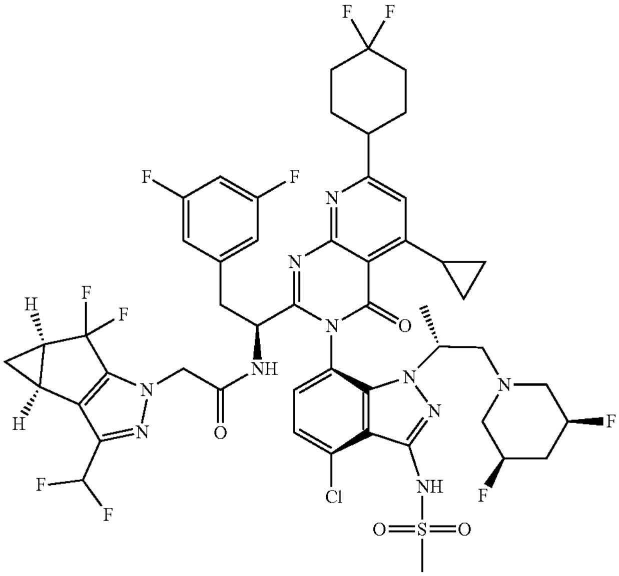 N-[(1S)-1-[(3P)-3-{4-chloro-1-[(2R)-1-[(3R,5S)-3,5-difluoropiperidin-1-yl]propan-2-yl]-3-methanesulfonamido-1H-indazol-7-yl}-5-cyclopropyl-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method: Column = ACQUITY BEH C18 (2.1 × 50 mm, 1.7 μm); Solvent A = 0.05% Trifluoroacetic Acid in water; Solvent B = 0.05% Trifluoroacetic Acid in ACN; Flow Rate = 0.6 mL/min; Gradient Method (min.)/% B: 0/3, 0.4/3, 2.5/98, 3.4/98; Wavelength = 210 nm to 400 nm.: retention time = 2.19 min.; observed ion = 1111.40 [M + H]+ 1H NMR (400 MHz, DMSO-d6, 298.2 K), Shift (ppm) = 9.47 (br s, 1H), 7.79 (br s, 1H), 7.41 (br s, 1H), 7.08 (s, 1H), 7.03-6.98 (m, 1H), 6.97-6.69 (m, 1H), 6.61 (d, J = 6 Hz, 2H), 4.61-4.58 (m, 3H), 4.43-4.32 (m, 2H), 3.78 (br s, 1H), 3.44-3.40 (m, 2H), 3.16-2.99 (m, 4H), 2.94-2.83 (m, 1H), 2.70-2.67 (m, 1H), 2.49-2.39 (m, 3H), 2.38-2.15 (m, 4H), 2.14-1.89 (m, 9H), 1.76-1.66 (m, 1H), 1.36-1.29 (m, 1H), 1.24 (s, 1H), 1.13-1.09 (m, 5H), 0.99-0.93 (m, 1H), 0.91-0.83 (m, 2H) |
| 717 (General Procedure B-2 using Amine B48 as the core reagent) | 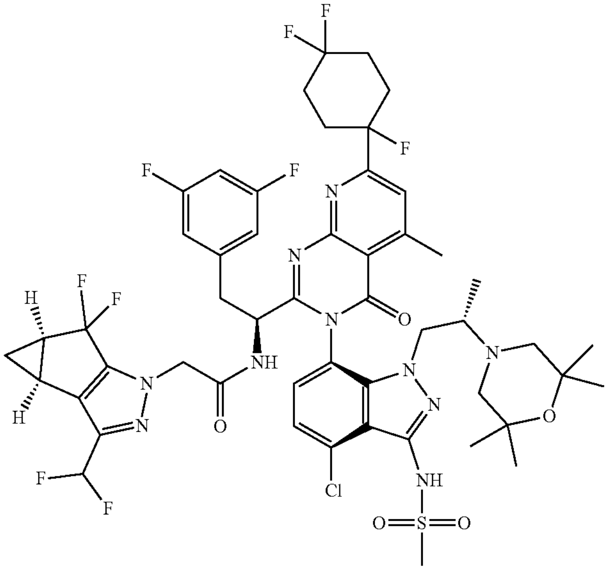 N-[(1S)-1-[(3P)-3-{4-chloro-3-methanesulfonamido-1-[(2S)-2-(2,2,6,6-tetramethylmorpholin-4-yl)propyl]-1H-indazol-7-yl}-5-methyl-4-oxo-7-(1,4,4-trifluorocyclohexyl)-3H,4H-pyrido[2,3-d]pyrimidin-2-yl]-2-(3,5- | LCMS method H: retention time = 2.20 min.; observed ion = 1125.40 [M + H]+ 1H NMR (400 MHz, DMSO-d6, 298.6 K), Shift (ppm) = 9.94 (br s, 1H), 9.57-9.46 (m, 1H), 7.82-7.73 (m, 1H), 7.71-7.69 (m, 1H), 7.56-7.48 (m, 1H), 7.05-6.72 (m, 2H), 6.50-6.43 (m, 2H), 4.64-4.60 (m, 2H), 4.57-4.51 (m, 1H), 3.99-3.88 (m, 1H), 3.87-3.76 (m, 1H), 3.25-3.17 (m, 4H), 2.97-2.89 (m, 1H), 2.87-2.80 (m, 4H), 2.47-2.39 (m, 3H), 2.30-2.08 (m, 7H), 1.98-1.89 (m, 2H), 1.85-1.79 (m, 2H), 1.43-1.33 (m, 1H), 0.90-0.75 (s, 10H), 0.70-0.61 (m, 6H) |

| Example No. (preparation of the Example) | Structure and IUPAC name | Characterising data (LCMS and/or NMR) |
|---|---|---|
| | difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | |
| 720 (General Procedure B using Amine B50 as the core reagent) | 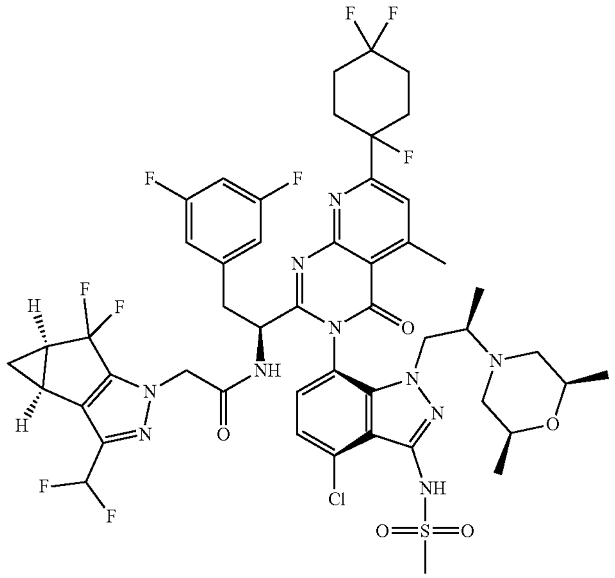 N-[(1S)-1-[(3P)-3-{4-chloro-1-[(2R)-2-[(2R,6S)-2,6-dimethylmorpholin-4-yl]propyl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS method F: retention time = 2.04 min.; observed ion = 1097.35 [M + H]+ 1H NMR (400 MHz, DMSO-d6, 298.2 K), Shift (ppm) = 10.01-9.83 (m, 2 H), 7.77-7.69 (m, 2 H), 7.56-7.47 (m, 1 H), 7.04-6.75 (m, 2 H), 6.45 (br d, J = 6.3 Hz, 2 H), 4.78-4.55 (m, 3 H), 3.85-3.75 (m, 2 H), 3.26-3.19 (m, 1 H), 3.24 (br d, J = 11.9 Hz, 1 H), 3.18-3.14 (m, 2 H), 2.94-2.86 (m, 2 H), 2.83-2.80 (m, 3 H), 2.60-2.53 (m, 2 H), 2.46-2.33 (m, 3 H), 2.28-2.12 (m, 8 H), 1.88-1.81 (m, 1 H), 1.69-1.62 (m, 1 H), 1.59-1.53 (m, 1 H), 1.42-1.36 (m, 1 H), 0.92-0.87 (m, 1 H), 0.84-0.77 (m, 9 H) |
| 722 (General Procedure B using Amine B51 as the core reagent) | 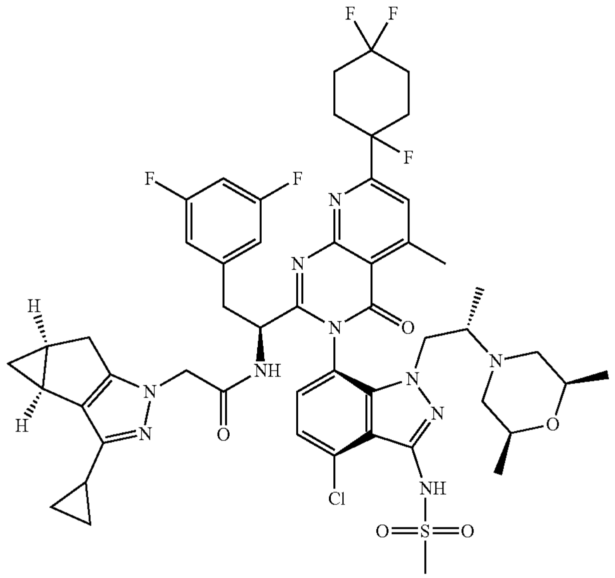 N-[(1S)-1-[(3P)-3-{4-chloro-1-[(2S)-2-[(2R,6S)-2,6-dimethylmorpholin-4-yl]propyl]-3-methanesulfonamido-1H-indazol-7-yl}-5-methyl-4-oxo-7-(1,4,4-trifluorocyclohexyl)-3H,4H-pyrido[2,3- | LCMS method F: retention time = 2.09 min.; observed ion = 1051.38 [M + H]+ 1H NMR (400 MHz, DMSO-d6, 298.1 K), Shift (ppm) = 9.96 (s, 1H), 9.29-9.08 (m, 1H), 7.72-7.66 (m, 2H), 7.48 (d, J = 7.2 Hz, 1H), 7.07-7.01 (m, 1H), 6.50-6.48 (m, 2H), 4.64-4.52 (m, 1H), 4.40-4.20 (m, 2H), 3.84-3.79 (m, 2H), 3.28-3.14 (m, 4H), 2.99-2.83 (m, 2H), 2.82 (s, 3H), 2.61-2.52 (m, 2H), 2.48-2.40 (m, 2H), 2.39-2.32 (m, 1H), 2.31-2.11 (m, 7H), 2.09-2.01 (m, 1H), 1.84-1.71 (m, 3H), 1.70-1.51 (m, 3H), 0.89-0.76 (m, 13H), 0.65-0.63 (m, 2H) |

| Example No. (preparation of the Example) | Structure and IUPAC name | Characterising data (LCMS and/or NMR) |
|---|---|---|
| | d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide | |
| 723 (General Procedure B using Amine B50 as the core reagent) | 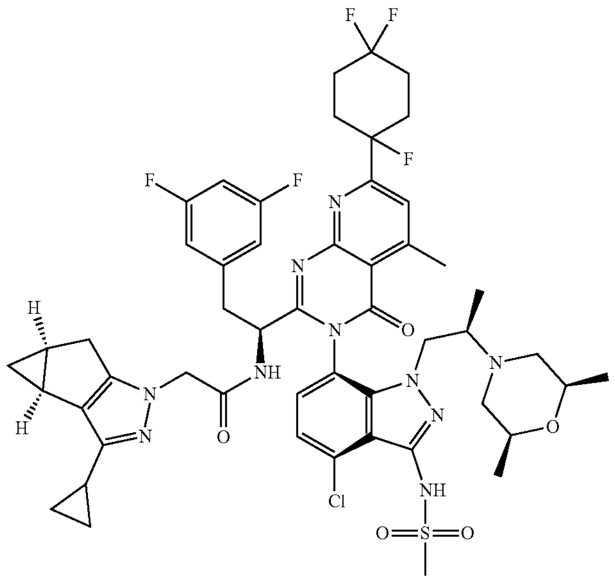 N-[(1S)-1-[(3P)-3-{4-chloro-1-[(2R)-2-[(2R,6S)-2,6-dimethylmorpholin-4-yl]propyl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide | LCMS method F: retention time = 2.07 min.; observed ion = 1051.42 [M + H]+ 1H NMR 1H NMR (400 MHz, DMSO-d6, 298.1 K), Shift (ppm) = 10.01-9.83 (m, 1 H), 9.22-8.96 (m, 1 H), 7.76-7.63 (m, 2 H), 7.54-7.40 (m, 1 H), 7.12-6.89 (m, 1 H), 6.56-6.40 (m, 2 H), 4.69-4.48 (m, 1 H), 4.42-4.34 (m, 1 H), 4.26-4.15 (m, 1 H), 3.86-3.72 (m, 2 H), 3.26-3.14 (m, 4 H), 3.00-2.85 (m, 2 H), 2.85-2.77 (m, 3 H), 2.68-2.54 (m, 2 H), 2.46-2.33 (m, 3 H), 2.29-2.12 (m, 7 H), 2.07-1.95 (m, 1 H), 1.90-1.75 (m, 3 H), 1.72-1.62 (m, 2 H), 1.59-1.51 (m, 1 H), 0.97-0.87 (m, 1 H), 0.93-0.86 (m, 1 H), 0.86-0.76 (m, 11 H), 0.68-0.48 (m, 2 H) |
| 724 (General Procedure B-2 using Amine B52 as the core reagent) | 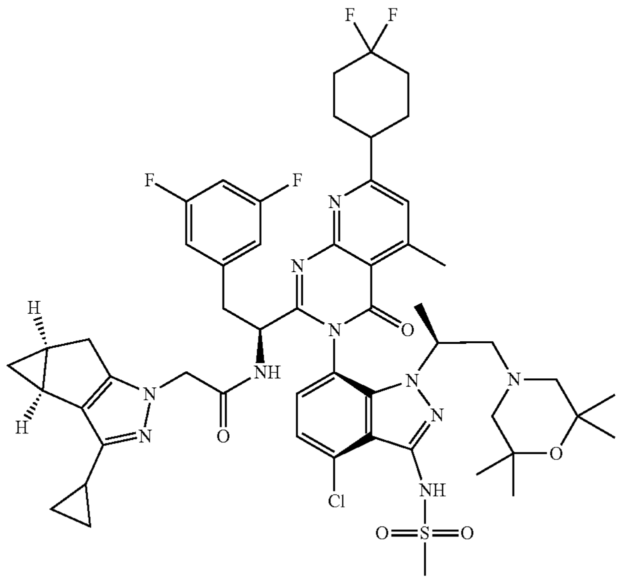 N-[(1S)-1-[(3P)-3-{4-chloro-3-methanesulfonamido-1-[(2S)-1-(2,2,6,6-tetramethylmorpholin-4-yl)propan-2-yl]-1H-indazol-7-yl}-7-(4,4-difluorocyclohexyl)-5- | LCMS method F: retention time = 2.52 min.; observed ion = 1061.50 [M + H]+ 1H NMR (400 MHz, DMSO-d6, 298.1 K), Shift (ppm) = 10.05-9.85 (m, 1H), 9.04-9.01 (m, 1H), 7.77-7.74 (m, 1H), 7.50-7.48 (m, 2H), 7.07-7.01 (m, 1H), 6.56-6.55 (m, 2H), 4.65-4.53 (m, 1H), 4.45-4.31 (m, 1H), 4.28-4.13 (m, 1H), 4.08-3.92 (m, 1H), 3.38-3.32 (m, 1H), 3.26-3.18 (m, 3H), 3.09-2.98 (m, 1H), 2.95-2.86 (m, 1H), 2.80-2.72 (m, 3H), 2.62-2.55 (m, 1H), 2.37-2.32 (m, 1H), 2.31-2.11 (m, 4H), 2.08-1.86 (m, 6H), 1.82-1.72 (m, 4H), 1.68-1.59 (m, 3H), 1.30-1.17 (m, 3H), 0.87-0.84 (m, 13H), 0.76-0.71 (m, 2H), 0.65-0.58 (m, 2H), −0.05-−0.06 (m, 1H) |

TABLE A-continued

| Example No. (preparation of the Example) | Structure and IUPAC name | Characterising data (LCMS and/or NMR) |
|---|---|---|
| | methyl-4-oxo-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide | |
| 729 (General Procedure B-2 using Amine B53 as the core reagent) | 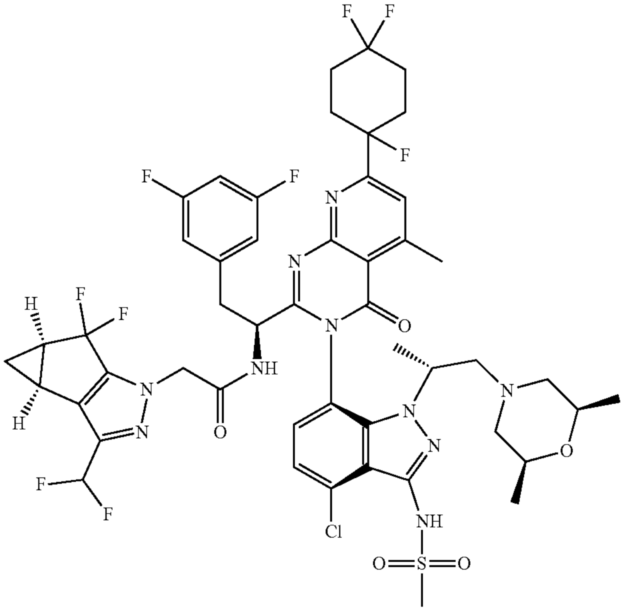<br>N-[(1S)-1-[(3P)-3-{4-chloro-1-[(2R)-1-[(2R,6S)-2,6-dimethylmorpholin-4-yl]propan-2-yl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS method F: retention time = 2.07 min.; observed ion = 1097.35 [M + H]+<br>1H NMR (400 MHz, DMSO-d6, 298.1 K), Shift (ppm) = 9.91-9.84 (m, 1H), 9.53-9.45 (m, 1H), 7.91-7.89 (m, 1H), 7.73-7.71 (m, 1H), 7.60-7.88 (m, 1H), 7.03-6.98 (m, 1H), 6.93-6.65 (m, 1H), 6.60-6.59 (m, 2H), 4.65-4.46 (m, 3H), 4.03-3.90 (m, 1H), 3.41-3.31 (m, 2H), 3.25-3.15 (m, 3H), 3.09-3.03 (m, 1H), 2.95-2.89 (m 1H), 2.85 (s, 3H), 2.67-2.59 (m, 1H), 2.40-2.34 (m, 4H), 2.28-2.09 (m, 8H), 1.75-1.55 (m, 2H), 1.39-1.31 (m, 1H), 1.25-1.15 (m, 4H), 0.98-0.95 (m, 3H), 0.90-0.86 (m, 1H), 0.85-0.82 (m, 3H) |

TABLE A-continued

| Example No. (preparation of the Example) | Structure and IUPAC name | Characterising data (LCMS and/or NMR) |
|---|---|---|
| 730 (General Procedure B-2 using Amine B53 as the core reagent) | 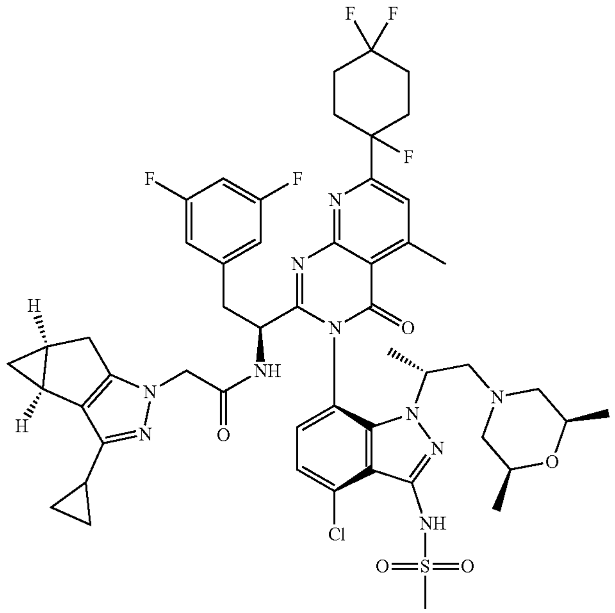 N-[(1S)-1-[(3P)-3-{4-chloro-1-[(2R)-1-[(2R,6S)-2,6-dimethylmorpholin-4-yl]propan-2-yl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide | LCMS Method: Column = Xbridge C18 (4.6 × 75 mm, 3.5 μm); Solvent A = 10 mM Ammonium Bicarbonate in water; Solvent B = ACN; Flow Rate = 1.3 mL/min; Gradient Method (min.)/% ACN: 0/5, 0.5/5, 1.0/15, 4.0/98, 7.0/98; Wavelength = 210 nm to 400 nm.: retention time = 5.11 min.; observed ion = 1049.62 [M − H]+ 1H NMR (400 MHz, DMSO-d6, 298.1 K), Shift (ppm) = 9.95-9.90 (m, 1H), 9.30-9.20 (m, 1H), 7.88-7.86 (m, 1H), 7.74-7.71 (m, 1H), 7.60-7.54 (m, 1H), 7.09-7.04 (m, 1H), 6.64-6.62 (m, 2H), 4.55-4.45 (m, 1H), 4.30-4.20 (m, 2H), 4.02-3.92 (m, 1H), 3.41-3.31 (m, 2H), 3.20-3.15 (m, 3H), 3.11-3.04 (m, 1H), 3.02-2.99 (m, 1H), 2.87-2.83 (m, 3H), 2.67-2.62 (m, 1H), 2.42-2.36 (m, 2H), 2.35-2.07 (m, 10H), 1.87-1.67 (m, 5H), 1.39-1.29 (m, 1H), 1.18-1.12 (m, 3H), 0.98-0.94 (m, 3H), 0.94-0.87 (m, 1H), 0.86-0.81 (m, 3H), 0.77-0.72 (m, 2H), 0.69-0.61 (m, 2H), 0--0.95 (m, 1H) |
| 732 (General Procedure B using Amine B54 as the core reagent) | 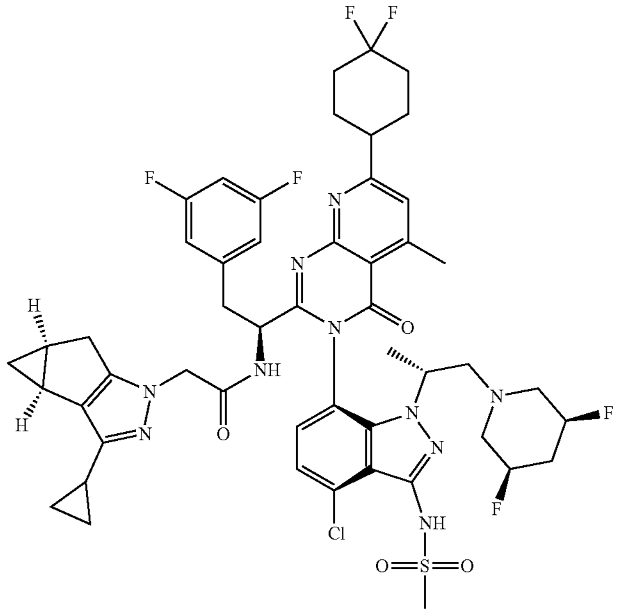 N-[(1S)-1-[(3P)-3-{4-chloro-1-[(2R)-1-[(3R,5S)-3,5-difluoropiperidin-1-yl]propan-2-yl]-3-methanesulfonamido-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2R*,4R*)-9- | LCMS Method: Column = X Bridge C18 (4.6 × 150 mm, 3.5 μm); Solvent A = 10 mM Ammonium Bicarbonate in Water; Solvent B = 100% Acetonitrile; Flow Rate = 1.0 mL/min; Gradient Method (min.)/% B: 0/5, 1/5, 3/15, 7/55, 11/98, 16/98; Wavelength = 210 nm to 400 nm.: retention time = 12.06 min.; observed ion = 1037.56 [M − H]+ 1H NMR (400 MHz, DMSO-d6, 298.1 K), Shift (ppm) = 9.91 (s, 1H), 9.27-9.20 (m, 1H), 7.86-7.85 (m, 1H), 7.55-7.53 (m, 1H), 7.43 (s, 1H), 7.09-7.04 (m, 1H), 6.67-6.66 (m, 2H), 4.47-4.14 (m, 5H), 3.85-3.75 (m, 1H), 3.47-3.39 (m, 1H), 3.20 (br s, 3H), 3.10-2.85 (m, 2H), 2.75-2.65 (m, 4H), 2.47-2.35 (m, 4H), 2.25-2.11 (m, 3H), 2.08-1.85 (m, 9H), 1.83-1.72 (m, 3H), 1.70-1.61 (m, 1H), 1.15-1.09 (m, 3H), 0.91-0.85 (m, 1H), 0.80-0.74 (m, 2H), 0.63-0.58 (m, 2H), −0.02-−0.05 (m, 1H) |

TABLE A-continued

| Example No. (preparation of the Example) | Structure and IUPAC name | Characterising data (LCMS and/or NMR) |
|---|---|---|
| | cyclopropyl-7,8-diazatricyclo[4.3.0.0$^{2}$,$^{4}$]nona-1(6),8-dien-7-yl]acetamide | |
| 733 (General Procedure B using Amine B55 as the core reagent) | 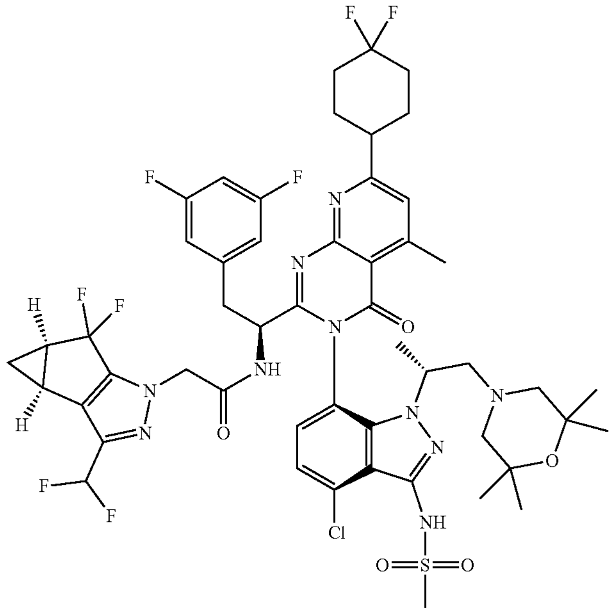 N-[(1S)-1-[(3P)-3-{4-chloro-3-methanesulfonamido-1-[(2R)-1-(2,2,6,6-tetramethylmorpholin-4-yl)propan-2-yl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2}$,$^{4}$]nona-1(6),8-dien-7-yl]acetamide | LCMS method I: retention time = 6.58 min.; observed ion = 1107.44 [M + H]+ 1H NMR (400 MHz, DMSO-d6, 298.2 K), Shift (ppm) = 9.88 (s, 1H), 9.53-9.47 (m, 1H), 7.93-7.84 (m, 1H), 7.64-7.54 (m, 1H), 7.49-7.44 (m, 1H), 7.05-6.96 (m, 1H), 6.93-6.64 (m, 1H), 6.61-6.57 (m, 2H), 4.66-4.46 (m, 3H), 3.96-3.85 (m, 1H), 3.42-3.37 (m, 1H), 3.23-3.17 (m, 3H), 3.06-3.00 (m, 1H), 2.93-2.87 (m, 1H), 2.76 (s, 3H), 2.66-2.60 (m, 1H), 2.47-2.38 (m, 2H), 2.32-2.27 (m, 1H), 2.22-2.15 (m, 2H), 2.09-1.92 (m, 8H), 1.80-1.74 (m, 2H), 1.37-1.31 (m, 1H), 1.29-1.24 (m, 3H), 1.00 (s, 6H), 0.87-0.84 (m, 1H), 0.69 (s, 6H) |
| 734 (General Procedure B using Amine B55 as the core reagent) | 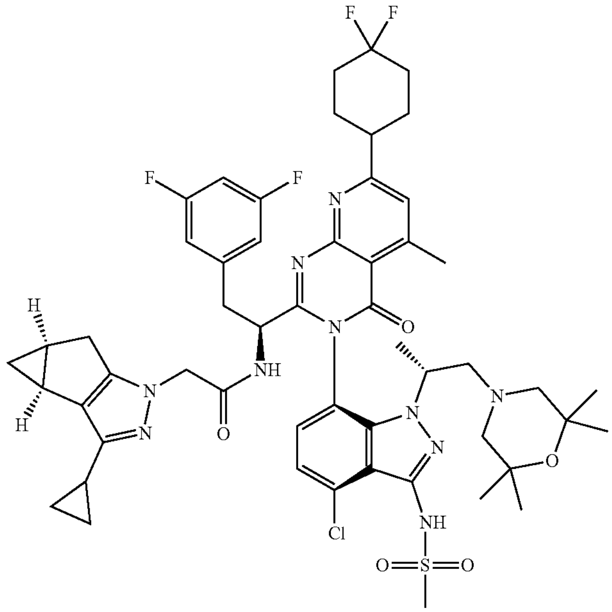 | LCMS Method: Column = Xbridge C18 (4.6 x 75 mm, 3.5 μm); Solvent A = 10 mM Ammonium Bicarbonate in water; Solvent B = ACN; Flow Rate = 1.3 mL/min; Gradient Method (min.)/% B: 0/5, 0.5/5, 1.0/15, 4.0/98, 7.0/98; Wavelength = 210 nm to 400 nm.: retention time = 4.96 min.; observed ion = 1059.65 [M − H]+ 1H NMR (400 MHz, DMSO-d6, 298.1 K), Shift (ppm) = 10.02-9.84 (m, 1H), 9.24-9.18 (m, 1H), 7.90-7.82 (m, 1H), 7.61-7.50 (m, 1H), 7.45 (s, 1H), 7.11-7.04 (m, 1H), 6.65-6.60 (m, 2H), 4.48-4.41 (m, 1H), 4.39-4.28 (m, 2H), 3.94-3.85 (m, 1H), 3.45-3.39 (m, 1H), 3.25 (s, 3H), 3.05-2.93 (m, 2H), 2.77 (s, 3H), 2.69-2.65 (m, 1H), 2.44-2.39 (m, 1H), 2.34-2.18 (m, 4H), 2.04-1.87 (m, 8H), 1.80-1.67 (m, 5H), 1.31-1.25 (m, 3H), 0.99 (s, 6H), 0.90-0.85 (m, 1H), 0.76-0.72 (m, 2H), 0.68 (s, 6H), 0.63-0.60 (m, 2H), 0--0.05 (m, 1H) |

TABLE A-continued

| Example No. (preparation of the Example) | Structure and IUPAC name | Characterising data (LCMS and/or NMR) |
|---|---|---|
| | N-[(1S)-1-[(3P)-3-{4-chloro-3-methanesulfonamido-1-[(2R)-1-(2,2,6,6-tetramethylmorpholin-4-yl)propan-2-yl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide | |
| 735 (General Procedure B-2 using Amine B56 as the core reagent) | 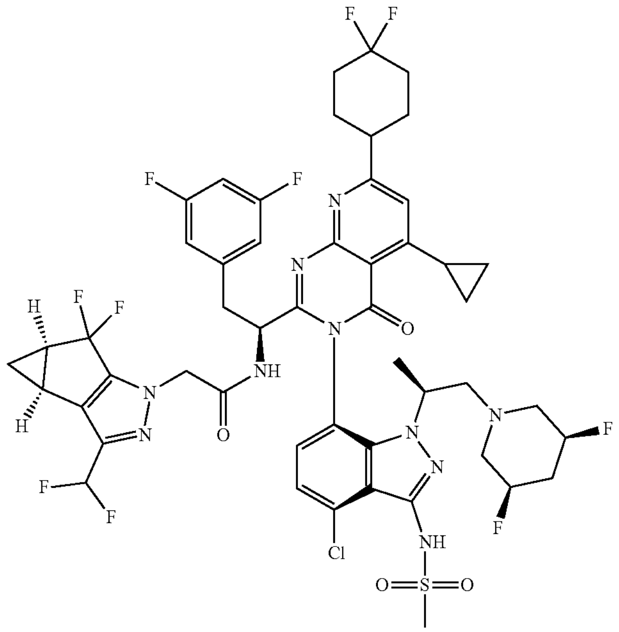 N-[(1S)-1-[(3P)-3-{4-chloro-1-[(2S)-1-[(3R,5S)-3,5-difluoropiperidin-1-yl]propan-2-yl]-3-methanesulfonamido-1H-indazol-7-yl}-5-cyclopropyl-7-(4,4-difluorocyclohexyl)-4-oxo-3H, 4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method: Column = X Bridge C18 (4.6 × 150 mm, 3.5nμm); Solvent A = 10 mM Ammonium Bicarbonate in Water; Solvent B = 100% Acetonitrile; Flow Rate = 1.0 mL/min; Gradient Method (min.)/% B: 0/5, 1/5, 3/15, 7/55, 11/98, 16/98; Wavelength = 210 nm to 400 nm.: retention time = 12.05 min.; observed ion = 1109.51 [M − H]+ 1H NMR (400 MHz, DMSO-d6, 298.1 K), Shift (ppm) = 9.47 (br s, 1H), 8.90-8.85 (m, 1H), 7.66-7.59 (m, 1H), 7.45-7.33 (m, 1H), 6.98-6.95 (m, 1H), 6.91-6.62 (m, 2H), 6.60-6.53 (m, 2H), 4.75-4.65 (m, 2H), 4.63-4.53 (m, 1H), 4.40-4.27 (m, 1H), 4.26-4.16 (m, 1H), 4.03-3.91 (m, 1H), 3.60-3.50 (m, 1H), 3.38-3.30 (m, 1H), 3.16 (s, 3H), 3.05-2.97 (m, 2H), 2.64-2.63 (m, 1H), 2.59-2.53 (m, 1H), 2.45-2.38 (m, 3H), 2.30-1.96 (m, 12H), 1.63-1.43 (m, 1H), 1.39-1.34 (m, 1H), 1.21-1.14 (m, 5H), 1.00-0.95 (m, 2H), 0.89-0.85 (m, 1H) |

TABLE A-continued

| Example No. (preparation of the Example) | Structure and IUPAC name | Characterising data (LCMS and/or NMR) |
|---|---|---|
| 738 (General Procedure B-2 using Amine B57 as the core reagent) | 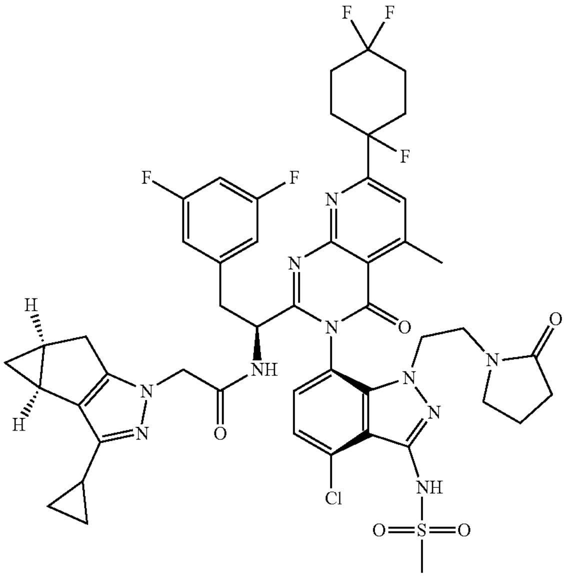 N-[(1S)-1-[(3P)-3-{4-chloro-3-methanesulfonamido-1-[2-(2-oxopyrrolidin-1-yl)ethyl]-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide | LCMS method F: retention time = 2.29 min.; observed ion = 1007.35 [M + H]+ 1H NMR (400 MHz, DMSO-d6, 298.2 K), Shift (ppm) = 9.96 (s, 1H), 9.12 (d, J = 8.4 Hz, 1H), 7.75 (d, J = 8 Hz, 1H), 7.65 (s, 1H), 7.50 (d, J = 4 Hz, 1H), 7.05-7.02 (m, 1H), 6.55 (d, J = 8 Hz, 2H), 4.48-4.46 (m, 1H), 4.34-4.19 (m, 2H), 3.95-3.89 (m, 1H), 3.87-3.71 (m, 1H), 3.35-3.31 (m, 2H), 3.26-3.24 (m, 4H), 3.05-3.01 (m, 1H), 2.84-2.75 (m, 4H), 2.67-2.60 (m, 1H), 2.43-2.40 (m, 2H), 2.34-2.30 (m, 1H), 2.59-2.04 (m, 9H), 1.77-1.65 (m, 5H), 0.77-0.75 (m, 1H), 0.74-0.73 (m, 2H), 0.59-0.57 (m, 2H), 0.00--0.05 (m, 1H) |
| 740 (General Procedure B-2 using Amine B58 as the core reagent) | 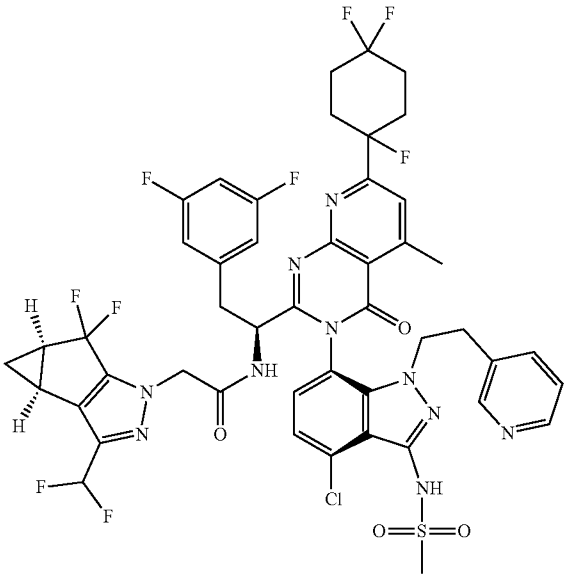 N-[(1S)-1-[(3P)-3-{4-chloro-3-methanesulfonamido-1-[2-(pyridin-3-yl)ethyl]-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS Method: Column = Acquity BEH C18 (2.1 × 50 mm, 1.7 um); Solvent A = 0.05% formic acid in water; Solvent B = 0.05% formic acid in ACN; Flow Rate = 0.6 mL/min; Gradient Method (min.)/% B: 0/3, 0.4/3, 2.5/98, 3.5/98; Wavelength = 215 nm and 254 nm.: retention time = 2.11 min.; observed ion = 1047.43 [M + H]+ 1H NMR (400 MHz, DMSO-d6, 298.1 K), Shift (ppm) = 9.89 (s, 1H), 9.43 (d, J = 8.4 Hz, 1H), 8.29-8.27 (m, 1H), 8.02-8.01 (m, 1H), 7.79 (d, J = 8 Hz, 1H), 7.67 (s, 1H), 7.52 (d, J = 7.6 Hz, 1H), 7.16 (d, J = 7.6 Hz, 1H), 7.05-7.01 (m, 2H), 6.96-6.86 (m, 1H), 6.58 (d, J = 6.4 Hz, 2H), 4.65-4.61 (m, 1H), 4.52-4.48 (m, 2H), 4.07-4.05 (m, 1H), 3.90-3.87 (m, 1H), 3.37-3.32 (m, 1H), 3.10 (s, 3H), 3.00-2.94 (m, 1H), 2.90-2.86 (m, 2H), 2.80 (s, 3H), 2.51-2.39 (m, 4H), 2.35-2.16 (m, 7H), 1.31-1.29 (m, 1H) |

TABLE A-continued

| Example No. (preparation of the Example) | Structure and IUPAC name | Characterising data (LCMS and/or NMR) |
|---|---|---|
| 741 (General Procedure B-2 using Amine B58 as the core reagent) | 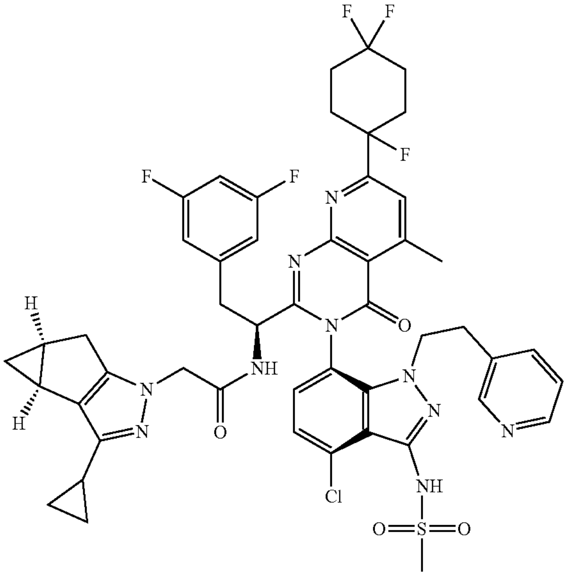 N-[(1S)-1-[(3P)-3-{4-chloro-3-methanesulfonamido-1-[2-(pyridin-3-yl)ethyl]-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide | LCMS method I: retention time = 5.89 min.; observed ion = 1001.55 [M + H]+ 1H NMR (400 MHz, DMSO-d6, 298.2 K), Shift (ppm) = 9.91 (s, 1H), 9.17 (m, 1H), 8.27-8.25 (m, 1H), 8.03 (d, 1H), 7.75-7.77 (d, 1H), 7.65 (s, 1H), 7.51-7.49 (d, 1H), 7.18-7.16 (m, 1H), 7.07-7.02 (m, 2H), 6.61-6.59 (d, 2H), 4.52 (t, 1H), 4.29-4.14 (m, 3H), 3.9 (m, 1H), 3.35-3.31 (m, 1H), 3.13 (s, 3H), 2.91-2.67 (m, 6H), 2.34-2.15 (m, 10H), 1.73-1.72 (m, 2H), 1.61 (m, 1H), 0.73-0.70 (m, 1H), 0.56-0.53 (m, 4H) |
| 742 (General Procedure B using Amine B52 as the core reagent) | 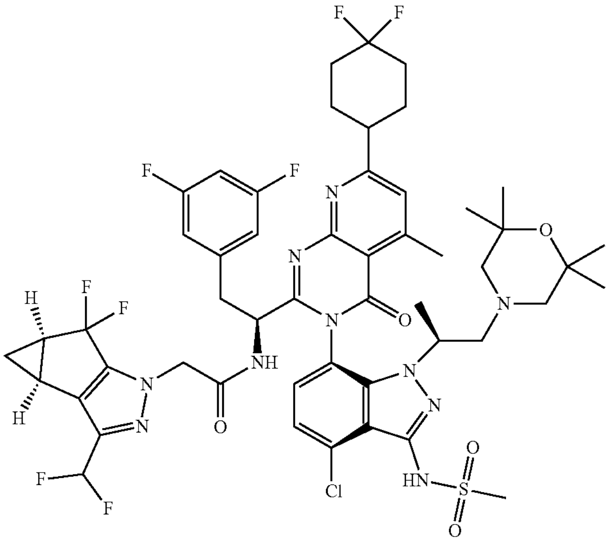 N-[(1S)-1-[(3P)-3-{4-chloro-3-methanesulfonamido-1-[(2S)-1-(2,2,6,6-tetramethylmorpholin-4-yl)propan-2-yl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS method F: retention time = 2.44 min.; observed ion = 1107.44 [M + H]+ 1H NMR (400 MHz, DMSO-d6, 298.2 K), Shift (ppm) = 9.97-9.88 (m, 1H), 9.43-9.28 (m, 1H), 7.85-7.75 (m, 1H), 7.59-7.48 (m, 2H), 7.06-6.98 (m, 1H), 6.97-6.68 (m, 1H), 6.58-6.50 (m, 2H), 4.77-4.70 (m, 1H), 4.67-4.58 (m, 1H), 4.57-4.48 (m, 1H), 4.04-3.92 (m, 1H), 3.39-3.34 (m, 1H), 3.23-3.16 (m, 3H), 3.09-2.97 (m, 1H), 2.94-2.84 (m, 1H), 2.79-2.73 (m, 3H), 2.59-2.54 (m, 1H), 2.47-2.42 (m, 2H), 2.28-2.15 (m, 3H), 2.11-1.91 (m, 7H), 1.84-1.74 (m, 2H), 1.69-1.60 (m, 2H), 1.40-1.29 (m, 1H), 1.26-1.17 (m, 3H), 0.85-0.78 (m, 12H) |

TABLE A-continued

| Example No. (preparation of the Example) | Structure and IUPAC name | Characterising data (LCMS and/or NMR) |
|---|---|---|
| 743 (General Procedure B-2 using Amine B59 as the core reagent) | 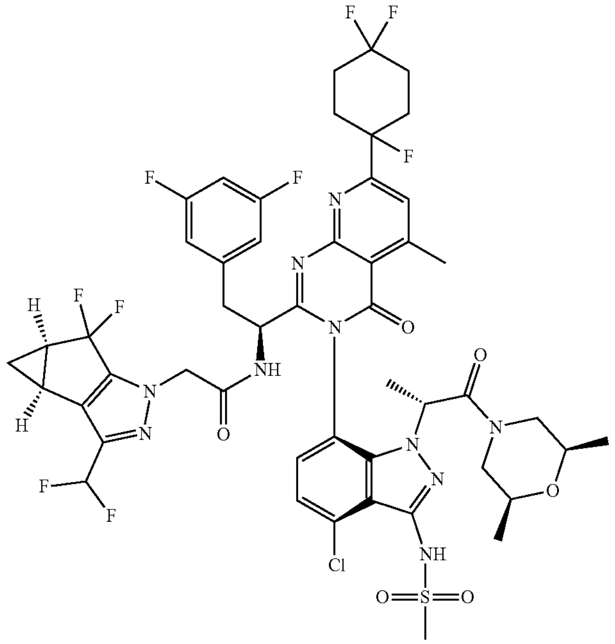 N-[(1S)-1-[(3P)-3-{4-chloro-1-[(2R)-1-[(2R,6S)-2,6-dimethylmorpholin-4-yl]-1-oxopropan-2-yl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS method F: retention time = 2.47 min.; observed ion = 1109.49 [M − H]+ 1H NMR (400 MHz, DMSO-d6, 298.1 K), Shift (ppm) = 10.08-9.95 (m, 1H), 8.70-8.60 (m, 1H), 7.88-7.78 (m, 1H), 7.75-7.70 (m, 1H), 7.62-7.50 (m, 1H), 7.04-6.73 (m, 2H), 6.67-6.61 (m, 2H), 5.25-5.08 (m, 1H), 4.77-4.69 (m, 1H), 4.50-4.42 (m, 2H), 3.94-3.86 (m, 1H), 3.31-3.16 (m, 6H), 2.97-2.80 (m, 5H), 2.44-2.33 (m, 4H), 2.30-2.10 (m, 6H), 2.04-1.91 (m, 1H), 1.65-1.49 (m, 3H), 1.37-1.29 (m, 1H), 1.05-0.97 (m, 3H), 0.87-0.70 (m, 2H), 0.63-0.42 (m, 3H) |
| 744 (General Procedure B-2 using Amine B59 as the core reagent) | 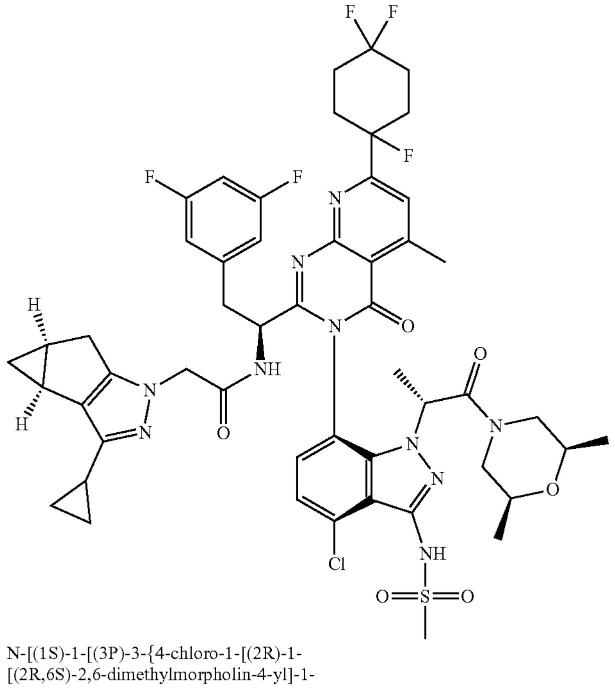 N-[(1S)-1-[(3P)-3-{4-chloro-1-[(2R)-1-[(2R,6S)-2,6-dimethylmorpholin-4-yl]-1-oxopropan-2-yl]-3-methanesulfonamido-1H-indazol-7-yl}-5-methyl-4-oxo-7-(1,4,4- | LCMS method F: retention time = 2.55 min.; observed ion = 1063.57 [M − H]+ 1H NMR (400 MHz, DMSO-d6, 298.1 K), Shift (ppm) = 10.05-9.95 (m, 1H), 8.32-8.26 (m, 1H), 7.81-7.79 (m, 1H), 7.76-7.71 (m, 1H), 7.53-7.51 (m, 1H), 7.05-7.00 (m, 1H), 6.70-6.60 (m, 2H), 5.25-5.10 (m, 1H), 4.60-4.45 (m, 1H), 4.28-3.94 (m, 2H), 3.90-3.85 (m, 1H), 3.28-3.15 (m, 6H), 3.05-2.95 (m, 1H), 2.90-2.85 (m, 4H), 2.45-2.05 (m, 11H), 1.95-1.65 (m, 4H), 1.60-1.50 (m, 3H), 1.05-0.95 (m, 3H), 0.93-0.88 (m, 1H), 0.80-0.55 (m, 7H), 0.00--0.05 (m, 1H) |

TABLE A-continued

| Example No. (preparation of the Example) | Structure and IUPAC name | Characterising data (LCMS and/or NMR) |
|---|---|---|
| | trifluorocyclohexyl)-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide | |
| 747 (General Procedure B-2 using Amine B61 as the core reagent) | 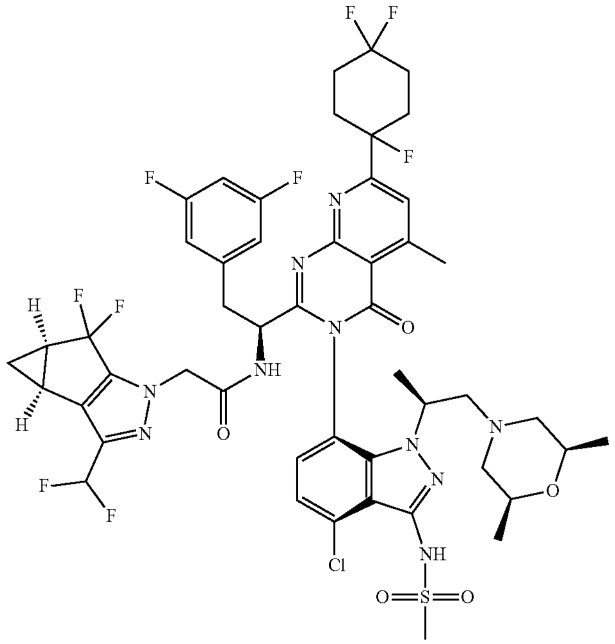 N-[(1S)-1-[(3P)-3-{4-chloro-1-[(2S)-1-[(2R,6S)-2,6-dimethylmorpholin-4-yl]propan-2-yl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS method F: retention time = 2.13 min.; observed ion = 1097.35 [M + H]+ 1H NMR (400 MHz, DMSO-d6, 298.2 K), Shift (ppm) = 9.95-9.85 (m, 1H), 9.59-9.36 (m, 1H), 7.85-7.80 (m, 1H), 7.75-7.66 (m, 1H), 7.65-7.59 (m, 1H), 7.05-6.95 (m, 1H), 6.94-6.70 (m, 1H), 6.65-6.55 (m, 2H), 4.85-4.75 (m, 1H), 4.60-4.50 (m, 2H), 4.12-4.01 (m, 1H), 3.38-3.25 (m, 2H), 3.21-3.10 (m, 4H), 2.95-2.90 (m, 1H), 2.88-2.83 (m, 3H), 2.55-2.50 (m, 1H), 2.46-2.35 (m, 4H), 2.27-2.05 (m, 8H), 1.75-1.70 (m, 1H), 1.58-1.50 (m, 1H), 1.38-1.32 (m, 1H), 1.22-1.18 (m, 3H), 0.95-0.91 (m, 3H), 0.89-0.65 (m, 2H), 0.55-0.42 (m, 3H) |
| 748 (General Procedure B-2 using Amine B62 as the core reagent) | 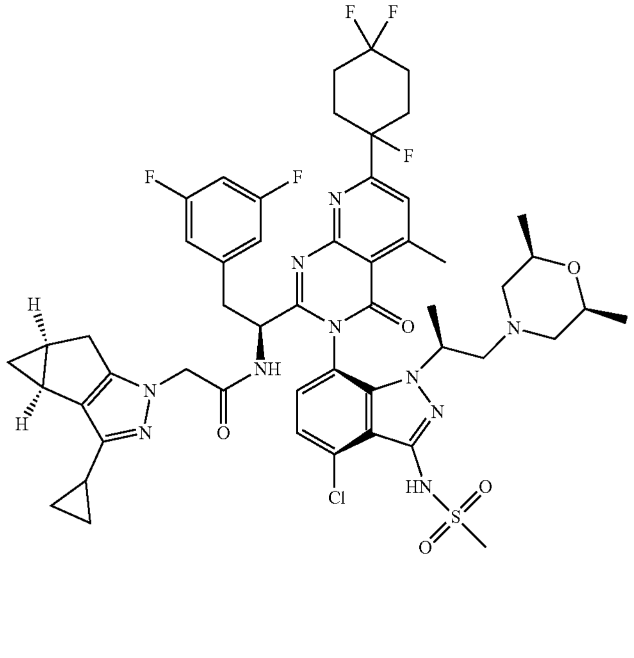 | LCMS method F: retention time = 2.16 min.; observed ion = 1051.42 [M + H]+ 1H NMR (400 MHz, DMSO-d6, 298.1 K), Shift (ppm) = 9.95-9.85 (m, 1H), 9.10-9.00 (m, 1H), 7.83-7.77 (m, 1H), 7.75-7.71 (m, 1H), 7.55-7.48 (m, 1H), 7.07-7.02 (m, 1H), 6.58-6.49 (m, 2H), 4.60-4.51 (m, 1H), 4.43-4.22 (m, 2H), 4.12-4.02 (m, 1H), 3.37-3.25 (m, 2H), 3.24-3.20 (m, 3H), 3.19-3.08 (m, 1H), 2.95-2.90 (m, 1H), 2.85-2.80 (m, 3H), 2.56-2.51 (m, 2H), 2.45-2.38 (m, 3H), 2.34-2.05 (m, 8H), 1.87-1.76 (m, 3H), 1.73-1.64 (m, 1H), 1.55-1.49 (m, 1H), 1.26-1.19 (m, 3H), 0.92 (m, 5H), 0.77-0.71 (m, 2H), 0.66-0.60 (m, 2H), 0.59-0.55 (m, 3H), 0.00--0.05 (m, 1H) |

TABLE A-continued

| Example No. (preparation of the Example) | Structure and IUPAC name | Characterising data (LCMS and/or NMR) |
|---|---|---|
| | N-[(1S)-1-[(3P)-3-{4-chloro-1-[(2S)-1-[(2R,6S)-2,6-dimethylmorpholin-4-yl]propan-2-yl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide | |
| 749 (General Procedure B using Amine B63 as the core reagent, where the general procedure was modified as follows: HATU and DIPEA were used as alternate coupling reagents) | 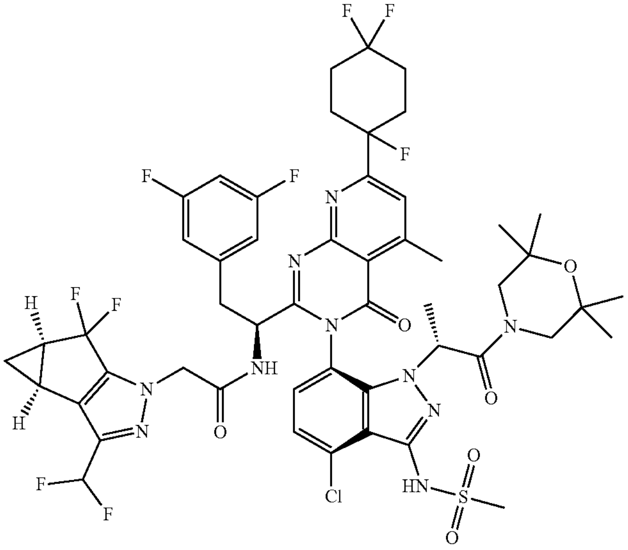 N-[(1S)-1-[(3P)-3-{4-chloro-3-methanesulfonamido-1-[(2R)-1-oxo-1-(2,2,6,6-tetramethylmorpholin-4-yl)propan-2-yl]-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide. | LCMS method F: retention time = 2.49 min.; observed ion = 1139.34 [M + H]+ 1H NMR (400 MHz, DMSO-d6, 298.2 K), Shift (ppm) = 10.06-9.92 (m, 1H), 8.84-8.52 (m, 1H), 7.88-7.81 (m, 1H), 7.76-7.68 (m, 1H), 7.60-7.46 (m, 1H), 7.03-6.70 (m, 2H), 6.65-6.54 (m, 2H), 5.18-4.90 (m, 1H), 4.71-4.58 (m, 1H), 4.53-4.44 (m, 1H), 4.42-4.34 (m, 1H), 3.85-3.67 (m, 1H), 3.29-3.21 (m, 4H), 3.09-3.01 (m, 1H), 2.96-2.91 (m, 3H), 2.83-2.72 (m, 1H), 2.44-2.33 (m, 4H), 2.31-2.08 (m, 8H), 1.69-1.56 (m, 3H), 1.37-1.31 (m, 1H), 1.27-1.18 (m, 1H), 1.05-0.96 (m, 9H), 0.77-0.61 (m, 3H) |
| 750 (General Procedure B using Amine B63 as the core reagent, where the general procedure was modified as follows: HATU and DIPEA were used as alternate coupling reagents) | 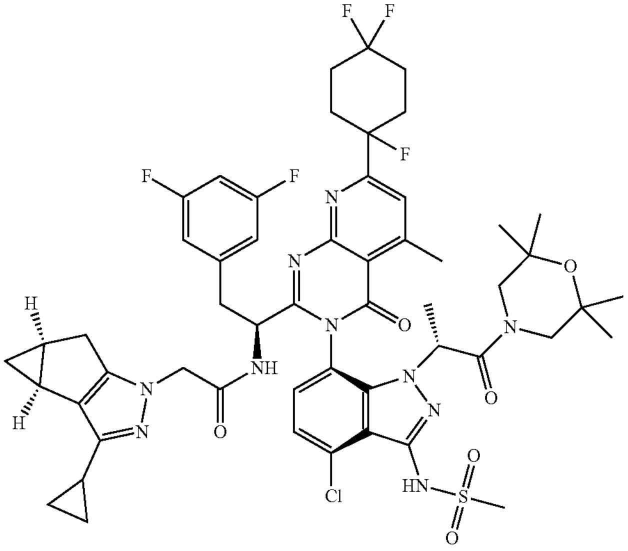 | LCMS method F: retention time = 2.57 min.; observed ion = 1093.41 [M + H]+ 1H NMR (400 MHz, DMSO-d6, 298.1 K), Shift (ppm) = 10.06-9.95 (m, 1H), 8.38-8.19 (m, 1H), 7.85-7.78 (m, 1H), 7.76-7.68 (m, 1H), 7.58-7.47 (m, 1H), 7.13-6.97 (m, 1H), 6.75-6.59 (m, 2H), 5.17-4.97 (m, 1H), 4.57-4.41 (m, 1H), 4.22-4.01 (m, 2H), 3.84-3.71 (m, 1H), 3.30-3.22 (m, 4H), 3.10-3.02 (m, 1H), 2.96-2.88 (m, 3H), 2.83-2.74 (m, 1H), 2.48-2.42 (m, 3H), 2.32-2.13 (m, 10H), 1.86-1.62 (m, 6H), 1.20-1.12 (m, 1H), 1.06-0.96 (m, 9H), 0.92-0.87 (m, 1H), 0.81-0.75 (m, 2H), 0.71-0.60 (m, 4H), −0.01-−0.03 (m, 1H) |

TABLE A-continued

| Example No. (preparation of the Example) | Structure and IUPAC name | Characterising data (LCMS and/or NMR) |
|---|---|---|
| | N-[(1S)-1-[(3P)-3-{4-chloro-3-methanesulfonamido-1-[(2R)-1-oxo-1-(2,2,6,6-tetramethylmorpholin-4-yl)propan-2-yl]-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide | |
| 753 (General Procedure B using Amine B64 as the core reagent) | 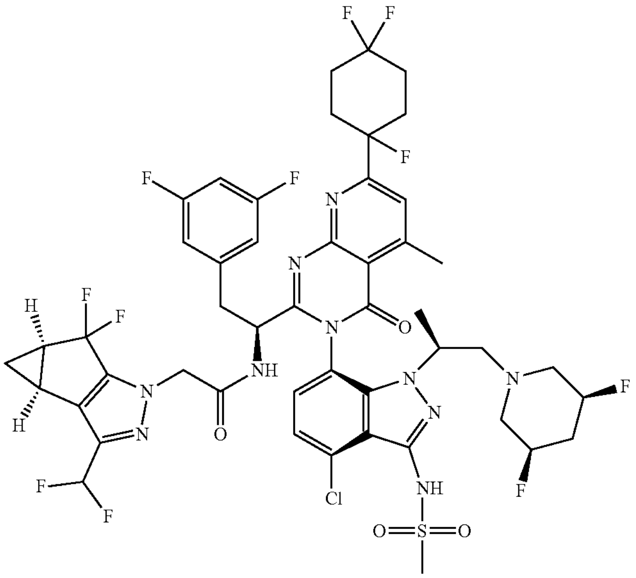 N-[(1S)-1-[(3P)-3-{4-chloro-1-[(2S)-1-[(3R,5S)-3,5-difluoropiperidin-1-yl]propan-2-yl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS method F: retention time = 2.78 min.; observed ion = 1103.22 [M + H]+ 1H NMR (400 MHz, DMSO-d6, 298.0 K), Shift (ppm) = 10.06-9.83 (m, 1H), 9.34-9.32 (m, 1H), 7.94-7.78 (m, 1H), 7.75-7.66 (m, 1H), 7.62-7.47 (m, 1H), 7.12-6.66 (m, 2H), 6.61-6.53 (m, 2H), 4.80-4.72 (m, 1H), 4.65-4.49 (m, 2H), 4.40-4.16 (m, 2H), 4.02-3.90 (m, 1H), 3.39-3.34 (m, 1H), 3.25-3.12 (m, 3H), 2.94-2.81 (m, 4H), 2.71-2.61 (m, 1H), 2.47-2.31 (m, 5H), 2.28-1.99 (m, 9H), 1.97-1.83 (m, 2H), 1.62-1.46 (m, 1H), 1.39-1.27 (m, 1H), 1.16-1.05 (m, 3H), 0.88-0.78 (m, 1H) |

TABLE A-continued

| Example No. (preparation of the Example) | Structure and IUPAC name | Characterising data (LCMS and/or NMR) |
|---|---|---|
| 754 (General Procedure B using Amine B64 as the core reagent) | 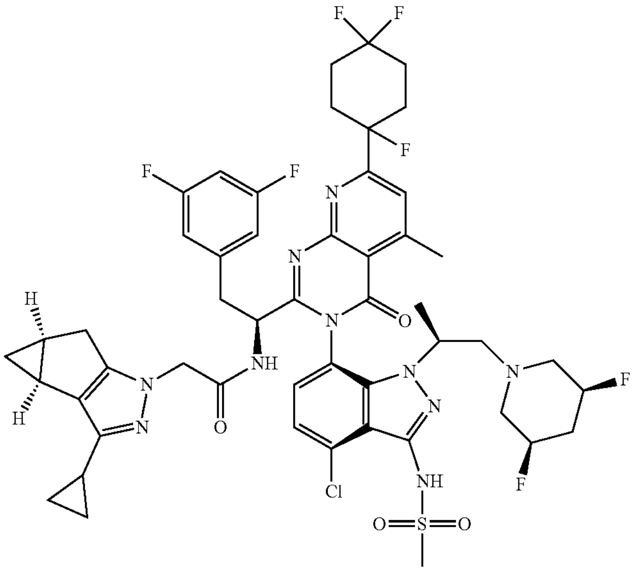 N-[(1S)-1-[(3P)-3-{4-chloro-1-[(2S)-1-[(3R,5S)-3,5-difluoropiperidin-1-yl]propan-2-yl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.0$^{2,4}$]nona-1(6),8-dien-7-yl]acetamide | LCMS method F: retention time = 2.46 min.; observed ion = 1057.57 [M + H]+ 1H NMR (400 MHz, DMSO-d6, 298.1 K), Shift (ppm) = 10.12-9.59 (m, 1 H), 9.09-8.71 (m, 1 H), 8.01-7.12 (m, 3 H), 7.09-6.95 (m, 1 H), 6.57-6.44 (m, 2 H), 4.76-4.59 (m, 1 H), 4.48-4.18 (m, 4 H), 3.95-3.73 (m, 1 H), 3.44-3.34 (m, 1 H), 3.20-2.83 (m, 7 H), 2.68-2.59 (m, 2 H), 2.46-2.41 (m, 2 H), 2.39-2.32 (m, 2 H), 2.28-2.10 (m, 9 H), 2.01-1.88 (m, 2 H), 1.83-1.74 (m, 2 H), 1.72-1.62 (m, 1 H), 1.56-1.44 (m, 1 H), 1.28-1.19 (m, 1 H), 1.17-1.07 (m, 3 H), 0.90-0.82 (m, 1 H), 0.77-0.71 (m, 2 H), 0.64-0.55 (m, 2 H), 0.04-0.10 (m, 1 H) |
| 755 (General Procedure B using Amine B65 as the core reagent, where the general procedure was modified as follows: HATU and DIPEA were used as alternate coupling reagents) | 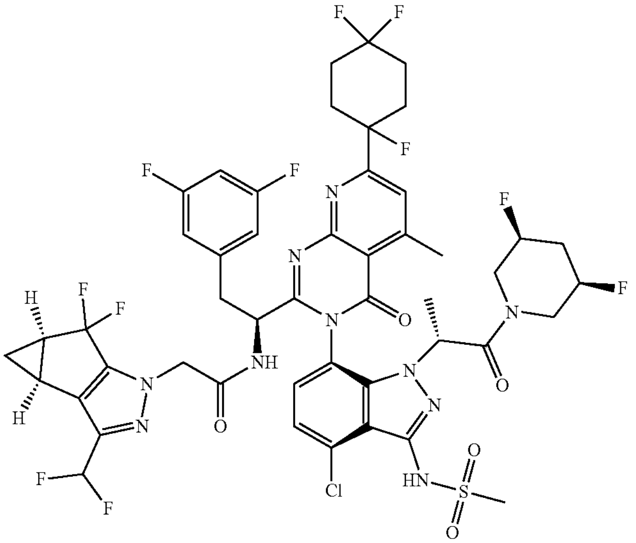 N-[(1S)-1-[(3P)-3-{4-chloro-1-[(2R)-1-[(3R,5S)-3,5-difluoropiperidin-1-yl]-1-oxopropan-2-yl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | LCMS method F: retention time = 2.34 min.; observed ion = 1115.34 [M − H]+ 1H NMR (400 MHz, DMSO-d6, 299.3 K), Shift (ppm) = 10.06-9.94 (m, 1H), 8.81-8.65 (m, 1H), 7.87-7.86 (m, 1H), 7.75-7.72 (m, 1H), 7.63-7.52 (m, 1H), 7.07-6.85 (m, 2H), 6.67-6.63 (m, 2H), 5.07-5.00 (m, 1H), 4.82-4.28 (m, 6H), 3.55-3.44 (m, 1H), 3.41-3.36 (m, 1H), 3.20-3.16 (m, 3H), 2.95-2.86 (m, 3H), 2.86-2.78 (m, 1H), 2.46-2.36 (m, 4H), 2.24-2.05 (m, 8H), 2.03-1.57 (m, 2H), 1.54-1.45 (m, 3H), 1.35-1.33 (m, 1H), 0.90-0.80 (m, 1H) |

TABLE A-continued

| Example No. (preparation of the Example) | Structure and IUPAC name | Characterising data (LCMS and/or NMR) |
| --- | --- | --- |
| 756 (General Procedure B using Amine B65 as the core reagent, where the general procedure was modified as follows: HATU and DIPEA were used as alternate coupling reagents) | 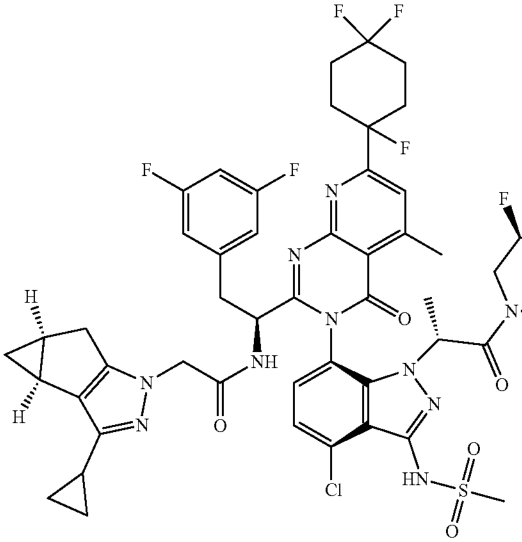<br>N-[(1S)-1-[(3P)-3-{4-chloro-1-[(2R)-1-[(3R,5S)-3,5-difluoropiperidin-1-yl]-1-oxopropan-2-yl]-3-methanesulfonamido-1H-indazol-7-yl}-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2R*,4R*)-9-cyclopropyl-7,8-diazatricyclo[4.3.0.$0^{2,4}$]nona-1(6),8-dien-7-yl]acetamide | LCMS Method: Column = Xbridge C18 (4.6 x 75 mm, 3.5 µm); Solvent A = 10 mM ammonium bicarbonate in water; Solvent B = ACN; Flow Rate = 1.3 mL/min; Gradient Method (min.)/% B: 0/5, 0.5/5, 1.0/15, 4.0/98, 7.0/98; Wavelength = 210 nm to 400 nm.: retention time = 4.66 min.; observed ion = 1071.37 [M + H]+ 1H NMR (400 MHz, DMSO-d6, 298.2 K), Shift (ppm) = 10.10-9.91 (m, 1H), 8.63-8.42 (m, 1H), 7.87-7.85 (m, 1H), 7.70-7.65 (m, 1H), 7.59-7.57 (m, 1H), 7.06-7.01 (m, 1H), 6.88-6.66 (m, 2H), 5.04-5.02 (m, 1H), 4.80-4.68 (m, 1H), 4.54-4.38 (m, 3H), 4.29-4.15 (m, 2H), 3.48-3.38 (m, 2H), 3.31-3.26 (m, 3H), 2.89-2.86 (m, 4H), 2.40-2.35 (m, 2H), 2.22-2.05 (m, 10H), 1.95-1.60 (m, 5H), 1.55-1.42 (m, 3H), 0.93-0.89 (m, 1H), 0.80-0.74 (m, 2H), 0.68-0.58 (m, 2H), −0.01-−0.10 (m, 1H) |

Crystalline Form Examples

Unless otherwise stated, the DSC method used herein is as follows: Instrument=TA Instruments DSC25; Pan=Tzero Pan; Lid=Tzero Hermetic Lid; Ramp=10° C./min; Maximum temperature=350° C.

Unless otherwise stated, the TGA method used herein is as follows: TGA Instrument=TA Instruments TGA55; Pan=Aluminum Cup; Ramp=10° C./min; Maximum temperature=350° C.

Unless otherwise stated, the XRPD analytical method used herein is as follows: Instrument=Rigaku MiniFlex 600; Tube anode=Cu (40 kV/15 mA); Detector=D/teX Ultra2; Scan range=3.0 to 40.0°2θ; Scan step size=0.01°2θ; Scan speed step=50°/min. During acquisition of an XRPD data, a K-Beta (Kβ) filter was absent.

Example 5A: First Seed Preparation of Crystalline Example 5

To a vial equipped with a stir bar and charged with N-[(1S)-1-[(3P)-3-(4-chloro-1-{2-[(3R,5S)-3,5-difluoropiperidin-1-yl]ethyl}-3-methanesulfonamido-1H-indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.$0^{2,4}$]nona-1(6),8-dien-7-yl]acetamide (Example 5, 25 mg, 23 µmol) was added ethanol (0.20 mL). The vial was heated at 70° C. with stirring until all solids dissolved. The stir bar was removed and the vial was then allowed to slowly cool to room temperature during which time a precipitate began to slowly form. The vial was allowed to stand at room temperature for 1 day. The precipitate was collected by filtration and the resulting solids were dried in a vacuum oven heated at 50° C. for 18 h. This material is referred to as Compound A (Form 1) or as Example 5A (Form 1) to distinguish between other crystalline polymorphs of the crystalline parent form of Example 5. The unique and crystalline nature of this material, the crystalline parent form of Example 5A (Form 1) ("Compound A (Form 1)"), was confirmed by X-ray powder diffraction ("XRPD") as shown in FIG. 1 and differential scanning calorimetry ("DSC") as shown in FIG. 2.

Figure 3:
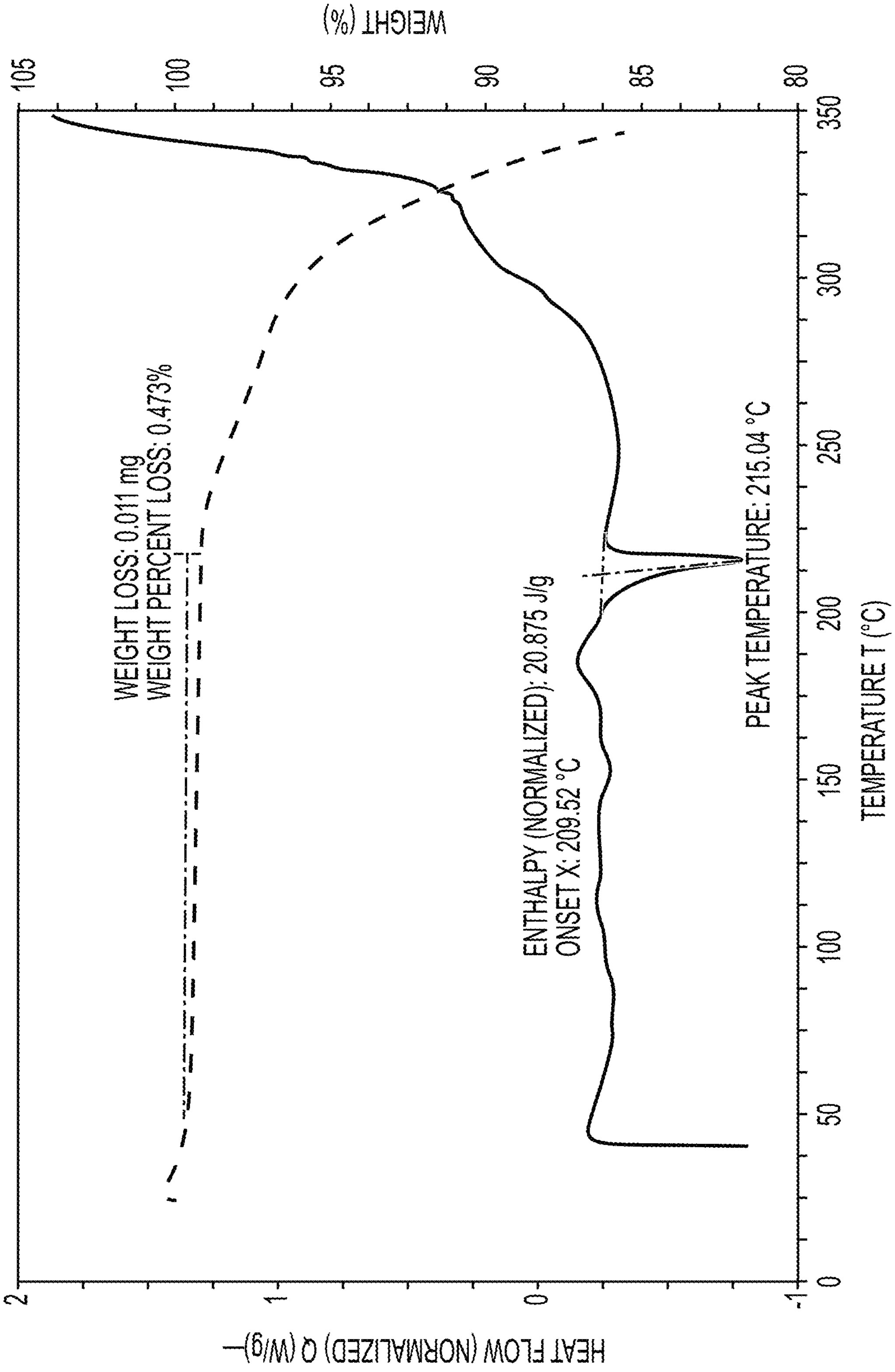
FIG. 3 depicts an overlay of DSC and Thermogravimetric analysis (TGA) thermograms of a crystalline form of the compound of Example 5A (Form 1) (Compound A (Form 1)) exhibiting a melting onset of about 209° C. and a weight loss of about 0.47 wt %.

DSC and TGA results: In FIG. 3 the overlay of DSC and TGA thermograms of Compound A (Form 1) exhibits a melting onset of about 209° C. and a weight loss of about 0.47 wt %.

XRPD result: See FIG. 1 for the XRPD pattern of Compound A (Form 1) and see Table 1 for a corresponding list of 2-theta peaks. This crystalline parent form of Compound A (Form 1) ( Example 5A (Form 1)) can be Used as Seed Crystals in Future Preparations of this Crystalline Form

TABLE 1

XRPD Peak List of Compound A (Form 1) (Example 5A (Form 1))

| Pos. [°2θ] | Rel. Int. [%] |
|---|---|
| 5.1 | 37.1 |
| 6.2 | 34.5 |
| 7.5 | 100.0 |
| 7.9 | 57.1 |
| 9.5 | 31.1 |
| 10.4 | 35.8 |
| 11.5 | 30.1 |
| 13.0 | 31.4 |
| 14.7 | 61.9 |
| 15.1 | 62.4 |
| 15.9 | 66.4 |
| 16.1 | 55.4 |
| 16.7 | 61.2 |
| 17.0 | 57.6 |
| 17.6 | 54.9 |
| 18.7 | 55.8 |
| 19.8 | 58.5 |
| 20.2 | 56.6 |
| 20.7 | 63.6 |
| 21.8 | 52.7 |
| 24.5 | 43.7 |
| 25.4 | 44.9 |
| 34.5 | 22.4 |

Example 11A: First Seed Preparation of Crystalline Example 11

To a vial charged with N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[$4.3.0.0^{2,4}$]nona-1(6),8-dien-7-yl]acetamide (Example 11, 25 mg) was added ethanol (0.4 mL). The mixture was vortexed, sonicated, and then briefly heated at 70° C. but the solids did not fully dissolve. Polarized Light Microscopy (PLM) of the solids indicated birefringence. The mixture was allowed to stand for 3 days at room temperature. The solids were collected by filtration and then washed with ethanol to afford 20 mg of a solid which was placed in a vacuum oven heated to 45-50° C. for approximately 18 h. The resulting material is referred to as Compound B (Form 1) or as Example 11A (Form 1) to distinguish between other crystalline polymorphs of the crystalline parent form of Example 11. The unique and crystalline nature of this material, the crystalline parent form of Example 11A (Form 1) ("Compound B (Form 1)"), was confirmed by XRPD as shown in FIG. 4 and DSC as shown in FIG. 5.

The procedure was repeated with slight modifications: To a vial equipped with a stir bar and charged with N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[$4.3.0.0^{2,4}$]nona-1(6),8-dien-7-yl]acetamide (58 mg) was added ethanol (5 mL). The vial was heated at 70° C. until all solids dissolved. The vial was then allowed to slowly cool to room temperature with stirring upon which a white precipitate formed. The mixture was stirred at room temperature for 3 days. The solids were collected by filtration and then analyzed by XRPD which confirmed that the material was Example 11A (Form 1) ("Compound B (Form 1)").

Figure 6:
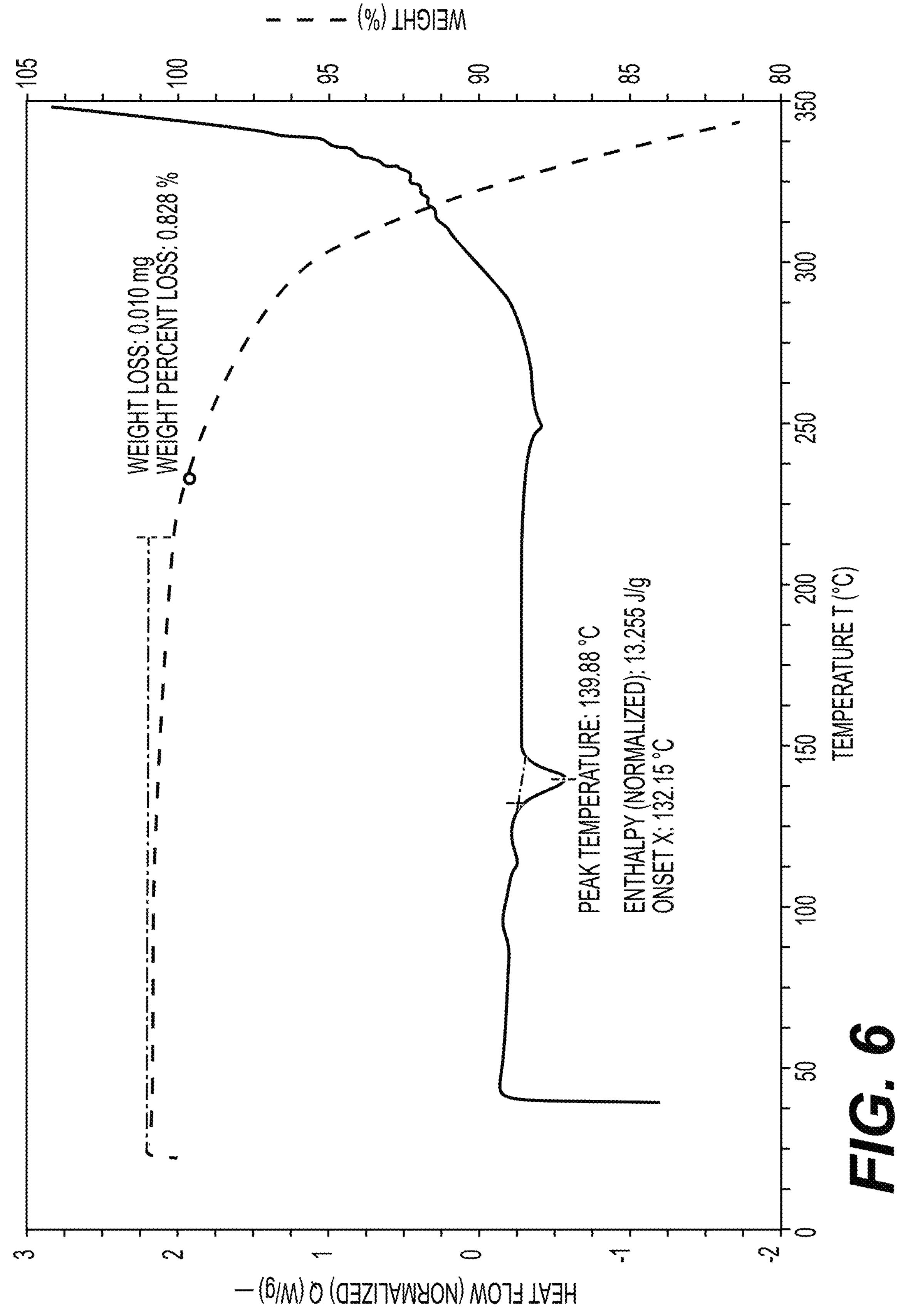
FIG. 6 depicts an overlay of DSC and TGA thermograms of a crystalline form of the compound of Example 11A (Form 1) (Compound B (Form 1)) exhibiting a melting onset of about 132° C. and a weight loss of about 0.83 wt %.

DSC and TGA results: In FIG. 6 the overlay of DSC and TGA thermograms of Compound B (Form 1)exhibits a melting onset of about 132° C. and a weight loss of about 0.83 wt %.

XRPD result: See FIG. 4 for the XRPD pattern of Compound B (Form 1) and see Table 2 for a corresponding list of 2-theta peaks. This crystalline parent form of Compound B (Form 1) can be used as seed crystals in future preparations of this crystalline form.

TABLE 2

XRPD Peak List of Compound B (Form 1) (Example 11A (Form 1))

| Pos. [°2θ] | Rel. Int. [%] |
|---|---|
| 4.0 | 24.0 |
| 6.3 | 17.7 |
| 7.9 | 100.0 |
| 9.3 | 17.1 |
| 9.7 | 17.8 |
| 10.5 | 12.0 |
| 12.6 | 13.0 |
| 12.9 | 12.9 |
| 13.9 | 13.4 |
| 14.5 | 14.3 |
| 15.2 | 44.8 |
| 15.9 | 67.5 |
| 16.7 | 42.4 |
| 18.7 | 33.2 |
| 19.0 | 32.7 |
| 20.0 | 57.0 |
| 20.9 | 22.6 |
| 21.2 | 19.0 |
| 21.8 | 14.5 |
| 22.3 | 11.6 |
| 22.9 | 14.5 |
| 24.6 | 14.5 |
| 25.0 | 17.3 |
| 25.6 | 23.1 |
| 26.0 | 24.2 |
| 27.0 | 11.1 |
| 28.4 | 13.0 |
| 29.2 | 11.1 |
| 30.8 | 11.2 |
| 31.6 | 9.8 |
| 32.1 | 13.0 |
| 32.8 | 8.6 |
| 33.7 | 9.2 |
| 34.7 | 7.6 |
| 35.1 | 7.3 |
| 35.7 | 7.8 |
| 37.0 | 6.8 |
| 37.7 | 7.5 |
| 38.6 | 7.6 |

Example 12A: First Seed Preparation of Crystalline Example 12

To a vial charged with N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8- diazatricyclo[4.3.0.0$^{2,4}$]nona-1(6),8-dien-7-yl]acetamide (Example 12, 25 mg) was added ethanol (0.1 mL). The mixture was briefly heated to 70° C. upon which the solids dissolved. The solution was allowed to slowly cool to room temperature and then was allowed to stand at room temperature for app. 18 h. The resulting solids were collected by filtration and then placed in a vacuum oven at 50° C. for 5 h to afford a material referred to as Compound C (Form 1) or as Example 12A (Form 1) to distinguish between other crystalline polymorphs of the crystalline parent form of Example 12. The unique and crystalline nature of this material, the crystalline parent form of Example 12A (Form 1) ("Compound C (Form 1)"), was confirmed by XRPD as shown in FIG. 7 and DSC as shown in FIG. 8.

The procedure was repeated with slight modifications: To a vial charged with N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide (100 mg) was added ethanol (5.0 mL). The mixture was heated at 70° C. until all solids dissolved. The solution was allowed to cool to room temperature upon which a precipitate was observed. The mixture was stirred at room temperature for 3 days. The solids were collected by filtration and then analyzed by XRPD which confirmed that the material was Example 12A (Form 1) ("Compound C (Form 1)").

DSC and TGA results: In FIG. 8 the overlay of DSC and TGA thermograms of Compound C (Form 1) exhibits a melting onset of about 123° C. and a weight loss of about 0.75 wt %.

XRPD result: See FIG. 7 for the XRPD pattern of Compound C (Form 1) and see Table 3 for a corresponding list of 2-theta peaks. This crystalline parent form of Compound C (Form 1) can be used as seed crystals in future preparations of this crystalline form.

TABLE 3

XRPD Peak List of Compound C (Form 1) (Example 12A (Form 1))

| Pos. [°2θ] | Rel. Int. [%] |
|---|---|
| 5.9 | 100.0 |
| 6.5 | 25.2 |
| 7.8 | 8.7 |
| 9.2 | 8.1 |
| 9.8 | 7.8 |
| 10.3 | 8.6 |
| 10.5 | 8.6 |
| 10.9 | 13.1 |
| 11.2 | 12.4 |
| 12.1 | 28.2 |
| 12.8 | 12.9 |
| 13.9 | 29.8 |
| 15.6 | 9.3 |
| 16.3 | 10.0 |
| 16.7 | 15.6 |
| 17.2 | 15.4 |
| 18.1 | 23.2 |
| 19.1 | 11.6 |
| 19.5 | 18.5 |
| 20.0 | 18.1 |
| 20.9 | 18.6 |
| 21.2 | 14.4 |
| 21.9 | 11.6 |
| 22.2 | 13.5 |
| 22.7 | 10.6 |
| 23.1 | 10.1 |

TABLE 3-continued

XRPD Peak List of Compound C (Form 1) (Example 12A (Form 1))

| Pos. [°2θ] | Rel. Int. [%] |
|---|---|
| 23.7 | 12.0 |
| 24.4 | 9.8 |
| 25.6 | 12.6 |
| 26.3 | 9.2 |
| 27.0 | 7.9 |
| 27.7 | 8.6 |
| 28.4 | 10.0 |
| 30.0 | 6.2 |
| 31.3 | 6.6 |
| 31.9 | 6.1 |
| 32.6 | 6.6 |
| 33.6 | 5.3 |
| 34.4 | 5.2 |
| 38.7 | 4.1 |

Example 13A: First Seed Preparation of Crystalline Example 13

To a vial equipped with a stir bar and charged with N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide (Example 13, 100 mg) was added 2-propanol (3.0 mL). The vial was placed on an 80° C. hot plate with stirring until all solids were dissolved. The vial was removed from the hot plate and the stir bar was removed from the vial, then the solution was allowed to cool to room temperature upon which a precipitate slowly formed. The solution was allowed to stand at room temperature for 2 days. The solids were collected by filtration and then were dried in a 50° C. vacuum oven for 18 hours to afford a material referred to as Compound D (Form 1) or as Example 13A (Form 1) to distinguish between other crystalline polymorphs of the crystalline parent form of Example 13. The unique and crystalline nature of this material, the crystalline parent form of Example 13A (Form 1) ("Compound D (Form 1)"), was confirmed by XRPD as shown in FIG. 9 and DSC as shown in FIG. 10.

DSC and TGA result: In FIG. 10 the overlay of DSC and TGA thermograms of Compound D (Form 1) exhibits a melting onset of about 216° C. and a weight loss of about 1.4 wt %.

XRPD result: See FIG. 9 for the XRPD pattern of Compound D (Form 1) and see Table 4 for a corresponding list of 2-theta peaks. This crystalline parent form of Compound D (Form 1) can be used as seed crystals in future preparations of this crystalline form.

TABLE 4

XRPD Peak List of Compound D (Form 1) (Example 13A (Form 1))

| Pos. [°2θ] | Rel. Int. [%] |
|---|---|
| 5.1 | 44.9 |
| 5.6 | 91.0 |
| 6.9 | 33.9 |
| 7.6 | 64.0 |
| 8.2 | 38.6 |
| 8.7 | 63.4 |
| 9.1 | 79.6 |

TABLE 4-continued

| XRPD Peak List of Compound D (Form 1) (Example 13A (Form 1)) | |
|---|---|
| Pos. [°2θ] | Rel. Int. [%] |
| 9.8 | 27.0 |
| 11.1 | 27.6 |
| 11.3 | 26.8 |
| 11.9 | 32.6 |
| 13.2 | 33.4 |
| 13.9 | 34.6 |
| 14.4 | 32.2 |
| 14.7 | 74.7 |
| 15.2 | 38.7 |
| 15.4 | 75.6 |
| 16.0 | 41.5 |
| 16.6 | 46.5 |
| 16.8 | 75.4 |
| 17.2 | 100.0 |
| 17.5 | 56.4 |
| 18.4 | 69.1 |
| 18.7 | 63.8 |
| 19.1 | 60.3 |
| 19.4 | 45.3 |
| 19.9 | 52.5 |
| 20.3 | 57.7 |
| 20.5 | 60.9 |
| 21.0 | 41.6 |
| 21.4 | 65.4 |
| 22.0 | 56.0 |
| 22.6 | 53.1 |
| 23.8 | 38.8 |
| 24.0 | 39.8 |
| 24.4 | 31.0 |
| 24.7 | 42.1 |
| 25.1 | 34.1 |
| 25.8 | 28.2 |
| 26.2 | 26.4 |
| 26.8 | 28.5 |
| 27.0 | 44.8 |
| 27.6 | 36.4 |
| 27.9 | 33.8 |
| 28.5 | 21.0 |
| 28.8 | 24.5 |
| 29.2 | 25.2 |
| 29.8 | 22.0 |
| 30.1 | 29.1 |
| 31.1 | 22.2 |
| 31.3 | 20.2 |
| 31.9 | 17.5 |
| 32.5 | 19.9 |
| 32.7 | 18.0 |
| 33.2 | 18.7 |
| 34.1 | 16.2 |
| 34.8 | 18.0 |
| 35.4 | 17.7 |
| 36.1 | 18.3 |
| 37.7 | 14.8 |
| 38.7 | 17.9 |
| 39.0 | 15.2 |
| 39.5 | 15.6 |
| 39.7 | 16.8 |

Example 135A: First Seed Preparation of Crystalline Example 135

To a vial equipped with a stir bar and charged with N-[(1S)-1-[(3P)-3-[4-chloro-3-methanesulfonamido-1-(3-methoxypropyl)-1H-indazol-7-yl]-7-(4,4-difluorocyclohexyl)-5-[(2-methoxyethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide (Example 135, 25 mg) was added ethanol (0.50 mL). The vial was placed on an 80° C. hot plate with stirring until all solids were dissolved. The vial was removed from the hot plate and the stir bar was removed from the vial, then the solution was allowed to cool to room temperature upon which a precipitate formed. The mixture was allowed to stand at room temperature for 1 day. The solids were collected by filtration and then were dried in a 50° C. vacuum oven for 18 h to afford a material referred to as Compound E (Form 1) or as Example 135A (Form 1) to distinguish between other crystalline polymorphs of the crystalline parent form of Example 135. The unique and crystalline nature of this material, the crystalline parent form of Example 135A (Form 1) ("Compound E (Form 1)"), was confirmed by XRPD as shown in FIG. 11 and DSC as shown in FIG. 12.

Figure 13:
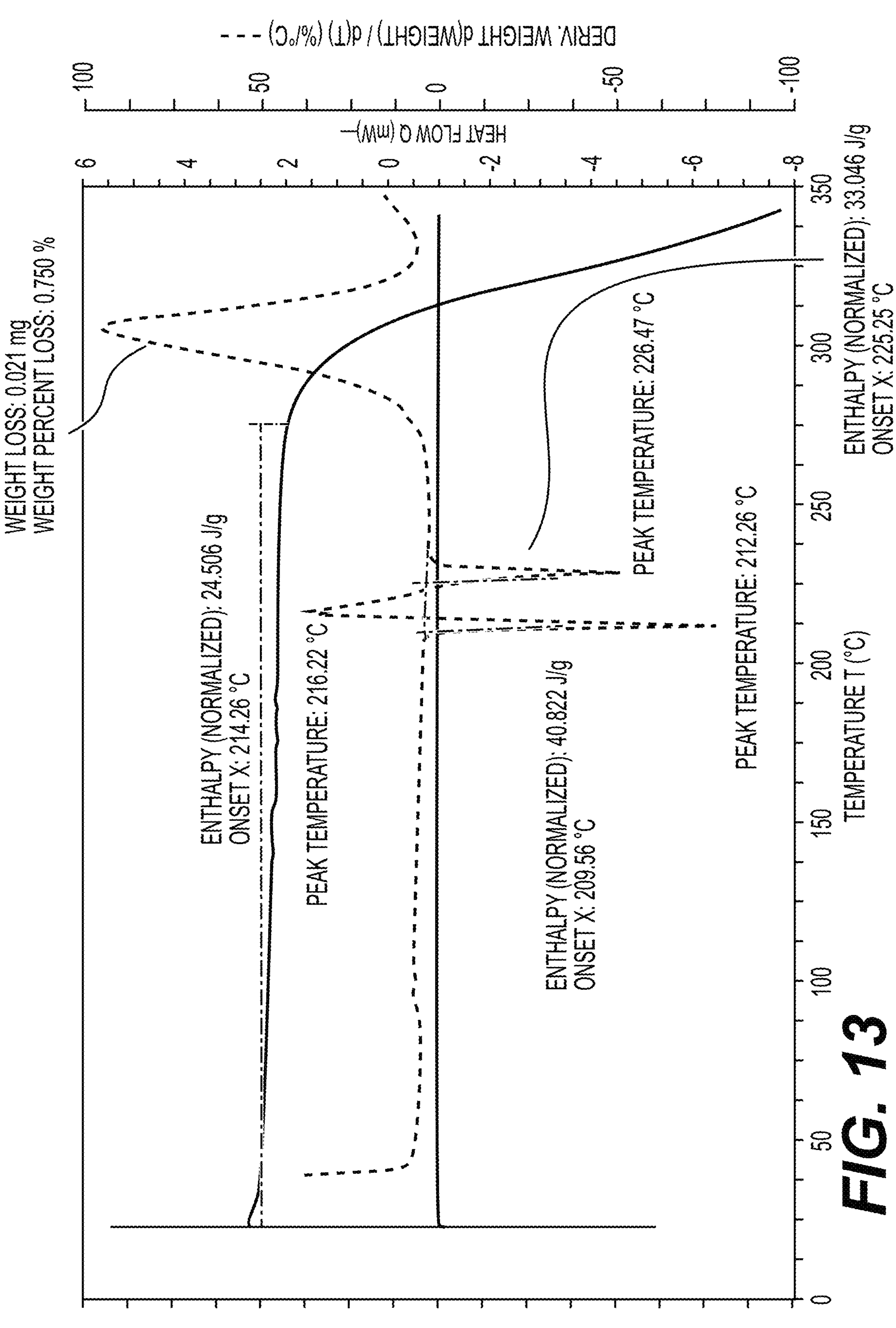
FIG. 13 depicts an overlay of DSC and TGA thermograms of a crystalline form of the compound of Example 135A (Form 1) (Compound E (Form 1)) exhibiting a melting onset of about 210° C., a second melting onset of about 225° C., and a weight loss of about 0.75 wt %.

DSC and TGA result: In FIG. 13 the overlay of DSC and TGA thermograms of Compound E (Form 1) exhibits a melting onset of about 210° C., a second melting onset of about 225° C., and a weight loss of about 0.75 wt %.

XRPD result: See FIG. 11 for the XRPD pattern of Compound E (Form 1) and see Table 5 for a corresponding list of 2-theta peaks. This crystalline parent form of Compound E (Form 1) can be used as seed crystals in future preparations of this crystalline form.

TABLE 5

| XRPD Peak List of Compound E (Form 1) (Example 135A (Form 1)) | | | | | |
|---|---|---|---|---|---|
| Pos. [°2θ] | Rel. Int. [%] | Pos. [°2θ] | Rel. Int. [%] | Pos. [°2θ] | Rel. Int. [%] |
| 6.5 | 29.4 | 17.5 | 22.4 | 26.9 | 21.8 |
| 7.4 | 58.5 | 18.3 | 20.0 | 27.2 | 19.3 |
| 8.1 | 100.0 | 18.6 | 20.0 | 27.6 | 14.5 |
| 9.0 | 25.1 | 19.3 | 85.1 | 28.3 | 30.6 |
| 9.6 | 61.4 | 20.0 | 23.4 | 28.7 | 25.3 |
| 10.2 | 17.7 | 20.4 | 55.7 | 29.4 | 27.4 |
| 11.5 | 43.4 | 21.2 | 38.0 | 30.1 | 22.4 |
| 12.7 | 33.5 | 21.5 | 21.4 | 30.8 | 14.7 |
| 13.1 | 39.9 | 22.1 | 95.4 | 31.4 | 11.2 |
| 13.5 | 19.2 | 17.5 | 22.4 | 31.6 | 15.3 |
| 13.7 | 25.1 | 22.6 | 20.3 | 32.1 | 17.3 |
| 14.1 | 30.4 | 23.1 | 41.7 | 33.2 | 16.4 |
| 14.6 | 25.6 | 23.5 | 25.3 | 34.3 | 10.7 |
| 14.7 | 25.7 | 25.0 | 27.4 | 34.5 | 8.9 |
| 15.0 | 27.5 | 25.3 | 69.9 | 36.0 | 9.6 |
| 15.9 | 62.0 | 25.5 | 71.9 | 36.5 | 10.8 |
| 16.4 | 36.4 | 25.9 | 26.1 | 37.3 | 10.7 |
| 16.8 | 19.5 | 26.1 | 38.9 | 38.5 | 9.7 |
| 17.2 | 51.2 | 26.6 | 27.1 | 39.1 | 10.1 |

Example 427A: First Seed Preparation of Crystalline Example 427

To a vial equipped with a stir bar and charged with N-[(1S)-1-[(3P)-3-[4-chloro-3-methanesulfonamido-1-(3-methoxypropyl)-1H-indazol-7-yl]-7-(4,4-difluorocyclohexyl)-5-(ethylamino)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide (Example 427, 25 mg) was added ethanol (0.50 mL). The vial was placed on an 80° C. hot plate with stirring until all solids dissolved. The vial was removed from the hot plate and the stir bar was removed from the vial. The solution was allowed to cool to room temperature upon which a precipitate was observed. The mixture was allowed to stand at room temperature for 1 day. The solids were collected by filtration and then dried in a 50° C. vacuum oven for 18 h to afford a material referred to as Compound F (Form 1) or as Example 427A (Form 1) to distinguish between other crystalline polymorphs of the crystalline parent form of Example 427. The unique and crystalline nature of this material, the crystalline parent form of Example 427A (Form 1) ("Compound F (Form 1)"), was confirmed by XRPD as shown in FIG. 14 and DSC as shown in FIG. 15.

DSC and TGA result: In FIG. 15 the overlay of DSC and TGA thermograms of Compound F (Form 1) exhibits a melting onset of about 227° C. and a weight loss of about 0.21 wt %.

XRPD result: See FIG. 14 for the XRPD pattern of Compound F (Form 1) and see Table 6 for a corresponding list of 2-theta peaks. This crystalline parent form of Compound F (Form 1) can be used as seed crystals in future preparations of this crystalline form.

TABLE 6

XRPD Peak List of Compound F (Form 1) (Example 427A (Form 1))

| Pos. [°2θ] | Rel. Int. [%] |
|---|---|
| 6.5 | 8.5 |
| 7.5 | 24.1 |
| 8.1 | 100.0 |
| 8.4 | 5.9 |
| 9.1 | 11.9 |
| 9.6 | 17.3 |
| 10.2 | 4.8 |
| 10.3 | 6.7 |
| 11.5 | 16.4 |
| 12.8 | 11.3 |
| 13.4 | 12.8 |
| 13.8 | 14.8 |
| 14.4 | 8.6 |
| 14.7 | 9.0 |
| 15.1 | 10.1 |
| 16.0 | 22.4 |
| 16.3 | 24.9 |
| 17.3 | 10.8 |
| 17.7 | 6.6 |
| 18.3 | 6.0 |
| 18.5 | 6.3 |
| 18.7 | 5.8 |
| 19.4 | 9.0 |
| 19.6 | 26.2 |
| 19.9 | 6.2 |
| 20.5 | 13.0 |
| 20.9 | 7.3 |
| 21.1 | 8.1 |
| 21.5 | 8.8 |
| 22.1 | 33.4 |
| 22.7 | 5.2 |
| 23.0 | 7.8 |
| 23.4 | 11.4 |
| 23.6 | 7.8 |
| 24.6 | 10.2 |
| 25.2 | 43.4 |
| 25.5 | 39.0 |
| 26.0 | 17.3 |
| 26.8 | 8.2 |
| 27.0 | 7.8 |
| 27.5 | 7.0 |
| 28.3 | 9.4 |
| 28.7 | 7.0 |
| 29.1 | 6.8 |
| 29.3 | 10.0 |
| 29.6 | 5.6 |
| 30.0 | 7.4 |
| 30.7 | 6.8 |
| 31.4 | 4.2 |
| 31.7 | 4.7 |
| 32.1 | 5.1 |
| 32.5 | 3.8 |
| 33.1 | 7.3 |
| 33.4 | 4.5 |
| 34.2 | 3.3 |
| 34.6 | 3.4 |

TABLE 6-continued

XRPD Peak List of Compound F (Form 1) (Example 427A (Form 1))

| Pos. [°2θ] | Rel. Int. [%] |
|---|---|
| 35.3 | 3.6 |
| 36.0 | 3.7 |
| 36.3 | 3.6 |
| 36.5 | 4.0 |
| 37.5 | 3.4 |
| 38.0 | 3.3 |
| 38.2 | 3.1 |
| 38.6 | 3.0 |
| 38.9 | 3.5 |
| 39.4 | 3.6 |
| 39.6 | 4.1 |

Example 448A: First Seed Preparation of Crystalline Example 448

To a vial equipped with a stir bar and charged with N-[(1S)-1-[(3P)-3-[4-chloro-3-methanesulfonamido-1-(3-methoxypropyl)-1H-indazol-7-yl]-7-(4,4-difluorocyclohexyl)-5-{[(2R,6S)-2,6-dimethylmorpholin-4-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide (Example 448, 50 mg) was added ethanol (1.0 mL). The vial was placed on an 80° C. hot plate with stirring until all the solids were dissolved. The vial was removed from the heat and the stir bar was removed from the vial. The solution was allowed to cool to room temperature upon which a precipitate was observed. The mixture was allowed to stand at room temperature for 1 day. The solids were collected by filtration and then were dried in a 50° C. vacuum oven for 18 h to afford a material referred to as Compound G (Form 1) or as Example 448A (Form 1) to distinguish between other crystalline polymorphs of the crystalline parent form of Example 448. The unique and crystalline nature of this material, the crystalline parent form of Example 448A (Form 1) ("Compound G (Form 1)"), was confirmed by XRPD as shown in FIG. 16 and DSC as shown in FIG. 17.

DSC and TGA result: In FIG. 17 the overlay of DSC and TGA thermograms of Compound G (Form 1) exhibits a melting onset of about 221° C. and a weight loss of about 0.28 wt %.

XRPD result: See FIG. 16 for the XRPD pattern of Compound G (Form 1) and see Table 7 for a corresponding list of 2-theta peaks. This crystalline parent form of Compound G (Form 1) can be used as seed crystals in future preparations of this crystalline form.

TABLE 7

XRPD Peak List of Compound G (Form 1) (Example 448A (Form 1))

| Pos. [°2θ] | Rel. Int. [%] |
|---|---|
| 5.0 | 68.6 |
| 6.8 | 41.3 |
| 8.1 | 38.3 |
| 9.4 | 20.2 |
| 9.7 | 30.1 |
| 10.0 | 100.0 |
| 10.3 | 19.0 |
| 10.9 | 14.9 |
| 11.4 | 17.5 |
| 11.9 | 42.6 |

TABLE 7-continued

| XRPD Peak List of Compound G (Form 1) (Example 448A (Form 1)) | |
|---|---|
| Pos. [°2θ] | Rel. Int. [%] |
| 12.6 | 15.1 |
| 13.7 | 32.9 |
| 14.1 | 47.2 |
| 14.4 | 15.2 |
| 14.9 | 33.1 |
| 16.0 | 22.0 |
| 16.3 | 47.1 |
| 16.9 | 25.8 |
| 17.2 | 28.9 |
| 18.0 | 46.1 |
| 18.2 | 49.9 |
| 19.6 | 48.6 |
| 19.9 | 41.4 |
| 20.1 | 33.4 |
| 20.4 | 30.2 |
| 20.7 | 38.6 |
| 21.0 | 34.2 |
| 21.4 | 81.5 |
| 21.8 | 37.7 |
| 22.7 | 40.6 |
| 23.1 | 37.5 |
| 23.4 | 32.3 |
| 23.6 | 23.4 |
| 24.9 | 30.8 |
| 25.3 | 26.1 |
| 25.8 | 19.3 |
| 26.2 | 33.3 |
| 27.4 | 28.1 |
| 27.7 | 17.0 |
| 28.5 | 26.3 |
| 29.0 | 27.0 |
| 29.4 | 19.3 |
| 29.8 | 21.3 |
| 30.1 | 17.6 |
| 31.2 | 16.6 |
| 31.5 | 16.1 |
| 32.3 | 13.8 |
| 33.1 | 17.2 |
| 34.1 | 15.7 |
| 35.1 | 12.6 |
| 35.7 | 12.8 |
| 36.7 | 10.9 |
| 37.3 | 16.1 |
| 39.4 | 11.3 |

Example 503A: First Seed Preparation of Crystalline Example 503

To a vial equipped with a stir bar and charged with N-[(1S)-1-[(3P)-3-(4-chloro-1-{2-[(2R,6S)-2,6-dimethylmorpholin-4-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide (Example 503, 189 mg) was added ethanol (10.0 mL). The mixture was heated to 60° C. until all solids dissolved. The solution was allowed to cool to room temperature with stirring upon which a precipitate was observed. The mixture was stirred at room temperature for 3 days. The solids were collected by filtration to afford 155 mg of a material referred to as Compound H (Form 1) or as Example 503A (Form 1) to distinguish between other crystalline polymorphs of the crystalline parent form of Example 503. The unique and crystalline nature of this material, the crystalline parent form of Example 503A (Form 1) ("Compound H (Form 1)"), was confirmed by XRPD as shown in FIG. 18 and DSC as shown in FIG. 19.

DSC and TGA result: In FIG. 19 the overlay of DSC and TGA thermograms of Compound H (Form 1)exhibits a melting onset of about 127° C. and a weight loss of about 1.5 wt %.

XRPD result: See FIG. 18 for the XRPD pattern of Compound H (Form 1) and see Table 8 for a corresponding list of 2-theta peaks. This crystalline parent form of Compound H (Form 1) can be used as seed crystals in future preparations of this crystalline form.

TABLE 8

| XRPD Peak List of Compound H (Form 1) (Example 503A (Form 1)) | |
|---|---|
| Pos. [°2θ] | Rel. Int. [%] |
| 6.1 | 100.0 |
| 6.7 | 69.0 |
| 7.6 | 15.0 |
| 8.5 | 94.7 |
| 9.2 | 22.1 |
| 9.7 | 37.2 |
| 11.0 | 31.1 |
| 11.6 | 11.6 |
| 12.0 | 34.8 |
| 12.3 | 24.2 |
| 13.0 | 26.1 |
| 13.4 | 28.6 |
| 14.1 | 22.9 |
| 14.3 | 17.2 |
| 15.1 | 14.4 |
| 15.3 | 30.5 |
| 16.4 | 14.0 |
| 16.6 | 14.4 |
| 17.2 | 24.2 |
| 17.9 | 12.2 |
| 18.4 | 74.5 |
| 19.4 | 34.1 |
| 19.6 | 65.2 |
| 20.3 | 41.9 |
| 20.7 | 21.9 |
| 21.5 | 25.2 |
| 21.9 | 34.9 |
| 22.3 | 19.0 |
| 23.0 | 41.3 |
| 24.0 | 15.3 |
| 24.3 | 18.7 |
| 24.8 | 30.6 |
| 25.3 | 22.2 |
| 25.9 | 43.5 |
| 26.9 | 16.0 |
| 27.1 | 12.9 |
| 28.1 | 12.3 |
| 28.6 | 12.2 |
| 29.6 | 13.5 |
| 30.4 | 9.9 |
| 30.6 | 11.0 |
| 31.0 | 10.0 |
| 31.2 | 12.8 |
| 31.6 | 13.7 |
| 32.9 | 9.0 |
| 33.4 | 9.1 |
| 33.7 | 10.6 |
| 34.2 | 10.7 |
| 34.9 | 10.1 |
| 35.6 | 7.8 |
| 36.4 | 6.9 |
| 36.8 | 6.7 |
| 37.4 | 6.9 |
| 37.9 | 10.3 |
| 38.5 | 6.3 |
| 39.5 | 7.3 |

Example 529A: First Seed Preparation of Crystalline Example 529

To a solution of N-[(1S)-1-[(3P)-3-{4-chloro-3-methanesulfonamido-1-[2-(2,2,6,6-tetramethylmorpholin-4-yl)

ethyl]-1H-indazol-7-yl}-7-(4,4-difluorocyclohexyl)-5-{[(2R,6S)-2,6-dimethylmorpholin-4-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide (15.5 g, 1.00 Eq, 14.0 mmol, single atropisomer) in DCM (150.00 mL) was added (2S,6R)-2,6-dimethylmorpholine (4.84 g, 3.00 Eq, 42.0 mmol). The mixture was stirred for 10 min. To the mixture was added sodium triacetoxyborohydride (8.90 g, 3.00 Eq, 42.0 mmol) and the mixture was stirred for 5 h. The mixture was diluted with water and then was extracted with dichloromethane (200 mL). The isolated organic layer was dried over $Na_2SO_4$, filtered, and the filtrate was concentrated under reduced pressure. The resulting residue was subjected to silica gel column chromatography (330 g column) eluting with 5-100% EtOAc in hexanes and the desired pure fractions were pooled and then concentrated under reduced pressure to afford N-((1S)-1-(3-(4-chloro-3-(methylsulfonamido)-1-(2-(2,2,6,6-tetramethylmorpholino)ethyl)-1H-indazol-7-yl)-7-(4,4-difluorocyclohexyl)-5-(((2S,6R)-2,6-dimethylmorpholino)methyl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (6.0 g, 34% yield), Example 529. Impure ("mixed") fractions resulting from the silica gel chromatography step described above were combined and then concentrated under reduced pressure. To the resulting solids was added isopropanol (50 mL) and the mixture was heated at 80° C. The solids did not dissolve completely before a distinct white precipitate began to form. The mixture was allowed to cool to room temp upon which significantly more precipitate was observed. The mixture was stirred at room temperature for 1 h. The solids were isolated by filtration and then were dried in a 45° C. vacuum overnight (app. 18 h) to afford 1.9 g of a material referred to as Compound J (Form 1) or as Example 529A (Form 1) to distinguish between other crystalline polymorphs of the crystalline parent form of Example 529. The unique and crystalline nature of this material, the crystalline parent form of Example 529A (Form 1) ("Compound J (Form 1)"), was confirmed by XRPD as shown in FIG. 20 and DSC as shown in FIG. 21.

DSC and TGA result: In FIG. 21 the overlay of DSC and TGA thermograms of Compound J (Form 1) exhibits a melting onset of about 235° C. and a weight loss of about 0.23 wt %.

XRPD result: See FIG. 20 for the XRPD pattern of Compound J (Form 1) and see Table 9 for a corresponding list of 2-theta peaks. This crystalline parent form of Compound J (Form 1) can be used as seed crystals in future preparations of this crystalline form.

TABLE 9

XRPD Peak List of Compound J (Form 1) (Example 529A (Form 1))

| Pos. [°2θ] | Rel. Int. [%] |
|---|---|
| 4.4 | 34.4 |
| 4.9 | 37.7 |
| 5.5 | 46.0 |
| 5.8 | 57.1 |
| 6.1 | 100.0 |
| 6.4 | 90.2 |
| 6.7 | 41.2 |
| 8.7 | 28.2 |
| 9.4 | 23.1 |
| 9.8 | 32.3 |
| 12.2 | 34.2 |
| 13.0 | 35.0 |
| 13.5 | 38.2 |
| 13.9 | 46.8 |
| 14.4 | 57.4 |
| 14.8 | 46.9 |
| 15.4 | 54.4 |
| 15.9 | 43.0 |
| 16.2 | 43.4 |
| 16.9 | 40.2 |
| 17.6 | 39.6 |
| 18.6 | 45.3 |
| 19.9 | 37.5 |
| 20.5 | 40.5 |
| 21.1 | 31.8 |
| 21.7 | 30.1 |
| 22.6 | 32.2 |
| 23.0 | 34.0 |
| 23.4 | 30.3 |
| 23.9 | 28.2 |
| 24.9 | 30.5 |
| 25.8 | 23.2 |
| 27.7 | 19.7 |
| 28.7 | 23.3 |
| 29.3 | 18.2 |
| 30.8 | 18.5 |
| 33.7 | 14.8 |
| 35.0 | 14.5 |

Example 538A: First Seed Preparation of Crystalline Example 538

To a vial equipped with a stir bar and charged with N-[(1S)-1-[(3P)-3-[4-chloro-3-methanesulfonamido-1-(3-methoxypropyl)-1H-indazol-7-yl]-5-[(3,3-difluoroazetidin-1-yl)methyl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide (Example 538, 40 mg) was added ethanol (1.0 mL). The vial was placed on an 80° C. hot plate with stirring until all solids were dissolved. The vial was removed from the heat and the stir bar was removed from the vial. The solution was allowed to cool to room temperature with stirring for app 18 h. The solids were collected by filtration and then were dried in a 50° C. vacuum oven for 18 hours to afford the material referred to as Compound K (Form 1) or as Example 538A (Form 1) to distinguish between other crystalline polymorphs of the crystalline parent form of Example 538. The unique and crystalline nature of this material, the crystalline parent form of Example 538 (Form 1) ("Compound K (Form 1)"), was confirmed by XRPD as shown in FIG. 22 and DSC as shown in FIG. 23.

DSC and TGA result: In FIG. 23 the overlay of DSC and TGA thermograms of Compound K (Form 1) exhibits a melting onset of about 162° C. and a weight loss of about 0.55 wt %.

XRPD result: See FIG. 22 for the XRPD pattern of Compound K (Form 1) and see Table 10 for a corresponding list of 2-theta peaks. This crystalline parent form of Compound K (Form 1)can be used as seed crystals in future preparations of this crystalline form.

TABLE 10

| XRPD Peak List of Compound K (Form 1) (Example 538A (Form 1)) | |
|---|---|
| Pos. [°2θ] | Rel. Int. [%] |
| 6.5 | 26.1 |
| 7.2 | 58.2 |
| 7.9 | 34.7 |
| 8.5 | 19.0 |
| 8.9 | 16.3 |
| 9.4 | 41.4 |
| 10.1 | 16.1 |
| 11.0 | 15.9 |
| 11.2 | 26.5 |
| 11.6 | 21.3 |
| 11.9 | 16.4 |
| 12.6 | 27.3 |
| 12.8 | 52.6 |
| 13.2 | 25.3 |
| 13.9 | 30.8 |
| 14.3 | 29.7 |
| 14.6 | 21.9 |
| 15.5 | 55.8 |
| 15.9 | 22.0 |
| 16.9 | 41.2 |
| 17.4 | 20.3 |
| 17.9 | 22.9 |
| 18.1 | 20.9 |
| 18.8 | 100.0 |
| 19.1 | 27.0 |
| 19.5 | 23.0 |
| 20.0 | 38.7 |
| 20.4 | 19.1 |
| 20.8 | 27.6 |
| 21.6 | 39.2 |
| 22.0 | 21.4 |
| 22.3 | 21.9 |
| 22.7 | 32.2 |
| 24.1 | 18.8 |
| 24.6 | 40.8 |
| 25.0 | 21.2 |
| 25.2 | 23.7 |
| 25.4 | 21.5 |
| 26.0 | 21.3 |
| 26.2 | 18.1 |
| 26.5 | 19.6 |
| 27.1 | 16.3 |
| 27.6 | 18.7 |
| 27.9 | 17.6 |
| 28.0 | 24.2 |
| 28.6 | 13.6 |
| 29.1 | 16.0 |
| 29.3 | 15.5 |
| 29.6 | 19.1 |
| 30.8 | 11.6 |
| 31.3 | 15.1 |
| 31.7 | 12.9 |
| 32.6 | 12.3 |
| 33.0 | 10.2 |
| 33.5 | 10.4 |
| 33.8 | 10.7 |
| 35.1 | 10.8 |
| 35.5 | 10.0 |
| 35.8 | 9.1 |
| 37.5 | 11.2 |
| 37.8 | 9.0 |
| 38.1 | 10.7 |
| 38.7 | 9.1 |
| 39.2 | 9.0 |

Crystallization of Example 13 Using Seed Crystals

To a 100 mL round bottom flask charged with NN-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide (1.75 g, 1.67 mmol) was added 2-propanol (20.000 mL). The mixture was heated to 80° C. with stirring. To the heated suspension was added Example 13A (Form 1) ("Compound D (Form 1)") (5 mg, crystalline seed crystals of Compound D (Form 1)). The slurry was allowed to cool to room temperature with stirring for 16 h. The solids were collected by filtration and were then dried in a 50° C. vacuum oven for 18 hours to afford N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide (1.65 g, 94% yield), a crystalline material. The material was analyzed by DSC, TGA, and XRPD which produced datasets that were substantially in accordance with the data described in FIG. 9 and FIG. 10, thereby confirming that the isolated material was Compound D (Form 1) (Example 13A (Form 1)).

IUPAC Chemical Names:

The IUPAC chemical names for each Example compound are provided herein and use P/M nomenclature to designate axial chirality. It is noted that at this time IUPAC chemical names using P/M nomenclature to designate axial chirality are not recognized by common software such tools such as ChemDraw or JChem. Table B below illustrates the difference between the two naming conventions for a list of representative Example compounds of the present invention. Often it is necessary to remove the "(3P)" portion of the IUPAC name to allow common software tools to convert the name to a chemical structure. For the Intermediate compounds disclosed herein, the chemical name provided may be the IUPAC chemical name using P/M nomenclature to designate axial chirality or the ChemDraw chemical name without P/M nomenclature. In instances where diastereomers may arise, many of the compounds disclosed in the Examples section were isolated as single stereoisomers (<5% of other diastereomers present in the mixture). The isolation of a single stereoisomer is reflected in the given chemical structure where stereochemistry is explicitly stated. Therefore, the designation of axial chirality in the given chemical structure supersedes any absence of axial chirality in the given chemical name.

TABLE B

| Example | IUPAC Name | ChemDraw Name |
|---|---|---|
| Example 5 | N-[(1S)-1-[(3P)-3-(4-chloro-1-{2-[(3R,5S)-3,5-difluoropiperidin-1-yl]ethyl}-3-methanesulfonamido-1H- | N-((S)-1-(3-(4-chloro-1-(2-((3S,5R)-3,5-difluoropiperidin-1-yl)ethyl)-3-(methylsulfonamido)- |

TABLE B-continued

| Example | IUPAC Name | ChemDraw Name |
|---|---|---|
| | indazol-7-yl)-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6), 8-dien-7-yl]acetamide | 1H-indazol-7-yl)-7-(4,4-difluorocyclohexyl)-5-methyl-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide |
| Example 11 | N-[(1S)-1-[(3P)-3-(4-chloro-1-{2-[(3R,5S)-3,5-difluoropiperidin-1-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | N-((S)-1-(3-(4-chloro-1-(2-((3S,5R)-3,5-difluoropiperidin-1-yl)ethyl)-3-(methylsulfonamido)-1H-indazol-7-yl)-5-methyl-4-oxo-7-(1,4,4-trifluorocyclohexyl)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide |
| Example 12 | N-[(1S)-1-[(3P)-3-(4-chloro-1-{2-[(3R,5S)-3,5-difluoropiperidin-1-ylethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | N-((S)-1-(3-(4-chloro-1-(2-((3S,5R)-3,5-difluoropiperidin-1-yl)ethyl)-3-(methylsulfonamido)-1H-indazol-7-yl)-5-methyl-4-oxo-7-(1,4,4-trifluorocyclohexyl)-3,4-dihydropyrido[2,3-d]pyrimidin-2-yl)-2-(3,5-difluorophenyl)ethyl)-2-((3bS,4aS)-3-cyclopropyl-3b,4,4a,5-tetrahydro-1H-cyclopropa[3,4]cyclopenta[1,2-c]pyrazol-1-yl)acetamide |
| Example 13 | N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-methyl-4-oxo-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6), 8-dien-7-yl]acetamide | N-((S)-1-(3-(4-chloro-3-(methylsulfonamido)-1-(2-(2,2,6,6-tetramethylmorpholino)ethyl)-1H-indazol-7-yl)-7-(4,4-difluorocyclohexyl)-5-methyl-4-oxo-3,4-dihydropyrido[2,3-d]pyrimidin-2-yl)-2-(3,5-difluorophenyl)ethyl)-2-((3bS,4aS)-3-cyclopropyl-3b,4,4a,5-tetrahydro-1H-cyclopropa[3,4]cyclopenta[1,2-c]pyrazol-1-yl)acetamide |
| Example 135 | N-[(1S)-1-[(3P)-3-[4-chloro-3-methanesulfonamido-1-(3-methoxypropyl)-1H-indazol-7-yl]-7-(4,4-difluorocyclohexyl)-5-[(2-methoxyethyl)amino]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6), 8-dien-7-yl]acetamide | N-((S)-1-(3-(4-chloro-1-(3-methoxypropyl)-3-(methylsulfonamido)-1H-indazol-7-yl)-7-(4,4-difluorocyclohexyl)-5-((2-methoxyethyl)amino)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide |
| Example 427 | N-[(1S)-1-[(3P)-3-[4-chloro-3-methanesulfonamido-1-(3-methoxypropyl)-1H-indazol-7-yl]-7-(4,4-difluorocyclohexyl)-5-(ethylamino)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | N-((S)-1-(3-(4-chloro-1-(3-methoxypropyl)-3-(methylsulfonamido)-1H-indazol-7-yl)-7-(4,4-difluorocyclohexyl)-5-(ethylamino)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide |
| Example 448 | N-[(1S)-1-[(3P)-3-[4-chloro-3-methanesulfonamido-1-(3-methoxypropyl)-1H-indazol-7-yl]-7-(4,4-difluorocyclohexyl)-5-{[(2R,6S)-2,6-dimethylmorpholin-4-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6), 8-dien-7-yl]acetamide | N-((S)-1-(3-(4-chloro-1-(3-methoxypropyl)-3-(methylsulfonamido)-1H-indazol-7-yl)-7-(4,4-difluorocyclohexyl)-5-(((2S,6R)-2,6-dimethylmorpholino)methyl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide |

TABLE B-continued

| Example | IUPAC Name | ChemDraw Name |
|---|---|---|
| Example 503 | N-[(1S)-1-[(3P)-3-(4-chloro-1-{2-[(2R,6S)-2,6-dimethylmorpholin-4-yl]ethyl}-3-methanesulfonamido-1H-indazol-7-yl)-5-methyl-4-oxo-7-(1,4,4-trifluorocyclohexyl)-3H,4H-pyrido[2,3-d]pyrimidin-2-yl]-2-(3,5-difluorophenyl)ethyl]-2-[(2S,4S)-9-cyclopropyl-7,8-diazatricyclo[4.3.0.0$^{2,4}$]nona-1(6),8-dien-7-yl]acetamide | N-((S)-1-(3-(4-chloro-1-(2-((2S,6R)-2,6-dimethylmorpholino)ethyl)-3-(methylsulfonamido)-1H-indazol-7-yl)-5-methyl-4-oxo-7-(1,4,4-trifluorocyclohexyl)-3,4-dihydropyrido[2,3-d]pyrimidin-2-yl)-2-(3,5-difluorophenyl)ethyl)-2-((3bS,4aS)-3-cyclopropyl-3b,4,4a,5-tetrahydro-1H-cyclopropa[3,4]cyclopenta[1,2-c]pyrazol-1-yl)acetamide |
| Example 529 | N-[(1S)-1-[(3P)-3-{4-chloro-3-methanesulfonamido-1-[2-(2,2,6,6-tetramethylmorpholin-4-yl)ethyl]-1H-indazol-7-yl}-7-(4,4-difluorocyclohexyl)-5-{[(2R,6S)-2,6-dimethylmorpholin-4-yl]methyl}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6), 8-dien-7-yl]acetamide | N-((S)-1-(3-(4-chloro-3-(methylsulfonamido)-1-(2-(2,2,6,6-tetramethylmorpholino)ethyl)-1H-indazol-7-yl)-7-(4,4-difluorocyclohexyl)-5-(((2S,6R)-2,6-dimethylmorpholino)methyl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide |
| Example 538 | N-[(1S)-1-[(3P)-3-[4-chloro-3-methanesulfonamido-1-(3-methoxypropyl)-1H-indazol-7-yl]-5-[(3,3-difluoroazetidin-1-yl)methyl]-7-(4,4-difluorocyclohexyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide | N-((S)-1-(3-(4-chloro-1-(3-methoxypropyl)-3-(methylsulfonamido)-1H-indazol-7-yl)-5-((3,3-difluoroazetidin-1-yl)methyl)-7-(4,4-difluorocyclohexyl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide |

Biological Methods

HIV cell culture assay—MT-2 cells, 293T cells and the proviral DNA clone of $NL_{4-3}$ virus were obtained from the NIH AIDS Research and Reference Reagent Program. MT-2 cells were propagated in RPMI 1640 media supplemented with 10% heat inactivated fetal bovine serum (FBS), 100 mg/ml penicillin G and up to 100 units/mL streptomycin. The 293T cells were propagated in DMEM media supplemented with 10% heat inactivated FBS, 100 mg/mL penicillin G and 100 mg/mL streptomycin. A recombinant $NL_{4-3}$ proviral clone, in which a section of the nef gene was replaced with the *Renilla* luciferase gene, was used to make the reference virus used in these studies. The recombinant virus was prepared through transfection of the recombinant $NL_{4-3}$ proviral clone into 293T cells using Transit-293 Transfection Reagent from Mirus Bio LLC (Madison, WI). Supernatant was harvested after 2-3 days and the amount of virus present was titered in MT-2 cells using luciferase enzyme activity as a marker by measuring luciferase enzyme activity. Luciferase was quantitated using the EnduRen Live Cell Substrate from Promega (Madison, WI). Antiviral activities of compounds toward the recombinant virus were quantified by measuring luciferase activity in MT-2 cells infected for 4-5 days with the recombinant virus in the presence of serial dilutions of the compound.

The 50% effective concentration ($EC_{50}$) was calculated by using the exponential form of the median effect equation where (Fa)=1/[1+($ED_{50}$/drug conc.)m](Johnson V A, Byington R T. Infectivity Assay. In Techniques in HIV Research. ed. Aldovini A, Walker B D. 71-76. New York: Stockton Press. 1990). Curve fitting and analysis were performed with ActivityBase XE Runner software version 9.1.0.4 using model 203 (ID Business Solutions, LTD, Guildford, UK).

Compound cytotoxicity and the corresponding $CC_{50}$ values were determined using the same protocol as described in the antiviral assay except that uninfected cells were used. Cytotoxicity was assessed on day 4 in uninfected MT2 cells by using an XTT (2,3-bis[2-Methoxy-4-nitro-5-sulfophenyl]-2H-tetrazolium-5-carboxyanilide inner salt)-based colorimetric assay (Sigma-Aldrich, St Louis, Mo).

Results: The $EC_{50}$ results and the 0050 results for Example compounds of the invention are shown in Table C below. As can be seen from the $EC_{50}$ values of Table C, the Example compounds of the invention demonstrate antiviral activity. Further, the Example compounds of the invention show significant selectivity for on-target antiviral activity versus cytotoxic activity, as can be seen from the comparison of the 00 values (provided in µM in Table C) and the $EC_{50}$ values (provided in nM in Table C) provided in Table C.

TABLE C

| Example No. | $EC_{50}$ (nM) | $CC_{50}$ (µM) |
|---|---|---|
| Example 1 | 0.009 | >0.050 |
| Example 2 | 0.008 | >0.050 |
| Example 3 | 0.009 | >0.050 |
| Example 4 | 0.007 | >0.050 |
| Example 5 | 0.009 | >20 |
| Example 6 | 0.006 | >0.050 |
| Example 7 | 0.009 | >0.050 |
| Example 9 | 0.009 | >0.050 |
| Example 10 | 0.060 | >0.050 |

TABLE C-continued

| Example No. | $EC_{50}$ (nM) | $CC_{50}$ (μM) |
|---|---|---|
| Example 11 | 0.009 | >20 |
| Example 12 | 0.012 | >20 |
| Example 13 | 0.011 | >20 |
| Example 14 | 0.009 | >0.050 |
| Example 15 | 0.010 | >0.050 |
| Example 17 | 0.012 | >0.050 |
| Example 24 | 0.007 | >0.050 |
| Example 26 | 0.011 | >0.050 |
| Example 40 | 0.028 | >0.050 |
| Example 41 | 0.015 | >0.050 |
| Example 42 | 0.021 | >0.050 |
| Example 43 | 0.021 | >0.050 |
| Example 48 | 0.018 | >0.050 |
| Example 59 | 0.011 | >0.050 |
| Example 60 | 0.012 | >0.050 |
| Example 72 | 0.029 | >0.050 |
| Example 77 | 0.018 | >0.050 |
| Example 78 | 0.016 | >0.050 |
| Example 84 | 0.016 | >0.050 |
| Example 85 | 0.016 | >0.050 |
| Example 86 | 0.011 | >0.050 |
| Example 87 | 0.019 | >0.050 |
| Example 88 | 0.021 | >0.050 |
| Example 89 | 0.014 | >0.050 |
| Example 90 | 0.018 | >0.050 |
| Example 94 | 0.023 | >0.050 |
| Example 105 | 0.011 | >0.050 |
| Example 112 | 0.013 | >0.050 |
| Example 114 | 0.013 | >0.050 |
| Example 115 | 0.016 | >0.050 |
| Example 116 | 0.012 | >0.050 |
| Example 121 | 0.027 | >0.050 |
| Example 128 | 0.013 | >0.050 |
| Example 129 | 0.024 | >0.050 |
| Example 130 | 0.013 | >0.050 |
| Example 134 | 0.022 | >0.050 |
| Example 135 | 0.013 | >0.050 |
| Example 149 | 0.018 | >0.050 |
| Example 150 | 0.017 | >0.050 |
| Example 154 | 0.019 | >0.050 |
| Example 155 | 0.027 | >0.050 |
| Example 158 | 0.011 | >0.050 |
| Example 159 | 0.017 | >0.050 |
| Example 160 | 0.023 | >0.050 |
| Example 165 | 0.031 | >0.050 |
| Example 166 | 0.019 | >0.050 |
| Example 167 | 0.024 | >0.050 |
| Example 168 | 0.018 | >0.050 |
| Example 170 | 0.032 | >0.050 |
| Example 176 | 0.018 | >0.050 |
| Example 187 | 0.032 | >0.050 |
| Example 189 | 0.035 | >0.050 |
| Example 191 | 0.024 | >0.050 |
| Example 195 | 0.037 | >0.050 |
| Example 199 | 0.023 | >0.050 |
| Example 207 | 0.013 | >0.050 |
| Example 208 | 0.009 | >0.050 |
| Example 211 | 0.012 | >0.050 |
| Example 214 | 0.015 | >0.050 |
| Example 227 | 0.016 | >0.050 |
| Example 229 | 0.013 | >0.050 |
| Example 230 | 0.006 | >0.050 |
| Example 231 | 0.010 | >0.050 |
| Example 232 | 0.009 | >0.050 |
| Example 237 | 0.006 | >0.050 |
| Example 239 | 0.021 | >0.050 |
| Example 240 | 0.026 | >0.050 |
| Example 241 | 0.018 | >0.050 |
| Example 245 | 0.019 | >0.050 |
| Example 246 | 0.028 | >0.050 |
| Example 247 | 0.047 | >0.050 |
| Example 248 | 0.018 | >0.050 |
| Example 257 | 0.027 | >0.050 |
| Example 259 | 0.025 | >0.050 |
| Example 266 | 0.034 | >0.050 |
| Example 267 | 0.015 | >0.050 |
| Example 268 | 0.015 | >0.050 |
| Example 269 | 0.018 | >0.050 |

TABLE C-continued

| Example No. | $EC_{50}$ (nM) | $CC_{50}$ (μM) |
|---|---|---|
| Example 270 | 0.011 | >0.050 |
| Example 271 | 0.015 | >0.050 |
| Example 273 | 0.020 | >0.050 |
| Example 275 | 0.012 | >0.050 |
| Example 276 | 0.016 | >0.050 |
| Example 277 | 0.009 | >0.050 |
| Example 278 | 0.005 | >0.050 |
| Example 279 | 0.036 | >0.050 |
| Example 280 | 0.006 | >0.050 |
| Example 281 | 0.011 | >0.050 |
| Example 283 | 0.008 | >0.050 |
| Example 285 | 0.009 | >0.050 |
| Example 287 | 0.010 | >0.050 |
| Example 288 | 0.008 | >0.050 |
| Example 289 | 0.025 | >0.050 |
| Example 290 | 0.023 | >0.050 |
| Example 291 | 0.012 | >0.050 |
| Example 292 | 0.016 | >0.050 |
| Example 298 | 0.016 | >0.050 |
| Example 307 | 0.023 | >0.050 |
| Example 310 | 0.019 | >0.050 |
| Example 311 | 0.013 | >0.050 |
| Example 312 | 0.021 | >0.050 |
| Example 315 | 0.025 | >0.050 |
| Example 321 | 0.020 | >0.050 |
| Example 322 | 0.009 | >0.050 |
| Example 324 | 0.014 | >0.050 |
| Example 325 | 0.009 | >0.050 |
| Example 327 | 0.008 | >0.050 |
| Example 354 | 0.022 | >0.050 |
| Example 356 | 0.029 | >0.050 |
| Example 360 | 0.010 | >0.050 |
| Example 370 | 0.009 | >0.020 |
| Example 371 | 0.009 | >0.020 |
| Example 375 | 0.014 | >0.020 |
| Example 376 | 0.016 | >0.020 |
| Example 381 | 0.007 | >0.020 |
| Example 382 | 0.037 | >0.020 |
| Example 384 | 0.025 | >0.020 |
| Example 387 | 0.039 | >0.020 |
| Example 393 | 0.035 | >0.020 |
| Example 395 | 0.034 | >0.020 |
| Example 396 | 0.020 | >0.020 |
| Example 401 | 0.012 | >0.020 |
| Example 405 | 0.034 | >0.020 |
| Example 409 | 0.014 | >0.020 |
| Example 413 | 0.013 | >0.020 |
| Example 414 | 0.010 | >0.020 |
| Example 415 | 0.013 | >0.020 |
| Example 416 | 0.012 | >0.020 |
| Example 417 | 0.007 | >0.020 |
| Example 418 | 0.019 | >0.020 |
| Example 419 | 0.011 | >0.020 |
| Example 420 | 0.011 | >0.020 |
| Example 421 | 0.012 | >0.020 |
| Example 424 | 0.012 | >0.020 |
| Example 427 | 0.010 | >0.020 |
| Example 428 | 0.020 | >0.020 |
| Example 429 | 0.019 | >0.020 |
| Example 430 | 0.011 | >0.020 |
| Example 431 | 0.010 | >0.020 |
| Example 432 | 0.182 | >0.020 |
| Example 433 | 0.037 | >0.020 |
| Example 434 | 0.010 | >0.020 |
| Example 435 | 0.009 | >0.020 |
| Example 444 | 0.009 | >0.020 |
| Example 445 | 0.015 | >0.020 |
| Example 446 | 0.009 | >0.020 |
| Example 448 | 0.009 | >0.020 |
| Example 449 | 0.009 | >0.020 |
| Example 453 | 0.008 | >0.020 |
| Example 454 | 0.010 | >0.020 |
| Example 456 | 0.010 | >0.020 |
| Example 457 | 0.007 | >0.020 |
| Example 458 | 0.007 | >0.020 |
| Example 459 | 0.005 | >0.020 |
| Example 462 | 0.019 | >0.020 |
| Example 467 | 0.017 | >0.020 |

TABLE C-continued

| Example No. | $EC_{50}$ (nM) | $CC_{50}$ (μM) |
|---|---|---|
| Example 471 | 0.038 | >0.020 |
| Example 472 | 0.087 | >0.020 |
| Example 473 | 0.008 | >0.020 |
| Example 474 | 0.011 | >0.020 |
| Example 475 | 0.004 | >0.020 |
| Example 476 | 0.005 | >0.020 |
| Example 477 | 0.013 | >0.020 |
| Example 479 | 0.004 | >0.020 |
| Example 480 | 0.005 | >0.020 |
| Example 484 | 0.006 | >0.020 |
| Example 485 | 0.016 | >0.020 |
| Example 488 | 0.009 | >0.020 |
| Example 489 | 0.018 | >0.020 |
| Example 491 | 0.009 | >0.020 |
| Example 495 | 0.010 | >0.020 |
| Example 498 | 0.018 | >0.020 |
| Example 500 | 0.049 | >0.020 |
| Example 501 | 0.016 | >0.020 |
| Example 502 | 0.019 | >0.020 |
| Example 503 | 0.008 | >0.020 |
| Example 504 | 0.049 | >0.020 |
| Example 505 | 0.013 | >0.020 |
| Example 506 | 0.027 | >0.020 |
| Example 507 | 0.021 | >0.020 |
| Example 508 | 0.012 | >0.020 |
| Example 509 | 0.006 | >0.020 |
| Example 512 | 0.006 | >0.020 |
| Example 513 | 0.017 | >0.020 |
| Example 514 | 0.014 | >0.020 |
| Example 515 | 0.016 | >0.020 |
| Example 517 | 0.009 | >0.020 |
| Example 519 | 0.024 | >0.020 |
| Example 521 | 0.079 | >0.020 |
| Example 522 | 0.014 | >0.020 |
| Example 523 | 0.012 | >0.020 |
| Example 525 | 0.016 | >0.020 |
| Example 526 | 0.014 | >0.020 |
| Example 527 | 0.012 | >0.020 |
| Example 528 | 0.006 | >0.020 |
| Example 529 | 0.017 | >1.0 |
| Example 530 | 0.008 | >0.020 |
| Example 531 | 0.021 | >0.020 |
| Example 535 | 0.057 | >0.020 |
| Example 536 | 0.025 | >0.020 |
| Example 538 | 0.007 | >0.020 |
| Example 539 | 0.006 | >0.020 |
| Example 543 | 0.014 | >0.020 |
| Example 546 | 0.017 | >0.020 |
| Example 549 | 0.258 | >0.020 |
| Example 550 | 0.012 | >0.020 |
| Example 552 | 0.006 | >0.020 |
| Example 553 | 0.024 | >0.020 |
| Example 556 | 0.014 | >0.020 |
| Example 557 | 0.007 | >0.020 |
| Example 561 | 0.013 | >0.020 |
| Example 563 | 0.019 | >0.020 |
| Example 564 | 0.012 | >0.020 |
| Example 565 | 0.011 | >0.020 |
| Example 566 | 0.079 | >0.020 |
| Example 567 | 0.009 | >0.020 |
| Example 568 | 0.010 | >0.020 |
| Example 569 | 0.012 | >0.020 |
| Example 570 | 0.029 | >0.020 |
| Example 571 | 0.014 | >0.020 |
| Example 572 | 0.015 | >0.020 |
| Example 573 | 0.012 | >0.020 |
| Example 574 | 0.019 | >0.020 |
| Example 575 | 0.012 | >0.020 |
| Example 576 | 0.010 | >0.020 |
| Example 577 | 0.014 | >0.020 |
| Example 578 | 0.008 | >0.020 |
| Example 579 | 0.011 | >0.020 |
| Example 581 | 0.015 | >0.020 |
| Example 582 | 0.017 | >0.020 |
| Example 583 | 0.031 | >0.020 |
| Example 584 | 0.015 | >0.020 |
| Example 585 | 0.012 | >0.020 |
| Example 586 | 0.016 | >0.020 |

TABLE C-continued

| Example No. | $EC_{50}$ (nM) | $CC_{50}$ (μM) |
|---|---|---|
| Example 588 | 0.008 | >0.020 |
| Example 589 | 0.005 | >0.020 |
| Example 590 | 0.013 | >0.020 |
| Example 591 | 0.006 | >0.020 |
| Example 592 | 0.006 | >0.020 |
| Example 593 | 0.017 | >0.020 |
| Example 594 | 0.011 | >0.020 |
| Example 595 | 0.014 | >0.020 |
| Example 596 | 0.029 | >0.020 |
| Example 597 | 0.021 | >0.020 |
| Example 598 | 0.009 | >0.020 |
| Example 599 | 0.007 | >0.020 |
| Example 600 | 0.008 | >0.020 |
| Example 601 | 0.008 | >0.020 |
| Example 602 | 0.017 | >0.020 |
| Example 603 | 0.004 | >0.020 |
| Example 604 | 0.011 | >0.020 |
| Example 605 | 0.018 | >0.020 |
| Example 606 | 0.026 | |
| Example 609 | 0.033 | |
| Example 610 | 0.017 | |
| Example 611 | 0.025 | |
| Example 612 | 0.028 | |
| Example 613 | 0.015 | |
| Example 615 | 0.027 | |
| Example 620 | 0.007 | |
| Example 621 | 0.005 | |
| Example 623 | 0.012 | >0.10 |
| Example 632 | 0.021 | >0.050 |
| Example 636 | 0.015 | >0.050 |
| Example 638 | 0.018 | >0.050 |
| Example 639 | 0.025 | >0.050 |
| Example 641 | 0.029 | >0.050 |
| Example 643 | 0.017 | >0.050 |
| Example 671 | 0.027 | >0.020 |
| Example 675 | 0.031 | >0.020 |
| Example 676 | 0.011 | >0.020 |
| Example 679 | 0.012 | >0.020 |
| Example 683 | 0.006 | >0.020 |
| Example 684 | 0.014 | >0.020 |
| Example 685 | 0.010 | >0.020 |
| Example 691 | 0.007 | >0.020 |
| Example 697 | 0.009 | >0.020 |
| Example 698 | 0.027 | >0.020 |
| Example 702 | 0.016 | >0.020 |
| Example 703 | 0.017 | >0.020 |
| Example 704 | 0.026 | >0.020 |
| Example 705 | 0.021 | |
| Example 706 | 0.015 | |
| Example 707 | 0.038 | |
| Example 711 | 0.026 | >0.020 |
| Example 714 | 0.024 | >0.020 |
| Example 716 | 0.035 | >0.020 |
| Example 717 | 0.032 | >0.020 |
| Example 720 | 0.007 | >0.020 |
| Example 722 | 0.007 | >0.020 |
| Example 723 | 0.012 | >0.020 |
| Example 724 | 0.036 | >0.020 |

TABLE C-continued

| Example No. | $EC_{50}$ (nM) | $CC_{50}$ (μM) |
|---|---|---|
| Example 729 | 0.023 | >0.020 |
| Example 730 | 0.032 | >0.020 |
| Example 732 | 0.013 | >0.020 |
| Example 733 | 0.037 | >0.020 |
| Example 734 | 0.038 | >0.020 |
| Example 735 | 0.018 | >0.020 |
| Example 738 | 0.043 | >0.020 |
| Example 740 | 0.021 | >0.020 |
| Example 741 | 0.040 | >0.020 |
| Example 742 | 0.026 | >0.020 |
| Example 743 | 0.016 | >0.020 |
| Example 744 | 0.017 | >0.020 |
| Example 746 | 0.008 | >0.020 |
| Example 747 | 0.017 | >0.020 |
| Example 748 | 0.024 | >0.020 |
| Example 749 | 0.018 | >0.020 |
| Example 750 | 0.028 | >0.020 |
| Example 753 | 0.026 | >0.020 |
| Example 754 | 0.075 | >0.020 |
| Example 755 | 0.027 | |
| Example 756 | 0.037 | |

The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

What is claimed:

1. A compound which is

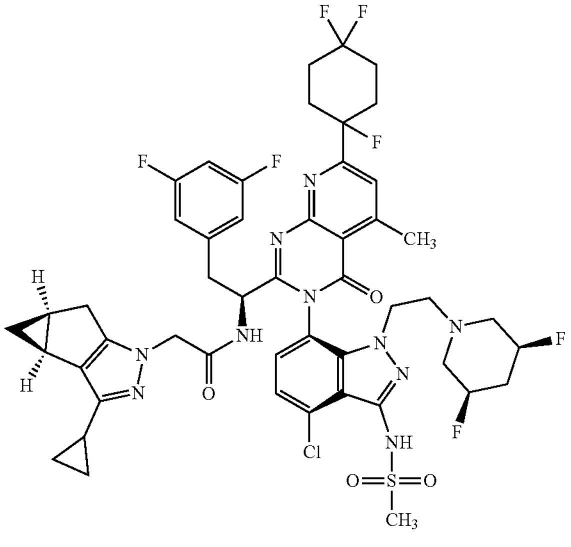

or a pharmaceutically acceptable salt thereof.

2. A compound which is:

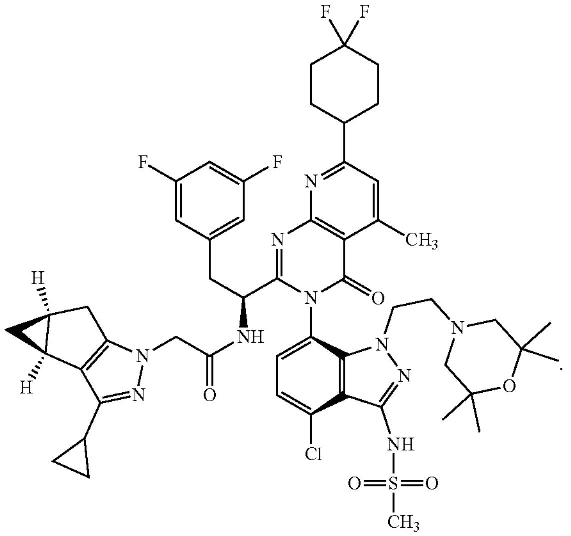

3. The compound or pharmaceutically acceptable salt according to claim 1, as a pharmaceutically acceptable salt.

4. The compound according to claim 2, wherein the compound is a crystalline compound and is characterized by having at least nine diffraction angles, when measured using Cu $K_\alpha$ radiation, selected from a group consisting of about 5.1, 5.6, 6.9, 7.6, 8.2, 8.7, 9.1, 9.8, 11.1, 11.3, 11.9, 13.2, 13.9, 14.4, 14.7, 15.2, 15.4, 16.0, 16.6, 16.8, 17.2, 17.5, 18.4, 18.7, 19.1, 19.4, 19.9, 20.3, 20.5, 21.0, 21.4, 22.0, 22.6, 23.8, 24.0, 24.4, 24.7, 25.1, 25.8, 26.2, 26.8, 27.0, 27.6, 27.9, 28.5, 28.8, 29.2, 29.8, 30.1, 31.1, 31.3, 31.9, 32.5, 32.7, 33.2, 34.1, 34.8, 35.4, 36.1, 37.7, 38.7, 39.0, 39.5, and 39.7 degrees±0.2° 2θ.

5. A pharmaceutical composition comprising a) the compound or pharmaceutically acceptable salt thereof as defined in claim 1, and b) a pharmaceutically acceptable excipient.

6. A combination of a) a compound or pharmaceutically acceptable salt thereof as defined in claim 1; and b) an agent used for treatment of AIDS or HIV infection selected from the group consisting of Dolutegravir, lamivudine, Fostemsavir, Cabotegravir, maraviroc, rilpivirine, atazanavir, Tenofovir, Alafenamide, EFdA, Doravirine, and darunavir.

7. The compound according to claim 2, wherein the compound is a crystalline compound and is characterized by a DSC thermogram having a melting onset of about 216° C.

* * * * *